US008871753B2

(12) United States Patent
Combs et al.

(10) Patent No.: US 8,871,753 B2
(45) Date of Patent: Oct. 28, 2014

(54) MACROCYCLIC COMPOUNDS AND THEIR USE AS KINASE INHIBITORS

(75) Inventors: Andrew Paul Combs, Kennett Square, PA (US); Richard B. Sparks, Boothwyn, PA (US); Eddy W. Yue, Landenberg, PA (US); Hao Feng, Aston, PA (US); Michael Jason Bower, Newark, DE (US); Wenyu Zhu, Media, PA (US)

(73) Assignee: Incyte Corporation, Wilmington, DE (US)

( * ) Notice: Subject to any disclaimer, the term of this patent is extended or adjusted under 35 U.S.C. 154(b) by 490 days.

(21) Appl. No.: 12/429,014

(22) Filed: Apr. 23, 2009

(65) Prior Publication Data
US 2009/0286778 A1 Nov. 19, 2009

Related U.S. Application Data

(60) Provisional application No. 61/047,547, filed on Apr. 24, 2008, provisional application No. 61/122,582, filed on Dec. 15, 2008.

(51) Int. Cl.
| C07D 239/48 | (2006.01) |
| C07D 487/08 | (2006.01) |
| C07D 498/04 | (2006.01) |
| C07D 498/18 | (2006.01) |
| A61K 31/505 | (2006.01) |
| C07D 413/14 | (2006.01) |
| C07D 407/12 | (2006.01) |
| C07D 403/12 | (2006.01) |
| C07D 409/12 | (2006.01) |
| C07D 417/14 | (2006.01) |
| C07D 403/14 | (2006.01) |
| C07D 413/12 | (2006.01) |

(52) U.S. Cl.
CPC ............ *C07D 239/48* (2013.01); *C07D 413/14* (2013.01); *C07D 407/12* (2013.01); *C07D 403/12* (2013.01); *C07D 409/12* (2013.01); *C07D 417/14* (2013.01); *C07D 403/14* (2013.01); *C07D 413/12* (2013.01); *C07D 498/04* (2013.01)
USPC .................... 514/183; 514/231.5; 514/252.13; 514/322; 514/422; 514/444; 540/450; 540/451; 540/454; 540/456; 540/457; 540/458; 540/460; 540/461

(58) Field of Classification Search
USPC ......... 540/450, 451, 454, 456, 457, 458, 460, 540/461; 514/183, 231.5, 252.13, 322, 422, 514/444
See application file for complete search history.

(56) References Cited

U.S. PATENT DOCUMENTS

| 5,521,184 | A | 5/1996 | Zimmermann |
| 6,537,959 | B2 | 3/2003 | Appel et al. |
| 6,919,484 | B2 | 7/2005 | Dolbier, Jr. et al. |
| 7,312,225 | B2 | 12/2007 | Luecking et al. |
| 2004/0198737 | A1 | 10/2004 | Cox et al. |
| 2004/0209895 | A1 | 10/2004 | Luecking et al. |
| 2004/0235841 | A1 | 11/2004 | Ren et al. |
| 2006/0194823 | A1 | 8/2006 | Kettschau et al. |
| 2006/0252782 | A1 | 11/2006 | Luecking et al. |
| 2007/0135461 | A1 | 6/2007 | Rodgers |
| 2008/0039482 | A1 | 2/2008 | Hartung et al. |

FOREIGN PATENT DOCUMENTS

| JP | 2005220116 | 8/2005 |
| WO | 9962908 | 12/1999 |
| WO | 9965909 | 12/1999 |
| WO | 0009495 | 2/2000 |
| WO | 0053595 | 9/2000 |
| WO | 0114402 | 3/2001 |
| WO | 0142246 | 6/2001 |
| WO | 0164655 | 9/2001 |
| WO | 0185717 | 11/2001 |
| WO | 0200196 | 1/2002 |
| WO | 03024967 | 3/2003 |
| WO | 03037347 | 5/2003 |
| WO | 03099771 | 12/2003 |
| WO | 2004005281 | 1/2004 |
| WO | 2004026881 | 4/2004 |
| WO | 2004046120 | 6/2004 |

(Continued)

OTHER PUBLICATIONS

Miyaura, N. et al., "Palladium-Catalyzed Cross-Coupling Reactions of Organoboron Compounds", Chem. Rev., 1995, 95:2457-2483.

(Continued)

*Primary Examiner* — Bruck Kifle
(74) *Attorney, Agent, or Firm* — Pepper Hamilton LLP

(57) ABSTRACT

The present invention relates to macrocyclic compounds of Formula I:

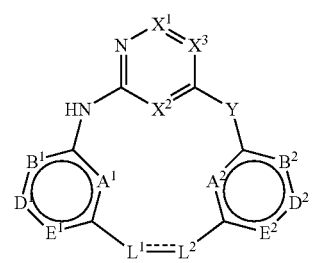

or pharmaceutically acceptable salts thereof or quaternary ammonium salts thereof wherein constituent members are provided herewith, as well as their compositions and methods of use, which are JAK/ALK inhibitors useful in the treatment of JAK/ALK-associated diseases including, for example, inflammatory and autoimmune disorders, as well as cancer.

62 Claims, No Drawings

(56) References Cited

FOREIGN PATENT DOCUMENTS

| | | |
|---|---|---|
| WO | 2004056786 | 7/2004 |
| WO | 2004072063 | 8/2004 |
| WO | 2004078682 | 9/2004 |
| WO | 2004079326 | 9/2004 |
| WO | 2004080980 | 9/2004 |
| WO | 2004099204 | 11/2004 |
| WO | 2004099205 | 11/2004 |
| WO | 2005005551 | 1/2005 |
| WO | 2005009967 | 2/2005 |
| WO | 2005010408 | 2/2005 |
| WO | 2005014552 | 2/2005 |
| WO | 2005028444 | 3/2005 |
| WO | 2005113556 | 12/2005 |
| WO | 2006056399 | 6/2006 |
| WO | 2006061415 | 6/2006 |
| WO | 2006066957 | 6/2006 |
| WO | 2006108695 | 10/2006 |
| WO | 2007003525 | 1/2007 |
| WO | 2007058627 | 5/2007 |
| WO | 2007058628 | 5/2007 |
| WO | 2007079982 | 7/2007 |
| WO | 2007147574 | 12/2007 |
| WO | 2007147575 | 12/2007 |

OTHER PUBLICATIONS

Espinet, P. et al., "The Mechanism of the Stille Reaction", Angewandte Chemie International Edition, 2004, 43 (36):4704-4734.

Heck, R.F. et al., "Palladium-catalyzed vinylic hydrogen substitution reactions with aryl, benzyl,and styryl halides", J. Org. Chem., 1972, 37(14):2320-2322.

Imada, Y. et al., "Flavin-catalyzed generation of diimide: an environmentally friendly method for the aerobic hydrogenation of olefins", J. Am. Chem. Soc., 2005, 127:14544-14545.

Hegarty, "The Chemistry of Functional Groups: The Chemistry of Diazonium and Diazo Groups", Wiley:New York, 1978, pt. 2, pp. 511-591 and Schnank, pt. 2, pp. 645-657.

Kalasi, P.S., "Organic Reactions Sterochemistry and Mechanism: Through Solved Problems": Chapter 6 (Sandmeyer Reaction), New Age Publishers, 4th ed., 2006.

Ende, D.J. et al., "A Caloricmetric Investigation to Safely Scale-Up a Curtius Rearrangement of Acryloyl Azide", J. Org. Proc. Res. Dev., 1998, 2:282-392.

McOmie, J.F.W. et al., "Demethylation of aryl methyl ethers by boron tribromide", Tetrahedron, 1968, 24(5):2289-2292.

Chinchilla, R. et al., The Sonogashira Reaction: A Booming Methodology in Synthetic Organic Chemistry, Chem., Rev., 2007, 107(3):874-922.

Spivak, J.L. et al., "Chronic Myeloproliferative Disorders", Hematology, 2003, 2003:200-224.

Berk, D.R. et al., "Portal, splenic, and superior mesenteric vein thrombosis in a patient with latent essential thrombocythemia and hyperhomocysteinemia", J. Clin. Gastroenterol., 2006, 40(3):227-8.

Brown, F.J. et al., "Hydroxyacetophenone-Derived Antagonists of the Peptidoleukotrienes", J. Med. Chem., 1989, 32:807-826.

International Search Report dated Sep. 21, 2010 received in International Application No. PCT/US2009/041555.

Moreau, E. et al. "Optimized N-phenyl-N'-(2-chloroethyl) urea as potential antineoplastic agents: Synthesis and growth inhibition activity", Bioorganic Med. Chem., 2005, 13:6703-6712.

Grabbe and Schwarz, "Immunoregulatory Mechanisms Involved in Elilcitation of allergic Contact Hypersensitivity", Immun. Today, 1998, 19(1):37-44.

Roudebush, R.E. et al., "Pharmacologic manipulation of a four day murine delayed type hypersensitivity model", Agents and Actions, 1993, 38(1-2):116-21.

Schindler, C. et al., "Cytokines and STAT signaling", Adv. Pharmacol., 2000, 47:113-74.

Berge S. et al., "Pharmaceutical Salts", Journal of Pharmaceutical Sciences, 1977, 66(1):1-2.

Blume-Jensen, P. et al., "Oncogenic Kinase Signaling", Nature, 2001, 411(6835):355-365.

Manning, G. et al., "The protein kinase complement of the human genome", Science, 2002, 298:1912-1934.

Bolen, J.B., "Nonreceptor tyrosine protein kinases", Oncogene, 1993, 8(8):2025-31.

Madhusudan, S. et al., "Tyrosine kinase inhibitors in cancer therapy", Clin. Biochem., 2004, 37(7):618-35.

Scott, M.J. et al., "Jaks, STATs, Cytokines, and Sepsis". Clin. Diagn. Lab Immunol., 2002, 9(6):1153-9.

Kawamura, M. et al.,"Molecular cloing of L-JAK, a Janus family protein-tyrosine kinase expressed in natural killer cells and activated leukocytes", Proc. Natl. Acad. Sci. USA, 1994, 91(14):6374-8.

Macchi, et al., "Mutations of Jak-3 gene in patients with autosonal severe combined immune deficiency (SCID)", Nature, 1995, 337:65-68.

Ortmann, R.A., et al., "Janus kinases and signal transducers and activators of transcription: their roles in cytokine signaling, development and immunorgeulation", Arthritis Res., 2000, 2(1):61-32.

Candotti, F.L. et al., "Molecular aspects of primary immunodeficiencies: lessons from cytokine and other signaling pathways", J. Clin. Invest., 2002, 109(10):1261-9.

Rodig, S.J. et al., "Disruption of the Jak 1 gene demonstrates obligatory and non-redundant roles of the Jaks in cytokine-induced biologic responses", Cell, 1998, 93(3):373-83.

Neubauer, H. et al., Jak2 deficiency defines an essential developmental checkpoint in definitive hematopoiesis:, Cell, 1998, 93(3):397-409.

Parganas, E. D. et al., "Jak2 is essential for signaling through a variety of cytokine receptors", Cell, 1998, 93(3):385-95.

Candotti, F. et al., "Structural and functional basis for JAK3-deficient severe combined immunodeficiency", Blood, 1997, 90(10):3996-4003.

Pernis, A.B. et al., "JAK-STAT signaling in asthma", J. Clin. Invest., 2002, 109(10):1279-83.

Seto, Y., et al., "Enhanced Th2 cell-mediated allergic inflammation in Tyk2-deficient mice", J. Immunol., 2003, 170 (2):1077-83.

Takemoto, S. et al., "Proliferation of adult T cell leukemia/lymphoma cells is associated with the constitutive activation of JAK/STAT proteins", Proc. Natl. Acad. Sci., USA, 1997, 94(25):13897-902.

Pedranzini, L. et al., "Pyridone 6, A Pan-Janus-Activated Kinase Inhibitor, induces Growth Inhibition of Multiple Myeloma Cells", Cancer Research, 2006, 66:9714-21.

Boudny, V., et al., "JAK/STAT signaling pathways and cancer. Janus kinases/signal transducers and activators of transcription", Neoplasm, 2002, 49:349-355.

Bowman, T. et al., "STATs in oncogenesis", Oncogene, 2000, 19:2474-2488.

Saemann, M.D. et al., "Prevention of CD40-triggered dendritic cell maturation and induction of T-Cell hyporeactivity by targeting of Janus kinases 3", Am. J. Transplant, 2003, 3(11):1341-9.

Cetkovic-Cvrlje, M. et al., "Targeting JAK3 with JANEX-1 for prevention of autoimmune type 1 diabetes in NOD mice", Clin. Immunol., 2003, 106(3):213-25.

Levine, R.L. et al., "Activating mutation in the tyrosine kinase JAK2 in polycythemia vera, essential thrombocythemia, and myeloiod metaplasia with myelofibrosis", Cancer Cell, 2005, 7:387-397.

Tefferi, A., "JAK and MPL mutations in myeloid malignancies", Leukemia & Lymphoma, 2008, 49(3):388-397.

Gottlieb, A.B. et al., "Psoriasis: Emerging Therapeutic Strategies", Nat. Rev. Drug Disc., 2005, 4:19-34.

Nickoloff B., et al., "Recent insights into the immunopathogenesis of psoriasis provide new therapeutic opportunities", Journal of Clin. Investigation, 2004, 113(12):1664-1675.

Lemp, "The Definition and Classification of Dry Eye Disease: Report of the Definition and Classification Subcommittee of the International Dry Eye workShop", The Ocular Surface, 2007, 5(2A):75-92.

Kimbal, A.B., et al., "Safety and efficacy of ABT-874, a fully human interleukin 12/23 monoclonal antibody, kn the trewatment of moderate to severe chronic plaque psoriasis", Arch. Dermatol., 2008, 144(2):200-7.

(56) References Cited

OTHER PUBLICATIONS

Soda, M. et al., "Identification of the transforming EML4-ALK fusion gene in non-small-cell lung cancer", Nature, 2007, 448:561-566.
Mosse, Y.P., "Identification of ALK as the Major Familial Neuroblastoma Predisposition Gene", Nature, 2008, 455 (7215):930-935 (AACR, 2008).
Remington's Pharmaceutical Sciences. 17th Ed., Mack Publishing Company, Easton, PA, 1985, p. 1418.
Greene & Wuts, Protective Groups in Organic Synthesis, 3rd ed., Wiley & Sons, Inc., New York, 1999.
Sriram, K. et al., "Induction of gp130-related cytokines and activation of JAK2/STAT3 pathway in astrocytes precedes up-regulation of glial fibrillary acidic protein inthe 1-methyl-4-phehnyl-1,2,3,6-tetrahydropyridine model of neurodegeneration", J. Biol. Chem., 2004, 279(19):19936-47. Epub Mar. 2, 2004.
Sonogashira, K. et al., "A convenient synthesis of acetylenes: catalytic substitutions of acetylenic hyudrogen with bromoalkenes, indoarenes and bromopyridines", Tetrahedron Letters, 1975, 16(50):4467-4470.
Dudley, A.C., et al., "A VEGF/JAK2/STAT5 axis may partially mediate endothelial cell tolerance to hypoxia", Biochem. J., 2005, 390(Pt 2):427-36.
Burger, R. et al., "Gp130 and ras mediated signaling in human plasma cell line INA-6: a cytokine-regulated tumor model for plasmacytoma", Hematol. J., 2001, 2:42-53.
Thompson, J.E. et al., "Photochemical preparation of a pyridone containing tetracycle: A JAK protein kinase inhibitor", Bioorganic& Medicinal Chemistry Letters, 2002, 12(8):1219-1223.
Current Protocols in Immunology, vol. 3, Coligan J.E. et al., Wiley Press: Methods in Molecular Biology: Vo. 225, Inflammation Protocols, Winyard, P.G. and Willoughby D.A., Humana Press, 2003.
Park et al., "Homogeneous Proximity Tyrosine Kinase Assays: Scintillation Proximity Assay versus Homgeneous Time-Resolved Fluorescence", Analytical Biochemistry, 1999, 269:94-104.
James, C. et al., "A unique clonal JAK2 mutation leading to constitutive signalling causes polycythaemia vera", Nature, 2005, 434:1144-1148.
Staerk, J. et al., "JAK1 and Tyk2 activation by the homologous polycythemia vera JAK2 V617F mutation", Journal of Biological Chemistry, 280:41893-41899.
"Cancer Prevention Overview," http://www.cancer.gov/cancertopics/pdq/prevention/overview/patient, printed Apr. 9, 2010.
Office Action dated Nov. 7, 2012 received in copending U.S. Appl. No. 12/692,078.
Yamaoka et al., "The Janus kinases (Jakes," Genome Biology (2004) 5(12):253-253.6.
Final Office Action dated Aug. 2, 2013 received in copending U.S. Appl. No. 12/692,078.
Notice of Allowance dated Feb. 27, 2014 received in copending U.S. Appl. No. 12/692,078.
Notice of Allowabiity dated May 8, 2014 received in copending U.S. Appl. No. 12/692,078.

MACROCYCLIC COMPOUNDS AND THEIR USE AS KINASE INHIBITORS

This application claims benefit of priority to U.S. provisional patent application Ser. No. 61/047,547 filed Apr. 24, 2008, and to U.S. provisional patent application Ser. No. 61/122,582 filed on Dec. 15, 2008, each of which is hereby incorporated by reference in its entirety.

FIELD OF THE INVENTION

The present invention relates to macrocyclic compounds, and compositions thereof as well as methods of use the same for treatment of Janus Kinase and/or Anaplastic Lymphoma Kinase (JAK/ALK)-associated diseases including, for example, inflammatory disorders, autoimmune disorders, skin disorders, myeloid proliferative disorders, as well as cancer.

BACKGROUND OF THE INVENTION

Protein kinases (PKs) are a group of enzymes that regulate diverse, important biological processes including cell growth, survival and differentiation, organ formation and morphogenesis, neovascularization, tissue repair and regeneration, among others. Protein kinases exert their physiological functions through catalyzing the phosphorylation of proteins (or other substrates such as lipids) and thereby modulating the cellular activities of the substrates in various biological contexts. In addition to the functions in normal tissues/organs, many protein kinases also play a central role in a host of human diseases including cancer. A subset of protein kinases (also referred to as oncogenic protein kinases), when dysregulated, can cause tumor formation and inappropriate tumor cell survival and proliferation, and further contribute to tumor progression [See e.g. Blume-Jensen P. et al, Nature 2001, 411(6835):355-365]. Thus far, oncogenic protein kinases represent one of the largest and most attractive groups of protein targets for cancer intervention and drug development.

Protein kinases can be categorized as receptor type and non-receptor type. Receptor tyrosine kinases (RTKs) have an extracellular portion, a transmembrane domain, and an intracellular portion, while non-receptor tyrosine kinases are entirely intracellular. RTK mediated signal transduction is typically initiated by extracellular interaction with a specific growth factor (ligand), typically followed by receptor dimerization, stimulation of the intrinsic protein tyrosine kinase activity, and receptor transphosphorylation. Binding sites are thereby created for intracellular signal transduction molecules and lead to the formation of complexes with a spectrum of cytoplasmic signaling molecules that facilitate cellular responses such as cell survival, proliferation, differentiation, metabolic effects, and changes in the extracellular microenvironment.

At present, at least nineteen (19) distinct RTK subfamilies have been identified. One RTK subfamily, designated the HER subfamily, includes EGFR, HER2, HER3 and HER4, and bind such ligands as epithelial growth factor (EGF), TGF-α, amphiregulin, HB-EGF, betacellulin and heregulin. A second family of RTKs, designated the insulin subfamily, includes the INS-R, the IGF-1R and the IR-R. A third family, the "PDGF" subfamily, includes the PDGF alpha and beta receptors, CSFIR, c-kit and FLK-II. Another subfamily of RTKs, referred to as the FLK subfamily, encompasses the Kinase insertDomain-Receptor fetal liver kinase-1 (KDR/FLK-1), the fetal liver kinase 4 (FLK-4) and the fms-like tyrosine kinase 1 (flt-1). Two other subfamilies of RTKs have been designated as the FGF receptor family (FGFR1, FGFR2, FGFR3 and FGFR4) and the Met subfamily (c-Met, Ron and Sea). For a detailed discussion of protein kinases, see for example, Blume-Jensen, P. et al., Nature. 2001, 411(6835): 355-365, and Manning, G. et al., Science. 2002, 298(5600): 1912-1934.

The non-receptor type of tyrosine kinases are also composed of numerous sub-families, including Src, Btk, Abl, Fak, and Jak. Each of these subfamilies can be further subdivided into multiple members that have been frequently linked to oncogenesis. The Src family, for example, is the largest and includes Src, Fyn, Lck and Fgr among others. For a detailed discussion of these kinases, see Bolen J B, "Non-receptor tyrosine protein kinases," Oncogene., 1993, 8(8):2025-31.

A significant number of tyrosine kinases (both receptor and nonreceptor) are associated with cancer (see Madhusudan S, Ganesan T S. Tyrosine kinase inhibitors in cancer therapy. Clin Biochem. 2004, 37(7):618-35.). Clinical studies suggest that overexpression or dysregulation of tyrosine kinases may also be of prognostic value. For example, members of the HER family of RTKs have been associated with poor prognosis in breast, colorectal, head and neck and lung cancer. Mutation of c-Kit tyrosine kinase has been associated with decreased survival in gastrointestinal stromal tumors. In acute myelogenous leukemia (AML), Flt-3 mutation predicts shorter disease free survival. VEGFR expression, which is important for tumor angiogenesis, is associated with a lower survival rate in lung cancer. Tie-1 kinase expression inversely correlates with survival in gastric cancer. BCR-Abl expression is an important predictor of response in chronic myelogenous leukemia (CML) and Src tyrosine kinase is an indicator of poor prognosis in all stages of colorectal cancer.

The immune system responds to injury and threats from pathogens. Cytokines are low-molecular weight polypeptides or glycoproteins that stimulate biological responses in virtually all cell types. For example, cytokines regulate many of the pathways involved in the host inflammatory response to sepsis. Cytokines influence cell differentiation, proliferation and activation, and they can modulate both proinflammatory and anti-inflammatory responses to allow the host to react appropriately to pathogens.

Binding of a cytokine to its cell surface receptor initiates intracellular signaling cascades that transduce the extracellular signal to the nucleus, ultimately leading to changes in gene expression. The pathway involving the Janus kinase family of protein tyrosine kinases (JAKs) and Signal Transducers and Activators of Transcription (STATs) is engaged in the signaling of a wide range of cytokines. Generally, cytokine receptors do not have intrinsic tyrosine kinase activity, and thus require receptor-associated kinases to propagate a phosphorylation cascade. JAKs fulfill this function. Cytokines bind to their receptors, causing receptor dimerization, and this enables JAKs to phosphorylate each other as well as specific tyrosine motifs within the cytokine receptors. STATs, and other proteins, recognize these phosphotyrosine motifs and are recruited to the receptor where they are activated by a JAK-dependent tyrosine phosphorylation events. Upon activation, STATs dissociate from the receptors and translocate to the nucleus to bind to specific DNA sites and alter transcription [Scott, M. J., C. J. Godshall, et al. (2002). "Jaks, STATs, Cytokines, and Sepsis." Clin Diagn Lab Immunol 9(6): 1153-9].

The Janus Kinase (JAK) family plays a role in the cytokine-dependent regulation of proliferation and function of cells involved in immune response. Currently, there are four known mammalian JAK family members: JAK1 (also known as Janus kinase-1), JAK2 (also known as Janus kinase-2), JAK3 (also known as Janus kinase, leukocyte; JAKL; L-JAK and Janus kinase-3) and TYK2 (also known as protein-tyrosine kinase 2). The JAK proteins range in size from 120 to 140 kDa and comprise seven conserved JAK homology (JH) domains; one of these is a functional catalytic kinase domain, and another is a pseudokinase domain potentially serving a regulatory function and/or serving as a docking site for STATs (Scott, Godshall et al. 2002, supra).

While JAK1, JAK2 and TYK2 are widely expressed, JAK3 is reported to be preferentially expressed in natural killer (NK) cells and activated T cells, suggesting a role in lymphoid activation (Kawamura, M., D. W. McVicar, et al. (1994). "Molecular cloning of L-JAK, a Janus family protein-tyrosine kinase expressed in natural killer cells and activated leukocytes." *Proc Natl Acad Sci* USA 91(14): 6374-8).

Not only do the cytokine-stimulated immune and inflammatory responses contribute to normal host defense, they also play roles in the pathogenesis of diseases. Pathologies such as severe combined immunodeficiency (SCID) can arise from hypoactivity, e.g. the inability of various cytokines to signal through JAK3 (Macchi, et al. Nature, 337:65-68, 1995). In contrast, hyperactive or inappropriate immune/inflammatory responses can contribute to the pathology of autoimmune diseases such as rheumatoid and psoriatic arthritis, asthma and systemic lupus erythematosus, inflammatory bowel disease, multiple sclerosis, type I diabetes mellitus, myasthenia gravis, thyroiditis, immunoglobulin nephropathies, myocarditis as well as illnesses such as scleroderma and osteoarthritis (Ortmann, R. A., T. Cheng, et al. (2000). "Janus kinases and signal transducers and activators of transcription: their roles in cytokine signaling, development and immunoregulation." *Arthritis Res* 2(1): 16-32). Furthermore, syndromes with a mixed presentation of autoimmune and immunodeficiency disease are quite common (Candotti, F., L. Notarangelo, et al. (2002). "Molecular aspects of primary immunodeficiencies: lessons from cytokine and other signaling pathways." *J Clin Invest* 109(10): 1261-9). Thus, therapeutic agents are typically aimed at augmentation or suppression of the immune and inflammatory pathways, accordingly.

Deficiencies in expression of various JAK family members have been associated with pathologies in rodents. Jak1−/− mice are runted at birth, fail to nurse, and die perinatally (Rodig, S. J., M. A. Meraz, et al. (1998). "Disruption of the Jak1 gene demonstrates obligatory and non-redundant roles of the Jaks in cytokine-induced biologic responses." *Cell* 93(3): 373-83). Jak2−/− mouse embryos are anemic and die around day 12.5 postcoitum due to the absence of definitive erythropoiesis. In addition, JAK2 deficiency resulted in cell-type specific deficiencies in the signaling of some cytokines such as those required for definitive erythropoiesis (Neubauer, H., A. Cumano, et al. (1998). *Cell* 93(3): 397-409; Parganas, E., D. Wang, et al. (1998). *Cell* 93(3): 385-95.). JAK3 appears to play a role in normal development and function of B and T lymphocytes. Mutations of JAK3 are reported to be responsible for autosomal recessive severe combined immunodeficiency (SCID) in humans (Candotti, F., S. A. Oakes, et al. (1997). "Structural and functional basis for JAK3-deficient severe combined immunodeficiency." *Blood* 90(10): 3996-4003).

The JAK/STAT pathway, and in particular all four members of the JAK family, are believed to play a role in the pathogenesis of the asthmatic response, chronic obstructive pulmonary disease, bronchitis other related inflammatory diseases of the lower respiratory tract, inflammatory diseases or conditions of the upper respiratory tract such as those affecting the nose and sinuses (e.g. rhinitis, sinusitis) whether classically allergic reactions or not, Systemic Inflammatory Response Syndrome (SIRS), and septic shock. See e.g., Pernis, A. B. and P. B. Rothman, "JAK-STAT signaling in asthma," J Clin Invest 109(10): 1279-83 (2002); and Seto, Y., H. Nakajima, et al., "Enhanced Th2 cell-mediated allergic inflammation in Tyk2-deficient mice." J Immunol 170(2): 1077-83 (2003).

The JAK/STAT pathway has also been implicated to play a role in inflammatory diseases/conditions of the eye including, but not limited to, dry eye disorder, iritis, uveitis, scleritis, conjunctivitis, as well as chronic allergic responses. Therefore, inhibition of JAK kinases may have a beneficial role in the therapeutic treatment of these diseases.

As used herein, "dry eye disorder" is intended to encompass the disease states summarized in a recent official report of the Dry Eye Workshop (DEWS), which defined dry eye as "a multifactorial disease of the tears and ocular surface that results in symptoms of discomfort, visual disturbance, and tear film instability with potential damage to the ocular surface. It is accompanied by increased osmolarity of the tear film and inflammation of the ocular surface." Lemp, "The Definition and Classification of Dry Eye Disease Report of the Definition and Classification Subcommittee of the International Dry Eye WorkShop", *The Ocular Surface,* 5(2), 75-92 April 2007, which is incorporated herein by reference in its entirety. Dry eye is also sometimes referred to as keratoconjunctivitis sicca. In some embodiments, the treatment of the dry eye disorder involves ameliorating a particular symptom of dry eye disorder, such as eye discomfort, visual disturbance, tear film instability, tear hyperosmolarity, and inflammation of the ocular surface.

The JAK/STAT pathway also plays a role in cancers of the immune system. In adult T cell leukemia/lymphoma (ATLL), human CD4+ T cells acquire a transformed phenotype, an event that correlates with acquisition of constitutive phosphorylation of JAKs and STATs. Furthermore, an association between JAK3 and STAT-1, STAT-3, and STAT-5 activation and cell-cycle progression was demonstrated by both propidium iodide staining and bromodeoxyuridine incorporation in cells of four ATLL patients tested. These results imply that JAK/STAT activation is associated with expansion of leukemic cells and that therapeutic approaches aimed at JAK/STAT inhibition may be considered to halt neoplastic growth (Takemoto, S., J. C. Mulloy, et al. (1997). "Proliferation of adult T cell leukemia/lymphoma cells is associated with the constitutive activation of JAK/STAT proteins." *Proc Natl Acad Sci USA* 94(25): 13897-902).

Blocking cytokine and growth factor signal transduction at the level of the JAK kinases holds promise for the treatment of a number of human cancers. For example, cytokines of the interleukin 6 (IL-6) family, which activate the signal transducer gp130, are major survival and growth factors for human multiple myeloma (MM) cells. The signal transduction of gp130 is believed to involve JAK1, JAK2 and Tyk2 and the downstream effectors STAT3 and the mitogen-activated protein kinase (MAPK) and AKT pathways. In IL-6-dependent MM cell lines treated with the JAK2 inhibitor pyridone 6 STAT3 phosphorylation and tumor cell proliferation and survival were inhibited (Pedranzini, L, et al, Cancer Research 66:9714-21, 2006.

Activation of JAK/STAT in cancers may occur by multiple mechanisms including cytokine stimulation (e.g. IL-6 or GM-CSF) or by a reduction in the endogenous suppressors of JAK signaling such as SOCS (suppressor of cytokine signaling) or PIAS (protein inhibitor of activated STAT) (Boudny, V., and Kovarik, J., *Neoplasm.* 49:349-355, 2002). Importantly, activation of STAT signaling, as well as other pathways downstream of JAKs (e.g. Akt), has been correlated with poor prognosis in many cancer types (Bowman, T., et al. *Oncogene* 19:2474-2488, 2000). Moreover, elevated levels of circulating cytokines that signal through JAK/STAT may adversely impact patient health as they are thought to play a causal role in cachexia and/or chronic fatigue. As such, JAK inhibition may be therapeutic for the treatment of cancer patients for reasons that extend beyond potential anti-tumor activity. The cachexia indication may gain further mechanistic support with the realization that the satiety factor leptin signals through JAKs.

Pharmacological targeting of Janus kinase 3 (JAK3) has been employed successfully to control allograft rejection and graft versus host disease (GVHD). In addition to its involvement in signaling of cytokine receptors, JAK3 is also engaged in the CD40 signaling pathway of peripheral blood monocytes. During CD40-induced maturation of myeloid dendritic cells (DCs), JAK3 activity is induced, and increases in costimulatory molecule expression, IL-12 production, and potent allogeneic stimulatory capacity are observed. A rationally designed JAK3 inhibitor WHI-P-154 prevented these effects arresting the DCs at an immature level, suggesting that immunosuppressive therapies targeting the tyrosine kinase JAK3 may also affect the function of myeloid cells (Saemann, M. D., C. Diakos, et al. (2003). "Prevention of CD40-triggered dendritic cell maturation and induction of T-cell hyporeactivity by targeting of Janus kinase 3." *Am J Transplant* 3(11): 1341-9). In the mouse model system, JAK3 was also shown to be an important molecular target for treatment of autoimmune insulin-dependent (type 1) diabetes mellitus. The rationally designed JAK3 inhibitor JANEX-1 exhibited potent immunomodulatory activity and delayed the onset of diabetes in the NOD mouse model of autoimmune type 1 diabetes (Cetkovic-Cvrlje, M., A. L. Dragt, et al. (2003). "Targeting JAK3 with JANEX-1 for prevention of autoimmune type 1 diabetes in NOD mice." *Clin Immunol* 106(3): 213-25).

It has been suggested that inhibition of JAK2 tyrosine kinase can be beneficial for patients with myeloproliferative disorders. (Levin, et al., *Cancer Cell*, vol. 7, 2005: 387-397) Myeloproliferative disorders (MPD) include polycythemia vera (PV), essential thrombocythemia (ET), myelofibrosis with myeloid metaplasia (MMM), chronic myelogenous leukemia (CML), chronic myelomonocytic leukemia (CMML), hypereosinophilic syndrome (HES), systemic mast cell disease (SMCD) and the like. Although myeloproliferative disorders (such as PV, ET and MMM) are thought to be caused by acquired somatic mutation in hematopoietic progenitors, the genetic basis for these diseases has not been known. However, it has been reported that hematopoietic cells from a majority of patients with PV and a significant number of patients with ET and MMM possess a recurrent somatic activating mutation in the JAK2 tyrosine kinase. It has also been reported that inhibition of the JAK2V617F kinase with a small molecule inhibitor leads to inhibition of proliferation of hematopoietic cells, suggesting that the JAK2 tyrosine kinase is a potential target for pharmacologic inhibition in patients with PV, ET and MMM. In addition, mutations in the receptor for thrombopoietin have also been described in MPD patients and due to the requirement of JAK2 for this receptor to signal, inhibition of JAKs may be therapeutic (Tefferi, A. *Leukemia & Lymphoma*, March 2008; 49(3): 388-397).

Inhibition of the JAK kinases is also envisioned to have therapeutic benefits in patients suffering from skin immune disorders such as psoriasis, and skin sensitization. In psoriasis vulgaris, the most common form of psoriasis, it has been generally accepted that activated T lymphocytes are important for the maintenance of the disease and its associated psoriatic plaques (Gottlieb, A. B., et al, *Nat Rev Drug Disc.*, 4:19-34). Psoriatic plaques contain a significant immune infiltrate, including leukocytes and monocytes, as well as multiple epidermal layers with increased keratinocyte proliferation. While the initial activation of immune cells in psoriasis occurs by an ill defined mechanism, the maintenance is believed to be dependent on a number of inflammatory cytokines, in addition to various chemokines and growth factors (JCI, 113:1664-1675). Many of these, including interleukins-2, -4, -6, -7, -12, -15, -18, and -23 as well as GM-CSF and IFNg, signal through the Janus (JAK) kinases (*Adv Pharmacol.* 2000; 47: 113-74). As such, blocking signal transduction at the level of JAK kinases may result in therapeutic benefits in patients suffering from psoriasis or other immune disorders of the skin (Kimbal, A. B., et al. Arch Dermatol. 2008 February; 144(2):200-7).

It has been known that certain therapeutics can cause immune reactions such as skin rash or diarrhea in some patients. For instance, administration of some of the new targeted anti-cancer agents such as Iressa, Erbitux, and Tarceva has induced acneiform rash with some patients. Another example is that some therapeutics used topically induce skin irritation, skin rash, contact dermatitis or allergic contact sensitization. For some patients, these immune reactions may be bothersome, but for others, the immune reactions such as rash or diarrhea may result in the inability to continue treatment. Although the driving force behind these immune reactions has not been elucidated completely at the present time, these immune reactions are likely linked to immune infiltrate.

Inhibitors of Janus kinases or related kinases are widely sought and several publications report effective classes of compounds. For example, certain inhibitors are reported in WO 99/65909, US 2004/0198737; WO 2004/099204; WO 2004/099205; and WO 01/42246. Heteroaryl substituted pyrroles and other compounds are reported in WO 2004/72063 and WO 99/62908. For another example, certain JAK inhibitors, including pyrrolopyridine and pyrrolopyrimidines, are reported in U.S. Ser. No. 11/637,545, filed Dec. 12, 2006.

Anaplastic lymphoma kinase (ALK), is a receptor tyrosine kinase, believed to play an important role in the development and function of the nervous system. ALK is normally expressed in the central nervous system, with peak expression during the neonatal period. However, due to chromosomal translocations, ALK is also aberrantly expressed and activated in some cancers in the form of oncogenic fusion proteins. ALK fusion proteins are responsible for approximately 5-10% of all non-Hodgkin's lymphomas. Additional mutations/translocations and increased expression have also been identified in lung cancer and neurological tumors (Soda, M., et al. Nature 448:561-566, 2007 and Mosse, Y P, AACR 2008). Accordingly, ALK inhibitors are useful for the treatment of ALK-related tumors, including anaplastic large cell lymphomas and non-Hodgkin lymphomas in addition to skin diseases and lung cancers.

The annual incidence of ALK positive lymphomas is about 100,000 worldwide. ALK is an excellent candidate for therapeutic intervention, as it plays an essential role in oncogenicity and its normal expression is mostly restricted to the central nervous system.

Hence, a specific ALK inhibitor could be an efficient treatment for ALK positive lymphomas with few associated clinical side effects. Accordingly, potential ALK inhibitors are highly desirable as potential treatments of ALK-related diseases/tumors. For example, certain ALK inhibitors such staurosporine derivatives are reported in WO2004079326.

Thus, new or improved agents which inhibit kinases such as Janus kinases and/or ALK are continually needed for developing new and more effective pharmaceuticals to treat cancer, myeloproliferative disorders, autoimmune diseases, and inflammatory diseases, to name a few. The compounds, compositions and methods described herein are directed toward these needs and other ends.

SUMMARY OF THE INVENTION

The present invention provides, inter alia, compounds of Formula I:

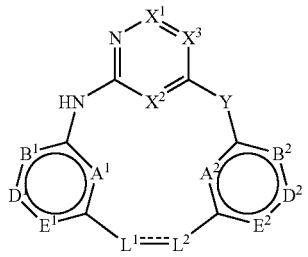

I or pharmaceutically acceptable salts thereof or quaternary ammonium salts thereof, wherein constituent members are provided below.

The present invention further provides pharmaceutical compositions comprising a compound of Formula I, or pharmaceutically acceptable salt thereof, and at least one pharmaceutically acceptable carrier.

The present invention further provides methods of modulating an activity of one or more JAK/ALK kinases, comprising contacting the kinases with a compound of Formula I, or pharmaceutically acceptable salt of the same.

The present invention further provides methods of inhibiting an activity of one or more JAK/ALK kinases, comprising contacting the kinases with a compound of Formula I, or pharmaceutically acceptable salt of the same.

The present invention further provides methods of treating one or more of the various JAK/ALK-associated diseases and disorders named herein by administering to a patient a therapeutically effective amount of a compound of Formula I, or pharmaceutically acceptable salt of the same.

The present invention further provides compounds of Formula I, or pharmaceutically acceptable salts thereof, for use in therapy.

The present invention further provides use of the compounds of Formula I, or pharmaceutically acceptable salts thereof, for the manufacture/preparation of a medicament for use in therapy.

DETAILED DESCRIPTION

The present invention provides, inter alia, compounds of Formula I:

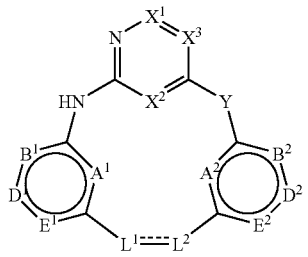

I or pharmaceutically acceptable salts thereof or quaternary ammonium salts thereof, wherein:

===== represents a single bond or a double bond;

$X^1$ is N or $CR^1$;

$X^2$ is N or $CR^2$;

$X^3$ is N or $CR^3$;

Y is O, S, S(O), $S(O)_2$, CR'R", or $NR^4$;

$A^1$ and $A^2$ are each, independently, selected from $CR^2$, N, $NR^6$, O, and S;

$B^1$, $B^2$, $E^1$, and $E^2$ are each, independently, selected from $CR^5$, N, $NR^6$, O, and S;

$D^1$ and $D^2$ are each, independently, selected from a bond, $CR^5$, N, $NR^6$, O, and S;

wherein the ring containing $A^1$, $B^1$, $D^1$, and $E^1$ is a 5- or 6-membered aromatic ring and wherein the ring containing $A^2$, $B^2$, $D^2$, and $E^2$ is a 5- or 6-membered aromatic ring;

$L^1$ and $L^2$ are each, independently selected from a bond, $-(CR^7R^8)_n-$, $-O-(CR^7R^8)_m-CR^{10}=$, $-S-(CR^7R^8)_m-CR^{10}=$, $-(CR^7R^8)_m-CR^{10}=$, $-(CR^7R^8)_m-NR^9-$, $-(CR^7R^8)_m-N=$, $-(CR^7R^8)_m-O-$, $-(CR^7R^8)_m-S-$, $-(CR^7R^8)_m-S(O)-$, $-(CR^7R^8)_m-S(O)_2-$, $-(CR^7R^8)_m-C(O)-$, $-C(O)NR^9-$, $-(CR^7R^8)_m-C(O)O-$, $-(CR^7R^8)_m-NR^9C(O)NR^9-$, $-(CR^7R^8)_m-OC(O)NR^9-$, $-(CR^7R^8)_m-NR^9C(O)O-$, $-(CR^7R^8)_m-NR^9-S(O)_2NR^9-$, $-(CR^7R^8)_m-S(O)NR^9-$, and $-(CR^7R^8)_m-S(O)_2NR^9-$;

wherein at least one of $L^1$ and $L^2$ is other than a bond;

$R^1$ and $R^3$ are each, independently, selected from H, halo, $C_{1-6}$ alkyl, $C_{2-6}$ alkenyl, $C_{2-6}$ alkynyl, $C_{1-6}$haloalkyl, CN, $NO_2$, $SF_5$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^g)NR^{c2}R^{d2}$, $NR^{c2}C(=NR^g)NR^{c2}R^{d2}$, $NR^{c2}S(O)_2NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

each $R^2$ is, independently, selected from H, halo, $C_{1-6}$ alkyl, $C_{2-6}$ alkenyl, $C_{2-6}$ alkynyl, $C_{1-6}$ haloalkyl, CN, $NO_2$, $SF_5$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^g)NR^{c2}R^{d2}$, $NR^{c2}C(=NR^g)NR^{c2}R^{d2}$, $NR^{c2}S(O)_2NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

each $R^5$ is, independently, H, $Cy^1$, halo, $C_{1-6}$ alkyl, $C_{2-6}$ alkenyl, $C_{2-6}$ alkynyl, $C_{1-6}$ haloalkyl, arylalkyl, heteroarylalkyl, cycloalkylalkyl, heterocycloalkylalkyl, halosulfanyl, CN, $NO_2$, $SF_5$, $OR^{a1}$, $SR^{a1}$, $C(O)R^{b1}$, $C(O)NR^{c1}R^{d1}$, $C(S)R^{b1}$, $C(S)NR^{c1}R^{d1}$, $C(O)OR^{a1}$, $OC(O)R^{b1}$, $-W^1-Q^1-Y^1-Z^1$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(S)R^{b1}$, $NR^{c1}C(S)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, $P(R^{f1})_2$, $P(OR^{e1})_2$, $P(O)R^{e1}R^{f1}$, or $P(O)OR^{e1}OR^{f1}$, wherein each of said $C_{1-6}$ alkyl, $C_{2-6}$ alkenyl, $C_{2-6}$ alkynyl, $C_{1-6}$ haloalkyl, arylalkyl, heteroarylalkyl, cycloalkylalkyl, or heterocycloalkylalkyl, is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $Cy^1$, halosulfanyl, CN, $NO_2$, $SF_5$, $OR^{a1}$, $SR^{a1}$, $C(O)R^{b1}$, $C(O)NR^{c1}R^{d1}$, $C(S)R^{b1}$, $C(S)NR^{c1}R^{d1}$, $C(O)OR^{a1}$, $OC(O)R^{b1}$, $-W^1-Q^1-Y^1-Z^1$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(S)R^{b1}$, $NR^{c1}C(S)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)NR^{c1}R^{d1}$, $S(O)R^{b1}$, $S(O)NR^{c1}R^{d1}$, $S(O)_2 R^{b1}$, $NR^{c1}S(O)_2R^{b1}$, $S(O)_2NR^{c1}R^{d1}$, $P(R^{f1})_2$, $P(OR^{e1})_2$, $P(O)R^{e1}R^{f1}$, and $P(O)OR^{e1}OR^{f1}$; or two adjacent $R^5$ on the same ring can link to form a fused cycloalkyl or fused heterocycloalkyl group, each optionally substituted by 1, 2, or 3 substituents independently selected from halo, $C_{1-6}$ alkyl, $C_{2-6}$ alkenyl, $C_{2-6}$ alkynyl, $C_{1-6}$ haloalkyl, arylalkyl, heteroarylalkyl, cycloalkylalkyl, heterocycloalkylalkyl, halosulfanyl, $Cy^1$, oxo, CN, $NO_2$, $OR^{a1}$, $SR^{a1}$, $C(O)R^{b1}$, $C(O)NR^{c1}R^{d1}$, $SF_5$, $C(S)R^{b1}$, $C(S)NR^{c1}R^{d1}$, $C(O)OR^{a1}$, $OC(O)R^{b1}$, $-W^1-Q^1-Y^1-Z^1$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(S)R^{b1}$, $NR^{c1}C(S)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)NR^{c1}R^{d1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, $P(R^{f1})_2$, $P(OR^{e1})_2$, $P(O)R^{e1}R^{f1}$, and $P(O)OR^{e1}OR^{f1}$, wherein each of said $C_{1-6}$ alkyl, $C_{2-6}$ alkenyl, $C_{2-6}$ alkynyl, $C_{1-6}$ haloalkyl, arylalkyl, heteroarylalkyl, cycloalkylalkyl, or heterocycloalkylalkyl, is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $Cy^1$, $-W^1-Q^1-Y^1-Z^1$, halosulfanyl, CN, $NO_2$, $SF_5$, $OR^{a1}$, $SR^{a1}$, $C(O)R^{b1}$, $C(O)NR^{c1}R^{d1}$, $C(O)OR^{a1}$, $OC(O)R^{b1}$, $OCH_2C(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)NR^{c1}R^{d1}$, $S(O)R^{b1}$, $S(O)NR^{c1}R^{d1}$, $S(O)_2 R^{b1}$, $NR^{c1}S(O)_2R^{b1}$, $S(O)_2NR^{c1}R^{d1}$, $P(R^{f1})_2$, $P(OR^{e1})_2$, $P(O)R^{e1}R^{f1}$, and $P(O)OR^{e1}OR^{f1}$;

$R^4$ and $R^6$ are each, independently, selected from H, $Cy^2$, $C_{1-6}$ alkyl, $C_{2-6}$ alkenyl, $C_{2-6}$ alkynyl, $C_{1-6}$ haloalkyl, arylalkyl, heteroarylalkyl, cycloalkylalkyl, heterocycloalkylalkyl, $-W^2-X^2-Y^2-Z^2$, $C(O)R^{b1}$, $C(O)NR^{c1}R^{d1}$, $C(O)OR^{a1}$, $C(=NR^g)NR^{c1}R^{d1}$, $S(O)R^{b1}$, $S(O)NR^{c1}R^{d1}$, $S(O)_2R^{b1}$, $S(O)_2 NR^{c1}R^{d1}$, $P(R^{f1})_2$, $P(OR^{e1})_2$, $P(O)R^{e1}R^{f1}$, and $P(O)OR^{e1}OR^{f1}$, wherein each of said $C_{1-6}$ alkyl, $C_{2-6}$ alkenyl, $C_{2-6}$ alkynyl, $C_{1-6}$ haloalkyl, arylalkyl, heteroarylalkyl, cycloalkylalkyl, or heterocycloalkylalkyl is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $Cy^2$, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $-W^2-Q^2-Y^2-Z^2$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)NR^{c1}R^{d1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, $P(R^{f1})_2$, $P(OR^{e1})_2$, $P(O)R^{e1}R^{f1}$, and $P(O)OR^{e1}OR^{f1}$;

$R^7$, $R^8$, and $R^{10}$ are each, independently, selected from H, $Cy^3$, halo, $C_{1-6}$ alkyl, $C_{2-6}$ alkenyl, $C_{2-6}$ alkynyl, $C_{1-6}$ haloalkyl, arylalkyl, heteroarylalkyl, cycloalkylalkyl, heterocycloalkylalkyl, $-W^3-Q^3-Y^3-Z^3$, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, $P(R^{f1})_2$, $P(OR^{e1})_2$, $P(O)R^{e1}R^{f1}$, and $P(O)OR^{e1}OR^{f1}$, wherein each of said $C_{1-6}$ alkyl, $C_{2-6}$ alkenyl, $C_{2-6}$ alkynyl, $C_{1-6}$ haloalkyl, arylalkyl, heteroarylalkyl, cycloalkylalkyl, or heterocycloalkylalkyl is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $Cy^3$, $-W^3-Q^3-Y^3-Z^3$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, $P(R^{f1})_2$, $P(OR^{e1})_2$, $P(O)R^{e1}R^{f1}$, and $P(O)OR^{e1}OR^{f1}$;

each $R^9$ is, independently, H, $Cy^4$, $C_{1-6}$ alkyl, $C_{2-6}$ alkenyl, $C_{2-6}$ alkynyl, $C_{1-6}$ haloalkyl, arylalkyl, heteroarylalkyl, cycloalkylalkyl, heterocycloalkylalkyl, $-W^4-Q^4-Y^4-Z^4$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^g)NR^{c1}R^{d1}$, $S(O)R^{b1}$, $S(O)NR^{c1}R^{d1}$, $S(O)_2R^{b1}$, $S(O)_2 NR^{c1}R^{d1}$, $P(R^{f1})_2$, $P(OR^{e1})_2$, $P(O)R^{e1}R^{f1}$, or $P(O)OR^{e1}OR^{f1}$ wherein each of said $C_{1-6}$ alkyl, $C_{2-6}$ alkenyl, $C_{2-6}$ alkynyl, $C_{1-6}$ haloalkyl, arylalkyl, heteroarylalkyl, cycloalkylalkyl, or heterocycloalkylalkyl is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $Cy^4$, $-W^4-Q^4-Y^4-Z^4$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, $P(R^{f1})_2$, $P(OR^{e1})_2$, $P(O)R^{e1}R^{f1}$, and $P(O)OR^{e1}OR^{f1}$;

$R^{11a}$, $R^{11b}$, $R^{12a}$, $R^{12b}$, and $R^{13}$ are each, independently, selected from H, $Cy^3$, halo, $C_{1-6}$ alkyl, $C_{2-6}$ alkenyl, $C_{2-6}$ alkynyl, $C_{1-6}$ haloalkyl, arylalkyl, heteroarylalkyl, cycloalkylalkyl, heterocycloalkylalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, $P(R^{f1})_2$, $P(OR^{e1})_2$, $P(O)R^{e1}R^{f1}$, and $P(O)OR^{e1}OR^{f1}$, wherein each of said $C_{1-6}$ alkyl, $C_{2-6}$ alkenyl, $C_{2-6}$ alkynyl, $C_{1-6}$ haloalkyl, arylalkyl, heteroarylalkyl, cycloalkylalkyl, or heterocycloalkylalkyl is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a1}$, $SR^{a1}$, $SF_5$, $C(O)R^{b1}$, $C(O)NR^{c1}R^{d1}$, $C(O)OR^{a1}$, $OC(O)R^{b1}$, $Cy^3$, $-W^3-Q^3-Y^3-Z^3$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, $P(R^{f1})_2$, $P(OR^{e1})_2$, $P(O)R^{e1}R^{f1}$, and $P(O)OR^{e1}OR^{f1}$;

R' and R'' are each, independently, selected from H, halo, $C_{1-4}$ alkyl, $C_{2-4}$ alkenyl, $C_{2-4}$ alkynyl, $C_{1-4}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^g)NR^{c2}R^{d2}$, $NR^{c2}C(=NR^g)NR^{c2}R^{d2}$, $NR^{c1}S(O)_2NR^{c1}R^{d1}$, $S(O)R^{b2}$, $S(O)NR^{c2}R^{d2}$, $S(O)_2R^{b2}$, $NR^{c2}S(O)_2R^{b2}$, and $S(O)_2 NR^{c2}R^{d2}$;

$W^1$, $W^2$, $W^3$, $W^4$, and $W^5$ are each, independently, selected from absent, $W^6$, $C_{1-6}$ alkylenyl, $C_{2-6}$ alkenylenyl, $C_{2-6}$ alkynylenyl, $(CR^{11a}R^{11b})_{p1}O(CR^{11a}R^{11b})_{p2}$, $(CR^{11a}R^{11b})_{p1}S(CR^{11a}R^{11b})_{p2}$, $(CR^{11a}R^{11b})_{p1}NR^e(CR^{11a}R^{11b})_{p2}$, $(CR^{11a}R^{11b})_{p1}C(O)(CR^{11a}R^{11b})_{p2}$, $(CR^{11a}R^{11b})_{p1}C(S)(CR^{11a}R^{11b})_{p2}$, $(CR^{11a}R^{11b})_{p1}C(O)O(CR^{11a}R^{11b})_{p2}$, $(CR^{11a}R^{11b})_{p1}C(O)NR^e(CR^{11a}R^{11b})_{p2}$, $(CR^{11a}R^{11b})_{p1}C(S)NR^e(CR^{11a}R^{11b})_{p2}$, $(CR^{11a}R^{11b})_{p1}S(O)(CR^{11a}R^{11b})_{p2}$, $(CR^{11a}R^{11b})_{p1}S(O)_2(CR^{11a}R^{11b})_{p2}$, $(CR^{11a}R^{11b})_{p1}S(O)NR^e(CR^{11a}R^{11b})_{p2}$, $(CR^{11a}R^{11b})_{p1}S(O)_2NR^e(CR^{11a}R^{11b})_{p2}$, $(CR^{11a}R^{11b})_{p1}NR^eC(O)NR^f(CR^{11a}R^{11b})_{p2}$, $(CR^{11a}R^{11b})_{p1}$ NR$^e$C(S)NR$^f$(CR$^{11a}$R$^{11b}$)$_{p2}$, (CR$^{11a}$R$^{11b}$)$_{p1}$NR$^e$S(O)$_2$NR$^f$(CR$^{11a}$R$^{11b}$)$_{p2}$, (CR$^{11a}$R$^{11b}$)$_{p1}$C(=NR$^g$)NR$^e$(CR$^{11a}$R$^{11b}$)$_{p2}$, (C$^{11a}$R$^{11b}$)$_{p1}$NR$^e$C(=NR$^g$)NR$^f$(CR$^{11a}$R$^{11b}$)$_{p2}$, O(CR$^{11a}$R$^{11b}$)$_{q1}$C(O), S(CR$^{11a}$R$^{11b}$)$_{q1}$C(O), NR$^e$(CR$^{11a}$R$^{11b}$)$_{q1}$C(O), C(O)(CR$^{11a}$R$^{11b}$)$_{q1}$C(O), NR$^e$(CR$^{11a}$R$^{11b}$)$_{q1}$NR$^f$, O(CR$^{11a}$R$^{11b}$)$_{q1}$NR$^f$, and O(CR$^{11a}$R$^{11b}$)$_{q1}$O, wherein each of the C$_{1-6}$ alkylenyl, C$_{2-6}$ alkenylenyl and C$_{2-6}$ alkynylenyl is optionally substituted by 1, 2, or 3 substituents independently selected from halo, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, C(=NR$^g$)NR$^c$R$^d$, NR$^c$C(=NR$^g$)NR$^c$R$^d$, NR$^c$S(O)$_2$NR$^c$R$^d$, S(O)R$^b$, S(O)NR$^c$R$^d$, S(O)$_2$R$^b$, NR$^c$S(O)$_2$R$^b$, and S(O)$_2$NR$^c$R$^d$;

each W$^6$ is independently selected from NR$^{e100}$C(O)NR$^{f100}$ and NR$^{e200}$C(O)CR$^{13}$R$_{f200}$, wherein R$^{e100}$ and R$^{f100}$ together with the intervening NC(O)N moiety to which they are attached form a 4-7 membered heterocycloalkyl group which is optionally substituted by 1, 2, or 3 substituents each independently selected from C$_{1-6}$ alkyl, C$_{1-6}$ haloalkyl, C$_{2-6}$ alkenyl, C$_{2-6}$ alkynyl, halo, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, C(=NR$^g$)NR$^c$R$^d$, NR$^c$C(=NR$^g$)NR$^c$R$^d$, NR$^c$S(O)$_2$NR$^c$R$^d$, S(O)R$^b$, S(O)NR$^c$R$^d$, S(O)$_2$R$^b$, NR$^c$S(O)$_2$R$^b$, and S(O)$_2$NR$^c$R$^d$, and wherein R$^{e200}$ and R$^{f200}$ together with the intervening NC(O)CR$^{13}$ moiety to which they are attached form a 4-7 membered heterocycloalkyl group which is optionally substituted by 1, 2, or 3 substituents each independently selected from C$_{1-6}$ alkyl, C$_{1-6}$ haloalkyl, C$_{2-6}$ alkenyl, C$_{2-6}$ alkynyl, halo, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, C(=NR$^g$)NR$^c$R$^d$, NR$^c$C(=NR$^g$)NR$^c$R$^d$, NR$^c$S(O)$_2$NR$^c$R$^d$, S(O)R$^b$, S(O)NR$^c$R$^d$, S(O)$_2$R$^b$, NR$^c$S(O)$_2$R$^b$, and S(O)$_2$NR$^c$R$^d$;

Q$^1$, Q$^2$, Q$^3$, Q$^4$, and Q$^5$ are each, independently, selected from aryl, cycloalkyl, heteroaryl, heterocycloalkyl, arylalkyl, heteroarylalkyl, cycloalkylalkyl, and heterocycloalkylalkyl, each optionally substituted by 1, 2, 3, 4, or 5 substituents independently selected from C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, heterocycloalkylalkyl, halo, CN, NO$_2$, OR$^a$, SR$^a$, SF$_5$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, C(=NR$^g$)NR$^c$R$^d$, NR$^c$C(=NR$^g$)NR$^c$R$^d$, NR$^c$S(O)$_2$NR$^c$R$^d$, S(O)R$^b$, S(O)NR$^c$R$^d$, S(O)$_2$R$^b$, NR$^c$S(O)$_2$R$^b$, and S(O)$_2$NR$^c$R$^d$;

Y$^1$, Y$^2$, Y$^3$, Y$^4$, and Y$^5$ are each, independently, selected from absent, C$_{1-6}$ alkylenyl, C$_{2-6}$ alkenylenyl, C$_{2-6}$ alkynylenyl, (CR$^{12a}$R$^{12b}$)$_{p3}$O(CR$^{12a}$R$^{12b}$)$_{p4}$, (CR$^{12a}$R$^{12b}$)$_{p3}$S(CR$^{12a}$R$^{12b}$)$_{p4}$, (CR$^{12a}$R$^{12b}$)$_{p3}$NR$^e$(CR$^{12a}$R$^{12b}$)$_{p4}$, (CR$^{12a}$R$^{12b}$)$_{p3}$C(O)(CR$^{12a}$R$^{12b}$)$_{p4}$, (CR$^{12a}$R$^{12b}$)$_{p3}$C(S)(CR$^{12a}$R$^{12b}$)$_{p4}$, (CR$^{12a}$R$^{12b}$)$_{p3}$C(O)O(CR$^{12a}$R$^{12b}$)$_{p4}$, (CR$^{12a}$R$^{12b}$)$_{p3}$C(O)NR$^e$(CR$^{12a}$R$^{12b}$)$_{p4}$, (CR$^{12a}$R$^{12b}$)$_{p3}$C(S)NR$^e$(CR$^{12a}$R$^{12b}$)$_{p4}$, (CR$^{12a}$R$^{12b}$)$_{p3}$S(O)(CR$^{12a}$R$^{12b}$)$_{p4}$, (CR$^{12a}$R$^{12b}$)$_{p3}$S(O)$_2$(CR$^{12a}$R$^{12b}$)$_{p4}$, (CR$^{12a}$R$^{12b}$)$_{p3}$S(O)NR$^e$(CR$^{12a}$R$^{12b}$)$_{p4}$, (CR$^{12a}$R$^{12b}$)$_{p3}$S(O)$_2$NR$^e$(CR$^{12a}$R$^{12b}$)$_{p4}$, (CR$^{12a}$R$^{12b}$)$_{p3}$NR$^e$C(O)NR$^f$(CR$^{12a}$R$^{12b}$)$_{p4}$, (CR$^{12a}$R$^{12b}$)$_{p3}$NR$^e$C(S)NR$^f$(CR$^{12a}$R$^{12b}$)$_{p4}$, (CR$^{12a}$R$^{12b}$)$_{p3}$NR$^e$S(O)$_2$NR$^f$(CR$^{12a}$R$^{12b}$)$_{p4}$, (CR$^{12a}$R$^{12b}$)$_{p3}$C(=NR$^g$)NR$^e$(CR$^{12a}$R$^{12b}$)$_{p4}$, (CR$^{12a}$R$^{12b}$)$_{p3}$NR$^e$C(=NR$^g$)NR$^f$(CR$^{12a}$R$^{12b}$)$_{p4}$, O(CR$^{12a}$R$^{12b}$)$_{q2}$C(O), S(CR$^{12a}$R$^{12b}$)$_{q2}$C(O), NR$^e$(CR$^{12a}$R$^{12b}$)$_{q2}$C(O), NR$^e$(CR$^{12a}$R$^{12b}$)$_{q2}$NR$^f$, O(CR$^{12a}$R$^{12b}$)$_{q2}$NR$^f$, and O(CR$^{12a}$R$^{12b}$)$_{q2}$O, wherein each of the C$_{1-6}$ alkylenyl, C$_{2-6}$ alkenylenyl and C$_{2-6}$ alkynylenyl is optionally substituted by 1, 2 or 3 substituents independently selected from C$_{1-6}$ alkyl, C$_{1-6}$ haloalkyl, C$_{2-6}$ alkenyl, C$_{2-6}$ alkynyl, halo, CN, NO$_2$, OR$^a$, SR$^a$, SF$_5$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, C(=NR$^g$)NR$^c$R$^d$, NR$^c$C(=NR$^g$)NR$^c$R$^d$, NR$^c$S(O)$_2$NR$^c$R$^d$, S(O)R$^b$, S(O)NR$^c$R$^d$, S(O)$_2$R$^b$, NR$^c$S(O)$_2$R$^b$, and S(O)$_2$NR$^c$R$^d$;

Z$^1$, Z$^2$, Z$^3$, Z$^4$, and Z$^5$ are each, independently, selected from H, halo, CN, NO$_2$, OH, C$_{1-6}$ alkoxy, C$_{1-6}$ haloalkoxy, amino, C$_{1-6}$ alkylamino, C$_{2-8}$ dialkylamino, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of the C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted by 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, aryl, cycloalkyl, heteroaryl, heterocycloalkyl, CN, NO$_2$, OR$^a$, SR$^a$, SF$_5$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, NR$^c$S(O)$_2$R$^b$, NR$^c$S(O)$_2$S(O)$_2$NR$^c$R$^d$, S(O)R$^b$, S(O)NR$^c$R$^d$, S(O)$_2$R$^b$, and S(O)$_2$NR$^c$R$^d$;

Cy$^1$, Cy$^2$, Cy$^3$, and Cy$^4$ are each, independently, selected from aryl, cycloalkyl, heteroaryl, and heterocycloalkyl, each optionally substituted by 1, 2, 3, 4, or 5 substituents independently selected from halo, C$_{1-6}$ alkyl, C$_{2-6}$ alkenyl, C$_{2-6}$ alkynyl, aryl, cycloalkyl, heteroaryl, heterocycloalkyl, SF$_5$, Cy$^5$, -L$^{b1}$-Cy$^5$, -W$^5$-Q$^5$-Y$^5$-Z$^5$, C$_{1-6}$ haloalkyl, halosulfanyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, C(=NR$^g$)NR$^{c1}$R$^{d1}$, NR$^{c1}$C(=NR$^g$)NR$^{c1}$R$^{d1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, and S(O)$_2$NR$^{c1}$R$^{d1}$;

Cy$^5$ and Cy$^6$ are each, independently, selected from aryl, cycloalkyl, heteroaryl, and heterocycloalkyl, each optionally substituted by 1, 2, 3, 4, or 5 substituents independently selected from halo, C$_{1-6}$ alkyl, C$_{2-6}$ alkenyl, C$_{2-6}$ alkynyl, aryl, cycloalkyl, heteroaryl, heterocycloalkyl, C$_{1-6}$ haloalkyl, arylalkyl, heteroarylalkyl, cycloalkylalkyl, heterocycloalkylalkyl, halosulfanyl, CN, NO$_2$, OR$^{a2}$, SR$^{a2}$, SF$_5$, C(O)R$^{b2}$, C(O)NR$^{c2}$R$^{d2}$, C(S)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, C(=NR$^g$)NR$^{c2}$R$^{d2}$, NR$^{c2}$C(=NR$^g$)NR$^{c2}$R$^{d2}$, NR$^{c2}$S(O)R$^{b2}$, S(O)R$^{b2}$, S(O)NR$^{c2}$R$^{d2}$, S(O)$_2$R$^{b2}$, NR$^{c2}$S(O)$_2$R$^{b2}$, and S(O)$_2$NR$^{c2}$R$^{d2}$;

L$^{b1}$ and L$^{b2}$ are each, independently, selected from C$_{1-4}$ alkylenyl, O, S, C(O), C(S), C(O)NR$^{b2}$, C(S)NR$^{c2}$, C(O)O, OC(O)NR$^{c2}$, NR$^{c2}$, NR$^{c2}$C(O)NR$^{d2}$, NR$^{c2}$C(S)NR$^{d2}$, C(=NR$^g$)NR$^{c2}$, NR$^{c2}$C(=NR$^g$)NR$^{d2}$, NR$^{c2}$S(O)$_2$NR$^{d2}$, S(O), S(O)NR$^{c2}$, S(O)$_2$, and S(O)$_2$NR$^{c2}$, wherein said C$_{1-4}$ alkylenyl is optionally substituted by 1, 2, 3, 4, 5, 6, 7, or 8 substituents each independently selected from halo, CN, C$_{1-6}$ alkyl, C$_{1-6}$ haloalkyl, OH, C$_{1-6}$ alkoxy, C$_{1-6}$ haloalkoxy, NH$_2$, NH(C$_{1-4}$ alkyl), and N(C$_{1-4}$ alkyl)$_2$;

R$^{a1}$, R$^{b1}$, R$^{c1}$, and R$^{d1}$ are each, independently, selected from H, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of said C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted with 1, 2, 3, 4, or 5 substituents independently selected from C$_{1-6}$ alkyl, halo, CN, Cy$^6$, -L$^{b2}$-Cy$^6$, OR$^{a2}$, SR$^{a2}$, SF$_5$, C(O)R$^{b2}$, C(O)NR$^{c2}$R$^{d2}$, C(S)R$^{b2}$, C(S)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(S)R$^{b2}$, NR$^{c2}$C(S)NR$^{c2}$R$^{d2}$, NR$^{c2}$C(O)

$OR^{a2}$, $C(=NR^g)NR^{c2}R^{d2}$, $NR^{c2}C(=NR^g)NR^{c2}R^{d2}$, $NR^{c2}S(O)_2NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

or $R^{c1}$ and $R^{d1}$ together with the N atom to which they are attached form a 4-, 5-, 6- or 7-membered heterocycloalkyl group or heteroaryl group, each optionally substituted with 1, 2, or 3 substituents independently selected from $C_{1-6}$ alkyl, $C_{1-6}$ haloalkyl, halo, CN, $Cy^6$, $-L^{b2}-Cy^6$, $OR^{a2}$, $SR^{a2}$, $SF_5$, $C(O)R^{b2}$, $C(O)NR^{c2}R^{d2}$, $C(S)R^{b2}$, $C(S)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(S)R^{b2}$, $NR^{c2}C(S)NR^{c2}R^{d2}$, $NR^{c2}C(O)OR^{a2}$, $C(=NR^g)NR^{c2}R^{d2}$, $NR^{c2}C(=NR^g)NR^{c2}R^{d2}$, $NR^{c2}S(O)_2NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

each $R^{e1}$ is, independently, H, $C_{1-6}$ alkyl, $C_{1-6}$ haloalkyl, $C_{2-6}$ alkenyl, ($C_{1-6}$ alkoxy)-$C_{1-6}$ alkyl, $C_{2-6}$ alkynyl, aryl, cycloalkyl, heteroaryl, heterocycloalkyl, arylalkyl, cycloalkylalkyl, heteroarylalkyl, or heterocycloalkylalkyl;

each $R^{f1}$ is, independently, H, $C_{1-6}$ alkyl, $C_{1-6}$ haloalkyl, $C_{2-6}$ alkenyl, $C_{2-6}$ alkynyl, aryl, cycloalkyl, heteroaryl, or heterocycloalkyl;

$R^{a2}$, $R^{b2}$, $R^{c2}$, and $R^{d2}$ are each, independently, selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

or $R^{c2}$ and $R^{d2}$ together with the N atom to which they are attached form a 4-, 5-, 6- or 7-membered heterocycloalkyl group or heteroaryl group, each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

each $R^a$ is independently selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl and heterocycloalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl and heterocycloalkyl is optionally substituted with 1, 2, 3, 4, or 5 substituents each independently selected from OH, CN, amino, halo, $C_{1-6}$ alkyl, $C_{1-6}$ haloalkyl, $C_{1-6}$ alkoxy, $C_{1-6}$ haloalkyl, aryl, arylalkyl, heteroaryl, heteroarylalkyl, cycloalkyl and heterocycloalkyl;

each $R^b$ is independently selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl and heterocycloalkylalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl and heterocycloalkylalkyl is optionally substituted with 1, 2, 3, 4, or 5 substituents each independently selected from OH, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl and heterocycloalkyl;

$R^c$ and $R^d$ are independently selected from H, $C_{1-10}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein each of the $C_{1-10}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl is optionally substituted with 1, 2, 3, 4, or 5 substituents each independently selected from OH, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl and heterocycloalkyl;

or $R^c$ and $R^d$ together with the N atom to which they are attached form a 4-, 5-, 6- or 7-membered heterocycloalkyl group that is optionally substituted with 1, 2, 3, 4, or 5 substituents each independently selected from OH, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl or heterocycloalkyl; and $R^e$ and $R^f$ are each, independently, selected from H, $C_{1-10}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein each of the $C_{1-10}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl is optionally substituted by OH, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl or heterocycloalkyl;

each $R^g$ is, independently, H, CN, or $NO_2$;
each p1 is, independently, 0, 1, or 2;
each p2 is, independently, 0, 1, or 2;
each p3 is, independently, 0, 1, or 2;
each p4 is, independently, 0, 1, or 2;
each q1 is, independently, 1 or 2;
each q2 is, independently, 1 or 2;
each n is, independently, 1, 2, or 3; and
each m is, independently, 0, 1, or 2.

In some embodiments, when the ring containing $A^1$, $B^1$, $D^1$, and $E^1$ is a benzene ring optionally substituted by one $C_{1-4}$ alkoxy, the ring containing $A^2$, $B^2$, $D^2$, and $E^2$ is a benzene ring optionally substituted by one $C_{1-4}$ alkoxy, one of $L^1$ and $L^2$ is $-C(O)NR^9-$, and the other is $-(CR^7R^8)_m-O-$, then $L^1\text{=}L^2$ is other than $-C(O)-NR^9-(CR^7R^8)_2-O-$.

In some embodiments, when the ring containing $A^1$, $B^1$, $D^1$, and $E^1$ is a benzene ring optionally substituted by one $C_{1-4}$ alkoxy, the ring containing $A^2$, $B^2$, $D^2$, and $E^2$ is a benzene ring optionally substituted by one $C_{1-4}$ alkoxy, one of $L^1$ and $L^2$ is $-(CR^7R^8)_m-C(O)-$, the other is $-(CR^7R^8)_m-NR^9-$, and $L^1\text{=}L^2$ is $-(CR^7R^8)_m-C(O)-NR^9-(CR^7R^8)_m-$, then at least one of m is 0;

In some embodiments, when the ring containing $A^1$, $B^1$, $D^1$, and $E^1$ is a benzene ring optionally substituted by one $C_{1-4}$ alkoxy, the ring containing $A^2$, $B^2$, $D^2$, and $E^2$ is a benzene ring optionally substituted by one $C_{1-4}$ alkoxy, $L^1\text{=}L^2$ is $-C(O)-NR^9-(CR^7R^8)-$, $X^2$ is N, $X^1$ is $CR^1$, and $X^3$ is $CR^3$, then at least one of $R^1$ and $R^3$ is other than H;

In some embodiments, when the ring containing $A^1$, $B^1$, $D^1$, and $E^1$ is a benzene ring optionally substituted by one $C_{1-4}$ alkoxy, the ring containing $A^2$, $B^2$, $D^2$, and $E^2$ is a benzene ring optionally substituted by one $C_{1-4}$ alkoxy, and both $L^1$ and $L^2$ are selected from $-(CR^7R^8)_m-O-$, then $L^1\text{=}L^2$ is other than $-O-(CR^7R^8)_4-O-$;

In some embodiments, when the ring containing $A^1$, $B^1$, $D^1$, and $E^1$ is a benzene ring optionally substituted by one $C_{1-4}$ alkoxy, the ring containing $A^2$, $B^2$, $D^2$, and $E^2$ is a benzene ring optionally substituted by one $C_{1-4}$ alkoxy, and both $L^1$ and $L^2$ are selected from $-O-(CR^7R^8)_m-CR^{10}=$, then $L^1\!=\!=\!=\!L^2$ is other than $-O-(CR^7R^8)-CR^{10}=CR^{10}-(CR^7R^8)-O-$; and In some embodiments, when $L^1$ is $-S(O)_2-$, $L^2$ is $-NH-$, $X^2$ is N, $X^1$ is CH, and $X^3$ is C—Br, Y is $-NH-$, the ring containing $A^1$, $B^1$, $D^1$, and $E^1$ is a benzene ring, and the ring containing $A^2$, $B^2$, $D^2$, and $E^2$ is a benzene ring, then the ring containing $A^2$, $B^2$, $D^2$, and $E^2$ is other than a benzene ring optionally substituted by OH.

In some embodiments, each $R^5$ is, independently, H, $Cy^1$, halo, $C_{1-6}$ alkyl, $C_{2-6}$ alkenyl, $C_{2-6}$ alkynyl, $C_{1-6}$ haloalkyl, halosulfanyl, CN, $NO_2$, $SF_5$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, $P(R^{f1})_2$, $P(OR^{e1})_2$, $P(O)R^{e1}R^{f1}$, or $P(O)OR^{e1}OR^{f1}$, wherein each of said $C_{1-6}$ alkyl, $C_{2-6}$ alkenyl, $C_{2-6}$ alkynyl, or $C_{1-6}$ haloalkyl is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, $Cy^1$, CN, $NO_2$, $SF_5$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)NR^{c1}R^{d1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, $P(R^{f1})_2$, $P(OR^{e1})_2$, $P(O)R^{e1}R^{f1}$, and $P(O)OR^{e1}OR^{f1}$.

In some embodiments, two adjacent $R^5$ on the same ring can link to form a fused cycloalkyl or fused heterocycloalkyl group, each optionally substituted by 1, 2, or 3 substituents independently selected from halo, $C_{1-6}$ alkyl, $C_{2-6}$ alkenyl, $C_{2-6}$ alkynyl, $C_{1-6}$ haloalkyl, arylalkyl, heteroarylalkyl, cycloalkylalkyl, heterocycloalkylalkyl, $Cy^1$, oxo, CN, $NO_2$, $OR^{a1}$, $SR^{a1}$, $C(O)R^{b1}$, $C(O)NR^{c1}R^{d1}$, $SF_5$, $C(S)R^{b1}$, $C(S)NR^{c1}R^{d1}$, $C(O)OR^{a1}$, $OC(O)R^{b1}$, $-W^1-Q^1-Y^1-Z^1$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(S)R^{b1}$, $NR^{c1}C(S)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)NR^{c1}R^{d1}$, $S(O)R^{b1}$, $S(O)NR^{c1}R^{d1}$, $S(O)_2R^{b1}$, $NR^cS(O)_2R^{b1}$, and $S(O)_2NR^{c1}R^{d1}$, wherein each of the $C_{1-6}$ alkyl, $C_{2-6}$ alkenyl, $C_{2-6}$ alkynyl, $C_{1-6}$ haloalkyl, arylalkyl, heteroarylalkyl, cycloalkylalkyl, or heterocycloalkylalkyl is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $Cy^1$, $-W^1-Q^1-Y^1-Z^1$, CN, $NO_2$, $SF_5$, $OR^{a1}$, $SR^{a1}$, $C(O)R^{b1}$, $C(O)NR^{c1}R^{d1}$, $C(O)OR^{a1}$, $OC(O)R^{b1}$, $OCH_2C(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)NR^{c1}R^{d1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$.

In some embodiments, two adjacent $R^5$ on the same ring can link to form a fused cycloalkyl or fused heterocycloalkyl group, each optionally substituted by 1, 2, or 3 substituents independently selected from halo, $C_{1-6}$ alkyl, $C_{2-6}$ alkenyl, $C_{2-6}$ alkynyl, $C_{1-6}$ haloalkyl, arylalkyl, heteroarylalkyl, cycloalkylalkyl, heterocycloalkylalkyl, $Cy^1$, CN, $NO_2$, $OR^{a1}$, $SR^{a1}$, $C(O)R^{b1}$, $C(O)NR^{c1}R^{d1}$, $SF_5$, $C(S)R^{b1}$, $C(S)NR^{c1}R^{d1}$, $C(O)OR^{a1}$, $OC(O)R^{b1}$, $-W^1-Q^1-Y^1-Z^1$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(S)R^{b1}$, $NR^{c1}C(S)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)NR^{c1}R^{d1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, $P(R^{f1})_2$, $P(OR^{e1})_2$, $P(O)R^{e1}R^{f1}$, and $P(O)OR^{e1}OR^{f1}$, wherein each of said $C_{1-6}$ alkyl, $C_{2-6}$ alkenyl, $C_{2-6}$ alkynyl, $C_{1-6}$ haloalkyl, arylalkyl, heteroarylalkyl, cycloalkylalkyl, or heterocycloalkylalkyl, is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $Cy^1$, $W^1-Q^1-Y^1-Z^1$, halosulfanyl, CN, $NO_2$, $SF_5$, $OR^{a1}$, $SR^{a1}$, $C(O)R^{b1}$, $C(O)NR^{c1}R^{d1}$, $C(O)OR^{a1}$, $OC(O)R^{b1}$, $OCH_2C(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)NR^{c1}R^{d1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, $P(R^{f1})_2$, $P(OR^{e1})_2$, $P(O)R^{e1}R^{f1}$, and $P(O)OR^{e1}OR^{f1}$.

In some embodiments, two adjacent $R^5$ on the same ring can link to form a fused cycloalkyl or fused heterocycloalkyl group, each optionally substituted by 1, 2, or 3 substituents independently selected from halo, $C_{1-6}$ alkyl, $C_{2-6}$ alkenyl, $C_{2-6}$ alkynyl, $C_{1-6}$ haloalkyl, halosulfanyl, $Cy^1$, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)NR^{c1}R^{d1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, $P(R^{f1})_2$, $P(OR^{e1})_2$, $P(O)R^{e1}R^{f1}$, and $P(O)OR^{e1}OR^{f1}$.

In some embodiments, $R^4$ and $R^6$ are each, independently, selected from H, $Cy^2$, $C_{1-6}$ alkyl, $C_{2-6}$ alkenyl, $C_{2-6}$ alkynyl, $C_{1-6}$ haloalkyl, $C(O)R^{b1}$, $C(O)NR^{c1}R^{d1}$, $C(O)OR^{a1}$, $C(=NR^g)NR^{c1}R^{d1}$, $S(O)R^{b1}$, $S(O)NR^{c1}R^{d1}$, $S(O)_2R^{b1}$, $S(O)_2 NR^{c1}R^{d1}$, $P(R^{f1})_2$, $P(OR^{e1})_2$, $P(O)R^{e1}R^{f1}$, and $P(O)OR^{e1}OR^{f1}$, wherein each of said $C_{1-6}$ alkyl, $C_{2-6}$ alkenyl, $C_{2-6}$ alkynyl, or $C_{1-6}$ haloalkyl is optionally substituted by 1, 2, 3, 4 or 5 substituents independently selected from halo, $C_{1-6}$ alkyl, $C_{2-6}$ alkenyl, $C_{2-6}$ alkynyl, $C_{1-6}$ haloalkyl, halosulfanyl, $Cy^2$, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, $P(R^{f1})_2$, $P(OR^{e1})_2$, $P(O)R^{e1}R^{f1}$, and $P(O)OR^{e1}OR^{f1}$.

In some embodiments, $R^7$, $R^8$, and $R^{10}$ are each, independently, selected from H, $Cy^3$, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)NR^{c1}R^{d1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, $P(R^{f1})_2$, $P(OR^{e1})_2$, $P(O)R^{e1}R^{f1}$, and P(O)OR$^{e1}$OR$^{f1}$, wherein each of said C$_{1-6}$ alkyl, C$_{2-6}$ alkenyl, C$_{2-6}$ alkynyl, or C$_{1-6}$ haloalkyl is optionally substituted by 1, 2, 3, 4 or 5 substituents independently selected from halo, C$_{1-6}$ alkyl, C$_{2-6}$ alkenyl, C$_{2-6}$ alkynyl, C$_{1-6}$ haloalkyl, halosulfanyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, C(=NR$^g$)NR$^{c1}$R$^{d1}$, NR$^{c1}$C(=NR$^g$)NR$^{c1}$R$^{d1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, S(O)$_2$NR$^{c1}$R$^{d1}$, P(R$^{f1}$)$_2$, P(OR$^{e1}$)$_2$, P(O)R$^{e1}$R$^{f1}$, and P(O)OR$^{e1}$OR$^{f1}$.

In some embodiments, each R$^9$ is, independently, H, Cy$^4$, C$_{1-6}$ alkyl, C$_{2-6}$ alkenyl, C$_{2-6}$ alkynyl, C$_{1-6}$ haloalkyl, C(O)R$^{b1}$, C(O)NR$^{c1}$R$^{d1}$, C(O)OR$^{a1}$, OC(O)R$^{b1}$, OC(O)NR$^{c1}$R$^{d1}$, C(=NR$^g$)NR$^{c1}$R$^{d1}$, S(O)R$^{b1}$, S(O)NR$^{c1}$R$^{d1}$, S(O)$_2$R$^{b1}$, S(O)$_2$ NR$^{c1}$R$^{d1}$, P(R$^{f1}$)$_2$, P(OR$^{e1}$)$_2$, P(O)R$^{e1}$R$^{f1}$, or P(O)OR$^{e1}$OR$^{f1}$ wherein each of said C$_{1-6}$ alkyl, C$_{2-6}$ alkenyl, C$_{2-6}$ alkynyl, or C$_{1-6}$ haloalkyl is optionally substituted by 1, 2, 3, 4 or 5 substituents independently selected from halo, C$_{1-6}$ alkyl, C$_{2-6}$ alkenyl, C$_{2-6}$ alkynyl, C$_{1-6}$ haloalkyl, halosulfanyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, C(=NR$^g$)NR$^{c1}$R$^{d1}$, NR$^{c1}$C(=NR$^g$)NR$^{c1}$R$^{d1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, S(O)$_2$NR$^{c1}$R$^{d1}$, P(R$^{f1}$)$_2$, P(OR$^{e1}$)$_2$, P(O)R$^{e1}$R$^{f1}$, and P(O)OR$^{e1}$OR$^{f1}$.

In some embodiments, Cy$^1$, Cy$^2$, Cy$^3$, and Cy$^4$ are each, independently, selected from aryl, cycloalkyl, heteroaryl, and heterocycloalkyl, each optionally substituted by 1, 2, 3, 4, or 5 substituents independently selected from halo, C$_{1-6}$ alkyl, C$_{2-6}$ alkenyl, C$_{2-6}$ alkynyl, aryl, cycloalkyl, heteroaryl, heterocycloalkyl, C$_{1-6}$ haloalkyl, halosulfanyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, C(=NR$^g$)NR$^{c1}$R$^{d1}$, NR$^{c1}$C(=NR$^g$)NR$^{c1}$R$^{d1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, and S(O)$_2$NR$^{c1}$R$^{d1}$.

In some embodiments, R$^{a1}$, R$^{b1}$, R$^{c1}$, and R$^{d1}$ are each, independently, selected from H, C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of said C$_{1-6}$ alkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted with 1, 2, 3, 4, or 5 substituents independently selected from C$_{1-6}$ alkyl, halo, CN, OR$^{a2}$, SR$^{a2}$, C(O)R$^{b2}$, C(O)NR$^{c2}$R$^{d2}$, C(O)OR$^{b2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, C(=NR$^g$)NR$^{c2}$R$^{d2}$, NR$^{c2}$C(=NR$^g$)NR$^{c2}$R$^{d2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, NR$^{c2}$S(O)$_2$R$^{b2}$, and S(O)$_2$NR$^{c2}$R$^{d2}$.

In some embodiments, R$^{c1}$ and R$^{d1}$ together with the N atom to which they are attached form a 4-, 5-, 6- or 7-membered heterocycloalkyl group or heteroaryl group, each optionally substituted with 1, 2, or 3 substituents independently selected from C$_{1-6}$ alkyl, halo, CN, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, C(=NR$^g$)NR$^{c2}$R$^{d2}$, NR$^{c2}$C(=NR$^g$)NR$^{c2}$R$^{d2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, NR$^{c2}$S(O)$_2$ R$^{b2}$, and S(O)$_2$NR$^{c2}$R$^{d2}$.

In some embodiments, when one of L$^1$ and L$^2$ is —C(O)NR$^9$—, and the other is —(CR$^7$R$^8$)$_m$—O—, then L$^1$====L$^2$ is other than —C(O)—NR$^9$—(CR$^7$R$^8$)$_2$—O—.

In some embodiments, when one of L$^1$ and L$^2$ is —(CR$^7$R$^8$)$_m$—C(O)—, the other is —(CR$^7$R$^8$)$_m$—NR$^9$—, and L$^1$====L$^2$ is —(CR$^7$R$^8$)$_m$—C(O)—NR$^9$—(CR$^7$R$^8$)$_m$—, then at least one of m is 0.

In some embodiments, when L$^1$====L$^2$ is —C(O)—NR$^9$—(CR$^7$R$^8$)—, X$^2$ is N, X$^1$ is CR$^1$, and X$^3$ is CR$^3$, then at least one of R$^1$ and R$^3$ is other than H.

In some embodiments, when both L$^1$ and L$^2$ are selected from —(CR$^7$R$^8$)$_m$—O—, then L$^1$====L$^2$ is other than —O—(CR$^7$R$^8$)$_4$—O—.

In some embodiments, when both L$^1$ and L$^2$ are selected from —O—(CR$^7$R$^8$)$_m$—CR$^{10}$=, then L$^1$====L$^2$ is other than —O—(CR$^7$R$^8$)—CR$^{10}$=CR$^{10}$—(CR$^7$R$^8$)—O—.

In some embodiments, the compound of Formula I is other than 6-Chloro-2,4,8,14,22-pentaazatetracyclo[14.3.1.1(3,7).1(9,13)]docosa-1(20),3(22),4,6,9(21),10,12,16,18-nonaen-15-one.

In some embodiments, the compound of Formula I is other than 6-Chloro-2,4,8,15,23-pentaazatetracyclo[15.3.1.1(3,7).1(9,13)]tricosa-1(21),3(23),4,6,9(22),10,12,17,19-nonaen-14-one.

In some embodiments, the compound of Formula I is other than 6-Chloro-2,4,8,15,23-pentaazatetracyclo[15.3.1.1(3,7).1(9,13)]tricosa-1(21),3(23),4,6,9(22),10,12,17,19-nonaen-16-one.

In some embodiments, the compound of Formula I is other than 6-Chloro-2,4,8,16,23-pentaazatetracyclo[15.3.1.1(3,7).1(9,13)]tricosa-1(21),3(23),4,6,9(22),10,12,17,19-nonaen-15-one.

In some embodiments, A$^1$ and A$^2$ are each, independently, selected from CR$^2$, N, NH, N(CH$_3$), O, and S. In some embodiments, one of A$^1$ and A$^2$ is selected from NH, N(CH$_3$), O, and S. In some embodiments, both A$^1$ and A$^2$ are independently selected from NH, N(CH$_3$), O, and S.

In some embodiments, A$^1$ and A$^2$ are each, independently, selected from CR$^2$ and N.

In some embodiments, the ring containing A$^1$, B$^1$, D$^1$, and E$^1$ is a 6-membered aromatic ring; B$^1$, D$^1$, and E$^1$ are each, independently, CR$^5$ or N; and A$^1$ is CR$^2$ or N.

In some embodiments, the ring containing A$^1$, B$^1$, D$^1$, and E$^1$ is a 6-membered aromatic ring; B$^1$, D$^1$, and E$^1$ are each, independently, CR$^5$; and A$^1$ is CR$^2$. In some embodiments, the ring containing A$^1$, B$^1$, D$^1$, and E$^1$ is a benzene ring, and the benzene ring can be substituted or unsubstituted.

In some embodiments, the ring containing A$^1$, B$^1$, D$^1$, and E$^1$ is a 6-membered aromatic ring wherein at least one of A$^1$, B$^1$, D$^1$, and E$^1$ is N. In some further embodiments, the 6-membered aromatic ring is selected from pyridine, pyrimidine, and pyrazine rings (the 6-membered aromatic rings such as pyridine, pyrimidine, and pyrazine can be substituted or unsubstituted). In yet further embodiments, the 6-membered aromatic ring is selected from pyridine and pyrimidine rings. In some embodiments, the 6-membered aromatic ring is a pyridine ring. In some embodiments wherein the ring containing A$^1$, B$^1$, D$^1$, and E$^1$ is a pyridine ring, D$^1$ is N. In some embodiments wherein the ring containing A$^1$, B$^1$, D$^1$, and E$^1$ is a pyridine ring, E$^1$ is N. In some embodiments wherein the ring containing A$^1$, B$^1$, D$^1$, and E$^1$ is a pyridine ring, B$^1$ is N. In some embodiments wherein the ring containing A$^1$, B$^1$, D$^1$, and E$^1$ is a pyridine ring, A$^1$ is N. In some embodiments, the 6-membered aromatic ring is a pyrimidine ring.

In some embodiments, the ring containing A$^1$, B$^1$, D$^1$, and E$^1$ is a 5-membered aromatic ring (optionally substituted). In some further embodiments, the 5-membered aromatic ring is selected from 1H-pyrrole, furan, thiophene, 1H-imidazole, 1H-pyrazole, oxazole, thiazole, isoxazole, and isothiazole (the 5-membered aromatic rings can be substituted or unsubstituted). In yet further embodiments, the 5-membered aromatic ring is selected from 1H-pyrrole, furan, and thiophene (each is optionally substituted). In still further embodiments, the 5-membered aromatic ring is a thiophene ring (optionally substituted).

In some embodiments, the ring containing $A^2$, $B^2$, $D^2$, and $E^2$ is a 6-membered aromatic ring; $B^2$, $D^2$, and $E^2$ are each, independently, $CR^5$ or N; and $A^2$ is $CR^2$ or N.

In some embodiments, the ring containing $A^2$, $B^2$, $D^2$, and $E^2$ is a 6-membered aromatic ring; $B^2$, $D^2$, and $E^2$ are each, independently, $CR^5$; and $A^2$ is $CR^2$.

In some embodiments, the ring containing $A^2$, $B^2$, $D^2$, and $E^2$ is a benzene ring, and the benzene ring can be substituted or unsubstituted.

In some embodiments, the ring containing $A^2$, $B^2$, $D^2$, and $E^2$ is a 6-membered aromatic ring, wherein at least one of $A^2$, $B^2$, $D^2$, and $E^2$ is N. In some further embodiments, the 6-membered aromatic ring is selected from pyridine, pyrimidine, and pyrazine rings (the 6-membered aromatic rings can be substituted or unsubstituted). In yet further embodiments, the 6-membered aromatic ring is selected from pyridine and pyrimidine rings. In some embodiments, the 6-membered aromatic ring is a pyridine ring. In some embodiments, the 6-membered aromatic ring is a pyrimidine ring.

In some embodiments, the ring containing $A^2$, $B^2$, $D^2$, and $E^2$ is a 5-membered aromatic ring. In some further embodiments, the 5-membered aromatic ring is selected from 1H-pyrrole, furan, thiophene, 1H-imidazole, 1H-pyrazole, oxazole, thiazole, isoxazole, and isothiazole rings (the 5-membered aromatic rings can be substituted or unsubstituted). In yet further embodiments, the 5-membered aromatic ring is selected from 1H-pyrrole, furan, and thiophene rings. In still further embodiments, the 5-membered aromatic ring is a thiophene ring.

In some embodiments, $X^1$ is $CR^1$.
In some embodiments, $X^1$ is N.
In some embodiments, $X^2$ is $CR^2$.
In some embodiments, $X^2$ is N.
In some embodiments, $X^3$ is $CR^3$.
In some embodiments, $X^3$ is N.
In some embodiments, Y is $NR^4$. In some embodiments, Y is NH. In some embodiments, Y is $N(C_{1-3}$ alkyl). In some embodiments, Y is $N-CH_3$.
In some embodiments, Y is O, S, SO, or $S(O)_2$.
In some embodiments, Y is O. In some embodiments, Y is S, SO, or $S(O)_2$. In some embodiments, Y is S. In some embodiments, Y is SO. In some embodiments, Y is $S(O)_2$.

In some embodiments, Y is CR'R". In some further embodiments, R' and R" are each, independently, selected from H, $C_{1-6}$ alkyl, and $C_{1-6}$ haloalkyl. In some yet further embodiments, R' and R" are each, independently, selected from H, $C_{1-3}$ alkyl, and $C_{1-3}$ haloalkyl. In some still further embodiments, R' and R" are each, independently, selected from H and $C_{1-3}$ alkyl. In some further, R' and R" are each, independently, selected from H and methyl. In some embodiments, R' and R" are both H.

In some embodiments, the ring containing $A^1$, $B^1$, $D^1$, and $E^1$ is a 6-membered aromatic ring; $B^1$, $D^1$, and $E^1$ are each, independently, $CR^5$ or N; $A^1$ is CH; the ring containing $A^2$, $B^2$, $D^2$, and $E^2$ is a 6-membered aromatic ring; $B^2$, $D^2$, and $E^2$ are each, independently, $CR^5$ or N; $A^2$ is CH; $X^1$ is $CR^1$; $X^2$ is N; $X^3$ is $CR^3$; and Y is $NR^4$. In some further embodiments, one of $B^1$, $D^1$, and $E^1$ is N, and the other two are each independently $CR^5$; $R^1$ is H; $R^3$ is H, halo, methyl, or $C_1$ haloalkyl; and $R^4$ is H or $C_{1-3}$ alkyl.

In some embodiments, $L^1$ and $L^2$ are each, independently, selected from a bond, $-(CR^7R^8)_n-$, $-O-(CR^7R^8)_m-CR^{10}=$, $-S-(CR^7R^8)_m-CR^{10}=$, $-(CR^7R^8)_m-CR^{10}=$, $-(CR^7R^8)_m-NR^9-$, $-(CR^7R^8)_m-O-$, $-(CR^7R^8)_m-S-$, $-(CR^7R^8)_m-S(O)-$, $-(CR^7R^8)_m-S(O)_2-$, $-(CR^7R^8)_m-C(O)-$, $-C(O)NR^9-$, $-(CR^7R^8)_m-C(O)O-$, $-(CR^7R^8)_m-NR^9C(O)NR^9-$, $-(CR^7R^8)_m-OC(O)NR^9-$, $-(CR^7R^8)_m-NR^9C(O)O-$, $-(CR^7R^8)_m-NR^9S(O)_2NR^9-$, $-(CR^7R^8)_m-S(O)NR^9-$, and $-(CR^7R^8)_m-S(O)_2NR^9-$.

In some embodiments, $L^1$ and $L^2$ are each, independently, selected from a bond, $-(CR^7R^8)_n-$, $-(CR^7R^8)_m-CR^{10}=$, $-O-(CR^7R^8)_m-CR^{10}=$, $-S(CR^7R^8)_m-CR^{10}=$, $-(CR^7R^8)_m-NR^9-$, $-(CR^7R^8)_m-O-$, $-(CR^7R^8)_m-S-$, $-(CR^7R^8)_m-S(O)-$, $-(CR^7R^8)_m-S(O)_2-$, $-(CR^7R^8)_m-C(O)-$, $-C(O)NR^9-$, $-(CR^7R^8)_m-C(O)O-$, $-(CR^7R^8)_m-S(O)NR^9-$, and $-(CR^7R^8)_m-S(O)_2NR^9-$.

In some embodiments, $L^1$ and $L^2$ are each, independently, selected from a bond, $-(CR^7R^8)_n-$, $-(CR^7R^8)_m-CR^{10}=$, $-(CR^7R^8)_m-NR^9-$, $-(CR^7R^8)_m-O-$, $-(CR^7R^8)_m-S-$, $-(CR^7R^8)_m-S(O)-$, $-(CR^7R^8)_m-S(O)_2-$, $-(CR^7R^8)_m-C(O)-$, $-C(O)NR^9-$, $-(CR^7R^8)_m-C(O)O-$, $-(CR^7R^8)_m-S(O)NR^9-$, and $-(CR^7R^8)_m-S(O)_2NR^9-$.

As used herein, when one of $L^1$ and $L^2$ is selected from $-O-(CR^7R^8)_m-CR^{10}=$, $-S-(CR^7R^8)_m-CR^{10}=$, $-(CR^7R^8)_m-CR^{10}=$, and $-(CR^7R^8)_m-N=$, the other is also selected from $-O-(CR^7R^8)_m-CR^{10}=$, $-S-(CR^7R^8)_m-CR^{10}=$, $-(CR^7R^8)_m-CR^{10}=$, and $-(CR^7R^8)_m-N=$ (although $L^1$ and $L^2$ can be the same or different in such embodiments). In such embodiments, the moiety formed by $L^1$ and $L^2$ together can include a moiety of "$-CR^{10}=CR^{10}-$" or "$-CR^{10}=N-$". In some further embodiments, the moiety formed by $L^1$ and $L^2$ together includes a moiety of $-CR^{10}=CR^{10}-$. In some embodiments, $L^1$ and $L^2$ together form $-(CR^7R^8)_m-CR^{10}=CR^{10}-(CR^7R^8)_m-$, $-O-(CR^7R^8)_m-CR^{10}=CR^{10}-(CR^7R^8)_m-$, $-S-(CR^7R^8)_m-CR^{10}=CR^{10}-(CR^7R^8)_m-$, $-O-(CR^7R^8)_m-CR^{10}=CR^{10}-(CR^7R^8)_m-O-$, $-O-(CR^7R^8)_m-CR^{10}=CR^{10}-(CR^7R^8)_m-S-$, or $-S-(CR^7R^8)_m-CR^{10}=CR^{10}-(CR^7R^8)_m-S-$.

In some embodiments, $L^1$ and $L^2$ are each, independently, selected from a bond, $-(CR^7R^8)_n-$, and $-(CR^7R^8)_m-CR^{10}=$.

In some embodiments, $L^1$ and $L^2$ together form $-(CR^7R^8)_m-CR^{10}=CR^{10}-(CR^7R^8)_m-$ or $-(CR^7R^8)_n-$.

In some embodiments, $L^1$ and $L^2$ together form $-CR^{10}=CR^{10}-$, $-(CR^7R^8)_2-$, or $-(CR^7R^8)_3-$.

In some embodiments, $L^1$ and $L^2$ together form $-CR^{10}=CR^{10}-$ or $-(CR^7R^8)_2-$. In some embodiments, $L^1$ and $L^2$ together form $-CH=CH-$ or $-CH_2-CH_2-$. In some embodiments, $L^1$ and $L^2$ together form $-CH=CH-$. In some embodiments, $L^1$ and $L^2$ together form $-CH_2-CH_2-$.

In some embodiments, $L^1$ and $L^2$ together form $-CR^{10}=CR^{10}-$ or $-CR^7R^8-CR^7R^8-$. In some embodiments, $L^1$ and $L^2$ together form $-CH=CH-$ or $-CH_2-CH_2-$. In some embodiments, $L^1$ and $L^2$ together form $-CH=CH-$. In some embodiments, $L^1$ and $L^2$ together form $-CH_2-CH_2-$.

In some embodiments, $L^1$ and $L^2$ together form $-CR^{10}=CR^{10}-$.

In some embodiments, $L^1$ and $L^2$ together form $-CR^7R^8-CR^7R^8-$.

In some embodiments, $L^1$ and $L^2$ together form $-(CR^7R^8)_3-$. In some embodiments, $L^1$ and $L^2$ together form $-(CH_2)_3-$.

In some embodiments, $L^1$ and $L^2$ together form $-(CR^7R^8)_4-$, $-(CR^7R^8)_5-$, or $-(CR^7R^8)_6-$. In some embodiments, $L^1$ and $L^2$ together form $-(CH_2)_4-$, $-(CH_2)_5-$, or $-(CH_2)_6-$.

In some embodiments, one of $L^1$ and $L^2$ is selected from $-(CR^7R^8)_m-O-$, $-(CR^7R^8)_m-S-$, $-(CR^7R^8)_m-S(O)-$, and $-(CR^7R^8)_m-S(O)_2-$; and the other is selected from a bond, $-(CR^7R^8)_n-$, $-(CR^7R^8)_m-O-$, $-(CR^7R^8)_m-S-$, $-(CR^7R^8)_m-S(O)-$, and $-(CR^7R^8)_m-S(O)_2-$.

In some embodiments:
$L^1$ and $L^2$ together form $-(CR^7R^8)_{t1}-S-$, $-(CR^7R^8)_{t1}-O-$, $-(CR^7R^8)_{t1}-S(O)-$, $-(CR^7R^8)_{t1}-S(O)_2-$, $-S-(CR^7R^8)_{t2}-S-$, $-O-(CR^7R^8)_{t2}-S-$, $-O-(CR^7R^8)_{t2}-S(O)-$, $-O-(CR^7R^8)_{t2}-S(O)_2-$, $-S-S-$, $-(CR^7R^8)_{t3}-O-(CR^7R^8)_{t4}-$, $-(CR^7R^8)_{t3}-S-(CR^7R^8)_{t4}-$, $-(CR^7R^8)_{t3}-S(O)-(CR^7R^8)_{t4}-$, or $-(CR^7R^8)_{t3}-S(O)_2-(CR^7R^8)_{t4}-$;
t1 is 1, 2, or 3;
t2 is 1 or 2;
t3 is 1, 2, or 3; and
t4 is 1 or 2.

In some embodiments:
$L^1$ and $L^2$ together form $-(CR^7R^8)_{t1}-S-$, $-(CR^7R^8)_{t1}-O-$, $-(CR^7R^8)_{t1}-S(O)-$, $-(CR^7R^8)_{t1}-S(O)_2-$, $-S-(CR^7R^8)_{t2}-S-$, $-O-(CR^7R^8)_{t2}-S-$, $-O-(CR^7R^8)_{t2}-S(O)-$, $-O-(CR^7R^8)_{t2}-S(O)_2-$, or $-S-S-$;
t1 is 1, 2, or 3; and
t2 is 1 or 2.

In some embodiments:
$L^1$ and $L^2$ together form $-(CR^7R^8)_{t3}-O-(CR^7R^8)_{t4}-$, $-(CR^7R^8)_{t3}-S-(CR^7R^8)_{t4}-$, $-(CR^7R^8)_{t3}-S(O)-(CR^7R^8)_{t4}-$, or $-(CR^7R^8)_{t3}-S(O)_2-(CR^7R^8)_{t4}-$,
t3 is 1, 2, or 3; and
t4 is 1 or 2.

In some embodiments, $L^1$ and $L^2$ together form $S-S$, $-(CR^7R^8)-S-$, $-(CR^7R^8)-S(O)-$, $-(CR^7R^8)-S(O)_2-$, $-(CR^7R^8)-O-$, $-(CR^7R^8)_2-O-$, $-O-(CR^7R^8)_2-O-$, $-O-(CR^7R^8)_2-S-$, $-O-(CR^7R^8)_2-S(O)-$, or $-O-(CR^7R^8)_2-S(O)_2-$.

In some embodiments, $L^1$ and $L^2$ together form $S-S$, $-(CH_2)-S-$, $-(CH_2)-S(O)-$, $-(CH_2)-S(O)_2-$, $-(CH_2)-O-$, $-(CH_2)_2-O-$, $-O-(CH_2)_2-O-$, $-O-(CH_2)_2-S-$, $-O-(CH_2)_2-S(O)-$, or $-O-(CH_2)_2-S(O)_2-$. In some embodiments, $L^1$ and $L^2$ together form $S-S$. In some embodiments, $L^1$ and $L^2$ together form $-(CH_2)-S-$, $-(CH_2)-S(O)-$, $-(CH_2)-S(O)_2-$, $-(CH_2)-O-$, $-(CH_2)_2-O-$, $-O-(CH_2)_2-O-$, $-O-(CH_2)_2-S-$, $-O-(CH_2)_2-S(O)-$, or $-O-(CH_2)_2-S(O)_2-$.

In some embodiments, $L^1$ and $L^2$ together form $-(CR^7R^8)-O-$, $-(CR^7R^8)-S-$, $-(CR^7R^8)-S(O)-$, $-(CR^7R^8)-S(O)_2-$, $-(CR^7R^8)_2-O-$, $-(CR^7R^8)_2-S-$, $-(CR^7R^8)_2-S(O)-$, $-(CR^7R^8)_2-S(O)_2-$, $-O-(CR^7R^8)_3-$, $-S-(CR^7R^8)_3-$, $-S(O)-(CR^7R^8)_3-$, or $-S(O)_2-(CR^7R^8)_3-$.

In some embodiments, $L^1$ and $L^2$ together form $-(CH_2)-O-$, $-(CH_2)-S-$, $-(CH_2)-S(O)-$, or $-(CH_2)-S(O)_2-$. In some embodiments, $L^1$ and $L^2$ together form $-(CH_2)-O-$ or $-(CH_2)-S-$.

In some embodiments, $L^1$ and $L^2$ together form $-(CH_2)-O-$.

In some embodiments, $L^1$ and $L^2$ together form $-(CH_2)-S-$.

In some embodiments, $L^1$ and $L^2$ together form $-(CH_2)-S(O)-$.

In some embodiments, $L^1$ and $L^2$ together form $-(CH_2)-S(O)_2-$.

In some embodiments, $L^1$ and $L^2$ together form $-(CH_2)_2-O-$, $-(CH_2)_2-S-$, $-(CH_2)_2-S(O)-$, or $-(CH_2)_2-S(O)_2-$. In some embodiments, $L^1$ and $L^2$ together form $-(CH_2)_2-O-$ or $-(CH_2)_2-S-$.

In some embodiments, $L^1$ and $L^2$ together form $-(CH_2)_2-O-$.

In some embodiments, $L^1$ and $L^2$ together form $-(CH_2)_2-S-$.

In some embodiments, $L^1$ and $L^2$ together form $-(CH_2)_2-S(O)-$.

In some embodiments, $L^1$ and $L^2$ together form $-(CH_2)_2-S(O)_2-$.

In some embodiments, $L^1$ and $L^2$ together form $-(CH_2)_3-O-$, $-(CH_2)_3-S-$, $-(CH_2)_3-S(O)-$, or $-(CH_2)_3-S(O)_2-$. In some embodiments, $L^1$ and $L^2$ together form $-(CH_2)_3-O-$ or $-(CH_2)_3-S-$.

In some embodiments, $L^1$ and $L^2$ together form $-(CH_2)_3-O-$.

In some embodiments, $L^1$ and $L^2$ together form $-(CH_2)_3-S-$.

In some embodiments, $L^1$ and $L^2$ together form $-(CH_2)_3-S(O)-$.

In some embodiments, $L^1$ and $L^2$ together form $-(CH_2)_3-S(O)_2-$.

In some embodiments, $L^1$ and $L^2$ together form $-(CR^7R^8)-O-(CR^7R^8)-$, $-(CR^7R^8)-S-(CR^7R^8)-$, $-(CR^7R^8)-S(O)-(CR^7R^8)-$, $-(CR^7R^8)-S(O)_2-(CR^7R^8)-$, $-(CR^7R^8)-O-(CR^7R^8)_2-$, $-(CR^7R^8)-S-(CR^7R^8)_2-$, $-(CR^7R^8)-S(O)-(CR^7R^8)_2-$, $-(CR^7R^8)-S(O)_2-(CR^7R^8)_2-$, $-(CR^7R^8)_2-O-(CR^7R^8)_2-$, $-(CR^7R^8)_2-S-(CR^7R^8)_2-$, $-(CR^7R^8)_2-S(O)-(CR^7R^8)_2-$, or $-(CR^7R^8)_2-S(O)_2-(CR^7R^8)_2-$.

In some embodiments, $L^1$ and $L^2$ together form $-(CH_2)-O-(CH_2)-$, $-(CH_2)-S-(CH_2)-$, $-(CH_2)-S(O)-(CH_2)-$, $-(CH_2)-S(O)_2-(CH_2)-$, $-(CH_2)-O-(CH_2)_2-$, $-(CH_2)-S-(CH_2)_2-$, $-(CH_2)-S(O)-(CH_2)_2-$, $-(CH_2)-S(O)_2-(CH_2)_2-$, $-(CH_2)_2-O-(CH_2)_2-$, $-(CH_2)_2-S-(CH_2)_2-$, $-(CH_2)_2-S(O)-(CH_2)_2-$, or $-(CH_2)_2-S(O)_2-(CH_2)_2-$.

In some embodiments, $L^1$ and $L^2$ together form $-(CH_2)-O-(CH_2)-$ or $-(CH_2)-S-(CH_2)-$.

In some embodiments, $L^1$ and $L^2$ together form $-(CH_2)-O-(CH_2)-$.

In some embodiments, $L^1$ and $L^2$ together form $-(CH_2)-S-(CH_2)-$.

In some embodiments, $L^1$ and $L^2$ together form $-(CH_2)-O-(CH_2)_2-$ or $-(CH_2)-S-(CH_2)_2-$.

In some embodiments, $L^1$ and $L^2$ together form $-(CH_2)-O-(CH_2)_2-$.

In some embodiments, $L^1$ and $L^2$ together form $-(CH_2)-S-(CH_2)_2-$.

In some embodiments, $L^1$ and $L^2$ together form $-(CH_2)_2-O-(CH_2)_2-$ or $-(CH_2)_2-S-(CH_2)_2-$.

In some embodiments, $L^1$ and $L^2$ together form $-(CH_2)_2-O-(CH_2)_2-$.

In some embodiments, $L^1$ and $L^2$ together form $-(CH_2)_2-S-(CH_2)_2-$.

In some embodiments, $L^1$ and $L^2$ together form $-O-(CH_2)_2-O-$, $-O-(CH_2)_2-S-$, $-O-(CH_2)_2-S$ (O)—, —O—(CH$_2$)$_2$—S(O)$_2$—, —S—(CH$_2$)$_2$—S—, —S(O)—(CH$_2$)$_2$—S(O)—, or —S(O)$_2$—(CH$_2$)$_2$—S(O)$_2$—.

In some embodiments, L$^1$ and L$^2$ together form —O—(CH$_2$)$_2$—O—, —O—(CH$_2$)$_2$—S—, —O—(CH$_2$)$_2$—S(O)—, or —O—(CH$_2$)$_2$—S(O)$_2$—.

In some embodiments, L$^1$ and L$^2$ together form —O—(CH$_2$)$_2$—O—.

In some embodiments, L$^1$ and L$^2$ together form —O—(CH$_2$)$_2$—S—.

In some embodiments, L$^1$ and L$^2$ together form —O—(CH$_2$)$_2$—S(O)—.

In some embodiments, L$^1$ and L$^2$ together form —O—(CH$_2$)$_2$—S(O)$_2$—.

In some embodiments, one of L$^1$ and L$^2$ is selected from —(CR$^7$R$^8$)$_m$—NR$^9$—, —(CR$^7$R$^8$)$_m$—S(O)$_2$, —(CR$^7$R$^8$)$_m$—C(O)—, —C(O)NR$^9$—, —(CR$^7$R$^8$)$_m$—S(O)NR$^9$—, and —(CR$^7$R$^8$)$_m$—S(O)$_2$NR$^9$—; and the other is selected from a bond, —(CR$^7$R$^8$)$_n$—, —(CR$^7$R$^8$)$_m$—NR$^9$—, —(CR$^7$R$^8$)$_m$—S(O)$_2$—, —(CR$^7$R$^8$)$_m$—C(O)—, —C(O)NR$^9$—, —(CR$^7$R$^8$)$_m$—S(O)NR$^9$—, and —(CR$^7$R$^8$)$_m$—S(O)$_2$NR$^9$—.

In some embodiments, L$^1$ and L$^2$ together form —(CR$^7$R$^8$)$_{t5}$—C(O)—, —(CR$^7$R$^8$)$_{t5}$—C(O)NR$^9$—, —C(O)NR$^9$—(CR$^7$R$^8$)$_{t5}$—, —C(O)NR$^9$—, —S(O)$_2$NR$^9$—(CR$^7$R$^8$)$_{t5}$—, —(CR$^7$R$^8$)$_{t5}$—S(O)$_2$NR$^9$—, or —S(O)$_2$NR$^9$—, wherein t5 is 1, 2, or 3.

In some embodiments, L$^1$ and L$^2$ together form —(CR$^7$R$^8$)$_{t5}$—C(O)—, —C(O)NR$^9$—, or —S(O)$_2$NR$^9$—, and wherein t5 is 1, 2, or 3.

In some embodiments, L$^1$ and L$^2$ together form —(CR$^7$R$^8$)—C(O)—, —(CR$^7$R$^8$)$_2$—C(O)—, or —(CR$^7$R$^8$)$_3$—C(O)—. In some embodiments, L$^1$ and L$^2$ together form —(CR$^7$R$^8$)—C(O)—. In some embodiments, L$^1$ and L$^2$ together form —(CR$^7$R$^8$)$_2$—C(O)—. In some embodiments, L$^1$ and L$^2$ together form —(CR$^7$R$^8$)$_3$—C(O)—.

In some embodiments, L$^1$ and L$^2$ together form —(CH$_2$)—C(O)—, —(CH$_2$)$_2$—C(O)—, or —(CH$_2$)$_3$—C(O)—. In some embodiments, L$^1$ and L$^2$ together form —(CH$_2$)—C(O)—. In some embodiments, L$^1$ and L$^2$ together form —(CH$_2$)$_2$—C(O)—. In some embodiments, L$^1$ and L$^2$ together form —(CH$_2$)$_3$—C(O)—.

In some embodiments, L$^1$ and L$^2$ together form —(CR$^7$R$^8$)—C(O)NR$^9$—, —C(O)NR$^9$—(CR$^7$R$^8$)—, or —C(O)NR$^9$—. In some embodiments, L$^1$ and L$^2$ together form —(CH$_2$)—C(O)NR$^9$—, —C(O)NR$^9$—(CH$_2$)—, or —C(O)NR$^9$—. In some embodiments, L$^1$ and L$^2$ together form —(CH$_2$)—C(O)NH—, —C(O)NH—(CH$_2$)—, or —C(O)NH—. In some embodiments, L$^1$ and L$^2$ together form —C(O)NH—(CH$_2$)—, or —C(O)NH—.

In some embodiments, L$^1$ and L$^2$ together form —(CH$_2$)—C(O)NH—.

In some embodiments, L$^1$ and L$^2$ together form —C(O)NH—(CH$_2$)—.

In some embodiments, L$^1$ and L$^2$ together form —C(O)NH—.

In some embodiments, L$^1$ and L$^2$ together form —(CR$^7$R$^8$)$_{t7}$—C(O)NR$^9$—(CR$^7$R$^8$)$_{t8}$, wherein t7 is 1 or 2 and t8 is 1 or 2. In some embodiments, L$^1$ and L$^2$ together form —(CR$^7$R$^8$)—C(O)NR$^9$—(CR$^7$R$^8$)—. In some embodiments, L$^1$ and L$^2$ together form —(CH$_2$)—C(O)NH—(CH$_2$)—.

In some embodiments, L$^1$ and L$^2$ together form —S(O)$_2$NR$^9$—(CR$^7$R$^8$)$_{t5}$—, —(CR$^7$R$^8$)$_{t5}$—S(O)$_2$NR$^9$—, or —S(O)$_2$NR$^9$—, wherein t5 is 1, 2, or 3.

In some embodiments, L$^1$ and L$^2$ together form —S(O)$_2$NR$^9$—(CR$^7$R$^8$)—, —(CR$^7$R$^8$)—S(O)$_2$NR$^9$—, or —S(O)$_2$NR$^9$—. In some further embodiments, R$^9$ is H or C$_{1-3}$ alkyl.

In some embodiments, L$^1$ and L$^2$ together form —S(O)$_2$NR$^9$—(CH$_2$)—, —(CH$_2$)—S(O)$_2$NR$^9$—, or —S(O)$_2$NR$^9$—. In some further embodiments, L$^1$ and L$^2$ together form —S(O)$_2$NH—(CH$_2$)—, —(CH$_2$)—S(O)$_2$NH—, or —S(O)$_2$NH—.

In some embodiments, L$^1$ and L$^2$ together form —S(O)$_2$NH—(CH$_2$)—.

In some embodiments, L$^1$ and L$^2$ together form —(CH$_2$)—S(O)$_2$NH—.

In some embodiments, L$^1$ and L$^2$ together form —S(O)$_2$NH—.

In some embodiments, L$^1$ and L$^2$ together form —(CR$^7$R$^8$)$_{t7}$—S(O)$_2$NR$^9$—(CR$^7$R$^8$)$_{t8}$—, wherein t7 is 1 or 2 and t8 is 1 or 2. In some embodiments, L$^1$ and L$^2$ together form —(CR$^7$R$^8$)—S(O)$_2$NR$^9$—(CR$^7$R$^8$).

In some embodiments, L$^1$ and L$^2$ together form —(CH$_2$)—S(O)$_2$NR$^9$—(CH$_2$)—.

In some embodiments, L$^1$ and L$^2$ together form —(CR$^7$R$^8$)$_m$—NR$^9$—C(O)NR$^9$—, —(CR$^7$R$^8$)$_m$—O—C(O)NR$^9$—, or —O—C(O)NR$^9$—(CR$^7$R$^8$)$_m$—.

In some embodiments, L$^1$ and L$^2$ together form —(CR$^7$R$^8$)—NR$^9$—C(O)NR$^9$—, —(CR$^7$R$^8$)—O—C(O)NR$^9$—, —O—C(O)NR$^9$—(CR$^7$R$^8$)—, —NR$^9$—C(O)NR$^9$—, or —O—C(O)NR$^9$—.

In some embodiments, L$^1$ and L$^2$ together form —(CH$_2$)—NR$^9$—C(O)NR$^9$—. In some embodiments, L$^1$ and L$^2$ together form —(CH$_2$)—NH—C(O)NH—.

In some embodiments, L$^1$ and L$^2$ together form —(CR$^7$R$^8$)—O—C(O)NR$^9$—. In some embodiments, L$^1$ and L$^2$ together form —(CH$_2$)—O—C(O)NH—.

In some embodiments, L$^1$ and L$^2$ together form —O—C(O)NR$^9$—(CR$^7$R$^8$)—. In some embodiments, L$^1$ and L$^2$ together form —O—C(O)NH—(CH$_2$)—.

In some embodiments, L$^1$ and L$^2$ together form —NR$^9$—C(O)NR$^9$—, or —O—C(O)NR$^9$—.

In some embodiments, L$^1$ and L$^2$ together form —NH—C(O)NH—.

In some embodiments, L$^1$ and L$^2$ together form —O—C(O)NH—.

In some embodiments, L$^1$ and L$^2$ together form —(CR$^7$R$^8$)$_m$—NR$^9$—(CR$^7$R$^8$)$_n$—.

In some embodiments, L$^1$ and L$^2$ together form —NR$^9$—(CR$^7$R$^8$)—. In some embodiments, L$^1$ and L$^2$ together form —NR$^9$—(CR$^7$R$^8$)—. In some embodiments, L$^1$ and L$^2$ together form —NR$^9$—(CR$^7$R$^8$)$_2$—. In some embodiments, L$^1$ and L$^2$ together form —NR$^9$—(CR$^7$R$^8$)$_3$—.

In some embodiments, L$^1$ and L$^2$ together form —NR$^9$—(CH$_2$)$_n$—. In some embodiments, L$^1$ and L$^2$ together form —NR$^9$—(CH$_2$)—. In some embodiments, L$^1$ and L$^2$ together form —NR$^9$—(CH$_2$)$_2$—. In some embodiments, L$^1$ and L$^2$ together form —NR$^9$—(CH$_2$)$_3$—.

In some embodiments, L$^1$ and L$^2$ together form —(CR$^7$R$^8$)$_{m2}$—NR$^9$—(CR$^7$R$^8$)$_n$—, wherein m2 is 1 or 2. In some embodiments, L$^1$ and L$^2$ together form —(CR$^7$R$^8$)—NR$^9$—(CR$^7$R$^8$)—, —(CR$^7$R$^8$)—NR$^9$—(CR$^7$R$^8$)$_2$—, or —(CR$^7$R$^8$)$_2$—NR$^9$—(CR$^7$R$^8$)$_2$—. In some further embodiments, L$^1$ and L$^2$ together form —(CR$^7$R$^8$)—NR$^9$—(CR$^7$R$^8$)— or —(CR$^7$R$^8$)—NR$^9$—(CR$^7$R$^8$)$_2$—. In some further embodiments, R$^9$ is H or C$_{1-3}$ alkyl.

In some embodiments, L$^1$ and L$^2$ together form —(CH$_2$)—NR$^9$—(CH$_2$)$_n$—, wherein m2 is 1 or 2. In some embodiments, L$^1$ and L$^2$ together form —(CH$_2$)—NR$^9$—(CH$_2$)—, —(CH$_2$)—NR$^9$—(CH$_2$)$_2$—, or —(CH$_2$)$_2$—NR$^9$—(CH$_2$)$_2$—. In some further embodiments, L$^1$ and L$^2$ together form —$(CH_2)$—$NR^9$—$(CH_2)$— or —$(CH_2)$—$NR^9$—$(CH_2)_2$—. In some further embodiments, $R^9$ is H or $C_{1-3}$ alkyl.

In some embodiments, $L^1$ and $L^2$ together form —$(CR^7R^8)$—$NR^9$—$(CR^7R^8)$—. In some embodiments, $L^1$ and $L^2$ together form —$(CH_2)$—$NR^9$—$(CH_2)$—.

In some embodiments, $L^1$ and $L^2$ together form —$NR^9$—$(CR^7R^8)_{t9}$—O— wherein t9 is 1, 2, or 3. In some embodiments, $L^1$ and $L^2$ together form —$NR^9$—$(CR^7R^8)$—O—. In some embodiments, $L^1$ and $L^2$ together form —$NR^9$—$(CR^7R^8)_2$—O—. In some embodiments, $L^1$ and $L^2$ together form —$NR^9$—$(CR^7R^8)_3$—O—.

In some embodiments, $L^1$ and $L^2$ together form —$NR^9$—$(CH_2)$—O—.

In some embodiments, $L^1$ and $L^2$ together form —$NR^9$—$(CH_2)_2$—O—.

In some embodiments, $L^1$ and $L^2$ together form —$NR^9$—$(CH_2)_3$—O—.

In some embodiments, one of $L^1$ and $L^2$ is selected from —$(CR^7R^8)_m$—$NR^9C(O)NR^9$—, —$(CR^7R^8)_m$—$OC(O)NR^9$—, —$(CR^7R^8)_m$—$NR^9C(O)O$—, and —$(CR^7R^8)_m$—$NR^9$—$S(O)_2NR^9$—; and the other is selected from a bond, —$(CR^7R^8)_n$—, —$(CR^7R^8)_m$—$NR^9$—, —$(CR^7R^8)_m$—O—, —$(CR^7R^8)_m$—S—, —$(CR^7R^8)_m$—$S(O)_2$—, —$(CR^7R^8)_m$—C(O), —$C(O)NR^9$—, —$(CR^7R^8)_m$—$S(O)NR^9$—, and —$(CR^7R^8)_m$—$S(O)_2NR^9$—.

In some embodiments, one of $L^1$ and $L^2$ is selected from —$(CR^7R^8)_m$—$NR^9C(O)NR^9$—, —$(CR^7R^8)_m$—$OC(O)NR^9$—, —$(CR^7R^8)_m$—$NR^9C(O)O$—, and —$(CR^7R^8)_m$—$NR^9$—$S(O)_2NR^9$—; and the other is selected from a bond, and —$(CR^7R^8)_n$.

In some embodiments, $L^1$ and $L^2$ together form —$(CR^7R^8)_m$—$NR^9C(O)NR^9$—$(CR^7R^8)_m$—, —$(CR^7R^8)_m$—$OC(O)NR^9$—$(CR^7R^8)_m$—, or —$(CR^7R^8)_m$—$NR^9$—$S(O)_2NR^9$—$(CR^7R^8)_m$—.

In some embodiments, $L^1$ and $L^2$ together form —$(CR^7R^8)_m$—$NR^9C(O)NR^9$—$(CR^7R^8)_m$—. In some embodiments, $L^1$ and $L^2$ together form —$NR^9C(O)NR^9$, —$NR^9C(O)NR^9$—$(CR^7R^8)_{m2}$—, or —$(CR^7R^8)_{m1}$—$NR^9C(O)NR^9$—$(CR^7R^8)$—, wherein m1 and m2 are each, independently 1 or 2.

In some embodiments, $L^1$ and $L^2$ together form —$NR^9C(O)NR^9$.

In some embodiments, $L^1$ and $L^2$ together form —$NR^9C(O)NR^9$—$(CR^7R^8)$—, —$NR^9C(O)NR^9$—$(CR^7R^8)_2$—, —$(CR^7R^8)$—$NR^9C(O)NR^9$—$(CR^7R^8)$—, —$(CR^7R^8)$—$NR^9C(O)NR^9$—$(CR^7R^8)_2$—, or —$(CR^7R^8)_2$—$NR^9C(O)NR^9$—$(CR^7R^8)_2$—.

In some embodiments, $L^1$ and $L^2$ together form —$(CH_2)_m$—$NR^9C(O)NR^9$—$(CH_2)_m$—. In some embodiments, $L^1$ and $L^2$ together form —$NR^9C(O)NR^9$, —$NR^9C(O)NR^9$—$(CH_2)_{m2}$—, or —$(CH_2)_{m1}$—$NR^9C(O)NR^9$—$(CH_2)_{m2}$— wherein m1 and m2 are each, independently 1 or 2.

In some embodiments, $L^1$ and $L^2$ together form —$NR^9C(O)NR^9$—$(CH_2)$—, —$NR^9C(O)NR^9$—$(CH_2)_2$—, —$(CH_2)$—$NR^9C(O)NR^9$—$(CH_2)$—, —$(CH_2)$—$NR^9C(O)NR^9$—$(CH_2)_2$—, or —$(CH_2)_2$—$NR^9C(O)NR^9$—$(CH_2)_2$—.

In some embodiments, $L^1$ and $L^2$ together form —$(CR^7R^8)_m$—$OC(O)NR^9$—$(CR^7R^8)_m$—.

In some embodiments, $L^1$ and $L^2$ together form —$OC(O)NR^9$—.

In some embodiments, $L^1$ and $L^2$ together form —$OC(O)NR^9$—$(CR^7R^8)$—, —$OC(O)NR^9$—$(CR^7R^8)_2$—, —$(CR^7R^8)$—$OC(O)NR^9$—, —$(CR^7R^8)_2$—$OC(O)NR^9$—, —$(CR^7R^8)$—$OC(O)NR^9$—$(CR^7R^8)$—, —$(CR^7R^8)$—$OC(O)NR^9$—$(CR^7R^8)_2$—, —$(CR^7R^8)_2$—$OC(O)NR^9$—$(CR^7R^8)$—, or —$(CR^7R^8)_2$—$OC(O)NR^9$—$(CR^7R^8)_2$—.

In some embodiments, $L^1$ and $L^2$ together form —$OC(O)NR^9$—$(CH_2)$—, —$OC(O)NR^9$—$(CH_2)_2$—, —$(CH_2)$—$OC(O)NR^9$—, —$(CH_2)_2$—$OC(O)NR^9$—, —$(CH_2)$—$OC(O)NR^9$—$(CH_2)$—, —$(CH_2)$—$OC(O)NR^9$—$(CH_2)_2$—, —$(CH_2)_2$—$OC(O)NR^9$—$(CH_2)$—, or —$(CH_2)_2$—$OC(O)NR^9$—$(CH_2)_2$—.

In some embodiments, $L^1$ and $L^2$ together form —$(CR^7R^8)_m$—$NR^9S(O)_2NR^9$—$(CR^7R^8)_m$—. In some embodiments, $L^1$ and $L^2$ together form —$NR^9S(O)_2NR^9$—, —$NR^9S(O)_2NR^9$—$(CR^7R^8)_{m2}$—, or —$(CR^7R^8)_{m1}$—$NR^9S(O)_2NR^9$—$(CR^7R^8)_{m2}$—, wherein m1 and m2 are each, independently 1 or 2.

In some embodiments, $L^1$ and $L^2$ together form —$NR^9S(O)_2NR^9$.

In some embodiments, $L^1$ and $L^2$ together form —$NR^9S(O)_2NR^9$—$(CR^7R^8)$—, —$NR^9S(O)_2NR^9$—$(CR^7R^8)_2$—, —$(CR^7R^8)$—$NR^9S(O)_2NR^9$—$(CR^7R^8)$—, —$(CR^7R^8)$—$NR^9S(O)_2NR^9$—$(CR^7R^8)_2$—, or —$(CR^7R^8)_2$—$NR^9S(O)_2NR^9$—$(CR^7R^8)_2$—.

In some embodiments, $L^1$ and $L^2$ together form —$CR^{10}$=$CR^{10}$—, —$(CH_2)_2$—, —$(CH_2)$—O—, —$(CH_2)$—S—, —$(CH_2)$—S(O)—, —$(CH_2)$—$S(O)_2$—, —$(CH_2)$—$NR^9$—, —C(O)—$NR^9$—, —$S(O)_2$—$NR^9$—, S—S—, —$(CH_2)_2$—O—, —$(CH_2)_2$—S—, —$(CH_2)_2$—S(O)—, —$(CH_2)_2$—$S(O)_2$—, —$(CH_2)_2$—C(O)—, —$(CH_2)_2$—$NR^9$—, —$(CH_2)$—$S(O)_2$—NH—, —$(CH_2)$—NH—$S(O)_2$—, —$(CH_2)$—C(O)—NH—, —$(CH_2)$—NH—C(O)—, —$(CH_2)$—O—$(CH_2)$—, —$(CH_2)$—S—$(CH_2)$—, —$(CH_2)$—$NR^9$—$(CH_2)$—, —$(CH_2)_3$—$NR^9$—, —$(CH_2)_2$—S—$(CH_2)$—, —O—$(CH_2)_2$—O—, —O—$(CH_2)_2$—S—, —O—$(CH_2)_2$—S(O)—, —O—$(CH_2)_2$—$S(O)_2$—, —S—$(CH_2)_2$—S—, —$NR^9$—$(CH_2)_2$—S—, or —$NR^9$—C(O)—$(CH_2)_2$—.

In some embodiments, $L^1$ and $L^2$ together form —CH=CH—, —$(CH_2)_2$—, —$(CH_2)$—O—, —$(CH_2)$—S—, —$(CH_2)$—S(O)—, —$(CH_2)$—$S(O)_2$—, —$(CH_2)$—$NR^9$—, —C(O)—NH—, —$S(O)_2$—NH—, S—S—, —$(CH_2)_2$—O—, —$(CH_2)_2$—S—, —$(CH_2)_2$—S(O)—, —$(CH_2)_2$—$S(O)_2$—, —$(CH_2)_2$—C(O)—, —$(CH_2)_2$—$NR^9$—, —$(CH_2)$—$S(O)_2$—NH—, —$(CH_2)$—NH—$S(O)_2$—, —$(CH_2)$—C(O)—NH—, —$(CH_2)$—NH—C(O)—, —$(CH_2)$—O—$(CH_2)$—, —$(CH_2)$—S—$(CH_2)$—, —$(CH_2)$—$NR^9$—$(CH_2)$—, —$(CH_2)_3$—$NR^9$—, —$(CH_2)_2$—S—$(CH_2)$—, —O—$(CH_2)_2$—O—, —O—$(CH_2)_2$—S—, —O—$(CH_2)_2$—S(O)—, —O—$(CH_2)_2$—$S(O)_2$—, —S—$(CH_2)_2$—S—, —$NR^9$—$(CH_2)_2$—S—, or —NH—C(O)—$(CH_2)_2$—, wherein each $R^9$ is independently selected from H, $C_{1-6}$ alkyl, and $C(O)R^{b1}$, and wherein $R^{b1}$ is selected from $C_{1-6}$ alkyl, aryl, and heteroaryl, each optionally substituted with 1, 2, or 3 substituents independently selected from halo, $C_{1-6}$ alkyl, and $C_{1-6}$ haloalkyl.

As used herein, unless specifically indicated, a linkage—a moiety that links two other moieties—can be attached to the other two moieties in either direction, if the linkage is asymmetric. For example, the moiety formed by $L^1$ and $L^2$ together in compounds of Formula I can be linked to the ring containing $A^1$, $B^1$, $D^1$, and $E^1$ and the containing $A^2$, $B^2$, $D^2$, and $E^2$ in either direction. For example, when $L^1$ and $L^2$ together form —O—$(CH_2)_2$—S—, the sulfur atom (S) can be linked to the ring containing $A^1$, $B^1$, $D^1$, and $E^1$, and oxygen atom (O) to the ring containing $A^2$, $B^2$, $D^2$, and $E^2$. Alternatively, when $L^1$ and $L^2$ together form —O—$(CH_2)_2$—S—, the oxygen atom (O) can be linked to the ring containing $A^1$, $B^1$, $D^1$, and $E^1$, and the sulfur atom (S) to the ring containing $A^2$, $B^2$, $D^2$, and $E^2$. For another example, when $W^1$ in -$W^1$-$Q^1$-$Y^1$-$Z^1$ is $O(CR^{11a}R^{11b})_{q1}NR^f$, $W^1$ can be linked to $Q^1$ either via the O or the N atom.

In some embodiments, the ring containing $A^1$, $B^1$, $D^1$, and $E^1$ is a 6-membered aromatic ring; $B^1$, $D^1$, and $E^1$ are each, independently, $CR^5$ or N; $A^1$ is CH; the ring containing $A^2$, $B^2$, $D^2$, and $E^2$ is a 6-membered aromatic ring; $B^2$, $D^2$, and $E^2$ are each, independently, $CR^5$ or N; $A^2$ is CH; $X^1$ is $CR^1$; $X^2$ is N; $X^3$ is $CR^3$; Y is $NR^4$; and $L^1$ and $L^2$ together form —$CR^{10}$=$CR^{10}$—, —$(CH_2)_2$—, —$(CH_2)$—O—, —$(CH_2)$—S—, —$(CH_2)$—S(O)—, —$(CH_2)$—S(O)$_2$—, —$(CH_2)$—$NR^9$—, —C(O)—$NR^9$—, —S(O)$_2$—$NR^9$—, S—S—, —$(CH_2)_2$—O—, —$(CH_2)_2$—S—, —$(CH_2)_2$—S(O)—, —$(CH_2)_2$—S(O)$_2$—, —$(CH_2)_2$—C(O)—, —$(CH_2)_2$—$NR^9$—, —$(CH_2)$—S(O)$_2$—NH—, —$(CH_2)$—NH—S(O)$_2$—, —$(CH_2)$—C(O)—NH—, —$(CH_2)$—NH—C(O)—, —$(CH_2)$—O—$(CH_2)$—, —$(CH_2)$—S—$(CH_2)$—, —$(CH_2)$—$NR^9$—$(CH_2)$—, —$(CH_2)_3$—$NR^9$—, —$(CH_2)_2$—S—$(CH_2)$—, —O—$(CH_2)_2$—O—, —O—$(CH_2)_2$—S—, —O—$(CH_2)_2$—S(O)—, —O—$(CH_2)_2$—S(O)$_2$—, —S—$(CH_2)_2$—S—, —$NR^9$—$(CH_2)_2$—S—, or —$NR^9$—C(O)—$(CH_2)_2$—. In some further embodiments, one of $B^1$, $D^1$, and $E^1$ is N, and the other two are each independently $CR^5$; $R^1$ is H; $R^3$ is H, halo, methyl, or $C_1$ haloalkyl; and $R^4$ is H or $C_{1-3}$ alkyl.

In some embodiments, the ring containing $A^1$, $B^1$, $D^1$, and $E^1$ is a 6-membered aromatic ring; $B^1$, $D^1$, and $E^1$ are each, independently, $CR^5$ or N; $A^1$ is CH; the ring containing $A^2$, $B^2$, $D^2$, and $E^2$ is a 6-membered aromatic ring; $B^2$, $D^2$, and $E^2$ are each, independently, $CR^5$ or N; $A^2$ is CH; $X^1$ is $CR^1$; $X^2$ is N; $X^3$ is $CR^3$; Y is $NR^4$; and $L^1$ and $L^2$ together form —CH=CH—, —$(CH_2)_2$—, —$(CH_2)$—O—, —$(CH_2)$—S—, —$(CH_2)$—S(O)—, —$(CH_2)$—S(O)$_2$—, —$(CH_2)$—$NR^9$—, —C(O)—$NR^9$—, —S(O)$_2$—$NR^9$—, or S—S—. In some further embodiments, $L^1$ and $L^2$ together form —CH=CH—, —$(CH_2)_2$—, —$(CH_2)$—O—, —$(CH_2)$—S—, —$(CH_2)$—S(O)—, —$(CH_2)$—S(O)$_2$—, or —$(CH_2)$—$NR^9$—. In yet further embodiments, $L^1$ and $L^2$ together form —$(CH_2)_2$—.

In some embodiments, the ring containing $A^1$, $B^1$, $D^1$, and $E^1$ is a 6-membered aromatic ring; $B^1$, $D^1$, and $E^1$ are each, independently, $CR^5$ or N; $A^1$ is CH; the ring containing $A^2$, $B^2$, $D^2$, and $E^2$ is a 6-membered aromatic ring; $B^2$, $D^2$, and $E^2$ are each, independently, $CR^5$ or N; $A^2$ is CH; $X^1$ is $CR^1$; $X^2$ is N; $X^3$ is $CR^3$; Y is $NR^4$; and $L^1$ and $L^2$ together form —CH=CH—, —$(CH_2)_2$—, —$(CH_2)$—O—, —$(CH_2)$—S—, —$(CH_2)$—S(O)—, —$(CH_2)$—S(O)$_2$—, or —$(CH_2)$—$NR^9$—. In some further embodiments, one of $B^1$, $D^1$, and $E^1$ is N, and the other two are each independently $CR^5$; $R^1$ is H; $R^3$ is H, halo, methyl, or $C_1$ haloalkyl; and $R^4$ is H or $C_{1-3}$ alkyl.

In some embodiments, the ring containing $A^1$, $B^1$, $D^1$, and $E^1$ is a 6-membered aromatic ring; $B^1$, $D^1$, and $E^1$ are each, independently, $CR^5$; $A^1$ is CH; the ring containing $A^2$, $B^2$, $D^2$, and $E^2$ is a 6-membered aromatic ring; $B^2$, $D^2$, and $E^2$ are each, independently, $CR^5$; $A^2$ is CH; $X^1$ is $CR^1$; $X^2$ is N; $X^3$ is $CR^3$; Y is $NR^4$; and $L^1$ and $L^2$ together form —CH=CH—, —$(CH_2)_2$—, —$(CH_2)$—O—, —$(CH_2)$—S—, —$(CH_2)$—S(O)—, —$(CH_2)$—S(O)$_2$—, —$(CH_2)$—$NR^9$—, —C(O)—$NR^9$—, —S(O)$_2$—$NR^9$—, or S—S—. In some further embodiments, $L^1$ and $L^2$ together form —CH=CH—, —$(CH_2)_2$—, —$(CH_2)$—O—, —$(CH_2)$—S—, —$(CH_2)$—S(O)—, —$(CH_2)$—S(O)$_2$—, or —$(CH_2)$—$NR^9$—. In yet further embodiments, $L^1$ and $L^2$ together form —$(CH_2)_2$—.

In some embodiments, the ring containing $A^1$, $B^1$, $D^1$, and $E^1$ is a 6-membered aromatic ring; $B^1$, $D^1$, and $E^1$ are each, independently, $CR^5$ or N; $A^1$ is CH; the ring containing $A^2$, $B^2$, $D^2$, and $E^2$ is a 6-membered aromatic ring; $B^2$, $D^2$, and $E^2$ are each, independently, $CR^5$ or N; $A^2$ is CH; $X^1$ is $CR^1$; $X^2$ is N; $X^3$ is $CR^3$; Y is $NR^4$; and $L^1$ and $L^2$ together form —$(CH_2)$—O—, —$(CH_2)$—S—, —$(CH_2)$—S(O)—, —$(CH_2)$—S(O)$_2$—, —$(CH_2)$—$NR^9$—, —$(CH_2)_2$—O—, —$(CH_2)_2$—S—, —$(CH_2)_2$—S(O)—, —$(CH_2)_2$—S(O)$_2$—, —$(CH_2)_2$—C(O)—, or —$(CH_2)_2$—$NR^9$—. In some further embodiments, one of $B^1$, $D^1$, and $E^1$ is N, and the other two are each independently $CR^5$; $R^1$ is H; $R^3$ is H, halo, methyl, or $C_1$ haloalkyl; and $R^4$ is H or $C_{1-3}$ alkyl. In yet further embodiments, $L^1$ and $L^2$ together form —$(CH_2)_2$—O—.

In some embodiments, the ring containing $A^1$, $B^1$, $D^1$, and $E^1$ is a 6-membered aromatic ring; $B^1$, $D^1$, and $E^1$ are each, independently, $CR^5$; $A^1$ is CH; the ring containing $A^2$, $B^2$, $D^2$, and $E^2$ is a 6-membered aromatic ring; $B^2$, $D^2$, and $E^2$ are each, independently, $CR^5$; $A^2$ is CH; $X^1$ is $CR^1$; $X^2$ is N; $X^3$ is $CR^3$; Y is $NR^4$; and $L^1$ and $L^2$ together form —$(CH_2)$—O—, —$(CH_2)$—S—, —$(CH_2)$—S(O)—, —$(CH_2)$—S(O)$_2$—, —$(CH_2)$—$NR^9$—, —$(CH_2)_2$—O—, —$(CH_2)_2$—S—, —$(CH_2)_2$—S(O)—, —$(CH_2)_2$—S(O)$_2$—, —$(CH_2)_2$—C(O)—, or —$(CH_2)_2$—$NR^9$—. In some further embodiments, one of $B^1$, $D^1$, and $E^1$ is N, and the other two are each independently $CR^5$; $R^1$ is H; $R^3$ is H, halo, methyl, or $C_1$ haloalkyl; and $R^4$ is H or $C_{1-3}$ alkyl. In yet further embodiments, $L^1$ and $L^2$ together form —$(CH_2)_2$—O—.

In some embodiments, each $R^9$ is, independently, H, $C_{1-6}$ alkyl, $C_{1-6}$ haloalkyl, C(O)$R^{b1}$, C(O)$NR^{c1}R^{d1}$, or C(O)$OR^{a1}$. In some further embodiments, each $R^9$ is, independently, H, $C_{1-6}$ alkyl, $C_{1-6}$ haloalkyl, C(O)$R^{b1}$, or C(O)$NR^{c1}R^{d1}$.

In some embodiments, each $R^9$ is, independently, H, $C_{1-6}$ alkyl, $C_{1-6}$ haloalkyl, C(=O)—($C_{1-6}$ alkyl), C(=O)-(arylalkyl), C(=O)$NH_2$, C(=O)$NH(C_{1-6}$ alkyl), C(=O)N($C_{1-6}$ alkyl)$_2$, C(=O)O—($C_{1-6}$ alkyl), or C(=O)O-(arylalkyl). In some embodiments, each $R^9$ is, independently, H, $C_{1-6}$ alkyl, $C_{1-6}$ haloalkyl, C(=O)—($C_{1-6}$ alkyl), C(=O)-(arylalkyl), C(=O)$NH_2$, C(=O)$NH(C_{1-6}$ alkyl), or C(=O)N($C_{1-4}$ alkyl)$_2$. In some embodiments, each $R^9$ is independently, H or $C_{1-6}$ alkyl. In some embodiments, each $R^9$ is independently, H or $C_{1-4}$ alkyl. In some embodiments, each $R^9$ is independently, H or $C_{1-3}$ alkyl. In some embodiments, each $R^9$ is H.

In some embodiments, each $R^9$ is, independently, H, $C_{1-6}$ alkyl, $C_{1-6}$ haloalkyl, or C(O)$R^{b1}$. In some further embodiments, each $R^9$ is, independently, H, $C_{1-6}$ alkyl, or C(O)$R^{b1}$, wherein $R^{b1}$ is selected from $C_{1-6}$ alkyl, $C_{2-6}$ alkenyl, $C_{2-6}$ alkynyl, aryl, heteroaryl, arylalkyl, heteroarylalkyl, and cycloalkylalkyl, each optionally substituted by 1, 2, 3, 4, or 5 substituents independently selected from halo, $C_{1-6}$ alkyl, $C_{1-6}$ haloalkyl, $C_{1-6}$ alkoxy, and $C_{1-6}$ haloalkoxy.

In some embodiments, each $R^9$ is, independently, H, $C_{1-6}$ alkyl, or C(O)$R^{b1}$. In some further embodiments, $R^{b1}$ is selected from aryl and heteroaryl, each optionally substituted by 1, 2, 3, 4, or 5 substituents independently selected from halo, $C_{1-6}$ alkyl, $C_{1-6}$ haloalkyl, $C_{1-6}$ alkoxy, and $C_{1-6}$ haloalkoxy. In yet further embodiments, $R^{b1}$ is selected from aryl and heteroaryl, each optionally substituted by 1, 2, or 3 substituents independently selected from halo, $C_{1-6}$ alkyl, and $C_{1-6}$ haloalkyl.

In some embodiments, $R^7$, $R^8$, and $R^{10}$ are each, independently, selected from H, halo, $C_{1-6}$ alkyl, $C_{2-6}$ alkenyl, $C_{2-6}$ alkynyl, $C_{1-6}$ haloalkyl, cycloalkyl, CN, $NO_2$, $OR^{a1}$, $SR^{a1}$, S(O)$R^{b1}$, S(O)$NR^{c1}R^{d1}$, S(O)$_2R^{b1}$, $NR^{c1}$S(O)$_2R^{b1}$, S(O)$_2NR^{c1}R^{d1}$, C(O)$R^{b1}$, C(O)$NR^{c1}R^{d1}$, C(O)$OR^{a1}$, $NR^{c1}$C(O)$R^{b1}$, $NR^{c1}$C(O)$NR^{c1}R^{d1}$, and $NR^{c1}R^{d1}$, wherein each of said $C_{1-6}$ alkyl, $C_{2-6}$ alkenyl, $C_{2-6}$ alkynyl, $C_{1-6}$ haloalkyl and cycloalkyl is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, cycloalkyl, CN, $NO_2$, $OR^{a1}$, $SR^{a1}$, S(O)$R^{b1}$, S(O)$NR^{c1}R^{d1}$, S(O)$_2R^{b1}$, $NR^{c1}$S(O)$_2R^{b1}$, S(O)$_2NR^{c1}R^{d1}$, C(O)$R^{b1}$, C(O)$NR^{c1}R^{d1}$, C(O)$OR^{a1}$, $NR^{c1}$C(O)$R^{b1}$, $NR^{c1}$C(O)$NR^{c1}R^{d1}$, and $NR^{c1}R^{d1}$.

In some embodiments, $R^7$, $R^8$, and $R^{10}$ are each, independently, selected from H, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, and $NR^{c1}R^{d1}$.

In some embodiments, $R^7$, $R^8$, and $R^{10}$ are each, independently, selected from H, halo, $C_{1-6}$ alkyl, $C_{2-6}$ alkenyl, $C_{2-6}$ alkynyl, $C_{1-6}$ haloalkyl, CN, $NO_2$, $OR^{a1}$, and $SR^{a1}$.

In some embodiments, $R^7$, $R^8$, and $R^{10}$ are each, independently, selected from H, halo, $C_{1-6}$ alkyl, $C_{1-6}$ haloalkyl, CN, $NO_2$, $OR^{a1}$, and $SR^{a1}$.

In some embodiments, $R^7$, $R^8$, and $R^{10}$ are each, independently, selected from H, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, or $NR^{c1}R^{d1}$.

In some embodiments, $R^7$, $R^8$, and $R^{10}$ are each, independently, selected from H, halo, $C_{1-6}$ alkyl, CN, $NO_2$, OH, $C_{1-6}$ alkoxy, $C_{1-6}$ haloalkoxy, and $C_{2-8}$ alkoxyalkoxy. In some embodiments, $R^7$, $R^8$, and $R^{10}$ are each, independently, selected from H, $C_{1-4}$ alkyl, OH, $C_{1-6}$ alkoxy, $C_{1-6}$ haloalkoxy, and $C_{2-8}$ alkoxyalkoxy.

In some embodiments, $R^7$ and $R^8$ are each, independently, selected from H, halo, $C_{1-6}$ alkyl, CN, $NO_2$, OH, $C_{1-6}$ alkoxy, $C_{1-6}$ haloalkoxy, and $C_{2-8}$ alkoxyalkoxy. In some further embodiments, $R^7$ and $R^8$ are each, independently, selected from H, halo, $C_{1-4}$ alkyl, CN, $NO_2$, $C_{1-4}$ alkoxy, $C_{1-4}$ haloalkoxy, and $C_{2-8}$ alkoxyalkoxy. In some further embodiments, $R^7$ and $R^8$ are each, independently, selected from H, halo, $C_{1-4}$ alkyl, OH, $C_{1-4}$ alkoxy, $C_{1-4}$ haloalkoxy, and $C_{2-8}$ alkoxyalkoxy. In some further embodiments, $R^7$ and $R^8$ are each, independently, selected from H, OH, $C_{1-4}$ alkoxy, $C_{1-4}$ haloalkoxy, and $C_{2-8}$ alkoxyalkoxy. In some further embodiments, $R^7$ and $R^8$ are each, independently, selected from H, OH, and $C_{2-8}$ alkoxyalkoxy.

In some embodiments, $R^7$ and $R^8$ are each, independently, selected from H and $C_{1-6}$ alkyl. In some further embodiments, $R^7$ and $R^8$ are each, independently, selected from H and $C_{1-4}$ alkyl.

In some embodiments, $R^7$ and $R^8$ are each, independently, selected from H and $C_{1-3}$ alkyl. In some further embodiments, $R^7$ and $R^8$ are each, independently, selected from H and methyl. In yet further embodiments, $R^7$ and $R^8$ are each H.

In some embodiments, each $R^{10}$ is, independently, selected from H, halo, and $C_{1-6}$ alkyl. In some embodiments, each $R^{10}$ is, independently, selected from H and $C_{1-6}$ alkyl. In some embodiments, each $R^{10}$ is, independently, selected from H and $C_{1-4}$ alkyl. In some embodiments, each $R^{10}$ is H.

In some embodiments, each $R^{10}$ is, independently, selected from H and $C_{1-3}$ alkyl. In some further embodiments, each $R^{10}$ is, independently, selected from H and methyl.

In some embodiments, $R^1$ is selected from H, halo, $C_{1-6}$ alkyl, $C_{1-6}$ haloalkyl, CN, $NO_2$, $OR^{a2}$, $C(O)R^{b2}$, $C(O)NR^{c2}R^{d2}$, $C(O)OR^{a2}$, and $NR^{c2}R^{d2}$.

In some embodiments, $R^1$ is selected from H, halo, $C_{1-6}$ alkyl, $C_{1-6}$ haloalkyl, CN, $NO_2$, —O—($C_{1-6}$ alkyl) and —O—($C_{1-6}$ haloalkyl).

In some embodiments, $R^1$ is selected from H, F, Cl, Br, methyl, ethyl, and $C_{1-2}$ haloalkyl.

In some embodiments, $R^1$ is selected from H, F, Cl, and Br.

In some embodiments, $R^1$ is selected from H, $CH_3$ and $CF_3$. In some further embodiments, $R^1$ is H or $CH_3$. In yet further embodiments, $R^1$ is H.

In some embodiments, each $R^2$ is, independently, selected from H, halo, $C_{1-6}$ alkyl, $C_{1-6}$ haloalkyl, CN, $NO_2$, $SF_5$, $OR^{a2}$, $C(O)R^{b2}$, $C(O)NR^{c2}R^{d2}$, $C(O)OR^{a2}$, $NR^{c2}C(O)R^{b2}$, $NR^{c2}C(O)NR^{c2}R^{d2}$, $NR^{c2}C(O)OR^{a2}$, $NR^{c2}S(O)_2NR^{c2}R^{d2}$, $NR^{c2}S(O)_2R^{b2}$, and $NR^{c2}R^{d2}$.

In some embodiments, each $R^2$ is, independently, selected from H, halo, $C_{1-6}$ alkyl, $C_{1-6}$ haloalkyl, CN, $NO_2$, $OR^{a2}$, $C(O)R^{b2}$, $C(O)NR^{c2}R^{d2}$, $C(O)OR^{a2}$, $NR^{c2}C(O)R^{b2}$, $NR^{c2}C(O)NR^{c2}R^{d2}$, $NR^{c2}C(O)OR^{a2}$, $NR^{c2}S(O)_2NR^{c2}R^{d2}$, $NR^{c2}S(O)_2R^{b2}$, and $NR^{c2}R^{d2}$.

In some embodiments, each $R^2$ is, independently, selected from H, halo, $C_{1-6}$ alkyl, $C_{1-6}$ haloalkyl, CN, $NO_2$, $OR^{a2}$, $C(O)R^{b2}$, $C(O)NR^{c2}R^{d2}$, $C(O)OR^{a2}$, $NR^{c2}C(O)R^{b2}$, $NR^{c2}C(O)NR^{c2}R^{d2}$, $NR^{c2}C(O)OR^{a2}$, $NR^{c2}S(O)_2R^{b2}$, and $NR^{c2}R^{d2}$.

In some embodiments, each $R^2$ is, independently, selected from H, halo, $C_{1-6}$ alkyl, $C_{1-6}$ haloalkyl, CN, $NO_2$, $OR^{a2}$, $C(O)R^{b2}$, $C(O)NR^{c2}R^{d2}$, $C(O)OR^{a2}$, and $NR^{c2}R^{d2}$.

In some embodiments, each $R^2$ is, independently, selected from H, halo, $C_{1-6}$ alkyl, $C_{1-6}$ haloalkyl, CN, $NO_2$, amino, $C_{1-4}$ alkylamino, $C_{2-8}$ dialkylamino, $NHC(=O)—(C_{1-4}$ alkyl), $NHC(=O)O$-(arylalkyl), $NHC(=O)O—(C_{1-4}$ alkyl), $NHC(=O)O$-(arylalkyl), $NHC(=O)NH_2$, $NHC(=O)NH—(C_{1-4}$ alkyl), $NHC(=O)N—(C_{1-4}$ alkyl)$_2$, $NHC(=O)NH$-(arylalkyl), $NHS(=O)_2—(C_{1-4}$ alkyl), and $NHS(=O)_2$-(arylalkyl).

In some embodiments, each $R^2$ is, independently, selected from H, halo, $C_{1-6}$ alkyl, $C_{1-6}$ haloalkyl, amino, $C_{1-4}$ alkylamino, $C_{2-8}$ dialkylamino, $NHC(=O)—(C_{1-4}$ alkyl), $NHC(=O)O$-(arylalkyl), $NHC(=O)O—(C_{1-4}$ alkyl), $NHC(=O)O$-(arylalkyl), $NHC(=O)NH_2$, $NHC(=O)NH—(C_{1-4}$ alkyl), $NHC(=O)N—(C_{1-4}$ alkyl)$_2$, $NHC(=O)NH$-(arylalkyl), $NHS(=O)_2—(C_{1-4}$ alkyl), and $NHS(=O)_2$-(arylalkyl).

In some embodiments, each $R^2$ is, independently, selected from H, halo, $C_{1-6}$ alkyl, and $C_{1-6}$ haloalkyl.

In some embodiments, each $R^2$ is, independently, selected from H, halo, $C_{1-3}$ alkyl, and $C_{1-3}$ haloalkyl. In some embodiments, each $R^2$ is, independently, selected from H, F, Cl, Br, methyl, ethyl, 1-propyl, 2-propyl, and $C_{1-2}$ haloalkyl. In some embodiments, each $R^2$ is, independently, selected from H, F, Cl, Br, methyl, ethyl, 1-propyl, 2-propyl, and $CF_3$. In some embodiments, each $R^2$ is, independently, selected from H, F, Cl, Br, methyl, and $CF_3$.

In some embodiments, each $R^2$ is, independently, selected from H, $CH_3$, $CF_3$, and halo. In some embodiments, each $R^2$ is, independently, selected from H, F, Cl, methyl, and $CF_3$. In some further embodiments, each $R^2$ is, independently, selected from H, F, and Cl.

In some embodiments, each $R^2$ is, independently, selected from H, $CH_3$ and $CF_3$. In some further embodiments, each $R^2$ is H.

In some embodiments, $R^3$ is selected from H, halo, $C_{1-6}$ alkyl, $C_{1-6}$ haloalkyl, CN, $NO_2$, $SF_5$, $OR^{a2}$, $C(O)R^{b2}$, $C(O)NR^{c2}R^{d2}$, $C(O)OR^{a2}$, $NR^{c2}C(O)R^{b2}$, $NR^{c2}C(O)NR^{c2}R^{d2}$, $NR^{c2}C(O)OR^{a2}$, $NR^{c2}S(O)_2NR^{c2}R^{d2}$, $NR^{c2}S(O)_2R^{b2}$, and $NR^{c2}R^{d2}$.

In some embodiments, $R^3$ is selected from H, halo, $C_{1-6}$ alkyl, $C_{1-6}$ haloalkyl, CN, $NO_2$, $SF_5$, $OR^{a2}$, $C(O)R^{b2}$, $C(O)NR^{c2}R^{d2}$, $C(O)OR^{a2}$, $NR^{c2}C(O)R^{b2}$, $NR^{c2}C(O)NR^{c2}R^{d2}$, $NR^{c2}C(O)OR^{a2}$, $NR^{c2}S(O)_2NR^{c2}R^{d2}$, $NR^{c2}S(O)_2R^{b2}$, and $NR^{c2}R^{d2}$.

In some embodiments, $R^3$ is selected from H, halo, $C_{1-6}$ alkyl, $C_{1-6}$ haloalkyl, CN, $NO_2$, $SF_5$, $OR^{a2}$, $C(O)R^{b2}$, $C(O)NR^{c2}R^{d2}$, $C(O)OR^{a2}$, and $NR^{c2}R^{d2}$.

In some embodiments, $R^3$ is selected from H, halo, $C_{1-6}$ alkyl, $C_{1-6}$ haloalkyl, amino, $C_{1-4}$ alkylamino, and $C_{2-8}$ dialkylamino.

In some embodiments, $R^3$ is selected from H, halo, $C_{1-3}$ alkyl, $C_{1-3}$ haloalkyl, $NH_2$, $NH(C_{1-3}$ alkyl), and $N(C_{1-3}$ alkyl)$_2$. In some embodiments, $R^3$ is selected from H, F, Cl, Br, methyl, ethyl, 1-propyl, 2-propyl, $C_{1-2}$ haloalkyl, $NH_2$, $NH(C_{1-3}$ alkyl), and $N(C_{1-3}$ alkyl)$_2$. In some embodiments, $R^3$ is selected from H, F, Cl, Br, methyl, ethyl, 1-propyl, 2-propyl, CF$_3$, NH$_2$, NH(C$_{1-3}$ alkyl), and N(C$_{1-3}$ alkyl)$_2$. In some embodiments, R$^3$ is selected from H, Cl, Br, methyl, CF$_3$, NH$_2$, NH(C$_{1-3}$ alkyl), and N(C$_{1-3}$ alkyl)$_2$.

In some embodiments, R$^3$ is selected from H, halo, C$_{1-6}$ alkyl, and C$_{1-6}$ haloalkyl.

In some embodiments, R$^3$ is selected from H, halo, C$_{1-3}$ alkyl, and C$_{1-3}$ haloalkyl. In some embodiments, R$^3$ is selected from H, F, Cl, Br, methyl, ethyl, 1-propyl, 2-propyl, and C$_{1-2}$ haloalkyl. In some embodiments, R$^3$ is selected from H, F, Cl, Br, methyl, ethyl, 1-propyl, 2-propyl, and CF$_3$. In some embodiments, R$^3$ is selected from H, F, Cl, Br, methyl, and CF$_3$.

In some embodiments, R$^3$ is selected from halo. In some embodiments, R$^3$ is selected from F, Cl, Br. In some further embodiments, R$^3$ is Cl.

In some embodiments, R$^1$ and R$^3$ are each, independently, selected from H, halo, C$_{1-6}$ alkyl, C$_{1-6}$ haloalkyl, CN, NO$_2$, SF$_5$, OR$^{a2}$, C(O)R$^{b2}$, C(O)NR$^{c2}$R$^{d2}$, C(O)OR$^{a2}$, NR$^{c2}$C(O)R$^{b2}$, NR$^{c2}$C(O)NR$^{c2}$R$^{d2}$, NR$^{c2}$C(O)OR$^{a2}$, NR$^{c2}$S(O)$_2$NR$^{c2}$R$^{d2}$, NR$^{c2}$S(O)$_2$R$^{b2}$, and NR$^{c2}$R$^{d2}$.

In some embodiments, R$^1$ and R$^3$ are each, independently, selected from H, halo, C$_{1-6}$ alkyl, C$_{1-6}$ haloalkyl, CN, NO$_2$, SF$_5$, OR$^{a2}$, C(O)R$^{b2}$, C(O)NR$^{c2}$R$^{d2}$, C(O)OR$^{a2}$, NR$^{c2}$C(O)R$^{b2}$, NR$^{c2}$C(O)NR$^{c2}$R$^{d2}$, NR$^{c2}$C(O)OR$^{a2}$, NR$^{c2}$S(O)$_2$R$^{b2}$, and NR$^{c2}$R$^{d2}$.

In some embodiments, R$^1$ and R$^3$ are each, independently, selected from H, halo, C$_{1-6}$ alkyl, C$_{1-6}$ haloalkyl, CN, NO$_2$, SF$_5$, OR$^{a2}$, C(O)R$^{b2}$, C(O)NR$^{c2}$R$^{d2}$, C(O)OR$^{a2}$ and NR$^{c2}$R$^{d2}$.

In some embodiments, R$^1$ and R$^3$ are each, independently, selected from H, halo, C$_{1-6}$ alkyl, C$_{1-6}$ haloalkyl, CN, NO$_2$, SF$_5$, amino, C$_{1-4}$ alkylamino, C$_{2-8}$ dialkylamino, NHC(=O)—(C$_{1-4}$ alkyl), NHC(=O)O-(arylalkyl), NHC(=O)O—(C$_{1-4}$ alkyl), NHC(=O)O-(arylalkyl), NHC(=O)NH$_2$, NHC(=O)NH—(C$_{1-4}$ alkyl), NHC(=O)N—(C$_{1-4}$ alkyl)$_2$, NHC(=O)NH-(arylalkyl), NHS(=O)$_2$—(C$_{1-4}$ alkyl), and NHS(=O)$_2$-(arylalkyl).

In some embodiments, R$^1$ and R$^3$ are each, independently, selected from H, halo, C$_{1-6}$ alkyl, C$_{1-6}$ haloalkyl, amino, C$_{1-4}$ alkylamino, C$_{2-8}$ dialkylamino, NHC(=O)—(C$_{1-4}$ alkyl), NHC(=O)O-(arylalkyl), NHC(=O)O—(C$_{1-4}$ alkyl), NHC(=O)O-(arylalkyl), NHC(=O)NH$_2$, NHC(=O)NH—(C$_{1-4}$ alkyl), NHC(=O)N—(C$_{1-4}$ alkyl)$_2$, NHC(=O)NH-(arylalkyl), NHS(=O)$_2$—(C$_{1-4}$ alkyl), and NHS(=O)$_2$-(arylalkyl).

In some embodiments, R$^1$ and R$^3$ are each, independently, selected from H, halo, C$_{1-6}$ alkyl, and C$_{1-6}$ haloalkyl.

In some embodiments, R$^1$ and R$^3$ are each, independently, selected from H, halo, C$_{1-3}$ alkyl, and C$_{1-3}$ haloalkyl. In some embodiments, R$^1$ and R$^3$ are each, independently, selected from H, F, Cl, Br, methyl, ethyl, 1-propyl, 2-propyl, and C$_{1-2}$ haloalkyl. In some embodiments, R$^1$ and R$^3$ are each, independently, selected from H, F, Cl, Br, methyl, ethyl, 1-propyl, 2-propyl, and CF$_3$. In some embodiments, R$^1$ and R$^3$ are each, selected from H, F, Cl, Br, methyl, and CF$_3$.

In some embodiments, one of R$^1$ and R$^3$ is SF$_5$. In some embodiments, R$^3$ is SF$_5$.

In some embodiments, R$^1$ is H and R$^3$ is selected from H, halo, C$_{1-3}$ alkyl, and C$_{1-3}$ haloalkyl.

In some embodiments, R$^1$ is H and R$^3$ is selected from halo, C$_1$ alkyl, and C$_1$ haloalkyl.

In some embodiments, R$^1$ is H and R$^3$ is selected from halo. In some embodiments, R$^1$ is H and R$^3$ is Cl.

In some embodiments, R$^1$ and R$^2$ are each, independently, selected from H, halo, C$_{1-6}$ alkyl, C$_{2-6}$ alkenyl, C$_{2-6}$ alkynyl, C$_{1-6}$ haloalkyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, C(=NR$^g$)NR$^{c2}$R$^{d2}$, NR$^{c2}$C(=NR$^g$)NR$^{c2}$R$^{d2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, NR$^{c2}$S(O)$_2$R$^{b2}$, or S(O)$_2$NR$^{c2}$R$^{d2}$.

In some embodiments, R$^1$ and R$^2$ are each, independently, selected from H, halo, C$_{1-6}$ alkyl, C$_{1-6}$ haloalkyl, CN, NO$_2$, OR$^{a2}$, C(O)R$^{b2}$, C(O)NR$^{c2}$R$^{d2}$, C(O)OR$^{a2}$, NR$^{c2}$C(O)R$^{b2}$, NR$^{c2}$C(O)NR$^{c2}$R$^{d2}$, NR$^{c2}$C(O)OR$^{a2}$, NR$^{c2}$S(O)$_2$NR$^{c2}$R$^{d2}$, NR$^{c2}$S(O)$_2$R$^{b2}$, and NR$^{c2}$R$^{d2}$.

In some embodiments, R$^1$ and R$^2$ are each, independently, selected from H, halo, C$_{1-6}$ alkyl, C$_{1-6}$ haloalkyl, CN, NO$_2$, OR$^{a2}$, C(O)R$^{b2}$, C(O)NR$^{c2}$R$^{d2}$, C(O)OR$^{a2}$, and NR$^{c2}$R$^{d2}$. In some further embodiments, R$^1$ and R$^2$ are each, independently, selected from H, halo, C$_{1-6}$ alkyl, and C$_{1-6}$ haloalkyl. In some embodiments, R$^1$ and R$^2$ are each, independently, selected from H, methyl, and ethyl. In some embodiments, R$^1$ and R$^2$ are each, independently, selected from H and methyl. In some further embodiments, R$^1$ and R$^2$ are H.

In some embodiments, R$^1$ and R$^2$ are each, independently, selected from H, F, Cl, Br, methyl, ethyl, and C$_{1-2}$ haloalkyl. In some further embodiments, R$^1$ and R$^2$ are each, independently, selected from H, F, Cl, methyl, and CF$_3$. In yet further embodiments, R$^1$ and R$^2$ are each, independently, selected from H and methyl. In still further embodiments, R$^1$ and R$^2$ are each H.

In some embodiments, R$^4$ is H or C$_{1-6}$ alkyl. In some embodiments, R$^4$ is H.

In some embodiments, each R$^5$ is, independently, selected from H, halo, C$_{1-6}$ alkyl, C$_{1-6}$ haloalkyl, Cy$^1$, -W$^1$-Q$^1$-Y$^1$-Z$^1$, CN, NO$_2$, SF$_5$, OR$^{a1}$, C(O)R$^{b1}$, C(O)NR$^{c1}$R$^{d1}$, C(O)OR$^{a1}$, NR$^{c1}$R$^{d1}$, NR$^{c1}$C(O)R$^{b1}$, S(O)$_2$R$^{b1}$, NR$^{c1}$S(O)$_2$NR$^{c1}$R$^{d1}$, NR$^{c1}$S(O)$_2$R$^{b1}$, and S(O)$_2$NR$^{c1}$R$^{d1}$, wherein each of said C$_{1-6}$ alkyl, C$_{2-6}$ alkenyl, C$_{2-6}$ alkynyl, or C$_{1-6}$ haloalkyl is optionally substituted by 1, 2, 3, 4, or 5 substituents each independently selected from halo, C$_{1-6}$ alkyl, C$_{2-6}$ alkenyl, C$_{2-6}$ alkynyl, C$_{1-6}$ haloalkyl, halosulfanyl, Cy$^1$, -W$^1$-Q$^1$-Y$^1$-Z$^1$, CN, NO$_2$, SF$_5$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, C(=NR$^g$)NR$^{c1}$R$^{d1}$, NR$^{c1}$C(=NR$^g$)NR$^{c1}$R$^{d1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, S(O)$_2$NR$^{c1}$R$^{d1}$, P(R$^{f1}$)$_2$, P(OR$^{e1}$)$_2$, P(O)R$^{e1}$R$^{f1}$, and P(O)OR$^{e1}$OR$^{f1}$.

In some embodiments, each R$^5$ is, independently, selected from H, halo, C$_{1-6}$ alkyl, C$_{1-6}$ haloalkyl, CN, NO$_2$, SF$_5$, OR$^{a1}$, C(O)R$^{b1}$, C(O)NR$^{c1}$R$^{d1}$, C(O)OR$^{a1}$, NR$^{c1}$R$^{d1}$, NR$^{c1}$C(O)R$^{b1}$, NR$^{c1}$S(O)$_2$NR$^{c1}$R$^{d1}$, S(O)$_2$R$^{b1}$, NR$^{c1}$S(O)$_2$R$^{b1}$, and S(O)$_2$NR$^{c1}$R$^{d1}$, wherein said C$_{1-6}$ alkyl, C$_{2-6}$ alkynyl, or C$_{1-6}$ haloalkyl, is optionally substituted by 1, 2, 3, 4 or 5 substituents each independently selected from halo, C$_{1-6}$ alkyl, C$_{2-6}$ alkenyl, C$_{2-6}$ alkynyl, C$_{1-6}$ haloalkyl, halosulfanyl, CN, NO$_2$, SF$_5$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, C(=NR$^g$)NR$^{c1}$R$^{d1}$, NR$^{c1}$C(=NR$^g$)NR$^{c1}$R$^{d1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, S(O)$_2$NR$^{c1}$R$^{d1}$, P(R$^{f1}$)$_2$, P(OR$^{e1}$)$_2$, P(O)R$^{e1}$R$^{f1}$, and P(O)OR$^{e1}$OR$^{f1}$.

In some embodiments:

each R$^5$ is, independently, selected from H, halo, C$_{1-6}$ alkyl, C$_{2-6}$ alkenyl, C$_{2-6}$ alkynyl, C$_{1-6}$ haloalkyl, Cy$^1$, -W$^1$-Q$^1$-Y$^1$-Z$^1$, CN, NO$_2$, OR$^{a1}$, C(O)R$^{b1}$, C(O)NR$^{c1}$R$^{d1}$, C(O)OR$^{a1}$, NR$^{c1}$R$^{d1}$, NR$^{c1}$C(O)R$^{b1}$, NR$^{c1}$C(O)NR$^{c1}$R$^{d1}$, NR$^{c1}$S(O)$_2$NR$^{c1}$R$^{d1}$, S(O)$_2$R$^{b1}$, NR$^{c1}$S(O)$_2$R$^{b1}$, and S(O)$_2$NR$^{c1}$R$^{d1}$, wherein each of said C$_{1-6}$ alkyl, C$_{2-6}$ alkenyl, C$_{2-6}$ alkynyl, or C$_{1-6}$ haloalkyl, is optionally substituted by 1, 2, 3, 4 or 5 substituents each independently selected from halo, C$_{1-6}$ alkyl, $C_{2-6}$ alkenyl, $C_{2-6}$ alkynyl, $C_{1-6}$ haloalkyl, halosulfanyl, CN, $NO_2$, $SF_5$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$; or each $R^5$ is, independently, selected from H, halo, $C_{1-6}$ alkyl, $C_{1-6}$ haloalkyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2NR^{c1}R^{d1}$, $S(O)_2R^{b1}$, $NR^{c1}S(O)_2R^{b1}$, and $S(O)_2NR^{c1}R^{d1}$, wherein said $C_{1-6}$ alkyl, $C_{2-6}$ alkenyl, $C_{2-6}$ alkynyl, or $C_{1-6}$ haloalkyl, is optionally substituted by 1, 2, 3, 4 or 5 substituents each independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $SF_5$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, $P(R^{f1})_2$, $P(OR^{e1})_2$, $P(O)R^{e1}R^{f1}$, and $P(O)OR^{e1}OR^{f1}$; and $R^{a1}$, $R^{b1}$, $R^{c1}$, and $R^{d1}$ are each, independently, selected from H, $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of said $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted with 1, 2, 3, 4, or 5 substituents independently selected from halo, $C_{1-4}$ alkyl, $C_{1-4}$ haloalkyl, $C_{1-4}$ hydroxylalkyl, $C_{1-4}$ cyanoalkyl, aryl, cycloalkyl, heteroaryl, heterocycloalkyl, CN, $NO_2$, OH, SH, $O(C_{1-4}$ alkyl), $O(C_{1-4}$ haloalkyl), O(aryl), O(arylalkyl), $S(C_{1-4}$ alkyl), $S(C_{1-4}$ haloalkyl), S(aryl), S(arylalkyl), amino, $C_{1-4}$ alkylamino, $C_{2-8}$ dialkylamino, C(=O)H, C(=O)—$(C_{1-4}$ alkyl), C(=O)-(arylalkyl), $C(=O)NH_2$, $C(=O)NH(C_{1-4}$ alkyl), $C(=O)N(C_{1-4}$ alkyl)$_2$, C(=O)OH, C(=O)O—$(C_{1-4}$ alkyl), C(=O)O-(arylalkyl), OC(=O)H, OC(=O)—$(C_{1-4}$ alkyl), OC(=O)-(arylalkyl), $OC(=O)NH_2$, $OC(=O)NH(C_{1-4}$ alkyl), OC(=O)NH-(arylalkyl), $OC(=O)N(C_{1-4}$ alkyl)$_2$, NHC(=O)—$(C_{1-4}$ alkyl), NHC(=O)O-(arylalkyl), NHC(=O)O—$(C_{1-4}$ alkyl), NHC(=O)O-(arylalkyl), $NHS(=O)_2$—$(C_{1-4}$ alkyl), $NHS(=O)_2$-(arylalkyl), $NHS(=O)_2$—$NH(C_{1-4}$ alkyl), $NHS(=O)_2$—$N(C_{1-4}$ alkyl)$_2$, $NHS(=O)_2$—NH(arylalkyl), $S(=O)_2$—$(C_{1-4}$ alkyl), $S(=O)_2$-(arylalkyl), $S(=O)_2NH(C_{1-4}$ alkyl) and $S(=O)_2NH$(arylalkyl);

or $R^{c1}$ and $R^{d1}$ together with the N atom to which they are attached form a 4-, 5-, 6- or 7-membered heterocycloalkyl group or heteroaryl group, each optionally substituted with 1, 2, or 3 substituents independently selected from halo, $C_{1-4}$ alkyl, $C_{1-4}$ haloalkyl, $C_{1-4}$ hydroxylalkyl, $C_{1-4}$ cyanoalkyl, aryl, cycloalkyl, heteroaryl, heterocycloalkyl, CN, $NO_2$, OH, SH, $O(C_{1-4}$ alkyl), $O(C_{1-4}$ haloalkyl), O(aryl), O(arylalkyl), $S(C_{1-4}$ alkyl), $S(C_{1-4}$ haloalkyl), S(aryl), S(arylalkyl), amino, $C_{1-4}$ alkylamino, $C_{2-8}$ dialkylamino, C(=O)H, C(=O)—$(C_{1-4}$ alkyl), C(=O)-(arylalkyl), $C(=O)NH_2$, $C(=O)NH(C_{1-4}$ alkyl), $C(=O)N(C_{1-4}$ alkyl)$_2$, C(=O)OH, C(=O)O—$(C_{1-4}$ alkyl), C(=O)O-(arylalkyl), OC(=O)H, OC(=O)—$(C_{1-4}$ alkyl), OC(=O)-(arylalkyl), $OC(=O)NH_2$, $OC(=O)NH(C_{1-4}$ alkyl), OC(=O)NH-(arylalkyl), $OC(=O)N(C_{1-4}$ alkyl)$_2$, NHC(=O)—$(C_{1-4}$ alkyl), NHC(=O)O-(arylalkyl), NHC(=O)O—$(C_{1-4}$ alkyl), NHC(=O)O-(arylalkyl), $NHS(=O)_2$—$(C_{1-4}$ alkyl), $NHS(=O)_2$-(arylalkyl), $NHS(=O)_2$—$NH(C_{1-4}$ alkyl), $NHS(=O)_2$—$N(C_{1-4}$ alkyl)$_2$, $NHS(=O)_2$—NH(arylalkyl), $S(=O)_2$—$(C_{1-4}$ alkyl), $S(=O)_2$-(arylalkyl), $S(=O)_2NH_2$, $S(=O)_2NH(C_{1-4}$ alkyl) and $S(=O)_2NH$(arylalkyl).

In some embodiments:
each $R^5$ is, independently, selected from H, halo, $C_{1-6}$ alkyl, $C_{1-6}$ haloalkyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2NR^{c1}R^{d1}$, $S(O)_2R^{b1}$, $NR^{c1}S(O)_2R^{b1}$, and $S(O)_2NR^{c1}R^{d1}$, wherein said $C_{1-6}$ alkyl, $C_{2-6}$ alkenyl, $C_{2-6}$ alkynyl, or $C_{1-6}$ haloalkyl, is optionally substituted by 1, 2, 3, 4 or 5 substituents each independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $SF_5$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, or $S(O)_2NR^{c1}R^{d1}$;

$R^{a1}$, $R^{b1}$, $R^{c1}$, and $R^{d1}$ are each, independently, selected from H, $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of said $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted with 1, 2, 3, 4, or 5 substituents independently selected from halo, $C_{1-4}$ alkyl, $C_{1-4}$ haloalkyl, $C_{1-4}$ hydroxylalkyl, $C_{1-4}$ cyanoalkyl, aryl, cycloalkyl, heteroaryl, heterocycloalkyl, CN, $NO_2$, OH, SH, $O(C_{1-4}$ alkyl), $O(C_{1-4}$ haloalkyl), O(aryl), O(arylalkyl), $S(C_{1-4}$ alkyl), $S(C_{1-4}$ haloalkyl), S(aryl), S(arylalkyl), amino, $C_{1-4}$ alkylamino, $C_{2-8}$ dialkylamino, C(=O)H, C(=O)—$(C_{1-4}$ alkyl), C(=O)-(arylalkyl), $C(=O)NH_2$, $C(=O)NH(C_{1-4}$ alkyl), $C(=O)N(C_{1-4}$ alkyl)$_2$, C(=O)OH, C(=O)O—$(C_{1-4}$ alkyl), C(=O)O-(arylalkyl), OC(=O)H, OC(=O)—$(C_{1-4}$ alkyl), OC(=O)-(arylalkyl), $OC(=O)NH_2$, $OC(=O)NH(C_{1-4}$ alkyl), OC(=O)NH-(arylalkyl), $OC(=O)N(C_{1-4}$ alkyl)$_2$, NHC(=O)—$(C_{1-4}$ alkyl), NHC(=O)O-(arylalkyl), NHC(=O)O—$(C_{1-4}$ alkyl), NHC(=O)O-(arylalkyl), $NHS(=O)_2$—$(C_{1-4}$ alkyl), $NHS(=O)_2$-(arylalkyl), $NHS(=O)_2$—$NH(C_{1-4}$ alkyl), $NHS(=O)_2$—$N(C_{1-4}$ alkyl)$_2$, $NHS(=O)_2$—NH(arylalkyl), $S(=O)_2$—$(C_{1-4}$ alkyl), $S(=O)_2$-(arylalkyl), $S(=O)_2NH_2$, $S(=O)_2NH(C_{1-4}$ alkyl) and $S(=O)_2NH$(arylalkyl);

or $R^{c1}$ and $R^{d1}$ together with the N atom to which they are attached form a 4-, 5-, 6- or 7-membered heterocycloalkyl group or heteroaryl group, each optionally substituted with 1, 2, or 3 substituents independently selected from halo, $C_{1-4}$ alkyl, $C_{1-4}$ haloalkyl, $C_{1-4}$ hydroxylalkyl, $C_{1-4}$ cyanoalkyl, aryl, cycloalkyl, heteroaryl, heterocycloalkyl, CN, $NO_2$, OH, SH, $O(C_{1-4}$ alkyl), $O(C_{1-4}$ haloalkyl), O(aryl), O(arylalkyl), $S(C_{1-4}$ alkyl), $S(C_{1-4}$ haloalkyl), S(aryl), S(arylalkyl), amino, $C_{1-4}$ alkylamino, $C_{2-8}$ dialkylamino, C(=O)H, C(=O)—$(C_{1-4}$ alkyl), C(=O)-(arylalkyl), $C(=O)NH_2$, $C(=O)NH(C_{1-4}$ alkyl), $C(=O)N(C_{1-4}$ alkyl)$_2$, C(=O)OH, C(=O)O—$(C_{1-4}$ alkyl), C(=O)O-(arylalkyl), OC(=O)H, OC(=O)—$(C_{1-4}$ alkyl), OC(=O)-(arylalkyl), $OC(=O)NH_2$, $OC(=O)NH(C_{1-4}$ alkyl), OC(=O)NH-(arylalkyl), $OC(=O)N(C_{1-4}$ alkyl)$_2$, NHC(=O)—$(C_{1-4}$ alkyl), NHC(=O)O-(arylalkyl), NHC(=O)O—$(C_{1-4}$ alkyl), NHC(=O)O-(arylalkyl), $NHS(=O)_2$—$(C_{1-4}$ alkyl), $NHS(=O)_2$-(arylalkyl), $NHS(=O)_2$—$NH(C_{1-4}$ alkyl), $NHS(=O)_2$—$N(C_{1-4}$ alkyl)$_2$, $NHS(=O)_2$—NH(arylalkyl), $S(=O)_2$—$(C_{1-4}$ alkyl), $S(=O)_2$-(arylalkyl), $S(=O)_2NH_2$, $S(=O)_2NH(C_{1-4}$ alkyl) and $S(=O)_2NH$(arylalkyl).

In some embodiments, at least one of $R^5$ is selected $C(O)NR^{c1}R^{d1}$ or $NR^{c1}R^{d1}$, wherein:

$R^{c1}$ and $R^{d1}$ are each, independently, selected from H, $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of said $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted with 1, 2, 3, 4, or 5 substituents independently selected from halo, $C_{1-4}$ alkyl, $C_{1-4}$ haloalkyl, $C_{1-4}$ hydroxylalkyl, $C_{1-4}$ cyanoalkyl, aryl, cycloalkyl, heteroaryl, heterocycloalkyl, CN, $NO_2$, OH, SH, $O(C_{1-4}$ alkyl), $O(C_{1-4}$ haloalkyl), O(aryl), O(arylalkyl), $S(C_{1-4}$ alkyl), $S(C_{1-4}$ haloalkyl), S(aryl), S(arylalkyl), amino, $C_{1-4}$ alkylamino, $C_{2-8}$ dialkylamino, C(=O)H, C(=O)—($C_{1-4}$ alkyl), C(=O)-(arylalkyl), C(=O)$NH_2$, C(=O)NH($C_{1-4}$ alkyl), C(=O)N($C_{1-4}$ alkyl)$_2$, C(=O)OH, C(=O)O—($C_{1-4}$ alkyl), C(=O)O-(arylalkyl), OC(=O)H, OC(=O)—($C_{1-4}$ alkyl), OC(=O)-(arylalkyl), OC(=O)$NH_2$, OC(=O)NH($C_{1-4}$ alkyl), OC(=O)NH-(arylalkyl), OC(=O)N($C_{1-4}$ alkyl)$_2$, NHC(=O)—($C_{1-4}$ alkyl), NHC(=O)O-(arylalkyl), NHC(=O)O—($C_{1-4}$ alkyl), NHC(=O)O-(arylalkyl), NHS(=O)$_2$—($C_{1-4}$ alkyl), NHS(=O)$_2$-(arylalkyl), NHS(=O)$_2$—NH($C_{1-4}$ alkyl), NHS(=O)$_2$—N($C_{1-4}$ alkyl)$_2$, NHS(=O)$_2$—NH(arylalkyl), S(=O)$_2$—($C_{1-4}$ alkyl), S(=O)$_2$-(arylalkyl), S(=O)$_2NH_2$, S(=O)$_2$NH($C_{1-4}$ alkyl) and S(=O)$_2$NH(arylalkyl);

or $R^{c1}$ and $R^{d1}$ together with the N atom to which they are attached form pyrrolidinyl, piperidinyl, piperazinyl, or morpholinyl, each optionally substituted with 1, 2, or 3 substituents independently selected from halo, $C_{1-4}$ alkyl, $C_{1-4}$ haloalkyl, $C_{1-4}$ hydroxylalkyl, $C_{1-4}$ cyanoalkyl, aryl, cycloalkyl, heteroaryl, heterocycloalkyl, CN, $NO_2$, OH, SH, $O(C_{1-4}$ alkyl), $O(C_{1-4}$ haloalkyl), O(aryl), O(arylalkyl), $S(C_{1-4}$ alkyl), $S(C_{1-4}$ haloalkyl), S(aryl), S(arylalkyl), amino, $C_{1-4}$ alkylamino, $C_{2-8}$ dialkylamino, C(=O)H, C(=O)—($C_{1-4}$ alkyl), C(=O)-(arylalkyl), C(=O)$NH_2$, C(=O)NH($C_{1-4}$ alkyl), C(=O)N($C_{1-4}$ alkyl)$_2$, C(=O)OH, C(=O)O—($C_{1-4}$ alkyl), C(=O)O-(arylalkyl), OC(=O)H, OC(=O)—($C_{1-4}$ alkyl), OC(=O)-(arylalkyl), OC(=O)$NH_2$, OC(=O)NH($C_{1-4}$ alkyl), OC(=O)NH-(arylalkyl), OC(=O)N($C_{1-4}$ alkyl)$_2$, NHC(=O)—($C_{1-4}$ alkyl), NHC(=O)O-(arylalkyl), NHC(=O)O—($C_{1-4}$ alkyl), NHC(=O)O-(arylalkyl), NHS(=O)$_2$—($C_{1-4}$ alkyl), NHS(=O)$_2$-(arylalkyl), NHS(=O)$_2$—NH($C_{1-4}$ alkyl), NHS(=O)$_2$—N($C_{1-4}$ alkyl)$_2$, NHS(=O)$_2$—NH(arylalkyl), S(=O)$_2$—($C_{1-4}$ alkyl), S(=O)$_2$-(arylalkyl), S(=O)$_2NH_2$, S(=O)$_2$NH($C_{1-4}$ alkyl) and S(=O)$_2$NH(arylalkyl).

In some embodiments, at least one of $R^5$ is selected C(O)$NR^{c1}R^{d1}$ or $NR^{c1}R^{d1}$, wherein:

$R^{c1}$ and $R^{d1}$ are each, independently, selected from H, $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of said $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted with 1, 2, 3, 4, or 5 substituents independently selected from halo, $C_{1-4}$ alkyl, $C_{1-4}$ haloalkyl, $C_{1-4}$ hydroxylalkyl, $C_{1-4}$ cyanoalkyl, aryl, cycloalkyl, heteroaryl, heterocycloalkyl, CN, $NO_2$, OH, SH, $O(C_{1-4}$ alkyl), $O(C_{1-4}$ haloalkyl), O(aryl), O(arylalkyl), $S(C_{1-4}$ alkyl), $S(C_{1-4}$ haloalkyl), S(aryl), S(arylalkyl), amino, $C_{1-4}$ alkylamino, $C_{2-8}$ dialkylamino, C(=O)H, C(=O)—($C_{1-4}$ alkyl), C(=O)-(arylalkyl), C(=O)$NH_2$, C(=O)NH($C_{1-4}$ alkyl), C(=O)N($C_{1-4}$ alkyl)$_2$, C(=O)OH, C(=O)O—($C_{1-4}$ alkyl), C(=O)O-(arylalkyl), OC(=O)H, OC(=O)—($C_{1-4}$ alkyl), OC(=O)-(arylalkyl), OC(=O)$NH_2$, OC(=O)NH($C_{1-4}$ alkyl), OC(=O)NH-(arylalkyl), OC(=O)N($C_{1-4}$ alkyl)$_2$, NHC(=O)—($C_{1-4}$ alkyl), NHC(=O)O-(arylalkyl), NHC(=O)O—($C_{1-4}$ alkyl), NHC(=O)O-(arylalkyl), NHS(=O)$_2$—($C_{1-4}$ alkyl), NHS(=O)$_2$-(arylalkyl), NHS(=O)$_2$—NH($C_{1-4}$ alkyl), NHS(=O)$_2$—N($C_{1-4}$ alkyl)$_2$, NHS(=O)$_2$—NH(arylalkyl), S(=O)$_2$—($C_{1-4}$ alkyl), S(=O)$_2$-(arylalkyl), S(=O)$_2NH_2$, S(=O)$_2$NH($C_{1-4}$ alkyl) and S(=O)$_2$NH(arylalkyl);

or $R^{c1}$ and $R^{d1}$ together with the N atom to which they are attached form pyrrolidinyl, piperidinyl or morpholinyl, each optionally substituted with 1, 2, or 3 substituents independently selected from halo, $C_{1-4}$ alkyl, $C_{1-4}$ haloalkyl, $C_{1-4}$ hydroxylalkyl, $C_{1-4}$ cyanoalkyl, aryl, cycloalkyl, heteroaryl, heterocycloalkyl, CN, $NO_2$, OH, SH, $O(C_{1-4}$ alkyl), $O(C_{1-4}$ haloalkyl), O(aryl), O(arylalkyl), $S(C_{1-4}$ alkyl), $S(C_{1-4}$ haloalkyl), S(aryl), S(arylalkyl), amino, $C_{1-4}$ alkylamino, $C_{2-8}$ dialkylamino, C(=O)H, C(=O)—($C_{1-4}$ alkyl), C(=O)-(arylalkyl), C(=O)$NH_2$, C(=O)NH($C_{1-4}$ alkyl), C(=O)N($C_{1-4}$ alkyl)$_2$, C(=O)OH, C(=O)O—($C_{1-4}$ alkyl), C(=O)O-(arylalkyl), OC(=O)H, OC(=O)—($C_{1-4}$ alkyl), OC(=O)-(arylalkyl), OC(=O)$NH_2$, OC(=O)NH($C_{1-4}$ alkyl), OC(=O)NH-(arylalkyl), OC(=O)N($C_{1-4}$ alkyl)$_2$, NHC(=O)—($C_{1-4}$ alkyl), NHC(=O)O-(arylalkyl), NHC(=O)O—($C_{1-4}$ alkyl), NHC(=O)O-(arylalkyl), NHS(=O)$_2$—($C_{1-4}$ alkyl), NHS(=O)$_2$-(arylalkyl), NHS(=O)$_2$—NH($C_{1-4}$ alkyl), NHS(=O)$_2$—N($C_{1-4}$ alkyl)$_2$, NHS(=O)$_2$—NH(arylalkyl), S(=O)$_2$—($C_{1-4}$ alkyl), S(=O)$_2$-(arylalkyl), S(=O)$_2NH_2$, S(=O)$_2$NH($C_{1-4}$ alkyl) and S(=O)$_2$NH(arylalkyl).

In some embodiments, each $R^5$ is, independently, selected from H, halo, $C_{1-6}$ alkyl, $C_{1-6}$ haloalkyl, CN, $NO_2$, $SF_5$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2NR^{c1}R^{d1}$, $S(O)_2R^{b1}$, $NR^{c1}S(O)_2R^{b1}$, and $S(O)_2NR^{c1}R^{d1}$.

In some embodiments, each $R^5$ is, independently, selected from H, halo, $C_{1-6}$ alkyl, $C_{1-6}$ haloalkyl, CN, $NO_2$, $SF_5$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $S(O)_2R^{b1}$, $NR^{c1}S(O)_2R^{b1}$, and $S(O)_2NR^{c1}R^{d1}$.

In some embodiments, each $R^5$ is independently selected from H, halo, $C_{1-6}$ alkyl, $C_{1-6}$ haloalkyl, CN, $NO_2$, $OR^{a1}$, $NR^{c1}R^{d1}$, $NR^{c1}S(O)_2R^{b1}$, $NR^{c1}S(O)_2NR^{c1}R^{d1}$, $S(O)R^{b1}$, $S(O)_2R^{b1}$, and $S(O)_2NR^{c1}R^{d1}$.

In some embodiments, each $R^5$ is independently selected from H, halo, $C_{1-6}$ alkyl, $C_{1-6}$ haloalkyl, CN, $NO_2$, $OR^{a1}$, $NR^{c1}R^{d1}$, $NR^{c1}S(O)_2R^{b1}$, $S(O)R^{b1}$, $S(O)_2R^{b1}$, and $S(O)_2NR^{c1}R^{d1}$.

In some embodiments, each $R^5$ is independently selected from H, $C_{1-6}$ alkyl, COOH, C(=O)—($C_{1-4}$ alkyl), S(=O)$_2$—($C_{1-4}$ alkyl), S(=O)$_2NH_2$, S(=O)$_2$NH($C_{1-4}$ alkyl), $NR^{c1}S(O)_2NR^{c1}R^{d1}$, $C(O)NR^{c1}R^{d1}$, and $NR^{c1}R^{d1}$.

In some embodiments, each $R^5$ is independently selected from H, $C_{1-6}$ alkyl, COOH, C(=O)—($C_{1-4}$ alkyl), S(=O)$_2$—($C_{1-4}$ alkyl), S(=O)$_2NH_2$, S(=O)$_2$NH($C_{1-4}$ alkyl), $C(O)NR^{c1}R^{d1}$ and $NR^{c1}R^{d1}$, wherein:

$R^{c1}$ and $R^{d1}$ are each, independently, selected from H, $C_{1-6}$ alkyl, aryl, heteroaryl, arylalkyl, and heteroarylalkyl, wherein each of said $C_{1-6}$ alkyl, aryl, heteroaryl, arylalkyl, heteroarylalkyl is optionally substituted with 1, 2, or 3 substituents independently selected from halo, $C_{1-4}$ alkyl, $C_{1-4}$ haloalkyl, $C_{1-4}$ hydroxylalkyl, $C_{1-4}$ cyanoalkyl, aryl, heteroaryl, OH, $O(C_{1-4}$ alkyl), $O(C_{1-4}$ haloalkyl), piperidinyl, pyrrolidinyl, morpholinyl, and piperizinyl optionally substituted with $C_{1-4}$ alkyl, aryl, or arylalkyl;

or $R^{c1}$ and $R^{d1}$ together with the N atom to which they are attached form pyrrolidinyl, piperidinyl, piperazinyl, or morpholinyl, each optionally substituted with 1, 2, or 3 substituents independently selected from $C_{1-4}$ alkyl, $C_{1-4}$ haloalkyl, $C_{1-4}$ hydroxylalkyl, aryl, arylalkyl, heteroaryl, heteroarylalkyl, OH, $O(C_{1-4}$ alkyl), and $O(C_{1-4}$ haloalkyl).

In some embodiments, two adjacent $R^5$ on the same ring can link to form a fused cycloalkyl or fused heterocycloalkyl group, each optionally substituted by 1, 2, or 3 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)NR^{c1}R^{d1}$, $S(O)R^{b1}$, S(O)

$NR^{c1}R^{d1}$, $S(O)_2R^{b1}$, $NR^{c1}S(O)_2R^{b1}$, $S(O)_2NR^{c1}R^{d1}$, $P(R^{f1})_2$, $P(OR^{e1})_2$, $P(O)R^{e1}R^{f1}$, and $P(O)OR^{e1}OR^{f1}$.

In some embodiments, two adjacent $R^5$ on the ring containing $A^1$, $B^1$, $D^1$, and $E^1$ can link to form a fused cycloalkyl or fused heterocycloalkyl group, each optionally substituted by 1, 2, or 3 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)NR^{c1}R^{d1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, $P(R^{f1})_2$, $P(OR^{e1})_2$, $P(O)R^{e1}R^{f1}$, and $P(O)OR^{e1}OR^{f1}$.

In some embodiments, two adjacent $R^5$ on the ring containing $A^2$, $B^2$, $D^2$, and $E^2$ can link to form a fused cycloalkyl or fused heterocycloalkyl group, each optionally substituted by 1, 2, or 3 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)NR^{c1}R^{d1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, $P(R^{f1})_2$, $P(OR^{e1})_2$, $P(O)R^{e1}R^{f1}$, and $P(O)OR^{e1}OR^{f1}$.

In some embodiments, at least one $R^5$ is other than H. In some embodiments, at least one $R^5$ on the ring containing $A^1$, $B^1$, $D^1$, and $E^1$ is other than H. In some embodiments, at least one $R^5$ on the ring containing $A^2$, $B^2$, $D^2$, and $E^2$ is other than H. In some embodiments, one or two $R^5$ on the ring containing $A^1$, $B^1$, $D^1$, and $E^1$ are other than H. In some embodiments, one $R^5$ on the ring containing $A^1$, $B^1$, $D^1$, and $E^1$ is other than H. In some embodiments, one or two $R^5$ on the ring containing $A^2$, $B^2$, $D^2$, and $E^2$ are other than H. In some embodiments, one $R^5$ on the ring containing $A^2$, $B^2$, $D^2$, and $E^2$ is other than H.

In some embodiments, at least one $R^5$ is selected from halo, $C_{1-6}$ alkyl, $C_{1-6}$ haloalkyl, cycloalkyl, aryl, hetroaryl, heterocycloalkylalkyl, $Cy^1$, $-W^1-Q^1-Y^1-Z^1$, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)NR^{c1}R^{d1}$, $NR^{c1}S(O)_2NR^{c1}R^{d1}$, $S(O)_2R^{b1}$, $NR^{c1}S(O)_2R^{b1}$, and $S(O)_2NR^{c1}R^{d1}$, wherein said $C_{1-6}$ alkyl, $C_{1-6}$ haloalkyl, cycloalkyl, aryl, hetroaryl, or heterocycloalkylalkyl, is optionally substituted by 1, 2, 3, 4 or 5 substituents each independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $SF_5$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, or $S(O)_2NR^{c1}R^{d1}$.

In some embodiments, at least one $R^5$ is selected from halo, $C_{1-6}$ alkyl, aryl, hetroaryl, heterocycloalkylalkyl, CN, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)NR^{c1}R^{d1}$, $NR^{c1}S(O)_2NR^{c1}R^{d1}$, $S(O)_2R^{b1}$, $NR^{c1}S(O)_2R^{b1}$, and $S(O)_2NR^{c1}R^{d1}$, wherein said $C_{1-6}$ alkyl, aryl, hetroaryl, or heterocycloalkylalkyl, is optionally substituted by 1, 2, 3, 4 or 5 substituents each independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $SF_5$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, or $S(O)_2NR^{c1}R^{d1}$.

In some embodiments, at least one $R^5$ is selected from $C(O)NR^{c1}R^{d1}$, $C(O)OR^{a1}$, $NR^{c1}R^{d1}$, $NR^{c1}C(O)R^{b1}$, $NR^{c1}C(O)NR^{c1}R^{d1}$, $NR^{c1}S(O)_2NR^{c1}R^{d1}$, $S(O)_2R^{b1}$, $NR^{c1}S(O)_2R^{b1}$, and $S(O)_2NR^{c1}R^{d1}$.

In some embodiments, at least one $R^5$ is $Cy^1$ or $-W^1-Q^1-Y^1-Z^1$.

In some embodiments, at least one $R^5$ is $Cy^1$. In some embodiments, at least one $R^5$ on the ring containing $A^1$, $B^1$, $D^1$, and $E^1$ is $Cy^1$. In some other embodiments, at least one $R^5$ on the ring containing $A^2$, $B^2$, $D^2$, and $E^2$ is $Cy^1$.

In some embodiments, at least one $R^5$ is $Cy^1$ that is selected from aryl and heteroaryl, each optionally substituted with 1, 2, or 3 substituents independently selected from $C_{1-6}$ alkyl, $C(O)-O-(C_{1-4}$ alkyl), $S(O)_2-(C_{1-4}$ alkyl), and piperazinyl, wherein the piperazinyl is optionally substituted with 1 or 2 substituents independently selected from $C_{1-6}$ alkyl, arylalkyl, aryl, heteroaryl, $C(O)R^{b1}$, $S(O)_2R^{b1}$, $C(O)NR^{c1}R^{d1}$, and $S(O)_2NR^{c1}R^{d1}$.

In some embodiments, at least one $R^5$ is $-W^1-Q^1-Y^1-Z^1$. In some embodiments, at least one $R^5$ on the ring containing $A^1$, $B^1$, $D^1$, and $E^1$ is $-W^1-Q^1-Y^1-Z^1$. In some other embodiments, at least one $R^5$ on the ring containing $A^2$, $B^2$, $D^2$, and $E^2$ is $-W^1-Q^1-Y^1-Z^1$.

In some embodiments, at least one $R^5$ is $-Q^1-Y^1-Z^1$, $-(CH_2)-Q^1-Y^1-Z^1$, $-O(CR^{11a}R^{11b})_{q1}C(O)-Q^1-Y^1-Z^1$, $-O(CR^{11a}R^{11b})_{p2}-Q^1-Y^1-Z^1$, $-(CR^{11a}R^{11b})_{p1}C(O)NR^e(CR^{11a}R^{11b})_{p2}-Q^1-Y^1-Z^1$, $-(CR^{11a}R^{11b})_{p1}C(O)NR^e-Q^1-Y^1-Z^1$, $-NR^e(CR^{11a}R^{11b})_{p2}-Q^1-Y^1-Z^1$, $-(CR^{11a}R^{11b})_{p2}NR^eC(O)-Q^1-Y^1-Z^1$, $-(CR^{11a}R^{11b})_{p1}NR^e-Q^1-Y^1-Z^1$, $-(CR^{11a}R^{11b})_{p1}O(CR^{11a}R^{11b})_{p2}-Q^1-Y^1-Z^1$, $-(CR^{11a}R^{11b})_{p1}S(CR^{11a}R^{11b})_{p2}-Q^1-Y^1-Z^1$, $-(CR^{11a}R^{11b})_{p1}S(O)(CR^{11a}R^{11b})_{p2}-Q^1-Y^1-Z^1$, $-(CR^{11a}R^{11b})_{p1}S(O)_2(CR^{11a}R^{11b})_{p2}-Q^1-Y^1-Z^1$, $-(CR^{11a}R^{11b})_{p1}NR^e(CR^{11a}R^{11b})_{p2}-Q^1-Y^1-Z^1$, $-NR^eS(O)(CR^{11a}R^{11b})_{p1}-Q^1-Y^1-Z^1$, $-S(O)NR^e(CR^{11a}R^{11b})_{p2}-Q^1-Y^1-Z^1$, $-NR^eS(O)_2(CR^{11a}R^{11b})_{p1}-Q^1-Y^1-Z^1$, $-S(O)_2NR^e(CR^{11a}R^{11b})_{p2}-Q^1-Y^1-Z^1$, $-NR^eC(O)(CR^{11a}R^{11b})_{p1}-Q^1-Y^1-Z^1$, $-C(O)NR^e(CR^{11a}R^{11b})_{p2}-Q^1-Y^1-Z^1$, or $-NR^eC(O)NR^f(CR^{11a}R^{11b})_{p2}-Q^1-Y^1-Z^1$.

In some embodiments, at least one $R^5$ on the ring containing $A^1$, $B^1$, $D^1$, and $E^1$ is $-Q^1-Y^1-Z^1$, $-(CH_2)-Q^1-Y^1-Z^1$, $-O(CR^{11a}R^{11b})_{q1}C(O)-Q^1-Y^1-Z^1$, $-O(CR^{11a}R^{11b})_{p2}-Q^1-Y^1-Z^1$, $-(CR^{11a}R^{11b})_{p1}C(O)NR^e(CR^{11a}R^{11b})_{p2}-Q^1-Y^1-Z^1$, $-(CR^{11a}R^{11b})_{p1}C(O)NR^e-Q^1-Y^1-Z^1$, $-NR^e(CR^{11a}R^{11b})_{p2}-Q^1-Y^1-Z^1$, $-(CR^{11a}R^{11b})_{p2}NR^eC(O)-Q^1-Y^1-Z^1$, $-(CR^{11a}R^{11b})_{p1}NR^e-Q^1-Y^1-Z^1$, $-(CR^{11a}R^{11b})_{p1}O(CR^{11a}R^{11b})_{p2}-Q^1-Y^1-Z^1$, $-(CR^{11a}R^{11b})_{p1}S(CR^{11a}R^{11b})_{p2}-Q^1-Y^1-Z^1$, $-(CR^{11a}R^{11b})_{p1}S(O)(CR^{11a}R^{11b})_{p2}-Q^1-Y^1-Z^1$, $-(CR^{11a}R^{11b})_{p1}S(O)_2(CR^{11a}R^{11b})_{p2}-Q^1-Y^1-Z^1$, $-(CR^{11a}R^{11b})_{p1}NR^e(CR^{11a}R^{11b})_{p2}-Q^1-Y^1-Z^1$, $-NR^eS(O)(CR^{11a}R^{11b})_{p1}-Q^1-Y^1-Z^1$, $-S(O)NR^e(CR^{11a}R^{11b})_{p2}-Q^1-Y^1-Z^1$, $-NR^eS(O)_2(CR^{11a}R^{11b})_{p1}-Q^1-Y^1-Z^1$, $-S(O)_2NR^e(CR^{11a}R^{11b})_{p2}-Q^1-Y^1-Z^1$, $-NR^eC(O)(CR^{11a}R^{11b})_{p1}-Q^1-Y^1-Z^1$, $-C(O)NR^e(CR^{11a}R^{11b})_{p2}-Q^1-Y^1-Z^1$, or $-NR^eC(O)NR^f(CR^{11a}R^{11b})_{p2}-Q^1-Y^1-Z^1$.

In some embodiments, at least one $R^5$ on the ring containing $A^2$, $B^2$, $D^2$, and $E^2$ is $-Q^1-Y^1-Z^1$, $-(CH_2)-Q^1-Y^1-Z^1$, $-O(CR^{11a}R^{11b})_{q1}C(O)-Q^1-Y^1-Z^1$, $-O(CR^{11a}R^{11b})_{p2}-Q^1-Y^1-Z^1$, $-(CR^{11a}R^{11b})_{p1}C(O)NR^e(CR^{11a}R^{11b})_{p2}-Q^1-Y^1-Z^1$, $-(CR^{11a}R^{11b})_{p1}C(O)NR^e-Q^1-Y^1-Z^1$, $-NR^e(CR^{11a}R^{11b})_{p2}-Q^1-Y^1-Z^1$, $-(CR^{11a}R^{11b})_{p2}NR^eC(O)-Q^1-Y^1-Z^1$, $-(CR^{11a}R^{11b})_{p1}NR^e-Q^1-Y^1-Z^1$, $-(CR^{11a}R^{11b})_{p1}O(CR^{11a}R^{11b})_{p2}-Q^1-Y^1-Z^1$, $-(CR^{11a}R^{11b})_{p1}S(CR^{11a}R^{11b})_{p2}-Q^1-Y^1-Z^1$, $-(CR^{11a}R^{11b})_{p1}S(O)(CR^{11a}R^{11b})_{p2}-Q^1-Y^1-Z^1$, $-(CR^{11a}R^{11b})_{p1}S(O)_2(CR^{11a}R^{11b})_{p2}-Q^1-Y^1-Z^1$, $-(CR^{11a}R^{11b})_{p1}NR^e(CR^{11a}R^{11b})_{p2}-Q^1-Y^1-Z^1$, $-NR^e(O)S(CR^{11a}R^{11b})_{p1}-Q^1-Y^1-Z^1$, $-S(O)NR^e(CR^{11a}R^{11b})_{p2}-Q^1-Y^1-Z^1$, $-NR^eS(O)_2(CR^{11a}R^{11b})_{p1}-Q^1-Y^1-Z^1$, $-S(O)_2NR^e(CR^{11a}R^{11b})_{p2}-Q^1-Y^1-Z^1$, $-NR^eC(O)(CR^{11a}R^{11b})_{p1}-Q^1-Y^1-Z^1$, $-C(O)NR^e(CR^{11a}R^{11b})_{p2}-Q^1-Y^1-Z^1$, or $-NR^eC(O)NR^f(CR^{11a}R^{11b})_{p2}-Q^1-Y^1-Z^1$.

In some embodiments, at least one $R^5$ on the ring containing $A^1$, $B^1$, $D^1$, and $E^1$ or on the ring containing $A^2$, $B^2$, $D^2$, and $E^2$ is $-W^1-Q^1-Y^1-Z^1$ that is selected from $-(CR^{11a}R^{11b})_{p1}$ $-Q^1-Y^1-Z^1$, $-(CR^{11a}R^{11b})_{p1}O(CR^{11a}R^{11b})_{p2}-Q^1-Y^1-Z^1$, $-(CR^{11a}R^{11b})_{p1}S(CR^{11a}R^{11b})_{p2}-Q^1-Y^1-Z^1$, $-(CR^{11a}R^{11b})_{p1}$ $S(O)(CR^{11a}R^{11b})_{p2}-Q^1-Y^1-Z^1$, $-(CR^{11a}R^{11b})_{p1}S(O)_2(CR^{11a}R^{11b})_{p2}-Q^1-Y^1-Z^1$, $-(CR^{11a}R^{11b})_{p1}NR^e(CR^{11a}R^{11b})_{p2}$ $-Q^1-Y^1-Z^1$, $-NR^eS(O)(CR^{11a}R^{11b})_{p1}-Q^1-Y^1-Z^1$, $-S(O)NR^e(CR^{11a}R^{11b})_{p2}-Q^1-Y^1-Z^1$, $-NR^eS(O)_2(CR^{11a}R^{11b})_{p1}-Q^1-Y^1-Z^1$, $-S(O)_2NR^e(CR^{11a}R^{11b})_{p2}-Q^1-Y^1-Z^1$, $-NR^eC(O)(CR^{11a}R^{11b})_{p1}-Q^1-Y^1-Z^1$, $-C(O)NR^e(CR^{11a}R^{11b})_{p2}-Q^1-Y^1-Z^1$, and $-NR^eC(O)NR^f(CR^{11a}R^{11b})_{p2}-Q^1-Y^1-Z^1$.

In some embodiments, at least one $R^5$ on the ring containing $A^1$, $B^1$, $D^1$, and $E^1$ or on the ring containing $A^2$, $B^2$, $D^2$, and $E^2$ is $-(CR^{11a}R^{11b})_{p1}O(CR^{11a}R^{11b})_{p2}-Q^1-Y^1-Z^1$, $-(CR^{11a}R^{11b})_{p1}S(CR^{11a}R^{11b})_{p2}-Q^1-Y^1-Z^1$, $-(CR^{11a}R^{11b})_{p1}$ $S(O)(CR^{11a}R^{11b})_{p2}-Q^1-Y^1-Z^1$, $-(CR^{11a}R^{11b})_{p1}S(O)_2(CR^{11a}R^{11b})_{p2}-Q^1-Y^1-Z^1$, $-(CR^{11a}R^{11b})_{p1}NR^e(CR^{11a}R^{11b})_{p2}$ $-Q^1-Y^1-Z^1$, $-NR^eS(O)(CR^{11a}R^{11b})_{p1}-Q^1-Y^1-Z^1$, $-S(O)NR^e(CR^{11a}R^{11b})_{p2}-Q^1-Y^1-Z^1$, $-NR^eS(O)_2(CR^{11a}R^{11b})_{p1}-Q^1-Y^1-Z^1$, $-S(O)_2NR^e(CR^{11a}R^{11b})_{p2}-Q^1-Y^1-Z^1$, $-NR^eC(O)(CR^{11a}R^{11b})_{p1}-Q^1-Y^1-Z^1$, $-C(O)NR^e(CR^{11a}R^{11b})_{p2}-Q^1-Y^1-Z^1$, or $-NR^eC(O)NR^f(CR^{11a}R^{11b})_{p2}-Q^1-Y^1-Z^1$.

In some embodiments, at least one $R^5$ is $-Q^1-Y^1-Z^1$, $-(CH_2)-Q^1-Y^1-Z^1$, $-O(CR^{11a}R^{11b})_{q1}C(O)-Q^1-Y^1-Z^1$, $-O(CR^{11a}R^{11b})_{p2}-Q^1-Y^1-Z^1$, $-(CR^{11a}R^{11b})_{p1}C(O)NR^e(CR^{11a}R^{11b})_{p2}-Q^1-Y^1-Z^1$, $-(CR^{11a}R^{11b})_{p1}C(O)NR^e-Q^1-Y^1-Z^1$, $-NR^e(CR^{11a}R^{11b})_{p2}-Q^1-Y^1-Z^1$, $-(CR^{11a}R^{11b})_{p2}NR^eC(O)-Q^1-Y^1-Z^1$, $-(CR^{11a}R^{11b})_{p1}NR^e-Q^1-Y^1-Z^1$, $-(CR^{11a}R^{11b})_{p1}O(CR^{11a}R^{11b})_{p2}-Q^1-Y^1-Z^1$, $-(CR^{11a}R^{11b})_{p1}$ $NR^e(CR^{11a}R^{11b})_{p2}-Q^1-Y^1-Z^1$, $-NR^eS(O)_2(CR^{11a}R^{11b})_{p1}$ $-Q^1-Y^1-Z^1$, $-NR^eC(O)(CR^{11a}R^{11b})_{p1}-Q^1-Y^1-Z^1$, $-C(O)NR^e(CR^{11a}R^{11b})_{p2}-Q^1-Y^1-Z^1$, or $-NR^eC(O)NR^f(CR^{11a}R^{11b})_{p2}-Q^1-Y^1-Z^1$.

In some embodiments, at least one $R^5$ on the ring containing $A^1$, $B^1$, $D^1$, and $E^1$ is at least one $R^5$ is $-Q^1-Y^1-Z^1$, $-(CH_2)-Q^1-Y^1-Z^1$, $-O(CR^{11a}R^{11b})_{q1}C(O)-Q^1-Y^1-Z^1$, $-O(CR^{11a}R^{11b})_{p2}-Q^1-Y^1-Z^1$, $-(CR^{11a}R^{11b})_{p1}C(O)NR^e(CR^{11a}R^{11b})_{p2}-Q^1-Y^1-Z^1$, $-(CR^{11a}R^{11b})_{p1}C(O)NR^e-Q^1-Y^1-Z^1$, $-NR^e(CR^{11a}R^{11b})_{p2}-Q^1-Y^1-Z^1$, $-(CR^{11a}R^{11b})_{p2}NR^eC(O)-Q^1-Y^1-Z^1$, $-(CR^{11a}R^{11b})_{p1}NR^e-Q^1-Y^1-Z^1$, $-(CR^{11a}R^{11b})_{p1}O(CR^{11a}R^{11b})_{p2}-Q^1-Y^1-Z^1$, $-NR^eC(O)(CR^{11a}R^{11b})_{p1}-Q^1-Y^1-Z^1$, $-C(O)NR^e(CR^{11a}R^{11b})_{p2}-Q^1-Y^1-Z^1$, or $-NR^eC(O)NR^f(CR^{11a}R^{11b})_{p2}-Q^1-Y^1-Z^1$.

In some embodiments, at least one $R^5$ on the ring containing $A^2$, $B^2$, $D^2$, and $E^2$ is $-Q^1-Y^1-Z^1$, $-(CH_2)-Q^1-Y^1-Z^1$, $-O(CR^{11a}R^{11b})^{q1}C(O)-Q^1-Y^1-Z^1$, $-O(CR^{11a}R^{11b})_{p2}-Q^1-Y^1-Z^1$, $-(CR^{11a}R^{11b})_{p1}C(O)NR^e(CR^{11a}R^{11b})_{p2}-Q^1-Y^1-Z^1$, $-(CR^{11a}R^{11b})_{p1}C(O)NR^e-Q^1-Y^1-Z^1$, $-NR^e(CR^{11a}R^{11b})_{p2}$ $-Q^1-Y^1-Z^1$, $-(CR^{11a}R^{11b})_{p2}NR^eC(O)-Q^1-Y^1-Z^1$, $-(CR^{11a}R^{11b})_{p1}NR^e-Q^1-Y^1-Z^1$, $-(CR^{11a}R^{11b})_{p1}O(CR^{11a}R^{11b})_{p2}-Q^1-Y^1-Z^1$, $-(CR^{11a}R^{11b})_{p1}NR^e(CR^{11a}R^{11b})_{p2}$ $-Q^1-Y^1-Z^1$, $-NR^eS(O)_2(CR^{11a}R^{11b})_{p1}-Q^1-Y^1-Z^1$, $-NR^eC(O)(CR^{11a}R^{11b})_{p1}-Q^1-Y^1-Z^1$, $-C(O)NR^e(CR^{11a}R^{11b})_{p2}-Q^1-Y^1-Z^1$, or $-NR^eC(O)NR^f(CR^{11a}R^{11b})_{p2}-Q^1-Y^1-Z^1$.

In some embodiments, at least one $R^5$ is (R5-A)

wherein:

each $R^Q$ is independently selected from selected from $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, heterocycloalkylalkyl, halo, CN, $NO_2$, $OR^a$, $SR^a$, $SF_5$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^g)NR^cR^d$, $NR^cC(=NR^g)NR^cR^d$, $NR^cS(O)_2NR^cR^d$, $S(O)R^b$, $S(O)NR^cR^d$, $S(O)_2R^b$, $NR^cS(O)_2R^b$, and $S(O)_2NR^cR^d$;

each p10 is independently 0, 1, or 2;

each p11 is independently 0, 1, or 2; and each t10 is independently 0, 1, 2, 3, 4, or 5.

In some embodiments of (R5-A), $W^1$ is absent, $C_{1-6}$ alkylenyl, $-O(CR^{11a}R^{11b})_{q1}C(O)-$, $-O(CR^{11a}R^{11b})_{p2}-$, $-(CR^{11a}R^{11b})_{p1}C(O)NR^e(CR^{11a}R^{11b})_{p2}-$, $-(CR^{11a}R^{11b})_{p1}$ $C(O)NR^e-$, $-NR^e(CR^{11a}R^{11b})_{p2}-$, $-(CR^{11a}R^{11b})_{p2}$ $NR^eC(O)-$, $-(CR^{11a}R^{11b})_{p1}NR^e-$, $-(CR^{11a}R^{11b})_{p1}O(CR^{11a}R^{11b})_{p2}-$, $-(CR^{11a}R^{11b})_{p1}S(CR^{11a}R^{11b})_{p2}-$, $-(CR^{11a}R^{11b})_{p1}S(O)(CR^{11a}R^{11b})_{p2}-$, $-(CR^{11a}R^{11b})_{p1}S(O)_2(CR^{11a}R^{11b})_{p2}-$, $-(CR^{11a}R^{11b})_{p1}NR^e(CR^{11a}R^{11b})_{p2}-$, $-NR^eS(O)(CR^{11a}R^{11b})_{p1}-$, $-S(O)NR^e(CR^{11a}R^{11b})_{p2}-$, $-NR^eS(O)_2(CR^{11a}R^{11b})_{p1}-$, $-S(O)_2NR^e(CR^{11a}R^{11b})_{p2}-$, $-NR^eC(O)(CR^{11a}R^{11b})_{p1}-$, $-C(O)NR^e(CR^{11a}R^{11b})_{p2}-$, or $-NR^eC(O)NR^f(CR^{11a}R^{11b})_{p2}-$.

In some embodiments of (R5-A), $W^1$ is absent, $-(CH_2)-$, $-O(CR^{11a}R^{11b})_{q1}C(O)-$, $-O(CR^{11a}R^{11b})_{p2}-$, $-(CR^{11a}R^{11b})_{p1}C(O)NR^e(CR^{11a}R^{11b})_{p2}-$, $-(CR^{11a}R^{11b})_{p1}$ $C(O)NR^e-$, $-NR^e(CR^{11a}R^{11b})_{p2}-$, $-(CR^{11a}R^{11b})_{p2}$ $NR^eC(O)-$, $-(CR^{11a}R^{11b})_{p1}NR^e-$, $-(CR^{11a}R^{11b})_{p1}O(CR^{11a}R^{11b})_{p2}-$, $-(CR^{11a}R^{11b})_{p1}S(CR^{11a}R^{11b})_{p2}-$, $-(CR^{11a}R^{11b})_{p1}S(O)(CR^{11a}R^{11b})_{p2}-$, $-(CR^{11a}R^{11b})_{p1}S(O)_2(CR^{11a}R^{11b})_{p2}-$, $-(CR^{11a}R^{11b})_{p1}NR^e(CR^{11a}R^{11b})_{p2}-$, $-NR^eS(O)(CR^{11a}R^{11b})_{p1}-$, $-S(O)NR^e(CR^{11a}R^{11b})_{p2}-$, $-NR^eS(O)_2(CR^{11a}R^{11b})_{p1}-$, $-S(O)_2NR^e(CR^{11a}R^{11b})_{p2}-$, $-NR^eC(O)(CR^{11a}R^{11b})_{p1}-$, $-C(O)NR^e(CR^{11a}R^{11b})_{p2}-$, or $-NR^eC(O)NR^f(CR^{11a}R^{11b})_{p2}-$.

In some embodiments, at least one $R^5$ is

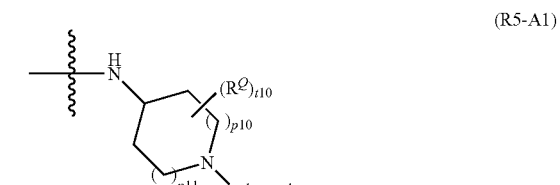

(R5-A1)

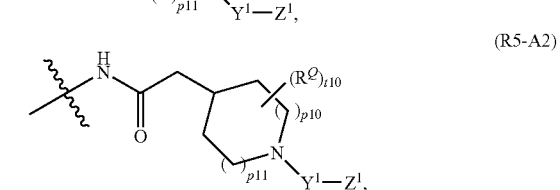

(R5-A2)

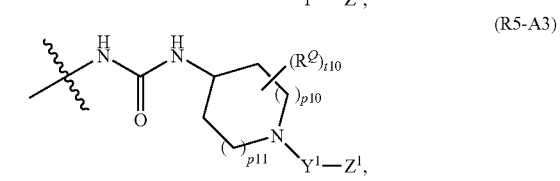

(R5-A3)

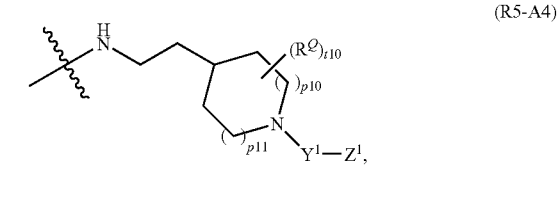

(R5-A4)

-continued

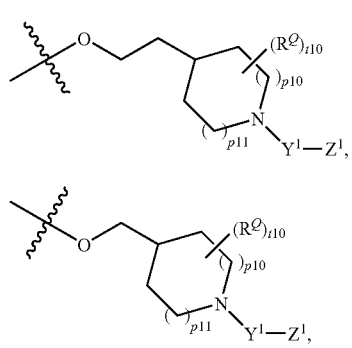

(R5-A5)

(R5-A6)

(R5-A7)

wherein:
each $R^Q$ is independently selected from selected from $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, heterocycloalkylalkyl, halo, CN, $NO_2$, $OR^a$, $SR^a$, $SF_5$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^g)NR^cR^d$, $NR^cC(=NR^g)NR^cR^d$, $NR^cS(O)_2NR^cR^d$, $S(O)R^b$, $S(O)NR^cR^d$, $S(O)_2R^b$, $NR^cS(O)_2R^b$, and $S(O)_2NR^cR^d$;

each p10 is independently 0, 1, or 2;
each p11 is independently 0, 1, or 2; and
each t10 is independently 0, 1, 2, 3, 4, or 5.

In some embodiments of (R5-A), (R5-A1), (R5-A2), (R5-A3), (R5-A4), (R5-A5), (R5-A6), or (R5-A7):
each $Y^1$ is independently selected from absent, $C_{1-6}$ alkylene, $(CR^{12a}R^{12b})_{p3}O(CR^{12a}R^{12b})_{p4}$, $(CR^{12a}R^{12b})_{p3}S(CR^{12a}R^{12b})_{p4}$, $(CR^{12a}R^{12b})_{p3}NR^e(CR^{12a}R^{12b})_{p4}$, $(CR^{12a}R^{12b})_{p3}C(O)(CR^{12a}R^{12b})_{p4}$, $(CR^{12a}R^{12b})_{p3}C(O)O(CR^{12a}R^{12b})_{p4}$, $C(S)NR^e$, $(CR^{12a}R^{12b})_{p3}C(O)NR^e(CR^{12a}R^{12b})_{p4}$, $(CR^{12a}R^{12b})_{p3}S(O)_2(CR^{12a}R^{12b})_{p4}$, $(CR^{12a}R^{12b})_{p3}S(O)_2NR^e(CR^{12a}R^{12b})_{p4}$, and $(CR^{12a}R^{12b})_{p3}NR^eC(O)NR^f(CR^{12a}R^{12b})_{p4}$; and
each $Z^1$ is independently selected from H, OH, CN, $C_{1-6}$ alkyl, aryl, cycloalkyl, heteroaryl, and heterocycloalkyl, wherein each of the $C_{1-6}$ alkyl, aryl, cycloalkyl, heteroaryl, and heterocycloalkyl is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $NR^cS(O)_2R^b$, $NR^cS(O)_2S(O)_2NR^cR^d$, $S(O)R^b$, $S(O)NR^cR^d$, $S(O)_2R^b$, and $S(O)_2NR^cR^d$.

In some embodiments of (R5-A), (R5-A1), (R5-A2), (R5-A3), (R5-A4), (R5-A5), (R5-A6), or (R5-A7):
each $Y^1$ is independently selected from absent, $(CH_2)$, $(CR^{12a}R^{12b})_{p3}O(CR^{12a}R^{12b})_{p4}$, $(CR^{12a}R^{12b})_{p3}S(CR^{12a}R^{12b})_{p4}$, $(CR^{12a}R^{12b})_{p3}NR^e(CR^{12a}R^{12b})_{p4}$, $(CR^{12a}R^{12b})_{p3}C(O)(CR^{12a}R^{12b})_{p4}$, $(CR^{12a}R^{12b})_{3}C(O)O(CR^{12a}R^{12b})_{p4}$, $C(S)NR^e$, $(CR^{12a}R^{12b})_{p3}C(O)NR^e(CR^{12a}R^{12b})_{p4}$, $(CR^{12a}R^{12b})_{p3}S(O)_2(CR^{12a}R^{12b})_{p4}$, $(CR^{12a}R^{12b})_{p3}S(O)_2NR^e(CR^{12a}R^{12b})_{p4}$, and $(CR^{12a}R^{12b})_{p3}NR^eC(O)NR^f(CR^{12a}R^{12b})_{p4}$; and
each $Z^1$ is independently selected from H, OH, CN, $C_{1-6}$ alkyl, aryl, cycloalkyl, heteroaryl, and heterocycloalkyl, wherein each of the $C_{1-6}$ alkyl, aryl, cycloalkyl, heteroaryl, and heterocycloalkyl is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $NR^cS(O)_2R^b$, $NR^cS(O)_2S(O)_2NR^cR^d$, $S(O)R^b$, $S(O)NR^cR^d$, $S(O)_2R^b$, and $S(O)_2NR^cR^d$.

In some embodiments of (R5-A), (R5-A1), (R5-A2), (R5-A3), (R5-A4), (R5-A5), (R5-A6), or (R5-A7), each $Z^1$ is independently selected from aryl and heteroaryl, each optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $NR^cS(O)_2R^b$, $NR^cS(O)_2S(O)_2NR^cR^d$, $S(O)R^b$, $S(O)NR^cR^d$, $S(O)_2R^b$, and $S(O)_2NR^cR^d$.

In some embodiments of (R5-A), (R5-A1), (R5-A2), (R5-A3), (R5-A4), (R5-A5), (R5-A6), or (R5-A7), each $Z^1$ is independently selected from phenyl, pyridinyl, 1H-pyrazolyl, isoxazolyl, 1,3-oxazolyl, 1,3-thiazolyl, 1H-imidazolyl, 1H-1,2,4-triazolyl, 1H-1,2,3-triazolyl, benzothiazolyl, [1,3]oxazolo[5,4-b]pyridinyl, 1,3,4-thiadiazolyl, furanyl, thienyl, pyrazinyl, pyrimidinyl, benzothiazolyl, furo[3,2-c]pyridinyl, 1,2,4-oxadiazolyl, 1,2,5-oxadiazolyl, 1,3-benzodioxol-5-yl, and indolyl, each optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $NR^cS(O)_2R^b$, $NR^cS(O)_2S(O)_2NR^cR^d$, $S(O)R^b$, $S(O)NR^cR^d$, $S(O)_2R^b$, and $S(O)_2NR^cR^d$.

In some embodiments, at least one $R^5$ is

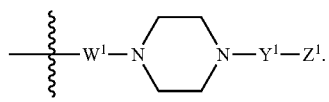

(R5-B)

In some embodiments of (R5-B), $W^1$ is absent, $C_{1-6}$ alkylenyl, $-O(CR^{11a}R^{11b})_{q1}C(O)-$, $-O(CR^{11a}R^{11b})_{p2}-$, $-(CR^{11a}R^{11b})_{p1}C(O)NR^e(CR^{11a}R^{11b})_{p2}-$, $-(CR^{11a}R^{11b})_{p1}C(O)NR^e-$, $-NR^e(CR^{11a}R^{11b})_{p2}-$, $-(CR^{11a}R^{11b})_{p2}NR^eC(O)-$, $-(CR^{11a}R^{11b})_{p1}NR^e-$, $-(CR^{11a}R^{11b})_{p1}O(CR^{11a}R^{11b})_{p2}-$, $-(CR^{11a}R^{11b})_{p1}S(CR^{11a}R^{11b})_{p2}-$, $-(CR^{11a}R^{11b})_{p1}S(O)(CR^{11a}R^{11b})_{p2}-$, $-(CR^{11a}R^{11b})_{p1}S(O)_2(CR^{11a}R^{11b})_{p2}-$, $-(CR^{11a}R^{11b})_{p1}NR^e(CR^{11a}R^{11b})_{p2}-$, $-NR^eS(O)(CR^{11a}R^{11b})_{p1}-$, $-S(O)NR^e(CR^{11a}R^{11b})_{p2}-$, $-NR^eS(O)_2(CR^{11a}R^{11b})_{p1}-$, $-S(O)_2NR^e(CR^{11a}R^{11b})_{p2}-$, $-NR^eC(O)(CR^{11a}R^{11b})_{p1}-$, $-C(O)NR^e(CR^{11a}R^{11b})_{p2}-$, or $-NR^eC(O)NR^f(CR^{11a}R^{11b})_{p2}-$.

In some embodiments of (R5-B), W$^1$ is absent, —(CH$_2$)—, —O(CR$^{11a}$R$^{11b}$)$_{q1}$C(O)—, —O(CR$^{11a}$R$^{11b}$)$_{p2}$—, —(CR$^{11a}$R$^{11b}$)$_{p1}$C(O)NR$^e$(CR$^{11a}$R$^{11b}$)$_{p2}$—, —(CR$^{11a}$R$^{11b}$)$_{p1}$C(O)NR$^e$—, —NR$^e$(CR$^{11a}$R$^{11b}$)$_{p2}$—, —(CR$^{11a}$R$^{11b}$)$_{p2}$NR$^e$C(O)—, —(CR$^{11a}$R$^{11b}$)$_{p1}$NR$^e$—, —(CR$^{11a}$R$^{11b}$)$_{p1}$O(CR$^{11a}$R$^{11b}$)$_{p2}$—, —(CR$^{11a}$R$^{11b}$)$_{p1}$S (CR$^{11a}$R$^{11b}$)$_{p2}$—, —(CR$^{11a}$R$^{11b}$)$_{p1}$S(O)(CR$^{11a}$R$^{11b}$)$_{p2}$—, —(CR$^{11a}$R$^{11b}$)$_{p1}$S(O)$_2$(CR$^{11a}$R$^{11b}$)$_{p2}$—, —(CR$^{11a}$R$^{11b}$)$_{p1}$NR$^e$(CR$^{11a}$R$^{11b}$)$_{p2}$—, —NR$^e$S(O)(CR$^{11a}$R$^{11b}$)$_{p1}$—, —S(O)NR$^e$(CR$^{11a}$R$^{11b}$)$_{p2}$—, —NR$^e$S(O)$_2$(CR$^{11a}$R$^{11b}$)$_{p1}$—, —S(O)$_2$NR$^e$(CR$^{11a}$R$^{11b}$)$_{p2}$—, —NR$^e$C(O)(CR$^{11a}$R$^{11b}$)$_{p1}$—, —C(O)NR$^e$(CR$^{11a}$R$^{11b}$)$_{p2}$—, or —NR$^e$C(O)NR$^f$(CR$^{11a}$R$^{11b}$)$_{p2}$—.

In some embodiments, at least one R$^5$ is

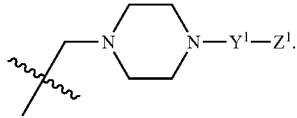

(R5-B1)

In some embodiments, at least one R$^5$ is

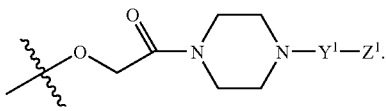

(R5-B2)

In some embodiments of (R5-B), (R5-B1), or (R5-B2):
each Y$^1$ is independently selected from absent, C$_{1-6}$ alkylene, (CR$^{12a}$R$^{12b}$)$_{p3}$O(CR$^{12a}$R$^{12b}$)$_{p4}$, (CR$^{12a}$R$^{12b}$)$_{p3}$S (CR$^{12a}$R$^{12b}$)$_{p4}$, (CR$^{12a}$R$^{12b}$)$_{p3}$NR$^e$(CR$^{12a}$R$^{12b}$)$_{p4}$, (CR$^{12a}$R$^{12b}$)$_{p3}$C(O)(CR$^{12a}$R$^{12b}$)$_{p4}$, (CR$^{12a}$R$^{12b}$)$_{p3}$C(O)O (CR$^{12a}$R$^{12b}$)$_{p4}$, C(S)NR$^e$, (CR$^{12a}$R$^{12b}$)$_{p3}$C(O)NR$^e$ (CR$^{12a}$R$^{12b}$)$_{p4}$, (CR$^{12a}$R$^{12b}$)$_{p3}$S(O)$_2$(CR$^{12a}$R$^{12b}$)$_{p4}$, (CR$^{12a}$R$^{12b}$)$_{p3}$S(O)$_2$NR$^e$(CR$^{12a}$R$^{12b}$)$_{p4}$, and (CR$^{12a}$R$^{12b}$)$_{p3}$NR$^e$C(O)NR$^f$(CR$^{12a}$R$^{12b}$)$_{p4}$; and each Z$^1$ is independently selected from H, OH, CN, C$_{1-6}$ alkyl, aryl, cycloalkyl, heteroaryl, and heterocycloalkyl, wherein each of the C$_{1-6}$ alkyl, aryl, cycloalkyl, heteroaryl, and heterocycloalkyl is optionally substituted by 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, aryl, cycloalkyl, heteroaryl, heterocycloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, NR$^c$S(O)$_2$R$^b$, NR$^c$S(O)$_2$S(O)$_2$NR$^c$R$^d$, S(O)R$^b$, S(O)NR$^c$R$^d$, S(O)$_2$R$^b$, and S(O)$_2$NR$^c$R$^d$.

In some embodiments of (R5-B), (R5-B1), or (R5-B2):
each Y$^1$ is independently selected from absent, (CH$_2$), (CR$^{12a}$R$^{12b}$)$_{p3}$O(CR$^{12a}$R$^{12b}$)$_{p4}$, (CR$^{12a}$R$^{12b}$)$_{p3}$S (CR$^{12a}$R$^{12b}$)$_{p4}$, (CR$^{12a}$R$^{12b}$)$_{p3}$NR$^e$(CR$^{12a}$R$^{12b}$)$_{p4}$, (CR$^{12a}$R$^{12b}$)$_{p3}$C(O)(CR$^{12a}$R$^{12b}$)$_{p4}$, (CR$^{12a}$R$^{12b}$)$_{p3}$C(O)O (CR$^{12a}$R$^{12b}$)$_{p4}$, C(S)NR$^e$, (CR$^{12a}$R$^{12b}$)$_{p3}$C(O)NR$^e$ (CR$^{12a}$R$^{12b}$)$_{p4}$, (CR$^{12a}$R$^{12b}$)$_{p3}$S(O)$_2$(CR$^{12a}$R$^{12b}$)$_{p4}$, (CR$^{12a}$R$^{12b}$)$_{p3}$S(O)$_2$NR$^e$(CR$^{12a}$R$^{12b}$)$_{p4}$, and (CR$^{12a}$R$^{12b}$)$_{p3}$NR$^e$C(O)NR$^f$(CR$^{12a}$R$^{12b}$)$_{p4}$; and each Z$^1$ is independently selected from H, OH, CN, C$_{1-6}$ alkyl, aryl, cycloalkyl, heteroaryl, and heterocycloalkyl, wherein each of the C$_{1-6}$ alkyl, aryl, cycloalkyl, heteroaryl, and heterocycloalkyl is optionally substituted by 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, aryl, cycloalkyl, heteroaryl, heterocycloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, NR$^c$S(O)$_2$R$^b$, NR$^c$S(O)$_2$S(O)$_2$NR$^c$R$^d$, S(O)R$^b$, S(O)NR$^c$R$^d$, S(O)$_2$R$^b$, and S(O)$_2$NR$^c$R$^d$.

In some embodiments of (R5-B), (R5-B1), or (R5-B2), each Z$^1$ is independently selected from aryl and heteroaryl, each optionally substituted by 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, aryl, cycloalkyl, heteroaryl, heterocycloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, NR$^c$S(O)$_2$R$^b$, NR$^c$S(O)$_2$S(O)$_2$NR$^c$R$^d$, S(O)R$^b$, S(O)NR$^c$R$^d$, S(O)$_2$R$^b$, and S(O)$_2$NR$^c$R$^d$.

In some embodiments of (R5-B), (R5-B1), or (R5-B2), each Z$^1$ is independently selected from phenyl, pyridinyl, 1H-pyrazolyl, isoxazolyl, 1,3-oxazolyl, 1,3-thiazolyl, 1H-imidazolyl, 1H-1,2,4-triazolyl, 1H-1,2,3-triazolyl, benzothiazolyl, [1,3]oxazolo[5,4-b]pyridinyl, 1,3,4-thiadiazolyl, furanyl, thienyl, pyrazinyl, pyrimidinyl, benzothiazolyl, furo[3,2-c]pyridinyl, 1,2,4-oxadiazolyl, 1,2,5-oxadiazolyl, 1,3-benzodioxol-5-yl, and indolyl, each optionally substituted by 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, aryl, cycloalkyl, heteroaryl, heterocycloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, NR$^c$S (O)$_2$R$^b$, NR$^c$S(O)$_2$S(O)$_2$NR$^c$R$^d$, S(O)R$^b$, S(O)NR$^c$R$^d$, S(O)$_2$ R$^b$, and S(O)$_2$NR$^c$R$^d$.

In some embodiments, Q$^1$, Q$^2$, Q$^3$, Q$^4$, and Q$^5$ are each, independently, selected cycloalkyl and heterocycloalkyl, each optionally substituted by 1, 2, 3, 4, or 5 substituents independently selected from halo, CN, NO$_2$, OH, C$_{1-6}$ alkyl, C$_{1-6}$ haloalkyl, C$_{2-8}$ alkoxyalkyl, C$_{1-6}$ alkoxy, C$_{1-6}$ haloalkoxy, C$_{2-8}$ alkoxyalkoxy, cycloalkyl, heterocycloalkyl, C(O)OR$^a$, C(O)NR$^c$R$^d$, amino, C$_{1-6}$ alkylamino and C$_{2-8}$ dialkylamino.

In some embodiments, each Q$^1$ is independently selected from aryl, heteroaryl, cycloalkyl, and heterocycloalkyl, each optionally substituted by 1, 2, 3, 4, or 5 substituents independently selected from halo, CN, NO$_2$, OH, C$_{1-6}$ alkyl, C$_{1-6}$ haloalkyl, C$_{2-8}$ alkoxyalkyl, C$_{1-6}$ alkoxy, C$_{1-6}$ haloalkoxy, C$_{2-8}$ alkoxyalkoxy, cycloalkyl, heterocycloalkyl, C(O)OR$^a$, C(O)NR$^c$R$^d$, amino, C$_{1-6}$ alkylamino and C$_{2-8}$ dialkylamino.

In some embodiments, each Q$^1$ is independently selected from cycloalkyl and heterocycloalkyl, each optionally substituted by 1, 2, 3, 4, or 5 substituents independently selected from halo, CN, NO$_2$, OH, C$_{1-6}$ alkyl, C$_{1-6}$ haloalkyl, C$_{2-8}$ alkoxyalkyl, C$_{1-6}$ alkoxy, C$_{1-6}$ haloalkoxy, C$_{2-8}$ alkoxyalkoxy, cycloalkyl, heterocycloalkyl, C(O)OR$^a$, C(O)NR$^c$R$^d$, amino, C$_{1-6}$ alkylamino and C$_{2-8}$ dialkylamino. In some further embodiments, each Q$^1$ is independently selected from such optionally substituted cycloalkyl. In other further embodiments, each Q$^1$ is independently selected from such optionally substituted heterocycloalkyl.

In some embodiments, each Q$^1$ is independently selected heterocycloalkyl optionally substituted by 1, 2, 3, 4, or 5 substituents independently selected from halo, CN, NO$_2$, OH, C$_{1-6}$ alkyl, C$_{1-6}$ haloalkyl, C$_{2-8}$ alkoxyalkyl, C$_{1-6}$ alkoxy, C$_{1-6}$ haloalkoxy, C$_{2-8}$ alkoxyalkoxy, cycloalkyl, heterocycloalkyl, C(O)OR$^a$, C(O)NR$^c$R$^d$, amino, C$_{1-6}$ alkylamino and C$_{2-8}$ dialkylamino.

In some embodiments, each Q$^1$ is independently selected from cyclopropyl, cyclobutyl, cyclopentyl, cyclohexyl, azetidinyl, pyrrolidinyl, piperidinyl, piperazinyl, (1H)-hexahydropyrrolo[1,2-a]pyrazin-2-yl, and (8H)-5,6-dihydro[1,2,4] triazolo[4,3-a]pyrazin-7-yl, each optionally substituted by 1, 2, 3, 4, or 5 substituents independently selected from halo, CN, NO$_2$, OH, C$_{1-6}$ alkyl, C$_{1-6}$ haloalkyl, C$_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^a$, $C(O)NR^cR^d$, amino, $C_{1-6}$ alkylamino and $C_{2-8}$ dialkylamino. In some further embodiments, each $Q^1$ is independently selected from cyclopropyl, cyclobutyl, cyclopentyl, and cyclohexyl, each optionally substituted by 1, 2, 3, 4, or 5 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^a$, $C(O)NR^cR^d$, amino, $C_{1-6}$ alkylamino and $C_{2-8}$ dialkylamino. In other further embodiments, each $Q^1$ is independently selected from azetidinyl, pyrrolidinyl, piperidinyl, and piperazinyl, each optionally substituted by 1, 2, 3, 4, or 5 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^a$, $C(O)NR^cR^d$, amino, $C_{1-6}$ alkylamino and $C_{2-8}$ dialkylamino.

In some embodiments, each $Q^1$ is independently selected from cyclopropyl, cyclobutyl, cyclopentyl, cyclohexyl, azetidinyl, pyrrolidinyl, piperidinyl, and piperazinyl, each optionally substituted by 1, 2, 3, 4, or 5 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^{a1}$, $C(O)NR^cR^d$, amino, $C_{1-6}$ alkylamino and $C_{2-8}$ dialkylamino. In some further embodiments, each $Q^1$ is independently selected from cyclopropyl, cyclobutyl, cyclopentyl, and cyclohexyl, each optionally substituted by 1, 2, 3, 4, or 5 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^a$, $C(O)NR^cR^d$, amino, $C_{1-6}$ alkylamino and $C_{2-8}$ dialkylamino. In other further embodiments, each $Q^1$ is independently selected from azetidinyl, pyrrolidinyl, piperidinyl, and piperazinyl, each optionally substituted by 1, 2, 3, 4, or 5 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^a$, $C(O)NR^cR^d$, amino, $C_{1-6}$ alkylamino and $C_{2-8}$ dialkylamino.

In some embodiments, each $Q^1$ is independently selected from cyclobutyl, cyclopentyl, cyclohexyl, pyrrolidinyl, piperidinyl, and piperazinyl, each optionally substituted by 1, 2, 3, 4, or 5 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^a$, $C(O)NR^cR^d$, amino, $C_{1-6}$ alkylamino and $C_{2-8}$ dialkylamino.

In some embodiments, each $Q^1$ is independently selected from cyclopropyl, cyclobutyl, cyclopentyl, cyclohexyl, azetidinyl, pyrrolidinyl, and piperidinyl, each optionally substituted by 1, 2, 3, 4, or 5 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^a$, $C(O)NR^cR^d$, amino, $C_{1-6}$ alkylamino and $C_{2-8}$ dialkylamino.

In some embodiments, each $Q^1$ is independently selected from pyrrolidinyl, piperidinyl, and piperazinyl, each optionally substituted by 1, 2, 3, 4, or 5 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^a$, $C(O)NR^cR^d$, amino, $C_{1-6}$ alkylamino and $C_{2-8}$ dialkylamino.

In some embodiments, each $Q^1$ is independently selected from pyrrolidinyl, and piperidinyl, each optionally substituted by 1, 2, 3, 4, or 5 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^a$, $C(O)NR^cR^d$, amino, $C_{1-6}$ alkylamino and $C_{2-8}$ dialkylamino.

In some embodiments, at least one $R^5$ is $-W^6-Q^1-Y^1-Z^1$.

In some embodiments, at least one $R^5$ is $-(CR^{11a}R^{11b})_{p1}S(CR^{11a}R^{11b})_{p2}-Q^1-Y^1-Z^1$, $-(CR^{11a}R^{11b})_{p1}S(O)(CR^{11a}R^{11b})_{p2}-Q^1-Y^1-Z^1$, $-(CR^{11a}R^{11b})_{p1}S(O)_2(CR^{11a}R^{11b})_{p2}-Q^1-Y^1-Z^1$, $-(CR^{11a}R^{11b})_{p1}S(O)NR^e(CR^{11a}R^{11b})_{p2}-Q^1-Y^1-Z^1$, $-(CR^{11a}R^{11b})_{p2}NR^eS(O)(CR^{11a}R^{11b})_{p1}-Q^1-Y^1-Z^1$, $(CR^{11a}R^{11b})_{p1}S(O)_2NR^e(CR^{11a}R^{11b})_{p2}-Q^1-Y^1-Z^1$, or $-(CR^{11a}R^{11b})_{p2}NR^eS(O)_2(CR^{11a}R^{11b})_{p1}-Q^1-Y^1-Z^1$.

In some embodiments, each $Y^1$ is independently selected from absent, $C_{1-6}$ alkylenyl, $(CR^{12a}R^{12b})_{p3}O(CR^{12a}R^{12b})_{p4}$, $(CR^{12a}R^{12b})_{p3}S(CR^{12a}R^{12b})_{p4}$, $(CR^{12a}R^{12b})_{p3}NR^e(CR^{12a}R^{12b})_{p4}$, $(CR^{12a}R^{12b})_{p3}C(O)(CR^{12a}R^{12b})_{p4}$, $(CR^{12a}R^{12b})_{p3}C(O)O(CR^{12a}R^{12b})_{p4}$, $C(S)NR^e$, $(CR^{12a}R^{12b})_{p3}C(O)NR^e(CR^{12a}R^{12b})_{p4}$, $(CR^{12a}R^{12b})_{p3}S(O)(CR^{12a}R^{12b})_{p4}$, $(CR^{12a}R^{12b})_{p3}S(O)_2NR^e(CR^{12a}R^{12b})_{p4}$, and $(CR^{12a}R^{12b})_{p3}NR^eC(O)NR^f(CR^{12a}R^{12b})_{p4}$.

In some embodiments, each $Y^1$ is independently selected from absent, $(CH_2)$, $(CR^{12a}R^{12b})_{p3}O(CR^{12a}R^{12b})_{p4}$, $(CR^{12a}R^{12b})_{p3}S(CR^{12a}R^{12b})_{p4}$, $(CR^{12a}R^{12b})_{p3}NR^e(CR^{12a}R^{12b})_{p4}$, $(CR^{12a}R^{12b})_{p3}C(O)(CR^{12a}R^{12b})_{p4}$, $(CR^{12a}R^{12b})_{p3}C(O)O(CR^{12a}R^{12b})_{p4}$, $C(S)NR^e$, $(CR^{12a}R^{12b})_{p3}C(O)NR^e(CR^{12a}R^{12b})_{p4}$, $(CR^{12a}R^{12b})_{p3}S(O)(CR^{12a}R^{12b})_{p4}$, $(CR^{12a}R^{12b})_{p3}S(O)_2NR^e(CR^{12a}R^{12a})_{p4}$, and $(CR^{12a}R^{12b})_{p3}NR^eC(O)NR^f(CR^{12a}R^{12b})_{p4}$.

In some embodiments, each $Y^1$ is independently selected from absent, $C_{1-6}$ alkylenyl, $(CR^{12a}R^{12b})_{p3}C(O)(CR^{12a}R^{12b})_{p4}$, $(CR^{12a}R^{12b})_{p3}C(O)O(CR^{12a}R^{12b})_{p4}$, $C(S)NR^e$, $(CR^{12a}R^{12b})_{p3}C(O)NR^e(CR^{12a}R^{12b})_{p4}$, $(CR^{12a}R^{12b})_{p3}S(O)_2(CR^{12a}R^{12b})_{p4}$, and $(CR^{12a}R^{12b})_{p3}NR^eC(O)NR^f(CR^{12a}R^{12b})_{p4}$.

In some embodiments, each $Y^1$ is independently selected from absent, $(CH_2)$, $(CR^{12a}R^{12b})_{p3}C(O)(CR^{12a}R^{12b})_{p4}$, $(CR^{12a}R^{12b})_{p3}C(O)O(CR^{12a}R^{12b})_{p4}$, $C(S)NR^e$, $(CR^{12a}R^{12b})_{p3}C(O)NR^e(CR^{12a}R^{12b})_{p4}$, $(CR^{12a}R^{12b})_{p3}S(O)_2(CR^{12a}R^{12b})_{p4}$, and $(CR^{12a}R^{12b})_{p3}NR^eC(O)NR^f(CR^{12a}R^{12b})_{p4}$.

In some embodiments, each $Y^1$ is independently selected from absent, $(CR^{12a}R^{12b})_{p3}O(CR^{12a}R^{12b})_{p4}$, $(CR^{12a}R^{12b})_{p3}S(CR^{12a}R^{12b})_{p4}$, $(CR^{12a}R^{12b})_{p3}NR^e(CR^{12a}R^{12b})_{p4}$, $(CR^{12a}R^{12b})_{p3}C(O)(CR^{12a}R^{12b})_{p4}$, $(CR^{12a}R^{12b})_{p3}C(O)NR^e(CR^{12a}R^{12b})_{p4}$, $(CR^{12a}R^{12b})_{p3}S(O)_2(CR^{12a}R^{12b})_{p4}$, $(CR^{12a}R^{12b})_{p3}S(O)_2NR^e(CR^{12a}R^{12b})_{p4}$, and $(CR^{12a}R^{12b})_{p3}NR^eC(O)NR^f(CR^{12a}R^{12b})_{p4}$.

In some embodiments, each $Z^1$ is independently selected from H, OH, CN, $C_{1-6}$ alkyl, aryl, cycloalkyl, heteroaryl, and heterocycloalkyl, wherein each of the $C_{1-6}$ alkyl, aryl, cycloalkyl, heteroaryl, and heterocycloalkyl is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $NR^cS(O)_2R^b$, $NR^cS(O)_2S(O)_2NR^cR^d$, $S(O)R^b$, $S(O)NR^cR^d$, $S(O)_2R^b$, and $S(O)_2NR^cR^d$.

In some embodiments, each $Z^1$ is independently selected from $C_{1-6}$ alkyl, $C_{1-6}$ haloalkyl, aryl, cycloalkyl, heteroaryl and heterocycloalkyl, each optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $NR^cS(O)_2R^b$, $NR^cS(O)_2S(O)_2NR^cR^d$, $S(O)R^b$, $S(O)NR^cR^d$, $S(O)_2R^b$, and $S(O)_2NR^cR^d$.

In some embodiments, each $Z^1$ is independently selected from aryl, cycloalkyl, heteroaryl and heterocycloalkyl, each optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $NR^cS(O)_2R^b$, $NR^cS(O)_2S(O)_2NR^cR^d$, $S(O)R^b$, $S(O)NR^cR^d$, $S(O)_2R^b$, and $S(O)_2NR^cR^d$.

In some embodiments, each $R^6$ is, independently, H, $C_{1-6}$ alkyl, $C_{2-6}$ alkenyl, $C_{2-6}$ alkynyl, $C_{1-6}$ haloalkyl, $C(O)R^{b1}$, $C(O)NR^{c1}R^{d1}$, $C(O)OR^{a1}$, $S(O)R^{b1}$, $S(O)_2R^{b1}$, or $S(O)_2NR^{c1}R^{d1}$. In some further embodiments, each $R^6$ is, independently, H, $C_{1-6}$ alkyl, $C_{2-6}$ alkenyl, $C_{2-6}$ alkynyl, or $C_{1-6}$ haloalkyl. In yet further embodiments, each $R^6$ is, independently, H or $C_{1-6}$ alkyl. In still further embodiments, each $R^6$ is H or $C_{1-3}$ alkyl.

In some embodiments, each $R^6$ is, independently, H, $C_{1-3}$ alkyl, $C_{2-3}$ alkenyl, $C_{2-3}$ alkynyl, or $C_{1-3}$ haloalkyl. In some further embodiments, each $R^6$ is, independently, H, $C_{1-3}$ alkyl, or $C_{1-3}$ haloalkyl. In some further embodiments, each $R^6$ is, independently, H or $C_{1-3}$ alkyl.

In some embodiments, each $R^6$ is, independently, H or methyl. In some embodiments, each $R^6$ is H. In some other embodiments, one $R^6$ is methyl.

In some embodiments, $R^{11a}$, $R^{11b}$, $R^{12a}$, and $R^{12b}$ are each, independently, selected from H, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$, wherein each of said $C_{1-6}$ alkyl, $C_{2-6}$ alkenyl, $C_{2-6}$ alkynyl, or $C_{1-6}$ haloalkyl, is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a1}$, $SR^{a1}$, $SF_5$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$.

In some embodiments, $R^{11a}$, $R^{11b}$, $R^{12a}$, and $R^{12b}$ are each, independently, selected from H, halo, $C_{1-6}$ alkyl, $C_{2-6}$ alkenyl, $C_{2-6}$ alkynyl, $C_{1-6}$ haloalkyl, CN, $NO_2$, OH, $C_{1-6}$ alkoxy, $C_{1-6}$ haloalkoxy, $C_{2-8}$ alkoxyalkyl, cycloalkyl, heterocycloalkyl, $C(O)OR^{a1}$, $C(O)NR^{c1}R^{d1}$, amino, $C_{1-6}$ alkylamino and $C_{2-8}$ dialkylamino.

In some embodiments, $R^{11a}$, $R^{11b}$, $R^{12a}$, and $R^{12b}$ are each, independently, selected from H and $C_{1-6}$ alkyl. In some further embodiments, $R^{11a}$, $R^{11b}$, $R^{12a}$, and $R^{12b}$ are each, independently, selected from H and $C_{1-3}$ alkyl.

In some embodiments, $R^{11a}$, $R^{11b}$, $R^{12a}$, and $R^{12b}$ are each, independently, selected from H and methyl. In some further embodiments, $R^{11a}$, $R^{11b}$, $R^{12a}$, and $R^{12b}$ are each H.

In some embodiments, each $R^{13}$ is independently selected from H, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$, wherein each of said $C_{1-6}$ alkyl, $C_{2-6}$ alkenyl, $C_{2-6}$ alkynyl, or $C_{1-6}$ haloalkyl, is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a1}$, $SR^{a1}$, $SF_5$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$, $P(R^{f1})_2$, $P(OR^{e1})_2$.

In some embodiments, each $R^{13}$ is independently selected from H, halo, $C_{1-6}$ alkyl, $C_{2-6}$ alkenyl, $C_{2-6}$ alkynyl, $C_{1-6}$ haloalkyl, CN, $NO_2$, OH, $C_{1-6}$ alkoxy, $C_{1-6}$ haloalkoxy, $C_{2-8}$ alkoxyalkyl, cycloalkyl, heterocycloalkyl, $C(O)OR^{a1}$, $C(O)NR^{c1}R^{d1}$, amino, $C_{1-6}$ alkylamino and $C_{2-8}$ dialkylamino. In some further embodiments, each $R^{13}$ is H or $C_{1-6}$ alkyl. In yet further embodiments, each $R^{13}$ is H.

In some embodiments, each p1 is, independently, 0 or 1. In some other embodiments, each p1 is, independently, 1 or 2.

In some embodiments, each p2 is, independently, 0 or 1. In some other embodiments, each p2 is, independently, 1 or 2.

In some embodiments, each p3 is, independently, 0 or 1. In some other embodiments, each p3 is, independently, 1 or 2.

In some embodiments, each p4 is, independently, 0 or 1. In some other embodiments, each p4 is, independently, 1 or 2.

In some embodiments, each q1 is 1. In some other embodiments, each q1 is 2.

In some embodiments, each q2 is 1. In some other embodiments, each q2 is 2.

In some embodiments, each n is, independently, 1 or 2. In some embodiments, n is 1. In some embodiments, n is 2.

In some embodiments, n is 3.

In some embodiments, each m is 0 or 1. In some embodiments, m is 0. In some embodiments, m is 1.

In some embodiments, m is 2.

In some embodiments, $X^1$ is CH; $X^2$ is N; $X^3$ is $CR^3$; $R^3$ is halo; Y is NH or $N(C_{1-3}$ alkyl); and at least one $R^5$ is selected from $C(O)NR^{c1}R^{d1}$, $C(O)OR^{a1}$, $NR^{c1}R^{d1}$, $NR^{c1}C(O)R^{b1}$, $NR^{c1}C(O)NR^{c1}R^{d1}$, $NR^{c1}S(O)_2NR^{c1}R^{d1}$, $S(O)_2R^{b1}$, $NR^{c1}S(O)_2R^{b1}$, $S(O)_2NR^{c1}R^{d1}$, $Cy^1$, and $W^1$-$Q^1$-$Y^1$-$Z^1$. In some further embodiments, at least one $R^5$ is -$W^1$-$Q^1$-$Y^1$-$Z^1$. In some further embodiments, at least one $R^5$ on the ring containing $A^1$, $B^1$, $D^1$, and $E^1$ is -$W^1$-$Q^1$-$Y^1$-$Z^1$. In some other embodiments, at least one $R^5$ on the ring containing $A^2$, $B^2$, $D^2$, and $E^2$ is -$W^1$-$Q^1$-$Y^1$-$Z^1$. In further embodiments, each $Q^1$ is independently selected from cycloalkyl and heterocycloalkyl, each optionally substituted by 1, 2, 3, 4, or 5 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^a$, $C(O)NR^cR^d$, amino, $C_{1-6}$ alkylamino and $C_{2-8}$ dialkylamino. In yet further embodiments, each $Q^1$ is independently selected from cyclopropyl, cyclobutyl, cyclopentyl, cyclohexyl, azetidinyl, pyrrolidinyl, piperidinyl, and piperazinyl, each optionally substituted by 1, 2, 3, 4, or 5 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^a$, $C(O)NR^cR^d$, amino, $C_{1-6}$ alkylamino and $C_{2-8}$ dialkylamino.

In some embodiments of the compounds of Formula I or pharmaceutically acceptable salts thereof, the ring containing $A^1$, $B^1$, $D^1$, and $E^1$ is a pyridine ring, wherein said pyridine ring is optionally substituted by $R^2$, if present, and optionally by 1 or 2 $R^5$; and the ring containing $A^2$, $B^2$, $D^2$, and $E^2$ is a benzene ring, wherein said benzene ring optionally substituted by $R^2$, if present, and optionally by 1, 2, or 3 $R^5$.

In some embodiments of the compounds of Formula I or pharmaceutically acceptable salts thereof, the ring containing $A^1$, $B^1$, $D^1$, and $E^1$ is a pyridine ring, wherein said pyridine ring is optionally substituted by 1 or 2 $R^5$; and the ring containing $A^2$, $B^2$, $D^2$, and $E^2$ is a benzene ring, wherein said benzene ring substituted by $-W^1-Q^1-Y^1-Z^1$ and optionally substituted by 1 or 2 $R^5$. In further embodiments, each $Q^1$ is independently selected from cycloalkyl and heterocycloalkyl, each optionally substituted by 1, 2, 3, 4, or 5 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^a$, $C(O)NR^cR^d$, amino, $C_{1-6}$ alkylamino and $C_{2-8}$ dialkylamino. In yet further embodiments, each $Q^1$ is independently selected from cyclopropyl, cyclobutyl, cyclopentyl, cyclohexyl, azetidinyl, pyrrolidinyl, piperidinyl, and piperazinyl, each optionally substituted by 1, 2, 3, 4, or 5 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^a$, $C(O)NR^cR^d$, amino, $C_{1-6}$ alkylamino and $C_{2-8}$ dialkylamino.

In some embodiments, the compounds of Formula I of the present invention have Formula II:

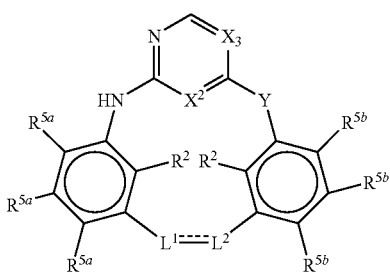

II wherein:
each $R^{5a}$ is, independently, selected from H, halo, $C_{1-6}$ alkyl, $C_{1-6}$ haloalkyl, CN, $NO_2$, $SF_5$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2NR^{c1}R^{d1}$, $S(O)_2R^{b1}$, $NR^{c1}S(O)_2R^{b1}$, and $S(O)_2NR^{c1}R^{d1}$;

or two adjacent $R^{5a}$ can link to form a fused cycloalkyl or fused heterocycloalkyl group, each optionally substituted by 1, 2, or 3 substituents independently selected from halo, $C_{1-6}$ alkyl, $C_{1-6}$ haloalkyl, CN, $NO_2$, $SF_5$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2NR^{c1}R^{d1}$, $S(O)_2R^{b1}$, $NR^{c1}S(O)_2R^{b1}$, and $S(O)_2NR^{c1}R^{d1}$; and each $R^{5b}$ is, independently, selected from H, halo, $C_{1-6}$ alkyl, $C_{1-6}$ haloalkyl, CN, $NO_2$, $SF_5$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2NR^{c1}R^{d1}$, $S(O)_2R^{b1}$, $NR^{c1}S(O)_2R^{b1}$, and $S(O)_2NR^{c1}R^{d1}$;

or two adjacent $R^{5b}$ can link to form a fused cycloalkyl or fused heterocycloalkyl group, each optionally substituted by 1, 2, or 3 substituents independently selected from halo, $C_{1-6}$ alkyl, $C_{1-6}$ haloalkyl, CN, $NO_2$, $SF_5$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2NR^{c1}R^{d1}$, $S(O)_2R^{b1}$, $NR^{c1}S(O)_2R^{b1}$, and $S(O)_2NR^{c1}R^{d1}$.

In some embodiments of the compounds of Formula II or pharmaceutically acceptable salts thereof:
each $R^{5a}$ is, independently, selected from H halo, $C_{1-6}$ alkyl, $C_{1-6}$ haloalkyl, CN, $NO_2$, $SF_5$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2NR^{c1}R^{d1}$, $S(O)_2R^{b1}$, $NR^{c1}S(O)_2R^{b1}$, and $S(O)_2NR^{c1}R^{d1}$; and
each $R^{5b}$ is, independently, selected from H halo, $C_{1-6}$ alkyl, $C_{1-6}$ haloalkyl, CN, $NO_2$, $SF_5$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2NR^{c1}R^{d1}$, $S(O)_2R^{b1}$, $NR^{c1}S(O)_2R^{b1}$, and $S(O)_2NR^{c1}R^{d1}$.

In some embodiments of the compounds of Formula II or pharmaceutically acceptable salts thereof, Y is O, S, or $NR^4$. In some further embodiments, Y is NH or $N(C_{1-3}$ alkyl). In yet further embodiments, Y is NH.

In some embodiments of the compounds of Formula II or pharmaceutically acceptable salts thereof, $X^3$ is N, and $X^2$ is $CR^2$.

In some embodiments of the compounds of Formula II or pharmaceutically acceptable salts thereof, each $R^2$ is, independently, selected from H, F, Cl, Br, methyl, and $CF_3$. In some further embodiments, each $R^2$ is H.

In some embodiments of the compounds of Formula II or pharmaceutically acceptable salts thereof, $X^2$ is N, and $X^3$ is $CR^3$. In some further embodiments, $R^3$ is halo. In yet further embodiments, $R^3$ is F or Cl. In still further embodiments, $R^3$ is Cl.

In some embodiments, the compounds of Formula II have Formula IIa:

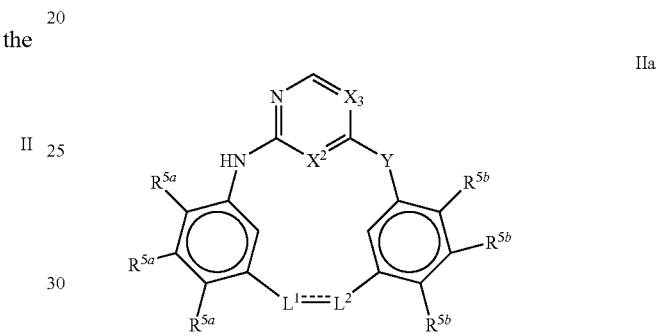

IIa

In some embodiments of the compounds of Formula IIa or pharmaceutically acceptable salts thereof, each $R^{5a}$ is independently selected from H, halo, $C_{1-6}$ alkyl, $C_{1-6}$ haloalkyl, $OR^{a1}$, $C(O)R^{b1}$, $C(O)NR^{c1}R^{d1}$, $C(O)OR^{a1}$, $S(O)_2R^{b1}$, $NR^{c1}S(O)_2NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, and $NR^{c1}S(O)_2R^{b1}$.

In some embodiments of the compounds of Formula IIa or pharmaceutically acceptable salts thereof, each $R^{5a}$ is independently selected from H, halo, $C_{1-6}$ alkyl, $C_{1-6}$ haloalkyl, $OR^{a1}$, $C(O)R^{b1}$, $NR^{c1}R^{d1}$, $NR^{c1}C(O)R^{b1}$, $NR^{c1}C(O)NR^{c1}R^{d1}$, $NR^{c1}C(O)OR^{a1}$, $NR^{c1}S(O)_2NR^{c1}R^{d1}$, and $NR^{c1}S(O)_2R^{b1}$.

In some embodiments of the compounds of Formula IIa or pharmaceutically acceptable salts thereof, each $R^{5a}$ is H.

In some embodiments of the compounds of Formula IIa or pharmaceutically acceptable salts thereof, one $R^{5a}$ is other than H.

In some embodiments of the compounds of Formula IIa or pharmaceutically acceptable salts thereof, two $R^{5a}$ are other than H.

In some embodiments of the compounds of Formula IIa or pharmaceutically acceptable salts thereof, three $R^{5a}$ are other than H.

In some embodiments of the compounds of Formula IIa or pharmaceutically acceptable salts thereof, at least one $R^{5a}$ is other than H.

In some embodiments of the compounds of Formula IIa or pharmaceutically acceptable salts thereof, at least one $R^{5a}$ is selected $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)NR^{c1}R^{d1}$, $NR^{c1}C(O)OR^{a1}$, $NR^{c1}S(O)_2NR^{c1}R^{d1}$, $S(O)_2R^{b1}$, $NR^{c1}S(O)_2R^{b1}$, and $S(O)_2NR^{c1}R^{d1}$, wherein:

$R^{a1}$, $R^{b1}$, $R^{c1}$, and $R^{d1}$ are each, independently, selected from H, $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of said $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted with 1, 2, 3, 4, or 5 substituents independently selected from halo, $C_{1-4}$ alkyl, $C_{1-4}$ haloalkyl, $C_{1-4}$ hydroxylalkyl, $C_{1-4}$ cyanoalkyl, aryl, cycloalkyl, heteroaryl, heterocycloalkyl, CN, $NO_2$, OH, SH, O($C_{1-4}$ alkyl), O($C_{1-4}$ haloalkyl), O(aryl), O(arylalkyl), S($C_{1-4}$ alkyl), S($C_{1-4}$ haloalkyl), S(aryl), S(arylalkyl), amino, $C_{1-4}$ alkylamino, $C_{2-8}$ dialkylamino, C(=O)H, C(=O)—($C_{1-4}$ alkyl), C(=O)-(arylalkyl), C(=O)$NH_2$, C(=O)NH($C_{1-4}$ alkyl), C(=O)N($C_{1-4}$ alkyl)$_2$, C(=O)OH, C(=O)O—($C_{1-4}$ alkyl), C(=O)O-(arylalkyl), OC(=O)H, OC(=O)—($C_{1-4}$ alkyl), OC(=O)-(arylalkyl), OC(=O)$NH_2$, OC(=O)NH($C_{1-4}$ alkyl), OC(=O)NH-(arylalkyl), OC(=O)N($C_{1-4}$ alkyl)$_2$, NHC(=O)—($C_{1-4}$ alkyl), NHC(=O)O-(arylalkyl), NHC(=O)O—($C_{1-4}$ alkyl), NHC(=O)O-(arylalkyl), NHS(=O)$_2$—($C_{1-4}$ alkyl), NHS(=O)$_2$-(arylalkyl), NHS(=O)$_2$—NH($C_{1-4}$ alkyl), NHS(=O)$_2$—N($C_{1-4}$ alkyl)$_2$, NHS(=O)$_2$—NH(arylalkyl), S(=O)$_2$—($C_{1-4}$ alkyl), S(=O)$_2$-(arylalkyl), S(=O)$_2$$NH_2$, S(=O)$_2$NH($C_{1-4}$ alkyl) and S(=O)$_2$NH(arylalkyl);

or $R^{c1}$ and $R^{d1}$ together with the N atom to which they are attached form a 4-, 5-, 6- or 7-membered heterocycloalkyl group or heteroaryl group, each optionally substituted with 1, 2, or 3 substituents independently selected from halo, $C_{1-4}$ alkyl, $C_{1-4}$ haloalkyl, $C_{1-4}$ hydroxylalkyl, $C_{1-4}$ cyanoalkyl, aryl, cycloalkyl, heteroaryl, heterocycloalkyl, CN, $NO_2$, OH, SH, O($C_{1-4}$ alkyl), O($C_{1-4}$ haloalkyl), O(aryl), O(arylalkyl), S($C_{1-4}$ alkyl), S($C_{1-4}$haloalkyl), S(aryl), S(arylalkyl), amino, $C_{1-4}$ alkylamino, $C_{2-8}$ dialkylamino, C(=O)H, C(=O)—($C_{1-4}$ alkyl), C(=O)-(arylalkyl), C(=O)$NH_2$, C(=O)NH($C_{1-4}$ alkyl), C(=O)N($C_{1-4}$ alkyl)$_2$, C(=O)OH, C(=O)O—($C_{1-4}$ alkyl), C(=O)O-(arylalkyl), OC(=O)H, OC(=O)—($C_{1-4}$ alkyl), OC(=O)-(arylalkyl), OC(=O)$NH_2$, OC(=O)NH($C_{1-4}$ alkyl), OC(=O)NH-(arylalkyl), OC(=O)N($C_{1-4}$ alkyl)$_2$, NHC(=O)—($C_{1-4}$ alkyl), NHC(=O)O-(arylalkyl), NHC(=O)O—($C_{1-4}$ alkyl), NHC(=O)O-(arylalkyl), NHS(=O)$_2$—($C_{1-4}$ alkyl), NHS(=O)$_2$-(arylalkyl), NHS(=O)$_2$—NH($C_{1-4}$ alkyl), NHS(=O)$_2$—N($C_{1-4}$ alkyl)$_2$, NHS(=O)$_2$—NH(arylalkyl), S(=O)$_2$—($C_{1-4}$ alkyl), S(=O)$_2$-(arylalkyl), S(=O)$_2$$NH_2$, S(=O)$_2$NH($C_{1-4}$ alkyl) and S(=O)$_2$NH(arylalkyl).

In some embodiments of the compounds of Formula IIa or pharmaceutically acceptable salts thereof, at least one of $R^{5a}$ is selected $NR^{c1}R^{d1}$, and $R^{c1}$ and $R^{d1}$ together with the N atom to which they are attached form pyrrolidinyl, piperidinyl or morpholinyl, each optionally substituted with 1, 2, or 3 substituents independently selected from halo, $C_{1-4}$ alkyl, $C_{1-4}$ haloalkyl, $C_{1-4}$ hydroxylalkyl, $C_{1-4}$ cyanoalkyl, aryl, cycloalkyl, heteroaryl, heterocycloalkyl, CN, $NO_2$, OH, SH, O($C_{1-4}$ alkyl), O($C_{1-4}$ haloalkyl), O(aryl), O(arylalkyl), S($C_{1-4}$ alkyl), S($C_{1-4}$haloalkyl), S(aryl), S(arylalkyl), amino, $C_{1-4}$ alkylamino, $C_{2-8}$ dialkylamino, C(=O)H, C(=O)—($C_{1-4}$ alkyl), C(=O)-(arylalkyl), C(=O)$NH_2$, C(=O)NH($C_{1-4}$ alkyl), C(=O)N($C_{1-4}$ alkyl)$_2$, C(=O)OH, C(=O)O—($C_{1-4}$ alkyl), C(=O)O-(arylalkyl), OC(=O)H, OC(=O)—($C_{1-4}$ alkyl), OC(=O)-(arylalkyl), OC(=O)$NH_2$, OC(=O)NH($C_{1-4}$ alkyl), OC(=O)NH-(arylalkyl), OC(=O)N($C_{1-4}$ alkyl)$_2$, NHC(=O)—($C_{1-4}$ alkyl), NHC(=O)O-(arylalkyl), NHC(=O)O—($C_{1-4}$ alkyl), NHC(=O)O-(arylalkyl), NHS(=O)$_2$—($C_{1-4}$ alkyl), NHS(=O)$_2$-(arylalkyl), NHS(=O)$_2$—NH($C_{1-4}$ alkyl), NHS(=O)$_2$—N($C_{1-4}$ alkyl)$_2$, NHS(=O)$_2$—NH(arylalkyl), S(=O)$_2$—($C_{1-4}$ alkyl), S(=O)$_2$-(arylalkyl), S(=O)$_2$$NH_2$, S(=O)$_2$NH($C_{1-4}$ alkyl) and S(=O)$_2$NH(arylalkyl).

In some embodiments of the compounds of Formula IIa or pharmaceutically acceptable salts thereof, each $R^{5b}$ is H.

In some embodiments of the compounds of Formula IIa or pharmaceutically acceptable salts thereof, one of $R^{5b}$ is other than H.

In some embodiments of the compounds of Formula IIa or pharmaceutically acceptable salts thereof, two of $R^{5b}$ are other than H.

In some embodiments of the compounds of Formula IIa or pharmaceutically acceptable salts thereof, three of $R^{5b}$ are other than H.

In some embodiments of the compounds of Formula IIa or pharmaceutically acceptable salts thereof, at least one of $R^{5b}$ is other than H.

In some embodiments, the compounds of Formula IIa have Formula IIb:

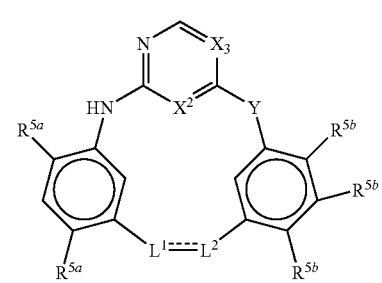

IIb

In some embodiments, the compounds of Formula IIa have Formula IIa-1:

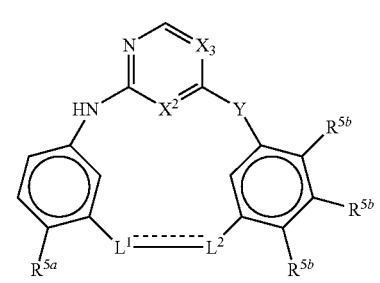

IIa-1

In some embodiments, the compounds of Formula IIa have Formula IIa-2:

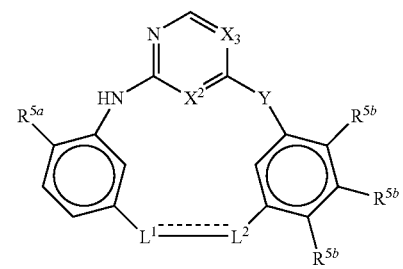

IIa-2

In some embodiments of the compounds of Formula IIa, IIb, IIa-1, IIa-2, $X^2$ is N; and $X^3$ is $CR^3$. In some further embodiments, $R^3$ is halo. In yet further embodiments, $R^3$ is F or Cl. In still further embodiments, $R^3$ is Cl.

In some embodiments, the compounds of Formula II have Formula IIc:

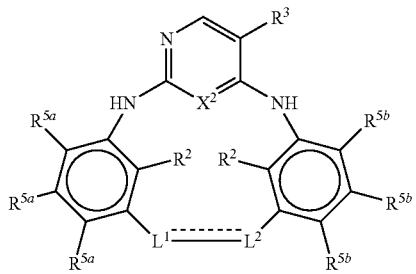

IIc

In some embodiments of the compounds of Formula IIc or pharmaceutically acceptable salts thereof, each $R^2$ is, independently, selected from H, F, Cl, Br, methyl, and $CF_3$. In some further embodiments, each $R^2$ is H.

In some embodiments of the compounds of Formula IIc or pharmaceutically acceptable salts thereof, $R^3$ is halo. In some further embodiments, $R^3$ is F or Cl. In yet further embodiments, $R^3$ is Cl.

In some embodiments, the compounds of Formula II have Formula IId:

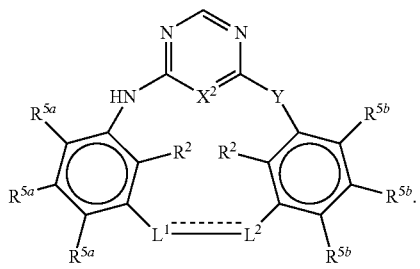

IId

In some embodiments of the compounds of Formula IId, or pharmaceutically acceptable salts thereof, Y is NH or $N(C_{1-3}$ alkyl). In some further embodiments, Y is NH.

In some embodiments of the compounds of Formula IId or pharmaceutically acceptable salts thereof, each $R^2$ is, independently, selected from H, F, Cl, Br, methyl, and $CF_3$. In some further embodiments, each $R^2$ is H.

In some embodiments of the compounds of Formula IId or IIe, $X^2$ is N.

In some embodiments, the compounds of Formula II have Formula IIe:

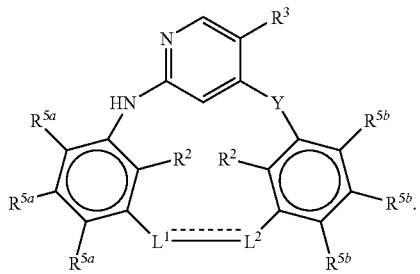

IIe

In some embodiments of the compounds of Formula IIe or pharmaceutically acceptable salts thereof, each $R^2$ is, independently, selected from H, F, Cl, Br, methyl, and $CF_3$. In some further embodiments, each $R^2$ is H.

In some embodiments of the compounds of Formula IIe or pharmaceutically acceptable salts thereof, Y is NH.

In some embodiments, the compounds of Formula I of the present invention have Formula IIIa:

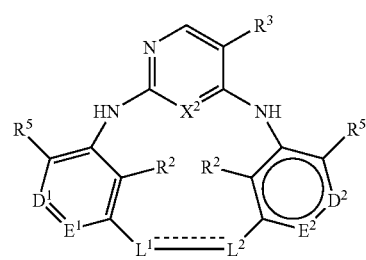

IIIa or are pharmaceutically acceptable salts thereof, wherein $D^1$, $E^1$, $D^2$, and $E^2$ are each, independently, $CR^5$ or N.

In some embodiments, the compounds of Formula I of the present invention have Formula IIIb:

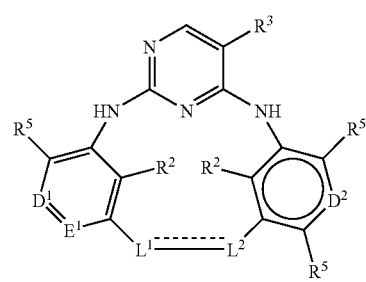

IIIb or are pharmaceutically acceptable salts thereof, wherein $D^1$, $E^1$, and $D^2$ are each, independently, $CR^5$ or N.

In some embodiments, the compounds of Formula I of the present invention have Formula IIIc:

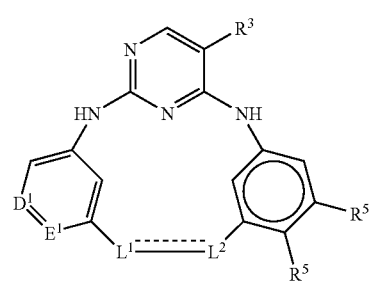

IIIc or are pharmaceutically acceptable salts thereof, wherein $D^1$ and $E^1$ are each, independently, $CR^5$ or N.

In some embodiments, the compounds of Formula I of the present invention have Formula IIId:

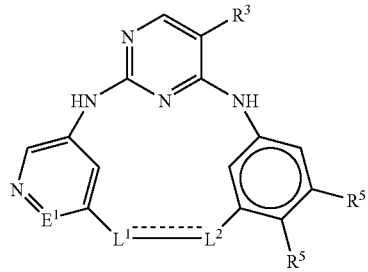

IIId or are pharmaceutically acceptable salts thereof, wherein $E^1$ is $CR^5$ or N.

In some embodiments, the compounds of Formula I of the present invention have Formula IIIe:

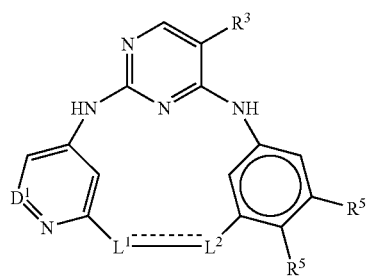

IIIe or are pharmaceutically acceptable salts thereof, wherein $D^1$ is $CR^5$ or N.

In some embodiments, the compounds of Formula I of the present invention have Formula IIIf:

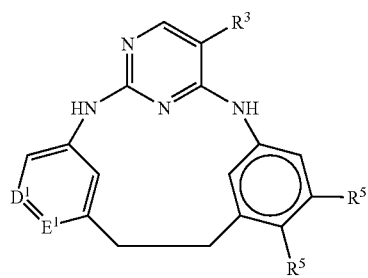

IIIf or are pharmaceutically acceptable salts thereof, wherein $D^1$ and $E^1$ are each, independently, $CR^5$ or N.

In some embodiments, the compounds of Formula I of the present invention have Formula IIIg:

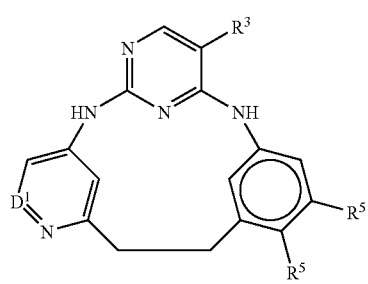

IIIg or are pharmaceutically acceptable salts thereof, wherein $D^1$ is $CR^5$ or N.

In some embodiments, the compounds of Formula I of the present invention have Formula IIIh:

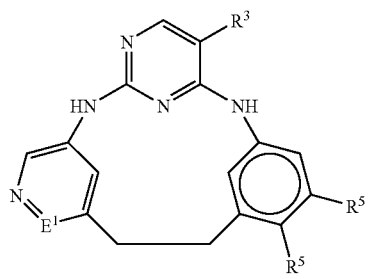

IIIh or are pharmaceutically acceptable salts thereof, wherein $E^1$ is $CR^5$ or N.

In some embodiments, the compounds of Formula I of the present invention have Formula IVa:

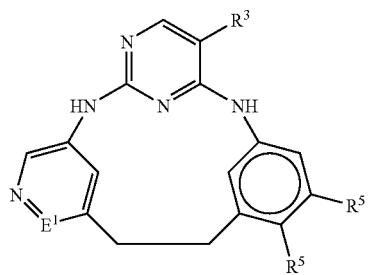

IVa or are pharmaceutically acceptable salts thereof.

In some embodiments, the compounds of Formula I of the present invention have Formula IVb:

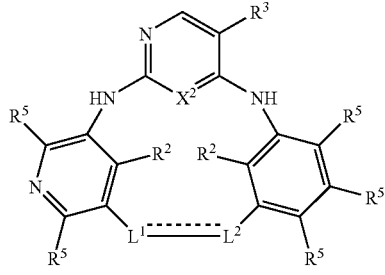

IVb or are pharmaceutically acceptable salts thereof.

In some embodiments, the compounds of Formula I of the present invention have Formula IVc:

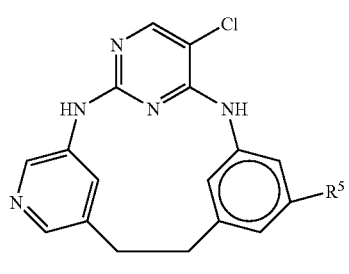

IVc or are pharmaceutically acceptable salts thereof.

In some embodiments, the compounds of Formula I of the present invention have Formula IVd:

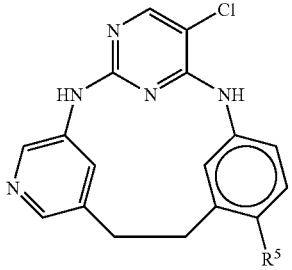

IVd or are pharmaceutically acceptable salts thereof.

In some embodiments, the compounds of Formula I of the present invention have Formula V:

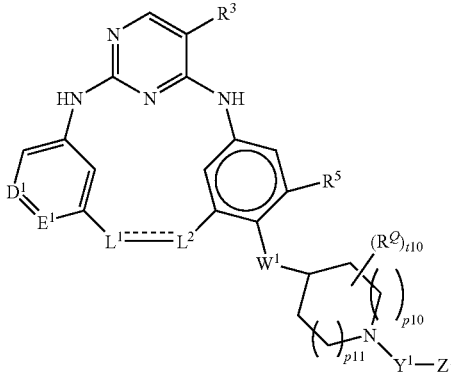

V or are pharmaceutically acceptable salts thereof, wherein:

$D^1$ and $E^1$, each, independently, $CR^5$ or N;

each $R^Q$ is independently selected from selected from $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, heterocycloalkylalkyl, halo, CN, $NO_2$, $OR^a$, $SR^a$, $SF_5$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^g)NR^cR^d$, $NR^cC(=NR^g)NR^cR^d$, $NR^cS(O)_2NR^cR^d$, $S(O)R^b$, $S(O)NR^cR^d$, $S(O)_2R^b$, $NR^cS(O)_2R^b$, and $S(O)_2NR^cR^d$;

p10 is 0 or 1;

p11 is 0 or 1; and t10 is 0, 1, 2, 3, 4, or 5.

In some embodiments, the compounds of Formula I of the present invention have Formula Va:

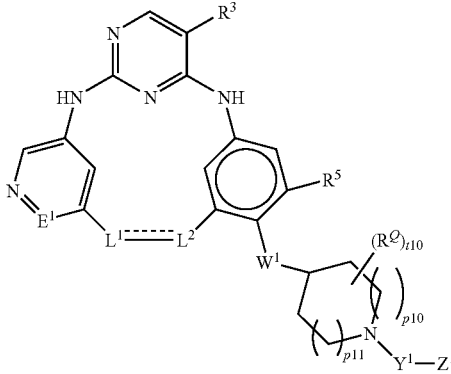

Va or are pharmaceutically acceptable salts thereof, wherein:

$E^1$ is $CR^5$ or N;

each $R^Q$ is independently selected from selected from $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, heterocycloalkylalkyl, halo, CN, $NO_2$, $OR^a$, $SR^a$, $SF_5$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^g)NR^cR^d$, $NR^cC(=NR^g)NR^cR^d$, $NR^cS(O)_2NR^cR^d$, $S(O)R^b$, $S(O)NR^cR^d$, $S(O)_2R^b$, $NR^cS(O)_2R^b$, and $S(O)_2NR^cR^d$;

p10 is 0 or 1;

p11 is 0 or 1; and t10 is 0, 1, 2, 3, 4, or 5.

In some embodiments of the compounds of Formula IIIa, IIIb, IIIc, IIId, IIIe, IIIf, IIIg, IIIh, IVa, IVb, IVc, IVd, V, or Va, or pharmaceutically acceptable salt thereof:

each $R^5$ is, independently, H, $Cy^1$, halo, $C_{1-6}$ alkyl, $C_{2-6}$ alkenyl, $C_{2-6}$ alkynyl, $C_{1-6}$ haloalkyl, halosulfanyl, CN, $NO_2$, $SF_5$, $OR^{a1}$, $SR^{a1}$, $C(O)R^{b1}$, $C(O)NR^{c1}R^{d1}$, $C(S)R^{b1}$, $C(S)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(S)R^{b1}$, $NR^{c1}C(S)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, or $-W^1-Q^1-Y^1-Z^1$;

or two adjacent $R^5$ on the same ring can link to form a fused cycloalkyl or fused heterocycloalkyl group, each optionally substituted by 1, 2, or 3 substituents independently selected from halo, $C_{1-6}$ alkyl, $C_{2-6}$ alkenyl, $C_{2-6}$ alkynyl, $C_{1-6}$ haloalkyl, arylalkyl, heteroarylalkyl, cycloalkylalkyl, heterocycloalkylalkyl, $Cy^1$, oxo, CN, $NO_2$, $OR^{a1}$, $SR^{a1}$, $C(O)R^{b1}$, $C(O)NR^{c1}R^{d1}$, $SF_5$, $C(S)R^{b1}$, $C(S)NR^{c1}R^{d1}$, $C(O)OR^{a1}$, $OC(O)R^{b1}$, $-W^1-Q^1-Y^1-Z^1$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(S)R^{b1}$, $NR^{c1}C(S)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)NR^{c1}R^{d1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$, wherein each of the $C_{1-6}$ alkyl, $C_{2-6}$ alkenyl, $C_{2-6}$ alkynyl, $C_{1-6}$ haloalkyl, arylalkyl, heteroarylalkyl, cycloalkylalkyl, or heterocycloalkylalkyl is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $Cy^1$, $-W^1-Q^1-Y^1-Z^1$, CN, $NO_2$, $SF_5$, $OR^{a1}$, $SR^{a1}$, $C(O)R^{b1}$, $C(O)NR^{c1}R^{d1}$, $C(O)OR^{a1}$, $OC(O)R^{b1}$, $OCH_2C(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)NR^{c1}R^{d1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$.

In some embodiments of the compounds of Formula IIIa, IIIb, IIIc, IIId, IIIe, IIIf, IIIg, IIIh, IVa, IVb, IVc, IVd, V, or Va, or pharmaceutically acceptable salt thereof:

each $R^5$ is, independently, H, $Cy^1$, halo, $C_{1-6}$ alkyl, $C_{2-6}$ alkenyl, $C_{2-6}$ alkynyl, $C_{1-6}$ haloalkyl, halosulfanyl, CN, $NO_2$, $SF_5$, $OR^{a1}$, $SR^{a1}$, $C(O)R^{b1}$, $C(O)NR^{c1}R^{d1}$, $C(S)R^{b1}$, $C(S)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(S)R^{b1}$, $NR^{c1}C(S)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, or $-W^1-Q^1-Y^1-Z^1$;

or two adjacent $R^5$ on the same ring can link to form a fused cycloalkyl or fused heterocycloalkyl group, each optionally substituted by 1, 2, or 3 substituents independently selected from halo, $C_{1-6}$ alkyl, $C_{2-6}$ alkenyl, $C_{2-6}$ alkynyl, $C_{1-6}$ haloalkyl, arylalkyl, heteroarylalkyl, cycloalkylalkyl, heterocycloalkylalkyl, $Cy^1$, CN, $NO_2$, $OR^{a1}$, $SR^{a1}$, $C(O)R^{b1}$, $C(O)NR^{c1}R^{d1}$, $SF_5$, $C(S)R^{b1}$, $C(S)NR^{c1}R^{d1}$, $C(O)OR^{a1}$, $OC(O)R^{b1}$, —$W^1$-$Q^1$-$Y^1$-$Z^1$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(S)R^{b1}$, $NR^{c1}C(S)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)NR^{c1}R^{d1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$, wherein each of the $C_{1-6}$ alkyl, $C_{2-6}$ alkenyl, $C_{2-6}$ alkynyl, $C_{1-6}$ haloalkyl, arylalkyl, heteroarylalkyl, cycloalkylalkyl, or heterocycloalkylalkyl is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $Cy^1$, -$W^1$-$Q^1$-$Y^1$-$Z^1$, CN, $NO_2$, $SF_5$, $OR^{a1}$, $SR^{a1}$, $C(O)R^{b1}$, $C(O)NR^{c1}R^{d1}$, $C(O)OR^{a1}$, $OC(O)R^{b1}$, $OCH_2C(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)NR^{c1}R^{d1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$.

In some embodiments, the compound of Formula IIIf is a compound of Formula IIIf-1:

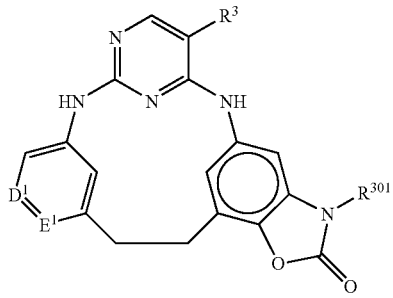

IIIf-1 wherein $R^{301}$ is selected from H, halo, $C_{1-6}$ alkyl, $C_{2-6}$ alkenyl, $C_{2-6}$ alkynyl, $C_{1-6}$ haloalkyl, arylalkyl, heteroarylalkyl, cycloalkylalkyl, heterocycloalkylalkyl, $Cy^1$, CN, $NO_2$, $OR^{a1}$, $SR^{a1}$, $C(O)R^{b1}$, $C(O)NR^{c1}R^{d1}$, $SF_5$, $C(S)R^{b1}$, $C(S)NR^{c1}R^{d1}$, $C(O)OR^{a1}$, $OC(O)R^{b1}$, -$W^1$-$Q^1$-$Y^1$-$Z^1$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(S)R^{b1}$, $NR^{c1}C(S)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)NR^{c1}R^{d1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$, wherein each of the $C_{1-6}$ alkyl, $C_{2-6}$ alkenyl, $C_{2-6}$ alkynyl, $C_{1-6}$ haloalkyl, arylalkyl, heteroarylalkyl, cycloalkylalkyl, or heterocycloalkylalkyl is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $Cy^1$, —$W^1$-$Q^1$-$Y^1$-$Z^1$, CN, $NO_2$, $SF_5$, $OR^{a1}$, $SR^{a1}$, $C(O)R^{b1}$, $C(O)NR^{c1}R^{d1}$, $C(O)OR^{a1}$, $OC(O)R^{b1}$, $OCH_2C(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)NR^{c1}R^{d1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$.

In some embodiments of compounds of Formula IIIf-1, $R^{301}$ is selected from H, $C_{1-6}$ alkyl, $C_{2-6}$ alkenyl, $C_{2-6}$ alkynyl, $C_{1-6}$ haloalkyl, arylalkyl, heteroarylalkyl, cycloalkylalkyl, heterocycloalkylalkyl, $Cy^1$, $C(O)R^{b1}$, $C(O)NR^{c1}R^{d1}$, $SF_5$, $C(S)R^{b1}$, $C(S)NR^{c1}R^{d1}$, $C(O)OR^{a1}$, $OC(O)R^{b1}$, -$W^1$-$Q^1$-$Y^1$-$Z^1$, $C(=NR^g)NR^{c1}R^{d1}$, $S(O)R^{b1}$, $S(O)NR^{c1}R^{d1}$, $S(O)_2R^{b1}$, and $S(O)_2NR^{c1}R^{d1}$, wherein each of the $C_{1-6}$ alkyl, $C_{2-6}$ alkenyl, $C_{2-6}$ alkynyl, $C_{1-6}$ haloalkyl, arylalkyl, heteroarylalkyl, cycloalkylalkyl, or heterocycloalkylalkyl is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $Cy^1$, -$W^1$-$Q^1$-$Y^1$-$Z^1$, CN, $NO_2$, $SF_5$, $OR^{a1}$, $SR^{a1}$, $C(O)R^{b1}$, $C(O)NR^{c1}R^{d1}$, $C(O)OR^{a1}$, $OC(O)R^{b1}$, $OCH_2C(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)NR^{c1}R^{d1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$. In some further embodiments, $R^{301}$ is selected from H, $C_{1-6}$ alkyl, and -$W^1$-$Q^1$-$Y^1$-$Z^1$, wherein the $C_{1-6}$ alkyl is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $Cy^1$, —$W^1$-$Q^1$-$Y^1$-$Z^1$, CN, $NO_2$, $SF_5$, $OR^{a1}$, $SR^{a1}$, $C(O)R^{b1}$, $C(O)NR^{c1}R^{d1}$, $C(O)OR^{a1}$, $OC(O)R^{b1}$, $OCH_2C(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)NR^{c1}R^{d1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$. In still further embodiments, $R^{301}$ is -$W^1$-$Q^1$-$Y^1$-$Z^1$.

In some embodiments of the compounds of Formula IIIa, IIIb, IIIc, IIId, IIIe, IIIf, IIIg, IIIh, IVa, IVb, IVc, IVd, V, or Va, or pharmaceutically acceptable salt thereof:

each $R^5$ is, independently, H, $Cy^1$, halo, $C_{1-6}$ alkyl, $C_{2-6}$ alkenyl, $C_{2-6}$ alkynyl, $C_{1-6}$ haloalkyl, halosulfanyl, CN, $NO_2$, $SF_5$, $OR^{a1}$, $SR^{a1}$, $C(O)R^{b1}$, $C(O)NR^{c1}R^{d1}$, $C(S)R^{b1}$, $C(S)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(S)R^{b1}$, $NR^{c1}C(S)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, or -$W^1$-$Q^1$-$Y^1$-$Z^1$;

or two adjacent $R^5$ on the same ring link to form a fused cycloalkyl or fused heterocycloalkyl group, each optionally substituted by 1, 2, or 3 substituents independently selected from halo, $C_{1-6}$ alkyl, $C_{2-6}$ alkenyl, $C_{2-6}$ alkynyl, $C_{1-6}$ haloalkyl, arylalkyl, heteroarylalkyl, cycloalkylalkyl, heterocycloalkylalkyl, halosulfanyl, $Cy^1$, CN, $NO_2$, $OR^{a1}$, $SR^{a1}$, $C(O)R^{b1}$, $C(O)NR^{c1}R^{d1}$, $C(S)R^{b1}$, $C(S)NR^{c1}R^{d1}$, $C(O)OR^{a1}$, $OC(O)R^{b1}$, -$W^1$-$Q^1$-$Y^1$-$Z^1$, $OC(O)NR^{c1}R^{d1}$, $NR^{c1}R^{d1}$, $NR^{c1}C(O)R^{b1}$.

In some embodiments of the compounds of Formula IIIa, IIIb, IIIc, IIId, IIIe, IIIf, IIIg, IIIh, IVa, IVb, IVc, IVd, V, or Va, or pharmaceutically acceptable salt thereof, at least one $R^5$ is -$W^1$-$Q^1$-$Y^1$-$Z^1$. In some further embodiments, at least one $R^5$ on the ring containing $A^2$, $B^2$, $D^2$, and $E^2$ is -$W^1$-$Q^1$-$Y^1$-$Z^1$.

In some embodiments of the compounds of Formula IIIa, IIIb, IIIc, IIId, IIIe, IIIf, IIIg, IIIh, IVa, IVb, IVc, IVd, V, or Va, or pharmaceutically acceptable salt thereof, at least one $R^5$ is $Cy^1$.

In some embodiments of the compounds of Formula IIIa, IIIb, IIIc, IIId, IIIe, IIIf, IIIg, IIIh, IVa, IVb, IVc, IVd, V, or Va, or pharmaceutically acceptable salt thereof, at least one $R^5$ is $Cy^1$ that is selected from aryl and heteroaryl, each optionally substituted with 1, 2, or 3 substituents independently selected from $C_{1-6}$ alkyl, $C(O)$—O—($C_{1-4}$ alkyl), $S(O)_2$—($C_{1-4}$ alkyl), and piperazinyl, wherein the piperazinyl is optionally substituted with 1 or 2 substituents independently selected from $C_{1-6}$ alkyl, arylalkyl, aryl, heteroaryl, $C(O)R^{b1}$, $S(O)_2R^{b1}$, $C(O)NR^{c1}R^{d1}$, and $S(O)_2NR^{c1}R^{d1}$.

In some embodiments of the compounds of Formula IIIa, IIIb, IIIc, IIId, IIIe, IIIf, IIIg, IIIh, IVa, IVb, IVc, IVd, V, or Va, or pharmaceutically acceptable salt thereof, at least one $R^5$ is -$Q^1$-$Y^1$-$Z^1$, —$(CH_2)$-$Q^1$-$Y^1$-$Z^1$, $O(CR^{11a}R^{11b})_{q1}C(O)$-$Q^1$-$Y^1$-$Z^1$, $O(CR^{11a}R^{11b})_{p2}$-$Q^1$-$Y^1$-$Z^1$, $(CR^{11a}R^{11b})_{p1}C(O)NR^e(CR^{11a}R^{11b})_{p2}$-$Q^1$-$Y^1$-$Z^1$, —$(CR^{11a}R^{11b})_{p1}C(O)NR^e$-$Q^1$-

$Y^1$-$Z^1$, —$NR^e(CR^{11a}R^{11b})_{p2}$-$Q^1$-$Y^1$-$Z^1$, $(CR^{11a}R^{11b})_{p2}$ $NR^eC(O)$-$Q^1$-$Y^1$-$Z^1$, —$(CR^{11a}R^{11b})_{p1}NR^e$-$Q^1$-$Y^1$-$Z^1$, —$(CR^{11a}R^{11b})_{p1}O(CR^{11a}R^{11b})_{p2}$-$Q^1$-$Y^1$-$Z^1$, —$(CR^{11a}R^{11b})_{p1}S(CR^{11a}R^{11b})_{p2}$-$Q^1$-$Y^1$-$Z^1$, —$(CR^{11a}R^{11b})_{p1}S(O)(CR^{11a}R^{11b})_{p2}$-$Q^1$-$Y^1$-$Z^1$, —$(CR^{11a}R^{11b})_{p1}S(O)_2(CR^{11a}R^{11b})_{p2}$-$Q^1$-$Y^1$-$Z^1$, —$(CR^{11a}R^{11b})_{p1}NR^e(CR^{11a}R^{11b})_{p2}$-$Q^1$-$Y^1$-$Z^1$, —$NR^eS(O)(CR^{11a}R^{11b})_{p1}$-$Q^1$-$Y^1$-$Z^1$, —$S(O)NR^e(CR^{11a}R^{11b})_{p2}$-$Q^1$-$Y^1$-$Z^1$, —$NR^eS(O)_2(CR^{11a}R^{11b})_{p1}$-$Q^1$-$Y^1$-$Z^1$, —$S(O)_2NR^e(CR^{11a}R^{11b})_{p2}$-$Q^1$-$Y^1$-$Z^1$, —$NR^eC(O)(CR^{11a}R^{11b})_{p1}$-$Q^1$-$Y^1$-$Z^1$, —$C(O)NR^e(CR^{11a}R^{11b})_{p2}$-$Q^1$-$Y^1$-$Z^1$, or —$NR^eC(O)NR^f(CR^{11a}R^{11b})_{p2}$-$Q^1$-$Y^1$-$Z^1$.

In some embodiments of the compounds of Formula IIIa, IIIb, IIIc, IIId, IIIe, IIIf, IIIg, IIIh, IVa, IVb, IVc, IVd, V, or Va, or pharmaceutically acceptable salt thereof, at least one $R^5$ is —$(CR^{11a}R^{11b})_{p1}$-$Q^1$-$Y^1$-$Z^1$, —$(CR^{11a}R^{11b})_{p1}O(CR^{11a}R^{11b})_{p2}$-$Q^1$-$Y^1$-$Z^1$, —$(CR^{11a}R^{11b})_{p1}S(CR^{11a}R^{11b})_{p2}$-$Q^1$-$Y^1$-$Z^1$, —$(CR^{11a}R^{11b})_{p1}S(O)(CR^{11a}R^{11b})_{p2}$-$Q^1$-$Y^1$-$Z^1$, —$(CR^{11a}R^{11b})_{p1}S(O)_2((CR^{11a}R^{11b})_{p2}$-$Q^1$-$Y^1$-$Z^1$, —$(CR^{11a}R^{11b})_{p1}NR^e(CR^{11a}R^{11b})_{p2}$-$Q^1$-$Y^1$-$Z^1$, —$NR^eS(O)(CR^{11a}R^{11b})_{p1}$-$Q^1$-$Y^1$-$Z^1$, —$S(O)NR^e(CR^{11a}R^{11b})_{p2}$-$Q^1$-$Y^1$-$Z^1$, —$NR^eS(O)_2(CR^{11a}R^{11b})_{p1}$-$Q^1$-$Y^1$-$Z^1$, —$S(O)_2NR^e(CR^{11a}R^{11b})_{p2}$-$Q^1$-$Y^1$-$Z^1$, —$NR^eC(O)(CR^{11a}R^{11b})_{p1}$-$Q^1$-$Y^1$-$Z^1$, —$C(O)NR^e(CR^{11a}R^{11b})_{p2}$-$Q^1$-$Y^1$-$Z^1$, or —$NR^eC(O)NR^f(CR^{11a}R^{11b})_{p2}$-$Q^1$-$Y^1$-$Z^1$. In some further embodiments, each $Q^1$ is independently selected from cycloalkyl and heterocycloalkyl, each optionally substituted by 1, 2, 3, 4, or 5 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^a$, $C(O)NR^cR^d$, amino, $C_{1-6}$ alkylamino and $C_{2-8}$ dialkylamino. In yet further embodiments, each $Q^1$ is independently selected from cyclopentyl, cyclohexyl, pyrrolidinyl, and piperidinyl, each optionally substituted by 1, 2, 3, 4, or 5 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^a$, $C(O)NR^cR^d$, amino, $C_{1-6}$ alkylamino and $C_{2-8}$ dialkylamino.

In some embodiments of the compounds of Formula IIIa, IIIb, IIIc, IIId, IIIe, IIIf, IIIg, IIIh, IVa, IVb, IVc, IVd, V, or Va, or pharmaceutically acceptable salt thereof, at least one $R^5$ is —$(CR^{11a}R^{11b})_{p1}O(CR^{11a}R^{11b})_{p2}$-$Q^1$-$Y^1$-$Z^1$, —$(CR^{11a}R^{11b})_{p1}S(CR^{11a}R^{11b})_{p2}$-$Q^1$-$Y^1$-$Z^1$, —$(CR^{11a}R^{11b})_{p1}S(O)(CR^{11a}R^{11b})_{p2}$-$Q^1$-$Y^1$-$Z^1$, —$(CR^{11a}R^{11b})_{p1}S(O)_2((CR^{11a}R^{11b})_{p2}$-$Q^1$-$Y^1$-$Z^1$, —$(CR^{11a}R^{11b})_{p1}NR^e(CR^{11a}R^{11b})_{p2}$-$Q^1$-$Y^1$-$Z^1$, —$NR^eS(O)(CR^{11a}R^{11b})_{p1}$-$Q^1$-$Y^1$-$Z^1$, —$S(O)NR^e(CR^{11a}R^{11b})_{p2}$-$Q^1$-$Y^1$-$Z^1$, —$NR^eS(O)_2(CR^{11a}R^{11b})_{p1}$-$Q^1$-$Y^1$-$Z^1$, —$S(O)_2NR^e(CR^{11a}R^{11b})_{p2}$-$Q^1$-$Y^1$-$Z^1$, —$NR^eC(O)(CR^{11a}R^{11b})_{p1}$-$Q^1$-$Y^1$-$Z^1$, —$C(O)NR^e(CR^{11a}R^{11b})_{p2}$-$Q^1$-$Y^1$-$Z^1$, or —$NR^eC(O)NR^f(CR^{11a}R^{11b})_{p2}$-$Q^1$-$Y^1$-$Z^1$. In some further embodiments, each $Q^1$ is independently selected from cycloalkyl and heterocycloalkyl, each optionally substituted by 1, 2, 3, 4, or 5 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^a$, $C(O)NR^cR^d$, amino, $C_{1-6}$ alkylamino and $C_{2-8}$ dialkylamino. In yet further embodiments, each $Q^1$ is independently selected from cyclopentyl, cyclohexyl, pyrrolidinyl, and piperidinyl, each optionally substituted by 1, 2, 3, 4, or 5 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^a$, $C(O)NR^cR^d$, amino, $C_{1-6}$ alkylamino and $C_{2-8}$ dialkylamino.

In some embodiments of the compounds of Formula IIIa, IIIb, IIIc, IIId, IIIe, IIIf, IIIg, IIIh, IVa, IVb, IVc, IVd, V, or Va, or pharmaceutically acceptable salt thereof, at least one $R^5$ is -$W^6$-$Q^1$-$Y^1$-$Z^1$. In some further embodiments, at least one $R^5$ on the ring containing $A^2$, $B^2$, $D^2$, and $E^2$ is -$W^6$-$Q^1$-$Y^1$-$Z^1$.

In some embodiments of the compounds of Formula IIIa, IIIb, IIIc, IIId, IIIe, IIIf, IIIg, IIIh, IVa, IVb, IVc, IVd, V, or Va, or pharmaceutically acceptable salt thereof, at least one $R^5$ is —$(CR^{11a}R^{11b})_{p1}S(CR^{11a}R^{11b})_{p2}$-$Q^1$-$Y^1$-$Z^1$, —$(CR^{11a}R^{11b})_{p1}S(O)(CR^{11a}R^{11b})_{p2}$-$Q^1$-$Y^1$-$Z^1$, —$(CR^{11a}R^{11b})_{p1}S(O)_2(CR^{11a}R^{11b})_{p2}$-$Q^1$-$Y^1$-$Z^1$, —$(CR^{11a}R^{11b})_{p1}S(O)NR^e(CR^{11a}R^{11b})_{p2}$-$Q^1$-$Y^1$-$Z^1$, —$(CR^{11a}R^{11b})_{p2}NR^eS(O)(CR^{11a}R^{11b})_{p1}$-$Q^1$-$Y^1$-$Z^1$, —$(CR^{11a}R^{11b})_{p1}S(O)_2NR^e(CR^{11a}R^{11b})_{p2}$-$Q^1$-$Y^1$-$Z^1$, or —$(CR^{11a}R^{11b})_{p2}NR^eS(O)_2(CR^{11a}R^{11b})_{p1}$-$Q^1$-$Y^1$-$Z^1$.

In some embodiments of the compounds of Formula IIIa, IIIb, IIIc, IIId, IIIe, IIIf, IIIg, IIIh, IVa, IVb, IVc, IVd, V, or Va, or pharmaceutically acceptable salt thereof, each $Q^1$ is independently selected from cyclopropyl, cyclobutyl, cyclopentyl, cyclohexyl, azetidinyl, pyrrolidinyl, piperidinyl, piperazinyl, (1H)-hexahydropyrrolo[1,2-a]pyrazin-2-yl, and (8H)-5,6-dihydro[1,2,4]triazolo[4,3-a]pyrazin-7-yl, each optionally substituted by 1, 2, 3, 4, or 5 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^a$, $C(O)NR^cR^d$, amino, $C_{1-6}$ alkylamino and $C_{2-8}$ dialkylamino. In some further embodiments, each $Q^1$ is independently selected from cyclopropyl, cyclobutyl, cyclopentyl, and cyclohexyl, each optionally substituted by 1, 2, 3, 4, or 5 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^a$, $C(O)NR^cR^d$, amino, $C_{1-6}$ alkylamino and $C_{2-8}$ dialkylamino. In other further embodiments, each $Q^1$ is independently selected from azetidinyl, pyrrolidinyl, piperidinyl, and piperazinyl, each optionally substituted by 1, 2, 3, 4, or 5 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^a$, $C(O)NR^cR^d$, amino, $C_{1-6}$ alkylamino and $C_{2-8}$ dialkylamino.

In some embodiments of the compounds of Formula IIIa, IIIb, IIIc, IIId, IIIe, IIIf, IIIg, IIIh, IVa, IVb, IVc, IVd, V, or Va, or pharmaceutically acceptable salt thereof, each $Q^1$ is independently selected from cyclopropyl, cyclobutyl, cyclopentyl, cyclohexyl, azetidinyl, pyrrolidinyl, piperidinyl, and piperazinyl, each optionally substituted by 1, 2, 3, 4, or 5 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^a$, $C(O)NR^cR^d$, amino, $C_{1-6}$ alkylamino and $C_{2-8}$ dialkylamino. In some further embodiments, each $Q^1$ is independently selected from cyclopropyl, cyclobutyl, cyclopentyl, and cyclohexyl, each optionally substituted by 1, 2, 3, 4, or 5 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^a$, $C(O)NR^cR^d$, amino, $C_{1-6}$ alkylamino and $C_{2-8}$ dialkylamino. In other further embodiments, each $Q^1$ is independently selected from azetidinyl, pyrrolidinyl, piperidinyl, and piperazinyl, each optionally substituted by 1, 2, 3, 4, or 5 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^a$, $C(O)NR^cR^d$, amino, $C_{1-6}$ alkylamino and $C_{2-8}$ dialkylamino.

In some embodiments of the compounds of Formula IIIa, IIIb, IIIc, IIId, IIIe, IIIf, IIIg, IIIh, IVa, IVb, IVc, IVd, V, or Va, or pharmaceutically acceptable salt thereof, each $Y^1$ is independently selected from absent, $C_{1-6}$ alkylenyl, $(CR^{12a}R^{12b})_{p3}O(CR^{12a}R^{12b})_{p4}$, $(CR^{12a}R^{12b})_{p3}S(CR^{12a}R^{12b})_{p4}$, $(CR^{12a}R^{12b})_{p3}NR^e(CR^{12a}R^{12b})_{p4}$, $(CR^{12a}R^{12b})_{p3}C(O)(CR^{12a}R^{12b})_{p4}$, $(CR^{12a}R^{12b})_{p3}C(O)O(CR^{12a}R^{12b})_{p4}$, $C(S)NR^e$, $(CR^{12a}R^{12b})_{p3}C(O)NR^e(CR^{12a}R^{12b})_{p4}$, $(CR^{12a}R^{12b})_{p3}S(O)_2(CR^{12a}R^{12b})_{p4}$, $(CR^{12a}R^{12b})_{p3}S(O)_2NR^e(CR^{12a}R^{12b})_{p4}$, and $(CR^{12a}R^{12b})_{p3}NR^eC(O)NR^f(CR^{12a}R^{12b})_{p4}$.

In some embodiments of the compounds of Formula IIIa, IIIb, IIIc, IIId, IIIe, IIIf, IIIg, IIIh, IVa, IVb, IVc, IVd, V, or Va, or pharmaceutically acceptable salt thereof, each $Y^1$ is independently selected from absent, $(CH_2)$, $(CR^{12a}R^{12b})_{p3}O(CR^{12a}R^{12b})_{p4}$, $(CR^{12a}R^{12b})_{p3}S(CR^{12a}R^{12b})_{p4}$, $(CR^{12a}R^{12b})_{p3}NR^e(CR^{12a}R^{12b})_{p4}$, $(CR^{12a}R^{12b})_{p3}C(O)(CR^{12a}R^{12b})_{p4}$, $(CR^{12a}R^{12b})_{p3}C(O)O(CR^{12a}R^{12b})_{p4}$, $C(S)NR^e$, $(CR^{12a}R^{12b})_{p3}C(O)NR^e(CR^{12a}R^{12b})_{p4}$, $(CR^{12a}R^{12b})_{p3}S(O)_2(CR^{12a}R^{12b})_{p4}$, $(CR^{12a}R^{12b})_{p3}S(O)_2NR^e(CR^{12a}R^{12b})_{p4}$, and $(CR^{12a}R^{12b})_{p3}NR^eC(O)NR^f(CR^{12a}R^{12b})_{p4}$.

In some embodiments of the compounds of Formula IIIa, IIIb, IIIc, IIId, IIIe, IIIf, IIIg, IIIh, IVa, IVb, IVc, IVd, V, or Va, or pharmaceutically acceptable salt thereof, each $Y^1$ is independently selected from absent, $C_{1-6}$ alkylenyl, $(CR^{12a}R^{12b})_{p3}C(O)(CR^{12a}R^{12b})_{p4}$, $(CR^{12a}R^{12b})_{p3}C(O)O(CR^{12a}R^{12b})_{p4}$, $C(S)NR^e$, $(CR^{12a}R^{12b})_{p3}C(O)NR^e(CR^{12a}R^{12b})_{p4}$, $(CR^{12a}R^{12b})_{p3}S(O)_2(CR^{12a}R^{12b})_{p4}$, and $(CR^{12a}R^{12b})_{p3}NR^eC(O)NR^f(CR^{12a}R^{12b})_{p4}$.

In some embodiments of the compounds of Formula IIIa, IIIb, IIIc, IIId, IIIe, IIIf, IIIg, IIIh, IVa, IVb, IVc, IVd, V, or Va, or pharmaceutically acceptable salt thereof, each $Y^1$ is independently selected from absent, $(CH_2)$, $(CR^{12a}R^{12b})_{p3}C(O)(CR^{12a}R^{12b})_{p4}$, $(CR^{12a}R^{12b})_{p3}C(O)O(CR^{12a}R^{12b})_{p4}$, $C(S)NR^e$, $(CR^{12a}R^{12b})_{p3}C(O)NR^e(CR^{12a}R^{12b})_{p4}$, $(CR^{12a}R^{12b})_{p3}S(O)_2(CR^{12a}R^{12b})_{p4}$, and $(CR^{12a}R^{12b})_{p3}NR^eC(O)NR^f(CR^{12a}R^{12b})_{p4}$.

In some embodiments of the compounds of Formula IIIa, IIIb, IIIc, IIId, IIIe, IIIf, IIIg, IIIh, IVa, IVb, IVc, IVd, V, or Va, or pharmaceutically acceptable salt thereof, each $Y^1$ is independently selected from absent, $(CR^{12a}R^{12b})_{p3}O(CR^{12a}R^{12b})_{p4}$, $(CR^{12a}R^{12b})_{p3}S(CR^{12a}R^{12b})_{p4}$, $(CR^{12a}R^{12b})_{p3}NR^e(CR^{12a}R^{12b})_{p4}$, $(CR^{12a}R^{12b})_{p3}C(O)(CR^{12a}R^{12b})_{p4}$, $(CR^{12a}R^{12b})_{p3}C(O)NR^e(CR^{12a}R^{12b})_{p4}$, $(CR^{12a}R^{12b})_{p3}S(O)_2(CR^{12a}R^{12b})_{p4}$, $(CR^{12a}R^{12b})_{p3}S(O)_2NR^e(CR^{12a}R^{12b})_{p4}$, and $(CR^{12a}R^{12b})_{p3}NR^eC(O)NR^f(CR^{12a}R^{12b})_{p4}$.

In some embodiments of the compounds of Formula IIIa, IIIb, IIIc, IIId, IIIe, IIIf, IIIg, IIIh, IVa, IVb, IVc, IVd, V, or Va, or pharmaceutically acceptable salt thereof, each $Z^1$ is independently selected from H, OH, CN, $C_{1-6}$ alkyl, aryl, cycloalkyl, heteroaryl, and heterocycloalkyl, wherein each of the $C_{1-6}$ alkyl, aryl, cycloalkyl, heteroaryl, and heterocycloalkyl is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $NR^cS(O)_2R^b$, $NR^cS(O)_2S(O)_2NR^cR^d$, $S(O)R^b$, $S(O)NR^cR^d$, $S(O)_2R^b$, and $S(O)_2NR^cR^d$.

In some embodiments of the compounds of Formula IIIa, IIIb, IIIc, IIId, IIIe, IIIf, IIIg, IIIh, IVa, IVb, IVc, IVd, V, or Va, or pharmaceutically acceptable salt thereof, each $Z^1$ is independently selected from $C_{1-6}$ alkyl, $C_{2-6}$ alkenyl, $C_{2-6}$ alkynyl, $C_{1-6}$ haloalkyl, aryl, cycloalkyl, heteroaryl and heterocycloalkyl, each optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $NR^cS(O)_2R^b$, $NR^cS(O)_2S(O)_2NR^cR^d$, $S(O)R^b$, $S(O)NR^cR^d$, $S(O)_2R^b$, and $S(O)_2NR^cR^d$.

In some embodiments of the compounds of Formula IIIa, IIIb, IIIc, IIId, IIIe, IIIf, IIIg, IIIh, IVa, IVb, IVc, IVd, V, or Va, or pharmaceutically acceptable salt thereof, each $Z^1$ is independently selected from $C_{1-6}$ alkyl, $C_{1-6}$ haloalkyl, aryl, cycloalkyl, heteroaryl and heterocycloalkyl, each optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $NR^cS(O)_2R^b$, $NR^cS(O)_2S(O)_2NR^cR^d$, $S(O)R^b$, $S(O)NR^cR^d$, $S(O)_2R^b$, and $S(O)_2NR^cR^d$.

In some embodiments of the compounds of Formula IIIa, IIIb, IIIc, IIId, IIIe, IIIf, IIIg, IIIh, IVa, IVb, IVc, IVd, V, or Va, or pharmaceutically acceptable salt thereof, each $Z^1$ is independently selected from aryl, cycloalkyl, heteroaryl and heterocycloalkyl, each optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $NR^cS(O)_2R^b$, $NR^cS(O)_2S(O)_2NR^cR^d$, $S(O)R^b$, $S(O)NR^cR^d$, $S(O)_2R^b$, and $S(O)_2NR^cR^d$.

In some embodiments, the compounds of Formula I of the present invention have Formula Ia:

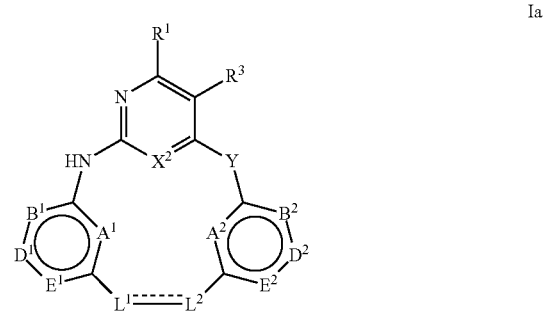

Ia or are pharmaceutically acceptable salts thereof, wherein $B^1$, $B^2$, $D^1$, $D^2$, $E^1$, and $E^2$ are each, independently, selected from $CR^5$ and N; and $A^1$ and $A^2$, are each, independently, selected from $CR^2$ and N.

In some embodiments of compounds of Formula Ia or pharmaceutically acceptable salts thereof, $X^2$ is N.

In some embodiments of compounds of Formula Ia or pharmaceutically acceptable salts thereof, $X^2$ is $CR^2$. In some further embodiments, $R^3$ is halo. In yet further embodiments, $R^3$ is F, Cl, or Br. In still further embodiments, $R^3$ is Cl.

In some embodiments of compounds of Formula Ia or pharmaceutically acceptable salts thereof, $B^1$, $B^2$, $D^1$, $D^2$, $E^1$, and $E^2$ are each, independently, selected from $CR^5$; and $A^1$ and $A^2$, are each, independently, selected from $CR^2$.

In some embodiments of compounds of Formula Ia or pharmaceutically acceptable salts thereof, the ring containing $A^1$, $B^1$, $D^1$, and $E^1$ is a benzene ring, and the benzene ring can be substituted or unsubstituted.

In some embodiments of compounds of Formula Ia or pharmaceutically acceptable salts thereof, the ring containing $A^1$, $B^1$, $D^1$, and $E^1$ is selected from pyridine and pyrimidine (which can be optionally substituted, for example by three $R^5$ and one $R^2$). In some embodiments, the ring is pyridine. In some embodiments, the ring is pyrimidine.

In some embodiments of compounds of Formula Ia or pharmaceutically acceptable salts thereof wherein the ring containing $A^1$, $B^1$, $D^1$, and $E^1$ is a pyridine ring, $D^1$ is N. In some embodiments of compounds of Formula Ia or pharmaceutically acceptable salts thereof wherein the ring containing $A^1$, $B^1$, $D^1$, and $E^1$ is a pyridine ring, $E^1$ is N. In some embodiments of compounds of Formula Ia or pharmaceutically acceptable salts thereof wherein the ring containing $A^1$, $B^1$, $D^1$, and $E^1$ is a pyridine ring, $B^1$ is N. In some embodiments of compounds of Formula Ia or pharmaceutically acceptable salts thereof wherein the ring containing $A^1$, $B^1$, $D^1$, and $E^1$ is a pyridine ring, $A^1$ is N.

In some embodiments of compounds of Formula Ia or pharmaceutically acceptable salts thereof, $B^2$, $D^2$, and $E^2$ are each, independently, selected from $CR^5$; and $A^2$ is $CR^2$.

In some embodiments of compounds of Formula Ia or pharmaceutically acceptable salts thereof, the ring containing $A^2$, $B^2$, $D^2$, and $E^2$ is selected from pyridine and pyrimidine (which can be optionally substituted, for example by three $R^5$ and one $R^2$). In some embodiments, the ring is pyridine. In some embodiments, the ring is pyrimidine.

In some embodiments of compounds of Formula Ia or pharmaceutically acceptable salts thereof, $R^1$ is selected from H, halo, $C_{1-6}$ alkyl, and $C_{1-6}$ haloalkyl. In some further embodiments, $R^1$ is H.

In some embodiments of compounds of Formula Ia or pharmaceutically acceptable salts thereof, each $R^2$ is, independently, selected from H, halo, $C_{1-6}$ alkyl, and $C_{1-6}$ haloalkyl. In some further embodiments, each $R^2$ is, independently, selected from H, halo, $C_{1-3}$ alkyl, and $C_{1-3}$ haloalkyl. In yet further embodiments, each $R^2$ is, independently, selected from H, F, Cl, Br, methyl, ethyl, 1-propyl, 2-propyl, and $C_{1-2}$ haloalkyl. In still further embodiments, each $R^2$ is, independently, selected from H, F, Cl, Br, methyl, ethyl, 1-propyl, 2-propyl, and $CF_3$. In some embodiments, each $R^2$ is, independently, selected from H, F, Cl, Br, methyl, and $CF_3$.

In some embodiments of compounds of Formula Ia or pharmaceutically acceptable salts thereof, each $R^2$ is, independently, selected from H, $CH_3$, $CF_3$, and halo. In some further embodiments, each $R^2$ is, independently, selected from H, F, Cl, methyl, and $CF_3$. In yet further embodiments, each $R^2$ is, independently, selected from H, F, and Cl.

In some embodiments of compounds of Formula Ia or pharmaceutically acceptable salts thereof, each $R^2$ is, independently, selected from H, $CH_3$ and $CF_3$. In some further embodiments, each $R^2$ is H, or $CH_3$. In yet further embodiments, each $R^2$ is H.

In some embodiments of compounds of Formula Ia or pharmaceutically acceptable salts thereof, $R^3$ is selected from H, halo, $C_{1-6}$ alkyl, and $C_{1-6}$ haloalkyl. In some embodiments, $R^3$ is selected from H, halo, $C_{1-3}$ alkyl, and $C_{1-3}$ haloalkyl. In some embodiments, $R^3$ is $C_{1-6}$ alkyl. In some embodiments, $R^3$ is $C_{1-3}$ alkyl. In some embodiments, $R^3$ is H, $CH_3$ or $CF_3$. In some embodiments, $R^3$ is H. In some embodiments, $R^3$ is $CH_3$. In some embodiments, $R^3$ is $CF_3$. In some embodiments, $R^3$ is halo. In some embodiments $R^3$ is chloro. In some embodiments, $R^3$ is bromo.

In some embodiments of compounds of Formula Ia or pharmaceutically acceptable salts thereof, $R^3$ is $SF_5$.

In some embodiments of compounds of Formula Ia or pharmaceutically acceptable salts thereof, $R^3$ is selected from amino, $C_{1-4}$ alkylamino, and $C_{2-8}$ dialkylamino. In some further embodiments, $R^3$ is selected from $NH_2$, $NH(C_{1-3}$ alkyl), and $N(C_{1-3}$ alkyl)$_2$.

In some embodiments of compounds of Formula Ia or pharmaceutically acceptable salts thereof:
$R^1$ is selected from H, halo, $C_{1-6}$ alkyl, and $C_{1-6}$ haloalkyl; and
$R^3$ is selected from H, halo, $C_{1-6}$ alkyl, and $C_{1-6}$ haloalkyl.

In some embodiments of compounds of Formula Ia or pharmaceutically acceptable salts thereof:
$R^1$ is H; and
$R^3$ is selected from H, halo, $C_{1-6}$ alkyl, and $C_{1-6}$ haloalkyl.

In some embodiments of compounds of Formula Ia or pharmaceutically acceptable salts thereof:
$R^1$ is H; and
$R^3$ is selected from H, halo, $C_{1-3}$ alkyl, and $C_{1-3}$ haloalkyl.

In some embodiments of compounds of Formula Ia or pharmaceutically acceptable salts thereof:
$R^1$ is H; and
$R^3$ is selected from H, F, Cl, Br, $C_{1-3}$ alkyl, and $CF_3$.

In some embodiments of compounds of Formula Ia or pharmaceutically acceptable salts thereof, each $R^5$ is independently selected from H, halo, $C_{1-6}$ alkyl, $C_{1-6}$ haloalkyl, $Cy^1$, -$W^1$-$Q^1$-$Y^1$-$Z^1$, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2NR^{c1}R^{d1}$, $S(O)_2R^{b1}$, $NR^{c1}S(O)_2R^{b1}$, and $S(O)_2NR^{c1}R^{d1}$.

In some embodiments of compounds of Formula Ia or pharmaceutically acceptable salts thereof, each $R^5$ is independently selected from H, halo, $C_{1-6}$ alkyl, $C_{1-6}$ haloalkyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2NR^{c1}R^{d1}$, $S(O)_2R^{b1}$, $NR^{c1}S(O)_2R^{b1}$, and $S(O)_2NR^{c1}R^{d1}$.

In some embodiments of compounds of Formula Ia or pharmaceutically acceptable salts thereof, each $R^5$ is independently selected from H, halo, $C_{1-6}$ alkyl, $C_{1-6}$ haloalkyl, CN, $NO_2$, $OR^{a1}$, $NR^{c1}R^{d1}$, $NR^{c1}S(O)_2R^{b1}$, $NR^{c1}S(O)_2NR^{c1}R^{d1}$, $S(O)R^{b1}$, $S(O)_2R^{b1}$ and $S(O)_2NR^{c1}R^{d1}$.

In some embodiments of compounds of Formula Ia or pharmaceutically acceptable salts thereof, at least one $R^5$ is -$W^1$-$Q^1$-$Y^1$-$Z^1$.

In some embodiments of compounds of Formula Ia or pharmaceutically acceptable salts thereof, at least one $R^5$ is $Cy^1$.

In some embodiments of compounds of Formula Ia or pharmaceutically acceptable salts thereof, two adjacent $R^5$ on the same ring can link to form a fused cycloalkyl or fused heterocycloalkyl group, each optionally substituted by 1, 2, or 3 substituents independently selected from halo, $C_{1-6}$ alkyl, $C_{1-6}$ haloalkyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2NR^{c1}R^{d1}$, $S(O)_2R^{b1}$, $NR^{c1}S(O)_2R^{b1}$, and $S(O)_2NR^{c1}R^{d1}$.

In some embodiments of compounds of Formula Ia or pharmaceutically acceptable salts thereof, two adjacent $R^5$ on the ring containing $A^1$, $B^1$, $D^1$, and $E^1$ can link to form a fused cycloalkyl or fused heterocycloalkyl group, each optionally substituted by 1, 2, or 3 substituents independently selected from halo, $C_{1-6}$ alkyl, $C_{1-6}$ haloalkyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2NR^{c1}R^{d1}$, $S(O)_2R^{b1}$, $NR^{c1}S(O)_2R^{b1}$, and $S(O)_2NR^{c1}R^{d1}$.

In some embodiments of compounds of Formula Ia or pharmaceutically acceptable salts thereof, two adjacent $R^5$ on the ring containing $A^2$, $B^2$, $D^2$, and $E^2$ can link to form a fused cycloalkyl or fused heterocycloalkyl group, each optionally substituted by 1, 2, or 3 substituents independently selected from halo, $C_{1-6}$ alkyl, $C_{1-6}$ haloalkyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2NR^{c1}R^{d1}$, $S(O)_2R^{b1}$, $NR^{c1}S(O)_2R^{b1}$, and $S(O)_2NR^{c1}R^{d1}$.

In some embodiments of compounds of Formula Ia or pharmaceutically acceptable salts thereof, Y is $NR^4$. In some embodiments, Y is NH or $N(C_{1-3}$ alkyl). In some embodiments, Y is NH. In some embodiments, Y is $N(C_{1-3}$ alkyl). In some embodiments, Y is $N$—$CH_3$.

In some embodiments of compounds of Formula Ia or pharmaceutically acceptable salts thereof, $L^1$ and $L^2$ are each, independently, selected from a bond, —$(CR^7R^8)_n$—, —O—$(CR^7R^8)_m$—$CR^{10}$=, —S—$(CR^7R^8)_m$—$CR^{10}$=, —$(CR^7R^8)_m$—$CR^{10}$=, —$(CR^7R^8)_m$—$NR^9$—, —$(CR^7R^8)_m$—O—, —$(CR^7R^8)_m$—S—, —$(CR^7R^8)_m$—S(O)—, —$(CR^7R^8)_m$—S(O)$_2$—, —$(CR^7R^8)_m$—C(O)—, —C(O)$NR^9$—, —$(CR^7R^8)_m$—C(O)O—, —$(CR^7R^8)_m$—$NR^9$C(O)$NR^9$—, —$(CR^7R^8)_m$—OC(O)$NR^9$—, —$(CR^7R^8)_m$—$NR^9$C(O)O—, —$(CR^7R^8)_m$—$NR^9$—S(O)$_2NR^9$—, —$(CR^7R^8)_m$—S(O)$NR^9$—, and —$(CR^7R^8)_m$—S(O)$_2NR^9$—.

In some embodiments of compounds of Formula Ia or pharmaceutically acceptable salts thereof, $L^1$ and $L^2$ are each, independently, selected from a bond, —$(CR^7R^8)_n$—, —$(CR^7R^8)_m$—$CR^{10}$=, —O—$(CR^7R^8)_m$—$CR^{10}$=, —S—$(CR^7R^8)_m$—$CR^{10}$=, —$(CR^7R^8)_m$—$NR^9$—, —$(CR^7R^8)_m$—O—, —$(CR^7R^8)_m$—S—, —$(CR^7R^8)_m$—S(O)—, —$(CR^7R^8)_m$—S(O)$_2$—, —$(CR^7R^8)_m$—C(O)—, —C(O)$NR^9$—, —$(CR^7R^8)_m$—C(O)O—, —$(CR^7R^8)_m$—S(O)$NR^9$—, and —$(CR^7R^8)_m$—S(O)$_2NR^9$—.

In some embodiments of compounds of Formula Ia or pharmaceutically acceptable salts thereof, $L^1$ and $L^2$ together form —$(CR^7R^8)_m$—$CR^{10}$=$CR^{10}$—$(CR^7R^8)_m$—, —O—$(CR^7R^8)_m$—$CR^{10}$=$CR^{10}$—$(CR^7R^8)_m$—, —S—$(CR^7R^8)_m$—$CR^{10}$=$CR^{10}$—$(CR^7R^8)_m$—, —O—$(CR^7R^8)_m$—$CR^{10}$=$CR^{10}$—$(CR^7R^8)_m$—O—, —O—$(CR^7R^8)_m$—$CR^{10}$=$CR^{10}$—$(CR^7R^8)_m$—S—, or —S—$(CR^7R^8)_m$—$CR^{10}$=$CR^{10}$—$(CR^7R^8)_m$—S—.

In some embodiments of compounds of Formula Ia or pharmaceutically acceptable salts thereof, $L^1$ and $L^2$ are each, independently, selected from a bond, —$(CR^7R^8)_n$—, —$(CR^7R^8)_m$—$CR^{10}$=, —$(CR^7R^8)_m$—$NR^9$—, —$(CR^7R^8)_m$—O—, —$(CR^7R^8)_m$—S—, —$(CR^7R^8)_m$—S(O)—, —$(CR^7R^8)_m$—S(O)$_2$—, —$(CR^7R^8)_m$—C(O)—, —C(O)$NR^9$—, —$(CR^7R^8)_m$—C(O)O—, —$(CR^7R^8)_m$—S(O)$NR^9$—, and —$(CR^7R^8)_m$—S(O)$_2NR^9$—.

In some embodiments of compounds of Formula Ia or pharmaceutically acceptable salts thereof, $L^1$ and $L^2$ are each, independently, selected from a bond, —$(CR^7R^8)_n$—, and —$(CR^7R^8)_m$—$CR^{10}$=.

In some embodiments of compounds of Formula Ia or pharmaceutically acceptable salts thereof, $L^1$ and $L^2$ together form —$(CR^7R^8)_m$—$CR^{10}$=$CR^{10}$—$(CR^7R^8)_m$— or —$(CR^7R^8)_m$—$(CR^7R^8)$—.

In some embodiments of compounds of Formula Ia or pharmaceutically acceptable salts thereof, $L^1$ and $L^2$ together form —$CR^{10}$=$CR^{10}$—, —$(CR^7R^8)_2$—, or —$(CR^7R^8)_3$—. In some further embodiments, $L^1$ and $L^2$ together form —$CR^{10}$=$CR^{10}$— or —$(CR^7R^8)_2$—. In yet further embodiments, $L^1$ and $L^2$ together form —CH=CH— or —$CH_2$—$CH_2$—. In some embodiments, $L^1$ and $L^2$ together form —CH=CH—. In some embodiments, $L^1$ and $L^2$ together form —$CH_2$—$CH_2$—.

In some embodiments of compounds of Formula Ia or pharmaceutically acceptable salts thereof, $L^1$ and $L^2$ together form —$CR^{10}$=$CR^{10}$— or —$CR^7R^8$—$CR^7R^8$—. In some further embodiments, $L^1$ and $L^2$ together form —CH=CH— or —$CH_2$—$CH_2$—. In some embodiments, $L^1$ and $L^2$ together form —CH=CH—. In some embodiments, $L^1$ and $L^2$ together form —$CH_2$—$CH_2$—.

In some embodiments of compounds of Formula Ia or pharmaceutically acceptable salts thereof, $L^1$ and $L^2$ together form —$(CR^7R^8)_3$—. In some further embodiments, $L^1$ and $L^2$ together form —$(CH_2)_3$—.

In some embodiments of compounds of Formula Ia or pharmaceutically acceptable salts thereof, one of $L^1$ and $L^2$ is selected from —$(CR^7R^8)_m$—O—, —$(CR^7R^8)_m$—S—, —$(CR^7R^8)_m$—S(O)—, and —$(CR^7R^8)_m$—S(O)$_2$—; and the other is selected from a bond, —$(CR^7R^8)_n$—, —$(CR^7R^8)_m$—O—, —$(CR^7R^8)_m$—S—, —$(CR^7R^8)_m$—S(O)—, and —$(CR^7R^8)_m$—S(O)$_2$—.

In some embodiments of compounds of Formula Ia or pharmaceutically acceptable salts thereof:

$L^1$ and $L^2$ together form —$(CR^7R^8)_{t1}$—S—, —$(CR^7R^8)_{t1}$—O—, —$(CR^7R^8)_{t1}$—S(O)—, —$(CR^7R^8)_{t1}$—S(O)$_2$—, —S—$(CR^7R^8)_{t2}$—S—, —O—$(CR^7R^8)_{t2}$—S—, —O—$(CR^7R^8)_{t2}$—S(O)—, —O—$(CR^7R^8)_{t2}$—S(O)$_2$—, —S—S—, —$(CR^7R^8)_{t3}$—O—$(CR^7R^8)_{t4}$—, —$(CR^7R^8)_{t3}$—S—$(CR^7R^8)_{t4}$—, —$(CR^7R^8)_{t3}$—S(O)—$(CR^7R^8)_{t4}$—, or —$(CR^7R^8)_{t3}$—S(O)$_2$—$(CR^7R^8)_{t4}$—;

t1 is 1, 2, or 3;

t2 is 1 or 2;

t3 is 1, 2, or 3; and t4 is 1 or 2.

In some embodiments of compounds of Formula Ia or pharmaceutically acceptable salts thereof:

$L^1$ and $L^2$ together form —$(CR^7R^8)_{t1}$—S—, —$(CR^7R^8)_{t1}$—O—, —$(CR^7R^8)_{t1}$—S(O)—, —$(CR^7R^8)_{t1}$—S(O)$_2$—, —S—$(CR^7R^8)_{t2}$—S—, —O—$(CR^7R^8)_{t2}$—S—, —O—$(CR^7R^8)_{t2}$—S(O)—, —O—$(CR^7R^8)_{t2}$—S(O)$_2$—, or —S—S—;

t1 is 1, 2, or 3; and t2 is 1 or 2.

In some embodiments of compounds of Formula Ia or pharmaceutically acceptable salts thereof:

$L^1$ and $L^2$ together form —$(CR^7R^8)_{t3}$—O—$(CR^7R^8)_{t4}$—, —$(CR^7R^8)_{t3}$—S—$(CR^7R^8)_{t4}$—, —$(CR^7R^8)_{t3}$—S(O)—$(CR^7R^8)_{t4}$—, or —$(CR^7R^8)_{t3}$—S(O)$_2$—$(CR^7R^8)_{t4}$—, t3 is 1, 2, or 3; and t4 is 1 or 2.

In some embodiments of compounds of Formula Ia or pharmaceutically acceptable salts thereof, $L^1$ and $L^2$ together form S—S, —$(CR^7R^8)$—S—, —$(CR^7R^8)$—S(O)—, —$(CR^7R^8)$—S(O)$_2$—, —$(CR^7R^8)$—O—, —$(CR^7R^8)_2$—O—, —O—$(CR^7R^8)_2$—O—, —O—$(CR^7R^8)_2$—S—, —O—$(CR^7R^8)_2$—S(O)—, or —O—$(CR^7R^8)_2$—S(O)$_2$—. In some further embodiments, $L^1$ and $L^2$ together form —$(CR^7R^8)$—S—, —$(CR^7R^8)$—S(O)—, —$(CR^7R^8)$—S(O)$_2$—, —$(CR^7R^8)$—O—, —$(CR^7R^8)_2$—O—, —O—$(CR^7R^8)_2$—O—, —O—$(CR^7R^8)_2$—S—, —O—$(CR^7R^8)_2$—S(O)—, or —O—$(CR^7R^8)_2$—S(O)$_2$—.

In some embodiments of compounds of Formula Ia or pharmaceutically acceptable salts thereof, $L^1$ and $L^2$ together form S—S, —$(CH_2)$—S—, —$(CH_2)$—S(O)—, —$(CH_2)$—S(O)$_2$—, —$(CH_2)$—O—, —$(CH_2)_2$—O—, —O—$(CH_2)_2$—O—, —O—$(CH_2)_2$—S—, —O—$(CH_2)_2$—S(O)—, or —O—$(CH_2)_2$—S(O)$_2$—. In some embodiments of compounds of Formula Ia or pharmaceutically acceptable salts thereof, $L^1$ and $L^2$ together form S—S. In some embodiments of compounds of Formula Ia or pharmaceutically acceptable salts thereof, $L^1$ and $L^2$ together form —$(CH_2)$—S—, —$(CH_2)$—S(O)—, —$(CH_2)$—S(O)$_2$—, —$(CH_2)$—O—, —$(CH_2)_2$—O—, —O—$(CH_2)_2$—, —O—$(CH_2)_2$—S—, —O—$(CH_2)_2$—S(O)—, or —O—$(CH_2)_2$—S(O)$_2$—.

In some embodiments of compounds of Formula Ia or pharmaceutically acceptable salts thereof, $L^1$ and $L^2$ together form —$(CR^7R^8)$—O, —$(CR^7R^8)$—S—, —$(CR^7R^8)$—S(O), —(CR$^7$R$^8$)—S(O)$_2$, —(CR$^7$R$^8$)$_2$—O—, —(CR$^7$R$^8$)$_2$—S—, —(CR$^7$R$^8$)$_2$—S(O)—, —(CR$^7$R$^8$)$_2$—S(O)$_2$—, —O—(CR$^7$R$^8$)$_3$—, —S—(CR$^7$R$^8$)$_3$—, —S(O)—(CR$^7$R$^8$)$_3$—, or —S(O)$_2$—(CR$^7$R$^8$)$_3$—.

In some embodiments of compounds of Formula Ia or pharmaceutically acceptable salts thereof, L$^1$ and L$^2$ together form —(CH$_2$)—O—, —(CH$_2$)—S—, —(CH$_2$)—S(O)—, or —(CH$_2$)—S(O)$_2$—. In some embodiments of compounds of Formula Ia or pharmaceutically acceptable salts thereof, L$^1$ and L$^2$ together form —(CH$_2$)—O— or —(CH$_2$)—S—.

In some embodiments of compounds of Formula Ia or pharmaceutically acceptable salts thereof, L$^1$ and L$^2$ together form —(CH$_2$)—O—.

In some embodiments of compounds of Formula Ia or pharmaceutically acceptable salts thereof, L$^1$ and L$^2$ together form —(CH$_2$)—S—.

In some embodiments of compounds of Formula Ia or pharmaceutically acceptable salts thereof, L$^1$ and L$^2$ together form —(CH$_2$)—S(O)—.

In some embodiments of compounds of Formula Ia or pharmaceutically acceptable salts thereof, L$^1$ and L$^2$ together form —(CH$_2$)—S(O)$_2$—.

In some embodiments of compounds of Formula Ia or pharmaceutically acceptable salts thereof, L$^1$ and L$^2$ together form —(CH$_2$)$_2$—O—, —(CH$_2$)$_2$—S—, —(CH$_2$)$_2$—S(O)—, or —(CH$_2$)$_2$—S(O)$_2$—. In some embodiments of compounds of Formula Ia or pharmaceutically acceptable salts thereof, L$^1$ and L$^2$ together form —(CH$_2$)$_2$—O— or —(CH$_2$)$_2$—S—.

In some embodiments of compounds of Formula Ia or pharmaceutically acceptable salts thereof, L$^1$ and L$^2$ together form —(CH$_2$)$_2$—O—.

In some embodiments of compounds of Formula Ia or pharmaceutically acceptable salts thereof, L$^1$ and L$^2$ together form —(CH$_2$)$_2$—S—.

In some embodiments of compounds of Formula Ia or pharmaceutically acceptable salts thereof, L$^1$ and L$^2$ together form —(CH$_2$)$_2$—S(O)—.

In some embodiments of compounds of Formula Ia or pharmaceutically acceptable salts thereof, L$^1$ and L$^2$ together form —(CH$_2$)$_2$—S(O)$_2$—.

In some embodiments of compounds of Formula Ia or pharmaceutically acceptable salts thereof, L$^1$ and L$^2$ together form —(CH$_2$)$_3$—O—, —(CH$_2$)$_3$—S—, —(CH$_2$)$_3$—S(O)—, or —(CH$_2$)$_3$—S(O)$_2$—. In some embodiments of compounds of Formula Ia or pharmaceutically acceptable salts thereof, L$^1$ and L$^2$ together form —(CH$_2$)$_3$—O— or —(CH$_2$)$_3$—S—.

In some embodiments of compounds of Formula Ia or pharmaceutically acceptable salts thereof, L$^1$ and L$^2$ together form —(CH$_2$)$_3$—O—.

In some embodiments of compounds of Formula Ia or pharmaceutically acceptable salts thereof, L$^1$ and L$^2$ together form —(CH$_2$)$_3$—S—.

In some embodiments of compounds of Formula Ia or pharmaceutically acceptable salts thereof, L$^1$ and L$^2$ together form —(CH$_2$)$_3$—S(O)—.

In some embodiments of compounds of Formula Ia or pharmaceutically acceptable salts thereof, L$^1$ and L$^2$ together form —(CH$_2$)$_3$—S(O)$_2$—.

In some embodiments of compounds of Formula Ia or pharmaceutically acceptable salts thereof, L$^1$ and L$^2$ together form —(CR$^7$R$^8$)—O—(CR$^7$R$^8$)—, —(CR$^7$R$^8$)—S—(CR$^7$R$^8$)—, —(CR$^7$R$^8$)—S(O)—(CR$^7$R$^8$)—, —(CR$^7$R$^8$)—S(O)$_2$—(CR$^7$R$^8$)—, —(CR$^7$R$^8$)—O—(CR$^7$R$^8$)$_2$—, —(CR$^7$R$^8$)—S—(CR$^7$R$^8$)$_2$—, —(CR$^7$R$^8$)—S(O)—(CR$^7$R$^8$)$_2$—, —(CR$^7$R$^8$)—S(O)$_2$—(CR$^7$R$^8$)$_2$—, —(CR$^7$R$^8$)$_2$—O—(CR$^7$R$^8$)$_2$—, —(CR$^7$R$^8$)$_2$—S—(CR$^7$R$^8$)$_2$—, —(CR$^7$R$^8$)$_2$—S(O)—(CR$^7$R$^8$)$_2$—, or —(CR$^7$R$^8$)$_2$—S(O)$_2$—(CR$^7$R$^8$)$_2$—.

In some embodiments of compounds of Formula Ia or pharmaceutically acceptable salts thereof, L$^1$ and L$^2$ together form —(CH$_2$)—O—(CH$_2$)—, —(CH$_2$)—S—(CH$_2$)—, —(CH$_2$)—S(O)—(CH$_2$)—, —(CH$_2$)—S(O)$_2$—(CH$_2$)—, —(CH$_2$)—O—(CH$_2$)$_2$—, —(CH$_2$)—S—(CH$_2$)$_2$—, —(CH$_2$)—S(O)—(CH$_2$)$_2$—, —(CH$_2$)—S(O)$_2$—(CH$_2$)$_2$—, —(CH$_2$)$_2$—O—(CH$_2$)$_2$—, —(CH$_2$)$_2$—S—(CH$_2$)$_2$—, —(CH$_2$)$_2$—S(O)—(CH$_2$)$_2$—, or —(CH$_2$)$_2$—S(O)$_2$—(CH$_2$)$_2$—.

In some embodiments of compounds of Formula Ia or pharmaceutically acceptable salts thereof, L$^1$ and L$^2$ together form —(CH$_2$)—O—(CH$_2$)— or —(CH$_2$)—S—(CH$_2$)—.

In some embodiments of compounds of Formula Ia or pharmaceutically acceptable salts thereof, L$^1$ and L$^2$ together form —(CH$_2$)—O—(CH$_2$)—.

In some embodiments of compounds of Formula Ia or pharmaceutically acceptable salts thereof, L$^1$ and L$^2$ together form —(CH$_2$)—S—(CH$_2$)—.

In some embodiments of compounds of Formula Ia or pharmaceutically acceptable salts thereof, L$^1$ and L$^2$ together form —(CH$_2$)—O—(CH$_2$)$_2$— or —(CH$_2$)—S—(CH$_2$)$_2$—.

In some embodiments of compounds of Formula Ia or pharmaceutically acceptable salts thereof, L$^1$ and L$^2$ together form —(CH$_2$)—O—(CH$_2$)$_2$—.

In some embodiments of compounds of Formula Ia or pharmaceutically acceptable salts thereof, L$^1$ and L$^2$ together form —(CH$_2$)—S—(CH$_2$)$_2$—.

In some embodiments of compounds of Formula Ia or pharmaceutically acceptable salts thereof, L$^1$ and L$^2$ together form —(CH$_2$)$_2$—O—(CH$_2$)$_2$— or —(CH$_2$)$_2$—S—(CH$_2$)$_2$—.

In some embodiments of compounds of Formula Ia or pharmaceutically acceptable salts thereof, L$^1$ and L$^2$ together form —(CH$_2$)$_2$—O—(CH$_2$)$_2$—.

In some embodiments of compounds of Formula Ia or pharmaceutically acceptable salts thereof, L$^1$ and L$^2$ together form —(CH$_2$)$_2$—S—(CH$_2$)$_2$—.

In some embodiments of compounds of Formula Ia or pharmaceutically acceptable salts thereof, L$^1$ and L$^2$ together form —O—(CH$_2$)$_2$—O—, —O—(CH$_2$)$_2$—S—, —O—(CH$_2$)$_2$—S(O)—, —O—(CH$_2$)$_2$—S(O)$_2$—, —S—(CH$_2$)$_2$—S—, —S(O)—(CH$_2$)$_2$—S(O)—, or —S(O)$_2$—(CH$_2$)$_2$—S(O)$_2$—.

In some embodiments of compounds of Formula Ia or pharmaceutically acceptable salts thereof, L$^1$ and L$^2$ together form —O—(CH$_2$)$_2$—O—, —O—(CH$_2$)$_2$—S—, —O—(CH$_2$)$_2$—S(O)—, or —O—(CH$_2$)$_2$—S(O)$_2$—.

In some embodiments of compounds of Formula Ia or pharmaceutically acceptable salts thereof, L$^1$ and L$^2$ together form —O—(CH$_2$)$_2$—O—.

In some embodiments of compounds of Formula Ia or pharmaceutically acceptable salts thereof, L$^1$ and L$^2$ together form —O—(CH$_2$)$_2$—S—.

In some embodiments of compounds of Formula Ia or pharmaceutically acceptable salts thereof, L$^1$ and L$^2$ together form —O—(CH$_2$)$_2$—S(O)—.

In some embodiments of compounds of Formula Ia or pharmaceutically acceptable salts thereof, L$^1$ and L$^2$ together form —O—(CH$_2$)$_2$—S(O)$_2$—.

In some embodiments of compounds of Formula Ia or pharmaceutically acceptable salts thereof, one of L$^1$ and L$^2$ is selected from —(CR$^7$R$^8$)$_m$—NR$^9$—, —(CR$^7$R$^8$)$_m$—S(O)$_2$—, —(CR$^7$R$^8$)$_m$—C(O)—, —C(O)NR$^9$—, —(CR$^7$R$^8$)$_m$—S(O)NR$^9$—, and —(CR$^7$R$^8$)$_m$—S(O)$_2$NR$^9$—; and the other is selected from a bond, —$(CR^7R^8)_n$—, —$(CR^7R^8)_m$—$NR^9$—, —$(CR^7R^8)_m$—$S(O)_2$—, —$(CR^7R^8)_m$—$C(O)$—, —$C(O)NR^9$—, —$(CR^7R^8)_m$—$S(O)NR^9$—, and —$(CR^7R^8)_m$—$S(O)_2NR^9$—.

In some embodiments of compounds of Formula Ia or pharmaceutically acceptable salts thereof, $L^1$ and $L^2$ together form —$(CR^7R^8)_{t5}$—$C(O)$—, —$(CR^7R^8)_{t5}$—$C(O)NR^9$—, —$C(O)NR^9$—$(CR^7R^8)_{t5}$—, —$C(O)NR^9$—, —$S(O)_2NR^9$—$(CR^7R^8)_{t5}$—, —$(CR^7R^8)_{t5}$—$S(O)_2NR^9$—, or —$S(O)_2NR^9$—, wherein t5 is 1, 2, or 3.

In some embodiments of compounds of Formula Ia or pharmaceutically acceptable salts thereof, $L^1$ and $L^2$ together form —$(CR^7R^8)_{t5}$—$C(O)$—, —$C(O)NR^9$—, or —$S(O)_2NR^9$—, and wherein t5 is 1, 2, or 3.

In some embodiments of compounds of Formula Ia or pharmaceutically acceptable salts thereof, $L^1$ and $L^2$ together form —$(CR^7R^8)$—$C(O)$—, —$(CR^7R^8)_2$—$C(O)$—, or —$(CR^7R^8)_3$—$C(O)$—. In some embodiments of compounds of Formula Ia or pharmaceutically acceptable salts thereof, $L^1$ and $L^2$ together form —$(CR^7R^8)$—$C(O)$—. In some embodiments of compounds of Formula Ia or pharmaceutically acceptable salts thereof, $L^1$ and $L^2$ together form —$(CR^7R^8)_2$—$C(O)$—. In some embodiments of compounds of Formula Ia or pharmaceutically acceptable salts thereof, $L^1$ and $L^2$ together form —$(CR^7R^8)_3$—$C(O)$—.

In some embodiments of compounds of Formula Ia or pharmaceutically acceptable salts thereof, $L^1$ and $L^2$ together form —$(CR^7R^8)$—$C(O)NR^9$—, —$C(O)NR^9$—$(CR^7R^8)$—, or —$C(O)NR^9$—. In some embodiments of compounds of Formula Ia or pharmaceutically acceptable salts thereof, $L^1$ and $L^2$ together form —$(CH_2)$—$C(O)NR^9$—, —$C(O)NR^9$—$(CH_2)$—, or —$C(O)NR^9$—. In some embodiments of compounds of Formula Ia or pharmaceutically acceptable salts thereof, $L^1$ and $L^2$ together form —$(CH_2)$—$C(O)NH$—, —$C(O)NH$—$(CH_2)$—, or —$C(O)NH$—.

In some embodiments of compounds of Formula Ia or pharmaceutically acceptable salts thereof, $L^1$ and $L^2$ together form —$(CH_2)$—$C(O)NH$—.

In some embodiments of compounds of Formula Ia or pharmaceutically acceptable salts thereof, $L^1$ and $L^2$ together form —$C(O)NH$—$(CH_2)$—.

In some embodiments of compounds of Formula Ia or pharmaceutically acceptable salts thereof, $L^1$ and $L^2$ together form —$C(O)NH$—.

In some embodiments of compounds of Formula Ia or pharmaceutically acceptable salts thereof, $L^1$ and $L^2$ together form —$(CR^7R^8)_{t7}$—$C(O)NR^9$—$(CR^7R^8)_{t8}$—, wherein t7 is 1 or 2 and t8 is 1 or 2. In some embodiments of compounds of Formula Ia or pharmaceutically acceptable salts thereof, $L^1$ and $L^2$ together form —$(CR^7R^8)$—$C(O)NR^9$—$(CR^7R^8)$. In some embodiments of compounds of Formula Ia or pharmaceutically acceptable salts thereof, $L^1$ and $L^2$ together form —$(CH_2)$—$C(O)NH$—$(CH_2)$—.

In some embodiments of compounds of Formula Ia or pharmaceutically acceptable salts thereof, $L^1$ and $L^2$ together form —$S(O)_2NR^9$—$(CR^7R^8)_{t5}$—, —$(CR^7R^8)_{t5}$—$S(O)_2NR^9$—, or —$S(O)_2NR^9$—, wherein t5 is 1, 2, or 3.

In some embodiments of compounds of Formula Ia or pharmaceutically acceptable salts thereof, $L^1$ and $L^2$ together form —$S(O)_2NR^9$—$(CR^7R^8)$—, —$(CR^7R^8)$—$S(O)_2NR^9$—, or —$S(O)_2NR^9$—. In some further embodiments, $R^9$ is H or $C_{1-3}$ alkyl.

In some embodiments of compounds of Formula Ia or pharmaceutically acceptable salts thereof, $L^1$ and $L^2$ together form —$S(O)_2NR^9$—$(CH_2)$—, —$(CH_2)$—$S(O)_2NR^9$—, or —$S(O)_2NR^9$—. In some further embodiments, $L^1$ and $L^2$ together form —$S(O)_2NH$—$(CH_2)$—, —$(CH_2)$—$S(O)_2NH$—, or —$S(O)_2NH$—.

In some embodiments of compounds of Formula Ia or pharmaceutically acceptable salts thereof, $L^1$ and $L^2$ together form —$S(O)_2NH$—$(CH_2)$—.

In some embodiments of compounds of Formula Ia or pharmaceutically acceptable salts thereof, $L^1$ and $L^2$ together form —$(CH_2)$—$S(O)_2NH$—.

In some embodiments of compounds of Formula Ia or pharmaceutically acceptable salts thereof, $L^1$ and $L^2$ together form —$S(O)_2NH$—.

In some embodiments of compounds of Formula Ia or pharmaceutically acceptable salts thereof, $L^1$ and $L^2$ together form —$(CR^7R^8)_{t7}$—$S(O)_2NR^9$—$(CR^7R^8)_{t8}$—, wherein t7 is 1 or 2 and t8 is 1 or 2. In some embodiments of compounds of Formula Ia or pharmaceutically acceptable salts thereof, $L^1$ and $L^2$ together form —$(CR^7R^8)$—$S(O)_2NR^9$—$(CR^7R^8)$.

In some embodiments of compounds of Formula Ia or pharmaceutically acceptable salts thereof, $L^1$ and $L^2$ together form —$(CH_2)$—$S(O)_2NR^9$—$(CH_2)$—.

In some embodiments of compounds of Formula Ia or pharmaceutically acceptable salts thereof, $L^1$ and $L^2$ together form —$(CR^7R^8)_m$—$NR^9$—$C(O)NR^9$—, —$(CR^7R^8)_m$—$O$—$C(O)NR^9$—, or —$O$—$C(O)NR^9$—$(CR^7R^8)_m$—.

In some embodiments of compounds of Formula Ia or pharmaceutically acceptable salts thereof, $L^1$ and $L^2$ together form —$(CR^7R^8)$—$NR^9$—$C(O)NR^9$—, —$(CR^7R^8)$—$O$—$C(O)NR^9$—, —$O$—$C(O)NR^9$—$(CR^7R^8)$—, —$NR^9$—$C(O)NR^9$—, or —$O$—$C(O)NR^9$—.

In some embodiments of compounds of Formula Ia or pharmaceutically acceptable salts thereof, $L^1$ and $L^2$ together form —$(CH_2)$—$NR^9$—$C(O)NR^9$—. In some embodiments of compounds of Formula Ia or pharmaceutically acceptable salts thereof, $L^1$ and $L^2$ together form —$(CH_2)$—$NH$—$C(O)NH$—.

In some embodiments of compounds of Formula Ia or pharmaceutically acceptable salts thereof, $L^1$ and $L^2$ together form —$(CR^7R^8)$—$O$—$C(O)NR^9$—. In some embodiments of compounds of Formula Ia or pharmaceutically acceptable salts thereof, $L^1$ and $L^2$ together form —$(CH_2)$—$O$—$C(O)NH$—.

In some embodiments of compounds of Formula Ia or pharmaceutically acceptable salts thereof, $L^1$ and $L^2$ together form —$O$—$C(O)NR^9$—$(CR^7R^8)$—. In some embodiments of compounds of Formula Ia or pharmaceutically acceptable salts thereof, $L^1$ and $L^2$ together form —$O$—$C(O)NH$—$(CH_2)$—.

In some embodiments of compounds of Formula Ia or pharmaceutically acceptable salts thereof, $L^1$ and $L^2$ together form —$NR^9$—$C(O)NR^9$—, or —$O$—$C(O)NR^9$—.

In some embodiments of compounds of Formula Ia or pharmaceutically acceptable salts thereof, $L^1$ and $L^2$ together form —$NH$—$C(O)NH$—.

In some embodiments of compounds of Formula Ia or pharmaceutically acceptable salts thereof, $L^1$ and $L^2$ together form —$O$—$C(O)NH$—.

In some embodiments of compounds of Formula Ia or pharmaceutically acceptable salts thereof, $L^1$ and $L^2$ together form —$(CR^7R^8)_m$—$NR^9$—$(CR^7R^8)_n$—.

In some embodiments of compounds of Formula Ia or pharmaceutically acceptable salts thereof, $L^1$ and $L^2$ together form —$NR^9$—$(CR^7R^8)$—. In some embodiments of compounds of Formula Ia or pharmaceutically acceptable salts thereof, $L^1$ and $L^2$ together form —$NR^9$—$(CR^7R^8)$—. In some embodiments of compounds of Formula Ia or pharmaceutically acceptable salts thereof, $L^1$ and $L^2$ together form —NR$^9$—(CR$^7$R$^8$)—. In some embodiments of compounds of Formula Ia or pharmaceutically acceptable salts thereof, L$^1$ and L$^2$ together form —NR$^9$—(CR$^7$R$^8$)$_2$—. In some embodiments of compounds of Formula Ia or pharmaceutically acceptable salts thereof, L$^1$ and L$^2$ together form —NR$^9$—(CR$^7$R$^8$)$_3$—.

In some embodiments of compounds of Formula Ia or pharmaceutically acceptable salts thereof, L$^1$ and L$^2$ together form —(CR$^7$R$^8$)$_{m2}$—NR$^9$—(CR$^7$R$^8$)$_n$—, wherein m2 is 1 or 2. In some embodiments of compounds of Formula Ia or pharmaceutically acceptable salts thereof, L$^1$ and L$^2$ together form —(CR$^7$R$^8$)—NR$^9$—(CR$^7$R$^8$)—, —(CR$^7$R$^8$)—NR$^9$—(CR$^7$R$^8$)$_2$—, or —(CR$^7$R$^8$)$_2$—NR$^9$—(CR$^7$R$^8$)$_2$—. In some further embodiments, L$^1$ and L$^2$ together form —(CR$^7$R$^8$)—NR$^9$—(CR$^7$R$^8$)— or —(CR$^7$R$^8$)—NR$^9$—(CR$^7$R$^8$)$_2$—. In some further embodiments, R$^9$ is H or C$_{1-3}$ alkyl.

In some embodiments of compounds of Formula Ia or pharmaceutically acceptable salts thereof, L$^1$ and L$^2$ together form —(CR$^7$R$^8$)—NR$^9$—(CR$^7$R$^8$)—. In some embodiments of compounds of Formula Ia or pharmaceutically acceptable salts thereof, L$^1$ and L$^2$ together form —(CH$_2$)—NR$^9$—(CH$_2$)—.

In some embodiments of compounds of Formula Ia or pharmaceutically acceptable salts thereof, L$^1$ and L$^2$ together form —NR$^9$—(CR$^7$R$^8$)$_{t9}$—O— wherein t9 is 1, 2, or 3. In some embodiments of compounds of Formula Ia or pharmaceutically acceptable salts thereof, L$^1$ and L$^2$ together form —NR$^9$—(CR$^7$R$^8$)—O—. In some embodiments of compounds of Formula Ia or pharmaceutically acceptable salts thereof, L$^1$ and L$^2$ together form —NR$^9$—(CR$^7$R$^8$)$_2$—O—. In some embodiments of compounds of Formula Ia or pharmaceutically acceptable salts thereof, L$^1$ and L$^2$ together form —NR$^9$—(CR$^7$R$^8$)$_3$—O—.

In some embodiments of compounds of Formula Ia or pharmaceutically acceptable salts thereof, L$^1$ and L$^2$ together form —NR$^9$—(CH$_2$)—O—.

In some embodiments of compounds of Formula Ia or pharmaceutically acceptable salts thereof, L$^1$ and L$^2$ together form —NR$^9$—(CH$_2$)$_2$—O—.

In some embodiments of compounds of Formula Ia or pharmaceutically acceptable salts thereof, L$^1$ and L$^2$ together form —NR$^9$—(CH$_2$)$_3$—O—.

In some embodiments of compounds of Formula Ia or pharmaceutically acceptable salts thereof, one of L$^1$ and L$^2$ is selected from —(CR$^7$R$^8$)$_m$—NR$^9$C(O)NR$^9$—, —(CR$^7$R$^8$)$_m$—OC(O)NR$^9$—, —(CR$^7$R$^8$)$_m$—NR$^9$C(O)O—, and —(CR$^7$R$^8$)$_m$—NR$^9$—S(O)$_2$NR$^9$—; and the other is selected from a bond, —(CR$^7$R$^8$)$_n$—, —(CR$^7$R$^8$)$_m$—NR$^9$—, —(CR$^7$R$^8$)$_m$—O—, —(CR$^7$R$^8$)$_m$—S—, —(CR$^7$R$^8$)$_m$—S(O)$_2$—, —(CR$^7$R$^8$)$_m$—C(O)—, —C(O)NR$^9$—, —(CR$^7$R$^8$)$_m$—S(O)NR$^9$—, and —(CR$^7$R$^8$)$_m$—S(O)$_2$NR$^9$—.

In some embodiments of compounds of Formula Ia or pharmaceutically acceptable salts thereof, one of L$^1$ and L$^2$ is selected from —(CR$^7$R$^8$)$_m$—NR$^9$C(O)NR$^9$—, —(CR$^7$R$^8$)$_m$—OC(O)NR$^9$—, —(CR$^7$R$^8$)$_m$—NR$^9$C(O)O—, and —(CR$^7$R$^8$)$_m$—NR$^9$—S(O)$_2$NR$^9$—; and the other is selected from a bond, and —(CR$^7$R$^8$)$_n$.

In some embodiments of compounds of Formula Ia or pharmaceutically acceptable salts thereof, L$^1$ and L$^2$ together form —(CR$^7$R$^8$)$_m$—NR$^9$C(O)NR$^9$—(CR$^7$R$^8$)$_m$—, —(CR$^7$R$^8$)$_m$—OC(O)NR$^9$—(CR$^7$R$^8$)$_m$—, or —(CR$^7$R$^8$)$_m$—NR$^9$—S(O)$_2$NR$^9$—(CR$^7$R$^8$)$_m$—.

In some embodiments of compounds of Formula Ia or pharmaceutically acceptable salts thereof, L$^1$ and L$^2$ together form —(CR$^7$R$^8$)$_m$—NR$^9$C(O)NR$^9$—(CR$^7$R$^8$)$_m$—. In some further embodiments, L$^1$ and L$^2$ together form —NR$^9$C(O) NR$^9$, —NR$^9$C(O)NR$^9$—(CR$^7$R$^8$)$_{m2}$—, or —(CR$^7$R$^8$)$_{m1}$—NR$^9$C(O)NR$^9$—(CR$^7$R$^8$)$_{m2}$—, wherein m1 and m2 are each, independently 1 or 2.

In some embodiments of compounds of Formula Ia or pharmaceutically acceptable salts thereof, L$^1$ and L$^2$ together form —NR$^9$C(O)NR$^9$—.

In some embodiments of compounds of Formula Ia or pharmaceutically acceptable salts thereof, L$^1$ and L$^2$ together form —NR$^9$C(O)NR$^9$—(CR$^7$R$^8$)—, —NR$^9$C(O)NR$^9$—(CR$^7$R$^8$)$_2$—, —(CR$^7$R$^8$)—NR$^9$C(O)NR$^9$—(CR$^7$R$^8$)—, —(CR$^7$R$^8$)—NR$^9$C(O)NR$^9$—(CR$^7$R$^8$)$_2$—, or —(CR$^7$R$^8$)$_2$—NR$^9$C(O)NR$^9$—(CR$^7$R$^8$)$_2$—.

In some embodiments of compounds of Formula Ia or pharmaceutically acceptable salts thereof, L$^1$ and L$^2$ together form —(CH$_2$)$_m$—NR$^9$C(O)NR$^9$—(CH$_2$)$_m$—. In some further embodiments, L$^1$ and L$^2$ together form —NR$^9$C(O)NR$^9$, —NR$^9$C(O)NR$^9$—(CH$_2$)$_m$—, or —(CH$_2$)$_{m1}$—NR$^9$C(O)NR$^9$—(CH$_2$)$_{m2}$— wherein m1 and m2 are each, independently 1 or 2.

In some embodiments of compounds of Formula Ia or pharmaceutically acceptable salts thereof, L$^1$ and L$^2$ together form —NR$^9$C(O)NR$^9$—(CH$_2$)—, —NR$^9$C(O)NR$^9$—(CH$_2$)$_2$—, —(CH$_2$)—NR$^9$C(O)NR$^9$—(CH$_2$)—, —(CH$_2$)—NR$^9$C(O)NR$^9$—(CH$_2$)$_2$—, or —(CH$_2$)$_2$—NR$^9$C(O)NR$^9$—(CH$_2$)$_2$—.

In some embodiments of compounds of Formula Ia or pharmaceutically acceptable salts thereof, L$^1$ and L$^2$ together form —(CR$^7$R$^8$)$_m$—OC(O)NR$^9$—(CR$^7$R$^8$)$_m$—.

In some embodiments of compounds of Formula Ia or pharmaceutically acceptable salts thereof, L$^1$ and L$^2$ together form —OC(O)NR$^9$—.

In some embodiments of compounds of Formula Ia or pharmaceutically acceptable salts thereof, L$^1$ and L$^2$ together form —OC(O)NR$^9$—(CR$^7$R$^8$)—, —OC(O)NR$^9$—(CR$^7$R$^8$)$_2$—, —(CR$^7$R$^8$)—OC(O)NR$^9$—, —(CR$^7$R$^8$)$_2$—OC(O)NR$^9$—, —(CR$^7$R$^8$)—OC(O)NR$^9$—(CR$^7$R$^8$)—, —(CR$^7$R$^8$)—OC(O)NR$^9$—(CR$^7$R$^8$)$_2$—, —(CR$^7$R$^8$)$_2$—OC(O)NR$^9$—(CR$^7$R$^8$)—, or —(CR$^7$R$^8$)$_2$—OC(O)NR$^9$—(CR$^7$R$^8$)$_2$—.

In some embodiments of compounds of Formula Ia or pharmaceutically acceptable salts thereof, L$^1$ and L$^2$ together form —OC(O)NR$^9$—(CH$_2$)—, —OC(O)NR$^9$—(CH$_2$)$_2$—, —(CH$_2$)—OC(O)NR$^9$—, —(CH$_2$)$_2$—OC(O)NR$^9$—, —(CH$_2$)—OC(O)NR$^9$—(CH$_2$)—, —(CH$_2$)—OC(O)NR$^9$—(CH$_2$)$_2$—, —(CH$_2$)$_2$—OC(O)NR$^9$—(CH$_2$)—, or —(CH$_2$)$_2$—OC(O)NR$^9$—(CH$_2$)$_2$—.

In some embodiments of compounds of Formula Ia or pharmaceutically acceptable salts thereof, L$^1$ and L$^2$ together form —(CR$^7$R$^8$)$_m$—NR$^9$S(O)$_2$NR$^9$—(CR$^7$R$^8$)$_m$—. In some further embodiments, L$^1$ and L$^2$ together form —NR$^9$S(O)$_2$NR$^9$—, —NR$^9$S(O)$_2$NR$^9$—(CR$^7$R$^8$)$_{m2}$—, or —(CR$^7$R$^8$)$_{m1}$—NR$^9$S(O)$_2$NR$^9$—(CR$^7$R$^8$)$_{m2}$—, wherein m1 and m2 are each, independently 1 or 2.

In some embodiments of compounds of Formula Ia or pharmaceutically acceptable salts thereof, L$^1$ and L$^2$ together form —NR$^9$S(O)$_2$NR$^9$.

In some embodiments of compounds of Formula Ia or pharmaceutically acceptable salts thereof, L$^1$ and L$^2$ together form —NR$^9$S(O)$_2$NR$^9$—(CR$^7$R$^8$)—, —NR$^9$S(O)$_2$NR$^9$—(CR$^7$R$^8$)$_2$—, —(CR$^7$R$^8$)—NR$^9$S(O)$_2$NR$^9$—(CR$^7$R$^8$)—, —(CR$^7$R$^8$)—NR$^9$S(O)$_2$NR$^9$—(CR$^7$R$^8$)$_2$—, or —(CR$^7$R$^8$)$_2$—NR$^9$S(O)$_2$NR$^9$—(CR$^7$R$^8$)$_2$—.

In some embodiments of compounds of Formula Ia or pharmaceutically acceptable salts thereof, R$^4$ is H or C$_{1-6}$ alkyl. In some further embodiments, R$^4$ is H or C$_{1-3}$ alkyl. In yet further embodiments, R$^4$ is H or methyl. In still further embodiments, R$^4$ is H.

In some embodiments of compounds of Formula Ia or pharmaceutically acceptable salts thereof:

each $R^5$ is, independently, selected from H, halo, $C_{1-6}$ alkyl, $C_{1-6}$ haloalkyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2NR^{c1}R^{d1}$, $S(O)_2R^{b1}$, $NR^{c1}S(O)_2R^{b1}$, and $S(O)_2NR^{c1}R^{d1}$, wherein said $C_{1-6}$ alkyl, $C_{2-6}$ alkenyl, $C_{2-6}$ alkynyl, or $C_{1-6}$ haloalkyl, is optionally substituted by 1, 2, 3, 4 or 5 substituents each independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $SF_5$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, or $S(O)_2NR^{c1}R^{d1}$;

$R^{a1}$, $R^{b1}$, $R^{c1}$, and $R^{d1}$ are each, independently, selected from H, $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of said $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted with 1, 2, 3, 4, or 5 substituents independently selected from halo, $C_{1-4}$ alkyl, $C_{1-4}$ haloalkyl, $C_{1-4}$ hydroxylalkyl, $C_{1-4}$ cyanoalkyl, aryl, cycloalkyl, heteroaryl, heterocycloalkyl, CN, $NO_2$, OH, SH, $O(C_{1-4}$ alkyl), $O(C_{1-4}$ haloalkyl), O(aryl), O(arylalkyl), $S(C_{1-4}$ alkyl), $S(C_{1-4}$ haloalkyl), S(aryl), S(arylalkyl), amino, $C_{1-4}$ alkylamino, $C_{2-8}$ dialkylamino, C(=O)H, C(=O)—($C_{1-4}$ alkyl), C(=O)-(arylalkyl), C(=O)$NH_2$, C(=O)NH($C_{1-4}$ alkyl), C(=O)N($C_{1-4}$ alkyl)$_2$, C(=O)OH, C(=O)O—($C_{1-4}$ alkyl), C(=O)O-(arylalkyl), OC(=O)H, OC(=O)—($C_{1-4}$ alkyl), OC(=O)-(arylalkyl), OC(=O)$NH_2$, OC(=O)NH($C_{1-4}$ alkyl), OC(=O)NH-(arylalkyl), OC(=O)N($C_{1-4}$ alkyl)$_2$, NHC(=O)—($C_{1-4}$ alkyl), NHC(=O)O-(arylalkyl), NHC(=O)O—($C_{1-4}$ alkyl), NHC(=O)O-(arylalkyl), NHS(=O)$_2$—($C_{1-4}$ alkyl), NHS(=O)$_2$-(arylalkyl), NHS(=O)$_2$—NH($C_{1-4}$ alkyl), NHS(=O)$_2$—N($C_{1-4}$ alkyl)$_2$, NHS(=O)$_2$—NH(arylalkyl), S(=O)$_2$—($C_{1-4}$ alkyl), S(=O)$_2$-(arylalkyl), S(=O)$_2$$NH_2$, S(=O)$_2$NH($C_{1-4}$ alkyl) and S(=O)$_2$NH(arylalkyl);

or $R^{c1}$ and $R^{d1}$ together with the N atom to which they are attached form a 4-, 5-, 6- or 7-membered heterocycloalkyl group, each optionally substituted with 1, 2, or 3 substituents independently selected from halo, $C_{1-4}$ alkyl, $C_{1-4}$ haloalkyl, $C_{1-4}$ hydroxylalkyl, $C_{1-4}$ cyanoalkyl, aryl, cycloalkyl, heteroaryl, heterocycloalkyl, CN, $NO_2$, OH, SH, $O(C_{1-4}$ alkyl), $O(C_{1-4}$ haloalkyl), O(aryl), O(arylalkyl), $S(C_{1-4}$ alkyl), $S(C_{1-4}$ haloalkyl), S(aryl), S(arylalkyl), amino, $C_{1-4}$ alkylamino, $C_{2-8}$ dialkylamino, C(=O)H, C(=O)—($C_{1-4}$ alkyl), C(=O)-(arylalkyl), C(=O)$NH_2$, C(=O)NH($C_{1-4}$ alkyl), C(=O)N($C_{1-4}$ alkyl)$_2$, C(=O)OH, C(=O)O—($C_{1-4}$ alkyl), C(=O)O-(arylalkyl), OC(=O)H, OC(=O)—($C_{1-4}$ alkyl), OC(=O)-(arylalkyl), OC(=O)$NH_2$, OC(=O)NH($C_{1-4}$ alkyl), OC(=O)NH-(arylalkyl), OC(=O)N($C_{1-4}$ alkyl)$_2$, NHC(=O)—($C_{1-4}$ alkyl), NHC(=O)O-(arylalkyl), NHC(=O)O—($C_{1-4}$ alkyl), NHC(=O)O-(arylalkyl), NHS(=O)$_2$—($C_{1-4}$ alkyl), NHS(=O)$_2$-(arylalkyl), NHS(=O)$_2$—NH($C_{1-4}$ alkyl), NHS(=O)$_2$—N($C_{1-4}$ alkyl)$_2$, NHS(=O)$_2$—NH(arylalkyl), S(=O)$_2$—($C_{1-4}$ alkyl), S(=O)$_2$-(arylalkyl), S(=O)$_2$$NH_2$, S(=O)$_2$NH($C_{1-4}$ alkyl) and S(=O)$_2$NH(arylalkyl).

In some embodiments of compounds of Formula Ia or pharmaceutically acceptable salts thereof, each $R^5$ is independently selected from H, $C_{1-6}$ alkyl, COOH, C(=O)—($C_{1-4}$ alkyl), S(=O)$_2$—($C_{1-4}$ alkyl), S(=O)$_2$$NH_2$, S(=O)$_2$NH($C_{1-4}$ alkyl), $C(O)NR^{c1}R^{d1}$, and $NR^{c1}R^{d1}$ wherein:

$R^{c1}$ and $R^{d1}$ are each, independently, selected from H, $C_{1-6}$ alkyl, aryl, heteroaryl, arylalkyl, and heteroarylalkyl, wherein each of said $C_{1-6}$ alkyl, aryl, heteroaryl, arylalkyl, heteroarylalkyl is optionally substituted with 1, 2, or 3 substituents independently selected from halo, $C_{1-4}$ alkyl, $C_{1-4}$ haloalkyl, $C_{1-4}$ hydroxylalkyl, $C_{1-4}$ cyanoalkyl, aryl, heteroaryl, OH, $O(C_{1-4}$ alkyl), $O(C_{1-4}$ haloalkyl), piperidinyl, pyrrolidinyl, morpholinyl, and piperizinyl optionally substituted with $C_{1-4}$ alkyl, aryl, or arylalkyl;

or $R^{c1}$ and $R^{d1}$ together with the N atom to which they are attached form pyrrolidinyl, piperidinyl, piperazinyl, or morpholinyl, each optionally substituted with 1, 2, or 3 substituents independently selected from $C_{1-4}$ alkyl, $C_{1-4}$ haloalkyl, $C_{1-4}$ hydroxylalkyl, aryl, arylalkyl, heteroaryl, heteroarylalkyl, OH, $O(C_{1-4}$ alkyl), and $O(C_{1-4}$ haloalkyl).

In some embodiments of compounds of Formula Ia or pharmaceutically acceptable salts thereof, each $R^6$ is, independently, H, $C_{1-6}$ alkyl, $C_{2-6}$ alkenyl, $C_{2-6}$ alkynyl, $C_{1-6}$ haloalkyl, $C(O)R^{b1}$, $C(O)NR^{c1}R^{d1}$, $C(O)OR^{a1}$, $S(O)R^{b1}$, $S(O)_2R^{b1}$, or $S(O)_2NR^{c1}R^{d1}$. In some further embodiments, each $R^6$ is, independently, H, $C_{1-6}$ alkyl, $C_{2-6}$ alkenyl, $C_{2-6}$ alkynyl, or $C_{1-6}$ haloalkyl.

In some embodiments of compounds of Formula Ia or pharmaceutically acceptable salts thereof, each $R^6$ is, independently, H or $C_{1-6}$ alkyl. In some further embodiments, each $R^6$ is, independently, H or $C_{1-3}$ alkyl. In yet further embodiments, each $R^6$ is, independently, H or methyl. In still further embodiments, each $R^6$ is H.

In some embodiments of compounds of Formula Ia or pharmaceutically acceptable salts thereof, $R^7$ and $R^8$ are each, independently, selected from H, halo, $C_{1-6}$ alkyl, CN, $NO_2$, OH, $C_{1-6}$ alkoxy, $C_{1-6}$ haloalkoxy, and $C_{2-8}$ alkoxyalkoxy. In some further embodiments, $R^7$ and $R^8$ are each, independently, selected from H, halo, $C_{1-4}$ alkyl, CN, $NO_2$, $C_{1-4}$ alkoxy, $C_{1-4}$ haloalkoxy, and $C_{2-8}$ alkoxyalkoxy. In some further embodiments, $R^7$ and $R^8$ are each, independently, selected from H, halo, $C_{1-4}$ alkyl, OH, $C_{1-4}$ alkoxy, $C_{1-4}$ haloalkoxy, and $C_{2-8}$ alkoxyalkoxy. In some further embodiments, $R^7$ and $R^8$ are each, independently, selected from H, OH, $C_{1-4}$ alkoxy, $C_{1-4}$ haloalkoxy, and $C_{2-8}$ alkoxyalkoxy. In some further embodiments, $R^7$ and $R^8$ are each, independently, selected from H, OH, and $C_{2-8}$ alkoxyalkoxy.

In some embodiments of compounds of Formula Ia or pharmaceutically acceptable salts thereof, each $R^{10}$ is, independently, selected from H, halo, and $C_{1-6}$ alkyl. In some embodiments, each $R^{10}$ is, independently, selected from H and $C_{1-6}$ alkyl. In some embodiments, each $R^{10}$ is, independently, selected from H and $C_{1-4}$ alkyl. In some further embodiments, each $R^{10}$ is H.

In some embodiments, the compounds of Formula Ia of the present invention have Formula Ia-1:

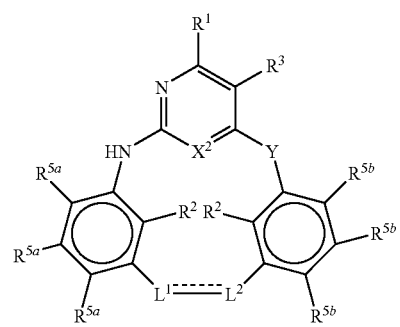

Ia-1 or are pharmaceutically acceptable salts thereof, wherein:

$R^1$ is H, halo, $C_{1-6}$ alkyl, $C_{1-6}$ haloalkyl, $NH_2$, $NH(C_{1-4}$ alkyl), $N(C_{1-4}$ alkyl$)_2$, or CN;

$R^3$ is H, halo, $C_{1-6}$ alkyl, $C_{1-6}$ haloalkyl, $NH_2$, $NH(C_{1-4}$ alkyl), $N(C_{1-4}$ alkyl$)_2$, or CN;

each $R^5$, is, independently, selected from H, halo, $C_{1-6}$ alkyl, $C_{1-6}$ haloalkyl, CN, $NO_2$, $SF_5$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2NR^{c1}R^{d1}$, $S(O)_2R^{b1}$, $NR^{c1}S(O)_2R^{b1}$, and $S(O)_2NR^{c1}R^{d1}$;

or two adjacent $R^{5a}$ can link to form a fused cycloalkyl or fused heterocycloalkyl group, each optionally substituted by 1, 2, or 3 substituents independently selected from halo, $C_{1-6}$ alkyl, $C_{1-6}$ haloalkyl, CN, $NO_2$, $SF_5$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2NR^{c1}R^{d1}$, $S(O)_2R^{b1}$, $NR^{c1}S(O)_2R^{b1}$, and $S(O)_2NR^{c1}R^{d1}$;

each $R^{5b}$ is, independently, selected from H, halo, $C_{1-6}$ alkyl, $C_{1-6}$ haloalkyl, CN, $NO_2$, $SF_5$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2NR^{c1}R^{d1}$, $S(O)_2R^{b1}$, $NR^{c1}S(O)_2R^{b1}$, and $S(O)_2NR^{c1}R^{d1}$;

or two adjacent $R^{5b}$ can link to form a fused cycloalkyl or fused heterocycloalkyl group, each optionally substituted by 1, 2, or 3 substituents independently selected from halo, $C_{1-6}$ alkyl, $C_{1-6}$ haloalkyl, CN, $NO_2$, $SF_5$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2NR^{c1}R^{d1}$, $S(O)_2R^{b1}$, $NR^{c1}S(O)_2R^{b1}$, and $S(O)_2NR^{c1}R^{d1}$; and Y is O, S, or $NR^4$.

In some embodiments of compounds of Formula Ia-1 or pharmaceutically acceptable salts thereof:

each $R^{5a}$ is, independently, selected from H, halo, $C_{1-6}$ alkyl, $C_{1-6}$ haloalkyl, CN, $NO_2$, $SF_5$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2NR^{c1}R^{d1}$, $S(O)_2R^{b1}$, $NR^{c1}S(O)_2R^{b1}$, and $S(O)_2NR^{c1}R^{d1}$; and each $R^{5b}$ is, independently, selected from H, halo, $C_{1-6}$ alkyl, $C_{1-6}$ haloalkyl, CN, $NO_2$, $SF_5$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2NR^{c1}R^{d1}$, $S(O)_2R^{b1}$, $NR^{c1}S(O)_2R^{b1}$, and $S(O)_2NR^{c1}R^{d1}$.

In some embodiments of the compounds of Formula Ia-1 or pharmaceutically acceptable salts thereof, each $R^{5a}$ is H.

In some embodiments of the compounds of Formula Ia-1 or pharmaceutically acceptable salts thereof, one $R^{5a}$ is other than H.

In some embodiments of the compounds of Formula Ia-1 or pharmaceutically acceptable salts thereof, two $R^{5a}$ are other than H.

In some embodiments of the compounds of Formula Ia-1 or pharmaceutically acceptable salts thereof, three $R^{5a}$ are other than H.

In some embodiments of the compounds of Formula Ia-1 or pharmaceutically acceptable salts thereof, at least one $R^{5a}$ is other than H.

In some embodiments of the compounds of Formula Ia-1 or pharmaceutically acceptable salts thereof, at least two $R^{5a}$ are other than H.

In some embodiments of the compounds of Formula Ia-1 or pharmaceutically acceptable salts thereof, each $R^{5b}$ is H.

In some embodiments of the compounds of Formula Ia-1 or pharmaceutically acceptable salts thereof, one $R^{5b}$ is other than H.

In some embodiments of the compounds of Formula Ia-1 or pharmaceutically acceptable salts thereof, two $R^{5b}$ are other than H.

In some embodiments of the compounds of Formula Ia-1 or pharmaceutically acceptable salts thereof, three $R^{5b}$ are other than H.

In some embodiments of the compounds of Formula Ia-1 or pharmaceutically acceptable salts thereof, at least one $R^{5b}$ is other than H.

In some embodiments of the compounds of Formula Ia-1 or pharmaceutically acceptable salts thereof, at least two $R^{5b}$ are other than H.

In some embodiments of compounds of Formula Ia-1 or pharmaceutically acceptable salts thereof, $R^1$ is H, halo, $C_{1-6}$ alkyl, $C_{1-6}$ haloalkyl, or CN; and $R^3$ is H, halo, $C_{1-6}$ alkyl, $C_{1-6}$ haloalkyl, or CN.

In some embodiments of compounds of Formula Ia-1 or pharmaceutically acceptable salts thereof:

$R^1$ is H, halo, $C_{1-3}$ alkyl, or $C_{1-3}$ haloalkyl;

$R^3$ is H, halo, $C_{1-3}$ alkyl, or $C_{1-3}$ haloalkyl;

each $R^5$, is, independently selected from H, halo, $C_{1-6}$ alkyl, $C_{1-6}$ haloalkyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}S(O)_2R^{b1}$, $NR^{c1}S(O)_2NR^{c1}R^{d1}$, $S(O)R^{b1}$, $S(O)_2R^{b1}$, and $S(O)_2NR^{c1}R^{d1}$;

each $R^{5b}$ is, independently, selected from H, halo, $C_{1-6}$ alkyl, $C_{1-6}$ haloalkyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}S(O)_2R^{b1}$, $NR^{c1}S(O)_2NR^{c1}R^{d1}$, $S(O)R^{b1}$, $S(O)_2R^{b1}$, and $S(O)_2NR^{c1}R^{d1}$;

Y is NH or $N(C_{1-3}$ alkyl); and $X^2$ is N.

In some embodiments, the compounds of Formula Ia-1 have Formula Ia-2:

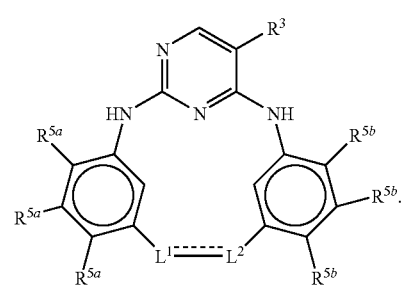

Ia-2

In some embodiments, the compounds of Formula Ia-2 have Formula Ia-2-a:

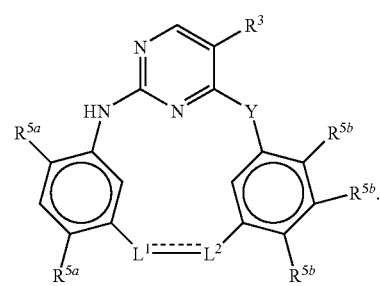

Ia-2-a

In some embodiments, the compounds of Formula Ia-2 have Formula Ia-2-b:

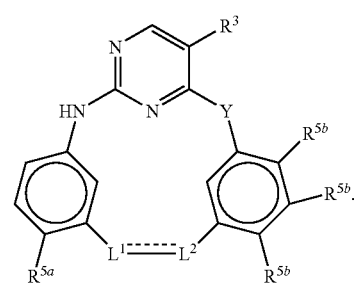

Ia-2-b

In some embodiments, the compounds of Formula Ia-2 have Formula Ia-2-c:

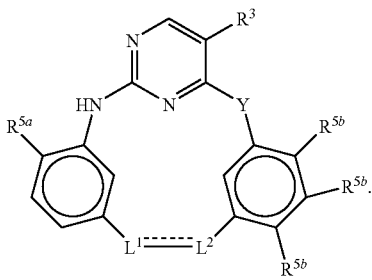

In some embodiments, the compounds of Formula Ia-2 have Formula Ia-2-d:

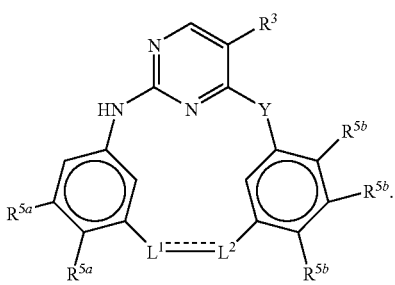

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

For compounds of the invention in which a variable appears more than once, each variable can be a different moiety selected from the Markush group defining the variable. For example, where a structure is described having two R groups that are simultaneously present on the same compound, then the two R groups can represent different moieties selected from the Markush group defined for R.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The term "n-membered" where n is an integer typically describes the number of ring-forming atoms in a moiety where the number of ring-forming atoms is n. For example, pyridine is an example of a 6-membered heteroaryl ring and thiophene is an example of a 5-membered heteroaryl group.

As used herein, the term "alkyl" is meant to refer to a saturated hydrocarbon group which is straight-chained or branched. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms. The term "alkylene" refers to a divalent alkyl linking group. An example of alkylene is methylene ($CH_2$).

As used herein, "alkenyl" refers to an alkyl group having one or more double carbon-carbon bonds. Example alkenyl groups include, but are not limited to, ethenyl, propenyl, cyclohexenyl, and the like. The term "alkenylenyl" refers to a divalent linking alkenyl group.

As used herein, "alkynyl" refers to an alkyl group having one or more triple carbon-carbon bonds. Example alkynyl groups include, but are not limited to, ethynyl, propynyl, and the like. The term "alkynylenyl" refers to a divalent linking alkynyl group.

As used herein, "haloalkyl" refers to an alkyl group having one or more halogen substituents. Example haloalkyl groups include, but are not limited to, $CF_3$, $C_2F_5$, $CHF_2$, $CCl_3$, $CHCl_2$, $C_2Cl_5$, $CH_2CF_3$, and the like.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms. In some embodiments, aryl groups have from 6 to about 10 carbon atoms.

As used herein, "cyclic" or "cyclo" refers to non-aromatic cyclic hydrocarbons including cyclized alkyl, alkenyl, and alkynyl groups that contain up to 20 ring-forming carbon atoms. Cyclic groups can include mono- or polycyclic (e.g., having 2, 3 or 4 fused rings) ring systems as well as spiro ring systems. A cyclic group can contain from 3 to about 15, from 3 to about 10, from 3 to about 8, from 3 to about 6, from 4 to about 6, from 3 to about 5, or from 5 to about 6 ring-forming carbon atoms. Ring-forming carbon atoms of a cyclic group can be optionally substituted by oxo or sulfido. Example cyclic groups include, but are not limited to, cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. Also included in the definition of "cyclic" are moieties that have one or more aromatic rings fused (i.e., having a bond in common with) to the cycloalkyl ring, for example, benzo or thienyl derivatives of pentane, pentene, hexane, and the like (e.g., 2,3-dihydro-IH-indene-1-yl, or IH-5 inden-2(3H)-one-1-yl).

As used herein, "heteroaryl" groups refer to an aromatic heterocycle having up to 20 ring-forming atoms and having at least one heteroatom ring member (ring-forming atom) such as sulfur, oxygen, or nitrogen. In some embodiments, the heteroaryl group has at least one or more heteroatom ring-forming atoms each independently selected from sulfur, oxygen, and nitrogen. Heteroaryl groups include monocyclic and polycyclic (e.g., having 2, 3 or 4 fused rings) systems. Examples of heteroaryl groups include without limitation, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 1 to about 5, from about 1 to about 4, from about 1 to about 3, from about 1 to about 2, carbon atoms as ringforming atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

As used herein, "heterocyclo" or "heterocyclic" refers to non-aromatic heterocycles having up to 20 ringforming atoms including cyclized alkyl, alkenyl, and alkynyl groups where one or more of the ringforming carbon atoms is replaced by a heteroatom such as an O, N, or S atom. Heterocyclic groups can be mono or polycyclic (e.g., both fused and spiro systems). Example heterocyclic groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, pyrrolidin-2-one-3-yl, and the like. Ringforming carbon atoms and heteroatoms of a heterocyclic group can be optionally substituted by oxo (i.e. =O) or sulfide (i.e. =S). For example, a ring-forming S atom can be substituted by 1 or 2 oxo [i.e., form a S(O) or S(O)2]. For another example, a ring-forming C atom can be substituted by oxo (i.e., form carbonyl). Accordingly, some non-limiting examples of heterocyclics include 2-oxo-oxazolidin-yl and 2-oxo-oxazolyl. Also included in the definition of heterocyclic are moieties that have one or more aromatic rings fused (i.e., having a bond in common with) to the nonaromatic heterocyclic ring, for example pyridinyl, thiophenyl, phthalimidyl, naphthalimidyl, and benzo derivatives of heterocycles such as indolene, isoindolene, isoindolin-1-one-3-yl, 4,5,6,7-tetrahydrothieno[2,3-c]pyridine-5-yl, 5,6-dihydrothieno[2,3-c]pyridin-7(4H)-one-5-yl, and 3,4-dihydroisoquinolin-1(2H)-one-3yl groups. Ringforming carbon atoms and heteroatoms of the heterocyclic group can be optionally substituted by oxo or sulfido. In some embodiments, the heterocyclic group has from 1 to about 20 carbon atoms, and in further embodiments from about 3 to about 20 carbon atoms. In some embodiments, the heterocyclic group contains 3 to about 14, 3 to about 7, or 5 to 6 ring-forming atoms. In some embodiments, the heterocyclic group has 1 to about 4, 1 to about 3, or 1 to 2 heteroatoms. In some embodiments, the heterocyclic group contains 0 to 3 double bonds. In some embodiments, the heterocyclic group contains 0 to 2 triple bonds.

As used herein, "halo" or "halogen" includes fluoro, chloro, bromo, and iodo.

As used herein, "halosulfanyl" refers to a sulfur group having one or more halogen substituents. Example halosulfanyl groups include pentahalosulfanyl groups such as $SF_5$.

As used herein, "alkoxy" refers to an —O-alkyl group. Example alkoxy groups include methoxy, ethoxy, propoxy (e.g., n-propoxy and isopropoxy), t-butoxy, and the like.

As used herein, "haloalkoxy" refers to an —O-haloalkyl group. An example haloalkoxy group is $OCF_3$.

As used herein, "cyanoalkyl" refers to an alkyl group substituted by a cyano group (CN). One example of cyanoalkyl is —$CH_2$—CN.

As used herein, "alkoxyalkoxy" refers to an alkoxy group substituted by an alkoxy group. One example of alkoxyalkoxy is —$OCH_2CH_2$—$OCH_3$.

As used herein, "arylalkyl" refers to a $C_{1-6}$ alkyl substituted by aryl and "cycloalkylalkyl" refers to $C_{1-6}$ alkyl substituted by cycloalkyl.

As used herein, "heteroarylalkyl" refers to a $C_{1-6}$ alkyl group substituted by a heteroaryl group, and "heterocycloalkylalkyl" refers to a $C_{1-6}$ alkyl substituted by heterocycloalkyl.

As used herein, "amino" refers to $NH_2$.

As used herein, "alkylamino" refers to an amino group substituted by an alkyl group.

As used herein, "dialkylamino" refers to an amino group substituted by two alkyl groups.

As used herein, "hydroxylalkyl" or "hydroxylalkyl" refers to an alkyl group substituted by a hydroxyl group. An example is —$CH_2OH$ or —$CH_2CH_2OH$.

As used here, C(O) refers to C(=O).
As used here, C(S) refers to C(=S).
As used here, S(O) refers to S(=O).
As used here, $S(O)_2$ refers to $S(=O)_2$.

As used herein, the term "optionally substituted" means that substitution is optional and therefore includes both unsubstituted and substituted atoms and moieties. A "substituted" atom or moiety indicates that any hydrogen on the designated atom or moiety can be replaced with a selection from the indicated substituent group, provided that the normal valency of the designated atom or moiety is not exceeded, and that the substitution results in a stable compound. For example, if a methyl group (i.e., $CH_3$) is optionally substituted, then 3 hydrogen atoms on the carbon atom can be replaced with substituent groups.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. Where a compound capable of stereoisomerism or geometric isomerism is designated in its structure or name without reference to specific R/S or cis/trans configurations, it is intended that all such isomers are contemplated.

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention further include hydrates and solvates, as well as anhydrous and non-solvated forms.

The term, "compound," as used herein is meant to include all stereoisomers, geometric isomers, tautomers, and isotopes of the structures depicted.

All compounds and pharmaceutically acceptable salts thereof, can be prepared or present together with other substances such as water and solvents (e.g. hydrates and solvates) or can be isolated.

Compounds of the invention can also include all isotopes of atoms occurring in the intermediates or final compounds. Isotopes include those atoms having the same atomic number but different mass numbers. For example, isotopes of hydrogen include tritium and deuterium.

In some embodiments, the compounds of the invention, or salts thereof, are substantially isolated. By "substantially isolated" is meant that the compound is at least partially or substantially separated from the environment in which is formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the compound of the invention, or salt thereof. Methods for isolating compounds and their salts are routine in the art.

Compounds of the invention are intended to include compounds with stable structures. As used herein, "stable compound" and "stable structure" are meant to indicate a compound that is sufficiently robust to survive isolation to a useful degree of purity from a reaction mixture, and formulation into an efficacious therapeutic agent.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g. a reaction temperature, that is about the temperature of the room in which the reaction is carried out, for example, a temperature from about 20° C. to about 30° C.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile (ACN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

The present invention also includes quaternary ammonium salts of the compounds described herein, where the compounds are primary amines, secondary amines, or tertiary amines. As used herein, "quaternary ammonium salts" refers to derivatives of the disclosed primary amine, secondary amine, or tertiary amine compounds wherein the parent amine compounds are modified by converting the amines to quaternary ammonium cations via alkylation (and the cations are balanced by anions such as $Cl^-$, $CH_3COO^-$, or $CF_3COO^-$), for example methylation or ethylation.

Synthesis

Compounds of the invention, including salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis,* $3^{rd}$ Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry, or by chromatographic methods such as high performance liquid chromatography (HPLC) or thin layer chromatography (TLC).

The compounds of invention can be prepared according to the synthetic procedures described below in the Example section.

As shown in Scheme 1a, macrocycle 1-2 of the present invention can be synthesized by cyclizing precursor 1-1 [wherein $Lg^1$ is a leaving group such as halo (e.g., chloro)] under acidic condition, or basic condition, or in the presence of a transition metal catalysis [such as a Palladium catalyst (e.g., $Pd(PPh_3)_4$) or a Pd(II) catalyst] to afford the desired macrocycle 1-2. Precursors 1-1 [wherein $Lg^1$ is a leaving group such as halo (e.g., chloro)], 1-1a [wherein $Lg^1$ is a leaving group such as halo (e.g., chloro)], 1-3 [wherein $Lg^1$ is a leaving group such as halo (e.g., chloro)], and 1-3a [wherein $Lg^1$ is a leaving group such as halo (e.g., chloro)] can undergo similar transformations to afford products 1-2, 1-4, and 1-4 respectively.

Scheme Ia
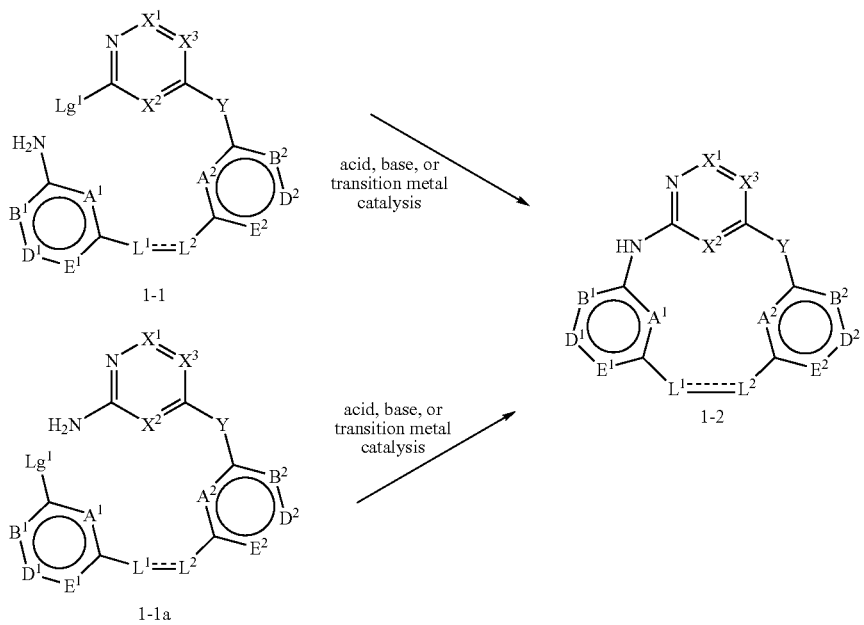
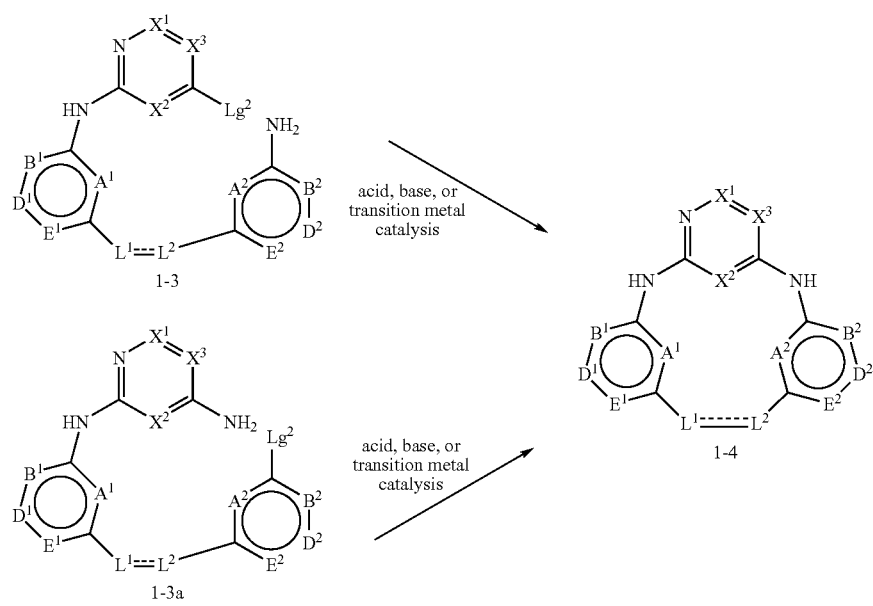

As shown in Scheme 1b, bis-olefin precursor 1-5 [wherein $L^{1f}$ and $L^{2f}$ can be independently selected from —$(CR^7R^8)_m$—, —$(CR^7R^8)_m$—O—, or —$(CR^7R^8)_m$—S—] can be cyclized in the presence of a metathesis catalyst (ruthenium, such as the Grubbs catalysts or molybdenum catalysts, such as the Hoveyda catalysts) to afford the desired macrocycle 1-6 that contains an olefin moiety of $CR^{10}$=$CR^{10}$. The olefin moiety of compound 1-6 can be further reduced under suitable hydrogenation conditions [such as in the presence of a palladium catalyst (e.g., 5% Pd/C)] to afford macrocycle 1-7.

As shown in Scheme 1b-1, macrocycle 1-7a can be obtained similarly according to the transformations described in Scheme 1b.

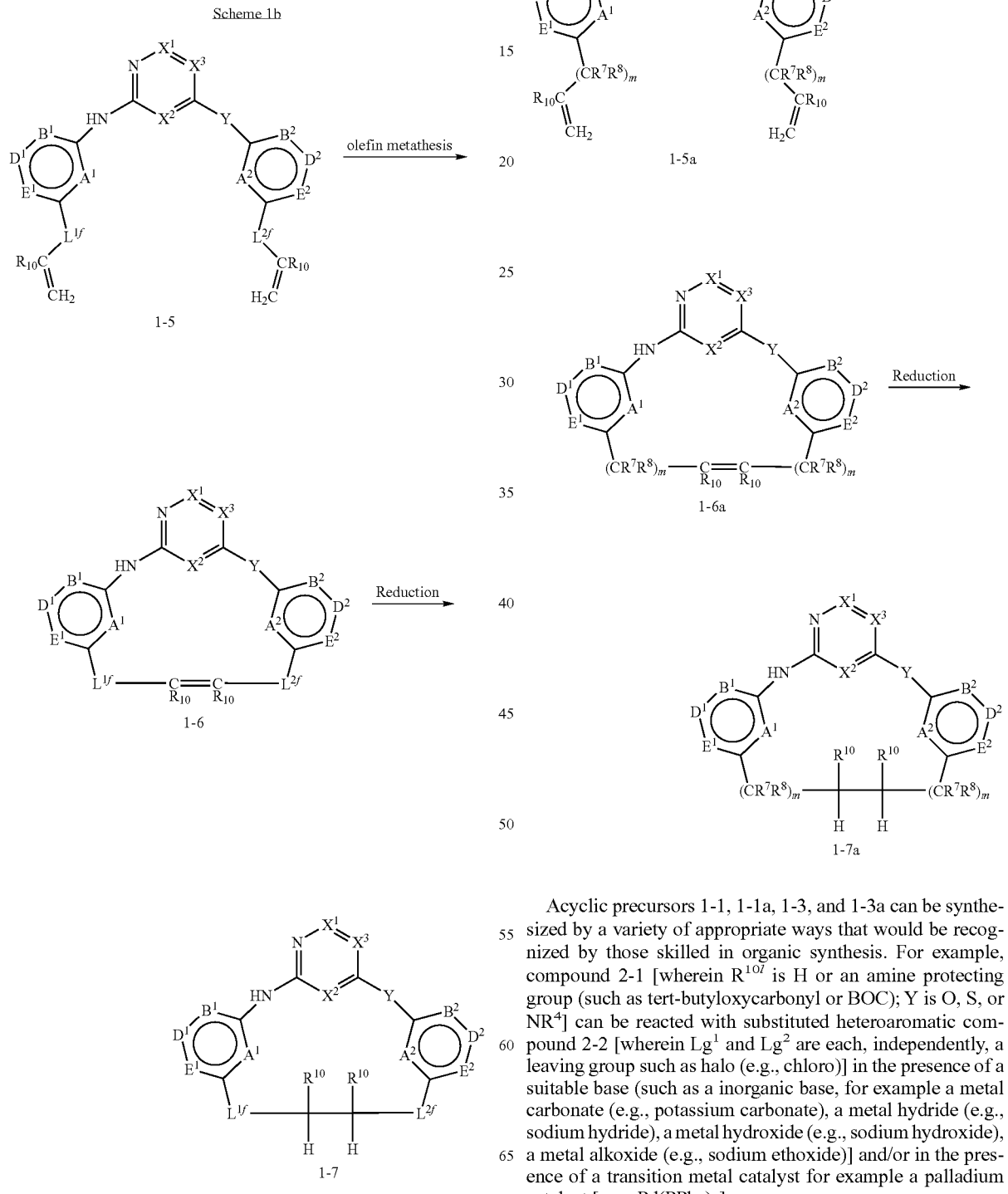

Acyclic precursors 1-1, 1-1a, 1-3, and 1-3a can be synthesized by a variety of appropriate ways that would be recognized by those skilled in organic synthesis. For example, compound 2-1 [wherein $R^{10l}$ is H or an amine protecting group (such as tert-butyloxycarbonyl or BOC); Y is O, S, or $NR^4$] can be reacted with substituted heteroaromatic compound 2-2 [wherein $Lg^1$ and $Lg^2$ are each, independently, a leaving group such as halo (e.g., chloro)] in the presence of a suitable base (such as a inorganic base, for example a metal carbonate (e.g., potassium carbonate), a metal hydride (e.g., sodium hydride), a metal hydroxide (e.g., sodium hydroxide), a metal alkoxide (e.g., sodium ethoxide)] and/or in the presence of a transition metal catalyst for example a palladium catalyst [e.g., $Pd(PPh_3)_4$].

Scheme 2

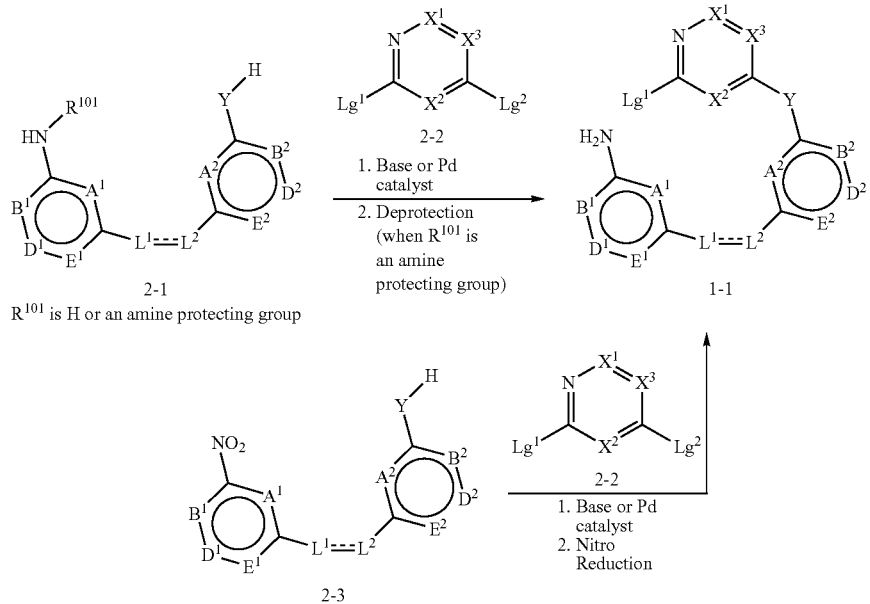

Precursors for the macrocycles of the present invention (for example, precursors 1-1, 1-1a, 1-3, 1-3a, and 1-5) can be prepared by a variety of methods. For example, Mitsunobu coupling, thioether formation, amine alkylation, amide formation, sulfonamide formation, urea formation and carbamate formation can be utilized in synthesizing these compounds. Some non-limiting examples are depicted in the following schemes.

As shown in Scheme 3a, compound 3-1 [wherein $R^{201}$ can be $NO_2$ or $NHR^{101}$; $R^{101}$ can be H or $Pg^4$; $Pg^4$ is an amine protecting group (such as tert-butyloxycarbonyl or BOC); $L^{1a}$ can be —$(CR^7R^8)_m$— (such as a bond or methylene) or $L^{1a}$ is selected from —$(CR^7R^8)_n$—, —$(CR^7R^8)_{m1}$—$NR^9$—, —$(CR^7R^8)_{m1}$—O—, —$(CR^7R^8)_{m1}$—S—, —$(CR^7R^8)_{m1}$—S(O)—, —$(CR^7R^8)_{m1}$—S(O)$_2$—, —$(CR^7R^8)_{m1}$—C(O)—, —$(CR^7R^8)_{m1}$—C(O)O—, —$(CR^7R^8)_{m1}$—$NR^9$C(O)$NR^9$—, —$(CR^7R^8)_{m1}$—OC(O)$NR^9$—, —$(CR^7R^8)_{m1}$—$NR^9$C(O)O—, —$(CR^7R^8)_{m1}$—$NR^9$—S(O)$_2NR^9$—, —$(CR^7R^8)_{m1}$—S(O)$NR^9$—, and —$(CR^7R^8)_{m1}$—S(O)$_2NR^9$—, wherein m1 is 1 or 2] can be reacted with compound 3-2 [wherein $Y^{10}$ can be OH, SH, $NHR^4$, or $NO_2$, wherein the OH, SH, or $NHR^4$ can also be protected by an appropriate protecting group; $L^{2a}$ is selected from —$(CR^7R^8)_n$—, —$(CR^7R^8)_{m1}$—$NR^9$—, —$(CR^7R^8)_{m1}$—O—, —$(CR^7R^8)_{m1}$—S—, —$(CR^7R^8)_{m1}$—S(O)—, —$(CR^7R^8)_{m1}$—S(O)$_2$—, —$(CR^7R^8)_{m1}$—C(O)—, —$(CR^7R^8)_{m1}$—C(O)O—, —$(CR^7R^8)_{m1}$—$NR^9$C(O)$NR^9$—, —$(CR^7R^8)_{m1}$—OC(O)$NR^9$—, —$(CR^7R^8)_{m1}$—$NR^9$C(O)O—, —$(CR^7R^8)_{m1}$—$NR^9$—S(O)$_2NR^9$—, —$(CR^7R^8)_{m1}$—S(O)$NR^9$—, and —$(CR^7R^8)_{m1}$—S(O)$_2NR^9$—, wherein m1 is 1 or 2; or $L^2$, can be —$(CR^7R^8)_m$— (such as a bond or methylene)] under Mitsunobu coupling reaction conditions to afford compound 3-3 [wherein $L^{1a}$ can be —$(CR^7R^8)_m$— and $L^{2a}$ is selected from —$(CR^7R^8)_n$—, —$(CR^7R^8)_{m1}$—$NR^9$—, —$(CR^7R^8)_{m1}$—O—, —$(CR^7R^8)_{m1}$—S—, —$(CR^7R^8)_{m1}$—S(O)—, —$(CR^7R^8)_{m1}$—S(O)$_2$—, —$(CR^7R^8)_{m1}$—C(O)—, —$(CR^7R^8)_{m1}$—C(O)O—, —$(CR^7R^8)_{m1}$—$NR^9$C(O)$NR^9$—, —$(CR^7R^8)_{m1}$—OC(O)$NR^9$—, —$(CR^7R^8)_{m1}$—$NR^9$C(O)O—, —$(CR^7R^8)_{m1}$—$NR^9$—S(O)$_2NR^9$—, —$(CR^7R^8)_{m1}$—S(O)$NR^9$—, and —$(CR^7R^8)_{m1}$—S(O)$_2NR^9$—, wherein m1 is 1 or 2; or $L^{2a}$ can be —$(CR^7R^8)_m$— and $L^{1a}$ is selected from —$(CR^7R^8)_n$—, —$(CR^7R^8)_{m1}$—$NR^9$—, —$(CR^7R^8)_{m1}$—O—, —$(CR^7R^8)_{m1}$—S—, —$(CR^7R^8)_{m1}$—S(O)—, —$(CR^7R^8)_{m1}$—S(O)$_2$—, —$(CR^7R^8)_{m1}$—C(O)—, —$(CR^7R^8)_{m1}$—C(O)O—, —$(CR^7R^8)_{m1}$—$NR^9$C(O)$NR^9$—, —$(CR^7R^8)_{m1}$—OC(O)$NR^9$—, —$(CR^7R^8)_{m1}$—$NR^9$C(O)O—, —$(CR^7R^8)_{m1}$—$NR^9$—S(O)$_2NR^9$—, —$(CR^7R^8)_{m1}$—S(O)$NR^9$—, and —$(CR^7R^8)_{m1}$—S(O)$_2NR^9$—, wherein m1 is 1 or 2.]. Compound 3-3 can undergo further chemical transformations if and when appropriate. For example, when $Y^{10}$ of compound 3-3 is a protected OH group, it can be deprotected according to the protecting group. For another example, when $Y^{10}$ of compound 3-3 is $NO_2$, it can be reduced to $NH_2$ under suitable conditions.

Compounds 3-4 and 3-5 [wherein $Lg^3$ is a leaving group such as halo (e.g., Br or Cl); $R^{201}$, $L^{1a}$, and $L^{2a}$ can be the same as those in compounds 3-1 and 3-2] can be reacted under basic conditions to afford compound 3-6. Alternatively compound 3-6 can be obtained by reacting compound 3-7 with compound 3-8 (wherein $Lg^3$, $R^{201}$, $L^{1a}$, and $L^{2a}$ can be the same as those in compounds 3-4 and 3-5). The $NO_2$ of compound 3-6 can be reduced to $NH_2$ under suitable conditions.

Scheme 3a

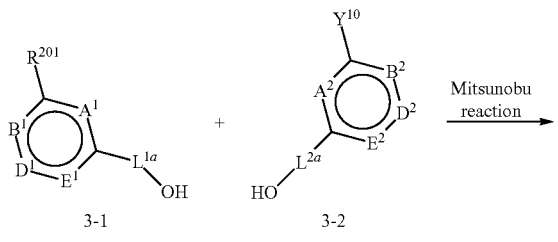

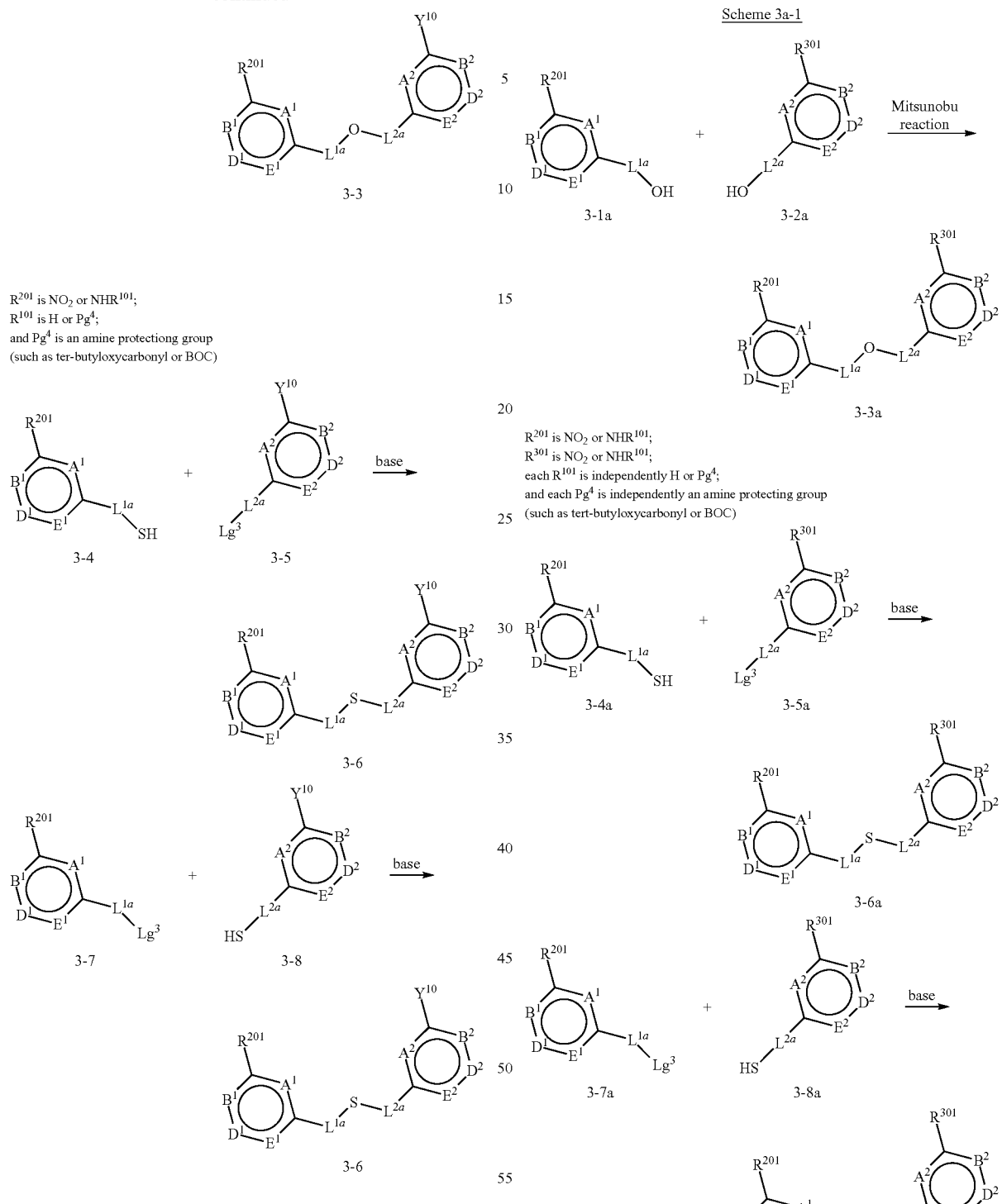

Useful intermediates 3-3a and 3-6a can be made according to the methods as shown in Scheme 3a-1 (similar to the reactions depicted in Scheme 3a, and wherein $R^{301}$ can be $NO_2$ or $NHR^{101}$; $R^{101}$, $R^{201}$, $L^{1a}$, and $L^{2a}$ can be the same as those in Scheme 3a). The protecting group $Pg^4$ of compound 3-3a and 3-6a, when present, can be removed under suitable conditions. Compounds 3-3a and 3-6a can undergo further chemical transformations when suitable reactive groups are present. For example, the $NO_2$ of compound 3-3a and 3-6a can be reduced to $NH_2$ under suitable conditions.

As shown in Scheme 3b, compounds 3-9a and 3-9b [wherein $R^{201}$, $L^{1a}$, and $L^{2a}$ can be the same as those in compounds 3-4 and 3-5] can be reacted under appropriate conditions to afford compound 3-10. For example, when $R^{102}$ is $Lg^3$ (a leaving group), amine alkylation can be carried out under basic conditions. When $R^{102}$ is —C(=O)H (i.e., compound 3-9a is an aldehyde), reductive aminations can be carried out. Similarly, compound 3-11c can be obtained by reacting compound 3-11a with compound 3-11b [wherein $L^{1a}$ and $L^{2a}$ can be the same as those in compounds 3-4 and 3-5] under suitable conditions. The protecting group $Pg^4$ of compound 3-10 or 3-11c can be removed under suitable conditions. Compounds 3-10 and 3-11c can undergo further chemical transformations when suitable reactive groups are present. For example, when $Y^{10}$ is $NO_2$, it can be reduced to $NH_2$ under suitable conditions.

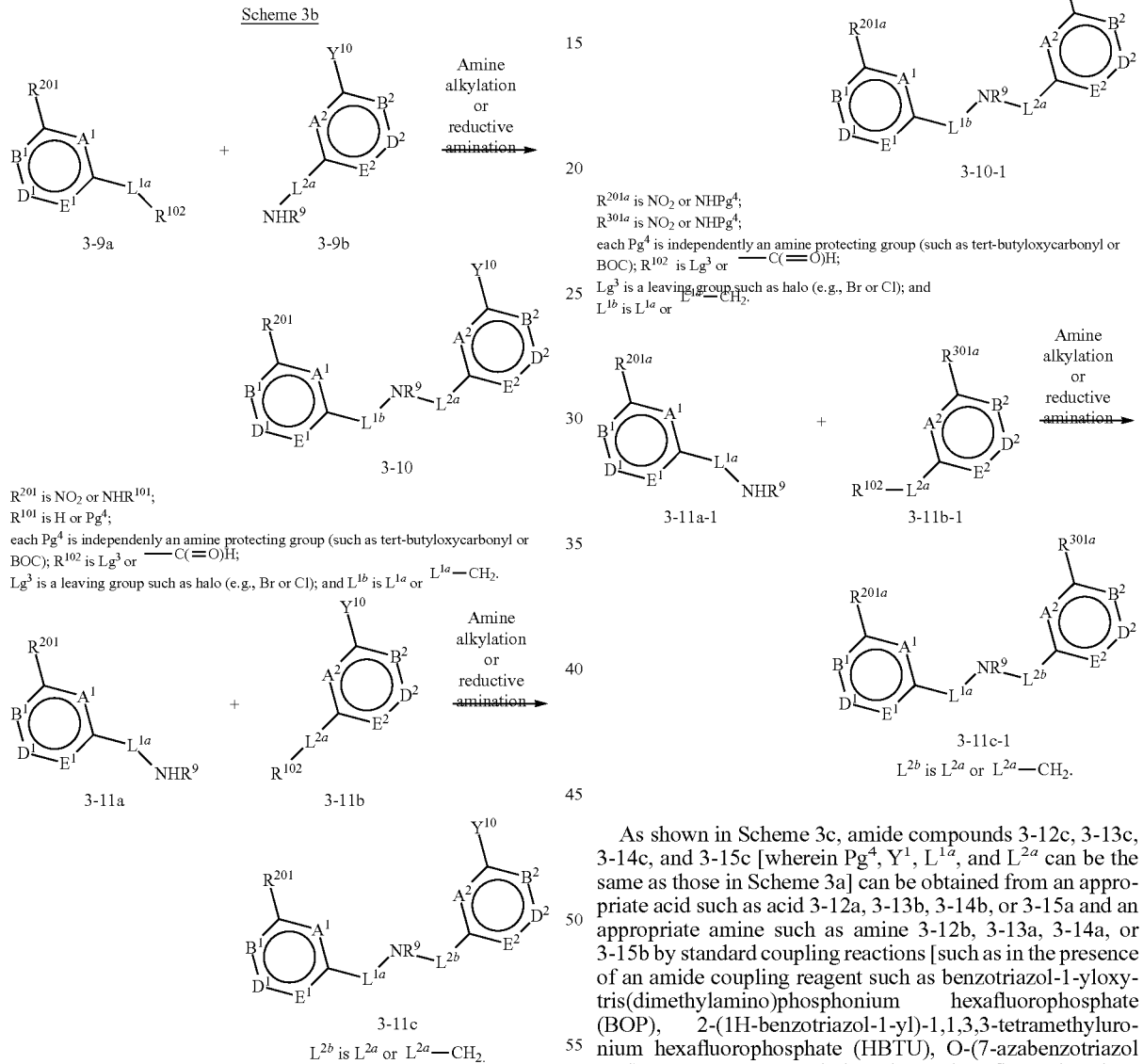

Useful intermediates 3-10-1 and 3-11c-1 can be made according to the methods outlined in Scheme 3b-1 (similar to the reactions depicted in Scheme 3b, and wherein $L^{1a}$ and $L^{2a}$ can be the same as those in Scheme 3a). The protecting group $Pg^4$ of compound 3-10-1 and 3-11c-1 can be removed under suitable conditions. Compounds 3-10-1 and 3-11c-1 can undergo further chemical transformations when suitable reactive groups are present. For example, the $NO_2$ of compound 3-10-1 and 3-11c-1 can be reduced to $NH_2$ under suitable conditions.

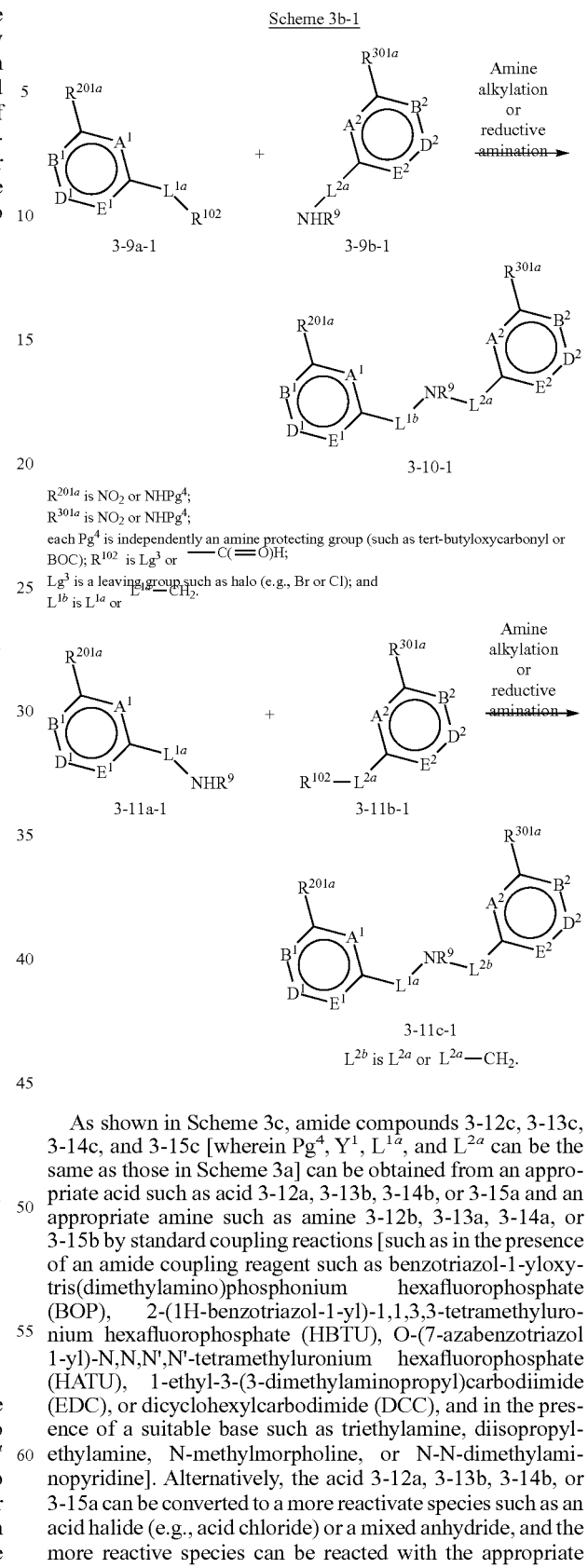

As shown in Scheme 3c, amide compounds 3-12c, 3-13c, 3-14c, and 3-15c [wherein $Pg^4$, $Y^1$, $L^{1a}$, and $L^{2a}$ can be the same as those in Scheme 3a] can be obtained from an appropriate acid such as acid 3-12a, 3-13b, 3-14b, or 3-15a and an appropriate amine such as amine 3-12b, 3-13a, 3-14a, or 3-15b by standard coupling reactions [such as in the presence of an amide coupling reagent such as benzotriazol-1-yloxy-tris(dimethylamino)phosphonium hexafluorophosphate (BOP), 2-(1H-benzotriazol-1-yl)-1,1,3,3-tetramethyluronium hexafluorophosphate (HBTU), O-(7-azabenzotriazol 1-yl)-N,N,N',N'-tetramethyluronium hexafluorophosphate (HATU), 1-ethyl-3-(3-dimethylaminopropyl)carbodiimide (EDC), or dicyclohexylcarbodiimide (DCC), and in the presence of a suitable base such as triethylamine, diisopropylethylamine, N-methylmorpholine, or N-N-dimethylaminopyridine]. Alternatively, the acid 3-12a, 3-13b, 3-14b, or 3-15a can be converted to a more reactivate species such as an acid halide (e.g., acid chloride) or a mixed anhydride, and the more reactive species can be reacted with the appropriate amine 3-12b, 3-13a, 3-14a, or 3-15b respectively.

The protecting group $Pg^4$ of compound 3-12c, 3-13c, 3-14c, or 3-15c can be removed under suitable conditions.

Compounds 3-12c, 3-13c, 3-14c, and 3-15c can undergo further transformation when suitable reactive groups are present. For example, when $Y^{10}$ is $NO_2$, it can be reduced to $NH_2$ under suitable conditions.

Scheme 3c

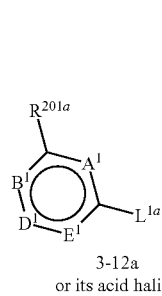

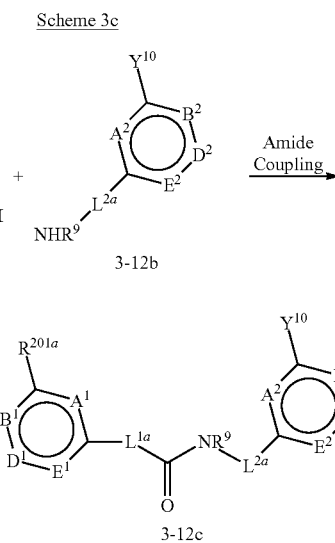

$R^{201a}$ is $NO_2$ or $NHPg^4$; and
$Pg^4$ is an amine protecting group (such as tert-butyloxycarbonyl or BOC).

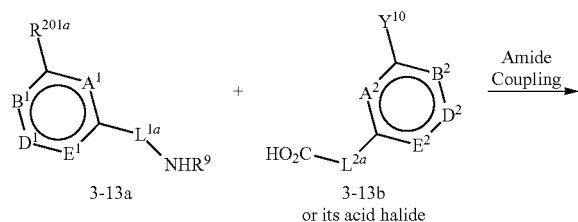

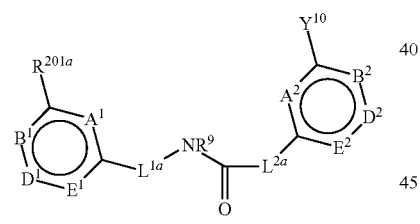

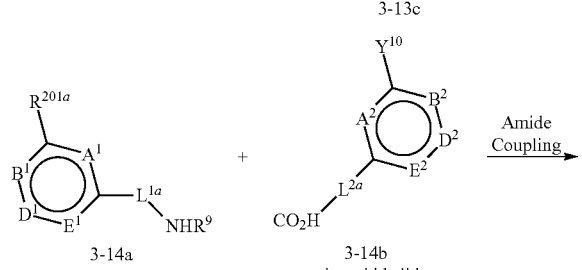

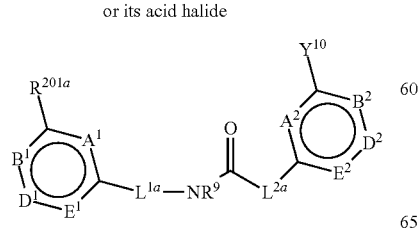

-continued

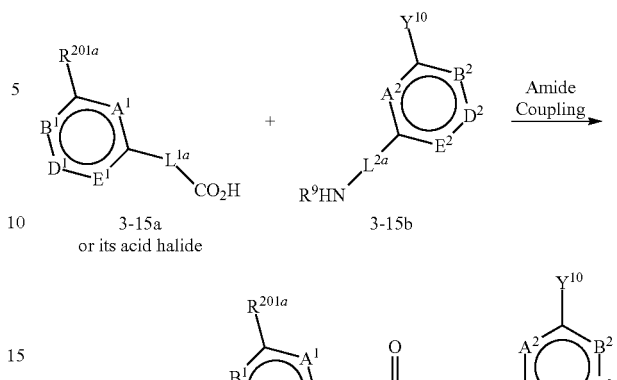

Useful intermediates 3-12c-1, 3-13c-1, 3-14c-1, and 3-15c-1 [wherein $Pg^4$, $L^{1a}$, and $L^{2a}$ can be the same as those in Scheme 3a] can be made according to the methods outlined in Scheme 3c-1 (similar to the reactions depicted in Scheme 3c). The protecting group $Pg^4$ of compounds 3-12c-1, 3-13c-1, 3-14c-1, and 3-15c-1 can be removed under suitable conditions. Compounds 3-12c-1, 3-13c-1, 3-14c-1, and 3-15c-1 can undergo further chemical transformations when suitable reactive groups are present. For example, the $NO_2$ of compounds 3-12c-1, 3-13c-1, 3-14c-1, and 3-15c-1 can be reduced to $NH_2$ under suitable conditions.

Scheme 3c-1

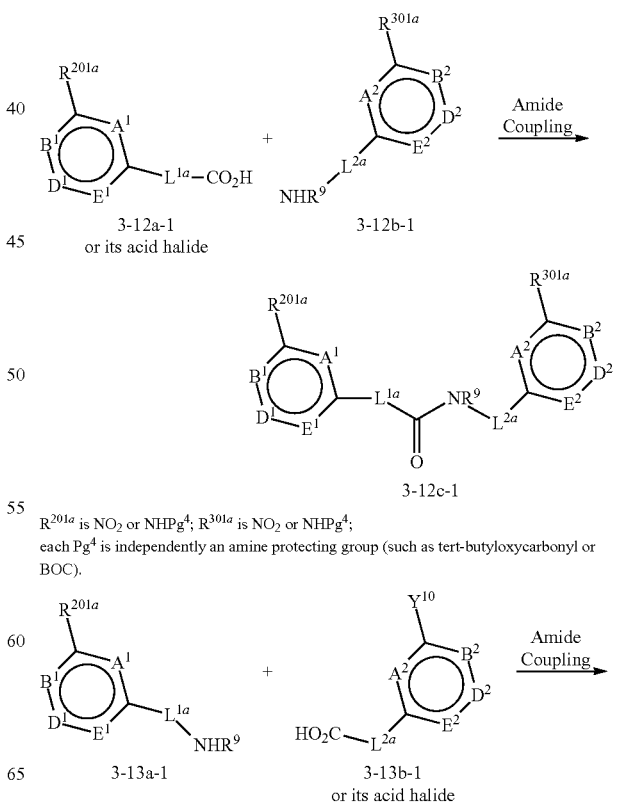

$R^{201a}$ is $NO_2$ or $NHPg^4$; $R^{301a}$ is $NO_2$ or $NHPg^4$;
each $Pg^4$ is independently an amine protecting group (such as tert-butyloxycarbonyl or BOC).

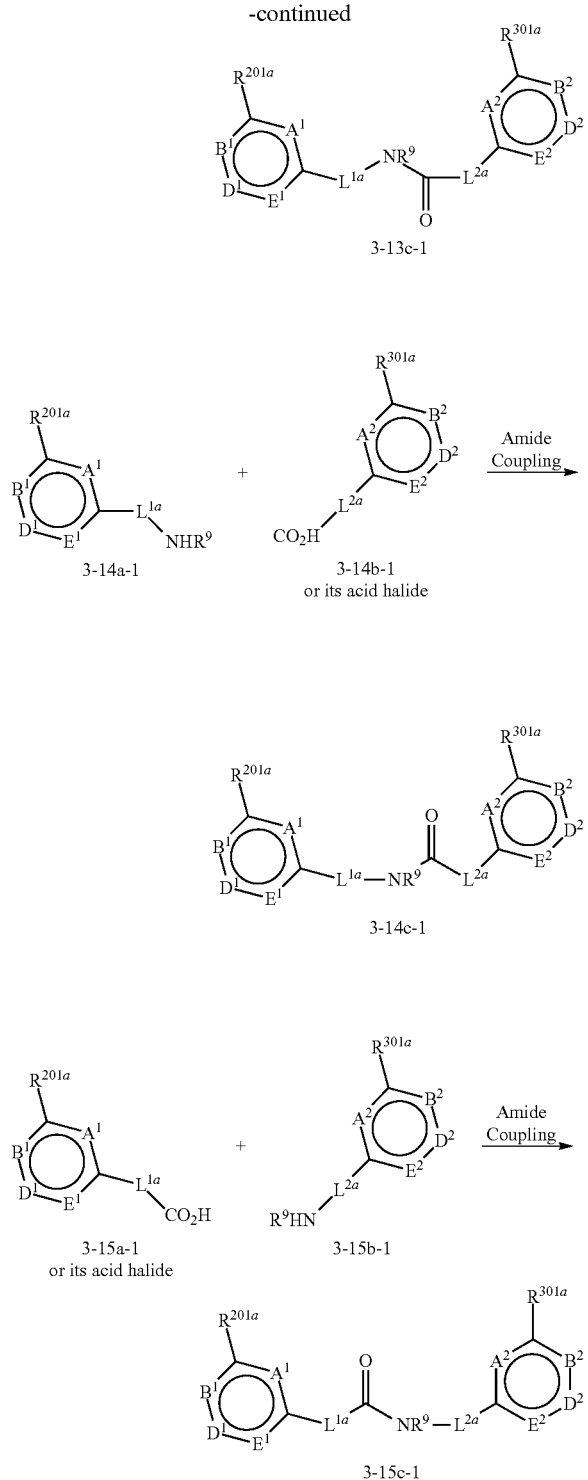
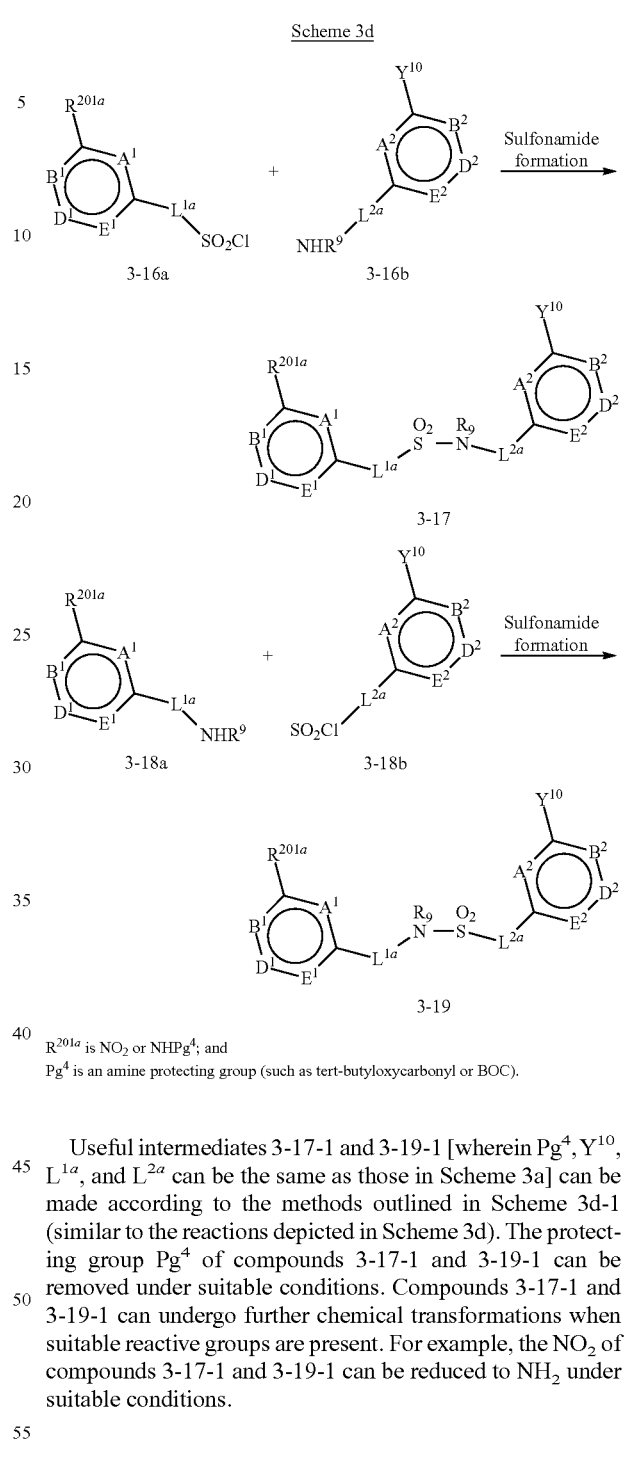

As shown in Scheme 3d, sulfonamide compounds 3-17 and 3-19 [wherein $Pg^4$, $Y^1$, $L^{1a}$, and $L^{2a}$ can be the same as those in Scheme 3a] can be obtained by reacting an appropriate sulfonyl halide (such as chloride) with an appropriate amine. The protecting group $Pg^4$ of compounds 3-17 or 3-19 can be removed under suitable conditions. Compounds 3-17 and 3-19 can undergo further chemical transformations when suitable reactive groups are present. For example, when $Y^{10}$ is $NO_2$, it can be reduced to $NH_2$ under suitable conditions.

$R^{201a}$ is $NO_2$ or $NHPg^4$; and
$Pg^4$ is an amine protecting group (such as tert-butyloxycarbonyl or BOC).

Useful intermediates 3-17-1 and 3-19-1 [wherein $Pg^4$, $Y^{10}$, $L^{1a}$, and $L^{2a}$ can be the same as those in Scheme 3a] can be made according to the methods outlined in Scheme 3d-1 (similar to the reactions depicted in Scheme 3d). The protecting group $Pg^4$ of compounds 3-17-1 and 3-19-1 can be removed under suitable conditions. Compounds 3-17-1 and 3-19-1 can undergo further chemical transformations when suitable reactive groups are present. For example, the $NO_2$ of compounds 3-17-1 and 3-19-1 can be reduced to $NH_2$ under suitable conditions.

Scheme 3d-1

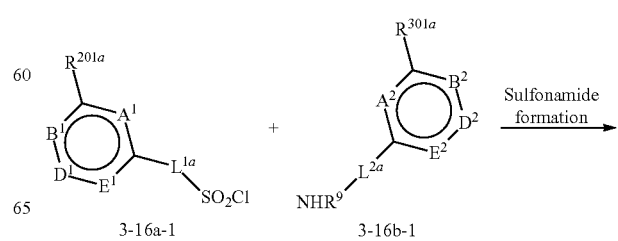

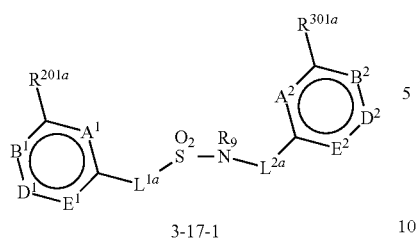

3-17-1

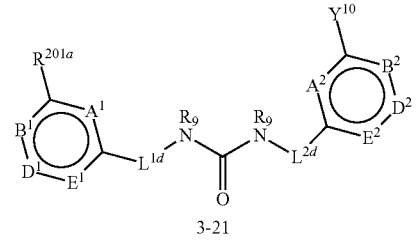

3-21

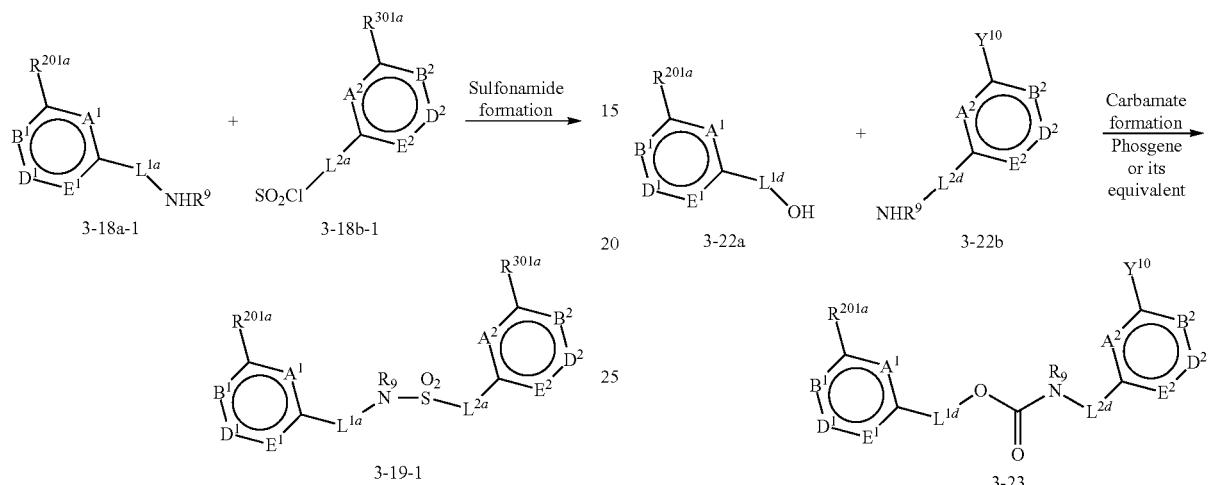

$R^{201a}$ is $NO_2$ or $NHPg^4$;
$R^{301a}$ is $NO_2$ or $NHPg^4$;
each $Pg^4$ is independently an amine protecting group (such as tert-butyloxycarbonyl or BOC).

As shown in Scheme 3e, urea compound 3-21 [wherein $R^{201a}$, $Pg^4$ and $Y^{10}$ can be the same as those in Scheme 3d; and $L^{1d}$ and $L^{2d}$ can be each, independently, —$(CR^7R^8)_m$— (such as a bond or methylene)] can be obtained by reacting two appropriate amines with phosgene [$C(=O)Cl_2$] or a phosgene equivalent [e.g., triphosgene, ethyl chloroformate, trichloromethyl chloroformate, or phenyl chlorocarbonate]. Similarly, carbamates 3-23 and 3-25 can be made by reacting an appropriate amine and an appropriate alcohol with phosgene or its equivalent. Sulfamide 3-25c can be made by reacting amines 3-25a and 3-25b with $SO_2Cl_2$ or its equivalent (such as other thionyl halides, e.g., $SO_2Br_2$). The protecting group $Pg^4$ of compounds 3-21, 3-23, or 3-25 can be removed under suitable conditions. Compounds 3-21, 3-23, and 3-25 can undergo further chemical transformations when suitable reactive groups are present. For example, when $Y^1$ (and/or $R^{201a}$) is $NO_2$, it can be reduced to $NH_2$ under suitable conditions.

Scheme 3e

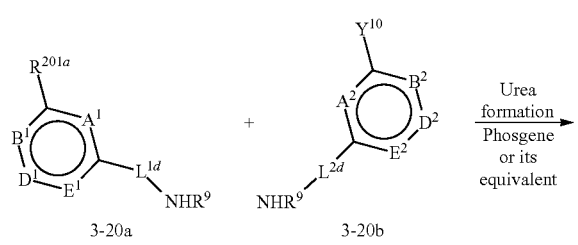



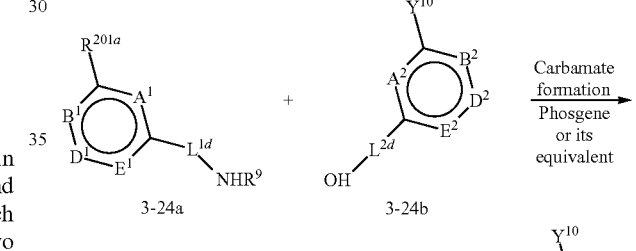

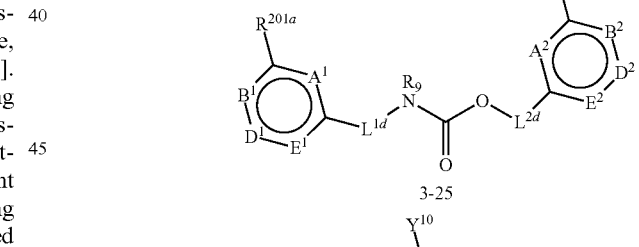

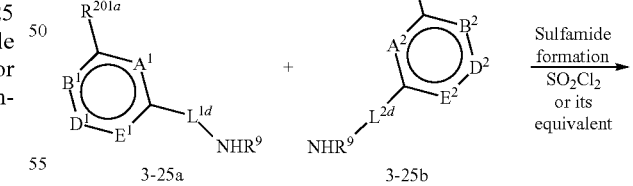

$R^{201a}$ is $NO_2$ or $NHPg^4$; and
$Pg^4$ is an amine protecting group (such as tert-butyloxycarbonyl or BOC).

Useful intermediates 3-21-1, 3-23-1, 3-25-1, or 3-25-1c [wherein $Pg^4$, $Y^{10}$, $L^{1a}$, and $L^{2a}$ can be the same as those in Scheme 3a] can be made according to the methods outlined in Scheme 3e-1 (similar to the reactions depicted in Scheme 3e). The protecting group $Pg^4$ of compounds 3-21, 3-23, or 3-25 can be removed under suitable conditions. Compounds 3-21, 3-23, or 3-25 can undergo further chemical transformations when suitable reactive groups are present. For example, the $NO_2$ of compound 3-21, 3-23, or 3-25 can be reduced to $NH_2$ under suitable conditions.

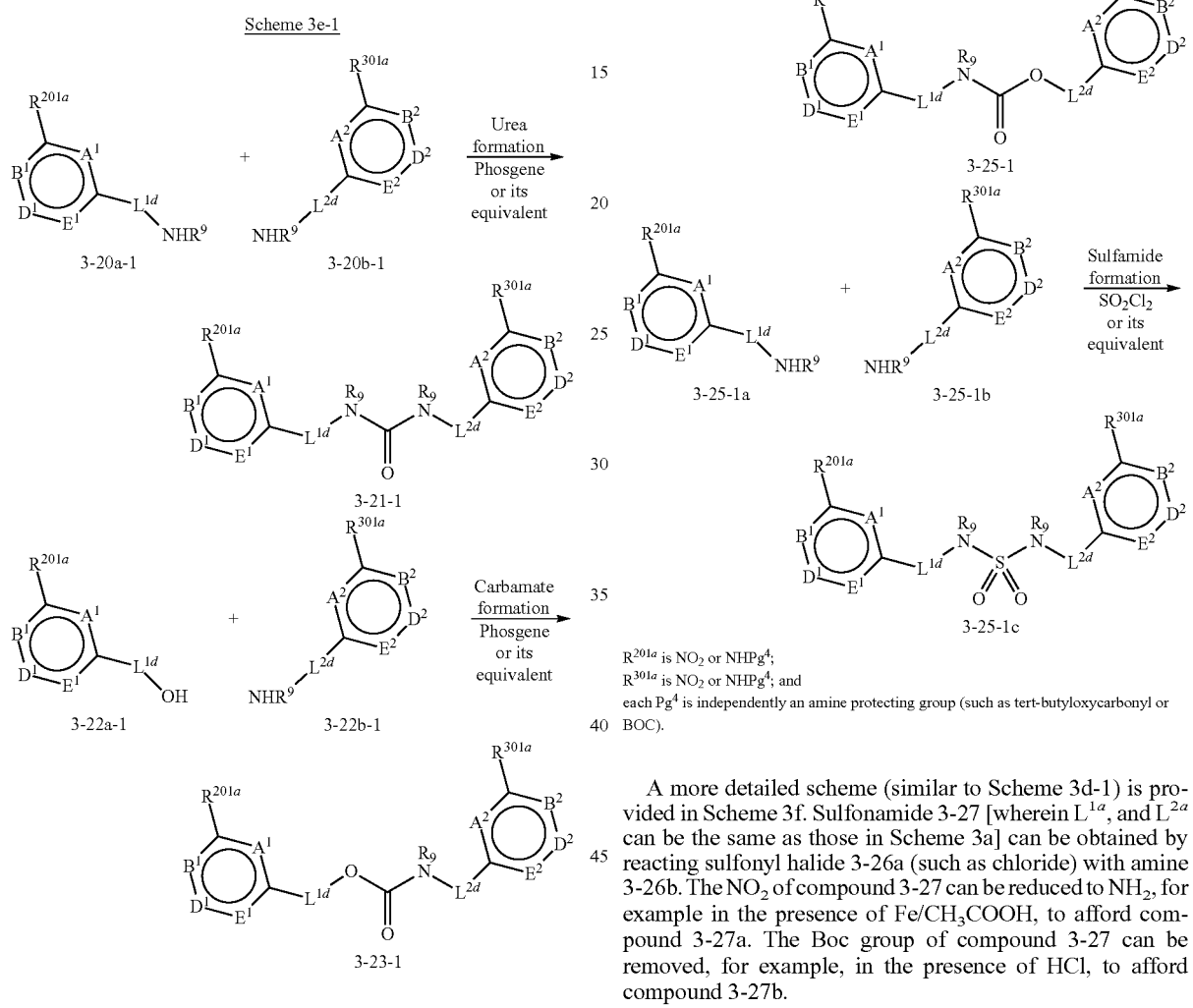

$R^{201a}$ is $NO_2$ or $NHPg^4$;
$R^{301a}$ is $NO_2$ or $NHPg^4$; and
each $Pg^4$ is independently an amine protecting group (such as tert-butyloxycarbonyl or BOC).

A more detailed scheme (similar to Scheme 3d-1) is provided in Scheme 3f. Sulfonamide 3-27 [wherein $L^{1a}$, and $L^{2a}$ can be the same as those in Scheme 3a] can be obtained by reacting sulfonyl halide 3-26a (such as chloride) with amine 3-26b. The $NO_2$ of compound 3-27 can be reduced to $NH_2$, for example in the presence of $Fe/CH_3COOH$, to afford compound 3-27a. The Boc group of compound 3-27 can be removed, for example, in the presence of HCl, to afford compound 3-27b.

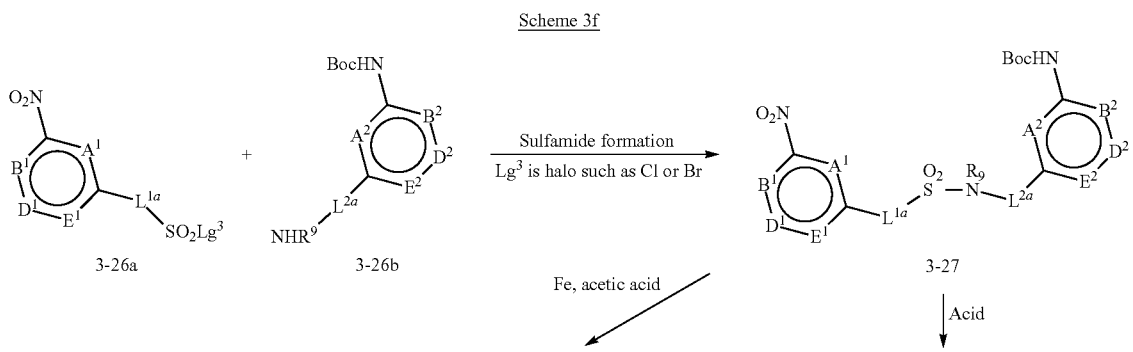

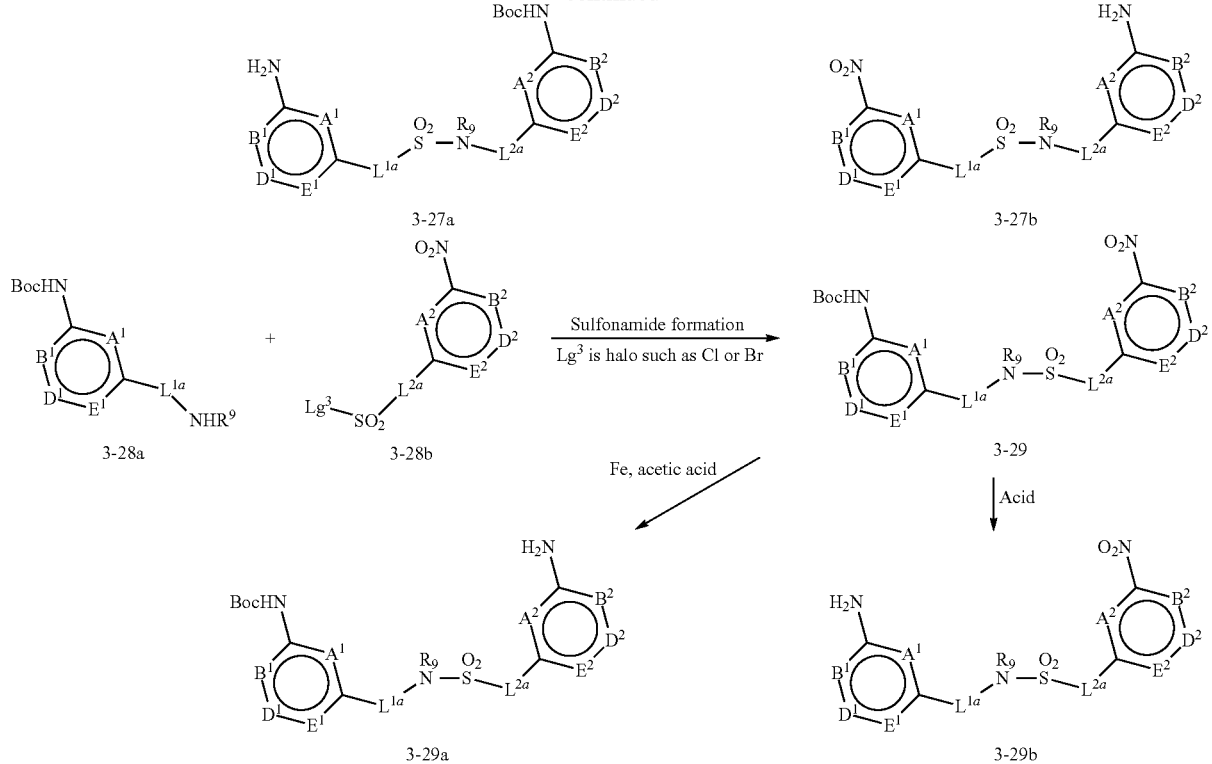

As shown in Scheme 4, macrocycle 4-2 [wherein $L^{1a}$ and $L^{2a}$ can be the same as those in Scheme 3a] can be cyclized from acyclic precursor 4-1 by intramolecular Mitsunobu reaction/coupling. Preferably, one of $L^{1a}$ and $L^{2a}$ of acyclic precursor 4-1 is a bond in the intramolecular Mitsunobu reactions/couplings.

In addition, many other intramolecular macrocyclizations can be useful for synthesizing the compounds of the present invention. For example, amine alkylations and reductive aminations can be useful for cyclizations as shown in Scheme 5a [wherein $L^{1a}$ and $L^{2a}$ can be the same as those in Scheme 3b].

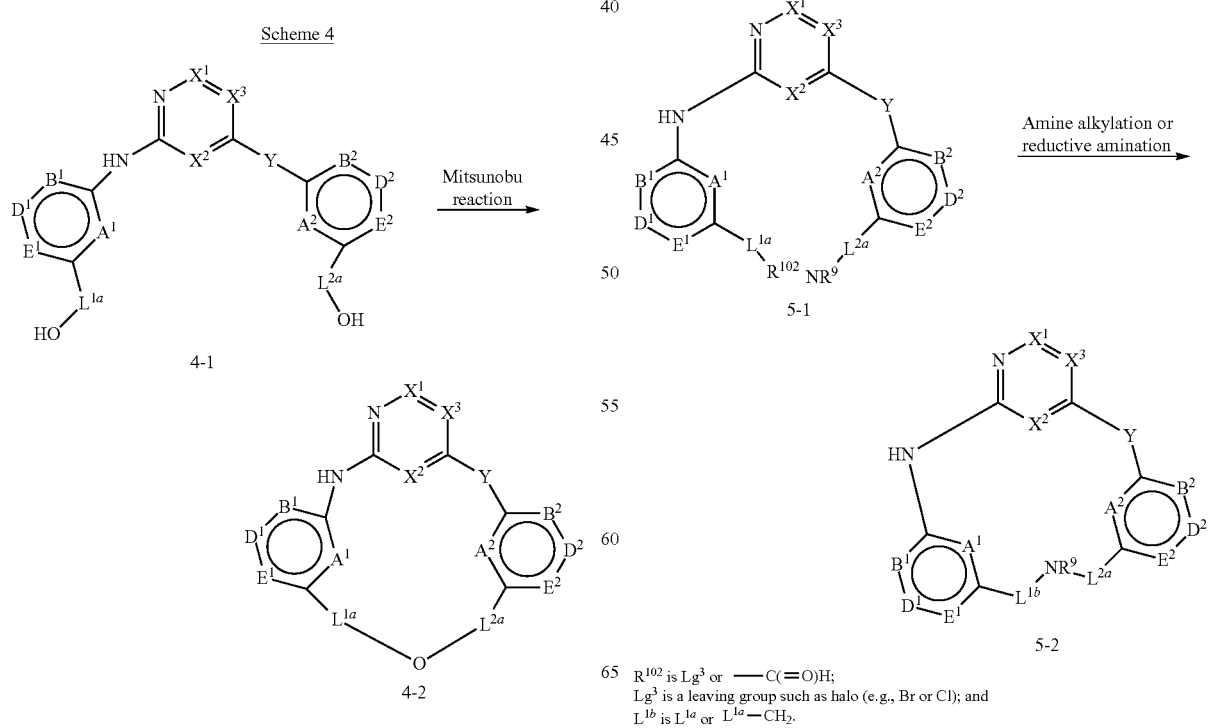

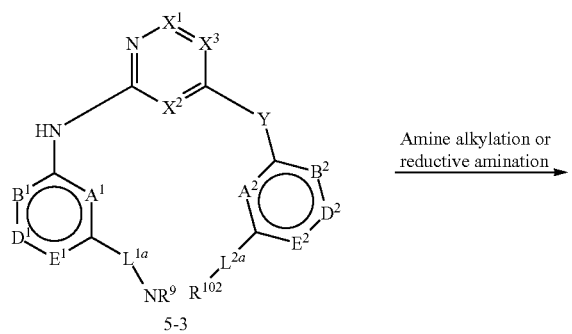
5-3
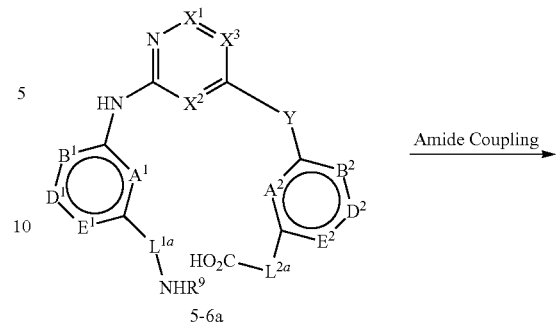
5-6a
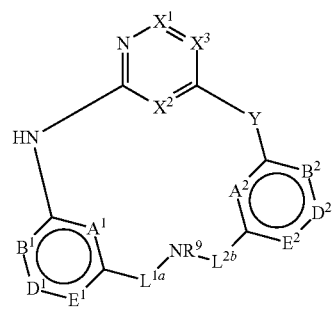
5-4
$L^{2b}$ is $L^{2a}$ or $L^{2a}$—$CH_2$.
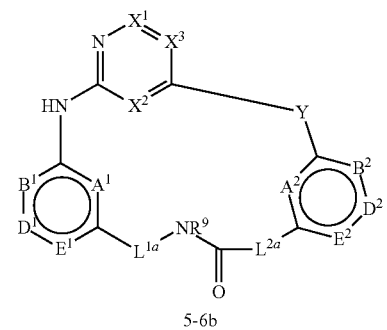
5-6b
Amide couplings can be useful for cyclizations as shown in Scheme 5b (similar to the reactions depicted in Scheme 3c, and wherein $L^{1a}$ and $L^{2a}$ can be the same as those in Scheme 3c).
Scheme 5b
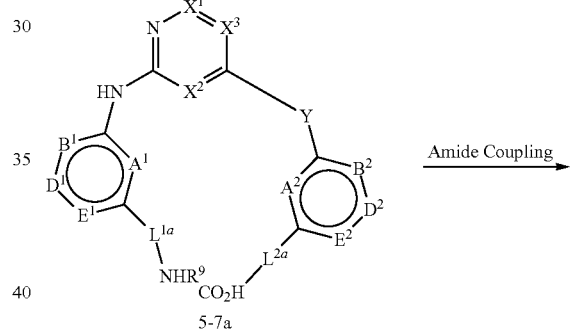
5-7a
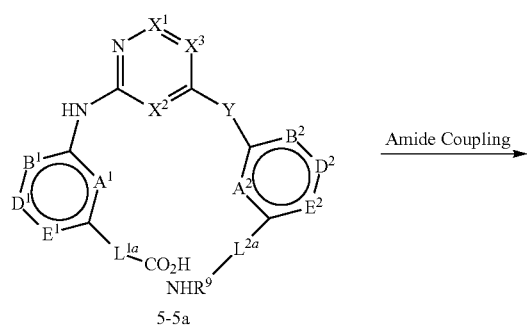
5-5a
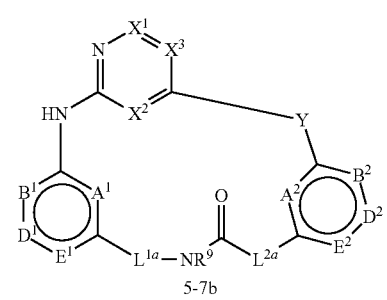
5-7b
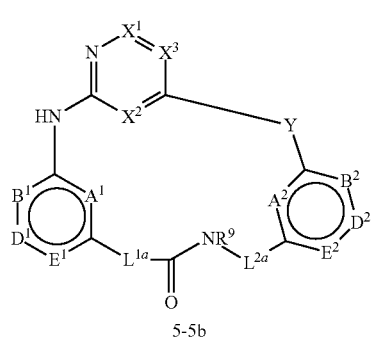
5-5b
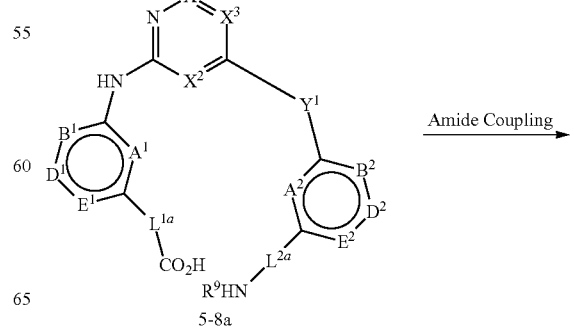
5-8a -continued

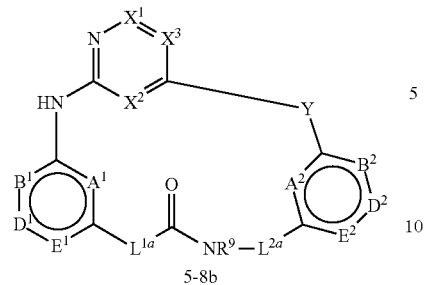

5-8b

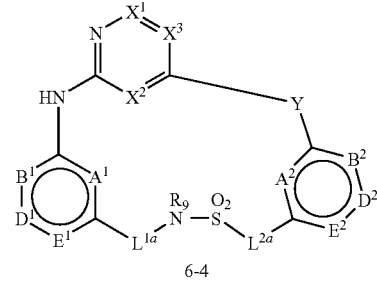

6-4

Sulfonamide formation can be useful for cyclization as shown in Scheme 6a (similar to the reactions depicted in Scheme 3d, and wherein $L^{1a}$ and $L^{2a}$ can be the same as those in Scheme 3d).

Urea formation and carbamate formation can be useful for cyclizations as shown in Scheme 6b (similar to the reactions depicted in Scheme 3e, and wherein $L^{1d}$ and $L^{2d}$ are the same as those in Scheme 3e).

Scheme 6a

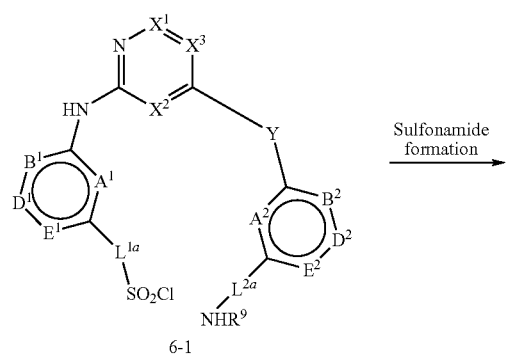

Scheme 6b

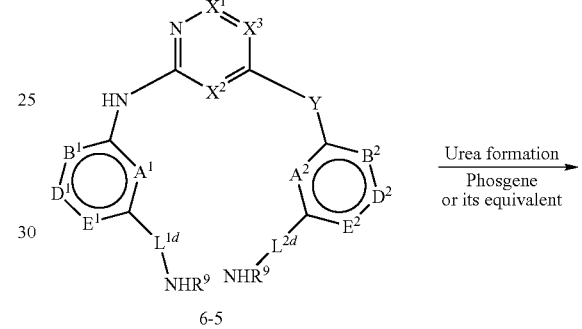

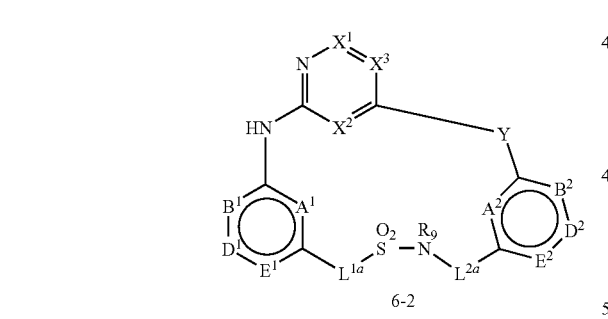

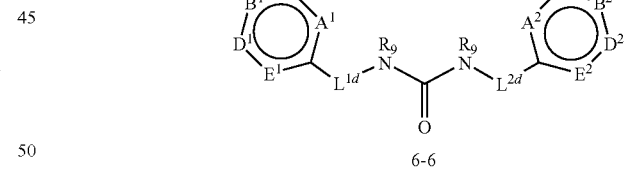

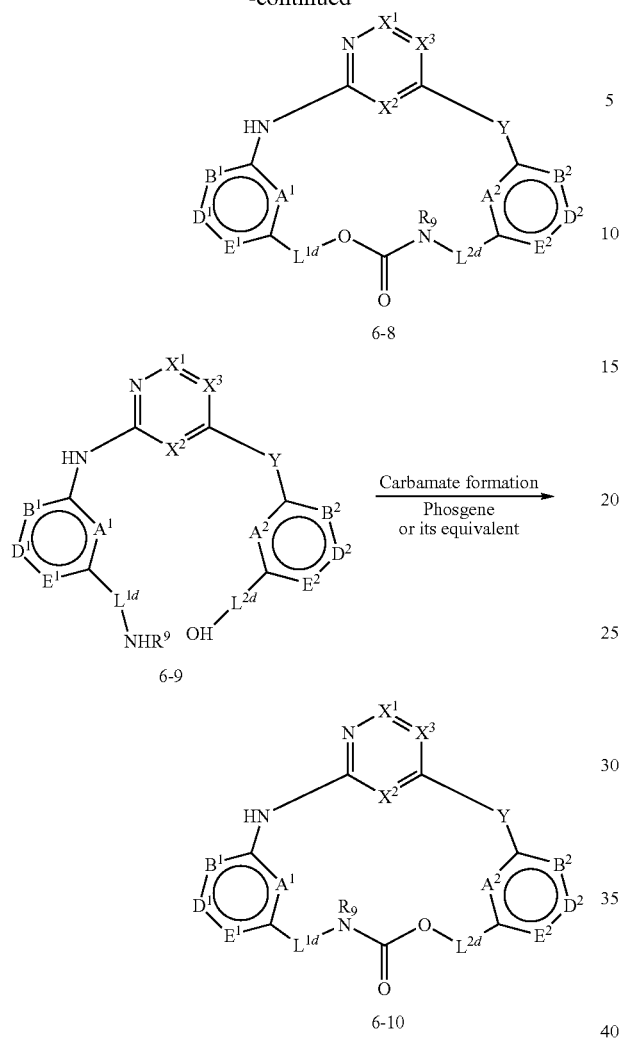

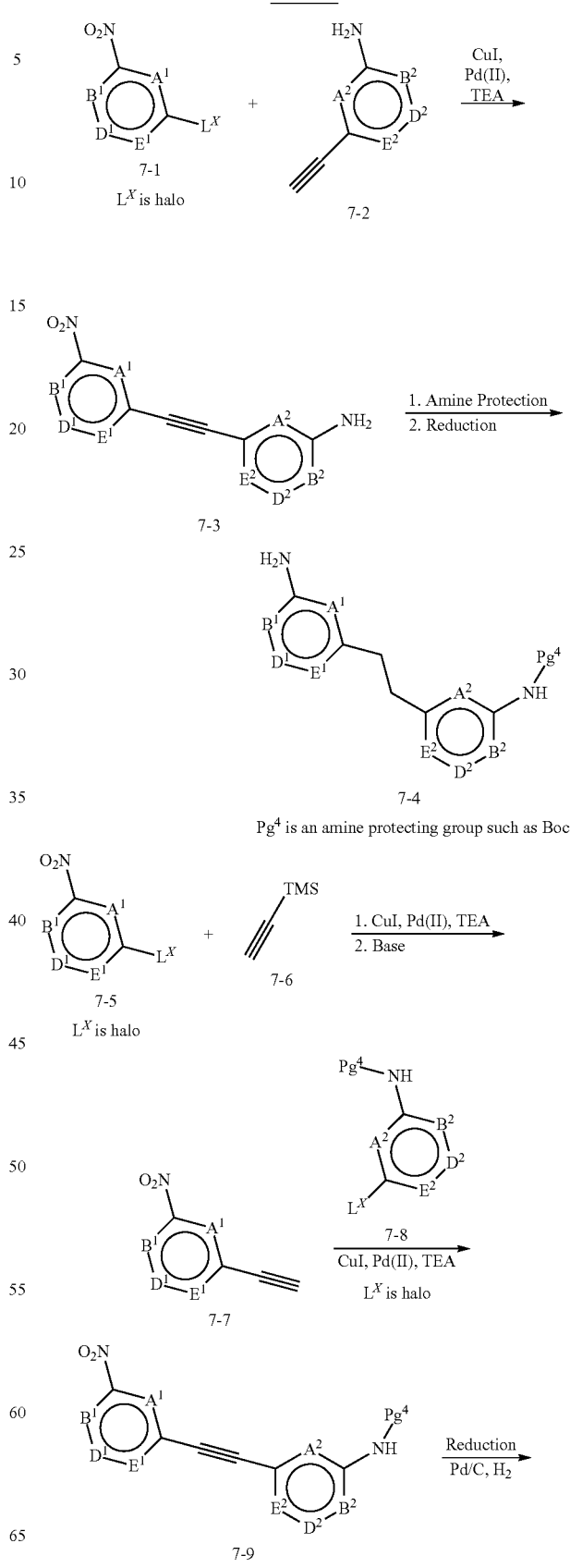

Scheme 7

Useful intermediates 7-4, 7-10, and 7-13 can be made according to the methods outlined in Scheme 7. Aryl halide or heteroaryl halide 7-1 can be reacted with alkyne 7-2 under Sonogashira coupling reaction conditions to afford alkyne 7-3. [See, K. Sonogashira, Y. Tohda, N. Hagihara (1975). "A convenient synthesis of acetylenes: catalytic substitutions of acetylenic hydrogen with bromoalkenes, iodoarenes and bromopyridines". *Tetrahedron Letters* 16 (50): 4467-4470.]. The amino group of alkyne 7-3 can be protected with a protecting group $Pg^4$, followed by the C≡C bond being reduced to a saturated bond by hydrogenation to afford intermediate 7-4.

Aryl halide or heteroaryl halide 7-5 can be reacted with silyl substituted acetylene 7-6 [e.g. (trimethylsilyl)-acetylene] under Sonogashira coupling reaction conditions, followed by removal of the silyl group under suitable conditions [e.g., in the presence of a base (e.g., $K_2CO_3$)] to afford alkyne 7-7. Alkyne 7-7 can be reacted with aryl halide or heteroaryl halide 7-8 under Sonogashira coupling reaction condition to afford alkyne 7-9. Alkyne 7-9 can be reduced via hydrogenation to produce intermediate 7-10. Aryl halide or heteroaryl halide 7-11 can be reacted with alkyne 7-12 under Sonogashira coupling reaction conditions, followed by hydrogenation to reduce the C≡C bond, to afford alkyne 7-13.

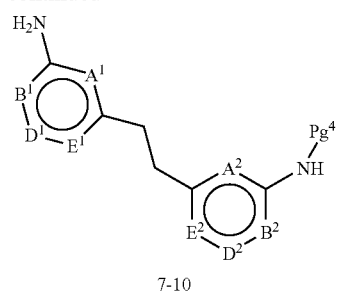
7-10
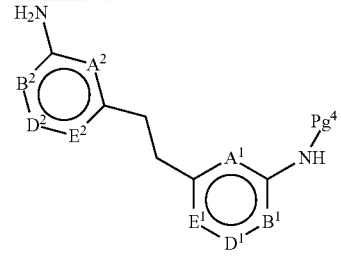
7-4a
Pg⁴ is an amine protecting group such as Boc
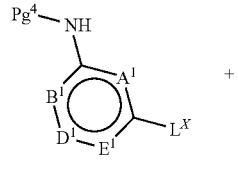
7-11
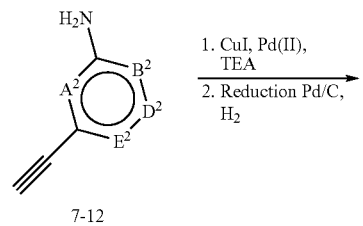
7-12
1. CuI, Pd(II), TEA
2. Reduction Pd/C, H$_2$
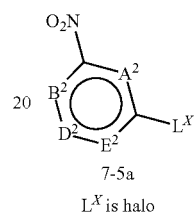
7-5a
L$^X$ is halo
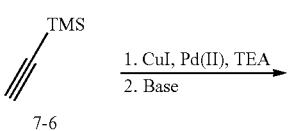
7-6
1. CuI, Pd(II), TEA
2. Base
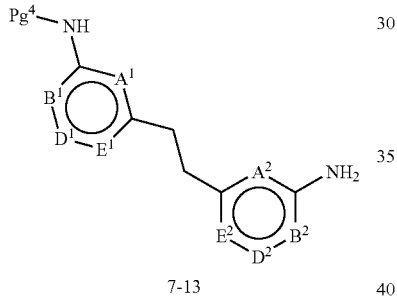
7-13
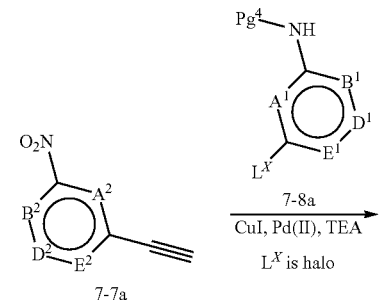
7-7a
7-8a
CuI, Pd(II), TEA
L$^X$ is halo
Useful intermediates 7-4a, 7-10a, and 7-13a can be made according to the methods outlined in Scheme 7-1 (similar to the reactions depicted in Scheme 7).
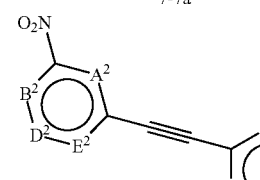
7-9a
Reduction
Pd/C, H$_2$
Scheme 7-1
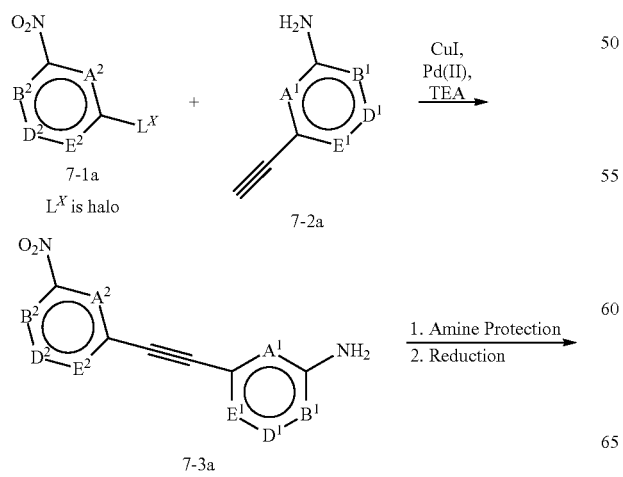
7-1a  L$^X$ is halo
7-2a
CuI, Pd(II), TEA
7-3a
1. Amine Protection
2. Reduction
7-11a
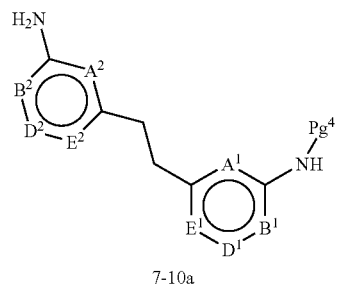
7-10a
+

-continued

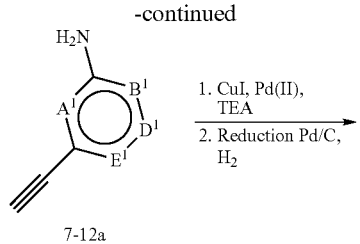

7-12a

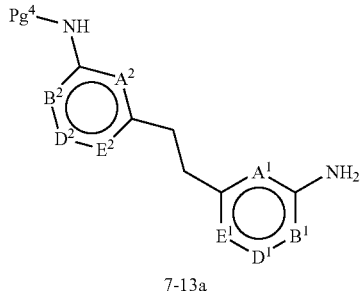

7-13a

Scheme 7-2

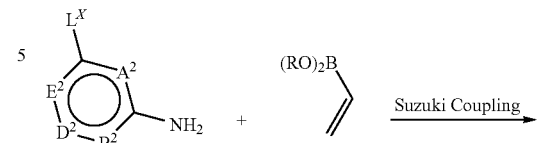

$L^X$ is a leaving group such as halo or OTf

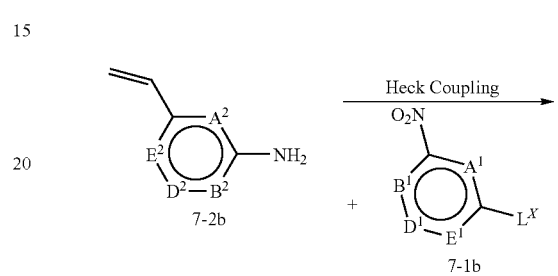

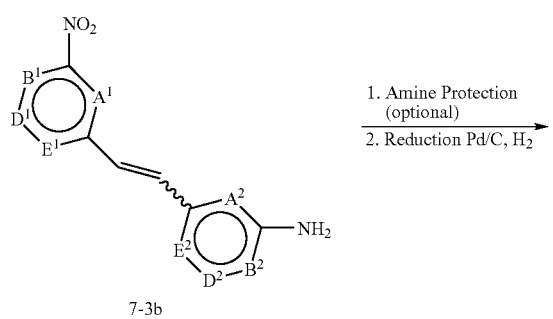

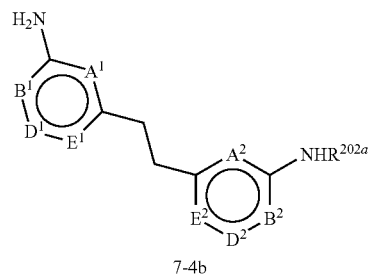

$R^{202a}$ is H or an amine protecting group such as Boc

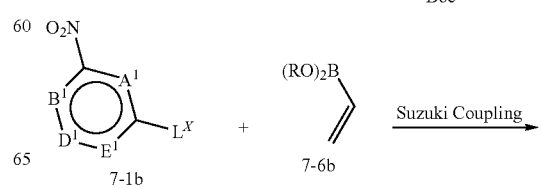

Useful intermediates 7-4b, 7-10b, and 7-13b can be made according to the methods outlined in Scheme 7-2. Aryl halide/triflate or heteroaryl halide/triflate 7-5b can be reacted with vinylboronate 7-6b (R groups can be each, independently, H (e.g., compound 7-6b is a vinylboronic acid when both R are H) or alklyl; or together with the —O—B—O— to which they are attached form an optionally substituted heterocycloalkyl) under Suzuki-Miyaura reaction condition/Suzuki coupling to form alkene 7-2b [for reviews of the Suzuki-Miyaura reaction, see e.g. Miyaura, N; Suzuki, A. Chem. Rev., 1995, 95:2457-2483]. Alternatively, a vinyl stannane (such as tributyl(vinyl)stannane, equivalent to vinylboronate 7-6b in the Suzuki-Miyaura reaction described herein) can be used to react with aryl halide or heteroaryl halide 7-5b to form alkene 7-2b under Stille reaction conditions [See e.g. P. Espinet, A. M. Echavarren "The Mechanisms of the Stille Reaction"; Angewandte Chemie International Edition; 43 (36): 4704-4734 (2004)]. Aryl halide/triflate or heteroaryl halide/triflate 7-1b can be reacted with alkene 7-2b under Heck coupling reaction conditions to afford alkene 7-3b. [See e.g. Heck, R. F.; Nolley, Jr., J. P., "Palladium-catalyzed vinylic hydrogen substitution reactions with aryl, benzyl, and styryl halides"; J. Org. Chem., 37(14): 2320-2322 (1972)]. The amino group of alkene 7-3b can optionally be protected by an amine protecting group such as Boc group, followed by reduction of the C=C bond to a saturated bond via hydrogenation to afford intermediate 7-4b under an appropriate condition such as palladium catalyzed hydrogenation or using a hydrazine compound. [See e.g. Y. Imada, H. Iida, T. Naota, *J. Am. Chem. Soc.*, 2005, 127, 14544-14545].

Intermediate 7-10b can be synthesized starting from aryl halide/triflate or heteroaryl halide/triflate 7-1b (also substituted with a nitro group) through similar chemical transformations to those described in the formation of intermediate 7-4b.

Alternatively, aryl halide/triflate or heteroaryl halide/triflate 7-11b can be reacted with alkene 7-12b under Heck coupling reaction conditions, followed by reduction of the C=C bond, for example, via hydrogenation, to afford intermediate 7-13b.

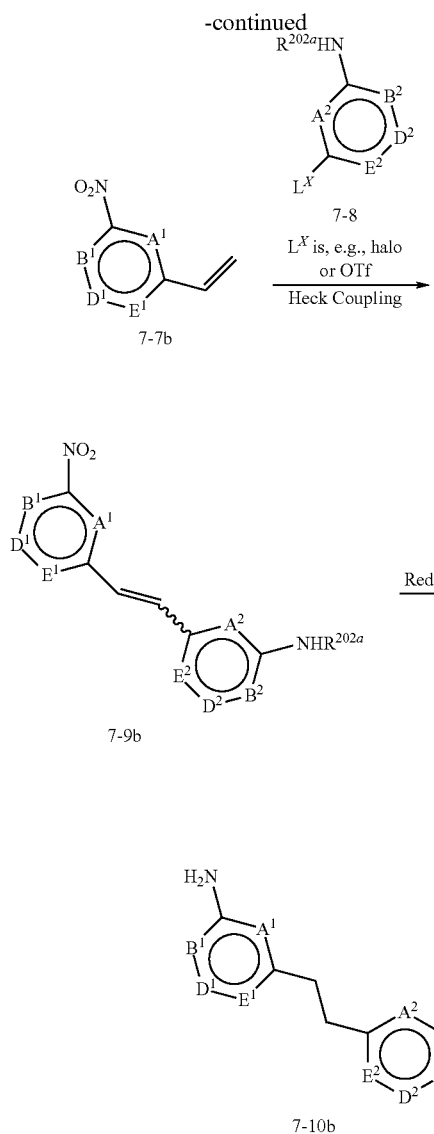
Useful intermediates 7-4c, 7-10c, and 7-13c can be made according to the methods outlined in Scheme 7-3 (similar to those depicted in Scheme 7-2).
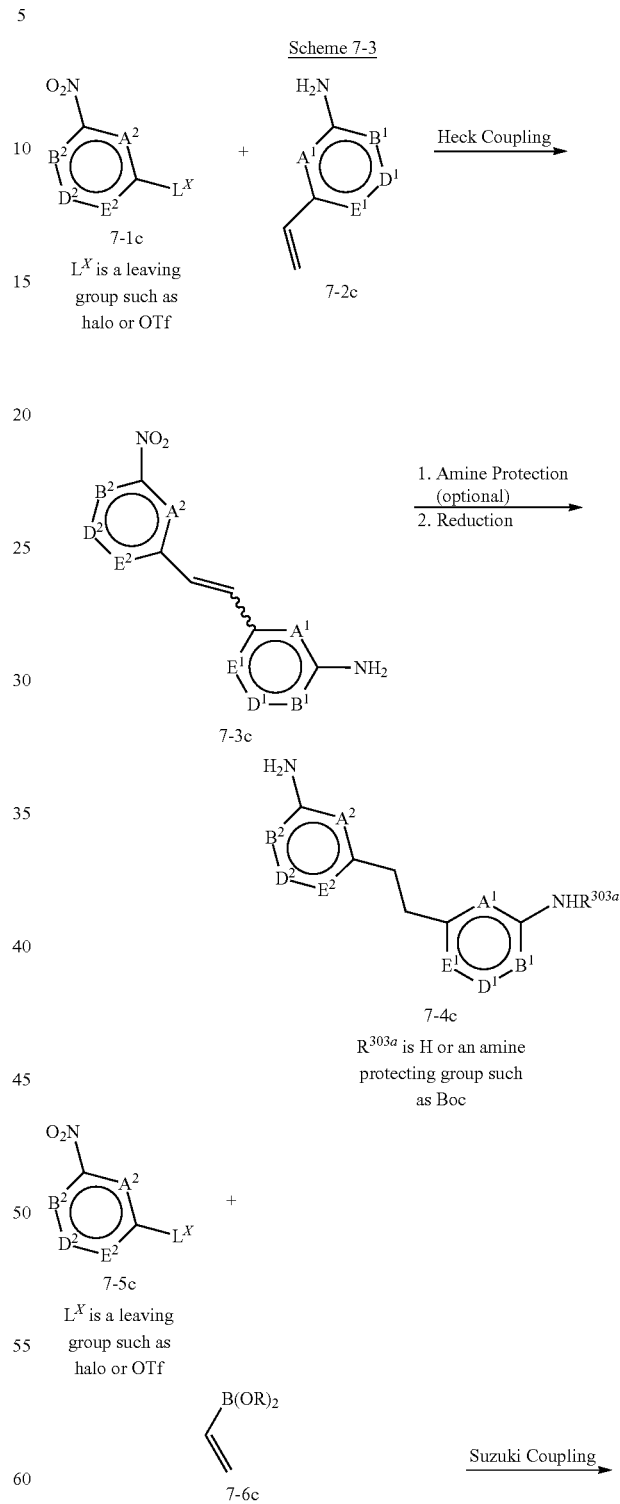

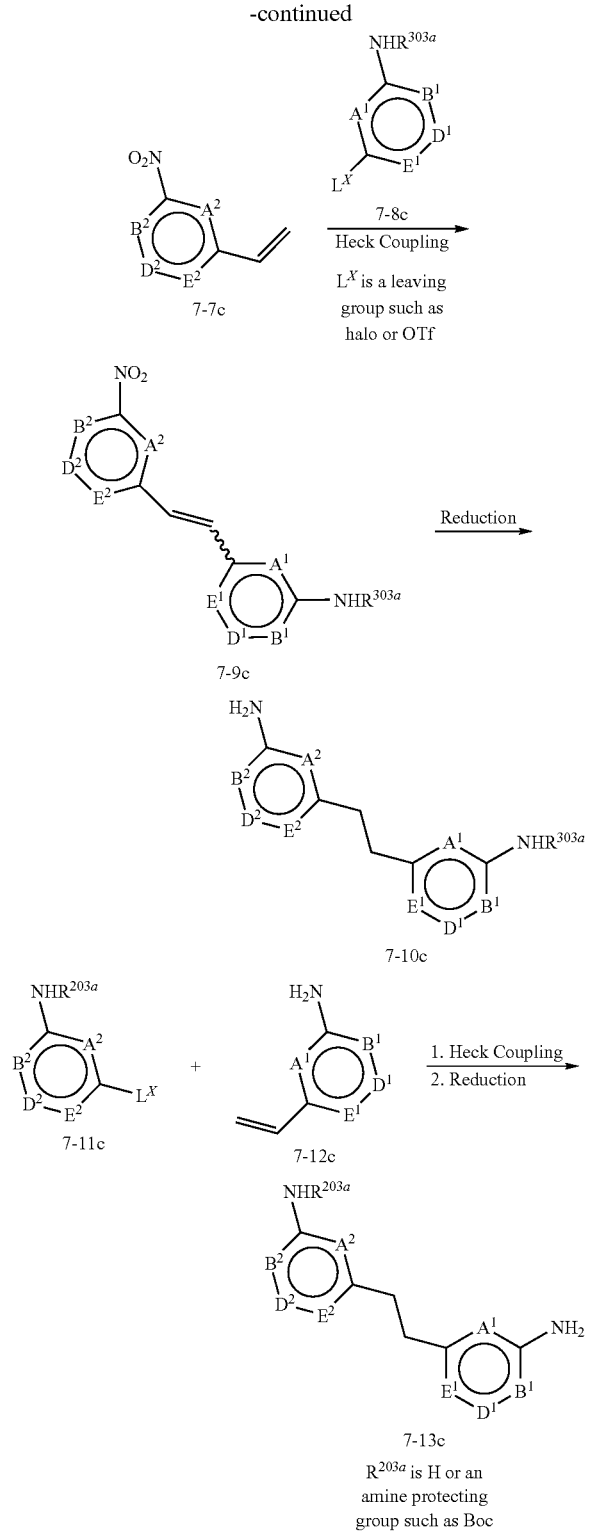

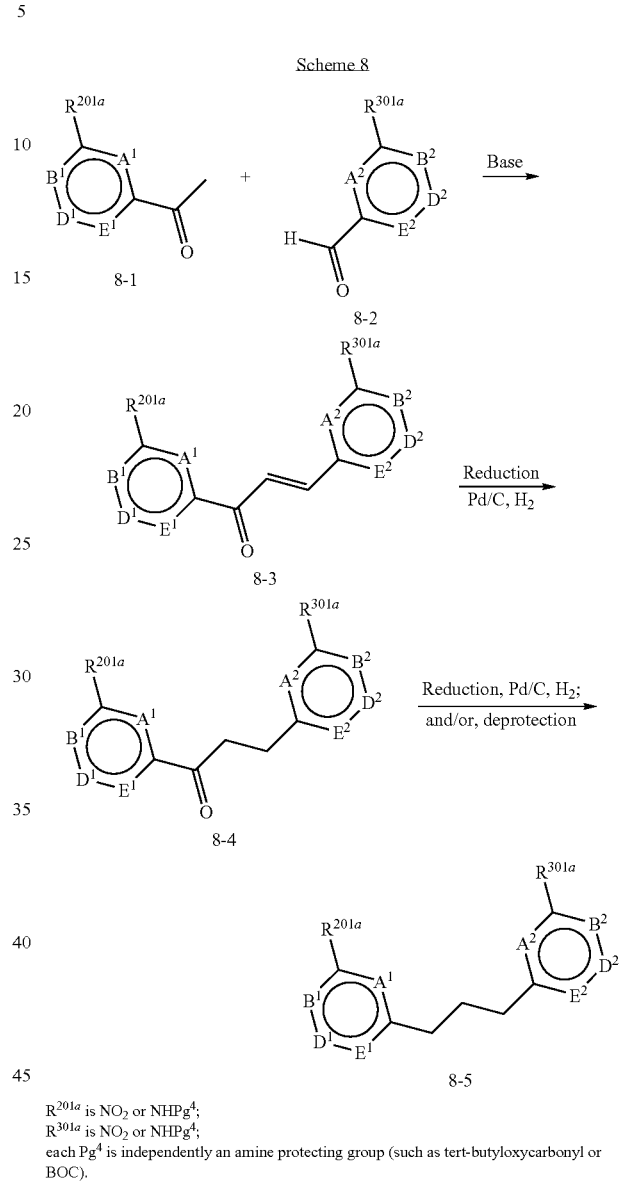

$R^{201}$ and $R^{301}$ groups of compounds 8-4 or 8-5 can undergo further chemical transformations. For example, the $NO_2$ group can be reduced to $NH_2$; and a protected amino group can be de-protected to $NH_2$.

$R^{201a}$ is $NO_2$ or $NHPg^4$;
$R^{301a}$ is $NO_2$ or $NHPg^4$;
each $Pg^4$ is independently an amine protecting group (such as tert-butyloxycarbonyl or BOC).

Useful intermediates 8-3a, 8-4a, and 8-5a can be made according to the methods outlined in Scheme 8-1 (similar to the reactions depicted in Scheme 8).

Scheme 8-1

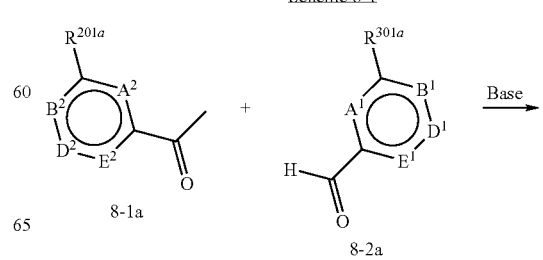

As shown in Scheme 8, aryl (or heteroaryl)methyl ketone 8-1 can be reacted with aryl (or heteroaryl) aldehyde 8-2 under basic conditions [(such as in the presence of an alkali metal hydroxide (e.g. NaOH)] to afford derivative 8-3. Intermediate 8-3 can be reduced via hydrogenation (such as in the presence of Pd/C, hydrogen and acetic acid) to afford compound 8-4, which further can be reduced to compound 8-5.

-continued

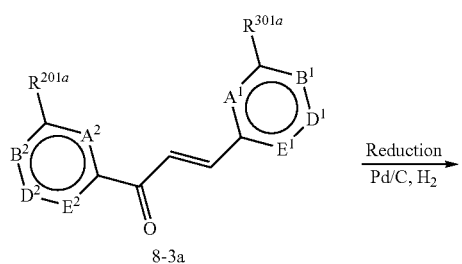
8-3a

Reduction
Pd/C, H₂

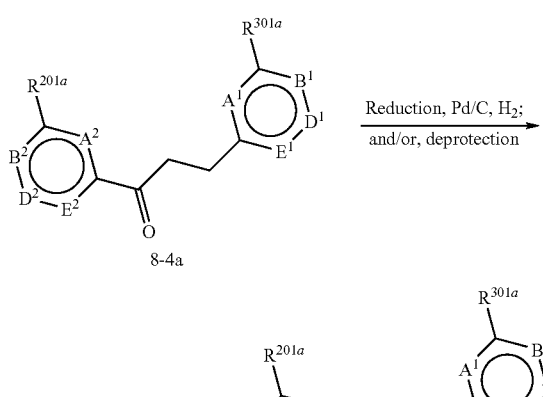
8-4a

Reduction, Pd/C, H₂;
and/or, deprotection

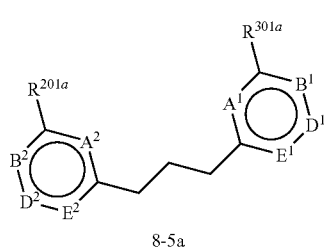
8-5a $R^{201a}$ is $NO_2$ or $NHPg^4$;
$R^{301a}$ is $NO_2$ or $NHPg^4$;
each $Pg^4$ is independently an amine protecting group (such as tert-butyloxycarbonyl or BOC).

Scheme 9

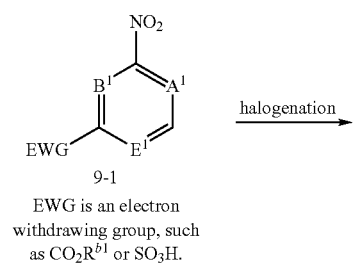
9-1

EWG is an electron withdrawing group, such as $CO_2R^{b1}$ or $SO_3H$.

halogenation

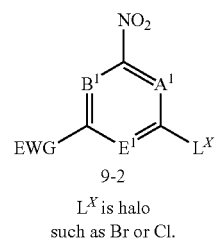
9-2

$L^X$ is halo such as Br or Cl.

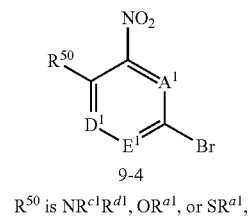
9-3

$HNR^{c1}R^{d1}$, $HOR^{a1}$, or $HSR^{a1}$,
Base

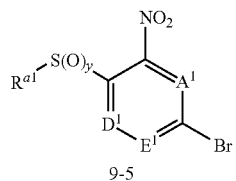
9-4

$R^{50}$ is $NR^{c1}R^{d1}$, $OR^{a1}$, or $SR^{a1}$, $R^{50}$ is $SR^{a1}$
Oxidation
mCPBA

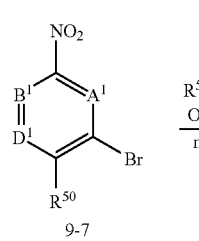
9-5

Some additional useful intermediates can be made by the methods outlined in Scheme 9. Aryl (or heteroaryl) compound 9-1 can be reacted with a halogenating reagent [such as bromine (Br₂), N-bromoacetamide (NBA), N-bromosuccinimide (NBS), 1,3-dibromo-5,5-dimethylhydantoin (DBDMH), 1,3-dichloro-5,5-dimethylhydantoin (DCDMH), N-chlorosuccinimide (NCS)] to afford halogenated compounds 9-2.

A fluorinated compound 9-3 can be reacted with an amine, an alcohol, or thioalcohol in the presence of a base (such as a tertiary amine, e.g., TEA) to form compound 9-4. Where $R^{50}$ is $SR^{a1}$, compound 9-4 can be oxidized to sulfinyl or sulfonyl compounds 9-5 (wherein y is 1 or 2), using an oxidizing reagent such as m-chloroperoxybenzoic acid (mCPBA).

A fluorinated compound 9-6 can be reacted with an amine, an alcohol, or thioalcohol in the presence of a base (such as a tertiary amine, e.g., triethylamine or TEA) to form compound 9-7. Where $R^{50}$ is $SR^{a1}$, compound 9-7 can be oxidized to sulfinyl or sulfonyl compound 9-8 (wherein y is 1 or 2), using an oxidizing reagent such as m-chloroperoxybenzoic acid (mCPBA). The nitro (NO₂) group of compound 9-8 can be reduced, for example, in the presence of Fe (or Zn) and acetic acid, followed by introduction of an amine protecting group (such as Boc), to afford compound 9-9.

-continued y is 1 or 2

Useful intermediates 9-2a, 9-4-a, 9-5a, 9-7a, 9-8a, and 9-9a can be made according to the methods outlined in Scheme 9-1 (similar to the reactions depicted in Scheme 9).

Scheme 9-1

EWG is an electron withdrawing group, such as $CO_2R^{b1}$ or $SO_3H$.

$L^X$ is halo such as Br or Cl.

y is 1 or 2

As shown in Scheme 10, compound 10-1 [Y is O, S, or $NR^4$; and $Lg^3$ is a leaving group such as halo (e.g., chloro)] can be reacted with substituted heteroaromatic compound 10-2 [wherein $Lg^1$ and $Lg^2$ are each, independently, a leaving group such as halo (e.g., chloro)] in the presence of a suitable base (such as an inorganic base, for example a metal carbonate (e.g., potassium carbonate), a metal hydride (e.g., sodium hydride), a metal hydroxide (e.g., sodium hydroxide), a metal alkoxide (e.g., sodium ethoxide)] and/or in the presence of a transition metal catalyst for example a palladium catalyst [e.g., $Pd(PPh_3)_4$] to afford compound 10-3. Reaction of compound 10-3 and alkene 10-4 under Heck coupling reaction conditions gives alkene compound 10-5. Reduction of the C=C bond (between the two aromatic rings) of compound 10-5 to a saturated bond under an appropriate condition such as palladium catalyzed hydrogenation or using a hydrazine compound, followed by optional deprotection (when $R^{101}$ is an amine protecting group) and ring closure step [in the presence of an acid (e.g. p-toluenesulfonic acid (PTSA) or HCl), or a Pd catalyst], gives compound 10-6.

Scheme 10

-continued

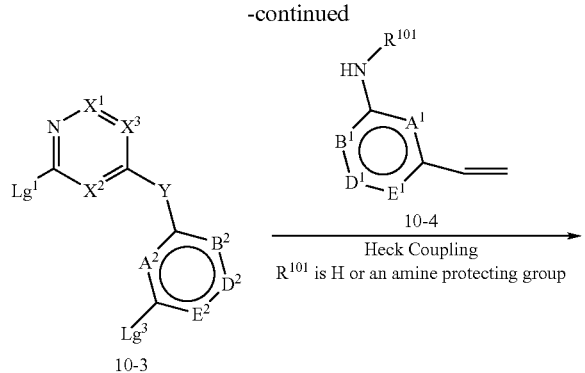

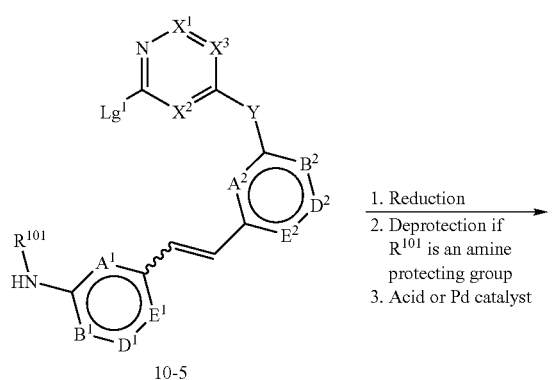

Similar to the chemical reactions/transformations depicted in Scheme 10, compound 11-6 can be synthesized according to the methods shown in Scheme 11 wherein alkene 11-4 is substituted with a nitro group.

Scheme 11

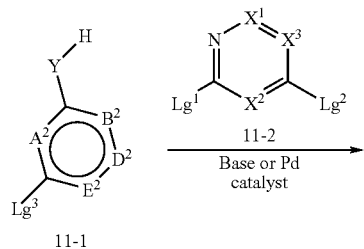

-continued

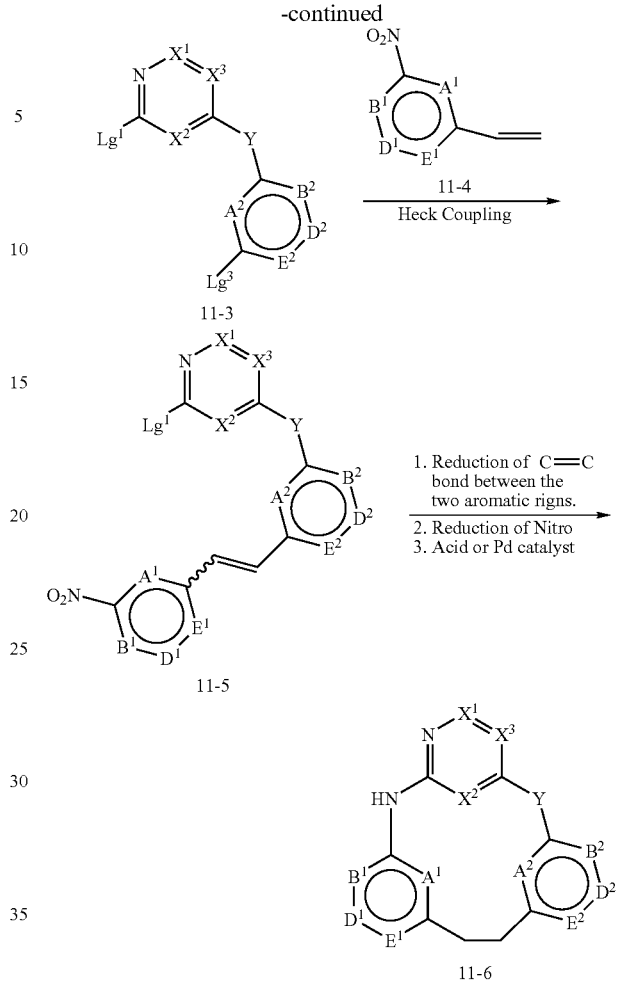

As shown in Scheme 12, arylamine 12-1 can be converted to its corresponding diazonium salt intermediate using $NaNO_2$ under acidic condition, followed by conversion of the diazonium salt to halide 12-2 [See e.g., "The Chemistry of Functional Groups. The Chemistry of Diazonium and Diazo Groups" Wiley: New York, 1978, the articles by Hegarty, pt. 2, pp. 511-591, and Schank, pt. 2, pp. 645-657; See also, P. S. Kalsi, "Organic Reactions Stereochemistry and Mechanism: Through Solved Problems"; Chapter 6, page 362 (Sandmeyer Reaction), New Age Publishers, 4th edition, 2006]. The compound 12-2 can be converted to a carbamate compound such as the BOC-protected amine 12-3 via Curtis rearrangement [See Ende, D. J. a.; DeVries, K. M.; Clifford, P. J.; Brenek, S. J. Org. Proc. Res. Dev. 1998, 2, 382-392.]. The nitro group of compound 12-3 can be reduced to amino, followed by coupling to compound 12-5 (for example, in the presence of a base or a Pd catalyst), to afford compound 12-6. Compound 12-6 can be reacted with alkene 12-7 under Heck Reaction conditions to afford compound 12-8. Reduction of the C=C bond (between the two aromatic rings) of compound 12-8 to a saturated bond via hydrogenation, followed by ring closure step (for example in the presence of a Pd catalyst or an acid such as HCl or PTSA), gives compound 12-9. Optional deprotection (when $R^{101}$ is an amine protecting group) of compound 12-9, followed by amide formation using an appropriation reactant such as an acid or acid halide 12-10, gives compound 12-11. The compound 12-11 (which can optionally be deprotected when $R^{150}$ is an amine protecting group) can undergo further chemical modifications such as acylation (where $R^{250}$ can be, e.g., —C(O)$Z^1$), sulfonylation (where $R^{250}$ can be, e.g., —S(O)$_2Z^1$), urea formation (where $R^{250}$ can be, e.g., —C(O)NH$Z^1$), carbamate formation (where $R^{250}$ can be, e.g., —C(O)O$Z^1$), or arylation/heteraylation (where $R^{250}$ can be, e.g., substituted aryl or heteroaryl).

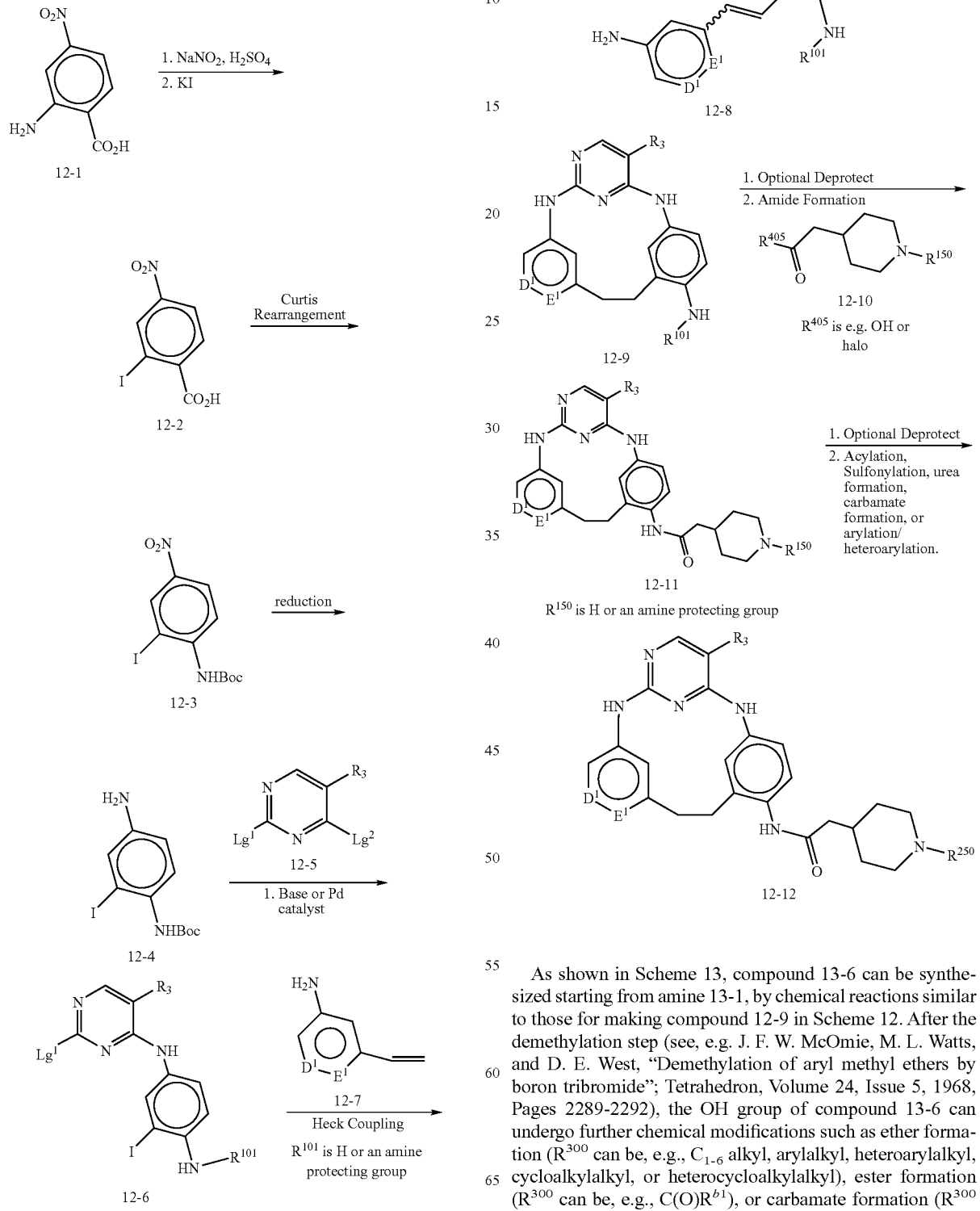

As shown in Scheme 13, compound 13-6 can be synthesized starting from amine 13-1, by chemical reactions similar to those for making compound 12-9 in Scheme 12. After the demethylation step (see, e.g. J. F. W. McOmie, M. L. Watts, and D. E. West, "Demethylation of aryl methyl ethers by boron tribromide"; Tetrahedron, Volume 24, Issue 5, 1968, Pages 2289-2292), the OH group of compound 13-6 can undergo further chemical modifications such as ether formation ($R^{300}$ can be, e.g., $C_{1-6}$ alkyl, arylalkyl, heteroarylalkyl, cycloalkylalkyl, or heterocycloalkylalkyl), ester formation ($R^{300}$ can be, e.g., C(O)$R^{b1}$), or carbamate formation ($R^{300}$ can be, e.g., C(O)N$R^{c1}R^{d1}$).

Scheme 13

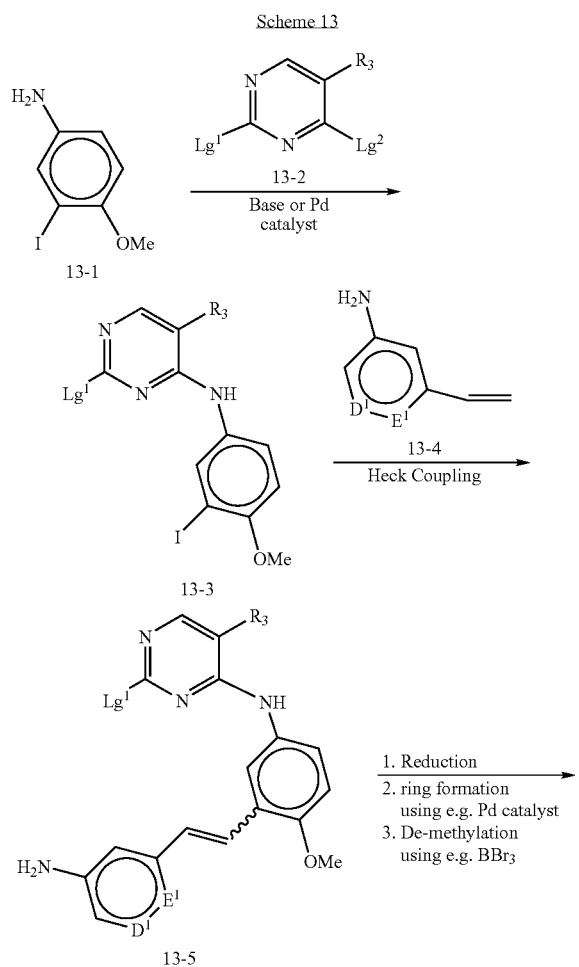
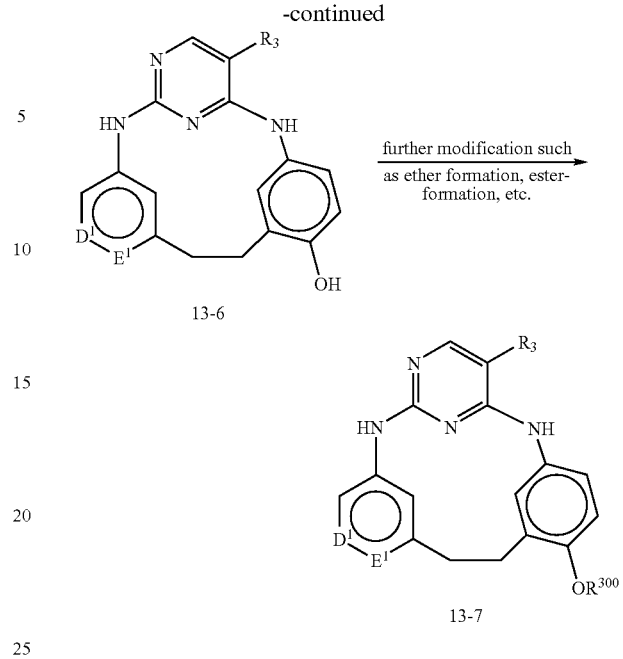

As shown in Scheme 14, compound 14-1 (with a hydroxyl group) can be reacted with an appropriation reactant such as halide 14-2, to give compound 14-3. The compound 14-3 can be deprotected (under appropriate conditions according to the amine protecting group of $R^{150}$, for example, under acidic condition when $R^{150}$ is Boc) followed by further chemical modifications such as acylation (where $R^{250}$ can be, e.g., —C(O)$Z^1$), sulfonylation (where $R^{250}$ can be, e.g., —S(O)$_2$$Z^1$), urea formation (where $R^{250}$ can be, e.g., —C(O)NH$Z^1$), carbamate formation (where $R^{250}$ can be, e.g., —C(O)O$Z^1$), arylation/heteroarylation (where $R^{250}$ can be, e.g., substituted aryl or heteroaryl).

Scheme 14

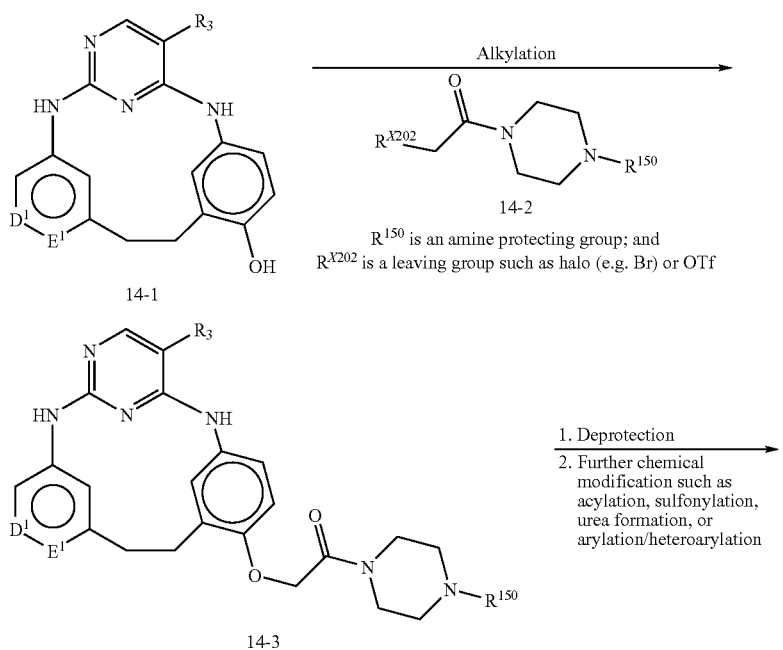

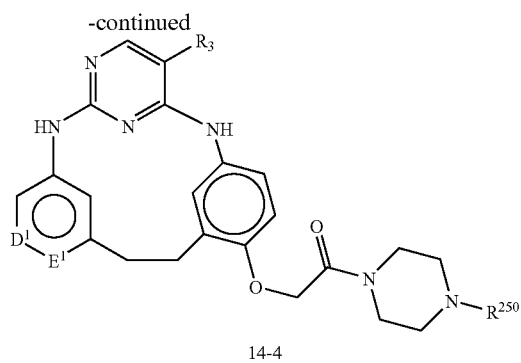

14-4

As shown in Scheme 15, the amino group of aromatic amine 15-1 can be protected by an amine protecting group such as Boc to afford compound 15-2. The amino group of aromatic amine 15-3 can be protected by an amine protecting group such as Boc to afford compound 15-4. Alkyne 15-2 can be reacted with aryl iodide 15-4 under Sonogashira coupling reaction condition to afford alkyne 15-5. [See e.g., K. Sonogashira, Y. Tohda, N. Hagihara; "A convenient synthesis of acetylenes: catalytic substitutions of acetylenic hydrogen with bromoalkenes, iodoarenes and bromopyridines"; Tetrahedron Letters 16 (50): 4467-4470 (1975); see also Rafael Chinchilla and Carmen Nájera, "The Sonogashira Reaction: A Booming Methodology in Synthetic Organic Chemistry"; Chem. Rev.; 2007; 107(3) pp 874-922.]. The reduction of the C≡C of alkyne 15-5 to carbon-carbon single bond and reduction of the nitro group to amino group can be carried out under appropriate reductive conditions, for example, by hydrogenation in the presence of a Pd catalyst (such as Pd/C) to afford compound 15-6. Amine 15-6 can be reacted with heteroaromatic compound 15-7 to give compound 15-8. Deprotection of compound 15-8 (under acid condition for Boc group, for example, in the present of an acid such as PTSA or HCl), followed by ring closure (an acid condition may also be used, for example, in the present of an acid such as PTSA or HCl), gives macrocycle 15-9. The amino group ($NH_2$) of macrocycle 15-9 can be converted to different moieties such as $NHC(O)R^{b1}$, $NHC(O)NR^{c1}R^{d1}$, $NHC(S)R^{b1}$, $NHC(S)NR^{c1}R^{d1}$, $NHC(O)OR^{a1}$, $NHS(O)_2NR^{c1}R^{d1}$, $NHS(O)_2R^{b1}$ by methods known to those skilled in the art.

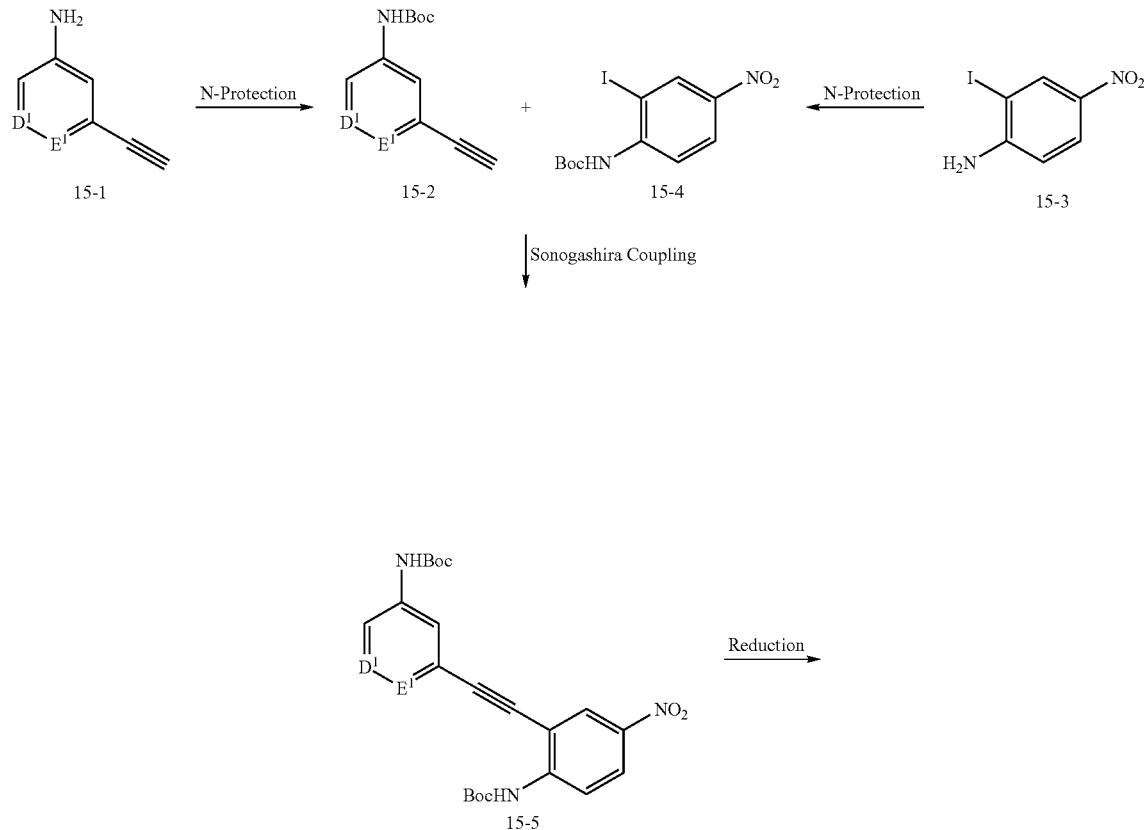

-continued

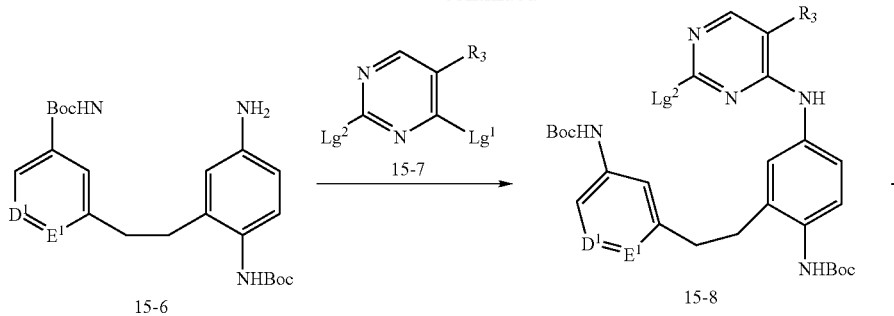

Additional starting materials and intermediates useful for making the compounds of the present invention can be obtained from chemical vendors such as Sigma-Aldrich or can be made according to methods described in the chemical art. For example, introducing pentafluorosulfanyl ($SF_5$) group to aromatic rings can be achieved according to the methods disclosed in U.S. Pat. No. 6,919,484 and/or the references cited therein.

Those skilled in the art can recognize that in all of the schemes described herein, if there are functional (reactive) groups present on a substituent group such as $R^1$, $R^2$, $R^3$, $R^4$, $R^5$, $R^6$, $R^7$, $R^8$, $R^9$, $R^{10}$, $L^1$, $L^2$, etc., further modification can be made if appropriate and/or desired. For example, a CN group can be hydrolyzed to afford an amide group; a carboxylic acid can be converted to an amide; a carboxylic acid can be converted to an ester, which in turn can be reduced to an alcohol, which in turn can be further modified. For another example, an OH group can be converted into a better leaving group such as mesylate, which in turn is suitable for nucleophilic substitution, such as by CN. For another example, an —S— can be oxidized to —S(O)— and/or —S(O)$_2$—. For yet another example, unsaturated bond such as C═C or C≡C can be reduced to saturated bond by hydrogenation. In some embodiments, a primary amine or a secondary amine moiety (present on a substituent group such as $R^1$, $R^2$, $R^3$, $R^4$, $R^5$, $R^6$, $R^7$, $R^8$, $R^9$, $R^{10}$, $L^1$, $L^2$, etc.) can be converted to amide, sulfonamide, urea, or thiourea moiety by reacting it with an appropriate reagent such as an acid chloride, a sulfonyl chloride, an isocyanate, or a thioisocyanate compound. In some embodiments, a primary amine, a secondary amine, or a tertiary amine moiety (present on a substituent group such as $R^1$, $R^2$, $R^3$, $R^4$, $R^5$, $R^6$, $R^7$, $R^8$, $R^9$, $R^{10}$, $L^1$, $L^2$, etc.) can be alkylated to form a quaternary ammonium salt. One skilled in the art will recognize further such modifications. Thus, a compound of Formula I (such as compound 1-2 of Scheme 1) having a substituent which contains a functional group can be converted to another compound of Formula I having a different substituent group.

As used herein, the term "reacting" refers to the bringing together of designated chemical reactants such that a chemical transformation takes place generating a compound different from any initially introduced into the system. Reacting can take place in the presence or absence of solvent.

Methods

Compounds of the invention can modulate activity of one or more Janus kinases (JAKs). The term "modulate" is meant to refer to an ability to increase or decrease the activity of one or more members of the JAK family of kinases. Accordingly, compounds of the invention can be used in methods of modulating a JAK by contacting the JAK with any one or more of the compounds or compositions described herein. In some embodiments, compounds of the present invention can act as inhibitors of one or more JAKs. In further embodiments, the compounds of the invention can be used to modulate activity of a JAK in an individual in need of modulation of the enzyme by administering a modulating amount of a compound of the invention.

JAKs to which the present compounds bind and/or modulate include any member of the JAK family. In some embodiments, the JAK is JAK1, JAK2, JAK3 or TYK2. In some embodiments, the JAK is JAK1 or JAK2. In some embodiments, the JAK is JAK2. In some embodiments, the JAK is JAK3. In some embodiments, the JAK is TYK2.

Another aspect of the present invention pertains to methods of treating a JAK-associated disease or disorder in an individual (e.g., patient) by administering to the individual a therapeutically effective amount or dose of a compound of the present invention or a pharmaceutical composition thereof. In some embodiments, the individual has been diagnosed to have a JAK-associated disease or disorder and is in need of treatment for the disease or disorder. A JAK-associated disease can include any disease, disorder or condition that is directly or indirectly linked to expression or activity of the JAK, including over expression and/or abnormal activity levels. A JAK-associated disease can also include any disease, disorder or condition that can be prevented, ameliorated, or cured by modulating JAK activity.

Examples of JAK-associated diseases include diseases involving the immune system including, for example, organ transplant rejection (e.g., allograft rejection and graft versus host disease).

Further examples of JAK-associated diseases include autoimmune diseases such as multiple sclerosis, rheumatoid arthritis, juvenile arthritis, psoriatic arthritis, type I diabetes, lupus, psoriasis, inflammatory bowel disease (e.g, ulcerative colitis and Crohn's disease), ankylosing spondylitis, myasthenia gravis, immunoglobulin nephropathies, autoimmune thyroid disorders, and the like. In some embodiments, the autoimmune disease is an autoimmune bullous skin disorder such as pemphigus vulgaris (PV) or bullous pemphigoid (BP). In some embodiments, JAK-associated diseases include rheumatoid arthritis.

Further examples of JAK-associated diseases include allergic conditions such as asthma, food allergies, atopic dermatitis and rhinitis. Further examples of JAK-associated diseases include viral diseases such as Epstein Barr Virus (EBV), Hepatitis B, Hepatitis C, HIV, HTLV 1, Varicella-Zoster Virus (VZV) and Human Papilloma Virus (HPV).

Further examples of JAK-associated diseases or conditions include skin disorders such as psoriasis (for example, psoriasis vulgaris), atopic dermatitis, alopecia greata, skin rash, skin irritation, skin sensitization (e.g., contact dermatitis or allergic contact dermatitis). For example, certain substances including some pharmaceuticals when topically applied can cause skin sensitization. In some embodiments, co-administration or sequential administration of at least one JAK inhibitor of the invention together with the agent causing unwanted sensitization can be helpful in treating such unwanted sensitization or dermatitis. In some embodiments, the skin disorder is treated by topical administration of at least one JAK inhibitor of the invention.

In further embodiments, the JAK-associated disease is cancer including those characterized by solid tumors (e.g., prostate cancer, renal cancer, hepatic cancer, colorectal cancer, pancreatic cancer, gastric cancer, breast cancer, lung cancer, cancers of the head and neck, thyroid cancer, glioblastoma, Kaposi's sarcoma, melanoma etc.), hematological cancers or malignancies [e.g., lymphoma, leukemia such as acute lymphoblastic leukemia, Chronic Lymphocytic Leukemia (CLL), myelodysplastic syndrome (MDS), acute myelogenous leukemia (AML), chronic myelogenous leukemia (CML), chronic myelomonocytic leukemia (CMML), or multiple myeloma, and other lymphoma related diseases including Castleman's disease, waldenstrom's macroglobulinemia and Poems syndrome], and skin cancer such as cutaneous T-cell lymphoma (CTCL) and cutaneous B-cell lymphoma. Examples of cutaneous T-cell lymphomas include Sezary syndrome and mycosis fungoides. Other kinase associated diseases may also include paraneoplastic syndromes associated with cytokine production in cancer.

JAK-associated diseases can further include those characterized by expression of a mutant JAK such as those having at least one mutation in the pseudo-kinase and/or kinase domain (e.g., JAK2V617F or JAK1R724H) or genetic or epigenetic alterations known or thought to result in dysregulated JAK activity (e.g. SOCS gene methylation or MPL mutation).

JAK-associated diseases can further include myeloproliferative disorders (MPDs) such as polycythemia vera (PV), essential thrombocythemia (ET), myelofibrosis with myeloid metaplasia (MMM), hypereosinophilic syndrome (HES), systemic mast cell disease (SMCD), and the like. In some embodiments, the myeloproliferative disorder is myelofibrosis with myeloid metaplasia (MMM). In some embodiments, the myeloproliferative disorder is selected from primary myelofibrosis (PMF). PMF has been known by a variety of terms including myelofibrosis with myeloid metaplasia (MMM), agnogenic myeloid metaplasia, and chronic idiopathic myelofibrosis. Myelofibrosis (MF) can present as a de novo disorder (PMF) or evolve from previous PV or ET [post-polycythemia vera myelofibrosis (Post-PV MF) or post-essential thrombocythemia myelofibrosis (Post-ET MF)]. Myelofibrosis develops in 10% to 20% of patients with PV (see e.g. J. L. Spivak, G. Barosi, G. Tognoni, T. Barbui, G. Finazzi, R. Marchioli, and M. Marchetti; "Chronic Myeloproliferative Disorders"; *Hematology*, January 2003; 2003: 200-224) and in 2% to 3% of patients with ET (See e.g. D. R. Berk and A. Ahmed; "Portal, splenic, and superior mesenteric vein thrombosis in a patient with latent essential thrombocythemia and hyperhomocysteinemia"; *J. Clin. Gastroenterol.*, 2006; 40: 3: 227-8).

Further JAK-associated diseases include inflammation and inflammatory diseases. Examples of inflammatory diseases include inflammatory diseases of the eye (e.g., iritis, uveitis, scleritis, conjunctivitis, or related disease), inflammatory diseases of the respiratory tract (e.g., the upper respiratory tract including the nose and sinuses such as rhinitis or sinusitis or the lower respiratory tract including bronchitis, chronic obstructive pulmonary disease, and the like), inflammatory myopathy (such as myocarditis), Systemic Inflammatory Response Syndrome (SIRS), septic shock, and other inflammatory diseases.

The JAK inhibitors described herein can further be used to treat ischemia reperfusion injuries or a disease or condition related to an inflammatory ischemic event such as stroke or cardiac arrest. The JAK inhibitors described herein can further be used to treat anorexia, cachexia, or fatigue such as that resulting from or associated with cancer. The JAK inhibitors described herein can further be used to treat restenosis, sclerodermitis, or fibrosis. The JAK inhibitors described herein can further be used to treat conditions associated with hypoxia or astrogliosis such as, for example, diabetic retinopathy, cancer, or neurodegeneration. See, e.g., Dudley, A. C. et al. *Biochem. J.* 2005, 390(Pt 2):427-36 and Sriram, K. et al. *J. Biol. Chem.* 2004, 279(19):19936-47. Epub 2004 Mar. 2.

The JAK/ALK inhibitors described herein can be used to treat any of the JAK-associated diseases, disorders or conditions and/or ALK-associated diseases, disorders or conditions, or any combination thereof. In some embodiments, the JAK inhibitors described herein can be used to treat any of the JAK-associated diseases diseases, disorders or conditions, or any combination thereof.

The JAK inhibitors described herein can further be used to treat any of the JAK-associated diseases or any combination thereof.

Certain compounds of the invention (the $IC_{50}$ of which with respect to ALK is less than about 10 μM) can also modulate activity of ALK kinases. The term "modulate" is meant to, in this context, refer to an ability to increase or decrease the activity of the ALK kinases. Certain compounds of the invention can be used in methods of modulating an ALK by contacting the ALK with any one or more of the compounds or compositions described herein. In some embodiments, certain compounds of the present invention (the $IC_{50}$ of which with respect to ALK is less than about 10 μM) can act as inhibitors of ALK. Certain compounds of the invention (the $IC_{50}$ of which with respect to ALK is less than about 10 μM) can be used to modulate activity of an ALK in an individual in need of modulation of the enzyme by administering a modulating amount of a compound of the invention.

Another aspect of the present invention pertains to methods of treating an ALK-associated disease or disorder in an individual (e.g., patient) by administering to the individual a therapeutically effective amount or dose of a compound of the present invention (the $IC_{50}$ of which with respect to ALK is less than about 10 μM) or a pharmaceutical composition thereof. In some embodiments, the individual is diagnosed to have an ALK-associated disease or disorder and is in need of treatment for the disease or disorder. An ALK-associated disease can include any disease, disorder or condition that is directly or indirectly linked to expression or activity of the ALK, including over expression and/or abnormal activity levels. An ALK-associated disease can also include any disease, disorder or condition that can be prevented, ameliorated, or cured by modulating ALK activity. Examples of ALK-associated diseases include diseases involving ALK-related tumors including anaplastic large cell lymphomas and non-Hodgkin lymphomas in addition to lung cancers.

Treatment of the diseases/disorders herein includes treating one or more symptoms associated with the diseases/disorders. For example, symptoms of a JAK-associated skin disorder (such as psoriasis, atopic dermatitis, skin rash, skin irritation, or skin sensitization) include itching (prutitus).

As used herein, the term "contacting" refers to the bringing together of indicated moieties in an in vitro system or an in vivo system. For example, "contacting" a JAK/ALK with a compound of the invention includes the administration of a compound of the present invention to an individual or patient, such as a human, having a JAK/ALK, as well as, for example, introducing a compound of the invention into a sample containing a cellular or purified preparation containing the JAK/ALK.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting/retarding the disease; for example, inhibiting/retarding a disease, condition or disorder in an individual who is experiencing or displaying the pathology or symptomatology of the disease, condition or disorder; and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease or completely eliminating/curing the disease. As used herein, treating a disease further includes treating one or more symptoms associated with the disease.

Combination Therapies

One or more additional pharmaceutical agents such as, for example, chemotherapeutics, anti-inflammatory agents, steroids, immunosuppressants, as well as Bcr-Abl, Flt-3, RAF, IKK, EGFR, MET, IGF1R, and FAK, ALK kinase inhibitors such as, for example, those described in WO 2006/056399, or other agents can be used in combination with the compounds of the present invention for treatment of JAK/ALK-associated diseases, disorders or conditions. The one or more additional pharmaceutical agents can be administered to a patient simultaneously or sequentially.

Examples of chemotherapeutics include proteosome inhibitors (e.g., bortezomib), thalidomide, revlimid, pomalidomide, DNA-damaging agents such as melphalan, doxorubicin, cyclophosphamide, vincristine, etoposide, carmustine, tubulin targeted agents (e.g. taxanes and vincristine), topoisomerase inhibitors (e.g. irinotecan), enzymes (e.g. L-asparaginase), antimetabolites (e.g. gemcitabine and hyroxyurea), and the like.

Examples of steroids include corticosteroids such as dexamethasone or prednisone.

Examples of Bcr-Abl inhibitors include the compounds, and pharmaceutically acceptable salts thereof, of the genera and species disclosed in U.S. Pat. No. 5,521,184, WO 04/005281, EP2005/009967, EP2005/010408, and U.S. Ser. No. 60/578,491.

Examples of suitable Flt-3 inhibitors include compounds, and their pharmaceutically acceptable salts, as disclosed in WO 03/037347, WO 03/099771, and WO 04/046120.

Examples of suitable RAF inhibitors include compounds, and their pharmaceutically acceptable salts, as disclosed in WO 00/09495 and WO 05/028444.

Examples of suitable FAK inhibitors include compounds, and their pharmaceutically acceptable salts, as disclosed in WO 04/080980, WO 04/056786, WO 03/024967, WO 01/064655, WO 00/053595, and WO 01/014402.

Examples of suitable ALK inhibitors include compounds, and their pharmaceutically acceptable salts, as disclosed in WO 04/079326.

In some embodiments, one or more of the compounds of the invention can be used in combination with one or more other kinase inhibitors including imatinib, particularly for treating patients resistant to imatinib or other kinase inhibitors.

In some embodiments, one or more JAK/ALK inhibitors of the invention can be used in combination with a chemotherapeutic in the treatment of cancer, such as multiple myeloma, and may improve the treatment response as compared to the response to the chemotherapeutic agent alone, without exacerbation of its toxic effects. Examples of additional pharmaceutical agents used in the treatment of multiple myeloma, for example, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, IGF1R, RAF and FAK kinase inhibitors. Additive or synergistic effects are desirable outcomes of combining a JAK/ALK inhibitor of the present invention with an additional agent. Furthermore, resistance of multiple myeloma cells to agents such as dexamethasone may be reversible upon treatment with a JAK/ALK inhibitor of the present invention. The agents can be combined with the present compounds in a single or continuous dosage form, or the agents can be administered simultaneously or sequentially as separate dosage forms.

In some embodiments, a corticosteroid such as dexamethasone is administered to a patient in combination with at least one JAK/ALK inhibitor where the dexamethasone is administered intermittently as opposed to continuously.

In some further embodiments, combinations of one or more JAK/ALK inhibitors of the invention with other therapeutic agents can be administered to a patient prior to, during, and/or after a bone marrow transplant or stem cell transplant.

Pharmaceutical Formulations and Dosage Forms

When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

This invention also includes pharmaceutical compositions which contain, as the active ingredient, one or more of the compounds of the invention above in combination with one or more pharmaceutically acceptable carriers (excipients). In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the invention may be milled using known milling procedures such as wet milling to obtain a particle size appropriate for tablet formation and for other formulation types. Finely divided (nano particulate) preparations of the compounds of the invention can be prepared by processes known in the art, for example see International Patent Application No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and can be generally administered in a pharmaceutically effective amount. For example, the dosage of the active compounds of the invention as employed for the treatment of a patient in need thereof (such as an adult human) may range from 0.1 to 3000 mg per day, depending on the route and frequency of administration. Such a dosage corresponds to 0.001 to 50 mg/kg per day. In some embodiments, the dosage of the active compounds of the invention as employed for the treatment of a patient in need thereof (such as an adult human) may range from 1 to 2000 mg per day, from 1 to 1000 mg per day, from 10 to 1000 mg per day, or from 10 to 500 mg per day. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient can be mixed with a pharmaceutical excipient to form a solid pre-formulation composition containing a homogeneous mixture of a compound of the present invention. When referring to these pre-formulation compositions as homogeneous, the active ingredient is typically dispersed evenly throughout the composition so that the composition can be readily subdivided into equally effective unit dosage forms such as tablets, pills and capsules. This solid pre-formulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect.

Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed hereinabove.

Labeled Compounds and Assay Methods

Another aspect of the present invention relates to labeled compounds of the invention (radio-labeled, fluorescent-labeled, etc.) that would be useful not only in radio-imaging but also in assays, both in vitro and in vivo, for localizing and quantitating the enzyme in tissue samples, including human, and for identifying ligands by inhibition binding of a labeled compound. Accordingly, the present invention includes enzyme assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^{2}$H (also written as D for deuterium), $^{3}$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the radio-labeled compounds will depend on the specific application of that radio-labeled compound. For example, for in vitro receptor labeling and competition assays, compounds that incorporate $^{3}$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled compound" is a compound that has incorporated at least one radionuclide. In some embodiments the radionuclide is selected from $^{3}$H, $^{14}$C, $^{125}$I, $^{35}$S and $^{82}$Br.

In some embodiments, the labeled compounds of the present invention contain a fluorescent label.

Synthetic methods for incorporating radio-isotopes and fluorescent labels into organic compounds are well known in the art.

A labeled compound of the invention (radio-labeled, fluorescent-labeled, etc.) can be used in a screening assay to identify/evaluate compounds. For example, a newly synthesized or identified compound (i.e., test compound) which is labeled can be evaluated for its ability to bind a JAK/ALK by monitoring its concentration variation when contacting with the JAK/ALK, through tracking the labeling. For another example, a test compound (labeled) can be evaluated for its ability to reduce binding of another compound which is known to bind to JAK/ALK (i.e., standard compound). Accordingly, the ability of a test compound to compete with the standard compound for binding to the JAK/ALK directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present invention also includes pharmaceutical kits useful, for example, in the treatment or prevention of JAK/ALK-associated diseases or disorders such as prostate cancer, renal cancer, hepatic cancer, breast cancer, lung cancer, and other diseases referred to herein which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. In some instances where the compounds of the examples were isolated by preparative HPLC in the presence of trifluoroacetic acid (TFA) or other acid (such as HCl), the compound may have been obtained as the corresponding salt. In some instances, the corresponding salt of an exemplary compound may be described as the mono-, di-, tri-, or tetrakis-acid salt (i.e. the molar ratio of the acid to the compound is 1:1, 2:1, 3:1 or 4:1), those skilled in the art would understand that other ratios of the acid to the compound may exist or form (for example 3:1, 2:1, 2.3:1, 0.8:1, or 0.5:1). Certain compounds of the Examples were found to be inhibitors of JAK/ALK according to one or more of the assays provided herein. In some embodiments, the $IC_{50}$ value for the compound of invention with respect one or more of JAK/ALK is less than about 100, 80, 50, 20, 10, 8, 5, 2, or 1 µM. In some embodiments, the $IC_{50}$ value for the compound of invention with respect to one or more of ALK is less than about 100, 80, 50, 20, 10, 8, 5, 2, or 1 µM. In some embodiments, the $IC_{50}$ value for the compound of invention with respect to one or more of JAK is less than about 100, 80, 50, 20, 10, 8, 5, 2, or 1 µM. In some embodiments, the $IC_{50}$ value for the compound of invention with respect to one or more of JAK/ALK is less than about 1000, 800, 500, 200, 100, 80, 50, 20, or 10 nM. Certain compounds described in Tables A1, B1, C1, and D1 and in the Example section were tested for inhibitory activity of JAK/ALK targets according to assays such as those described herein or those known in the art [e.g., ALK assays described in WO 04/079326; and TYK2 assays described by James E. Thompson et. al, "Photochemical preparation of a pyridone containing tetracycle: A JAK protein kinase inhibitor," *Bioorganic & Medicinal Chemistry Letters*, Volume 12, Issue 8, 22 Apr. 2002, Pages 1219-1223]. For instance, Examples A1-A8, B1-B3, B5-B18, C1, C3, C6-C10, and D1-D16 were found to have $IC_{50}$ values less than 1000 nM, 800 nM, 500 nM, 200 nM, or 100 nM for at least one of JAK1, JAK2, JAK3, TYK2, and ALK. Some exemplary data of the compounds of the invention are shown in Tables A1, B1, C1, and D1 in the experimental section.

In some embodiments, percentage inhibition of the compound of invention to ALK was measured at a concentration of 500 nM or 1 mM. In some embodiments, the percentage inhibition measured is about 1% to about 20%, about 20% to about 50%, about 50% to about 80%, about 80% to about 100%, about 1% to about 50%, or about 50% to about 100%.

EXAMPLES

Example A1

(14Z)-6-Chloro-2,4,8,22-tetraazatetracyclo[14.3.1.1 (3,7).1(9,13)]docosa-1(20),3(22),4,6,9(21),10,12,14, 16,18-decaene trifluoroacetate

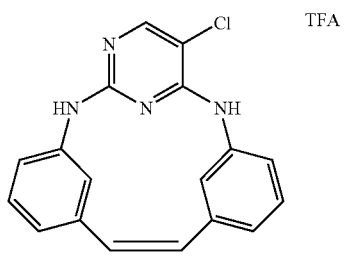 [SMILES: "TFA" ; Clc1cnc2nc1Nc1cccc(c1)/C=C\c1cccc(c1)N2]

Step A:
2,5-Dichloro-N-(3-vinylphenyl)pyrimidin-4-amine trifluoroacetate

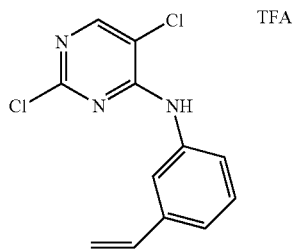 [SMILES: "TFA" ; C=Cc1cccc(Nc2nc(Cl)ncc2Cl)c1]

3-Vinylaniline (200 mg, 2.0 mmol) [Aldrich] was stirred in N,N-dimethylformamide (10 mL) and cooled to 0° C. Sodium hydride (96 mg, 4 mmol) was added in portions which caused significant foaming. The mixture was stirred for 5 minutes after the addition was complete. 2,4,5-Trichloropyrimidine (190 µl, 2.0 mmol) [Aldrich] was added dropwise and the mixture was stirred for 30 minutes at 0° C. and at room temperature (rt or RT) overnight. Neutralization with acetic acid and purification by preparative LCMS (pH 2) gave the desired product as a trifluoroacetate salt (400 mg, 60%). LCMS for $C_{12}H_9Cl_2N_3$ $(M+H)^+$: m/z=266.1.

Step B: 5-Chloro-N,N'-bis(3-vinylphenyl)pyrimidine-2,4-diamine trifluoroacetate

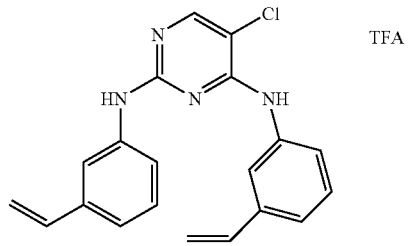 [SMILES: "TFA" ; C=Cc1cccc(Nc2ncc(Cl)c(Nc3cccc(C=C)c3)n2)c1]

A solution of 2,5-dichloro-N-(3-vinylphenyl)pyrimidin-4-amine trifluoroacetate (150 mg, 0.56 mmol) and 3-vinylaniline (200 mg, 1.0 mmol) in 2-methoxyethanol (3.8 mL) and 3 N hydrogen chloride in ethanol (0.56 mL) were mixed and heated to 150° C. for 30 minutes in a microwave. Purification by preparative LCMS (pH 2) gave the desired product as a trifluoroacetate salt (150 mg, 60%). LCMS for $C_{20}H_{17}ClN_4$ $(M+H)^+$: m/z=349.1.

Step C: (14Z)-6-Chloro-2,4,8,22-tetraazatetracyclo [14.3.1.1(3,7).1(9,13)]docosa-1(20),3(22),4,6,9(21), 10,12,14,16,18-decaene trifluoroacetate A solution of 5-chloro-N,N'-bis(3-vinylphenyl)pyrimidine-2,4-diamine trifluoroacetate (21 mg, 0.045 mmol) in 1,2-dichloroethane (20 mL) was degassed by bubbling nitrogen for 5 minutes. Benzylidene-bis(tricyclohexylphosphine) dichlororuthenium (11 mg, 0.013 mmol) was added and the mixture was heated to 130° C. for 20 minutes in a microwave. The mixture was evaporated to give a dark mixture which was suspended in acetonitrile and filtered. The filtrate was purified by preparative LCMS (pH 2) to give the desired product as a trifluoroacetate salt (1.7 mg, 9%). LCMS for $C_{18}H_{14}ClN_4$ $(M+H)^+$: m/z=321.1. $^1$H NMR (400 MHz, $CD_3Cl$): δ 8.85 (s, 1H), 8.75 (s, 1H), 7.90 (s, 1H), 7.55 (s, 1H), 7.25 (m, 3H), 7.02 (m, 4H), 6.60 (s, 2H).

Example A2

6-Chloro-2,4,8,22-tetraazatetracyclo[14.3.1.1(3,7).1(9,13)]docosa-1(20),3(22),4,6,9(21),10,12,16,18-nonaene trifluoroacetate

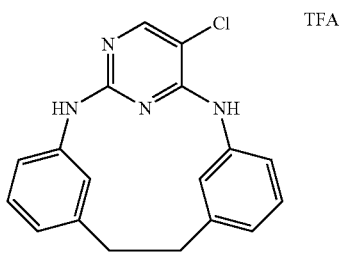 [SMILES: "TFA" ; Clc1cnc2nc1Nc1cccc(c1)CCc1cccc(c1)N2]

To a solution of (14Z)-6-chloro-2,4,8,22-tetraazatetracyclo[14.3.1.1(3,7).1(9,13)]docosa-1(20),3(22),4,6,9(21),10,12,14,16,18-decaene trifluoroacetate (21 mg, 0.045 mmol) in ethanol (1 mL) was added 5% palladium on carbon (5 mg) and the mixture was purged and degassed with hydrogen three times. The mixture was stirred for 1 hour with balloon pressure of hydrogen. Filtration through celite and purification by preparative LCMS (pH 2) gave the desired product as a trifluoroacetate salt (1.7 mg, 30%). LCMS for $C_{18}H_{16}ClN_4$ $(M+H)^+$: m/z=323.1. $^1$H NMR (400 MHz, $CD_3OD$): δ 7.75 (m, 2H), 7.30 (m, 1H), 7.22 (m, 1H), 7.12 (m, 1H), 7.03 (m, 2H), 6.90 (m, 1H), 3.00 (s, 4H).

Example A3

2,4,8,22-Tetraazatetracyclo[14.3.1.1(3,7).1(9,13)]docosa-1(20),3(22),4,6,9(21),10,12,16,18-nonaene trifluoroacetate

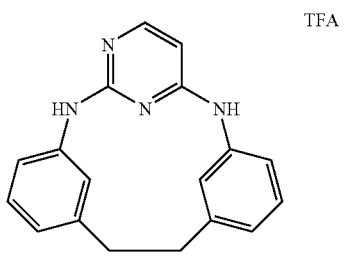 [SMILES: "TFA" ; c1cc2cc(c1)Nc1ccnc(n1)Nc1cccc(c1)CC2]

Also isolated from the reaction mixture in Example A2 was the dechlorinated product as a trifluoroacetate salt (0.7 mg, 20%). LCMS for $C_{18}H_{17}N_4$ $(M+H)^+$: m/z=289.1.

Example A4

6-Chloro-2,4,8,23-tetraazatetracyclo[15.3.1.1(3,7).1(9,13)]tricosa-1(21),3(23),4,6,9(22),10,12,17,19-nonaene

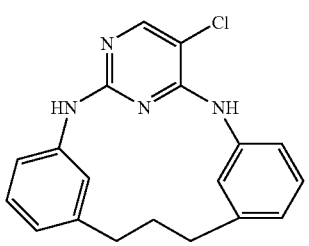 [SMILES: Clc1cnc2nc1Nc1cccc(c1)CCCc1cccc(c1)N2]

Step A: (2E)-1,3-bis(3-Nitrophenyl)prop-2-en-1-one

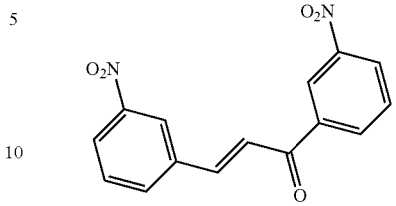

3-Nitroacetophenone (2.23 g, 0.0135 mol) [Aldrich] and 3-nitrobenzaldehyde (2.04 g, 0.0135 mol) [Aldrich] were dissolved in methanol (20 mL), and sodium hydroxide (1.3 g, 0.032 mol) was added. The mixture was stirred for 16 hours. The solid formed was filtered and washed with water to give the desired product (3.6 g, 89%). LCMS for $C_{15}H_{11}N_2O_5$ $(M+H)^+$: m/z=299.1.

Step B: 3,3'-Propane-1,3-diyldianiline

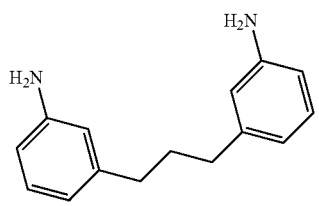 [SMILES: Nc1cccc(CCCc2cccc(N)c2)c1]

To a solution of (2E)-1,3-bis(3-nitrophenyl)prop-2-en-1-one (2.8 g, 0.0094 mol) in N,N-dimethylformamide (20 mL) was added 10% (by wt.) palladium on carbon and acetic acid (2.0 mL). The mixture was degassed with vacuum and purged with hydrogen three times before shaking on a Parr shaker for 72 hours under a hydrogen atmosphere. The mixture was filtered through celite, evaporated and purified by preparative LCMS (pH 10) to give the desired product (101 mg, 5%). LCMS for $C_{15}H_{19}N_2$ $(M+H)^+$: m/z=227.2.

Step C: N-{3-[3-(3-Aminophenyl)propyl]phenyl}-2,5-dichloropyrimidin-4-amine

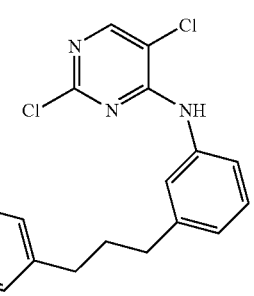

To a solution of 3,3'-propane-1,3-diyldianiline (41.0 mg, 0.181 mmol) in N,N-dimethylformamide (1.0 mL), potassium carbonate (72 mg, 0.52 mmol) was added followed by 2,4,5-trichloropyrimidine (20 μL, 0.17 mmol). The mixture was stirred for 2.5 hours and purified by preparative LCMS (pH 10) to give the desired product (21 mg, 32%). LCMS for $C_{19}H_{19}Cl_2N_4$ $(M+H)^+$: m/z=373.1.

Step D: 6-Chloro-2,4,8,23-tetraazatetracyclo[15.3.1.1(3,7).1(9,13)]tricosa-1(21),3(23),4,6,9(22),10,12,17,19-nonaene N-{3-[3-(3-Aminophenyl)propyl]phenyl}-2,5-dichloropyrimidin-4-amine (20 mg, 0.05 mmol) was stirred in 2-methoxyethanol (1.0 mL) and a solution of hydrogen chloride in ethanol (0.75 mL, 3.5 M). The mixture was heated to 150° C. for 30 minutes in a microwave. Purification by preparative LCMS gave the desired product (6.5 mg, 37%). LCMS for $C_{19}H_{18}ClN_4$ (M+H)$^+$: m/z=337.

Example A5

6-Chloro-2,4,8,23-tetraazatetracyclo[15.3.1.1(3,7).1(9,13)]tricosa-1(21),3(23),4,6,9(22),10,12,17,19-nonaen-16-one trifluoroacetate

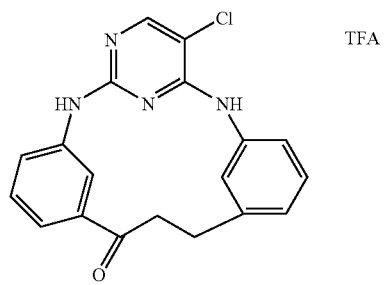 [SMILES: O=C1CCc2cccc(c2)Nc2nc(ncc2Cl)Nc2cccc1c2]

Step A: 1,3-Bis(3-aminophenyl)propan-1-one bis(trifluoroacetate)

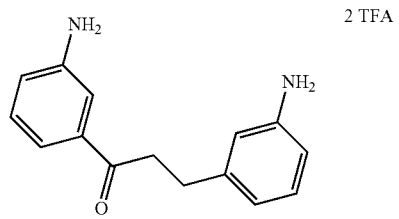 [SMILES: Nc1cccc(CCC(=O)c2cccc(N)c2)c1 ; "2 TFA"]

The desired compound was prepared according to the procedure of Example A4, step B in 8.8% yield. LCMS for $C_{15}H_{17}N_4O$ (M+H)$^+$: m/z=241.1.

Step B: 6-Chloro-2,4,8,23-tetraazatetracyclo[15.3.1.1(3,7).1(9,13)]tricosa-1(21),3(23),4,6,9(22),10,12,17,19-nonaen-16-one trifluoroacetate The desired compound was prepared according to the procedure of Example A4, steps C-D, using 1,3-bis(3-aminophenyl)propan-1-one bis(trifluoroacetate) as a starting material (16% yield). LCMS for $C_{19}H_{16}ClN_4O$ (M+H)$^+$: m/z=351.1.

Example A6

6-Chloro-19-methyl-17-morpholin-4-yl-2,4,8,22-tetraazatetracyclo[14.3.1.1(3,7).1(9,13)]docosa-1(20),3(22),4,6,9(21),10,12,16,18-nonaene trifluoroacetate

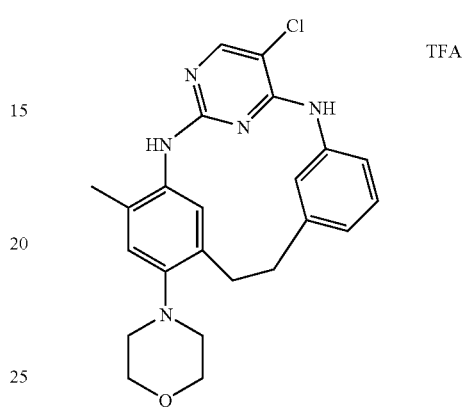

Step A. 4-(2-Bromo-5-methyl-4-nitrophenyl)morpholine

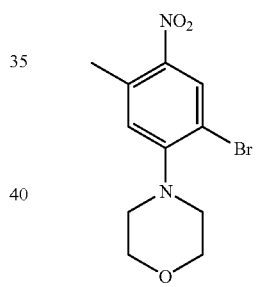

1-Bromo-2-fluoro-4-methyl-5-nitrobenzene (1.0 g, 4.3 mmol) [Aldrich] was stirred in N,N-dimethylformamide (10 mL) with potassium carbonate (1.5 g, 11.0 mmol), and morpholine (0.56 mL, 6.4 mmol) was added. The mixture was stirred for 3 hours and diluted with saturated sodium bicarbonate solution. Extraction with ethyl acetate gave the desired compound (1.0 g, 77%). LCMS for $C_{11}H_{14}BrN_2O_3$ (M+H)$^+$: m/z=301.0.

Step B. 5-Bromo-2-methyl-4-morpholin-4-ylaniline

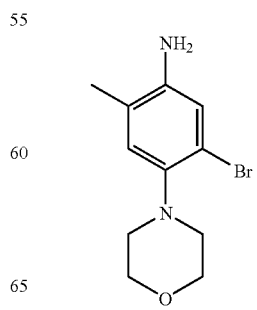

Iron powder (320 mg, 5.8 mmol) was stirred in ethanol (12 mL) with 1 N HCl solution (0.6 mL, 0.6 mmol) and heated at 60° C. for 2 hours. 5 N aqueous Ammonium chloride solution (1.0 mL, 5.0 mmol) and 4-(2-bromo-5-methyl-4-nitrophenyl) morpholine (350 mg, 1.2 mmol) were added and the mixture was heated at 60° C. for 30 minutes. The mixture was filtered through celite and the collected solids were washed with ethanol. The combined filtrates were evaporated to give the desired compound (0.24 g, 75%). LCMS for $C_{11}H_{16}BrN_2O$ $(M+H)^+$: m/z=271.0.

Step C. tert-Butyl (5-bromo-2-methyl-4-morpholin-4-ylphenyl)carbamate

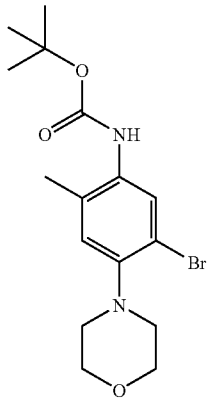 [SMILES: Cc1cc(N2CCOCC2)c(Br)cc1NC(=O)OC(C)(C)C]

5-Bromo-2-methyl-4-morpholin-4-ylaniline (550 mg, 2.0 mmol) was stirred in ethanol (15 mL) and di-tert-butyldicarbonate (440 mg, 2.0 mmol) was added. The mixture was stirred for 16 hours and evaporated. Purification by silica gel chromatography gave the desired compound (523 mg, 70%). LCMS for $C_{16}H_{24}BrN_2O_3$ $(M+H)^+$: m/z=371.0.

Step D. tert-Butyl {5-[(3-aminophenyl)ethynyl]-2-methyl-4-morpholin-4-ylphenyl}carbamate

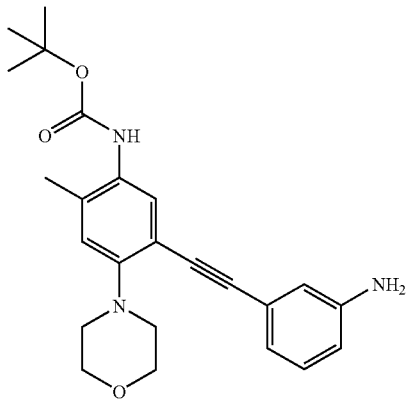 [SMILES: Cc1cc(N2CCOCC2)c(C#Cc2cccc(N)c2)cc1NC(=O)OC(C)(C)C]

tert-Butyl (5-bromo-2-methyl-4-morpholin-4-ylphenyl) carbamate (110 mg, 0.3 mmol), copper(I) iodide (4 mg, 0.02 mmol) and bis(triphenylphosphine)palladium(II) chloride (10 mg, 0.01 mmol) were stirred in tetrahydrofuran (0.5 mL) and triethylamine (50 µL, 0.4 mmol) was added. 3-Ethynylaniline (100 µL, 1.0 mmol) was added and the mixture was heated to 80° C. for 1 hour. The mixture was filtered through celite and purified by preparative LCMS (pH 2). The product fractions were neutralized with saturated sodium bicarbonate solution, evaporated to remove acetonitrile and extracted with ethyl acetate. The extracts were evaporated to give the desired compound (25 mg, 31%). LCMS for $C_{24}H_{30}N_3O_3$ $(M+H)^+$: m/z=408.1.

Step E. tert-Butyl {5-[2-(3-aminophenyl)ethyl]-2-methyl-4-morpholin-4-ylphenyl}carbamate

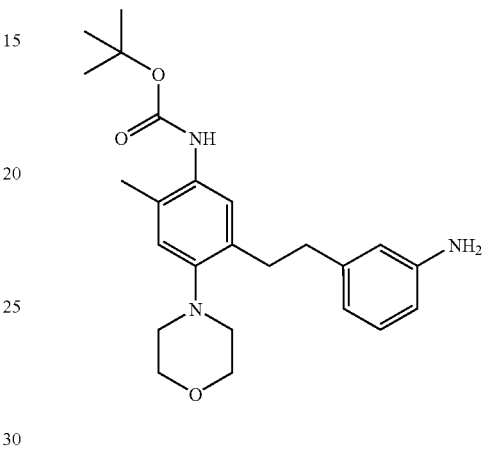

tert-Butyl {5-[(3-aminophenyl)ethynyl]-2-methyl-4-morpholin-4-ylphenyl}carbamate (62 mg, 0.15 mmol) was stirred in methanol (2 mL) and 10% palladium on carbon (50 mg). The mixture was stirred under a balloon pressure of hydrogen gas for 3 hours. The mixture was filtered through celite and evaporated to give the desired compound (63 mg, 100%). LCMS for $C_{24}H_{34}N_3O_3$ $(M+H)^+$: m/z=412.1.

Step F. tert-Butyl [5-(2-{3-[(2,5-dichloropyrimidin-4-yl)amino]phenyl}ethyl)-2-methyl-4-morpholin-4-ylphenyl]carbamate

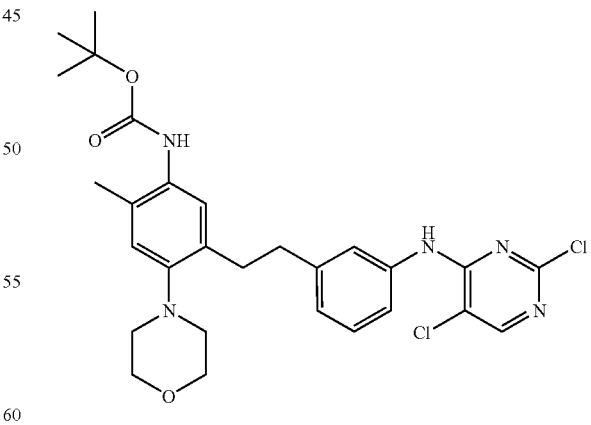

tert-Butyl {5-[2-(3-aminophenyl)ethyl]-2-methyl-4-morpholin-4-ylphenyl}carbamate (31 mg, 0.08 mmol) and potassium carbonate (16 mg, 0.11 mmol) were stirred in N,N-dimethylformamide (1 mL) and 2,4,5-trichloropyrimidine (9 µL, 0.08 mmol) was added. The mixture was stirred for 16 hours (or 16 h) and diluted with saturated sodium bicarbonate solution. The mixture was extracted with ethyl acetate and evaporated to give the desired compound (12 mg, 14%). LCMS for $C_{28}H_{34}NCl_2N_3O_3$ (M+H)$^+$: m/z=558.1.

Step H. 6-Chloro-19-methyl-17-morpholin-4-yl-2,4,8,22-tetraazatetracyclo[14.3.1.1(3,7).1(9,13)]docosa-1(20),3(22),4,6,9(21),10,12,16,18-nonaene trifluoroacetate tert-Butyl [5-(2-{3-[(2,5-dichloropyrimidin-4-yl)amino]phenyl}ethyl)-2-methyl-4-morpholin-4-ylphenyl]carbamate (12 mg, 0.02 mmol) was stirred in 2-methoxyethanol (1 mL) and 3 N hydrogen chloride in ethanol (0.2 mL) and heated to 130° C. for 20 minutes in a microwave. Purification by preparative LCMS (pH 2) gave the desired compound as a trifluoroacetic acid salt (2.2 mg, 20%). $^1$H NMR (300 MHz, CDCl$_3$): δ 11.20 (s, 1H), 7.95 (s, 1H), 7.85 (s, 1H), 7.62 (s, 1H), 7.42 (s, 1H), 7.04 (m, 1H), 6.92 (m, 1H), 6.85 (m, 1H), 3.89 (m, 4H), 3.10 (m, 4H), 2.91 (m, 4H), 2.33 (s, 3H). LCMS for $C_{23}H_{25}ClN_5O$ (M+H)$^+$: m/z=422.0.

Example A7

6-Chloro-19-methyl-2,4,8,22-tetraazatetracyclo[14.3.1.1(3,7).1(9,13)]docosa-1(20),3(22),4,6,9(21),10,12,16,18-nonaene trifluoroacetate

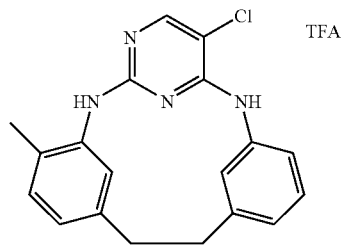 [SMILES: Cc1ccc2cc1Nc1ncc(Cl)c(n1)Nc1cccc(c1)CC2]

The desired compound was prepared according to the procedure of Example A6, steps C-H using 5-bromo-2-methylaniline [Aldrich] as the starting material in 7% yield. LCMS for $C_{19}H_{18}ClN_4$ (M+H)$^+$: m/z=337.0. $^1$H NMR (300 MHz, CDCl$_3$): δ 11.20 (s, 1H), 7.95 (s, 1H), 7.85 (s, 1H), 7.62 (s, 1H), 7.42 (s, 1H), 7.14 (m, 1H), 7.08 (m, 1H), 7.00 (m, 1H), 6.87 (m, 1H), 2.98 (m, 4H), 2.33 (s, 3H).

Example A8

6-Chloro-10-(isopropylsulfonyl)-2,4,8,22-tetraazatetracyclo[14.3.1.1(3,7).1(9,13)]docosa-1(20),3(22),4,6,9(21),10,12,16,18-nonaene trifluoroacetate

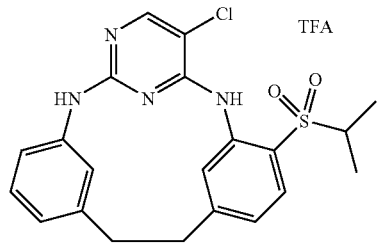 [SMILES: CC(C)S(=O)(=O)c1ccc2cc1Nc1nc(ncc1Cl)Nc1cccc(c1)CC2]

Step A. 4-Bromo-1-(isopropylthio)-2-nitrobenzene

4-Bromo-1-fluoro-2-nitrobenzene (1.0 g, 4.5 mmol) [Aldrich] and potassium carbonate (1.6 g, 11 mmol) were stirred in N,N-dimethylformamide (10 mL), and 2-propanethiol (0.42 mL, 4.5 mmol) was added. The mixture was heated to 100° C. for 16 hours. The mixture was cooled to rt, diluted with water (100 mL), and extracted with ethyl acetate. The extracts were washed with brine, dried over sodium sulfate, and evaporated to give the desired compound (1.2 g, 96%). $^1$H NMR (300 MHz, CDCl$_3$): δ 8.27 (s, 1H), 7.62 (d, 1H), 7.38 (d, 1H), 3.55 (m, 1H), 1.40 (d, 6H).

Step B.
4-Bromo-1-(isopropylsulfonyl)-2-nitrobenzene

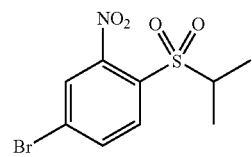 [SMILES: CC(C)S(=O)(=O)c1ccc(Br)cc1[N+](=O)[O-]]

4-Bromo-1-(isopropylsulfonyl)-2-nitrobenzene (750 mg, 2.7 mmol) was stirred in 1,2-dichloroethane (40 mL) with m-chloroperbenzoic acid (1.5 g, 6.1 mmol) for 16 hours. The suspension was filtered and the collected solids were washed with 1,2-dichloroethane. The combined filtrates were evaporated and purified by silica gel chromatography to give the desired compound (600 mg, 70%). LCMS for $C_9H_{11}BrNO_4S$ (M+H)$^+$: m/z=307.8.

Step C. 3-{[4-(Isopropylsulfonyl)-3-nitrophenyl]ethynyl}aniline

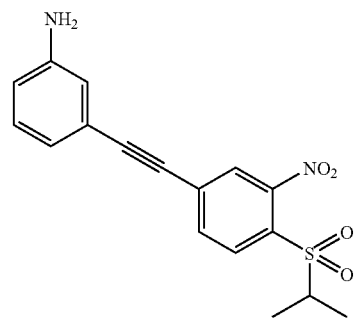 [SMILES: CC(C)S(=O)(=O)c1ccc(C#Cc2cccc(N)c2)cc1[N+](=O)[O-]]

4-Bromo-1-(isopropylsulfonyl)-2-nitrobenzene (390 mg, 1.3 mmol), bis(triphenylphosphine)palladium(II) chloride (60 mg, 0.08 mmol) and copper(I) iodide (20 mg, 0.1 mmol) were stirred in tetrahydrofuran (5 mL) with triethylamine (250 μL, 1.8 mmol). 3-Ethynylaniline (100 μL, 1.0 mmol) was added and the mixture was stirred at rt for 1.5 hours. The mixture was evaporated, diluted with saturated aqueous sodium bicarbonate and extracted with ethyl acetate. The extracts were dried over sodium sulfate, filtered and evaporated to give the desired compound (250 mg, 60%). LCMS for $C_{17}H_{17}N_2O_4S$ (M+H)$^+$: m/z=345.1.

Step D. tert-Butyl (3-{[isopropylsulfonyl)-3-nitrophenyl]ethynyl}phenyl)carbamate

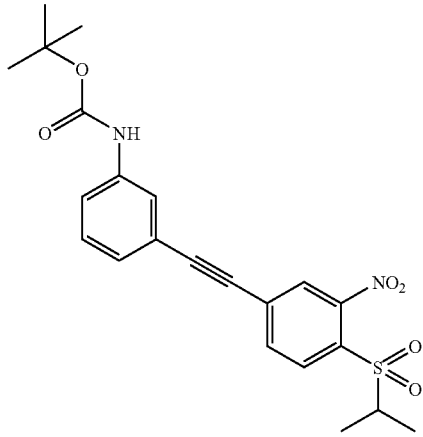 [SMILES: CC(C)S(=O)(=O)c1ccc(C#Cc2cccc(NC(=O)OC(C)(C)C)c2)cc1[N+](=O)[O-]]

3-{[4-(Isopropylsulfonyl)-3-nitrophenyl]ethynyl}aniline (390 mg, 1.1 mmol) was stirred in ethanol (5 mL) and di-tert-butyldicarbonate (250 mg, 1.1 mmol) was added. The mixture was stirred for 16 hours and evaporated to give the desired compound (280 mg, 55%). $^1$H NMR (300 MHz, DMSO-d$_6$): δ 11.91 (s, 1H), 10.36 (s, 1H), 8.35 (s, 1H), 7.92 (s, 1H), 7.83 (m, 2H), 7.28 (m, 2H), 7.15 (m, 1H), 7.07 (m, 1H), 3.18 (m, 1H), 3.01 (m, 4H), 1.32 (d, 6H).

Step E. 6-Chloro-10-(isopropylsulfonyl)-2,4,8,22-tetraazatetracyclo[14.3.1.1(3,7).1(9,13)]docosa-1(20),3(22),4,6,9(21),10,12,16,18-nonaene trifluoroacetate The desired compound was prepared according to the procedure of Example A6, steps D-G using tert-butyl (3-{[isopropylsulfonyl)-3-nitrophenyl]ethynyl}phenyl)carbamate as the starting material. LCMS for $C_{21}H_{22}ClN_4O_2S$ (M+H)$^+$: m/z=429.1. $^1$H NMR (300 MHz, CDCl$_3$): δ 9.61 (s, 1H), 8.39 (s, 1H), 8.08 (s, 2H), 7.80 (s, 1H), 7.50 (m, 1H), 7.38 (m, 1H), 7.22 (m, 1H), 3.78 (m, 1H), 1.48 (s, 9H), 1.25 (d, 6H).

Example A9

4-({[6-Chloro-2,4,8,22-tetraazatetracyclo[14.3.1.1(3,7).1(9,13)]docosa-1(20),3(22),4,6,9(21),10,12,16,18-nonaen-12-yl]oxy}acetyl)-N-(4-cyanophenyl)piperazine-1-carboxamide trifluoroacetate

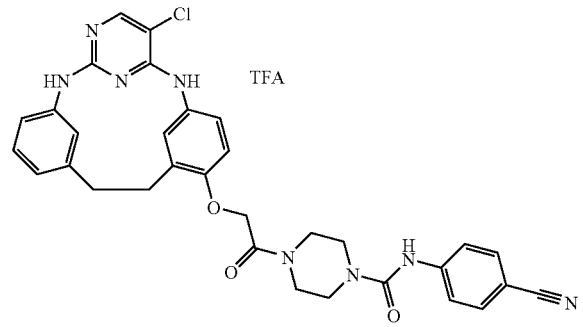 [SMILES: N#Cc1ccc(NC(=O)N2CCN(C(=O)COc3ccc4cc3CCc3cccc(c3)Nc3ncc(Cl)c(n3)N4)CC2)cc1]

Step A. 2-Iodo-1-methoxy-4-nitrobenzene

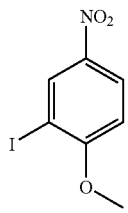

2-Methoxy-5-nitroaniline (10.0 g, 0.060 mol) was stirred in water (150 mL) and concentrated (conc.) sulfuric acid (12 mL, 0.22 mol). The solution was cooled below 5° C. with an ice-salt bath, and a solution of sodium nitrite (4.8 g, 0.070 mol) in water (40 mL) was added dropwise while maintaining the temperature below 5° C. A solution of potassium iodide (16.8 g, 0.101 mol) was added and the mixture was heated to 90° C. for 1 hour. Cooling to 0° C. gave dark red crystals which were filtered, washed with water, and dried. Purification by silica gel chromatography using ethyl acetate/hexanes gave the desired compound (13.6 g, 75%). $^1$H NMR (300 MHz, DMSO-d$_6$): δ 8.57 (s, 1H), 8.28 (d, 1H), 7.19 (d, 1H), 3.98 (s, 3H). LCMS for $C_7H_7INO_3$ (M+H)$^+$: m/z=280.1.

Step B. tert-Butyl{3-[(2-methoxy-5-nitrophenyl)ethynyl]phenyl}carbamate

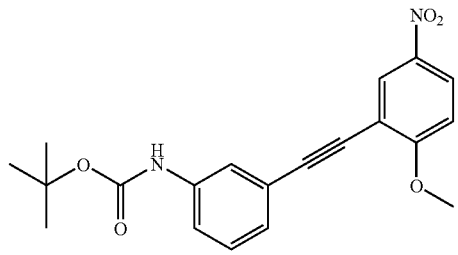 [SMILES: COc1ccc([N+](=O)[O-])cc1C#Cc1cccc(NC(=O)OC(C)(C)C)c1]

tert-Butyl (3-ethynylphenyl)carbamate was stirred with 2-iodo-1-methoxy-4-nitrobenzene (2.60 g, 9.31 mmol) and bis(triphenylphosphine)palladium(II) chloride (163 mg, 0.23 mmol) in N,N-dimethylformamide (15 mL), and triethylamine (2.59 mL, 18.6 mmol) was added. The reaction mixture was heated at 80° C. for 15 minutes. Purification by preparative LCMS (pH 10) gave the desired compound (1.38 g, 40%). $^1$H NMR (300 MHz, DMSO-d$_6$): δ 9.53 (s, 1H), 8.25 (m, 2H), 7.71 (s, 1H), 7.42 (d, 1H), 7.25 (m, 2H), 7.18 (d, 1H), 4.00 (s, 3H), 1.42 (s, 9H). LCMS for $C_{20}H_{21}N_2O_5$ (M+H)$^+$: m/z=369.1.

Step C. tert-Butyl{3-[2-(5-amino-2-methoxyphenyl)ethyl]phenyl}carbamate

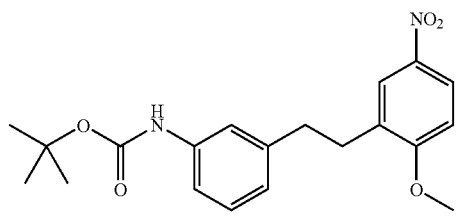 [SMILES: COc1ccc([N+](=O)[O-])cc1CCc1cccc(NC(=O)OC(C)(C)C)c1]

tert-Butyl{3-[(2-methoxy-5-nitrophenyl)ethynyl]phenyl}carbamate (63 mg, 0.17 mmol) and 10% palladium on carbon (122 mg, 0.10 mmol) were stirred in N,N-dimethylformamide (3.0 mL) under an atmosphere of hydrogen for 16 hours. The mixture was diluted with ethyl acetate (9.0 mL) and filtered through celite. Evaporation of the filtrate gave the desired compound (55 mg, 94%). LCMS for $C_{20}H_{27}N_2O_3$ (M+H)$^+$: m/z=343.2.

Step D. tert-Butyl[3-(2-{5-[(2,5-dichloropyrimidin-4-yl)amino]-2-methoxyphenyl}ethyl)phenyl]carbamate

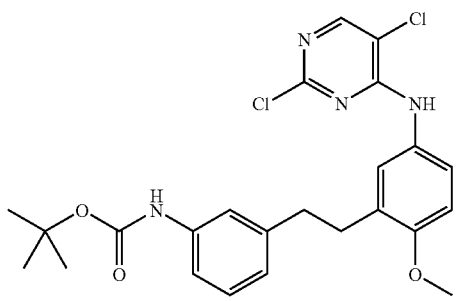 [SMILES: COc1ccc(Nc2nc(Cl)ncc2Cl)cc1CCc1cccc(NC(=O)OC(C)(C)C)c1]

tert-Butyl{3-[2-(5-amino-2-methoxyphenyl)ethyl]phenyl}carbamate (55 mg, 0.16 mmol), potassium carbonate (67 mg, 0.48 mmol), and 2,4,5-trichloropyrimidine (18 µL, 0.16 mmol) were stirred in N,N-dimethylformamide (1.5 mL) for 30 minutes. Purification by preparative LCMS (pH 2) gave the desired compound (75 mg, 95%). $^1$H NMR (300 MHz, DMSO-$d_6$): δ 9.40 (s, 1H), 9.25 (s, 1H), 8.30 (s, 1H), 7.40 (m, 3H), 7.20 (m, 1H), 7.12 (m, 1H), 6.99 (d, 1H) 6.80 (d, 1H), 3.80 (s, 3H), 2.77 (m, 4H), 1.42 (s, 9H). LCMS for $C_{24}H_{27}Cl_2N_4O_3$ (M+H)$^+$: m/z=489.1.

Step E. 6-Chloro-12-methoxy-2,4,8,22-tetraazatetracyclo[14.3.1.1(3,7).1(9,13)]docosa-1(20),3(22),4,6,9(21),10,12,16,18-nonaene trifluoroacetate

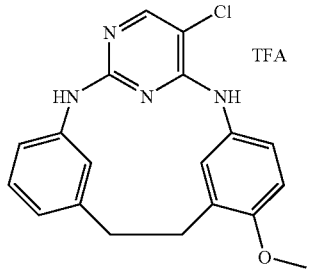 [SMILES: COc1ccc2cc1CCc1cccc(c1)Nc1ncc(Cl)c(n1)N2]

tert-Butyl[3-(2-{5-[(2,5-dichloropyrimidin-4-yl)amino]-2-methoxyphenyl}ethyl)phenyl]carbamate (343 mg, 0.70 mmol) was stirred in 2-methoxyethanol (104 mL) with 3 M hydrogen chloride in ethanol (12 mL) and heated at 130° C. for 20 minutes in a microwave, (4 batches of 29 mL). Purification by preparative LCMS (pH 2) gave the desired compound (168 mg, 51%). $^1$H NMR (300 MHz, DMSO-$d_6$) δ 9.53 (s, 1H), 9.40 (s, 1H), 8.14 (s, 1H), 7.91, (s, 1H), 7.60 (s, 1H), 7.03 (m, 2H), 6.81 (m, 3H), 3.79 (s, 3H), 2.85 (s, 4H). LCMS for $C_{19}H_{18}ClN_4O$ (M+H)$^+$: m/z=353.1.

Step F. 6-Chloro-2,4,8,22-tetraazatetracyclo[14.3.1.1(3,7).1(9,13)]docosa-1(20),3(22),4,6,9(21),10,12,16,18-nonaen-12-ol

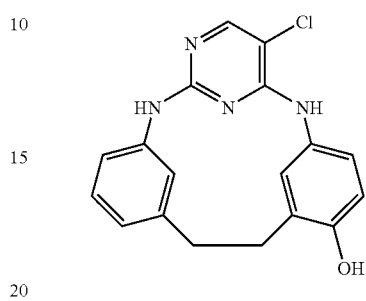

A solution of 6-chloro-12-methoxy-2,4,8,22-tetraazatetracyclo[14.3.1.1(3,7).1(9,13)]docosa-1(20),3(22),4,6,9(21),10,12,16,18-nonaene trifluoroacetate (157 mg, 0.34 mmol) in methylene chloride (2.5 mL) was cooled to −78° C. and 1 M boron tribromide in methylene chloride (1.68 mL, 1.68 mmol) was added slowly. The mixture was allowed to warm to room temperature and stir for 16 hours. The mixture was cooled to −78° C. and saturated sodium bicarbonate solution was added. The resulting suspension was filtered and the collected solid was washed with water and ethyl acetate to give the desired compound (113 mg, 100%). $^1$H NMR (300 MHz, DMSO-$d_6$): δ 9.45 (s, 1H), 9.25 (s, 1H), 8.09 (s, 1H), 7.92 (s, 1H), 7.48 (s, 1H), 7.08 (m, 1H), 6.81 (m, 3H), 6.71 (d, 1H), 2.82 (s, 4H). LCMS for $C_{18}H_{16}ClN_4O$ (M+H)$^+$: m/z=339.1.

Step G. 6-Chloro-12-(2-oxo-2-piperazin-1-ylethoxy)-2,4,8,22-tetraazatetracyclo[14.3.1.1(3,7).1(9,13)]docosa-1(20),3(22),4,6,9(21),10,12,16,18-nonaene bis(trifluoroacetate)

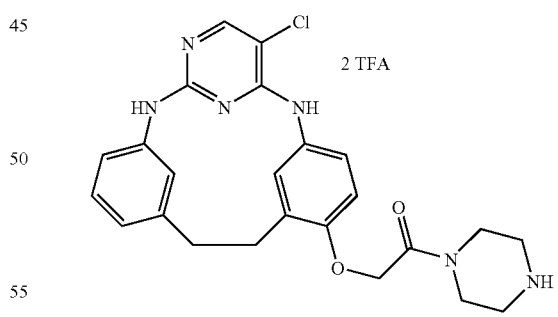

6-Chloro-2,4,8,22-tetraazatetracyclo[14.3.1.1(3,7).1(9,13)]docosa-1(20),3(22),4,6,9(21),10,12,16,18-nonaen-12-ol (100 mg, 0.30 mmol), potassium carbonate (102 mg, 0.74 mmol), and tert-butyl 4-(bromoacetyl)piperazine-1-carboxylate (181 mg, 0.59 mmol) were stirred in N,N-dimethylformamide (2 mL) for 16 hours at 70° C. Purification by preparative LCMS (pH 2) and treatment with 1:1 trifluoroacetic acid and methylene chloride followed by evaporation gave the desired compound (33 mg, 19%). LCMS for $C_{24}H_{26}ClN_6O_2$ (M+H)$^+$: m/z=465.2.

Step H. 4-({[6-Chloro-2,4,8,22-tetraazatetracyclo[14.3.1.1(3,7).1(9,13)]docosa-1(20),3(22),4,6,9(21),10,12,16,18-nonaene12-yl]oxy}acetyl)-N-(4-cyanophenyl)piperazine-1-carboxamide trifluoroacetate 6-Chloro-12-(2-oxo-2-piperazin-1-ylethoxy)-2,4,8,22-tetraazatetracyclo[14.3.1.1(3,7).1(9,13)]docosa-1(20),3(22),4,6,9(21),10,12,16,18-nonaene trifluoroacetate (10.0 mg, 0.017 mmol) was stirred in N,N-dimethylformamide (0.5 mL) and methylene chloride (0.5 mL) with triethylamine (12.0 μL, 0.086 mmol), and 4-isocyanatobenzonitrile (2.7 mg, 0.019 mmol) was added. Purification by preparative LCMS (pH 2) gave the desired compound (8%). LCMS for $C_{32}H_{30}ClN_8O_3$ (M+H)$^+$: m/z=609.2.

Example A10

4-(6-Chloropyridin-3-yl)-4-({[6-chloro-2,4,8,22-tetraazatetracyclo[14.3.1.1(3,7).1(9,13)]docosa-1(20),3(22),4,6,9(21),10,12,16,18-nonaen-12-yl]oxy}acetyl)piperazine-1-carboxamide bis(trifluoroacetate)

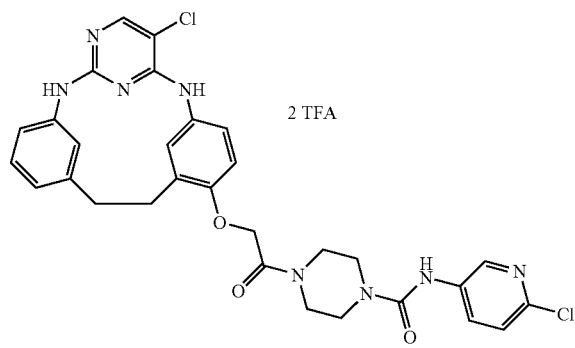 [SMILES: O=C(COc1ccc2cc1CCc1cccc(c1)Nc1ncc(Cl)c(n1)N2)N1CCN(C(=O)Nc2ccc(Cl)nc2)CC1 ; "2 TFA"]

The desired compound was prepared according to the procedure of Example A9, step H using 2-chloro-5-isocyanato-pyridine as the starting material in 19% yield. LCMS for $C_{30}H_{29}Cl_2N_8O_3$ (M+H)$^+$: m/z=619.2.

Example A11

4-({[6-Chloro-2,4,8,22-tetraazatetracyclo[14.3.1.1(3,7).1(9,13)]docosa-1(20),3(22),4,6,9(21),10,12,16,18-nonaen-12-yl]oxy}acetyl)-N-(1-methyl-1H-indol-4-yl)piperazine-1-carboxamide trifluoroacetate

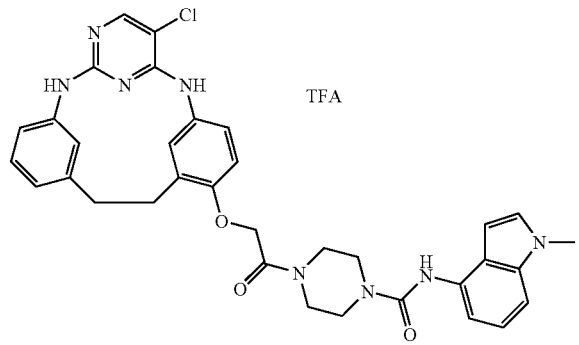 [SMILES: "TFA" ; Cn1ccc2c(NC(=O)N3CCN(C(=O)COc4ccc5cc4CCc4cccc(c4)Nc4ncc(Cl)c(n4)N5)CC3)cccc21]

The desired compound was prepared according to the procedure of Example A9, step H using 4-isocyanato-1-methyl-1H-indole as the starting material in 15% yield. LCMS for $C_{34}H_{34}ClN_8O_3$ (M+H)$^+$: m/z=637.2.

Example A12

12-[2-(4-Acetylpiperazin-1-yl)-2-oxoethoxy]-6-chloro-2,4,8,22-tetraazatetracyclo[14.3.1.1(3,7).1(9,13)]docosa-1(20),3(22),4,6,9(21),10,12,16,18-nonaene trifluoroacetate


The desired compound was prepared according to the procedure of Example A9, step H using isocyanato-ethane as the starting material in 57% yield. $^1$H NMR (300 MHz, DMSO-d$_6$): δ 9.42 (s, 1H), 9.31 (s, 1H), 8.10 (s, 1H), 7.97 (s, 1H), 7.60 (m, 1H), 7.08 (m, 1H), 6.99 (d, 1H), 6.85 (d, 1H), 6.80 (m, 2H), 6.59 (m, 1H), 4.82 (s, 2H), 3.30 (m, 8H), 3.03 (m, 2H), 2.90 (m, 4H), 1.00 (t, 3H). LCMS for $C_{27}H_{31}ClN_7O_3$ (M+H)$^+$: m/z=536.2.

Example A13

4-({[6-Chloro-2,4,8,22-tetraazatetracyclo[14.3.1.1(3,7).1(9,13)]docosa-1(20),3(22),4,6,9(21),10,12,16,18-nonaen-12-yl]oxy}acetyl)-N-phenylpiperazine-1-carboxamide trifluoroacetate


The desired compound was prepared according to the procedure of Example A9, step H using phenyl isocyanate as the starting material in 46% yield. $^1$H NMR (300 MHz, DMSO-d$_6$): δ 9.38 (s, 1H), 9.24 (s, 1H), 8.60 (s, 1H), 8.10 (s, 1H), 7.99 (s, 1H), 7.60 (s, 1H), 7.43 (d, 2H), 7.20 (m, 2H), 7.08 (m, 1H), 6.90 (m, 5H), 4.89 (s, 2H), 3.50 (m, 8H), 2.89 (m, 4H). LCMS for $C_{31}H_{31}ClN_7O_3$ (M+H)$^+$: m/z=584.2.

Example A14

6-Chloro-12-(cyclopentyloxy)-2,4,8,22-tetraazatetracyclo[14.3.1.1(3,7).1(9,13)]docosa-1(20),3(22),4,6,9(21),10,12,16,18-nonaene trifluoroacetate

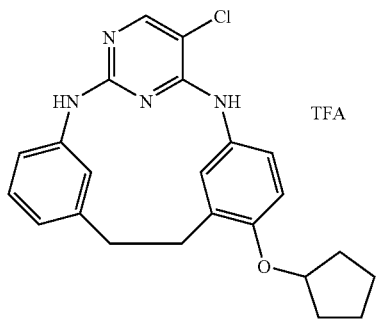 [SMILES: "TFA" ; Clc1cnc2nc1Nc1ccc(OC3CCCC3)c(c1)CCc1cccc(c1)N2]

The desired compound was prepared according to the procedure of Example A9, step G using cyclopentyl bromide as the starting material in 32% yield. LCMS for $C_{23}H_{24}ClN_4O$ (M+H)$^+$: m/z=407.2.

Example A15

2-{[6-Chloro-2,4,8,22-tetraazatetracyclo[14.3.1.1(3,7).1(9,13)]docosa-1(20),3(22),4,6,9(21),10,12,16,18-nonaen-12-yl]oxy}acetamide trifluoroacetate

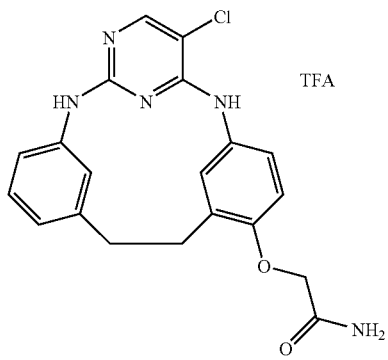 [SMILES: "TFA" ; NC(=O)COc1ccc2cc1CCc1cccc(c1)Nc1ncc(Cl)c(n1)N2]

The desired compound was prepared according to the procedure of Example A9, step G using 2-bromoacetamide as the starting material in 56% yield. $^1$H NMR (300 MHz, DMSO-d$_6$): δ 9.40 (s, 1H), 9.28 (s, 1H), 8.10 (s, 1H), 7.97 (s, 1H), 7.63 (s, 1H), 7.43 (s, 1H), 7.38 (s, 1H), 7.09 (m, 1H), 6.99 (d, 1H), 6.83 (d, 1H), 6.79 (m, 2H), 4.42 (s, 2H), 2.89 (m, 4H). LCMS for $C_{20}H_{19}ClN_5O_2$ (M+H)$^+$: m/z=396.1.

Example A16

2-{[6-Chloro-2,4,8,22-tetraazatetracyclo[14.3.1.1(3,7).1(9,13)]docosa-1(20),3(22),4,6,9(21),10,12,16,18-nonaen-12-yl]oxy}-N-phenylpropanamide trifluoroacetate

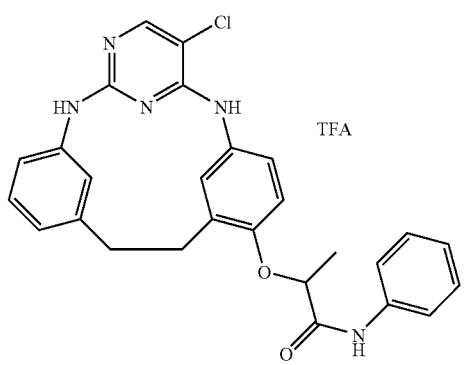 [SMILES: "TFA" ; CC(Oc1ccc2cc1CCc1cccc(c1)Nc1ncc(Cl)c(n1)N2)C(=O)Nc1ccccc1]

The desired compound was prepared according to the procedure of Example A9, step G using 2-bromo-N-phenylpropanamide as the starting material in 69% yield. $^1$H NMR (300 MHz, DMSO-d$_6$): δ 10.10 (s, 1H), 9.42 (s, 1H), 9.28 (s, 1H), 8.10 (s, 1H), 7.97 (s, 1H), 7.63 (m, 3H), 7.28 (m, 2H), 7.04 (m, 2H), 6.96 (d, 1H), 6.80 (m, 3H), 4.83 (m, 1H), 2.95 (m, 4H), 1.58 (d, 3H). LCMS for $C_{27}H_{24}ClN_5O_2$ (M+H)$^+$: m/z=486.2.

Example A17 tert-Butyl 4-({[6-chloro-2,4,8,22-tetraazatetracyclo[14.3.1.1(3,7).1(9,13)]docosa-1(20),3(22),4,6,9(21),10,12,16,18-nonaen-12-yl]oxy}acetyl)piperazine-1-carboxylate trifluoroacetate

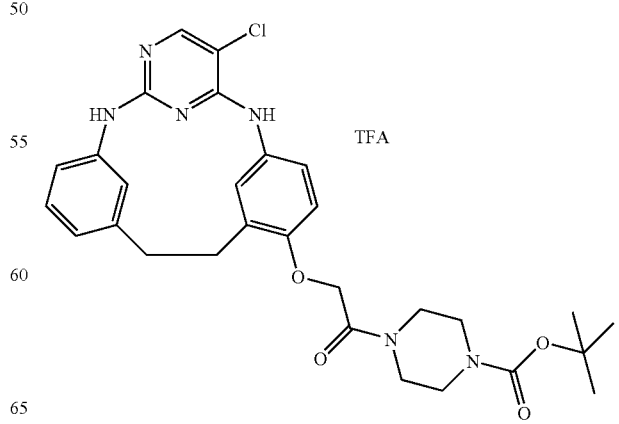

The desired compound (the boc intermediate) was also prepared and isolated in Example A9, step G in 19% yield. LCMS for $C_{29}H_{30}ClN_8O_3$ (M+H)$^+$: m/z=565.2

Example A18

2-{[6-Chloro-2,4,8,22-tetraazatetracyclo[14.3.1.1(3, 7).1(9,13)]docosa-1(20),3(22),4,6,9(21),10,12,16,18-nonaen-12-yl]oxy}-N-phenylacetamide trifluoroacetate

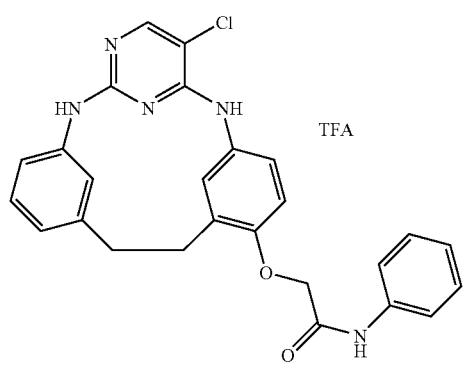 [SMILES: "TFA" ; O=C(COc1ccc2cc1CCc1cccc(c1)Nc1ncc(Cl)c(n1)N2)Nc1ccccc1]

The desired compound was prepared according to the procedure of Example A9, step G using 2-bromo-N-phenylacetamide as the starting material in 50% yield. $^1$H NMR (300 MHz, DMSO-d$_6$): δ 10.08 (s, 1H), 9.52 (s, 1H), 9.40 (s, 1H), 8.12 (s, 1H), 7.97 (s, 1H), 7.63 (m, 3H), 7.33 (m, 2H), 7.09 (m, 2H), 6.99 (d, 1H), 6.85 (d, 1H), 6.83 (m, 2H), 4.72 (s, 2H), 2.99 (m, 4H). LCMS for $C_{26}H_{23}ClN_5O_2$ (M+H)$^+$: m/z=472.2.

Example A19

N-Benzyl-4-(2-{[6-chloro-2,4,8,18,22-pentaazatetracyclo[14.3.1.1(3,7).1(9,13)]docosa-1(20),3(22),4,6,9 (21),10,12,16,18-nonaen-12-yl]amino}-2-oxoethyl) piperidine-1-carboxamide bis(trifluoroacetate)

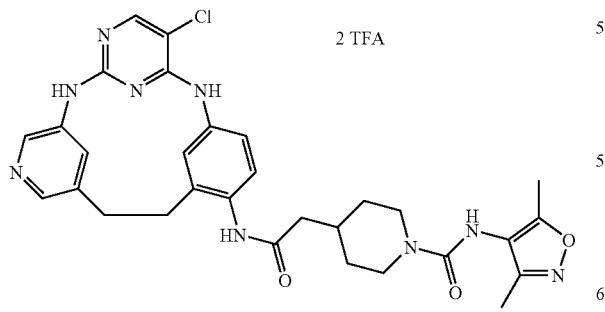

The desired compound was prepared according to the procedure of Example A9, step H using N-[6-chloro-2,4,8,18, 22-pentaazatetracyclo[14.3.1.1(3,7).1(9,13)]docosa-1(20),3 (22),4,6,9(21),10,12,16,18-nonaen-12-yl]-2-piperidin-4-ylacetamide tris(trifluoroacetate) and 4-isocyanato-3,5-dimethylisoxazole as starting materials in 30% yield. LCMS for $C_{30}H_{33}ClN_9O_3$ (M+H)$^+$: m/z=602.2.

Example A20

12-[2-(4-Acetylpiperazin-1-yl)-2-oxoethoxy]-6-chloro-2,4,8,22-tetraazatetracyclo[14.3.1.1(3,7).1(9, 13)]docosa-1(20),3(22),4,6,9(21),10,12,16,18-nonaene trifluoroacetate

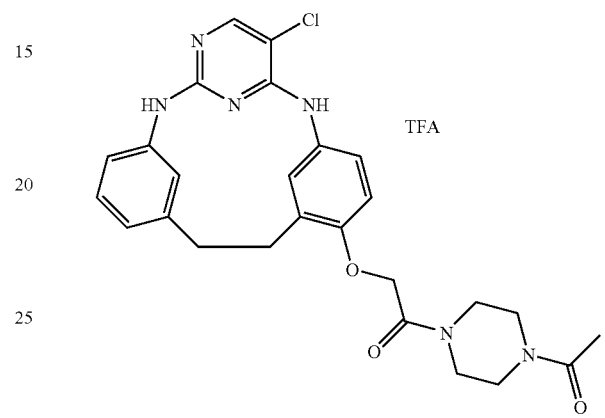

6-Chloro-12-(2-oxo-2-piperazin-1-ylethoxy)-2,4,8,22-tetraazatetracyclo[14.3.1.1(3,7).1(9,13)]docosa-1(20),3(22), 4,6,9(21),10,12,16,18-nonaene trifluoroacetate (11.1 mg, 0.019 mmol) was stirred in N,N-dimethylformamide (1.0 mL) with N,N-diisopropylethylamine (17 μL, 0.096 mmol), and acetyl chloride (1.5 μL, 0.021 mmol) was added. Purification by preparative LCMS (pH 2) gave the desired compound (46%). LCMS for $C_{26}H_{28}ClN_6O_3$ (M+H)$^+$: m/z=507.2.

Example A21

6-Chloro-11-methoxy-2,4,8,22-tetraazatetracyclo [14.3.1.1(3,7).1(9,13)]docosa-1(20),3(22),4,6,9(21), 10,12,16,18-nonaene trifluoroacetate

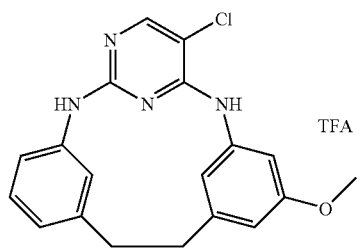 [SMILES: "TFA" ; COc1cc2cc(c1)Nc1nc(ncc1Cl)Nc1cccc(c1)CC2]

161

Step A. 3,5-Dinitrobromobenzene

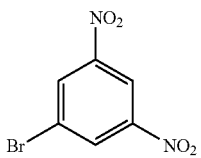

m-Dinitrobenzene (5.0 g, 0.030 mol) was stirred in sulfuric acid (50 mL) and heated to 85° C. N-Bromosuccinimide (5.0 g, 0.030 mol) was added in portions over 1.5 hours while maintaining a temperature of 85° C. The cooled mixture was poured into ice water and the precipitate was collected, washed with water and recrystallized from methanol to give the desired compound (5.9 g, 80%). LCMS for $C_6H_4BrN_2O_4$ (M+H)$^+$: m/z=248.1.

Step B. 1-Bromo-3-methoxy-5-nitrobenzene

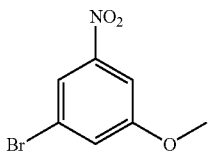

3,5-Dinitrobromobenzene (1.25 g, 5.06 mmol) was stirred in methanol (12 mL) and a solution of sodium methoxide (0.5 M in methanol, 12.6 mL) was added. The mixture was heated to 60° C. for 2 hours and cooled to RT. The mixture was quenched with hydrogen chloride solution (1 N) and extracted with dichloromethane. Evaporation and purification by silica chromatography using ethyl acetate and hexanes gave the desired compound (1.0 g, 80%). LCMS for $C_7H_7BrNO_3$ (M+H)$^+$: m/z=232.1.

Step C. tert-Butyl {3-[(E)-2-(3-methoxy-5-nitrophenyl)vinyl]phenyl}carbamate

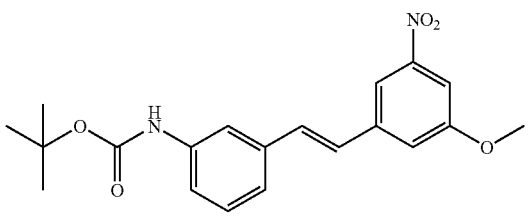 [SMILES: COc1cc(/C=C/c2cccc(NC(=O)OC(C)(C)C)c2)cc([N+](=O)[O-])c1]

1-Bromo-3-methoxy-5-nitrobenzene (0.50 g, 2.00 mmol), tert-butyl (3-vinylphenyl)carbamate (0.56 g, 2.15 mmol), tetra-N-butylammonium chloride (59.9 mg, 0.22 mmol), palladium acetate (48 mg, 0.22 mmol), and triethylamine (0.75 mL, 5.39 mmol) were stirred in N,N-dimethylformamide (5.7 mL) and heated to 110° C. for 20 hours. The mixture was cooled to RT, ethyl acetate and brine were added. The ethyl acetate was separated and the aqueous layer was extracted two more times with ethyl acetate. The combined ethyl acetate extracts were dried over sodium sulfate, filtered, and concentrated. Purification by silica chromatography using ethyl acetate and hexanes gave the desired compound (0.45 g, 60%). LCMS for $C_{20}H_{23}N_2O_5$ (M+H)$^+$: m/z=371.2.

Step D. 6-Chloro-11-methoxy-2,4,8,22-tetraazatetracyclo[14.3.1.1(3,7).1(9,13)]docosa-1(20),3(22),4,6,9(21),10,12,16,18-nonaene trifluoroacetate The desired compound was prepared according to the procedure of Example A9, steps C-E using tert-Butyl {3-[(E)-2-(3-methoxy-5-nitrophenyl)vinyl]phenyl}carbamate as the starting material in 37% yield over 3 steps. $^1$H NMR (300 MHz, DMSO-d$_6$): δ 9.41 (s, 1H), 9.23 (s, 1H), 8.17 (s, 1H), 7.92 (s, 1H), 7.40 (s, 1H), 7.12 (m, 1H), 6.91 (d, 1H), 6.83 (d, 1H), 6.71 (m, 1H), 6.60 (m, 1H), 3.72 (s, 3H), 2.82 (m, 4H). LCMS for $C_{19}H_{18}ClN_4O$ (M+H)$^+$: m/z=353.1.

Example A22

6-Chloro-2,4,8,22-tetraazatetracyclo[14.3.1.1(3,7).1(9,13)]docosa-1(20),3(22),4,6,9(21),10,12,16,18-nonaen-11-ol trifluoroacetate

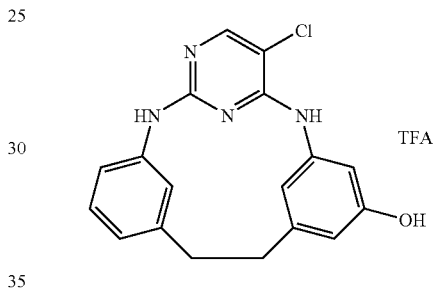

The desired compound was prepared according to the procedure of Example A9, step F using 6-chloro-11-methoxy-2,4,8,22-tetraazatetracyclo[14.3.1.1(3,7).1(9,13)]docosa-1(20),3(22),4,6,9(21),10,12,16,18-nonaene trifluoroacetate as the starting material in 94% yield. $^1$H NMR (300 MHz, DMSO-d$_6$): δ 9.43 (s, 1H), 9.23 (s, 1H), 8.12 (s, 1H), 7.93 (s, 1H), 7.20 (s, 1H), 7.12 (m, 1H), 6.91 (d, 1H), 6.81 (d, 1H), 6.51 (m, 1H), 6.40 (m, 1H), 2.82 (m, 4H). LCMS for $C_{18}H_{16}ClN_4O$ (M+H)$^+$: m/z=339.1.

Example A23

2-{[6-Chloro-2,4,8,22-tetraazatetracyclo[14.3.1.1(3,7).1(9,13)]docosa-1(20),3(22),4,6,9(21),10,12,16,18-nonaen-11-yl]oxy}acetyl)acetamide trifluoroacetate

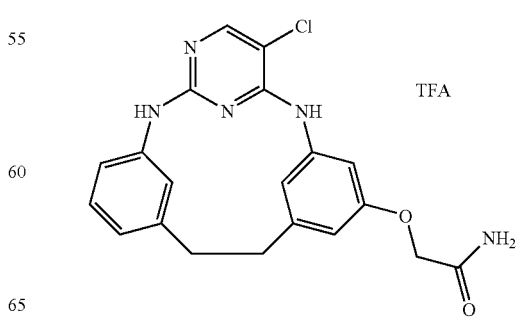

The desired compound was prepared according to the procedure of Example A9, step G using 6-chloro-2,4,8,22-tetraazatetracyclo[14.3.1.1(3,7).1(9,13)]docosa-1(20),3(22),4,6,9(21),10,12,16,18-nonaen-11-ol trifluoroacetate and 2-bromoacetamide as starting materials in 40% yield. $^1$H NMR (300 MHz, DMSO-d$_6$): δ 9.40 (s, 1H), 9.20 (s, 1H), 8.10 (s, 1H), 7.97 (s, 1H), 7.50 (s, 1H), 7.40 (m, 2H), 7.09 (m, 1H), 6.90 (d, 1H), 6.81 (d, 1H), 6.75 (s, 1H), 6.60 (s, 1H), 4.38 (s, 2H), 2.81 (m, 4H). LCMS for C$_{20}$H$_{19}$ClN$_5$O$_2$ (M+H)$^+$: m/z=396.1.

Example A24

2-{[6-Chloro-2,4,8,22-tetraazatetracyclo[14.3.1.1(3,7).1(9,13)]docosa-1(20),3(22),4,6,9(21),10,12,16,18-nonaen-11-yl]oxy}-N-phenylacetamide trifluoroacetate

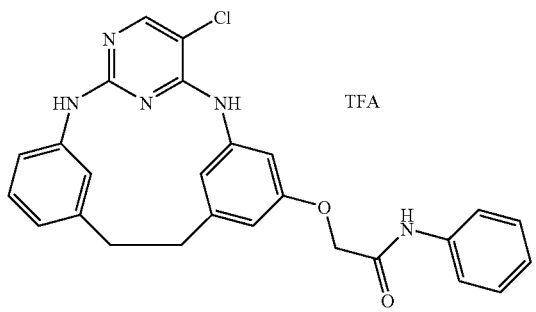 [SMILES: O=C(COc1cc2cc(c1)Nc1nc(ncc1Cl)Nc1cccc(c1)CC2)Nc1ccccc1]

The desired compound was prepared according to the procedure of Example A9, step G using 6-chloro-2,4,8,22-tetraazatetracyclo[14.3.1.1(3,7).1(9,13)]docosa-1(20),3(22),4,6,9(21),10,12,16,18-nonaen-11-ol trifluoroacetate and 2-bromo-N-phenylacetamide as the starting material in 30% yield. $^1$H NMR (300 MHz, DMSO-d$_6$): δ 10.08 (s, 1H), 9.32 (s, 1H), 9.16 (s, 1H), 8.12 (s, 1H), 7.97 (s, 1H), 7.63 (m, 2H), 7.43 (s, 1H), 7.30 (m, 2H), 7.09 (m, 2H), 6.90 (d, 1H), 6.80 (m, 2H), 6.68 (s, 1H), 4.62 (s, 2H), 2.80 (s, 4H). LCMS for C$_{26}$H$_{23}$ClN$_5$O$_2$ (M+H)$^+$: m/z=472.2.

Example A25

6-Chloro-10-methoxy-2,4,8,22-tetraazatetracyclo[14.3.1.1(3,7).1(9,13)]docosa-1(20),3(22),4,6,9(21),10,12,16,18-nonaene trifluoroacetate

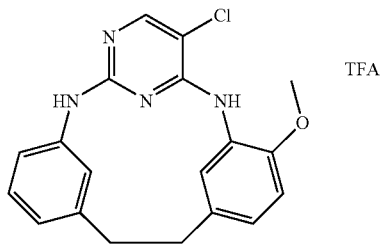 [SMILES: COc1ccc2cc1Nc1nc(ncc1Cl)Nc1cccc(c1)CC2]

The desired compound was prepared according to the procedure of Example A9, steps B-E using 4-iodo-1-methoxy-2-nitrobenzene as the starting material in 38% yield over 4 steps. $^1$H NMR (300 MHz, DMSO-d$_6$): δ 9.45 (s, 1H), 8.20 (s, 1H), 8.12 (s, 1H), 7.87 (s, 1H), 7.80 (s, 1H), 7.18 (m, 1H), 7.00 (m, 2H), 6.91 (d, 1H), 6.83 (d, 1H), 3.80 (s, 3H), 2.82 (s, 4H). LCMS for C$_{19}$H$_{18}$ClN$_4$O (M+H)$^+$: m/z=353.1.

Example A26

6-Chloro-2,4,8,22-tetraazatetracyclo[14.3.1.1(3,7).1(9,13)]docosa-1(20),3(22),4,6,9(21),10,12,16,18-nonaen-10-ol trifluoroacetate

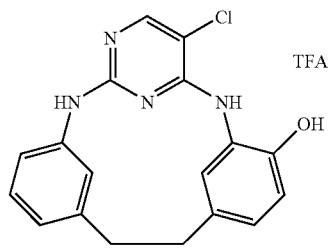 [SMILES: Oc1ccc2cc1Nc1nc(ncc1Cl)Nc1cccc(c1)CC2]

The desired compound was prepared according to the procedure of Example A9, step F using 6-chloro-10-methoxy-2,4,8,22-tetraazatetracyclo[14.3.1.1(3,7).1(9,13)]docosa-1(20),3(22),4,6,9(21),10,12,16,18-nonaene trifluoroacetate as the starting material in 96% yield. $^1$H NMR (300 MHz, DMSO-d$_6$): δ 9.32 (s, 1H), 8.12 (s, 1H), 7.88 (m, 2H), 7.77 (s, 1H), 7.18 (m, 1H), 6.92 (d, 1H), 6.81 (m, 3H), 2.82 (m, 4H). LCMS for C$_{18}$H$_{16}$ClN$_4$O (M+H)$^+$: m/z=339.1.

Example A27 tert-Butyl 4-({[6-chloro-2,4,8,22-tetraazatetracyclo[14.3.1.1(3,7).1(9,13)]docosa-1(20),3(22),4,6,9(21),10,12,16,18-nonaen-12-yl]amino}carbonyl)piperidine-1-carboxylate trifluoroacetate

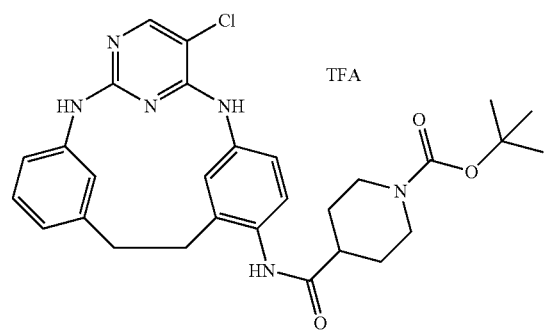 [SMILES: CC(C)(C)OC(=O)N1CCC(C(=O)Nc2ccc3cc2CCc2cccc(c2)Nc2ncc(Cl)c(n2)N3)CC1]

To a solution of 1-(tert-butoxycarbonyl)piperidine-4-carboxylic acid (25.0 mg, 0.109 mmol) in N,N-dimethylformamide (1.0 mL), N,N,N',N'-tetramethyl-O-(7-azabenzotriazol-1-yl)uronium hexafluorophosphate (124 mg, 0.33 mmol) and N,N-diisopropylethylamine (48 μL, 0.27 mmol) were added, and the mixture was stirred for 15 minutes. A solution of 6-chloro-2,4,8,22-tetraazatetracyclo[14.3.1.1(3,7).1(9,13)]docosa-1(20),3(22),4,6,9(21),10,12,16,18-nonaen-12-amine dihydrochloride (53.7 mg, 0.13 mmol) in N,N-dimethylformamide (1.0 mL) and N,N-diisopropylethylamine (48 μL, 0.27 mmol) was added to the previous solution and stirred for 3 hours at room temperature. The precipitate was filtered, washed with water and dried under vacuum. Purification by

Example A28

N-[6-Chloro-2,4,8,22-tetraazatetracyclo[14.3.1.1(3,7).1(9,13)]docosa-1(20), 3(22),4,6,9(21),10,12,16,18-nonaen-12-yl]piperidine-4-carboxamide bis(trifluoroacetate)

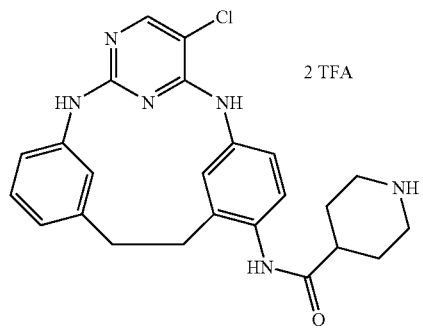 [SMILES: O=C(Nc1ccc2cc1CCc1cccc(c1)Nc1ncc(Cl)c(n1)N2)C1CCNCC1 ; "2 TFA"]

tert-Butyl 4-({[6-chloro-2,4,8,22-tetraazatetracyclo[14.3.1.1(3,7).1(9,13)]docosa-1(20),3(22),4,6,9(21),10,12,16,18-nonaen-12-yl]amino}carbonyl)piperidine-1-carboxylate (35 mg, 0.064 mmol) was treated with trifluoroacetic acid (1.0 mL) and methylene chloride (1.0 mL) for 10 minutes and evaporated to give the desired compound (35 mg, 100% yield). $^1$H NMR (300 MHz, DMSO-d$_6$): δ 9.42 (s, 2H), 9.25 (s, 1H), 8.60 (m, 1H), 8.28 (m, 1H), 8.13 (s, 1H), 8.00 (s, 1H), 7.75 (s, 1H), 7.20 (d, 1H), 7.05 (m, 2H), 6.91 (d, 1H), 6.77 (d, 1H), 3.38 (m, 2H), 2.80 (m, 7H), 2.01 (m, 2H), 1.82 (m, 2H). LCMS for $C_{24}H_{26}ClN_6O$ (M+H)$^+$: m/z=449.2.

Example A29

1-Acetyl-N-[6-chloro-2,4,8,22-tetraazatetracyclo[14.3.1.1(3,7).1(9,13)]docosa-1(20),3(22),4,6,9(21),10,12,16,18-nonaen-12-yl]piperidine-4-carboxamide trifluoroacetate

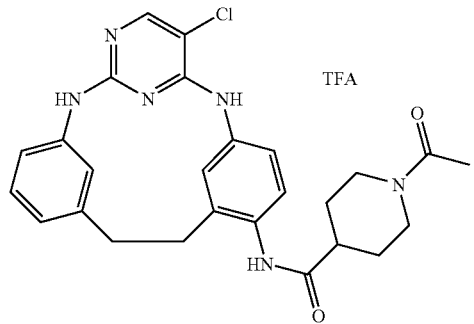 [SMILES: "TFA" ; CC(=O)N1CCC(C(=O)Nc2ccc3cc2CCc2cccc(c2)Nc2ncc(Cl)c(n2)N3)CC1]

The desired compound was prepared according to the procedure of Example A20, using N-[6-chloro-2,4,8,22-tetraazatetracyclo[14.3.1.1(3,7).1(9,13)]docosa-1(20), 3(22),4,6,9(21),10,12,16,18-nonaen-12-yl]piperidine-4-carboxamide bis(trifluoroacetate) and acetyl chloride as starting materials in 16% yield. LCMS for $C_{26}H_{28}ClN_6O_2$ (M+H)$^+$: m/z=491.2.

Example A30

1-Benzoyl-N-[6-chloro-2,4,8,22-tetraazatetracyclo[14.3.1.1(3,7).1(9,13)]docosa-1(20),3(22),4,6,9(21),10,12,16,18-nonaen-12-yl]piperidine-4-carboxamide trifluoroacetate

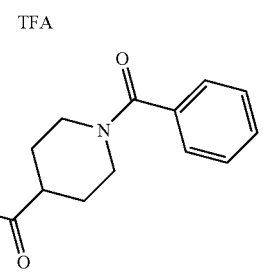

The desired compound was prepared according to the procedure of Example A20, using N-[6-chloro-2,4,8,22-tetraazatetracyclo[14.3.1.1(3,7).1(9,13)]docosa-1(20), 3(22),4,6,9(21),10,12,16,18-nonaen-12-yl]piperidine-4-carboxamide bis(trifluoroacetate) and benzoyl chloride as starting materials in 18% yield. LCMS for $C_{31}H_{30}ClN_6O_2$ (M+H)$^+$: m/z=553.2.

Example A31

1-(1,3-Benzodioxol-5-ylcarbonyl)-N-[6-chloro-2,4,8,22-tetraazatetracyclo[14.3.1.1(3,7).1(9,13)]docosa-1(20),3(22),4,6,9(21),10,12,16,18-nonaen-12-yl]piperidine-4-carboxamide trifluoroacetate

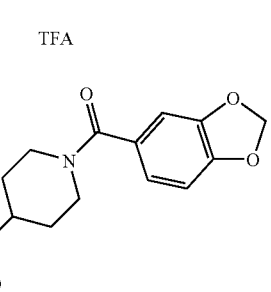

The desired compound was prepared according to the procedure of Example A20, using N-[6-chloro-2,4,8,22-tetraazatetracyclo[14.3.1.1(3,7).1(9,13)]docosa-1(20), 3(22),4,6,9(21),10,12,16,18-nonaen-12-yl]piperidine-4-carboxamide bis(trifluoroacetate) and 1,3-benzodioxole-5- carbonyl chloride as starting materials in 16% yield. LCMS for $C_{32}H_{30}ClN_6O_4$ (M+H)+: m/z=597.2.

Example A32

N-[6-Chloro-2,4,8,22-tetraazatetracyclo[14.3.1.1(3,7).1(9,13)]docosa-1(20), 3(22),4,6,9(21),10,12,16,18-nonaen-12-yl]-1-(2-furoyl)piperidine-4-carboxamide trifluoroacetate

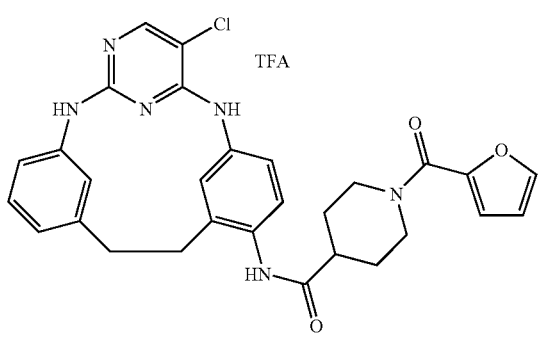 [SMILES: "TFA" ; O=C(Nc1ccc2cc1CCc1cccc(c1)Nc1ncc(Cl)c(n1)N2)C1CCN(C(=O)c2ccco2)CC1]

The desired compound was prepared according to the procedure of Example A20, using N-[6-chloro-2,4,8,22-tetraazatetracyclo[14.3.1.1(3,7).1(9,13)]docosa-1(20), 3(22),4,6,9(21),10,12,16,18-nonaen-12-yl]piperidine-4-carboxamide bis(trifluoroacetate) and 2-furancarbonyl chloride as starting materials in 16% yield. LCMS for $C_{29}H_{28}ClN_6O_3$ (M+H)+: m/z=543.2.

Example A33

N-[6-Chloro-2,4,8,22-tetraazatetracyclo[14.3.1.1(3,7).1(9,13)]docosa-1(20), 3(22),4,6,9(21),10,12,16,18-nonaen-12-yl]-1-(4-cyanobenzoyl)piperidine-4-carboxamide trifluoroacetate

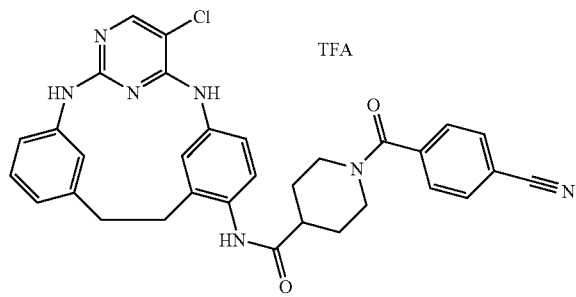 [SMILES: "TFA" ; N#Cc1ccc(C(=O)N2CCC(C(=O)Nc3ccc4cc3CCc3cccc(c3)Nc3ncc(Cl)c(n3)N4)CC2)cc1]

The desired compound was prepared according to the procedure of Example A20, using N-[6-chloro-2,4,8,22-tetraazatetracyclo[14.3.1.1(3,7).1(9,13)]docosa-1(20),3(22),4,6,9(21),10,12,16,18-nonaen-12-yl]piperidine-4-carboxamide bis(trifluoroacetate) and 4-cyanobenzoyl chloride as starting materials in 20% yield. LCMS for $C_{32}H_{29}ClN_7O_2$ (M+H)+: m/z=578.2.

Example A34

N-[6-Chloro-2,4,8,22-tetraazatetracyclo[14.3.1.1(3,7).1(9,13)]docosa-1(20), 3(22),4,6,9(21),10,12,16,18-nonaen-12-yl]-1-[(3,5-dimethylisoxazol-4-yl)carbonyl]piperidine-4-carboxamide trifluoroacetate

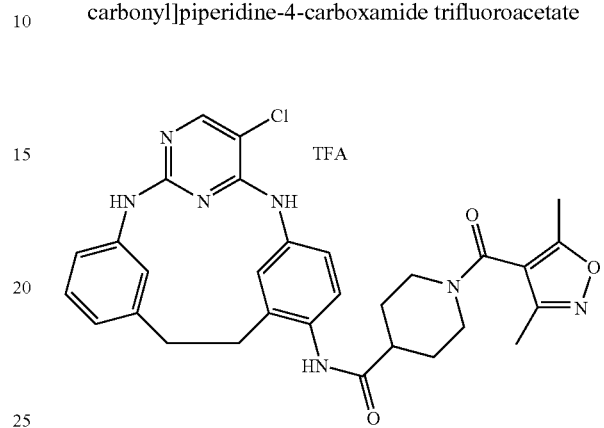

The desired compound was prepared according to the procedure of Example A20, using N-[6-chloro-2,4,8,22-tetraazatetracyclo[14.3.1.1(3,7).1(9,13)]docosa-1(20),3(22),4,6,9(21),10,12,16,18-nonaen-12-yl]piperidine-4-carboxamide bis(trifluoroacetate) and 3,5-dimethylisoxazole-4-carbonyl chloride as starting materials in 36% yield. LCMS for $C_{30}H_{31}ClN_7O_3$ (M+H)+: m/z=572.2.

Example A35

N-[6-Chloro-2,4,8,22-tetraazatetracyclo[14.3.1.1(3,7).1(9,13)]docosa-1(20),3(22),4,6,9(21),10,12,16,18-nonaen-12-yl]-1-(phenylacetyl)piperidine-4-carboxamide trifluoroacetate

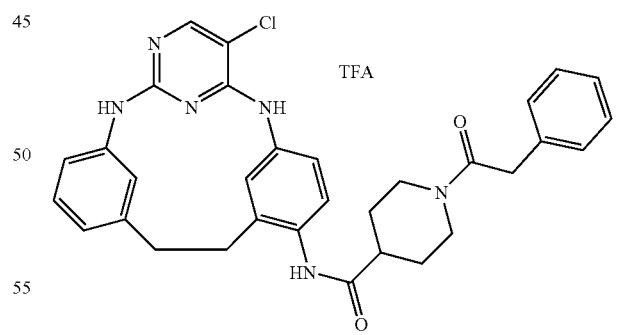

The desired compound was prepared according to the procedure of Example A20, using N-[6-chloro-2,4,8,22-tetraazatetracyclo[14.3.1.1(3,7).1(9,13)]docosa-1(20), 3(22),4,6,9(21),10,12,16,18-nonaen-12-yl]piperidine-4-carboxamide bis(trifluoroacetate) and benzeneacetyl chloride as starting materials in 70% yield. 1H NMR (300 MHz, DMSO-$d_6$): δ 9.61 (s, 1H), 9.44 (s, 1H), 9.32 (s, 1H), 8.18 (s, 1H), 7.97 (s, 1H), 7.72 (s, 1H), 7.20 (m, 7H), 7.03 (m, 2H), 6.89 (d, 1H), 6.79 (d, 1H), 4.42 (d, 1H), 4.01 (d, 1H), 3.73 (s, 2H), 3.02 (m, 1H), 2.81 (m, 4H), 2.63 (m, 2H), 1.80 (m, 2H), 1.41 (m, 2H). LCMS for $C_{32}H_{32}ClN_6O_2$ (M+H)$^+$: m/z=567.2.

Example A36

N(4)-[6-Chloro-2,4,8,22-tetraazatetracyclo[14.3.1.1 (3,7).1(9,13)]docosa-1(20),3(22),4,6,9(21),10,12,16, 18-nonaen-12-yl]-N(1)-phenylpiperidine-1,4-dicarboxamide trifluoroacetate

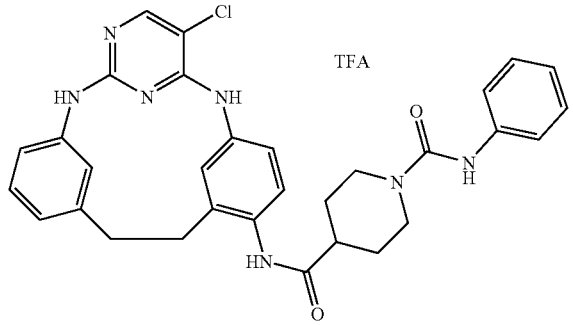 [SMILES: "TFA" ; O=C(Nc1ccc2cc1CCc1cccc(c1)Nc1ncc(Cl)c(n1)N2)C1CCN(C(=O)Nc2ccccc2)CC1]

The desired compound was prepared according to the procedure of Example A9, step H using N-[6-chloro-2,4,8,22-tetraazatetracyclo[14.3.1.1(3,7).1(9,13)]docosa-1(20),3(22), 4,6,9(21),10,12,16,18-nonaen-12-yl]piperidine-4-carboxamide bis(trifluoroacetate) and phenyl isocyante as starting materials in 31% yield. LCMS for $C_{31}H_{31}ClN_7O_2$ (M+H)$^+$: m/z=568.2.

Example A37

N(4)-[6-Chloro-2,4,8,22-tetraazatetracyclo[14.3.1.1 (3,7).1(9,13)]docosa-1(20),3(22),4,6,9(21),10,12,16, 18-nonaen-12-yl]-N(1)-(4-cyanophenyl)piperidine-1, 4-dicarboxamide trifluoroacetate

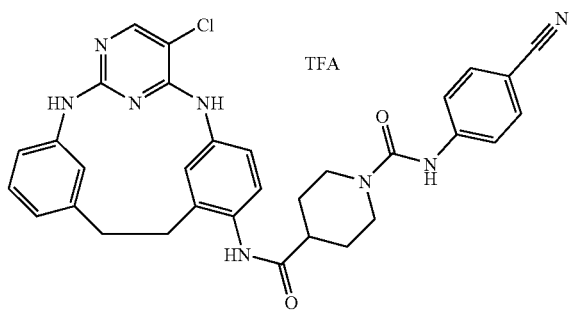 [SMILES: "TFA" ; N#Cc1ccc(NC(=O)N2CCC(C(=O)Nc3ccc4cc3CCc3cccc(c3)Nc3ncc(Cl)c(n3)N4)CC2)cc1]

The desired compound was prepared according to the procedure of Example A9, step H using N-[6-chloro-2,4,8,22-tetraazatetracyclo[14.3.1.1(3,7).1(9,13)]docosa-1(20),3(22), 4,6,9(21),10,12,16,18-nonaen-12-yl]piperidine-4-carboxamide bis(trifluoroacetate) and 4-isocyanatobenzonitrile as starting materials in 44% yield. $^1$H NMR (300 MHz, DMSO-d$_6$): δ 9.43 (s, 1H), 9.33 (m, 2H), 9.01 (s, 1H), 8.12 (s, 1H), 8.00 (s, 1H), 7.75 (s, 1H), 7.65 (s, 4H), 7.20 (d, 1H), 7.04 (m, 2H), 6.87 (d, 1H), 6.78 (d, 1H), 4.20 (d, 2H), 2.90 (m, 6H), 2.69 (m, 1H), 1.89 (m, 2H), 1.61 (m, 2H). LCMS for $C_{32}H_{30}ClN_8O_2$ (M+H)$^+$: m/z=593.2.

Example A38

N(4)-[6-Chloro-2,4,8,22-tetraazatetracyclo[14.3.1.1 (3,7).1(9,13)]docosa-1(20),3(22),4,6,9(21),10,12,16, 18-nonaen-12-yl]-N(1)-(3-methoxyphenyl)piperidine-1,4-dicarboxamide trifluoroacetate

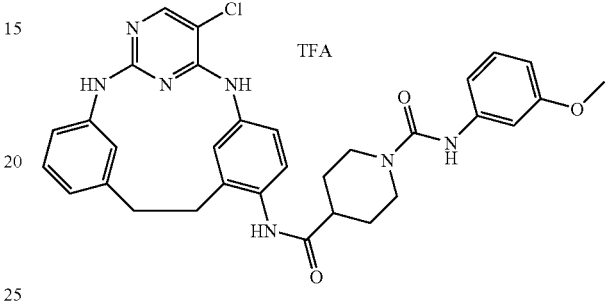

The desired compound was prepared according to the procedure of Example A9, step H using N-[6-chloro-2,4,8,22-tetraazatetracyclo[14.3.1.1(3,7).1(9,13)]docosa-1(20),3(22), 4,6,9(21),10,12,16,18-nonaen-12-yl]piperidine-4-carboxamide bis(trifluoroacetate) and 1-isocyanato-3-methoxybenzene as starting materials in 66% yield. $^1$H NMR (300 MHz, DMSO-d$_6$): δ 9.49 (s, 1H), 9.40 (s, 1H), 9.33 (s, 1H), 8.49 (s, 1H), 8.17 (s, 1H), 7.98 (s, 1H), 7.72 (s, 1H), 7.10 (m, 5H), 6.87 (d, 1H), 6.79 (d, 1H), 6.48 (d, 1H), 4.20 (d, 2H), 3.68 (s, 3H), 2.87 (m, 6H), 2.66 (m, 1H), 1.89 (m, 2H), 1.61 (m, 2H). LCMS for $C_{32}H_{33}ClN_7O_3$ (M+H)$^+$: m/z=598.2.

Example A39

N(4)-[6-Chloro-2,4,8,22-tetraazatetracyclo[14.3.1.1 (3,7).1(9,13)]docosa-1(20),3(22),4,6,9(21),10,12,16, 18-nonaen-12-yl]-N(1)-[2-(methylthio)phenyl]piperidine-1,4-dicarboxamide trifluoroacetate

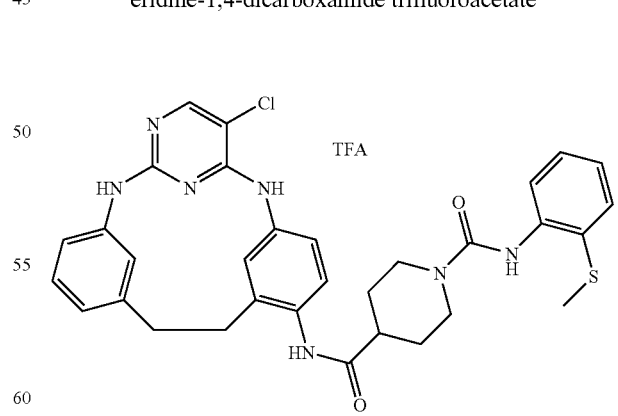

The desired compound was prepared according to the procedure of Example A9, step H using N-[6-chloro-2,4,8,22-tetraazatetracyclo[14.3.1.1(3,7).1(9,13)]docosa-1(20),3(22), 4,6,9(21),10,12,16,18-nonaen-12-yl]piperidine-4-carboxamide bis(trifluoroacetate) and 1-isocyanato-2-

(methylthio)benzene as starting materials in 49% yield. LCMS for $C_{32}H_{32}ClN_7O_2S$ (M+H)$^+$: m/z=614.2.

Example A40

N(1)-(6-Chloropyridin-3-yl)-N(4)-[6-chloro-2,4,8, 22-tetraazatetracyclo[14.3.1.1(3,7).1(9,13)]docosa-1 (20),3(22),4,6,9(21),10,12,16,18-nonaen-12-yl]piperidine-1,4-dicarboxamide bis(trifluoroacetate)

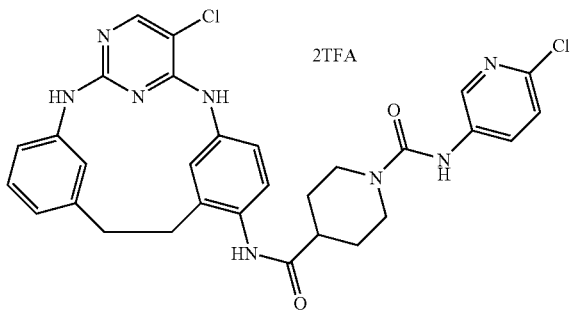 [SMILES: O=C(Nc1ccc2cc1CCc1cccc(c1)Nc1ncc(Cl)c(n1)N2)C1CCN(C(=O)Nc2ccc(Cl)nc2)CC1 ; "2TFA"]

The desired compound was prepared according to the procedure of Example A9, step H using N-[6-chloro-2,4,8,22-tetraazatetracyclo[14.3.1.1(3,7).1(9,13)]docosa-1(20), 3(22),4,6,9(21),10,12,16,18-nonaen-12-yl]piperidine-4-carboxamide bis(trifluoroacetate) and 2-chloro-5-isocyanatopyridine as starting materials in 23% yield. LCMS for $C_{30}H_{29}Cl_2N_8O_2$ (M+H)$^+$: m/z=603.2.

Example A41

N(4)-[6-Chloro-2,4,8,22-tetraazatetracyclo[14.3.1.1 (3,7).1(9,13)]docosa-1(20),3(22),4,6,9(21),10,12,16, 18-nonaen-12-yl]-N(1)-(1-methyl-1H-indol-4-yl) piperidine-1,4-dicarboxamide trifluoroacetate

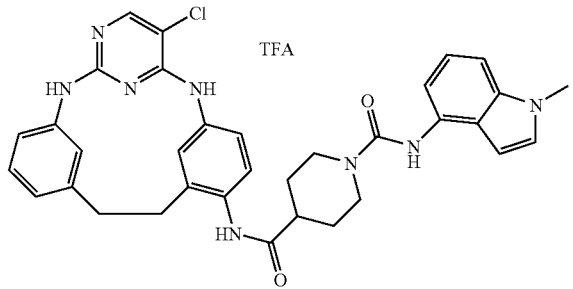 [SMILES: Cn1ccc2c(NC(=O)N3CCC(C(=O)Nc4ccc5cc4CCc4cccc(c4)Nc4ncc(Cl)c(n4)N5)CC3)cccc21]

The desired compound was prepared according to the procedure of Example A9, step H using N-[6-chloro-2,4,8,22-tetraazatetracyclo[14.3.1.1(3,7).1(9,13)]docosa-1(20), 3(22),4,6,9(21),10,12,16,18-nonaen-12-yl]piperidine-4-carboxamide bis(trifluoroacetate) and 4-isocyanato-1-methyl-1H-indole as starting materials in 34% yield. LCMS for $C_{34}H_{34}ClN_8O_2$ (M+H)$^+$: m/z=621.2.

Example A42

N-[6-Chloro-2,4,8,22-tetraazatetracyclo[14.3.1.1(3, 7).1(9,13)]docosa-1(20), 3(22),4,6,9(21),10,12,16, 18-nonaen-12-yl]-1-(phenylsulfonyl)piperidine-4-carboxamide trifluoroacetate

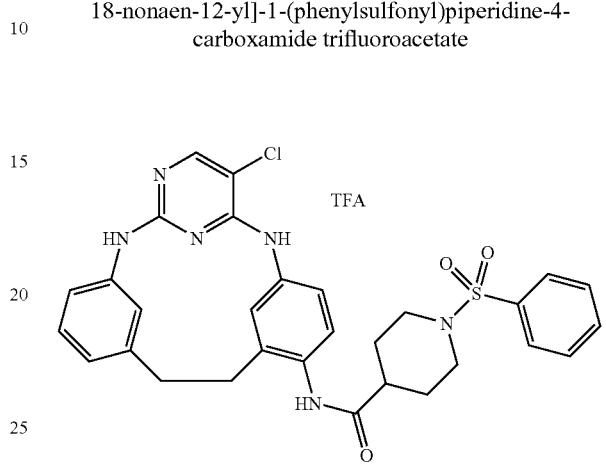

N-[6-chloro-2,4,8,22-tetraazatetracyclo[14.3.1.1(3,7).1 (9,13)]docosa-1(20), 3(22),4,6,9(21),10,12,16,18-nonaen-12-yl]piperidine-4-carboxamide bis(trifluoroacetate) (10.0 mg, 0.018 mmol) was stirred in N,N-dimethylformamide (1.0 mL) with N,N-diisopropylethylamine (16 μL, 0.089 mmol), and benzenesulfonyl chloride (2.5 μL, 0.020 mmol) was added. Purification by preparative LCMS (pH 2) gave the desired compound (18%). LCMS for $C_{30}H_{30}ClN_6O_3S$ (M+H)$^+$: m/z=589.2.

Example A43

1-(Anilinocarbonothioyl)-N-[6-chloro-2,4,8,22-tetraazatetracyclo[14.3.1.1(3,7).1(9,13)]docosa-1(20),3 (22),4,6,9(21),10,12,16,18-nonaen-12-yl]piperidine-4-carboxamide trifluoroacetate

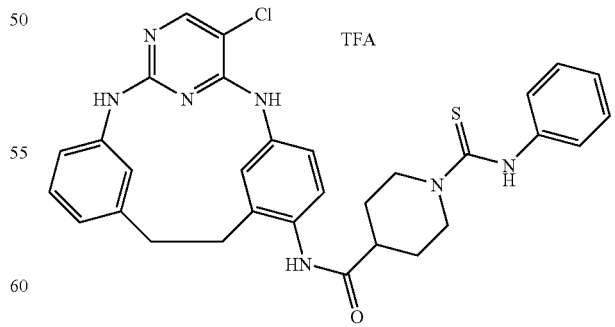

The desired compound was prepared according to the procedure of Example A9, step H using N-[6-chloro-2,4,8,22-tetraazatetracyclo[14.3.1.1(3,7).1(9,13)]docosa-1(20), 3(22),4,6,9(21),10,12,16,18-nonaen-12-yl]piperidine-4-carboxamide bis(trifluoroacetate) and isothiocyanatobenzene as starting materials in 28% yield. LCMS for $C_{31}H_{30}ClN_7OS$ (M+H)$^+$: m/z=584.2.

Example A44

N-[6-Chloro-2,4,8,22-tetraazatetracyclo[14.3.1.1(3,7).1(9,13)]docosa-1(20), 3(22),4,6,9(21),10,12,16,18-nonaen-12-yl]piperidine-3-carboxamide bis(trifluoroacetate)

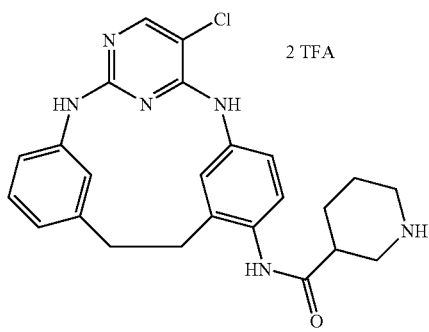 [SMILES: O=C(Nc1ccc2cc1CCc1cccc(c1)Nc1ncc(Cl)c(n1)N2)C1CCCNC1 ; "2 TFA"]

The desired compound was prepared according to the procedures of Examples A-27 and A-28 using 1-(tert-butoxycarbonyl)piperidine-3-carboxylic acid as the starting material in 53% yield. LCMS for $C_{24}H_{26}ClN_6O$ (M+H)$^+$: m/z=449.2.

Example A45

(3R)—N-[6-chloro-2,4,8,22-tetraazatetracyclo[14.3.1.1(3,7).1(9,13)]docosa-1(20),3(22),4,6,9(21),10,12,16,18-nonaen-12-yl]pyrrolidine-3-carboxamide bis(trifluoroacetate)

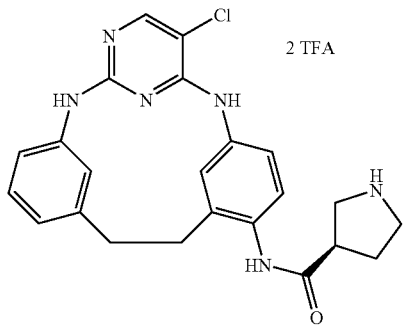 [SMILES: O=C(Nc1ccc2cc1CCc1cccc(c1)Nc1ncc(Cl)c(n1)N2)[C@@H]1CCNC1 ; "2 TFA"]

The desired compound was prepared according to the procedures of Examples A-27 and A-28 using (3R)-1-(tert-bu-toxycarbonyl)pyrrolidine-3-carboxylic acid as the starting material in 37% yield. LCMS for $C_{23}H_{24}ClN_6O$ (M+H)$^+$: m/z=435.2.

Example A46

N-[6-Chloro-2,4,8,22-tetraazatetracyclo[14.3.1.1(3,7).1(9,13)]docosa-1(20), 3(22),4,6,9(21),10,12,16,18-nonaen-12-yl]-2-piperidin-4-ylacetamide bis(trifluoroacetate)

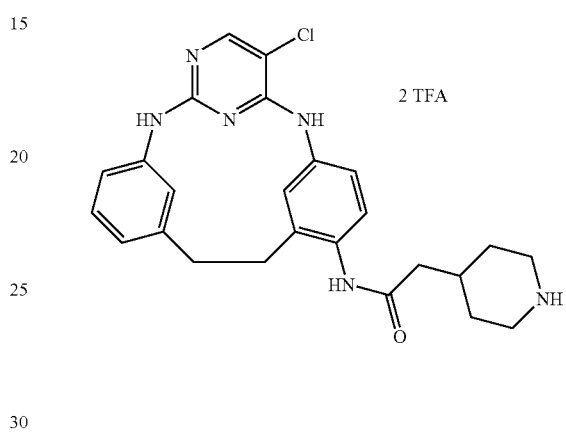

The desired compound was prepared according to the procedures of Examples A-27 and A-28 using [1-(tert-butoxycarbonyl)piperidin-4-yl]acetic acid as the starting material in 53% yield. LCMS for $C_{25}H_{28}ClN_6O$ (M+H)$^+$: m/z=463.2.

Example A47

1-Acetyl-N-[6-chloro-2,4,8,22-tetraazatetracyclo[14.3.1.1(3,7).1(9,13)]docosa-1(20),3(22),4,6,9(21),10,12,16,18-nonaen-12-yl]piperidine-3-carboxamide trifluoroacetate

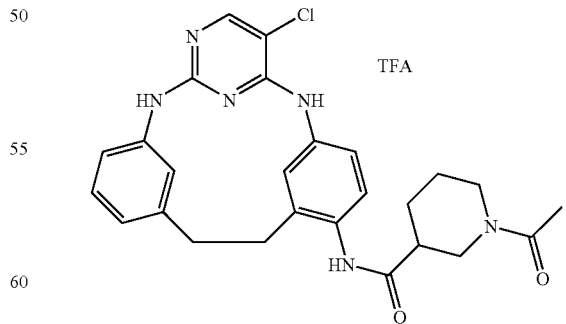

The desired compound was prepared according to the procedure of Example A20, using N-[6-chloro-2,4,8,22-tetraazatetracyclo[14.3.1.1(3,7).1(9,13)]docosa-1(20), 3(22),4,6,9(21),10,12,16,18-nonaen-12-yl]piperidine-3- carboxamide bis(trifluoroacetate) and acetyl chloride as starting materials in 34% yield. LCMS for $C_{26}H_{28}ClN_6O_2$ $(M+H)^+$: m/z=491.2.

Example A48

1-Benzoyl-N-[6-chloro-2,4,8,22-tetraazatetracyclo[14.3.1.1(3,7).1(9,13)]docosa-1(20),3(22),4,6,9(21),10,12,16,18-nonaen-12-yl]piperidine-3-carboxamide trifluoroacetate

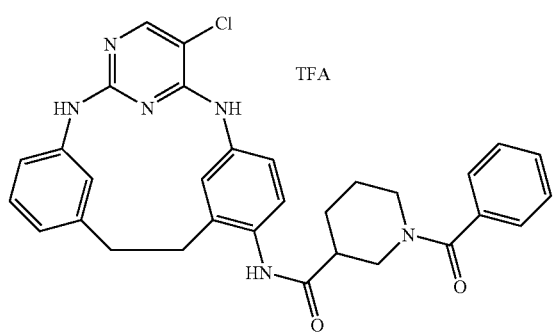 [SMILES: "TFA" ; O=C(Nc1ccc2cc1CCc1cccc(c1)Nc1ncc(Cl)c(n1)N2)C1CCCN(C(=O)c2ccccc2)C1]

The desired compound was prepared according to the procedure of Example A20, using N-[6-chloro-2,4,8,22-tetraazatetracyclo[14.3.1.1(3,7).1(9,13)]docosa-1(20),3(22),4,6,9(21),10,12,16,18-nonaen-12-yl]piperidine-3-carboxamide bis(trifluoroacetate) and benzoyl chloride as starting materials in 36% yield. LCMS for $C_{31}H_{30}ClN_6O_2$ $(M+H)^+$: m/z=553.2.

Example A49

N(3)-[6-Chloro-2,4,8,22-tetraazatetracyclo[14.3.1.1(3,7).1(9,13)]docosa-1(20),3(22),4,6,9(21),10,12,16,18-nonaen-12-yl]-N(1)-ethylpiperidine-1,3-dicarboxamide trifluoroacetate

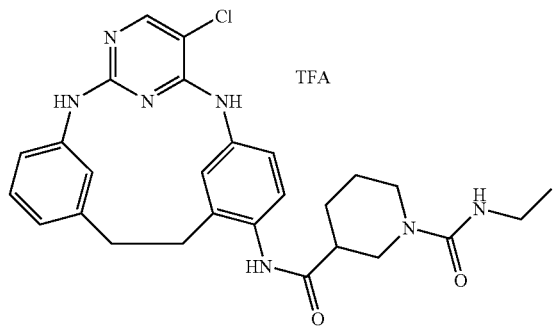 [SMILES: "TFA" ; CCNC(=O)N1CCCC(C(=O)Nc2ccc3cc2CCc2cccc(c2)Nc2ncc(Cl)c(n2)N3)C1]

The desired compound was prepared according to the procedure of Example A9, step H using N-[6-chloro-2,4,8,22-tetraazatetracyclo[14.3.1.1(3,7).1(9,13)]docosa-1(20),3(22),4,6,9(21),10,12,16,18-nonaen-12-yl]piperidine-3-carboxamide bis(trifluoroacetate) and isocyanato-ethane as starting materials in 36% yield. LCMS for $C_{27}H_{31}ClN_7O_2$ $(M+H)^+$: m/z=520.2.

Example A50

N(3)-[6-Chloro-2,4,8,22-tetraazatetracyclo[14.3.1.1(3,7).1(9,13)]docosa-1(20),3(22),4,6,9(21),10,12,16,18-nonaen-12-yl]-N(1)-phenylpiperidine-1,3-dicarboxamide trifluoroacetate

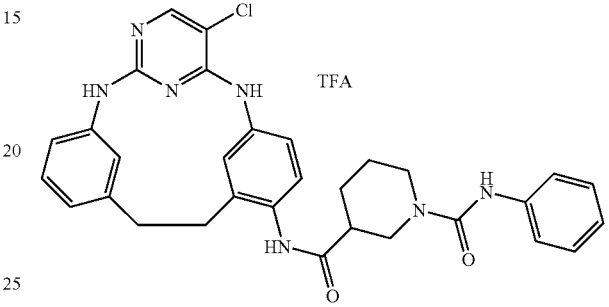

The desired compound was prepared according to the procedure of Example A9, step H using N-[6-chloro-2,4,8,22-tetraazatetracyclo[14.3.1.1(3,7).1(9,13)]docosa-1(20),3(22),4,6,9(21),10,12,16,18-nonaen-12-yl]piperidine-3-carboxamide bis(trifluoroacetate) and phenyl isocyanate as starting materials in 42% yield. $^1$H NMR (300 MHz, DMSO-$d_6$): δ 9.43 (s, 1H), 9.40 (s, 1H), 9.38 (s, 1H), 8.59 (s, 1H), 8.14 (s, 1H), 8.00 (s, 1H), 7.72 (s, 1H), 7.44 (d, 2H), 7.21 (m, 3H), 7.04 (m, 2H), 6.90 (m, 2H), 4.22 (d, 1H), 4.10 (d, 1H), 2.90 (m, 6H), 2.63 (m, 1H), 2.03 (m, 1H), 1.72 (m, 2H), 1.47 (m, 1H). LCMS for $C_{31}H_{31}ClN_7O_2$ $(M+H)^+$: m/z=568.2.

Example A51

(3R)-1-Acetyl-N-[6-chloro-2,4,8,22-tetraazatetracyclo[14.3.1.1(3,7).1(9,13)]docosa-1(20),3(22),4,6,9(21),10,12,16,18-nonaen-12-yl]pyrrolidine-3-carboxamide trifluoroacetate

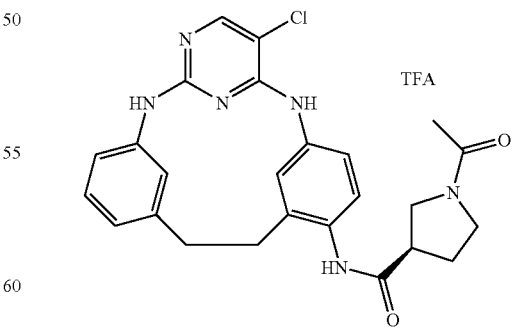

The desired compound was prepared according to the procedure of Example A20, using (3R)—N-[6-chloro-2,4,8,22-tetraazatetracyclo[14.3.1.1(3,7).1(9,13)]docosa-1(20),3(22),4,6,9(21),10,12,16,18-nonaen-12-yl]pyrrolidine-3- carboxamide bis(trifluoroacetate) and acetyl chloride as starting materials in 43% yield. LCMS for $C_{25}H_{26}ClN_6O_2$ (M+H)$^+$: m/z=477.2.

Example A52

(3R)-1-Benzoyl-N-[6-chloro-2,4,8,22-tetraazatetracyclo[14.3.1.1(3,7).1(9,13)]docosa-1(20),3(22),4,6,9(21),10,12,16,18-nonaen-12-yl]pyrrolidine-3-carboxamide trifluoroacetate

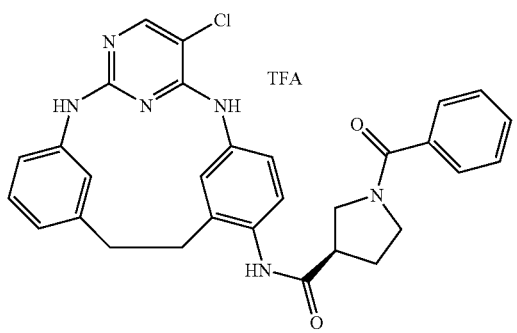 [SMILES: "TFA" ; O=C(Nc1ccc2cc1CCc1cccc(c1)Nc1ncc(Cl)c(n1)N2)[C@@H]1CCN(C(=O)c2ccccc2)C1]

The desired compound was prepared according to the procedure of Example A20, using (3R)—N-[6-chloro-2,4,8,22-tetraazatetracyclo[14.3.1.1(3,7).1(9,13)]docosa-1(20),3(22),4,6,9(21),10,12,16,18-nonaen-12-yl]pyrrolidine-3-carboxamide bis(trifluoroacetate) and benzoyl chloride as starting materials in 40% yield. LCMS for $C_{30}H_{28}ClN_6O_2$ (M+H)$^+$: m/z=539.2.

Example A53

(3R)—N(3)-[6-Chloro-2,4,8,22-tetraazatetracyclo[14.3.1.1(3,7).1(9,13)]docosa-1(20),3(22),4,6,9(21),10,12,16,18-nonaen-12-yl]-N(1)-ethylpyrrolidine-1,3-dicarboxamide trifluoroacetate

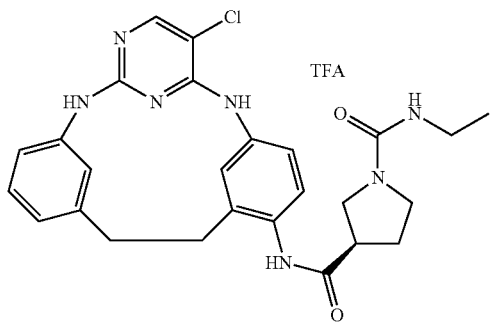 [SMILES: CCNC(=O)N1CC[C@@H](C(=O)Nc2ccc3cc2CCc2cccc(c2)Nc2ncc(Cl)c(n2)N3)C1]

The desired compound was prepared according to the procedure of Example A9, step H using (3R)—N-[6-chloro-2,4,8,22-tetraazatetracyclo[14.3.1.1(3,7).1(9,13)]docosa-1(20),3(22),4,6,9(21),10,12,16,18-nonaen-12-yl]pyrrolidine-3- carboxamide bis(trifluoroacetate) and isocyanato-ethane as starting materials in 40% yield. LCMS for $C_{26}H_{29}ClN_7O_2$ (M+H)$^+$: m/z=506.2.

Example A54

(3R)—N(3)-[6-Chloro-2,4,8,22-tetraazatetracyclo[14.3.1.1(3,7).1(9,13)]docosa-1(20),3(22),4,6,9(21),10,12,16,18-nonaen-12-yl]-N(1)-phenylpyrrolidine-1,3-dicarboxamide trifluoroacetate

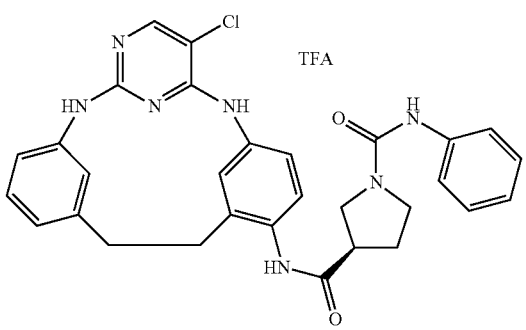 [SMILES: O=C(Nc1ccc2cc1CCc1cccc(c1)Nc1ncc(Cl)c(n1)N2)[C@@H]1CCN(C(=O)Nc2ccccc2)C1]

The desired compound was prepared according to the procedure of Example A9, step H using (3R)—N-[6-chloro-2,4,8,22-tetraazatetracyclo[14.3.1.1(3,7).1(9,13)]docosa-1(20),3(22),4,6,9(21),10,12,16,18-nonaen-12-yl]pyrrolidine-3-carboxamide bis(trifluoroacetate) and phenyl isocyanate as starting materials in 46% yield. $^1$H NMR (300 MHz, DMSO-d$_6$): δ 9.53 (s, 1H), 9.42 (s, 1H), 9.34 (s, 1H), 8.21 (s, 1H), 8.14 (s, 1H), 8.00 (s, 1H), 7.78 (s, 1H), 7.50 (d, 2H), 7.20 (m, 3H), 7.08 (m, 2H), 6.90 (m, 2H), 6.78 (d, 1H), 3.70 (m, 1H), 3.60 (m, 2H), 3.40 (m, 1H), 3.27 (m, 1H), 2.87 (m, 4H), 2.19 (m, 2H). LCMS for $C_{30}H_{29}ClN_7O_2$ (M+H)$^+$: m/z=554.2.

Example A55

2-(1-Acetylpiperidin-4-yl)-N-[6-chloro-2,4,8,22-tetraazatetracyclo[14.3.1.1(3,7).1(9,13)]docosa-1(20),3(22),4,6,9(21),10,12,16,18-nonaen-12-yl]acetamide trifluoroacetate

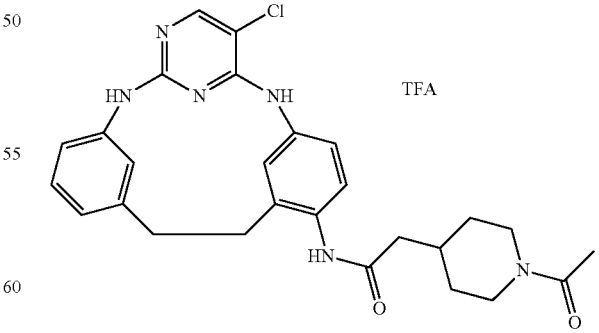

The desired compound was prepared according to the procedure of Example A20, using N-[6-chloro-2,4,8,22-tetraazatetracyclo[14.3.1.1(3,7).1(9,13)]docosa-1(20), 3(22),4,6,9(21),10,12,16,18-nonaen-12-yl]-2-piperidin-4- ylacetamide bis(trifluoroacetate) and acetyl chloride as starting materials in 58% yield. LCMS for $C_{27}H_{30}ClN_6O_2$ (M+H)+: m/z=505.2.

Example A56

2-(1-Benzoylpiperidin-4-yl)-N-[6-chloro-2,4,8,22-tetraazatetracyclo[14.3.1.1(3,7).1(9,13)]docosa-1(20),3(22),4,6,9(21),10,12,16,18-nonaen-12-yl]acetamide trifluoroacetate

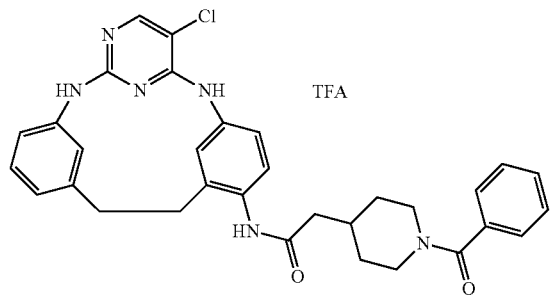 [SMILES: O=C(CC1CCN(C(=O)c2ccccc2)CC1)Nc1ccc2cc1CCc1cccc(c1)Nc1ncc(Cl)c(n1)N2]

The desired compound was prepared according to the procedure of Example A20, using N-[6-chloro-2,4,8,22-tetraazatetracyclo[14.3.1.1(3,7).1(9,13)]docosa-1(20), 3(22),4,6,9(21),10,12,16,18-nonaen-12-yl]-2-piperidin-4-ylacetamide bis(trifluoroacetate) and benzoyl chloride as starting materials in 58% yield. LCMS for $C_{32}H_{32}ClN_6O_2$ (M+H)+: m/z=567.2.

Example A57

4-(2-{[6-Chloro-2,4,8,22-tetraazatetracyclo[14.3.1.1(3,7).1(9,13)]docosa-1(20),3(22),4,6,9(21),10,12,16,18-nonaen-12-yl]amino}-2-oxoethyl)-N-ethylpiperidine-1-carboxamide trifluoroacetate

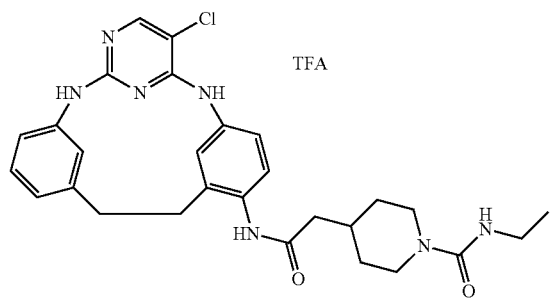 [SMILES: CCNC(=O)N1CCC(CC(=O)Nc2ccc3cc2CCc2cccc(c2)Nc2ncc(Cl)c(n2)N3)CC1]

The desired compound was prepared according to the procedure of Example A9, step H using N-[6-chloro-2,4,8,22-tetraazatetracyclo[14.3.1.1(3,7).1(9,13)]docosa-1(20), 3(22),4,6,9(21),10,12,16,18-nonaen-12-yl]-2-piperidin-4-ylacetamide bis(trifluoroacetate) and isocyanato-ethane as starting materials in 77% yield. 1H NMR (300 MHz, DMSO-d6): δ 9.65 (s, 1H), 9.60 (s, 1H), 9.30 (s, 1H), 8.20 (s, 1H), 7.92 (s, 1H), 7.73 (s, 1H), 7.24 (d, 1H), 7.12 (m, 1H), 7.04 (d, 1H), 6.87 (d, 1H), 6.80 (d, 1H), 6.40 (s, 1H), 3.92 (d, 2H), 3.01 (m, 2H), 2.90 (m, 4H), 2.62 (m, 2H), 2.28 (d, 2H), 1.92 (m, 1H), 1.61 (m, 2H), 1.12 (m, 2H), 1.00 (t, 3H). LCMS for $C_{28}H_{33}ClN_7O_2$ (M+H)+: m/z=534.2.

Example A58

4-(2-{[6-Chloro-2,4,8,22-tetraazatetracyclo[14.3.1.1(3,7).1(9,13)]docosa-1(20),3(22),4,6,9(21),10,12,16,18-nonaen-12-yl]amino}-2-oxoethyl)-N-phenylpiperidine-1-carboxamide trifluoroacetate

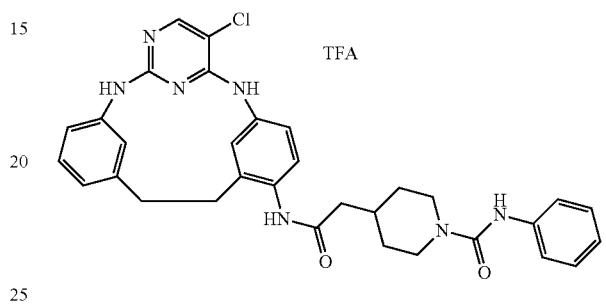

The desired compound was prepared according to the procedure of Example A9, step H using N-[6-chloro-2,4,8,22-tetraazatetracyclo[14.3.1.1(3,7).1(9,13)]docosa-1(20), 3(22),4,6,9(21),10,12,16,18-nonaen-12-yl]-2-piperidin-4-ylacetamide bis(trifluoroacetate) and phenyl isocyanate as starting materials in 53% yield. 1H NMR (300 MHz, DMSO-d6): δ 9.49 (s, 1H), 9.38 (s, 1H), 9.35 (s, 1H), 8.47 (s, 1H), 8.12 (s, 1H), 7.99 (s, 1H), 7.72 (s, 1H), 7.43 (d, 2H), 7.20 (m, 3H), 7.04 (m, 2H), 6.90 (m, 2H), 6.78 (d, 1H), 4.15 (d, 2H), 2.82 (m, 6H), 2.30 (d, 2H), 2.00 (m, 1H), 1.72 (m, 2H), 1.20 (m, 2H). LCMS for $C_{32}H_{33}ClN_7O_2$ (M+H)+: m/z=582.2.

Example A59

N(4)-[6-Chloro-2,4,8,22-tetraazatetracyclo[14.3.1.1(3,7).1(9,13)]docosa-1(20),3(22),4,6,9(21),10,12,16,18-nonaen-12-yl]-N(1)-ethylpiperidine-1,4-dicarboxamide trifluoroacetate

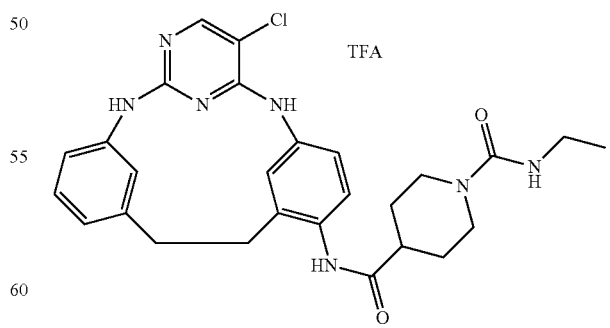

The desired compound was prepared according to the procedure of Example A9, step H using N-[6-chloro-2,4,8,22-tetraazatetracyclo[14.3.1.1(3,7).1(9,13)]docosa-1(20),3(22),4,6,9(21),10,12,16,18-nonaen-12-yl]piperidine-4- carboxamide bis(trifluoroacetate) and isocyanato-ethane as starting materials in 25% yield. LCMS for $C_{27}H_{31}ClN_7O_2$ (M+H)$^+$: m/z=520.2.

Example A60

Ethyl ({[4-({[6-chloro-2,4,8,22-tetraazatetracyclo[14.3.1.1(3,7).1(9,13)]docosa-1(20),3(22),4,6,9(21),10,12,16,18-nonaen-12-yl]amino}carbonyl)piperidin-1-yl]carbonyl}amino)acetate trifluoroacetate

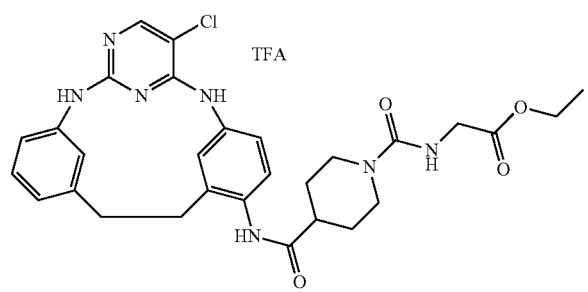 [SMILES: CCOC(=O)CNC(=O)N1CCC(C(=O)Nc2ccc3cc2CCc2cccc(c2)Nc2ncc(Cl)c(n2)N3)CC1]

The desired compound was prepared according to the procedure of Example A9, step H using N-[6-chloro-2,4,8,22-tetraazatetracyclo[14.3.1.1(3,7).1(9,13)]docosa-1(20),3(22),4,6,9(21),10,12,16,18-nonaen-12-yl]piperidine-4-carboxamide bis(trifluoroacetate) and ethyl isocyanatoacetate as starting materials in 35% yield. LCMS for $C_{29}H_{33}ClN_7O_4$ (M+H)$^+$: m/z=578.2.

Example A61

N(4)-[6-Chloro-2,4,8,22-tetraazatetracyclo[14.3.1.1(3,7).1(9,13)]docosa-1(20),3(22),4,6,9(21),10,12,16,18-nonaen-12-yl]-N(1)-cyclopentylpiperidine-1,4-dicarboxamide trifluoroacetate

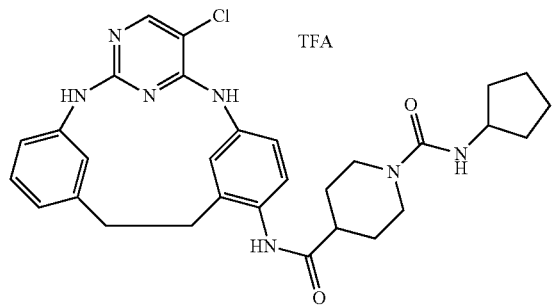 [SMILES: O=C(Nc1ccc2cc1CCc1cccc(c1)Nc1ncc(Cl)c(n1)N2)C1CCN(C(=O)NC2CCCC2)CC1]

The desired compound was prepared according to the procedure of Example A9, step H using N-[6-chloro-2,4,8,22-tetraazatetracyclo[14.3.1.1(3,7).1(9,13)]docosa-1(20),3(22),4,6,9(21),10,12,16,18-nonaen-12-yl]piperidine-4-carboxamide bis(trifluoroacetate) and isocyanatocyclopentane as starting materials in 31% yield. LCMS for $C_{30}H_{35}ClN_7O_2$ (M+H)$^+$: m/z=560.2.

Example A62

N(3)-[6-Chloro-2,4,8,22-tetraazatetracyclo[14.3.1.1(3,7).1(9,13)]docosa-1(20),3(22),4,6,9(21),10,12,16,18-nonaen-12-yl]-N(1)-cyclopentylpiperidine-1,3-dicarboxamide trifluoroacetate

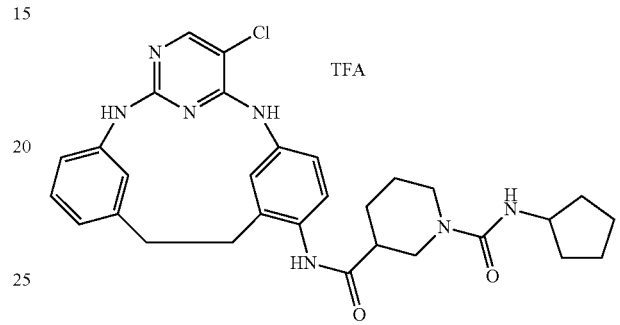

The desired compound was prepared according to the procedure of Example A9, step H using N-[6-chloro-2,4,8,22-tetraazatetracyclo[14.3.1.1(3,7).1(9,13)]docosa-1(20),3(22),4,6,9(21),10,12,16,18-nonaen-12-yl]piperidine-3-carboxamide bis(trifluoroacetate) and isocyanatocyclopentane as starting materials in 58% yield. LCMS for $C_{30}H_{35}ClN_7O_2$ (M+H)$^+$: m/z=560.2.

Example A63

(3R)—N(3)-[6-Chloro-2,4,8,22-tetraazatetracyclo[14.3.1.1(3,7).1(9,13)]docosa-1(20),3(22),4,6,9(21),10,12,16,18-nonaen-12-yl]-N(1)-cyclopentylpyrrolidine-1,3-dicarboxamide trifluoroacetate

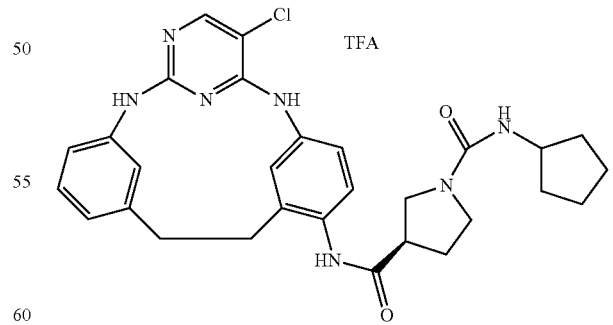

The desired compound was prepared according to the procedure of Example A9, step H using (3R)—N-[6-chloro-2,4,8,22-tetraazatetracyclo[14.3.1.1(3,7).1(9,13)]docosa-1(20),3(22),4,6,9(21),10,12,16,18-nonaen-12-yl]pyrrolidine-3-carboxamide bis(trifluoroacetate) and

Example A64

4-(2-{[6-Chloro-2,4,8,22-tetraazatetracyclo[14.3.1.1(3,7).1(9,13)]docosa-1(20),3(22),4,6,9(21),10,12,16,18-nonaen-12-yl]amino}-2-oxoethyl)-N-cyclopentylpiperidine-1-carboxamide trifluoroacetate

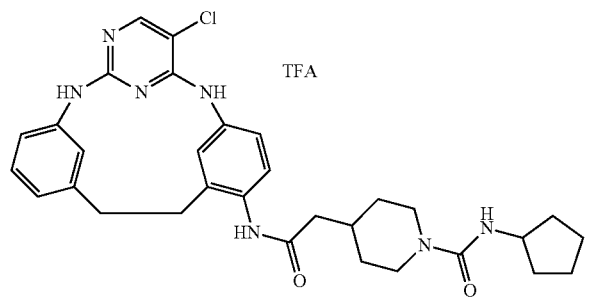 [SMILES: O=C(CC1CCN(C(=O)NC2CCCC2)CC1)Nc1ccc2cc1CCc1cccc(c1)Nc1ncc(Cl)c(n1)N2]

The desired compound was prepared according to the procedure of Example A9, step H using N-[6-chloro-2,4,8,22-tetraazatetracyclo[14.3.1.1(3,7).1(9,13)]docosa-1(20),3(22),4,6,9(21),10,12,16,18-nonaen-12-yl]-2-piperidin-4-ylacetamide bis(trifluoroacetate) and isocyanatocyclopentane as starting materials in 68% yield. LCMS for $C_{31}H_{37}ClN_7O_2$ (M+H)$^+$: m/z=574.2.

Example A65

N-[6-Chloro-2,4,8,22-tetraazatetracyclo[14.3.1.1(3,7).1(9,13)]docosa-1(20), 3(22),4,6,9(21),10,12,16,18-nonaen-12-yl]-2-cyanoacetamide trifluoroacetate

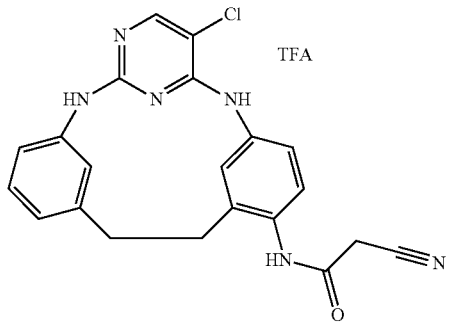 [SMILES: N#CCC(=O)Nc1ccc2cc1CCc1cccc(c1)Nc1ncc(Cl)c(n1)N2]

The desired compound was prepared according to the procedure of Example A27 using cyanoacetic acid as the starting material in 26% yield. $^1$H NMR (300 MHz, DMSO-d$_6$): δ 9.70 (s, 1H), 9.50 (m, 1H), 9.48 (s, 1H), 8.17 (s, 1H), 7.92 (s, 1H), 7.78 (s, 1H), 7.25 (d, 1H), 7.04 (m, 2H), 6.87 (d, 1H), 6.81 (d, 1H), 3.92 (s, 2H), 2.88 (m, 4H). LCMS for $C_{21}H_{18}ClN_6O$ (M+H)$^+$: m/z=405.1.

Example A66

2-[(Anilinocarbonyl)amino]-N-[6-chloro-2,4,8,22-tetraazatetracyclo[14.3.1.1(3,7).1(9,13)]docosa-1(20),3(22),4,6,9(21),10,12,16,18-nonaen-12-yl]acetamide trifluoroacetate

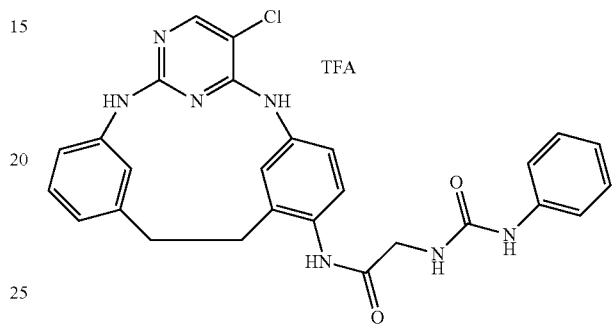

The desired compound was prepared according to the procedure of Example A9, step H using 2-amino-N-[6-chloro-2,4,8,22-tetraazatetracyclo[14.3.1.1(3,7).1(9,13)]docosa-1(20),3(22),4,6,9(21),10,12,16,18-nonaen-12-yl]acetamide bis(trifluoroacetate) and phenyl isocyanate as starting materials in 38% yield. LCMS for $C_{27}H_{25}ClN_7O_2$ (M+H)$^+$: m/z=514.2.

Example A67

3-[(Anilinocarbonyl)amino]-N-[6-chloro-2,4,8,22-tetraazatetracyclo[14.3.1.1(3,7).1(9,13)]docosa-1(20),3(22),4,6,9(21),10,12,16,18-nonaen-12-yl]propanamide trifluoroacetate

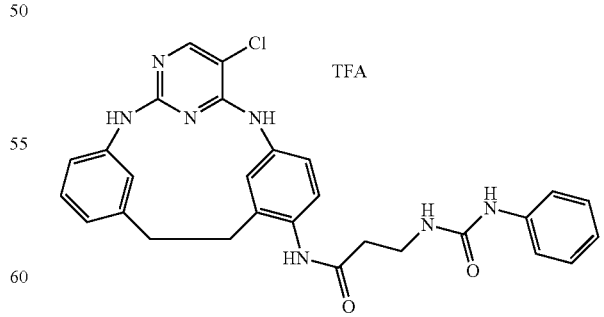

The desired compound was prepared according to the procedure of Example A9, step H using 3-amino-N-[6-chloro-2,4,8,22-tetraazatetracyclo[14.3.1.1(3,7).1(9,13)]docosa-1(20),3(22),4,6,9(21),10,12,16,18-nonaen-12-yl]

propanamide bis(trifluoroacetate) and phenyl isocyanate as starting materials in 35% yield. LCMS for $C_{28}H_{27}ClN_7O_2$ (M+H)$^+$: m/z=528.2.

Example A68

(2S)-2-[(Anilinocarbonyl)amino]-N-[6-chloro-2,4,8,22-tetraazatetracyclo[14.3.1.1(3,7).1(9,13)]docosa-1(20),3(22),4,6,9(21),10,12,16,18-nonaen-12-yl]-3-hydroxypropanamide trifluoroacetate

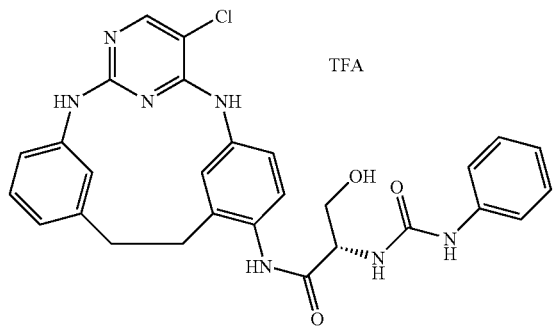 [SMILES: O=C(Nc1ccccc1)N[C@@H](CO)C(=O)Nc1ccc2cc1CCc1cccc(c1)Nc1ncc(Cl)c(n1)N2]

The desired compound was prepared according to the procedure of Example A9, step H using (2S)-2-amino-N-[6-chloro-2,4,8,22-tetraazatetracyclo[14.3.1.1(3,7).1(9,13)]docosa-1(20),3(22),4,6,9(21),10,12,16,18-nonaen-12-yl]-3-hydroxypropanamide bis(trifluoroacetate) and phenyl isocyanate as starting materials in 36% yield. LCMS for $C_{28}H_{27}ClN_7O_3$ (M+H)$^+$: m/z=544.2.

Example A69

(2S)—N(2)-[6-Chloro-2,4,8,22-tetraazatetracyclo[14.3.1.1(3,7).1(9,13)]docosa-1(20),3(22),4,6,9(21),10,12,16,18-nonaen-12-yl]-N(1)-phenylpyrrolidine-1,2-dicarboxamide trifluoroacetate

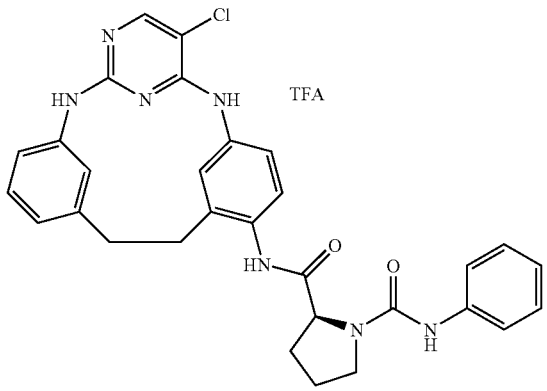 [SMILES: O=C(Nc1ccc2cc1CCc1cccc(c1)Nc1ncc(Cl)c(n1)N2)[C@@H]1CCCN1C(=O)Nc1ccccc1]

The desired compound was prepared according to the procedure of Example A9, step H using (2S)—N-[6-chloro-2,4,8,22-tetraazatetracyclo[14.3.1.1(3,7).1(9,13)]docosa-1(20),3(22),4,6,9(21),10,12,16,18-nonaen-12-yl]pyrrolidine-2-carboxamide bis(trifluoroacetate) and phenyl isocyanate as starting materials in 44% yield. $^1$H NMR (300 MHz, DMSO-d$_6$): δ 9.43 (s, 2H), 9.36 (s, 1H), 8.30 (s, 1H), 8.11 (s, 1H), 7.98 (s, 1H), 7.72 (s, 1H), 7.58 (d, 2H), 7.25 (m, 3H), 7.04 (m, 2H), 6.95 (m, 1H), 6.85 (d, 1H), 4.53 (m, 1H), 3.68 (m, 1H), 3.50 (m, 1H), 2.85 (m, 4H), 2.20 (m, 1H), 2.01 (m, 3H). LCMS for $C_{30}H_{29}ClN_7O_2$ (M+H)$^+$: m/z=554.2.

Example A70 tert-Butyl 4-(2-{[6-chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)piperidine-1-carboxylate bis(trifluoroacetate)

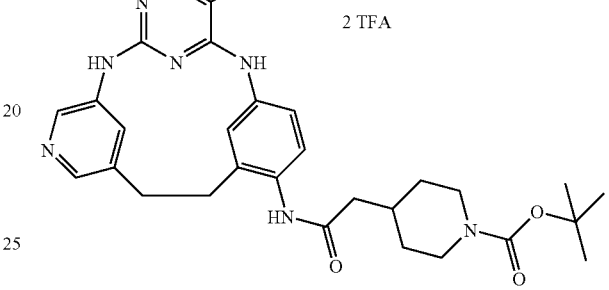

The desired compound was prepared according to the procedure of Example A27 using 6-chloro-2,4,8,18,22-pentaazatetracyclo[14.3.1.1(3,7).1(9,13)]docosa-1(20),3(22),4,6,9(21),10,12,16,18-nonaen-12-amine tris(trifluoroacetate) and [1-(tert-butoxycarbonyl)piperidin-4-yl]acetic acid as the starting materials in 59% yield. LCMS for $C_{29}H_{35}ClN_7O_3$ (M+H)$^+$: m/z=564.2.

Example A71

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate)

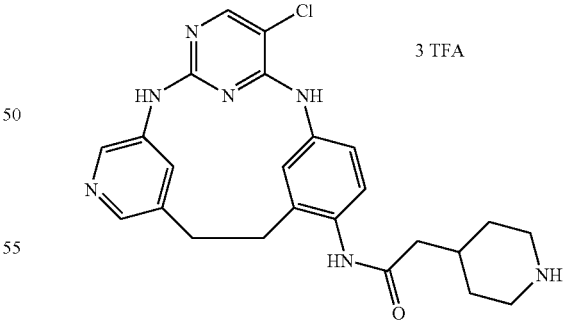

The desired compound was prepared according to the procedure of Example A28 using tert-butyl 4-(2-{[6-chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)piperidine-1-carboxylate as the starting material in 100% yield. $^1$H NMR (300 MHz, DMSO-d$_6$): δ 9.40 (s, 1H), 9.36 (s, 1H), 9.25 (s, 1H), 8.10 (s, 1H), 8.00 (s, 1H), 7.72 (s, 1H), 7.22 (d, 1H), 7.03 (m, 2H), 6.87 (m, 1H), 6.72 (d, 1H), 6.69 (s, 2H), 3.42 (d, 2H), 2.85 (m, 4H), 2.50 (m, 3H), 2.30 (m, 2H), 1.80 (d, 2H), 1.25 (m, 2H). LCMS for $C_{24}H_{27}ClN_7O$ $(M+H)^+$: m/z=464.2.

Example A72

1-(Aminosulfonyl)-N-[6-chloro-2,4,8,22-tetraazatetracyclo[14.3.1.1(3,7).1(9,13)]docosa-1(20),3(22),4,6,9(21),10,12,16,18-nonaen-12-yl]piperidine-4-carboxamide trifluoroacetate

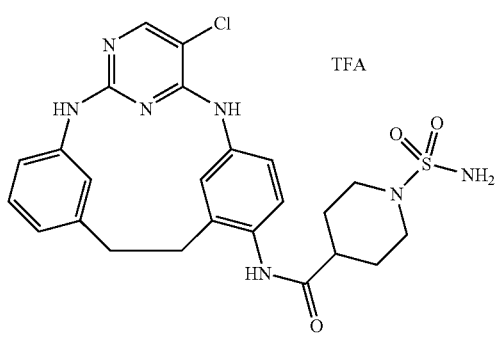 [SMILES: "TFA" ; NS(=O)(=O)N1CCC(C(=O)Nc2ccc3cc2CCc2cccc(c2)Nc2ncc(Cl)c(n2)N3)CC1]

To a solution of N-[6-chloro-2,4,8,22-tetraazatetracyclo[14.3.1.1(3,7).1(9,13)]docosa-1(20), 3(22),4,6,9(21),10,12,16,18-nonaen-12-yl]piperidine-4-carboxamide bis(trifluoroacetate) (10.0 mg, 0.018 mmol) in 1,4-dioxane (1.0 mL) was added sulfamide (17.1 mg, 0.18 mmol) and the mixture was heated to 130° C. in a microwave for 10 minutes. Purification by preparative LCMS (pH 2) gave the desired compound (0.8 mg, 7% yield). LCMS for $C_{24}H_{27}ClN_7O_3S$ $(M+H)^+$: m/z=528.2.

Example A73

1-(Aminosulfonyl)-N-[6-chloro-2,4,8,22-tetraazatetracyclo[14.3.1.1(3,7).1(9,13)]docosa-1(20),3(22),4,6,9(21),10,12,16,18-nonaen-12-yl]piperidine-3-carboxamide trifluoroacetate

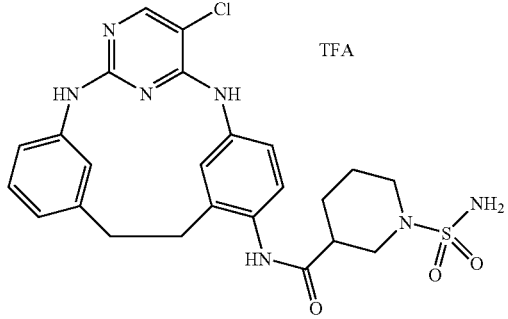 [SMILES: "TFA" ; NS(=O)(=O)N1CCCC(C(=O)Nc2ccc3cc2CCc2cccc(c2)Nc2ncc(Cl)c(n2)N3)C1]

The desired compound was prepared according to the procedure of Example A72 using N-[6-chloro-2,4,8,22-tetraazatetracyclo[14.3.1.1(3,7).1(9,13)]docosa-1(20),3(22),4,6,9(21),10,12,16,18-nonaen-12-yl]piperidine-3-carboxamide bis(trifluoroacetate) as the starting material in 33% yield. LCMS for $C_{24}H_{27}ClN_7O_3S$ $(M+H)^+$: m/z=528.2.

Example A74

(3R)-1-(Aminosulfonyl)-N-[6-chloro-2,4,8,22-tetraazatetracyclo[14.3.1.1(3,7).1(9,13)]docosa-1(20),3(22),4,6,9(21),10,12,16,18-nonaen-12-yl]pyrrolidine-3-carboxamide trifluoroacetate

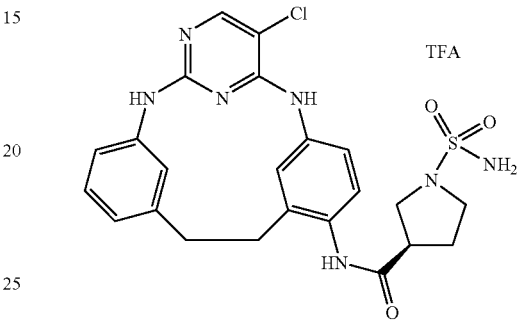

The desired compound was prepared according to the procedure of Example A72 using (3R)—N-[6-chloro-2,4,8,22-tetraazatetracyclo[14.3.1.1(3,7).1(9,13)]docosa-1(20),3(22),4,6,9(21),10,12,16,18-nonaen-12-yl]pyrrolidine-3-carboxamide bis(trifluoroacetate) as the starting material in 30% yield. LCMS for $C_{23}H_{25}ClN_7O_3S$ $(M+H)^+$: m/z=514.2.

Example A75

2-[1-(Aminosulfonyl)piperidin-4-yl]-N-[6-chloro-2,4,8,22-tetraazatetracyclo[14.3.1.1(3,7).1(9,13)]docosa-1(20),3(22),4,6,9(21),10,12,16,18-nonaen-12-yl]acetamide trifluoroacetate

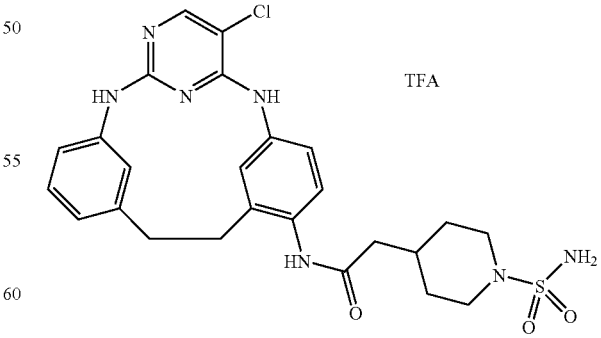

The desired compound was prepared according to the procedure of Example A72 using N-[6-chloro-2,4,8,22-tetraazatetracyclo[14.3.1.1(3,7).1(9,13)]docosa-1(20), 3(22),4,6,9(21),10,12,16,18-nonaen-12-yl]-2-piperidin-4-ylacetamide bis(trifluoroacetate) as the starting material in 39% yield. LCMS for $C_{25}H_{29}ClN_7O_3S$ (M+H)⁺: m/z=542.2.

Example A76

2-(1-Acetylpiperidin-4-yl)-N-[6-chloro-2,4,8,18,22-pentaazatetracyclo[14.3.1.1(3,7).1(9,13)]docosa-1(20),3(22),4,6,9(21),10,12,16,18-nonaen-12-yl]acetamide bis(trifluoroacetate)

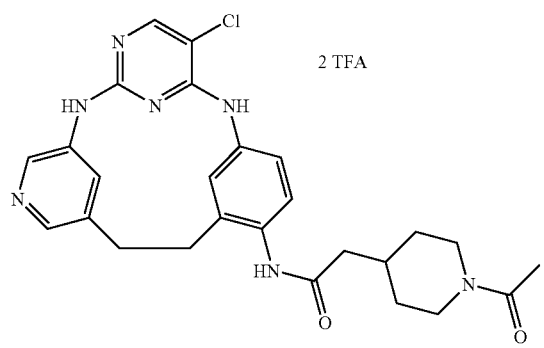 [SMILES: CC(=O)N1CCC(CC(=O)Nc2ccc3cc2CCc2cncc(c2)Nc2ncc(Cl)c(n2)N3)CC1 ; "2 TFA"]

The desired compound was prepared according to the procedure of Example A20, using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and acetyl chloride as starting materials in 43% yield. ¹H NMR (300 MHz, DMSO-$d_6$): δ 10.02 (s, 2H), 9.40 (s, 1H), 9.01 (s, 1H), 8.31 (s, 2H), 8.20 (s, 1H), 7.65 (s, 1H), 7.31 (d, 1H), 7.08 (d, 1H), 4.38 (d, 1H), 3.81 (d, 1H), 3.00 (m, 6H), 2.52 (m, 1H), 2.32 (m, 2H), 2.00 (s, 3H), 1.75 (m, 2H), 1.20 (m, 2H). LCMS for $C_{26}H_{29}ClN_7O_2$ (M+H)⁺: m/z=506.2.

Example A77

4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-phenylpiperidine-1-carboxamide bis(trifluoroacetate)

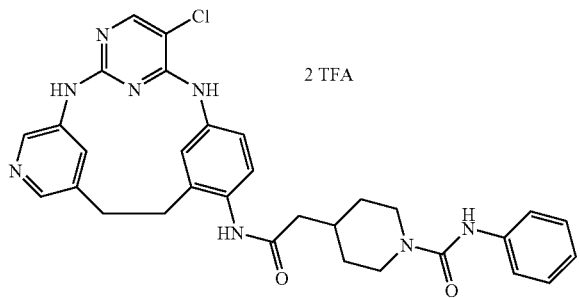 [SMILES: O=C(CC1CCN(C(=O)Nc2ccccc2)CC1)Nc1ccc2cc1CCc1cncc(c1)Nc1ncc(Cl)c(n1)N2 ; "2 TFA"]

The desired compound was prepared according to the procedure of Example A9, step H using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and phenyl isocyanate as starting materials in 51% yield. LCMS for $C_{31}H_{32}ClN_8O_2$ (M+H)⁺: m/z=583.2.

Example A78

2-[1-(Aminosulfonyl)piperidin-4-yl]-N-[6-chloro-2,4,8,18,22pentaazatetracyclo[14.3.1.1(3,7).1(9,13)]docosa-1(20),3(22),4,6,9(21),10,12,16,18-nonaen-12-yl]acetamide bis(trifluoroacetate)

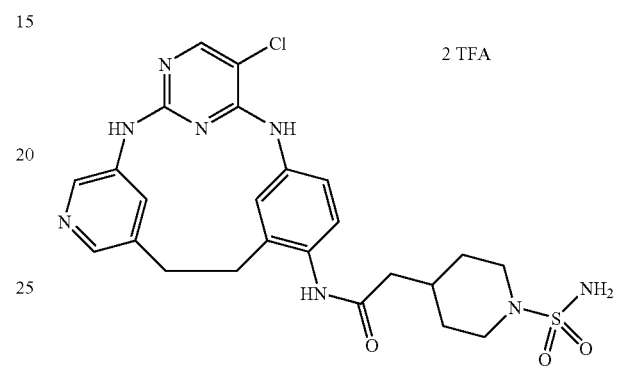

The desired compound was prepared according to the procedure of Example A72 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) as the starting material in 30% yield. LCMS for $C_{24}H_{28}ClN_8O_3S$ (M+H)⁺: m/z=543.2.

Example A79

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(methylsulfonyl)piperidin-4-yl]acetamide bis(trifluoroacetate)

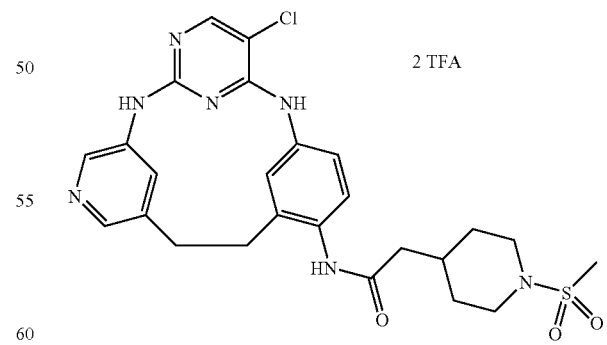

The desired compound was prepared according to the procedure of Example A42, using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and methanesulfonyl chloride as starting materials in 43% yield. LCMS for $C_{25}H_{29}ClN_7O_3S$ (M+H)+: m/z=542.2.

Example A80

4-(2-{[6-Chloro-2,4,8,22-tetraazatetracyclo[14.3.1.1 (3,7).1(9,13)]docosa-1(20),3(22),4,6,9(21),10,12,16, 18-nonaen-12-yl]amino}-2-oxoethyl)-N,N-dimethylpiperidine-1-carboxamide trifluoroacetate

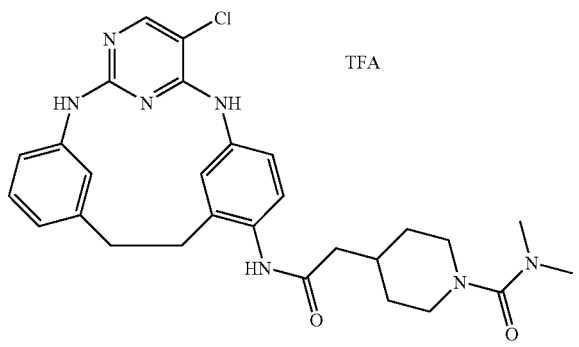 [SMILES: "TFA" ; CN(C)C(=O)N1CCC(CC(=O)Nc2ccc3cc2CCc2cccc(c2)Nc2ncc(Cl)c(n2)N3)CC1]

The desired compound was prepared according to the procedure of Example A9, step H using N-[6-chloro-2,4,8,22-tetraazatetracyclo[14.3.1.1(3,7).1(9,13)]docosa-1(20), 3(22),4,6,9(21),10,12,16,18-nonaen-12-yl]-2-piperidin-4-ylacetamide bis(trifluoroacetate) and N,N-dimethylcarbamoyl chloride as starting materials in 48% yield. $^1$H NMR (300 MHz, DMSO-d$_6$): δ 9.57 (s, 1H), 9.43 (s, 1H), 9.32 (s, 1H), 8.17 (s, 1H), 7.97 (s, 1H), 7.72 (s, 1H), 7.21 (d, 1H), 7.10 (m, 1H), 7.01 (d, 1H), 6.88 (d, 1H), 6.80 (d, 1H), 3.57 (d, 2H), 2.91 (m, 2H), 2.83 (m, 2H), 2.71 (m, 8H), 2.32 (d, 2H), 1.93 (m, 1H), 1.70 (m, 2H), 1.20 (m, 2H). LCMS for $C_{28}H_{33}ClN_7O_2$ (M+H)+: m/z=534.2.

Example A81

N-[6-Chloro-2,4,8,22-tetraazatetracyclo[14.3.1.1(3, 7).1(9,13)]docosa-1(20),3(22),4,6,9(21),10,12,16,18-nonaen-12-yl]-2-{1-[(dimethylamino)sulfonyl]piperidin-4-yl}acetamide trifluoroacetate

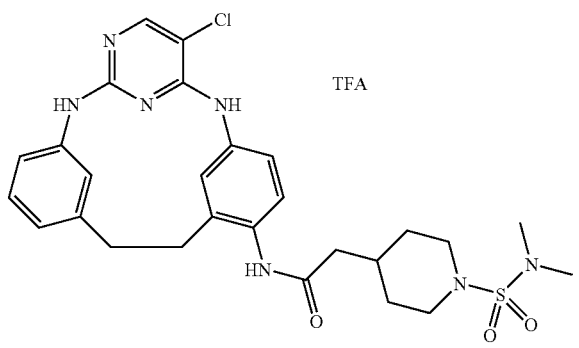 [SMILES: "TFA" ; CN(C)S(=O)(=O)N1CCC(CC(=O)Nc2ccc3cc2CCc2cccc(c2)Nc2ncc(Cl)c(n2)N3)CC1]

The desired compound was prepared according to the procedure of Example A42, using N-[6-chloro-2,4,8,22-tetraazatetracyclo[14.3.1.1(3,7).1(9,13)]docosa-1(20), 3(22),4, 6,9(21),10,12,16,18-nonaen-12-yl]-2-piperidin-4-ylacetamide bis(trifluoroacetate) and dimethylsulfamoyl chloride as starting materials in 38% yield. $^1$H NMR (300 MHz, DMSO-d$_6$): δ 9.42 (s, 1H), 9.36 (s, 1H), 9.29 (s, 1H), 8.12 (s, 1H), 8.00 (s, 1H), 7.76 (s, 1H), 7.21 (d, 1H), 7.05 (m, 2H), 6.89 (d, 1H), 6.79 (d, 1H), 3.58 (d, 2H), 2.88 (m, 6H), 2.76 (s, 6H), 2.30 (d, 2H), 1.91 (m, 1H), 1.76 (m, 2H), 1.21 (m, 2H). LCMS for $C_{27}H_{33}ClN_7O_3S$ (M+H)+: m/z=570.2.

Example A82

N-[6-Chloro-2,4,8,22-tetraazatetracyclo[14.3.1.1(3, 7).1(9,13)]docosa-1(20),3(22),4,6,9(21),10,12,16,18-nonaen-12-yl]-2-[1-(isopropylsulfonyl)piperidin-4-yl]acetamide trifluoroacetate

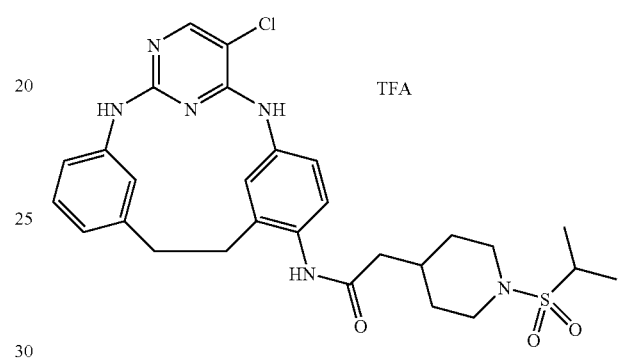

The desired compound was prepared according to the procedure of Example A42, using N-[6-chloro-2,4,8,22-tetraazatetracyclo[14.3.1.1(3,7).1(9,13)]docosa-1(20),3(22),4, 6,9(21),10,12,16,18-nonaen-12-yl]-2-piperidin-4-ylacetamide bis(trifluoroacetate) and propane-2-sulfonyl chloride as starting materials in 27% yield. LCMS for $C_{28}H_{34}ClN_6O_3S$ (M+H)+: m/z=569.2.

Example A83

N-[6-Chloro-2,4,8,22-tetraazatetracyclo[14.3.1.1(3, 7).1(9,13)]docosa-1(20),3(22),4,6,9(21),10,12,16,18-nonaen-12-yl]-2-[1-(ethylsulfonyl)piperidin-4-yl] acetamide trifluoroacetate


The desired compound was prepared according to the procedure of Example A42, using N-[6-chloro-2,4,8,22-tetraazatetracyclo[14.3.1.1(3,7).1(9,13)]docosa-1(20),3(22),4, 6,9(21),10,12,16,18-nonaen-12-yl]-2-piperidin-4-ylacetamide bis(trifluoroacetate) and ethanesulfonyl chloride as starting materials in 41% yield. $^1$H NMR (300 MHz, DMSO-d$_6$): δ 9.40 (s, 1H), 9.36 (s, 1H), 9.28 (s, 1H), 8.12 (s, 1H), 7.98 (s, 1H), 7.73 (s, 1H), 7.21 (d, 1H), 7.04 (m, 2H), 6.87 (d, 1H), 6.78 (d, 1H), 3.60 (m, 2H), 3.01 (m, 2H), 2.83 (m, 6H), 2.27 (m, 2H), 1.91 (m, 1H), 1.78 (m, 2H), 1.22 (m, 2H), 1.20 (m, 3H). LCMS for C$_{27}$H$_{32}$ClN$_6$O$_3$S (M+H)$^+$: m/z=555.2.

Example A84

4-(2-{[6-Chloro-2,4,8,22-tetraazatetracyclo[14.3.1.1 (3,7).1(9,13)]docosa-1(20),3(22),4,6,9(21),10,12,16, 18-nonaen-12-yl]amino}-2-oxoethyl)-N-isopropylpiperidine-1-carboxamide trifluoroacetate

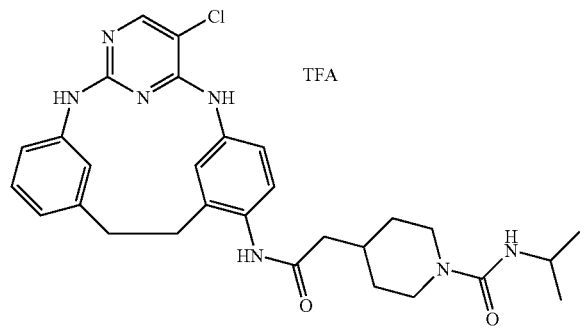 [SMILES: CC(C)NC(=O)N1CCC(CC(=O)Nc2ccc3cc2CCc2cccc(c2)Nc2ncc(Cl)c(n2)N3)CC1]

The desired compound was prepared according to the procedure of Example A9, step H using N-[6-chloro-2,4,8,22-tetraazatetracyclo[14.3.1.1(3,7).1(9,13)]docosa-1(20),3(22), 4,6,9(21),10,12,16,18-nonaen-12-yl]-2-piperidin-4-ylacetamide bis(trifluoroacetate) and 2-isocyanatopropane as starting materials in 41% yield. $^1$H NMR (300 MHz, DMSO-d$_6$): δ 9.43 (s, 1H), 9.33 (s, 1H), 9.31 (s, 1H), 8.12 (s, 1H), 7.98 (s, 1H), 7.73 (s, 1H), 7.21 (d, 1H), 7.04 (m, 2H), 6.87 (d, 1H), 6.78 (d, 1H), 6.09 (m, 1H), 3.95 (m, 2H), 3.72 (m, 1H), 2.83 (m, 4H), 2.62 (m, 2H), 2.27 (m, 2H), 1.91 (m, 1H), 1.62 (m, 2H), 1.12 (m, 2H), 1.00 (d, 6H). LCMS for C$_{29}$H$_{35}$ClN$_7$O$_3$ (M+H)$^+$: m/z=548.2.

Example A85

N-(tert-Butyl)-4-(2-{[6-chloro-2,4,8,22-tetraazatetracyclo[14.3.1.1(3,7).1(9,13)]docosa-1(20),3(22),4,6,9 (21),10,12,16,18-nonaen-12-yl]amino}-2-oxoethyl) piperidine-1-carboxamide trifluoroacetate

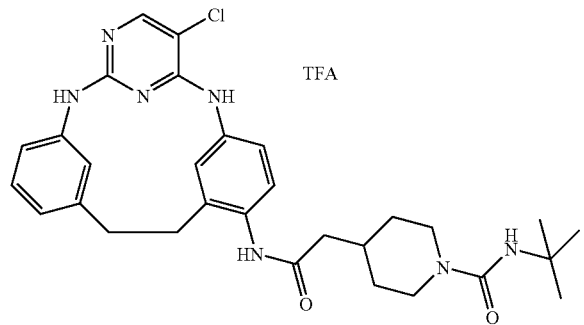 [SMILES: CC(C)(C)NC(=O)N1CCC(CC(=O)Nc2ccc3cc2CCc2cccc(c2)Nc2ncc(Cl)c(n2)N3)CC1]

The desired compound was prepared according to the procedure of Example A9, step H using N-[6-chloro-2,4,8,22-tetraazatetracyclo[14.3.1.1(3,7).1(9,13)]docosa-1(20), 3(22),4,6,9(21),10,12,16,18-nonaen-12-yl]-2-piperidin-4-ylacetamide bis(trifluoroacetate) and 2-isocyanato-2-methyl-propane as starting materials in 48% yield. $^1$H NMR (300 MHz, DMSO-d$_6$): δ 9.43 (s, 1H), 9.32 (m, 2H), 8.13 (s, 1H), 8.00 (s, 1H), 7.72 (s, 1H), 7.22 (d, 1H), 7.09 (m, 1H), 7.01 (d, 1H), 6.89 (d, 1H), 6.75 (d, 1H), 5.71 (s, 1H), 3.91 (d, 2H), 2.90 (m, 2H), 2.82 (m, 2H), 2.61 (m, 2H), 2.25 (d, 2H), 1.90 (m, 1H), 1.62 (m, 2H), 1.23 (s, 9H), 1.10 (m, 2H). LCMS for C$_{30}$H$_{37}$ClN$_7$O$_2$ (M+H)$^+$: m/z=562.3.

Example A86

N-[6-Chloro-2,4,8,22-tetraazatetracyclo[14.3.1.1(3, 7).1(9,13)]docosa-1(20),3(22),4,6,9(21),10,12,16,18-nonaen-12-yl]-2-{1-[(5-methylisoxazol-3-yl)carbonyl]piperidin-4-yl}acetamide trifluoroacetate

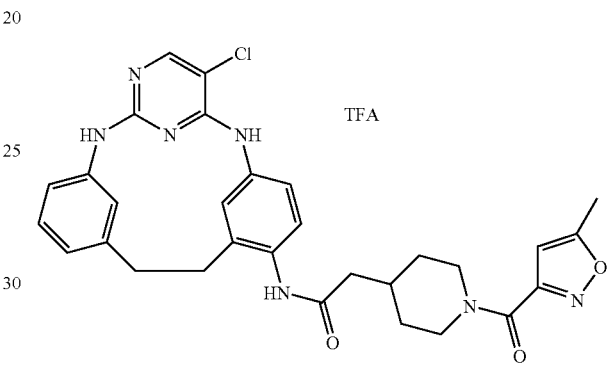

The desired compound was prepared according to the procedure of Example A20, using N-[6-chloro-2,4,8,22-tetraazatetracyclo[14.3.1.1(3,7).1(9,13)]docosa-1(20),3(22),4, 6,9(21),10,12,16,18-nonaen-12-yl]-2-piperidin-4-ylacetamide bis(trifluoroacetate) and 5-methoxyisoxazole-3-carbonyl chloride as starting materials in 31% yield. $^1$H NMR (300 MHz, DMSO-d$_6$): δ 9.45 (s, 1H), 9.36 (s, 2H), 8.12 (s, 1H), 7.98 (s, 1H), 7.73 (s, 1H), 7.21 (d, 1H), 7.04 (m, 2H), 6.87 (d, 1H), 6.78 (d, 1H), 6.41 (s, 1H), 4.42 (m, 1H), 3.88 (m, 1H), 3.13 (m, 2H), 2.83 (m, 4H), 2.45 (s, 3H), 2.30 (m, 2H), 2.10 (m, 1H), 1.80 (m, 2H), 1.20 (m, 2H). LCMS for C$_{30}$H$_{31}$ClN$_7$O$_3$S (M+H)$^+$: m/z=572.2.

Example A87

N-[6-Chloro-2,4,8,22-tetraazatetracyclo[14.3.1.1(3, 7).1(9,13)]docosa-1(20),3(22),4,6,9(21),10,12,16,18-nonaen-12-yl]-2-[1-(pyrazin-2-ylcarbonyl)piperidin-4-yl]acetamide bis(trifluoroacetate)

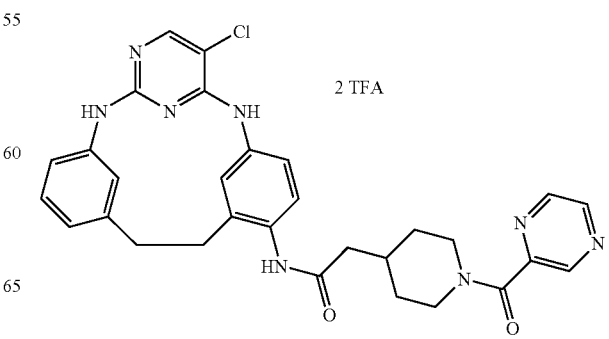

The desired compound was prepared according to the procedure of Example A20, using N-[6-chloro-2,4,8,22-tetraazatetracyclo[14.3.1.1(3,7).1(9,13)]docosa-1(20), 3(22),4,6,9(21),10,12,16,18-nonaen-12-yl]-2-piperidin-4-ylacetamide bis(trifluoroacetate) and pyrazine-2-carbonyl chloride as starting materials in 36% yield. $^1$H NMR (300 MHz, DMSO-d$_6$): δ 9.42 (s, 1H), 9.35 (s, 1H), 9.30 (s, 1H), 8.80 (s, 1H), 8.72 (s, 1H), 8.68 (s, 1H), 8.11 (s, 1H), 7.99 (s, 1H), 7.73 (s, 1H), 7.21 (d, 1H), 7.04 (m, 2H), 6.87 (d, 1H), 6.78 (d, 1H), 4.49 (m, 2H), 3.65 (m, 1H), 3.12 (m, 1H), 2.81 (m, 4H), 2.31 (m, 2H), 2.10 (m, 1H), 1.83 (m, 1H), 1.68 (m, 1H), 1.22 (m, 2H). LCMS for $C_{30}H_{30}ClN_8O_2$ (M+H)$^+$: m/z=569.2.

Example A88

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-[1-(2,2-dimethylpropanoyl)piperidin-4-yl]acetamide trifluoroacetate

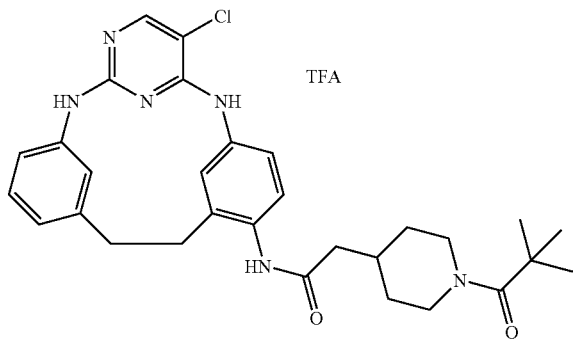 [SMILES: "TFA" ; CC(C)(C)C(=O)N1CCC(CC(=O)Nc2ccc3cc2CCc2cccc(c2)Nc2ncc(Cl)c(n2)N3)CC1]

The desired compound was prepared according to the procedure of Example A20, using N-[6-chloro-2,4,8,22-tetraazatetracyclo[14.3.1.1(3,7).1(9,13)]docosa-1(20),3(22),4,6,9(21),10,12,16,18-nonaen-12-yl]-2-piperidin-4-ylacetamide bis(trifluoroacetate) and 2,2-dimethylpropanoyl chloride as starting materials in 31% yield. $^1$H NMR (300 MHz, DMSO-d$_6$): δ 9.50 (s, 1H), 9.33 (s, 1H), 9.30 (s, 1H), 8.13 (s, 1H), 7.98 (s, 1H), 7.77 (s, 1H), 7.21 (d, 1H), 7.04 (m, 2H), 6.87 (d, 1H), 6.79 (d, 1H), 4.27 (m, 2H), 2.81 (m, 6H), 2.25 (m, 2H), 2.01 (m, 1H), 1.76 (m, 2H), 1.19 (s, 9H), 1.04 (m, 2H). LCMS for $C_{30}H_{36}ClN_6O_2$ (M+H)$^+$: m/z=547.2.

Example A89

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-(1-isobutyrylpiperidin-4-yl)acetamide trifluoroacetate

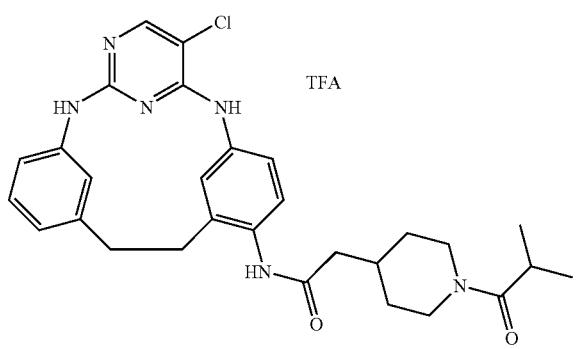 [SMILES: "TFA" ; CC(C)C(=O)N1CCC(CC(=O)Nc2ccc3cc2CCc2cccc(c2)Nc2ncc(Cl)c(n2)N3)CC1]

The desired compound was prepared according to the procedure of Example A20, using N-[6-chloro-2,4,8,22-tetraazatetracyclo[14.3.1.1(3,7).1(9,13)]docosa-1(20), 3(22),4,6,9(21),10,12,16,18-nonaen-12-yl]-2-piperidin-4-ylacetamide bis(trifluoroacetate) and isobutyryl chloride as starting materials in 41% yield. $^1$H NMR (300 MHz, DMSO-d$_6$): δ 9.45 (s, 1H), 9.38 (s, 1H), 9.31 (s, 1H), 8.12 (s, 1H), 7.98 (s, 1H), 7.73 (s, 1H), 7.21 (d, 1H), 7.04 (m, 2H), 6.87 (d, 1H), 6.78 (d, 1H), 4.40 (m, 2H), 3.95 (m, 2H), 3.03 (m, 1H), 2.83 (m, 4H), 2.27 (m, 2H), 2.01 (m, 1H), 1.76 (m, 2H), 1.10 (m, 2H), 1.00 (m, 6H). LCMS for $C_{29}H_{34}ClN_6O_2$ (M+H)$^+$: m/z=533.2.

Example A90

N-[6-Chloro-2,4,8,22-tetraazatetracyclo[14.3.1.1(3,7).1(9,13)]docosa-1(20), 3(22),4,6,9(21),10,12,16,18-nonaen-12-yl]-2-(1-propionylpiperidin-4-yl)acetamide trifluoroacetate

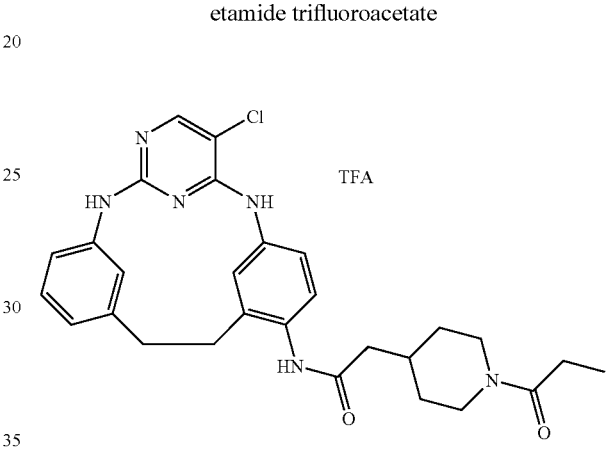

The desired compound was prepared according to the procedure of Example A20, using N-[6-chloro-2,4,8,22-tetraazatetracyclo[14.3.1.1(3,7).1(9,13)]docosa-1(20), 3(22),4,6,9(21),10,12,16,18-nonaen-12-yl]-2-piperidin-4-ylacetamide bis(trifluoroacetate) and propanoyl chloride as starting materials in 31% yield. LCMS for $C_{28}H_{32}ClN_6O_2$ (M+H)$^+$: m/z=519.2.

Example A91

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(methylsulfonyl)pyrrolidin-3-yl]acetamide bis(trifluoroacetate)

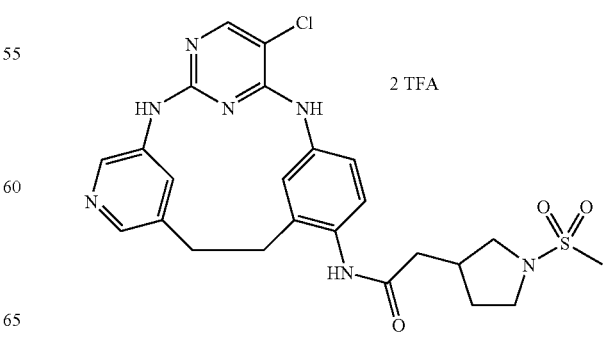

The desired compound was prepared according to the procedure of Example A42, using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-pyrrolidin-3-ylacetamide tris(trifluoroacetate) and methanesulfonyl chloride as starting materials in 48% yield. $^1$H NMR (300 MHz, DMSO-d$_6$): δ 10.10 (s, 1H), 9.48 (s, 1H), 9.41 (s, 1H), 9.08 (s, 1H), 8.33 (s, 2H), 8.21 (s, 1H), 7.69 (s, 1H), 7.32 (d, 1H), 7.09 (d, 1H), 3.95 (s, 2H), 3.44 (m, 1H), 3.37 (m, 1H), 3.25 (m, 1H), 3.00 (m, 4H), 2.90 (s, 3H), 2.62 (m, 1H), 2.05 (m, 1H), 1.62 (m, 2H). LCMS for C$_{24}$H$_{27}$ClN$_7$O$_3$S (M+H)$^+$: m/z=528.2.

Example A92

3-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-phenylpyrrolidine-1-carboxamide bis(trifluoroacetate)

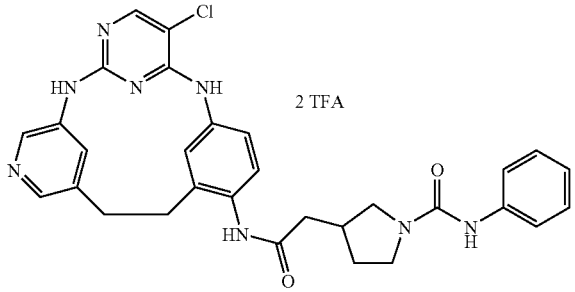 [SMILES: O=C(CC1CCN(C(=O)Nc2ccccc2)C1)Nc1ccc2cc1CCc1cncc(c1)Nc1ncc(Cl)c(n1)N2 ; "2 TFA"]

The desired compound was prepared according to the procedure of Example A9, step H using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-pyrrolidin-3-ylacetamide tris(trifluoroacetate) and phenyl isocyanate as starting materials in 44% yield. $^1$H NMR (300 MHz, DMSO-d$_6$): δ 10.08 (s, 1H), 9.42 (m, 2H), 9.07 (s, 1H), 8.32 (m, 2H), 8.21 (s, 1H), 8.13 (s, 1H), 7.68 (s, 1H), 7.50 (d, 2H), 7.31 (d, 1H), 7.20 (m, 2H), 7.07 (d, 1H), 6.89 (m, 1H), 3.60 (m, 2H), 3.40 (m, 1H), 3.12 (m, 1H), 2.99 (m, 4H), 2.60 (m, 1H), 2.09 (m, 2H), 1.67 (m, 2H). LCMS for C$_{30}$H$_{30}$ClN$_8$O$_2$ (M+H)$^+$: m/z=569.2.

Example A93

3-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-methylpyrrolidine-1-carboxamide bis(trifluoroacetate)

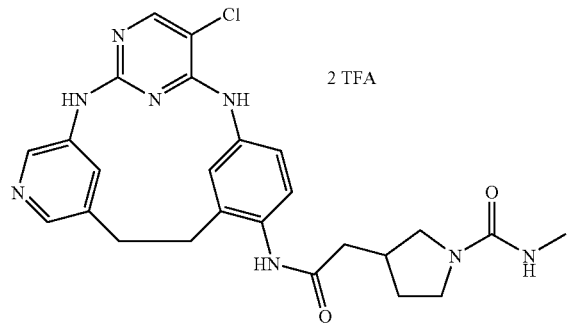 [SMILES: CNC(=O)N1CCC(CC(=O)Nc2ccc3cc2CCc2cncc(c2)Nc2ncc(Cl)c(n2)N3)C1 ; "2 TFA"]

The desired compound was prepared according to the procedure of Example A9, step H using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-pyrrolidin-3-ylacetamide tris(trifluoroacetate) and methyl isocyanate as starting materials in 59% yield. $^1$H NMR (300 MHz, DMSO-d$_6$): δ 10.04 (s, 1H), 9.40 (m, 2H), 9.05 (s, 1H), 8.32 (m, 2H), 8.21 (s, 1H), 7.68 (m, 1H), 7.30 (m, 1H), 7.07 (m, 1H), 6.03 (m, 1H), 3.40 (m, 3H), 3.20 (m, 2H), 2.99 (m, 4H), 2.55 (s, 3H), 2.00 (m, 2H), 1.60 (m, 2H). LCMS for C$_{25}$H$_{28}$ClN$_8$O$_2$ (M+H)$^+$: m/z=507.2.

Example A94

2-(1-Acetylpyrrolidin-3-yl)-N-[6-chloro-2,4,8,18,22-pentaazatetracyclo[14.3.1.1(3,7).1(9,13)]docosa-1(20),3(22),4,6,9(21),10,12,16,18-nonaen-12-yl]acetamide bis(trifluoroacetate)

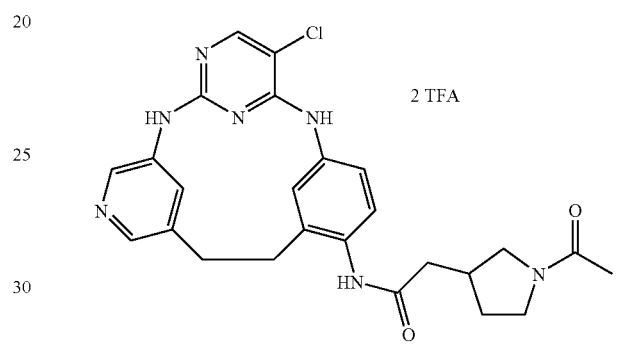

The desired compound was prepared according to the procedure of Example A20, using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-pyrrolidin-3-ylacetamide tris(trifluoroacetate) and acetyl chloride as starting materials in 39% yield. $^1$H NMR (300 MHz, DMSO-d$_6$): δ 10.08 (s, 1H), 9.40 (m, 2H), 9.07 (s, 1H), 8.32 (m, 2H), 8.21 (s, 1H), 7.67 (m, 1H), 7.30 (m, 1H), 7.07 (m, 1H), 3.50 (m, 4H), 3.17 (m, 1H), 2.99 (m, 4H), 2.08 (m, 2H), 1.91 (s, 3H), 1.60 (m, 2H). LCMS for C$_{25}$H$_{27}$ClN$_7$O$_2$ (M+H)$^+$: m/z=492.2.

Example A95

4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N,N-dimethylpiperidine-1-carboxamide bis(trifluoroacetate)

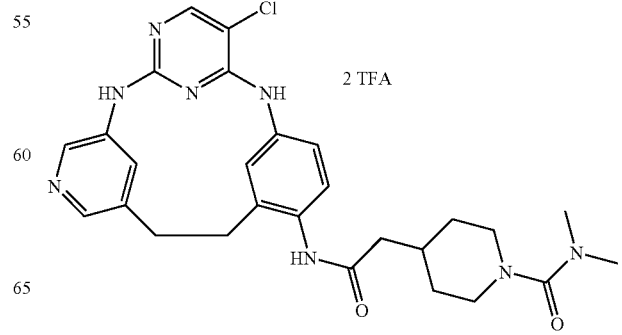

The desired compound was prepared according to the procedure of Example A20, using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and N,N-dimethylcarbamoyl chloride as starting materials in 84% yield. LCMS for $C_{27}H_{32}ClN_8O_2$ $(M+H)^+$: m/z=535.2.

Example A96

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(dimethylamino)sulfonyl]piperidin-4-yl}acetamide bis(trifluoroacetate)

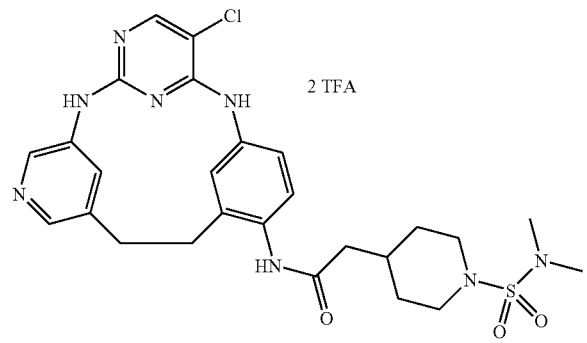 [SMILES: CN(C)S(=O)(=O)N1CCC(CC(=O)Nc2ccc3cc2CCc2cncc(c2)Nc2ncc(Cl)c(n2)N3)CC1 ; "2 TFA"]

The desired compound was prepared according to the procedure of Example A42, using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and dimethylsulfamoyl chloride as starting materials in 48% yield. $^1$H NMR (300 MHz, DMSO-$d_6$): δ 10.02 (s, 1H), 9.40 (m, 2H), 9.02 (s, 1H), 8.31 (m, 2H), 8.21 (s, 1H), 7.68 (m, 1H), 7.30 (m, 1H), 7.07 (m, 1H), 3.58 (m, 2H), 2.99 (m, 4H), 2.85 (m, 2H), 2.72 (s, 6H), 2.32 (m, 2H), 1.91 (m, 1H), 1.77 (m, 2H), 1.25 (m, 2H). LCMS for $C_{26}H_{32}ClN_8O_3S$ $(M+H)^+$: m/z=571.2.

Example A97

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(isopropylsulfonyl)piperidin-4-yl]acetamide bis(trifluoroacetate)

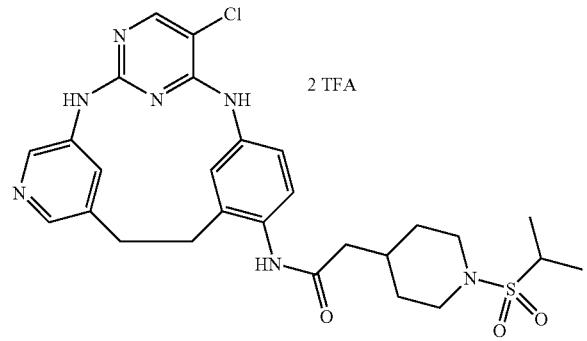 [SMILES: CC(C)S(=O)(=O)N1CCC(CC(=O)Nc2ccc3cc2CCc2cncc(c2)Nc2ncc(Cl)c(n2)N3)CC1 ; "2 TFA"]

The desired compound was prepared according to the procedure of Example A42, using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and propane-2-sulfonyl chloride as starting materials in 25% yield. LCMS for $C_{27}H_{33}ClN_7O_3S$ $(M+H)^+$: m/z=570.2.

Example A98

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(ethylsulfonyl)piperidin-4-yl]acetamide bis(trifluoroacetate)

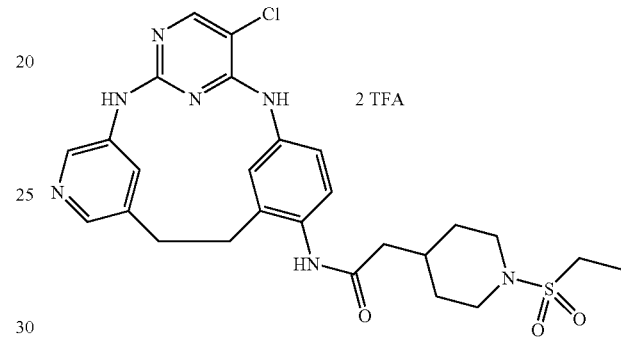

The desired compound was prepared according to the procedure of Example A42, using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and ethanesulfonyl chloride as starting materials in 45% yield. $^1$H NMR (300 MHz, DMSO-$d_6$): δ 10.00 (s, 1H), 9.40 (m, 2H), 8.98 (s, 1H), 8.28 (m, 2H), 8.21 (s, 1H), 7.65 (m, 1H), 7.30 (m, 1H), 7.07 (m, 1H), 3.60 (m, 2H), 2.99 (m, 6H), 2.81 (m, 2H), 2.32 (m, 2H), 1.91 (m, 1H), 1.80 (m, 2H), 1.25 (m, 2H), 1.20 (t, 3H). LCMS for $C_{26}H_{31}ClN_7O_3S$ $(M+H)^+$: m/z=556.2.

Example A99

4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-isopropylpiperidine-1-carboxamide bis(trifluoroacetate)

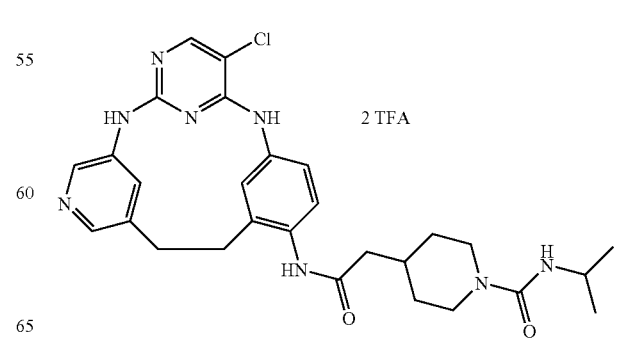

The desired compound was prepared according to the procedure of Example A9, step H using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and 2-isocyanatopropane as starting materials in 58% yield. $^1$H NMR (300 MHz, DMSO-d$_6$): δ 10.08 (s, 1H), 9.40 (m, 2H), 9.05 (s, 1H), 8.33 (m, 2H), 8.20 (s, 1H), 7.63 (m, 1H), 7.30 (m, 1H), 7.09 (m, 1H), 6.09 (m, 1H), 3.92 (m, 2H), 3.75 (m, 1H), 2.97 (s, 4H), 2.62 (m, 2H), 2.28 (m, 2H), 1.91 (m, 1H), 1.64 (m, 2H), 1.09 (m, 2H), 1.00 (d, 6H). LCMS for $C_{28}H_{34}ClN_8O_2$ (M+H)$^+$: m/z=549.2.

Example A100

4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-methylpiperidine-1-carboxamide bis(trifluoroacetate)

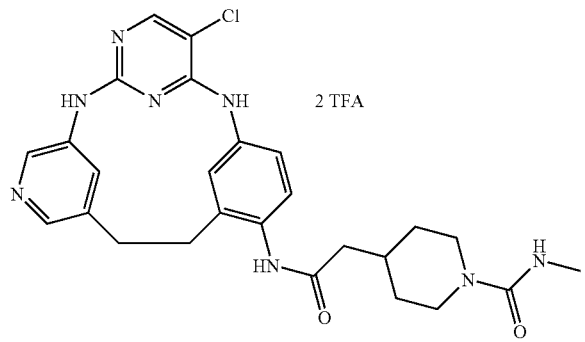 [SMILES: CNC(=O)N1CCC(CC(=O)Nc2ccc3cc2CCc2cncc(c2)Nc2ncc(Cl)c(n2)N3)CC1 ; "2 TFA"]

The desired compound was prepared according to the procedure of Example A9, step H using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and methyl isocyanate as starting materials in 43% yield. $^1$H NMR (300 MHz, DMSO-d$_6$): δ 10.08 (s, 1H), 9.40 (m, 2H), 9.05 (s, 1H), 8.33 (m, 2H), 8.20 (s, 1H), 7.63 (m, 1H), 7.30 (m, 1H), 7.09 (m, 1H), 6.38 (m, 1H), 3.92 (m, 2H), 2.97 (s, 4H), 2.68 (m, 2H), 2.55 (s, 3H), 2.28 (m, 2H), 1.91 (m, 1H), 1.64 (m, 2H), 1.09 (m, 2H). LCMS for $C_{26}H_{30}ClN_8O_2$ (M+H)$^+$: m/z=521.2.

Example A101

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(5-methylisoxazol-3-yl)carbonyl]piperidin-4-yl}acetamide bis(trifluoroacetate)

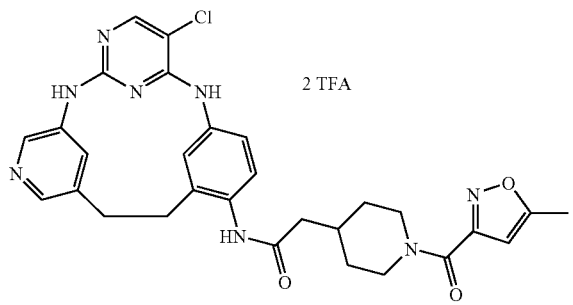

The desired compound was prepared according to the procedure of Example A20, using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and 5-methylisoxazole-3-carbonyl chloride as starting materials in 56% yield. LCMS for $C_{29}H_{30}ClN_8O_3$ (M+H)$^+$: m/z=573.2.

Example A102

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(pyrazin-2-ylcarbonyl)piperidin-4-yl]acetamide tris(trifluoroacetate)

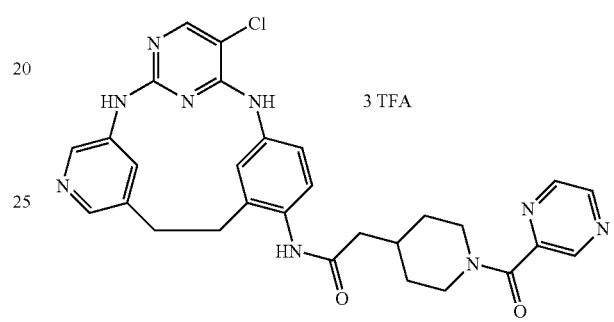

The desired compound was prepared according to the procedure of Example A20, using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and pyrazine-2-carbonyl chloride as starting materials in 46% yield. $^1$H NMR (300 MHz, DMSO-d$_6$): δ 10.10 (s, 1H), 9.40 (m, 2H), 9.05 (s, 1H), 8.80 (s, 1H), 8.71 (s, 1H), 8.67 (s, 1H), 8.32 (d, 2H), 8.20 (s, 1H), 7.65 (s, 1H), 7.30 (d, 1H), 7.04 (d, 1H), 4.52 (d, 1H), 3.62 (d, 1H), 3.12 (m, 1H), 2.98 (m, 4H), 2.88 (m, 1H), 2.34 (m, 2H), 2.12 (m, 1H), 1.82 (m, 1H), 1.70 (m, 1H), 1.25 (m, 2H). LCMS for $C_{29}H_{29}ClN_9O_2$ (M+H)$^+$: m/z=570.2.

Example A103

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-(1-isobutyrylpiperidin-4-yl)acetamide bis(trifluoroacetate)

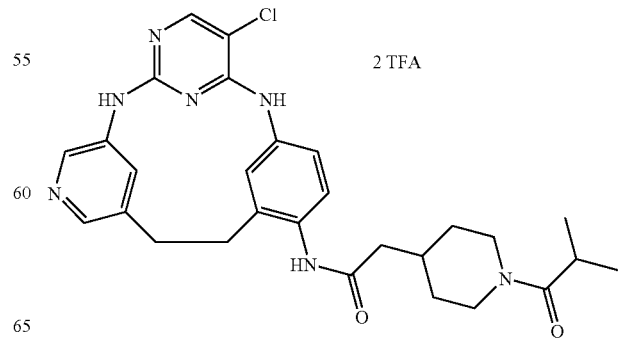

The desired compound was prepared according to the procedure of Example A20, using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and isobutyryl chloride as starting materials in 32% yield. LCMS for $C_{28}H_{33}ClN_7O_2$ (M+H)$^+$: m/z=534.2.

Example A104

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-(1-propionylpiperidin-4-yl)acetamide bis(trifluoroacetate)

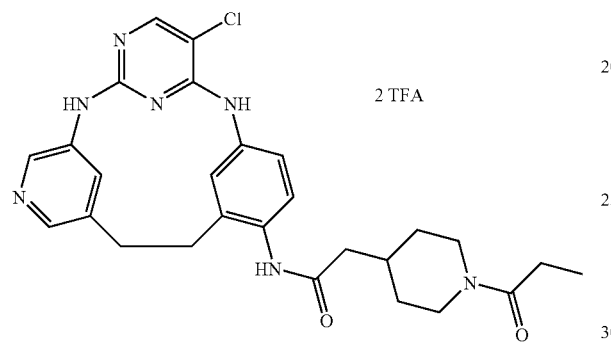

The desired compound was prepared according to the procedure of Example A20, using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and propanoyl chloride as starting materials in 20% yield. LCMS for $C_{27}H_{31}ClN_7O_2$ (M+H)$^+$: m/z=520.2.

Example A105

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-pyrrolidin-3-ylacetamide tris(trifluoroacetate)

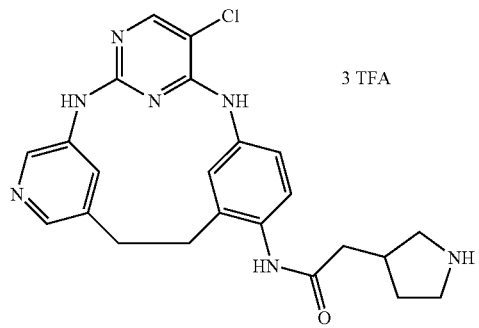 [SMILES: "3 TFA" ; O=C(CC1CCNC1)Nc1ccc2cc1CCc1cncc(c1)Nc1ncc(Cl)c(n1)N2]

The desired compound was prepared according to the procedures of Examples A-27 and A-28 using 6-chloro-2,4,8,18,22-pentaazatetracyclo[14.3.1.1(3,7).1(9,13)]docosa-1(20),3(22),4,6,9(21),10,12,16,18-nonaen-12-amine bis(trifluoroacetate) and 2-(1-(tert-butoxycarbonyl)pyrrolidin-3-yl)acetic acid as the starting materials in 51% yield. $^1$H NMR (300 MHz, DMSO-d$_6$): δ 10.04 (s, 1H), 9.50 (s, 1H), 9.40 (s, 1H), 9.00 (s, 1H), 8.72 (m, 2H), 8.31 (s, 1H), 8.29 (s, 1H), 8.21 (s, 1H), 7.68 (s, 1H), 7.30 (d, 1H), 7.08 (d, 1H), 3.98 (s, 2H), 3.40 (m, 1H), 3.27 (m, 1H), 2.97 (m, 4H), 2.58 (m, 2H), 2.11 (m, 1H), 1.61 (m, 2H). LCMS for $C_{23}H_{25}ClN_7O$ (M+H)$^+$: m/z=450.2.

Example A106

(2S)—N-[6-Chloro-2,4,8,22-tetraazatetracyclo[14.3.1.1(3,7).1(9,13)]docosa-1(20),3(22),4,6,9(21),10,12,16,18-nonaen-12-yl]-2-hydroxypropanamide trifluoroacetate

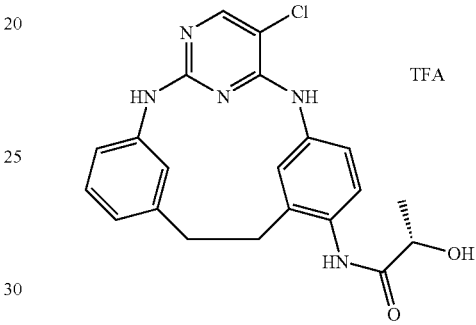

The desired compound was prepared according to the procedure of Example A27 using (S)-2-hydroxypropanoic acid as the starting material in 35% yield. LCMS for $C_{21}H_{21}ClN_5O_2$ (M+H)$^+$: m/z=410.1.

Example A107

2-Amino-N-[6-chloro-2,4,8,22-tetraazatetracyclo[14.3.1.1(3,7).1(9,13)]docosa-1(20),3(22),4,6,9(21),10,12,16,18-nonaen-12-yl]acetamide bis(trifluoroacetate)

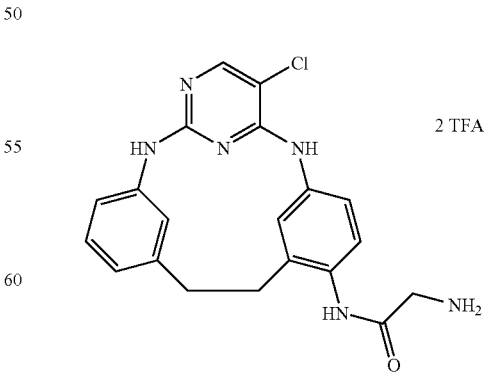

The desired compound was prepared according to the procedures of Examples A-27 and A-28 using N-α-(tert-butoxycarbonyl)glycine as the starting material in 45% yield. LCMS for $C_{20}H_{20}ClN_6O$ (M+H)$^+$: m/z=395.1.

Example A108

3-Amino-N-[6-chloro-2,4,8,22-tetraazatetracyclo[14.3.1.1(3,7).1(9,13)]docosa-1(20),3(22),4,6,9(21),10,12,16,18-nonaen-12-yl]propanamide bis(trifluoroacetate)

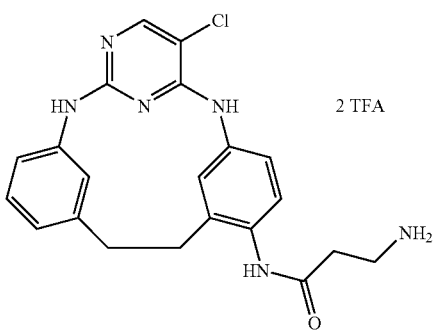 [SMILES: NCCC(=O)Nc1ccc2cc1CCc1cccc(c1)Nc1ncc(Cl)c(n1)N2 ; "2 TFA"]

The desired compound was prepared according to the procedures of Examples A-27 and A-28 using 3-[(tert-butoxycarbonyl)amino]propionic acid as the starting material in 37% yield. LCMS for $C_{21}H_{22}ClN_6O$ (M+H)$^+$: m/z=409.2.

Example A109

(2S)-2-Amino-N-[6-chloro-2,4,8,22-tetraazatetracyclo[14.3.1.1(3,7).1(9,13)]docosa-1(20),3(22),4,6,9(21),10,12,16,18-nonaen-12-yl]-3-hydroxypropanamide bis(trifluoroacetate)

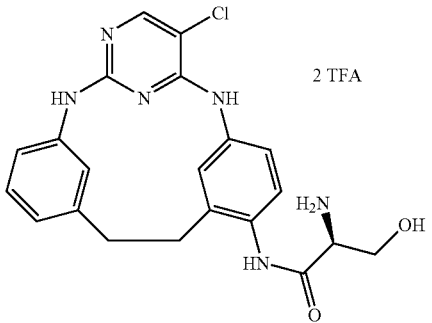 [SMILES: N[C@@H](CO)C(=O)Nc1ccc2cc1CCc1cccc(c1)Nc1ncc(Cl)c(n1)N2 ; "2 TFA"]

The desired compound was prepared according to the procedures of Examples A-27 and A-28 using (2S)-2-[(tert-butoxycarbonyl)amino]-3-hydroxypropionic acid as the starting material in 29% yield. LCMS for $C_{21}H_{22}ClN_6O_2$ (M+H)$^+$: m/z=425.1.

Example A110

(2S)—N-[6-Chloro-2,4,8,22-tetraazatetracyclo[14.3.1.1(3,7).1(9,13)]docosa-1(20),3(22),4,6,9(21),10,12,16,18-nonaen-12-yl]pyrrolidine-2-carboxamide bis(trifluoroacetate)

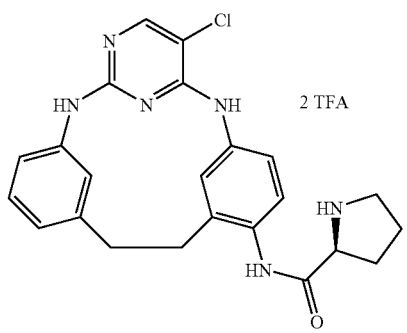 [SMILES: O=C(Nc1ccc2cc1CCc1cccc(c1)Nc1ncc(Cl)c(n1)N2)[C@@H]1CCCN1 ; "2 TFA"]

The desired compound was prepared according to the procedures of Examples A-27 and A-28 using (2S)-1-(tert-butoxycarbonyl)pyrrolidine-2-carboxylic acid as the starting material in 45% yield. LCMS for $C_{23}H_{24}ClN_6O$ (M+H)$^+$: m/z=435.2.

Example A111

4-(2-{[6-Chloro-2,4,8,22-tetraazatetracyclo[14.3.1.1(3,7).1(9,13)]docosa-1(20),3(22),4,6,9(21),10,12,16,18-nonaen-12-yl]amino}-2-oxoethyl)-1,1-dimethylpiperidinium bis(trifluoroacetate)

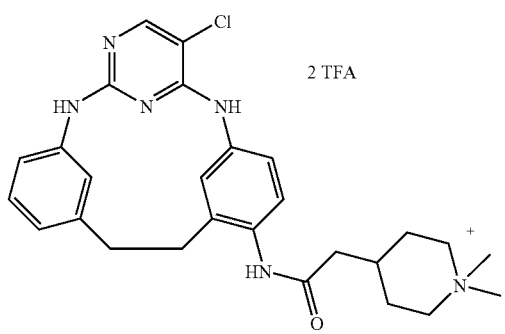

N-[6-chloro-2,4,8,22-tetraazatetracyclo[14.3.1.1(3,7).1(9,13)]docosa-1(20), 3(22),4,6,9(21),10,12,16,18-nonaen-12-yl]-2-piperidin-4-ylacetamide bis(trifluoroacetate) (11.6 mg, 0.020 mmol), potassium carbonate (5.6 mg, 0.040 mmol) and methyl iodide (12.5 mL, 0.020 mmol) were stirred in acetonitrile (1.0 mL) for 30 minutes. Purification by preparative LCMS (pH 2) gave the desired compound (58%). $^1$H NMR (300 MHz, DMSO-d$_6$): δ 9.52 (s, 1H), 9.39 (s, 1H), 9.33 (s, 1H), 8.18 (s, 1H), 8.00 (s, 1H), 7.78 (s, 1H), 7.22 (d, 1H), 7.05 (m, 2H), 6.87 (d, 1H), 6.77 (d, 1H), 3.38 (m, 4H), 3.07 (s, 3H), 3.03 (s, 3H), 2.88 (m, 4H), 2.40 (d, 2H), 2.03 (m, 1H), 1.78 (m, 4H). LCMS for $C_{27}H_{33}ClN_6O$ (M+H)$^+$: m/z=492.2.

Example A112

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(2,2-dimethylpropanoyl)piperidin-4-yl]acetamide bis(trifluoroacetate)

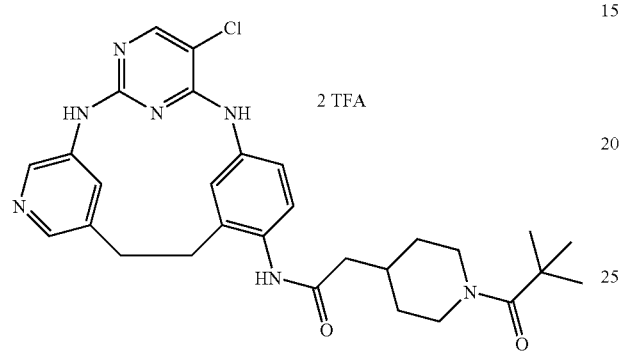

The desired compound was prepared according to the procedure of Example A20, using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and 2,2-dimethylpropanoyl chloride as starting materials in 32% yield. LCMS for $C_{29}H_{35}ClN_7O_2$ (M+H)$^+$: m/z=548.2.

Example A113

N-(tert-Butyl)-4-(2-{[6-chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)piperidine-1-carboxamide bis(trifluoroacetate)

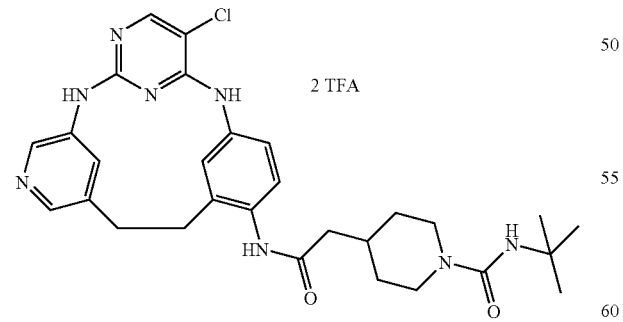

The desired compound was prepared according to the procedure of Example A9, step H using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and 2-isocyanato-2-methyl-propane as starting materials in 32% yield. LCMS for $C_{29}H_{36}ClN_8O_2$ (M+H)$^+$: m/z=563.3.

Example A114 tert-Butyl-4-(2-{[6-chloro-2,4,8,22-tetraazatetracyclo[14.3.1.1(3,7).1(9,13)]docosa-1(20),3(22),4,6,9(21),10,12,16,18-nonaen-12-yl]amino}-2-oxoethyl)piperazine-1-carboxylate tris(trifluoroacetate)

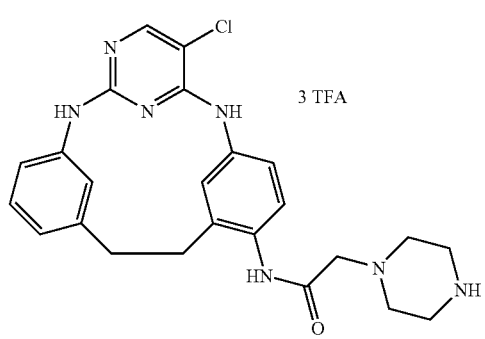 [SMILES: "3 TFA" ; O=C(CN1CCNCC1)Nc1ccc2cc1CCc1cccc(c1)Nc1ncc(Cl)c(n1)N2]

The desired compound was prepared according to the procedures of Examples A-27 and A-28 using [4-(tert-butoxycarbonyl)piperazin-1-yl]acetic acid as starting material in 70% yield. LCMS for $C_{24}H_{27}ClN_7O$ (M+H)$^+$: m/z=464.2.

Example A115

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-piperazin-1-acetamide tetrakis(trifluoroacetate)

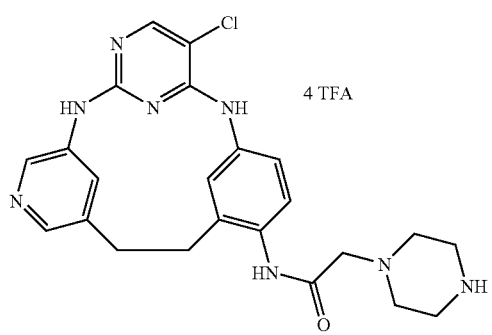 [SMILES: O=C(CN1CCNCC1)Nc1ccc2cc1CCc1cncc(c1)Nc1ncc(Cl)c(n1)N2 ; "4 TFA"]

The desired compound was prepared according to the procedures of Examples A-27 and A-28 using 6-chloro-2,4,8,18,22-pentaazatetracyclo[14.3.1.1(3,7).1(9,13)]docosa-1(20),3(22),4,6,9(21),10,12,16,18-nonaen-12-amine bis(trifluoroacetate) and [4-(tert-butoxycarbonyl)piperazin-1- yl]acetic acid as starting materials in 37% yield. LCMS for $C_{23}H_{26}ClN_8O$ (M+H)$^+$: m/z=465.2.

Example A116

N-[6-Chloro-2,4,8,22-tetraazatetracyclo[14.3.1.1(3,7).1(9,13)]docosa-1(20),3(22),4,6,9(21),10,12,16,18-nonaen-12-yl]-3piperidin-4-ylpropanamide bis(trifluoroacetate)

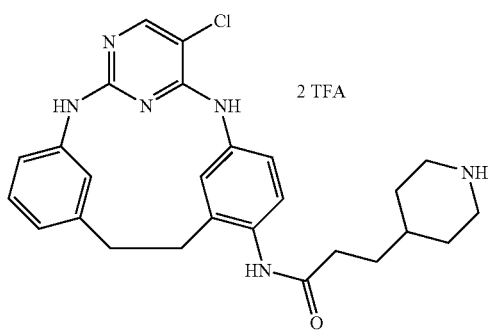 [SMILES: O=C(CCC1CCNCC1)Nc1ccc2cc1CCc1cccc(c1)Nc1ncc(Cl)c(n1)N2 ; "2 TFA"]

The desired compound was prepared according to the procedures of Examples A-27 and A-28 using 3-[1-(tert-butoxycarbonyl)piperidin-4-yl]propanoic acid as the starting material in 43% yield. LCMS for $C_{26}H_{30}ClN_6O$ (M+H)$^+$: m/z=477.2.

Example A117

N-[6-Chloro-2,4,8,18,22-pentaaazatetracyclo[14.3.1.1(3,7).1(9,13)]docosa-1(20),3(22),4,6,9(21),10,12,16,18-nonaen-12-yl]-3piperidin-4-ylpropanamide tris(trifluoroacetate)

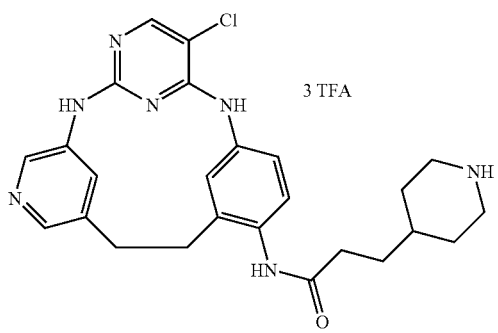 [SMILES: "3 TFA" ; O=C(CCC1CCNCC1)Nc1ccc2cc1CCc1cncc(c1)Nc1ncc(Cl)c(n1)N2]

The desired compound was prepared according to the procedures of Examples A-27 and A-28 using 6-chloro-2,4,8,18,22-pentaazatetracyclo[14.3.1.1(3,7).1(9,13)]docosa-1(20),3(22),4,6,9(21),10,12,16,18-nonaen-12-amine bis(trifluoroacetate) and 3-[1-(tert-butoxycarbonyl)piperidin-4- yl]propanoic acid as starting materials in 53% yield. LCMS for $C_{25}H_{29}ClN_7O$ (M+H)$^+$: m/z=478.2.

Example A118

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-(4-[1,3]oxazolo[5,4-b]pyridin-2-ylpiperazin-1-yl)acetamide tris(trifluoroacetate)

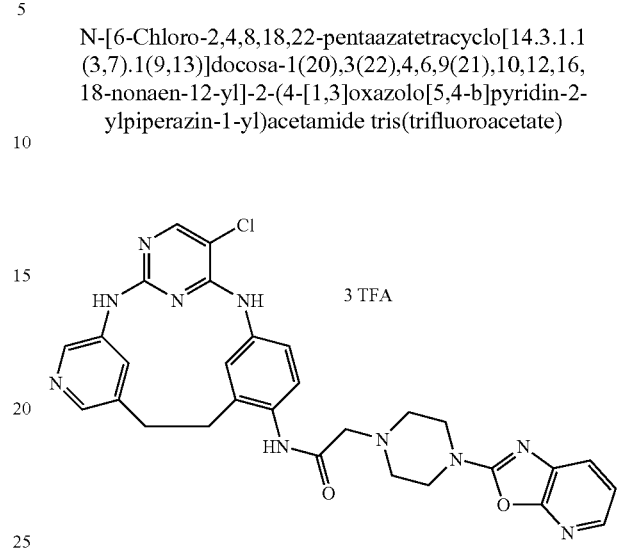

N-[6-Chloro-2,4,8,18,22pentaazatetracyclo[14.3.1.1(3,7).1(9,13)]docosa-1(20),3(22),4,6,9(21),10,12,16,18-nonaen-12-yl]-2-piperazin-1-acetamide bis(trifluoroacetate) (8.2 mg, 0.010 mmol) and [1,3]oxazolo[5,4-b]pyridine-2-thiol (3.7 mg, 0.024 mmol) were stirred in 1,4-dioxane (1 mL) and heated to 70° C. for 16 hours. The mixture was evaporated and stirred in ethanol (1 mL). Silver nitrate (7.2 mg, 0.043 mmol) and ammonium hydroxide solution (14.5 M in water) were added and the mixture was stirred at RT for 3 hours. Purification by preparative LCMS (pH 2) gave the desired compound in 17% yield. LCMS for $C_{29}H_{28}ClN_{10}O_2$ (M+H)$^+$: m/z=583.2.

Example A119

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{4-[(5-methylisoxazol-3-yl)carbonyl]piperazin-1-yl}acetamide tris(trifluoroacetate)

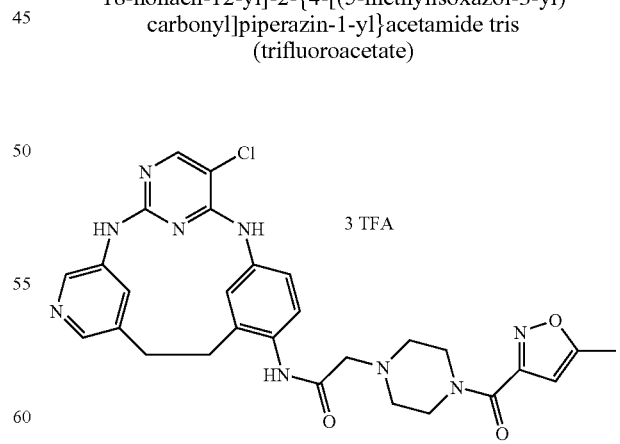

The desired compound was prepared according to the procedure of Example A20, using N-[6-chloro-2,4,8,18,22pentaazatetracyclo[14.3.1.1(3,7).1(9,13)]docosa-1(20),3(22),4,6,9(21),10,12,16,18-nonaen-12-yl]-2-piperazin-1-acetamide tris(trifluoroacetate) and 5-methylisoxazole-3- carbonyl chloride as starting materials in 70% yield. LCMS for $C_{28}H_{29}ClN_9O_3$ (M+H)$^+$: m/z=574.2.

Example A120

N-[6-Chloro-2,4,8,22-tetraazatetracyclo[14.3.1.1(3,7).1(9,13)]docosa-1(20),3(22),4,6,9(21),10,12,16,18-nonaen-12-yl]-1-[(5-methylisoxazol-3-yl)carbonyl]piperidine-4-carboxamide trifluoroacetate

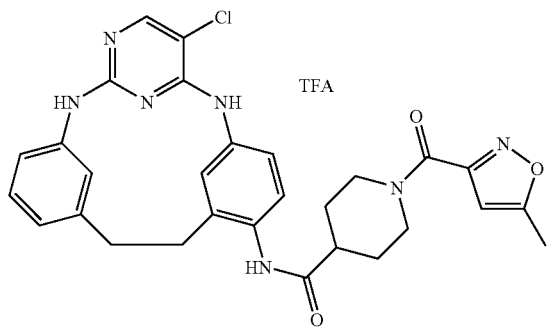 [SMILES: "TFA" ; Cc1cc(C(=O)N2CCC(C(=O)Nc3ccc4cc3CCc3cccc(c3)Nc3ncc(Cl)c(n3)N4)CC2)no1]

The desired compound was prepared according to the procedure of Example A20, using N-[6-chloro-2,4,8,22-tetraazatetracyclo[14.3.1.1(3,7).1(9,13)]docosa-1(20), 3(22),4,6,9(21),10,12,16,18-nonaen-12-yl]piperidine-4-carboxamide bis(trifluoroacetate) and 5-methylisoxazole-3-carboxyl chloride as starting materials in 12% yield. LCMS for $C_{29}H_{29}ClN_7O_3$ (M+H)$^+$: m/z=558.2.

Example A121

N-[6-Chloro-2,4,8,22-tetraazatetracyclo[14.3.1.1(3,7).1(9,13)]docosa-1(20),3(22),4,6,9(21),10,12,16,18-nonaen-12-yl]-1-[(5-methylisoxazol-3-yl)carbonyl]piperidine-3-carboxamide trifluoroacetate

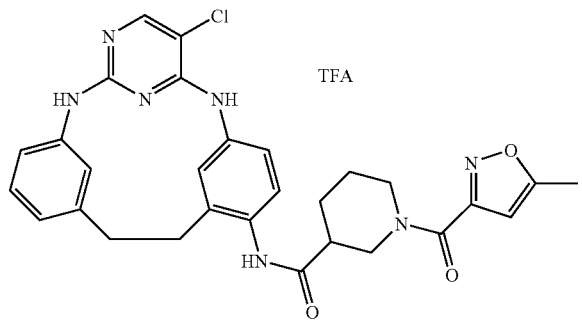 [SMILES: "TFA" ; Cc1cc(C(=O)N2CCCC(C(=O)Nc3ccc4cc3CCc3cccc(c3)Nc3ncc(Cl)c(n3)N4)C2)no1]

The desired compound was prepared according to the procedure of Example A20, using N-[6-chloro-2,4,8,22-tetraazatetracyclo[14.3.1.1(3,7).1(9,13)]docosa-1(20), 3(22),4, 6,9(21),10,12,16,18-nonaen-12-yl]piperidine-3-carboxamide bis(trifluoroacetate) and 5-methylisoxazole-3-carbonyl chloride as starting materials in 62% yield. LCMS for $C_{29}H_{29}ClN_7O_3$ (M+H)$^+$: m/z=558.2.

Example A122

(3R)—N-[6-Chloro-2,4,8,22-tetraazatetracyclo[14.3.1.1(3,7).1(9,13)]docosa-1(20),3(22),4,6,9(21),10,12,16,18-nonaen-12-yl]-1-[(5-methylisoxazol-3-yl)carbonyl]pyrrolidine-4-carboxamide trifluoroacetate

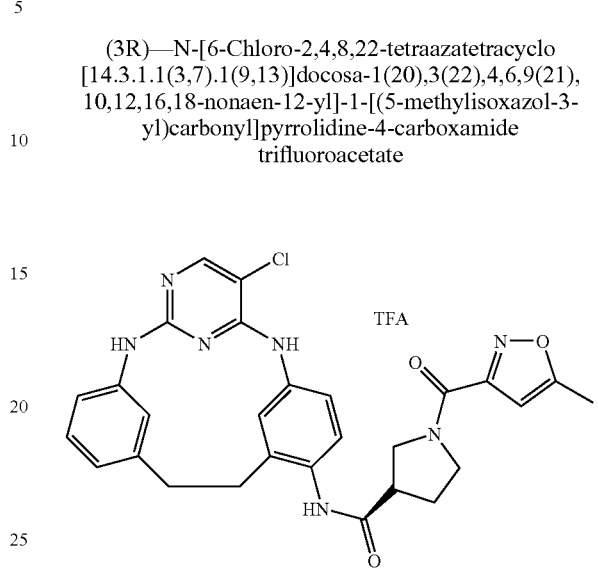

The desired compound was prepared according to the procedure of Example A20, using (3R)—N-[6-chloro-2,4,8,22-tetraazatetracyclo[14.3.1.1(3,7).1(9,13)]docosa-1(20),3(22),4,6,9(21),10,12,16,18-nonaen-12-yl]pyrrolidine-3-carboxamide bis(trifluoroacetate) and 5-methylisoxazole-3-carbonyl chloride as starting materials in 60% yield. $^1$H NMR (300 MHz, DMSO-d$_6$): δ 9.57 (m, 1H), 9.47 (s, 1H), 9.38 (s, 1H), 8.12 (s, 1H), 7.98 (s, 1H), 7.73 (s, 1H), 7.21 (m, 1H), 7.04 (m, 2H), 6.87 (d, 2H), 6.78 (m, 1H), 6.50 (s, 1H), 3.78 (m, 4H), 3.30 (m, 1H), 2.82 (m, 4H), 2.46 (s, 3H), 2.20 (m, 2H). LCMS for $C_{28}H_{27}ClN_7O_3$ (M+H)$^+$: m/z=544.2.

Example A123

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-{4-[(5-methylisoxazol-3-yl)carbonyl]piperazin-1-yl}acetamide bis(trifluoroacetate)

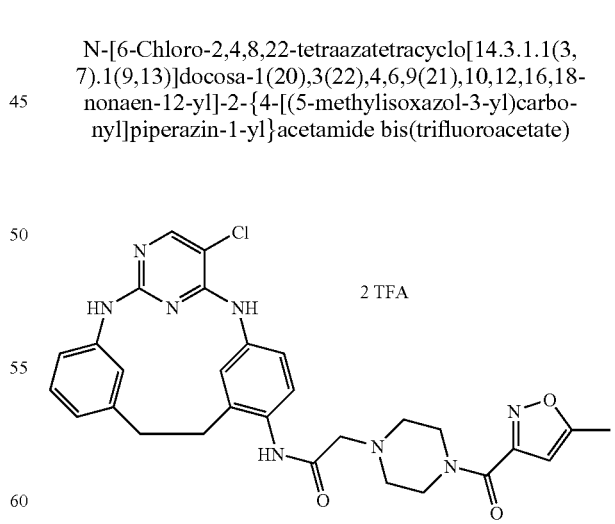

The desired compound was prepared according to the procedure of Example A20, using tert-butyl-4-(2-[{6-chloro-2,4,8,22-tetraazatetracyclo[14.3.1.1(3,7).1(9,13)]docosa-1(20),3(22),4,6,9(21),10,12,16,18-nonaen-12-yl]amino}-2-oxoethyl)piperazine-1-carboxylate bis(trifluoroacetate) and 5-methylisoxazole-3-carbonyl chloride as starting materials in 56% yield. LCMS for $C_{29}H_{30}ClN_8O_3$ (M+H)$^+$: m/z=573.2.

Example A124

N-[6-Chloro-2,4,8,22-tetraazatetracyclo[14.3.1.1(3,7).1(9,13)]docosa-1(20),3(22),4,6,9(21),10,12,16,18-nonaen-12-yl]-3-{1-[(5-methylisoxazol-3-yl)carbonyl]piperidin-4-yl}propanamide trifluoroacetate

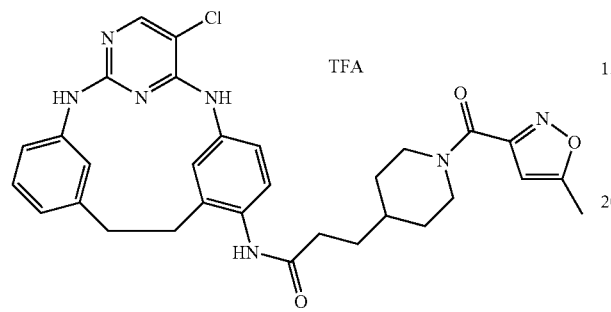

The desired compound was prepared according to the procedure of Example A20, using N-[6-chloro-2,4,8,22-tetraazatetracyclo[14.3.1.1(3,7).1(9,13)]docosa-1(20),3(22),4,6,9(21),10,12,16,18-nonaen-12-yl]-3piperidin-4-ylpropanamide bis(trifluoroacetate) and 5-methylisoxazole-3-carbonyl chloride as starting materials in 54% yield. $^1$H NMR (300 MHz, DMSO-d$_6$): δ 9.43 (s, 1H), 9.34 (m, 2H), 8.12 (s, 1H), 7.98 (s, 1H), 7.73 (s, 1H), 7.21 (d, 1H), 7.04 (m, 2H), 6.87 (d, 1H), 6.78 (d, 1H), 6.40 (s, 1H), 4.42 (m, 2H), 3.88 (m, 2H), 3.03 (m, 2H), 2.83 (m, 4H), 2.45 (s, 3H), 2.27 (m, 2H), 1.80 (m, 2H), 1.60 (m, 2H), 1.10 (m, 1H). LCMS for $C_{31}H_{33}ClN_7O_3$ (M+H)$^+$: m/z=586.2.

Example A125

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-3-{1-[(5-methylisoxazol-3-yl)carbonyl]piperidin-4-yl}propanamide bis(trifluoroacetate)

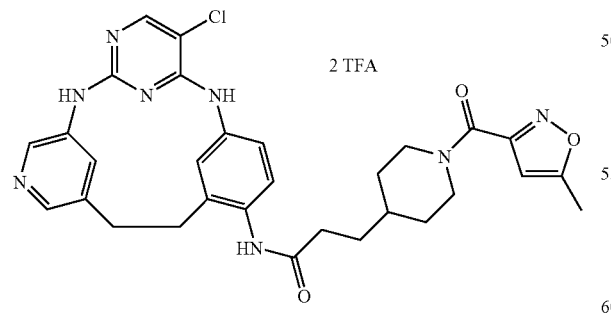

The desired compound was prepared according to the procedure of Example A20, using N-[6-chloro-2,4,8,18,22-pentaazatetracyclo[14.3.1.1(3,7).1(9,13)]docosa-1(20),3(22),4,6,9(21),10,12,16,18-nonaen-12-yl]-3piperidin-4-ylpropanamide tris(trifluoroacetate) and 5-methylisoxazole-3-carbonyl chloride as starting materials in 48% yield. $^1$H NMR (300 MHz, DMSO-d$_6$): δ 10.04 (s, 1H), 9.40 (s, 2H), 9.02 (m, 1H), 8.30 (s, 2H), 8.21 (s, 1H), 7.68 (s, 1H), 7.30 (d, 1H), 7.04 (d, 1H), 6.40 (s, 1H), 4.42 (m, 2H), 3.88 (m, 2H), 3.03 (m, 2H), 2.97 (m, 4H), 2.45 (s, 3H), 2.40 (m, 2H), 1.80 (m, 2H), 1.60 (m, 2H), 1.10 (m, 1H). LCMS for $C_{30}H_{32}ClN_8O_3$ (M+H)$^+$: m/z=587.2.

Example A126

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-(1-[1,3]oxazolo[5,4-b]pyridin-2-ylpiperidin-4-yl)acetamide bis(trifluoroacetate)

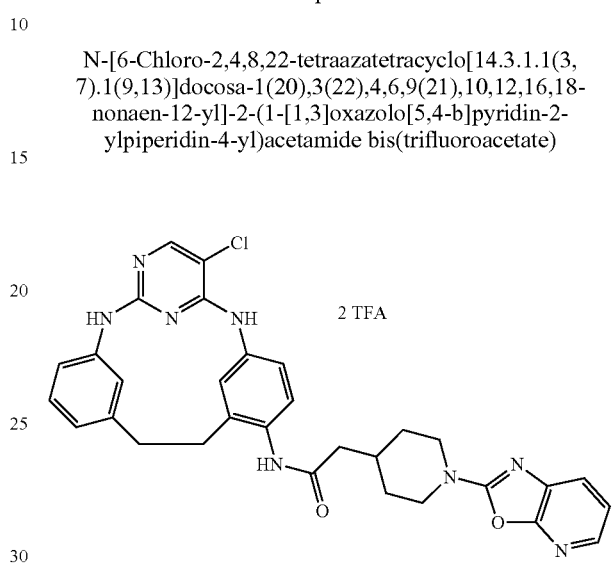

The desired compound was prepared according to the procedure of Example A118 using N-[6-chloro-2,4,8,22-tetraazatetracyclo[14.3.1.1(3,7).1(9,13)]docosa-1(20),3(22),4,6,9(21),10,12,16,18-nonaen-12-yl]-2-piperidin-4-ylacetamide bis(trifluoroacetate) as the starting material in 12% yield. LCMS for $C_{31}H_{30}ClN_8O_2$ (M+H)$^+$: m/z=581.2.

Example A127

2-(4-Acetylpiperazin-1-yl)-N-[6-chloro-2,4,8,18,22-pentaazatetracyclo[14.3.1.1(3,7).1(9,13)]docosa-1(20),3(22),4,6,9(21),10,12,16,18-nonaen-12-yl]acetamide tris(trifluoroacetate)

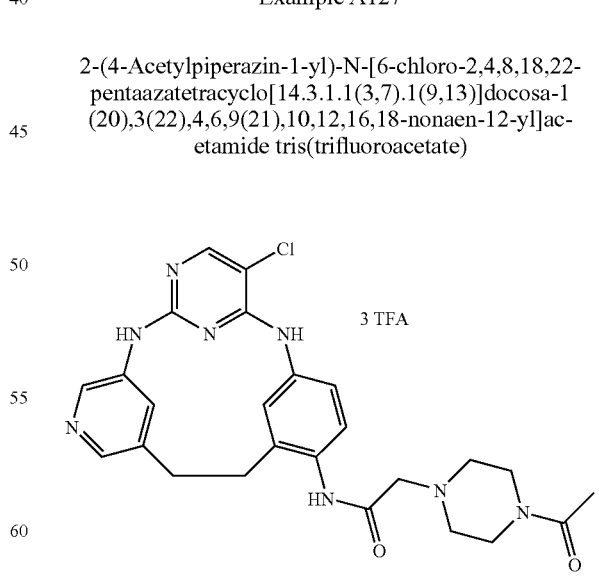

The desired compound was prepared according to the procedure of Example A20, using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperazin-1-

Example A128

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(isoxazol-5-ylcarbonyl)piperidin-4-yl]acetamide bis(trifluoroacetate)

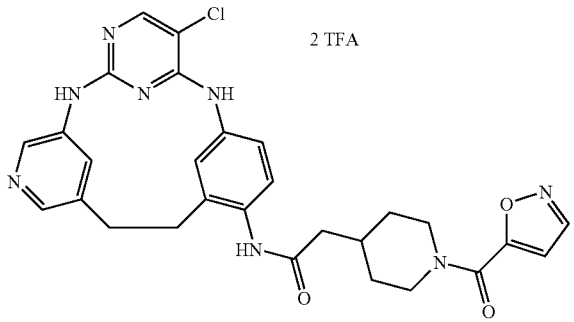 [SMILES: O=C(CC1CCN(C(=O)c2ccno2)CC1)Nc1ccc2cc1CCc1cncc(c1)Nc1ncc(Cl)c(n1)N2 ; "2 TFA"]

The desired compound was prepared according to the procedure of Example A20, using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and isoxazole-5-carbonyl chloride as starting materials in 59% yield. $^1$H NMR (300 MHz, DMSO-$d_6$): δ 9.50 (d, 2H), 9.16 (s, 1H), 8.83 (s, 1H), 8.40 (s, 2H), 8.33 (s, 1H), 7.78 (s, 1H), 7.40 (d, 1H), 7.19 (d, 1H), 7.00 (s, 1H), 4.52 (m, 1H), 3.88 (m, 1H), 3.32 (m, 1H), 3.03 (s, 4H), 2.42 (m, 2H), 2.21 (m, 1H), 1.93 (m, 2H), 1.39 (m, 2H). LCMS for $C_{28}H_{28}ClN_8O_3$ (M+H)$^+$: m/z=559.2.

Example A129

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(1-methyl-1H-pyrazol-4-yl)carbonyl]piperidin-4-yl}acetamide bis(trifluoroacetate)

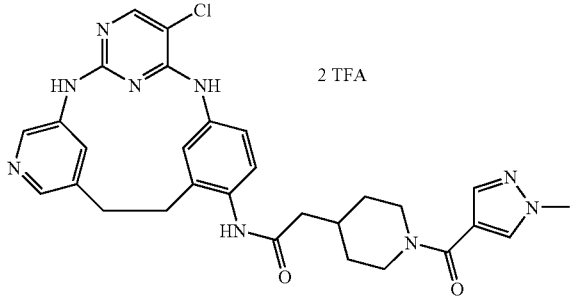 [SMILES: Cn1cc(C(=O)N2CCC(CC(=O)Nc3ccc4cc3CCc3cncc(c3)Nc3ncc(Cl)c(n3)N4)CC2)cn1 ; "2 TFA"]

The desired compound was prepared according to the procedure of Example A20, using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and 1-methyl-1H-pyrazoleacetamide tris(trifluoroacetate) and acetyl chloride as starting materials in 35% yield. LCMS for $C_{25}H_{28}ClN_8O_2$ (M+H)$^+$: m/z=507.2.

4-carbonyl chloride as starting materials in 42% yield. LCMS for $C_{29}H_{31}ClN_9O_2$ (M+H)$^+$: m/z=572.2.

Example A130

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(1-methyl-1H-pyrazol-3-yl)carbonyl]piperidin-4-yl}acetamide bis(trifluoroacetate)

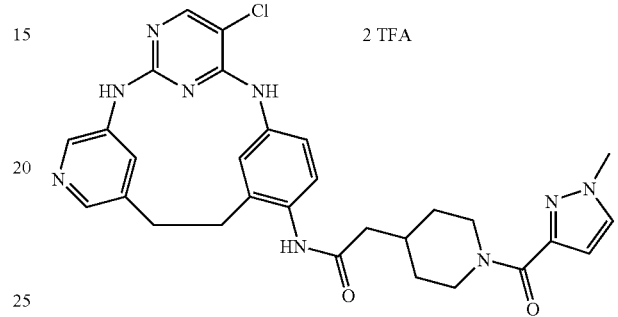

The desired compound was prepared according to the procedure of Example A20, using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and 1-methyl-1H-pyrazole-3-carbonyl chloride as starting materials in 36% yield. $^1$H NMR (300 MHz, DMSO-$d_6$): δ 10.08 (s, 1H), 9.41 (s, 2H), 9.02 (s, 1H), 8.30 (m, 2H), 8.20 (s, 1H), 7.72 (s, 1H), 7.65 (s, 1H), 7.30 (d, 1H), 7.05 (d, 1H), 6.47 (s, 1H), 4.52 (m, 2H), 3.83 (s, 3H), 3.12 (m, 1H), 2.98 (m, 4H), 2.77 (m, 1H), 2.32 (m, 2H), 2.12 (m, 1H), 1.80 (m, 2H), 1.20 (m, 2H). LCMS for $C_{29}H_{31}ClN_9O_2$ (M+H)$^+$: m/z=572.2.

Example A131

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(5-methylisoxazol-4-yl)carbonyl]piperidin-4-yl}acetamide bis(trifluoroacetate)

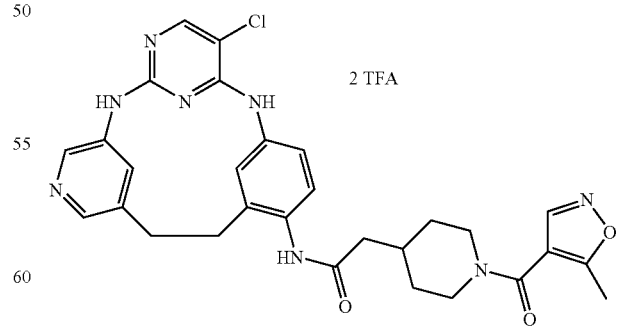

The desired compound was prepared according to the procedure of Example A20, using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4- ylacetamide tris(trifluoroacetate) and 5-methylisoxazole-4-carbonyl chloride as starting materials in 44% yield. ¹H NMR (300 MHz, DMSO-d₆): δ 10.05 (s, 1H), 9.41 (s, 2H), 9.02 (s, 1H), 8.65 (s, 1H), 8.33 (s, 2H), 8.20 (s, 1H), 7.65 (s, 1H), 7.30 (d, 1H), 7.05 (d, 1H), 4.42 (m, 1H), 3.70 (m, 1H), 3.12 (m, 2H), 2.98 (m, 4H), 2.49 (s, 3H), 2.30 (m, 2H), 2.12 (m, 1H), 1.80 (m, 2H), 1.20 (m, 2H). LCMS for $C_{29}H_{30}ClN_8O_3$ (M+H)⁺: m/z=573.2.

Example A132

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(4-methyl-1,3-oxazol-5-yl)carbonyl]piperidin-4-yl}acetamide bis(trifluoroacetate)

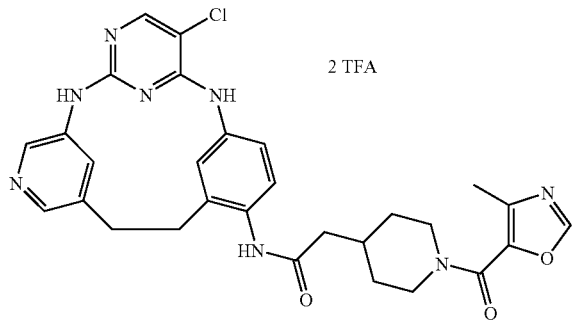 [SMILES: Cc1ncoc1C(=O)N1CCC(CC(=O)Nc2ccc3cc2CCc2cncc(c2)Nc2ncc(Cl)c(n2)N3)CC1 ; "2 TFA"]

The desired compound was prepared according to the procedure of Example A20, using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and 4-methyl-1,3-oxazole-5-carbonyl chloride as starting materials in 37% yield. ¹H NMR (300 MHz, DMSO-d₆): δ 10.02 (s, 1H), 9.41 (m, 2H), 9.02 (s, 1H), 8.40 (s, 1H), 8.30 (s, 2H), 8.20 (s, 1H), 7.65 (s, 1H), 7.30 (d, 1H), 7.05 (d, 1H), 4.52 (m, 2H), 3.12 (m, 1H), 2.98 (m, 4H), 2.32 (m, 2H), 2.21 (s, 3H), 2.12 (m, 1H), 1.80 (m, 2H), 1.20 (m, 2H). LCMS for $C_{29}H_{30}ClN_8O_3$ (M+H)⁺: m/z=573.2.

Example A133

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(1,3-thiazol-2-ylcarbonyl)piperidin-4-yl]acetamide bis(trifluoroacetate)

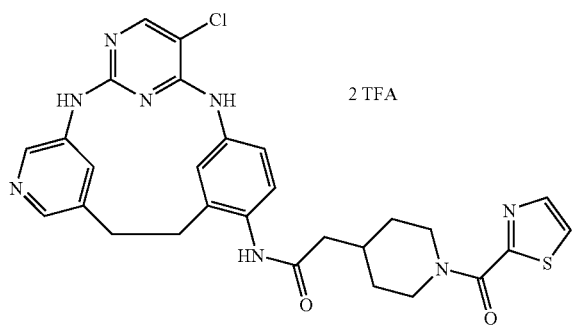 [SMILES: O=C(CC1CCN(C(=O)c2nccs2)CC1)Nc1ccc2cc1CCc1cncc(c1)Nc1ncc(Cl)c(n1)N2 ; "2 TFA"]

The desired compound was prepared according to the procedure of Example A20, using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and 1,3-thiazole-2-carbonyl chloride as starting materials in 37% yield. ¹H NMR (300 MHz, DMSO-d₆): δ 10.04 (s, 1H), 9.41 (m, 2H), 9.02 (s, 1H), 8.30 (m, 2H), 8.20 (s, 1H), 8.00 (m, 2H), 7.65 (s, 1H), 7.30 (d, 1H), 7.05 (d, 1H), 5.20 (m, 1H), 4.48 (m, 1H), 3.22 (m, 2H), 2.98 (m, 4H), 2.32 (m, 2H), 2.12 (m, 1H), 1.80 (m, 2H), 1.25 (m, 2H). LCMS for $C_{28}H_{28}ClN_8O_2S$ (M+H)⁺: m/z=575.2.

Example A134

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(1-methyl-1H-imidazol-5yl)carbonyl]piperidin-4-yl}acetamide bis(trifluoroacetate)

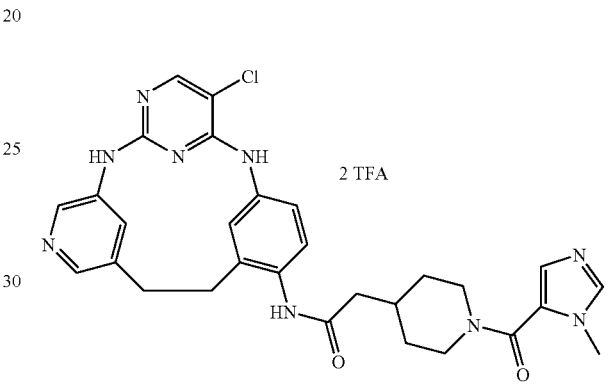

The desired compound was prepared according to the procedure of Example A20, using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and 1-methyl-1H-imidazole-5-carbonyl chloride as starting materials in 31% yield. ¹H NMR (300 MHz, DMSO-d₆): δ 9.97 (s, 1H), 9.41 (s, 1H), 9.38 (s, 1H), 8.97 (s, 1H), 8.91 (s, 1H), 8.22 (m, 3H), 7.85 (s, 1H), 7.65 (s, 1H), 7.30 (d, 1H), 7.05 (d, 1H), 4.00 (m, 2H), 3.83 (s, 3H), 2.98 (m, 6H), 2.32 (m, 2H), 2.12 (m, 1H), 1.80 (m, 2H), 1.20 (m, 2H). LCMS for $C_{29}H_{31}ClN_9O_2$ (M+H)⁺: m/z=572.2.

Example A135

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(isoxazol-3-ylcarbonyl)piperidin-4-yl]acetamide bis(trifluoroacetate)

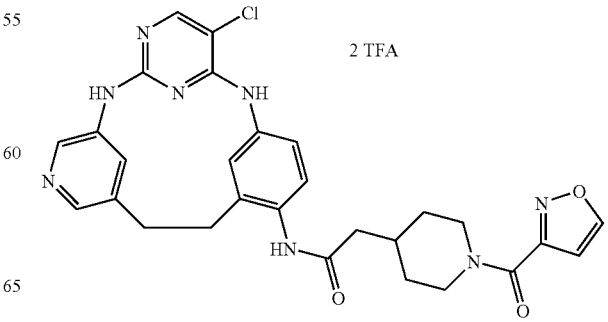

The desired compound was prepared according to the procedure of Example A27 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and isoxazole-3-carboxylic acid as starting materials in 37% yield. $^1$H NMR (300 MHz, DMSO-d$_6$): δ 10.04 (s, 1H), 9.41 (m, 2H), 9.02 (m, 2H), 8.30 (m, 2H), 8.20 (s, 1H), 7.64 (s, 1H), 7.30 (d, 1H), 7.05 (d, 1H), 6.80 (s, 1H), 4.52 (m, 1H), 3.83 (m, 1H), 3.18 (m, 2H), 2.98 (m, 4H), 2.32 (m, 2H), 2.12 (m, 1H), 1.80 (m, 2H), 1.20 (m, 2H). LCMS for C$_{28}$H$_{28}$ClN$_8$O$_3$ (M+H)$^+$: m/z=559.2.

Example A136

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(1H-1,2,4-triazol-3-ylcarbonyl)piperidin-4-yl]acetamide bis(trifluoroacetate)

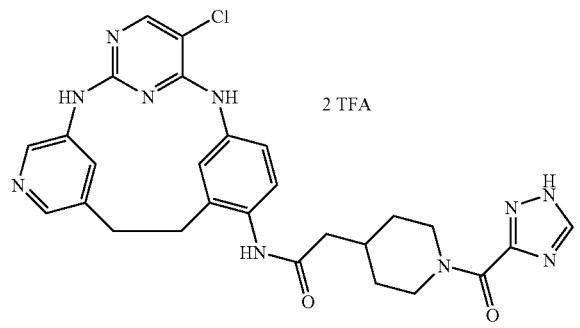 [SMILES: O=C(CC1CCN(C(=O)c2nc[nH]n2)CC1)Nc1ccc2cc1CCc1cncc(c1)Nc1ncc(Cl)c(n1)N2 ; "2 TFA"]

The desired compound was prepared according to the procedure of Example A27 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and 1H-1,2,4-triazole-3-carboxylic acid as starting materials in 43% yield. LCMS for C$_{27}$H$_{28}$ClN$_{10}$O$_2$ (M+H)$^+$: m/z=559.2.

Example A137

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(1H-1,2,3-triazol-4-ylcarbonyl)piperidin-4-yl]acetamide bis(trifluoroacetate)

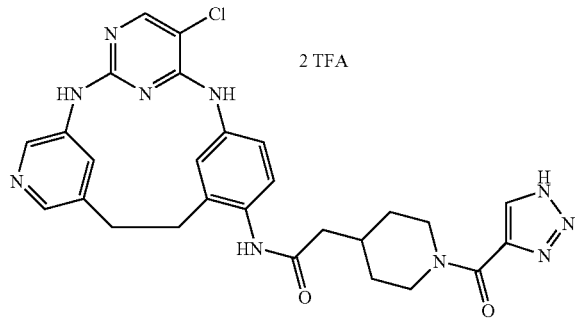 [SMILES: O=C(CC1CCN(C(=O)c2c[nH]nn2)CC1)Nc1ccc2cc1CCc1cncc(c1)Nc1ncc(Cl)c(n1)N2 ; "2 TFA"]

The desired compound was prepared according to the procedure of Example A27 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and 2H-1,2,3-triazole-4-carboxylic acid as starting materials in 48% yield. $^1$H NMR (300 MHz, DMSO-d$_6$): δ 10.12 (s, 1H), 9.41 (m, 2H), 9.15 (s, 1H), 8.32 (m, 2H), 8.21 (m, 2H), 7.65 (s, 1H), 7.30 (d, 1H), 7.05 (d, 1H), 4.52 (m, 2H), 3.19 (m, 2H), 2.99 (m, 4H), 2.32 (m, 2H), 2.12 (m, 1H), 1.80 (m, 2H), 1.20 (m, 2H). LCMS for C$_{27}$H$_{28}$ClN$_{10}$O$_2$ (M+H)$^+$: m/z=559.2.

Example A138

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(1,2,5-oxadiazol-3-ylcarbonyl)piperidin-4-yl]acetamide bis(trifluoroacetate)

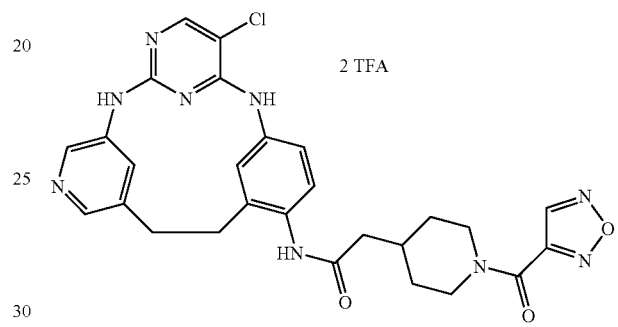

The desired compound was prepared according to the procedure of Example A20, using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and 1,2,5-oxadiazole-3-carbonyl chloride as starting materials in 33% yield. $^1$H NMR (300 MHz, DMSO-d$_6$): δ 10.08 (s, 1H), 9.41 (s, 2H), 9.02 (s, 1H), 8.30 (m, 2H), 8.20 (s, 1H), 7.72 (s, 1H), 7.65 (s, 1H), 7.30 (d, 1H), 7.05 (d, 1H), 6.47 (s, 1H), 4.38 (m, 1H), 4.02 (m, 1H), 3.19 (m, 2H), 2.98 (m, 4H), 2.32 (m, 2H), 2.12 (m, 1H), 1.80 (m, 2H), 1.20 (m, 2H). LCMS for C$_{27}$H$_{27}$ClN$_9$O$_3$ (M+H)$^+$: m/z=560.2.

Example A139

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(1,3-oxazol-2-ylcarbonyl)piperidin-4-yl]acetamide bis(trifluoroacetate)

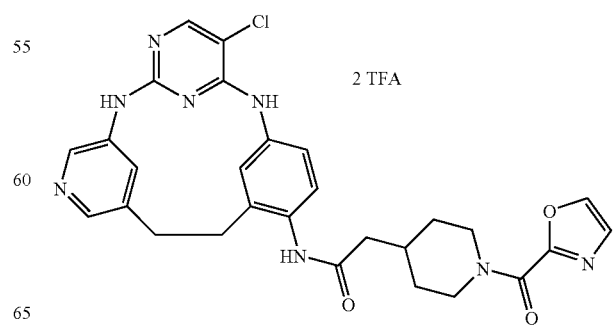

The desired compound was prepared according to the procedure of Example A27 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and 1,3-oxazole-2-carboxylic acid as starting materials in 31% yield. LCMS for $C_{28}H_{28}ClN_8O_3$ (M+H)$^+$: m/z=559.2.

Example A140

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-(1-isopropylpiperidin-4-yl)acetamide tris(trifluoroacetate)

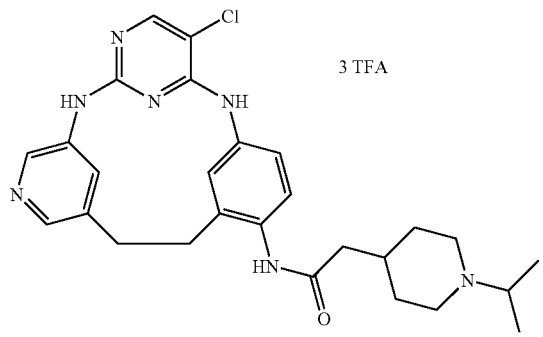 [SMILES: "3 TFA" ; CC(C)N1CCC(CC(=O)Nc2ccc3cc2CCc2cncc(c2)Nc2ncc(Cl)c(n2)N3)CC1]

The desired compound was prepared according to the procedure of Example A111, using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and 2-bromopropane as starting materials in 28% yield. LCMS for $C_{27}H_{33}ClN_7O$ (M+H)$^+$: m/z=506.2.

Example A141

4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-(2-cyanophenyl)piperidine-1-carboxamide bis(trifluoroacetate)

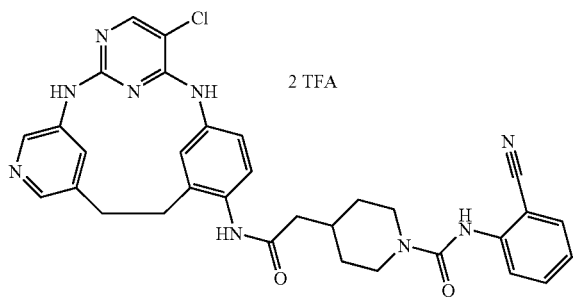 [SMILES: N#Cc1ccccc1NC(=O)N1CCC(CC(=O)Nc2ccc3cc2CCc2cncc(c2)Nc2ncc(Cl)c(n2)N3)CC1 ; "2 TFA"]

The desired compound was prepared according to the procedure of Example A9, step H using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and 2-isocyanatobenzonitrile as starting materials in 57% yield. LCMS for $C_{32}H_{31}ClN_9O_2$ (M+H)$^+$: m/z=608.2.

Example A142

4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-(3-cyanophenyl)piperidine-1-carboxamide bis(trifluoroacetate)

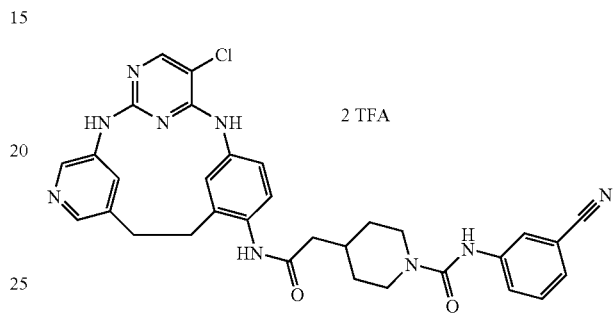

The desired compound was prepared according to the procedure of Example A9, step H using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and 3-isocyanatobenzonitrile as starting materials in 8% yield. LCMS for $C_{32}H_{31}ClN_9O_2$ (M+H)$^+$: m/z=608.2.

Example A143

4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-(4-cyanophenyl)piperidine-1-carboxamide bis(trifluoroacetate)

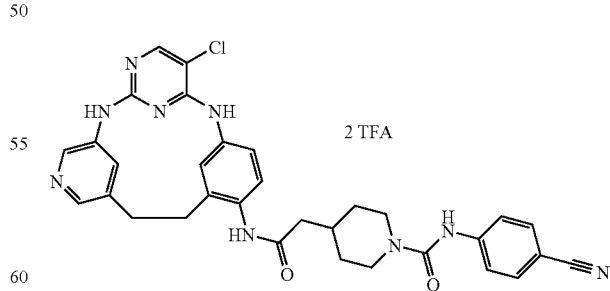

The desired compound was prepared according to the procedure of Example A9, step H using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and 4-isocyanatobenzonitrile as starting materials in 35% yield. LCMS for $C_{32}H_{31}ClN_9O_2$ (M+H)$^+$: m/z=608.2.

Example A144

4-(2-{[6-Chloro-2,4,8,18,22-pentaazatetracyclo [14.3.1.1(3,7).1(9,13)]docosa-1(20),3(22),4,6,9(21), 10,12,16,18-nonaen-12-yl]amino}-2-oxoethyl)-N-pyridin-3-ylpiperidine-1-carboxamide bis (trifluoroacetate)

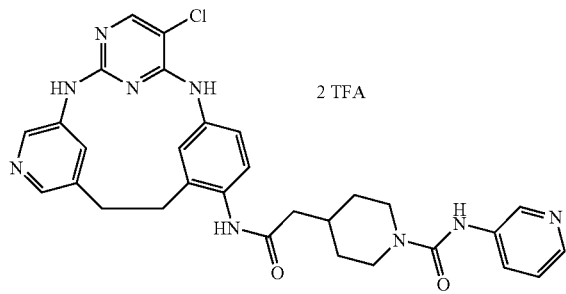 [SMILES: O=C(CC1CCN(C(=O)Nc2cccnc2)CC1)Nc1ccc2cc1CCc1cncc(c1)Nc1ncc(Cl)c(n1)N2 ; "2 TFA"]

The desired compound was prepared according to the procedure of Example A9, step H using N-[6-chloro-2,4,8,18, 22-pentaazatetracyclo[14.3.1.1(3,7).1(9,13)]docosa-1(20),3 (22),4,6,9(21),10,12,16,18-nonaen-12-yl]-2-piperidin-4-ylacetamide tris(trifluoroacetate) and 3-isocyanatopyridine as starting materials in 46% yield. $^1$H NMR (300 MHz, DMSO-d$_6$): δ 10.00 (s, 1H), 9.41 (m, 2H), 9.24 (s, 1H), 8.98 (s, 2H), 8.40 (m, 1H), 8.30 (m, 3H), 8.20 (s, 1H), 7.72 (m, 1H), 7.65 (s, 1H), 7.30 (d, 1H), 7.05 (d, 1H), 4.15 (m, 2H), 2.98 (m, 6H), 2.32 (m, 2H), 2.12 (m, 1H), 1.80 (m, 2H), 1.20 (m, 2H). LCMS for $C_{30}H_{31}ClN_9O_2$ (M+H)$^+$: m/z=584.2.

Example A145

4-(2-{[6-Chloro-2,4,8,18,22-pentaazatetracyclo [14.3.1.1(3,7).1(9,13)]docosa-1(20),3(22),4,6,9(21), 10,12,16,18-nonaen-12-yl]amino}-2-oxoethyl)-N-(3, 5-dimethylisoxazol-4-yl)piperidine-1-carboxamide bis(trifluoroacetate)

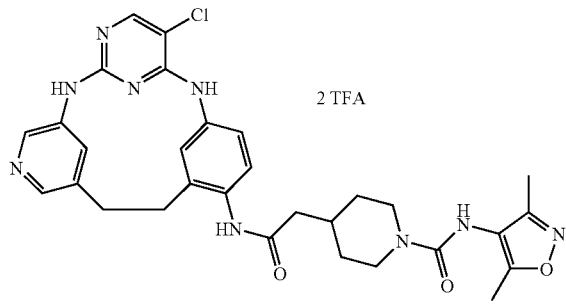 [SMILES: Cc1noc(C)c1NC(=O)N1CCC(CC(=O)Nc2ccc3cc2CCc2cncc(c2)Nc2ncc(Cl)c(n2)N3)CC1 ; "2 TFA"]

The desired compound was prepared according to the procedure of Example A9, step H using N-[6-chloro-2,4,8,18, 22-pentaazatetracyclo[14.3.1.1(3,7).1(9,13)]docosa-1(20),3 (22),4,6,9(21),10,12,16,18-nonaen-12-yl]-2-piperidin-4-ylacetamide tris(trifluoroacetate) and 4-isocyanato-3,5-dimethylisoxazole as starting materials in 30% yield. $^1$H NMR (300 MHz, DMSO-d$_6$): δ 10.02 (s, 1H), 9.41 (m, 2H), 9.00 (s, 1H), 8.30 (m, 2H), 8.20 (s, 1H), 7.88 (s, 1H), 7.67 (s, 1H), 7.30 (d, 1H), 7.05 (d, 1H), 4.02 (m, 2H), 2.98 (m, 4H), 2.80 (m, 2H), 2.32 (m, 2H), 2.20 (s, 3H), 2.12 (m, 4H), 1.80 (m, 2H), 1.20 (m, 2H). LCMS for $C_{30}H_{33}ClN_9O_3$ (M+H)$^+$: m/z=602.2.

Example A146

4-(2-{[6-Chloro-2,4,8,18,22-pentaazatetracyclo [14.3.1.1(3,7).1(9,13)]docosa-1(20),3(22),4,6,9(21), 10,12,16,18-nonaen-12-yl]amino}-2-oxoethyl)-N-(2-fluorophenyl)piperidine-1-carboxamide bis (trifluoroacetate)

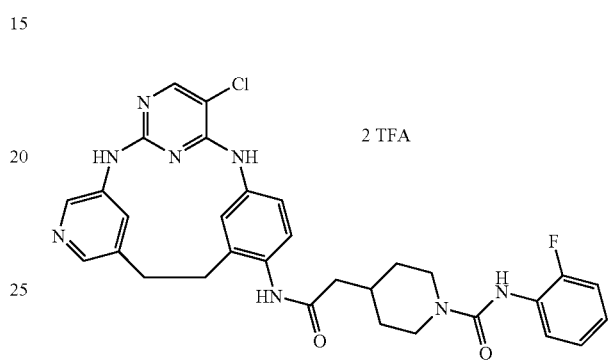

The desired compound was prepared according to the procedure of Example A9, step H using N-[6-chloro-2,4,8,18, 22-pentaazatetracyclo[14.3.1.1(3,7).1(9,13)]docosa-1(20),3 (22),4,6,9(21),10,12,16,18-nonaen-12-yl]-2-piperidin-4-ylacetamide tris(trifluoroacetate) and 1-fluoro-2-isocyanatobenzene as starting materials in 51% yield. $^1$H NMR (300 MHz, DMSO-d$_6$): δ 10.04 (s, 1H), 9.41 (m, 2H), 9.02 (s, 1H), 8.25 (m, 4H), 7.65 (s, 1H), 7.30 (m, 2H), 7.05 (m, 4H), 4.09 (m, 2H), 2.98 (m, 4H), 2.83 (m, 2H), 2.32 (m, 2H), 2.02 (m, 1H), 1.75 (m, 2H), 1.21 (m, 2H). LCMS for $C_{31}H_{31}ClFN_8O_2$ (M+H)$^+$: m/z=601.2.

Example A147

4-(2-{[6-Chloro-2,4,8,18,22-pentaazatetracyclo [14.3.1.1(3,7).1(9,13)]docosa-1(20),3(22),4,6,9(21), 10,12,16,18-nonaen-12-yl]amino}-2-oxoethyl)-N-(3-fluorophenyl)piperidine-1-carboxamide bis (trifluoroacetate)

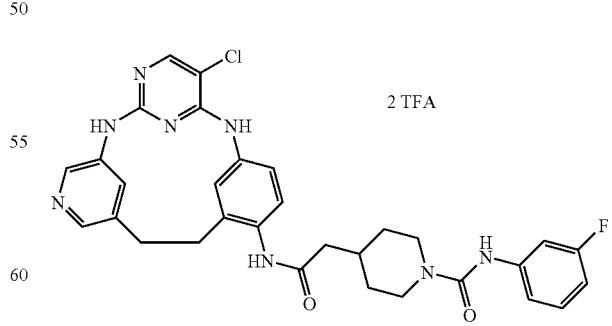

The desired compound was prepared according to the procedure of Example A9, step H using N-[6-chloro-2,4,8,18, 22-pentaazatetracyclo[14.3.1.1(3,7).1(9,13)]docosa-1(20),3 (22),4,6,9(21),10,12,16,18-nonaen-12-yl]-2-piperidin-4- ylacetamide tris(trifluoroacetate) and 1-fluoro-3-isocyanatobenzene as starting materials in 39% yield. LCMS for $C_{31}H_{31}ClFN_8O_2$ (M+H)$^+$: m/z=601.2.

Example A148

4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-(4-fluorophenyl)piperidine-1-carboxamide bis(trifluoroacetate)

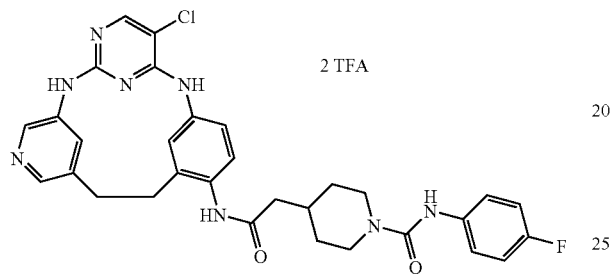

The desired compound was prepared according to the procedure of Example A9, step H using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and 1-fluoro-4-isocyanatobenzene as starting materials in 32% yield. LCMS for $C_{31}H_{31}ClFN_8O_2$ (M+H)$^+$: m/z=601.2.

Example A149

4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-(2-methylphenyl)piperidine-1-carboxamide bis(trifluoroacetate)

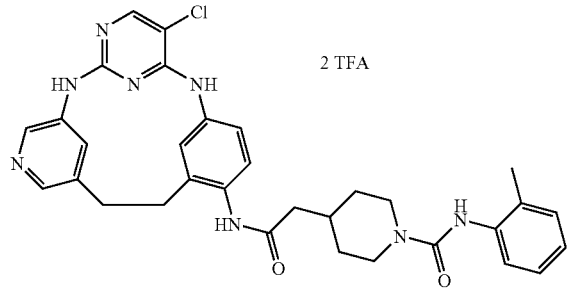 [SMILES: Cc1ccccc1NC(=O)N1CCC(CC(=O)Nc2ccc3cc2CCc2cncc(c2)Nc2ncc(Cl)c(n2)N3)CC1 ; "2 TFA"]

The desired compound was prepared according to the procedure of Example A9, step H using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and 1-isocyanato-2-methylbenzene as starting materials in 31% yield. LCMS for $C_{32}H_{34}ClN_8O_2$ (M+H)$^+$: m/z=597.2.

Example A150

4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-(3-methylphenyl)piperidine-1-carboxamide bis(trifluoroacetate)

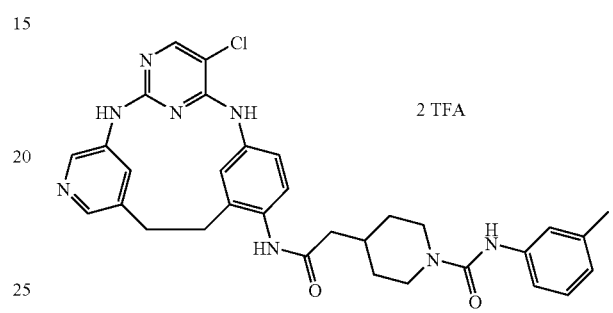

The desired compound was prepared according to the procedure of Example A9, step H using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and 1-isocyanato-3-methylbenzene as starting materials in 27% yield. LCMS for $C_{32}H_{34}ClN_8O_2$ (M+H)$^+$: m/z=597.2.

Example A151

4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-(4-methylphenyl)piperidine-1-carboxamide bis(trifluoroacetate)

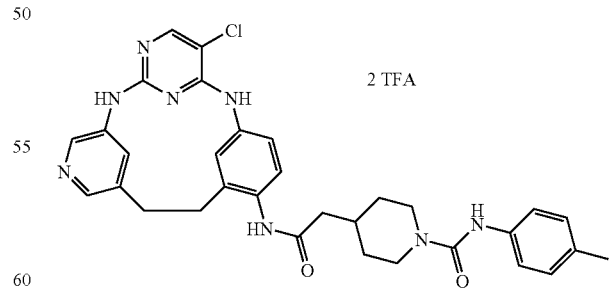

The desired compound was prepared according to the procedure of Example A9, step H using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and 1-isocyanato-4- methylbenzene as starting materials in 30% yield. LCMS for $C_{32}H_{34}ClN_8O_2$ (M+H)⁺: m/z=597.2.

Example A152

4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-(2-methoxyphenyl)piperidine-1-carboxamide bis(trifluoroacetate)

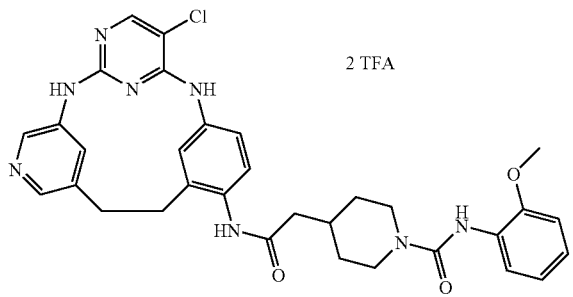 [SMILES: COc1ccccc1NC(=O)N1CCC(CC(=O)Nc2ccc3cc2CCc2cncc(c2)Nc2ncc(Cl)c(n2)N3)CC1 ; "2 TFA"]

The desired compound was prepared according to the procedure of Example A9, step H using N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and 1-isocyanato-2-methoxybenzene as starting materials in 30% yield. LCMS for $C_{32}H_{34}ClN_8O_3$ (M+H)⁺: m/z=613.2.

Example A153

4-(2-{[6-chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-(3-methoxyphenyl)piperidine-1-carboxamide bis(trifluoroacetate)

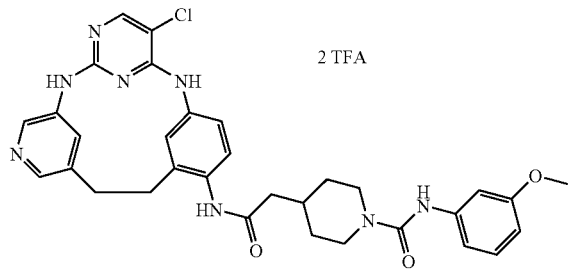 [SMILES: COc1cccc(NC(=O)N2CCC(CC(=O)Nc3ccc4cc3CCc3cncc(c3)Nc3ncc(Cl)c(n3)N4)CC2)c1 ; "2 TFA"]

The desired compound was prepared according to the procedure of Example A9, step H using N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and 1-isocyanato-3- methoxybenzene as starting materials in 26% yield. LCMS for $C_{32}H_{34}ClN_8O_3$ (M+H)⁺: m/z=613.2.

Example A154

4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-(4-methoxyphenyl)piperidine-1-carboxamide bis(trifluoroacetate)

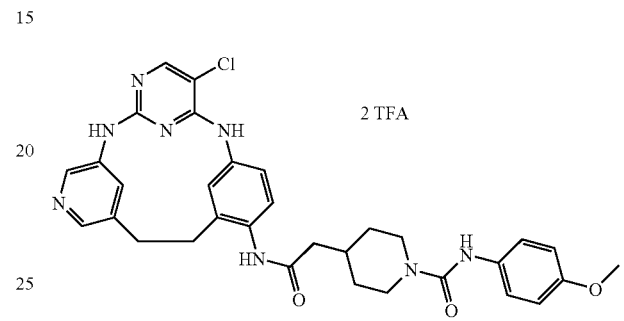

The desired compound was prepared according to the procedure of Example A9, step H using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and 1-isocyanato-4-methoxybenzene as starting materials in 26% yield. LCMS for $C_{32}H_{34}ClN_8O_3$ (M+H)⁺: m/z=613.2.

Example A155

N-Benzyl-4-(2-{[6-chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)piperidine-1-carboxamide bis(trifluoroacetate)

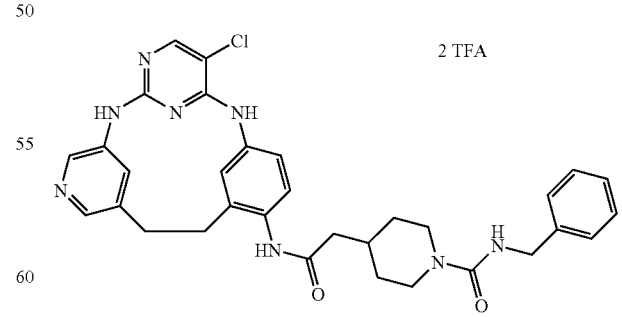

The desired compound was prepared according to the procedure of Example A9, step H using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4- ylacetamide tris(trifluoroacetate) and benzyl isocyanate as starting materials in 35% yield. LCMS for $C_{32}H_{34}ClN_8O_2$ (M+H)$^+$: m/z=597.2.

Example A156

N-[6-Chloro-2,4,8,18,22-pentaazatetracyclo[14.3.1.1 (3,7).1(9,13)]docosa-1(20),3(22),4,6,9(21),10,12,16, 18-nonaen-12-yl]-2-{1-[(3,5-dimethylisoxazol-4-yl) carbonyl]piperidin-4-yl}acetamide bis (trifluoroacetate)

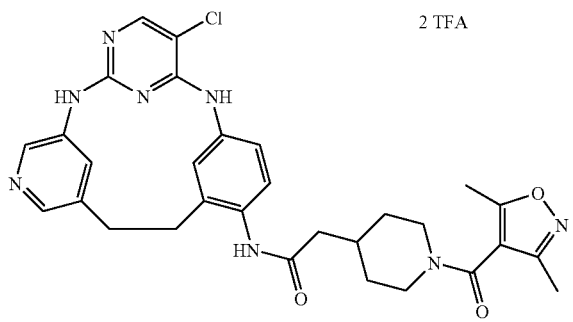 [SMILES: Cc1noc(C)c1C(=O)N1CCC(CC(=O)Nc2ccc3cc2CCc2cncc(c2)Nc2ncc(Cl)c(n2)N3)CC1 ; "2 TFA"]

The desired compound was prepared according to the procedure of Example A20, using N-[6-chloro-2,4,8,18,22-pentaazatetracyclo[14.3.1.1(3,7).1(9,13)]docosa-1(20),3(22),4, 6,9(21),10,12,16,18-nonaen-12-yl]-2-piperidin-4-ylacetamide tris(trifluoroacetate) and 3,5-dimethylisoxazole-4-carbonyl chloride as starting materials (43% yield). LCMS for $C_{30}H_{32}ClN_8O_3$ (M+H)$^+$: m/z=587.2.

Example A157

2-[1-(1,3-Benzothiazol-2-yl)piperidin-4-yl]-N-[6-chloro-2,4,8,18,22-pentaazatetracyclo[14.3.1.1(3,7) .1(9,13)]docosa-1(20),3(22),4,6,9(21),10,12,16,18-nonaen-12-yl]acetamide tris(trifluoroacetate)

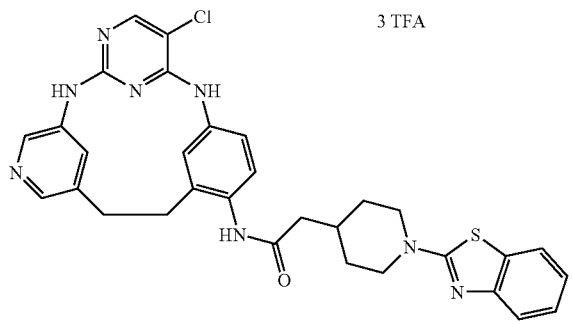 [SMILES: "3 TFA" ; O=C(CC1CCN(c2nc3ccccc3s2)CC1)Nc1ccc2cc1CCc1cncc(c1)Nc1ncc(Cl)c(n1)N2]

A solution of N-[6-chloro-2,4,8,18,22-pentaazatetracyclo [14.3.1.1(3,7).1(9,13)]docosa-1(20),3(22),4,6,9(21),10,12, 16,18-nonaen-12-yl]-2-piperidin-4-ylacetamide tris(trifluoroacetate) (10 mg, 0.0144 mmol), 2-chloro-benzothiazole (20.7 mg, 0.122 mmol) was heated at 80° C. for 1 hour. Then the solution was diluted with MeOH and purified on LC/MS using pH2 buffer to give the desired compound in 11% yield. LCMS for $C_{31}H_{30}ClN_8OS$ (M+H)$^+$: m/z=597.2.

Example A158

N-[6-Chloro-2,4,8,18,22-pentaazatetracyclo[14.3.1.1 (3,7).1(9,13)]docosa-1(20),3(22),4,6,9(21),10,12,16, 18-nonaen-12-yl]-2-(1-[1,3]oxazolo[5,4-b]pyridin-2-ylpiperidin-4-yl)acetamide tris(trifluoroacetate)

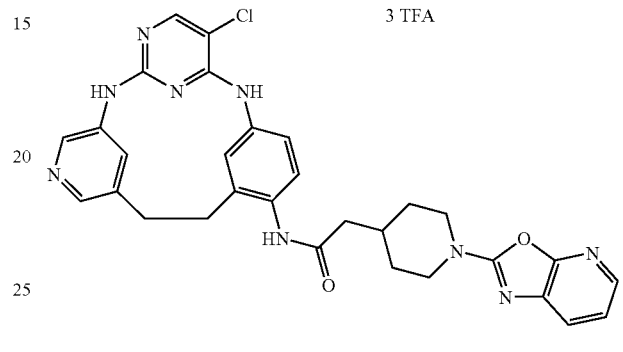

The desired compound was prepared according to the procedure of Example A118, using N-[6-chloro-2,4,8,18,22-pentaazatetracyclo[14.3.1.1(3,7).1(9,13)]docosa-1(20),3 (22),4,6,9(21),10,12,16,18-nonaen-12-yl]-2-piperidin-4-ylacetamide tris(trifluoroacetate) as the starting material in 14% yield. LCMS for $C_{30}H_{29}ClN_9O_2$ (M+H)$^+$: m/z=582.2.

Example A159

N-[6-Chloro-2,4,8,18,22-pentaazatetracyclo[14.3.1.1 (3,7).1(9,13)]docosa-1(20),3(22),4,6,9(21),10,12,16, 18-nonaen-12-yl]-2-[1-(1,3-thiazol-2-yl)piperidin-4-yl]acetamide tris(trifluoroacetate)

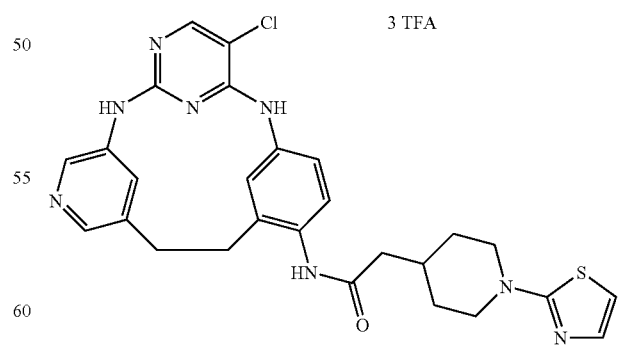

The desired compound was prepared according to the procedure of Example A157, using N-[6-chloro-2,4,8,18,22-pentaazatetracyclo[14.3.1.1(3,7).1(9,13)]docosa-1(20),3 (22),4,6,9(21),10,12,16,18-nonaen-12-yl]-2-piperidin-4-

Example A160

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(2-methyl-3-furoyl)piperidin-4-yl]acetamide bis(trifluoroacetate)

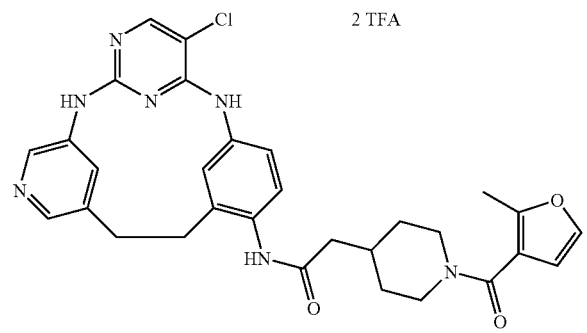 [SMILES: Cc1occc1C(=O)N1CCC(CC(=O)Nc2ccc3cc2CCc2cncc(c2)Nc2ncc(Cl)c(n2)N3)CC1 ; "2 TFA"]

The desired compound was prepared according to the procedure of Example A27, using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide bis(trifluoroacetate) and 2-methyl-3-furoic acid as starting materials in 60% yield. LCMS for $C_{30}H_{31}ClN_7O_3$ (M+H)$^+$: m/z=572.2.

Example A161

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(3-methyl-2-furoyl)piperidin-4-yl]acetamide bis(trifluoroacetate)

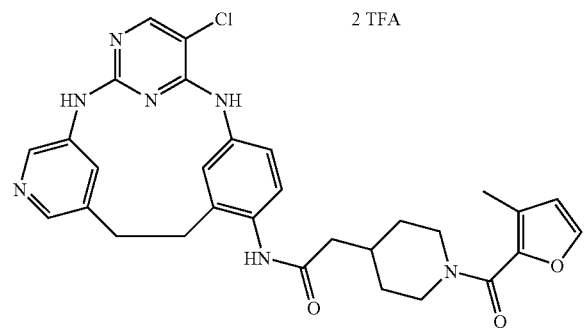 [SMILES: Cc1ccoc1C(=O)N1CCC(CC(=O)Nc2ccc3cc2CCc2cncc(c2)Nc2ncc(Cl)c(n2)N3)CC1 ; "2 TFA"]

The desired compound was prepared according to the procedure of Example A27, using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and 2-chloro-1,3-thiazole as starting materials in 12% yield. LCMS for $C_{27}H_{28}ClN_8OS$ (M+H)$^+$: m/z=547.2.

Example A162

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(5-methyl-2-furoyl)piperidin-4-yl]acetamide bis(trifluoroacetate)

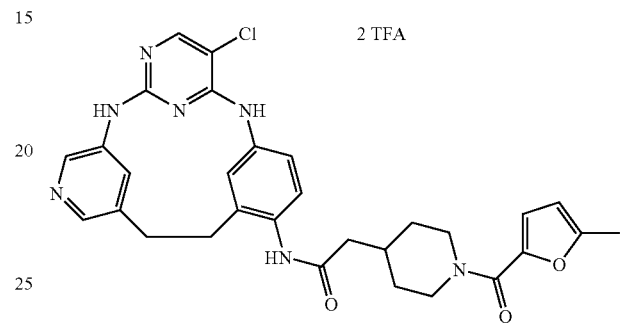

The desired compound was prepared according to the procedure of Example A27, using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide bis(trifluoroacetate) and 3-methyl-2-furoic acid as starting materials in 51% yield. LCMS for $C_{30}H_{31}ClN_7O_3$ (M+H)$^+$: m/z=572.2.

The desired compound was prepared according to the procedure of Example A27, using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide bis(trifluoroacetate) and 5-methyl-2-furoic acid as starting materials in 46% yield. LCMS for $C_{30}H_{31}ClN_7O_3$ (M+H)$^+$: m/z=572.2.

Example A163

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(5-methyl-1H-pyrazol-3-yl)carbonyl]piperidin-4-yl}acetamide bis(trifluoroacetate)

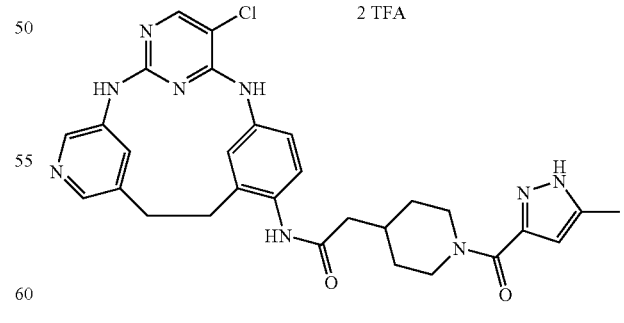

The desired compound was prepared according to the procedure of Example A27, using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide bis(trifluoroacetate) and 5-methyl-1H-pyrazole- 3-carboxylic acid as starting materials in 29% yield. LCMS for $C_{29}H_{31}ClN_9O_2$ (M+H)$^+$: m/z=572.2.

Example A164

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(1-methyl-1H-imidazol-2-yl)carbonyl]piperidin-4-yl}acetamide bis(trifluoroacetate)

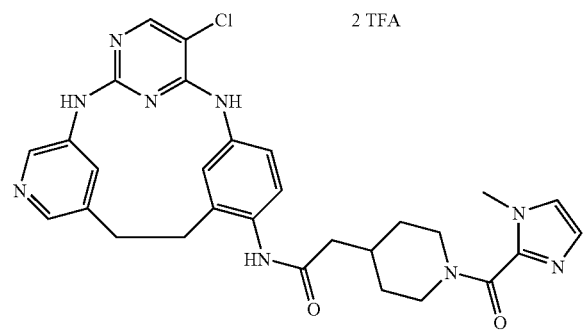 [SMILES: Cn1ccnc1C(=O)N1CCC(CC(=O)Nc2ccc3cc2CCc2cncc(c2)Nc2ncc(Cl)c(n2)N3)CC1 ; "2 TFA"]

The desired compound was prepared according to the procedure of Example A27, using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide bis(trifluoroacetate) and 1-methyl-1H-imidazole-2-carboxylic acid as starting materials in 70% yield. LCMS for $C_{29}H_{31}ClN_9O_2$ (M+H)$^+$: m/z=572.2.

Example A165

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(3-methylisoxazol-4-yl)carbonyl]piperidin-4-yl}acetamide bis(trifluoroacetate)

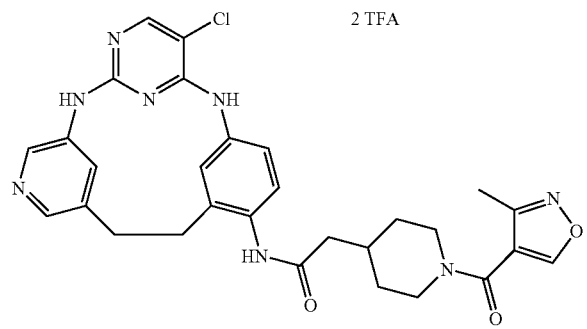 [SMILES: Cc1nocc1C(=O)N1CCC(CC(=O)Nc2ccc3cc2CCc2cncc(c2)Nc2ncc(Cl)c(n2)N3)CC1 ; "2 TFA"]

The desired compound was prepared according to the procedure of Example A27, using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide bis(trifluoroacetate) and 3-methylisoxazole-4- carboxylic acid as starting materials in 55% yield. LCMS for $C_{29}H_{30}ClN_8O_3$ (M+H)$^+$: m/z=573.2.

Example A166

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(4-methyl-1,2,5-oxadiazol-3-yl)carbonyl]piperidin-4-yl}acetamide bis(trifluoroacetate)

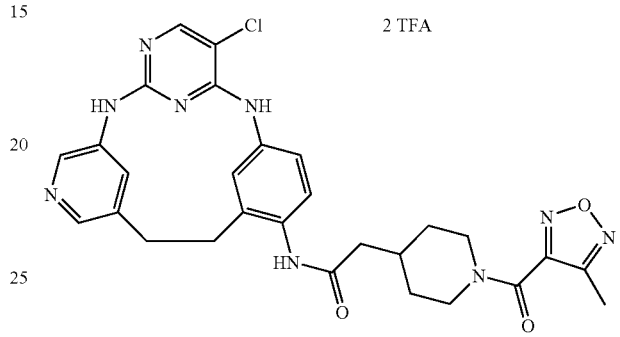

The desired compound was prepared according to the procedure of Example A27, using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide bis(trifluoroacetate) and 4-methyl-1,2,5-oxadiazole-3-carboxylic acid as starting materials in 44% yield. LCMS for $C_{28}H_{29}ClN_9O_3$ (M+H)$^+$: m/z=574.2.

Example A167

2-{1-[(4-Amino-1,2,5-oxadiazol-3-yl)carbonyl]piperidin-4-yl}-N-[6-chloro-2,4,8,18,22-pentaazatetracyclo[14.3.1.1(3,7).1(9,13)]docosa-1(20),3(22),4,6,9(21),10,12,16,18-nonaen-12-yl]acetamide tris(trifluoroacetate)

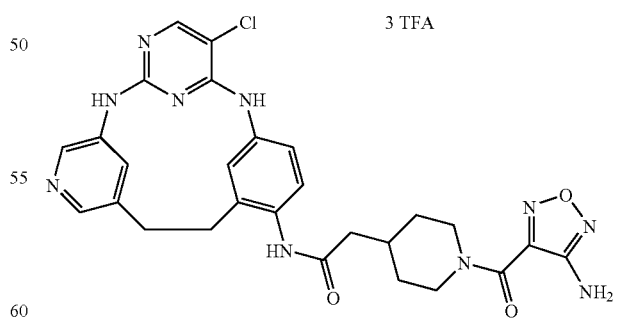

The desired compound was prepared according to the procedure of Example A27, using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide bis(trifluoroacetate) and 4-amino-1,2,5- oxadiazole-3-carboxylic acid as starting materials in 41% yield. LCMS for $C_{27}H_{28}ClN_{10}O_3$ (M+H)$^+$: m/z=575.2.

Example A168

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(isothiazol-5-ylcarbonyl)piperidin-4-yl]acetamide bis(trifluoroacetate)

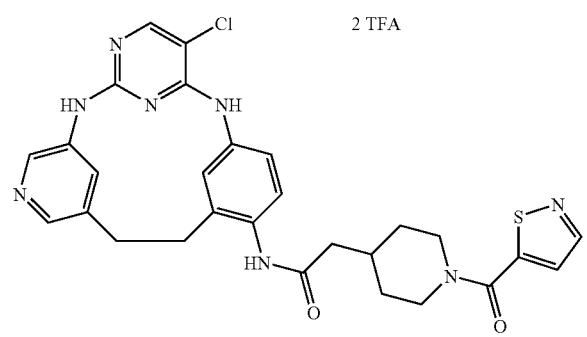 [SMILES: O=C(CC1CCN(C(=O)c2ccns2)CC1)Nc1ccc2cc1CCc1cncc(c1)Nc1ncc(Cl)c(n1)N2 ; "2 TFA"]

The desired compound was prepared according to the procedure of Example A27, using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide bis(trifluoroacetate) and isothiazole-5-carboxylic acid as starting materials in 55% yield. LCMS for $C_{28}H_{28}ClN_8O_2S$ (M+H)$^+$: m/z=575.2.

Example A169

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(5-fluoropyrimidin-2-yl)piperidin-4-yl]acetamide tris(trifluoroacetate)

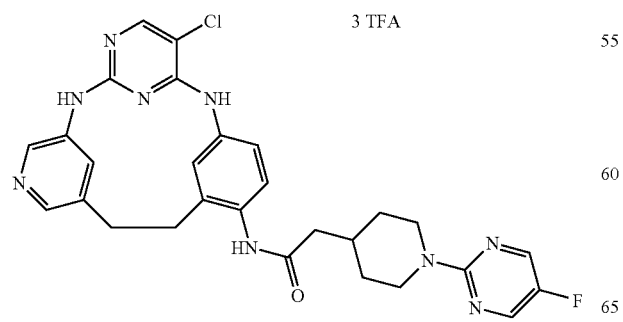

Step A.
[1-(5-Fluoropyrimidin-2-yl)piperidin-4-yl]acetic acid trifluoroacetate

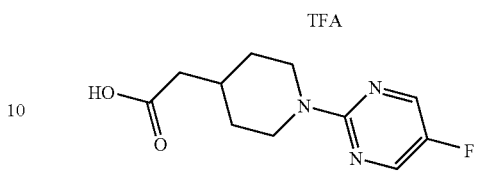

Methyl piperidin-4-ylacetate (100 mg, 0.6 mmol), 2-chloro-5-fluoropyrimidine (250 mg, 1.9 mmol) and N,N-diisopropylethylamine (330 µL, 1.9 mmol) were stirred in N-methylpyrrolidinone (1 mL) and heated to 150° C. for 20 minutes in a microwave. Purification by preparative LCMS (pH 2) gave the ester intermediate which was saponified by stirring in methanol (1 mL) and 2 N aqueous sodium hydroxide solution (1 mL) for 1 hour. Neutralization and purification by preparative LCMS gave the desired compound in 50% yield. LCMS for $C_{11}H_{15}FN_3O_2$ (M+H)$^+$: m/z=240.1.

Step B. N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(5-fluoropyridin-2-yl)piperidin-4-yl]acetamide tris(trifluoroacetate)

A solution of [1-(5-fluoropyrimidin-2-yl)piperidin-4-yl]acetic acid trifluoroacetate (9.0 mg, 0.029 mmol), N,N,N',N'-tetramethyl-O-(7-azabenzotriazol-1-yl)uronium hexafluorophosphate (17 mg, 0.043 mmol) and N,N-diisopropylethylamine (12.6 µL, 0.0722 mmol) in N,N-dimethylformamide (0.5 mL) was stirred for 15 minutes. To this reaction mixture, a solution of 6-chloro-2,4,8,18,22-pentaazatetracyclo[14.3.1.1(3,7).1(9,13)]docosa-1(20),3(22),4,6,9(21),10,12,16,18-nonaen-12-amine tris(trifluoroacetate) and N,N-diisopropylethylamine (12.6 µL, 0.0722 mmol) in N,N-dimethylformamide (0.5 mL) was added and the mixture was stirred for 1.5 hours. Purification by preparative LCMS (pH 2) gave the desired compound in 68% yield. LCMS for $C_{28}H_{25}ClFN_9O$ (M+H)$^+$: m/z=560.2.

Example A170

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-(1-pyridin-2-ylpiperidin-4-yl)acetamide tris(trifluoroacetate)

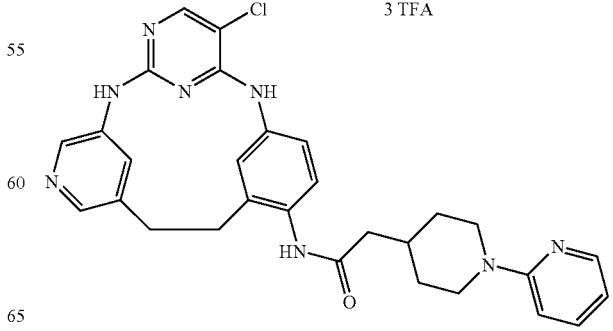

Step A. (1-Pyridin-2-ylpiperidin-4-yl)acetic acid trifluoroacetate

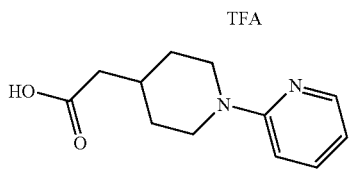 [SMILES: "TFA" ; O=C(O)CC1CCN(c2ccccn2)CC1]

The desired compound was prepared according to the procedure of Example A169, step A using 2-fluoropyridine as starting material in 30% yield. LCMS for $C_{12}H_{17}N_2O_2$ $(M+H)^+$: m/z=221.1.

Step B. N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-(1-pyridin-2-ylpiperidin-4-yl)acetamide tris(trifluoroacetate)

The desired compound was prepared according to the procedure of Example A169, step B using (1-pyridin-2-ylpiperidin-4-yl)acetic acid trifluoroacetate as starting material in 50% yield. LCMS for $C_{29}H_{30}ClN_8O$ $(M+H)^+$: m/z=541.2.

Example A171

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-(1-pyrazin-2-ylpiperidin-4-yl)acetamide tris(trifluoroacetate)

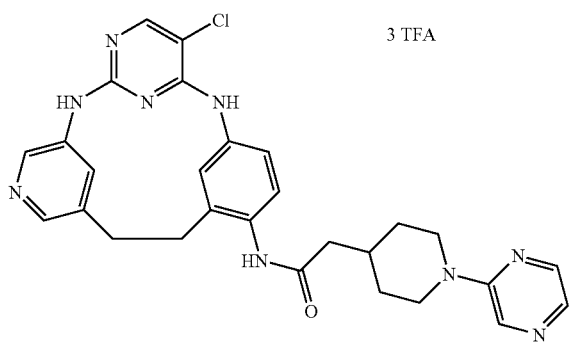 [SMILES: O=C(CC1CCN(c2cnccn2)CC1)Nc1ccc2cc1CCc1cncc(c1)Nc1ncc(Cl)c(n1)N2]

Step A. (1-Pyrazin-2-ylpiperidin-4-yl)acetic acid trifluoroacetate

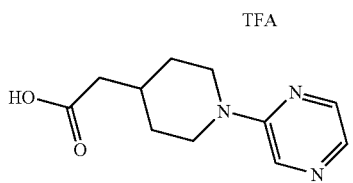 [SMILES: O=C(O)CC1CCN(c2cnccn2)CC1]

The desired compound was prepared according to the procedure of Example A169, step A using 2-chloropyrazine as starting material in 50% yield. LCMS for $C_{11}H_{16}N_3O_2$ $(M+H)^+$: m/z=222.1.

Step B. N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-(1-pyrazin-2-ylpiperidin-4-yl)acetamide tris(trifluoroacetate)

The desired compound was prepared according to the procedure of Example A169, step B using (1-pyrazin-2-ylpiperidin-4-yl)acetic acid trifluoroacetate as starting material in 34% yield. LCMS for $C_{28}H_{29}ClN_9O$ $(M+H)^+$: m/z=542.2.

Example A172

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-(1-pyrimidin-2-ylpiperidin-4-yl)acetamide tris(trifluoroacetate)

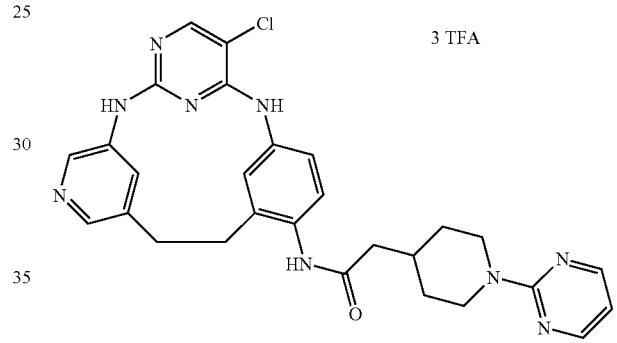

Step A. (1-Pyrimidin-2-ylpiperidin-4-yl)acetic acid trifluoroacetate

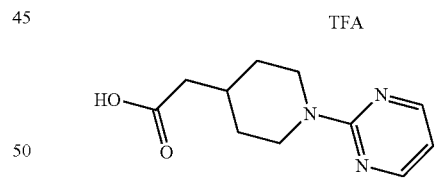

The desired compound was prepared according to the procedure of Example A169, step A using 2-chloropyrimidine as starting material in 40% yield. LCMS for $C_{11}H_{16}N_3O_2$ $(M+H)^+$: m/z=222.1.

Step B. N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-(1-pyrimidin-2-ylpiperidin-4-yl)acetamide tris(trifluoroacetate)

The desired compound was prepared according to the procedure of Example A169, step B using (1-pyrimidin-2-ylpiperidin-4-yl)acetic acid trifluoroacetate as starting material in 70% yield. $^1$H NMR (300 MHz, DMSO-d$_6$): δ 10.10 (s, 1H), 9.41 (m, 2H), 9.10 (s, 1H), 8.37 (m, 4H), 8.22 (s, 1H), 7.68 (s, 1H), 7.31 (m, 1H), 7.09 (m, 1H), 6.59 (m, 1H), 4.62 (m, 2H), 2.92 (m, 6H), 2.30 (m, 2H), 2.10 (m, 1H), 1.79 (m, 2H), 1.10 (m, 2H). LCMS for $C_{28}H_{29}ClN_9O$ (M+H)$^+$: m/z=542.2.

Example A173

N-[6-Chloro-2,4,8,18,22-pentaazatetracyclo[14.3.1.1 (3,7).1(9,13)]docosa-1(20),3(22),4,6,9(21),10,12,16, 18-nonaen-12-yl]-2-[1-(6-methylpyridazin-3-yl)piperidin-4-yl]acetamide tris(trifluoroacetate)

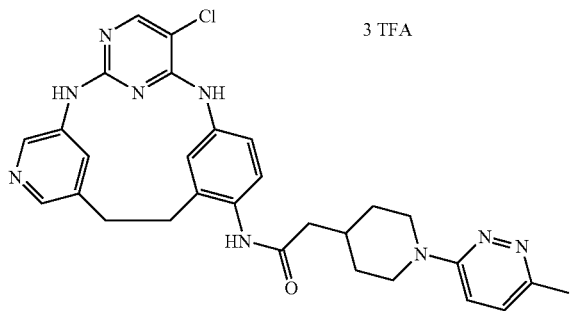 [SMILES: Cc1ccc(N2CCC(CC(=O)Nc3ccc4cc3CCc3cncc(c3)Nc3ncc(Cl)c(n3)N4)CC2)nn1]

Step A.
[1-(6-Methylpyridazin-3-yl)piperidin-4-yl]acetic acid trifluoroacetate

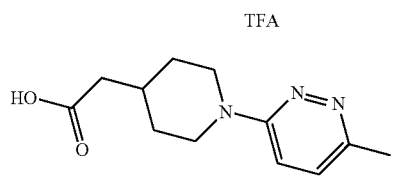 [SMILES: Cc1ccc(N2CCC(CC(=O)O)CC2)nn1]

The desired compound was prepared according to the procedure of Example A169, step A using 3-chloro-6-methylpyridazine as starting material in 10% yield. LCMS for $C_{12}H_{18}N_3O_2$ (M+H)$^+$: m/z=236.1.

Step B. N-[6-Chloro-2,4,8,18,22-pentaazatetracyclo [14.3.1.1(3,7).1(9,13)]docosa-1(20),3(22),4,6,9(21), 10,12,16,18-nonaen-12-yl]-2-[1-(6-methylpyridazin-3-yl)piperidin-4-yl)acetamide tris(trifluoroacetate)

The desired compound was prepared according to the procedure of Example A169, step B using [1-(6-methylpyridazin-3-yl)piperidin-4-yl)acetic acid trifluoroacetate as starting material in 62% yield. LCMS for $C_{29}H_{30}ClN_9O$ (M+H)$^+$: m/z=556.2.

Example A174

N-[6-Chloro-2,4,8,22-tetraazatetracyclo[14.3.1.1(3, 7).1(9,13)]docosa-1(20),3(22),4,6,9(21),10,12,16,18-nonaen-12-yl]-2-[1-(1,3,4-thiadiazol-2-yl)piperidin-4-yl]acetamide tris(trifluoroacetate)

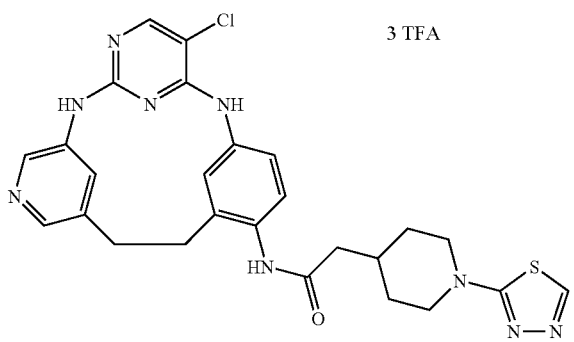 [SMILES: O=C(CC1CCN(c2nncs2)CC1)Nc1ccc2cc1CCc1cncc(c1)Nc1ncc(Cl)c(n1)N2]

Step A.
[1-(1,3,4-Thiadiazol-2-yl)piperidin-4-yl]acetic acid trifluoroacetate

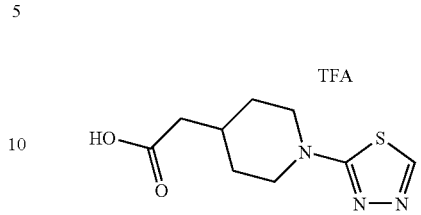

The desired compound was prepared according to the procedure of Example A169, step A using 2-bromo-1,3,4-thiadiazole as starting material in 30% yield. LCMS for $C_9H_{14}N_3O_2S$ (M+H)$^+$: m/z=228.1.

Step B. N-[6-Chloro-2,4,8,18,22-pentaazatetracyclo [14.3.1.1(3,7).1(9,13)]docosa-1(20),3(22),4,6,9(21), 10,12,16,18-nonaen-12-yl]-2-[1-(1,3,4-thiadiazol-2-yl)piperidin-4-yl]acetamide tris(trifluoroacetate)

The desired compound was prepared according to the procedure of Example A169, step B using [1-(1,3,4-thiadiazol-2-yl)piperidin-4-yl]acetic acid trifluoroacetate as starting material in 79% yield. LCMS for $C_{26}H_{27}ClN_9OS$ (M+H)$^+$: m/z=548.2.

Example A175

N-[6-Chloro-2,4,8,22-tetraazatetracyclo[14.3.1.1(3, 7).1(9,13)]docosa-1(20),3(22),4,6,9(21),10,12,16,18-nonaen-12-yl]-2-{1-[(5-methyl-1H-pyrazol-3-yl)carbonyl]piperidin-4-yl}acetamide bis(trifluoroacetate)

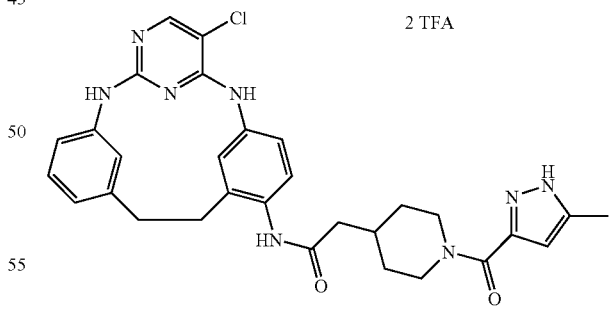

The desired compound was prepared according to the procedure of Example A27 using of N-[6-chloro-2,4,8,22-tetraazatetracyclo[14.3.1.1(3,7).1(9,13)]docosa-1(20), 3(22),4, 6,9(21),10,12,16,18-nonaen-12-yl]piperidine-4-carboxamide bis(trifluoroacetate) and 5-methyl-1H-pyrazole-3-carboxylic acid as starting materials in 27% yield. LCMS for $C_{30}H_{32}ClN_8O_2$ (M+H)$^+$: m/z=571.2.

Example A176

N-[6-Chloro-2,4,8,18,22-pentaazatetracyclo[14.3.1.1 (3,7).1(9,13)]docosa-1(20),3(22),4,6,9(21),10,12,16, 18-nonaen-12-yl]-2-[1-(4-methylpyridin-2-yl)piperidin-4-yl]acetamide tris(trifluoroacetate)

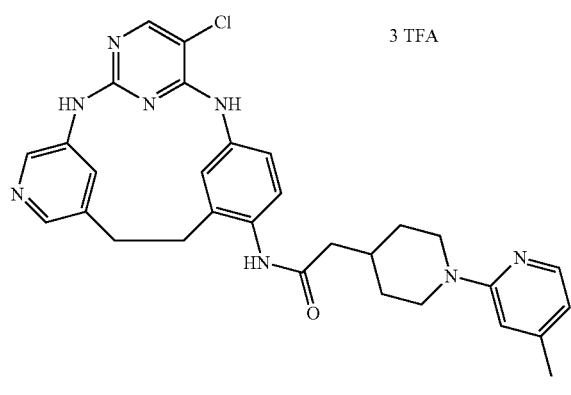 [SMILES: Cc1ccnc(N2CCC(CC(=O)Nc3ccc4cc3CCc3cncc(c3)Nc3ncc(Cl)c(n3)N4)CC2)c1]

Step A.
[1-(4-Methylpyridin-2-yl)piperidin-4-yl]acetic acid trifluoroacetate

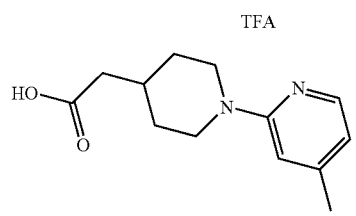 [SMILES: Cc1ccnc(N2CCC(CC(=O)O)CC2)c1]

The desired compound was prepared according to the procedure of Example A169, step A using 2-fluoro-4-methylpyridine as starting material in 8% yield. LCMS for $C_{13}H_{19}N_2O_2$ $(M+H)^+$: m/z=235.1.

Step B. N-[6-Chloro-2,4,8,18,22-pentaazatetracyclo [14.3.1.1(3,7).1(9,13)]docosa-1(20),3(22),4,6,9(21), 10,12,16,18-nonaen-12-yl]-2-[1-(4-ethylpyridin-2-yl)piperidin-4-yl]acetamide tris(trifluoroacetate)

The desired compound was prepared according to the procedure of Example A169, step B using [1-(4-methylpyridin-2-yl)piperidin-4-yl]acetic acid trifluoroacetate as starting material in 38% yield. LCMS for $C_{30}H_{32}ClN_8O$ $(M+H)^+$: m/z=555.2.

Example A177

N-[6-Chloro-2,4,8,18,22-pentaazatetracyclo[14.3.1.1 (3,7).1(9,13)]docosa-1(20),3(22),4,6,9(21),10,12,16, 18-nonaen-12-yl]-2-[1-(3-cyanopyridin-2-yl)piperidin-4-yl]acetamide tris(trifluoroacetate)

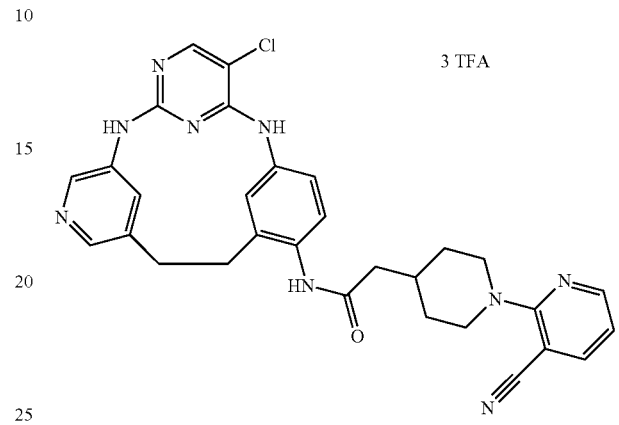

Step A.
[1-(3-Cyanopyridin-2-yl)piperidin-4-yl]acetic acid trifluoroacetate

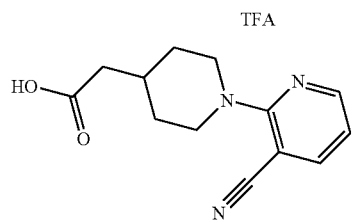 [SMILES: N#Cc1cccnc1N1CCC(CC(=O)O)CC1]

The desired compound was prepared according to the procedure of Example A169, step A using 2-chloronicotinonitrile as starting material in 33% yield. LCMS for $C_{13}H_{16}N_3O_2$ $(M+H)^+$: m/z=246.1.

Step B. N-[6-Chloro-2,4,8,18,22-pentaazatetracyclo [14.3.1.1(3,7).1(9,13)]docosa-1(20),3(22),4,6,9(21), 10,12,16,18-nonaen-12-yl]-2-[6-(3-cyanopyridin-2-yl)piperidin-4-yl]acetamide tris(trifluoroacetate)

The desired compound was prepared according to the procedure of Example A169, step B using [1-(3-cyanopyridin-2-yl)piperidin-4-yl]acetic acid trifluoroacetate as starting material in 38% yield. LCMS for $C_{30}H_{29}ClN_9O$ $(M+H)^+$: m/z=566.2.

Example A178

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(4-cyanopyridin-2-yl)piperidin-4-yl]acetamide tris(trifluoroacetate)

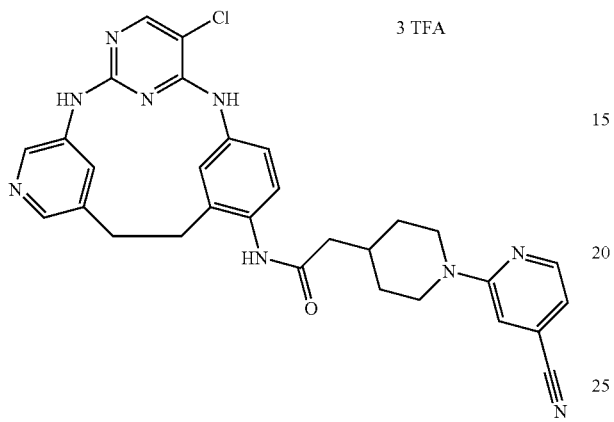

Step A.
[1-(4-Cyanopyridin-2-yl)piperidin-4-yl]acetic acid trifluoroacetate

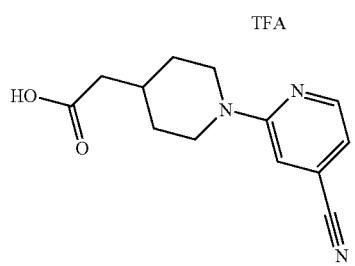 [SMILES: N#Cc1ccnc(N2CCC(CC(=O)O)CC2)c1]

The desired compound was prepared according to the procedure of Example A169, step A using 2-chloroisonicotinonitrile as starting material in 12% yield. LCMS for $C_{13}H_{16}N_3O_2$ (M+H)$^+$: m/z=246.1.

Step B. N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[6-(4-cyanopyridin-2-yl)piperidin-4-yl]acetamide tris(trifluoroacetate)

The desired compound was prepared according to the procedure of Example A169, step B using [1-(4-cyanopyridin-2-yl)piperidin-4-yl]acetic acid trifluoroacetate as starting material in 22% yield. LCMS for $C_{30}H_{29}ClN_9O$ (M+H)$^+$: m/z=566.2.

Example A179

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(5-cyanopyridin-2-yl)piperidin-4-yl]acetamide tris(trifluoroacetate)

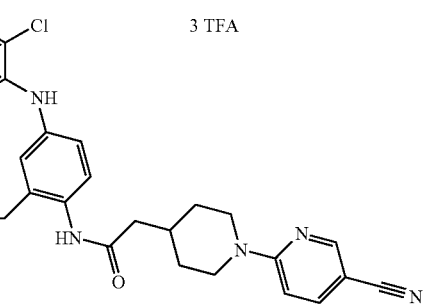

Step A.
[1-(5-Cyanopyridin-2-yl)piperidin-4-yl]acetic acid trifluoroacetate

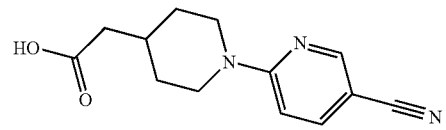

The desired compound was prepared according to the procedure of Example A169, step A using 6-chloronicotinonitrile as starting material in 19% yield. LCMS for $C_{13}H_{16}N_3O_2$ (M+H)$^+$: m/z=246.1.

Step B. N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[6-(5-cyanopyridin-2-yl)piperidin-4-yl]acetamide tris(trifluoroacetate)

The desired compound was prepared according to the procedure of Example A169, step B using [1-(5-cyanopyridin-2-yl)piperidin-4-yl]acetic acid trifluoroacetate as starting material in 22% yield. LCMS for $C_{30}H_{29}ClN_9O$ (M+H)$^+$: m/z=566.2.

Example A180

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(6-chloropyridin-2-yl)piperidin-4-yl]acetamide tris(trifluoroacetate)

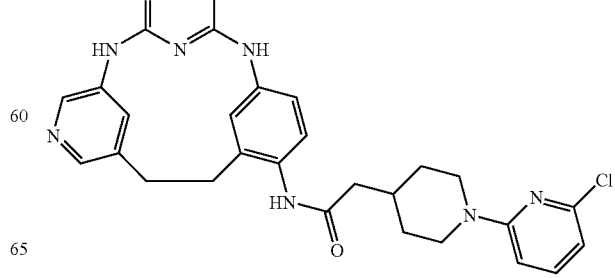

Step A.
[1-(6-Chloropyridin-2-yl)piperidin-4-yl]acetic acid trifluoroacetate

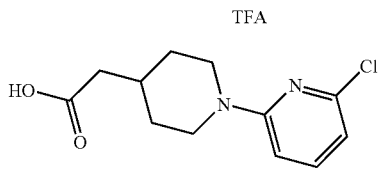 [SMILES: "TFA" ; O=C(O)CC1CCN(c2cccc(Cl)n2)CC1]

The desired compound was prepared according to the procedure of Example A169, step A using 2,6-dichloropyridine as starting material in 100% yield. LCMS for $C_{12}H_{16}ClN_2O_2$ $(M+H)^+$: m/z=255.1.

Step B. N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(6-chloropyridin-2-yl)piperidin-4-yl]acetamide tris(trifluoroacetate)

The desired compound was prepared according to the procedure of Example A169, step B using [1-(6-chloropyridin-2-yl)piperidin-4-yl]acetic acid trifluoroacetate as starting material in 13% yield. LCMS for $C_{29}H_{29}Cl_2N_8O$ $(M+H)^+$: m/z=575.2.

Example A181

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(6-fluoropyridin-2-yl)piperidin-4-yl]acetamide tris(trifluoroacetate)

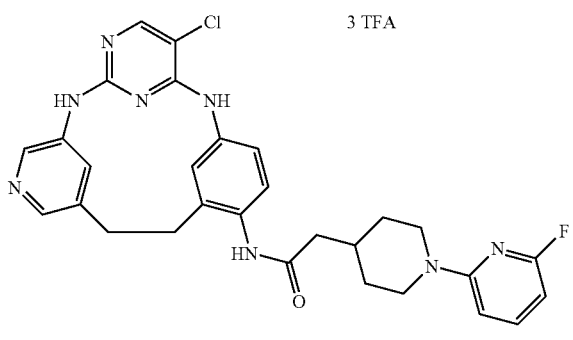 [SMILES: "3 TFA" ; O=C(CC1CCN(c2cccc(F)n2)CC1)Nc1ccc2cc1CCc1cncc(c1)Nc1ncc(Cl)c(n1)N2]

Step A.
[1-(6-Fluoropyridin-2-yl)piperidin-4-yl]acetic acid trifluoroacetate

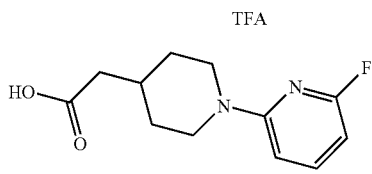 [SMILES: "TFA" ; O=C(O)CC1CCN(c2cccc(F)n2)CC1]

The desired compound was prepared according to the procedure of Example A169, step A using 2,6-difluoropyridine as starting material in 39% yield. LCMS for $C_{12}H_{16}FN_2O_2$ $(M+H)^+$: m/z=239.1.

Step B. N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(6-fluoropyridin-2-yl)piperidin-4-yl]acetamide tris(trifluoroacetate)

The desired compound was prepared according to the procedure of Example A169, step B using [1-(6-fluoropyridin-2-yl)piperidin-4-yl]acetic acid trifluoroacetate as starting material in 24% yield. LCMS for $C_{29}H_{29}ClFN_8O$ $(M+H)^+$: m/z=559.2.

Example A182

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(2-methylpyrimidin-4-yl)piperidin-4-yl]acetamide tris(trifluoroacetate)

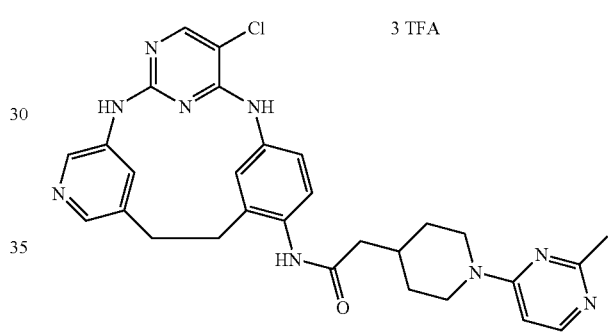

Step A.
[1-(2-Methylpyrimidin-2-yl)piperidin-4-yl]acetic acid trifluoroacetate

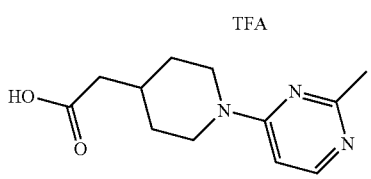 [SMILES: "TFA" ; Cc1nccc(N2CCC(CC(=O)O)CC2)n1]

The desired compound was prepared according to the procedure of Example A169, step A using 4-chloro-2-methylpyrimidine as starting material in 66% yield. LCMS for $C_{12}H_{18}N_3O_2$ $(M+H)^+$: m/z=236.1.

Step B. N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(2-methylpyrimidin-4-yl)piperidin-4-yl]acetamide tris(trifluoroacetate)

The desired compound was prepared according to the procedure of Example A169, step B using [1-(2-methylpyrimidin-4-yl)piperidin-4-yl]acetic acid trifluoroacetate as starting material in 45% yield. LCMS for $C_{29}H_{31}ClN_9O$ (M+H)$^+$: m/z=556.2.

Example A183

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-[1-(1,3,4-thiadiazol-2-yl)piperidin-4-yl]acetamide bis(trifluoroacetate)

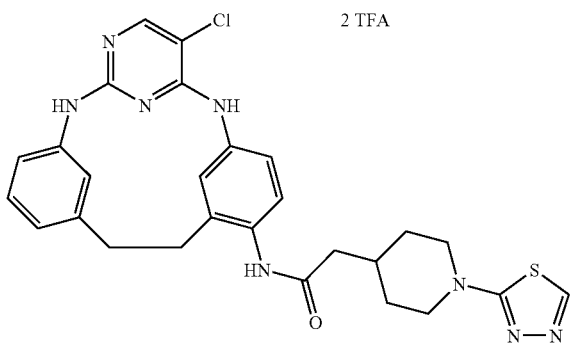 [SMILES: O=C(CC1CCN(c2nncs2)CC1)Nc1ccc2cc1CCc1cccc(c1)Nc1ncc(Cl)c(n1)N2 ; "2 TFA"]

The desired compound was prepared according to the procedure of Example A169, step B using 6-chloro2,4,8,22-tetraazatetracyclo[14.3.1.1(3,7).1(9,13)]docosa1(20),3(22),4,6,9(21),10,12,16,18-nonaen-12-amine dihydrochloride and [1-(1,3,4-thiadiazol-2-yl)piperidin-4-yl]acetic acid trifluoroacetate as starting materials in 27% yield. LCMS for $C_{27}H_{28}ClN_8OS$ (M+H)$^+$: m/z=547.2.

Example A184

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-[1-(pyridin-3-ylcarbonyl)piperidin-4-yl]acetamide bis(trifluoroacetate)

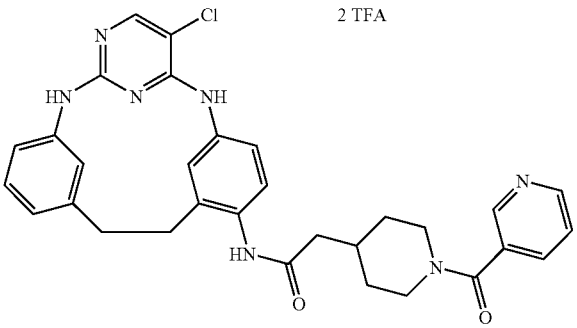 [SMILES: O=C(CC1CCN(C(=O)c2cccnc2)CC1)Nc1ccc2cc1CCc1cccc(c1)Nc1ncc(Cl)c(n1)N2 ; "2 TFA"]

The desired compound was prepared according to the procedure of Example A20 using N-[6-chloro-2,4,8,22-tetraazatetracyclo[14.3.1.1(3,7).1(9,13)]docosa-1(20),3(22),4,6,9(21),10,12,16,18-nonaen-12-yl]piperidine-4-carboxamide bis(trifluoroacetate) and nicotinoyl chloride as starting materials in 70% yield. LCMS for $C_{31}H_{31}ClN_7O_2$ (M+H)$^+$: m/z=568.2.

Example A185

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-(1-isonicotinoylpiperidin-4-yl)acetamide bis(trifluoroacetate)

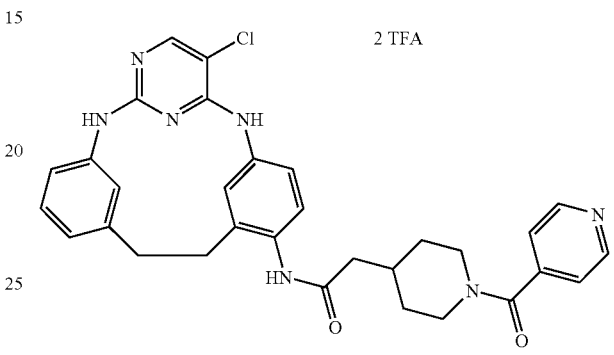

The desired compound was prepared according to the procedure of Example A20 using of N-[6-chloro-2,4,8,22-tetraazatetracyclo[14.3.1.1(3,7).1(9,13)]docosa-1(20), 3(22),4,6,9(21),10,12,16,18-nonaen-12-yl]piperidine-4-carboxamide bis(trifluoroacetate) and isonicotinoyl chloride as starting materials in 60% yield. LCMS for LCMS for $C_{31}H_{31}ClN_7O_2$ (M+H)$^+$: m/z=568.2.

Example A186

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-[1-(4-cyanobenzoyl)piperidin-4-yl]acetamide trifluoroacetate

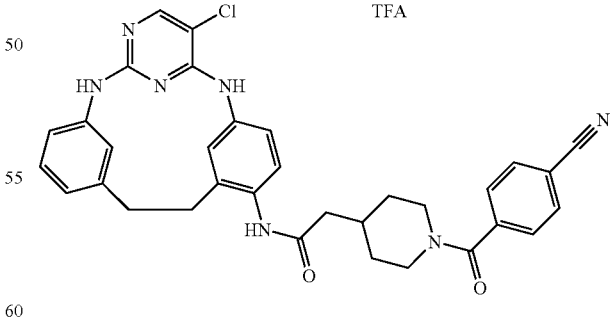

The desired compound was prepared according to the procedure of Example A20 using of N-[6-chloro-2,4,8,22-tetraazatetracyclo[14.3.1.1(3,7).1(9,13)]docosa-1(20), 3(22),4,6,9(21),10,12,16,18-nonaen-12-yl]piperidine-4-carboxamide bis(trifluoroacetate) and 4-cyanobenzoyl chloride as starting materials in 53% yield. LCMS for C$_{33}$H$_{31}$ClN$_7$O$_2$ (M+H)$^+$: m/z=592.2.

Example A187

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-[1-(3-cyanobenzoyl)piperidin-4-yl]acetamide trifluoroacetate

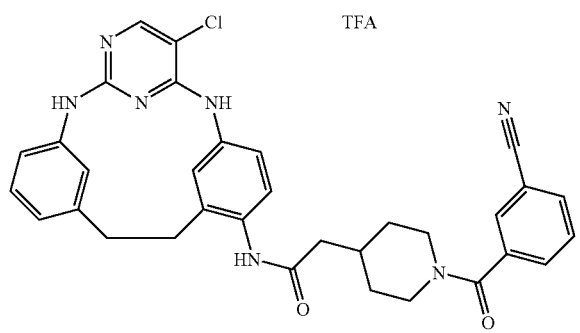 [SMILES: "TFA" ; N#Cc1cccc(C(=O)N2CCC(CC(=O)Nc3ccc4cc3CCc3cccc(c3)Nc3ncc(Cl)c(n3)N4)CC2)c1]

The desired compound was prepared according to the procedure of Example A20 using of N-[6-chloro-2,4,8,22-tetraazatetracyclo[14.3.1.1(3,7).1(9,13)]docosa-1(20),3(22),4,6,9(21),10,12,16,18-nonaen-12-yl]piperidine-4-carboxamide bis(trifluoroacetate) and 3-cyanobenzoyl chloride as starting materials in 16% yield. LCMS for C$_{33}$H$_{31}$ClN$_7$O$_2$ (M+H)$^+$: m/z=592.2.

Example A188

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(pyridin-3-ylcarbonyl)piperidin-4-yl]acetamide tris(trifluoroacetate)

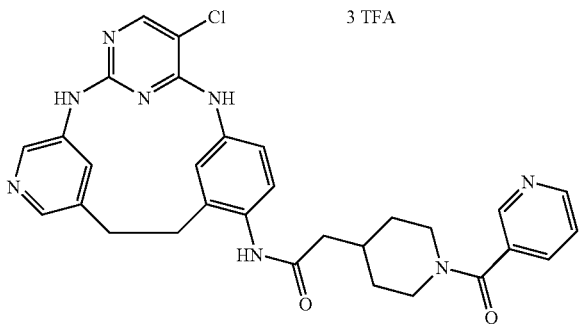 [SMILES: "3 TFA" ; O=C(CC1CCN(C(=O)c2cccnc2)CC1)Nc1ccc2cc1CCc1cncc(c1)Nc1ncc(Cl)c(n1)N2]

The desired compound was prepared according to the procedure of Example A20 using of N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide bis(trifluoroacetate) and nicotinoyl chloride as starting materials in 37% yield. LCMS for C$_{30}$H$_{30}$ClN$_8$O$_2$ (M+H)$^+$: m/z=569.2.

Example A189

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-(1-isonicotinoylpiperidin-4-yl)acetamide tris(trifluoroacetate)

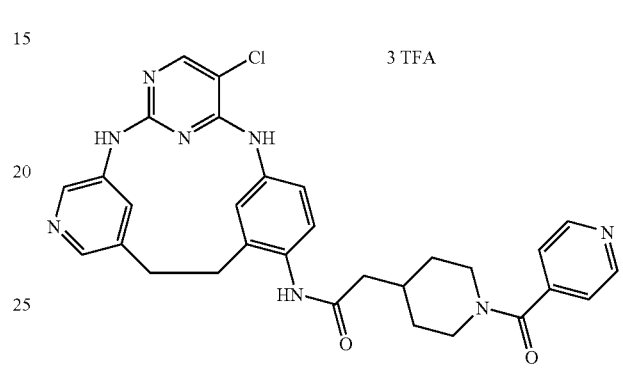

The desired compound was prepared according to the procedure of Example A20 using of N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide bis(trifluoroacetate) and isonicotinoyl chloride as starting materials in 43% yield. LCMS for C$_{30}$H$_{30}$ClN$_8$O$_2$ (M+H)$^+$: m/z=569.2.

Example A190

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(4-cyanobenzoyl)piperidin-4-yl]acetamide bis(trifluoroacetate)

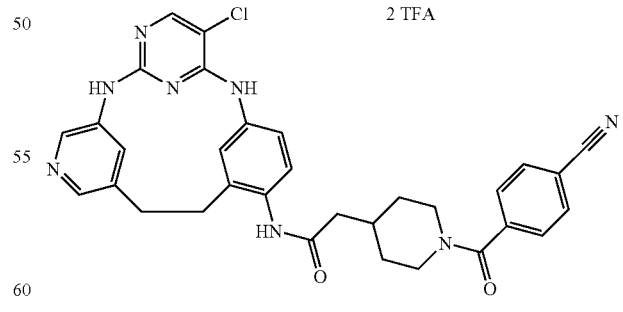

The desired compound was prepared according to the procedure of Example A20 using of N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide bis(trifluoroacetate) and 4-cyanobenzoyl Example A191

N-[6-Chloro-2,4,8,18,22-pentaazatetracyclo[14.3.1.1
(3,7).1(9,13)]docosa-1(20),3(22),4,6,9(21),10,12,16,
18-nonaen-12-yl]-2-[1-(3-cyanobenzoyl)piperidin-4-
yl]acetamide bis(trifluoroacetate)

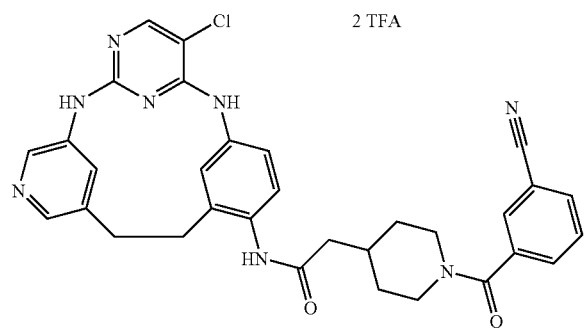 [SMILES: N#Cc1cccc(C(=O)N2CCC(CC(=O)Nc3ccc4cc3CCc3cncc(c3)Nc3ncc(Cl)c(n3)N4)CC2)c1 ; "2 TFA"]

The desired compound was prepared according to the procedure of Example A20 using of N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide bis(trifluoroacetate) and 3-cyanobenzoyl chloride as starting materials in 14% yield. LCMS for $C_{32}H_{30}ClN_8O_2$ (M+H)$^+$: m/z=593.2.

Example A192

2-(1-Benzoylpiperidin-4-yl)-N-[6-chloro-2,4,8,18,
22-pentaazatetracyclo[14.3.1.1(3,7).1(9,13)]docosa-
1(20),3(22),4,6,9(21),10,12,16,18-nonaen-12-yl]
acetamide bis(trifluoroacetate)

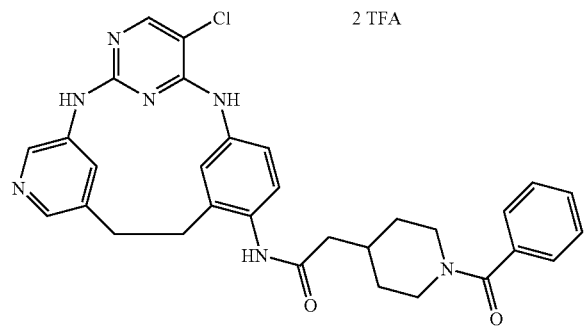

The desired compound was prepared according to the procedure of Example A20 using of N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide bis(trifluoroacetate) and benzoyl chloride as starting materials in 48% yield. LCMS for $C_{31}H_{31}ClN_7O_2$ (M+H)$^+$: m/z=568.2.

Example A193

N-[6-Chloro-2,4,8,18,22-pentaazatetracyclo[14.3.1.1
(3,7).1(9,13)]docosa-1(20),3(22),4,6,9(21),10,12,16,
18-nonaen-12-yl]-2-[1-(4-fluorobenzoyl)piperidin-4-
yl]acetamide bis(trifluoroacetate)

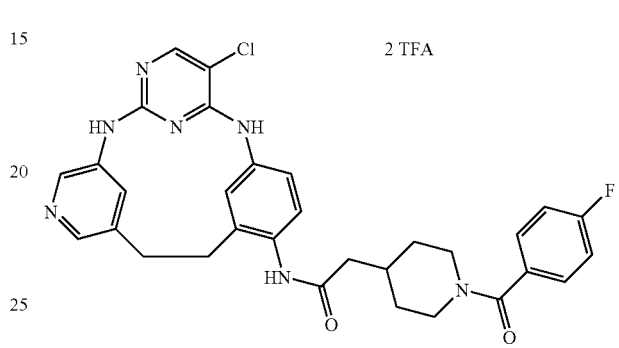

The desired compound was prepared according to the procedure of Example A20 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and 4-fluorobenzoyl chloride as starting materials in 26% yield. LCMS for $C_{31}H_{30}ClFN_7O_2$ (M+H)$^+$: m/z=586.2.

Example A194

N-[6-Chloro-2,4,8,18,22-pentaazatetracyclo[14.3.1.1
(3,7).1(9,13)]docosa-1(20),3(22),4,6,9(21),10,12,16,
18-nonaen-12-yl]-2-[1-(2,4-difluorobenzoyl)piperi-
din-4-yl]acetamide bis(trifluoroacetate)

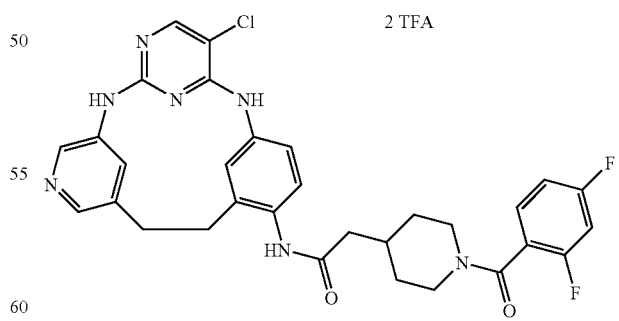

The desired compound was prepared according to the procedure of Example A20 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and 2,4-difluorobenzoyl

Example A195

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(phenylsulfonyl)piperidin-4-yl]acetamide bis(trifluoroacetate)

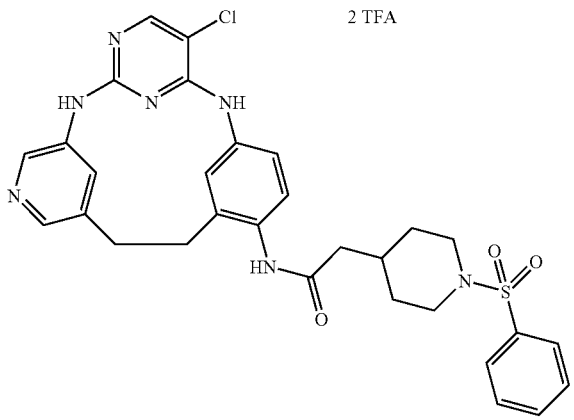 [SMILES: O=C(CC1CCN(S(=O)(=O)c2ccccc2)CC1)Nc1ccc2cc1CCc1cncc(c1)Nc1ncc(Cl)c(n1)N2 ; "2 TFA"]

The desired compound was prepared according to the procedure of Example A42 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and benzenesulfonyl chloride as starting materials in 44% yield. LCMS for $C_{30}H_{31}ClN_7O_3S$ (M+H)$^+$: m/z=604.2.

Example A196

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(3-methoxyphenyl)sulfonyl]piperidin-4-yl}acetamide bis(trifluoroacetate)

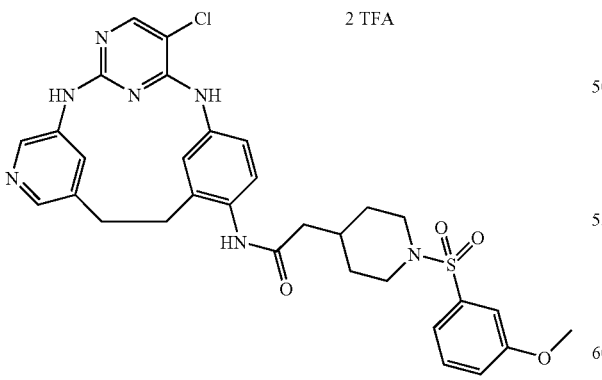

The desired compound was prepared according to the procedure of Example A42 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and 3-methoxybenzenesulfonyl chloride as starting materials in 28% yield. LCMS for $C_{31}H_{33}ClN_7O_4S$ (M+H)$^+$: m/z=634.2.

Example A197

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(4-methoxyphenyl)sulfonyl]piperidin-4-yl}acetamide bis(trifluoroacetate)

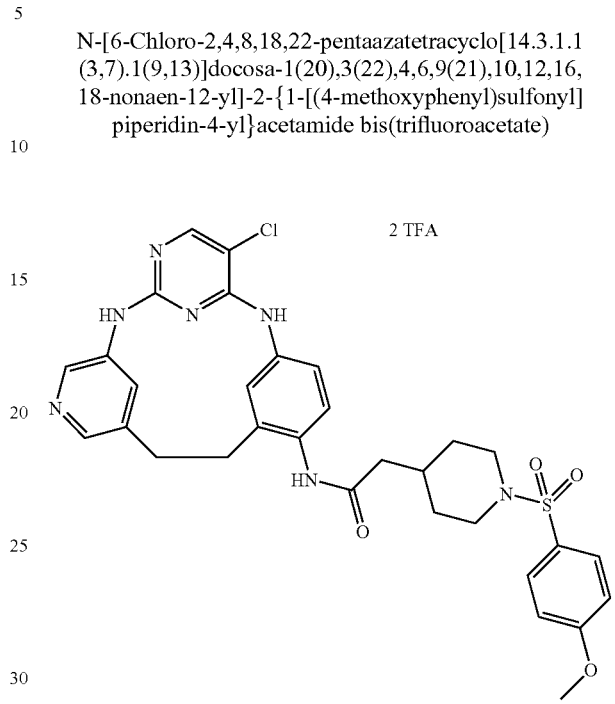

The desired compound was prepared according to the procedure of Example A42 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and 4-methoxybenzenesulfonyl chloride as starting materials in 41% yield. LCMS for $C_{31}H_{33}ClN_7O_4S$ (M+H)$^+$: m/z=634.2.

Example A198

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(2-cyanophenyl)sulfonyl]piperidin-4-yl}acetamide bis(trifluoroacetate)

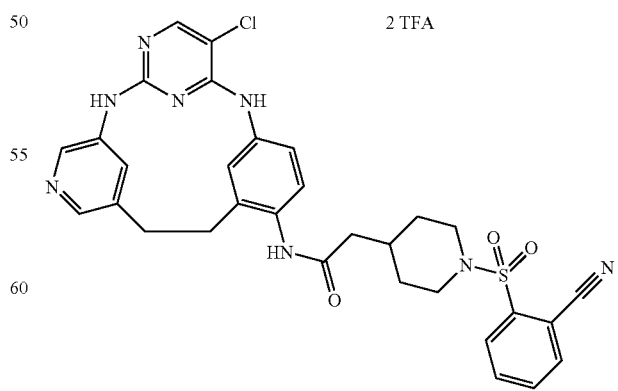

The desired compound was prepared according to the procedure of Example A42 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and 2-cyanobenzenesulfonyl chloride as starting materials in 20% yield. LCMS for $C_{31}H_{30}ClN_8O_3S$ (M+H)$^+$: m/z=629.2.

Example A199

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(4-cyanophenyl)sulfonyl]piperidin-4-yl}acetamide bis(trifluoroacetate)

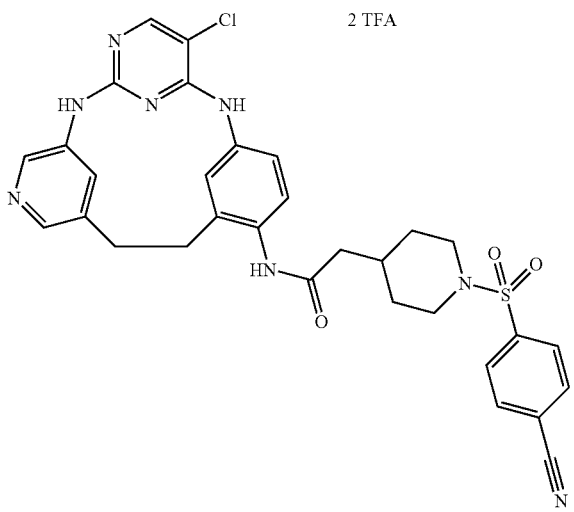 [SMILES: N#Cc1ccc(S(=O)(=O)N2CCC(CC(=O)Nc3ccc4cc3CCc3cncc(c3)Nc3ncc(Cl)c(n3)N4)CC2)cc1 ; "2 TFA"]

The desired compound was prepared according to the procedure of Example A42 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and 4-cyanobenzenesulfonyl chloride as starting materials in 22% yield. LCMS for $C_{31}H_{30}ClN_8O_3S$ (M+H)$^+$: m/z=629.2.

Example A200

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(5-methylisoxazol-4-yl)sulfonyl]piperidin-4-yl}acetamide bis(trifluoroacetate)

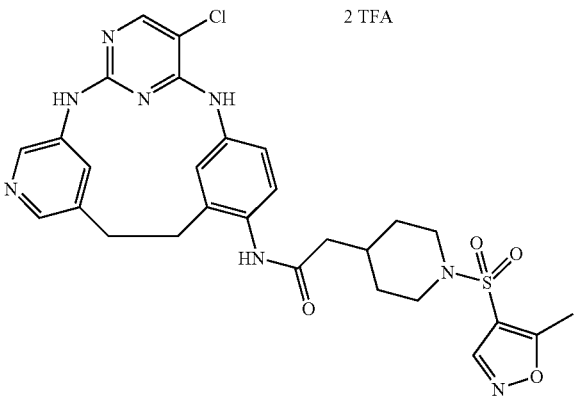 [SMILES: Cc1oncc1S(=O)(=O)N1CCC(CC(=O)Nc2ccc3cc2CCc2cncc(c2)Nc2ncc(Cl)c(n2)N3)CC1 ; "2 TFA"]

The desired compound was prepared according to the procedure of Example A42 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and 5-methylisoxazole-4-sulfonyl chloride as starting materials in 12% yield. LCMS for $C_{28}H_{30}ClN_8O_4S$ (M+H)$^+$: m/z=609.2.

Example A201

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(2-furylsulfonyl)piperidin-4-yl]acetamide bis(trifluoroacetate)

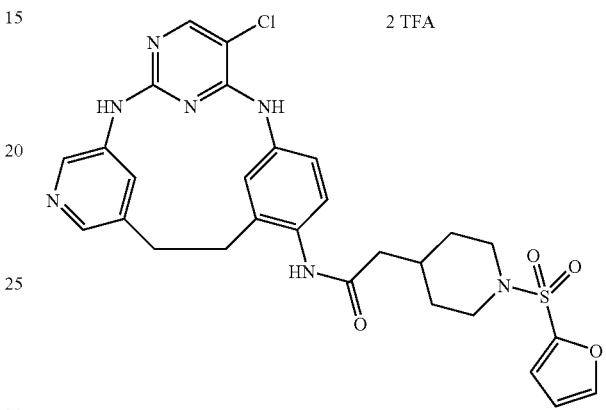

The desired compound was prepared according to the procedure of Example A42 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and furan-2-sulfonyl chloride as starting materials in 8% yield. LCMS for $C_{28}H_{29}ClN_7O_4S$ (M+H)$^+$: m/z=594.2.

Example A202

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(pyridin-3-ylsulfonyl)piperidin-4-yl]acetamide tris(trifluoroacetate)

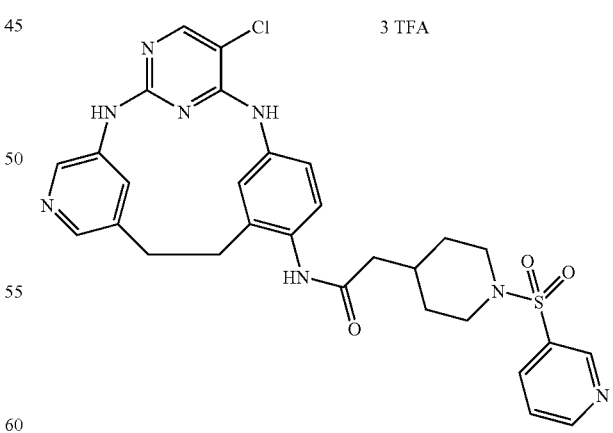

The desired compound was prepared according to the procedure of Example A42 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and pyridine-3-sulfonyl chloride hydrochloride as starting materials in 31% yield. LCMS for $C_{29}H_{30}ClN_8O_3S$ (M+H)$^+$: m/z=605.2.

Example A203

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-[1-(4-fluorobenzoyl)piperidin-4-yl]acetamide trifluoroacetate

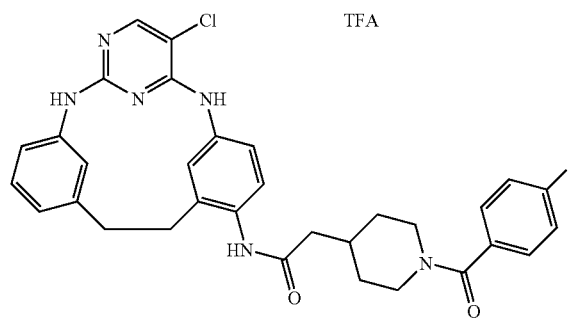

The desired compound was prepared according to the procedure of Example A20 using N-[6-chloro-2,4,8,22-tetraazatetracyclo[14.3.1.1(3,7).1(9,13)]docosa-1(20),3(22),4,6,9(21),10,12,16,18-nonaen-12-yl]piperidine-4-carboxamide bis(trifluoroacetate) and 4-fluorobenzoyl chloride as starting materials in 20% yield. LCMS for $C_{32}H_{31}ClFN_6O_2$ (M+H)$^+$: m/z=585.2.

Example A204

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-[1-(2,4-difluorobenzoyl)piperidin-4-yl]acetamide trifluoroacetate

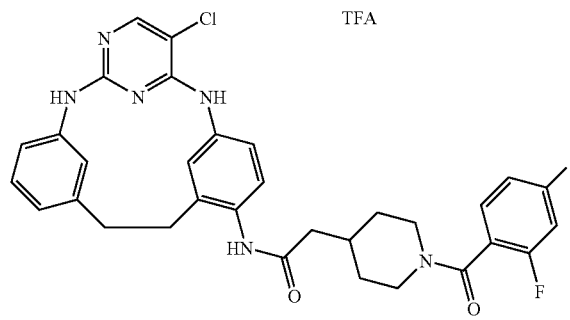

The desired compound was prepared according to the procedure of Example A20 using N-[6-chloro-2,4,8,22-tetraazatetracyclo[14.3.1.1(3,7).1(9,13)]docosa-1(20),3(22),4,6,9(21),10,12,16,18-nonaen-12-yl]piperidine-4-carboxamide bis(trifluoroacetate) and 2,4-difluorobenzoyl chloride as starting materials in 12% yield. LCMS for $C_{32}H_{30}ClF_2N_6O_2$ (M+H)$^+$: m/z=603.2.

Example A205

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-[1-(phenylsulfonyl)piperidin-4-yl]acetamide trifluoroacetate

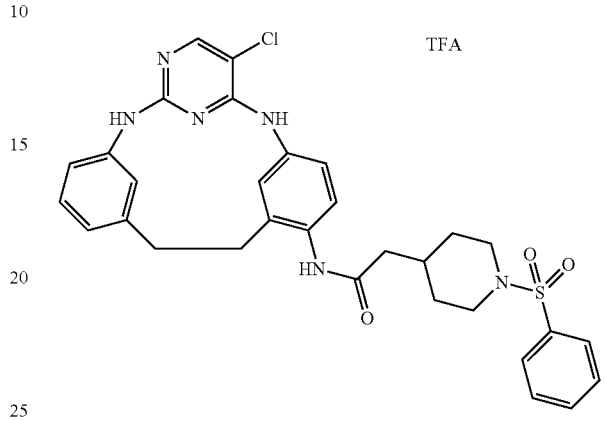

The desired compound was prepared according to the procedure of Example A42 using N-[6-chloro-2,4,8,22-tetraazatetracyclo[14.3.1.1(3,7).1(9,13)]docosa-1(20),3(22),4,6,9(21),10,12,16,18-nonaen-12-yl]piperidine-4-carboxamide bis(trifluoroacetate) and benzenesulfonyl chloride as starting materials in 26% yield. LCMS for $C_{31}H_{32}ClN_6O_3S$ (M+H)$^+$: m/z=603.2.

Example A206

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-{1-[(3-methoxyphenyl)sulfonyl]piperidin-4-yl}acetamide trifluoroacetate

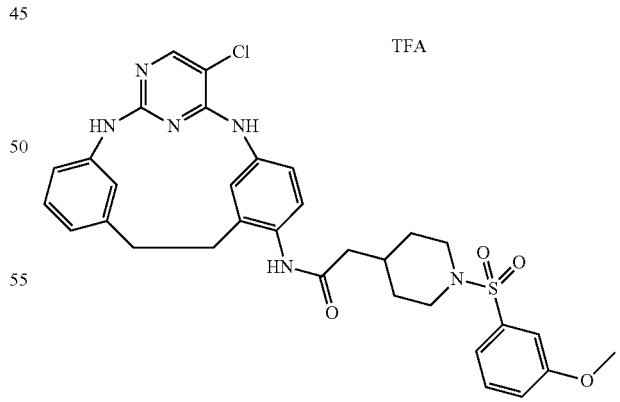

The desired compound was prepared according to the procedure of Example A42 using N-[6-chloro-2,4,8,22-tetraazatetracyclo[14.3.1.1(3,7).1(9,13)]docosa-1(20),3(22),4,6,9(21),10,12,16,18-nonaen-12-yl]piperidine-4-carboxamide bis(trifluoroacetate) and 3-methoxybenzenesulfonyl chloride

Example A207

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-{1-[(4-methoxyphenyl)sulfonyl]piperidin-4-yl}acetamide trifluoroacetate

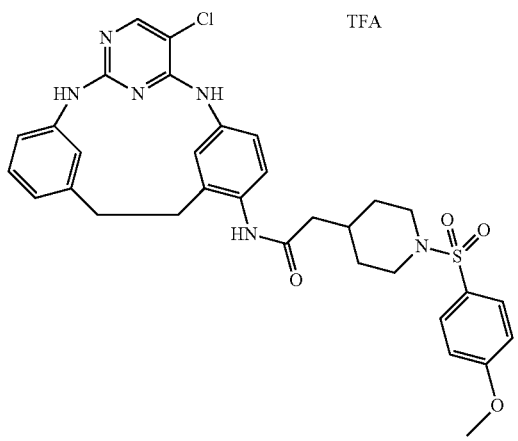 [SMILES: COc1ccc(S(=O)(=O)N2CCC(CC(=O)Nc3ccc4cc3CCc3cccc(c3)Nc3ncc(Cl)c(n3)N4)CC2)cc1]

The desired compound was prepared according to the procedure of Example A42 using N-[6-chloro-2,4,8,22-tetraazatetracyclo[14.3.1.1(3,7).1(9,13)]docosa-1(20),3(22),4,6,9(21),10,12,16,18-nonaen-12-yl]piperidine-4-carboxamide bis(trifluoroacetate) and 4-methoxybenzenesulfonyl chloride as starting materials in 20% yield. LCMS for $C_{32}H_{34}ClN_6O_4S$ $(M+H)^+$: m/z=633.2.

Example A208

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-{1-[(2-cyanophenyl)sulfonyl]piperidin-4-yl}acetamide trifluoroacetate

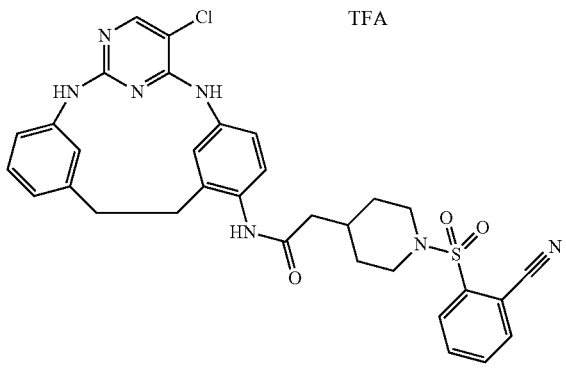 [SMILES: N#Cc1ccccc1S(=O)(=O)N1CCC(CC(=O)Nc2ccc3cc2CCc2cccc(c2)Nc2ncc(Cl)c(n2)N3)CC1]

The desired compound was prepared according to the procedure of Example A42 using N-[6-chloro-2,4,8,22-tetraazatetracyclo[14.3.1.1(3,7).1(9,13)]docosa-1(20),3(22),4,6,9(21),10,12,16,18-nonaen-12-yl]piperidine-4-carboxamide bis(trifluoroacetate) and 2-cyanobenzenesulfonyl chloride as starting materials in 26% yield. LCMS for $C_{32}H_{31}ClN_7O_3S$ $(M+H)^+$: m/z=628.2.

Example A209

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-{1-[(4-cyanophenyl)sulfonyl]piperidin-4-yl}acetamide trifluoroacetate

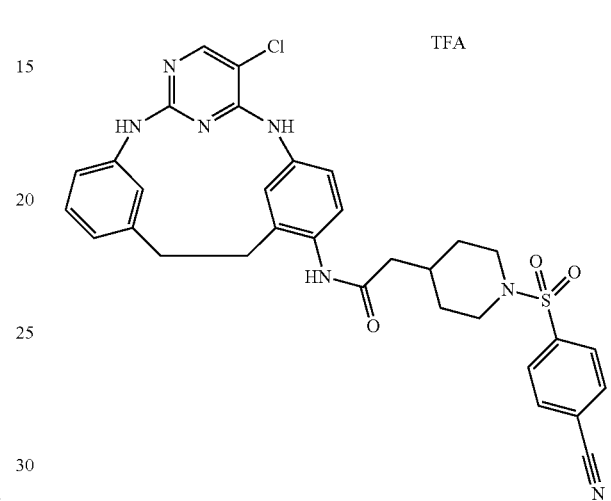

The desired compound was prepared according to the procedure of Example A42 using N-[6-chloro-2,4,8,22-tetraazatetracyclo[14.3.1.1(3,7).1(9,13)]docosa-1(20),3(22),4,6,9(21),10,12,16,18-nonaen-12-yl]piperidine-4-carboxamide bis(trifluoroacetate) and 4-cyanobenzenesulfonyl chloride as starting materials in 21% yield. LCMS for $C_{32}H_{31}ClN_7O_3S$ $(M+H)^+$: m/z=628.2.

Example A210

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-{1-[(5-methylisoxazol-4-yl)sulfonyl]piperidin-4-yl}acetamide trifluoroacetate

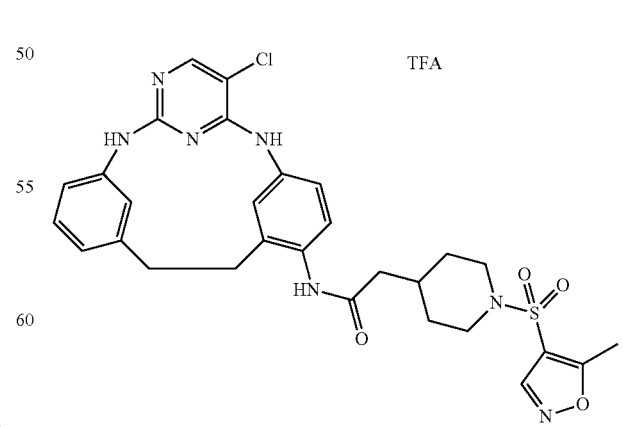

The desired compound was prepared according to the procedure of Example A42 using N-[6-chloro-2,4,8,22-tetraazatetracyclo[14.3.1.1(3,7).1(9,13)]docosa-1(20),3(22),4,6,9 (21),10,12,16,18-nonaen-12-yl]piperidine-4-carboxamide bis(trifluoroacetate) and 5-methylisoxazole-4-sulfonyl chloride as starting materials in 21% yield. LCMS for $C_{29}H_{31}ClN_7O_4S$ (M+H)$^+$: m/z=608.2.

Example A211

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-[1-(2-furylsulfonyl)piperidin-4-yl]acetamide trifluoroacetate

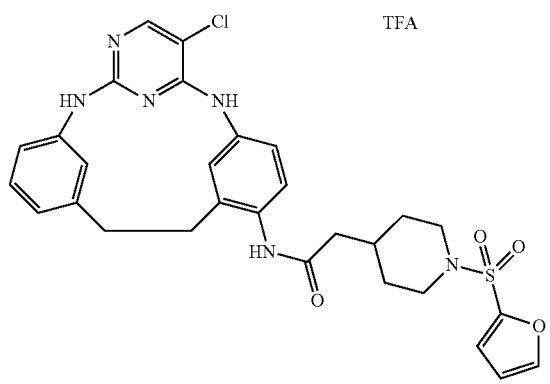 [SMILES: O=C(CC1CCN(S(=O)(=O)c2ccco2)CC1)Nc1ccc2cc1CCc1cccc(c1)Nc1ncc(Cl)c(n1)N2]

The desired compound was prepared according to the procedure of Example A42 using N-[6-chloro-2,4,8,22-tetraazatetracyclo[14.3.1.1(3,7).1(9,13)]docosa-1(20),3(22),4,6,9 (21),10,12,16,18-nonaen-12-yl]piperidine-4-carboxamide bis(trifluoroacetate) and furan-2-sulfonyl chloride as starting materials in 24% yield. LCMS for $C_{29}H_{30}ClN_6O_4S$ (M+H)$^+$: m/z=593.2.

Example A212

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-[1-(pyridin-3-ylsulfonyl)piperidin-4-yl]acetamide bis(trifluoroacetate)

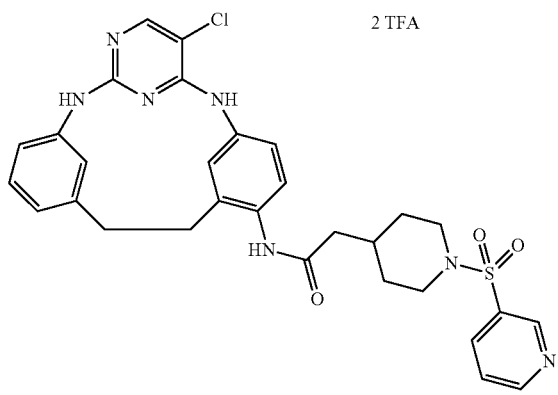 [SMILES: O=C(CC1CCN(S(=O)(=O)c2cccnc2)CC1)Nc1ccc2cc1CCc1cccc(c1)Nc1ncc(Cl)c(n1)N2 ; "2 TFA"]

The desired compound was prepared according to the procedure of Example A42 using N-[6-chloro-2,4,8,22-tetraazatetracyclo[14.3.1.1(3,7).1(9,13)]docosa-1(20),3(22),4,6,9 (21),10,12,16,18-nonaen-12-yl]piperidine-4-carboxamide bis(trifluoroacetate) and pyridine-3-sulfonyl chloride hydrochloride as starting materials in 28% yield. LCMS for $C_{30}H_{31}ClN_7O_3S$ (M+H)$^+$: m/z=604.2.

Example A213

N-[6-Chloro-2,4,8,18,22-pentaazatetracyclo[14.3.1.1 (3,7).1(9,13)]docosa-1(20),3(22),4,6,9(21),10,12,16, 18-nonaen-12-yl]-2-{1-[(5-cyclopropylisoxazol-4-yl) carbonyl]piperidin-4-yl}acetamide bis (trifluoroacetate)

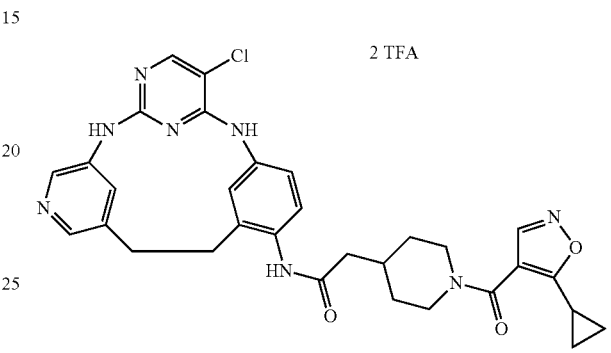

The desired compound was prepared according to the procedure of Example A27 using N-[6-chloro-2,4,8,18,22-pentaazatetracyclo[14.3.1.1(3,7).1(9,13)]docosa-1(20),3(22),4, 6,9(21),10,12,16,18-nonaen-12-yl]-2-piperidin-4-ylacetamide tris(trifluoroacetate) and 5-cyclopropylisoxazole-4-carboxylic acid as starting materials in 18% yield. LCMS for $C_{31}H_{32}ClN_8O_3$ (M+H)$^+$: m/z=599.2.

Example A214

N-[6-Chloro-2,4,8,18,22-pentaazatetracyclo[14.3.1.1 (3,7).1(9,13)]docosa-1(20),3(22),4,6,9(21),10,12,16, 18-nonaen-12-yl]-2-{1-[(5-isopropylisoxazol-3-yl) carbonyl]piperidin-4-yl}acetamide bis (trifluoroacetate)

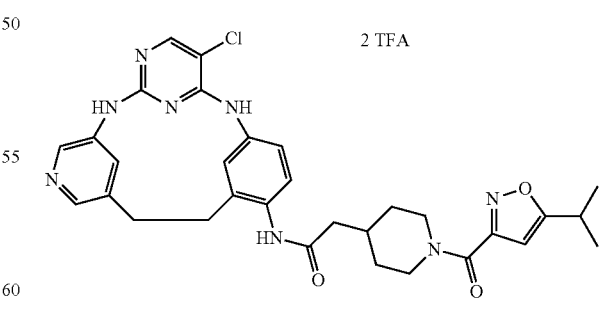

The desired compound was prepared according to the procedure of Example A27 using N-[6-chloro-2,4,8,18,22-pentaazatetracyclo[14.3.1.1(3,7).1(9,13)]docosa-1(20),3(22),4, 6,9(21),10,12,16,18-nonaen-12-yl]-2-piperidin-4-ylacetamide tris(trifluoroacetate) and 5-isopropylisoxazole- 3-carboxylic acid as starting materials in 18% yield. LCMS for $C_{31}H_{34}ClN_8O_3$ (M+H)$^+$: m/z=601.2.

Example A215

N-[6-Chloro-2,4,8,18,22-pentaazatetracyclo[14.3.1.1 (3,7).1(9,13)]docosa-1(20),3(22),4,6,9(21),10,12,16, 18-nonaen-12-yl]-2-{1-[(3-methoxyisoxazol-5-yl) carbonyl]piperidin-4-yl}acetamide bis (trifluoroacetate)

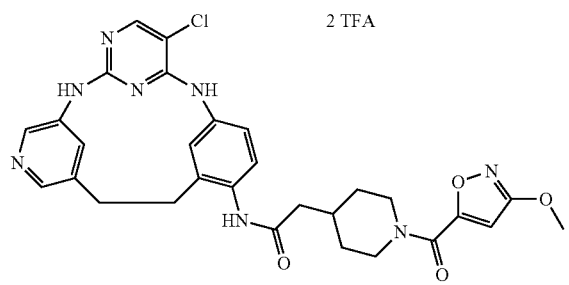 [SMILES: COc1cc(C(=O)N2CCC(CC(=O)Nc3ccc4cc3CCc3cncc(c3)Nc3ncc(Cl)c(n3)N4)CC2)on1 ; "2 TFA"]

The desired compound was prepared according to the procedure of Example A27 using N-[6-chloro-2,4,8,18,22-pentaazatetracyclo[14.3.1.1(3,7).1(9,13)]docosa-1(20),3(22),4, 6,9(21),10,12,16,18-nonaen-12-yl]-2-piperidin-4-ylacetamide tris(trifluoroacetate) and 3-methoxyisoxazole-5-carboxylic acid as starting materials in 24% yield. LCMS for $C_{29}H_{30}ClN_8O_4$ (M+H)$^+$: m/z=589.2.

Example A216

N-[6-Chloro-2,4,8,18,22-pentaazatetracyclo[14.3.1.1 (3,7).1(9,13)]docosa-1(20),3(22),4,6,9(21),10,12,16, 18-nonaen-12-yl]-2-{1-[(4-methyl-1,3-thiazol-5-yl) carbonyl]piperidin-4-yl}acetamide bis (trifluoroacetate)

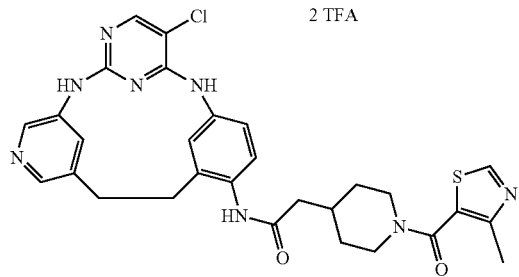 [SMILES: Cc1ncsc1C(=O)N1CCC(CC(=O)Nc2ccc3cc2CCc2cncc(c2)Nc2ncc(Cl)c(n2)N3)CC1 ; "2 TFA"]

The desired compound was prepared according to the procedure of Example A27 using N-[6-chloro-2,4,8,18,22-pentaazatetracyclo[14.3.1.1(3,7).1(9,13)]docosa-1(20),3(22),4, 6,9(21),10,12,16,18-nonaen-12-yl]-2-piperidin-4-ylacetamide tris(trifluoroacetate) and 4-methyl-1,3-thiazole- 5-carboxylic acid as starting materials in 62% yield. LCMS for $C_{29}H_{30}ClN_8O_2S$ (M+H)$^+$: m/z=589.2.

Example A217

2-{1-[(2-Amino-1,3-thiazol-4-yl)carbonyl]piperidin-4-yl}-N-[6-chloro-2,4,8,18,22-pentaazatetracyclo [14.3.1.1(3,7).1(9,13)]docosa-1(20),3(22),4,6,9(21), 10,12,16,18-nonaen-12-yl]acetamide tris (trifluoroacetate)

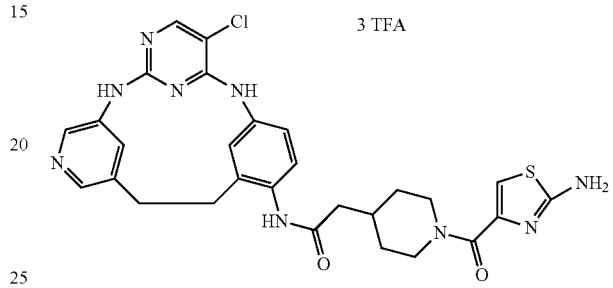

The desired compound was prepared according to the procedure of Example A27 using N-[6-chloro-2,4,8,18,22-pentaazatetracyclo[14.3.1.1(3,7).1(9,13)]docosa-1(20),3(22),4, 6,9(21),10,12,16,18-nonaen-12-yl]-2-piperidin-4-ylacetamide tris(trifluoroacetate) and 2-amino-1,3-thiazole-4-carboxylic acid hydrobromide as starting materials in 36% yield. LCMS for $C_{28}H_{29}ClN_9O_2S$ (M+H)$^+$: m/z=590.2.

Example A218

N-[6-Chloro-2,4,8,18,22-pentaazatetracyclo[14.3.1.1 (3,7).1(9,13)]docosa-1(20),3(22),4,6,9(21),10,12,16, 18-nonaen-12-yl]-2-{1-[(5-isopropylisoxazol-4-yl) carbonyl]piperidin-4-yl}acetamide bis (trifluoroacetate)

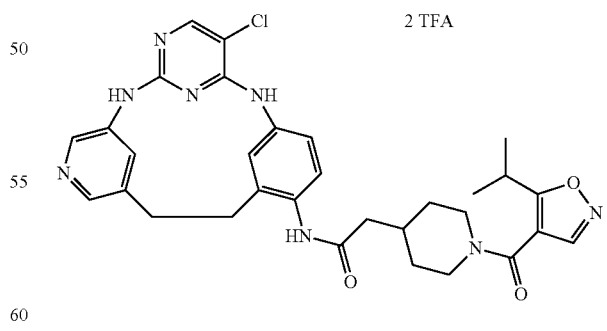

The desired compound was prepared according to the procedure of Example A27 using N-[6-chloro-2,4,8,18,22-pentaazatetracyclo[14.3.1.1(3,7).1(9,13)]docosa-1(20),3(22),4, 6,9(21),10,12,16,18-nonaen-12-yl]-2-piperidin-4-ylacetamide tris(trifluoroacetate) and 5-isopropylisoxazole- 4-carboxylic acid as starting materials in 18% yield. LCMS for $C_{31}H_{34}ClN_8O_3$ (M+H)$^+$: m/z=601.2.

Example A219

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-(1-phenylpiperidin-4-yl)acetamide tris(trifluoroacetate)

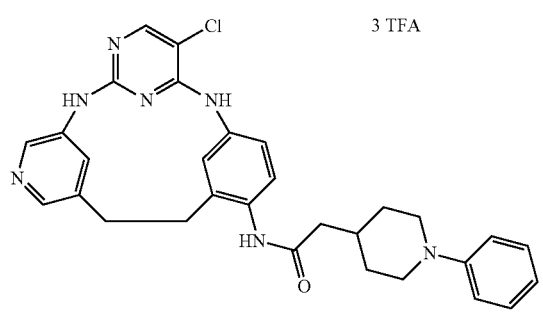 [SMILES: "3 TFA" ; O=C(CC1CCN(c2ccccc2)CC1)Nc1ccc2cc1CCc1cncc(c1)Nc1ncc(Cl)c(n1)N2]

Step A. (1-Phenylpiperidin-4-yl)acetic acid trifluoroacetate

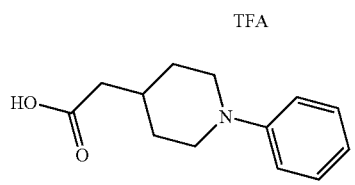 [SMILES: O=C(O)CC1CCN(c2ccccc2)CC1]

Methyl piperidin-4-ylacetate (100 mg, 0.60 mmol) and phenylboronic acid (120 mg, 0.95 mmol) were stirred in dimethyl sulfoxide (1 mL) with copper diacetate (230 mg, 1.3 mmol) and 1,8-diazabicyclo[5.4.0]undec-7-ene (190 μL, 1.3 mmol). The mixture was heated at 130° C. for 30 minutes in a microwave. Purification by preparative LCMS gave the desired ester. The ester intermediate (22 mg) was stirred with a 1N solution of sodium hydroxide in water (1 mL) and methanol (1 mL) at rt for 1 hour. Acetic acid was added and the mixture was purified by preparative LCMS to give the desired compound in 5% yield. LCMS for $C_{13}H_{18}NO_2$ (M+H)$^+$: m/z=220.1.

Step B. N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-(1-phenylpiperidin-4-yl)acetamide tris(trifluoroacetate)

The desired compound was prepared according to the procedure of Example A169, step B using (1-phenylpiperidin-4-yl)acetic acid trifluoroacetate as starting material in 17% yield. LCMS for $C_{30}H_{31}ClN_7O$ (M+H)$^+$: m/z=540.2.

Example A220

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(2-cyanophenyl)piperidin-4-yl]acetamide tris(trifluoroacetate)

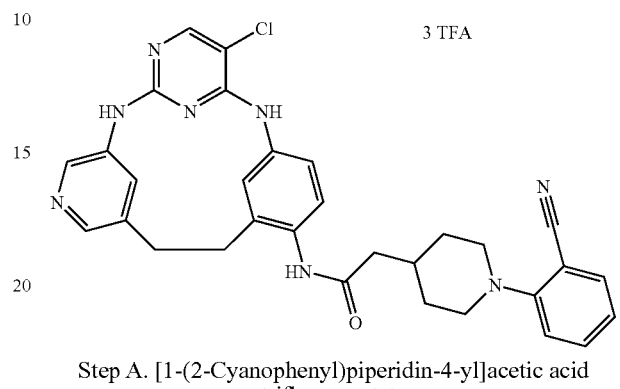

Step A. [1-(2-Cyanophenyl)piperidin-4-yl]acetic acid trifluoroacetate

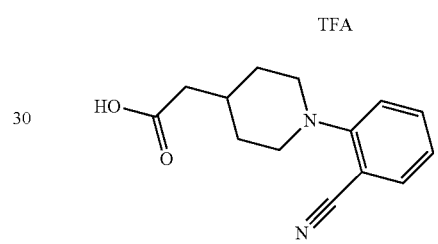

The desired compound was prepared according to the procedure of Example A169, step A using 2-chlorobenzonitrile as starting material in 39% yield. LCMS for $C_{14}H_{17}N_2O_2$ (M+H)$^+$: m/z=245.1.

Step B. N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(2-cyanophenyl)piperidin-4-yl]acetamide tris(trifluoroacetate)

The desired compound was prepared according to the procedure of Example A169, step B using [1-(2-cyanophenyl)piperidin-4-yl]acetic acid trifluoroacetate as starting material in 40% yield. LCMS for $C_{31}H_{30}ClN_8O$ (M+H)$^+$: m/z=565.2.

Example A221

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(4-cyanophenyl)piperidin-4-yl]acetamide tris(trifluoroacetate)

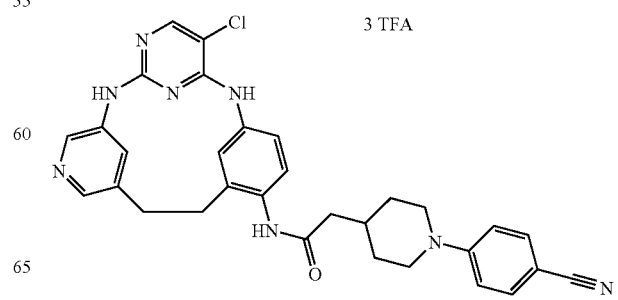

Step A. [1-(4-Cyanophenyl)piperidin-4-yl]acetic acid trifluoroacetate

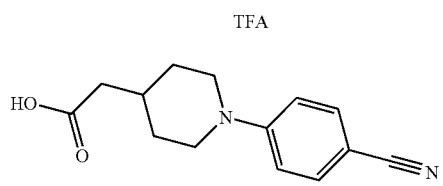 [SMILES: N#Cc1ccc(N2CCC(CC(=O)O)CC2)cc1]

The desired compound was prepared according to the procedure of Example A169, step A using 4-chlorobenzonitrile as starting material in 38% yield. LCMS for $C_{14}H_{17}N_2O_2$ (M+H)$^+$: m/z=245.1.

Step B. N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(4-cyanophenyl)piperidin-4-yl]acetamide tris(trifluoroacetate)

The desired compound was prepared according to the procedure of Example A169, step B using [1-(4-cyanophenyl)piperidin-4-yl]acetic acid trifluoroacetate as starting material in 57% yield. LCMS for $C_{31}H_{30}ClN_8O$ (M+H)$^+$: m/z=565.2.

Example A222

2-[1-(3-Chloro-2-cyanophenyl)piperidin-4-yl]-N-[6-chloro-2,4,8,18,22-pentaazatetracyclo[14.3.1.1(3,7).1(9,13)]docosa-1(20),3(22),4,6,9(21),10,12,16,18-nonaen-12-yl]acetamide tris(trifluoroacetate)

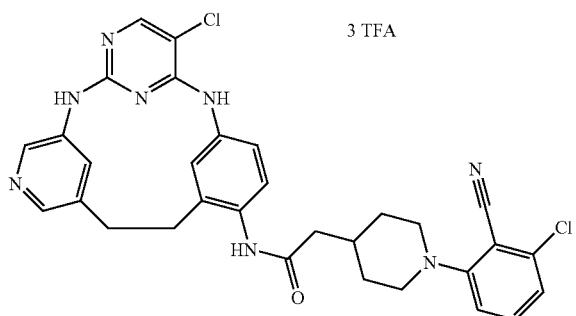

Step A. [1-(3-Chloro-2-cyanophenyl)piperidin-4-yl]-acetic acid trifluoroacetate

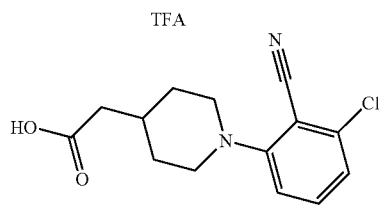 [SMILES: N#Cc1c(Cl)cccc1N1CCC(CC(=O)O)CC1]

The desired compound was prepared according to the procedure of Example A169, step A using 2,6-dichlorobenzonitrile as starting material in 27% yield. LCMS for $C_{14}H_{16}ClN_2O_2$ (M+H)$^+$: m/z=279.1.

Step B. 2-[1-(3-Chloro-2-cyanophenyl)piperidin-4-yl]-N-[6-chloro-2,4,8,18,22-pentaazatetracyclo[14.3.1.1(3,7).1(9,13)]docosa-1(20),3(22),4,6,9(21),10,12,16,18-nonaen-12-yl]acetamide tris(trifluoroacetate)

The desired compound was prepared according to the procedure of Example A169, step B using [1-(3-Chloro-2-cyanophenyl)piperidin-4-yl]acetic acid trifluoroacetate as starting material in 18% yield. LCMS for $C_{31}H_{29}Cl_2N_8O$ (M+H)$^+$: m/z=599.2.

Example A223

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(2-chlorophenyl)sulfonyl]piperidin-4-yl}acetamide bis(trifluoroacetate)

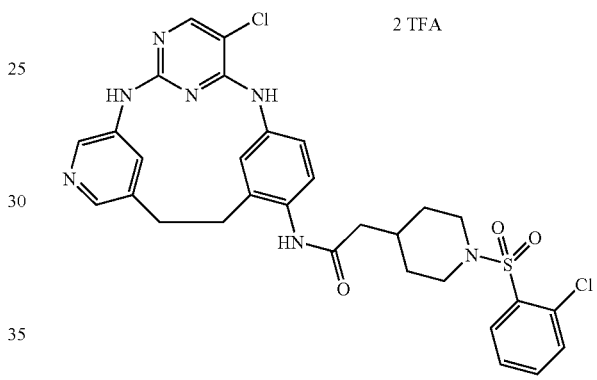

The desired compound was prepared according to the procedure of Example A42 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and 2-chlorobenzenesulfonyl chloride as starting materials in 22% yield. LCMS for $C_{30}H_{30}Cl_2N_7O_3S$ (M+H)$^+$: m/z=638.2.

Example A224

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-(1-{[2-(trifluoromethyl)phenyl]sulfonyl}piperidin-4-yl)acetamide bis(trifluoroacetate)

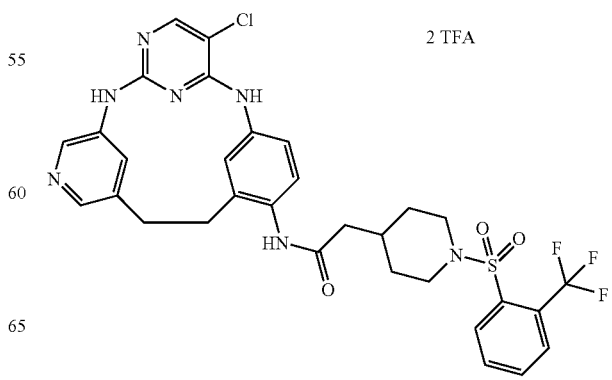

The desired compound was prepared according to the procedure of Example A42 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and 2-(trifluoromethyl)benzenesulfonyl chloride as starting materials in 14% yield. LCMS for $C_{31}H_{30}ClF_3N_7O_3S$ (M+H)+: m/z=672.2.

Example A225

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(2-methylphenyl)sulfonyl]piperidin-4-yl}acetamide bis(trifluoroacetate)

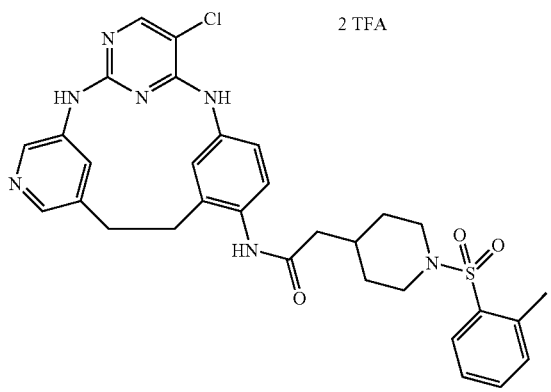 [SMILES: Cc1ccccc1S(=O)(=O)N1CCC(CC(=O)Nc2ccc3cc2CCc2cncc(c2)Nc2ncc(Cl)c(n2)N3)CC1 ; "2 TFA"]

The desired compound was prepared according to the procedure of Example A42 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and 2-methylbenzenesulfonyl chloride as starting materials in 18% yield. LCMS for $C_{31}H_{33}ClN_7O_3S$ (M+H)+: m/z=618.2.

Example A226

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(2-fluorophenyl)sulfonyl]piperidin-4-yl}acetamide bis(trifluoroacetate)

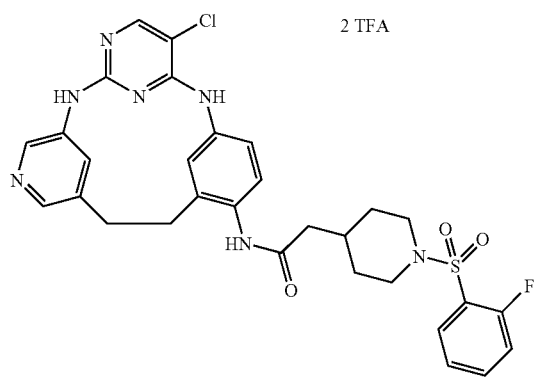 [SMILES: O=C(CC1CCN(S(=O)(=O)c2ccccc2F)CC1)Nc1ccc2cc1CCc1cncc(c1)Nc1ncc(Cl)c(n1)N2 ; "2 TFA"]

The desired compound was prepared according to the procedure of Example A42 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and 2-fluorobenzenesulfonyl chloride as starting materials in 16% yield. LCMS for $C_{30}H_{30}ClFN_7O_3S$ (M+H)+: m/z=622.2.

Example A227

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-(1-{[2-(trifluoromethoxy)phenyl]sulfonyl}piperidin-4-yl)acetamide bis(trifluoroacetate)

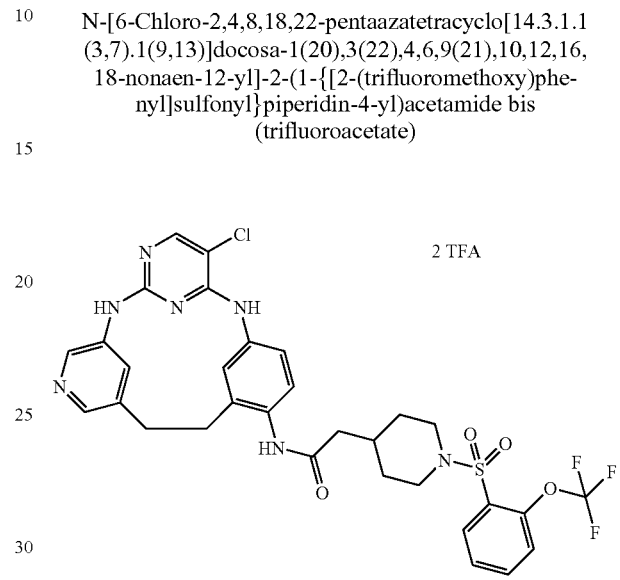

The desired compound was prepared according to the procedure of Example A42 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and 2-(trifluoromethoxy)benzenesulfonyl chloride as starting materials in 16% yield. LCMS for $C_{31}H_{30}ClF_3N_7O_4S$ (M+H)+: m/z=688.2.

Example A228

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(3-cyanophenyl)sulfonyl]piperidin-4-yl}acetamide bis(trifluoroacetate)

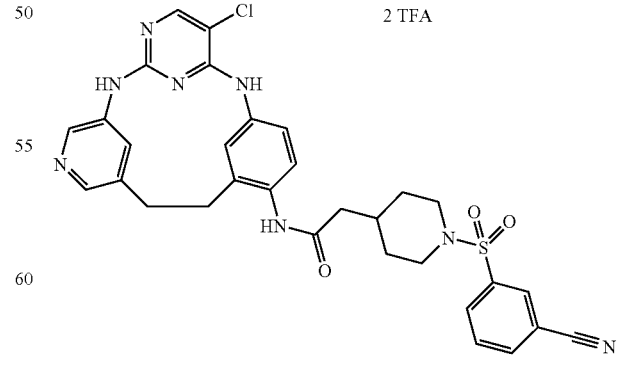

The desired compound was prepared according to the procedure of Example A42 using N-[6-chloro-2,4,8,18,22-pentaazatetracyclo[14.3.1.1(3,7).1(9,13)]docosa-1(20),3(22),4, 6,9(21),10,12,16,18-nonaen-12-yl]-2-piperidin-4-ylacetamide tris(trifluoroacetate) and 3-cyanobenzenesulfonyl chloride as starting materials in 25% yield. LCMS for $C_{31}H_{30}ClN_8O_3S$ (M+H)+: m/z=629.2.

Example A229

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(1-methyl-1H-imidazol-4-yl)sulfonyl]piperidin-4-yl}acetamide bis (trifluoroacetate)

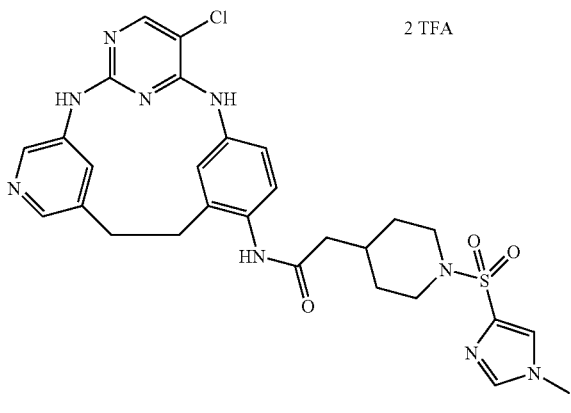 [SMILES: Cn1cnc(S(=O)(=O)N2CCC(CC(=O)Nc3ccc4cc3CCc3cncc(c3)Nc3ncc(Cl)c(n3)N4)CC2)c1 ; "2 TFA"]

The desired compound was prepared according to the procedure of Example A42 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and 1-methyl-1H-imidazole-4-sulfonyl chloride as starting materials in 17% yield. LCMS for $C_{28}H_{31}ClN_9O_3S$ (M+H)+: m/z=608.2.

Example A230

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(1,2-dimethyl-1H-imidazol-4-yl)sulfonyl]piperidin-4-yl}acetamide bis (trifluoroacetate)

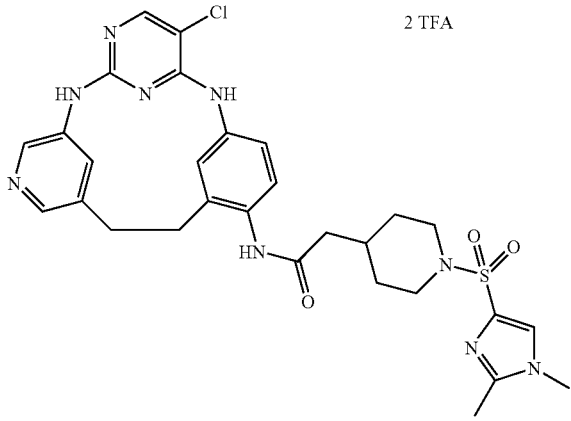 [SMILES: Cc1nc(S(=O)(=O)N2CCC(CC(=O)Nc3ccc4cc3CCc3cncc(c3)Nc3ncc(Cl)c(n3)N4)CC2)cn1C ; "2 TFA"]

The desired compound was prepared according to the procedure of Example A42 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and 1,2-dimethyl-1H-imidazole-4-sulfonyl chloride as starting materials in 24% yield. LCMS for $C_{29}H_{33}ClN_9O_3S$ (M+H)+: m/z=622.2.

Example A231

N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(3,5-dimethylisoxazol-4-yl)sulfonyl]piperidin-4-yl}acetamide bis (trifluoroacetate)

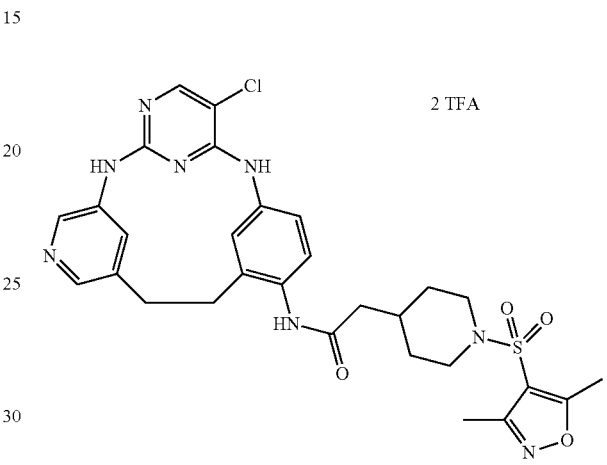

The desired compound was prepared according to the procedure of Example A42 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and 3,5-dimethylisoxazole-4-sulfonyl chloride as starting materials in 17% yield. LCMS for $C_{29}H_{32}ClN_8O_4S$ (M+H)+: m/z=623.2.

Example A232

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(2,4-dimethyl-1,3-thiazol-5-yl)sulfonyl]piperidin-4-yl}acetamide bis (trifluoroacetate)

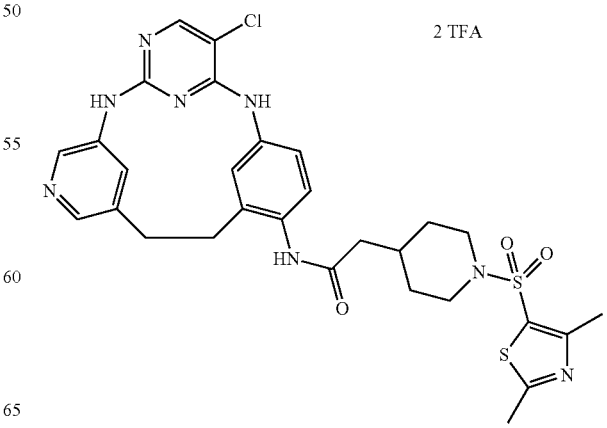

The desired compound was prepared according to the procedure of Example A42 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and 2,4-dimethyl-1,3-thiazole-5-sulfonyl chloride as starting materials in 22% yield. LCMS for $C_{29}H_{32}ClN_8O_3S_2$ (M+H)$^+$: m/z=639.2.

Example A233

N-[6-Chloro-2,4,8,18,22-pentaazatetracyclo[14.3.1.1 (3,7).1(9,13)]docosa-1(20),3(22),4,6,9(21),10,12,16, 18-nonaen-12-yl]-2-[1-(2-cyano-3-methoxyphenyl) piperidin-4-yl]acetamide tris(trifluoroacetate)

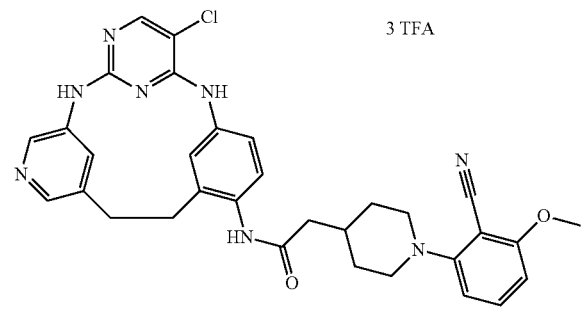 [SMILES: "3 TFA" ; COc1cccc(N2CCC(CC(=O)Nc3ccc4cc3CCc3cncc(c3)Nc3ncc(Cl)c(n3)N4)CC2)c1C#N]

Step A.
[1-(2-Cyano-3-methoxyphenyl)piperidin-4-yl]acetic acid trifluoroacetate

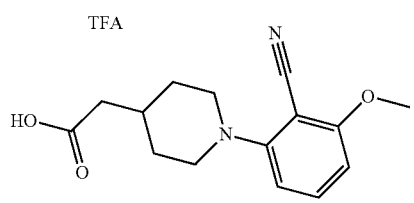 [SMILES: "TFA" ; COc1cccc(N2CCC(CC(=O)O)CC2)c1C#N]

The desired compound was prepared according to the procedure of Example A169, step A using 2-fluoro-6-methoxybenzonitrile as starting material in 4% yield. LCMS for $C_{15}H_{19}N_2O_3$ (M+H)$^+$: m/z=275.1.

Step B. N-[6-Chloro-2,4,8,18,22-pentaazatetracyclo [14.3.1.1(3,7).1(9,13)]docosa-1(20),3(22),4,6,9(21), 10,12,16,18-nonaen-12-yl]-2-[1-(2-cyano-3-methoxyphenyl)piperidin-4-yl]acetamide tris (trifluoroacetate)

The desired compound was prepared according to the procedure of Example A169, step B using [1-(2-cyano-3-methoxyphenyl)piperidin-4-yl]acetic acid trifluoroacetate as starting material in 27% yield. LCMS for $C_{32}H_{32}ClN_8O_2$ (M+H)$^+$: m/z=595.2.

Example A234

N-[6-Chloro-2,4,8,18,22-pentaazatetracyclo[14.3.1.1 (3,7).1(9,13)]docosa-1(20),3(22),4,6,9(21),10,12,16, 18-nonaen-12-yl]-2-[1-(2-cyano-3-fluorophenyl) piperidin-4-yl]acetamide tris(trifluoroacetate)

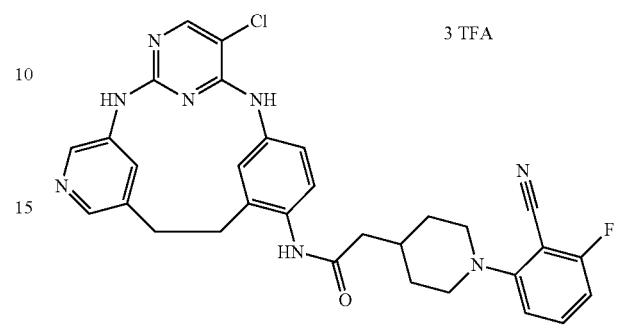

Step A.
[1-(2-Cyano-3-fluorophenyl)piperidin-4-yl]acetic acid trifluoroacetate

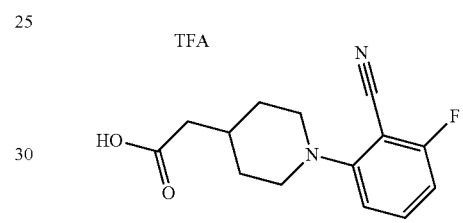

The desired compound was prepared according to the procedure of Example A169, step A using 2,6-difluorobenzonitrile as starting material in 43% yield. LCMS for $C_{14}H_{16}FN_2O_2$ (M+H)$^+$: m/z=263.1.

Step B. N-[6-Chloro-2,4,8,18,22-pentaazatetracyclo [14.3.1.1(3,7).1(9,13)]docosa-1(20),3(22),4,6,9(21), 10,12,16,18-nonaen-12-yl]-2-[6-(2-cyano-3-fluorophenyl)piperidin-4-yl]acetamide tris (trifluoroacetate)

The desired compound was prepared according to the procedure of Example A169, step B using [1-(2-cyano-3-fluorophenyl)piperidin-4-yl]acetic acid trifluoroacetate as starting material in 8% yield. LCMS for $C_{31}H_{29}ClFN_8O$ (M+H)$^+$: m/z=583.2.

Example A235

N-[6-Chloro-2,4,8,18,22-pentaazatetracyclo[14.3.1.1 (3,7).1(9,13)]docosa-1(20),3(22),4,6,9(21),10,12,16, 18-nonaen-12-yl]-2-{1-[2-cyano-3-(trifluoromethyl) phenyl]piperidin-4-yl}acetamide tris (trifluoroacetate)

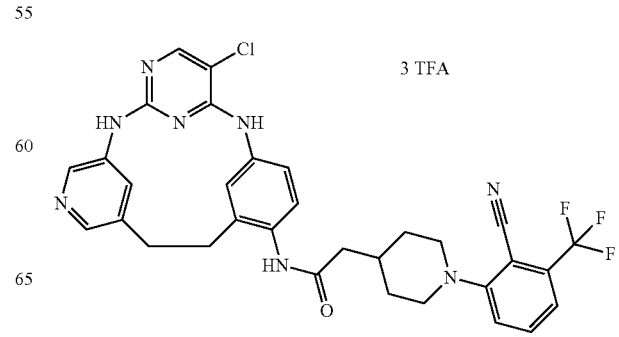

Step A. {1-[2-Cyano-3-(trifluoromethyl)phenyl]piperidin-4-yl}acetic acid trifluoroacetate

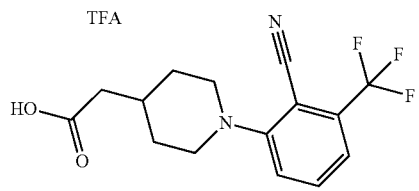 [SMILES: "TFA" ; N#Cc1c(N2CCC(CC(=O)O)CC2)cccc1C(F)(F)F]

The desired compound was prepared according to the procedure of Example A169, step A using 2-fluoro-6-(trifluoromethyl)benzonitrile as starting material in 42% yield. LCMS for $C_{15}H_{16}F_3N_2O_2$ (M+H)$^+$: m/z=313.1.

Step B. N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[2-cyano-3-(trifluoromethyl)phenyl]piperidin-4-yl}acetamide tris(trifluoroacetate)

The desired compound was prepared according to the procedure of Example A169, step B using {1-[2-cyano-3-(trifluoromethyl)phenyl]piperidin-4-yl}acetic acid trifluoroacetate as starting material in 23% yield. LCMS for $C_{32}H_{29}ClF_3N_8O$ (M+H)$^+$: m/z=633.2.

Example A236

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(2-cyano-3-methylphenyl)piperidin-4-yl]acetamide tris(trifluoroacetate)

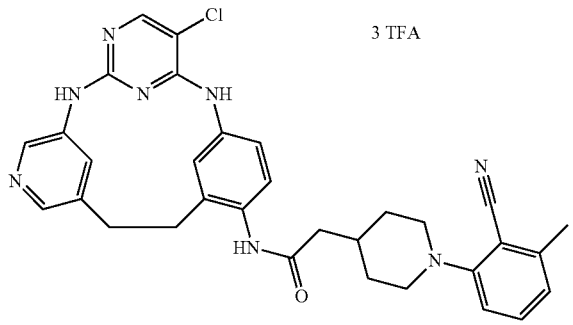 [SMILES: "3 TFA" ; Cc1cccc(N2CCC(CC(=O)Nc3ccc4cc3CCc3cncc(c3)Nc3ncc(Cl)c(n3)N4)CC2)c1C#N]

Step A.
[1-(2-Cyano-3-methylphenyl)piperidin-4-yl]acetic acid trifluoroacetate

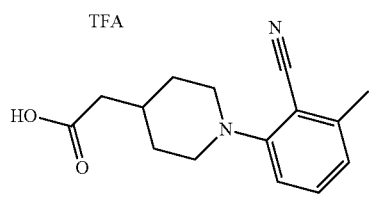 [SMILES: "TFA" ; Cc1cccc(N2CCC(CC(=O)O)CC2)c1C#N]

The desired compound was prepared according to the procedure of Example A169, step A using 2-chloro-6-methylbenzonitrile as starting material in 4% yield. LCMS for $C_{15}H_{19}N_2O_2$ (M+H)$^+$: m/z=259.1.

Step B. N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[6-(2-cyano-3-ethylphenyl)piperidin-4-yl]acetamide tris(trifluoroacetate)

The desired compound was prepared according to the procedure of Example A169, step B using [1-(2-cyano-3-methylphenyl)piperidin-4-yl]acetic acid trifluoroacetate as starting material in 35% yield. LCMS for $C_{32}H_{32}ClN_8O$ (M+H)$^+$: m/z=579.2.

Example A237

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[2-cyano-5-(trifluoromethyl)phenyl]piperidin-4-yl}acetamide tris(trifluoroacetate)

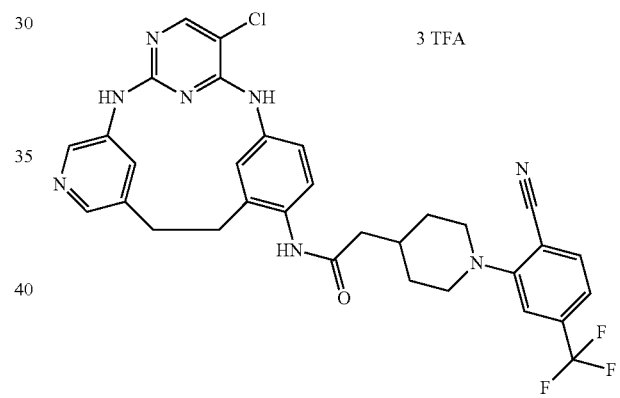

Step A. {1-[2-Cyano-5-(trifluoromethyl)phenyl]piperidin-4-yl}acetic acid trifluoroacetate

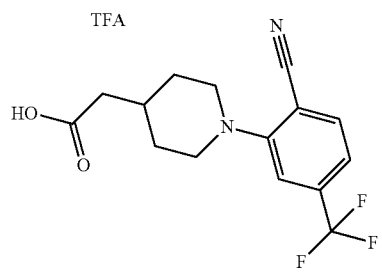 [SMILES: "TFA" ; N#Cc1ccc(C(F)(F)F)cc1N1CCC(CC(=O)O)CC1]

The desired compound was prepared according to the procedure of Example A169, step A using 2-fluoro-4-(trifluoromethyl)benzonitrile as starting material in 9% yield. LCMS for $C_{15}H_{16}F_3N_2O_2$ (M+H)$^+$: m/z=313.1.

Step B. N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[2-cyano-5-(trifluoromethyl)phenyl]piperidin-4-yl}acetamide tris (trifluoroacetate)

The desired compound was prepared according to the procedure of Example A169, step B using {1-[2-cyano-5-(trifluoromethyl)phenyl]piperidin-4-yl}acetic acid trifluoroacetate as starting material in 32% yield. LCMS for $C_{32}H_{29}ClF_3N_8O$ (M+H)$^+$: m/z=633.2.

Example A238

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(3-cyano-6-methylpyridin-2-yl)piperidin-4-yl]acetamide tris(trifluoroacetate)

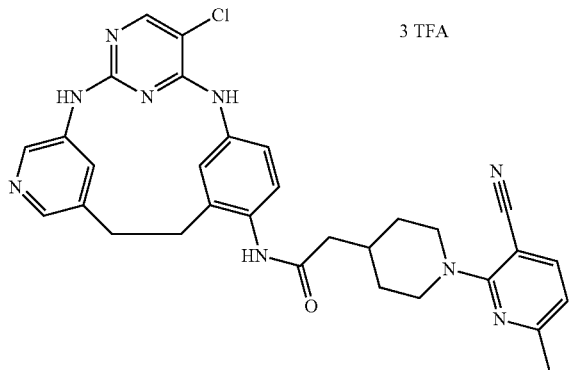 [SMILES: "3 TFA" ; Cc1ccc(C#N)c(N2CCC(CC(=O)Nc3ccc4cc3CCc3cncc(c3)Nc3ncc(Cl)c(n3)N4)CC2)n1]

Step A. [1-(3-Cyano-6-methylpyridin-2-yl)piperidin-4-yl]acetic acid trifluoroacetate

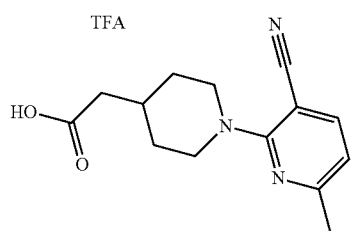 [SMILES: "TFA" ; Cc1ccc(C#N)c(N2CCC(CC(=O)O)CC2)n1]

The desired compound was prepared according to the procedure of Example A169, step A using 2-chloro-6-methylnicotinonitrile as starting material in 4% yield. LCMS for $C_{14}H_{18}N_3O_2$ (M+H)$^+$: m/z=260.1.

Step B. N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(3-cyano-6-methylpyridin-2-yl)piperidin-4-yl]acetamide tris (trifluoroacetate)

The desired compound was prepared according to the procedure of Example A169, step B using [1-(3-cyano-6-methylpyridin-2-yl)piperidin-4-yl]acetic acid trifluoroacetate as starting material in 23% yield. LCMS for $C_{31}H_{31}ClN_9O$ (M+H)$^+$: m/z=580.2.

Example A239

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(3-cyano-4,6-dimethylpyridin-2-yl)piperidin-4-yl]acetamide tris (trifluoroacetate)

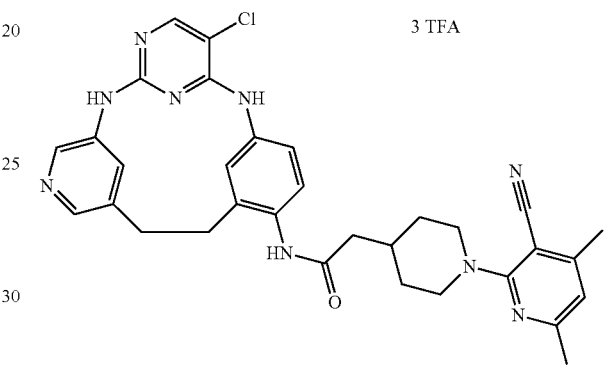

Step A. [1-(3-Cyano-4,6-dimethylpyridin-2-yl)piperidin-4-yl]acetic acid trifluoroacetate

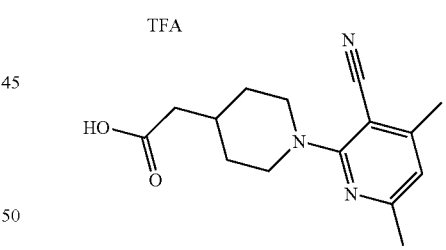

The desired compound was prepared according to the procedure of Example A169, step A using 2-chloro-3-cyano-4,6-dimethylpyridine as starting material in 59% yield. LCMS for $C_{15}H_{20}N_3O_2$ (M+H)+: m/z=274.1.

Step B. N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(3-cyano-4,6-dimethylpyridin-2-yl)piperidin-4-yl]acetamide tris (trifluoroacetate)

The desired compound was prepared according to the procedure of Example A169, step B using [1-(3-cyano-4,6-dimethylpyridin-2-yl)piperidin-4-yl]acetic acid trifluoroacetate as starting material in 25% yield. LCMS for $C_{32}H_{33}ClN_9O_2$ (M+H)$^+$: m/z=594.2.

Example A240

2-[1-(5-Chloro-4-cyanopyridin-3-yl)piperidin-4-yl]-N-[6-chloro-2,4,8,18,22-pentaazatetracyclo[14.3.1.1(3,7).1(9,13)]docosa-1(20),3(22),4,6,9(21),10,12,16,18-nonaen-12-yl]acetamide tris(trifluoroacetate)

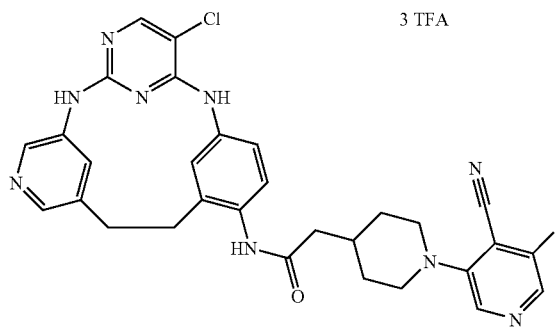

Step A. [1-(5-Chloro-4-cyanopyridin-3-yl)piperidin-4-yl]acetic acid trifluoroacetate

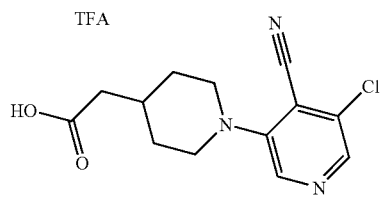 [SMILES: N#Cc1c(Cl)cncc1N1CCC(CC(=O)O)CC1]

The desired compound was prepared according to the procedure of Example A169, step A using 3,5-dichloroisonicotinonitrile as starting material in 50% yield. LCMS for $C_{13}H_{15}ClN_3O_2$ (M+H)$^+$: m/z=280.1.

Step B. 2-[1-(5-Chloro-4-cyanopyridin-3-yl)piperidin-4-yl]-N-[6-chloro-2,4,8,18,22-pentaazatetracyclo[14.3.1.1(3,7).1(9,13)]docosa-1(20),3(22),4,6,9(21),10,12,16,18-nonaen-12-yl]acetamide tris(trifluoroacetate)

The desired compound was prepared according to the procedure of Example A169, step B using [1-(5-chloro-4-cyan-opyridin-3-yl)piperidin-4-yl]acetic acid trifluoroacetate as starting material in 17% yield. LCMS for $C_{30}H_{28}Cl_2N_9O$ (M+H)$^+$: m/z=600.2.

Example A241

2-[1-(6-Chloro-3-cyano-5-fluoropyridin-2-yl)piperidin-4-yl]-N-[6-chloro-2,4,8,18,22-pentaazatetracyclo[14.3.1.1(3,7).1(9,13)]docosa-1(20),3(22),4,6,9(21),10,12,16,18-nonaen-12-yl]acetamide tris(trifluoroacetate)

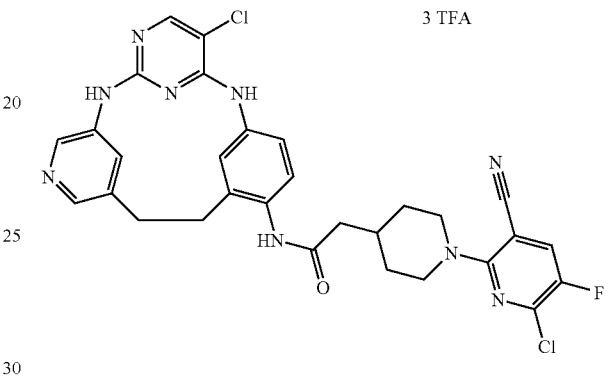

Step A. [1-(6-Chloro-3-cyano-5-fluoropyridin-2-yl)piperidin-4-yl]acetic acid trifluoroacetate

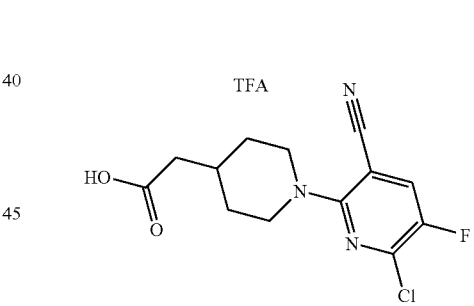

The desired compound was prepared according to the procedure of Example A169, step A using 2,6-dichloro-5-fluoronicotinonitrile as starting material in 8% yield. LCMS for $C_{13}H_{14}ClFN_3O_2$ (M+H)$^+$: m/z=298.1.

Step B. 2-[1-(6-Chloro-3-cyano-5-fluoropyridin-2-yl)piperidin-4-yl]-N-[6-chloro-2,4,8,18,22-pentaazatetracyclo[14.3.1.1(3,7).1(9,13)]docosa-1(20),3(22),4,6,9(21),10,12,16,18-nonaen-12-yl]acetamide tris(trifluoroacetate)

The desired compound was prepared according to the procedure of Example A169, step B using [1-(6-chloro-3-cyano-5-fluoropyridin-2-yl)piperidin-4-yl]acetic acid trifluoroacetate as starting material in 9% yield. LCMS for $C_{30}H_{27}Cl_2FN_9O$ (M+H)⁺: m/z=618.2.

Example A242

N-[6-Chloro-2,4,8,18,22-pentaazatetracyclo[14.3.1.1 (3,7).1(9,13)]docosa-1(20),3(22),4,6,9(21),10,12,16, 18-nonaen-12-yl]-2-(1-pyridin-4-ylpiperidin-4-yl) acetamide tris(trifluoroacetate)

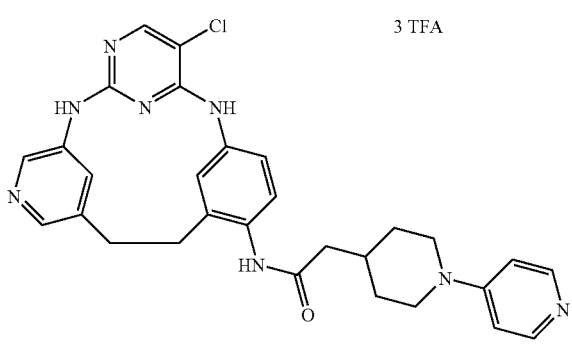 [SMILES: O=C(CC1CCN(c2ccncc2)CC1)Nc1ccc2cc1CCc1cncc(c1)Nc1ncc(Cl)c(n1)N2]

Step A. (1-Pyridin-4-ylpiperidin-4-yl)acetic acid trifluoroacetate

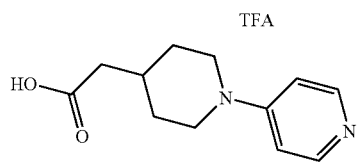 [SMILES: O=C(O)CC1CCN(c2ccncc2)CC1]

The desired compound was prepared according to the procedure of Example A169, step A using 4-bromopyridine hydrochloride as starting material in 99% yield. LCMS for $C_{12}H_{17}N_2O_2$ (M+H)⁺: m/z=221.1.

Step B. N-[6-Chloro-2,4,8,18,22-pentaazatetracyclo [14.3.1.1(3,7).1(9,13)]docosa-1(20),3(22),4,6,9(21), 10,12,16,18-nonaen-12-yl]-2-(1-pyridin-4-ylpiperidin-4-yl)acetamide tris(trifluoroacetate)

The desired compound was prepared according to the procedure of Example A169, step B using (1-pyridin-4-ylpiperidin-4-yl)acetic acid trifluoroacetate as starting material in 8% yield. LCMS for $C_{29}H_{30}ClN_8O$ (M+H)⁺: m/z=541.2.

Example A243

N-[6-Chloro-2,4,8,18,22-pentaazatetracyclo[14.3.1.1 (3,7).1(9,13)]docosa-1(20),3(22),4,6,9(21),10,12,16, 18-nonaen-12-yl]-2-[1-(3-fluoropyridin-4-yl)piperidin-4-yl]acetamide tris(trifluoroacetate)

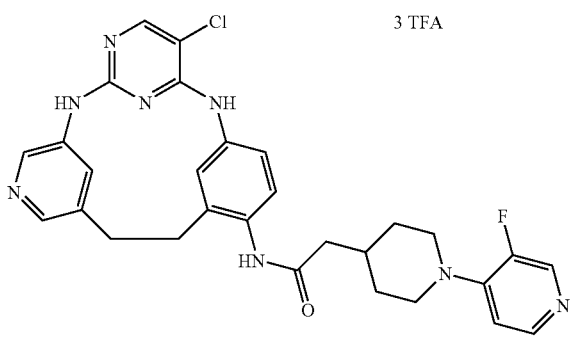 [SMILES: O=C(CC1CCN(c2ccncc2F)CC1)Nc1ccc2cc1CCc1cncc(c1)Nc1ncc(Cl)c(n1)N2]

Step A. [1-(3-Fluoropyridin-4-yl)piperidin-4-yl]acetic acid trifluoroacetate

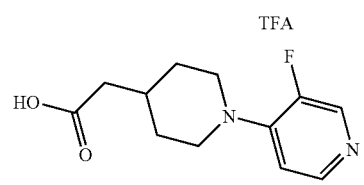 [SMILES: O=C(O)CC1CCN(c2ccncc2F)CC1]

The desired compound was prepared according to the procedure of Example A169, step A using 4-bromo-3-fluoropyridine hydrochloride as starting material in 82% yield. LCMS for $C_{12}H_{16}FN_2O_2$ (M+H)⁺: m/z=239.1.

Step B. N-[6-Chloro-2,4,8,18,22-pentaazatetracyclo [14.3.1.1(3,7).1(9,13)]docosa-1(20),3(22),4,6,9(21), 10,12,16,18-nonaen-12-yl]-2-[1-(3-fluoropyridin-4-yl)piperidin-4-yl]acetamide tris(trifluoroacetate)

The desired compound was prepared according to the procedure of Example A169, step B using [1-(3-fluoropyridin-4-yl)piperidin-4-yl]acetic acid trifluoroacetate as starting material in 24% yield. LCMS for $C_{29}H_{29}FN_8O$ (M+H)⁺: m/z=559.2.

Example A244

N-[6-Chloro-2,4,8,18,22-pentaazatetracyclo[14.3.1.1 (3,7).1(9,13)]docosa-1(20),3(22),4,6,9(21),10,12,16, 18-nonaen-12-yl]-2-[1-(2-fluoropyridin-4-yl)piperidin-4-yl]acetamide tris(trifluoroacetate)

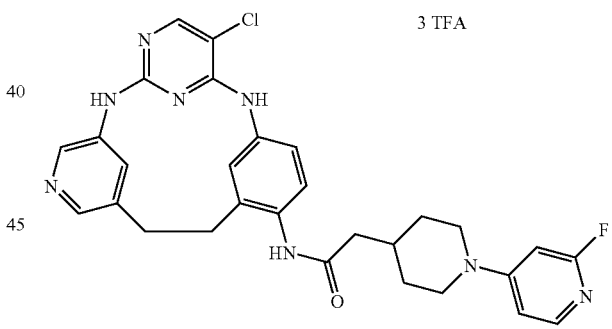

Step A. [1-(2-Fluoropyridin-4-yl)piperidin-4-yl]acetic acid trifluoroacetate

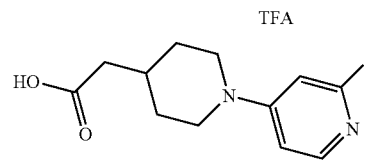

The desired compound was prepared according to the procedure of Example A169, step A using 4-bromo-2-fluoropyridine as starting material in 13% yield. LCMS for $C_{12}H_{16}FN_2O_2$ (M+H)⁺: m/z=239.1.

Step B. N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(2-fluoropyridin-4-yl)piperidin-4-yl]acetamide tris(trifluoroacetate)

The desired compound was prepared according to the procedure of Example A169, step B using [1-(2-fluoropyridin-4-yl)piperidin-4-yl]acetic acid trifluoroacetate as starting material in 23% yield. LCMS for $C_{29}H_{29}ClFN_8O$ (M+H)$^+$: m/z=559.2.

Example A245

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(cyanoacetyl)piperidin-4-yl]acetamide bis(trifluoroacetate)

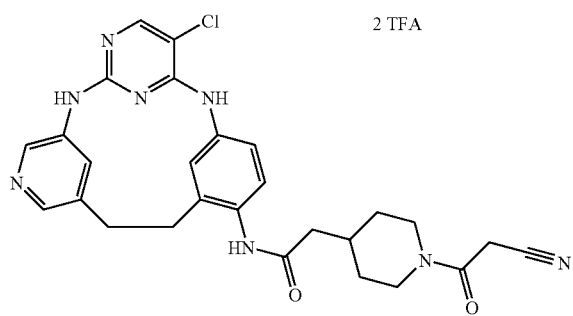 [SMILES: N#CCC(=O)N1CCC(CC(=O)Nc2ccc3cc2CCc2cncc(c2)Nc2ncc(Cl)c(n2)N3)CC1 ; "2 TFA"]

The desired compound was prepared according to the procedure of Example A27 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide tris(trifluoroacetate) and cyanoacetic acid as starting materials in 41% yield. LCMS for $C_{27}H_{28}ClN_8O_2$ (M+H)$^+$: m/z=531.2.

Example A246

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(1,3-oxazol-2-yl)piperidin-4-yl]acetamide tris(trifluoroacetate)

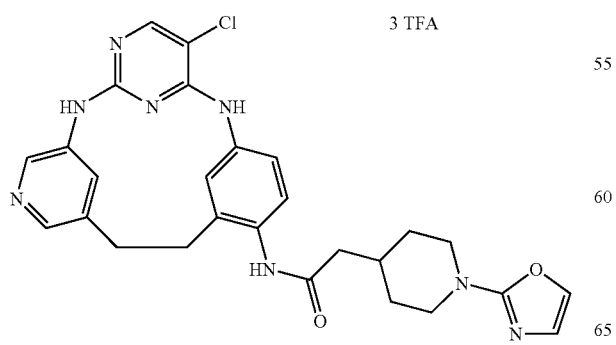

Step A. [1-(1,3-Oxazol-2-yl)piperidin-4-yl]acetic acid trifluoroacetate

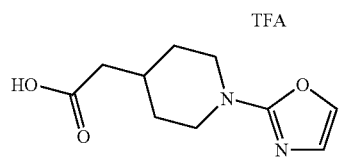 [SMILES: O=C(O)CC1CCN(c2ncco2)CC1]

The desired compound was prepared according to the procedure of Example A169, step A using 2-chloro-1,3-oxazole as starting material in 20% yield. LCMS for $C_{10}H_{15}N_2O_3$ (M+H)$^+$: m/z=211.1.

Step B. N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(1,3-oxazol-2-yl)piperidin-4-yl]acetamide tris(trifluoroacetate)

The desired compound was prepared according to the procedure of Example A169, step B using [1-(1,3-oxazol-2-yl)piperidin-4-yl]acetic acid trifluoroacetate as starting material in 8% yield. LCMS for $C_{27}H_{28}ClN_8O_2$ (M+H)$^+$: m/z=531.2.

Example A247

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(5-methylisoxazol-3-yl)piperidin-4-yl]acetamide bis(trifluoroacetate)

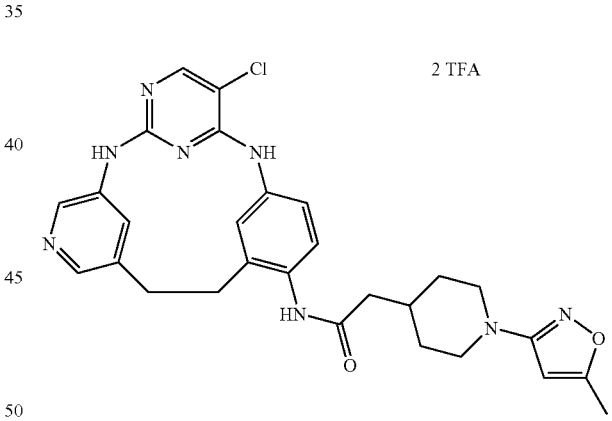

Step A. [1-(5-Methylisoxazol-3-yl)piperidin-4-yl]acetic acid trifluoroacetate

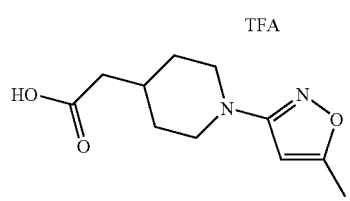 [SMILES: Cc1cc(N2CCC(CC(=O)O)CC2)no1]

The desired compound was prepared according to the procedure of Example A169, step A using 3-chloro-2,5-dimethyl-isoxazolium chloride as starting material in 10% yield. LCMS for $C_{11}H_{17}N_2O_3$ (M+H)$^+$: m/z=225.1.

Step B. N-[6-Chloro-2,4,8,18,22-pentaazatetracyclo [14.3.1.1(3,7).1(9,13)]docosa-1(20),3(22),4,6,9(21), 10,12,16,18-nonaen-12-yl]-2-[1-(5-methylisoxazol-3-yl)piperidin-4-yl]acetamide tris(trifluoroacetate)

The desired compound was prepared according to the procedure of Example A169, step B using [1-(5-methylisoxazol-3-yl)piperidin-4-yl]acetic acid trifluoroacetate as starting material in 14% yield. LCMS for $C_{28}H_{30}ClN_8O_2$ (M+H)$^+$: m/z=545.2.

Example A248

N-[6-Chloro-2,4,8,22-tetraazatetracyclo[14.3.1.1(3, 7).1(9,13)]docosa-1(20),3(22),4,6,9(21),10,12,16,18-nonaen-12-yl]-2-[1-(5-methylisoxazol-3-yl)piperidin-4-yl]acetamide trifluoroacetate

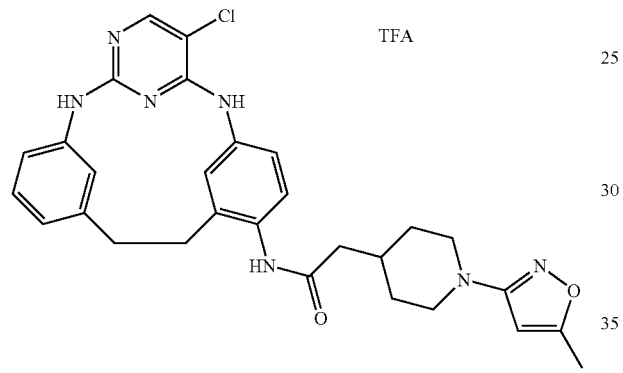

The desired compound was prepared according to the procedure of Example A169, step B using 6-chloro2,4,8,22-tetraazatetracyclo[14.3.1.1(3,7).1(9,13)]docosa1(20),3(22), 4,6,9(21),10,12,16,18-nonaen-12-amine dihydrochloride and [1-(5-methylisoxazol-3-yl)piperidin-4-yl]acetic acid trifluoroacetate as starting materials in 8% yield. LCMS for $C_{29}H_{31}ClN_7O_2$ (M+H)$^+$: m/z=544.2.

Example A249

6-Chloro-12-{2-oxo-2-[3-(trifluoromethyl)-5,6-dihydro[1,2,4]triazolo[4,3-a]pyrazin-7(8H)-yl]ethoxy}-2, 4,8,18,22pentaazatetracyclo[14.3.1.1(3,7).1(9,13)] docosa1(20),3(22),4,6,9(21),10,12,16,18-nonaene bis(trifluoroacetate)

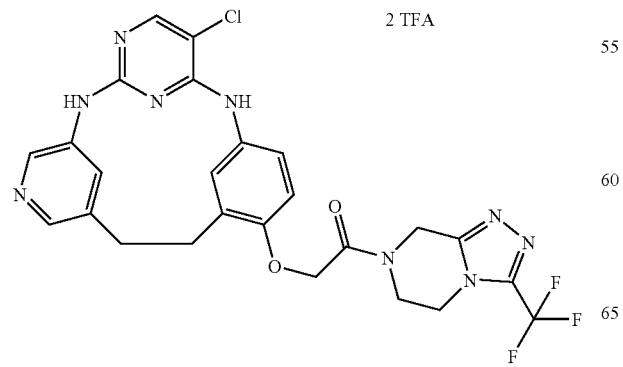

Step A. 7-(Chloroacetyl)-3-(trifluoromethyl)-5,6,7,8-tetrahydro[1,2,4]triazolo[4,3-a]pyrazine

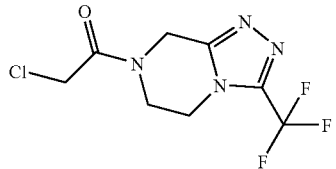 [SMILES: O=C(CCl)N1CCn2c(nnc2C(F)(F)F)C1]

Bromoacetic acid (300 mg, 2.2 mmol) and 3-(trifluoromethyl)-5,6,7,8-tetrahydro[1,2,4]triazolo[4,3-a]pyrazine hydrochloride (490 mg, 2.2 mmol) were stirred in dichloromethane (5 mL) with N-(3-dimethylaminopropyl)-N'-ethylcarbodiimide hydrochloride (412 mg, 2.2 mmol) and N,N-diisopropylethylamine (560 mL, 3.2 µmol) for 3 hours at rt. The mixture was washed with water, dried over sodium sulfate and evaporated to give the desired compound in 33% yield. LCMS for $C_8H_8ClF_3N_4O$ (M+H)$^+$: m/z=269.0.

Step B. 6-Chloro-12-{2-oxo-2-[3-(trifluoromethyl)-5,6-dihydro[1,2,4]triazolo[4,3-a]pyrazin-7(8H)-yl] ethoxy}-2,4,8,18,22-pentaazatetracyclo[14.3.1.1(3, 7). 1(9,13)]docosa-1(20),3(22),4,6,9(21),10,12,16, 18-nonaene bis(trifluoroacetate)

The desired compound was prepared according to the procedure of Example A9, step G using 6-chloro-2,4,8,18,22-pentaazatetracyclo[14.3.1.1(3,7).1(9,13)]docosa-1(20),3 (22),4,6,9(21),10,12,16,18-nonaen-12-ol and 7-(chloroacetyl)-3-(trifluoromethyl)-5,6,7,8-tetrahydro[1,2, 4]triazolo[4,3-a]pyrazine as starting materials in 30% yield. LCMS for $C_{25}H_{22}ClF_3N_9O_2$ (M+H)$^+$: m/z=572.2.

Example B1

(14Z)-6-Methyl-2,4,8,22-tetraazatetracyclo[14.3.1.1 (3,7).1(9,13)]docosa-1(20),3(22),4,6,9(21),10,12,14, 16,18-decaene trifluoroacetate

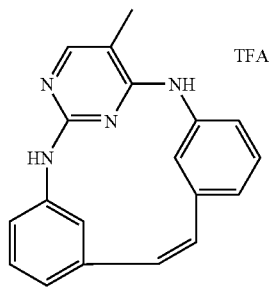 [SMILES: Cc1cnc2nc1Nc1cccc(c1)/C=C\c1cccc(c1)N2]

Step A: 2-Chloro-5-methyl-N-(3-vinylphenyl)pyrimidin-4-amine

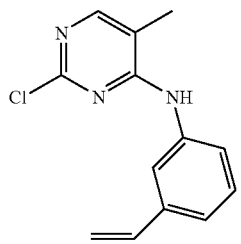 [SMILES: C=Cc1cccc(Nc2nc(Cl)ncc2C)c1]

This compound was prepared according to the procedure of Example A1, step A, using 2,4-dichloro-5-methylpyrimidine and 3-vinylaniline as the starting materials in 39% yield. LCMS calculated for $C_{13}H_{13}ClN_3$ (M+H)$^+$: m/z=246.1.

Step B: 5-Methyl-N,N'-bis(3-vinylphenyl)pyrimidine-2,4-diamine trifluoroacetate

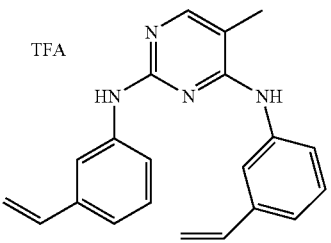 [SMILES: C=Cc1cccc(Nc2ncc(C)c(Nc3cccc(C=C)c3)n2)c1]

This compound was prepared according to the procedure of Example A1, step B, using 2-chloro-5-methyl-N-(3-vinylphenyl)pyrimidin-4-amine and 3-vinylaniline as the starting materials in 64% yield. LCMS calculated for $C_{21}H_{21}N_4$ (M+H)$^+$: m/z=329.3.

Step C: (14Z)-6-Methyl-2,4,8,22-tetraazatetracyclo[14.3.1.1(3,7).1(9,13)]docosa-1(20),3(22),4,6,9(21),10,12,14,16,18-decaene trifluoroacetate This compound was prepared according to the procedure of Example A1, step C using 5-methyl-N,N'-bis(3-vinylphenyl)pyrimidine-2,4-diamine trifluoroacetate as the starting materials in 17% yield. LCMS calculated for $C_{19}H_{17}N_4$(M+H)$^+$: m/z=301.1. $^1$H NMR (400 MHz, DMSO-$d_6$): δ 10.02 (brs, 1H), 9.62 (brs, 1H), 8.67 (s, 1H), 8.50 (s, 1H), 7.91 (s, 1H), 7.32-7.14 (m, 3H), 7.05-6.95 (m, 3H), 6.74-6.66 (m, 2H), 2.14 (s, 3H).

Example B2

6-Methyl-2,4,8,22-tetraazatetracyclo[14.3.1.1(3,7).1(9,13)]docosa-1(20),3(22),4,6,9(21),10,12,16,18-nonaene trifluoroacetate

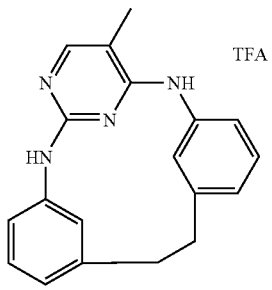 [SMILES: Cc1cnc2nc1Nc1cccc(c1)CCc1cccc(c1)N2]

This compound was prepared according to the procedure of Example A2, using (14Z)-6-methyl-2,4,8,22-tetraazatetracyclo[14.3.1.1(3,7).1(9,13)]docosa-1(20),3(22),4,6,9(21),10,12,14,16,18-decaene trifluoroacetate as the starting material in 65% yield. LCMS calculated for $C_{19}H_{19}N_4$(M+H)$^+$: m/z=303.2. $^1$H NMR (400 MHz, DMSO-$d_6$): δ 10.15 (s, 1H), 9.87 (s, 1H), 7.89 (s, 1H), 7.79 (s, 1H), 7.73 (s, 1H), 7.25 (t, 1H), 7.17 (t, 1H), 7.02 (m, 2H), 6.95 (d, 1H), 6.87 (dd, 1H), 2.95 (s, 4H), 2.14 (s, 3H).

Example B3

6-Bromo-2,4,8,22-tetraazatetracyclo[14.3.1.1(3,7).1(9,13)]docosa-1(20),3(22),4,6,9(21),10,12,16,18-nonaene trifluoroacetate

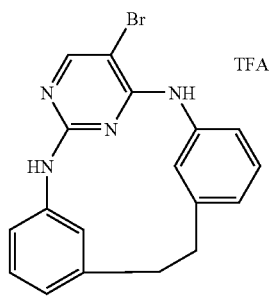 [SMILES: Brc1cnc2nc1Nc1cccc(c1)CCc1cccc(c1)N2]

Step A: tert-Butyl {3-[(3-aminophenyl)ethynyl]phenyl}carbamate

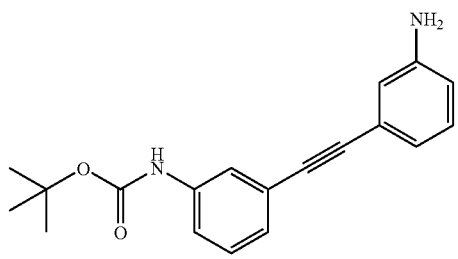 [SMILES: CC(C)(C)OC(=O)Nc1cccc(C#Cc2cccc(N)c2)c1]

A solution of 3-ethynylaniline (1.16 g, 9.87 mmol) and tert-butyl (3-iodophenyl)carbamate (3.0 g, 9.4 mmol) in THF (28 mL) was treated with bis(triphenylphosphine)palladium (II) chloride (330 mg, 0.47 mmol), copper(I) iodide (140 mg, 0.75 mmol) and N,N-diisopropylethylamine (3.27 ml, 18.8 mmol), and stirred at 25° C. overnight. The reaction was diluted with water and extracted with ethyl acetate three times. The combined organic solutions were dried with sodium sulfate, filtered, and concentrated in vacuo. The crude residue was purified by flash column chromatography to yield the desired product (1.42 g, 49%). LCMS for $C_{19}H_{21}N_2O_2$ (M+H)$^+$: m/z=309.1.

Step B: tert-Butyl {3-[2-(3-aminophenyl)ethyl]phenyl}carbamate

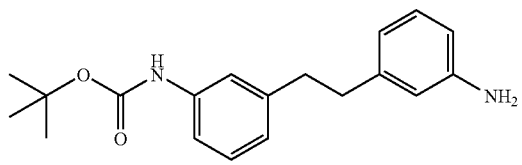 [SMILES: CC(C)(C)OC(=O)Nc1cccc(CCc2cccc(N)c2)c1]

To a solution of tert-butyl {3-[(3-aminophenyl)ethynyl]phenyl}carbamate (0.5 g, 2.0 mmol) in methanol (10 mL) was added 10% palladium on carbon (0.50 g, 0.43 mmol) and the mixture was stirred under an atmosphere of hydrogen for 24 h. The reaction mixture was filtered through a pad of celite, rinsed with methanol and dichloromethane. The solvents were evaporated to give a crude oil. This material was purified by flash column chromatography to yield the desired product (430 mg, 85%). LCMS for $C_{19}H_{25}N_2O_2(M+H)^+$: m/z=313.2.

Step C: tert-Butyl [3-(2-{3-[(5-bromo-2-chloropyrimidin-4-yl)amino]phenyl}ethyl)phenyl]carbamate

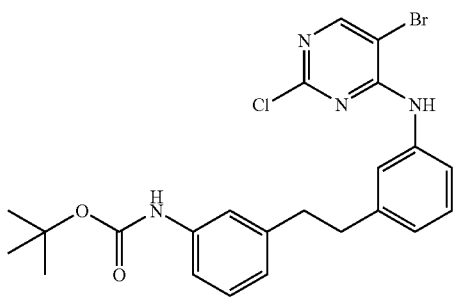 [SMILES: CC(C)(C)OC(=O)Nc1cccc(CCc2cccc(Nc3nc(Cl)ncc3Br)c2)c1]

This compound was prepared according to the procedure of Example B5, step G using 5-bromo-2,4-dichloropyrimidine and tert-butyl {3-[2-(3-aminophenyl)ethyl]phenyl}carbamate as the starting materials in 70% yield. LCMS calculated for $C_{23}H_{25}BrClN_4O_2$ $(M+H)^+$: m/z=503.1, 505.1.

Step D: 6-Bromo-2,4,8,22-tetraazatetracyclo[14.3.1.1(3,7).1(9,13)]docosa-1(20),3(22),4,6,9(21),10,12,16,18-nonaene trifluoroacetate This compound was prepared according to the procedure of Example B5, step H using tert-butyl [3-(2-{3-[(5-bromo-2-chloropyrimidin-4-yl)amino]phenyl}ethyl)phenyl]carbamate as the starting material in 43% yield. LCMS calculated for $C_{18}H_{16}BrN_4$ $(M+H)^+$: m/z=367.2, 369.2. $^1$H NMR (400 MHz, $CD_3OD$): δ 8.16 (s, 1H), 7.73 (s, 1H), 7.69 (s, 1H), 7.29 (m, 1H), 7.21 (t, 1H), 7.13 (d, 1H), 7.00-7.08 (m, 2H), 6.90 (d, 1H), 2.99 (m, 4H).

Example B5

Methyl 6-chloro-2,4,8,22-tetraazatetracyclo[14.3.1.1(3,7).1(9,13)]docosa-1(20),3(22),4,6,9(21),10,12,16,18-nonaene-11-carboxylate trifluoroacetate

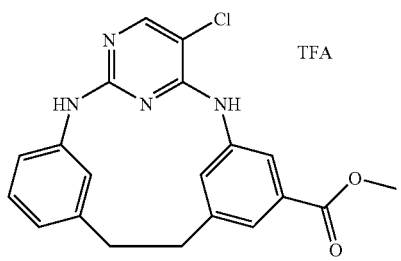 [SMILES: "TFA" ; COC(=O)c1cc2cc(c1)Nc1nc(ncc1Cl)Nc1cccc(c1)CC2]

Step A: 3-Bromo-5-nitrobenzoic acid

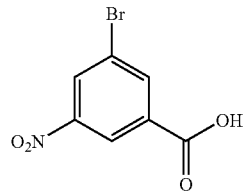 [SMILES: O=C(O)c1cc(Br)cc([N+](=O)[O-])c1]

m-Nitrobenzoic acid (11.2 g, 67.0 mmol) was taken up in sulfuric acid (30 mL) and heated to 60° C. To this solution was added N-bromosuccinimide (14.3 g, 80.4 mmol) in three portions each over a 15 minute period. After stirring for 2 h, the mixture was poured into crushed ice (100 g) to precipitate a solid. The solid was filtered, washed with water followed by hexanes to give the desired product (16 g, 97%). LCMS for $C_7H_3BrNO_4$ $(M-H)^+$: m/z=244.0, 246.0.

Step B: Methyl 3-bromo-5-nitrobenzoate

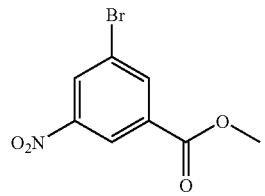

A solution of 3-bromo-5-nitrobenzoic acid (15.4 g, 62.6 mmol) in methanol (120 mL) and sulfuric acid (1.7 mL, 31 mmol) was heated to reflux overnight. After cooling to 0° C. for 0.5 h, the precipitated solid was filtered to give the desired product as a white solid (15.5 g, 95%). LCMS for $C_8H_7BrNO_4$ $(M+H)^+$: m/z=260.0, 262.0.

Step C: Methyl 3-nitro-5-[(trimethylsilyl)ethynyl]benzoate

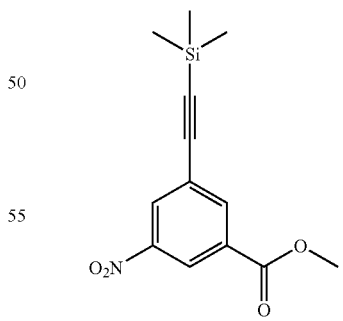

A solution of methyl 3-bromo-5-nitrobenzoate (0.331 g, 1.27 mmol), (trimethylsilyl)acetylene (0.27 mL, 1.9 mmol), bis(triphenylphosphine)palladium(II) chloride (45 mg, 0.064 mmol), copper(I) iodide (19 mg, 0.10 mmol) and triethylamine (0.26 mL, 1.9 mol) in DMF (5 mL) was stirred at room temperature overnight. The solution was diluted with ethyl acetate and 1 N HCl. The aqueous layer was extracted with ethyl acetate once, and the combined organic solutions were washed with brine, dried over MgSO₄, filtered and concentrated. The residue was purified by silica gel chromatography (10% ethyl acetate in hexanes) to give the desired product (310 mg, 88%). LCMS for $C_{13}H_{16}NO_4Si$ (M+H)⁺: m/z=278.1.

Step D: Methyl 3-ethynyl-5-nitrobenzoate

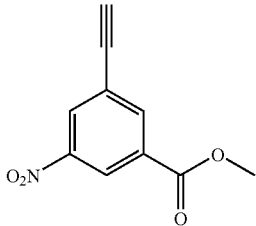

Methyl 3-nitro-5-[(trimethylsilyl)ethynyl]benzoate (7.9 g, 28 mmol) was dissolved in THF (90 mL) and methanol (90 mL) and then potassium carbonate (2.0 g, 14 mmol) was added. The resulting solution was stirred at room temperature for 1 hour. The reaction was quenched with 1 N HCl, and the solvent was removed in vacuo. The aqueous residue was extracted with ethyl acetate twice. The combined organic solutions were washed with brine, dried over Na₂SO₄, filtered and concentrated to give a solid. The solid was washed with ether to give the desired product (4 g, 68%). LCMS for $C_{10}H_8NO_4$ (M+H)⁺: m/z=206.0.

Step E: Methyl 3-({3-[(tert-butoxycarbonyl)amino]phenyl}ethynyl)-5-nitrobenzoate

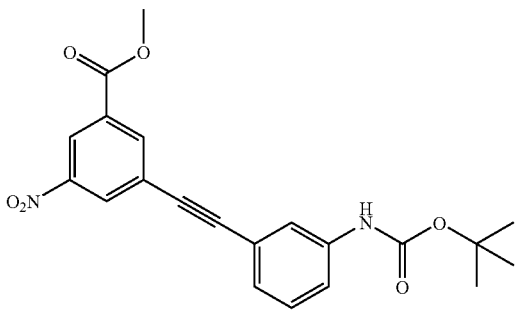 [SMILES: COC(=O)c1cc(C#Cc2cccc(NC(=O)OC(C)(C)C)c2)cc([N+](=O)[O-])c1]

A solution of methyl 3-ethynyl-5-nitrobenzoate (1.45 g, 7.08 mmol), tert-butyl (3-iodophenyl)carbamate (2.26 g, 7.08 mmol) in THF (28 mL) was treated with bis(triphenylphosphine)palladium(II) chloride (248 mg, 0.354 mmol), copper (I) iodide (108 mg, 0.566 mmol) and N,N-diisopropylethylamine (2.47 mL, 14.2 mmol) and stirred at 25° C. overnight. The reaction was diluted with water and extracted with ethyl acetate three times. The combined organic solutions were dried with sodium sulfate, filtered, and concentrated in vacuo.

The crude residue was purified by flash column chromatography to yield the desired product (1.85 g, 66%). LCMS for $C_{21}H_{20}N_2O_6Na$ (M+Na)⁺: m/z=419.3.

Step F: Methyl 3-amino-5-(2-{3-[(tert-butoxycarbonyl)amino]phenyl}ethyl)benzoate

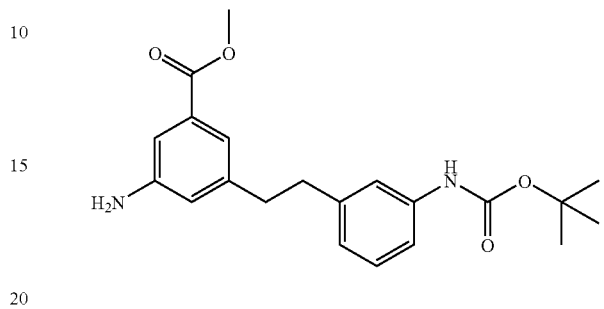

To a solution of methyl 3-({3-[(tert-butoxycarbonyl)amino]phenyl}ethynyl)-5-nitrobenzoate (1.85 g, 4.67 mmol) in methanol (50 mL) was added 10% palladium on carbon (1.85 g, 1.58 mmol), and the mixture was hydrogenated under 55 psi of H₂ for 72 hours with shaking. The solution was filtered through a pad of celite, and filtrate was concentrated. The residue was purified by flash column chromatography to give the desired product as a yellow oil (1.70 g, 98%). LCMS for $C_{21}H_{27}N_2O_4$ (M+H)⁺: m/z=371.1.

Step G: Methyl 3-(2-{3-[(tert-butoxycarbonyl)amino]phenyl}ethyl)-5-[(2,5-dichloropyrimidin-4-yl)amino]benzoate

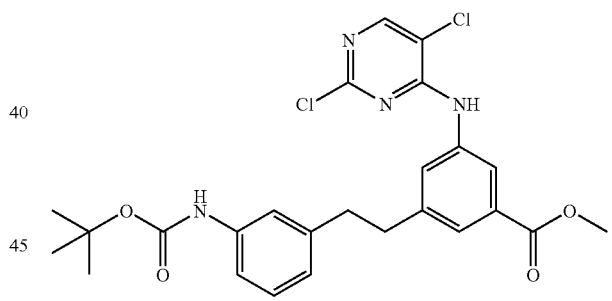

A solution of 2,4,5-trichloropyrimidine (0.371 mL, 3.24 mmol) and methyl 3-amino-5-(2-{3-[(tert-butoxycarbonyl)amino]phenyl}ethyl)benzoate (1.20 g, 3.24 mmol) in DMF (20 mL) and potassium carbonate (895 mg, 6.48 mmol) were stirred at 60° C. overnight. The reaction mixture was diluted with 1 N HCl and extracted with ethyl acetate three times. The combined organic solutions were dried with sodium sulfate, filtered, and concentrated in vacuo. The crude residue was purified by flash column chromatography to yield the desired product (1.20 g, 72%). LCMS for $C_{25}H_{26}Cl_2N_4O_4Na$ (M+Na)⁺: m/z=539.3, 541.3.

Step H: Methyl 6-chloro-2,4,8,22-tetraazatetracyclo[14.3.1.1(3,7).1(9,13)]docosa-1(20),3(22),4,6,9(21),10,12,16,18-nonaene-11-carboxylate trifluoroacetate A solution of methyl 3-(2-{3-[(tert-butoxycarbonyl)amino]phenyl}ethyl)-5-[(2,5-dichloropyrimidin-4-yl)amino]benzoate (124 mg, 0.240 mmol), 4.0 M of hydrogen chloride in 1,4-dioxane (0.21 mL, 0.84 mmol) in 2-methoxyethanol (16 mL) was microwaved at 130° C. for 5 minutes. Purification by preparative LCMS gave the desired product as a white solid (51 mg, 43%). LCMS for $C_{20}H_{18}ClN_4O_2$ (M+H)$^+$: m/z=381.3. $^1$H NMR (400 MHz, DMSO-d$_6$): δ 9.44 (m, 2H), 8.16 (s, 1H), 8.04 (m, 1H), 7.83 (m, 1H), 7.74 (m, 1H), 7.61 (m, 1H), 7.12 (t, J=7.5 Hz, 1H), 6.88 (m, 1H), 6.82 (m, 1H), 3.83 (s, 3H), 2.94 (m, 2H), 2.87 (m, 2H).

Example B6

6-Chloro-2,4,8,22-tetraazatetracyclo[14.3.1.1(3,7).1(9,13)]docosa-1(20),3(22),4,6,9(21),10,12,16,18-nonaene-11-carboxylic acid trifluoroacetate

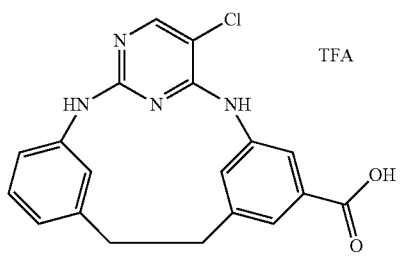 [SMILES: O=C(O)c1cc2cc(c1)Nc1nc(ncc1Cl)Nc1cccc(c1)CC2]

A solution of methyl 6-chloro-2,4,8,22-tetraazatetracyclo[14.3.1.1(3,7).1(9,13)]docosa-1(20),3(22),4,6,9(21),10,12,16,18-nonaene-11-carboxylate trifluoroacetate (45 mg, 90.9 μmol) in acetonitrile (5 mL) and 2.0 M of sodium hydroxide in water (227 μL, 0.455 mmol) were stirred at 25° C. overnight. Purification by preparative LCMS gave the desired product as a white solid (16 mg, 48%). LCMS for $C_{19}H_{16}ClN_4O_2$ (M+H)$^+$: m/z=367.1. $^1$H NMR (400 MHz, DMSO-d$_6$): δ 9.33 (s, 1H), 9.28 (s, 1H), 8.12 (s, 1H), 8.01 (m, 1H), 7.86 (m, 1H), 7.71 (m, 1H), 7.58 (m, 1H), 7.11 (t, 1H), 6.91 (m, 1H), 6.82 (m, 1H), 2.93 (m, 2H), 2.87 (m, 2H).

Example B7

6-Chloro-N-(3-chloro-4-fluorophenyl)-2,4,8,22-tetraazatetracyclo[14.3.1.1(3,7).1(9,13)]docosa-1(20),3(22),4,6,9(21),10,12,16,18-nonaene-11-carboxamide trifluoroacetate

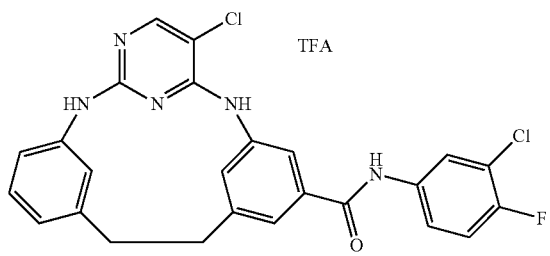 [SMILES: O=C(Nc1ccc(F)c(Cl)c1)c1cc2cc(c1)Nc1nc(ncc1Cl)Nc1cccc(c1)CC2]

To a solution of methyl 6-chloro-2,4,8,22-tetraazatetracyclo[14.3.1.1(3,7).1(9,13)]docosa-1(20),3(22),4,6,9(21),10,12,16,18-nonaene-11-carboxylate (13.5 mg, 0.0354 mmol) in methylene chloride (0.4 mL) was added 3-chloro-4-fluoroaniline (10.3 mg, 0.0709 mmol). The resulting solution was cooled down to 0° C. and treated with 2.0 M of trimethylaluminum in toluene (35.4 μL, 0.0709 mmol) under an atmosphere of nitrogen. After stirring at 25° C. for 2 h, the reaction mixture was quenched with 1 M potassium sodium tartrate solution dropwise at 0° C. The aqueous layer was extracted with ethyl acetate once, and the combined organic solutions were dried over Na$_2$SO$_4$, filtered, and concentrated. Purification by preparative LCMS gave the desired product as a white solid (13.2 mg, 75%). LCMS for $C_{25}H_{19}Cl_2FN_5O$ (M+H)$^+$: m/z=494.2. $^1$H NMR (400 MHz DMSO-d$_6$): δ 10.35 (s, 1H), 9.40 (s, 1H), 9.38 (s, 1H), 8.11 (s, 1H), 8.00 (dd, 1H), 7.93 (m, 1H), 7.83 (m, 1H), 7.65 (m, 1H), 7.60 (m, 1H), 7.55 (m, 1H), 7.36 (t, 1H), 7.07 (t, 1H), 6.85 (m, 1H), 6.79 (m, 1H), 2.92 (m, 2H), 2.89 (m, 2H).

Example B8

6-Chloro-11-[(4-methylpiperazin-1-yl)carbonyl]-2,4,8,22-tetraazatetracyclo[14.3.1.1(3,7).1(9,13)]docosa-1(20),3(22),4,6,9(21),10,12,16,18-nonaene trifluoroacetate

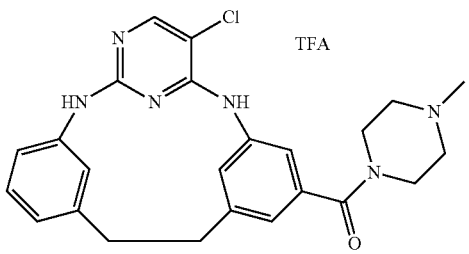 [SMILES: CN1CCN(C(=O)c2cc3cc(c2)Nc2nc(ncc2Cl)Nc2cccc(c2)CC3)CC1]

The desired compound was prepared according to the procedure of Example B7, using methyl 6-chloro-2,4,8,22-tetraazatetracyclo[14.3.1.1(3,7).1(9,13)]docosa-1(20),3(22),4,6,9(21),10,12,16,18-nonaene-11-carboxylate and 4-(aminomethyl)pyridine as the starting materials in 55% yield. LCMS for $C_{24}H_{26}ClN_6O$ (M+H)$^+$: m/z=449.4. $^1$H NMR (400 MHz, DMSO-d$_6$): δ 10.01 (br s, 1H), 9.40 (s, 1H), 9.23 (s, 1H), 8.15 (s, 1H), 7.92 (m, 2H), 7.14 (m, 3H), 6.92 (m, 1H), 6.83 (m, 1H), 3.43 (bs, 4H), 3.08 (br s, 4H), 2.86 (m, 4H), 2.82 (s, 3H).

Example B9

6-Chloro-N-(4-morpholin-4-ylphenyl)-2,4,8,22-tetraazatetracyclo[14.3.1.1(3,7).1(9,13)]docosa-1(20),3(22),4,6,9(21),10,12,16,18-nonaene-11-carboxamide trifluoroacetate

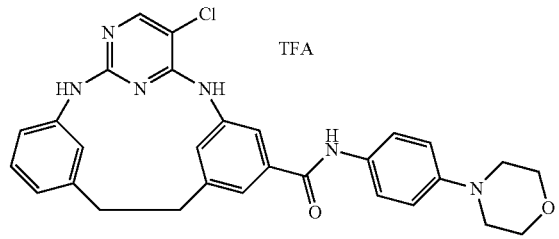 [SMILES: O=C(Nc1ccc(N2CCOCC2)cc1)c1cc2cc(c1)Nc1nc(ncc1Cl)Nc1cccc(c1)CC2]

The desired compound was prepared according to the procedure of Example B7, using methyl 6-chloro-2,4,8,22-tetraazatetracyclo[14.3.1.1(3,7).1(9,13)]docosa-1(20),3(22),4,6,9(21),10,12,16,18-nonaene-11-carboxylate and 4-morpholin-4-ylaniline as the starting materials in 45% yield. LCMS for $C_{29}H_{28}ClN_6O_2$ (M+H)$^+$: m/z=527.4. $^1$H NMR (400 MHz, DMSO-d$_6$): δ 10.04 (s, 1H), 9.37 (s, 1H), 9.32 (s, 1H), 8.14 (s, 1H), 7.92 (m, 2H), 7.61 (m, 4H), 7.12 (t, 1H), 6.92 (m, 3H), 6.82 (d, 1H), 3.73 (m, 4H), 3.06 (m, 4H), 2.94 (m, 4H).

Example B10

6-Chloro-N-[4-(2-hydroxyethyl)phenyl]-2,4,8,22-tetraazatetracyclo[14.3.1.1(3,7).1(9,13)]docosa-1(20),3(22),4,6,9(21),10,12,16,18-nonaene-11-carboxamide trifluoroacetate

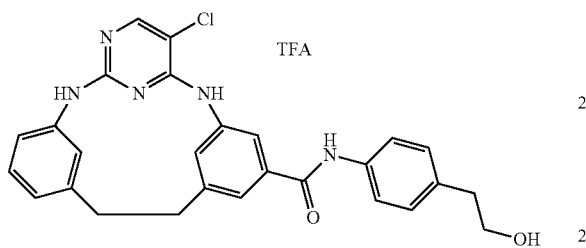

The desired compound was prepared according to the procedure of Example B7, using methyl 6-chloro-2,4,8,22-tetraazatetracyclo[14.3.1.1(3,7).1(9,13)]docosa-1(20),3(22),4,6,9(21),10,12,16,18-nonaene-11-carboxylate and p-aminophenylethanol as the starting materials in 41% yield. LCMS for $C_{27}H_{25}ClN_5O_2$(M+H)$^+$: m/z=486.3. $^1$H NMR (400 MHz, DMSO-d$_6$): δ 10.15 (s, 1H), 9.42 (m, 2H), 8.15 (s, 1H), 7.94 (m, 1H), 7.89 (m, 1H), 7.64 (m, 4H), 7.17 (m, 3H), 6.92 (m, 1H), 6.84 (m, 1H), 3.56 (t, 2H), 2.93 (m, 4H), 2.85 (s, 1H), 2.67 (t, 2H).

Example B11

6-Chloro-N-(pyridin-4-ylmethyl)-2,4,8,22-tetraazatetracyclo[14.3.1.1(3,7).1(9,13)]docosa-1(20),3(22),4,6,9(21),10,12,16,18-nonaene-11-carboxamide bis(trifluoroacetate)

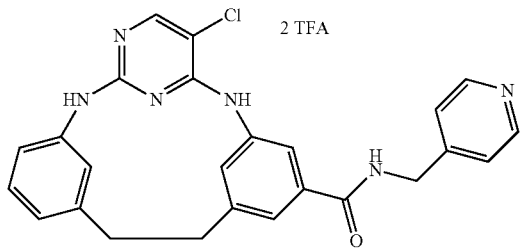 [SMILES: O=C(NCc1ccncc1)c1cc2cc(c1)Nc1nc(ncc1Cl)Nc1cccc(c1)CC2 ; "2 TFA"]

The desired compound was prepared according to the procedure of Example B7, using methyl 6-chloro-2,4,8,22-tetraazatetracyclo[14.3.1.1(3,7).1(9,13)]docosa-1(20),3(22),4,6,9(21),10,12,16,18-nonaene-11-carboxylate and 4-(aminomethyl)pyridine as the starting materials in 53% yield. LCMS for $C_{25}H_{22}ClN_6O$ (M+H)$^+$: m/z=457.3. $^1$H NMR (400 MHz, DMSO-d$_6$): δ 9.45 (s, 1H), 9.39 (s, 1H), 9.27 (t, 1H), 8.78 (s, 1H), 8.76 (s, 1H), 8.15 (s, 1H), 7.94 (m, 1H), 7.88 (m, 1H), 7.83 (d, 1H), 7.63 (m, 1H), 7.59 (m, 1H), 7.12 (t, 1H), 6.91 (m, 1H), 6.84 (m, 1H), 4.67 (d, 2H), 2.94 (m, 4H).

Example B12

1-{[6-Chloro-2,4,8,22-tetraazatetracyclo[14.3.1.1(3,7).1(9,13)]docosa-1(20), 3(22),4,6,9(21),10,12,16,18-nonaen-11-yl]carbonyl}piperidin-3-ol trifluoroacetate

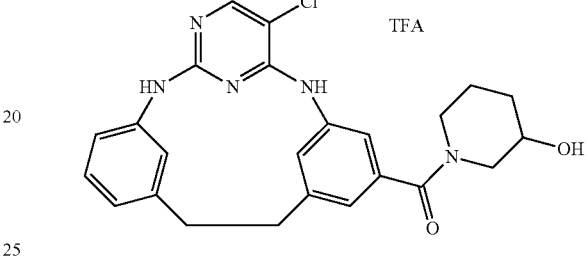

The desired compound was prepared according to the procedure of Example B7, using methyl 6-chloro-2,4,8,22-tetraazatetracyclo[14.3.1.1(3,7).1(9,13)]docosa-1(20),3(22),4,6,9(21),10,12,16,18-nonaene-11-carboxylate and piperidin-3-ol as the starting materials in 33% yield. LCMS for $C_{24}H_{25}ClN_5O_2$ (M+H)$^+$: m/z=450.4. $^1$H NMR (400 MHz, DMSO-d$_6$): δ 9.38 (s, 1H), 9.24 (s, 1H), 8.13 (s, 1H), 7.91 (m, 1H), 7.86 (m, 1H), 7.12 (m, 2H), 6.92 (m, 3H), 6.82 (m, 1H), 4.14 (m, 0.5H), 3.84 (m, 0.5H), 3.10 (m, 1H), 2.87 (m, 4H), 1.84 (m, 1H), 1.64 (m, 1H), 1.38 (m, 2H).

Example B13

6-Chloro-N-(3-chlorophenyl)-2,4,8,22-tetraazatetracyclo[14.3.1.1(3,7).1(9,13)]docosa-1(20),3(22),4,6,9(21),10,12,16,18-nonaene-11-carboxamide trifluoroacetate

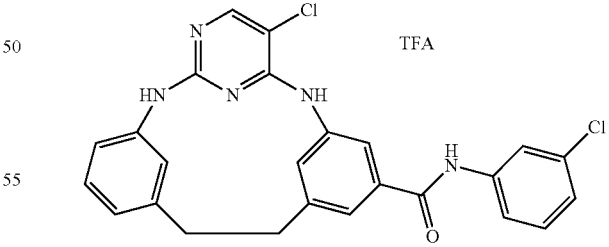

The desired compound was prepared according to the procedure of Example B7, using methyl 6-chloro-2,4,8,22-tetraazatetracyclo[14.3.1.1(3,7).1(9,13)]docosa-1(20),3(22),4,6,9(21),10,12,16,18-nonaene-11-carboxylate and m-chloroaniline as the starting materials in 55% yield. LCMS for $C_{25}H_{20}Cl_2N_5O$ (M+H)$^+$: m/z=476.2. $^1$H NMR (400 MHz, DMSO-d$_6$): δ 10.33 (s, 1H), 9.31 (s, 1H), 9.27 (s, 1H), 8.09 (s, 1H), 7.93 (m, 1H), 7.89 (m, 1H), 7.86 (m, 1H), 7.63 (m, 2H), 7.55 (m, 1H), 7.32 (t, 1H), 7.09 (m, 2H), 6.87 (m, 1H), 6.79 (m, 1H), 2.91 (m, 4H).

Example B14

6-Chloro-N-(2-chlorophenyl)-2,4,8,22-tetraazatetracyclo[14.3.1.1(3,7).1(9,13)]docosa-1(20),3(22),4,6,9(21),10,12,16,18-nonaene-11-carboxamide trifluoroacetate

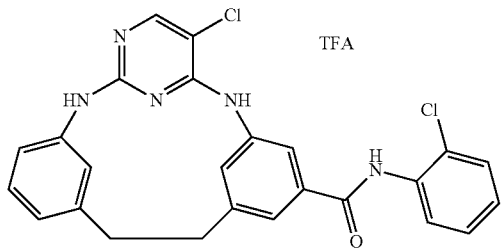 [SMILES: O=C(Nc1ccccc1Cl)c1cc2cc(c1)Nc1nc(ncc1Cl)Nc1cccc(c1)CC2]

The desired compound was prepared according to the procedure of Example B7, using methyl 6-chloro-2,4,8,22-tetraazatetracyclo[14.3.1.1(3,7).1(9,13)]docosa-1(20),3(22),4,6,9(21),10,12,16,18-nonaene-11-carboxylate and o-chloroaniline as the starting materials in 46% yield. LCMS for $C_{25}H_{20}Cl_2N_5O$ (M+H)$^+$: m/z=476.2. $^1$H NMR (400 MHz, DMSO-$d_6$): δ 10.02 (s, 1H), 9.39 (s, 1H), 9.38 (s, 1H), 8.14 (s, 1H), 7.97 (m, 1H), 7.90 (m, 1H), 7.70 (m, 1H), 7.65 (m, 1H), 7.55 (m, 2H), 7.37 (m, 1H), 7.27 (m, 1H), 7.12 (t, 1H), 6.92 (m, 1H), 6.83 (m, 1H), 2.94 (m, 4H).

Example B15

6-Chloro-N-(4-chlorophenyl)-2,4,8,22-tetraazatetracyclo[14.3.1.1(3,7).1(9,13)]docosa-1(20),3(22),4,6,9(21),10,12,16,18-nonaene-11-carboxamide trifluoroacetate

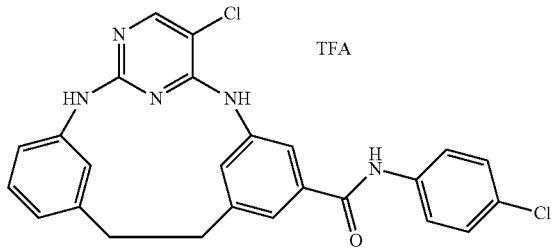 [SMILES: O=C(Nc1ccc(Cl)cc1)c1cc2cc(c1)Nc1nc(ncc1Cl)Nc1cccc(c1)CC2]

The desired compound was prepared according to the procedure of Example B7, using methyl 6-chloro-2,4,8,22-tetraazatetracyclo[14.3.1.1(3,7).1(9,13)]docosa-1(20),3(22),4,6,9(21),10,12,16,18-nonaene-11-carboxylate and p-chloroaniline as the starting materials in 48% yield. LCMS for $C_{25}H_{20}Cl_2N_5O$ (M+H)$^+$: m/z=476.2. $^1$H NMR (400 MHz, DMSO-$d_6$): δ 10.35 (s, 1H), 9.38 (s, 1H), 9.34 (s, 1H), 8.14 (s, 1H), 7.97 (m, 1H), 7.89 (m, 1H), 7.80 (m, 1H), 7.78 (m, 1H), 7.65 (m, 1H), 7.59 (m, 1H), 7.41 (m, 1H), 7.39 (m, 1H), 7.12 (t, 1H), 6.92 (m, 1H), 6.84 (m, 1H), 2.93 (m, 4H).

Example B16

N-(tert-Butyl)-6-chloro-2,4,8,22-tetraazatetracyclo[14.3.1.1(3,7).1(9,13)]docosa-1(20),3(22),4,6,9(21),10,12,16,18-nonaene-11-sulfonamide trifluoroacetate

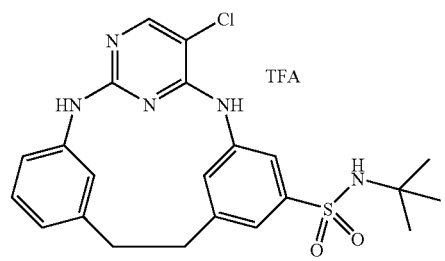 [SMILES: CC(C)(C)NS(=O)(=O)c1cc2cc(c1)Nc1nc(ncc1Cl)Nc1cccc(c1)CC2]

Step A. 3-Bromo-5-nitrobenzenesulfonic acid

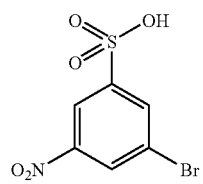 [SMILES: O=[N+]([O-])c1cc(Br)cc(S(=O)(=O)O)c1]

The desired compound was prepared according to the procedure of Example B5, step A using 3-nitrobenzenesulfonic acid as the starting material in 61% yield. LCMS for $C_6H_3BrNO_5S$ (M−H)$^+$: m/z=280.1, 282.1.

Step B. 3-Bromo-N-(tert-butyl)-5-nitrobenzenesulfonamide

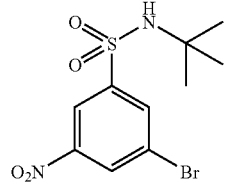 [SMILES: CC(C)(C)NS(=O)(=O)c1cc(Br)cc([N+](=O)[O-])c1]

A solution of 3-bromo-5-nitrobenzenesulfonic acid (1.86 g, 6.59 mmol) in toluene (37 mL) and phosphorus pentachloride (2.75 g, 13.2 mmol) were heated at 100° C. overnight. The reaction mixture was cooled to 0° C. and treated with tert-butylamine (1.03 mL, 9.89 mmol) and N,N-diisopropylethylamine (5.74 mL, 33.0 mmol). After stirring at 25° C. for 30 min, the reaction mixture was diluted with 1 N HCl and extracted with ethyl acetate three times. The combined organic layers were dried with sodium sulfate, filtered, and concentrated in vacuo. The crude residue was purified by flash column chromatography to yield the desired product (2.2 g, 98%). ¹H NMR (400 MHz, (400 MHz, DMSO-$d_6$): δ 8.62 (m, 1H), 8.56 (m, 1H), 8.37 (m, 1H), 8.03 (s, 1H), 1.32 (s, 9H).

Step C. 3-[(3-Aminophenyl)ethynyl]-N-(tert-butyl)-5-nitrobenzenesulfonamide

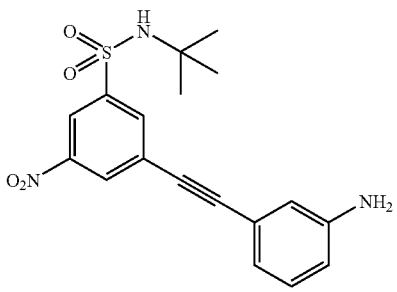 [SMILES: CC(C)(C)NS(=O)(=O)c1cc(C#Cc2cccc(N)c2)cc([N+](=O)[O-])c1]

The desired compound was prepared according to the procedure of Example B5, step E using 3-bromo-N-(tert-butyl)-5-nitrobenzenesulfonamide and 3-ethynylaniline as the starting materials in 32% yield. LCMS for $C_{18}H_{20}N_3O_4S$ (M+H)⁺: m/z=374.2.

Step D. tert-Butyl [3-({3-[(tert-butylamino)sulfonyl]-5-nitrophenyl}ethynyl)phenyl]carbamate

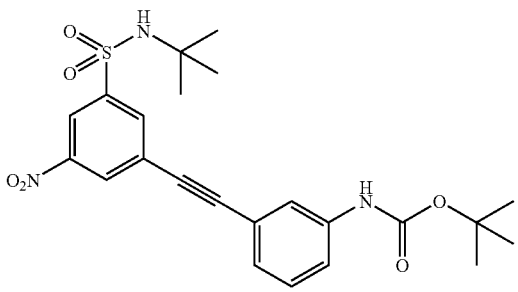 [SMILES: CC(C)(C)NS(=O)(=O)c1cc(C#Cc2cccc(NC(=O)OC(C)(C)C)c2)cc([N+](=O)[O-])c1]

A solution of 3-[(3-aminophenyl)ethynyl]-N-(tert-butyl)-5-nitrobenzenesulfonamide (180 mg, 0.482 mmol), di-tert-butyldicarbonate (116 mg, 0.53 mmol), ethanol (5 mL) and N,N-diisopropylethylamine (84.0 mL, 0.482 mmol) was stirred at 25° C. overnight. The reaction mixture was concentrated in vacuo. The crude residue was purified by flash column chromatography to yield the desired product (186 mg, 81%). LCMS calculated for $C_{23}H_{27}N_3O_6SNa$ (M+Na)⁺: m/z=496.1.

Step E. tert-Butyl [3-(2-{3-amino-5-[(tert-butylamino)sulfonyl]phenyl}ethyl)phenyl]carbamate

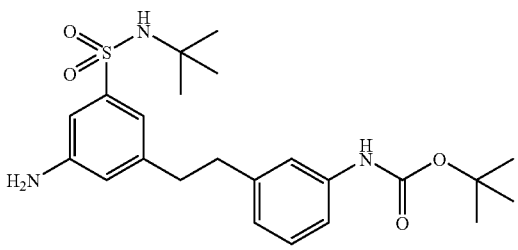 [SMILES: CC(C)(C)NS(=O)(=O)c1cc(N)cc(CCc2cccc(NC(=O)OC(C)(C)C)c2)c1]

The desired compound was prepared according to the procedure of Example B5, step F using tert-butyl [3-({3-[(tert-butylamino)sulfonyl]-5-nitrophenyl}ethynyl)phenyl]carbamate as a starting material in 58% yield. LCMS for $C_{23}H_{33}N_3O_4SNa$ (M+Na)⁺: m/z=470.4.

Step F. tert-Butyl [3-(2-{3-[(tert-butylamino)sulfonyl]-5-[(2,5-dichloropyrimidin-4-yl)amino]phenyl}ethyl)phenyl]carbamate

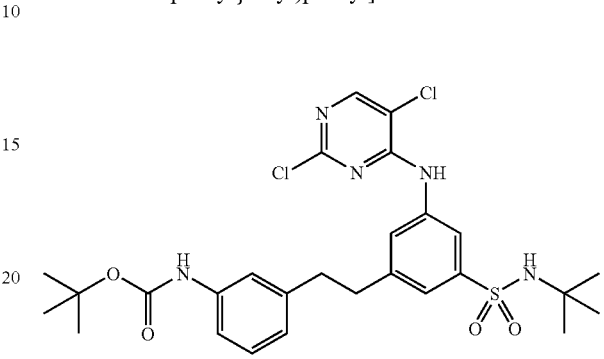

The desired compound was prepared according to the procedure of Example B5, step G using tert-butyl [3-(2-{3-amino-5-[(tert-butylamino)sulfonyl]phenyl}ethyl)phenyl]carbamate and 2,4,5-trichloropyrimidine as the starting materials in 35% yield. LCMS for $C_{27}H_{33}Cl_2N_5O_4SNa$ (M+Na)⁺: m/z=616.2, 618.2.

Step G. N-(tert-Butyl)-6-chloro-2,4,8,22-tetraazatetracyclo[14.3.1.1(3,7).1(9,13)]docosa-1(20),3(22),4,6,9(21),10,12,16,18-nonaene-11-sulfonamide trifluoroacetate The desired compound was prepared according to the procedure of Example B5, step H using tert-butyl [3-(2-{3-[(tert-butylamino)sulfonyl]-5-[(2,5-dichloropyrimidin-4-yl)amino]phenyl}ethyl)phenyl]carbamate as a starting material in 53% yield. LCMS for $C_{22}H_{25}ClN_5O_2S$ (M+H)⁺: m/z=458.3. ¹H NMR (400 MHz, DMSO-$d_6$): δ 9.51 (s, 1H), 9.43 (s, 1H), 8.16 (s, 1H), 7.94 (m, 1H), 7.82 (s, 1H), 7.58 (m, 1H), 7.46 (m, 1H), 7.44 (s, 1H), 7.11 (t, 1H), 6.91 (m, 1H), 6.81 (m, 1H), 2.95 (m, 2H), 2.86 (m, 2H), 1.08 (s, 9H).

Example B17

6-Bromo-N-(tert-butyl)-2,4,8,22-tetraazatetracyclo[14.3.1.1(3,7).1(9,13)]docosa-1(20),3(22),4,6,9(21),10,12,16,18-nonaene-11-sulfonamide trifluoroacetate

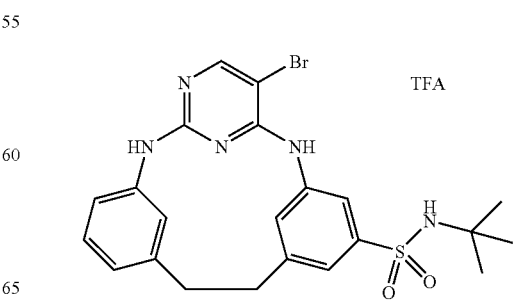

Example B18

6-Bromo-2,4,8,22-tetraazatetracyclo[14.3.1.1(3,7).1(9,13)]docosa-1(20),3(22),4,6,9(21),10,12,16,18-nonaene-11-sulfonamide trifluoroacetate

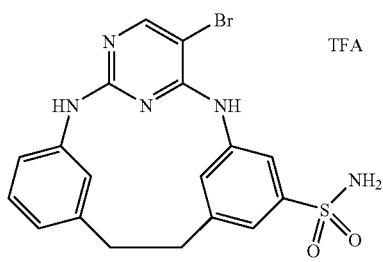 [SMILES: NS(=O)(=O)c1cc2cc(c1)Nc1nc(ncc1Br)Nc1cccc(c1)CC2]

Step A. tert-Butyl [3-(2-{3-[(5-bromo-2-chloropyrimidin-4-yl)amino]-5-[(tert-butylamino)sulfonyl]phenyl}ethyl)phenyl]carbamate

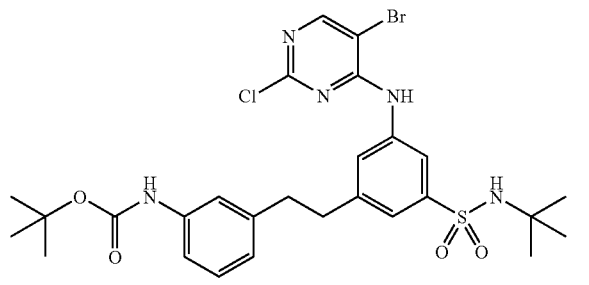 [SMILES: CC(C)(C)NS(=O)(=O)c1cc(CCc2cccc(NC(=O)OC(C)(C)C)c2)cc(Nc2nc(Cl)ncc2Br)c1]

The desired compound was prepared according to the procedure of Example B5, step G using tert-butyl [3-(2-{3-amino-5-[(tert-butylamino)sulfonyl]phenyl}ethyl)phenyl]carbamate and 5-bromo-2,4-dichloropyrimidine as the starting materials in 44% yield. LCMS for $C_{27}H_{33}BrClN_5O_4SNa$ (M+Na)$^+$: m/z=660.3, 662.3.

Step B. 6-Bromo-N-(tert-butyl)-2,4,8,22-tetraazatetracyclo[14.3.1.1(3,7).1(9,13)]docosa-1(20),3(22),4,6,9(21),10,12,16,18-nonaene-11-sulfonamide trifluoroacetate

6-Bromo-2,4,8,22-tetraazatetracyclo[14.3.1.1(3,7).1(9,13)]docosa-1(20),3(22),4,6,9(21),10,12,16,18-nonaene-11-sulfonamide trifluoroacetate The desired compounds were prepared according to the procedure of Example B5, step H using tert-butyl [3-(2-{3-[(5-bromo-2-chloropyrimidin-4-yl)amino]-5-[(tert-butylamino)sulfonyl]phenyl}ethyl)phenyl]carbamate as the starting material in 31% (Example B17) and 23% (Example B18) yield respectively.

Example B17: LCMS for $C_{22}H_{25}BrN_5O_2S$ (M+H)$^+$: m/z=502.2, 504.2. $^1$H NMR (400 MHz, DMSO-$d_6$): δ 9.45 (s, 1H), 9.34 (s, 1H), 8.23 (s, 1H), 7.89 (s, 1H), 7.79 (s, 1H), 7.58 (m, 1H), 7.46 (s, 1H), 7.43 (s, 1H), 7.11 (t, 1H), 6.89 (m, 1H), 6.81 (m, 1H), 2.97 (m, 2H), 2.89 (m, 2H), 1.07 (s, 9H).

Example B18: LCMS for $C_{18}H_{17}BrN_5O_2S$ (M+H)$^+$: m/z=446.2, 448.2. $^1$H NMR (400 MHz, DMSO-$d_6$): δ 9.43 (s, 1H), 9.30 (s, 1H), 8.22 (s, 1H), 7.93 (m, 1H), 7.84 (m, 1H), 7.60 (m, 1H), 7.47 (m, 1H), 7.29 (s, 2H), 7.11 (t, 1H), 6.89 (m, 1H), 6.83 (m, 1H), 2.96 (m, 2H), 2.91 (m, 2H).

Example B19

6-Chloro-2,4,8,22-tetraazatetracyclo[14.3.1.1(3,7).1(9,13)]docosa-1(20),3(22),4,6,9(21),10,12,16,18-nonaen-12-amine dihydrochloride

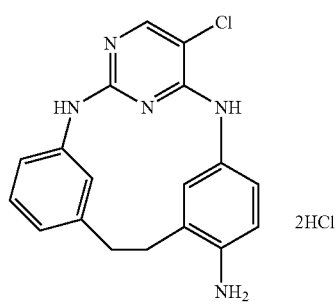 [SMILES: Nc1ccc2cc1CCc1cccc(c1)Nc1ncc(Cl)c(n1)N2 ; "2HCl"]

Step A: tert-Butyl (2-iodo-4-nitrophenyl)carbamate

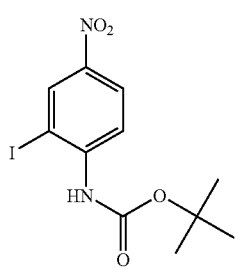 [SMILES: CC(C)(C)OC(=O)Nc1ccc([N+](=O)[O-])cc1I]

To a solution of 2-iodo-4-nitroaniline (20.0 g, 75.8 mmol) in THF (150 mL) at 0° C. was added sodium hydride (2.18 g, 90.9 mmol). After stirring for 0.5 h, di-tert-butyldicarbonate (17.4 g, 79.5 mmol) was added to the reaction flask and the reaction mixture was warmed to rt and stirred overnight. LCMS showed 50% conversion of the starting materials (SM). The reaction solution was cooled down to 0° C. and another 0.7 eq NaH was added. After stirring overnight, the reaction solution was diluted with water and ethyl acetate. The organic solution was separated and washed with brine, dried over $Na_2SO_4$, filtered, and concentrated. The crude product was purified with silica gel chromatography (20% ethyl acetate/hexanes) to give the desired product as white solid (17.2 g, 62%). LCMS calculated for $C_{11}H_{14}IN_2O_4$(M+H)$^+$: m/z=365.0.

Step B: tert-Butyl (3-ethynylphenyl)carbamate

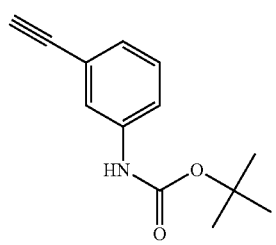 [SMILES: C#Cc1cccc(NC(=O)OC(C)(C)C)c1]

A solution of 3-ethynylaniline (20.2 g, 172 mmol) and di-tert-butyldicarbonate (41.4 g, 190 mmol) in ethanol (310 ml) was stirred at 25° C. overnight. Then the reaction solution was concentrated. The crude residue was purified by flash column chromatography to yield the desired product (37.5 g, 100%). LCMS calculated for $C_{13}H_{16}NO_2(M+H)^+$: m/z=218.1.

Step C: tert-Butyl [3-({2-[(tert-butoxycarbonyl) amino]-5-nitrophenyl}ethynyl)phenyl]carbamate

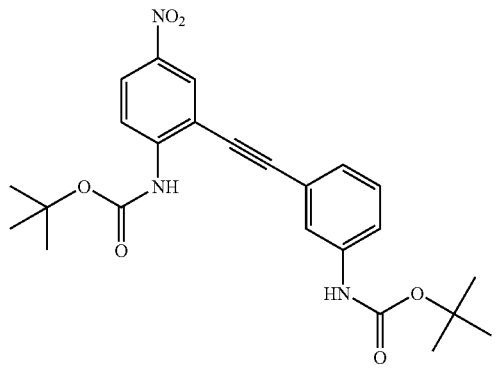 [SMILES: CC(C)(C)OC(=O)Nc1cccc(C#Cc2cc([N+](=O)[O-])ccc2NC(=O)OC(C)(C)C)c1]

A solution of tert-butyl (3-ethynylphenyl)carbamate (12.7 g, 58.5 mmol), tert-butyl (2-iodo-4-nitrophenyl)carbamate (14.2 g, 39.0 mmol), bis(triphenylphosphine)palladium(II) chloride (1.37 g, 1.95 mmol), and copper(I) iodide (371 mg, 1.95 mmol) in THF (200 mL) was treated with N,N-diisopropylethylamine (7.47 mL, 42.9 mmol) dropwise and stirred at 20° C. overnight. The reaction mixture was concentrated and diluted with water (200 mL) and ethyl acetate (200 mL). The organic layer was separated, washed with brine, dried with sodium sulfate, filtered, and concentrated to give a yellow/brown solid which was washed with ethyl acetate to give the desired product as light yellow solid (15 g, 85%). LCMS calculated for $C_{24}H_{27}N_3O_6Na$ (M+Na)$^+$: m/z=476.2.

Step D: tert-Butyl [3-(2-{5-amino-2-[(tert-butoxycarbonyl)amino]phenyl}ethyl)phenyl]carbamate

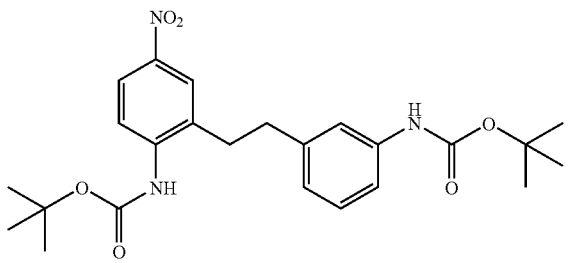 [SMILES: CC(C)(C)OC(=O)Nc1cccc(CCc2cc([N+](=O)[O-])ccc2NC(=O)OC(C)(C)C)c1]

To a solution of tert-butyl [3-({2-[(tert-butoxycarbonyl) amino]-5-nitrophenyl}ethynyl)phenyl]carbamate (15.0 g, 33.1 mmol) in DMF (234 mL) was added 10% Palladium on carbon (13.1 g, 11.2 mmol). The solution was shaken under 55 psi $H_2$ atmosphere for 72 h. The solution was filtered through a pad of celite. The filtrate was concentrated and purified with silica gel chromatography (45% ethyl acetate/hexanes) to give an intermediate as yellow oil. To a solution of the intermediate in methanol (200 mL) was added 10% Palladium on carbon (12 g). The resulting solution was shaken under 55 psi $H_2$ atmosphere overnight. The reaction mixture was filtered through a pad of celite and the filtrate was concentrated. The crude product was purified with a short pad of silica gel to give the desire product (11.5 g, 81%). LCMS calculated for $C_{24}H_{33}N_3O_4Na$ (M+Na)$^+$: m/z=450.2.

Step E: tert-Butyl [3-(2-{2-[(tert-butoxycarbonyl) amino]-5-[(2,5-dichloropyrimidin-4-yl)amino] phenyl}ethyl)phenyl]carbamate

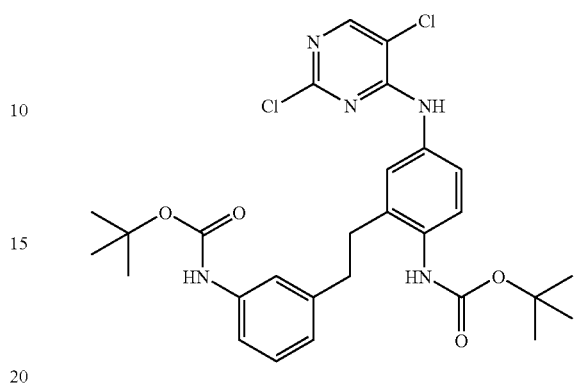

A solution of tert-butyl [3-(2-{5-amino-2-[(tert-butoxycarbonyl)amino]phenyl}ethyl)phenyl]carbamate (8.15 g, 19.1 mmol) in DMF (19 mL) was treated with potassium carbonate (3.42 g, 24.8 mol) and stirred at 25° C. for 5 minutes. The reaction mixture was treated with 2,4,5-trichloropyrimidine (2.40 mL, 21.0 mmol) dropwise and stirred at 20° C. overnight. The reaction mixture was poured into water (200 mL) and extracted with ethyl acetate (300 mL). The organic layer was separated and washed with brine (50 mL), dried with sodium sulfate, filtered, and concentrated to give a crude orange oil. The residue was purified with silica gel chromatography to give the desired product (10.9 g, 99.5%). LCMS calculated for $C_{28}H_{33}Cl_2N_5O_4Na$ (M+Na)$^+$: m/z=596.0, 598.0.

Step F: 6-Chloro-2,4,8,22-tetraazatetracyclo[14.3.1.1 (3,7).1(9,13)]docosa-1(20),3(22),4,6,9(21),10,12,16, 18-nonaen-12-amine dihydrochloride A solution of tert-butyl [3-(2-{2-[(tert-butoxycarbonyl) amino]-5-[(2,5-dichloropyrimidin-4-yl)amino] phenyl}ethyl)phenyl]carbamate (4.70 g, 8.18 mmol) in acetonitrile (750 mL), water (75 mL) and 2-butanol (1.0 mL) was treated with 4.0 M of hydrogen chloride in 1,4-dioxane (7.2 mL, 28.6 mmol) and refluxed for 20 hours. The reaction mixture was concentrated and the tan solid was triturated with dichloromethane and methanol to give the desired product (2.83 g, 84%). LCMS calculated for $C_{18}H_{17}ClN_5(M+H)^+$: m/z=338.1. $^1H$ NMR (400 MHz, DMSO-d$_6$): δ 8.37 (s, 1H), 7.89 (s, 1H), 7.79 (s, 1H), 7.59 (m, 1H), 7.43 (m, 3H), 7.36 (d, 1H), 7.17 (m, 2H), 6.91 (dd, 2H), 3.08 (d, 4H).

Example B20

6-Chloro-2,4,8,18,22-pentaazatetracyclo[14.3.1.1(3,7).1(9,13)]docosa-1(20),3(22),4,6,9(21),10,12,16,18-nonaen-12-amine tris(trifluoroacetate)

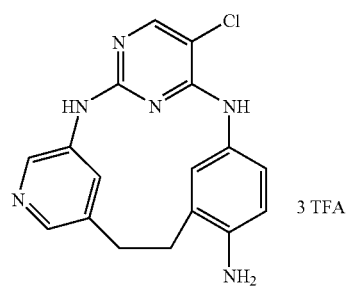 [SMILES: Nc1ccc2cc1CCc1cncc(c1)Nc1ncc(Cl)c(n1)N2]

Step A: tert-Butyl {5-[(trimethylsilyl)ethynyl]pyridin-3-yl}carbamate

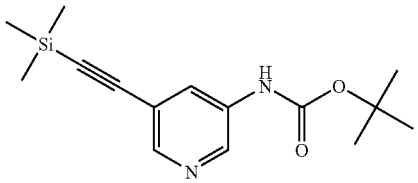 [SMILES: CC(C)(C)OC(=O)Nc1cncc(C#C[Si](C)(C)C)c1]

To a solution of tert-butyl (5-bromopyridin-3-yl)carbamate (3.00 g, 11.0 mmol) and THF (30 mL) was added (trimethylsilyl)acetylene (1.60 g, 16.3 mmol), (triphenylphosphine)palladium(II) chloride (0.31 g, 0.44 mmol), copper(I) iodide (84 mg, 0.44 mmol) and triethylamine (1.7 mL, 12 mmol) under nitrogen atmosphere. The mixture was heated at 50° C. overnight. The solvent removed in vacuo. The residue was diluted with EtOAc and water. The organic layer was separated, dried over sodium sulfate, filtered, and concentrated in vacuo. The crude residue was purified by flash column chromatography to yield the desired product (2.0 g, 63%). LCMS calculated for $C_{15}H_{23}N_2O_2Si(M+H)^+$: m/z=291.1.

Step B: tert-Butyl (5-ethynylpyridin-3-yl)carbamate

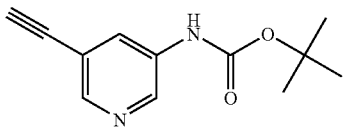 [SMILES: C#Cc1cncc(NC(=O)OC(C)(C)C)c1]

This compound was prepared according to the procedure of Example B5 step D, using tert-butyl {5-[(trimethylsilyl)ethynyl]pyridin-3-yl}carbamate as the starting material in 66% yield. LCMS calculated for $C_{12}H_{15}N_2O_2(M+H)^+$: m/z=219.1.

Step C: tert-Butyl [5-({2-[(tert-butoxycarbonyl)amino]-5-nitrophenyl}ethynyl)pyridin-3-yl]carbamate

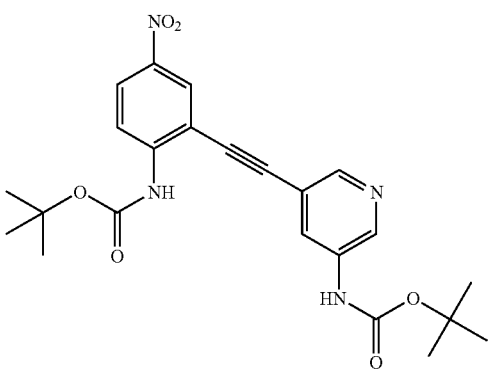

This compound was prepared according to the procedure of Example B19 step C, using tert-butyl (5-ethynylpyridin-3-yl)carbamate and tert-butyl (2-iodo-4-nitrophenyl)carbamate as the starting material in 85% yield. LCMS calculated for $C_{23}H_{27}N_4O_6(M+H)^+$: m/z=455.1.

Step D: tert-Butyl [5-({5-amino-2-[(tert-butoxycarbonyl)amino]phenyl}ethynyl)pyridin-3-yl]carbamate

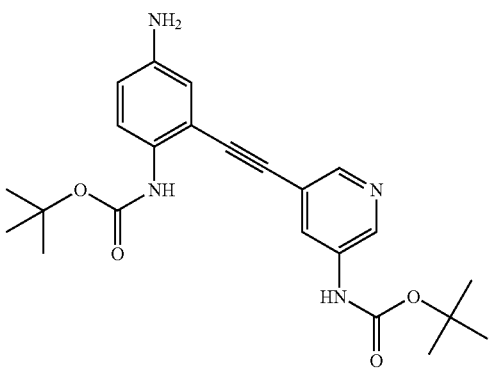

A mixture of tert-butyl [5-({2-[(tert-butoxycarbonyl)amino]-5-nitrophenyl}ethynyl)pyridin-3-yl]carbamate (1.60 g, 3.52 mmol), methanol (37 mL), acetic acid (7.3 mL), water (3.7 mL) and iron (905 mg, 16.2 mmol) was stirred at 60° C. for 3 h. The reaction mixture was filtered through a pad of celite and washed with ethyl acetate and extracted with ethyl acetate once. The combined organic solutions were dried with sodium sulfate, filtered, and concentrated in vacuo. The crude residue was purified by flash column chromatography to yield the desired product (1.40 g, 94%). LCMS calculated for $C_{23}H_{29}N_4O_4(M+H)^+$: m/z=425.1.

Step E: tert-Butyl [5-(2-{5-amino-2-[(tert-butoxycarbonyl)amino]phenyl}ethyl)pyridin-3-yl]carbamate

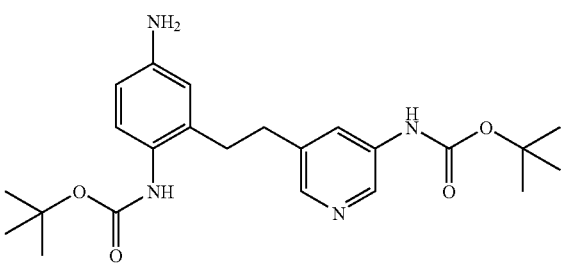 [SMILES: CC(C)(C)OC(=O)Nc1cncc(CCc2cc(N)ccc2NC(=O)OC(C)(C)C)c1]

To a solution of tert-butyl [5-({5-amino-2-[(tert-butoxycarbonyl)amino]phenyl}ethynyl)pyridin-3-yl]carbamate (1.50 g, 3.53 mmol) in methanol (30 mL) was added 10% palladium on carbon (150 mg, 0.141 mmol), and the mixture was hydrogenated under 25 psi of $H_2$ for 2 hours with shaking. The solution was filtered through a pad of celite, and filtrate was concentrated. The residue was purified by flash column chromatography to give the desired product (1.40 g, 92%). LCMS calculated for $C_{23}H_{33}N_4O_4(M+H)^+$: m/z=429.1.

Step F: tert-Butyl [5-(2-{2-[(tert-butoxycarbonyl)amino]-5-[(2,5-dichloropyrimidin-4-yl)amino]phenyl}ethyl)pyridin-3-yl]carbamate

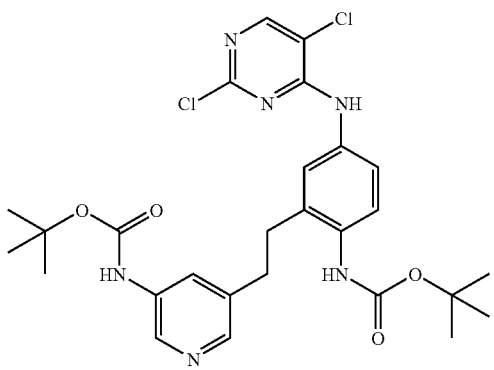 [SMILES: CC(C)(C)OC(=O)Nc1cncc(CCc2cc(Nc3nc(Cl)ncc3Cl)ccc2NC(=O)OC(C)(C)C)c1]

This compound was prepared according to the procedure of Example B19 step E, using tert-butyl [5-(2-{5-amino-2-[(tert-butoxycarbonyl)amino]phenyl}ethyl)pyridin-3-yl]carbamate and 2,4,5-trichloropyrimidine as the starting materials in 43% yield. LCMS calculated for $C_{27}H_{33}Cl_2N_6O_4(M+H)^+$: m/z=575.1, 577.1.

Step G: 2-[2-(5-Aminopyridin-3-yl)ethyl]-N(4)-(2,5-dichloropyrimidin-4-yl)benzene-1,4-diamine trihydrochloride

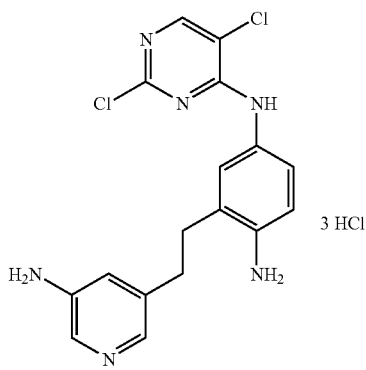 [SMILES: Nc1cncc(CCc2cc(Nc3nc(Cl)ncc3Cl)ccc2N)c1 ; "3 HCl"]

A solution of 4.0 M of hydrogen chloride in 1,4-dioxane (30 mL, 120 mmol), tert-butyl [5-(2-{2-[(tert-butoxycarbonyl)amino]-5-[(2,5-dichloropyrimidin-4-yl)amino]phenyl}ethyl)pyridin-3-yl]carbamate (860 mg, 1.49 mmol) and methanol (15 mL) was stirred at 25° C. for 1 hour. The solvent was removed in vacuo. The crude residue was dissolved in DCM and triturated with ether to give the desired product (0.57 g, 73%). LCMS calculated for $C_{17}H_{17}Cl_2N_6$ $(M+H)^+$: m/z=375.0, 377.0.

Step H: 6-Chloro-2,4,8,18,22-pentaazatetracyclo[14.3.1.1(3,7).1(9,13)]docosa-1(20),3(22),4,6,9(21),10,12,16,18-nonaen-12-amine tris(trifluoroacetate)

To a solution of 2-[2-(5-aminopyridin-3-yl)ethyl]-N(4)-(2,5-dichloropyrimidin-4-yl)benzene-1,4-diamine trihydrochloride (450 mg, 0.928 mmol) in 1,4-dioxane (9.0 mL) and DMF (3.0 mL) and N,N-diisopropylethylamine (647 µL, 3.71 mmol). The mixture was stirred at room temperature for 5 minutes. The reaction mixture was treated with tris(dibenzylideneacetone)dipalladium (128 mg, 0.139 mmol) and (9,9-dimethyl-9H-xanthene-4,5-diyl)bis(diphenylphosphine) (161 mg, 0.278 mmol) and cesium carbonate (605 mg, 1.86 mmol). The mixture was degassed with $N_2$ and heated in microwave at 160° C. for 30 minutes. The reaction solution was concentrated in vacuo. The residue was dissolved in DMSO, filtered and purified on preparative LCMS to give the desired product (120 mg, 23%). LCMS calculated for $C_{17}H_{16}ClN_6(M+H)^+$: m/z=339.1. $^1$H NMR (400 MHz, DMSO-$d_6$): δ 9.99 (s, 1H), 9.29 (s, 1H), 8.96 (s, 1H), 8.33 (d, 1H), 8.30 (d, 1H), 8.18 (s, 1H), 7.53 (s, 1H), 6.91-6.99 (m, 2H), 2.71-3.02 (m, 4H).

Example B21

6-Chloro-2,4,8,22-tetraazatetracyclo[14.3.1.1(3,7).1(9,13)]docosa-1(20),3(22),4,6,9(21),10,12,16,18-nonaen-11-amine bis(trifluoroacetate)

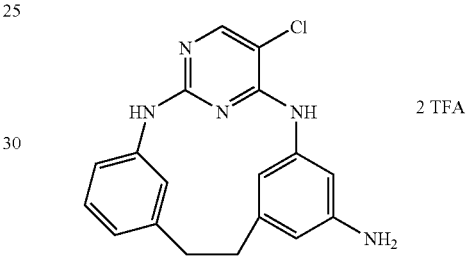

Step A: tert-Butyl [6-chloro-2,4,8,22-tetraazatetracyclo[14.3.1.1(3,7).1(9,13)]docosa-1(20),3(22),4,6,9(21),10,12,16,18-nonaen-11-yl]carbamate

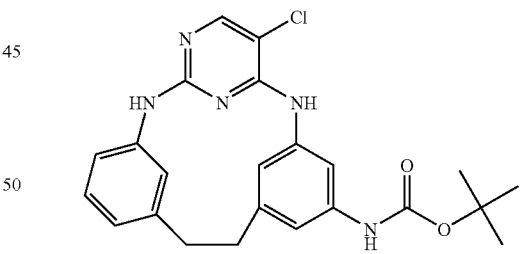

To a solution of 6-chloro-2,4,8,22-tetraazatetracyclo[14.3.1.1(3,7).1(9,13)]docosa-1(20),3(22),4,6,9(21),10,12,16,18-nonaene-11-carboxylic acid (9.2 mg, 25.1 µmol) in tert-butyl alcohol (0.16 mL) was added triethylamine (3.5 µL, 25.1 µmol) and diphenylphosphonic azide (5.4 µL, 25.1 µmol). The resulting mixture was heated at 85° C. overnight. The reaction mixture was diluted with DMSO and purified with preparative LCMS to give the desired product (6 mg, 55%). $^1$H NMR (400 MHz, DMSO-$d_6$): δ 9.33 (s, 1H), 9.22 (s, 1H), 8.09 (s, 1H), 7.92 (s, 1H), 7.31 (m, 2H), 7.08 (t, 1H), 7.03 (s, 1H), 6.88 (dd, 1H), 6.80 (dd, 1H), 2.80 (d, 4H), 1.46 (s, 9H). LCMS calculated for $C_{23}H_{25}ClN_5O_2(M+H)^+$: m/z=438.2.

Step B: 6-Chloro-2,4,8,22-tetraazatetracyclo [14.3.1.1(3,7).1(9,13)]docosa-1(20),3(22),4,6,9(21), 10,12,16,18-nonaen-11-amine bis(trifluoroacetate)

A solution of tert-butyl [6-chloro-2,4,8,22-tetraazatetracyclo[14.3.1.1(3,7).1(9,13)]docosa-1(20),3(22),4,6,9(21),10,12,16,18-nonaen-11-yl]carbamate (134 mg, 0.306 mmol), 4.0 M of hydrogen chloride in 1,4-dioxane (229 μL, 918 μmol) and methylene chloride (11 mL) was stirred at 25° C. overnight. The reaction solution was concentrated and the residue was dissolved in methanol and purified with preparative LCMS to yield the desired product (102 mg, 74%). $^1$H NMR (400 MHz, DMSO-$d_6$): δ 9.40 (s, 1H), 9.32 (s, 1H), 8.14 (s, 1H), 7.89 (m, 1H), 7.64 (s, 1H), 7.10 (dd, 1H), 6.87 (m, 2H), 6.81 (m, 2H), 2.87 (m, 4H). LCMS calculated for $C_{18}H_{17}ClN_5$(M+H)$^+$: m/z=338.1.

Example B22

Methyl 6-chloro-2,4,8,22-tetraazatetracyclo[14.3.1.1(3,7).1(9,13)]docosa-1(20),3(22),4,6,9(21),10,12,16,18-nonaene-12-carboxylate trifluoroacetate

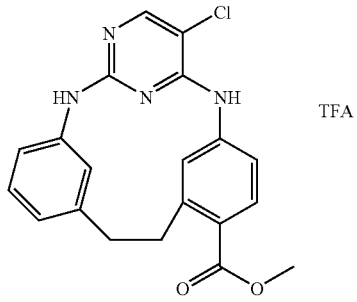 [SMILES: COC(=O)c1ccc2cc1CCc1cccc(c1)Nc1ncc(Cl)c(n1)N2]

Step A: 2-Iodo-4-nitrobenzoic acid

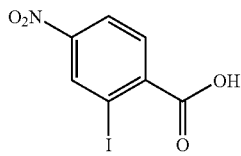 [SMILES: O=C(O)c1ccc([N+](=O)[O-])cc1I]

To a solution of 2-amino-4-nitrobenzoic acid (14.5 g, 79.6 mmol) in 2.0 M of sulfuric acid aqueous solution (398 mL, 796 mmol) was added a solution of sodium nitrite (8.24 g, 0.119 mol) in water dropwise at 0° C. After the addition, the resulting solution was stirred at same temperature for 1 hour, then a solution of potassium iodide (19.8 g, 0.119 mol) in water was added dropwise at 0° C. The resulting mixture was stirred at rt for 72 hours. The precipitate was filtered and washed by water to give the desired product (19.5 g, 83%). LCMS calculated for $C_7H_{51}NO_4$(M+H)$^+$: m/z=294.0.

Step B: Methyl 2-iodo-4-nitrobenzoate

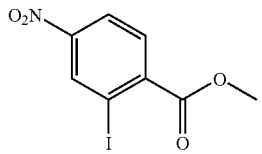

A solution of 2-iodo-4-nitrobenzoic acid (9 g, 30.7 mmol), methanol (88 mL) and sulfuric acid (0.82 mL, 15.4 mmol) was heated to reflux overnight. The reaction solution was cooled down to 0° C. for 30 minutes. The solid was filtered to give the desired product (5.90 g, 62%). LCMS calculated for $C_8H_{71}NO_4$(M+H)$^+$: m/z=308.0.

Step C: Methyl 2-({3-[(tert-butoxycarbonyl)amino]phenyl}ethynyl)-4-nitrobenzoate

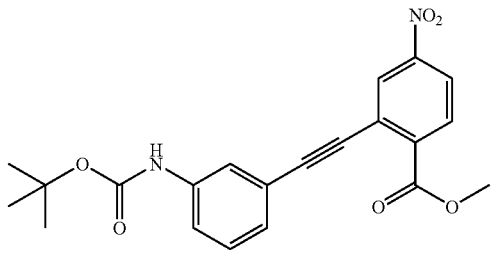 [SMILES: COC(=O)c1ccc([N+](=O)[O-])cc1C#Cc1cccc(NC(=O)OC(C)(C)C)c1]

This compound was prepared according to the procedure of Example B19 step C, using tert-butyl (3-ethynylphenyl)carbamate and methyl 2-iodo-4-nitrobenzoate as the starting materials in 87% yield. LCMS calculated for $C_{21}H_{21}N_2O_6$ (M+H)$^+$: m/z=397.1.

Step D: Methyl 4-amino-2-(2-{3-[(tert-butoxycarbonyl)amino]phenyl}ethyl)benzoate

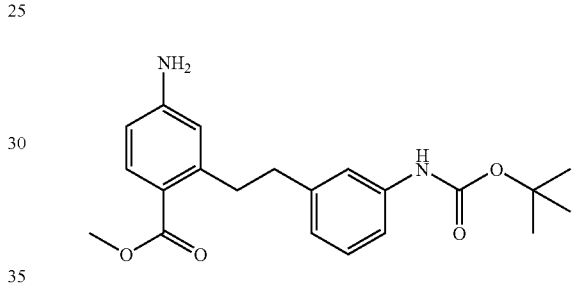

This compound was prepared according to the procedure of Example B19 step D, using methyl 2-({3-[(tert-butoxycarbonyl)amino]phenyl}ethynyl)-4-nitrobenzoate as the starting material in 83% yield. LCMS calculated for $C_{21}H_{27}N_2O_4$ (M+H)$^+$: m/z=371.1.

Step E: Methyl 2-(2-{3-[(tert-butoxycarbonyl)amino]phenyl}ethyl)-4-[(2,5-dichloropyrimidin-4-yl)amino]benzoate

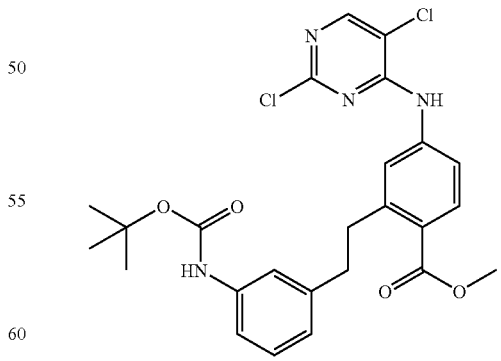

This compound was prepared according to the procedure of Example B19 step E, using methyl 4-amino-2-(2-{3-[(tert-butoxycarbonyl)amino]phenyl}ethyl)benzoate as the starting material in 29% yield. LCMS calculated for $C_{25}H_{27}Cl_2N_4O_4$ (M+H)$^+$: m/z=517.1.

Step F: Methyl 6-chloro-2,4,8,22-tetraazatetracyclo[14.3.1.1(3,7).1(9,13)]docosa-1(20),3(22),4,6,9(21),10,12,16,18-nonaene-12-carboxylate trifluoroacetate This compound was prepared according to the procedure of Example B19 step F, using methyl 2-(2-{3-[(tert-butoxycarbonyl)amino]phenyl}ethyl)-4-[(2,5-dichloropyrimidin-4-yl)amino]benzoate as the starting material in 62% yield. LCMS calculated for $C_{20}H_{18}ClN_4O_2(M+H)^+$: m/z=381.1. $^1$H NMR (400 MHz, DMSO-$d_6$): δ 9.49 (m, 2H), 8.18 (s, 1H), 8.03 (m, 1H), 7.90 (m, 1H), 7.83 (d, 1H), 7.17 (dd, 1H), 7.08 (dd, 1H), 6.97 (m, 1H), 6.77 (m, 1H), 3.82 (s, 3H), 3.22 (m, 2H), 2.93 (m, 2H).

Example B23

[6-Chloro-2,4,8,22-tetraazatetracyclo[14.3.1.1(3,7).1(9,13)]docosa-1(20),3(22),4,6,9(21),10,12,16,18-nonaen-12-yl]methanol trifluoroacetate

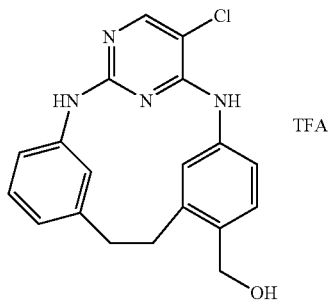 [SMILES: OCc1ccc2cc1CCc1cccc(c1)Nc1ncc(Cl)c(n1)N2]

To a solution of methyl 6-chloro-2,4,8,22-tetraazatetracyclo[14.3.1.1(3,7).1(9,13)]docosa-1(20),3(22),4,6,9(21),10,12,16,18-nonaene-12-carboxylate (1.06 g, 2.78 mmol) in dichloromethane (DCM, 44 mL) was added 1.0 M of diisobutylaluminum hydride in methylene chloride (12.5 mL, 12.5 mmol) at 0° C. The resulting solution was allowed to warm up to rt for 2 hours. The reaction was quenched with 1 N HCl and diluted with ethyl acetate. The organic solution was dried over sodium sulfate and concentrated; and the residue was dissolve in DMSO/methanol and purified with preparative LCMS to give the desired product (629 mg, 48%). $^1$H NMR (400 MHz, DMSO-$d_6$): δ 9.63 (s, 1H), 9.49 (s, 1H), 8.17 (s, 1H), 7.97 (m, 1H), 7.69 (d, 1H), 7.30 (d, 1H), 7.10 (dd, 1H), 7.04 (dd, 1H), 6.87 (m, 1H), 6.84 (m, 1H), 4.54 (s, 2H), 2.90 (m, 4H). LCMS calculated for $C_{19}H_{18}ClN_4O$ (M+H)$^+$: m/z=353.2.

Example B24

[6-Chloro-2,4,8,22-tetraazatetracyclo[14.3.1.1(3,7).1(9,13)]docosa-1(20),3(22),4,6,9(21),10,12,16,18-nonaen-11-yl]methanol trifluoroacetate

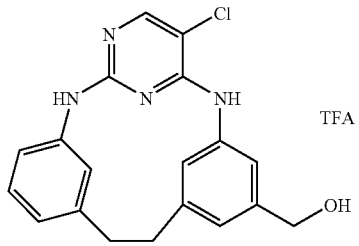 [SMILES: OCc1cc2cc(c1)Nc1nc(ncc1Cl)Nc1cccc(c1)CC2]

The desired compound was prepared according to the procedure of Example B23, using methyl 6-chloro-2,4,8,22-tetraazatetracyclo[14.3.1.1(3,7).1(9,13)]docosa-1(20),3(22),4,6,9(21),10,12,16,18-nonaene-11-carboxylate as the starting material in 60% yield. $^1$H NMR (400 MHz, DMSO-$d_6$): δ 9.50 (s, 1H), 9.40 (s, 1H), 8.14 (s, 1H), 7.88 (m, 1H), 7.60 (m, 1H), 7.10 (dd, 1H), 7.04 (m, 1H), 6.95 (m, 1H), 6.87 (m, 2H), 4.44 (s, 2H), 2.87 (m, 4H). LCMS calculated for $C_{19}H_{18}ClN_4O$ (M+H)$^+$: m/z=353.2.

Example B25

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-N'-[(3S)-pyrrolidin-3-yl]urea trihydrochloride

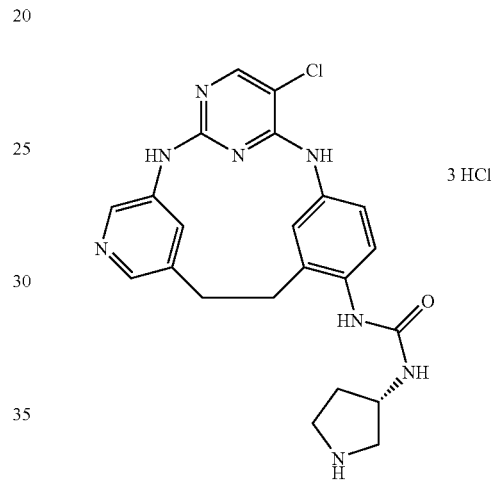

Step A: tert-Butyl (3S)-3-[({[6-chloro-2,4,8,18,22-pentaazatetracyclo[14.3.1.1(3,7).1(9,13)]docosa-1(20),3(22),4,6,9(21),10,12,16,18-nonaen-12-yl]amino}carbonyl)amino]pyrrolidine-1-carboxylate

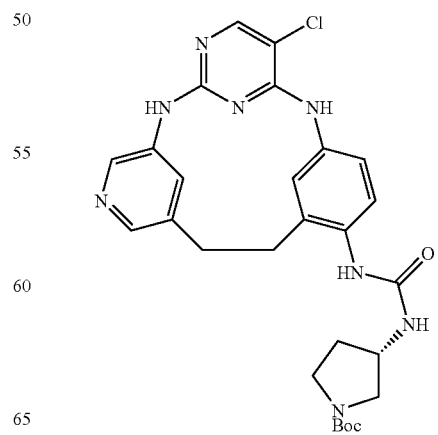

To a solution of 20% phosgene in toluene (0.49 mL, 0.93 mmol) was added a solution of tert-butyl (3S)-3-aminopyrrolidine-1-carboxylate (38 mg, 0.20 mmol) and triethylamine (102 µL, 0.734 mmol) in THF (0.5 mL). The resulting solution was stirred for 2 hours then concentrated. To the isolated solids was added DCM (0.75 mL) followed by 6-chloro-2,4,8,18,22-pentaazatetracyclo[14.3.1.1(3,7).1(9,13)]docosa-1(20),3(22),4,6,9(21),10,12,16,18-nonaen-12-amine bis(trifluoroacetate) (70 mg, 0.1 mmol) and triethylamine (73 µL, 0.52 mmol). The resulting mixture was stirred at room temperature overnight and concentrated. The residue was purified by flash column chromatography to yield the desired product (34 mg, 50%). LCMS calculated for $C_{27}H_{32}ClN_8O_3$ (M+H)$^+$: m/z=551.1.

Step B: N-[6-Chloro-2,4,8,18,22-pentaazatetracyclo [14.3.1.1(3,7).1(9,13)]docosa-1(20),3(22),4,6,9(21), 10,12,16,18-nonaen-12-yl]-N'-[(3S)-pyrrolidin-3-yl] urea dihydrochloride To the product from the previous step was added a solution of hydrogen chloride in 1,4-dioxane (4.0 M, 0.8 mL, 3 mmol). The mixture was stirred for 2 hours then the solvent evaporated and the solids dried under vacuum to give the desired product (33 mg, 46%). LCMS calculated for $C_{22}H_{24}ClN_8O$ (M+H)$^+$: m/z=451.0.

Example B26

N-[6-Chloro-2,4,8,22-tetraazatetracyclo[14.3.1.1(3, 7).1(9,13)]docosa-1(20), 3(22),4,6,9(21),10,12,16, 18-nonaen-12-yl]acetamide trifluoroacetate

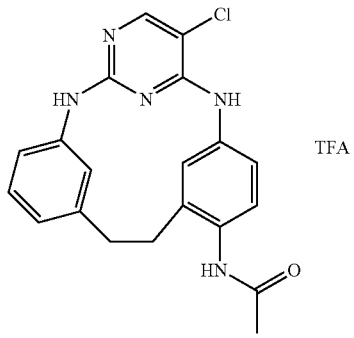 [SMILES: CC(=O)Nc1ccc2cc1CCc1cccc(c1)Nc1ncc(Cl)c(n1)N2]

6-Chloro-2,4,8,22-tetraazatetracyclo[14.3.1.1(3,7).1(9, 13)]docosa-1(20),3(22),4,6,9(21),10,12,16,18-nonaen-12-amine dihydrochloride (20 mg, 0.06 mmol) in DCM (0.3 mL) was treated with triethylamine (24.8 µL, 0.178 mmol) and acetyl chloride (5.1 µL, 0.071 mmol). The reaction mixture was stirred at room temperature overnight. The solvent was evaporated and the crude residue was dissolved in a mixture of acetonitrile and methanol and purified by preparative LCMS to give the desired product (10.4 mg, 35%). LCMS calculated for $C_{20}H_{19}ClN_5O$ (M+H)$^+$: m/z=380.2.

Example B27

N-[6-Chloro-2,4,8,22-tetraazatetracyclo[14.3.1.1(3, 7).1(9,13)]docosa-1(20), 3(22),4,6,9(21),10,12,16, 18-nonaen-12-yl]cyclopropanecarboxamide trifluoroacetate

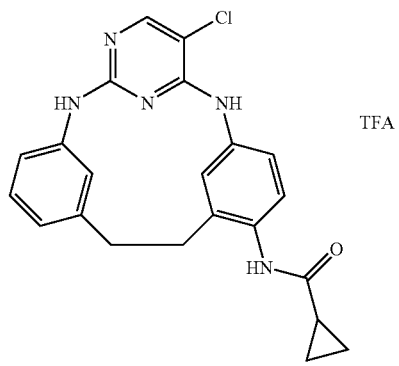 [SMILES: "TFA" ; O=C(Nc1ccc2cc1CCc1cccc(c1)Nc1ncc(Cl)c(n1)N2)C1CC1]

The desired compound was prepared according to the procedure of Example B26, using 6-chloro-2,4,8,22-tetraazatetracyclo[14.3.1.1(3,7).1(9,13)]docosa-1(20),3(22),4,6,9(21), 10,12,16,18-nonaen-12-amine dihydrochloride and cyclopropanecarbonyl chloride as the starting materials in 30% yield. LCMS for $C_{22}H_{21}ClN_5O$ (M+H)$^+$: m/z=406.3.

Example B28

N-[6-Chloro-2,4,8,22-tetraazatetracyclo[14.3.1.1(3, 7).1(9,13)]docosa-1(20), 3(22),4,6,9(21),10,12,16, 18-nonaen-12-yl]-2-methoxyacetamide trifluoroacetate

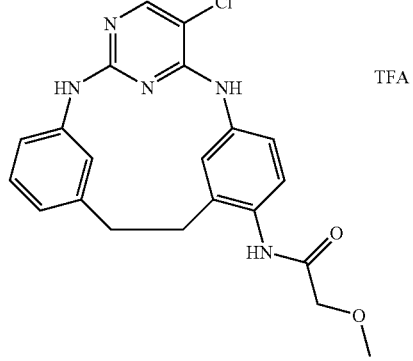

The desired compound was prepared according to the procedure of Example B26, using 6-chloro-2,4,8,22-tetraazatetracyclo[14.3.1.1(3,7).1(9,13)]docosa-1(20),3(22),4,6,9(21), 10,12,16,18-nonaen-12-amine dihydrochloride and methoxyacetyl chloride as the starting materials in 40% yield. LCMS for $C_{21}H_{21}ClN_5O_2$(M+H)$^+$: m/z=410.3. $^1$H NMR (400 MHz, CDCl$_3$): δ 11.84 (s, 1H), 8.42 (s, 1H), 8.08 (d, 1H), 7.85 (m, 3H), 7.27 (m, 2H), 7.11 (d, 1H), 7.01 (m, 2H), 4.10 (s, 2H), 3.79 (s, 3H), 2.92 (t, 4H).

Example B29

N-[6-Chloro-2,4,8,22-tetraazatetracyclo[14.3.1.1(3,7).1(9,13)]docosa-1(20), 3(22),4,6,9(21),10,12,16,18-nonaen-12-yl]benzamide trifluoroacetate

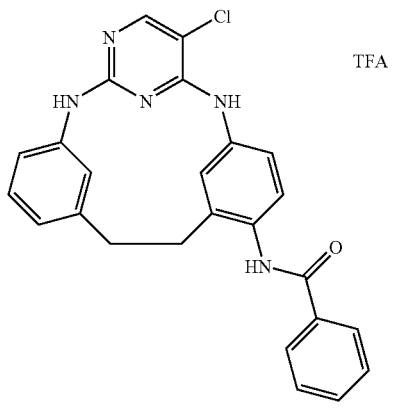 [SMILES: "TFA" ; O=C(Nc1ccc2cc1CCc1cccc(c1)Nc1ncc(Cl)c(n1)N2)c1ccccc1]

The desired compound was prepared according to the procedure of Example B26, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and benzoyl chloride as the starting materials in 45% yield. LCMS for $C_{25}H_{21}ClN_5O$ (M+H)$^+$: m/z=442.0. $^1$H NMR (400 MHz, DMSO-d$_6$): δ 9.91 (s, 1H), 9.38 (s, 1H), 9.25 (s, 1H), 8.12 (s, 1H), 8.08 (s, 1H), 7.98 (d, 2H), 7.83 (s, 1H), 7.57 (m, 3H), 7.21 (d, 1H), 7.09 (m, 2H), 6.86 (d, 1H), 6.75 (d, 1H), 2.86 (dd, 4H).

Example B30

N-[6-Chloro-2,4,8,22-tetraazatetracyclo[14.3.1.1(3,7).1(9,13)]docosa-1(20), 3(22),4,6,9(21),10,12,16,18-nonaen-12-yl]nicotinamide bis(trifluoroacetate)

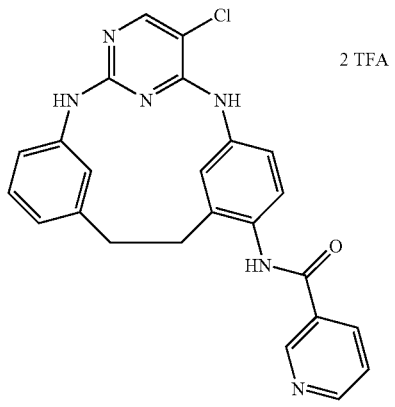 [SMILES: O=C(Nc1ccc2cc1CCc1cccc(c1)Nc1ncc(Cl)c(n1)N2)c1cccnc1 ; "2 TFA"]

The desired compound was prepared according to the procedure of Example B26, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and nicotinoyl chloride hydrochloride as the starting materials in 40% yield. LCMS for $C_{24}H_{20}ClN_6O$ (M+H)$^+$: m/z=443.0. $^1$H NMR (400 MHz, DMSO-d$_6$): δ 10.18 (s, 1H), 9.76 (s, 1H), 9.69 (s, 1H), 9.19 (s, 1H), 8.81 (d, 1H), 8.41 (d, 1H), 8.21 (s, 1H), 7.97 (s, 1H), 7.85 (s, 1H), 7.66 (m, 1H), 7.25 (d, 1H), 7.10 (m, 2H), 6.88 (d, 1H), 6.81 (d, 1H), 2.92 (dd, 4H).

Example B31

N-[6-Chloro-2,4,8,22-tetraazatetracyclo[14.3.1.1(3,7).1(9,13)]docosa-1(20), 3(22),4,6,9(21),10,12,16,18-nonaen-12-yl]-1-methyl-1H-pyrazole-3-carboxamide trifluoroacetate

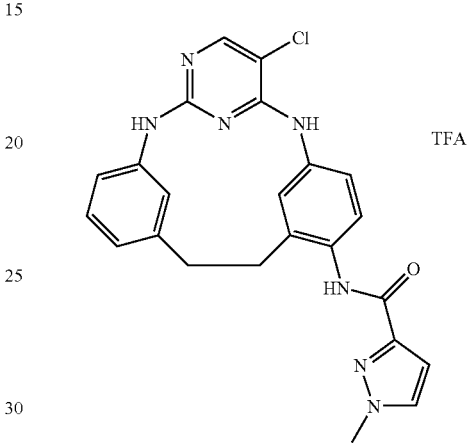

The desired compound was prepared according to the procedure of Example B26, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 1-methyl-1H-pyrazole-3-carbonyl chloride as the starting materials in 27% yield. LCMS for $C_{23}H_{21}ClN_7O$ (M+H)$^+$: m/z=446.3. $^1$H NMR (400 MHz, DMSO-d$_6$): δ 9.59 (m, 3H), 8.19 (s, 1H), 7.99 (s, 1H), 7.83 (s, 1H), 7.79 (s, 1H), 7.36 (d, 1H), 7.08 (m, 2H), 6.87 (d, 1H), 6.79 (d, 1H), 6.75 (s, 1H), 3.97 (s, 3H), 2.90 (dd, 4H).

Example B32

N-[6-Chloro-2,4,8,22-tetraazatetracyclo[14.3.1.1(3,7).1(9,13)]docosa-1(20), 3(22),4,6,9(21),10,12,16,18-nonaen-12-yl]-2-phenylacetamide trifluoroacetate

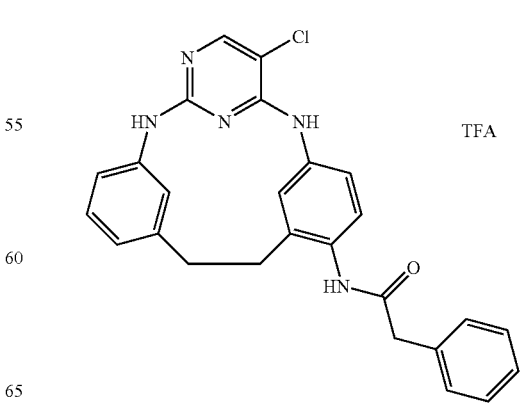

The desired compound was prepared according to the procedure of Example B26, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and benzeneacetyl chloride as the starting materials in 11% yield. LCMS for $C_{26}H_{23}ClN_5O$ (M+H)⁺: m/z=456.3.

Example B33

N-[6-Chloro-2,4,8,22-tetraazatetracyclo[14.3.1.1(3,7).1(9,13)]docosa-1(20), 3(22),4,6,9(21),10,12,16,18-nonaen-12-yl]-2-furamide trifluoroacetate

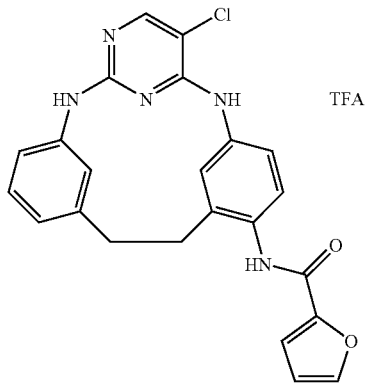 [SMILES: "TFA" ; O=C(Nc1ccc2cc1CCc1cccc(c1)Nc1ncc(Cl)c(n1)N2)c1ccco1]

The desired compound was prepared according to the procedure of Example B26, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 2-furancarbonyl chloride as the starting materials in 41% yield. LCMS for $C_{23}H_{19}ClN_5O_2$ (M+H)⁺: m/z=432.0.

Example B34

N-[6-Chloro-2,4,8,22-tetraazatetracyclo[14.3.1.1(3,7).1(9,13)]docosa-1(20),3(22),4,6,9(21),10,12,16,18-nonaen-12-yl]thiophene-2-carboxamide trifluoroacetate

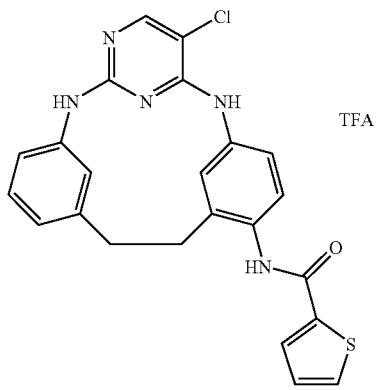 [SMILES: "TFA" ; O=C(Nc1ccc2cc1CCc1cccc(c1)Nc1ncc(Cl)c(n1)N2)c1cccs1]

The desired compound was prepared according to the procedure of Example B26, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 2-thiophenecarbonyl chloride as the starting materials in 41% yield. LCMS for $C_{23}H_{19}ClN_5OS$ (M+H)⁺: m/z=448.0.

Example B35

N-[6-Chloro-2,4,8,22-tetraazatetracyclo[14.3.1.1(3,7).1(9,13)]docosa-1(20), 3(22),4,6,9(21),10,12,16,18-nonaen-12-yl]-2-methylbenzamide trifluoroacetate

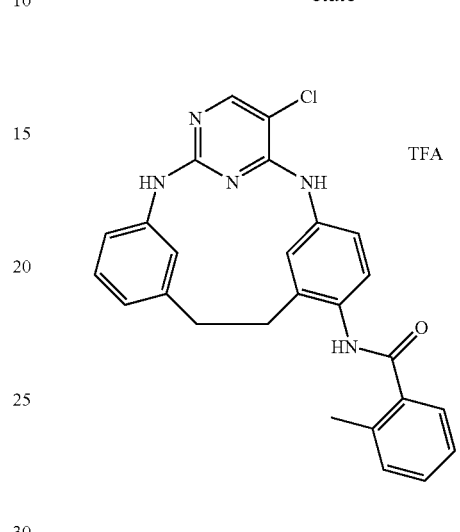

The desired compound was prepared according to the procedure of Example B26, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 2-methylbenzoyl chloride as the starting materials in 36% yield. LCMS for $C_{26}H_{23}ClN_5O$ (M+H)⁺: m/z=456.1.

Example B36

N-[6-Chloro-2,4,8,22-tetraazatetracyclo[14.3.1.1(3,7).1(9,13)]docosa-1(20), 3(22),4,6,9(21),10,12,16,18-nonaen-12-yl]-2-methoxybenzamide trifluoroacetate

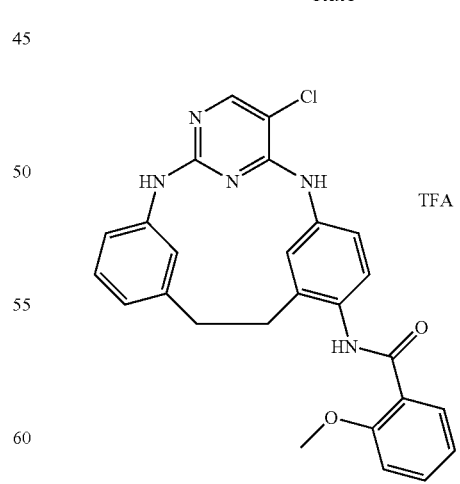

The desired compound was prepared according to the procedure of Example B26, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 2-methoxybenzoyl chloride as the starting materials in 38% yield. LCMS for $C_{26}H_{23}ClN_5O_2(M+H)^+$: m/z=472.3.

Example B37

N-[6-Chloro-2,4,8,22-tetraazatetracyclo[14.3.1.1(3,7).1(9,13)]docosa-1(20), 3(22),4,6,9(21),10,12,16,18-nonaen-12-yl]pyridine-2-carboxamide bis(trifluoroacetate)

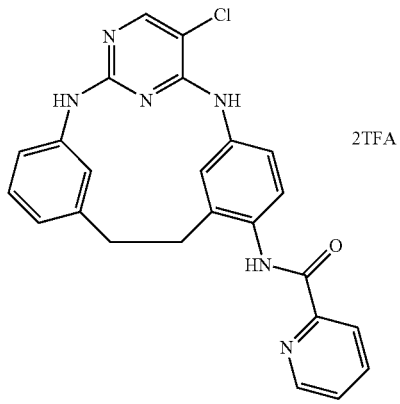 [SMILES: O=C(Nc1ccc2cc1CCc1cccc(c1)Nc1ncc(Cl)c(n1)N2)c1ccccn1 ; "2TFA"]

The desired compound was prepared according to the procedure of Example B26, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and pyridine-2-carbonyl chloride hydrochloride as the starting materials in 24% yield. LCMS for $C_{24}H_{20}ClN_6O$ $(M+H)^+$: m/z=443.3.

Example B38

N-[6-Chloro-2,4,8,22-tetraazatetracyclo[14.3.1.1(3,7).1(9,13)]docosa-1(20), 3(22),4,6,9(21),10,12,16,18-nonaen-12-yl]-2-fluorobenzamide trifluoroacetate

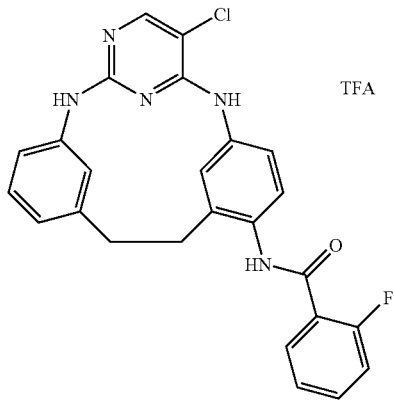 [SMILES: "TFA" ; O=C(Nc1ccc2cc1CCc1cccc(c1)Nc1ncc(Cl)c(n1)N2)c1ccccc1F]

The desired compound was prepared according to the procedure of Example B26, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 2-fluorobenzoyl chloride as the starting materials in 24% yield. LCMS for $C_{25}H_{20}ClFN_5O$ $(M+H)^+$: m/z=460.0.

Example B39

N-[6-Chloro-2,4,8,22-tetraazatetracyclo[14.3.1.1(3,7).1(9,13)]docosa-1(20), 3(22),4,6,9(21),10,12,16,18-nonaen-12-yl]isonicotinamide bis(trifluoroacetate)

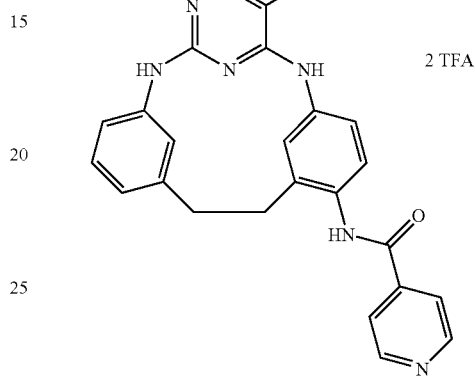

The desired compound was prepared according to the procedure of Example B26, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and isonicotinoyl chloride hydrochloride as the starting materials in 37% yield. LCMS for $C_{24}H_{20}ClN_6O$ $(M+H)^+$: m/z=443.3.

Example B40

N-[6-Chloro-2,4,8,22-tetraazatetracyclo[14.3.1.1(3,7).1(9,13)]docosa-1(20), 3(22),4,6,9(21),10,12,16,18-nonaen-12-yl]-3,5-dimethylisoxazole-4-carboxamide trifluoroacetate

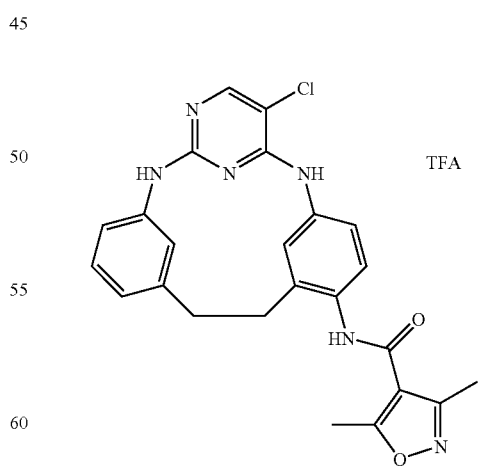

The desired compound was prepared according to the procedure of Example B26, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 3,5- dimethylisoxazole-4-carbonyl chloride as the starting materials in 34% yield. LCMS for $C_{24}H_{22}ClN_6O_2(M+H)^+$: m/z=461.3.

Example B41

2-Chloro-N-[6-chloro-2,4,8,22-tetraazatetracyclo [14.3.1.1(3,7).1(9,13)]docosa-1(20),3(22),4,6,9(21), 10,12,16,18-nonaen-12-yl]benzamide hydrochloride

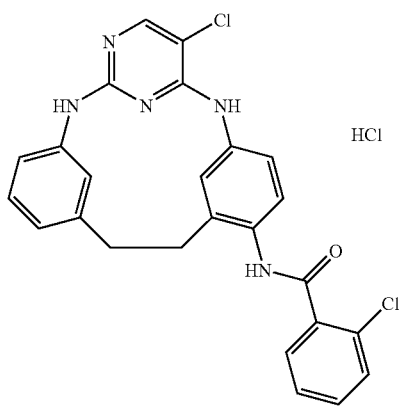 [SMILES: O=C(Nc1ccc2cc1CCc1cccc(c1)Nc1ncc(Cl)c(n1)N2)c1ccccc1Cl ; Cl]

The desired compound was prepared according to the procedure of Example B26, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 2-chlorobenzoyl chloride as the starting materials in 24% yield. LCMS for $C_{25}H_{20}Cl_2N_5O$ $(M+H)^+$: m/z=476.2.

Example B42

3-Chloro-N-[6-chloro-2,4,8,22-tetraazatetracyclo [14.3.1.1(3,7).1(9,13)]docosa-1(20),3(22),4,6,9(21), 10,12,16,18-nonaen-12-yl]benzamide hydrochloride

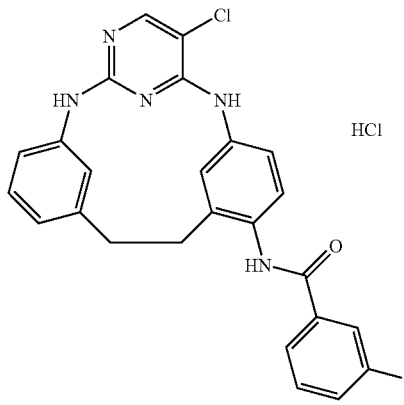

The desired compound was prepared according to the procedure of Example B26, using 6-chloro-2,4,8,22-tetraazatetracyclo[14.3.1.1(3,7).1(9,13)]docosa-1(20),3(22),4,6,9(21), 10,12,16,18-nonaen-12-amine dihydrochloride and 3-chlorobenzoyl chloride as the starting materials in 60% yield. LCMS for $C_{25}H_{20}Cl_2N_5O$ $(M+H)^+$: m/z=476.3.

Example B43

4-Chloro-N-[6-chloro-2,4,8,22-tetraazatetracyclo [14.3.1.1(3,7).1(9,13)]docosa-1(20),3(22),4,6,9(21), 10,12,16,18-nonaen-12-yl]benzamide hydrochloride

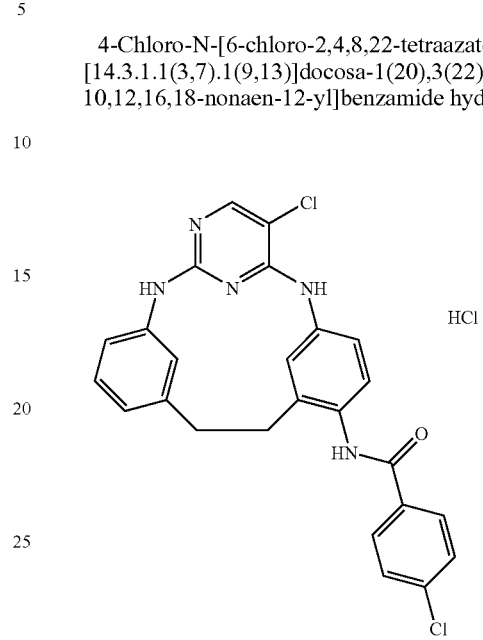

The desired compound was prepared according to the procedure of Example B26, using 6-chloro-2,4,8,22-tetraazatetracyclo[14.3.1.1(3,7).1(9,13)]docosa-1(20),3(22),4,6,9(21), 10,12,16,18-nonaen-12-amine dihydrochloride and 4-chlorobenzoyl chloride as the starting materials in 66% yield. LCMS for $C_{25}H_{20}Cl_2N_5O$ $(M+H)^+$: m/z=476.2.

Example B44

N-[6-Chloro-2,4,8,22-tetraazatetracyclo[14.3.1.1(3, 7).1(9,13)]docosa-1(20), 3(22),4,6,9(21),10,12,16, 18-nonaen-12-yl]pyrazine-2-carboxamide bis(trifluoroacetate)

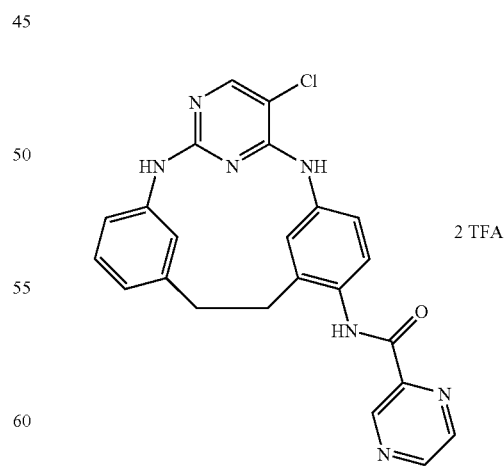

The desired compound was prepared according to the procedure of Example B26, using 6-chloro-2,4,8,22-tetraazatetracyclo[14.3.1.1(3,7).1(9,13)]docosa-1(20),3(22),4,6,9(21), 10,12,16,18-nonaen-12-amine dihydrochloride and pyrazine-2-carbonyl chloride as the starting materials in 23% yield. LCMS for $C_{23}H_{19}ClN_7O$ (M+H)$^+$: m/z=444.3.

Example B45

4-(Acetylamino)-N-[6-chloro-2,4,8,22-tetraazatetracyclo[14.3.1.1(3,7).1(9,13)]docosa-1(20),3(22),4,6,9 (21),10,12,16,18-nonaen-12-yl]benzamide trifluoroacetate

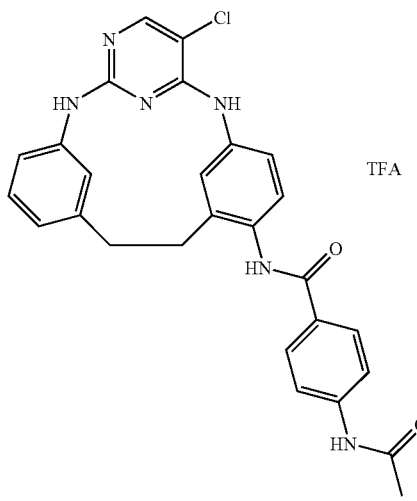

The desired compound was prepared according to the procedure of Example B26, using 6-chloro-2,4,8,22-tetraazatetracyclo[14.3.1.1(3,7).1(9,13)]docosa-1(20),3(22),4,6,9(21), 10,12,16,18-nonaen-12-amine dihydrochloride and 4-acetamidobenzoyl chloride as the starting materials in 25% yield. LCMS for $C_{27}H_{24}ClN_6O_2$(M+H)$^+$: m/z=499.3.

Example B46

N-[6-Chloro-2,4,8,22-tetraazatetracyclo[14.3.1.1(3, 7).1(9,13)]docosa-1(20), 3(22),4,6,9(21),10,12,16, 18-nonaen-12-yl]-3-methylbenzamide trifluoroacetate

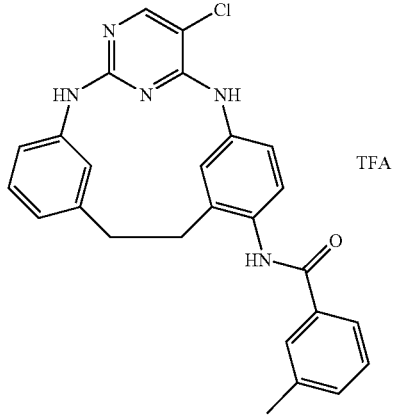 [SMILES: "TFA" ; Cc1cccc(C(=O)Nc2ccc3cc2CCc2cccc(c2)Nc2ncc(Cl)c(n2)N3)c1]

The desired compound was prepared according to the procedure of Example B26, using 6-chloro-2,4,8,22-tetraazatet-
racyclo[14.3.1.1(3,7).1(9,13)]docosa-1(20),3(22),4,6,9(21), 10,12,16,18-nonaen-12-amine dihydrochloride and 3-methylbenzoyl chloride as the starting materials in 38% yield. LCMS for $C_{26}H_{23}ClN_5O$ (M+H)$^+$: m/z=456.0.

Example B47

N-[6-Chloro-2,4,8,22-tetraazatetracyclo[14.3.1.1(3, 7).1(9,13)]docosa-1(20), 3(22),4,6,9(21),10,12,16, 18-nonaen-12-yl]-4-methylbenzamide trifluoroacetate

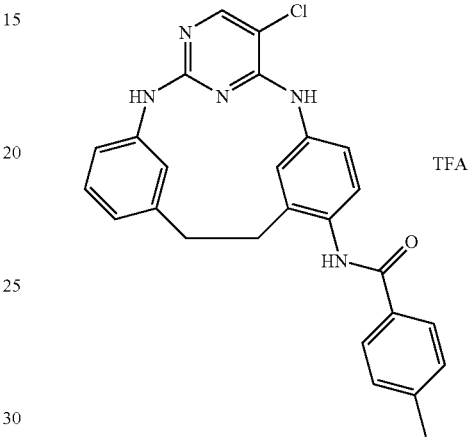

The desired compound was prepared according to the procedure of Example B26, using 6-chloro-2,4,8,22-tetraazatetracyclo[14.3.1.1(3,7).1(9,13)]docosa-1(20),3(22),4,6,9(21), 10,12,16,18-nonaen-12-amine dihydrochloride and 4-methylbenzoyl chloride as the starting materials in 39% yield. LCMS for $C_{26}H_{23}ClN_5O$ (M+H)$^+$: m/z=456.2.

Example B48

N-[6-Chloro-2,4,8,22-tetraazatetracyclo[14.3.1.1(3, 7).1(9,13)]docosa-1(20), 3(22),4,6,9(21),10,12,16, 18-nonaen-12-yl]-3-fluorobenzamide trifluoroacetate

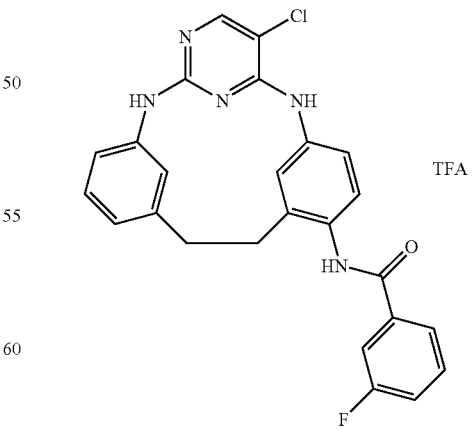

The desired compound was prepared according to the procedure of Example B26 7, using 6-chloro-2,4,8,22-tetraazatetracyclo[14.3.1.1(3,7).1(9,13)]docosa-1(20),3(22),4,6,9

(21),10,12,16,18-nonaen-12-amine dihydrochloride and 3-fluorolbenzoyl chloride as the starting materials in 32% yield. LCMS for $C_{25}H_{20}ClFN_5O$ (M+H)$^+$: m/z=460.3.

Example B49

N-[6-Chloro-2,4,8,22-tetraazatetracyclo[14.3.1.1(3, 7).1(9,13)]docosa-1(20), 3(22),4,6,9(21),10,12,16, 18-nonaen-12-yl]-4-fluorobenzamide trifluoroacetate

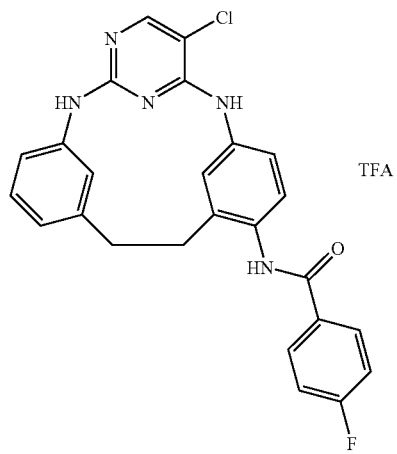 [SMILES: "TFA" ; O=C(Nc1ccc2cc1CCc1cccc(c1)Nc1ncc(Cl)c(n1)N2)c1ccc(F)cc1]

The desired compound was prepared according to the procedure of Example B26, using 6-chloro-2,4,8,22-tetraazatetracyclo[14.3.1.1(3,7).1(9,13)]docosa-1(20),3(22),4,6,9(21), 10,12,16,18-nonaen-12-amine dihydrochloride and 4-fluorobenzoyl chloride as the starting materials in 36% yield. LCMS for $C_{25}H_{20}ClFN_5O$ (M+H)$^+$: m/z=460.3. $^1$H NMR (400 MHz, DMSO-d$_6$): δ 9.95 (s, 1H), 9.49 (s, 1H), 9.40 (s, 1H), 8.17 (s, 1H), 8.06 (m, 3H), 7.83 (s, 1H), 7.38 (t, 2H), 7.21 (d, 1H), 7.09 (m, 2H), 6.86 (d, 1H), 6.78 (d, 1H), 2.86 (dd, 4H).

Example B50

N-[6-Chloro-2,4,8,22-tetraazatetracyclo[14.3.1.1(3, 7).1(9,13)]docosa-1(20), 3(22),4,6,9(21),10,12,16, 18-nonaen-12-yl]-1-methyl-1H-pyrrole-2-carboxamide trifluoroacetate

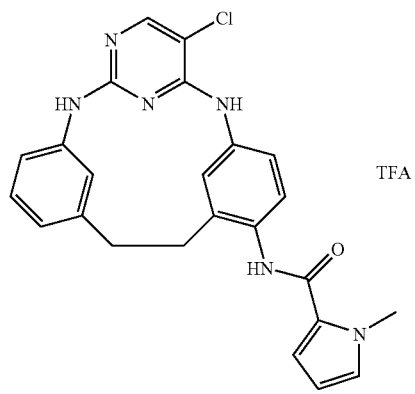 [SMILES: Cn1cccc1C(=O)Nc1ccc2cc1CCc1cccc(c1)Nc1ncc(Cl)c(n1)N2]

The desired compound was prepared according to the procedure of Example B26, using 6-chloro-2,4,8,22-tetraazatetracyclo[14.3.1.1(3,7).1(9,13)]docosa-1(20),3(22),4,6,9(21), 10,12,16,18-nonaen-12-amine dihydrochloride and 1-methyl-1H-pyrrole-2-carbonyl chloride as the starting materials in 29% yield. LCMS for $C_{24}H_{22}ClN_6O$ (M+H)$^+$: m/z=445.1.

Example B51

N-[6-Chloro-2,4,8,22-tetraazatetracyclo[14.3.1.1(3, 7).1(9,13)]docosa-1(20), 3(22),4,6,9(21),10,12,16, 18-nonaen-12-yl]-1-methyl-1H-imidazole-5-carboxamide bis(trifluoroacetate)

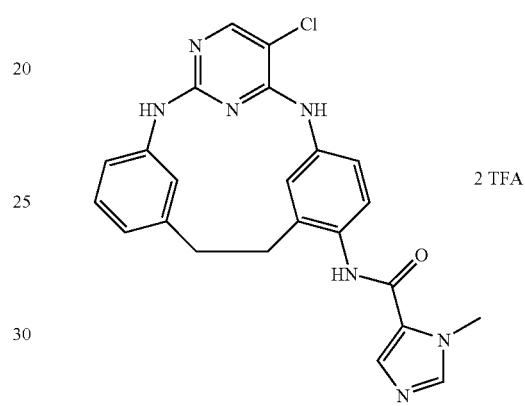

The desired compound was prepared according to the procedure of Example B26, using 6-chloro-2,4,8,22-tetraazatetracyclo[14.3.1.1(3,7).1(9,13)]docosa-1(20),3(22),4,6,9(21), 10,12,16,18-nonaen-12-amine dihydrochloride and 1-methyl-1H-imidazole-5-carbonyl chloride as the starting materials in 26% yield. LCMS for $C_{23}H_{21}ClN_7O$ (M+H)$^+$: m/z=446.3.

Example B52

N-[6-Chloro-2,4,8,22-tetraazatetracyclo[14.3.1.1(3, 7).1(9,13)]docosa-1(20), 3(22),4,6,9(21),10,12,16, 18-nonaen-12-yl]-1,3-thiazole-2-carboxamide trifluoroacetate

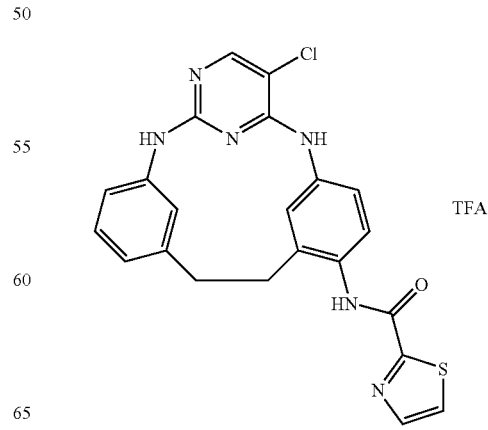

The desired compound was prepared according to the procedure of Example B26, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 1,3-thiazole-2-carbonyl chloride as the starting materials in 31% yield. LCMS for $C_{22}H_{18}ClN_6OS$ (M+H)$^+$: m/z=449.0. $^1$H NMR (400 MHz, DMSO-d$_6$): δ 10.30 (s, 1H), 9.45 (s, 1H), 9.36 (s, 1H), 8.14 (m, 3H), 8.02 (s, 1H), 7.83 (s, 1H), 7.37 (d, 1H), 7.09 (m, 2H), 6.86 (d, 1H), 6.77 (d, 1H), 2.86 (dd, 4H).

Example B53

N-[6-Chloro-2,4,8,22-tetraazatetracyclo[14.3.1.1(3,7).1(9,13)]docosa-1(20), 3(22),4,6,9(21),10,12,16,18-nonaen-12-yl]isoxazole-5-carboxamide trifluoroacetate

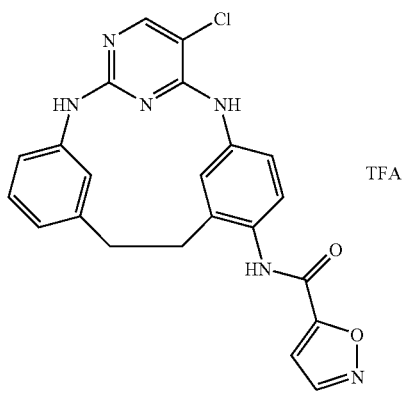 [SMILES: "TFA" ; O=C(Nc1ccc2cc1CCc1cccc(c1)Nc1ncc(Cl)c(n1)N2)c1ccno1]

The desired compound was prepared according to the procedure of Example B26, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and isoxazole-5-carbonyl chloride as the starting materials in 40% yield. LCMS for $C_{22}H_{18}ClN_6O_2$(M+H)$^+$: m/z=433.0.

Example B54

N-[6-Chloro-2,4,8,22-tetraazatetracyclo[14.3.1.1(3,7).1(9,13)]docosa-1(20), 3(22),4,6,9(21),10,12,16,18-nonaen-12-yl]propanamide trifluoroacetate

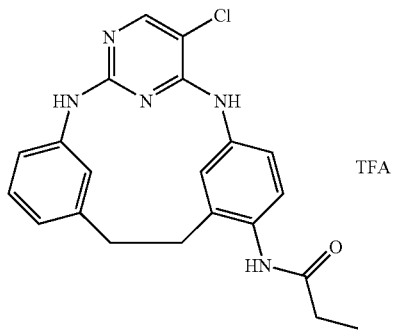 [SMILES: CCC(=O)Nc1ccc2cc1CCc1cccc(c1)Nc1ncc(Cl)c(n1)N2]

The desired compound was prepared according to the procedure of Example B26, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and propanoyl chloride as the starting materials in 24% yield. LCMS for $C_{21}H_{21}ClN_5O$ (M+H)$^+$: m/z=394.3.

Example B55

N-[6-Chloro-2,4,8,22-tetraazatetracyclo[14.3.1.1(3,7).1(9,13)]docosa-1(20), 3(22),4,6,9(21),10,12,16,18-nonaen-12-yl]-2-methylpropanamide trifluoroacetate

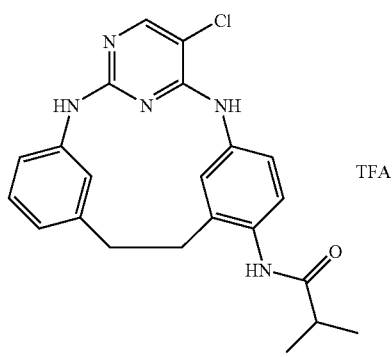 [SMILES: CC(C)C(=O)Nc1ccc2cc1CCc1cccc(c1)Nc1ncc(Cl)c(n1)N2]

The desired compound was prepared according to the procedure of Example B26, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and isobutyryl chloride as the starting materials in 24% yield. LCMS for $C_{22}H_{23}ClN_5O$ (M+H)$^+$: m/z=408.3.

Example B56

N-[6-Chloro-2,4,8,22-tetraazatetracyclo[14.3.1.1(3,7).1(9,13)]docosa-1(20), 3(22),4,6,9(21),10,12,16,18-nonaen-12-yl]butanamide trifluoroacetate

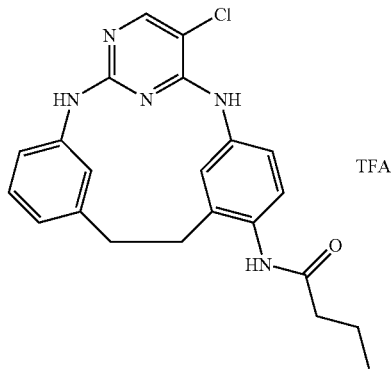 [SMILES: CCCC(=O)Nc1ccc2cc1CCc1cccc(c1)Nc1ncc(Cl)c(n1)N2]

The desired compound was prepared according to the procedure of Example B26, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and butylryl chloride as the starting materials in 26% yield. LCMS for $C_{22}H_{23}ClN_5O$ (M+H)$^+$: m/z=408.3.

Example B57

N-[6-Chloro-2,4,8,22-tetraazatetracyclo[14.3.1.1(3, 7).1(9,13)]docosa-1(20), 3(22),4,6,9(21),10,12,16, 18-nonaen-12-yl]cyclobutanecarboxamide hydrochloride

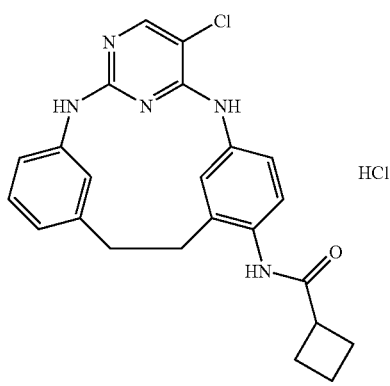 [SMILES: O=C(Nc1ccc2cc1CCc1cccc(c1)Nc1ncc(Cl)c(n1)N2)C1CCC1 ; Cl]

The desired compound was prepared according to the procedure of Example B26, using 6-chloro-2,4,8,22-tetraazatetracyclo[14.3.1.1(3,7).1(9,13)]docosa-1(20),3(22),4,6,9(21), 10,12,16,18-nonaen-12-amine dihydrochloride and cyclobutanecarboxylic acid chloride as the starting materials in 40% yield. LCMS for $C_{23}H_{23}ClN_5O$ (M+H)$^+$: m/z=420.3.

Example B58

N-[6-Chloro-2,4,8,22-tetraazatetracyclo[14.3.1.1(3, 7).1(9,13)]docosa-1(20), 3(22),4,6,9(21),10,12,16, 18-nonaen-12-yl]-2,2-dimethylpropanamide trifluoroacetate

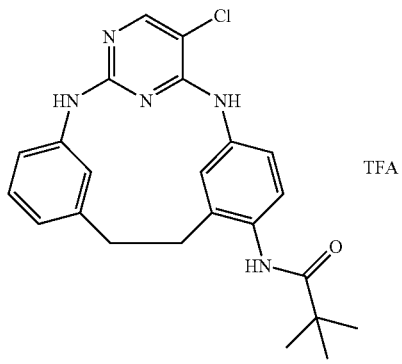 [SMILES: "TFA" ; CC(C)(C)C(=O)Nc1ccc2cc1CCc1cccc(c1)Nc1ncc(Cl)c(n1)N2]

The desired compound was prepared according to the procedure of Example B26, using 6-chloro-2,4,8,22-tetraazatetracyclo[14.3.1.1(3,7).1(9,13)]docosa-1(20),3(22),4,6,9(21), 10,12,16,18-nonaen-12-amine dihydrochloride and 2,2-dimethylpropanoyl chloride as the starting materials in 14% yield. LCMS for $C_{23}H_{25}ClN_5O$ (M+H)$^+$: m/z=422.3.

Example B59

N-[6-Chloro-2,4,8,22-tetraazatetracyclo[14.3.1.1(3, 7).1(9,13)]docosa-1(20), 3(22),4,6,9(21),10,12,16, 18-nonaen-12-yl]-3-furamide trifluoroacetate

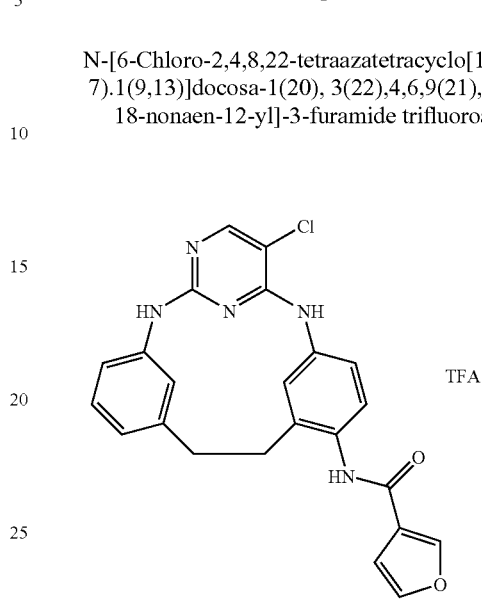

The desired compound was prepared according to the procedure of Example B26, using 6-chloro-2,4,8,22-tetraazatetracyclo[14.3.1.1(3,7).1(9,13)]docosa-1(20),3(22),4,6,9(21), 10,12,16,18-nonaen-12-amine dihydrochloride and 3-furoyl chloride as the starting materials in 22% yield. LCMS for $C_{23}H_{19}ClN_5O_2$(M+H)$^+$: m/z=432.3.

Example B60

N-[6-Chloro-2,4,8,22-tetraazatetracyclo[14.3.1.1(3, 7).1(9,13)]docosa-1(20), 3(22),4,6,9(21),10,12,16, 18-nonaen-12-yl]cyclopentanecarboxamide trifluoroacetate

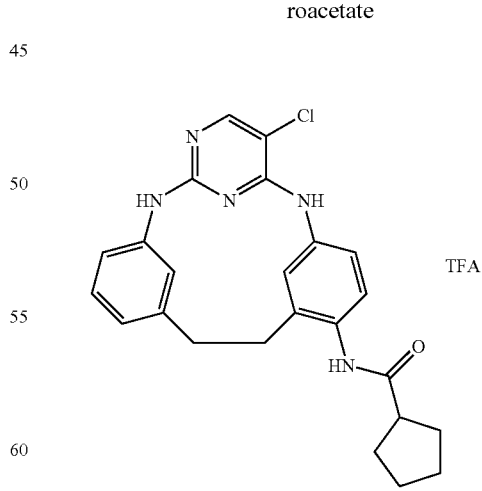

The desired compound was prepared according to the procedure of Example B26, using 6-chloro-2,4,8,22-tetraazatetracyclo[14.3.1.1(3,7).1(9,13)]docosa-1(20),3(22),4,6,9(21), 10,12,16,18-nonaen-12-amine dihydrochloride and cyclopentanecarbonyl chloride as the starting materials in 22% yield. LCMS for $C_{24}H_{25}ClN_5O$ (M+H)$^+$: m/z=434.3.

Example B61

N-[6-Chloro-2,4,8,22-tetraazatetracyclo[14.3.1.1(3,7).1(9,13)]docosa-1(20), 3(22),4,6,9(21),10,12,16,18-nonaen-12-yl]-2-methylbutanamide trifluoroacetate

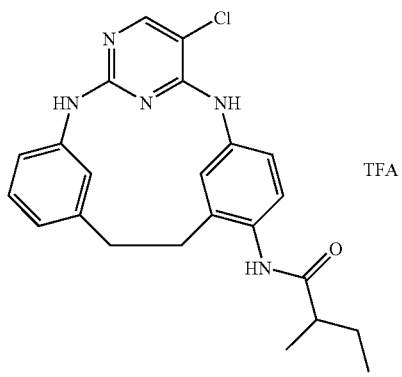 [SMILES: "TFA" ; CCC(C)C(=O)Nc1ccc2cc1CCc1cccc(c1)Nc1ncc(Cl)c(n1)N2]

The desired compound was prepared according to the procedure of Example B26, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and DL-2-methylbutrylchloride as the starting materials in 27% yield. LCMS for $C_{23}H_{25}ClN_5O$ (M+H)$^+$: m/z=422.3. $^1$H NMR (400 MHz, DMSO-d$_6$): δ 9.37 (s, 1H), 9.29 (s, 1H), 9.22 (s, 1H), 8.10 (s, 1H), 8.01 (s, 1H), 7.75 (s, 1H), 7.19 (d, 1H), 7.05 (m, 2H), 6.86 (d, 1H), 6.75 (d, 1H), 2.82 (dd, 4H), 2.16 (s, 1H), 1.61 (m, 1H), 1.40 (m, 1H), 1.12 (d, 3H), 0.91 (t, 3H).

Example B62

N-[6-Chloro-2,4,8,22-tetraazatetracyclo[14.3.1.1(3,7).1(9,13)]docosa-1(20), 3(22),4,6,9(21),10,12,16,18-nonaen-12-yl]thiophene-3-carboxamide trifluoroacetate

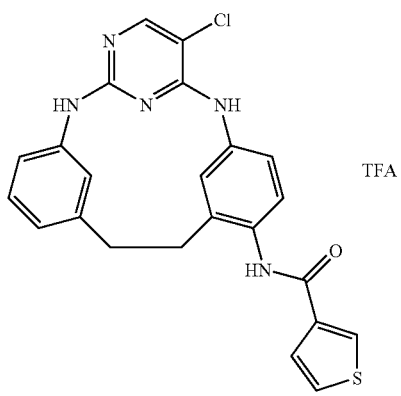 [SMILES: "TFA" ; O=C(Nc1ccc2cc1CCc1cccc(c1)Nc1ncc(Cl)c(n1)N2)c1ccsc1]

The desired compound was prepared according to the procedure of Example B26, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and thiophene-3-carbonyl chloride as the starting materials in 21% yield. LCMS for $C_{23}H_{19}ClN_5OS$ (M+H)$^+$: m/z=448.3.

Example B63

N-[6-Chloro-2,4,8,22-tetraazatetracyclo[14.3.1.1(3,7).1(9,13)]docosa-1(20), 3(22),4,6,9(21),10,12,16,18-nonaen-12-yl]cyclohexanecarboxamide trifluoroacetate

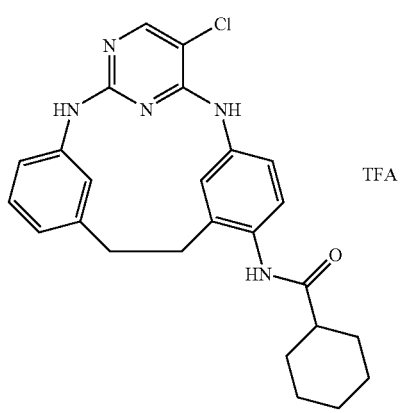 [SMILES: "TFA" ; O=C(Nc1ccc2cc1CCc1cccc(c1)Nc1ncc(Cl)c(n1)N2)C1CCCCC1]

The desired compound was prepared according to the procedure of Example B26, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and cyclohexanecarbonyl chloride as the starting materials in 20% yield. LCMS for $C_{25}H_{27}ClN_5O$ (M+H)$^+$: m/z=448.3.

Example B64

N-[6-Chloro-2,4,8,22-tetraazatetracyclo[14.3.1.1(3,7).1(9,13)]docosa-1(20), 3(22),4,6,9(21),10,12,16,18-nonaen-12-yl]-4-cyanobenzamide trifluoroacetate The desired compound was prepared according to the procedure of Example B26, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 4-cyanobenzoyl chloride as the starting materials in 7% yield. LCMS for $C_{26}H_{20}ClN_6O$ (M+H)$^+$: m/z=467.3.

Example B65

N-[6-Chloro-2,4,8,22-tetraazatetracyclo[14.3.1.1(3,7).1(9,13)]docosa-1(20), 3(22),4,6,9(21),10,12,16,18-nonaen-12-yl]-3-cyanobenzamide trifluoroacetate

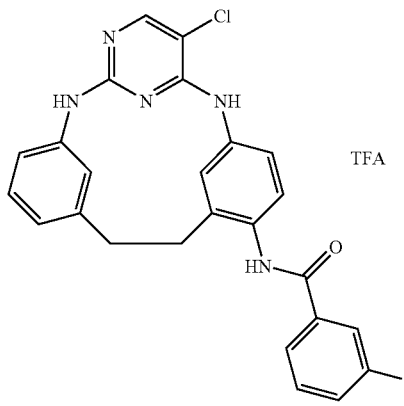

The desired compound was prepared according to the procedure of Example B26 7, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 3-cyanobenzoyl chloride as the starting materials in 8% yield. LCMS for $C_{26}H_{20}ClN_6O$ (M+H)$^+$: m/z=467.4.

Example B66

N-[6-Chloro-2,4,8,22-tetraazatetracyclo[14.3.1.1(3,7).1(9,13)]docosa-1(20), 3(22),4,6,9(21),10,12,16,18-nonaen-12-yl]-3-methoxybenzamide trifluoroacetate

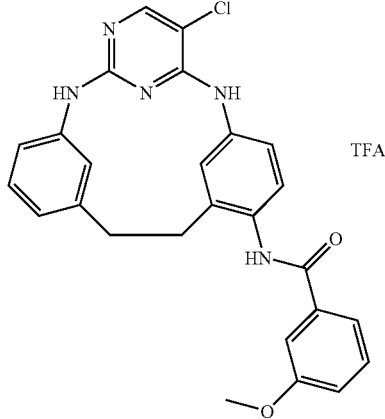 [SMILES: COc1cccc(C(=O)Nc2ccc3cc2CCc2cccc(c2)Nc2ncc(Cl)c(n2)N3)c1]

The desired compound was prepared according to the procedure of Example B26, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 3-methoxybenzoyl chloride as the starting materials in 14% yield. LCMS for $C_{26}H_{23}ClN_5O_2$(M+H)$^+$: m/z=472.2.

Example B67

N-[6-Chloro-2,4,8,22-tetraazatetracyclo[14.3.1.1(3,7).1(9,13)]docosa-1(20), 3(22),4,6,9(21),10,12,16,18-nonaen-12-yl]-4-methoxybenzamide trifluoroacetate

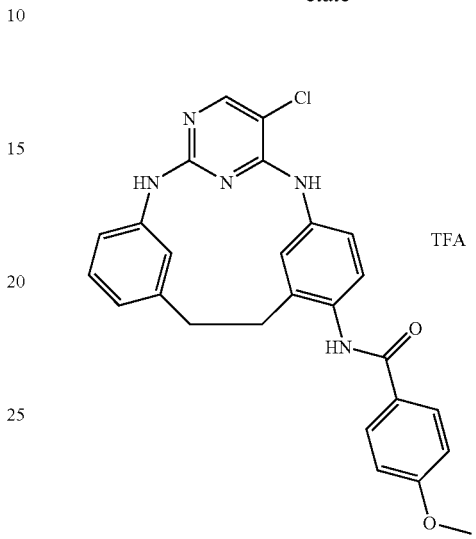

The desired compound was prepared according to the procedure of Example B26, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 4-methoxybenzoyl chloride as the starting materials in 10% yield. LCMS for $C_{26}H_{23}ClN_5O_2$(M+H)$^+$: m/z=472.3.

Example B68

N-[6-Chloro-2,4,8,22-tetraazatetracyclo[14.3.1.1(3,7).1(9,13)]docosa-1(20), 3(22),4,6,9(21),10,12,16,18-nonaen-12-yl]-5-methylisoxazole-3-carboxamide trifluoroacetate

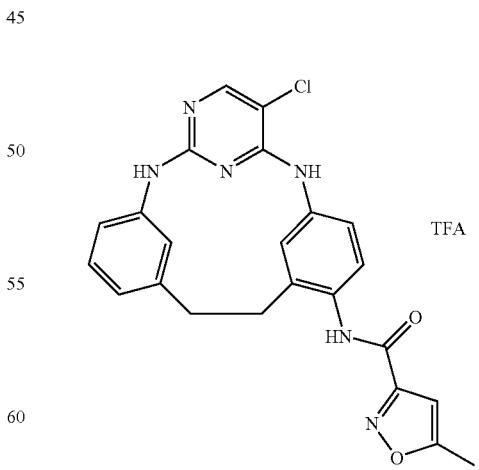

The desired compound was prepared according to the procedure of Example B26, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 5-methylisoxazole-3-carbonyl chloride as the starting materials in 21% yield. LCMS for $C_{23}H_{20}ClN_6O_2(M+H)^+$: m/z=447.0.

Example B69

6-Chloro-N-[6-chloro-2,4,8,22-tetraazatetracyclo [14.3.1.1(3,7).1(9,13)]docosa-1(20),3(22),4,6,9(21), 10,12,16,18-nonaen-12-yl]nicotinamide bis(trifluoroacetate)

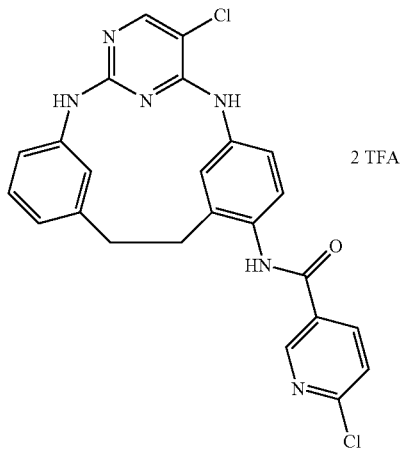 [SMILES: O=C(Nc1ccc2cc1CCc1cccc(c1)Nc1ncc(Cl)c(n1)N2)c1ccc(Cl)nc1 ; "2 TFA"]

The desired compound was prepared according to the procedure of Example B26, using 6-chloro-2,4,8,22-tetraazatetracyclo[14.3.1.1(3,7).1(9,13)]docosa-1(20),3(22),4,6,9(21), 10,12,16,18-nonaen-12-amine dihydrochloride and 6-chloronicotinoyl chloride as the starting materials in 19% yield. LCMS for $C_{24}H_{19}Cl_2N_6O$ $(M+H)^+$: m/z=476.9, 478.9.

Example B70

2-Chloro-N-[6-chloro-2,4,8,22-tetraazatetracyclo [14.3.1.1(3,7).1(9,13)]docosa-1(20),3(22),4,6,9(21), 10,12,16,18-nonaen-12-yl]nicotinamide bis(trifluoroacetate)

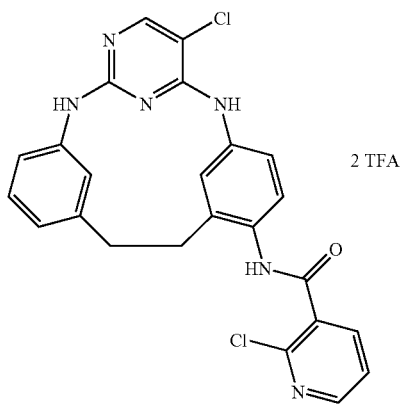 [SMILES: O=C(Nc1ccc2cc1CCc1cccc(c1)Nc1ncc(Cl)c(n1)N2)c1cccnc1Cl ; "2 TFA"]

The desired compound was prepared according to the procedure of Example B26, using 6-chloro-2,4,8,22-tetraazatetracyclo[14.3.1.1(3,7).1(9,13)]docosa-1(20),3(22),4,6,9(21), 10,12,16,18-nonaen-12-amine dihydrochloride and 2-chloronicotinoyl chloride as the starting materials in 12% yield. LCMS for $C_{24}H_{19}Cl_2N_6O$ $(M+H)^+$: m/z=477.2, 479.2.

Example B71

N-[6-Chloro-2,4,8,22-tetraazatetracyclo[14.3.1.1(3, 7).1(9,13)]docosa-1(20), 3(22),4,6,9(21),10,12,16, 18-nonaen-12-yl]-1,3-benzodioxole-5-carboxamide trifluoroacetate

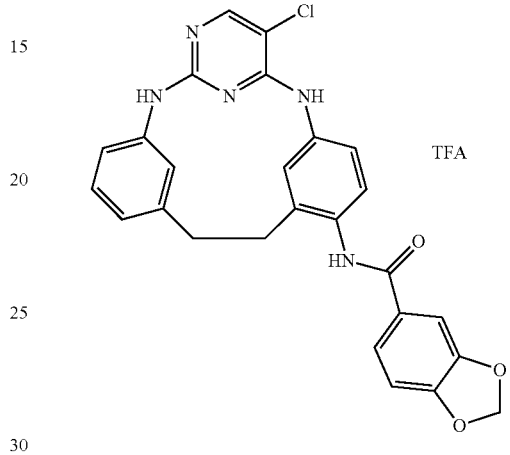

The desired compound was prepared according to the procedure of Example B26, using 6-chloro-2,4,8,22-tetraazatetracyclo[14.3.1.1(3,7).1(9,13)]docosa-1(20),3(22),4,6,9(21), 10,12,16,18-nonaen-12-amine dihydrochloride and 1,3-benzodioxole-5-carbonyl chloride as the starting materials in 7% yield. LCMS for $C_{26}H_{21}ClN_5O_3(M+H)^+$: m/z=486.2.

Example B72

N-[6-Chloro-2,4,8,22-tetraazatetracyclo[14.3.1.1(3, 7).1(9,13)]docosa-1(20), 3(22),4,6,9(21),10,12,16, 18-nonaen-12-yl]quinoxaline-2-carboxamide bis (trifluoroacetate)

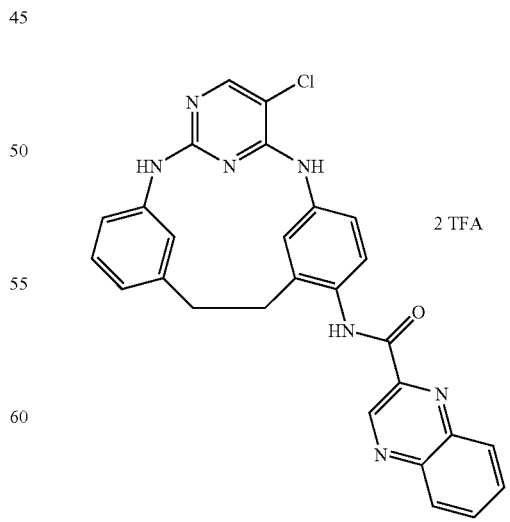

The desired compound was prepared according to the procedure of Example B26, using 6-chloro-2,4,8,22-tetraazatetracyclo[14.3.1.1(3,7).1(9,13)]docosa-1(20),3(22),4,6,9(21), 10,12,16,18-nonaen-12-amine dihydrochloride and quinoxaline-2-carbonyl chloride as the starting materials in 14% yield. LCMS for $C_{27}H_{21}ClN_7O$ (M+H)$^+$: m/z=494.3.

Example B73

4-tert-Butyl-N-[6-chloro-2,4,8,22-tetraazatetracyclo [14.3.1.1(3,7).1(9,13)]docosa-1(20),3(22),4,6,9(21), 10,12,16,18-nonaen-12-yl]benzamide trifluoroacetate

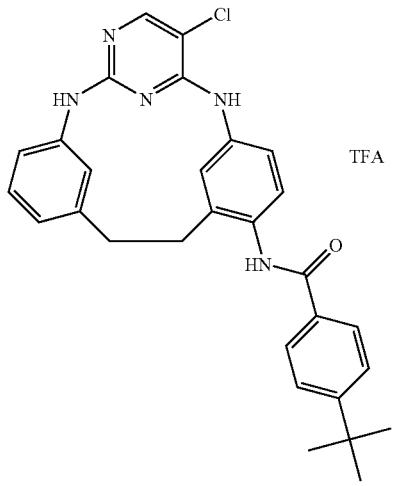 [SMILES: "TFA" ; CC(C)(C)c1ccc(C(=O)Nc2ccc3cc2CCc2cccc(c2)Nc2ncc(Cl)c(n2)N3)cc1]

The desired compound was prepared according to the procedure of Example B26, using 6-chloro-2,4,8,22-tetraazatetracyclo[14.3.1.1(3,7).1(9,13)]docosa-1(20),3(22),4,6,9(21), 10,12,16,18-nonaen-12-amine dihydrochloride and 4-(1,1-dimethylethyl)-benzoyl chloride as the starting materials in 30% yield. LCMS for $C_{29}H_{29}ClN_5O$ (M+H)$^+$: m/z=498.4.

Example B74

N-[6-Chloro-2,4,8,22-tetraazatetracyclo[14.3.1.1(3, 7).1(9,13)]docosa-1(20), 3(22),4,6,9(21),10,12,16, 18-nonaen-12-yl]-1,3-benzothiazole-2-carboxamide trifluoroacetate

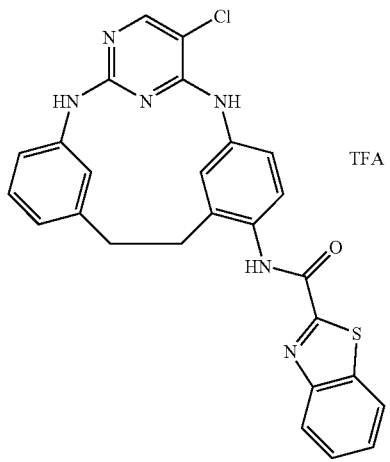 [SMILES: "TFA" ; O=C(Nc1ccc2cc1CCc1cccc(c1)Nc1ncc(Cl)c(n1)N2)c1nc2ccccc2s1]

The desired compound was prepared according to the procedure of Example B26, using 6-chloro-2,4,8,22-tetraazatetracyclo[14.3.1.1(3,7).1(9,13)]docosa-1(20),3(22),4,6,9(21), 10,12,16,18-nonaen-12-amine dihydrochloride and 1,3-benzothiazole-2-carbonyl chloride as the starting materials in 20% yield. LCMS for $C_{26}H_{20}ClN_6OS$ (M+H)$^+$: m/z=499.2.

Example B75

N-[6-Chloro-2,4,8,22-tetraazatetracyclo[14.3.1.1(3, 7).1(9,13)]docosa-1(20), 3(22),4,6,9(21),10,12,16, 18-nonaen-12-yl]-4-(trifluoromethyl)benzamide trifluoroacetate

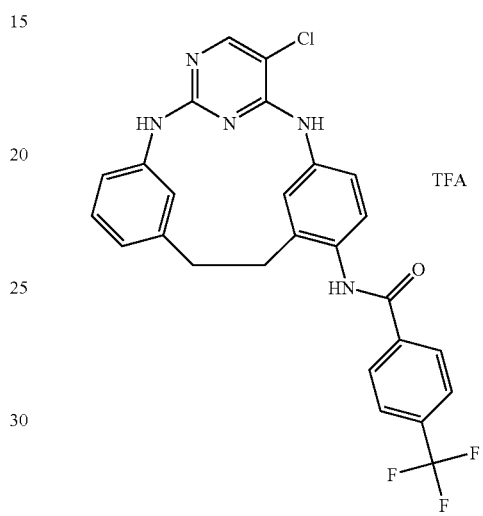

The desired compound was prepared according to the procedure of Example B26, using 6-chloro-2,4,8,22-tetraazatetracyclo[14.3.1.1(3,7).1(9,13)]docosa-1(20),3(22),4,6,9(21), 10,12,16,18-nonaen-12-amine dihydrochloride and 4-(trifluoromethyl)benzoyl chloride as the starting materials in 22% yield. LCMS for $C_{26}H_{20}ClF_3N_5O$ (M+H)$^+$: m/z=510.0.

Example B76

N-[6-Chloro-2,4,8,22-tetraazatetracyclo[14.3.1.1(3, 7).1(9,13)]docosa-1(20), 3(22),4,6,9(21),10,12,16, 18-nonaen-12-yl]-3-(trifluoromethyl)benzamide trifluoroacetate

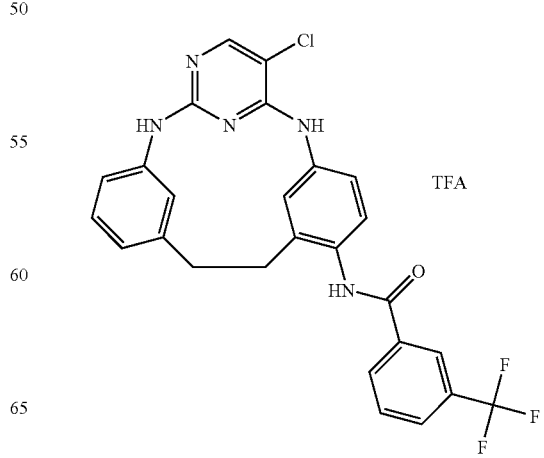

The desired compound was prepared according to the procedure of Example B26, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 3-(trifluoromethyl)benzoyl chloride as the starting materials in 24% yield. LCMS for $C_{26}H_{20}ClF_3N_5O$ (M+H)$^+$: m/z=510.0.

Example B77

N-[6-Chloro-2,4,8,22-tetraazatetracyclo[14.3.1.1(3,7).1(9,13)]docosa-1(20), 3(22),4,6,9(21),10,12,16,18-nonaen-12-yl]-6-(trifluoromethyl)nicotinamide bis(trifluoroacetate)

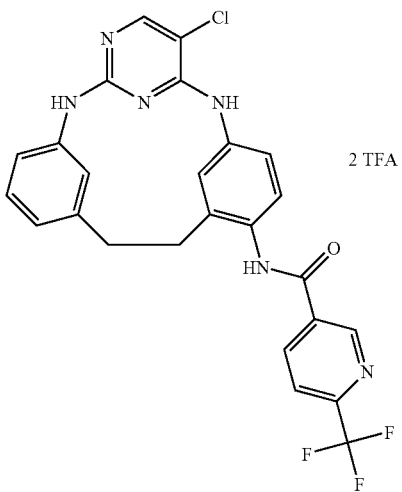 [SMILES: O=C(Nc1ccc2cc1CCc1cccc(c1)Nc1ncc(Cl)c(n1)N2)c1ccc(C(F)(F)F)nc1 ; "2 TFA"]

The desired compound was prepared according to the procedure of Example B26, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 6-(trifluoromethyl)nicotinoyl chloride as the starting materials in 18% yield. LCMS for $C_{25}H_{19}ClF_3N_6O$ (M+H)$^+$: m/z=511.0.

Example B78

N-[6-Chloro-2,4,8,22-tetraazatetracyclo[14.3.1.1(3,7).1(9,13)]docosa-1(20),3(22),4,6,9(21),10,12,16,18-nonaen-12-yl]-4-methyl-1,3-oxazole-5-carboxamide trifluoroacetate

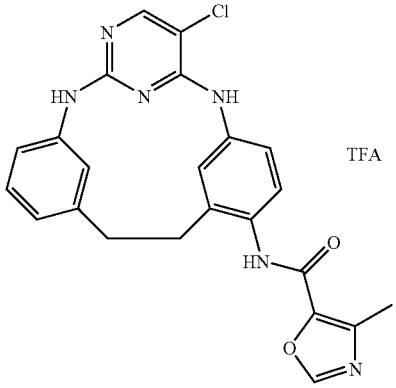 [SMILES: "TFA" ; Cc1ncoc1C(=O)Nc1ccc2cc1CCc1cccc(c1)Nc1ncc(Cl)c(n1)N2]

The desired compound was prepared according to the procedure of Example B26, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 4-methyl-1,3-oxazole-5-carbonyl chloride as the starting materials in 24% yield. LCMS for $C_{23}H_{20}ClN_6O_2$(M+H)$^+$: m/z=447.0.

Example B79

N-[6-Chloro-2,4,8,22-tetraazatetracyclo[14.3.1.1(3,7).1(9,13)]docosa-1(20), 3(22),4,6,9(21),10,12,16,18-nonaen-12-yl]-1-benzofuran-5-carboxamide trifluoroacetate

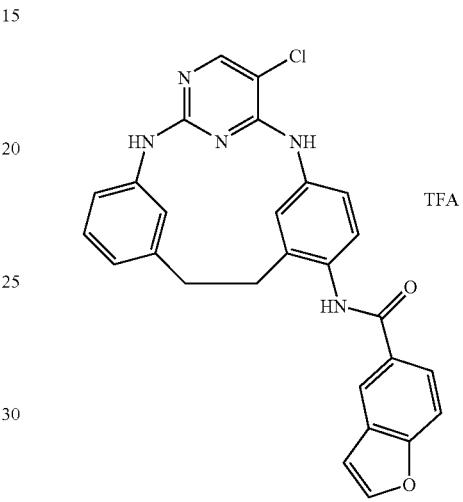

The desired compound was prepared according to the procedure of Example B26, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 1-benzofuran-5-carbonyl chloride as the starting materials in 13% yield. LCMS for $C_{27}H_{21}ClN_5O_2$(M+H)$^+$: m/z=482.2.

Example B80

N-[6-Chloro-2,4,8,22-tetraazatetracyclo[14.3.1.1(3,7).1(9,13)]docosa-1(20),3(22),4,6,9(21),10,12,16,18-nonaen-12-yl]pyrazolo[1,5-a]pyridine-3-carboxamide bis(trifluoroacetate)

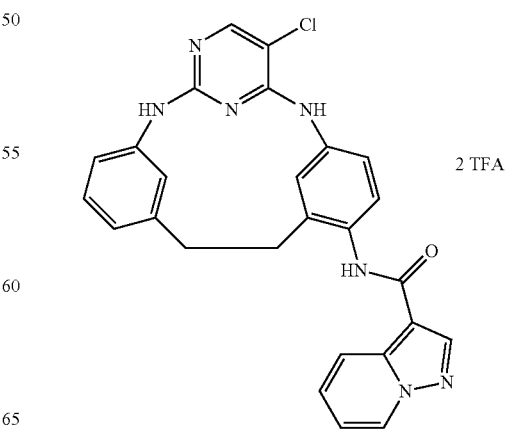

The desired compound was prepared according to the procedure of Example B26, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and pyrazolo[1,5-a]pyridine-3-carbonyl chloride as the starting materials in 17% yield. LCMS for $C_{26}H_{21}ClN_7O$ (M+H)$^+$: m/z=482.0.

Example B81

N-[6-Chloro-2,4,8,22-tetraazatetracyclo[14.3.1.1(3,7).1(9,13)]docosa-1(20), 3(22),4,6,9(21),10,12,16,18-nonaen-12-yl]pyrrolidine-1-carboxamide trifluoroacetate

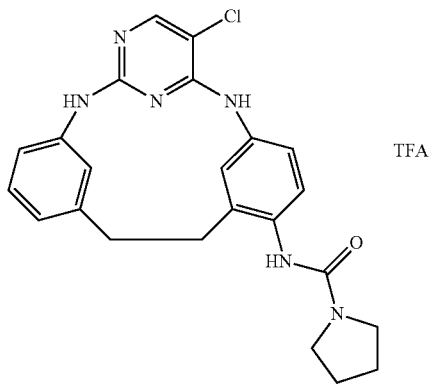 [SMILES: O=C(Nc1ccc2cc1CCc1cccc(c1)Nc1ncc(Cl)c(n1)N2)N1CCCC1]

The desired compound was prepared according to the procedure of Example B26, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 1-pyrrolidinecarbonyl chloride as the starting materials in 20% yield. LCMS for $C_{23}H_{24}ClN_6O$ (M+H)$^+$: m/z=435.0.

Example B82

N-[6-Chloro-2,4,8,22-tetraazatetracyclo[14.3.1.1(3,7).1(9,13)]docosa-1(20), 3(22),4,6,9(21),10,12,16,18-nonaen-12-yl]-4-(dimethylamino)benzamide bis(trifluoroacetate)

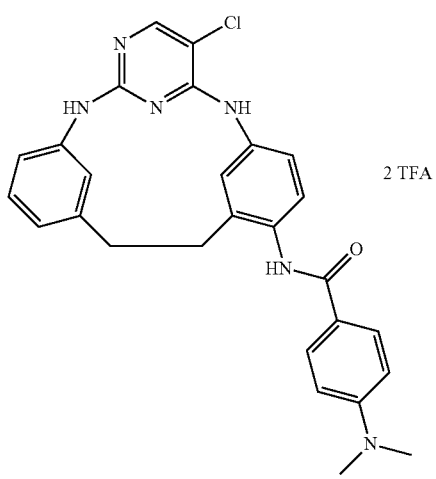 [SMILES: CN(C)c1ccc(C(=O)Nc2ccc3cc2CCc2cccc(c2)Nc2ncc(Cl)c(n2)N3)cc1 ; "2 TFA"]

The desired compound was prepared according to the procedure of Example B26, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 4-(dimethylamino)benzoyl chloride as the starting materials in 8% yield. LCMS for $C_{27}H_{26}ClN_6O$ (M+H)$^+$: m/z=485.0.

Example B83

N-[6-Chloro-2,4,8,22-tetraazatetracyclo[14.3.1.1(3,7).1(9,13)]docosa-1(20), 3(22),4,6,9(21),10,12,16,18-nonaen-12-yl]-N'-phenylurea trifluoroacetate

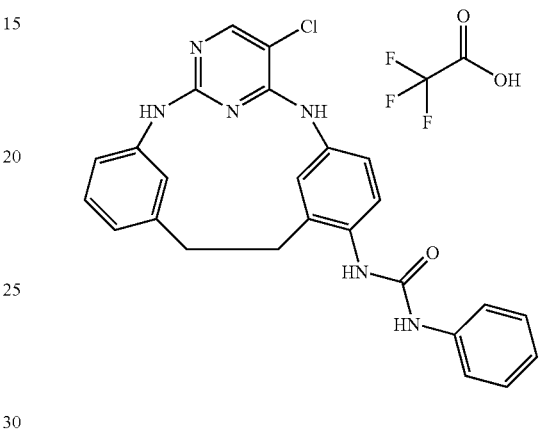

A solution of 6-chloro-2,4,8,22-tetraazatetracyclo[14.3.1.1(3,7).1(9,13)]docosa-1(20),3(22),4,6,9(21),10,12,16,18-nonaen-12-amine dihydrochloride (20 mg, 0.049 mmol) in DCM (0.3 mL) was treated with triethylamine (20.4 μL, 0.146 mmol) and phenyl isocyanate (7.9 μL, 0.073 mmol). The reaction mixture was stirred at room temperature overnight. The solvent was evaporated and the crude residue was dissolved in a mixture of acetonitrile/methanol and purified by preparative LCMS to give the desired product (6.0 mg, 21%). LCMS calculated for $C_{25}H_{22}ClN_6O$ (M+H)$^+$: m/z=457.3. $^1$H NMR (400 MHz, DMSO-d$_6$): δ 9.54 (s, 1H), 9.44 (s, 1H), 9.04 (s, 1H), 8.17 (s, 1H), 8.00 (d, 2H), 7.69 (m, 2H), 7.45 (t, 2H), 7.25 (t, 2H), 7.09 (t, 1H), 7.00 (d, 1H), 6.95 (t, 1H), 6.84 (m, 2H), 2.92 (m, 4H).

Example B84

N-(2-Chlorophenyl)-N'-[6-chloro-2,4,8,22-tetraazatetracyclo[14.3.1.1(3,7).1(9,13)]docosa-1(20),3(22),4,6,9(21),10,12,16,18-nonaen-12-yl]urea trifluoroacetate

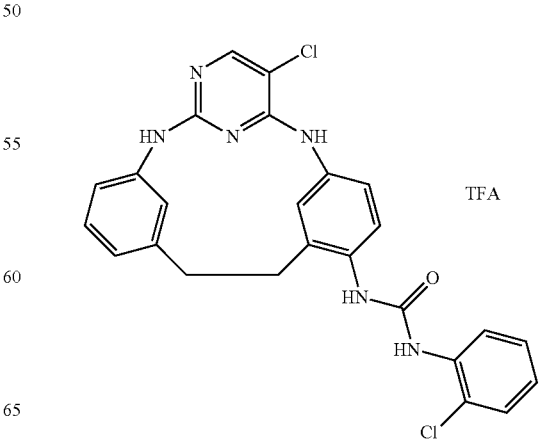

The desired compound was prepared according to the procedure of Example B83, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 1-chloro-2-isocyanatobenzene as the starting materials in 11% yield. LCMS for $C_{25}H_{21}Cl_2N_6O$ (M+H)$^+$: m/z=491.2.

Example B85

N-(3-Chlorophenyl)-N'-[6-chloro-2,4,8,22-tetraazatetracyclo[14.3.1.1(3,7).1(9,13)]docosa-1(20),3(22),4,6,9(21),10,12,16,18-nonaen-12-yl]urea trifluoroacetate

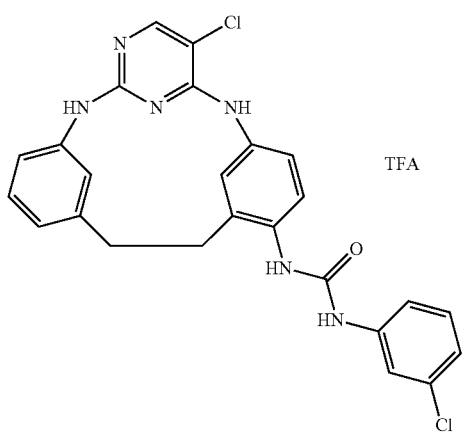 [SMILES: O=C(Nc1cccc(Cl)c1)Nc1ccc2cc1CCc1cccc(c1)Nc1ncc(Cl)c(n1)N2]

The desired compound was prepared according to the procedure of Example B83, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 1-chloro-3-isocyanatobenzene as the starting materials in 22% yield. LCMS for $C_{25}H_{21}Cl_2N_6O$ (M+H)$^+$: m/z=491.0.

Example B86

N-(4-Chlorophenyl)-N'-[6-chloro-2,4,8,22-tetraazatetracyclo[14.3.1.1(3,7).1(9,13)]docosa-1(20),3(22),4,6,9(21),10,12,16,18-nonaen-12-yl]urea trifluoroacetate

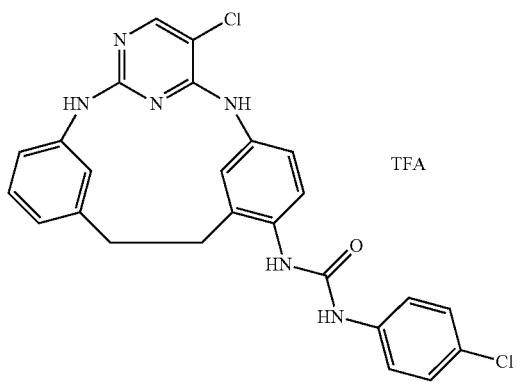 [SMILES: O=C(Nc1ccc(Cl)cc1)Nc1ccc2cc1CCc1cccc(c1)Nc1ncc(Cl)c(n1)N2]

The desired compound was prepared according to the procedure of Example B83, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 1-chloro-4-isocyanatobenzene as the starting materials in 29% yield. LCMS for $C_{25}H_{21}Cl_2N_6O$ (M+H)$^+$: m/z=491.0.

Example B87

N-(tert-Butyl)-N'-[6-chloro-2,4,8,22-tetraazatetracyclo[14.3.1.1(3,7).1(9,13)]docosa-1(20),3(22),4,6,9(21),10,12,16,18-nonaen-12-yl]urea trifluoroacetate

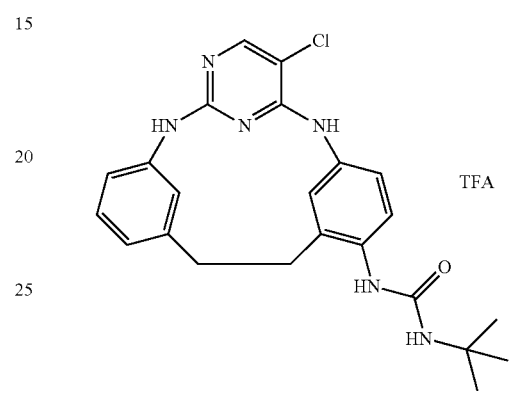

The desired compound was prepared according to the procedure of Example B83, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 2-methyl-2-isocyanatopropane as the starting materials in 7% yield. LCMS for $C_{23}H_{26}ClN_6O$ (M+H)$^+$: m/z=437.3.

Example B88

N-[6-Chloro-2,4,8,22-tetraazatetracyclo[14.3.1.1(3,7).1(9,13)]docosa-1(20), 3(22),4,6,9(21),10,12,16,18-nonaen-12-yl]-N'-cyclopentylurea trifluoroacetate

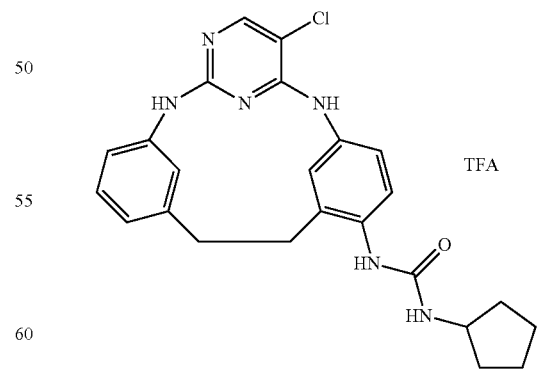

The desired compound was prepared according to the procedure of Example B83, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and isocyanatocyclopentane as the starting materials in 31% yield. LCMS for $C_{24}H_{26}ClN_6O$ (M+H)$^+$: m/z=449.2.

Example B89

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-3-thienylurea trifluoroacetate

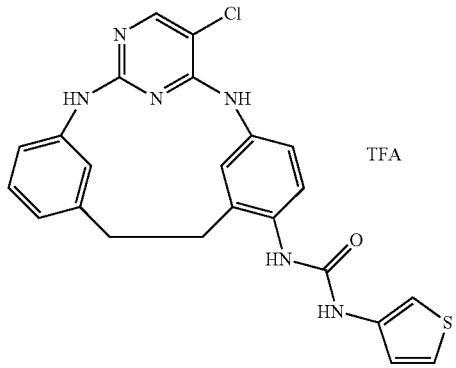 [SMILES: O=C(Nc1ccsc1)Nc1ccc2cc1CCc1cccc(c1)Nc1ncc(Cl)c(n1)N2]

The desired compound was prepared according to the procedure of Example B83, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 3-isocyanatothiophene as the starting materials in 7% yield. LCMS for $C_{23}H_{20}ClN_6OS$ (M+H)$^+$: m/z=463.4.

Example B90

N-[6-Chloro-2,4,8,22-tetraazatetracyclo[14.3.1.1(3,7).1(9,13)]docosa-1(20), 3(22),4,6,9(21),10,12,16,18-nonaen-12-yl]-N'-(3-methylphenyl)urea trifluoroacetate

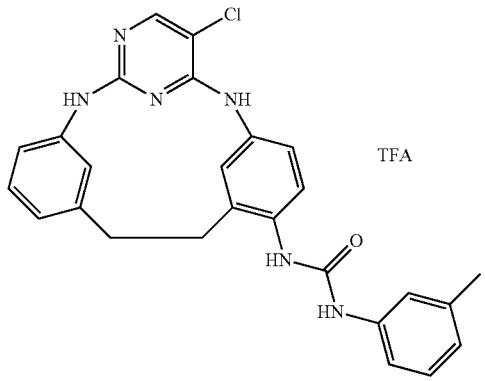 [SMILES: Cc1cccc(NC(=O)Nc2ccc3cc2CCc2cccc(c2)Nc2ncc(Cl)c(n2)N3)c1]

The desired compound was prepared according to the procedure of Example B83, using 6-chloro-2,4,8,22-tetraazatetracyclo[14.3.1.1(3,7).1(9,13)]docosa-1(20),3(22),4,6,9(21), 10,12,16,18-nonaen-12-amine dihydrochloride and 3-methyl-1-isocyanatobenzene as the starting materials in 17% yield. LCMS for $C_{26}H_{24}ClN_6O$ (M+H)$^+$: m/z=471.3.

Example B91

N-[6-Chloro-2,4,8,22-tetraazatetracyclo[14.3.1.1(3,7).1(9,13)]docosa-1(20), 3(22),4,6,9(21),10,12,16,18-nonaen-12-yl]-N'-(2-methylphenyl)urea trifluoroacetate

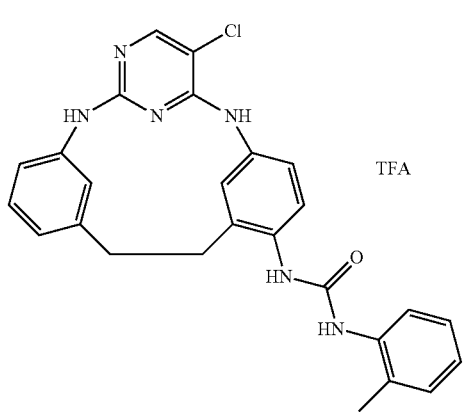 [SMILES: Cc1ccccc1NC(=O)Nc1ccc2cc1CCc1cccc(c1)Nc1ncc(Cl)c(n1)N2]

The desired compound was prepared according to the procedure of Example B83, using 6-chloro-2,4,8,22-tetraazatetracyclo[14.3.1.1(3,7).1(9,13)]docosa-1(20),3(22),4,6,9(21), 10,12,16,18-nonaen-12-amine dihydrochloride and 2-methyl-1-isocyanatobenzene as the starting materials in 14% yield. LCMS for $C_{26}H_{24}ClN_6O$ (M+H)$^+$: m/z=471.3.

Example B92

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-(4-methylphenyl)urea trifluoroacetate

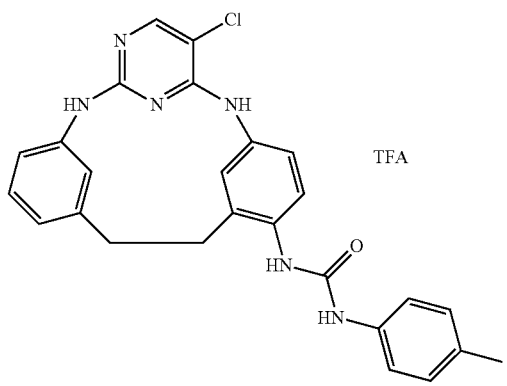 [SMILES: Cc1ccc(NC(=O)Nc2ccc3cc2CCc2cccc(c2)Nc2ncc(Cl)c(n2)N3)cc1]

The desired compound was prepared according to the procedure of Example B83, using 6-chloro-2,4,8,22-tetraazatetracyclo[14.3.1.1(3,7).1(9,13)]docosa-1(20),3(22),4,6,9(21), 10,12,16,18-nonaen-12-amine dihydrochloride and 4-methyl-1-isocyanatobenzene as the starting materials in 21% yield. LCMS for $C_{26}H_{24}ClN_6O$ (M+H)$^+$: m/z=471.3.

Example B93

N-benzyl-N'-[6-chloro-2,4,8,22-tetraazatetracyclo[14.3.1.1(3,7).1(9,13)]docosa-1(20),3(22),4,6,9(21),10,12,16,18-nonaen-12-yl]urea trifluoroacetate

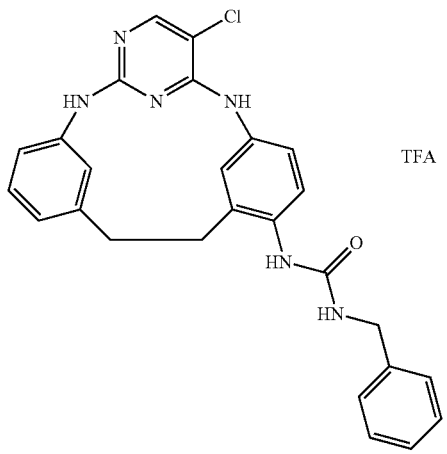 [SMILES: O=C(NCc1ccccc1)Nc1ccc2cc1CCc1cccc(c1)Nc1ncc(Cl)c(n1)N2]

The desired compound was prepared according to the procedure of Example B83 3, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and benzyl isocyanate as the starting materials in 17% yield. LCMS for $C_{26}H_{24}ClN_6O$ (M+H)$^+$: m/z=471.3.

Example B94

N-[6-Chloro-2,4,8,22-tetraazatetracyclo[14.3.1.1(3,7).1(9,13)]docosa-1(20), 3(22),4,6,9(21),10,12,16,18-nonaen-12-yl]-N'-(3,5-dimethylisoxazol-4-yl)urea trifluoroacetate

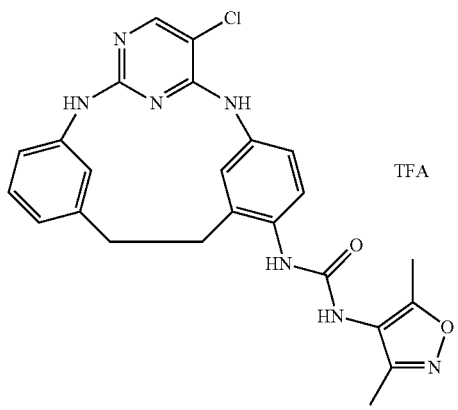 [SMILES: Cc1noc(C)c1NC(=O)Nc1ccc2cc1CCc1cccc(c1)Nc1ncc(Cl)c(n1)N2]

The desired compound was prepared according to the procedure of Example B83, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 4-isocyanato-3,5-dimethylisoxazole as the starting materials in 18% yield. LCMS for $C_{24}H_{23}ClN_7O_2$(M+H)$^+$: m/z=476.4.

Example B95

N-[6-Chloro-2,4,8,22-tetraazatetracyclo[14.3.1.1(3,7).1(9,13)]docosa-1(20), 3(22),4,6,9(21),10,12,16,18-nonaen-12-yl]-N'-(3-cyanophenyl)urea trifluoroacetate

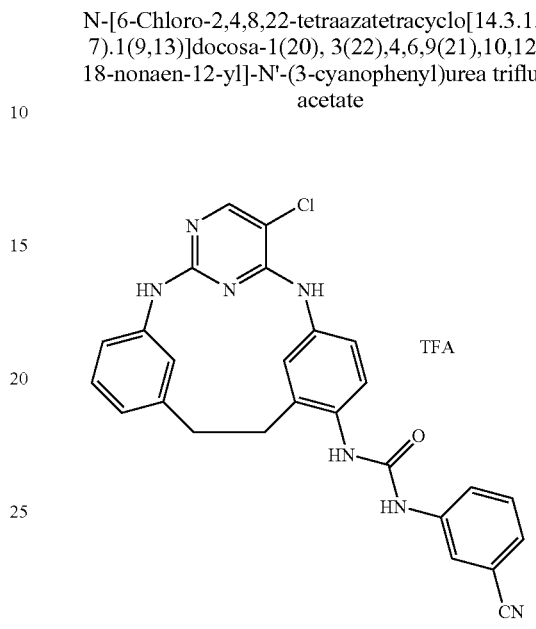

The desired compound was prepared according to the procedure of Example B83, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 3-isocyanatobenzonitrile as the starting materials in 20% yield. LCMS for $C_{26}H_{21}ClN_7O$ (M+H)$^+$: m/z=482.3.

Example B96

N-[6-Chloro-2,4,8,22-tetraazatetracyclo[14.3.1.1(3,7).1(9,13)]docosa-1(20), 3(22),4,6,9(21),10,12,16,18-nonaen-12-yl]-N'-(4-cyanophenyl)urea trifluoroacetate

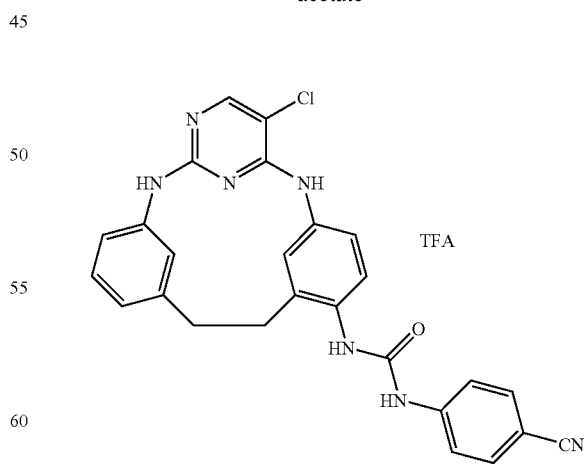

The desired compound was prepared according to the procedure of Example B83, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 4-isocyanatobenzonitrile as the starting materials in 19% yield. LCMS for $C_{26}H_{21}ClN_7O$ (M+H)$^+$: m/z=482.3.

Example B97

N-[6-Chloro-2,4,8,22-tetraazatetracyclo[14.3.1.1(3,7).1(9,13)]docosa-1(20), 3(22),4,6,9(21),10,12,16,18-nonaen-12-yl]-N'-(2-ethylphenyl)urea trifluoroacetate

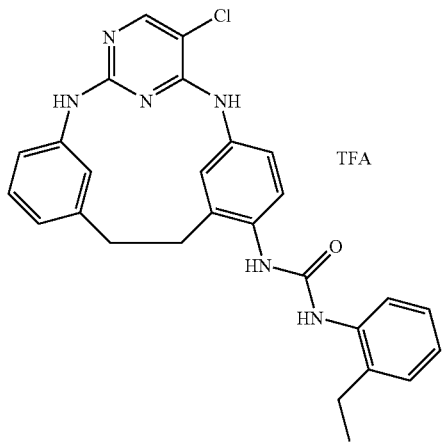 [SMILES: "TFA" ; CCc1ccccc1NC(=O)Nc1ccc2cc1CCc1cccc(c1)Nc1ncc(Cl)c(n1)N2]

The desired compound was prepared according to the procedure of Example B83, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 1-ethyl-2-isocyanatobenzene as the starting materials in 22% yield. LCMS for $C_{27}H_{26}ClN_6O$ (M+H)$^+$: m/z=485.3.

Example B98

N-[6-Chloro-2,4,8,22-tetraazatetracyclo[14.3.1.1(3,7).1(9,13)]docosa-1(20), 3(22),4,6,9(21),10,12,16,18-nonaen-12-yl]-N'-(4-ethylphenyl)urea trifluoroacetate

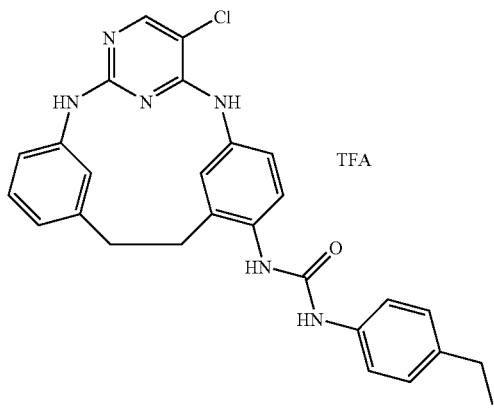 [SMILES: "TFA" ; CCc1ccc(NC(=O)Nc2ccc3cc2CCc2cccc(c2)Nc2ncc(Cl)c(n2)N3)cc1]

The desired compound was prepared according to the procedure of Example B83, using 6-chloro-2,4,8,22-tetraazatetracyclo[14.3.1.1(3,7).1(9,13)]docosa-1(20),3(22),4,6,9(21), 10,12,16,18-nonaen-12-amine dihydrochloride and 4-ethylphenyl isocyanate as the starting materials in 20% yield. LCMS for $C_{27}H_{26}ClN_6O$ (M+H)$^+$: m/z=485.3.

Example B99

N-[6-Chloro-2,4,8,22-tetraazatetracyclo[14.3.1.1(3,7).1(9,13)]docosa-1(20), 3(22),4,6,9(21),10,12,16,18-nonaen-12-yl]-N'-(3-ethylphenyl)urea trifluoroacetate

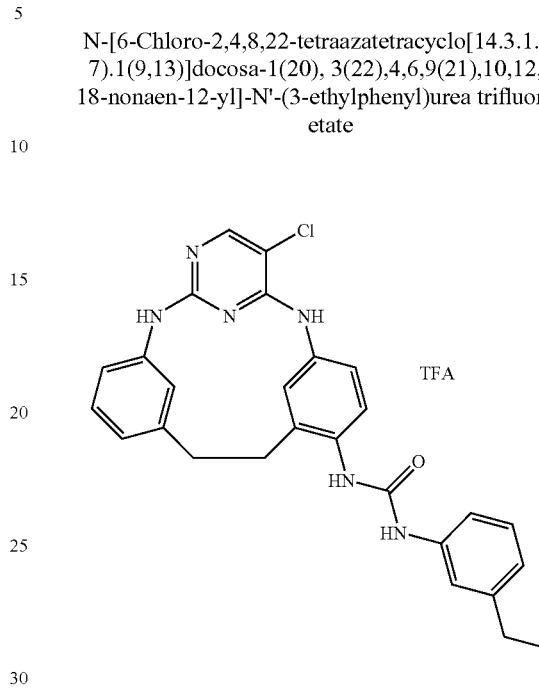

The desired compound was prepared according to the procedure of Example B83, using 6-chloro-2,4,8,22-tetraazatetracyclo[14.3.1.1(3,7).1(9,13)]docosa-1(20),3(22),4,6,9(21), 10,12,16,18-nonaen-12-amine dihydrochloride and 3-ethylphenyl isocyanate as the starting materials in 22% yield. LCMS for $C_{27}H_{26}ClN_6O$ (M+H)$^+$: m/z=485.3.

Example B100

N-[6-Chloro-2,4,8,22-tetraazatetracyclo[14.3.1.1(3,7).1(9,13)]docosa-1(20), 3(22),4,6,9(21),10,12,16,18-nonaen-12-yl]-N'-(3-methoxyphenyl)urea trifluoroacetate

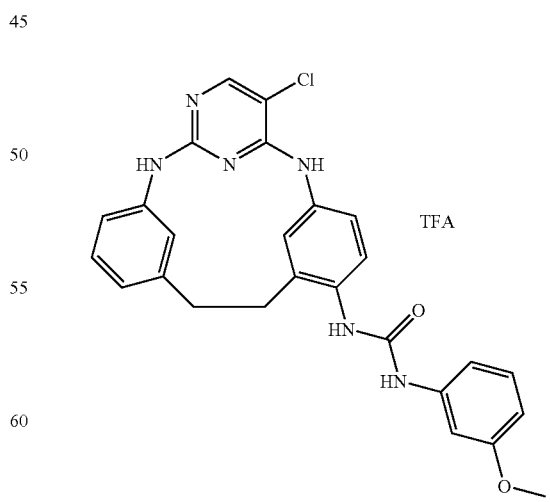

The desired compound was prepared according to the procedure of Example B83, using 6-chloro-2,4,8,22-tetraazatetracyclo[14.3.1.1(3,7).1(9,13)]docosa-1(20),3(22),4,6,9(21), 10,12,16,18-nonaen-12-amine dihydrochloride and 1-isocyanato-3-methoxybenzene as the starting materials in 17% yield. LCMS for $C_{26}H_{24}ClN_6O_2(M+H)^+$: m/z=487.3.

Example B101

N-[6-Chloro-2,4,8,22-tetraazatetracyclo[14.3.1.1(3,7).1(9,13)]docosa-1(20), 3(22),4,6,9(21),10,12,16,18-nonaen-12-yl]-N'-(4-methoxyphenyl)urea trifluoroacetate

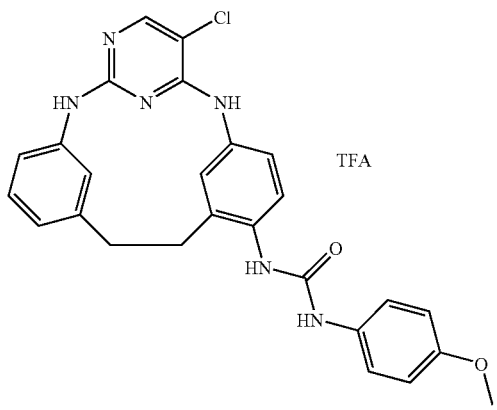 [SMILES: "TFA" ; COc1ccc(NC(=O)Nc2ccc3cc2CCc2cccc(c2)Nc2ncc(Cl)c(n2)N3)cc1]

The desired compound was prepared according to the procedure of Example B83 3, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 1-isocyanato-4-methoxybenzene as the starting materials in 18% yield. LCMS for $C_{26}H_{24}ClN_6O_2(M+H)^+$: m/z=487.3.

Example B102

N-[6-Chloro-2,4,8,22-tetraazatetracyclo[14.3.1.1(3,7).1(9,13)]docosa-1(20), 3(22),4,6,9(21),10,12,16,18-nonaen-12-yl]-N'-(2-methoxyphenyl)urea trifluoroacetate

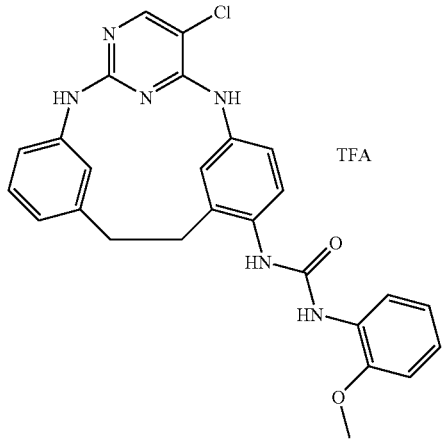 [SMILES: "TFA" ; COc1ccccc1NC(=O)Nc1ccc2cc1CCc1cccc(c1)Nc1ncc(Cl)c(n1)N2]

The desired compound was prepared according to the procedure of Example B83, using 6-chloro-2,4,8,22-tetraazatetracyclo[14.3.1.1(3,7).1(9,13)]docosa-1(20),3(22),4,6,9(21), 10,12,16,18-nonaen-12-amine dihydrochloride and 1-isocyanato-2-methoxybenzene as the starting materials in 19% yield. LCMS for $C_{26}H_{24}ClN_6O_2(M+H)^+$: m/z=487.0.

Example B103

N-[6-Chloro-2,4,8,22-tetraazatetracyclo[14.3.1.1(3,7).1(9,13)]docosa-1(20), 3(22),4,6,9(21),10,12,16,18-nonaen-12-yl]-N'-(2,3-dihydro-1H-inden-5-yl)urea trifluoroacetate

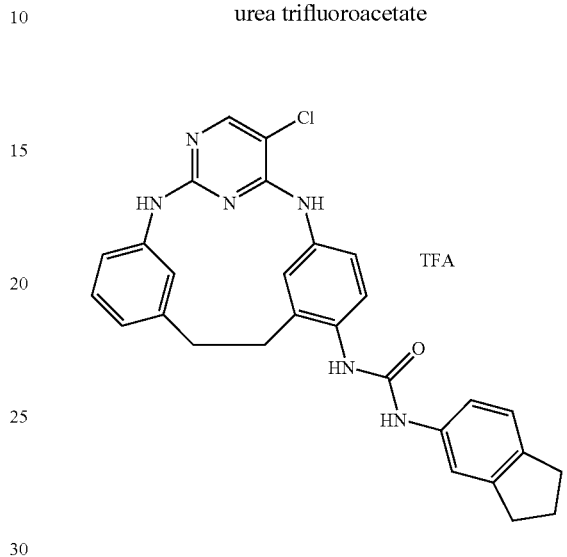

The desired compound was prepared according to the procedure of Example B83, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 5-isocyanatoindane as the starting materials in 16% yield. LCMS for $C_{28}H_{26}ClN_6O(M+H)^+$: m/z=497.1.

Example B104

N-[6-Chloro-2,4,8,22-tetraazatetracyclo[14.3.1.1(3,7).1(9,13)]docosa-1(20), 3(22),4,6,9(21),10,12,16,18-nonaen-12-yl]-N'-(2-isopropylphenyl)urea trifluoroacetate

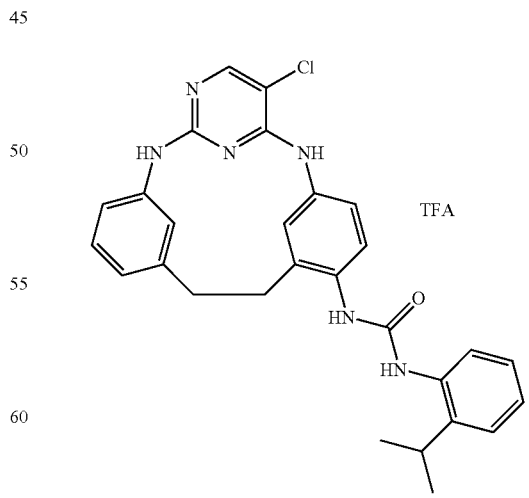

The desired compound was prepared according to the procedure of Example B83, using 6-chloro-2,4,8,22-tetraazatetracyclo[14.3.1.1(3,7).1(9,13)]docosa-1(20),3(22),4,6,9(21), 10,12,16,18-nonaen-12-amine dihydrochloride and 1-isocyanato-2-isopropylbenzene as the starting materials in 22% yield. LCMS for $C_{28}H_{28}ClN_6O$ (M+H)$^+$: m/z=499.1.

Example B105

N-[6-Chloro-2,4,8,22-tetraazatetracyclo[14.3.1.1(3,7).1(9,13)]docosa-1(20), 3(22),4,6,9(21),10,12,16,18-nonaen-12-yl]-N'-(2-propylphenyl)urea trifluoroacetate

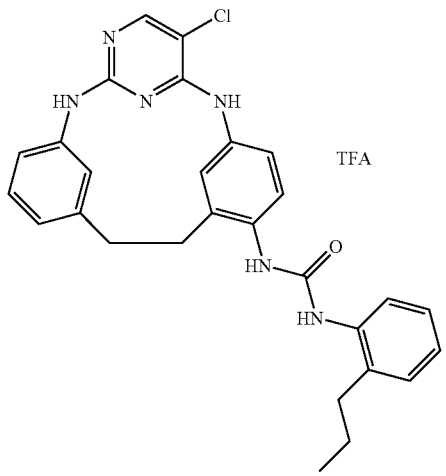 [SMILES: "TFA" ; CCCc1ccccc1NC(=O)Nc1ccc2cc1CCc1cccc(c1)Nc1ncc(Cl)c(n1)N2]

The desired compound was prepared according to the procedure of Example B83 I, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 1-isocyanato-2-propylbenzene as the starting materials in 27% yield. LCMS for $C_{28}H_{28}ClN_6O$ (M+H)$^+$: m/z=499.0.

Example B106

N-[6-Chloro-2,4,8,22-tetraazatetracyclo[14.3.1.1(3,7).1(9,13)]docosa-1(20), 3(22),4,6,9(21),10,12,16,18-nonaen-12-yl]-N'-(2-ethoxyphenyl)urea trifluoroacetate

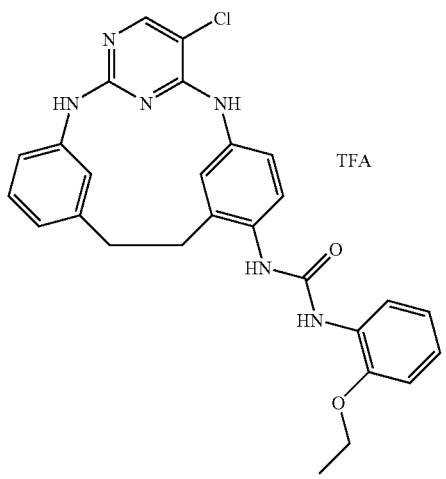 [SMILES: "TFA" ; CCOc1ccccc1NC(=O)Nc1ccc2cc1CCc1cccc(c1)Nc1ncc(Cl)c(n1)N2]

The desired compound was prepared according to the procedure of Example B83, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 1-ethoxy-2-isocyanatobenzene as the starting materials in 22% yield. LCMS for $C_{27}H_{26}ClN_6O_2$(M+H)$^+$: m/z=501.0.

Example B107

N-[6-Chloro-2,4,8,22-tetraazatetracyclo[14.3.1.1(3,7).1(9,13)]docosa-1(20), 3(22),4,6,9(21),10,12,16,18-nonaen-12-yl]-N'-[2-(methylthio)phenyl]urea trifluoroacetate

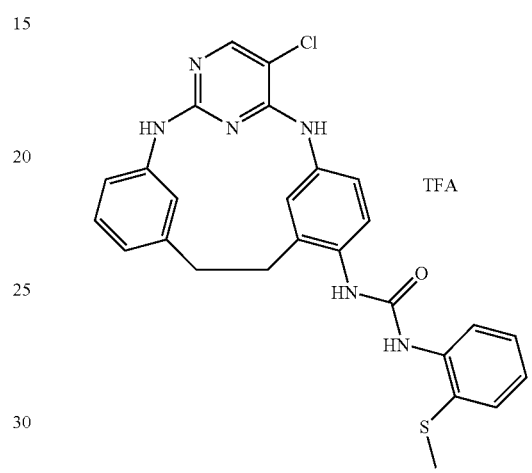

The desired compound was prepared according to the procedure of Example B83, using 6-chloro-2,4,8,22-tetraazatetracyclo[14.3.1.1(3,7).1(9,13)]docosa-1(20),3(22),4,6,9(21), 10,12,16,18-nonaen-12-amine dihydrochloride and 1-isocyanato-2-(methylthio)benzene as the starting materials in 20% yield. LCMS for $C_{26}H_{24}ClN_6OS$ (M+H)$^+$: m/z=503.0.

Example B108

N-[2-(Chloromethyl)phenyl]-N'-[6-chloro-2,4,8,22-tetraazatetracyclo[14.3.1.1(3,7).1(9,13)]docosa-1(20),3(22),4,6,9(21),10,12,16,18-nonaen-12-yl]urea trifluoroacetate

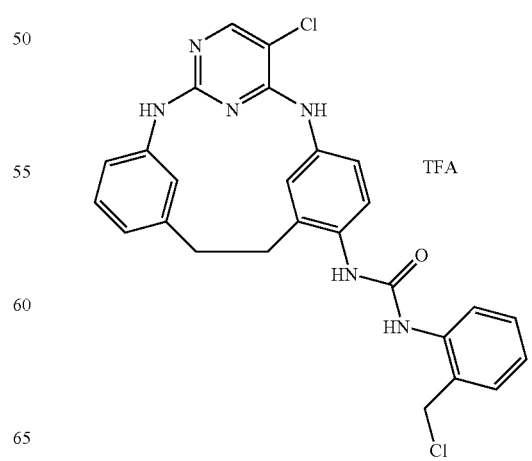

The desired compound was prepared according to the procedure of Example B83, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 1-(chloromethyl)-2-isocyanatobenzene as the starting materials in 6% yield. LCMS for $C_{26}H_{23}Cl_2N_6O$ (M+H)$^+$: m/z=505.3, 507.3.

Example B109

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-(5,6,7,8-tetrahydronaphthalen-1-yl)urea trifluoroacetate

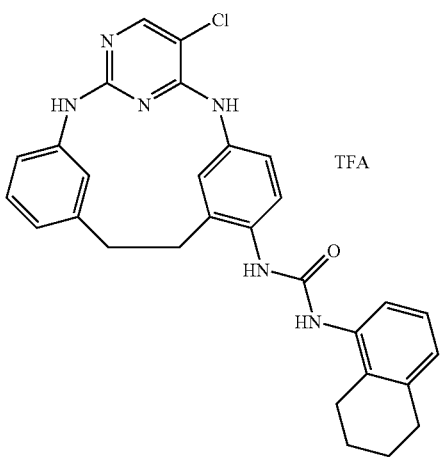 [SMILES: "TFA" ; O=C(Nc1ccc2cc1CCc1cccc(c1)Nc1ncc(Cl)c(n1)N2)Nc1cccc2c1CCCC2]

The desired compound was prepared according to the procedure of Example B83, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 5-isocyanato-1,2,3,4-tetrahydronaphthalene as the starting materials in 4% yield. LCMS for $C_{29}H_{28}ClN_6O$ (M+H)$^+$: m/z=511.3.

Example B110

N-(2-tert-Butylphenyl)-N'-[6-chloro-2,4,8,22-tetraazatetracyclo[14.3.1.1(3,7).1(9,13)]docosa-1(20),3(22),4,6,9(21),10,12,16,18-nonaen-12-yl]urea trifluoroacetate

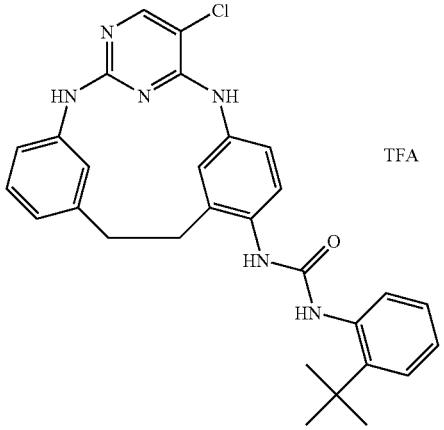 [SMILES: CC(C)(C)c1ccccc1NC(=O)Nc1ccc2cc1CCc1cccc(c1)Nc1ncc(Cl)c(n1)N2]

The desired compound was prepared according to the procedure of Example B83, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 1-tert-butyl-2-isocyanatobenzene as the starting materials in 28% yield. LCMS for $C_{29}H_{30}ClN_6O$ (M+H)$^+$: m/z=513.3.

Example B111

N-[6-Chloro-2,4,8,22-tetraazatetracyclo[14.3.1.1(3,7).1(9,13)]docosa-1(20), 3(22),4,6,9(21),10,12,16,18-nonaen-12-yl]-N'-[2-(trifluoromethyl)phenyl]urea trifluoroacetate

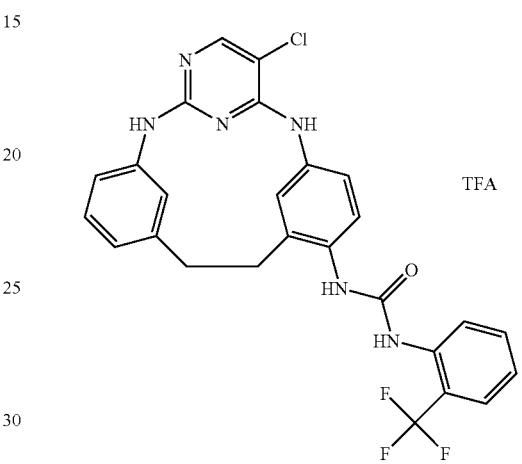

The desired compound was prepared according to the procedure of Example B83 I, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 1-isocyanato-2-(trifluoromethyl)benzene as the starting materials in 16% yield. LCMS for $C_{26}H_{21}ClF_3N_6O$ (M+H)$^+$: m/z=525.3.

Example B112

N-[6-Chloro-2,4,8,22-tetraazatetracyclo[14.3.1.1(3,7).1(9,13)]docosa-1(20), 3(22),4,6,9(21),10,12,16,18-nonaen-12-yl]-N'-[3-(trifluoromethyl)phenyl]urea trifluoroacetate

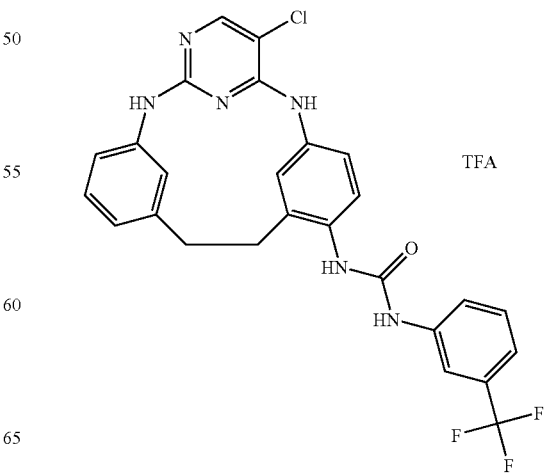

The desired compound was prepared according to the procedure of Example B83, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 1-isocyanato-3-(trifluoromethyl)benzene as the starting materials in 21% yield. LCMS for $C_{26}H_{21}ClF_3N_6O$ (M+H)$^+$: m/z=525.0.

Example B113

N-[6-Chloro-2,4,8,22-tetraazatetracyclo[14.3.1.1(3,7).1(9,13)]docosa-1(20), 3(22),4,6,9(21),10,12,16,18-nonaen-12-yl]-N'-(2,6-dichlorophenyl)urea trifluoroacetate

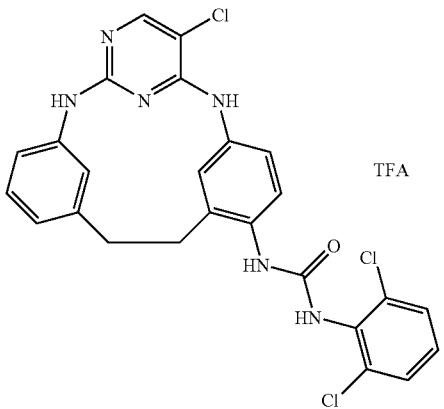 [SMILES: O=C(Nc1ccc2cc1CCc1cccc(c1)Nc1ncc(Cl)c(n1)N2)Nc1c(Cl)cccc1Cl]

The desired compound was prepared according to the procedure of Example B83, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 1,3-dichloro-2-isocyanatobenzene as the starting materials in 21% yield. LCMS for $C_{25}H_{20}Cl_3N_6O$ (M+H)$^+$: m/z=525.0, 527.0.

Example B114

N-[6-Chloro-2,4,8,22-tetraazatetracyclo[14.3.1.1(3,7).1(9,13)]docosa-1(20), 3(22),4,6,9(21),10,12,16,18-nonaen-12-yl]-N'-methylurea trifluoroacetate

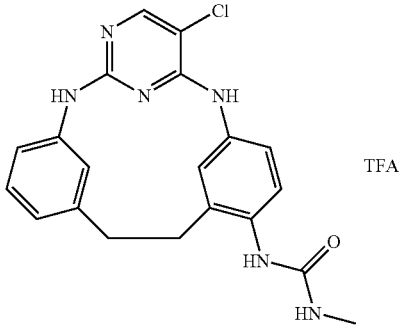 [SMILES: CNC(=O)Nc1ccc2cc1CCc1cccc(c1)Nc1ncc(Cl)c(n1)N2]

The desired compound was prepared according to the procedure of Example B83, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and methyl isocyanate as the starting materials in 29% yield. LCMS for $C_{20}H_{20}ClN_6O$ (M+H)$^+$: m/z=395.0.

Example B115

N-[6-Chloro-2,4,8,22-tetraazatetracyclo[14.3.1.1(3,7).1(9,13)]docosa-1(20), 3(22),4,6,9(21),10,12,16,18-nonaen-12-yl]-N'-ethylurea trifluoroacetate

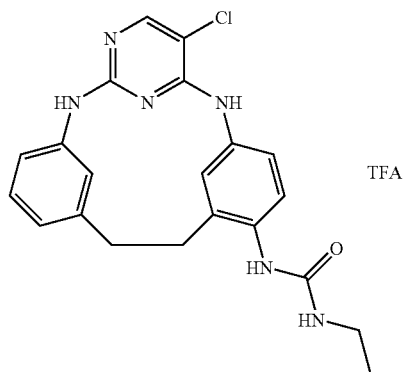 [SMILES: CCNC(=O)Nc1ccc2cc1CCc1cccc(c1)Nc1ncc(Cl)c(n1)N2]

The desired compound was prepared according to the procedure of Example B83, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and ethyl isocyanate as the starting materials in 23% yield. LCMS for $C_{21}H_{22}ClN_6O$ (M+H)$^+$: m/z=409.0.

Example B116

N-[6-Chloro-2,4,8,22-tetraazatetracyclo[14.3.1.1(3,7).1(9,13)]docosa-1(20), 3(22),4,6,9(21),10,12,16,18-nonaen-12-yl]-N'-isopropylurea trifluoroacetate

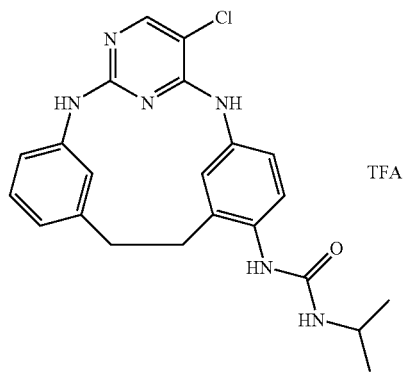 [SMILES: CC(C)NC(=O)Nc1ccc2cc1CCc1cccc(c1)Nc1ncc(Cl)c(n1)N2]

The desired compound was prepared according to the procedure of Example B83, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 2-isocyanatopropane as the starting materials in 24% yield. LCMS for $C_{22}H_{24}ClN_6O$ (M+H)$^+$: m/z=423.4.

Example B117

N-[6-Chloro-2,4,8,22-tetraazatetracyclo[14.3.1.1(3,7).1(9,13)]docosa-1(20), 3(22),4,6,9(21),10,12,16,18-nonaen-12-yl]-N'-(2-furylmethyl)urea trifluoroacetate

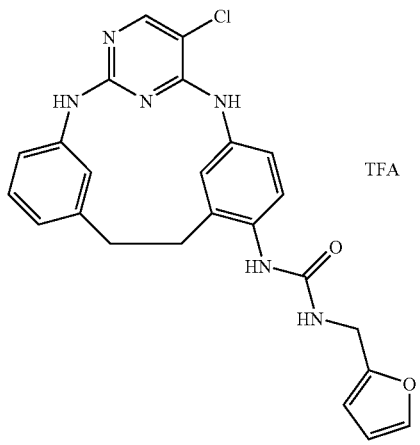 [SMILES: O=C(NCc1ccco1)Nc1ccc2cc1CCc1cccc(c1)Nc1ncc(Cl)c(n1)N2]

The desired compound was prepared according to the procedure of Example B83, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 2-(isocyanatomethyl)furan as the starting materials in 33% yield. LCMS for $C_{24}H_{22}ClN_6O_2$(M+H)$^+$: m/z=461.2. $^1$H NMR (400 MHz, DMSO-d$_6$): δ 9.50 (s, 1H), 9.38 (s, 1H), 8.12 (s, 1H), 7.99 (s, 1H), 7.79 (s, 1H), 7.65 (m, 3H), 7.09 (t, 1H), 6.96 (m, 2H), 6.88 (d, 1H), 6.79 (d, 1H), 6.40 (d, 1H), 6.27 (d, 1H), 4.29 (d, 2H), 2.86 (m, 4H).

Example B118

N-[6-Chloro-2,4,8,22-tetraazatetracyclo[14.3.1.1(3,7).1(9,13)]docosa-1(20), 3(22),4,6,9(21),10,12,16,18-nonaen-12-yl]-N'-(2-methyl-3-furyl)urea trifluoroacetate

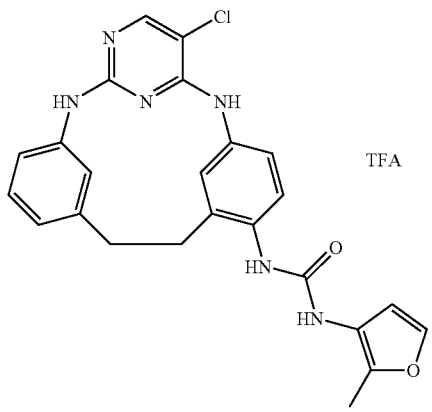 [SMILES: Cc1occc1NC(=O)Nc1ccc2cc1CCc1cccc(c1)Nc1ncc(Cl)c(n1)N2]

The desired compound was prepared according to the procedure of Example B83, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 3-isocyanato-2-methylfuran as the starting materials in 24% yield. LCMS for $C_{24}H_{22}ClN_6O_2$(M+H)$^+$: m/z=461.3.

Example B119

N-[6-Chloro-2,4,8,22-tetraazatetracyclo[14.3.1.1(3,7).1(9,13)]docosa-1(20), 3(22),4,6,9(21),10,12,16,18-nonaen-12-yl]-N'-cyclohexylurea trifluoroacetate

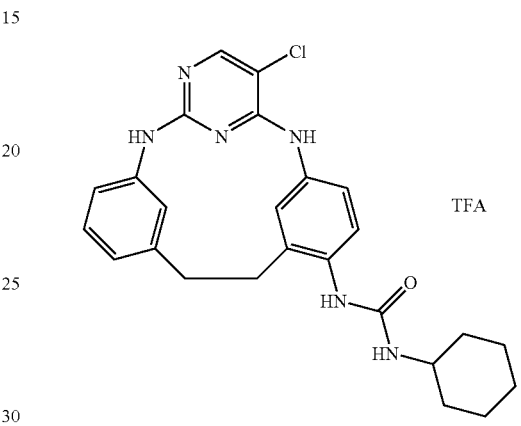

The desired compound was prepared according to the procedure of Example B83, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and cyclohexylisocyanate as the starting materials in 35% yield. LCMS for $C_{25}H_{28}ClN_6O$ (M+H)$^+$: m/z=463.4.

Example B120

N-[6-Chloro-2,4,8,22-tetraazatetracyclo[14.3.1.1(3,7).1(9,13)]docosa-1(20), 3(22),4,6,9(21),10,12,16,18-nonaen-12-yl]-N'-(4-methyl-2-thienyl)urea trifluoroacetate

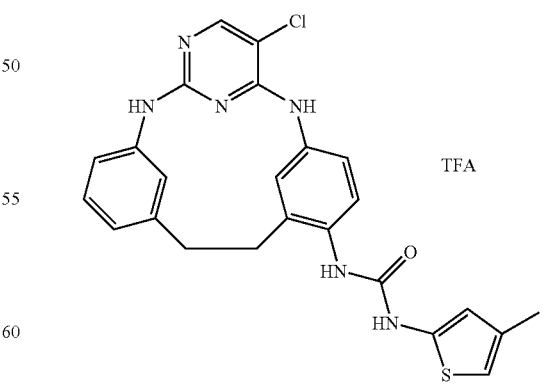

The desired compound was prepared according to the procedure of Example B83 3, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 2-isocyanato-4-methylthiophene as the starting materials in 30% yield. LCMS for $C_{24}H_{22}ClN_6OS$ (M+H)$^+$: m/z=477.3.

Example B121

N-(6-Chloropyridin-3-yl)-N'-[6-chloro-2,4,8,22-tetraazatetracyclo[14.3.1.1(3,7).1(9,13)]docosa-1(20),3(22),4,6,9(21),10,12,16,18-nonaen-12-yl]urea bis(trifluoroacetate)

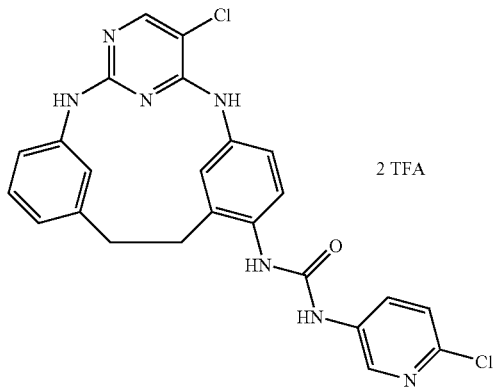 [SMILES: O=C(Nc1ccc(Cl)nc1)Nc1ccc2cc1CCc1cccc(c1)Nc1ncc(Cl)c(n1)N2 ; "2 TFA"]

The desired compound was prepared according to the procedure of Example B83, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 2-chloro-5-isocyanatopyridine as the starting materials in 15% yield. LCMS for $C_{24}H_{20}Cl_2N_7O$ (M+H)$^+$: m/z=492.3, 494.3.

Example B122

N-(2-Chloro-6-methylphenyl)-N'-[6-chloro-2,4,8,22-tetraazatetracyclo[14.3.1.1(3,7).1(9,13)]docosa-1(20),3(22),4,6,9(21),10,12,16,18-nonaen-12-yl]urea trifluoroacetate

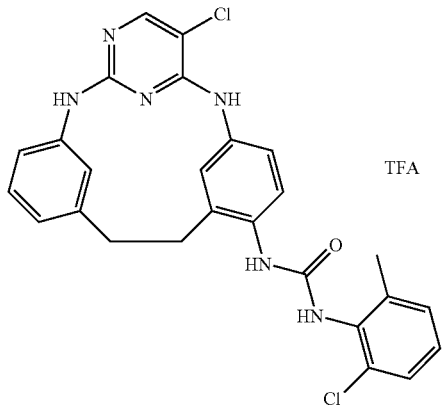 [SMILES: "TFA" ; Cc1cccc(Cl)c1NC(=O)Nc1ccc2cc1CCc1cccc(c1)Nc1ncc(Cl)c(n1)N2]

The desired compound was prepared according to the procedure of Example B83 using 6-chloro-2,4,8,22-tetraazatetracyclo[14.3.1.1(3,7).1(9,13)]docosa-1(20),3(22),4,6,9(21), 10,12,16,18-nonaen-12-amine dihydrochloride and 1-chloro-2-isocyanato-3-methylbenzene as the starting materials in 24% yield. LCMS for $C_{26}H_{23}Cl_2N_6O$ (M+H)$^+$: m/z=505.3, 507.3.

Example B123

N-(5-Chloro-2-methylphenyl)-N'-[6-chloro-2,4,8,22-tetraazatetracyclo[14.3.1.1(3,7).1(9,13)]docosa-1(20),3(22),4,6,9(21),10,12,16,18-nonaen-12-yl]urea trifluoroacetate

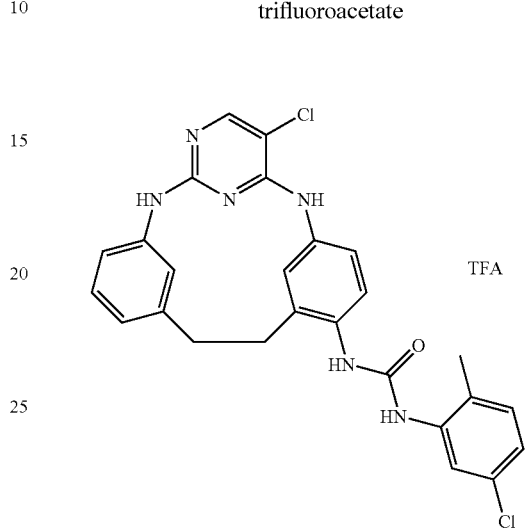

The desired compound was prepared according to the procedure of Example B83 using 6-chloro-2,4,8,22-tetraazatetracyclo[14.3.1.1(3,7).1(9,13)]docosa-1(20),3(22),4,6,9(21), 10,12,16,18-nonaen-12-amine dihydrochloride and 4-chloro-2-isocyanato-1-methylbenzene as the starting materials in 9% yield. LCMS for $C_{26}H_{23}Cl_2N_6O$ (M+H)$^+$: m/z=505.2, 507.2.

Example B124

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-1-naphthylurea trifluoroacetate

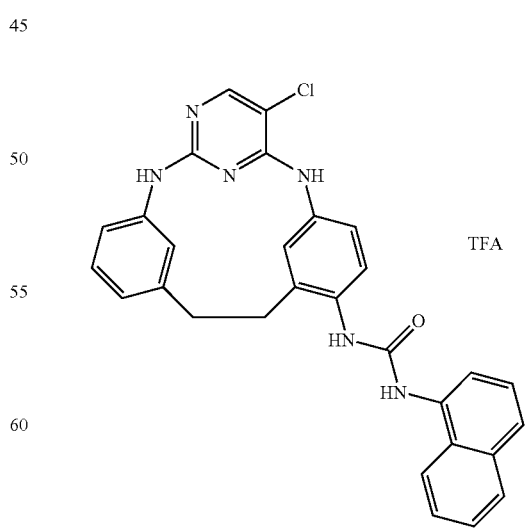

The desired compound was prepared according to the procedure of Example B83 using 6-chloro-2,4,8,22-tetraazatetracyclo[14.3.1.1(3,7).1(9,13)]docosa-1(20),3(22),4,6,9(21), 10,12,16,18-nonaen-12-amine dihydrochloride and 1-isocyanato-naphthalene as the starting materials in 14% yield. LCMS for $C_{29}H_{24}ClN_6O$ (M+H)$^+$: m/z=507.2.

Example B125

N-[6-Chloro-2,4,8,22-tetraazatetracyclo[14.3.1.1(3, 7).1(9,13)]docosa-1(20), 3(22),4,6,9(21),10,12,16, 18-nonaen-12-yl]-N'-(1-methyl-1H-indol-4-yl)urea trifluoroacetate

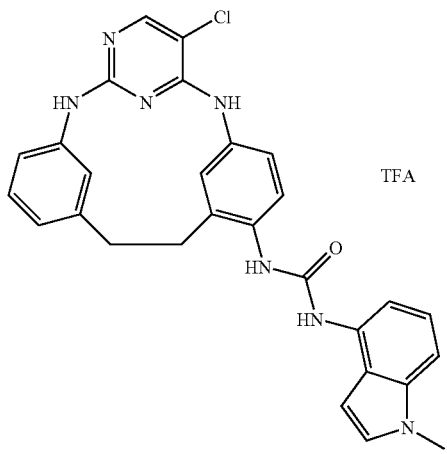 [SMILES: Cn1ccc2c(NC(=O)Nc3ccc4cc3CCc3cccc(c3)Nc3ncc(Cl)c(n3)N4)cccc21]

The desired compound was prepared according to the procedure of Example B83, using 6-chloro-2,4,8,22-tetraazatetracyclo[14.3.1.1(3,7).1(9,13)]docosa-1(20),3(22),4,6,9(21), 10,12,16,18-nonaen-12-amine dihydrochloride and 4-isocyanato-1-methyl-1H-indole as the starting materials in 14% yield. LCMS for $C_{28}H_{25}ClN_7O$ (M+H)$^+$: m/z=510.2.

Example B126

N-(2-sec-Butylphenyl)-N'-[6-chloro-2,4,8,22-tetraazatetracyclo[14.3.1.1(3,7).1(9,13)]docosa-1(20),3 (22),4,6,9(21),10,12,16,18-nonaen-12-yl]urea trifluoroacetate

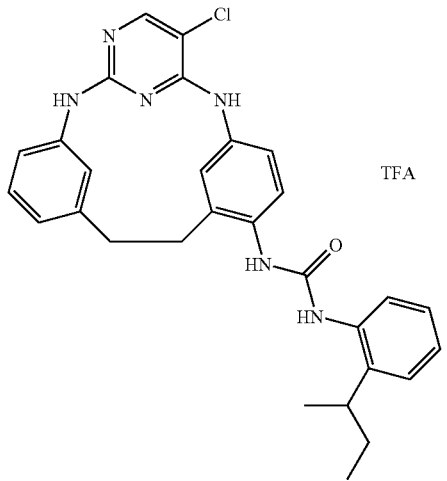 [SMILES: CCC(C)c1ccccc1NC(=O)Nc1ccc2cc1CCc1cccc(c1)Nc1ncc(Cl)c(n1)N2]

The desired compound was prepared according to the procedure of Example B83, using 6-chloro-2,4,8,22-tetraazatetracyclo[14.3.1.1(3,7).1(9,13)]docosa-1(20),3(22),4,6,9(21), 10,12,16,18-nonaen-12-amine dihydrochloride and 1-sec-butyl-2-isocyanatobenzene as the starting materials in 11% yield. LCMS for $C_{29}H_{30}ClN_6O$ (M+H)$^+$: m/z=513.3.

Example B127

N-1-Adamantyl-N'-[6-chloro-2,4,8,22-tetraazatetracyclo[14.3.1.1(3,7).1(9,13)]docosa-1(20),3(22),4,6,9 (21),10,12,16,18-nonaen-12-yl]urea trifluoroacetate

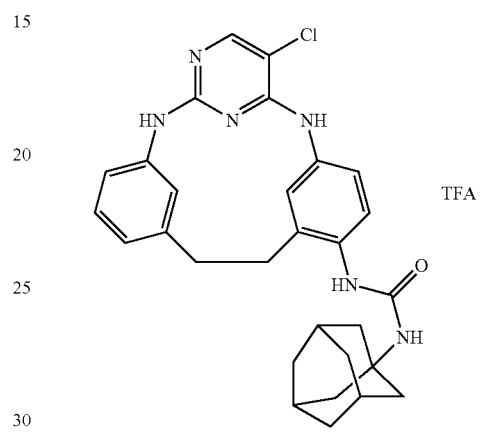

The desired compound was prepared according to the procedure of Example B83, using 6-chloro-2,4,8,22-tetraazatetracyclo[14.3.1.1(3,7).1(9,13)]docosa-1(20),3(22),4,6,9(21), 10,12,16,18-nonaen-12-amine dihydrochloride and 1-isocyanatoadamantane as the starting materials in 16% yield. LCMS for $C_{29}H_{32}ClN_6O$ (M+H)$^+$: m/z=515.3.

Example B128 2

N-[6-Chloro-2,4,8,22-tetraazatetracyclo[14.3.1.1(3, 7).1(9,13)]docosa-1(20), 3(22),4,6,9(21),10,12,16, 18-nonaen-12-yl]-N'-[2-(difluoromethoxy)phenyl] urea trifluoroacetate

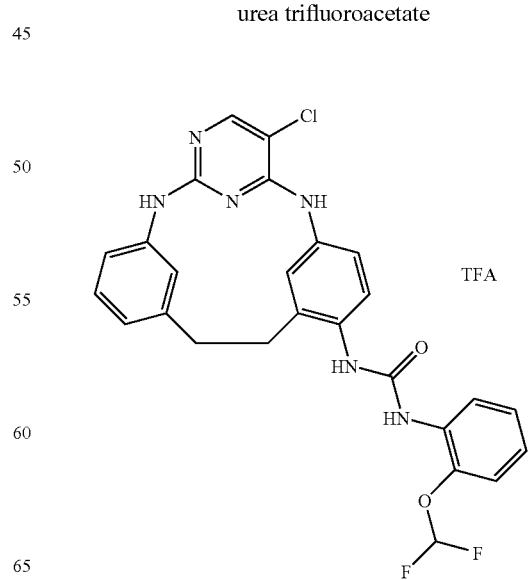

The desired compound was prepared according to the procedure of Example B83, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 1-(difluoromethoxy)-2-isocyanatobenzene as the starting materials in 25% yield. LCMS for $C_{26}H_{22}ClF_2N_6O_2(M+H)^+$: m/z=523.3.

Example B129

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-(2,2-dimethyl-2,3-dihydro-1-benzofuran-7-yl)urea trifluoroacetate

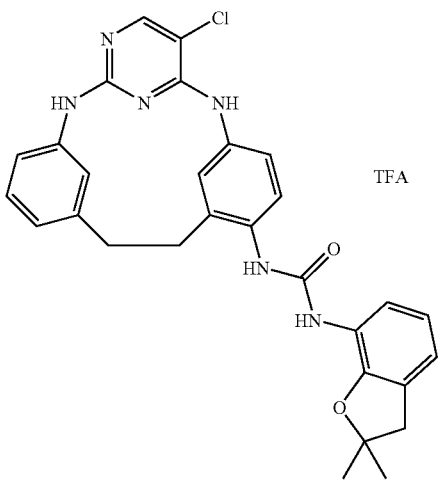 [SMILES: CC1(C)Cc2cccc(NC(=O)Nc3ccc4cc3CCc3cccc(c3)Nc3ncc(Cl)c(n3)N4)c2O1]

The desired compound was prepared according to the procedure of Example B83, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 7-isocyanato-2,2-dimethyl-2,3-dihydro-1-benzofuran as the starting materials in 10% yield. LCMS for $C_{29}H_{28}ClN_6O_2$ $(M+H)^+$: m/z=527.3.

Example B130

N-Biphenyl-2-yl-N'-[6-chloro-2,4,8,22-tetraazatetracyclo[14.3.1.1(3,7).1(9,13)]docosa-1(20),3(22),4,6,9(21),10,12,16,18-nonaen-12-yl]urea trifluoroacetate

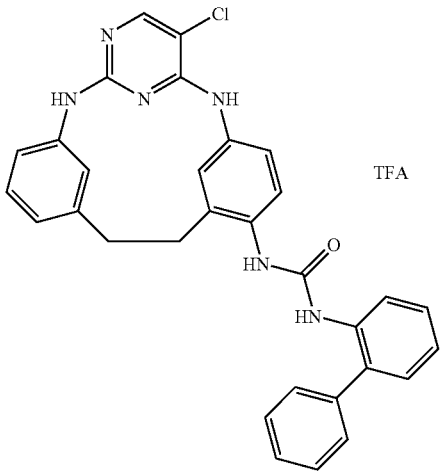 [SMILES: O=C(Nc1ccc2cc1CCc1cccc(c1)Nc1ncc(Cl)c(n1)N2)Nc1ccccc1-c1ccccc1]

The desired compound was prepared according to the procedure of Example B83, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 2-isocyanatobiphenyl as the starting materials in 27% yield. LCMS for $C_{31}H_{26}ClN_6O$ $(M+H)^+$: m/z=533.3.

Example B131

N-[6-Chloro-2,4,8,22-tetraazatetracyclo[14.3.1.1(3,7).1(9,13)]docosa-1(20), 3(22),4,6,9(21),10,12,16,18-nonaen-12-yl]-N'-[2-(trifluoromethoxy)phenyl]urea trifluoroacetate

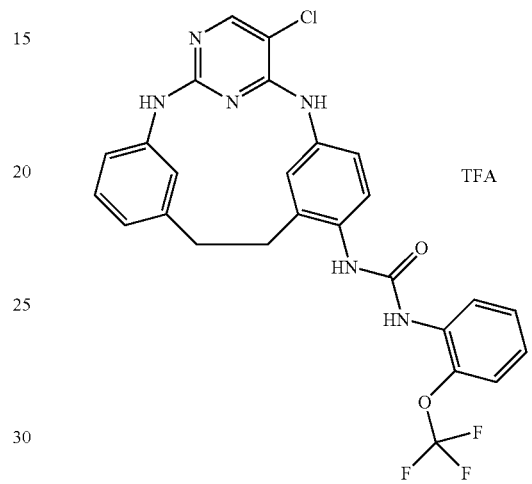

The desired compound was prepared according to the procedure of Example B83, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 1-isocyanato-2-(trifluoromethoxy)benzene as the starting materials in 29% yield. LCMS for $C_{26}H_{21}ClF_3N_6O_2(M+H)^+$: m/z=541.3. $^1$H NMR (400 MHz, DMSO-d$_6$): δ 9.44 (s, 1H), 9.31 (s, 1H), 8.78 (s, 1H), 8.55 (s, 1H), 8.19 (d, 1H), 8.12 (s, 1H), 8.01 (s, 1H), 7.74 (s, 1H), 7.58 (d, 1H), 7.37 (m, 2H), 7.09 (m, 3H), 6.88 (d, 1H), 6.80 (d, 1H), 2.92 (dd, 4H).

Example B132

N-[6-Chloro-2,4,8,22-tetraazatetracyclo[14.3.1.1(3,7).1(9,13)]docosa-1(20), 3(22),4,6,9(21),10,12,16,18-nonaen-12-yl]-N'-[4-(trifluoromethoxy)phenyl]urea trifluoroacetate

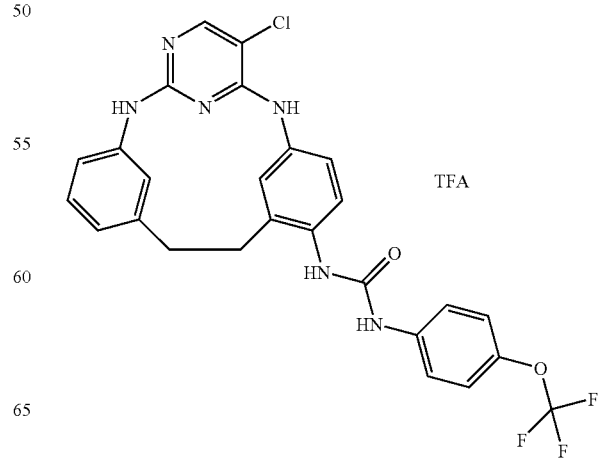

The desired compound was prepared according to the procedure of Example B83, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 1-isocyanato-4-(trifluoromethoxy)benzene as the starting materials in 24% yield. LCMS for $C_{26}H_{21}ClF_3N_6O_2$ (M+H)$^+$: m/z=541.3.

Example B133

N-[6-Chloro-2,4,8,22-tetraazatetracyclo[14.3.1.1(3,7).1(9,13)]docosa-1(20), 3(22),4,6,9(21),10,12,16,18-nonaen-12-yl]-N'-(6-morpholin-4-ylpyridin-2-yl)urea bis(trifluoroacetate)

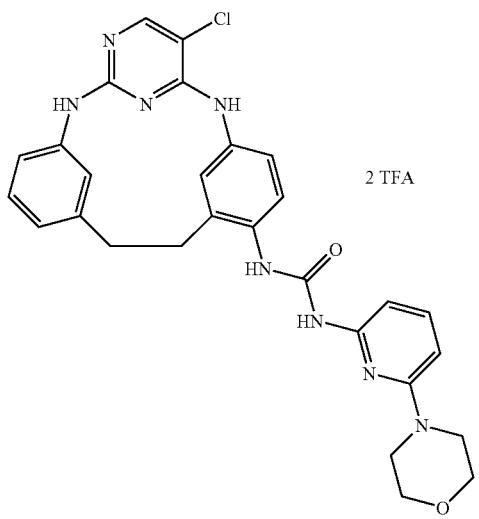 [SMILES: O=C(Nc1cccc(N2CCOCC2)n1)Nc1ccc2cc1CCc1cccc(c1)Nc1ncc(Cl)c(n1)N2 ; "2 TFA"]

The desired compound was prepared according to the procedure of Example B83, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 4-(6-isocyanatopyridin-2-yl)morpholine as the starting materials in 11% yield. LCMS for $C_{28}H_{28}ClN_8O_2$ (M+H)$^+$: m/z=543.3.

Example B134

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-N'-(2-furylmethyl)urea bis(trifluoroacetate)

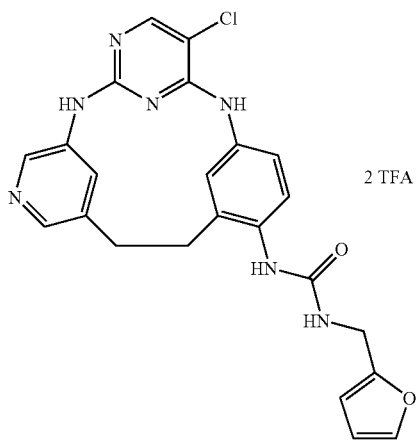 [SMILES: O=C(NCc1ccco1)Nc1ccc2cc1CCc1cncc(c1)Nc1ncc(Cl)c(n1)N2 ; "2 TFA"]

The desired compound was prepared according to the procedure of Example B83, using 6-chloro-2,4,8,18,22-pentaazatetracyclo[14.3.1.1(3,7).1(9,13)]docosa-1(20),3(22),4,6,9(21),10,12,16,18-nonaen-12-amine bis(trifluoroacetate) and 2-(isocyanatomethyl)furan as the starting materials in 34% yield. LCMS for $C_{23}H_{21}ClN_7O_2$ (M+H)$^+$: m/z=462.1. $^1$H NMR (400 MHz, DMSO-d$_6$): δ 9.96 (s, 1H), 9.31 (s, 1H), 8.97 (m, 1H), 8.30 (m, 2H), 8.18 (s, 1H), 7.89 (m, 1H), 7.71 (d, 1H), 7.60 (d, 1H), 7.56 (d, 1H), 6.95-7.02 (m, 2H), 6.41 (dd, 1H), 6.28 (dd, 1H), 4.29 (d, 2H), 2.96 (m, 4H).

Example B135

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-N'-methylurea bis(trifluoroacetate)

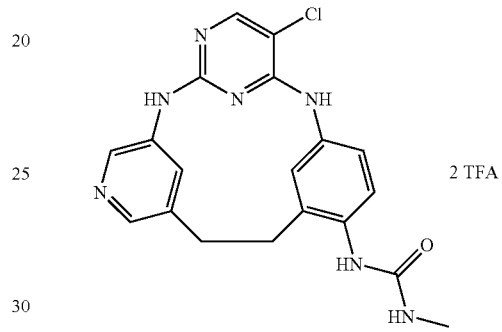

The desired compound was prepared according to the procedure of Example B83, using 6-chloro-2,4,8,18,22-pentaazatetracyclo[14.3.1.1(3,7).1(9,13)]docosa-1(20),3(22),4,6,9(21),10,12,16,18-nonaen-12-amine bis(trifluoroacetate) and methyl isocyanate as the starting materials in 52% yield. LCMS for $C_{19}H_{19}ClN_7O$ (M+H)$^+$: m/z=396.1. $^1$H NMR (400 MHz, DMSO-d$_6$): δ 9.97 (s, 1H), 9.31 (s, 1H), 8.99 (m, 1H), 8.30 (m, 2H), 8.18 (s, 1H), 7.84 (m, 1H), 7.65 (d, 1H), 7.56 (d, 1H), 6.98 (dd, 1H), 6.40 (bs, 1H), 2.96 (m, 4H), 2.64 (d, 3H).

Example B136

N-[6-Chloro-2,4,8,22-tetraazatetracyclo[14.3.1.1(3,7).1(9,13)]docosa-1(20), 3(22),4,6,9(21),10,12,16,18-nonaen-12-yl]benzenesulfonamide trifluoroacetate

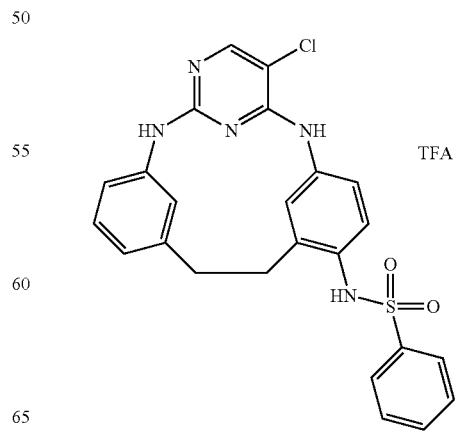

A solution of 6-chloro-2,4,8,22-tetraazatetracyclo[14.3.1.1(3,7).1(9,13)]docosa-1(20),3(22),4,6,9(21),10,12,16,18-nonaen-12-amine dihydrochloride (20 mg, 0.049 mmol) in DCM (0.3 mL) was treated with triethylamine (20.4 µL, 0.146 mmol) and benzenesulfonyl chloride (9.3 µL, 0.073 mmol). The reaction mixture was stirred at room temperature overnight. The solvent was evaporated and the crude residue was dissolved in a mixture of acetonitrile and methanol and purified by preparative LCMS to give the desired product (15 mg, 52%). LCMS calculated for $C_{24}H_{21}ClN_5O_2S$ (M+H)$^+$: m/z=478.2. $^1$H NMR (400 MHz, DMSO-d$_6$): δ 9.60 (s, 1H), 9.47 (s, 1H), 9.26 (s, 1H), 8.13 (s, 1H), 7.79 (d, 2H), 7.70 (d, 2H), 7.63 (m, 1H), 7.57 (t, 2H), 7.05 (t, 1H), 6.92 (d, 1H), 6.84 (d, 1H), 6.71 (m, 2H), 2.81 (d, 2H), 2.65 (d, 2H).

Example B137

2-Chloro-N-[6-chloro-2,4,8,22-tetraazatetracyclo[14.3.1.1(3,7).1(9,13)]docosa-1(20),3(22),4,6,9(21),10,12,16,18-nonaen-12-yl]benzenesulfonamide trifluoroacetate

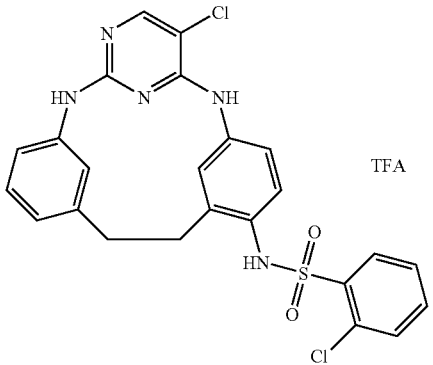 [SMILES: "TFA" ; O=S(=O)(Nc1ccc2cc1CCc1cccc(c1)Nc1ncc(Cl)c(n1)N2)c1ccccc1Cl]

The desired compound was prepared according to the procedure of Example B136, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 2-chlorobenzenesulfonyl chloride as the starting materials in 17% yield. LCMS for $C_{24}H_{20}Cl_2N_5O_2S$ (M+H)$^+$: m/z=512.0, 514.0.

Example B138

3-Chloro-N-[6-chloro-2,4,8,22-tetraazatetracyclo[14.3.1.1(3,7).1(9,13)]docosa-1(20),3(22),4,6,9(21),10,12,16,18-nonaen-12-yl]benzenesulfonamide trifluoroacetate

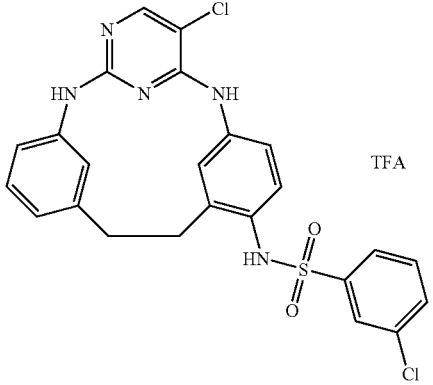 [SMILES: "TFA" ; O=S(=O)(Nc1ccc2cc1CCc1cccc(c1)Nc1ncc(Cl)c(n1)N2)c1cccc(Cl)c1]

The desired compound was prepared according to the procedure of Example B136, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 3-chlorobenzenesulfonyl chloride as the starting materials in 28% yield. LCMS for $C_{24}H_{20}Cl_2N_5O_2S$ (M+H)$^+$: m/z=511.9, 513.9. $^1$H NMR (400 MHz, DMSO-d$_6$): δ 9.77 (s, 1H), 9.47 (s, 1H), 9.26 (s, 1H), 8.13 (s, 1H), 7.81 (d, 2H), 7.77-7.60 (m, 4H), 7.05 (t, 1H), 6.92 (d, 1H), 6.84 (d, 1H), 6.71 (m, 2H), 2.81 (d, 2H), 2.65 (d, 2H).

Example B139

4-Chloro-N-[6-chloro-2,4,8,22-tetraazatetracyclo[14.3.1.1(3,7).1(9,13)]docosa-1(20),3(22),4,6,9(21),10,12,16,18-nonaen-12-yl]benzenesulfonamide trifluoroacetate

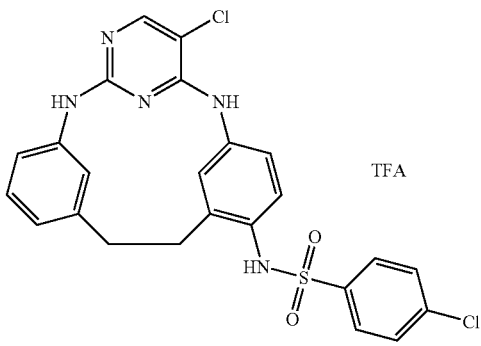 [SMILES: "TFA" ; O=S(=O)(Nc1ccc2cc1CCc1cccc(c1)Nc1ncc(Cl)c(n1)N2)c1ccc(Cl)cc1]

The desired compound was prepared according to the procedure of Example B136, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 4-chlorobenzenesulfonyl chloride as the starting materials in 26% yield. LCMS for $C_{24}H_{20}Cl_2N_5O_2S$ (M+H)$^+$: m/z=511.9, 513.9.

Example B140

N-[6-Chloro-2,4,8,22-tetraazatetracyclo[14.3.1.1(3,7).1(9,13)]docosa-1(20), 3(22),4,6,9(21),10,12,16,18-nonaen-12-yl]methanesulfonamide trifluoroacetate

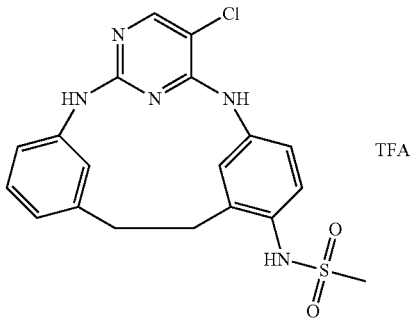 [SMILES: CS(=O)(=O)Nc1ccc2cc1CCc1cccc(c1)Nc1ncc(Cl)c(n1)N2]

The desired compound was prepared according to the procedure of Example B136, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and methanesulfonyl chloride as the starting materials in 12% yield. LCMS for $C_{19}H_{19}ClN_5O_2S$ (M+H)$^+$: m/z=416.2.

Example B141

N-[6-Chloro-2,4,8,22-tetraazatetracyclo[14.3.1.1(3,7).1(9,13)]docosa-1(20), 3(22),4,6,9(21),10,12,16,18-nonaen-12-yl]ethanesulfonamide trifluoroacetate

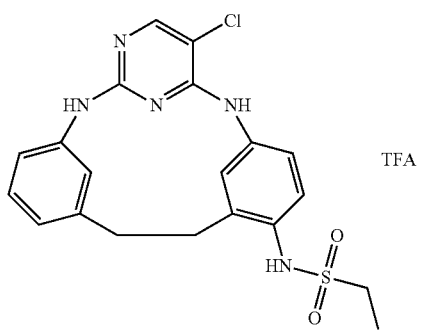 [SMILES: CCS(=O)(=O)Nc1ccc2cc1CCc1cccc(c1)Nc1ncc(Cl)c(n1)N2]

The desired compound was prepared according to the procedure of Example B136, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and ethanesulfonyl chloride as the starting materials in 8% yield. LCMS for $C_{20}H_{21}ClN_5O_2S$ (M+H)$^+$: m/z=430.3.

Example B142

N-[6-Chloro-2,4,8,22-tetraazatetracyclo[14.3.1.1(3,7).1(9,13)]docosa-1(20), 3(22),4,6,9(21),10,12,16,18-nonaen-12-yl]propane-1-sulfonamide trifluoroacetate

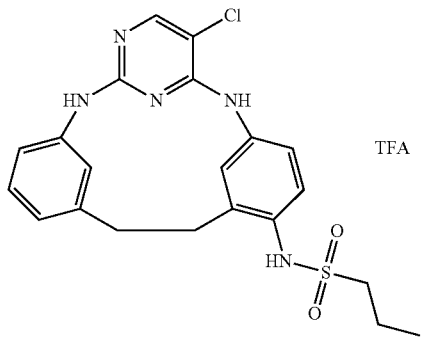 [SMILES: CCCS(=O)(=O)Nc1ccc2cc1CCc1cccc(c1)Nc1ncc(Cl)c(n1)N2]

The desired compound was prepared according to the procedure of Example B136, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 1-propanesulfonyl chloride as the starting materials in 7% yield. LCMS for $C_{21}H_{23}ClN_5O_2S$ (M+H)$^+$: m/z=444.3.

Example B143

N-[6-Chloro-2,4,8,22-tetraazatetracyclo[14.3.1.1(3,7).1(9,13)]docosa-1(20), 3(22),4,6,9(21),10,12,16,18-nonaen-12-yl]propane-2-sulfonamide trifluoroacetate

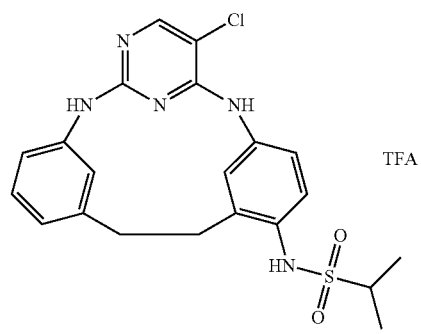 [SMILES: CC(C)S(=O)(=O)Nc1ccc2cc1CCc1cccc(c1)Nc1ncc(Cl)c(n1)N2]

The desired compound was prepared according to the procedure of Example B136, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and propane-2-sulfonyl chloride as the starting materials in 7% yield. LCMS for $C_{21}H_{23}ClN_5O_2S$ (M+H)$^+$: m/z=444.2.

Example B144

N-[6-Chloro-2,4,8,22-tetraazatetracyclo[14.3.1.1(3,7).1(9,13)]docosa-1(20), 3(22),4,6,9(21),10,12,16,18-nonaen-12-yl]-1-methyl-1H-imidazole-4-sulfonamide bis(trifluoroacetate)

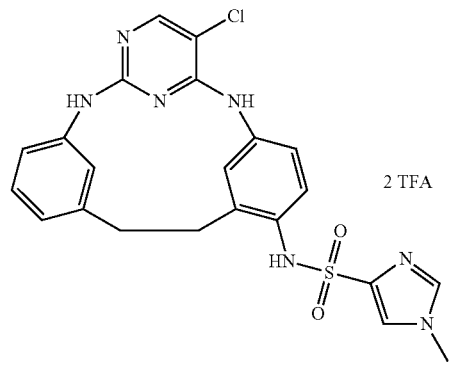 [SMILES: Cn1cnc(S(=O)(=O)Nc2ccc3cc2CCc2cccc(c2)Nc2ncc(Cl)c(n2)N3)c1 ; "2 TFA"]

The desired compound was prepared according to the procedure of Example B136, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 1-methyl-1H-imidazole-4-sulfonyl chloride as the starting materials in 8% yield. LCMS for $C_{22}H_{21}ClN_7O_2S$ (M+H)$^+$: m/z=482.2.

Example B145

N-[6-Chloro-2,4,8,22-tetraazatetracyclo[14.3.1.1(3, 7).1(9,13)]docosa-1(20), 3(22),4,6,9(21),10,12,16, 18-nonaen-12-yl]-5-methylisoxazole-4-sulfonamide trifluoroacetate

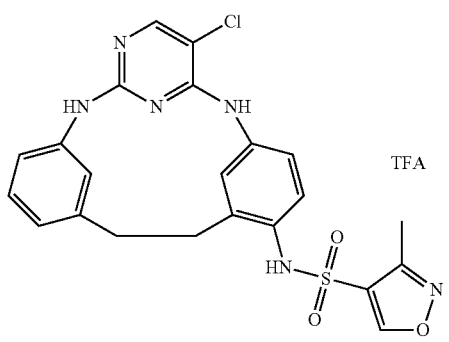 [SMILES: "TFA" ; Cc1nocc1S(=O)(=O)Nc1ccc2cc1CCc1cccc(c1)Nc1ncc(Cl)c(n1)N2]

The desired compound was prepared according to the procedure of Example B136, using 6-chloro-2,4,8,22-tetraazatetracyclo[14.3.1.1(3,7).1(9,13)]docosa-1(20),3(22),4,6,9 (21),10,12,16,18-nonaen-12-amine dihydrochloride and 5-methylisoxazole-4-sulfonyl chloride as the starting materials in 7% yield. LCMS for $C_{22}H_{20}ClN_6O_3S$ (M+H)$^+$: m/z=483.3.

Example B146

N-[6-Chloro-2,4,8,22-tetraazatetracyclo[14.3.1.1(3, 7).1(9,13)]docosa-1(20), 3(22),4,6,9(21),10,12,16, 18-nonaen-12-yl]thiophene-2-sulfonamide trifluoroacetate

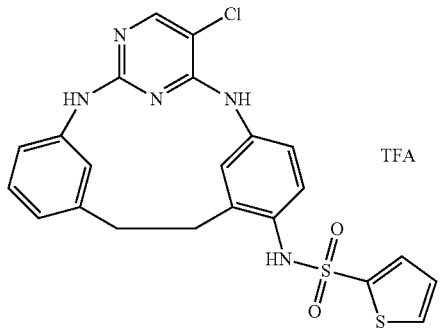 [SMILES: "TFA" ; O=S(=O)(Nc1ccc2cc1CCc1cccc(c1)Nc1ncc(Cl)c(n1)N2)c1cccs1]

The desired compound was prepared according to the procedure of Example B136, using 6-chloro-2,4,8,22-tetraazatetracyclo[14.3.1.1(3,7).1(9,13)]docosa-1(20),3(22),4,6,9 (21),10,12,16,18-nonaen-12-amine dihydrochloride and 2-thiophenesulfonyl chloride as the starting materials in 25% yield. LCMS for $C_{22}H_{19}ClN_5O_2S_2$(M+H)$^+$: m/z=484.2.

Example B147

N-[6-Chloro-2,4,8,22-tetraazatetracyclo[14.3.1.1(3, 7).1(9,13)]docosa-1(20), 3(22),4,6,9(21),10,12,16, 18-nonaen-12-yl]-1-phenylmethanesulfonamide trifluoroacetate

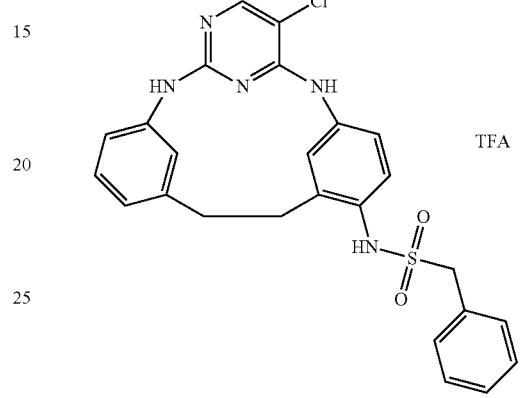

The desired compound was prepared according to the procedure of Example B136, using 6-chloro-2,4,8,22-tetraazatetracyclo[14.3.1.1(3,7).1(9,13)]docosa-1(20),3(22),4,6,9 (21),10,12,16,18-nonaen-12-amine dihydrochloride and phenylmethanesulfonyl chloride as the starting materials in 25% yield. LCMS for $C_{25}H_{23}ClN_5O_2S$ (M+H)$^+$: m/z=492.3.

Example B148

N-[6-Chloro-2,4,8,22-tetraazatetracyclo[14.3.1.1(3, 7).1(9,13)]docosa-1(20), 3(22),4,6,9(21),10,12,16, 18-nonaen-12-yl]-3-methylbenzenesulfonamide trifluoroacetate

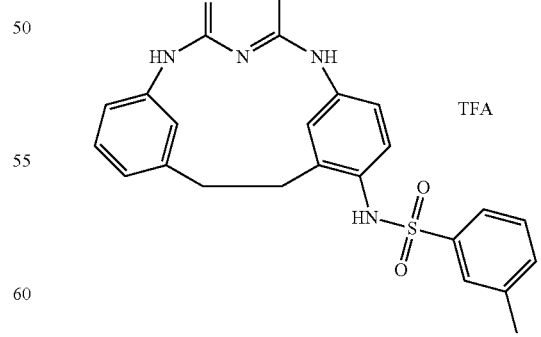

The desired compound was prepared according to the procedure of Example B136, using 6-chloro-2,4,8,22-tetraazatetracyclo[14.3.1.1(3,7).1(9,13)]docosa-1(20),3(22),4,6,9 (21),10,12,16,18-nonaen-12-amine dihydrochloride and 3-methylbenzenesulfonyl chloride as the starting materials in 17% yield. LCMS for $C_{25}H_{23}ClN_5O_2S$ (M+H)$^+$: m/z=492.3.

Example B149

N-[6-Chloro-2,4,8,22-tetraazatetracyclo[14.3.1.1(3,7).1(9,13)]docosa-1(20), 3(22),4,6,9(21),10,12,16,18-nonaen-12-yl]-2-methylbenzenesulfonamide trifluoroacetate

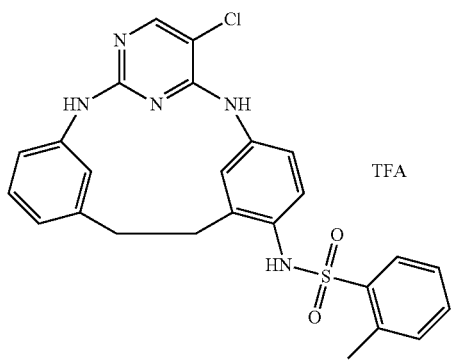 [SMILES: Cc1ccccc1S(=O)(=O)Nc1ccc2cc1CCc1cccc(c1)Nc1ncc(Cl)c(n1)N2]

The desired compound was prepared according to the procedure of Example B136, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 2-methylbenzenesulfonyl chloride as the starting materials in 22% yield. LCMS for $C_{25}H_{23}ClN_5O_2S$ (M+H)$^+$: m/z=492.3. $^1$H NMR (400 MHz, DMSO-d$_6$): δ 9.58 (s, 1H), 9.37 (s, 1H), 9.13 (s, 1H), 8.10 (s, 1H), 7.82 (s, 1H), 7.78 (s, 1H), 7.65 (d, 1H), 7.51 (t, 1H), 7.42 (d, 1H), 7.30 (t, 1H), 7.06 (t, 1H), 6.92 (d, 1H), 6.85 (d, 1H), 6.69 (t, 2H), 2.83 (d, 2H), 2.65 (d, 2H), 2.60 (s, 3H).

Example B150

N-[6-Chloro-2,4,8,22-tetraazatetracyclo[14.3.1.1(3,7).1(9,13)]docosa-1(20), 3(22),4,6,9(21),10,12,16,18-nonaen-12-yl]-4-methylbenzenesulfonamide trifluoroacetate

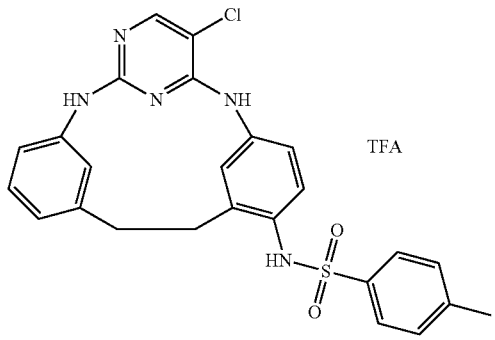 [SMILES: Cc1ccc(S(=O)(=O)Nc2ccc3cc2CCc2cccc(c2)Nc2ncc(Cl)c(n2)N3)cc1]

The desired compound was prepared according to the procedure of Example B136, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 4-methylbenzenesulfonyl chloride as the starting materials in 19% yield. LCMS for $C_{25}H_{23}ClN_5O_2S$ (M+H)$^+$: m/z=492.3.

Example B151

N-[6-Chloro-2,4,8,22-tetraazatetracyclo[14.3.1.1(3,7).1(9,13)]docosa-1(20),3(22),4,6,9(21),10,12,16,18-nonaen-12-yl]-1,2-dimethyl-1H-imidazole-4-sulfonamide bis(trifluoroacetate)

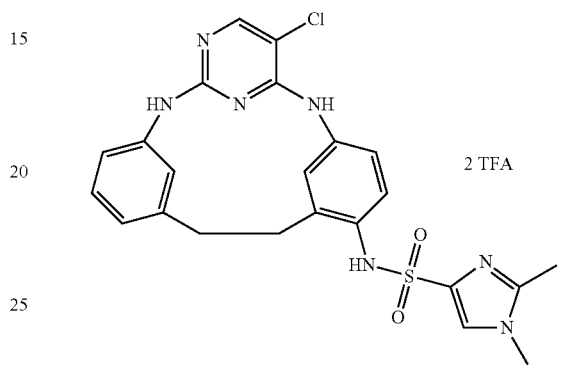

The desired compound was prepared according to the procedure of Example B136, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 1,2-dimethyl-1H-imidazole-4-sulfonyl chloride as the starting materials in 21% yield. LCMS for $C_{23}H_{23}ClN_7O_2S$ (M+H)$^+$: m/z=496.3.

Example B152

N-[6-Chloro-2,4,8,22-tetraazatetracyclo[14.3.1.1(3,7).1(9,13)]docosa-1(20),3(22),4,6,9(21),10,12,16,18-nonaen-12-yl]-3,5-dimethylisoxazole-4-sulfonamide trifluoroacetate

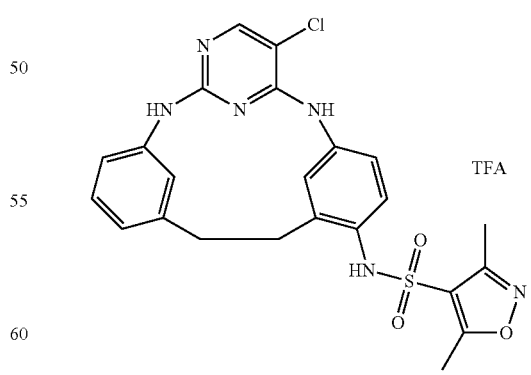

The desired compound was prepared according to the procedure of Example B136, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 3,5- dimethylisoxazole-4-sulfonyl chloride as the starting materials in 14% yield. LCMS for $C_{23}H_{22}ClN_6O_3S$ (M+H)$^+$: m/z=497.2.

Example B153

N-[6-Chloro-2,4,8,22-tetraazatetracyclo[14.3.1.1(3,7).1(9,13)]docosa-1(20),3(22),4,6,9(21),10,12,16,18-nonaen-12-yl]-3-cyanobenzenesulfonamide trifluoroacetate

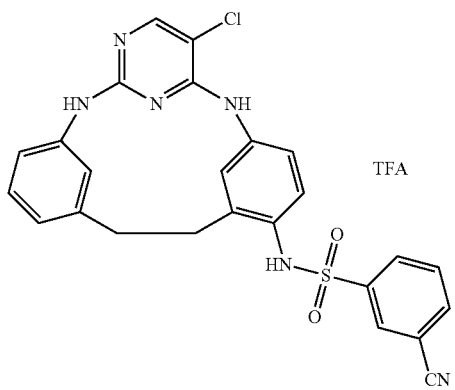 [SMILES: "TFA" ; N#Cc1cccc(S(=O)(=O)Nc2ccc3cc2CCc2cccc(c2)Nc2ncc(Cl)c(n2)N3)c1]

The desired compound was prepared according to the procedure of Example B136, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 3-cyanobenzenesulfonyl chloride as the starting materials in 8% yield. LCMS for $C_{25}H_{20}ClN_6O_2S$ (M+H)$^+$: m/z=503.3.

Example B154

N-[6-Chloro-2,4,8,22-tetraazatetracyclo[14.3.1.1(3,7).1(9,13)]docosa-1(20), 3(22),4,6,9(21),10,12,16,18-nonaen-12-yl]-4-cyanobenzenesulfonamide trifluoroacetate

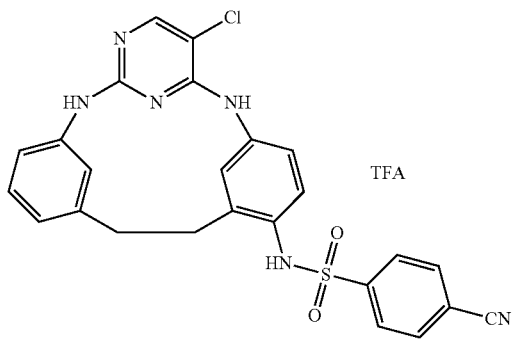 [SMILES: "TFA" ; N#Cc1ccc(S(=O)(=O)Nc2ccc3cc2CCc2cccc(c2)Nc2ncc(Cl)c(n2)N3)cc1]

The desired compound was prepared according to the procedure of Example B136, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 4-cyanobenzenesulfonyl chloride as the starting materials in 7% yield. LCMS for $C_{25}H_{20}ClN_6O_2S$ (M+H)$^+$: m/z=503.3.

Example B155

N-[6-Chloro-2,4,8,22-tetraazatetracyclo[14.3.1.1(3,7).1(9,13)]docosa-1(20), 3(22),4,6,9(21),10,12,16,18-nonaen-12-yl]-2-cyanobenzenesulfonamide trifluoroacetate

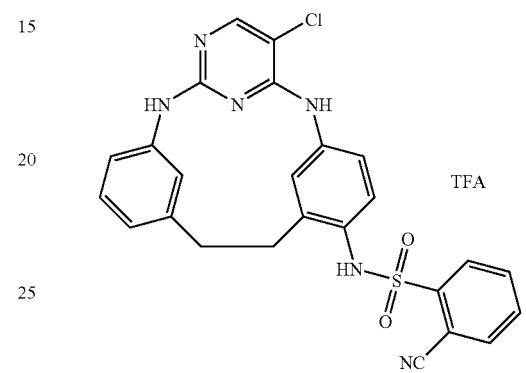

The desired compound was prepared according to the procedure of Example B136, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 2-cyanobenzenesulfonyl chloride as the starting materials in 10% yield. LCMS for $C_{25}H_{20}ClN_6O_2S$ (M+H)$^+$: m/z=503.1.

Example B156

N-[6-Chloro-2,4,8,22-tetraazatetracyclo[14.3.1.1(3,7).1(9,13)]docosa-1(20), 3(22),4,6,9(21),10,12,16,18-nonaen-12-yl]-4-methoxybenzenesulfonamide trifluoroacetate

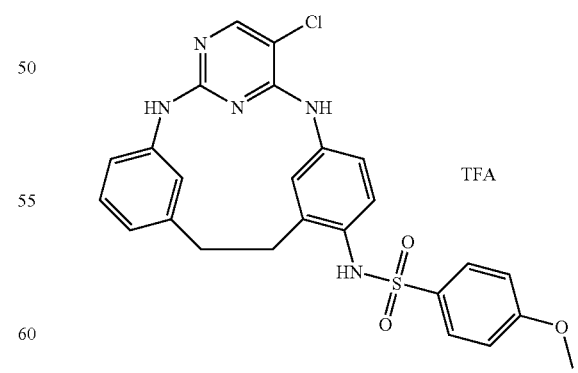

The desired compound was prepared according to the procedure of Example B136, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 4-methoxybenzenesulfonyl chloride as the starting materials in 16% yield. LCMS for $C_{25}H_{23}ClN_5O_3S$ (M+H)⁺: m/z=508.0.

Example B157

N-[6-Chloro-2,4,8,22-tetraazatetracyclo[14.3.1.1(3,7).1(9,13)]docosa-1(20), 3(22),4,6,9(21),10,12,16,18-nonaen-12-yl]-3-methoxybenzenesulfonamide trifluoroacetate

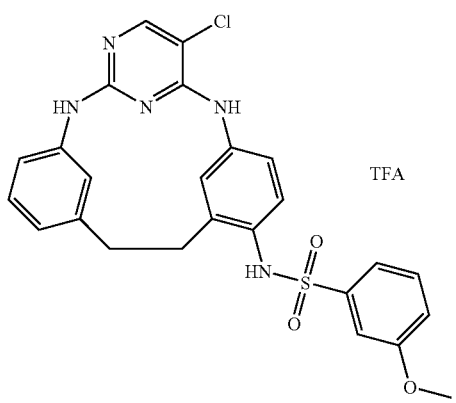 [SMILES: COc1cccc(S(=O)(=O)Nc2ccc3cc2CCc2cccc(c2)Nc2ncc(Cl)c(n2)N3)c1]

The desired compound was prepared according to the procedure of Example B136, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 3-methoxybenzenesulfonyl chloride as the starting materials in 16% yield. LCMS for $C_{25}H_{23}ClN_5O_3S$ (M+H)⁺: m/z=508.0.

Example B158

N-[6-Chloro-2,4,8,22-tetraazatetracyclo[14.3.1.1(3,7).1(9,13)]docosa-1(20), 3(22),4,6,9(21),10,12,16,18-nonaen-12-yl]cyclopropanesulfonamide trifluoroacetate

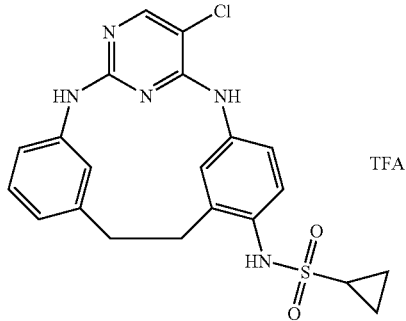 [SMILES: O=S(=O)(Nc1ccc2cc1CCc1cccc(c1)Nc1ncc(Cl)c(n1)N2)C1CC1]

The desired compound was prepared according to the procedure of Example B136, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and cyclopropanesulfonyl chloride as the starting materials in 17% yield. LCMS for $C_{21}H_{21}ClN_5O_2S$ (M+H)⁺: m/z=442.0.

Example B159

3-({[6-Chloro-2,4,8,22-tetraazatetracyclo[14.3.1.1(3,7).1(9,13)]docosa-1(20),3(22),4,6,9(21),10,12,16,18-nonaen-12-yl]amino}sulfonyl)benzoic acid trifluoroacetate

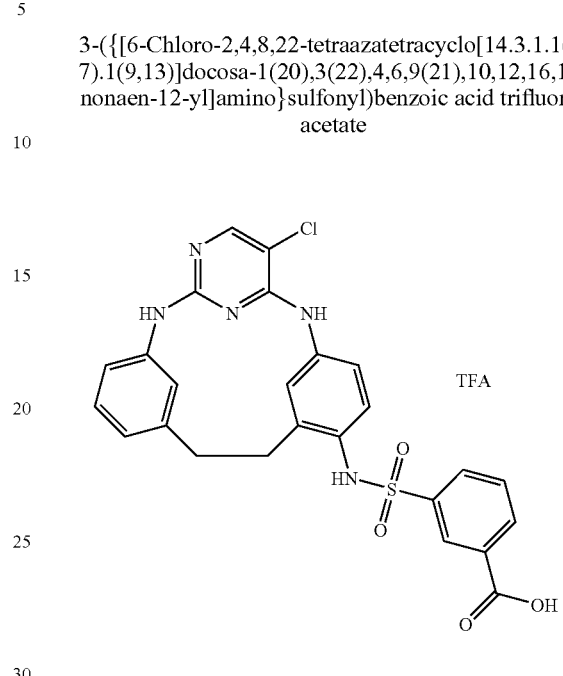

The desired compound was prepared according to the procedure of Example B136, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 3-(chlorosulfonyl)benzoic acid as the starting materials in 22% yield. LCMS for $C_{25}H_{21}ClN_5O_4S$ (M+H)⁺: m/z=522.0.

Example B160

N-[6-Chloro-2,4,8,22-tetraazatetracyclo[14.3.1.1(3,7).1(9,13)]docosa-1(20), 3(22),4,6,9(21),10,12,16,18-nonaen-12-yl]quinoline-8-sulfonamide bis(trifluoroacetate)

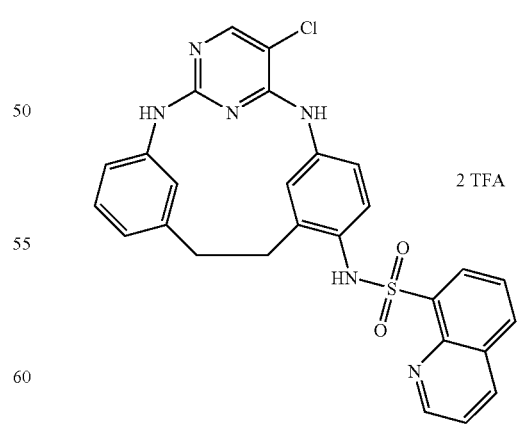

The desired compound was prepared according to the procedure of Example B136, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and quinolin-8-sulfonyl chloride as the starting materials in 18% yield. LCMS for $C_{27}H_{22}ClN_6O_2S$ (M+H)$^+$: m/z=529.0.

Example B161

N-[4-({[6-Chloro-2,4,8,22-tetraazatetracyclo [14.3.1.1(3,7).1(9,13)]docosa-1(20),3(22),4,6,9(21), 10,12,16,18-nonaen-12-yl]amino}sulfonyl)phenyl] acetamide trifluoroacetate

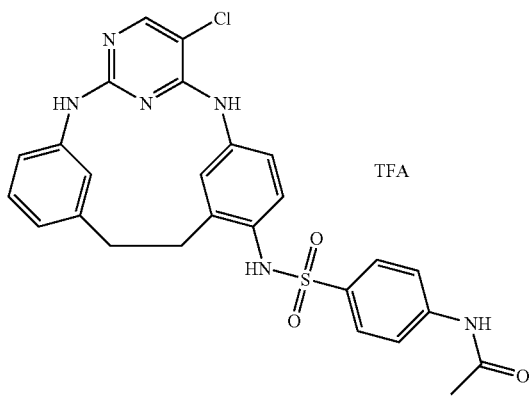 [SMILES: "TFA" ; CC(=O)Nc1ccc(S(=O)(=O)Nc2ccc3cc2CCc2cccc(c2)Nc2ncc(Cl)c(n2)N3)cc1]

The desired compound was prepared according to the procedure of Example B136, using 6-chloro-2,4,8,22-tetraazatetracyclo[14.3.1.1(3,7).1(9,13)]docosa-1(20),3(22),4,6,9 (21),10,12,16,18-nonaen-12-amine dihydrochloride and p-acetaminobenzenesulfonyl chloride as the starting materials in 19% yield. LCMS for $C_{26}H_{24}ClN_6O_3S$ (M+H)$^+$: m/z=535.0.

Example B162

N-[6-Chloro-2,4,8,22-tetraazatetracyclo[14.3.1.1(3, 7).1(9,13)]docosa-1(20), 3(22),4,6,9(21),10,12,16, 18-nonaen-12-yl]-4-(trifluoromethyl)benzenesulfonamide trifluoroacetate

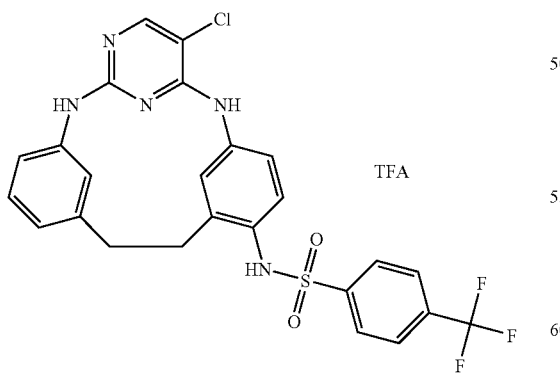

The desired compound was prepared according to the procedure of Example B136, using 6-chloro-2,4,8,22-tetraazatetracyclo[14.3.1.1(3,7).1(9,13)]docosa-1(20),3(22),4,6,9 (21),10,12,16,18-nonaen-12-amine dihydrochloride and 4-(trifluoromethyl)benzenesulfonyl chloride as the starting materials in 17% yield. LCMS for $C_{25}H_{20}ClF_3N_5O_2S$ (M+H)$^+$: m/z=546.3.

Example B163

N-[6-Chloro-2,4,8,22-tetraazatetracyclo[14.3.1.1(3, 7).1(9,13)]docosa-1(20), 3(22),4,6,9(21),10,12,16, 18-nonaen-12-yl]-3-(trifluoromethyl)benzenesulfonamide trifluoroacetate

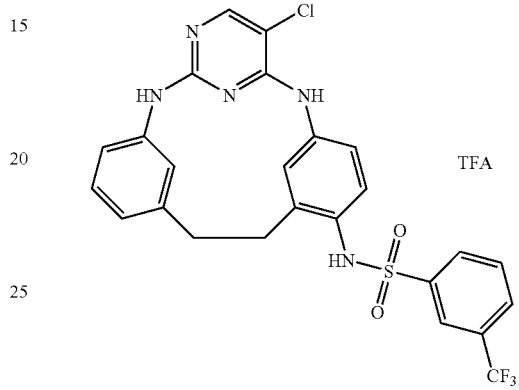

The desired compound was prepared according to the procedure of Example B136, using 6-chloro-2,4,8,22-tetraazatetracyclo[14.3.1.1(3,7).1(9,13)]docosa-1(20),3(22),4,6,9 (21),10,12,16,18-nonaen-12-amine dihydrochloride and 3-(trifluoromethyl)benzenesulfonyl chloride as the starting materials in 24% yield. LCMS for $C_{25}H_{20}ClF_3N_5O_2S$ (M+H)$^+$: m/z=546.3.

Example B164

N-[6-Chloro-2,4,8,22-tetraazatetracyclo[14.3.1.1(3, 7).1(9,13)]docosa-1(20), 3(22),4,6,9(21),10,12,16, 18-nonaen-12-yl]-2-(trifluoromethyl)benzenesulfonamide trifluoroacetate

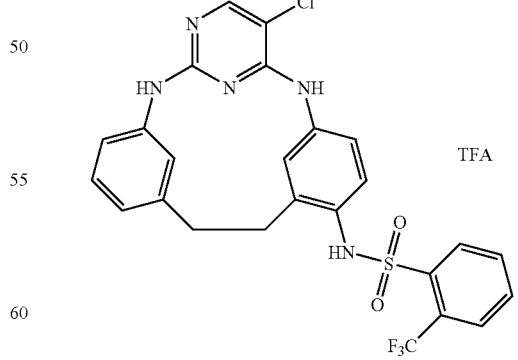

The desired compound was prepared according to the procedure of Example B136, using 6-chloro-2,4,8,22-tetraazatetracyclo[14.3.1.1(3,7).1(9,13)]docosa-1(20),3(22),4,6,9 (21),10,12,16,18-nonaen-12-amine dihydrochloride and

Example B165

N-[6-Chloro-2,4,8,22-tetraazatetracyclo[14.3.1.1(3,7).1(9,13)]docosa-1(20),3(22),4,6,9(21),10,12,16,18-nonaen-12-yl]-4-methyl-3,4-dihydro-2H-1,4-benzoxazine-7-sulfonamide trifluoroacetate

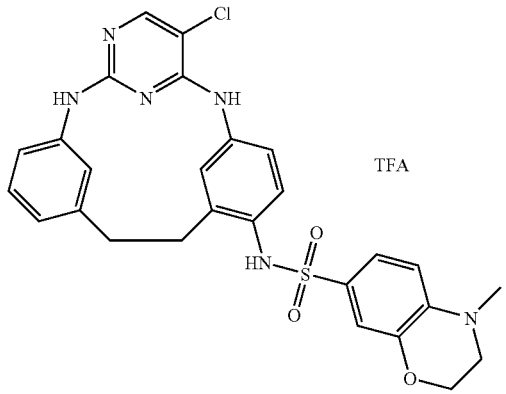 [SMILES: "TFA" ; CN1CCOc2cc(S(=O)(=O)Nc3ccc4cc3CCc3cccc(c3)Nc3ncc(Cl)c(n3)N4)ccc21]

The desired compound was prepared according to the procedure of Example B136, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 4-methyl-3,4-dihydro-2H-1,4-benzoxazine-7-sulfonyl chloride as the starting materials in 27% yield. LCMS for $C_{27}H_{26}ClN_6O_3S$ (M+H)$^+$: m/z=549.3.

Example B166 tert-Butyl (3S)-3-[({[6-chloro-2,4,8,22-tetraazatetracyclo[14.3.1.1(3,7).1(9,13)]docosa-1(20),3(22),4,6,9(21),10,12,16,18-nonaen-12-yl]amino}carbonyl)amino]pyrrolidine-1-carboxylate

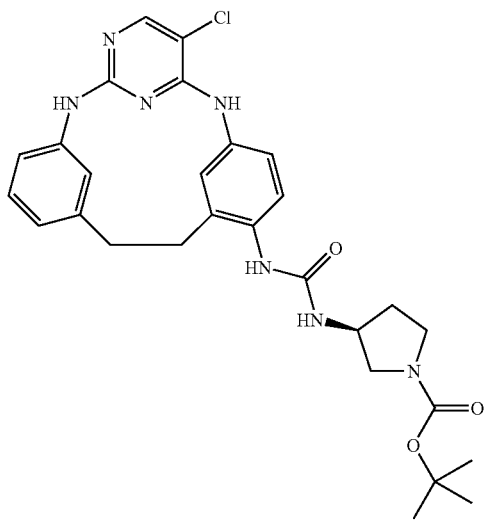 [SMILES: CC(C)(C)OC(=O)N1CC[C@H](NC(=O)Nc2ccc3cc2CCc2cccc(c2)Nc2ncc(Cl)c(n2)N3)C1]

The desired compound was prepared according to the procedure of Example B25 step A, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and tert-butyl (3S)-3-aminopyrrolidine-1-carboxylate as the starting materials in 47% yield. LCMS for $C_{28}H_{33}ClN_7O_3$ (M+H)$^+$: m/z=550.3.

Example B167

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-[(3S)-pyrrolidin-3-yl]urea bis(trifluoroacetate)

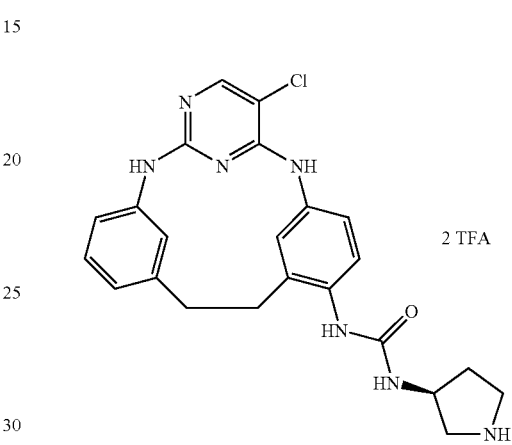

The desired compound was prepared according to the procedure of Example B25 step B, using tert-butyl (3S)-3-[({[6-chloro-2,4,8,22-tetraazatetracyclo[14.3.1.1(3,7).1(9,13)]docosa-1(20),3(22),4,6,9(21),10,12,16,18-nonaen-12-yl]amino}carbonyl)amino]pyrrolidine-1-carboxylate as the starting material in 46% yield. LCMS for $C_{23}H_{25}ClN_7O$ (M+H)$^+$: m/z=450.4.

Example B168

N-[(3S)-1-Acetylpyrrolidin-3-yl]-N'-[6-chloro-2,4,8,22-tetraazatetracyclo[14.3.1.1(3,7).1(9,13)]docosa-1(20),3(22),4,6,9(21),10,12,16,18-nonaen-12-yl]urea trifluoroacetate

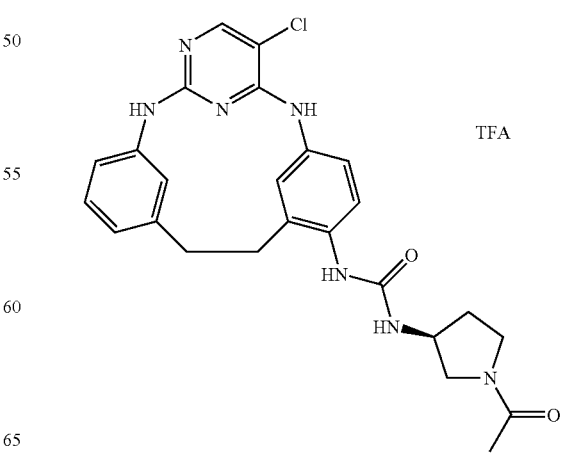

The desired compound was prepared according to the procedure of Example B26, using N-[6-chloro-2,4,8,22-tetraazatetracyclo[14.3.1.1(3,7).1(9,13)]docosa-1(20),3(22),4,6,9(21),10,12,16,18-nonaen-12-yl]-N'-[(3S)-pyrrolidin-3-yl]urea dihydrochloride and acetyl chloride as the starting materials in 36% yield. LCMS for $C_{25}H_{27}ClN_7O_2(M+H)^+$: m/z=492.3.

Example B169

(3S)-3-[({[6-Chloro-2,4,8,22-tetraazatetracyclo[14.3.1.1(3,7).1(9,13)]docosa-1(20),3(22),4,6,9(21),10,12,16,18-nonaen-12-yl]amino}carbonyl)amino]-N-methylpyrrolidine-1-carboxamide Trifluoracetate

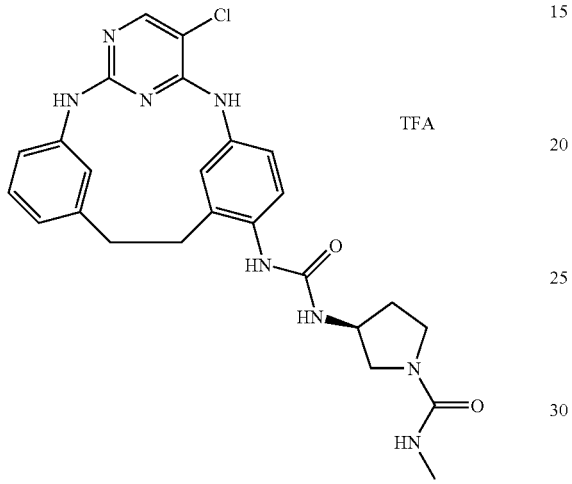

The desired compound was prepared according to the procedure of Example B183, using N-[6-chloro-2,4,8,22-tetraazatetracyclo[14.3.1.1(3,7).1(9,13)]docosa-1(20),3(22),4,6,9(21),10,12,16,18-nonaen-12-yl]-N'-[(3S)-pyrrolidin-3-yl]urea dihydrochloride and methyl isocyanate as the starting materials in 50% yield. LCMS for $C_{25}H_{28}ClN_8O_2(M+H)^+$: m/z=507.2.

Example B170

N-[(3S)-1-Benzoylpyrrolidin-3-yl]-N'-[6-chloro-2,4,8,22-tetraazatetracyclo[14.3.1.1(3,7).1(9,13)]docosa-1(20),3(22),4,6,9(21),10,12,16,18-nonaen-12-yl]urea trifluoroacetate

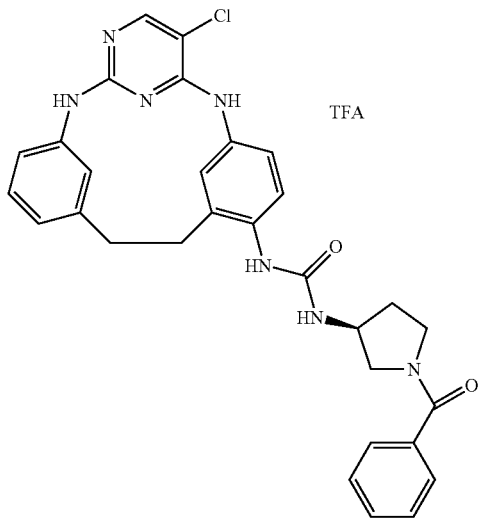 [SMILES: O=C(Nc1ccc2cc1CCc1cccc(c1)Nc1ncc(Cl)c(n1)N2)N[C@H]1CCN(C(=O)c2ccccc2)C1]

The desired compound was prepared according to the procedure of Example B26, using N-[6-chloro-2,4,8,22-tetraazatetracyclo[14.3.1.1(3,7).1(9,13)]docosa-1(20),3(22),4,6,9(21),10,12,16,18-nonaen-12-yl]-N'-[(3S)-pyrrolidin-3-yl]urea dihydrochloride and benzoyl chloride as the starting materials in 39% yield. LCMS for $C_{30}H_{29}ClN_7O_2(M+H)^+$: m/z=554.3. $^1$H NMR (400 MHz, DMSO-d$_6$): δ 9.55 (s, 1H), 9.40 (s, 1H), 8.15 (s, 1H), 7.98 (m, 1H), 7.71-7.41 (m, 8H), 7.09 (m, 1H), 6.99-6.78 (m, 4H), 4.18 (d, 1H), 3.76-3.48 (m, 3H), 3.42-3.25 (m, 1H), 2.86 (d, 4H), 2.17 (m, 1H), 1.85 (m, 1H).

Example B171

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-[(3S)-1-(pyridin-3-ylcarbonyl)pyrrolidin-3-yl]urea bis(trifluoroacetate)

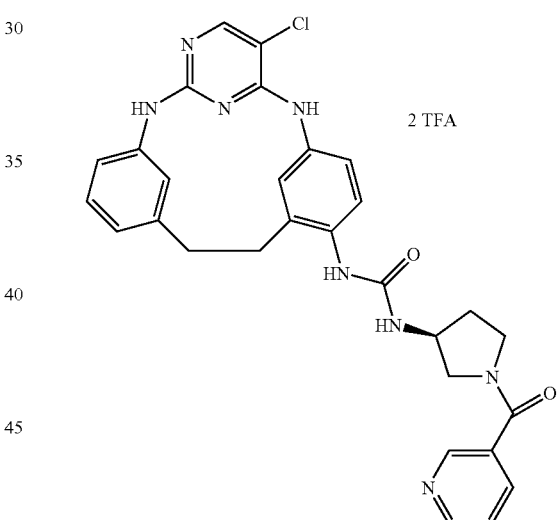

The desired compound was prepared according to the procedure of Example B26, using N-[6-chloro-2,4,8,22-tetraazatetracyclo[14.3.1.1(3,7).1(9,13)]docosa-1(20),3(22),4,6,9(21),10,12,16,18-nonaen-12-yl]-N'-[(3S)-pyrrolidin-3-yl]urea dihydrochloride and nicotinoyl chloride hydrochloride as the starting materials in 42% yield. LCMS for $C_{29}H_{28}ClN_8O_2(M+H)^+$: m/z=555.3. $^1$H NMR (400 MHz, DMSO-d$_6$): δ 9.77 (s, 1H), 9.62 (s, 1H), 8.79 (s, 1H), 8.69 (s, 1H), 8.19 (s, 1H), 8.07 (m, 1H), 7.95 (d, 1H), 7.75-7.52 (m, 4H), 7.09 (m, 1H), 6.99-6.78 (m, 4H), 4.20 (d, 1H), 3.77-3.50 (m, 3H), 3.41-3.20 (m, 1H), 2.86 (d, 4H), 2.17 (m, 1H), 1.85 (m, 1H).

Example B172

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-[(3S)-1-(methylsulfonyl)pyrrolidin-3-yl]urea trifluoroacetate

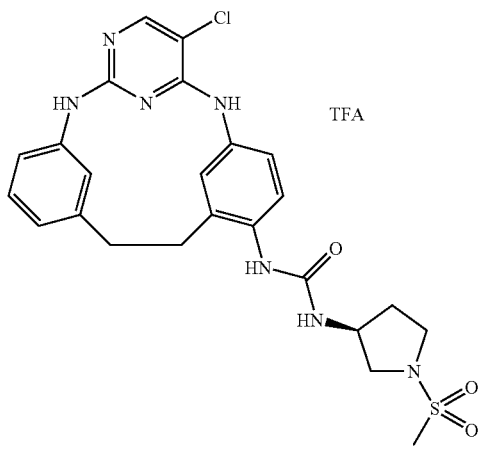 [SMILES: CS(=O)(=O)N1CC[C@H](NC(=O)Nc2ccc3cc2CCc2cccc(c2)Nc2ncc(Cl)c(n2)N3)C1]

The desired compound was prepared according to the procedure of Example B136, using N-[6-chloro-2,4,8,22-tetraazatetracyclo[14.3.1.1(3,7).1(9,13)]docosa-1(20),3(22),4,6,9(21),10,12,16,18-nonaen-12-yl]-N'-[(3S)-pyrrolidin-3-yl]urea dihydrochloride as the starting material in 16% yield. LCMS for $C_{24}H_{27}ClN_7O_3S$ (M+H)$^+$: m/z=528.1.

Example B173

N-[(3S)-1-Benzylpyrrolidin-3-yl]-N'-[6-chloro-2,4,8,22-tetraazatetracyclo[14.3.1.1(3,7).1(9,13)]docosa-1(20),3(22),4,6,9(21),10,12,16,18-nonaen-12-yl]urea bis(trifluoroacetate)

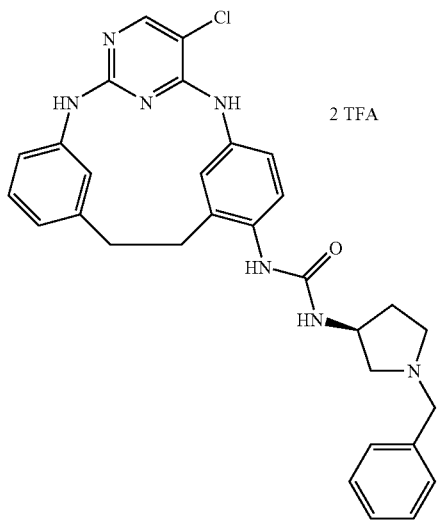 [SMILES: O=C(Nc1ccc2cc1CCc1cccc(c1)Nc1ncc(Cl)c(n1)N2)N[C@H]1CCN(Cc2ccccc2)C1 ; "2 TFA"]

The desired compound was prepared according to the procedure of Example B192, using N-[6-chloro-2,4,8,22-tetraazatetracyclo[14.3.1.1(3,7).1(9,13)]docosa-1(20),3(22),4,6,9(21),10,12,16,18-nonaen-12-yl]-N'-[(3S)-pyrrolidin-3-yl]urea dihydrochloride and benzaldehyde as the starting materials in 9% yield. LCMS for $C_{30}H_{31}ClN_7O$ (M+H)$^+$: m/z=540.1.

Example B174 tert-Butyl (3R)-3-[({[6-chloro-2,4,8,22-tetraazatetracyclo[14.3.1.1(3,7).1(9,13)]docosa-1(20),3(22),4,6,9(21),10,12,16,18-nonaen-12-yl]amino}carbonyl)amino]pyrrolidine-1-carboxylate

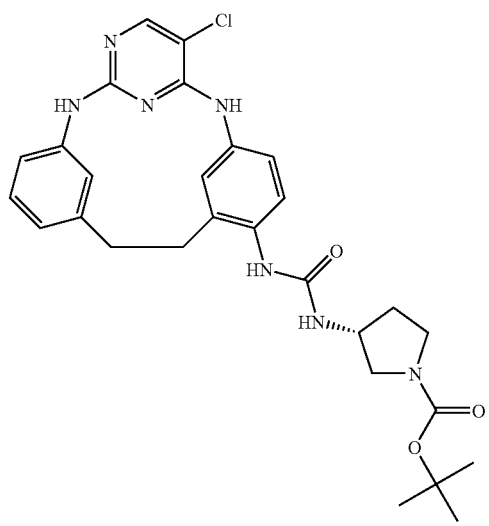 [SMILES: CC(C)(C)OC(=O)N1CC[C@@H](NC(=O)Nc2ccc3cc2CCc2cccc(c2)Nc2ncc(Cl)c(n2)N3)C1]

The desired compound was prepared according to the procedure of Example B25 step A, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and tert-butyl (3R)-3-aminopyrrolidine-1-carboxylate as the starting materials in 27% yield. LCMS for $C_{28}H_{33}ClN_7O_3$ (M+H)$^+$: m/z=550.3.

Example B175

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-[(3R)-pyrrolidin-3-yl]urea dihydrochloride

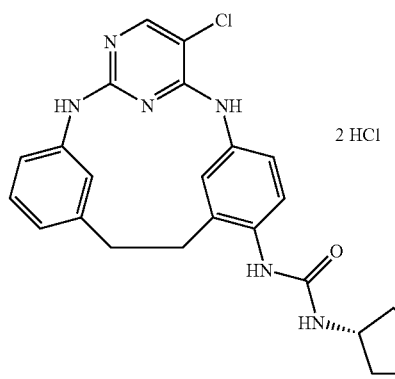

The desired compound was prepared according to the procedure of Example B25 step B, using tert-butyl (3R)-3-[({[6-chloro-2,4,8,22-tetraazatetracyclo[14.3.1.1(3,7).1(9,13)]docosa-1(20),3(22),4,6,9(21),10,12,16,18-nonaen-12-yl]amino}carbonyl)amino]pyrrolidine-1-carboxylate as the starting material in 25% yield. LCMS for $C_{23}H_{25}ClN_7O$ (M+H)$^+$: m/z=450.0. $^1$H NMR (400 MHz, DMSO-d$_6$): δ 10.20 (s, 1H), 10.05 (s, 1H), 9.38-9.15 (br, 2H), 8.28 (s, 1H), 8.20 (s, 1H), 7.89 (s, 1H), 7.75 (d, 1H), 7.64 (m, 1H), 7.15 (t, 1H), 6.96 (d, 1H), 6.87 (m, 1H), 4.20 (m, 1H), 3.68 (d, 1H), 3.45 (d, 1H), 3.39-3.10 (m, 2H), 2.99 (m, 4H), 2.17 (m, 1H), 1.80 (m, 1H).

Example B176

N-[(3R)-1-Benzoylpyrrolidin-3-yl]-N'-[6-chloro-2,4,8,22-tetraazatetracyclo[14.3.1.1(3,7).1(9,13)]docosa-1(20),3(22),4,6,9(21),10,12,16,18-nonaen-12-yl]urea trifluoroacetate

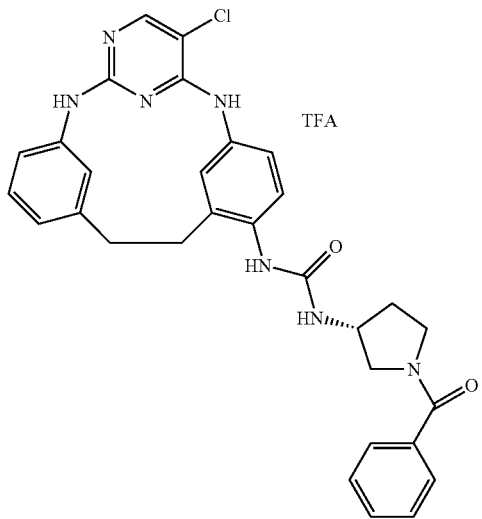 [SMILES: O=C(Nc1ccc2cc1CCc1cccc(c1)Nc1ncc(Cl)c(n1)N2)N[C@@H]1CCN(C(=O)c2ccccc2)C1]

The desired compound was prepared according to the procedure of Example B26, using N-[6-chloro-2,4,8,22-tetraazatetracyclo[14.3.1.1(3,7).1(9,13)]docosa-1(20),3(22),4,6,9(21),10,12,16,18-nonaen-12-yl]-N'-[(3R)-pyrrolidin-3-yl]urea dihydrochloride and benzoyl chloride as the starting materials in 18% yield. LCMS for $C_{30}H_{29}ClN_7O_2$(M+H)$^+$: m/z=554.1.

Example B177

N-[(3R)-1-Acetylpyrrolidin-3-yl]-N'-[6-chloro-2,4,8,22-tetraazatetracyclo[14.3.1.1(3,7).1(9,13)]docosa-1(20),3(22),4,6,9(21),10,12,16,18-nonaen-12-yl]urea trifluoroacetate

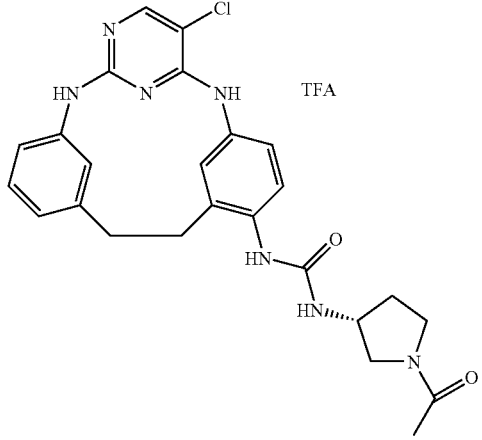 [SMILES: CC(=O)N1CC[C@@H](NC(=O)Nc2ccc3cc2CCc2cccc(c2)Nc2ncc(Cl)c(n2)N3)C1]

The desired compound was prepared according to the procedure of Example B26, using N-[6-chloro-2,4,8,22-tetraazatetracyclo[14.3.1.1(3,7).1(9,13)]docosa-1(20),3(22),4,6,9(21),10,12,16,18-nonaen-12-yl]-N'-[(3R)-pyrrolidin-3-yl]urea dihydrochloride and acetyl chloride as the starting materials in 18% yield. LCMS for $C_{25}H_{27}ClN_7O_2$(M+H)$^+$: m/z=492.1.

Example B178

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-[(3R)-1-(methylsulfonyl)pyrrolidin-3-yl]urea trifluoroacetate

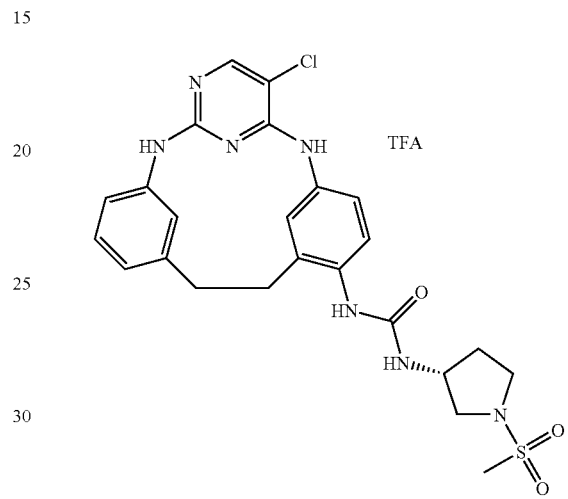

The desired compound was prepared according to the procedure of Example B136, using N-[6-chloro-2,4,8,22-tetraazatetracyclo[14.3.1.1(3,7).1(9,13)]docosa-1(20),3(22),4,6,9(21),10,12,16,18-nonaen-12-yl]-N'-[(3R)-pyrrolidin-3-yl]urea dihydrochloride as the starting material in 18% yield. LCMS for $C_{24}H_{27}ClN_7O_3S$ (M+H)$^+$: m/z=528.1.

Example B179

(3R)-3-[({[6-Chloro-2,4,8,22-tetraazatetracyclo[14.3.1.1(3,7).1(9,13)]docosa-1(20),3(22),4,6,9(21),10,12,16,18-nonaen-12-yl]amino}carbonyl)amino]pyrrolidine-1-sulfonamide trifluoroacetate

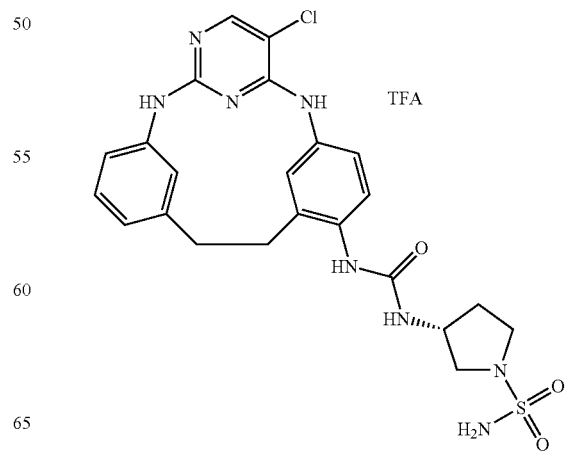

A suspension of N-[6-chloro-2,4,8,22-tetraazatetracyclo[14.3.1.1(3,7).1(9,13)]docosa-1(20),3(22),4,6,9(21),10,12,16,18-nonaen-12-yl]-N'-[(3R)-pyrrolidin-3-yl]urea dihydrochloride (15 mg, 0.029 mmol) and sulfamide (13.8 mg, 0.143 mmol) in pyridine (0.4 mL, 5 mmol) was heated to 130° C. for 3 minutes in a microwave reactor. The crude mixture was dissolved in methanol and purified by preparative LCMS to give the desired product (2.4 mg, 13%). LCMS for $C_{23}H_{26}ClN_8O_2S$ (M+H)$^+$: m/z=529.3.

Example B180 tert-Butyl 4-[({[6-chloro-2,4,8,22-tetraazatetracyclo[14.3.1.1(3,7).1(9,13)]docosa-1(20),3(22),4,6,9(21),10,12,16,18-nonaen-12-yl]amino}carbonyl)amino]piperidine-1-carboxylate

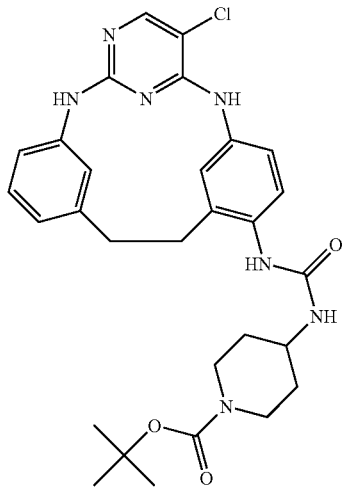 [SMILES: CC(C)(C)OC(=O)N1CCC(NC(=O)Nc2ccc3cc2CCc2cccc(c2)Nc2ncc(Cl)c(n2)N3)CC1]

The desired compound was prepared according to the procedure of Example B25 step A, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and tert-butyl 4-aminopiperidine-1-carboxylate as the starting materials in 33% yield. LCMS for $C_{29}H_{35}ClN_7O_3$(M+H)$^+$: m/z=564.4.

Example B181

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-piperidin-4-ylurea dihydrochloride

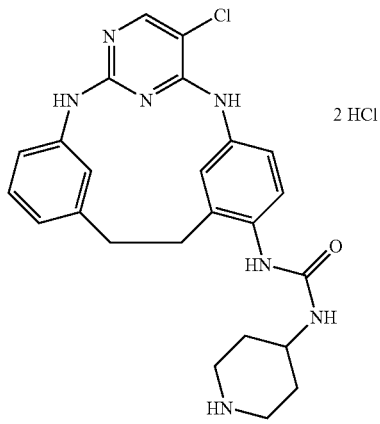 [SMILES: O=C(Nc1ccc2cc1CCc1cccc(c1)Nc1ncc(Cl)c(n1)N2)NC1CCNCC1 ; "2 HCl"]

The desired compound was prepared according to the procedure of Example B25 step B, using tert-butyl 4-[({[6-chloro-2,4,8,22-tetraazatetracyclo[14.3.1.1(3,7).1(9,13)]docosa-1(20),3(22),4,6,9(21),10,12,16,18-nonaen-12-yl]amino}carbonyl)amino]piperidine-1-carboxylate as the starting material in 30% yield. LCMS for $C_{24}H_{27}ClN_7O$ (M+H)$^+$: m/z=464.0.

Example B182

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-[1-(methylsulfonyl)piperidin-4-yl]urea trifluoroacetate

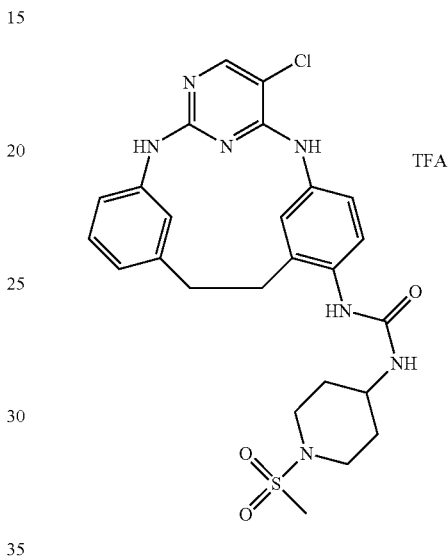

The desired compound was prepared according to the procedure of Example B136, using N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-piperidin-4-ylurea dihydrochloride as the starting material in 11% yield. LCMS for $C_{25}H_{29}ClN_7O_3S$ (M+H)$^+$: m/z=542.0.

Example B183

4-[({[6-Chloro-2,4,8,22-tetraazatetracyclo[14.3.1.1(3,7).1(9,13)]docosa-1(20),3(22),4,6,9(21),10,12,16,18-nonaen-12-yl]amino}carbonyl)amino]piperidine-1-sulfonamide trifluoroacetate

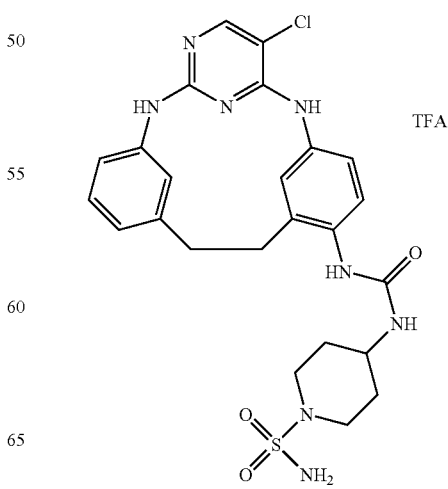

The desired compound was prepared according to the procedure of Example B179, using 4-[({[6-chloro-2,4,8,22-tetraazatetracyclo[14.3.1.1(3,7).1(9,13)]docosa-1(20),3(22),4,6,9(21),10,12,16,18-nonaen-12-yl]amino}carbonyl)amino]piperidine-1-sulfonamide trifluoroacetate as the starting material in 7% yield. LCMS for $C_{24}H_{28}ClN_8O_3S$ (M+H)$^+$: m/z=543.2.

Example B184

N-[6-Chloro-2,4,8,22-tetraazatetracyclo[14.3.1.1(3,7).1(9,13)]docosa-1(20),3(22),4,6,9(21),10,12,16,18-nonaen-12-yl]sulfamide trifluoroacetate

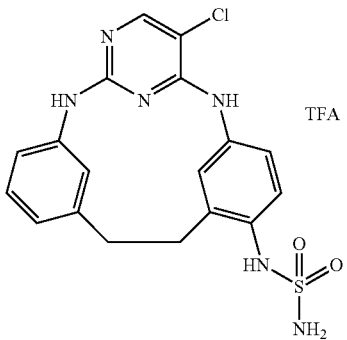 [SMILES: NS(=O)(=O)Nc1ccc2cc1CCc1cccc(c1)Nc1ncc(Cl)c(n1)N2]

The desired compound was prepared according to the procedure of Example B179, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride as the starting material in 25% yield. LCMS for $C_{18}H_{18}ClN_6O_2S$ (M+H)$^+$: m/z=417.2.

Example B185 tert-Butyl {2-[({[6-chloro-2,4,8,22-tetraazatetracyclo[14.3.1.1(3,7).1(9,13)]docosa-1(20),3(22),4,6,9(21),10,12,16,18-nonaen-12-yl]amino}carbonyl)amino]ethyl}carbamate

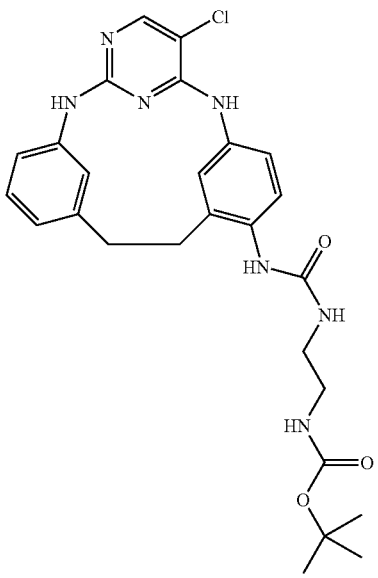 [SMILES: CC(C)(C)OC(=O)NCCNC(=O)Nc1ccc2cc1CCc1cccc(c1)Nc1ncc(Cl)c(n1)N2]

To a solution of 6-chloro-2,4,8,22-tetraazatetracyclo[14.3.1.1(3,7).1(9,13)]docosa-1(20),3(22),4,6,9(21),10,12,16,18-nonaen-12-amine dihydrochloride (314 mg, 0.764 mmol) in DCM (3.4 mL) were added N,N-diisopropylethylamine (0.53 mL, 3.1 mmol) and 20% phosgene in toluene (0.53 mL, 0.99 mmol). After stirring for 2 hours, N-(2-aminoethyl)(tert-butoxy)carboxamide (0.182 mL, 1.15 mmol) was added to reaction flask and stirred overnight. The resulting precipitate was filtered and washed with DCM to yield the desired product (326 mg, 81%). LCMS calculated for $C_{26}H_{31}ClN_7O_3$(M+H)$^+$: m/z=524.3.

Example B186

N-{2-[({[6-Chloro-2,4,8,22-tetraazatetracyclo[14.3.1.1(3,7).1(9,13)]docosa-1(20),3(22),4,6,9(21),10,12,16,18-nonaen-12-yl]amino}carbonyl)amino]ethyl}acetamide trifluoroacetate

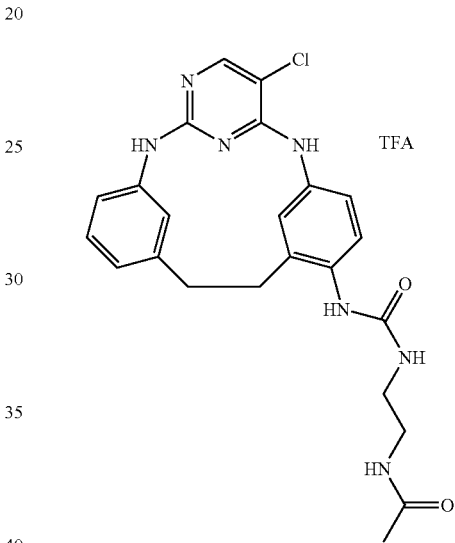

Step A: N-(2-Aminoethyl)-N'-[6-chloro-2,4,8,22-tetraazatetracyclo[14.3.1.1(3,7).1(9,13)]docosa-1(20),3(22),4,6,9(21),10,12,16,18-nonaen-12-yl]urea dihydrochloride

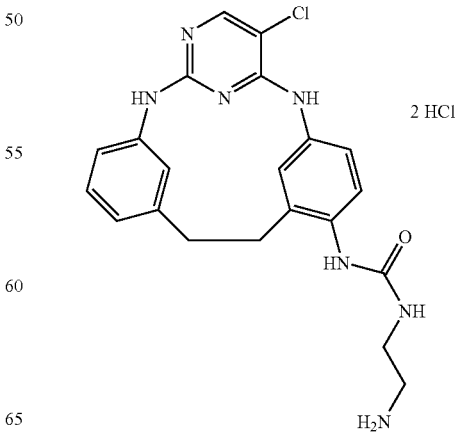

To a solution of tert-butyl {2-[({[6-chloro-2,4,8,22-tetraazatetracyclo[14.3.1.1(3,7).1(9,13)]docosa-1(20),3(22),4,6,9(21),10,12,16,18-nonaen-12-yl]amino}carbonyl)amino]ethyl}carbamate (326 mg, 0.622 mmol) in DCM (12 mL) was added 4.0 M of hydrogen chloride in 1,4-dioxane (0.544 mL, 2.18 mmol). After stirring overnight, the reaction solution was diluted with ether. The resulting precipitate was filtered and dried under vacuum to give the desired product (245 mg, 79%). LCMS calculated for $C_{21}H_{23}ClN_7O$ (M+H)$^+$: m/z=424.2.

Step B: N-{2-[({[6-chloro-2,4,8,22-tetraazatetracyclo[14.3.1.1(3,7).1(9,13)]docosa-1(20),3(22),4,6,9(21),10,12,16,18-nonaen-12-yl]amino}carbonyl)amino]ethyl}acetamide trifluoroacetate The desired compound was prepared according to the procedure of Example B26, using N-(2-aminoethyl)-N'-[6-chloro-2,4,8,22-tetraazatetracyclo[14.3.1.1(3,7).1(9,13)]docosa-1(20),3(22),4,6,9(21),10,12,16,18-nonaen-12-yl]urea dihydrochloride and acetyl chloride as the starting materials in 48% yield. LCMS for $C_{23}H_{25}ClN_7O_2$(M+H)$^+$: m/z=466.2.

Example B187

N-{2-[({[6-Chloro-2,4,8,22-tetraazatetracyclo[14.3.1.1(3,7).1(9,13)]docosa-1(20),3(22),4,6,9(21),10,12,16,18-nonaen-12-yl]amino}carbonyl)amino]ethyl}methanesulfonamide trifluoroacetate

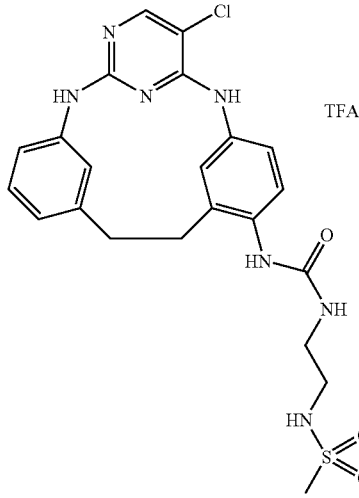

The desired compound was prepared according to the procedure of Example B136, using N-(2-aminoethyl)-N'-[6-chloro-2,4,8,22-tetraazatetracyclo[14.3.1.1(3,7).1(9,13)]docosa-1(20),3(22),4,6,9(21),10,12,16,18-nonaen-12-yl] urea dihydrochloride as the starting material in 38% yield. LCMS for $C_{22}H_{25}ClN_7O_3S$ (M+H)$^+$: m/z=502.2.

Example B188

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-(2-{[(isopropylamino)carbonyl]amino}ethyl)urea trifluoroacetate

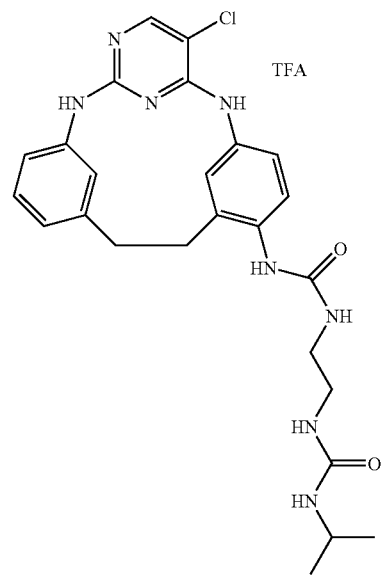 [SMILES: CC(C)NC(=O)NCCNC(=O)Nc1ccc2cc1CCc1cccc(c1)Nc1ncc(Cl)c(n1)N2]

The desired compound was prepared according to the procedure of Example B83, using N-(2-aminoethyl)-N'-[6-chloro-2,4,8,22-tetraazatetracyclo[14.3.1.1(3,7).1(9,13)]docosa-1(20),3(22),4,6,9(21),10,12,16,18-nonaen-12-yl] urea dihydrochloride and 2-isocyanatopropane as the starting materials in 24% yield. LCMS for $C_{25}H_{30}ClN_8O_2$(M+H)$^+$: m/z=509.5.

Example B189

N-{2-[({[6-Chloro-2,4,8,22-tetraazatetracyclo[14.3.1.1(3,7).1(9,13)]docosa-1(20),3(22),4,6,9(21),10,12,16,18-nonaen-12-yl]amino}carbonyl)amino]ethyl}benzamide trifluoroacetate

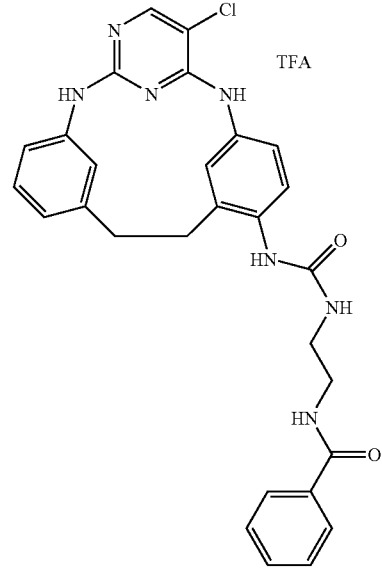 [SMILES: O=C(NCCNC(=O)c1ccccc1)Nc1ccc2cc1CCc1cccc(c1)Nc1ncc(Cl)c(n1)N2]

The desired compound was prepared according to the procedure of Example B26, using N-(2-aminoethyl)-N'-[6-chloro-2,4,8,22-tetraazatetracyclo[14.3.1.1(3,7).1(9,13)]docosa-1(20),3(22),4,6,9(21),10,12,16,18-nonaen-12-yl] urea dihydrochloride and benzoyl chloride as the starting materials in 18% yield. LCMS for $C_{28}H_{27}ClN_7O_2(M+H)^+$: m/z=528.5.

Example B190

N-{2-[({[6-Chloro-2,4,8,22-tetraazatetracyclo[14.3.1.1(3,7).1(9,13)]docosa-1(20),3(22),4,6,9(21),10,12,16,18-nonaen-12-yl]amino}carbonyl)amino]ethyl}pyridine-2-carboxamide trifluoroacetate

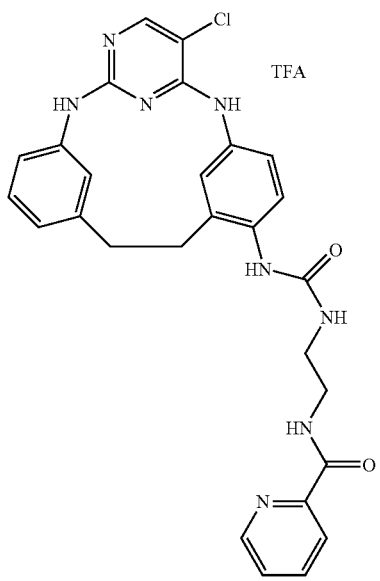 [SMILES: O=C(NCCNC(=O)c1ccccn1)Nc1ccc2cc1CCc1cccc(c1)Nc1ncc(Cl)c(n1)N2]

The desired compound was prepared according to the procedure of Example B26, using N-(2-aminoethyl)-N'-[6-chloro-2,4,8,22-tetraazatetracyclo[14.3.1.1(3,7).1(9,13)]docosa-1(20),3(22),4,6,9(21),10,12,16,18-nonaen-12-yl] urea dihydrochloride and pyridine-2-carbonyl chloride as the starting materials in 12% yield. LCMS for $C_{27}H_{26}ClN_8O_2$ $(M+H)^+$: m/z=529.3.

Example B191

6-Chloro-11-(piperazin-1-ylmethyl)-2,4,8,22-tetraazatetracyclo[14.3.1.1(3,7).1(9,13)]docosa-1(20),3(22),4,6,9(21),10,12,16,18-nonaene dihydrochloride

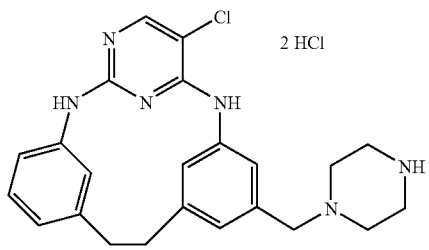 [SMILES: Clc1cnc2nc1Nc1cc(cc(CN3CCNCC3)c1)CCc1cccc(c1)N2 ; "2 HCl"]

Step A: tert-Butyl 4-{[6-chloro-2,4,8,22-tetraazatetracyclo[14.3.1.1(3,7).1(9,13)]docosa-1(20),3(22),4,6,9(21),10,12,16,18-nonaen-11-yl]methyl}piperazine-1-carboxylate

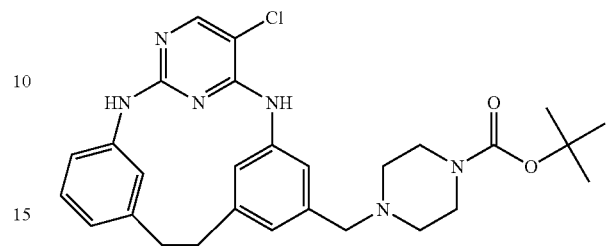

To a solution of [6-chloro-2,4,8,22-tetraazatetracyclo[14.3.1.1(3,7).1(9,13)]docosa-1(20),3(22),4,6,9(21),10,12,16,18-nonaen-11-yl]methanol trifluoroacetate (0.731 g, 1.56 mmol) in THF (15 mL) was added methanesulfonyl chloride (151 µL, 1.95 mmol) and N,N-diisopropylethylamine (0.93 mL, 5.32 mmol) at 0° C. The resulting reaction solution was stirred at same temperature for 2 hours. The reaction solution was diluted with DMF (8 mL) and N-tert-butoxycarbonylpiperazine (396 mg, 2.13 mmol) was added, followed by N,N-diisopropylethylamine (0.818 mL, 4.70 mmol). The reaction solution was stirred at 40° C. overnight. The reaction solution was diluted with 1 N HCl solution and ethyl acetate and the aqueous layer was extracted with ethyl acetate once. The aqueous layer was neutralized with 50% NaOH solution to pH 10, and then extracted with EtOAc twice. The combined organic solutions were dried over sodium sulfate, filtered and concentrated. The residue was purified by flash column chromatography to yield the desired product (410 mg, 50%). LCMS calculated for $C_{28}H_{34}ClN_6O_2(M+H)^+$: m/z=521.2.

Step B: 6-Chloro-11-(piperazin-1-ylmethyl)-2,4,8,22-tetraazatetracyclo[14.3.1.1(3,7).1(9,13)]docosa-1(20),3(22),4,6,9(21),10,12,16,18-nonaene dihydrochloride The desired compound was prepared according to the procedure of Example B186 step A, using tert-butyl 4-{[6-chloro-2,4,8,22-tetraazatetracyclo[14.3.1.1(3,7).1(9,13)]docosa-1(20),3(22),4,6,9(21),10,12,16,18-nonaen-11-yl]methyl}piperazine-1-carboxylate as the starting materials in 98% yield. LCMS for $C_{23}H_{26}ClN_6(M+H)^+$: m/z=421.2.

Example B192

6-Chloro-11-{[4-(4-fluorobenzyl)piperazin-1-yl]methyl}-2,4,8,22-tetraazatetracyclo[14.3.1.1(3,7).1(9,13)]docosa-1(20),3(22),4,6,9(21),10,12,16,18-nonaene tris(trifluoroacetate)

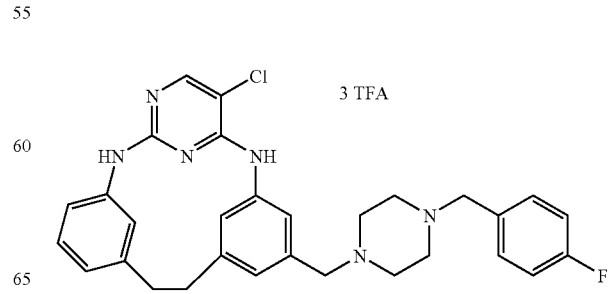

To a mixture of 6-chloro-11-(piperazin-1-ylmethyl)-2,4,8,22-tetraazatetracyclo[14.3.1.1(3,7).1(9,13)]docosa-1(20),3(22),4,6,9(21),10,12,16,18-nonaene dihydrochloride (37.1 mg, 75.1 μmol) and 4-fluorobenzaldehyde (12 μL, 110 μmol) in DMF (0.5 mL) was added sodium triacetoxyborohydride (32 mg, 0.15 mmol). The reaction was stirred at room temperature overnight. The reaction solution was diluted with methanol and purified by preparative LCMS to give the desired product as white solid (15.3 mg, 23%). LCMS calculated for $C_{30}H_{31}ClFN_6(M+H)^+$: m/z=529.3. $^1$H NMR (400 MHz, DMSO-$d_6$): δ 9.65 (s, 1H), 9.44 (s, 1H), 8.19 (s, 1H), 7.85 (m, 2H), 7.46 (m, 2H), 7.25 (m, 2H), 7.13 (m, 3H), 6.91 (m, 1H), 6.86 (m, 1H), 4.11 (bd, 4H), 3.13 (bs, 8H), 2.87 (m, 4H).

Example B193

6-Chloro-11-({4-[4-(pyrimidin-2-yloxy)benzyl]piperazin-1-yl}methyl)-2,4,8,22-tetraazatetracyclo[14.3.1.1(3,7).1(9,13)]docosa-1(20),3(22),4,6,9(21),10,12,16,18-nonaene tris(trifluoroacetate)

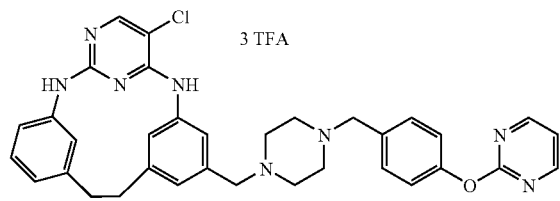 [SMILES: Clc1cnc2nc1Nc1cc(cc(CN3CCN(Cc4ccc(Oc5ncccn5)cc4)CC3)c1)CCc1cccc(c1)N2]

The desired compound was prepared according to the procedure of Example B192, using 6-chloro-11-(piperazin-1-ylmethyl)-2,4,8,22-tetraazatetracyclo[14.3.1.1(3,7).1(9,13)]docosa-1(20),3(22),4,6,9(21),10,12,16,18-nonaene dihydrochloride and 4-(pyrimidin-2-yloxy)benzaldehyde as the starting materials in 50% yield. LCMS for $C_{34}H_{34}ClN_8O$ $(M+H)^+$: m/z=605.3.

Example B194

6-Chloro-11-{[4-(4-nitrobenzyl)piperazin-1-yl]methyl}-2,4,8,22-tetraazatetracyclo[14.3.1.1(3,7).1(9,13)]docosa-1(20),3(22),4,6,9(21),10,12,16,18-nonaene tris(trifluoroacetate)

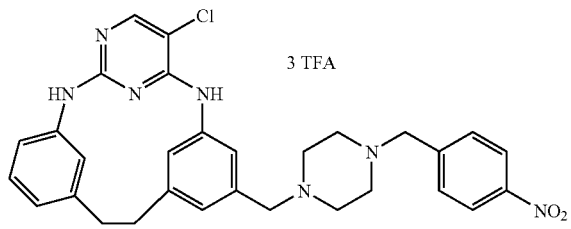 [SMILES: O=[N+]([O-])c1ccc(CN2CCN(Cc3cc4cc(c3)Nc3nc(ncc3Cl)Nc3cccc(c3)CC4)CC2)cc1]

The desired compound was prepared according to the procedure of Example B192, using 6-chloro-11-(piperazin-1-ylmethyl)-2,4,8,22-tetraazatetracyclo[14.3.1.1(3,7).1(9,13)]docosa-1(20),3(22),4,6,9(21),10,12,16,18-nonaene dihydrochloride and p-nitrobenzaldehyde as the starting materials in 41% yield. LCMS for $C_{30}H_{31}ClN_7O_2(M+H)^+$: m/z=556.3.

Example B195

6-Chloro-11-[(4-{4-[(4-chlorophenyl)sulfonyl]benzyl}piperazin-1-yl)methyl]-2,4,8,22-tetraazatetracyclo[14.3.1.1(3,7).1(9,13)]docosa-1(20),3(22),4,6,9(21),10,12,16,18-nonaene tris(trifluoroacetate)

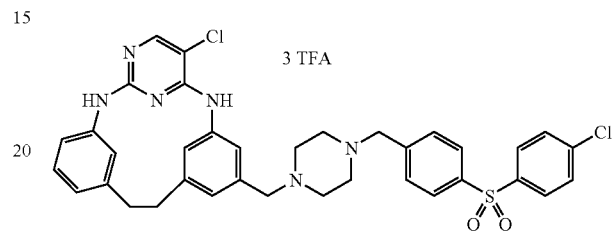

The desired compound was prepared according to the procedure of Example B192, using 6-chloro-11-(piperazin-1-ylmethyl)-2,4,8,22-tetraazatetracyclo[14.3.1.1(3,7).1(9,13)]docosa-1(20),3(22),4,6,9(21),10,12,16,18-nonaene dihydrochloride and 4-[(4-chlorophenyl)sulfonyl]benzaldehyde as the starting materials in 28% yield. LCMS for $C_{36}H_{35}Cl_2N_6O_2S$ $(M+H)^+$: m/z=685.3, 687.3.

Example B196

11-({4-[(4-Bromo-2-thienyl)methyl]piperazin-1-yl}methyl)-6-chloro-2,4,8,22-tetraazatetracyclo[14.3.1.1(3,7).1(9,13)]docosa-1(20),3(22),4,6,9(21),10,12,16,18-nonaene tris(trifluoroacetate)

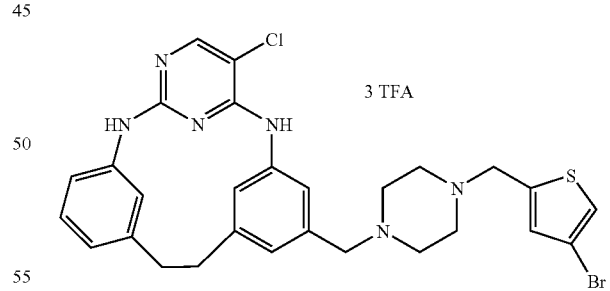

The desired compound was prepared according to the procedure of Example B192, using 6-chloro-11-(piperazin-1-ylmethyl)-2,4,8,22-tetraazatetracyclo[14.3.1.1(3,7).1(9,13)]docosa-1(20),3(22),4,6,9(21),10,12,16,18-nonaene dihydrochloride and 4-bromothiophene-2-carbaldehyde as the starting materials in 29% yield. LCMS for $C_{28}H_{29}BrClN_6S$ $(M+H)^+$: m/z=595.2. $^1$H NMR (400 MHz, DMSO-$d_6$): δ 9.46 (s, 1H), 9.30 (s, 1H), 8.15 (s, 1H), 7.87 (m, 2H), 7.64 (s, 1H), 7.14 (m, 4H), 6.92 (m, 1H), 6.84 (m, 1H), 4.20 (bs, 2H), 3.89 (bs, 2H), 3.30 (bs, 2H), 3.01 (bs, 4H), 2.87 (m, 6H).

Example B197

6-Chloro-11-{[4-(4-methoxybenzyl)piperazin-1-yl]methyl}-2,4,8,22-tetraazatetracyclo[14.3.1.1(3,7).1(9,13)]docosa-1(20),3(22),4,6,9(21),10,12,16,18-nonaene tris(trifluoroacetate)

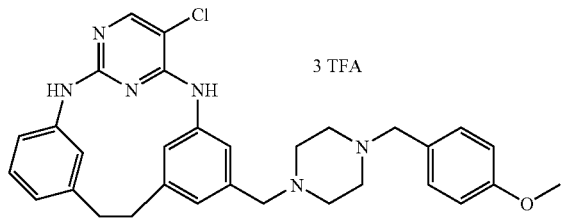 [SMILES: COc1ccc(CN2CCN(Cc3cc4cc(c3)Nc3nc(ncc3Cl)Nc3cccc(c3)CC4)CC2)cc1]

The desired compound was prepared according to the procedure of Example B192, using 6-chloro-11-(piperazin-1-ylmethyl)-2,4,8,22-tetraazatetracyclo[14.3.1.1(3,7).1(9,13)]docosa-1(20),3(22),4,6,9(21),10,12,16,18-nonaene dihydrochloride and 4-methoxybenzaldehyde as the starting materials in 32% yield. LCMS for $C_{31}H_{34}ClN_6O$ (M+H)$^+$: m/z=541.3.

Example B198

6-Chloro-11-{[4-(3-methoxybenzyl)piperazin-1-yl]methyl}-2,4,8,22-tetraazatetracyclo[14.3.1.1(3,7).1(9,13)]docosa-1(20),3(22),4,6,9(21),10,12,16,18-nonaene tris(trifluoroacetate)

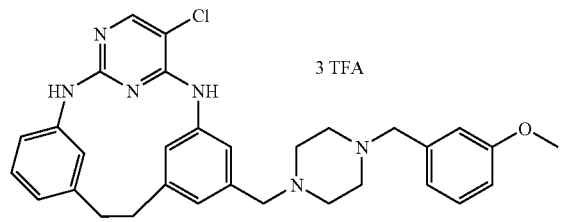 [SMILES: COc1cccc(CN2CCN(Cc3cc4cc(c3)Nc3nc(ncc3Cl)Nc3cccc(c3)CC4)CC2)c1]

The desired compound was prepared according to the procedure of Example B192, using 6-chloro-11-(piperazin-1-ylmethyl)-2,4,8,22-tetraazatetracyclo[14.3.1.1(3,7).1(9,13)]docosa-1(20),3(22),4,6,9(21),10,12,16,18-nonaene dihydrochloride and 3-methoxybenzaldehyde as the starting materials in 41% yield. LCMS for $C_{31}H_{34}ClN_6O$ (M+H)$^+$: m/z=541.3.

Example B199

6-Chloro-11-{[4-(4-chlorobenzyl)piperazin-1-yl]methyl}-2,4,8,22-tetraazatetracyclo[14.3.1.1(3,7).1(9,13)]docosa-1(20),3(22),4,6,9(21),10,12,16,18-nonaene tris(trifluoroacetate)

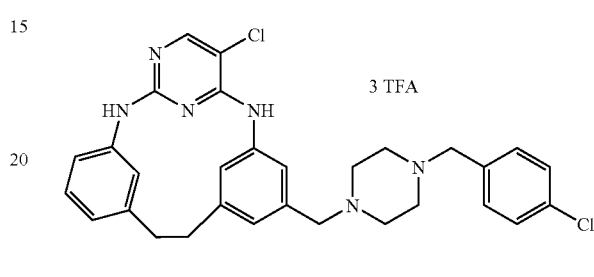

The desired compound was prepared according to the procedure of Example B192, using 6-chloro-11-(piperazin-1-ylmethyl)-2,4,8,22-tetraazatetracyclo[14.3.1.1(3,7).1(9,13)]docosa-1(20),3(22),4,6,9(21),10,12,16,18-nonaene dihydrochloride and 4-chlorobenzaldehyde as the starting materials in 30% yield. LCMS for $C_{30}H_{31}Cl_2N_6$(M+H)$^+$: m/z=545.3, 547.3.

Example B200

6-Chloro-N-phenyl-2,4,8,22-tetraazatetracyclo[14.3.1.1(3,7).1(9,13)]docosa-1(20),3(22),4,6,9(21),10,12,16,18-nonaene-12-carboxamide trifluoroacetate

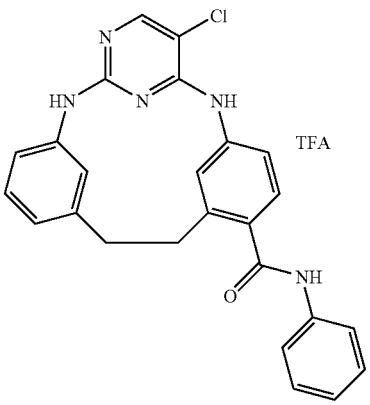 [SMILES: O=C(Nc1ccccc1)c1ccc2cc1CCc1cccc(c1)Nc1ncc(Cl)c(n1)N2]

The desired compound was prepared according to the procedure of Example B7, using methyl 6-chloro-2,4,8,22-tetraazatetracyclo[14.3.1.1(3,7).1(9,13)]docosa-1(20),3(22),4,6,9(21),10,12,16,18-nonaene-12-carboxylate and aniline as the starting materials in 51% yield. LCMS for $C_{25}H_{21}ClN_5O$ (M+H)$^+$: m/z=442.1. $^1$H NMR (400 MHz, DMSO-d$_6$): δ 10.32 (s, 1H), 9.38 (s, 1H), 9.32 (s, 1H), 8.14 (s, 1H), 8.05 (m, 1H), 7.90 (m, 1H), 7.74 (m, 2H), 7.41 (d, 1H), 7.32 (m, 2H), 7.17 (dd, 1H), 7.08 (m, 2H), 6.88 (m, 1H), 6.76 (m, 1H), 3.05 (m, 2H), 2.93 (m, 2H).

Example B201 I

N-[6-Chloro-2,4,8,22-tetraazatetracyclo[14.3.1.1(3,7).1(9,13)]docosa-1(20),3(22),4,6,9(21),10,12,16,18-nonaen-11-yl]pyridine-2-carboxamide trifluoroacetate

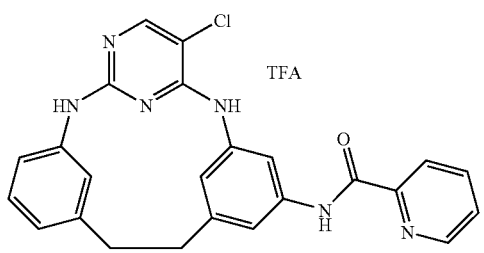 [SMILES: O=C(Nc1cc2cc(c1)Nc1nc(ncc1Cl)Nc1cccc(c1)CC2)c1ccccn1]

The desired compound was prepared according to the procedure of Example B26, using 6-chloro-2,4,8,22-tetraazatetracyclo[14.3.1.1(3,7).1(9,13)]docosa-1(20),3(22),4,6,9(21), 10,12,16,18-nonaen-11-amine bis(trifluoroacetate) and pyridine-2-carbonyl chloride as the starting materials in 35% yield. LCMS for $C_{24}H_{20}ClN_6O$ (M+H)$^+$: m/z=443.2. $^1H$ NMR (400 MHz, DMSO-$d_6$): δ 10.54 (s, 1H), 9.51 (s, 2H), 8.72 (m, 1H), 8.16 (s, 1H), 8.13 (m, 1H), 8.05 (m, 1H), 7.92 (m, 1H), 7.75 (m, 1H), 7.66 (m, 1H), 7.49 (m, 1H), 7.45 (m, 1H), 7.11 (dd, 1H), 6.89 (m, 1H), 6.84 (m, 1H), 2.89 (m, 4H).

Example B202

N-[6-Chloro-2,4,8,22-tetraazatetracyclo[14.3.1.1(3,7).1(9,13)]docosa-1(20),3(22),4,6,9(21),10,12,16,18-nonaen-11-yl]-N'-phenylurea trifluoroacetate

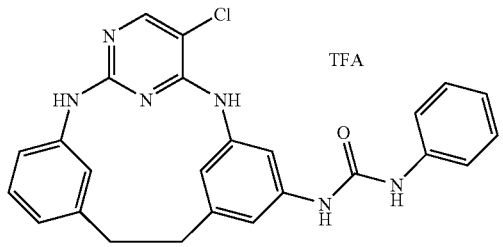 [SMILES: O=C(Nc1ccccc1)Nc1cc2cc(c1)Nc1nc(ncc1Cl)Nc1cccc(c1)CC2]

The desired compound was prepared according to the procedure of Example B83, using 6-chloro-2,4,8,22-tetraazatetracyclo[14.3.1.1(3,7).1(9,13)]docosa-1(20),3(22),4,6,9(21), 10,12,16,18-nonaen-11-amine bis(trifluoroacetate) and phenyl isocyanate as the starting materials in 28% yield. LCMS for $C_{25}H_{22}ClN_6O$ (M+H)$^+$: m/z=457.2. $^1H$ NMR (400 MHz, DMSO-$d_6$): δ 9.39 (s, 1H), 9.28 (s, 1H), 8.69 (s, 1H), 8.64 (s, 1H), 8.08 (s, 1H), 7.90 (m, 1H), 7.40 (m, 2H), 7.31 (m, 1H), 7.22 (m, 3H), 7.06 (dd, 1H), 7.01 (m, 1H), 6.89 (m, 2H), 6.78 (m, 1H), 2.80 (m, 4H).

Example B203

N-[6-Chloro-2,4,8,22-tetraazatetracyclo[14.3.1.1(3,7).1(9,13)]docosa-1(20),3(22),4,6,9(21),10,12,16,18-nonaen-11-yl]benzenesulfonamide trifluoroacetate

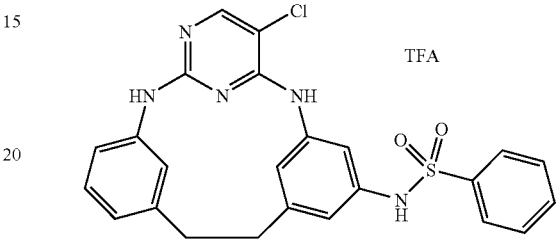

The desired compound was prepared according to the procedure of Example B136, using 6-chloro-2,4,8,22-tetraazatetracyclo[14.3.1.1(3,7).1(9,13)]docosa-1(20),3(22),4,6,9 (21),10,12,16,18-nonaen-11-amine bis(trifluoroacetate) and benzenesulfonyl chloride as the starting materials in 42% yield. LCMS for $C_{24}H_{21}ClN_5O_2S$ (M+H)$^+$: m/z=478.1. $^1H$ NMR (400 MHz, DMSO-$d_6$): δ 10.24 (s, 1H), 9.55 (s, 1H), 9.50 (s, 1H), 8.15 (s, 1H), 7.76 (m, 3H), 7.50 (m, 3H), 7.40 (m, 1H), 7.10 (dd, 1H), 6.94 (m, 1H), 6.88 (m, 1H), 6.80 (m, 1H), 6.69 (m, 1H), 2.74 (m, 4H).

Example B204

N-[6-Chloro-2,4,8,22-tetraazatetracyclo[14.3.1.1(3,7).1(9,13)]docosa-1(20),3(22),4,6,9(21),10,12,16,18-nonaen-11-yl]-1,3-benzothiazole-2-carboxamide trifluoroacetate

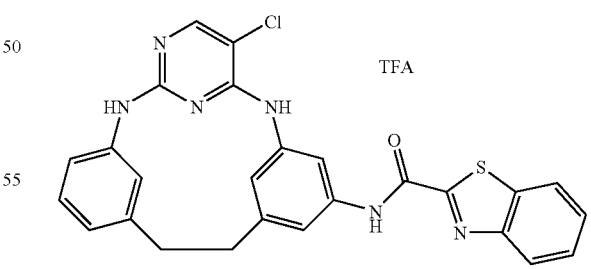

The desired compound was prepared according to the procedure of Example B26, using 6-chloro-2,4,8,22-tetraazatetracyclo[14.3.1.1(3,7).1(9,13)]docosa-1(20),3(22),4,6,9(21), 10,12,16,18-nonaen-1-amine bis(trifluoroacetate) and 1,3-benzothiazole-2-carbonyl chloride as the starting materials in 43% yield. LCMS for $C_{26}H_{20}ClN_6OS$ (M+H)$^+$: m/z=499.2. $^1H$ NMR (400 MHz, DMSO-$d_6$): δ 11.06 (s, 1H), 9.38 (s, 2H), 8.25 (m, 2H), 8.13 (s, 1H), 7.94 (m, 1H), 7.62 (m, 5H), 7.11 (dd, 1H), 6.89 (m, 1H), 6.83 (m, 1H), 2.88 (m, 4H).

Example B205

N-[6-Chloro-2,4,8,22-tetraazatetracyclo[14.3.1.1(3,7).1(9,13)]docosa-1(20),3(22),4,6,9(21),10,12,16,18-nonaen-11-yl]-5-methylisoxazole-3-carboxamide trifluoroacetate

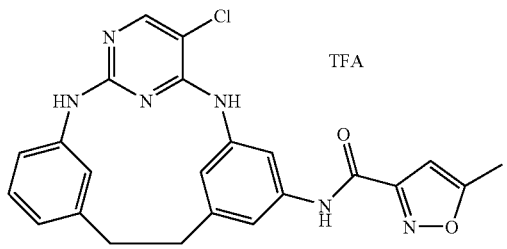 [SMILES: Cc1cc(C(=O)Nc2cc3cc(c2)Nc2nc(ncc2Cl)Nc2cccc(c2)CC3)no1]

The desired compound was prepared according to the procedure of Example B26, using 6-chloro-2,4,8,22-tetraazatetracyclo[14.3.1.1(3,7).1(9,13)]docosa-1(20),3(22),4,6,9(21),10,12,16,18-nonaen-11-amine bis(trifluoroacetate) and 5-methylisoxazole-3-carbonyl chloride as the starting materials in 42% yield. LCMS for $C_{23}H_{20}ClN_6O_2(M+H)^+$: m/z=447.2. $^1$H NMR (400 MHz, DMSO-$d_6$): δ 10.59 (s, 1H), 9.59 (s, 2H), 8.17 (s, 1H), 7.88 (m, 1H), 7.59 (m, 1H), 7.49 (m, 1H), 7.35 (m, 1H), 7.11 (dd, 1H), 6.89 (m, 1H), 6.84 (m, 1H), 6.64 (m, 1H), 2.88 (m, 4H), 2.48 (s, 3H).

Example B206

N-[6-Chloro-2,4,8,22-tetraazatetracyclo[14.3.1.1(3,7).1(9,13)]docosa-1(20),3(22),4,6,9(21),10,12,16,18-nonaen-11-yl]isoxazole-5-carboxamide trifluoroacetate

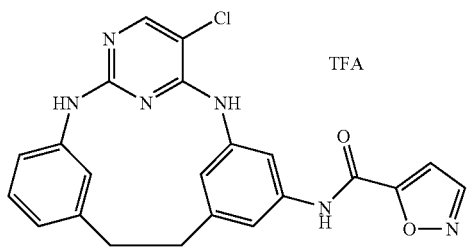 [SMILES: O=C(Nc1cc2cc(c1)Nc1nc(ncc1Cl)Nc1cccc(c1)CC2)c1ccno1]

The desired compound was prepared according to the procedure of Example B26, using 6-chloro-2,4,8,22-tetraazatetracyclo[14.3.1.1(3,7).1(9,13)]docosa-1(20),3(22),4,6,9(21),10,12,16,18-nonaen-11-amine bis(trifluoroacetate) and isoxazole-5-carbonyl chloride as the starting materials in 45% yield. LCMS for $C_{22}H_{18}ClN_6O_2(M+H)^+$: m/z=433.1. $^1$H NMR (400 MHz, DMSO-$d_6$): δ 10.65 (s, 1H), 9.49 (s, 1H), 8.75 (d, 1H), 8.12 (s, 1H), 7.84 (m, 1H), 7.56 (m, 1H), 7.48 (m, 1H), 7.27 (m, 1H), 7.20 (d, 1H), 7.06 (dd, 1H), 6.85 (m, 1H), 6.82 (m, 1H), 2.84 (m, 4H).

Example B207

N-[6-Chloro-2,4,8,22-tetraazatetracyclo[14.3.1.1(3,7).1(9,13)]docosa-1(20),3(22),4,6,9(21),10,12,16,18-nonaen-11-yl]-1-methyl-1H-pyrazole-3-carboxamide trifluoroacetate

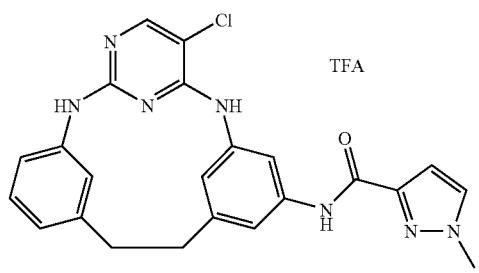 [SMILES: Cn1ccc(C(=O)Nc2cc3cc(c2)Nc2nc(ncc2Cl)Nc2cccc(c2)CC3)n1]

The desired compound was prepared according to the procedure of Example B26, using 6-chloro-2,4,8,22-tetraazatetracyclo[14.3.1.1(3,7).1(9,13)]docosa-1(20),3(22),4,6,9(21),10,12,16,18-nonaen-11-amine bis(trifluoroacetate) and 1-methyl-1H-pyrazole-3-carbonyl chloride as the starting materials in 47% yield. LCMS for $C_{23}H_{21}ClN_7O$ (M+H)$^+$: m/z=446.2. $^1$H NMR (400 MHz, DMSO-$d_6$): δ 9.93 (s, 1H), 9.76 (s, 1H), 9.70 (s, 1H), 8.20 (s, 1H), 7.88 (m, 1H), 7.82 (d, 1H), 7.64 (m, 1H), 7.42 (m, 1H), 7.36 (m, 1H), 7.11 (dd, 1H), 6.87 (m, 2H), 6.73 (d, 1H), 3.94 (s, 3H), 2.86 (m, 4H).

Example B208

N-[6-Chloro-2,4,8,22-tetraazatetracyclo[14.3.1.1(3,7).1(9,13)]docosa-1(20),3(22),4,6,9(21),10,12,16,18-nonaen-11-yl]-1-methyl-1H-imidazole-5-carboxamide trifluoroacetate

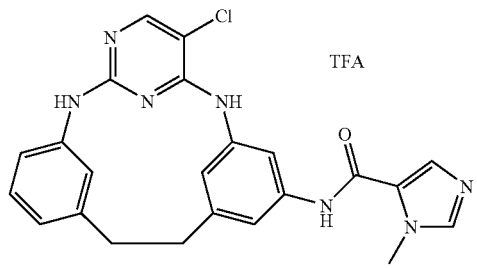 [SMILES: Cn1cncc1C(=O)Nc1cc2cc(c1)Nc1nc(ncc1Cl)Nc1cccc(c1)CC2]

The desired compound was prepared according to the procedure of Example B26, using 6-chloro-2,4,8,22-tetraazatetracyclo[14.3.1.1(3,7).1(9,13)]docosa-1(20),3(22),4,6,9(21), 10,12,16,18-nonaen-11-amine bis(trifluoroacetate) and 1-methyl-1H-imidazole-5-carbonyl chloride hydrochloride as the starting materials in 29% yield. LCMS for C$_{23}$H$_{21}$ClN$_7$O (M+H)$^+$: m/z=446.2.

Example B209

N-[6-Chloro-2,4,8,22-tetraazatetracyclo[14.3.1.1(3,7).1(9,13)]docosa-1(20),3(22),4,6,9(21),10,12,16,18-nonaen-11-yl]-1,3-thiazole-2-carboxamide trifluoroacetate

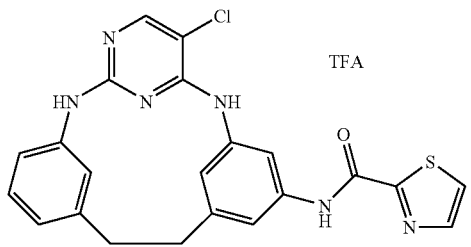 [SMILES: O=C(Nc1cc2cc(c1)Nc1nc(ncc1Cl)Nc1cccc(c1)CC2)c1nccs1]

The desired compound was prepared according to the procedure of Example B26, using 6-chloro-2,4,8,22-tetraazatetracyclo[14.3.1.1(3,7).1(9,13)]docosa-1(20),3(22),4,6,9(21),10,12,16,18-nonaen-11-amine bis(trifluoroacetate) and 1,3-thiazole-2-carbonyl chloride as the starting materials in 37% yield. LCMS for C$_{22}$H$_{18}$ClN$_6$OS (M+H)$^+$: m/z=449.2. $^1$H NMR (400 MHz, DMSO-d$_6$): δ 10.67 (s, 1H), 9.57 (m, 2H), 8.13 (s, 1H), 8.07 (m, 2H), 7.84 (m, 1H), 7.60 (m, 1H), 7.45 (m, 1H), 7.40 (m, 1H), 7.07 (dd, 1H), 6.85 (m, 2H), 2.84 (m, 4H).

Example B210

N-[6-Chloro-2,4,8,22-tetraazatetracyclo[14.3.1.1(3,7).1(9,13)]docosa-1(20),3(22),4,6,9(21),10,12,16,18-nonaen-11-yl]-4-methyl-1,3-oxazole-5-carboxamide trifluoroacetate

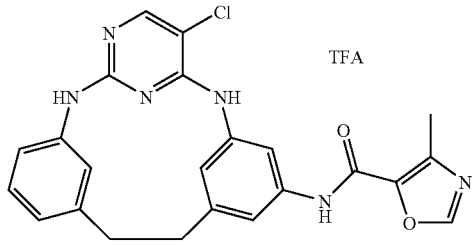 [SMILES: Cc1ncoc1C(=O)Nc1cc2cc(c1)Nc1nc(ncc1Cl)Nc1cccc(c1)CC2]

The desired compound was prepared according to the procedure of Example B26, using 6-chloro-2,4,8,22-tetraazatetracyclo[14.3.1.1(3,7).1(9,13)]docosa-1(20),3(22),4,6,9(21),10,12,16,18-nonaen-11-amine bis(trifluoroacetate) and 4-methyl-1,3-oxazole-5-carbonyl chloride as the starting materials in 55% yield. LCMS for C$_{23}$H$_{20}$ClN$_6$O$_2$(M+H)$^+$: m/z=447.2. $^1$H NMR (400 MHz, DMSO-d$_6$): δ 10.20 (s, 1H), 9.69 (s, 1H), 9.63 (s, 1H), 8.48 (d, 1H), 8.15 (s, 1H), 7.82 (m, 1H), 7.55 (m, 1H), 7.43 (m, 1H), 7.29 (m, 1H), 7.07 (dd, 1H), 6.84 (m, 2H), 2.84 (m, 4H), 2.36 (s, 3H).

Example B211

N-[6-Chloro-2,4,8,22-tetraazatetracyclo[14.3.1.1(3,7).1(9,13)]docosa-1(20),3(22),4,6,9(21),10,12,16,18-nonaen-11-yl]cyclobutanecarboxamide trifluoroacetate

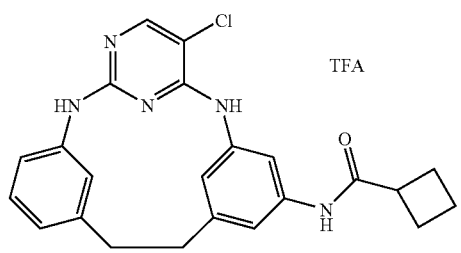 [SMILES: O=C(Nc1cc2cc(c1)Nc1nc(ncc1Cl)Nc1cccc(c1)CC2)C1CCC1]

The desired compound was prepared according to the procedure of Example B26, using 6-chloro-2,4,8,22-tetraazatetracyclo[14.3.1.1(3,7).1(9,13)]docosa-1(20),3(22),4,6,9(21),10,12,16,18-nonaen-11-amine bis(trifluoroacetate) and cyclobutanecarboxylic acid chloride as the starting materials in 51% yield. LCMS for C$_{23}$H$_{23}$ClN$_5$O (M+H)$^+$: m/z=420.2.

Example B212

N-[6-Chloro-2,4,8,22-tetraazatetracyclo[14.3.1.1(3,7).1(9,13)]docosa-1(20),3(22),4,6,9(21),10,12,16,18-nonaen-11-yl]-N'-(4-cyanophenyl)urea trifluoroacetate

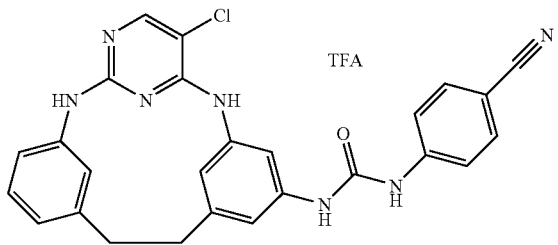 [SMILES: N#Cc1ccc(NC(=O)Nc2cc3cc(c2)Nc2nc(ncc2Cl)Nc2cccc(c2)CC3)cc1]

The desired compound was prepared according to the procedure of Example B83, using 6-chloro-2,4,8,22-tetraazatetracyclo[14.3.1.1(3,7).1(9,13)]docosa-1(20),3(22),4,6,9(21),10,12,16,18-nonaen-11-amine bis(trifluoroacetate) and 4-isocyanatobenzonitrile as the starting materials in 52% yield. LCMS for C$_{26}$H$_{21}$ClN$_7$O (M+H)$^+$: m/z=482.2. $^1$H NMR (400 MHz, DMSO-d$_6$): δ 9.55 (s, 1H), 9.49 (s, 1H), 9.35 (s, 1H), 8.97 (s, 1H), 8.12 (s, 1H), 7.86 (m, 1H), 7.67 (m, 2H), 7.59 (m, 2H), 7.33 (m, 1H), 7.23 (m, 1H), 7.05 (m, 2H), 6.83 (m, 2H), 2.82 (m, 4H).

Example B213

N-[6-Chloro-2,4,8,22-tetraazatetracyclo[14.3.1.1(3,7).1(9,13)]docosa-1(20),3(22),4,6,9(21),10,12,16,18-nonaen-11-yl]-N'-(2-fluorophenyl)urea trifluoroacetate

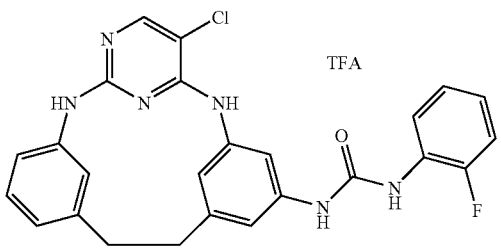 [SMILES: O=C(Nc1cc2cc(c1)Nc1nc(ncc1Cl)Nc1cccc(c1)CC2)Nc1ccccc1F]

The desired compound was prepared according to the procedure of Example B83, using 6-chloro-2,4,8,22-tetraazatetracyclo[14.3.1.1(3,7).1(9,13)]docosa-1(20),3(22),4,6,9(21),10,12,16,18-nonaen-11-amine bis(trifluoroacetate) and 1-fluoro-2-isocyanatobenzene as the starting materials in 43% yield. LCMS for $C_{25}H_{21}ClFN_6O$ (M+H)$^+$: m/z=475.2.

Example B214

N-[6-Chloro-2,4,8,22-tetraazatetracyclo[14.3.1.1(3,7).1(9,13)]docosa-1(20),3(22),4,6,9(21),10,12,16,18-nonaen-11-yl]-N'-(3-fluorophenyl)urea trifluoroacetate

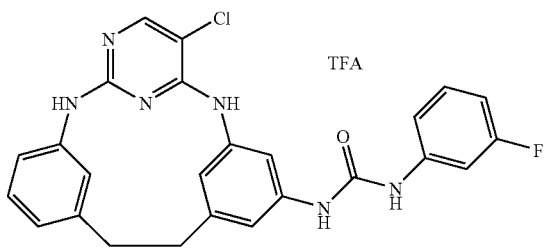 [SMILES: O=C(Nc1cccc(F)c1)Nc1cc2cc(c1)Nc1nc(ncc1Cl)Nc1cccc(c1)CC2]

The desired compound was prepared according to the procedure of Example B83, using 6-chloro-2,4,8,22-tetraazatetracyclo[14.3.1.1(3,7).1(9,13)]docosa-1(20),3(22),4,6,9(21),10,12,16,18-nonaen-11-amine bis(trifluoroacetate) and 1-fluoro-3-isocyanatobenzene as the starting materials in 49% yield. LCMS for $C_{25}H_{21}ClFN_6O$ (M+H)$^+$: m/z=475.2.
$^1$H NMR (400 MHz, DMSO-d$_6$): δ 9.56 (s, 1H), 9.47 (s, 1H), 9.03 (m, 1H), 8.81 (m, 1H), 8.12 (s, 1H), 7.86 (m, 1H), 7.40 (m, 1H), 7.31 (m, 1H), 7.24 (m, 2H), 7.05 (m, 3H), 6.84 (m, 2H), 6.68 (m, 1H), 2.82 (m, 4H).

Example B215

N-[6-Chloro-2,4,8,22-tetraazatetracyclo[14.3.1.1(3,7).1(9,13)]docosa-1(20),3(22),4,6,9(21),10,12,16,18-nonaen-11-yl]-N'-cyclopentylurea trifluoroacetate

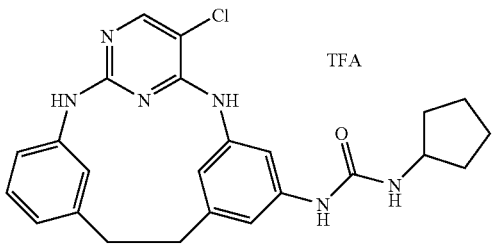 [SMILES: O=C(Nc1cc2cc(c1)Nc1nc(ncc1Cl)Nc1cccc(c1)CC2)NC1CCCC1]

The desired compound was prepared according to the procedure of Example B83, using 6-chloro-2,4,8,22-tetraazatetracyclo[14.3.1.1(3,7).1(9,13)]docosa-1(20),3(22),4,6,9(21),10,12,16,18-nonaen-11-amine bis(trifluoroacetate) and isocyanatocyclopentane as the starting materials in 39% yield. LCMS for $C_{24}H_{26}ClN_6O$ (M+H)$^+$: m/z=449.2.

Example B216

N-[6-Chloro-2,4,8,22-tetraazatetracyclo[14.3.1.1(3,7).1(9,13)]docosa-1(20),3(22),4,6,9(21),10,12,16,18-nonaen-11-yl]-2-cyanobenzenesulfonamide trifluoroacetate

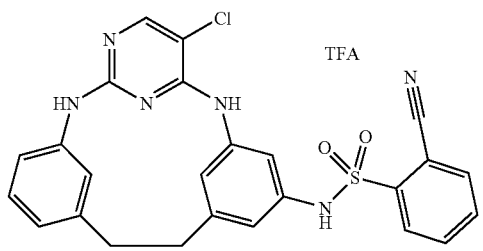 [SMILES: N#Cc1ccccc1S(=O)(=O)Nc1cc2cc(c1)Nc1nc(ncc1Cl)Nc1cccc(c1)CC2]

The desired compound was prepared according to the procedure of Example B136, using 6-chloro-2,4,8,22-tetraazatetracyclo[14.3.1.1(3,7).1(9,13)]docosa-1(20),3(22),4,6,9(21),10,12,16,18-nonaen-11-amine bis(trifluoroacetate) and -cyanobenzenesulfonyl chloride as the starting materials in 27% yield. LCMS for $C_{25}H_{20}ClN_6O_2S$ (M+H)$^+$: m/z=503.1.

Example B217

6-Chloro-11-{[4-(6-chloropyridin-2-yl)piperazin-1-yl]methyl}-2,4,8,22-tetraazatetracyclo[14.3.1.1(3,7).1(9,13)]docosa-1(20),3(22),4,6,9(21),10,12,16,18-nonaene tris(trifluoroacetate)

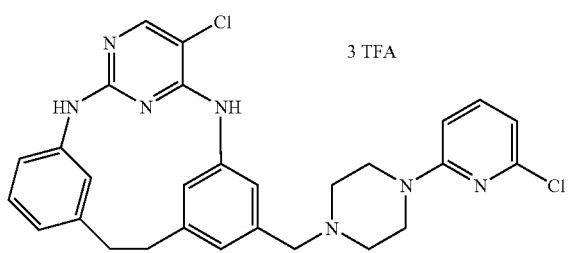 [SMILES: Clc1cccc(N2CCN(Cc3cc4cc(c3)Nc3nc(ncc3Cl)Nc3cccc(c3)CC4)CC2)n1]

To a solution of 6-chloro-11-(piperazin-1-ylmethyl)-2,4,8,22-tetraazatetracyclo[14.3.1.1(3,7).1(9,13)]docosa-1(20),3(22),4,6,9(21),10,12,16,18-nonaene dihydrochloride (31.5 mg, 0.064 mmol) in DMF (0.30 mL) were added 2,6-dichloro-pyridine (20.0 mg, 0.135 mmol) and N,N-diisopropylethylamine (44.4 µL, 0.255 mmol). The reaction was microwaved at 180° C. for 15 minutes. The reaction solution was diluted with methanol and purified with preparative LCMS to give the desired product as white solid (8.5 mg, 21%). LCMS for $C_{28}H_{28}Cl_2N_7$(M+H)$^+$: m/z=532.2.

Example B218

6-Chloro-11-{[4-(2-chloropyrimidin-4-yl)piperazin-1-yl]methyl}-2,4,8,22-tetraazatetracyclo[14.3.1.1(3,7).1(9,13)]docosa-1(20),3(22),4,6,9(21),10,12,16,18-nonaene tris(trifluoroacetate)

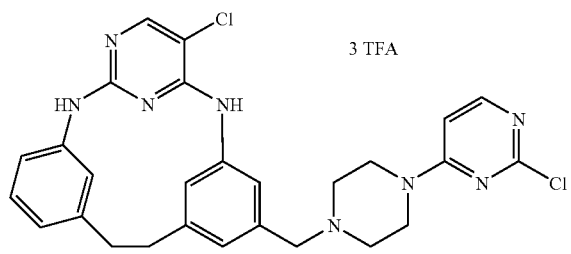 [SMILES: Clc1nccc(N2CCN(Cc3cc4cc(c3)Nc3nc(ncc3Cl)Nc3cccc(c3)CC4)CC2)n1]

To a solution of 6-chloro-11-(piperazin-1-ylmethyl)-2,4,8,22-tetraazatetracyclo[14.3.1.1(3,7).1(9,13)]docosa-1(20),3(22),4,6,9(21),10,12,16,18-nonaene dihydrochloride (21.0 mg, 0.0425 mmol) in DMF (0.6 mL) were added 2,4-dichloropyrimidine (6.6 mg, 0.045 mmol) and N,N-diisopropylethylamine (29.6 µL, 0.170 mmol). The resulting mixture was stirred at 70° C. for 2 h. The reaction solution was diluted with methanol and purified by preparative LCMS to give the desired product (8.2 mg 31%). LCMS for $C_{27}H_{27}Cl_2N_8(M+H)^+$: m/z=533.2.

Example B219 tert-Butyl (3R)-3-({[6-chloro-2,4,8,22-tetraazatetracyclo[14.3.1.1(3,7).1(9,13)]docosa-1(20),3(22),4,6,9(21),10,12,16,18-nonaen-12-yl]methyl}amino)pyrrolidine-1-carboxylate bis(trifluoroacetate)

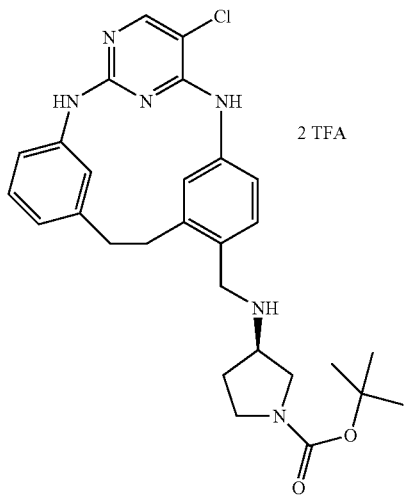 [SMILES: CC(C)(C)OC(=O)N1CC[C@@H](NCc2ccc3cc2CCc2cccc(c2)Nc2ncc(Cl)c(n2)N3)C1 ; "2 TFA"]

The desired compound was prepared according to the procedure of Example B191 step A, using [6-chloro-2,4,8,22-tetraazatetracyclo[14.3.1.1(3,7).1(9,13)]docosa-1(20),3(22),4,6,9(21),10,12,16,18-nonaen-12-yl]methanol trifluoroacetate and tert-butyl (3R)-3-aminopyrrolidine-1-carboxylate as the starting materials in 52% yield. LCMS for $C_{28}H_{34}ClN_6O_2(M+H)^+$: m/z=521.3.

Example B220 tert-Butyl (3S)-3-({[6-chloro-2,4,8,22-tetraazatetracyclo[14.3.1.1(3,7).1(9,13)]docosa-1(20),3(22),4,6,9(21),10,12,16,18-nonaen-12-yl]methyl}amino)pyrrolidine-1-carboxylate bis(trifluoroacetate)

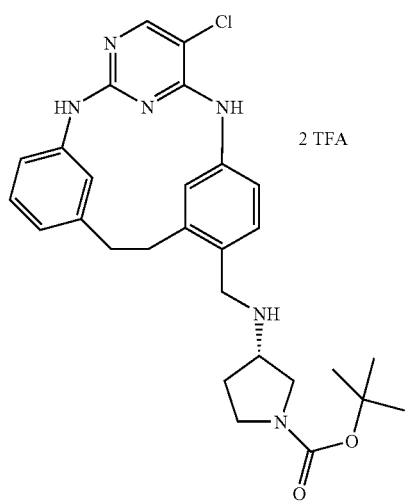 [SMILES: CC(C)(C)OC(=O)N1CC[C@H](NCc2ccc3cc2CCc2cccc(c2)Nc2ncc(Cl)c(n2)N3)C1 ; "2 TFA"]

The desired compound was prepared according to the procedure of Example B191 step A, using [6-chloro-2,4,8,22-tetraazatetracyclo[14.3.1.1(3,7).1(9,13)]docosa-1(20),3(22),4,6,9(21),10,12,16,18-nonaen-12-yl]methanol trifluoroacetate and tert-butyl (3S)-3-aminopyrrolidine-1-carboxylate as the starting materials in 47% yield. LCMS for $C_{28}H_{34}ClN_6O_2(M+H)^+$: m/z=521.3.

Example B221 tert-Butyl 4-{[6-chloro-2,4,8,22-tetraazatetracyclo[14.3.1.1(3,7).1(9,13)]docosa-1(20),3(22),4,6,9(21),10,12,16,18-nonaen-12-yl]methyl}piperazine-1-carboxylate bis(trifluoroacetate)

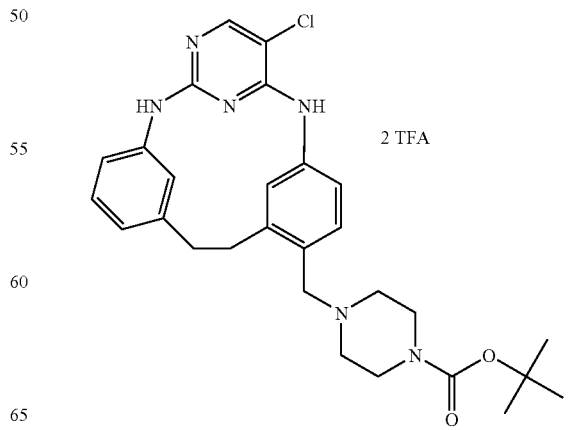

The desired compound was prepared according to the procedure of Example B191 step A, using [6-chloro-2,4,8,22-tetraazatetracyclo[14.3.1.1(3,7).1(9,13)]docosa-1(20),3(22),4,6,9(21),10,12,16,18-nonaen-12-yl]methanol trifluoroacetate and tert-butyl piperazine-1-carboxylate as the starting materials in 63% yield. LCMS for $C_{28}H_{34}ClN_6O_2$ (M+H)$^+$: m/z=521.3.

Example B222

(3R)—N-{[6-Chloro-2,4,8,22-tetraazatetracyclo[14.3.1.1(3,7).1(9,13)]docosa-1(20),3(22),4,6,9(21),10,12,16,18-nonaen-12-yl]methyl}pyrrolidin-3-amine tris(trifluoroacetate)

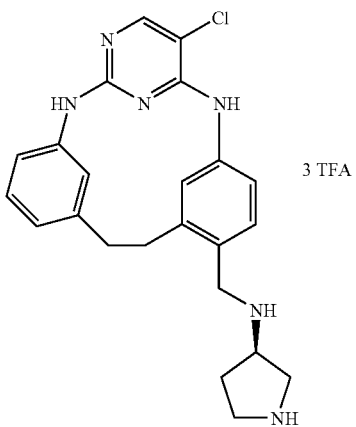 [SMILES: "3 TFA" ; Clc1cnc2nc1Nc1ccc(CN[C@@H]3CCNC3)c(c1)CCc1cccc(c1)N2]

The desired compound was prepared according to the procedure of Example B191 step B, using tert-butyl (3R)-3-({[6-chloro-2,4,8,22-tetraazatetracyclo[14.3.1.1(3,7).1(9,13)]docosa-1(20),3(22),4,6,9(21),10,12,16,18-nonaen-12-yl]methyl}amino)pyrrolidine-1-carboxylate bis(trifluoroacetate) as the starting material in 67% yield. LCMS for $C_{23}H_{26}ClN_6$(M+H)$^+$: m/z=421.3.

Example B223

(3S)—N-{[6-Chloro-2,4,8,22-tetraazatetracyclo[14.3.1.1(3,7).1(9,13)]docosa-1(20),3(22),4,6,9(21),10,12,16,18-nonaen-12-yl]methyl}pyrrolidin-3-amine tris(trifluoroacetate)

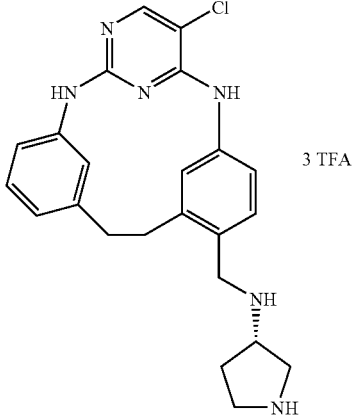 [SMILES: "3 TFA" ; Clc1cnc2nc1Nc1ccc(CN[C@H]3CCNC3)c(c1)CCc1cccc(c1)N2]

The desired compound was prepared according to the procedure of Example B191 step B, using tert-butyl (3S)-3-({[6-chloro-2,4,8,22-tetraazatetracyclo[14.3.1.1(3,7).1(9,13)]docosa-1(20),3(22),4,6,9(21),10,12,16,18-nonaen-12-yl]methyl}amino)pyrrolidine-1-carboxylate bis(trifluoroacetate) as the starting material in 72% yield. LCMS for $C_{23}H_{26}ClN_6$(M+H)$^+$: m/z=421.3.

Example B224

6-Chloro-12-(piperazin-1-ylmethyl)-2,4,8,22-tetraazatetracyclo[14.3.1.1(3,7).1(9,13)]docosa-1(20),3(22),4,6,9(21),10,12,16,18-nonaene tris(trifluoroacetate)

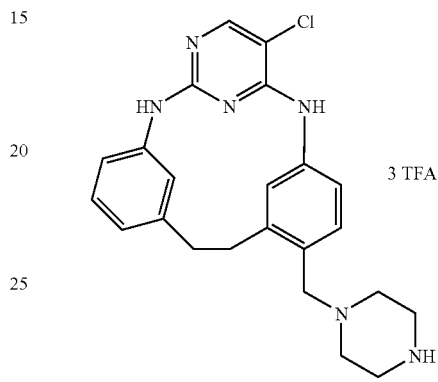

The desired compound was prepared according to the procedure of Example B191 step B, using tert-butyl 4-{[6-chloro-2,4,8,22-tetraazatetracyclo[14.3.1.1(3,7).1(9,13)]docosa-1(20),3(22),4,6,9(21),10,12,16,18-nonaen-12-yl]methyl}piperazine-1-carboxylate trifluoroacetate as the starting materials in 47% yield. LCMS for $C_{23}H_{26}ClN_6$(M+H)$^+$: m/z=421.3.

Example B225

12-[(4-Acetylpiperazin-1-yl)methyl]-6-chloro-2,4,8,22-tetraazatetracyclo[14.3.1.1(3,7).1(9,13)]docosa-1(20),3(22),4,6,9(21),10,12,16,18-nonaene bis(trifluoroacetate)

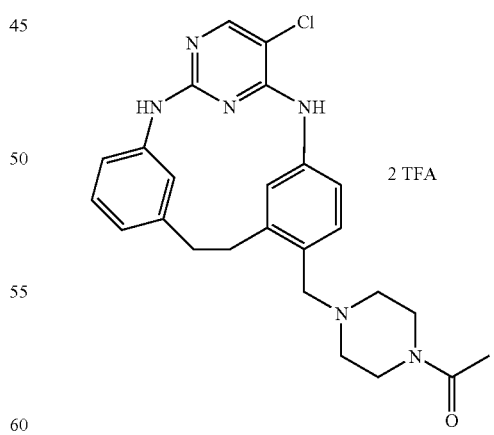

The desired compound was prepared according to the procedure of Example B26, using 6-chloro-12-(piperazin-1-ylmethyl)-2,4,8,22-tetraazatetracyclo[14.3.1.1(3,7).1(9,13)]docosa-1(20),3(22),4,6,9(21),10,12,16,18-nonaene tris(trifluoroacetate) and acetyl chloride as the starting materials in 52% yield. LCMS for $C_{25}H_{28}ClN_6O$ (M+H)$^+$: m/z=463.2.

Example B226

N-[(3S)-1-Acetylpyrrolidin-3-yl]-N'-[6-chloro-2,4,8,18,22-pentaazatetracyclo[14.3.1.1(3,7).1(9,13)]docosa-1(20),3(22),4,6,9(21),10,12,16,18-nonaen-12-yl]urea bis(trifluoroacetate)

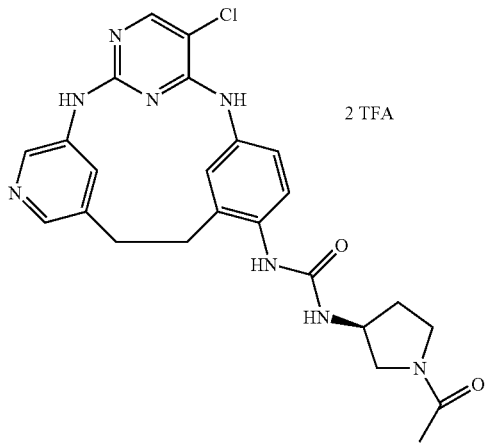 [SMILES: CC(=O)N1CC[C@H](NC(=O)Nc2ccc3cc2CCc2cncc(c2)Nc2ncc(Cl)c(n2)N3)C1 ; "2 TFA"]

The desired compound was prepared according to the procedure of Example B26, using N-[6-Chloro-2,4,8,18,22-pentaazatetracyclo[14.3.1.1(3,7).1(9,13)]docosa-1(20),3(22),4,6,9(21),10,12,16,18-nonaen-12-yl]-N'-[(3S)-pyrrolidin-3-yl]urea dihydrochloride and acetyl chloride as the starting materials in 18% yield. LCMS for $C_{24}H_{26}ClN_8O_2(M+H)^+$: m/z=493.2.

Example B227

N-[(3S)-1-benzoylpyrrolidin-3-yl]-N'-[6-chloro-2,4,8,18,22-pentaazatetracyclo[14.3.1.1(3,7).1(9,13)]docosa-1(20),3(22),4,6,9(21),10,12,16,18-nonaen-12-yl]urea bis(trifluoroacetate)

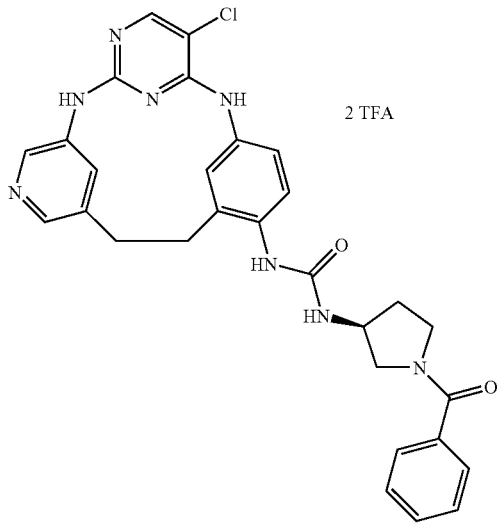 [SMILES: O=C(Nc1ccc2cc1CCc1cncc(c1)Nc1ncc(Cl)c(n1)N2)N[C@H]1CCN(C(=O)c2ccccc2)C1 ; "2 TFA"]

The desired compound was prepared according to the procedure of Example B26, using N-[6-Chloro-2,4,8,18,22-pentaazatetracyclo[14.3.1.1(3,7).1(9,13)]docosa-1(20),3(22),4,6,9(21),10,12,16,18-nonaen-12-yl]-N'-[(3S)-pyrrolidin-3-yl]urea dihydrochloride and benzoyl chloride as the starting materials in 23% yield. LCMS for $C_{29}H_{28}ClN_8O_2(M+H)^+$: m/z=555.3.

Example B228

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-[(3S)-1-(cyclopropylcarbonyl)pyrrolidin-3-yl]urea trifluoroacetate


The desired compound was prepared according to the procedure of Example B26, using N-[6-chloro-2,4,8,22-tetraazatetracyclo[14.3.1.1(3,7).1(9,13)]docosa-1(20),3(22),4,6,9(21),10,12,16,18-nonaen-12-yl]-N'-[(3S)-pyrrolidin-3-yl]urea dihydrochloride and cyclopropanecarbonyl chloride as the starting materials in 10% yield. LCMS for $C_{27}H_{29}ClN_7O_2(M+H)^+$: m/z=518.2.

Example B229

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-[(3S)-1-isobutyrylpyrrolidin-3-yl]urea trifluoroacetate

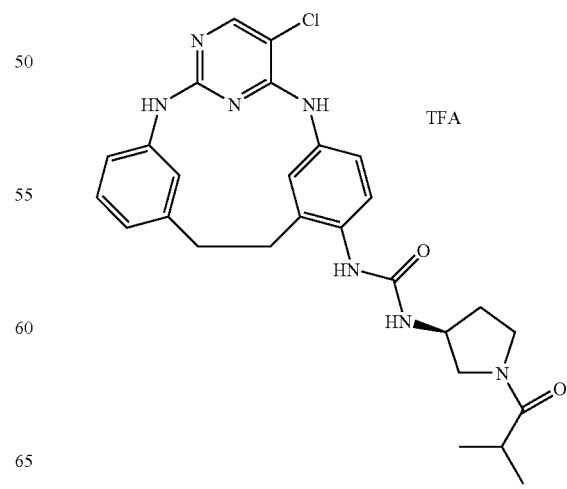

The desired compound was prepared according to the procedure of Example B26, using N-[6-chloro-2,4,8,22-tetraazatetracyclo[14.3.1.1(3,7).1(9,13)]docosa-1(20),3(22),4,6,9(21),10,12,16,18-nonaen-12-yl]-N'-[(3S)-pyrrolidin-3-yl]urea dihydrochloride and isobutyryl chloride as the starting materials in 9% yield. LCMS for $C_{27}H_{31}ClN_7O_2$ (M+H)$^+$: m/z=520.2.

Example B230

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-[(3S)-1-(isoxazol-5-ylcarbonyl)pyrrolidin-3-yl]urea trifluoroacetate

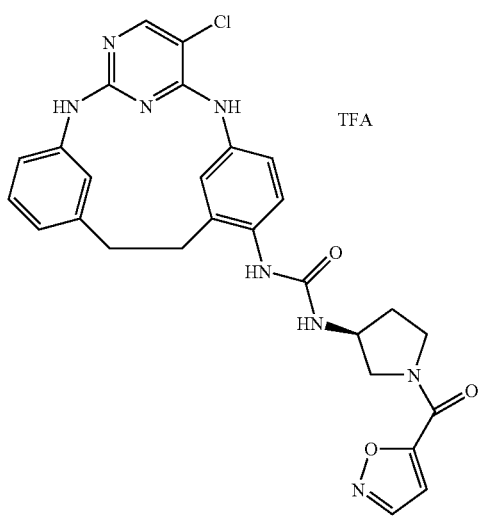 [SMILES: "TFA" ; O=C(Nc1ccc2cc1CCc1cccc(c1)Nc1ncc(Cl)c(n1)N2)N[C@H]1CCN(C(=O)c2ccno2)C1]

The desired compound was prepared according to the procedure of Example B26, using N-[6-chloro-2,4,8,22-tetraazatetracyclo[14.3.1.1(3,7).1(9,13)]docosa-1(20),3(22),4,6,9(21),10,12,16,18-nonaen-12-yl]-N'-[(3S)-pyrrolidin-3-yl]urea dihydrochloride and isoxazole-5-carbonyl chloride as the starting materials in 8% yield. LCMS for $C_{27}H_{26}ClN_8O_3$ (M+H)$^+$: m/z=545.3.

Example B231

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-[(3S)-1-(1,3-thiazol-2-ylcarbonyl)pyrrolidin-3-yl]urea trifluoroacetate

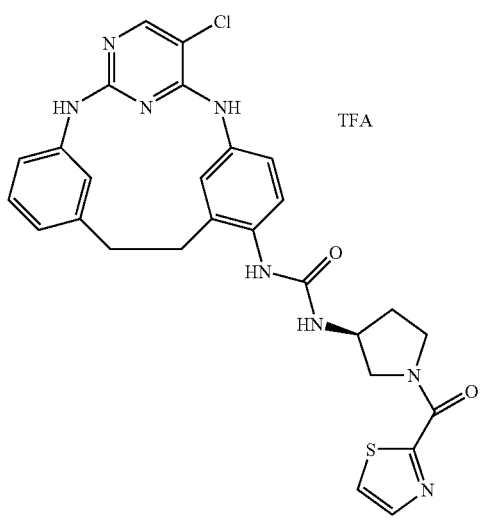 [SMILES: "TFA" ; O=C(Nc1ccc2cc1CCc1cccc(c1)Nc1ncc(Cl)c(n1)N2)N[C@H]1CCN(C(=O)c2nccs2)C1]

The desired compound was prepared according to the procedure of Example B26, using N-[6-chloro-2,4,8,22-tetraazatetracyclo[14.3.1.1(3,7).1(9,13)]docosa-1(20),3(22),4,6,9(21),10,12,16,18-nonaen-12-yl]-N'-[(3S)-pyrrolidin-3-yl]urea dihydrochloride and 1,3-thiazole-2-carbonyl chloride as the starting materials in 8% yield. LCMS for $C_{27}H_{26}ClN_8O_2S$ (M+H)$^+$: m/z=561.3.

Example B232

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-{(3S)-1-[(1-methyl-1H-pyrazol-3-yl)carbonyl]pyrrolidin-3-yl}urea bis(trifluoroacetate)

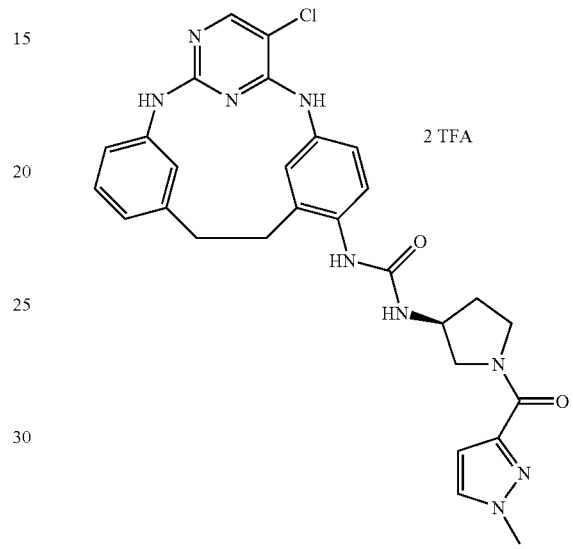

The desired compound was prepared according to the procedure of Example B26, using N-[6-chloro-2,4,8,22-tetraazatetracyclo[14.3.1.1(3,7).1(9,13)]docosa-1(20),3(22),4,6,9(21),10,12,16,18-nonaen-12-yl]-N'-[(3S)-pyrrolidin-3-yl]urea dihydrochloride and 1-methyl-1H-pyrazole-3-carbonyl chloride as the starting materials in 9% yield. LCMS for $C_{28}H_{29}ClN_9O_2$ (M+H)$^+$: m/z=558.3.

Example B233

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-[(3S)-1-(pyridin-2-ylcarbonyl)pyrrolidin-3-yl]urea bis(trifluoroacetate)

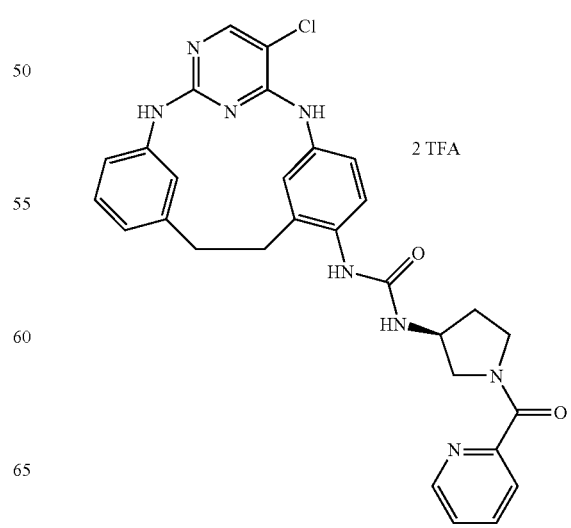

The desired compound was prepared according to the procedure of Example B26, using N-[6-chloro-2,4,8,22-tetraazatetracyclo[14.3.1.1(3,7).1(9,13)]docosa-1(20),3(22),4,6,9(21),10,12,16,18-nonaen-12-yl]-N'-[(3S)-pyrrolidin-3-yl]urea dihydrochloride and pyridine-2-carbonyl chloride hydrochloride as the starting materials in 6% yield. LCMS for $C_{29}H_{28}ClN_8O_2(M+H)^+$: m/z=555.2.

Example B234

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-[(3S)-1-isonicotinoylpyrrolidin-3-yl]urea bis(trifluoroacetate)

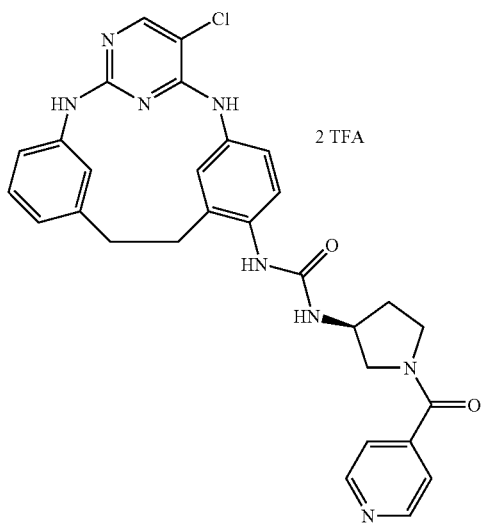 [SMILES: O=C(Nc1ccc2cc1CCc1cccc(c1)Nc1ncc(Cl)c(n1)N2)N[C@H]1CCN(C(=O)c2ccncc2)C1 ; "2 TFA"]

The desired compound was prepared according to the procedure of Example B26, using N-[6-chloro-2,4,8,22-tetraazatetracyclo[14.3.1.1(3,7).1(9,13)]docosa-1(20),3(22),4,6,9(21),10,12,16,18-nonaen-12-yl]-N'-[(3S)-pyrrolidin-3-yl]urea dihydrochloride and isonicotinoyl chloride hydrochloride as the starting materials in 6% yield. LCMS for $C_{29}H_{28}ClN_8O_2(M+H)^+$: m/z=555.0.

Example B235

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-[(3S)-1-(4-cyanobenzoyl)pyrrolidin-3-yl]urea trifluoroacetate

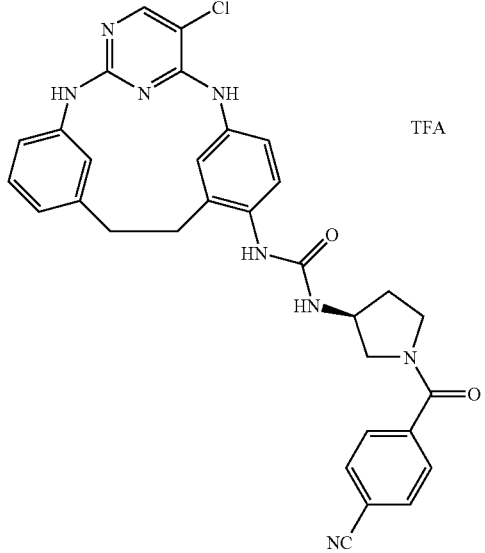

The desired compound was prepared according to the procedure of Example B267, using N-[6-chloro-2,4,8,22-tetraazatetracyclo[14.3.1.1(3,7).1(9,13)]docosa-1(20),3(22),4,6,9(21),10,12,16,18-nonaen-12-yl]-N'-[(3S)-pyrrolidin-3-yl]urea dihydrochloride and 4-cyanobenzoyl chloride as the starting materials in 9% yield. LCMS for $C_{31}H_{28}ClN_8O_2(M+H)^+$: m/z=579.3.

Example B236 tert-Butyl [(3R)-1-({[6-chloro-2,4,8,22-tetraazatetracyclo[14.3.1.1(3,7).1(9,13)]docosa-1(20),3(22),4,6,9(21),10,12,16,18-nonaen-12-yl]amino}carbonyl)pyrrolidin-3-yl]carbamate

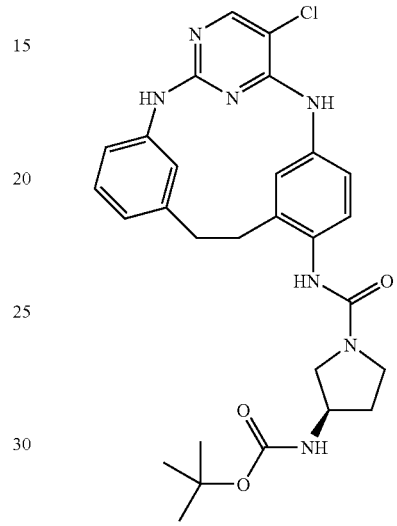

To a mixture of 6-chloro-2,4,8,22-tetraazatetracyclo[14.3.1.1(3,7).1(9,13)]docosa-1(20),3(22),4,6,9(21),10,12,16,18-nonaen-12-amine dihydrochloride (30 mg, 0.07 mmol) and pyridine (18.9 µL, 0.234 mmol) in methylene chloride (0.4 mL) was added 20% phosgene in toluene (1:4, phosgene:toluene, 50.2 µL, 0.0950 mmol). The resulting mixture was stirred for 1 hour before adding tert-butyl (3R)-pyrrolidin-3-ylcarbamate (14.3 mg, 0.0767 mmol) and pyridine (13.0 µL, 0.161 mmol). The mixture was allowed to stir overnight. It was diluted with methanol and purified by preparative LCMS (pH 10) to give the desired product. LCMS calculated for $C_{28}H_{33}ClN_7O_3$ (M+H)$^+$: m/z=550.2.

Example B237 tert-Butyl 3-[({[6-chloro-2,4,8,22-tetraazatetracyclo[14.3.1.1(3,7).1(9,13)]docosa-1(20),3(22),4,6,9(21),10,12,16,18-nonaen-12-yl]amino}carbonyl)amino]piperidine-1-carboxylate

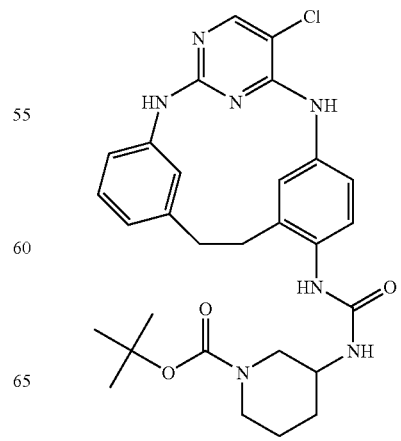

The desired compound was prepared according to the procedure of Example B236, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and tert-butyl 3-aminopiperidine-1-carboxylate as the starting materials in 20% yield. LCMS for $C_{29}H_{35}ClN_7O_3$ (M+H)$^+$: m/z=564.2.

Example B238

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-piperidin-3-ylurea bis(trifluoroacetate)

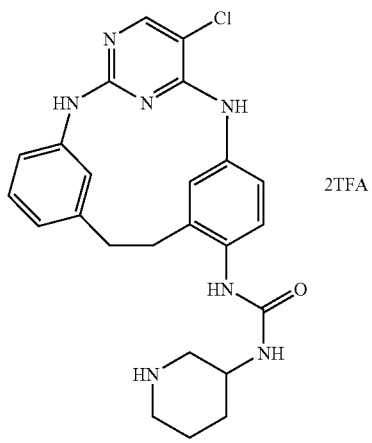 [SMILES: O=C(Nc1ccc2cc1CCc1cccc(c1)Nc1ncc(Cl)c(n1)N2)NC1CCCNC1 ; "2TFA"]

The desired compound was prepared according to the procedure of Example B21, step B, using tert-butyl 3-[({[6-chloro-2,4,8,22-tetraazatetracyclo[14.3.1.1(3,7).1(9,13)]docosa-1(20),3(22),4,6,9(21),10,12,16,18-nonaen-12-yl]amino}carbonyl)amino]piperidine-1-carboxylate as the starting material in 80% yield. LCMS for $C_{24}H_{27}ClN_7O$ (M+H)$^+$: m/z=464.4.

Example B239

N'-[6-Chloro-2,4,8,22-tetraazatetracyclo[14.3.1.1(3,7).1(9,13)]docosa-1(20),3(22),4,6,9(21),10,12,16,18-nonaen-12-yl]-N,N-dimethylurea trifluoroacetate

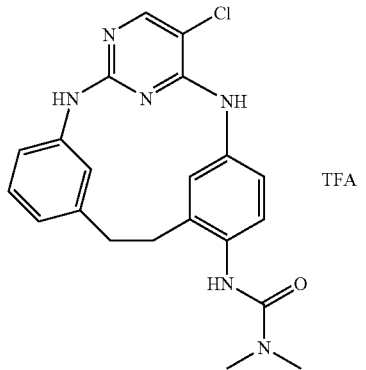 [SMILES: "TFA" ; CN(C)C(=O)Nc1ccc2cc1CCc1cccc(c1)Nc1ncc(Cl)c(n1)N2]

The desired compound was prepared according to the procedure of Example B236, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and dimethylamine hydrochloride as the starting materials in 14% yield. LCMS for $C_{21}H_{22}ClN_6O$ (M+H)$^+$: m/z=409.1.

Example B240

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-cyclopropylurea trifluoroacetate

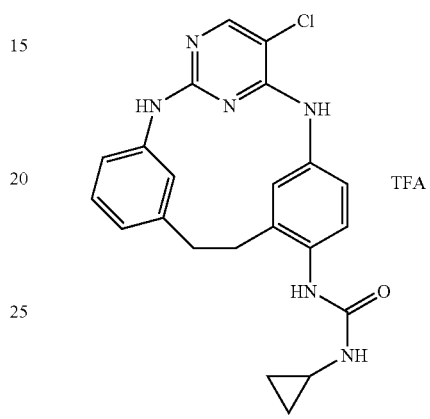

The desired compound was prepared according to the procedure of Example B236, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and cyclopopylamine as the starting materials in 10% yield. LCMS for $C_{22}H_{22}ClN_6O$ (M+H)$^+$: m/z=421.1.

Example B241

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-(2-hydroxyethyl)urea trifluoroacetate

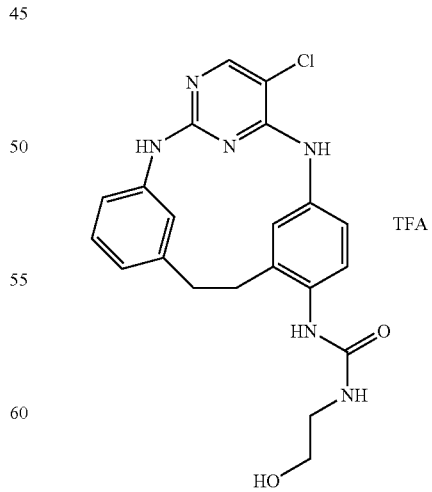

The desired compound was prepared according to the procedure of Example B236, using 6-chloro-2,4,8,22-tetraazatetracyclo[14.3.1.1(3,7).1(9,13)]docosa-1(20),3(22),4,6,9

(21),10,12,16,18-nonaen-12-amine dihydrochloride and ethanolamine as the starting materials in 9% yield. LCMS for $C_{21}H_{22}ClN_6O_2$ (M+H)+: m/z=425.1.

Example B242

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-(2-hydroxy-1-methylethyl)urea trifluoroacetate

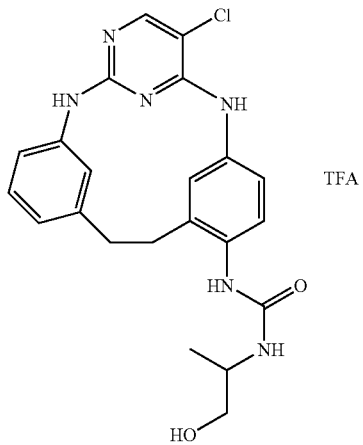 [SMILES: "TFA" ; CC(CO)NC(=O)Nc1ccc2cc1CCc1cccc(c1)Nc1ncc(Cl)c(n1)N2]

The desired compound was prepared according to the procedure of Example B236, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 2-amino-1-propanol as the starting materials in 12% yield. LCMS for $C_{22}H_{24}ClN_6O_2$ (M+H)+: m/z=439.1.

Example B243

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-(2-methoxyethyl)urea trifluoroacetate

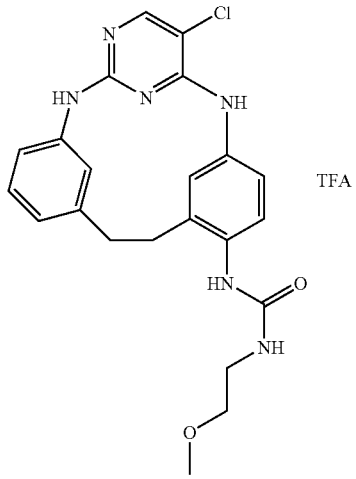 [SMILES: "TFA" ; COCCNC(=O)Nc1ccc2cc1CCc1cccc(c1)Nc1ncc(Cl)c(n1)N2]

The desired compound was prepared according to the procedure of Example B236, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 2-methoxyethylamine as the starting materials in 8% yield. LCMS for $C_{22}H_{24}ClN_6O_2$ (M+H)+: m/z=439.1.

Example B244

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-1H-1,2,4-triazol-3-ylurea trifluoroacetate

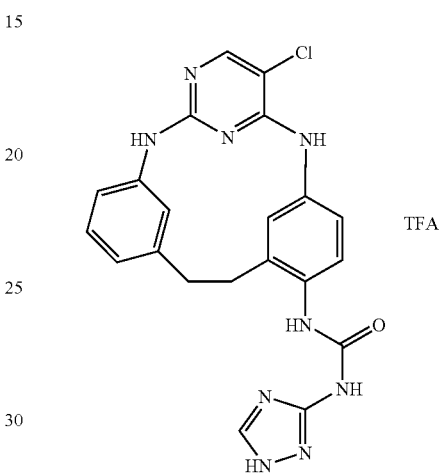

The desired compound was prepared according to the procedure of Example B236, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 3-amino-1,2,4-triazole as the starting materials in 8% yield. LCMS for $C_{21}H_{19}ClN_9O$ (M+H)+: m/z=448.0.

Example B245

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-1,3-thiazol-2-ylurea trifluoroacetate

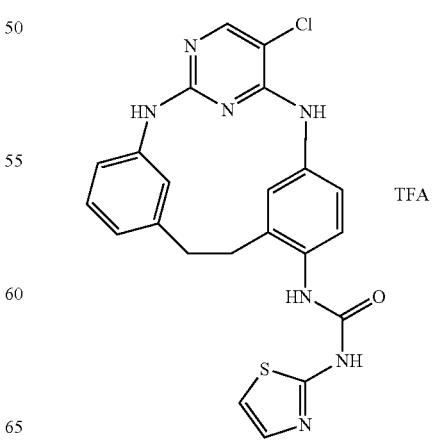

The desired compound was prepared according to the procedure of Example B236, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 2-aminothiazole as the starting materials in 10% yield. LCMS for $C_{22}H_{19}ClN_7OS$ (M+H)$^+$: m/z=464.0. $^1$HNMR (400 MHz, DMSO) δ 9.49 (s, 1H), 9.41 (s, 1H), 8.48 (s, 1H), 8.14 (s, 1H), 8.00 (s, 1H), 7.75-7.71 (m, 2H), 7.39 (d, 2H), 7.12-7.03 (m, 3H), 6.87 (d, 1H), 6.82 (d, 1H), 2.92 (m, 4H).

Example B246

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-(pyridin-4-ylmethyl)ureabis(trifluoroacetate)

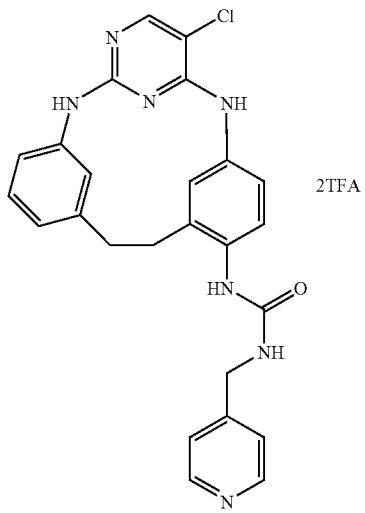 [SMILES: O=C(NCc1ccncc1)Nc1ccc2cc1CCc1cccc(c1)Nc1ncc(Cl)c(n1)N2 ; "2TFA"]

The desired compound was prepared according to the procedure of Example B236, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 4-(aminomethyl)pyridine as the starting materials in 11% yield. LCMS for $C_{25}H_{23}ClN_7O$ (M+H)$^+$: m/z=472.1.

Example B247

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-(2-methoxy-1-methylethyl)ureatrifluoroacetate

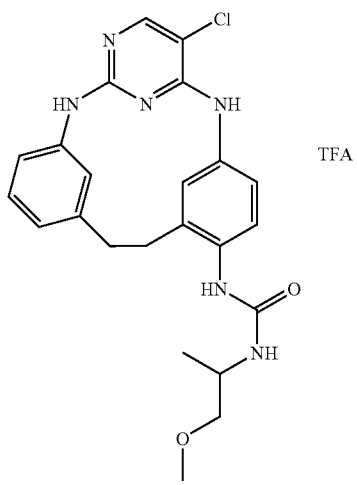 [SMILES: COCC(C)NC(=O)Nc1ccc2cc1CCc1cccc(c1)Nc1ncc(Cl)c(n1)N2]

The desired compound was prepared according to the procedure of Example B236, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 1-methoxypropan-2-amine as the starting materials in 20% yield. LCMS for $C_{23}H_{26}ClN_6O_2$ (M+H)$^+$: m/z=453.5. $^1$HNMR (400 MHz, DMSO) δ 9.58 (s, 1H), 9.45 (s, 1H), 8.13 (s, 1H), 7.98 (s, 1H), 7.74-7.70 (m, 2H), 7.62 (d, 1H), 7.09 (t, 1H), 6.94 (d, 1H), 6.87 (d, 1H), 6.81 (d, 1H), 6.55 (d, 1H), 3.83 (m, 1H), 3.38-3.25 (m, 5H), 2.88 (m, 4H), 1.09 (d, 3H).

Example B248

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-(5-methyl-1,3-thiazol-2-yl)urea trifluoroacetate

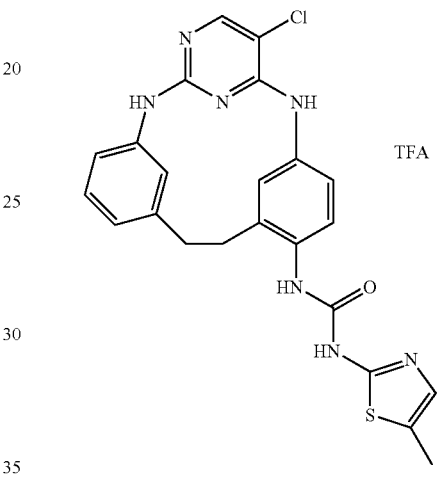

The desired compound was prepared according to the procedure of Example B236, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 5-methyl-1,3-thiazol-2-amine as the starting materials in 11% yield. LCMS calculated for $C_{23}H_{21}ClN_7OS$ (M+H)$^+$: m/z=478.0.

Example B249

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-(4-methyl-1,3-thiazol-2-yl)ureatrifluoroacetate

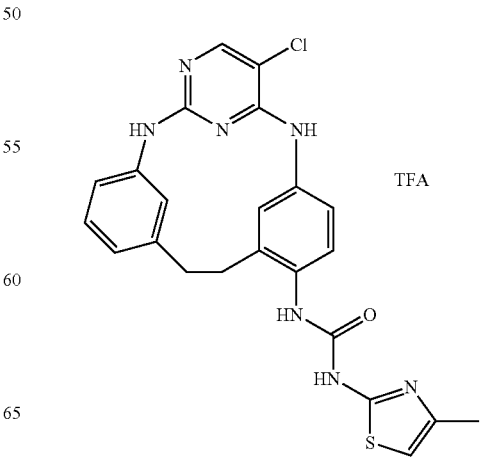

The desired compound was prepared according to the procedure of Example B236, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 4-methyl-1,3-thiazol-2-amine as the starting materials in 11% yield. LCMS for $C_{23}H_{21}ClN_7OS$ (M+H)$^+$: m/z=478.0.

Example B250

2-[({[6-Chloro-2,4,8,22-tetraazatetracyclo[14.3.1.1(3,7).1(9,13)]docosa-1(20),3(22),4,6,9(21),10,12,16,18-nonaen-12-yl]amino}carbonyl)amino]-1,3-thiazole-4-carboxylic acid trifluoroacetate

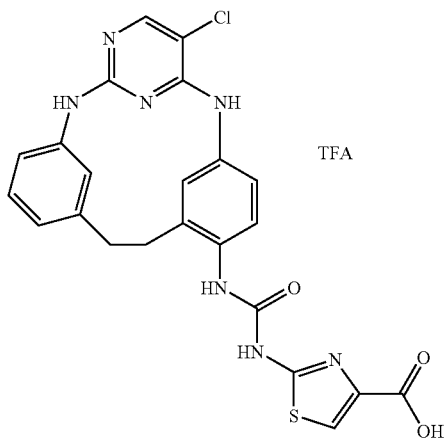 [SMILES: O=C(Nc1nc(C(=O)O)cs1)Nc1ccc2cc1CCc1cccc(c1)Nc1ncc(Cl)c(n1)N2]

The desired compound was prepared according to the procedure of Example B236, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 2-amino-1,3-thiazole-4-carboxylic acid hydrobromide as the starting materials in 7% yield. LCMS for $C_{23}H_{19}ClN_7O_3S$ (M+H)$^+$: m/z=508.0.

Example B251

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-1H-tetrazol-5-ylurea trifluoroacetate

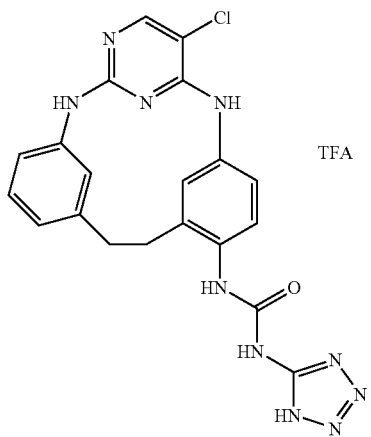 [SMILES: O=C(Nc1nnn[nH]1)Nc1ccc2cc1CCc1cccc(c1)Nc1ncc(Cl)c(n1)N2]

The desired compound was prepared according to the procedure of Example B236, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 1H-tetrazol-5-amine as the starting materials in 5% yield. LCMS for $C_{20}H_{18}ClN_{10}O$ (M+H)$^+$: m/z=449.1.

Example B252

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-(5-chloro-1,3-thiazol-2-yl)urea trifluoroacetate

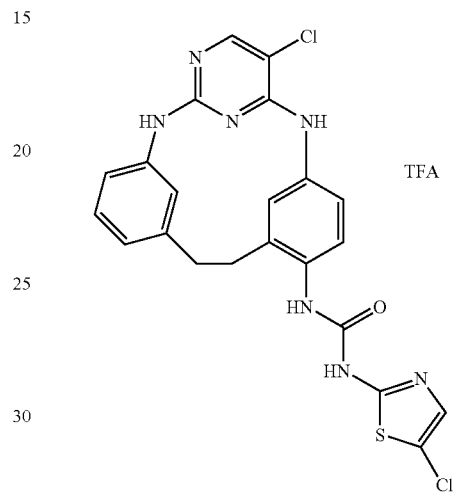

The desired compound was prepared according to the procedure of Example B236, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 5-chloro-1,3-thiazol-2-amine hydrochloride as the starting materials in 4% yield. LCMS for $C_{22}H_{18}Cl_2N_7OS$ (M+H)$^+$: m/z=498.0.

Example B253

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-pyridin-2-ylurea bis(trifluoroacetate)

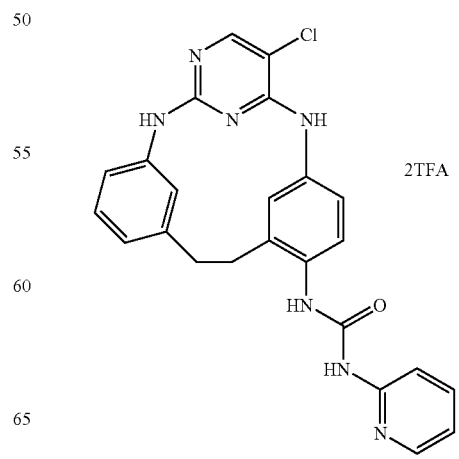

The desired compound was prepared according to the procedure of Example B236, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 2-pyridinamine as the starting materials in 4% yield. LCMS for $C_{24}H_{21}ClN_7O$ (M+H)$^+$: m/z=458.1.

Example B254
N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-(2-morpholin-4-ylethyl)urea bis(trifluoroacetate)

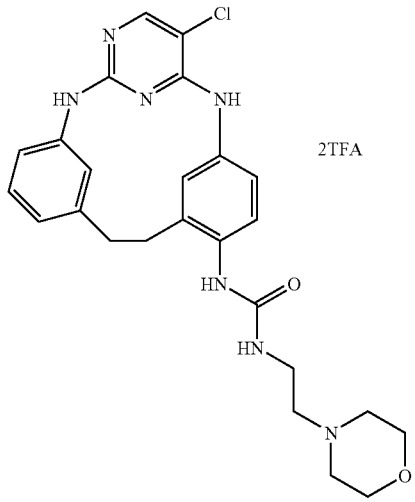 [SMILES: O=C(NCCN1CCOCC1)Nc1ccc2cc1CCc1cccc(c1)Nc1ncc(Cl)c(n1)N2 ; "2TFA"]

The desired compound was prepared according to the procedure of Example B236, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and N-(2-aminoethyl)morpholine as the starting materials in 31% yield. LCMS for $C_{25}H_{29}ClN_7O_2$ (M+H)$^+$: m/z=494.3. $^1$HNMR (300 MHz, CD$_3$OD) δ 8.10 (s, 1H), 7.83 (s, 1H), 7.76 (s, 1H), 7.57 (d, 1H), 7.21 (t, 1H), 7.06 (d, 1H), 7.00 (d, 1H), 6.91 (d, 1H), 4.09 (m, 2H), 3.79 (m, 2H), 3.64 (m, 4H), 3.35 (m, 2H), 3.20 (m, 2H), 3.05 (m, 4H).

Example B255
N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-(2-pyrrolidin-1-ylethyl)urea bis(trifluoroacetate)

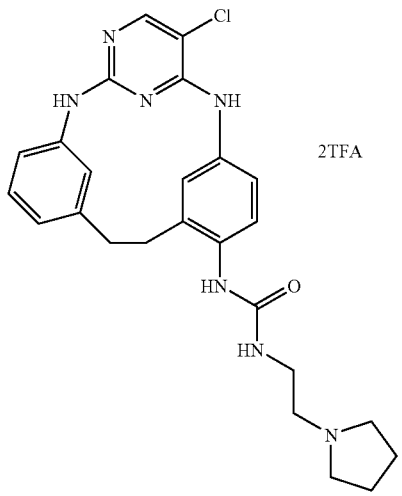 [SMILES: O=C(NCCN1CCCC1)Nc1ccc2cc1CCc1cccc(c1)Nc1ncc(Cl)c(n1)N2 ; "2TFA"]

The desired compound was prepared according to the procedure of Example B236, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 1-pyrrolidineethanamine as the starting materials in 33% yield. LCMS for $C_{25}H_{29}ClN_7O$ (M+H)$^+$: m/z=478.2.

Example B256
N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-[2-(1-methylpyrrolidin-2-yl)ethyl]urea bis(trifluoroacetate)

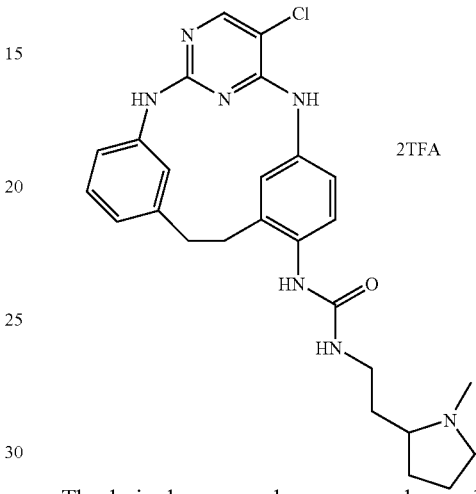

The desired compound was prepared according to the procedure of Example B236, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 2-(1-methyllpyrrolidin-2-yl)ethanamine as the starting materials in 37% yield. LCMS for $C_{26}H_{31}ClN_7O$ (M+H)$^+$: m/z=492.2. $^1$HNMR (300 MHz, CD$_3$OD) δ 8.11 (s, 1H), 7.83 (s, 1H), 7.76 (s, 1H), 7.55 (d, 1H), 7.21 (t, 1H), 7.06 (d, 1H), 6.99 (d, 1H), 6.91 (d, 1H), 3.68 (m, 1H), 3.32 (m, 2H), 3.19 (m, 2H), 3.02 (m, 4H), 2.95 (m, 2H), 2.45 (m, 1H), 2.25-1.92 (m, 4H), 1.80 (m, 2H).

Example B257
N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-[2-(2-oxopyrrolidin-1-yl)ethyl]urea trifluoroacetate

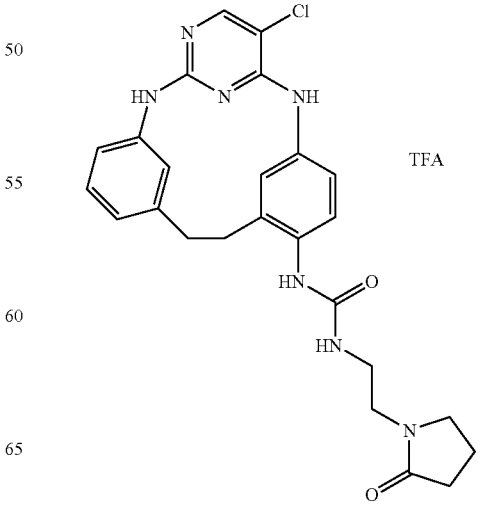

The desired compound was prepared according to the procedure of Example B236, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 1-(2-aminoethyl)pyrrolidin-2-one hydrochloride as the starting materials in 34% yield. LCMS for $C_{25}H_{27}ClN_7O_2$ $(M+H)^+$: m/z=492.1.

Example B258
N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-(2-piperidin-1-ylethyl)urea bis(trifluoroacetate)

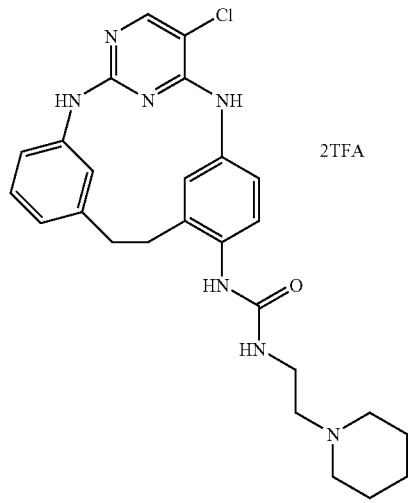 [SMILES: O=C(NCCN1CCCCC1)Nc1ccc2cc1CCc1cccc(c1)Nc1ncc(Cl)c(n1)N2 ; "2TFA"]

The desired compound was prepared according to the procedure of Example B236, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 1-piperidineethanamine as the starting materials in 42% yield. LCMS for $C_{26}H_{31}ClN_7O$ $(M+H)^+$: m/z=492.2.

Example B259
tert-Butyl 4-{2-[({[6-chloro-2,4,8,22-tetraazatetracyclo[14.3.1.1(3,7).1(9,13)]docosa-1(20),3(22),4,6,9(21),10,12,16,18-nonaen-12-yl]amino}carbonyl)amino]ethyl}piperazine-1-carboxylate

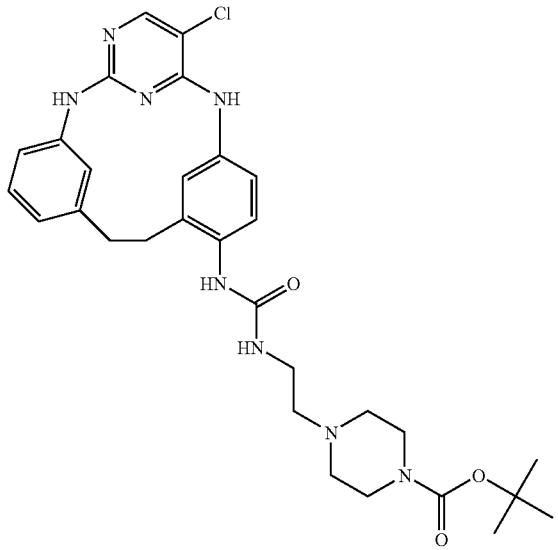 [SMILES: CC(C)(C)OC(=O)N1CCN(CCNC(=O)Nc2ccc3cc2CCc2cccc(c2)Nc2ncc(Cl)c(n2)N3)CC1]

The desired compound was prepared according to the procedure of Example B236, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and tert-butyl 4-(2-aminoethyl)piperazine-1-carboxylate as the starting materials in 10% yield. LCMS for $C_{30}H_{38}ClN_8O_3$ $(M+H)^+$: m/z=593.2.

Example B260
N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-(2-piperazin-1-ylethyl)urea trihydrochloride

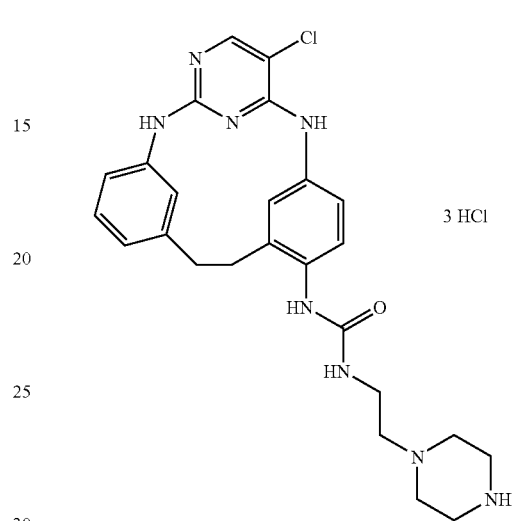

The desired compound was prepared according to the procedure of Example B25, step B, using tert-butyl 4-{2-[({[6-chloro-2,4,8,22-tetraazatetracyclo[14.3.1.1(3,7).1(9,13)]docosa-1(20),3(22),4,6,9(21),10,12,16,18-nonaen-12-yl]amino}carbonyl)amino]ethyl}piperazine-1-carboxylate as the starting material in 90% yield. LCMS for $C_{25}H_{30}ClN_8O$ $(M+H)^+$: m/z=493.2.

Example B261
N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-[(3S)-1-methylpyrrolidin-3-yl]urea bis(trifluoroacetate)

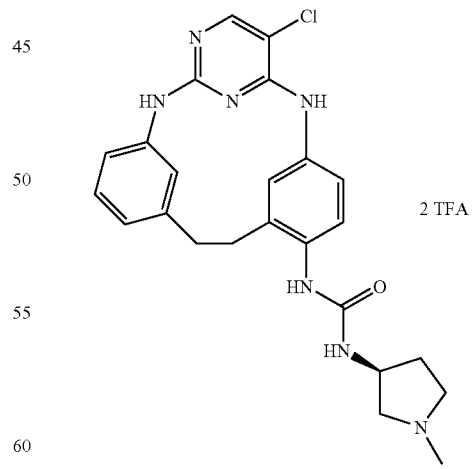

The desired compound was prepared according to the procedure of Example B192, using N-[6-chloro-2,4,8,22-tetraazatetracyclo[14.3.1.1(3,7).1(9,13)]docosa-1(20),3(22),4,6,9(21),10,12,16,18-nonaen-12-yl]-N'-[(3S)-pyrrolidin-3-yl]urea dihydrochloride and formaldehyde as the starting materials in 20% yield. LCMS for $C_{24}H_{27}ClN_7O$ $(M+H)^+$: m/z=464.1.

Example B262

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-[(3S)-1-pyrimidin-2-ylpyrrolidin-3-yl]urea bis(trifluoroacetate)

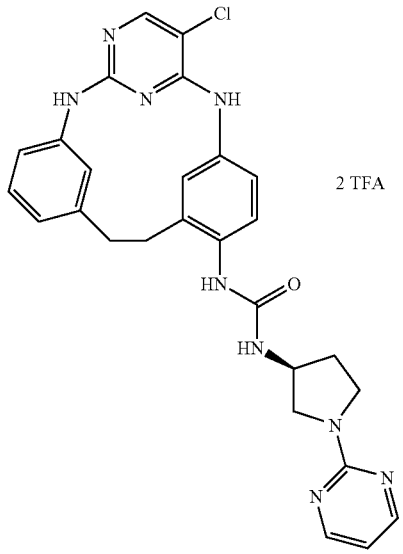 [SMILES: O=C(Nc1ccc2cc1CCc1cccc(c1)Nc1ncc(Cl)c(n1)N2)N[C@H]1CCN(c2ncccn2)C1 ; "2 TFA"]

A mixture of N-[6-chloro-2,4,8,22-tetraazatetracyclo[14.3.1.1(3,7).1(9,13)]docosa-1(20),3(22),4,6,9(21),10,12,16,18-nonaen-12-yl]-N'-[(3S)-pyrrolidin-3-yl]urea (18 mg, 0.040 mmol), 2-chloropyrimidine (8.5 mg, 0.074 mmol), and N,N-diisopropylethylamine (14 µL, 0.080 mmol) in isopropyl alcohol (0.4 mL) was heated in a microwave at 100° C. for 10 minutes. The mixture was diluted with methanol and purified by preparative LCMS (pH 2) to give of the desired product as a white solid (12.5 mg, 36%). LCMS for $C_{27}H_{27}ClN_9O$ $(M+H)^+$: m/z=528.3.

Example B263

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-{1-[(5-methylisoxazol-3-yl)carbonyl]piperidin-4-yl}urea trifluoroacetate

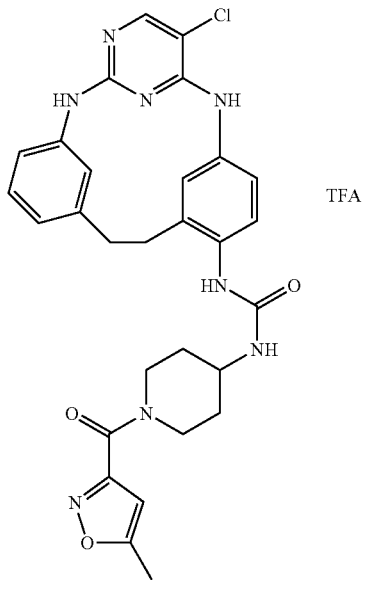 [SMILES: "TFA" ; Cc1cc(C(=O)N2CCC(NC(=O)Nc3ccc4cc3CCc3cccc(c3)Nc3ncc(Cl)c(n3)N4)CC2)no1]

The desired compound was prepared according to the procedure of Example B26, using N-[6-chloro-2,4,8,22-tetraazatetracyclo[14.3.1.1(3,7).1(9,13)]docosa-1(20),3(22),4,6,9(21),10,12,16,18-nonaen-12-yl]-N'-piperidin-4-ylurea trihydrochloride and 5-methylisoxazole-3-carbonyl chloride as the starting materials in 10% yield. LCMS for $C_{29}H_{30}ClN_8O_3(M+H)^+$: m/z=573.0.

Example B264

N-[6-chloro-2,4,8,22-tetraazatetracyclo[14.3.1.1(3,7).1(9,13)]docosa-1(20),3(22),4,6,9(21),10,12,16,18-nonaen-12-yl]-N'-{1-[(5-methylisoxazol-4-yl)carbonyl]piperidin-4-yl}urea trifluoroacetate

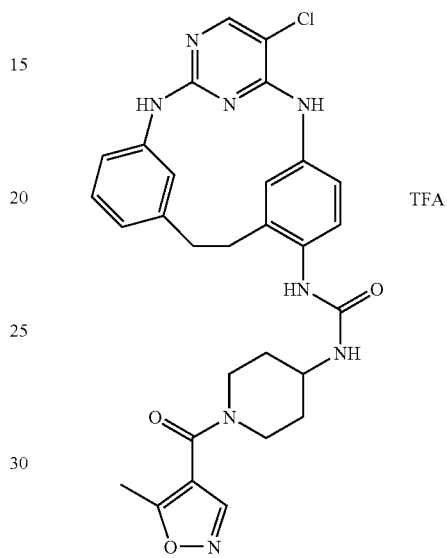

The desired compound was prepared according to the procedure of Example B26, using N-[6-chloro-2,4,8,22-tetraazatetracyclo[14.3.1.1(3,7).1(9,13)]docosa-1(20),3(22),4,6,9(21),10,12,16,18-nonaen-12-yl]-N'-piperidin-4-ylurea trihydrochloride and 5-methylisoxazole-4-carbonyl chloride as the starting materials in 10% yield. LCMS for $C_{29}H_{30}ClN_8O_3(M+H)^+$: m/z=573.0.

Example B265

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-N'-{(3S)-1-[(5-methylisoxazol-3-yl)carbonyl]pyrrolidin-3-yl}urea bis(trifluoroacetate)

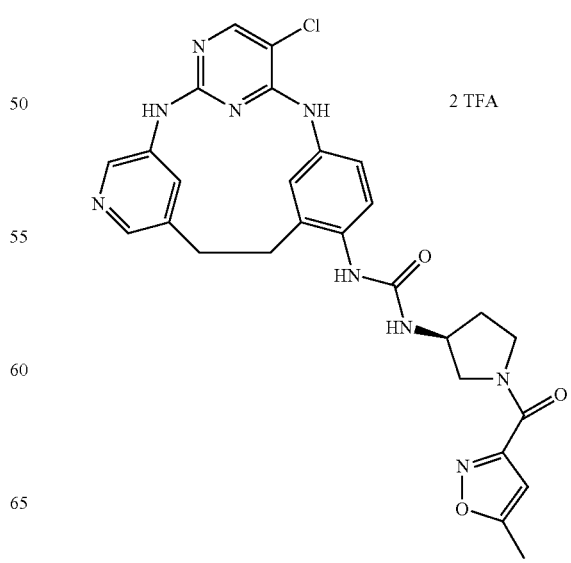

The desired compound was prepared according to the procedure of Example B26, using N-[6-chloro-2,4,8,18,22-pentaazatetracyclo[14.3.1.1(3,7).1(9,13)]docosa-1(20),3(22),4,6,9(21),10,12,16,18-nonaen-12-yl]-N'-[(3S)-pyrrolidin-3-yl]urea trihydrochloride and 5-methylisoxazole-3-carbonyl chloride as the starting materials in 28% yield. LCMS for $C_{27}H_{27}ClN_9O_3(M+H)^+$: m/z=560.1.

Example B266

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-N'-{(3S)-1-[(5-methylisoxazol-4-yl)carbonyl]pyrrolidin-3-yl}urea bis(trifluoroacetate)

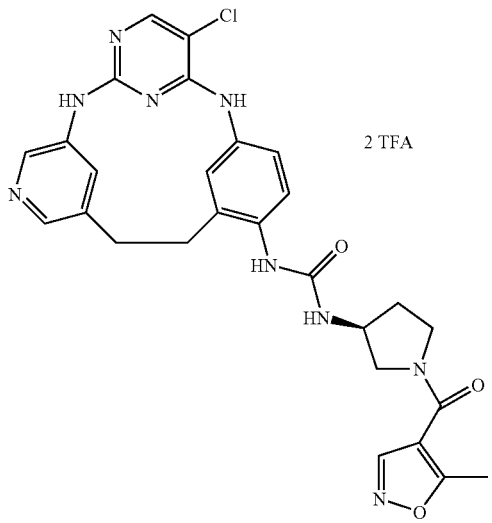 [SMILES: Cc1oncc1C(=O)N1CC[C@H](NC(=O)Nc2ccc3cc2CCc2cncc(c2)Nc2ncc(Cl)c(n2)N3)C1 ; "2 TFA"]

The desired compound was prepared according to the procedure of Example B26, using N-[6-chloro-2,4,8,18,22-pentaazatetracyclo[14.3.1.1(3,7).1(9,13)]docosa-1(20),3(22),4,6,9(21),10,12,16,18-nonaen-12-yl]-N'-[(3S)-pyrrolidin-3-yl]urea trihydrochloride and 5-methylisoxazole-4-carbonyl chloride as the starting materials in 17% yield. LCMS for $C_{27}H_{27}ClN_9O_3(M+H)^+$: m/z=560.0.

Example B267

N-[6-chloro-2,4,8,18,22-pentaazatetracyclo[14.3.1.1(3,7).1(9,13)]docosa-1(20),3(22),4,6,9(21),10,12,16,18-nonaen-12-yl]-N'-[(3S)-1-(1H-pyrazol-4-ylcarbonyl)pyrrolidin-3-yl]urea bis(trifluoroacetate)

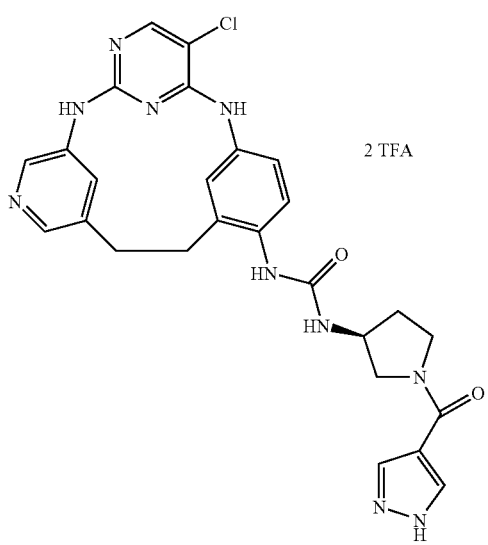 [SMILES: O=C(Nc1ccc2cc1CCc1cncc(c1)Nc1ncc(Cl)c(n1)N2)N[C@H]1CCN(C(=O)c2cn[nH]c2)C1 ; "2 TFA"]

To a mixture of N-[6-chloro-2,4,8,18,22-pentaazatetracyclo[14.3.1.1(3,7).1(9,13)]docosa-1(20),3(22),4,6,9(21),10,12,16,18-nonaen-12-yl]-N'-[(3S)-pyrrolidin-3-yl]urea trihydrochloride (10 mg, 0.02 mmol), 1H-pyrazole-4-carboxylic acid (3.2 mg, 0.029 mmol) and triethylamine (10.6 μL, 0.076 mmol) in DMF (0.2 mL) was added benzothiazol-1-yloxytris (dimethylamino)phosphonium hexafluorophosphate (15.2 mg, 0.034 mmol). The resulting solution was stirred overnight at room temperature. The reaction solution was diluted with methanol and purified with preparative LCMS to give the desired product (1.1 mg, 6%). LCMS for $C_{26}H_{26}ClN_{10}O_2$ $(M+H)^+$: m/z=545.4.

Example B268

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-N'-[(3S)-1-(1H-pyrazol-5-ylcarbonyl)pyrrolidin-3-yl]urea bis(trifluoroacetate)

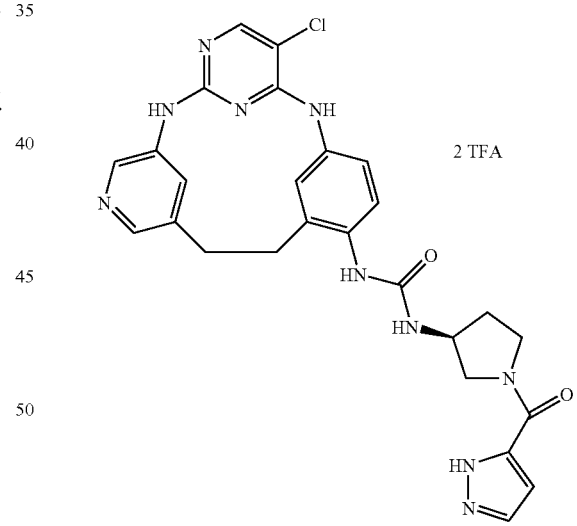

The desired compound was prepared according to the procedure of Example B267, using N-[6-chloro-2,4,8,18,22-pentaazatetracyclo[14.3.1.1(3,7).1(9,13)]docosa-1(20),3(22),4,6,9(21),10,12,16,18-nonaen-12-yl]-N'-[(3S)-pyrrolidin-3-yl]urea trihydrochloride and 1H-pyrazole-5-carboxylic acid as the starting materials in 11% yield. LCMS for $C_{26}H_{26}ClN_{10}O_2(M+H)^+$: m/z=545.3.

Example B269

N-[6-Chloro-2,4,8,18,22-pentaazatetracyclo[14.3.1.1 (3,7).1(9,13)]docosa-1(20),3(22),4,6,9(21),10,12,16, 18-nonaen-12-yl]-N'-{(3S)-1-[(1-methyl-1H-pyrazol-4-yl)carbonyl]pyrrolidin-3-yl}urea bis (trifluoroacetate)

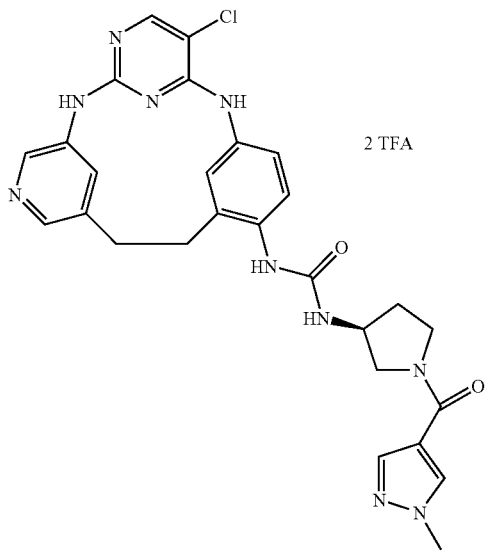 [SMILES: Cn1cc(C(=O)N2CC[C@H](NC(=O)Nc3ccc4cc3CCc3cncc(c3)Nc3ncc(Cl)c(n3)N4)C2)cn1 ; "2 TFA"]

The desired compound was prepared according to the procedure of Example B267, using N-[6-chloro-2,4,8,18,22-pentaazatetracyclo[14.3.1.1(3,7).1(9,13)]docosa-1(20),3 (22),4,6,9(21),10,12,16,18-nonaen-12-yl]-N'-[(3S)-pyrrolidin-3-yl]urea trihydrochloride and 1-methyl-1H-pyrazole-4-carboxylic acid as the starting materials in 22% yield. LCMS for $C_{27}H_{28}ClN_{10}O_2(M+H)^+$: m/z=559.3.

Example B270

N-[6-Chloro-2,4,8,18,22-pentaazatetracyclo[14.3.1.1 (3,7).1(9,13)]docosa-1(20),3(22),4,6,9(21),10,12,16, 18-nonaen-12-yl]-N'-{(3S)-1-[(5-cyclopropylisoxazol-3-yl)carbonyl]pyrrolidin-3-yl}urea bis (trifluoroacetate)

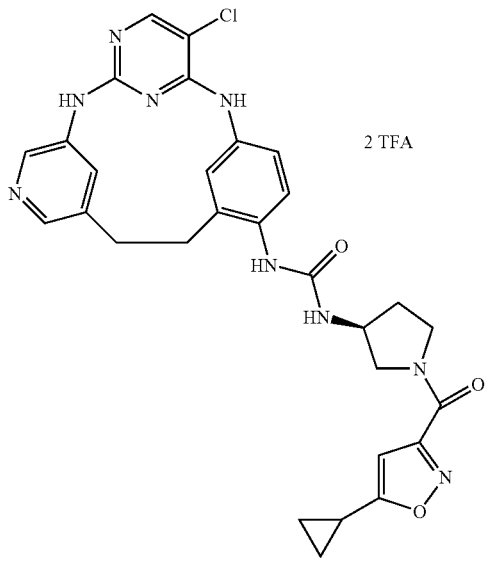 [SMILES: O=C(Nc1ccc2cc1CCc1cncc(c1)Nc1ncc(Cl)c(n1)N2)N[C@H]1CCN(C(=O)c2cc(C3CC3)on2)C1 ; "2 TFA"]

The desired compound was prepared according to the procedure of Example B267, using N-[6-chloro-2,4,8,18,22-pentaazatetracyclo[14.3.1.1(3,7).1(9,13)]docosa-1(20),3 (22),4,6,9(21),10,12,16,18-nonaen-12-yl]-N'-[(3S)-pyrrolidin-3-yl]urea trihydrochloride and 5-cyclopropylisoxzole-3-carboxylic acid as the starting materials in 18% yield. LCMS for $C_{29}H_{29}ClN_9O_3(M+H)^+$: m/z=586.3.

Example B271

N-[6-Chloro-2,4,8,18,22-pentaazatetracyclo[14.3.1.1 (3,7).1(9,13)]docosa-1(20),3(22),4,6,9(21),10,12,16, 18-nonaen-12-yl]-N'-[(3S)-1-(isoxazol-5-ylcarbonyl) pyrrolidin-3-yl]urea bis(trifluoroacetate)

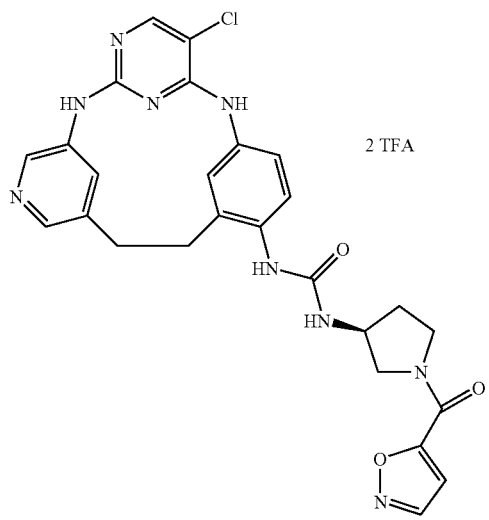 [SMILES: O=C(Nc1ccc2cc1CCc1cncc(c1)Nc1ncc(Cl)c(n1)N2)N[C@H]1CCN(C(=O)c2ccno2)C1 ; "2 TFA"]

The desired compound was prepared according to the procedure of Example B26, using N-[6-chloro-2,4,8,18,22-pentaazatetracyclo[14.3.1.1(3,7).1(9,13)]docosa-1(20),3(22),4, 6,9(21),10,12,16,18-nonaen-12-yl]-N'-[(3S)-pyrrolidin-3-yl]urea trihydrochloride and isoxazole-5-carbonyl chloride as the starting materials in 7% yield. LCMS for $C_{26}H_{25}ClN_9O_3(M+H)^+$: m/z=546.2.

Example B272

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-N'-{(3S)-1-[(1-methyl-1H-pyrazol-3-yl)carbonyl]pyrrolidin-3-yl}urea bis(trifluoroacetate)

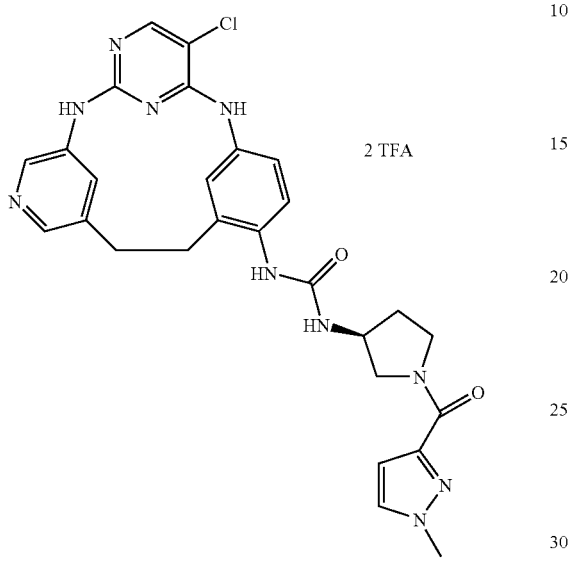

The desired compound was prepared according to the procedure of Example B26, using N-[6-chloro-2,4,8,18,22-pentaazatetracyclo[14.3.1.1(3,7).1(9,13)]docosa-1(20),3(22),4,6,9(21),10,12,16,18-nonaen-12-yl]-N'-[(3S)-pyrrolidin-3-yl]urea trihydrochloride and 1-methyl-1H-pyrazole-3-carbonyl chloride as the starting materials in 9% yield. LCMS for $C_{27}H_{28}ClN_{10}O_2$(M+H)$^+$: m/z=559.2.

Example B273

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-N'-{(3S)-1-[(4-methyl-1,3-oxazol-5-yl)carbonyl]pyrrolidin-3-yl}urea bis(trifluoroacetate)

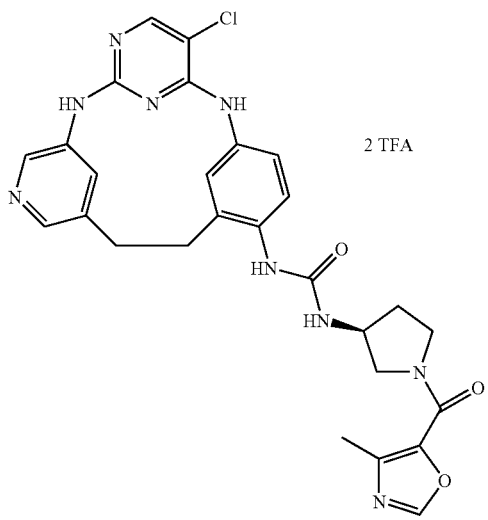 [SMILES: Cc1ncoc1C(=O)N1CC[C@H](NC(=O)Nc2ccc3cc2CCc2cncc(c2)Nc2ncc(Cl)c(n2)N3)C1 ; "2 TFA"]

The desired compound was prepared according to the procedure of Example B26, using N-[6-chloro-2,4,8,18,22-pentaazatetracyclo[14.3.1.1(3,7).1(9,13)]docosa-1(20),3(22),4,6,9(21),10,12,16,18-nonaen-12-yl]-N'-[(3S)-pyrrolidin-3-yl]urea trihydrochloride and 4-methyl-1,3-oxazole-5-carbonyl chloride as the starting materials in 7% yield. LCMS for $C_{27}H_{27}ClN_9O_3$(M+H)$^+$: m/z=560.2.

Example B274

N-[6-chloro-2,4,8,18,22-pentaazatetracyclo[14.3.1.1(3,7).1(9,13)]docosa-1(20),3(22),4,6,9(21),10,12,16,18-nonaen-12-yl]-N'-{(3S)-1-[(3,5-dimethylisoxazol-4-yl)carbonyl]pyrrolidin-3-yl}urea bis(trifluoroacetate)

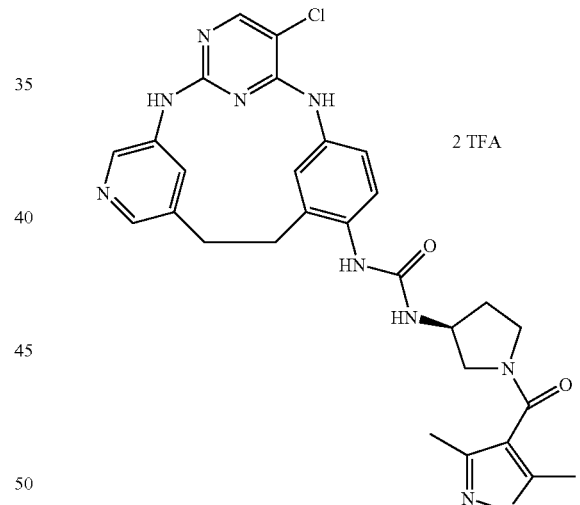

The desired compound was prepared according to the procedure of Example B26, using N-[6-chloro-2,4,8,18,22-pentaazatetracyclo[14.3.1.1(3,7).1(9,13)]docosa-1(20),3(22),4,6,9(21),10,12,16,18-nonaen-12-yl]-N'-[(3S)-pyrrolidin-3-yl]urea trihydrochloride and 3,5-dimethylisoxazole-4-carbonyl chloride as the starting materials in 19% yield. LCMS for $C_{28}H_{29}ClN_9O_3$(M+H)$^+$: m/z=574.3.

Example B275

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-N'-[(3S)-1-[1,3]oxazolo[5,4-b]pyridin-2-ylpyrrolidin-3-yl]urea tris(trifluoroacetate)

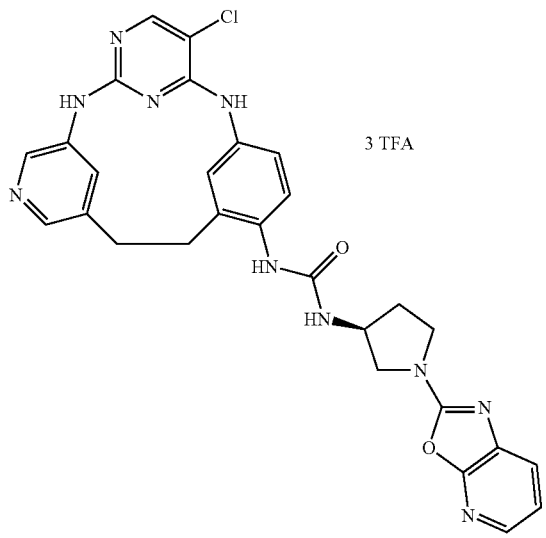 [SMILES: "3 TFA" ; O=C(Nc1ccc2cc1CCc1cncc(c1)Nc1ncc(Cl)c(n1)N2)N[C@H]1CCN(c2nc3cccnc3o2)C1]

A mixture of N-[6-chloro-2,4,8,18,22-pentaazatetracyclo[14.3.1.1(3,7).1(9,13)]docosa-1(20),3(22),4,6,9(21),10,12,16,18-nonaen-12-yl]-N'-[(3S)-pyrrolidin-3-yl]urea trihydrochloride (15 mg, 0.027 mmol), [1,3]oxazole[5,4-b]pyridine-2-thiol (4.9 mg, 0.032 mmol) and triethylamine (14.9 μL, 0.107 mol) in 1,4-dioxane (0.1 mL) was stirred at 70° C. for 3 hours. The solvent was removed in vacuo. To the residue was added ethanol (0.2 mL), silver nitrate (9 mg, 0.05 mmol) and 29% ammonium hydroxide in water (30 μL, 0.2 mmol). The resulting solution was stirred overnight at room temperature. The reaction solution was diluted with methanol and purified with preparative LCMS to give the desired product (1.7 mg, 7%). LCMS for $C_{28}H_{26}ClN_{10}O_2(M+H)^+$: m/z=569.0.

Example B276

6-Chloro-N-(4-methylpyrimidin-2-yl)-2,4,8,22-tetraazatetracyclo[14.3.1.1(3,7).1(9,13)]docosa-1(20),3(22),4,6,9(21),10,12,16,18-nonaen-12-amine bis(trifluoroacetate)

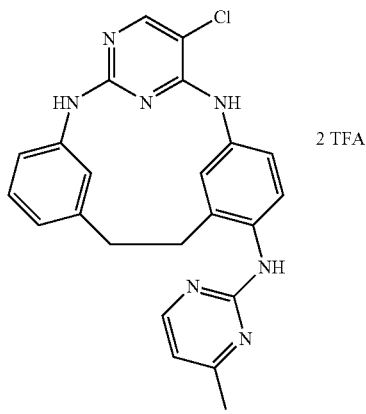 [SMILES: Cc1ccnc(Nc2ccc3cc2CCc2cccc(c2)Nc2ncc(Cl)c(n2)N3)n1 ; "2 TFA"]

A mixture of 6-chloro-2,4,8,22-tetraazatetracyclo[14.3.1.1(3,7).1(9,13)]docosa-1(20),3(22),4,6,9(21),10,12,16,18-nonaen-12-amine dihydrochloride (15 mg, 0.036 mmol), 2-chloro-4-methylpyrimidine (5.8 mg, 0.045 mmol) and N,N-diisopropylethylamine (22 μL, 0.13 mmol) in isopropyl alcohol (0.2 mL) was heated at 180° C. for 40 min in the microwave reactor. The reaction solution was diluted with methanol and purified with preparative LCMS to give the desired product (2.4 mg, 8%). LCMS for $C_{23}H_{21}ClN_7(M+H)^+$: m/z=430.3.

Example B277

2-{[6-Chloro-2,4,8,22-tetraazatetracyclo[14.3.1.1(3,7).1(9,13)]docosa-1(20),3(22),4,6,9(21),10,12,16,18-nonaen-12-yl]amino}pyrimidin-4-ol bis(trifluoroacetate)

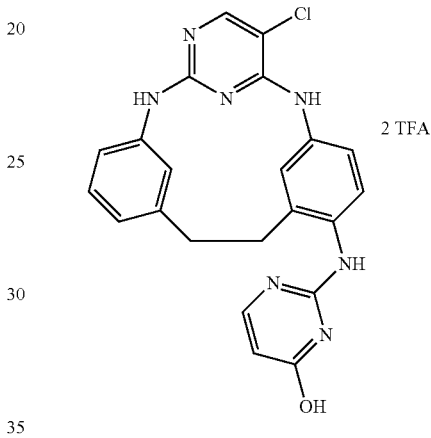

The desired compound was prepared according to the procedure of Example B276, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 2-chloro-4-methoxypyrimidine as the starting materials in 16% yield. LCMS for $C_{22}H_{19}ClN_7O$ $(M+H)^+$: m/z=432.3.

Example B278

Ethyl 2-{[6-chloro-2,4,8,22-tetraazatetracyclo[14.3.1.1(3,7).1(9,13)]docosa-1(20),3(22),4,6,9(21),10,12,16,18-nonaen-12-yl]amino}-1,3-oxazole-4-carboxylate bis(trifluoroacetate)


The desired compound was prepared according to the procedure of Example B276, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and ethyl-2-chloro-1,3-oxazole-4-carboxylate as the starting materials in 5% yield. LCMS for $C_{24}H_{22}ClN_6O_3(M+H)^+$: m/z=477.2.

Example B279

6-Chloro-N-(4-phenylpyrimidin-2-yl)-2,4,8,22-tetraazatetracyclo[14.3.1.1(3,7).1(9,13)]docosa-1(20),3(22),4,6,9(21),10,12,16,18-nonaen-12-amine tris(trifluoroacetate)

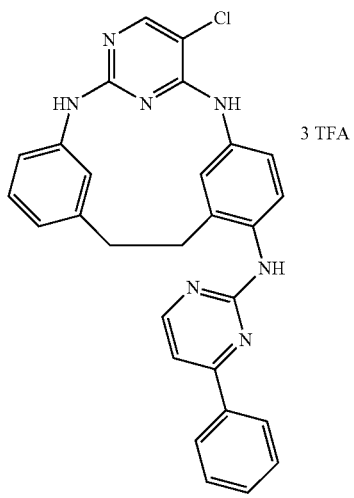 [SMILES: "3 TFA" ; Clc1cnc2nc1Nc1ccc(Nc3nccc(-c4ccccc4)n3)c(c1)CCc1cccc(c1)N2]

3 TFA

The desired compound was prepared according to the procedure of Example B276, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 2-chloro-4-phenylpyrimidine as the starting materials in 8% yield. LCMS for $C_{28}H_{23}ClN_7(M+H)^+$: m/z=492.4.

Example B280

2-Chloro-N-[6-chloro-2,4,8,22-tetraazatetracyclo[14.3.1.1(3,7).1(9,13)]docosa-1(20),3(22),4,6,9(21),10,12,16,18-nonaen-12-yl]-6-methylpyrimidine-4-carboxamide bis(trifluoroacetate)

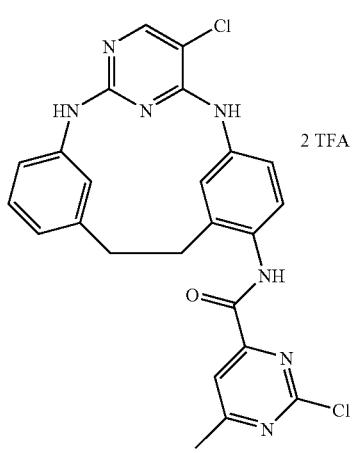 [SMILES: Cc1cc(C(=O)Nc2ccc3cc2CCc2cccc(c2)Nc2ncc(Cl)c(n2)N3)nc(Cl)n1 ; "2 TFA"]

2 TFA

The desired compound was prepared according to the procedure of Example B276, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and methyl-2-chloro-6-methylpyrimidine-4-carboxylate as the starting materials in 8% yield. LCMS for $C_{24}H_{20}Cl_2N_7O(M+H)^+$: m/z=492.3.

Example B281

N-[4-(4-Aminopiperidin-1-yl)pyrimidin-2-yl]-6-chloro-2,4,8,22-tetraazatetracyclo[14.3.1.1(3,7).1(9,13)]docosa-1(20),3(22),4,6,9(21),10,12,16,18-nonaen-12-amine tris(trifluoroacetate)

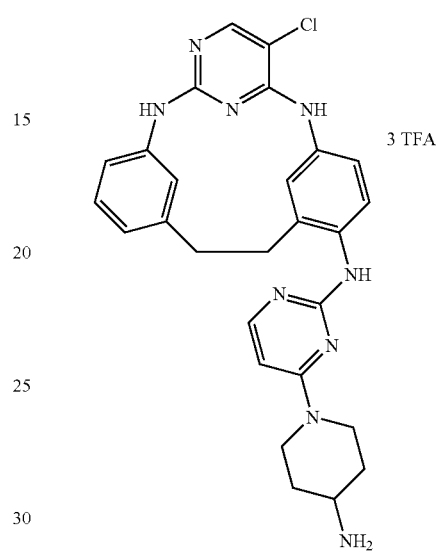

3 TFA

To a solution of 6-chloro-2,4,8,22-tetraazatetracyclo[14.3.1.1(3,7).1(9,13)]docosa-1(20),3(22),4,6,9(21),10,12,16,18-nonaen-12-amine dihydrochloride (10 mg, 0.02 mmol) in 2-methoxyethanol (0.2 mL) was added tert-butyl [1-(2-chloropyrimidin-4-yl)piperidin-4-yl]carbamate (9.1 mg, 0.029 mmol) and 4.0 M hydrogen chloride in 1,4-dioxane (9.1 µL, 0.036 mmol). The solution was heated at 130° C. for 15 min. The reaction solution was diluted with methanol and purified with preparative LCMS to give the desired product (7.0 mg, 30%). LCMS for $C_{27}H_{29}ClN_9(M+H)^+$: m/z=514.1.

Example B282

N-[4-(4-Aminopiperidin-1-yl)pyrimidin-2-yl]-6-chloro-2,4,8,18,22-pentaazatetracyclo[14.3.1.1(3,7).1(9,13)]docosa-1(20),3(22),4,6,9(21),10,12,16,18-nonaen-12-amine tetrakis(trifluoroacetate)

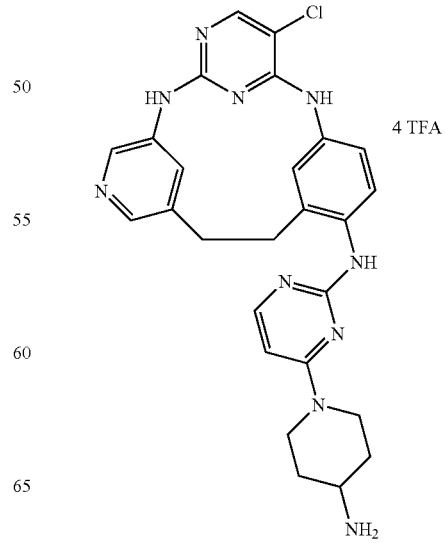

4 TFA

The desired compound was prepared according to the procedure of Example B281, using 6-chloro-2,4,8,18,22-pentaazatetracyclo[14.3.1.1(3,7).1(9,13)]docosa-1(20),3(22),4,6,9(21),10,12,16,18-nonaen-12-amine trihydrochloride and tert-butyl [1-(2-chloropyrimidin-4-yl)piperidin-4-yl]carbamate as the starting materials in 31% yield. LCMS for $C_{26}H_{28}ClN_{10}$ (M+H)$^+$: m/z=515.1.

Example B283

N-[(3S)-1-Benzylpyrrolidin-3-yl]-N'-[6-chloro-2,4,8,22-tetraazatetracyclo[14.3.1.1(3,7).1(9,13)]docosa-1(20),3(22),4,6,9(21),10,12,16,18-nonaen-12-yl]-N-methylurea

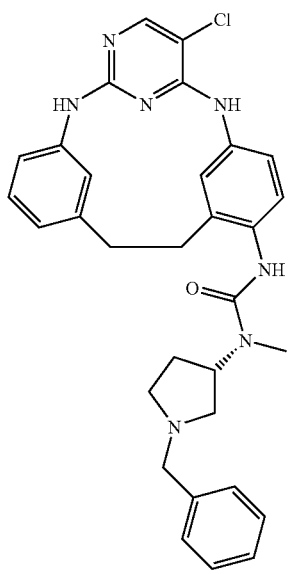

The desired compound was prepared according to the procedure of Example B236, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and (3S)-1-benzyl-N-methylpyrrolidin-3-amine as the starting materials in 32% yield. LCMS for $C_{31}H_{33}ClN_7O$ (M+H)$^+$: m/z=554.3.

Example B284

N-[(3S)-1-Benzylpyrrolidin-3-yl]-N'-[6-chloro-2,4,8,18,22-pentaazatetracyclo[14.3.1.1(3,7).1(9,13)]docosa-1(20),3(22),4,6,9(21),10,12,16,18-nonaen-12-yl]-N-methylurea

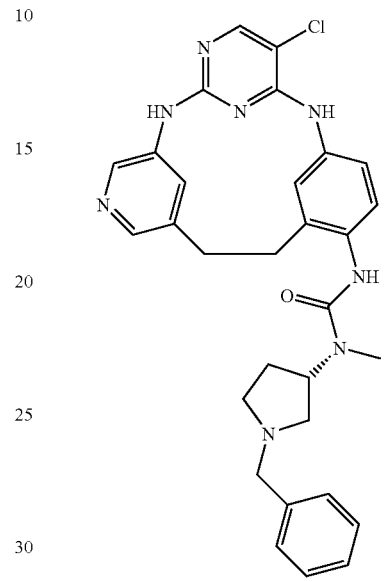

The desired compound was prepared according to the procedure of Example B236, using 6-chloro-2,4,8,18,22-pentaazatetracyclo[14.3.1.1(3,7).1(9,13)]docosa-1(20),3(22),4,6,9(21),10,12,16,18-nonaen-12-amine and (3S)-1-benzyl-N-methylpyrrolidin-3-amine as the starting materials in 33% yield. LCMS for $C_{30}H_{32}ClN_8O$ (M+H)$^+$: m/z=555.3.

Example B285

N-[6-Chloro-2,4,8,18,22-pentaazatetracyclo[14.3.1.1(3,7).1(9,13)]docosa-1(20),3(22),4,6,9(21),10,12,16,18-nonaen-12-yl]piperazine-1-carboxamidetrihydrochloride

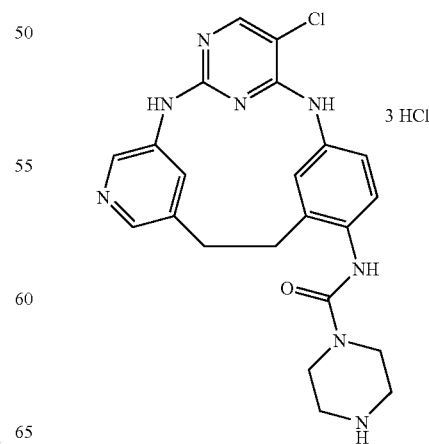

Step A: tert-Butyl 4-({[6-chloro-2,4,8,18,22-pentaazatetracyclo[14.3.1.1(3,7).1(9,13)]docosa-1(20),3(22),4,6,9(21),10,12,16,18-nonaen-12-yl]amino}carbonyl)piperazine-1-carboxylate

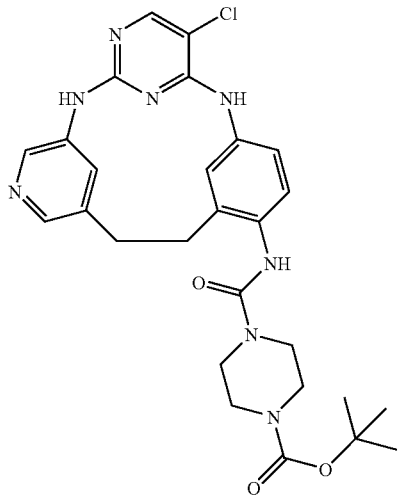 [SMILES: CC(C)(C)OC(=O)N1CCN(C(=O)Nc2ccc3cc2CCc2cncc(c2)Nc2ncc(Cl)c(n2)N3)CC1]

The desired compound was prepared according to the procedure of Example B236, using 6-chloro-2,4,8,18,22-pentaazatetracyclo[14.3.1.1(3,7).1(9,13)]docosa-1(20),3(22),4,6,9(21),10,12,16,18-nonaen-12-amine and tert-butyl piperidine-1-carboxylate as the starting materials in 54% yield. LCMS for $C_{27}H_{32}ClN_8O_3$ (M+H)$^+$: m/z=551.3.

Step B: N-[6-Chloro-2,4,8,18,22-pentaazatetracyclo[14.3.1.1(3,7).1(9,13)]docosa-1(20),3(22),4,6,9(21),10,12,16,18-nonaen-12-yl]piperazine-1-carboxamidetrihydrochloride The desired compound was prepared according to the procedure of Example B21, step B, using tert-butyl 4-({[6-chloro-2,4,8,18,22-pentaazatetracyclo[14.3.1.1(3,7).1(9,13)]docosa-1(20),3(22),4,6,9(21),10,12,16,18-nonaen-12-yl]amino}carbonyl)piperazine-1-carboxylate as the starting material in 96% yield. LCMS for $C_{22}H_{24}ClN_8O$ (M+H)$^+$: m/z=451.4.

Example B286

4-Benzoyl-N-[6-chloro-2,4,8,18,22-pentaazatetracyclo[14.3.1.1(3,7).1(9,13)]docosa-1(20),3(22),4,6,9(21),10,12,16,18-nonaen-12-yl]piperazine-1-carboxamide bis(trifluoroacetate)

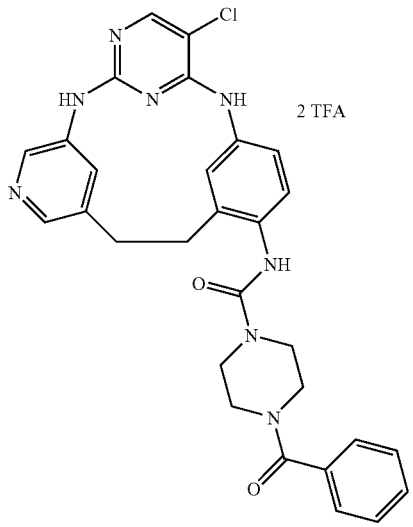 [SMILES: O=C(Nc1ccc2cc1CCc1cncc(c1)Nc1ncc(Cl)c(n1)N2)N1CCN(C(=O)c2ccccc2)CC1 ; "2 TFA"]

The desired compound was prepared according to the procedure of Example B26, using N-[6-chloro-2,4,8,18,22-pentaazatetracyclo[14.3.1.1(3,7).1(9,13)]docosa-1(20),3(22),4,6,9(21),10,12,16,18-nonaen-12-yl]piperazine-1-carboxamide trihydrochloride and benzoyl chloride as the starting materials in 45% yield. LCMS for $C_{29}H_{28}ClN_8O_2$ (M+H)$^+$: m/z=555.3.

Example B287

4-Benzyl-N-[6-chloro-2,4,8,18,22-pentaazatetracyclo[14.3.1.1(3,7).1(9,13)]docosa-1(20),3(22),4,6,9(21),10,12,16,18-nonaen-12-yl]piperazine-1-carboxamidetris(trifluoroacetate)

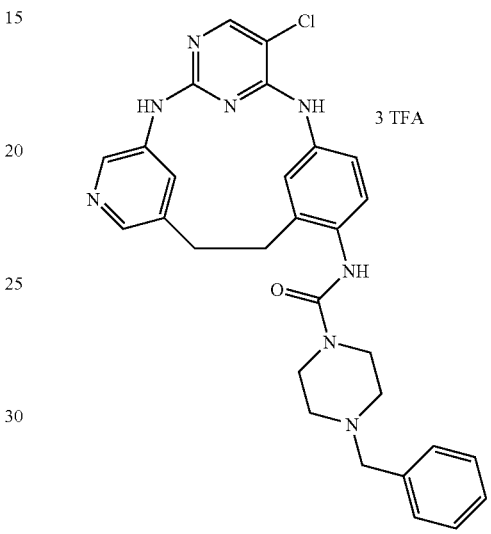

The desired compound was prepared according to the procedure of Example B192, using N-[6-chloro-2,4,8,18,22-pentaazatetracyclo[14.3.1.1(3,7).1(9,13)]docosa-1(20),3(22),4,6,9(21),10,12,16,18-nonaen-12-yl]piperazine-1-carboxamide trihydrochloride and benzaldehyde as the starting materials in 22% yield. LCMS for $C_{29}H_{30}ClN_8O$ (M+H)$^+$: m/z=541.3.

Example B288

N'-[6-Chloro-2,4,8,18,22-pentaazatetracyclo[14.3.1.1(3,7).1(9,13)]docosa-1(20),3(22),4,6,9(21),10,12,16,18-nonaen-12-yl]-N-methyl-N-[(3S)-pyrrolidin-3-yl]urea tris(trifluoroacetate)

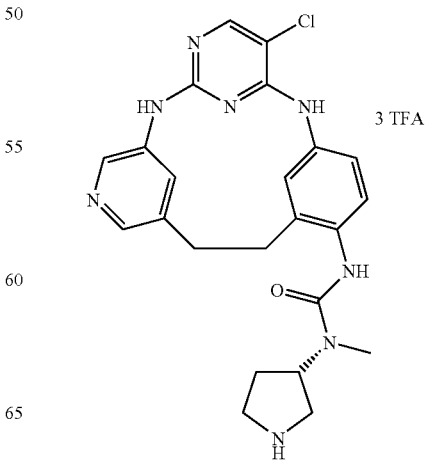

449

Step A: N-[(3S)-1-Benzylpyrrolidin-3-yl]N'-[6-chloro-2,4,8,18,22-pentaazatetracyclo[14.3.1.1(3,7).1(9,13)]docosa-1(20),3(22),4,6,9(21),10,12,16,18-nonaen-12-yl]-N-methylurea

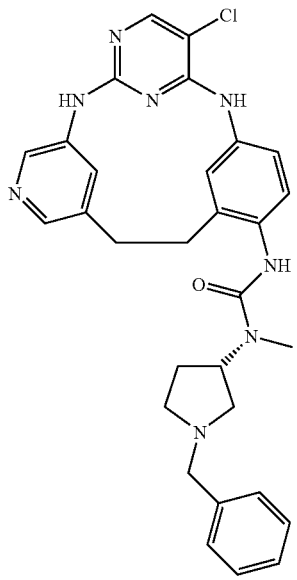

The desired compound was prepared according to the procedure of Example B236, using 6-chloro-2,4,8,18,22-pentaazatetracyclo[14.3.1.1(3,7).1(9,13)]docosa-1(20),3(22),4,6,9(21),10,12,16,18-nonaen-12-amine and (3S)-1-benzyl-N-methylpyrrolidin-3-amine as the starting materials in 33% yield. LCMS for $C_{30}H_{32}ClN_8O$ (M+H)$^+$: m/z=555.3.

Step B: N'-[6-Chloro-2,4,8,18,22-pentaazatetracyclo[14.3.1.1(3,7).1(9,13)]docosa-1(20),3(22),4,6,9(21),10,12,16,18-nonaen-12-yl]-N-methyl-N-[(3S)-pyrrolidin-3-yl]urea tris(trifluoroacetate)

To a mixture of N-[(3S)-1-benzylpyrrolidin-3-yl]N'-[6-chloro-2,4,8,18,22-pentaazatetracyclo[14.3.1.1(3,7).1(9,13)]docosa-1(20),3(22),4,6,9(21),10,12,16,18-nonaen-12-yl]-N-methylurea (45 mg, 0.037 mmol) and 10% palladium on carbon (50 mg, 0.05 mmol) in methanol (0.5 mL) was added ammonium formate (32 mg, 0.51 mmol). The reaction solution was stirred at 65° C. overnight. The reaction solution was cooled to room temperature and diluted with methanol and purified with preparative LCMS to give the desired product (1.2 mg, 2%). LCMS for $C_{23}H_{26}ClN_8O$ (M+H)$^+$: m/z=465.2.

450

Example B289

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-4-pyridin-2-ylpiperazine-1-carboxamide tris(trifluoroacetate)

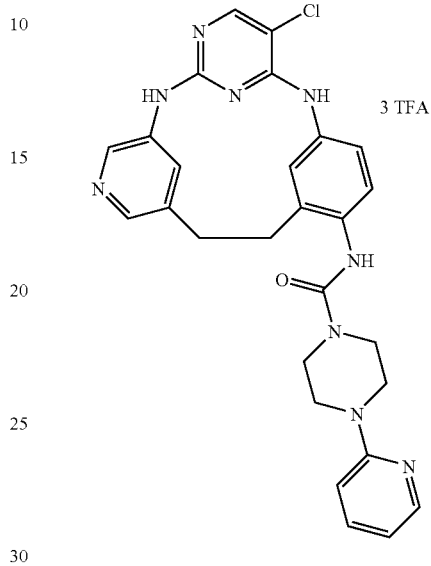

The desired compound was prepared according to the procedure of Example B236, using 6-chloro-2,4,8,18,22-pentaazatetracyclo[14.3.1.1(3,7).1(9,13)]docosa-1(20),3(22),4,6,9(21),10,12,16,18-nonaen-12-amine and N-(2-pyridyl)piperazine as the starting materials in 27% yield. LCMS for $C_{27}H_{27}ClN_9O$ (M+H)$^+$: m/z=528.3.

Example B290

N-[6-Chloro-2,4,8,22-tetraazatetracyclo[14.3.1.1(3,7).1(9,13)]docosa-1(20),3(22),4,6,9(21),10,12,16,18-nonaen-12-yl]-4-pyridin-2-ylpiperazine-1-carboxamide bis(trifluoroacetate)

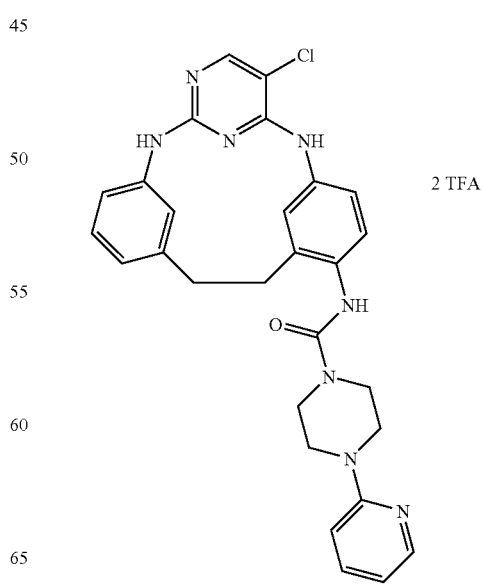

The desired compound was prepared according to the procedure of Example B236, using 6-chloro-2,4,8,22-tetraazatetracyclo[14.3.1.1(3,7).1(9,13)]docosa-1(9,13),3(22),4,6,9(21),10,12,16,18-nonaen-12-amine dihydrochloride and N-(2-pyridyl)piperazine as the starting materials in 18% yield. LCMS for $C_{28}H_{28}ClN_8O$ (M+H)$^+$: m/z=527.3.

Example B291
N-[(3S)-1-Benzoylpyrrolidin-3-yl]-N'-[6-chloro-2,4,8,18,22-pentaazatetracyclo[14.3.1.1(3,7).1(9,13)]docosa-1(20),3(22),4,6,9(21),10,12,16,18-nonaen-12-yl]-N-methylurea bis(trifluoroacetate)

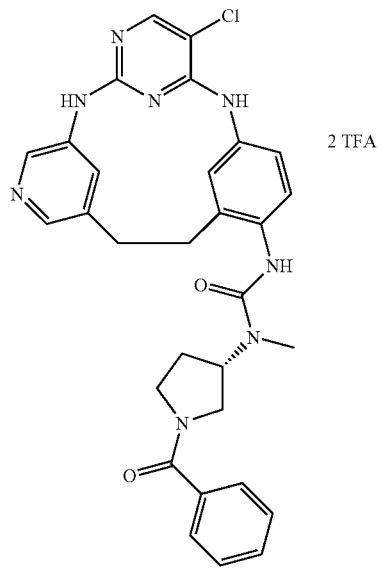 [SMILES: CN(C(=O)Nc1ccc2cc1CCc1cncc(c1)Nc1ncc(Cl)c(n1)N2)[C@H]1CCN(C(=O)c2ccccc2)C1 ; "2 TFA"]

The desired compound was prepared according to the procedure of Example B26, using N'-[6-chloro-2,4,8,18,22-pentaazatetracyclo[14.3.1.1(3,7).1(9,13)]docosa-1(20),3(22),4,6,9(21),10,12,16,18-nonaen-12-yl]-N-methyl-N-[(3S)-pyrrolidin-3-yl]urea trihydrochloride and benzoyl chloride as the starting materials in 14% yield. LCMS for $C_{30}H_{30}ClN_8O_2$ (M+H)$^+$: m/z=569.3.

Example B292
N-[6-Chloro-2,4,8,18,22-pentaazatetracyclo[14.3.1.1(3,7).1(9,13)]docosa-1(20),3(22),4,6,9(21),10,12,16,18-nonaen-12-yl]-4-phenylpiperazine-1-carboxamide tris(trifluoroacetate)

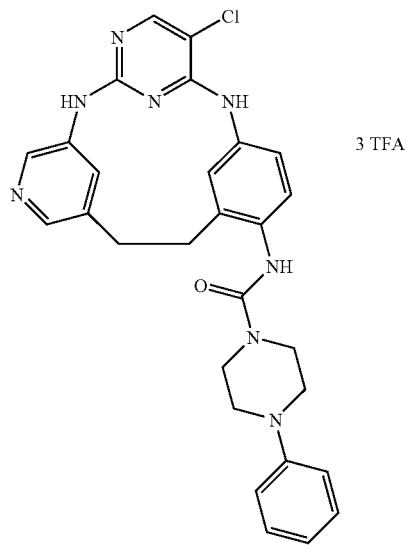 [SMILES: "3 TFA" ; O=C(Nc1ccc2cc1CCc1cncc(c1)Nc1ncc(Cl)c(n1)N2)N1CCN(c2ccccc2)CC1]

The desired compound was prepared according to the procedure of Example B236, using 6-chloro-2,4,8,18,22-pentaazatetracyclo[14.3.1.1(3,7).1(9,13)]docosa-1(20),3(22),4,6,9(21),10,12,16,18-nonaen-12-amine trihydrochloride and 1-phenylpiperazine as the starting materials in 28% yield. LCMS for $C_{28}H_{28}ClN_8O$ (M+H)$^+$: m/z=527.2. $^1$HNMR (300 MHz, CD$_3$OD) δ 9.29 (s, 1H), 8.30 (d, 2H), 8.16 (s, 1H), 7.72 (s, 1H), 7.33 (t, 2H), 7.24 (d, 1H), 7.13 (d, 3H), 6.99 (t, 1H), 3.79 (t, 4H), 3.35 (m, 4H), 3.11 (q, 4H).

Example B293
N-[6-Chloro-2,4,8,18,22-pentaazatetracyclo[14.3.1.1(3,7).1(9,13)]docosa-1(20),3(22),4,6,9(21),10,12,16,18-nonaen-12-yl]-4-pyridin-4-ylpiperazine-1-carboxamide tetrakis(trifluoroacetate)

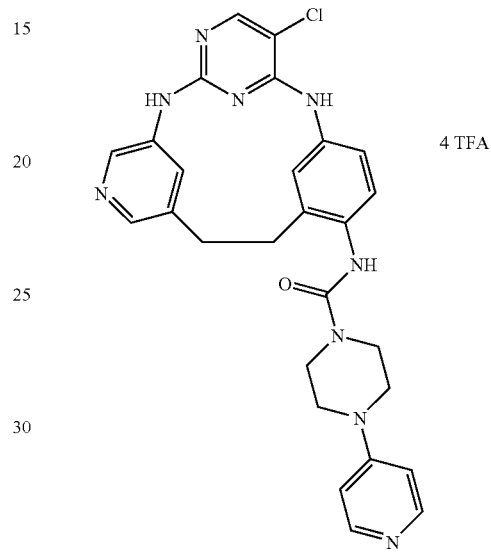

The desired compound was prepared according to the procedure of Example B236, using 6-chloro-2,4,8,18,22-pentaazatetracyclo[14.3.1.1(3,7).1(9,13)]docosa-1(20),3(22),4,6,9(21),10,12,16,18-nonaen-12-amine trihydrochloride and 1-pyridin-4-ylpiperazine as the starting materials in 19% yield. LCMS for $C_{27}H_{27}ClN_9O$ (M+H)$^+$: m/z=528.3.

Example B294
N-[6-Chloro-2,4,8,18,22-pentaazatetracyclo[14.3.1.1(3,7).1(9,13)]docosa-1(20),3(22),4,6,9(21),10,12,16,18-nonaen-12-yl]-4-pyrazin-2-ylpiperazine-1-carboxamide tetrakis(trifluoroacetate)

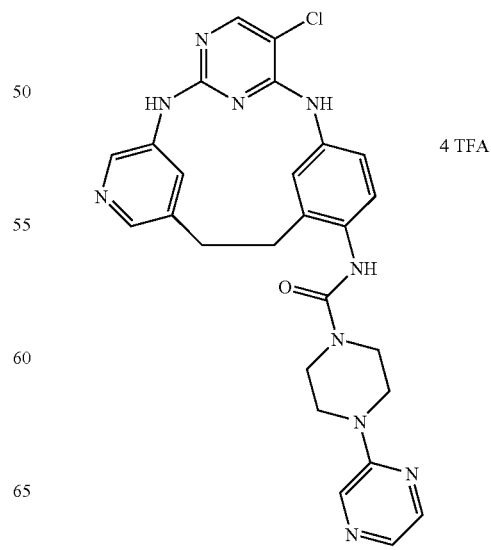

The desired compound was prepared according to the procedure of Example B236, using 6-chloro-2,4,8,18,22-pentaazatetracyclo[14.3.1.1(3,7).1(9,13)]docosa-1(20),3(22),4,6,9(21),10,12,16,18-nonaen-12-amine trihydrochloride and 2-piperazin-1-ylpyrazine as the starting materials in 19% yield. LCMS for $C_{26}H_{26}ClN_{10}O$ (M+H)$^+$: m/z=529.3.

Example B295

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-4-(2-fluorophenyl)piperazine-1-carboxamide tris(trifluoroacetate)

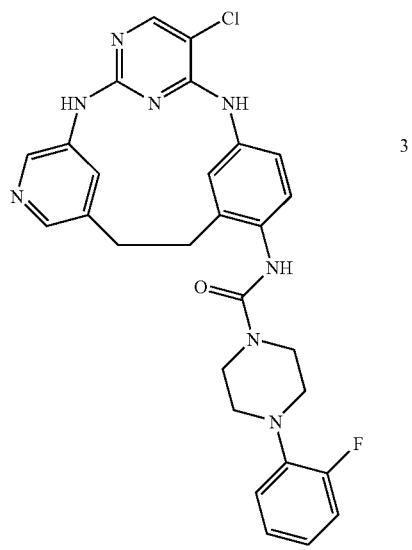

3 TFA

The desired compound was prepared according to the procedure of Example B236, using 6-chloro-2,4,8,18,22-pentaazatetracyclo[14.3.1.1(3,7).1(9,13)]docosa-1(20),3(22),4,6,9(21),10,12,16,18-nonaen-12-amine trihydrochloride and 1-(2-fluorophenyl)piperazine as the starting materials in 23% yield. LCMS for $C_{28}H_{27}ClFN_8O$ (M+H)$^+$: m/z=545.3.

Example B296

6-Chloro-N-[4-(hexahydropyrrolo[1,2-a]pyrazin-2(1H)-ylcarbonyl)-2,3-oxazol-2-yl]-2,4,8,22-tetraazatetracyclo[14.3.1.1(3,7).1(9,13)]docosa-1(20),3(22),4,6,9(21),10,12,16,18-nonaen-12-amine bis(trifluoroacetate)

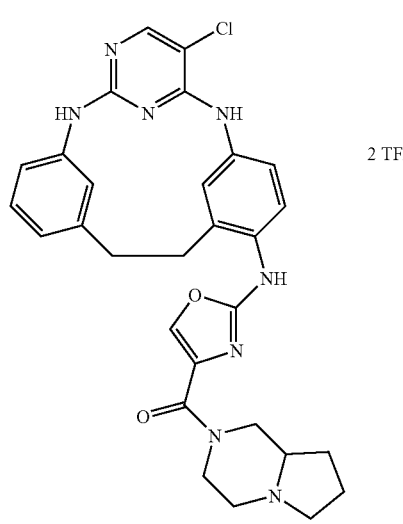

2 TFA

The desired compound was prepared according to the procedure of Example B7, using methyl ethyl 2-{[6-chloro-2,4,8,22-tetraazatetracyclo[14.3.1.1(3,7).1(9,13)]docosa-1(20),3(22),4,6,9(21),10,12,16,18-nonaen-12-yl]amino}-1,3-oxazole-4-carboxylate bis(trifluoroacetate) and octahydropyrrolo[1,2-a]pyrazine as the starting materials in 25% yield. LCMS for $C_{29}H_{30}ClN_8O_2$ (M+H)$^+$: m/z=557.3.

Example B297

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-4-(4-fluorophenyl)piperazine-1-carboxamide tris(trifluoroacetate)

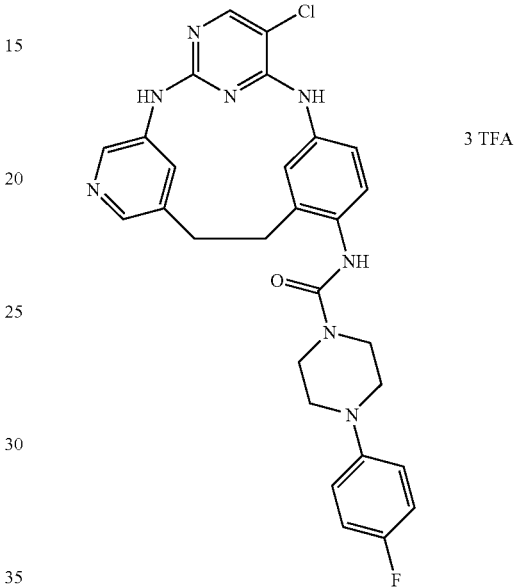

3 TFA

The desired compound was prepared according to the procedure of Example B236, using 6-chloro-2,4,8,18,22-pentaazatetracyclo[14.3.1.1(3,7).1(9,13)]docosa-1(20),3(22),4,6,9(21),10,12,16,18-nonaen-12-amine trihydrochloride and N-(4-fluorophenyl)piperazine as the starting materials in 17% yield. LCMS for $C_{28}H_{27}ClFN_8O$ (M+H)$^+$: m/z=545.3.

Example B298

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-4-(2-methoxyphenyl)piperazine-1-carboxamide tris(trifluoroacetate)

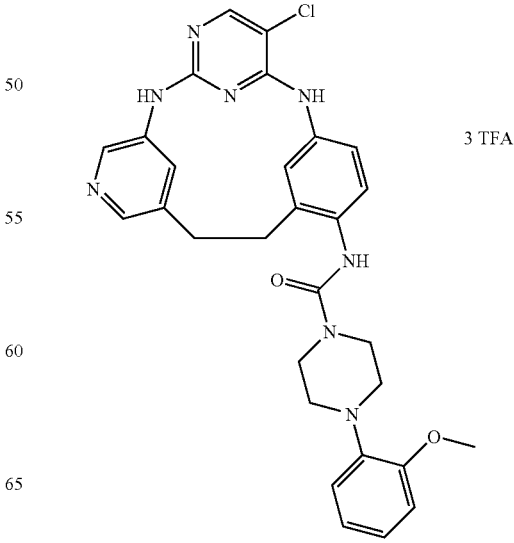

3 TFA

The desired compound was prepared according to the procedure of Example B236, using 6-chloro-2,4,8,18,22-pentaazatetracyclo[14.3.1.1(3,7).1(9,13)]docosa-1(20),3(22),4,6,9(21),10,12,16,18-nonaen-12-amine trihydrochloride and 1-(2-methoxyphenyl)piperazine as the starting materials in 25% yield. LCMS for $C_{29}H_{30}ClN_8O_2$ (M+H)$^+$: m/z=557.4.

Example B299

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-4-(4-methoxyphenyl)piperazine-1-carboxamide tris(trifluoroacetate)

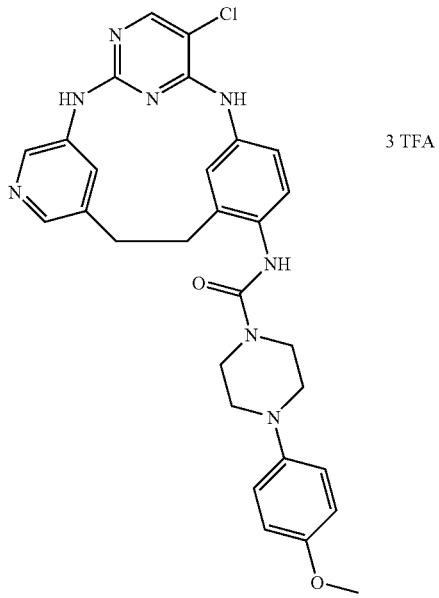 [SMILES: "3 TFA" ; COc1ccc(N2CCN(C(=O)Nc3ccc4cc3CCc3cncc(c3)Nc3ncc(Cl)c(n3)N4)CC2)cc1]

The desired compound was prepared according to the procedure of Example B236, using 6-chloro-2,4,8,18,22-pentaazatetracyclo[14.3.1.1(3,7).1(9,13)]docosa-1(20),3(22),4,6,9(21),10,12,16,18-nonaen-12-amine trihydrochloride and 1-(4-methoxyphenyl)piperazine as the starting materials in 12% yield. LCMS for $C_{29}H_{30}ClN_8O_2$ (M+H)$^+$: m/z=557.3.

Example B300

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-4-(2-cyanophenyl)piperazine-1-carboxamide tris(trifluoroacetate)

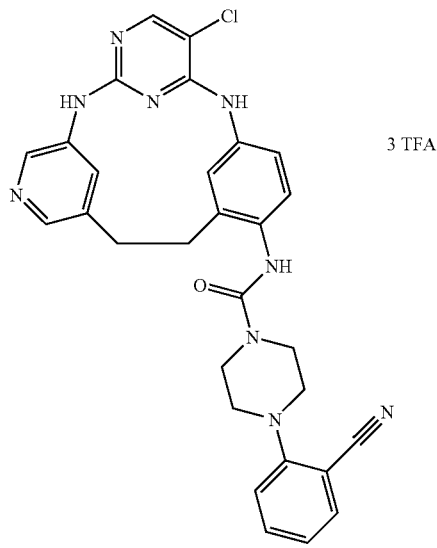 [SMILES: "3 TFA" ; N#Cc1ccccc1N1CCN(C(=O)Nc2ccc3cc2CCc2cncc(c2)Nc2ncc(Cl)c(n2)N3)CC1]

The desired compound was prepared according to the procedure of Example B236, using 6-chloro-2,4,8,18,22-pentaazatetracyclo[14.3.1.1(3,7).1(9,13)]docosa-1(20),3(22),4,6,9(21),10,12,16,18-nonaen-12-amine trihydrochloride and 2-piperazin-1-yl-benzonitrile as the starting materials in 18% yield. LCMS for $C_{29}H_{27}ClN_9O$ (M+H)$^+$: m/z=552.2.

Example B301

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-4-[5-(trifluoromethyl)pyridin-2-yl]piperazine-1-carboxamide tris(trifluoroacetate)

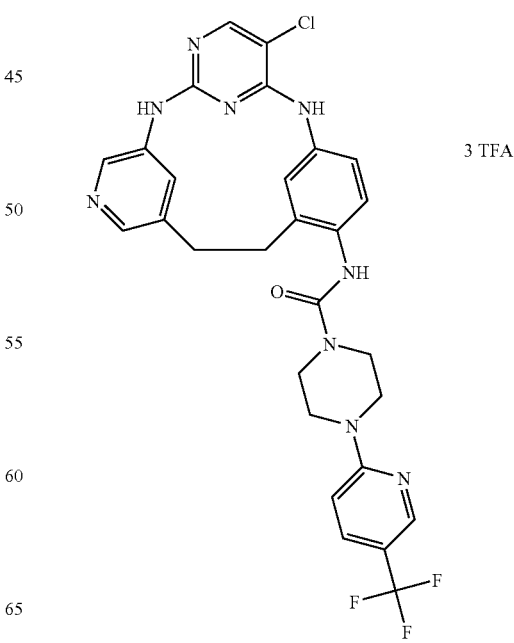

The desired compound was prepared according to the procedure of Example B236, using 6-chloro-2,4,8,18,22-pentaazatetracyclo[14.3.1.1(3,7).1(9,13)]docosa-1(20),3(22),4,6,9(21),10,12,16,18-nonaen-12-amine trihydrochloride and 1-[5-(trifluoromethyl)pyridine-2-yl]piperazine as the starting materials in 18% yield. LCMS for $C_{28}H_{26}ClF_3N_9O$ (M+H)$^+$: m/z=596.3.

Example B302

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-4-[3-chloro-5-(trifluoromethyl)pyridin-2-yl]piperazine-1-carboxamide tris(trifluoroacetate)

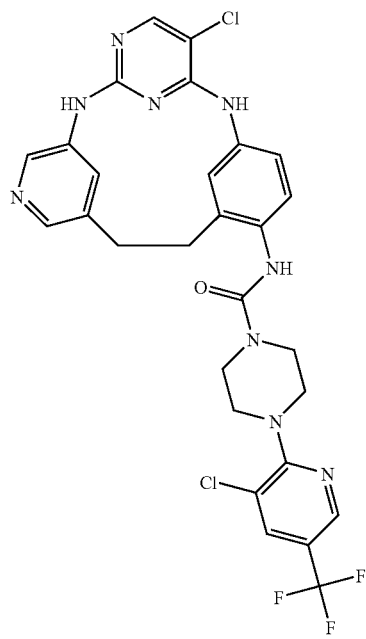

The desired compound was prepared according to the procedure of Example B236, using 6-chloro-2,4,8,18,22-pentaazatetracyclo[14.3.1.1(3,7).1(9,13)]docosa-1(20),3(22),4,6,9(21),10,12,16,18-nonaen-12-amine trihydrochloride and 1-[3-chloro-5-(trifluoromethyl)pyridine-2-yl]piperazine as the starting materials in 19% yield. LCMS for $C_{28}H_{25}Cl_2F_3N_9O$ (M+H)$^+$: m/z=630.3.

Example B303

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-4-(4-cyanophenyl)piperazine-1-carboxamide tris(trifluoroacetate)

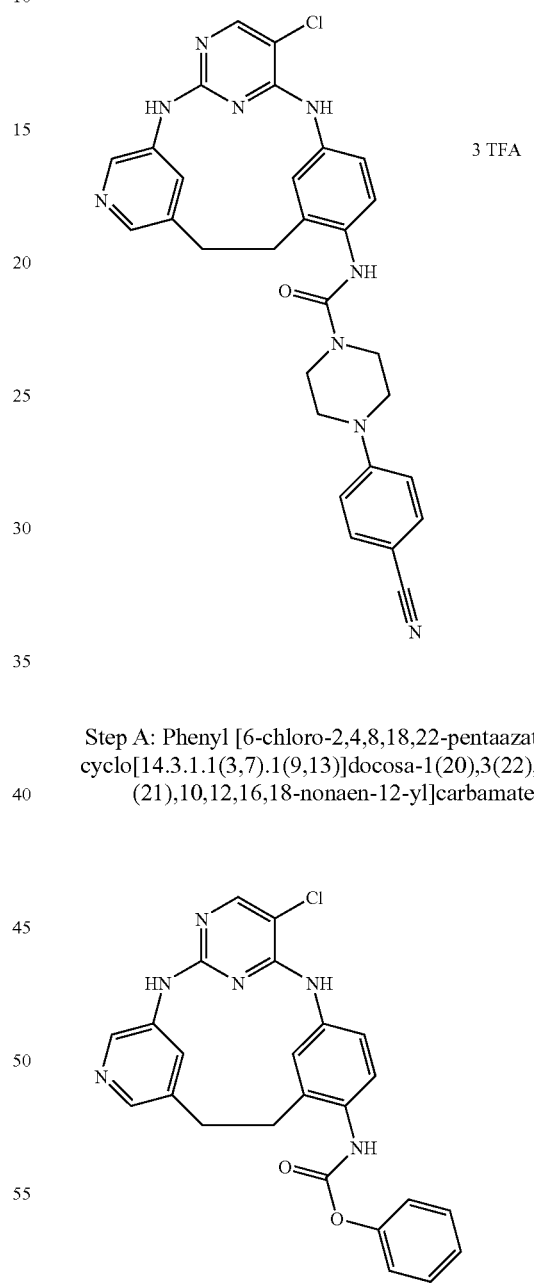

Step A: Phenyl [6-chloro-2,4,8,18,22-pentaazatetracyclo[14.3.1.1(3,7).1(9,13)]docosa-1(20),3(22),4,6,9(21),10,12,16,18-nonaen-12-yl]carbamate To a solution of 6-chloro-2,4,8,18,22-pentaazatetracyclo[14.3.1.1(3,7).1(9,13)]docosa-1(20),3(22),4,6,9(21),10,12,16,18-nonaen-12-amine trihydrochloride (100.0 mg, 0.223 mmol) in pyridine (1 mL) was added carbonochloridic acid, phenyl ester (42.0 µL, 0.335 mmol). The reaction solution was stirred at room temperature overnight. The reaction solution was concentrated and diluted with water. The resulting precipitate was filtered and dried under vacuum to give the desired product (100 mg, 88%). LCMS for $C_{24}H_{20}ClN_6O_2$ $(M+H)^+$: m/z=459.2.

Step B: N-[6-Chloro-2,4,8,18,22-pentaazatetracyclo [14.3.1.1(3,7).1(9,13)]docosa-1(20),3(22),4,6,9(21), 10,12,16,18-nonaen-12-yl]-4-(4-cyanophenyl)piperazine-1-carboxamide tris(trifluoroacetate)

A mixture of phenyl [6-chloro-2,4,8,18,22-pentaazatetracyclo[14.3.1.1(3,7).1(9,13)]docosa-1(20),3(22),4,6,9(21), 10,12,16,18-nonaen-12-yl]carbamate (12 mg, 0.026 mmol), 4-piperazin-1-ylbenzonitrile hydrochloride (9.0 mg, 0.040 mmol) and triethylamine (11 mL, 0.078 mmol) and chloroform (0.2 mL) was stirred at 70° C. overnight. The solvent was removed in vacuo and the residue was dissolved in methanol and purified with preparative LCMS to give the desired product (6.1 mg, 30%). LCMS for $C_{29}H_{27}ClN_9O$ $(M+H)^+$: m/z=552.3.

Example B304

N-[6-Chloro-2,4,8,18,22-pentaazatetracyclo[14.3.1.1 (3,7).1(9,13)]docosa-1(20),3(22),4,6,9(21),10,12,16, 18-nonaen-12-yl]-4-(3-methoxyphenyl)piperazine-1-carboxamide tris(trifluoroacetate)

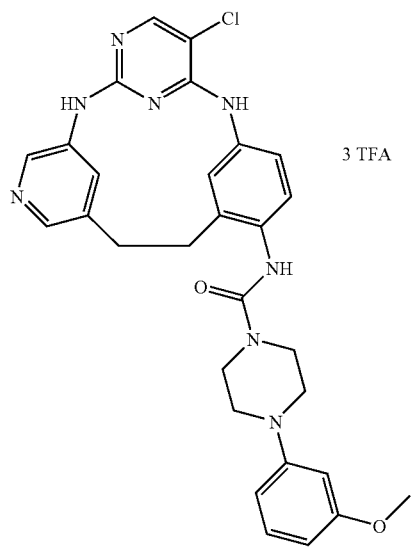 [SMILES: "3 TFA" ; COc1cccc(N2CCN(C(=O)Nc3ccc4cc3CCc3cncc(c3)Nc3ncc(Cl)c(n3)N4)CC2)c1]

The desired compound was prepared according to the procedure of Example B303, using phenyl [6-chloro-2,4,8,18, 22-pentaazatetracyclo[14.3.1.1(3,7).1(9,13)]docosa-1(20),3 (22),4,6,9(21),10,12,16,18-nonaen-12-yl]carbamate and 1-(3-methoxyphenyl)piperazine dihydrochloride as the starting materials in 45% yield. LCMS for $C_{29}H_{30}ClN_8O_2$ $(M+H)^+$: m/z=557.4.

Example B305

N-[6-Chloro-2,4,8,18,22-pentaazatetracyclo[14.3.1.1 (3,7).1(9,13)]docosa-1(20),3(22),4,6,9(21),10,12,16, 18-nonaen-12-yl]-4-(2-chlorophenyl)piperazine-1-carboxamide bis(trifluoroacetate)

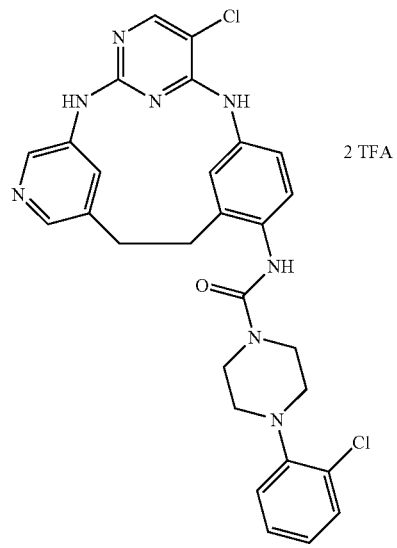 [SMILES: O=C(Nc1ccc2cc1CCc1cncc(c1)Nc1ncc(Cl)c(n1)N2)N1CCN(c2ccccc2Cl)CC1 ; "2 TFA"]

The desired compound was prepared according to the procedure of Example B303, using phenyl [6-chloro-2,4,8,18, 22-pentaazatetracyclo[14.3.1.1(3,7).1(9,13)]docosa-1(20),3 (22),4,6,9(21),10,12,16,18-nonaen-12-yl]carbamate and 1-(2-chlorophenyl)piperazine hydrochloride as the starting materials in 40% yield. LCMS for $C_{28}H_{27}Cl_2N_8O$ $(M+H)^+$: m/z=561.3.

Example B306

N-[6-Chloro-2,4,8,18,22-pentaazatetracyclo[14.3.1.1 (3,7).1(9,13)]docosa-1(20),3(22),4,6,9(21),10,12,16, 18-nonaen-12-yl]-4-(3-chlorophenyl)piperazine-1-carboxamide tris(trifluoroacetate)

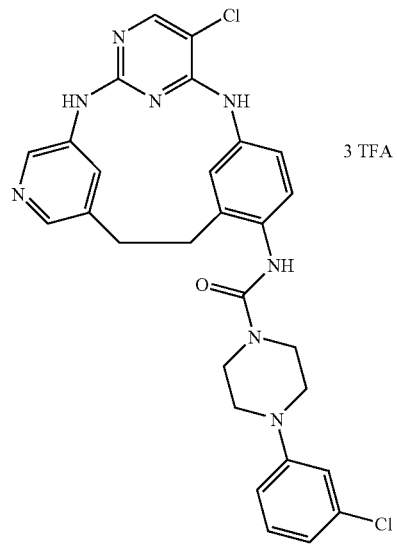 [SMILES: "3 TFA" ; O=C(Nc1ccc2cc1CCc1cncc(c1)Nc1ncc(Cl)c(n1)N2)N1CCN(c2cccc(Cl)c2)CC1]

The desired compound was prepared according to the procedure of Example B303, using phenyl [6-chloro-2,4,8,18,22-pentaazatetracyclo[14.3.1.1(3,7).1(9,13)]docosa-1(20),3(22),4,6,9(21),10,12,16,18-nonaen-12-yl]carbamate and 1-(3-chlorophenyl)piperazine hydrochloride as the starting materials in 45% yield. LCMS for $C_{28}H_{27}Cl_2N_8O$ (M+H)$^+$: m/z=561.3.

Example B307
N-[6-Chloro-2,4,8,18,22-pentaazatetracyclo[14.3.1.1(3,7).1(9,13)]docosa-1(20),3(22),4,6,9(21),10,12,16,18-nonaen-12-yl]-4-(4-chlorophenyl)piperazine-1-carboxamide tris(trifluoroacetate)

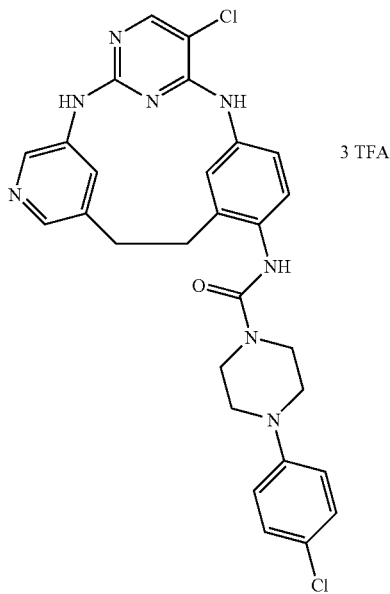 [SMILES: "3 TFA" ; O=C(Nc1ccc2cc1CCc1cncc(c1)Nc1ncc(Cl)c(n1)N2)N1CCN(c2ccc(Cl)cc2)CC1]

The desired compound was prepared according to the procedure of Example B303, using phenyl [6-chloro-2,4,8,18,22-pentaazatetracyclo[14.3.1.1(3,7).1(9,13)]docosa-1(20),3(22),4,6,9(21),10,12,16,18-nonaen-12-yl]carbamate and 1-(4-chlorophenyl)piperazine hydrochloride as the starting materials in 47% yield. LCMS for $C_{28}H_{27}Cl_2N_8O$ (M+H)$^+$: m/z=561.3.

Example B308
N-[6-Chloro-2,4,8,18,22-pentaazatetracyclo[14.3.1.1(3,7).1(9,13)]docosa-1(20),3(22),4,6,9(21),10,12,16,18-nonaen-12-yl]-4-(6-methylpyrazin-2-yl)piperazine-1-carboxamide tris(trifluoroacetate)

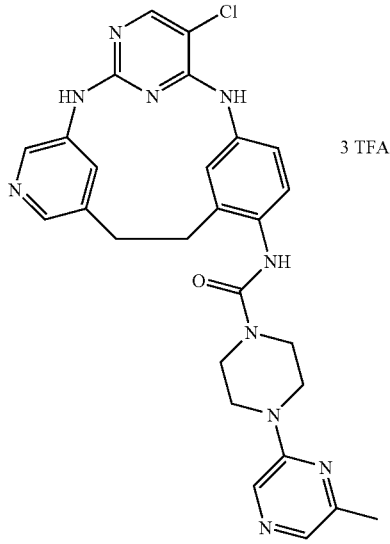 [SMILES: "3 TFA" ; Cc1cncc(N2CCN(C(=O)Nc3ccc4cc3CCc3cncc(c3)Nc3ncc(Cl)c(n3)N4)CC2)n1]

The desired compound was prepared according to the procedure of Example B303, using phenyl [6-chloro-2,4,8,18,22-pentaazatetracyclo[14.3.1.1(3,7).1(9,13)]docosa-1(20),3(22),4,6,9(21),10,12,16,18-nonaen-12-yl]carbamate and 2-methyl-6-piperazin-1-ylpyrazine as the starting materials in 32% yield. LCMS for $C_{27}H_{28}ClN_{10}O$ (M+H)$^+$: m/z=543.3.

Example B309
N-[6-Chloro-2,4,8,18,22-pentaazatetracyclo[14.3.1.1(3,7).1(9,13)]docosa-1(20),3(22),4,6,9(21),10,12,16,18-nonaen-12-yl]-4-pyrimidin-2-ylpiperazine-1-carboxamide tris(trifluoroacetate)

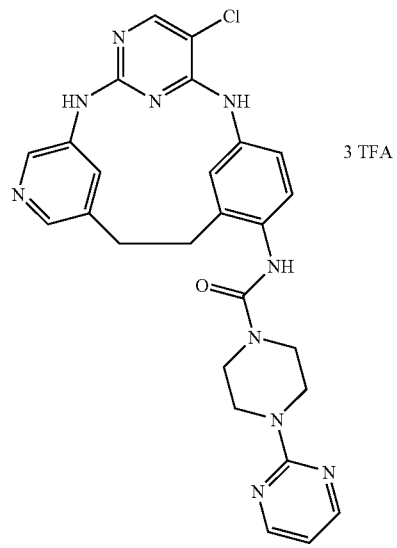 [SMILES: "3 TFA" ; O=C(Nc1ccc2cc1CCc1cncc(c1)Nc1ncc(Cl)c(n1)N2)N1CCN(c2ncccn2)CC1]

The desired compound was prepared according to the procedure of Example B303, using phenyl [6-chloro-2,4,8,18,22-pentaazatetracyclo[14.3.1.1(3,7).1(9,13)]docosa-1(20),3(22),4,6,9(21),10,12,16,18-nonaen-12-yl]carbamate and 2-piperazin-1-ylpyrimidine as the starting materials in 39% yield. LCMS for $C_{26}H_{26}ClN_{10}O$ (M+H)$^+$: m/z=529.3. $^1$HNMR (400 MHz, CD$_3$OD) δ 9.30 (s, 1H), 8.40 (m, 2H), 8.29 (d, 2H), 8.15 (s, 1H), 7.71 (s, 2H), 7.23 (d, 1H), 7.13 (d, 1H), 6.68 (t, 1H), 3.93 (t, 4H), 3.68 (m, 4H), 3.10 (m, 4H).

Example B310

N-[6-Chloro-2,4,8,18,22-pentaazatetracyclo[14.3.1.1 (3,7).1(9,13)]docosa-1(20),3(22),4,6,9(21),10,12,16, 18-nonaen-12-yl]-4-(5-cyanopyridin-2-yl)piperazine-1-carboxamide tris(trifluoroacetate)

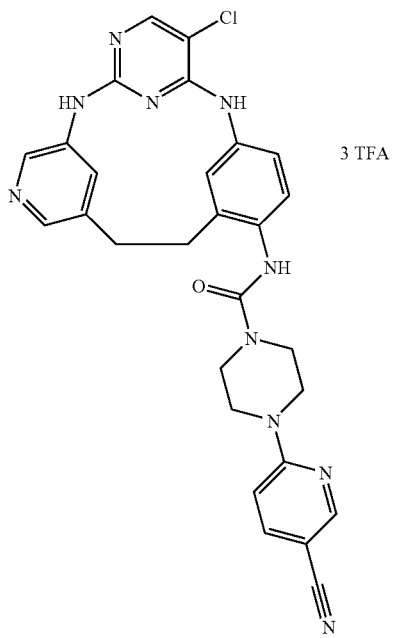 [SMILES: "3 TFA" ; N#Cc1ccc(N2CCN(C(=O)Nc3ccc4cc3CCc3cncc(c3)Nc3ncc(Cl)c(n3)N4)CC2)nc1]

The desired compound was prepared according to the procedure of Example B303, using phenyl [6-chloro-2,4,8,18, 22-pentaazatetracyclo[14.3.1.1(3,7).1(9,13)]docosa-1(20),3 (22),4,6,9(21),10,12,16,18-nonaen-12-yl]carbamate and 6-piperazin-1-ylnicotinonitrile as the starting materials in 44% yield. LCMS for $C_{28}H_{26}ClN_{10}O$ (M+H)$^+$: m/z=553.3.

Example B311

N-[6-Chloro-2,4,8,18,22-pentaazatetracyclo[14.3.1.1 (3,7).1(9,13)]docosa-1(20),3(22),4,6,9(21),10,12,16, 18-nonaen-12-yl]-4-(3-cyanopyridin-2-yl)piperazine-1-carboxamide tris(trifluoroacetate)

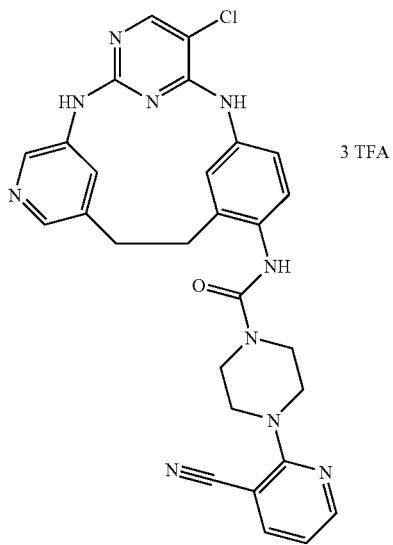 [SMILES: "3 TFA" ; N#Cc1cccnc1N1CCN(C(=O)Nc2ccc3cc2CCc2cncc(c2)Nc2ncc(Cl)c(n2)N3)CC1]

The desired compound was prepared according to the procedure of Example B303, using phenyl [6-chloro-2,4,8,18, 22-pentaazatetracyclo[14.3.1.1(3,7).1(9,13)]docosa-1(20),3 (22),4,6,9(21),10,12,16,18-nonaen-12-yl]carbamate and 2-piperazin-1-ylnicotinonitrile as the starting materials in 32% yield. LCMS for $C_{28}H_{26}ClN_{10}O$ (M+H)$^+$: m/z=553.3.

Example B312

N-[6-Chloro-2,4,8,18,22-pentaazatetracyclo[14.3.1.1 (3,7).1(9,13)]docosa-1(20),3(22),4,6,9(21),10,12,16, 18-nonaen-12-yl]-3-phenylpyrrolidine-1-carboxamide bis(trifluoroacetate)

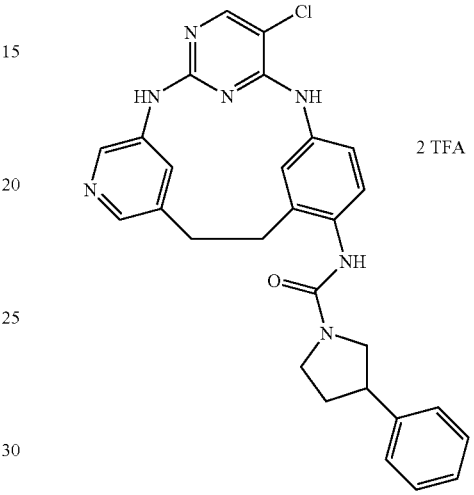

The desired compound was prepared according to the procedure of Example B303, using phenyl [6-chloro-2,4,8,18, 22-pentaazatetracyclo[14.3.1.1(3,7).1(9,13)]docosa-1(20),3 (22),4,6,9(21),10,12,16,18-nonaen-12-yl]carbamate and 3-phenylpyrrolidine as the starting materials in 38% yield. LCMS for $C_{28}H_{27}ClN_7O$ (M+H)$^+$: m/z=512.3. $^1$HNMR (400 MHz, CD$_3$OD) δ 9.29 (s, 1H), 8.28 (d, 2H), 8.13 (s, 1H), 7.70 (s, 1H), 7.35 (d, 4H), 7.26 (m, 2H), 7.12 (d, 1H), 3.98 (t, 1H), 3.77 (t, 1H), 3.62-3.49 (m, 4H), 3.11 (m, 5H).

Example B313

N-[6-Chloro-2,4,8,18,22-pentaazatetracyclo[14.3.1.1 (3,7).1(9,13)]docosa-1(20),3(22),4,6,9(21),10,12,16, 18-nonaen-12-yl]-3-pyrazin-2-ylpyrrolidine-1-carboxamide tetrakis(trifluoroacetate)

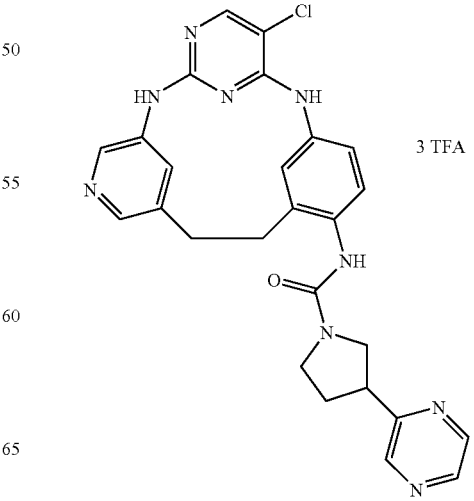

The desired compound was prepared according to the procedure of Example B303, using phenyl [6-chloro-2,4,8,18,22-pentaazatetracyclo[14.3.1.1(3,7).1(9,13)]docosa-1(20),3(22),4,6,9(21),10,12,16,18-nonaen-12-yl]carbamate and 2-pyrrolidin-3-ylpyrazine trihydrochloride as the starting materials in 33% yield. LCMS for $C_{26}H_{25}ClN_9O$ (M+H)$^+$: m/z=514.2.

Example B314

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-4-phenylpiperidine-1-carboxamide bis(trifluoroacetate)

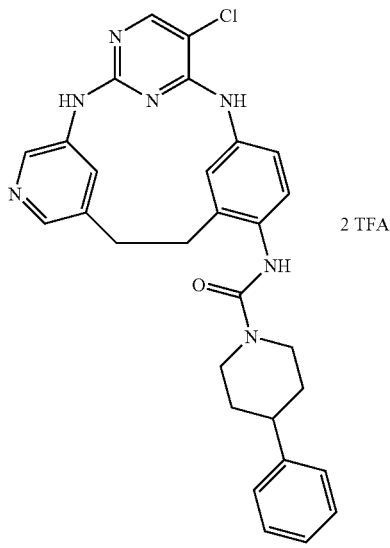 [SMILES: O=C(Nc1ccc2cc1CCc1cncc(c1)Nc1ncc(Cl)c(n1)N2)N1CCC(c2ccccc2)CC1 ; "2 TFA"]

The desired compound was prepared according to the procedure of Example B303, using phenyl [6-chloro-2,4,8,18,22-pentaazatetracyclo[14.3.1.1(3,7).1(9,13)]docosa-1(20),3(22),4,6,9(21),10,12,16,18-nonaen-12-yl]carbamate and 4-phenylpiperidine as the starting materials in 32% yield. LCMS for $C_{29}H_{29}ClN_7O$ (M+H)$^+$: m/z=526.3.

Example B315

N-[6-Chloro-2,4,8,18,22-pentaazatetracyclo[14.3.1.1(3,7).1(9,13)]docosa-1(20),3(22),4,6,9(21),10,12,16,18-nonaen-12-yl]hexahydropyrrolo[1,2-a]pyrazine-2(1H)-carboxamide tris(trifluoroacetate)

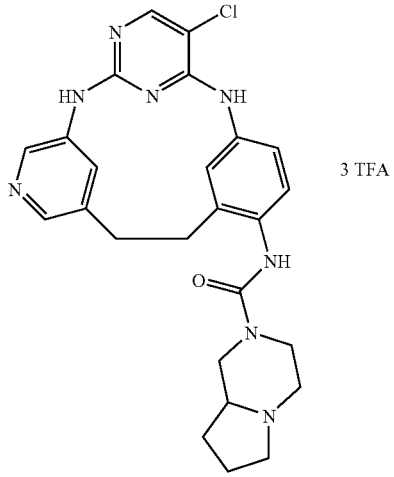 [SMILES: "3 TFA" ; O=C(Nc1ccc2cc1CCc1cncc(c1)Nc1ncc(Cl)c(n1)N2)N1CCN2CCCC2C1]

The desired compound was prepared according to the procedure of Example B303, using phenyl [6-chloro-2,4,8,18,22-pentaazatetracyclo[14.3.1.1(3,7).1(9,13)]docosa-1(20),3(22),4,6,9(21),10,12,16,18-nonaen-12-yl]carbamate and octahydropyrrolo[1,2-a]pyrazine as the starting materials in 29% yield. LCMS for $C_{25}H_{28}ClN_8O$ (M+H)$^+$: m/z=491.1.

Example B316

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-3-(trifluoromethyl)-5,6-dihydro[1,2,4]triazolo[4,3-a]pyrazine-7(8H)-carboxamide tris(trifluoroacetate)

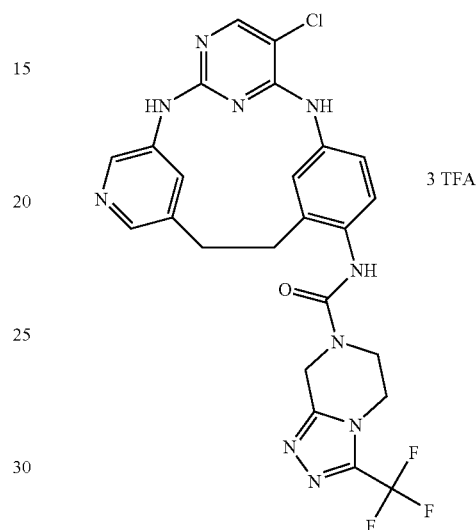

The desired compound was prepared according to the procedure of Example B303, using phenyl [6-chloro-2,4,8,18,22-pentaazatetracyclo[14.3.1.1(3,7).1(9,13)]docosa-1(20),3(22),4,6,9(21),10,12,16,18-nonaen-12-yl]carbamate and 3-(trifluoromethyl)-5,6,7,8-tetrahydro[1,2,4]triazolo[4,3,-a]pyrazine hydrochloride as the starting materials in 13% yield. LCMS for $C_{24}H_{21}ClF_3N_{10}O$ (M+H)$^+$: m/z=557.1.

Example B317

4-Acetyl-N-[6-chloro-2,4,8,18,22-pentaazatetracyclo[14.3.1.1(3,7).1(9,13)]docosa-1(20),3(22),4,6,9(21),10,12,16,18-nonaen-12-yl]piperazine-1-carboxamide bis(trifluoroacetate)

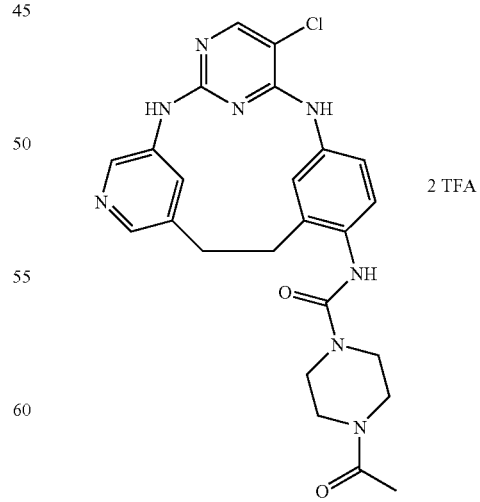

The desired compound was prepared according to the procedure of Example B303, using phenyl [6-chloro-2,4,8,18,22-pentaazatetracyclo[14.3.1.1(3,7).1(9,13)]docosa-1(20),3(22),4,6,9(21),10,12,16,18-nonaen-12-yl]carbamate and 1-acetylpiperazine as the starting materials in 42% yield. LCMS for $C_{24}H_{26}ClN_8O_2$ (M+H)$^+$: m/z=493.4.

Example B318

N-[6-Chloro-2,4,8,18,22-pentaazatetracyclo[14.3.1.1 (3,7).1(9,13)]docosa-1(20),3(22),4,6,9(21),10,12,16, 18-nonaen-12-yl]-4-(methylsulfonyl)piperazine-1-carboxamide bis(trifluoroacetate)

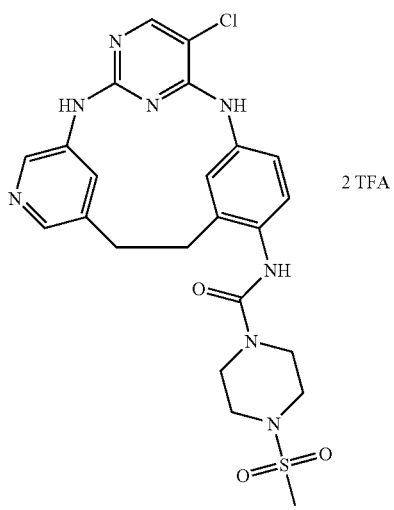 [SMILES: CS(=O)(=O)N1CCN(C(=O)Nc2ccc3cc2CCc2cncc(c2)Nc2ncc(Cl)c(n2)N3)CC1 ; "2 TFA"]

The desired compound was prepared according to the procedure of Example B303, using phenyl [6-chloro-2,4,8,18, 22-pentaazatetracyclo[14.3.1.1(3,7).1(9,13)]docosa-1(20),3 (22),4,6,9(21),10,12,16,18-nonaen-12-yl]carbamate and 1-(methylsulfonyl)piperazine as the starting materials in 37% yield. LCMS for $C_{23}H_{26}ClN_8O_3S$ (M+H)$^+$: m/z=529.3.

Example B319

N-[6-Chloro-2,4,8,18,22-pentaazatetracyclo[14.3.1.1 (3,7).1(9,13)]docosa-1(20),3(22),4,6,9(21),10,12,16, 18-nonaen-12-yl]-4-(phenylsulfonyl)piperazine-1-carboxamide bis(trifluoroacetate)

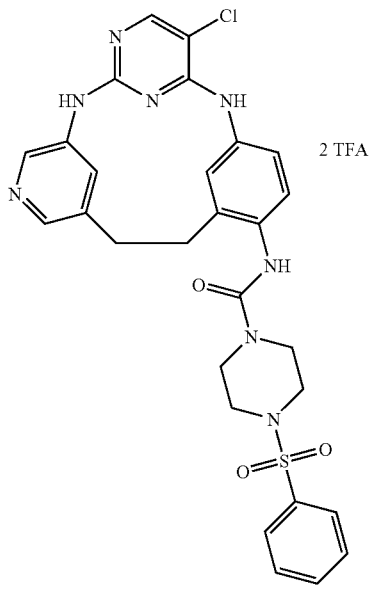 [SMILES: O=C(Nc1ccc2cc1CCc1cncc(c1)Nc1ncc(Cl)c(n1)N2)N1CCN(S(=O)(=O)c2ccccc2)CC1 ; "2 TFA"]

The desired compound was prepared according to the procedure of Example B303, using phenyl [6-chloro-2,4,8,18, 22-pentaazatetracyclo[14.3.1.1(3,7).1(9,13)]docosa-1(20),3 (22),4,6,9(21),10,12,16,18-nonaen-12-yl]carbamate and 1-(phenylsulfonyl)piperazine as the starting materials in 29% yield. LCMS for $C_{28}H_{28}ClN_8O_3S$ (M+H)$^+$: m/z=591.3.

Example B320

N-[6-Chloro-2,4,8,18,22-pentaazatetracyclo[14.3.1.1 (3,7).1(9,13)]docosa-1(20),3(22),4,6,9(21),10,12,16, 18-nonaen-12-yl]-3-methyl-4-phenylpiperazine-1-carboxamide tris(trifluoroacetate)

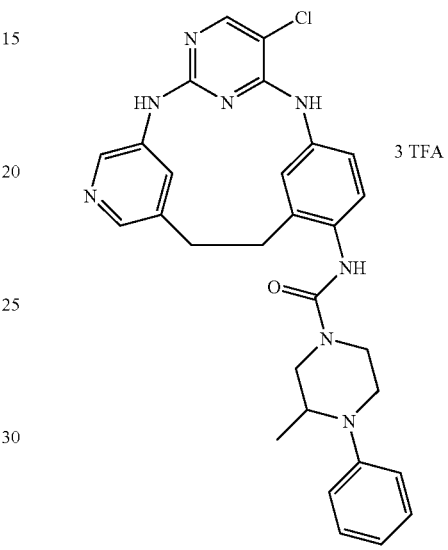

The desired compound was prepared according to the procedure of Example B303, using phenyl [6-chloro-2,4,8,18, 22-pentaazatetracyclo[14.3.1.1(3,7).1(9,13)]docosa-1(20),3 (22),4,6,9(21),10,12,16,18-nonaen-12-yl]carbamate and 2-methyl-1-phenylpiperazine as the starting materials in 54% yield. LCMS for $C_{29}H_{30}ClN_8O$ (M+H)$^+$: m/z=541.4.

Example B321

N-[6-Chloro-2,4,8,18,22-pentaazatetracyclo[14.3.1.1 (3,7).1(9,13)]docosa-1(20),3(22),4,6,9(21),10,12,16, 18-nonaen-12-yl]-3-(phenylsulfonyl)pyrrolidine-1-carboxamide bis(trifluoroacetate)

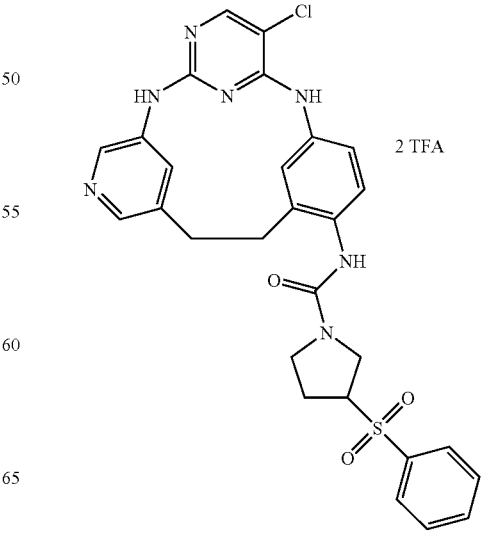

The desired compound was prepared according to the procedure of Example B303, using phenyl [6-chloro-2,4,8,18,22-pentaazatetracyclo[14.3.1.1(3,7).1(9,13)]docosa-1(20),3(22),4,6,9(21),10,12,16,18-nonaen-12-yl]carbamate and 3-(phenylsulfonyl)pyrrolidine as the starting materials in 32% yield. LCMS for $C_{28}H_{27}ClN_7O_3S$ (M+H)$^+$: m/z=576.2. $^1$HNMR (400 MHz, DMSO) δ 10.01 (s, 1H), 9.37 (s, 1H), 9.02 (s, 1H), 8.29 (s, 2H), 8.20 (s, 1H), 7.91 (m, 3H), 7.80 (t, 1H), 7.69 (t, 2H), 7.62 (s, 1H), 7.14 (d, 1H), 7.02 (d, 1H), 4.21 (m, 1H), 3.80 (d, 1H), 3.60 (t, 1H), 3.43 (m, 2H), 2.98 (m, 4H), 2.23 (m, 2H).

Example B322

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-4-cyano-4-phenylpiperidine-1-carboxamide bis(trifluoroacetate)

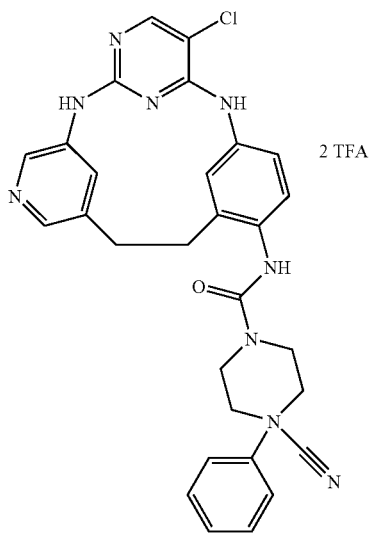

The desired compound was prepared according to the procedure of Example B303, using phenyl [6-chloro-2,4,8,18,22-pentaazatetracyclo[14.3.1.1(3,7).1(9,13)]docosa-1(20),3(22),4,6,9(21),10,12,16,18-nonaen-12-yl]carbamate and 4-phenylpiperidine-4-carbonitrile as the starting materials in 50% yield. LCMS for $C_{30}H_{28}ClN_8O$ (M+H)$^+$: m/z=551.2. $^1$HNMR (400 MHz, DMSO) δ 9.98 (s, 1H), 9.36 (s, 1H), 8.99 (s, 1H), 8.29 (m, 3H), 8.20 (s, 1H), 7.63 (s, 1H), 7.58 (d, 2H), 7.47 (t, 2H), 7.39 (t, 1H), 7.15 (d, 1H), 7.03 (t, 1H), 4.30 (d, 2H), 3.13 (t, 2H), 2.98 (m, 4H), 2.21 (d, 2H), 1.99 (t, 2H).

Example B323

N-[6-chloro-2,4,8,22-tetraazatetracyclo[14.3.1.1(3,7).1(9,13)]docosa-1(20),3(22),4,6,9(21),10,12,16,18-nonaen-12-yl]-N'-cyanourea trifluoroacetate

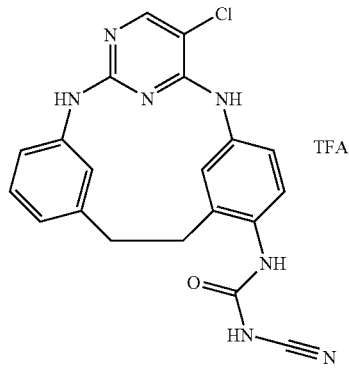 [SMILES: "TFA" ; N#CNC(=O)Nc1ccc2cc1CCc1cccc(c1)Nc1ncc(Cl)c(n1)N2]

The desired compound was prepared according to the procedure of Example B236, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and cyanamide as the starting materials in 14% yield. LCMS for $C_{20}H_{17}ClN_7O$ (M+H)$^+$: m/z=406.1.

Example B324

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-hydroxyurea trifluoroacetate

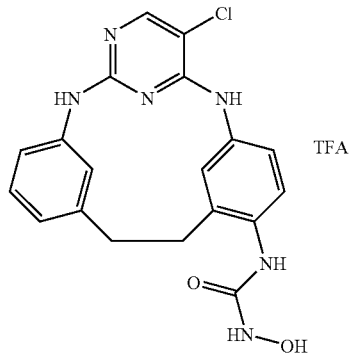 [SMILES: "TFA" ; O=C(NO)Nc1ccc2cc1CCc1cccc(c1)Nc1ncc(Cl)c(n1)N2]

The desired compound was prepared according to the procedure of Example B236, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and hydroxylamine as the starting materials in 11% yield. LCMS for $C_{19}H_{18}ClN_6O_2$ (M+H)$^+$: m/z=397.1.

Example B325

N-{2-[({[6-Chloro-2,4,8,22-tetraazatetracyclo[14.3.1.1(3,7).1(9,13)]docosa-1(20),3(22),4,6,9(21),10,12,16,18-nonaen-12-yl]amino}carbonyl)amino]ethyl}ethanesulfonamide trifluoroacetate

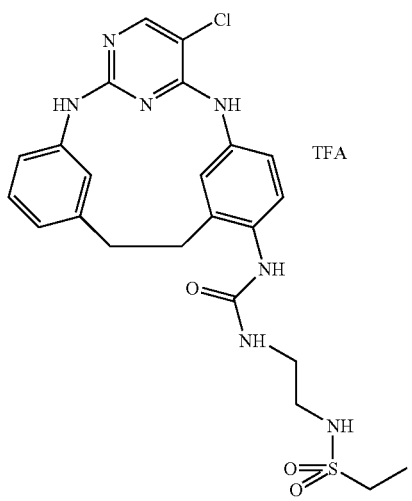 [SMILES: "TFA" ; CCS(=O)(=O)NCCNC(=O)Nc1ccc2cc1CCc1cccc(c1)Nc1ncc(Cl)c(n1)N2]

The desired compound was prepared according to the procedure of Example B136, using N-(2-aminoethyl)-N'-[6-chloro-2,4,8,22-tetraazatetracyclo[14.3.1.1(3,7).1(9,13)]docosa-1(20),3(22),4,6,9(21),10,12,16,18-nonaen-12-yl]urea dihydrochloride and ethanesulfonyl chloride as the starting materials in 27% yield. LCMS for $C_{23}H_{27}ClN_7O_3S$ (M+H)$^+$: m/z=516.3.

Example B326

N-{2-[({[6-Chloro-2,4,8,22-tetraazatetracyclo[14.3.1.1(3,7).1(9,13)]docosa-1(20),3(22),4,6,9(21),10,12,16,18-nonaen-12-yl]amino}carbonyl)amino]ethyl}propane-1-sulfonamide trifluoroacetate

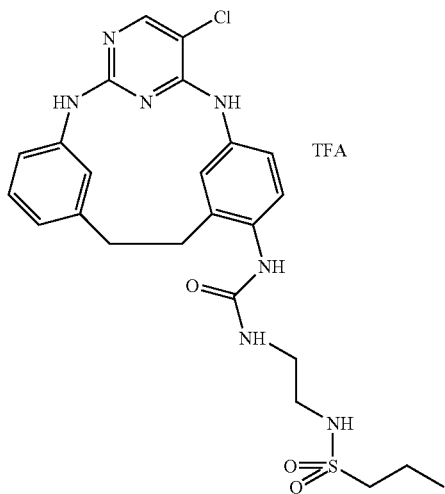 [SMILES: "TFA" ; CCCS(=O)(=O)NCCNC(=O)Nc1ccc2cc1CCc1cccc(c1)Nc1ncc(Cl)c(n1)N2]

The desired compound was prepared according to the procedure of Example B136, using N-(2-aminoethyl)-N'-[6-chloro-2,4,8,22-tetraazatetracyclo[14.3.1.1(3,7).1(9,13)]docosa-1(20),3(22),4,6,9(21),10,12,16,18-nonaen-12-yl]urea dihydrochloride and 1-propanesulfonyl chloride as the starting materials in 32% yield. LCMS for $C_{24}H_{29}ClN_7O_3S$ (M+H)$^+$: m/z=530.3.

Example B327

N-{2-[({[6-Chloro-2,4,8,22-tetraazatetracyclo[14.3.1.1(3,7).1(9,13)]docosa-1(20),3(22),4,6,9(21),10,12,16,18-nonaen-12-yl]amino}carbonyl)amino]ethyl}cyclopropanesulfonamide trifluoroacetate

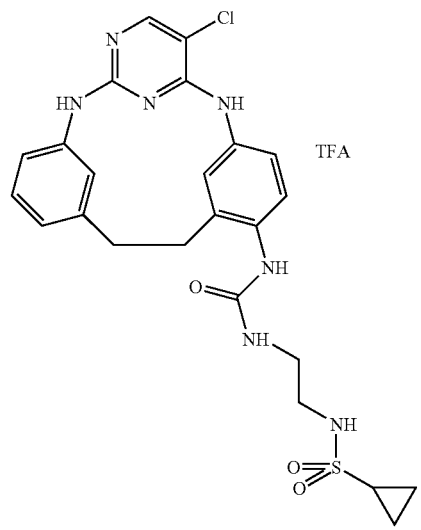 [SMILES: "TFA" ; O=C(NCCNS(=O)(=O)C1CC1)Nc1ccc2cc1CCc1cccc(c1)Nc1ncc(Cl)c(n1)N2]

The desired compound was prepared according to the procedure of Example B136, using N-(2-aminoethyl)-N'-[6-chloro-2,4,8,22-tetraazatetracyclo[14.3.1.1(3,7).1(9,13)]docosa-1(20),3(22),4,6,9(21),10,12,16,18-nonaen-12-yl]urea dihydrochloride and cyclopropanesulfonyl chloride as the starting materials in 23% yield. LCMS for $C_{24}H_{27}ClN_7O_3S$ (M+H)$^+$: m/z=528.3.

Example B328

N-[6-chloro-2,4,8,22-tetraazatetracyclo[14.3.1.1(3,7).1(9,13)]docosa-1(20),3(22),4,6,9(21),10,12,16,18-nonaen-12-yl]-N'-(2-{[(dimethylamino)sulfonyl]amino}ethyl)urea trifluoroacetate

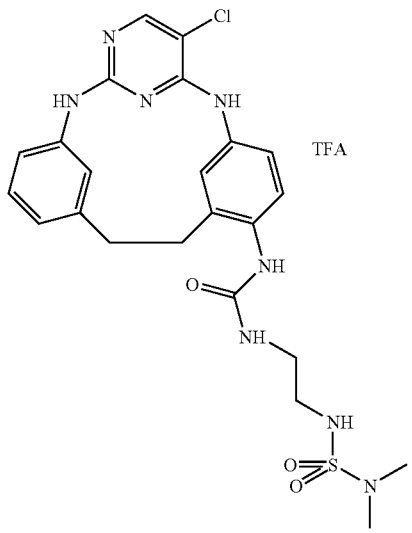 [SMILES: "TFA" ; CN(C)S(=O)(=O)NCCNC(=O)Nc1ccc2cc1CCc1cccc(c1)Nc1ncc(Cl)c(n1)N2]

The desired compound was prepared according to the procedure of Example B136, using N-(2-aminoethyl)-N'-[6-chloro-2,4,8,22-tetraazatetracyclo[14.3.1.1(3,7).1(9,13)]docosa-1(20),3(22),4,6,9(21),10,12,16,18-nonaen-12-yl]urea dihydrochloride and dimethylsulfamoyl chloride as the starting materials in 18% yield. LCMS for $C_{23}H_{28}ClN_8O_3S$ $(M+H)^+$: m/z=531.3.

Example B329

N-{2-[({[6-Chloro-2,4,8,22-tetraazatetracyclo[14.3.1.1(3,7).1(9,13)]docosa-1(20),3(22),4,6,9(21),10,12,16,18-nonaen-12-yl]amino}carbonyl)amino]ethyl}benzenesulfonamide trifluoroacetate

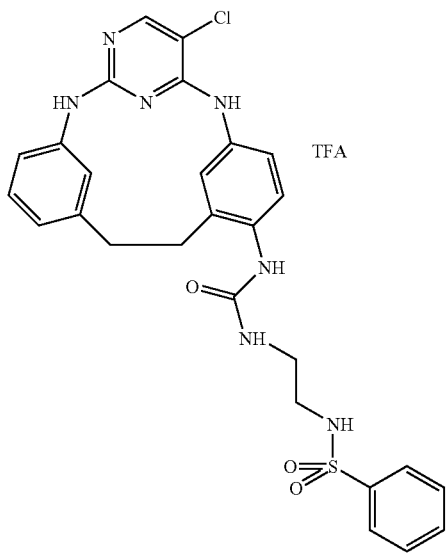 [SMILES: "TFA" ; O=C(NCCNS(=O)(=O)c1ccccc1)Nc1ccc2cc1CCc1cccc(c1)Nc1ncc(Cl)c(n1)N2]

The desired compound was prepared according to the procedure of Example B136, using N-(2-aminoethyl)-N'-[6-chloro-2,4,8,22-tetraazatetracyclo[14.3.1.1(3,7).1(9,13)]docosa-1(20),3(22),4,6,9(21),10,12,16,18-nonaen-12-yl]urea dihydrochloride and benzenesulfonyl chloride as the starting materials in 22% yield. LCMS for $C_{27}H_{27}ClN_7O_3S$ $(M+H)^+$: m/z=564.3.

Example B330

5-Chloro-N-{2-[({[6-chloro-2,4,8,22-tetraazatetracyclo[14.3.1.1(3,7).1(9,13)]docosa-1(20),3(22),4,6,9(21),10,12,16,18-nonaen-12-yl]amino}carbonyl)amino]ethyl}thiophene-2-sulfonamide trifluoroacetate

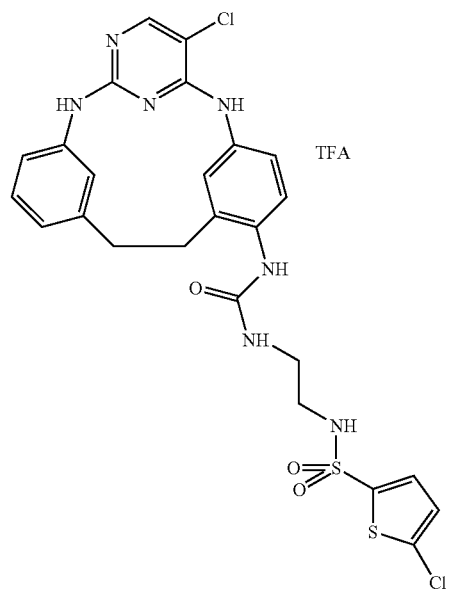 [SMILES: "TFA" ; O=C(NCCNS(=O)(=O)c1ccc(Cl)s1)Nc1ccc2cc1CCc1cccc(c1)Nc1ncc(Cl)c(n1)N2]

The desired compound was prepared according to the procedure of Example B136, using N-(2-aminoethyl)-N'-[6-chloro-2,4,8,22-tetraazatetracyclo[14.3.1.1(3,7).1(9,13)]docosa-1(20),3(22),4,6,9(21),10,12,16,18-nonaen-12-yl]urea dihydrochloride and 5-chlorothiophene-2-sulfonyl chloride as the starting materials in 11% yield. LCMS for $C_{25}H_{24}Cl_2N_7O_3S_2(M+H)^+$: m/z=604.2, 606.3.

Example B331

6-Chloro-N-{2-[({[6-chloro-2,4,8,22-tetraazatetracyclo[14.3.1.1(3,7).1(9,13)]docosa-1(20),3(22),4,6,9(21),10,12,16,18-nonaen-12-yl]amino}carbonyl)amino]ethyl}pyridine-3-sulfonamide trifluoroacetate

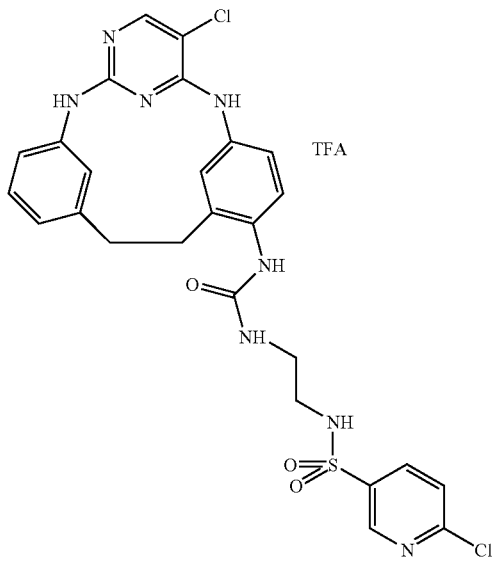 [SMILES: "TFA" ; O=C(NCCNS(=O)(=O)c1ccc(Cl)nc1)Nc1ccc2cc1CCc1cccc(c1)Nc1ncc(Cl)c(n1)N2]

The desired compound was prepared according to the procedure of Example B136, using N-(2-aminoethyl)-N'-[6-chloro-2,4,8,22-tetraazatetracyclo[14.3.1.1(3,7).1(9,13)]docosa-1(20),3(22),4,6,9(21),10,12,16,18-nonaen-12-yl] urea dihydrochloride and 6-chloropyridien-3-sulfonyl chloride as the starting materials in 9% yield. LCMS for $C_{26}H_{25}Cl_2N_8O_3S$ (M+H)$^+$: m/z=599.2, 601.3.

Example B332

N-{2-[({[6-chloro-2,4,8,22-tetraazatetracyclo[14.3.1.1(3,7).1(9,13)]docosa-1(20),3(22),4,6,9(21),10,12,16,18-nonaen-12-yl]amino}carbonyl)amino]ethyl}-1-methyl-1H-pyrazole-3-sulfonamide trifluoroacetate

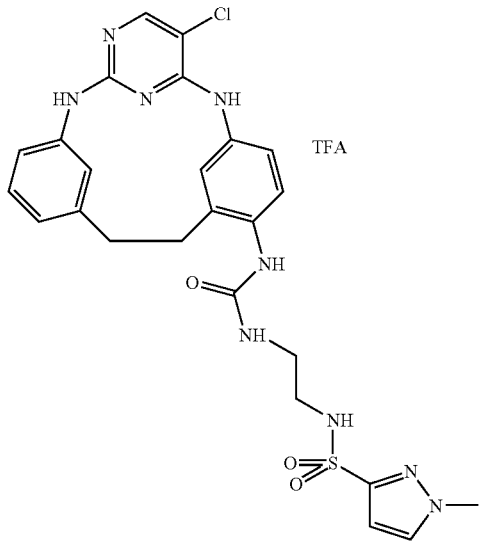 [SMILES: "TFA" ; Cn1ccc(S(=O)(=O)NCCNC(=O)Nc2ccc3cc2CCc2cccc(c2)Nc2ncc(Cl)c(n2)N3)n1]

The desired compound was prepared according to the procedure of Example B136, using N-(2-aminoethyl)-N'-[6-chloro-2,4,8,22-tetraazatetracyclo[14.3.1.1(3,7).1(9,13)]docosa-1(20),3(22),4,6,9(21),10,12,16,18-nonaen-12-yl] urea dihydrochloride and 1-methyl-1H-pyrazole-3-sulfonyl chloride as the starting materials in 17% yield. LCMS for $C_{25}H_{27}ClN_9O_3S$ (M+H)$^+$: m/z=568.3.

Example B333

6-Chloro-N-[1,3]oxazolo[5,4-b]pyridin-2-yl-2,4,8,22-tetraazatetracyclo[14.3.1.1(3,7).1(9,13)]docosa-1(20),3(22),4,6,9(21),10,12,16,18-nonaen-12-amine tris(trifluoroacetate)

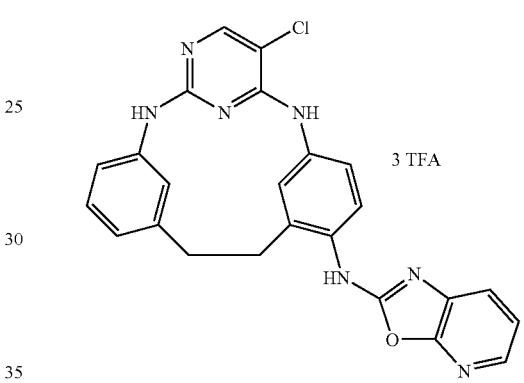

A microwave tube was charged with palladium acetate (1.09 mg, 0.00487 mmol) and dicyclohexyl(2',4',6'-triisopropylbiphenyl-2-yl)phosphine (6.9 mg, 0.015 mmol). The vessel was evacuated and backfilled with nitrogen (this process was repeated a total of 3 times) and tert-butyl alcohol (1.0 mL) and water (0.351 µL, 0.0195 mmol) were added via syringe. After addition of the water, the solution was heated to 80° C. for 1 min. A second microwave tube was charged with 6-chloro-2,4,8,22-tetraazatetracyclo[14.3.1.1(3,7).1(9,13)]docosa-1(20),3(22),4,6,9(21),10,12,16,18-nonaen-12-amine dihydrochloride (20.0 mg, 0.0487 mmol), 2-chloro[1,3]oxazolo[5,4-b]pyridine (7.5 mg, 0.049 mmol) and potassium carbonate (33.6 mg, 0.243 mmol). The vessel was evacuated and backfilled with nitrogen and the activated catalyst solution was transferred from the first reaction vessel into the second via cannula. The reaction was microwaved on 200 watts, 120° C. for 30 minutes. The reaction solution was diluted with DMSO, filtered and purified with preparative LCMS to give the desired product as off-white solid (4.2 mg, 11%). LCMS for $C_{24}H_{19}ClN_7O$ (M+H)$^+$: m/z=456.3.

Example B334

1-[6-Chloro-2,4,8,18,22-pentaazatetracyclo[14.3.1.1 (3,7).1(9,13)]docosa-1(20),3(22),4,6,9(21),10,12,16, 18-nonaen-12-yl]-N-methylmethanamine trihydrochloride

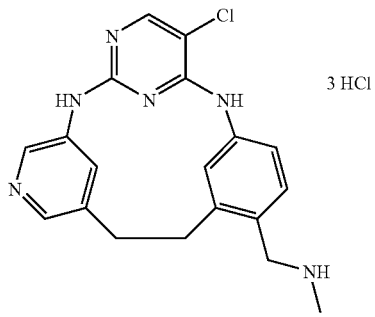 [SMILES: CNCc1ccc2cc1CCc1cncc(c1)Nc1ncc(Cl)c(n1)N2 ; "3 HCl"]

Step A: (2-Iodo-4-nitrophenyl)methanol

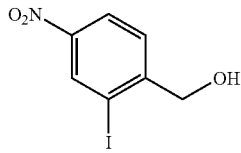 [SMILES: O=[N+]([O-])c1ccc(CO)c(I)c1]

To a solution of methyl 2-iodo-4-nitrobenzoate (25.6 g, 83.4 mmol) in THF (400 mL) was added lithium tetrahydroborate (2.2 g, 92 mmol). The reaction solution was stirred at rt for 2 h and cooled down to 0° C., and water was added dropwise. After stirring for 10 min, ethyl acetate was added. The organic solution was separated and washed with brine, dried over $Na_2SO_4$, filtered and concentrated. The residue was purified with flash chromatography (30% ethyl acetate/hexs) to give the desired product as yellow solid (15.6 g, 67%). LCMS calculated for $C_7H_7INO_3(M+H)^+$: m/z=280.0.

Step B: 2-Iodo-4-nitrobenzyl methanesulfonate

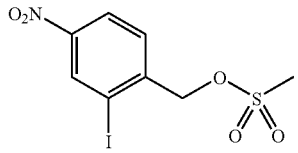 [SMILES: CS(=O)(=O)OCc1ccc([N+](=O)[O-])cc1I]

To a solution of (2-iodo-4-nitrophenyl)methanol (6.01 g, 21.5 mmol) in methylene chloride (50 mL) was added N,N-diisopropylethylamine (7.50 mL, 43.1 mmol) and methanesulfonyl chloride (1.83 mL, 23.7 mmol) at 0° C. The reaction solution was stirred at same temperature for 2 hours. The reaction was quenched with water, and aqueous layer was extracted with DCM once. The combined organic solutions were washed with brine, dried over $Na_2SO_4$, filtered and concentrated The crude product was purified by flash column chromatography to give the desired product (6.15 g, 80%). LCMS calculated for $C_8H_9NO_5S$ $(M+H)^+$: m/z=358.0.

Step C: 1-(2-Iodo-4-nitrophenyl)-N-methylmethanamine hydrochloride

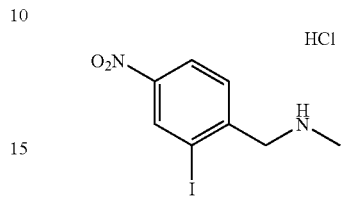

A solution of 2-iodo-4-nitrobenzyl methanesulfonate (6.00 g, 0.0168 mol) in DMF (50 mL) was treated with N,N-diisopropylethylamine (8.78 mL, 0.0504 mol) and 33% methylamine in ethanol (6.79 mL, 0.0504 mol) and stirred at 20° C. overnight. The reaction mixture was poured into water (200 mL) and extracted with ethyl acetate (300 mL). The organic layer was separated and washed with brine (50 mL), dried over sodium sulfate, filtered, and concentrated to a crude orange oil. The crude material was dissolve in 10 mL methanol and treated 4 N HCl in dioxane and diluted with ethyl ether. The precipitate was filtered and dried under vacuum to give the desired product (5 g, 90.58%). LCMS calculated for $C_8H_{10}IN_2O_2(M+H)^+$: m/z=293.1.

Step D: tert-Butyl (2-iodo-4-nitrobenzyl)methylcarbamate

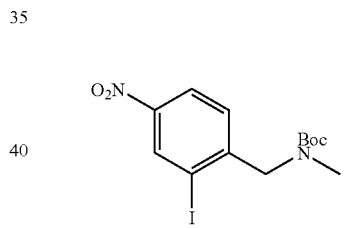

To a solution of 1-(2-iodo-4-nitrophenyl)-N-methylmethanamine hydrochloride (5.00 g, 15.2 mmol) in ethanol (36 mL) was added di-tert-butyldicarbonate (3.49 g, 16.0 mmol). The resulting solution was stirred at room temperature overnight. Solvent was evaporated in vacuo. The residue was purified by flash column chromatography to yield the desired product (4.90 g, 82%). LCMS calculated for $C_{13}H_{17}IN_2O_4Na$ $(M+Na)^+$: m/z=415.0.

Step E: tert-Butyl (4-amino-2-iodobenzyl)methylcarbamate

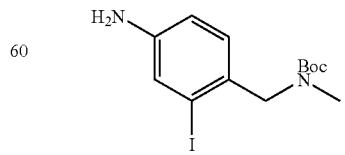

Into the reaction was added tert-butyl (2-iodo-4-nitrobenzyl)methylcarbamate (4.90 g, 12.5 mmol), methanol (85 mL), acetic acid (14.2 mL) and iron (4.19 g, 75.0 mmol) powder. The reaction solution was heated at 50° C. for 1.5 h. After cooling to room temperature, the reaction solution was diluted with ethyl acetate and a saturated sodium carbonate solution. The reaction mixture was filtered through a pad of celite and washed with EtOAc. The aqueous layer was extracted with ethyl acetate once. The combined organic solutions were washed with brine, dried over $Na_2SO_4$, filtered and concentrated. The residue was purified by flash column chromatography to yield the desired product (4.10 g, 91%). LCMS calculated for $C_{13}H_{19}IN_2O_2Na$ $(M+H)^+$: m/z=385.1.

Step F: tert-Butyl {4-[(2,5-dichloropyrimidin-4-yl)amino]-2-iodobenzyl}methylcarbamate

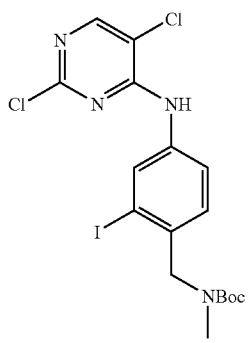 [SMILES: CN(Cc1ccc(Nc2nc(Cl)ncc2Cl)cc1I)C(=O)OC(C)(C)C]

The desired compound was prepared according to the procedure of Example B5, step G using tert-butyl (4-amino-2-iodobenzyl)methylcarbamate and 2,4,5-trichloropyrimidine as the starting materials in 57% yield. LCMS for $C_{17}H_{20}Cl_2IN_4O_2$ $(M+H)^+$: m/z=509.1, 511.1.

Step G: tert-Butyl {2-[(E)-2-(5-aminopyridin-3-yl)vinyl]-4-[(2,5-dichloropyrimidin-4-yl)amino]phenyl}carbamate

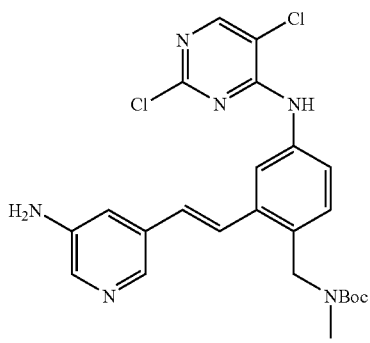

To a solution of tert-butyl {4-[(2,5-dichloropyrimidin-4-yl)amino]-2-iodobenzyl}methylcarbamate (3.30 g, 6.48 mmol) in acetonitrile (40 mL), THF (30 mL) and water (30 mL) was added 5-vinylpyridin-3-amine (1.56 g, 13.0 mmol), sodium carbonate (1.37 g, 13.0 mmol), palladium acetate (43.6 mg, 0.194 mmol) and trisodium 3,3',3''-phosphinetriyl-tris(4,6-dimethylbenzenesulfonate) (381 mg, 0.583 mmol). The reaction flask was evacuated and backfilled with nitrogen (this process was repeated a total of 3 times). The reaction solution was heated at 80° C. for 16 hours. The aqueous layer was separated and extracted with ethyl acetate once. The combined organic solutions were washed with brine, dried over $Na_2SO_4$, filtered and concentrated. The residue was purified by flash column chromatography to yield the desired product (2.40 g, 78%). LCMS for $C_{24}H_{27}Cl_2N_6O_2$ $(M+H)^+$: m/z=501.3, 503.3.

Step H: tert-Butyl {2-[2-(5-aminopyridin-3-yl)ethyl]-4-[(2,5-dichloropyrimidin-4-yl)amino]benzyl}carbamate

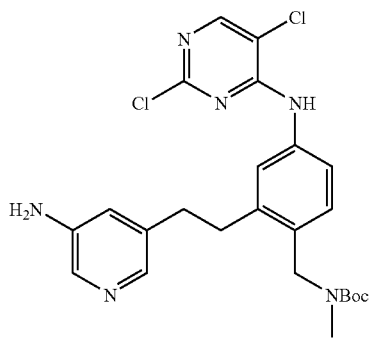 [SMILES: CN(Cc1ccc(Nc2nc(Cl)ncc2Cl)cc1CCc1cncc(N)c1)C(=O)OC(C)(C)C]

To a solution of tert-butyl {2-[(E)-2-(5-aminopyridin-3-yl)vinyl]-4-[(2,5-dichloropyrimidin-4-yl)amino]benzyl}carbamate (90.0 mg, 0.185 mmol) in THF (4 mL) was added p-toluenesulfonylhydrazide (0.515 g, 2.76 mmol). The reaction solution was heated to reflux at 90° C., then a solution of sodium acetate (0.363 g, 4.42 mmol) in water (3.7 mL, 20 mmol) was added dropwise over 4 h period. Another portion of p-toluenesulfonylhydrazide (0.343 g, 1.84 mmol) was added to reaction flask, then a solution of sodium acetate (0.242 g, 2.95 mmol) in water was added dropwise overnight under reflux. The reaction solution was diluted with ethyl acetate. Aqueous layer was extracted with ethyl acetate twice. The combined organic solutions were washed with brine, dried over $Na_2SO_4$, filtered and concentrated. The residue was purified by flash column chromatography to yield the desired product (56 mg, 62%). LCMS for $C_{24}H_{29}Cl_2N_6O_2$ $(M+H)^+$: m/z=503.3, 505.3.

Step I: tert-Butyl {[6-chloro-2,4,8,18,22-pentaazatetracyclo[14.3.1.1(3,7).1(9,13)]docosa-1(20),3(22),4,6,9(21),10,12,16,18-nonaen-12-yl]methyl}methylcarbamate

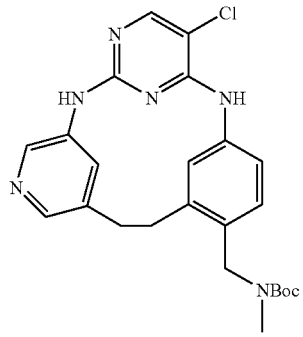 [SMILES: CN(Cc1ccc2cc1CCc1cncc(c1)Nc1ncc(Cl)c(n1)N2)C(=O)OC(C)(C)C]

This compound was prepared according to the procedure of Example B20 step H, using tert-butyl {2-[2-(5-aminopyridin-3-yl)ethyl]-4-[(2,5-dichloropyrimidin-4-yl)amino]benzyl}carbamate as the starting materials in 99% yield. LCMS calculated for $C_{24}H_{28}ClN_6O_2(M+H)^+$: m/z=467.3.

Step J: 1-[6-Chloro-2,4,8,18,22-pentaazatetracyclo[14.3.1.1(3,7).1(9,13)]docosa-1(20),3(22),4,6,9(21),10,12,16,18-nonaen-12-yl]-N-methylmethanamine trihydrochloride The desired compound was prepared according to the procedure of Example B21, step B, using tert-butyl {[6-chloro-2,4,8,18,22-pentaazatetracyclo[14.3.1.1(3,7).1(9,13)]docosa-1(20),3(22),4,6,9(21),10,12,16,18-nonaen-12-yl]methyl}methylcarbamate as the starting material in 73% yield. LCMS for $C_{19}H_{20}ClN_6$ $(M+H)^+$: m/z=367.2.

Example B335

N-{[6-Chloro-2,4,8,18,22-pentaazatetracyclo[14.3.1.1(3,7).1(9,13)]docosa-1(20),3(22),4,6,9(21),10,12,16,18-nonaen-12-yl]methyl}-N-methyl-1-[(5-methylisoxazol-3-yl)carbonyl]piperidine-4-carboxamide bis(trifluoroacetate)

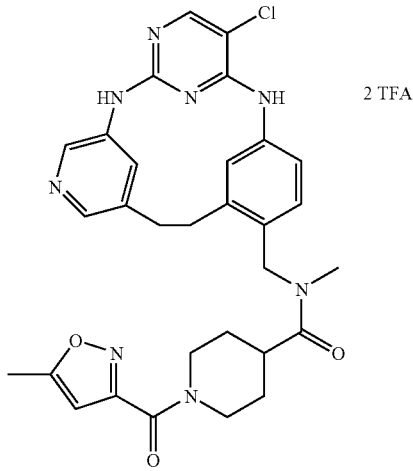 [SMILES: Cc1cc(C(=O)N2CCC(C(=O)N(C)Cc3ccc4cc3CCc3cncc(c3)Nc3ncc(Cl)c(n3)N4)CC2)no1 ; "2 TFA"]

Step A: tert-Butyl 4-{[{[6-chloro-2,4,8,18,22-pentaazatetracyclo[14.3.1.1(3,7).1(9,13)]docosa-1(20),3(22),4,6,9(21),10,12,16,18-nonaen-12-yl]methyl}(methyl)amino]carbonyl}piperidine-1-carboxylate bis(trifluoroacetate)

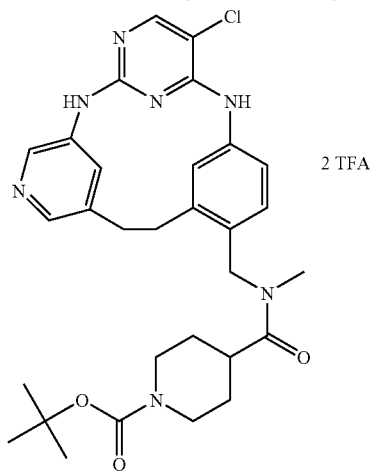 [SMILES: CN(Cc1ccc2cc1CCc1cncc(c1)Nc1ncc(Cl)c(n1)N2)C(=O)C1CCN(C(=O)OC(C)(C)C)CC1 ; "2 TFA"]

The desired compound was prepared according to the procedure of Example B267, using 1-[6-Chloro-2,4,8,18,22-pentaazatetracyclo[14.3.1.1(3,7).1(9,13)]docosa-1(20),3(22),4,6,9(21),10,12,16,18-nonaen-12-yl]-N-methylmethanamine trihydrochloride and 1-(tert-butoxycarbonyl)piperidine-4-carboxylic acid as the starting materials in 49% yield. LCMS for $C_{30}H_{37}ClN_7O_3(M+H)^+$: m/z=578.4.

Step B: N-{[6-Chloro-2,4,8,18,22-pentaazatetracyclo[14.3.1.1(3,7).1(9,13)]docosa-1(20),3(22),4,6,9(21),10,12,16,18-nonaen-12-yl]methyl}-N-methylpiperidine-4-carboxamide trihydrochloride

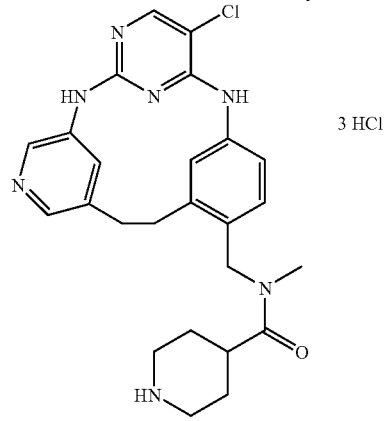

The desired compound was prepared according to the procedure of Example B21, step B, using tert-butyl 4-{[{[6-chloro-2,4,8,18,22-pentaazatetracyclo[14.3.1.1(3,7).1(9,13)]docosa-1(20),3(22),4,6,9(21),10,12,16,18-nonaen-12-yl]methyl}(methyl)amino]carbonyl}piperidine-1-carboxylate bis(trifluoroacetate) as the starting material in 84% yield. LCMS for $C_{25}H_{29}ClN_7O$ $(M+H)^+$: m/z=478.3.

Step C: N-{[6-Chloro-2,4,8,18,22-pentaazatetracyclo[14.3.1.1(3,7).1(9,13)]docosa-1(20),3(22),4,6,9(21),10,12,16,18-nonaen-12-yl]methyl}-N-methyl-1-[(5-methylisoxazol-3-yl)carbonyl]piperidine-4-carboxamide bis(trifluoroacetate)

The desired compound was prepared according to the procedure of Example B267, using N-{[6-Chloro-2,4,8,18,22-pentaazatetracyclo[14.3.1.1(3,7).1(9,13)]docosa-1(20),3(22),4,6,9(21),10,12,16,18-nonaen-12-yl]methyl}-N-methylpiperidine-4-carboxamide trihydrochloride and 5-methylisoxazole-3-carboxylic acid as the starting materials in 64% yield. LCMS for $C_{30}H_{32}ClN_8O_3(M+H)^+$: m/z=587.3.

Example B336

N-{[6-Chloro-2,4,8,18,22-pentaazatetracyclo[14.3.1.1(3,7).1(9,13)]docosa-1(20),3(22),4,6,9(21),10,12,16,18-nonaen-12-yl]methyl}-1-(isoxazol-5-ylcarbonyl)-N-methylpiperidine-4-carboxamide bis(trifluoroacetate)

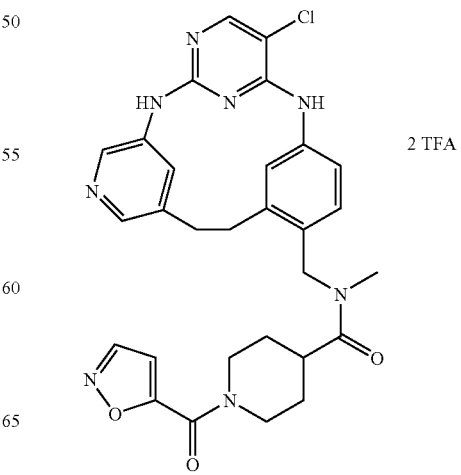

The desired compound was prepared according to the procedure of Example B267, using N-{[6-chloro-2,4,8,18,22-pentaazatetracyclo[14.3.1.1(3,7).1(9,13)]docosa-1(20),3(22),4,6,9(21),10,12,16,18-nonaen-12-yl]methyl}-N-methylpiperidine-4-carboxamide trihydrochloride and isoxazole-5-carboxylic acid as the starting materials in 62% yield. LCMS for $C_{29}H_{30}ClN_8O_3(M+H)^+$: m/z=573.3.

Example B337

N(4)-{[6-chloro-2,4,8,18,22-pentaazatetracyclo[14.3.1.1(3,7).1(9,13)]docosa-1(20),3(22),4,6,9(21),10,12,16,18-nonaen-12-yl]methyl}-N(4)-methyl-N(1)-phenylpiperidine-1,4-dicarboxamide bis(trifluoroacetate)

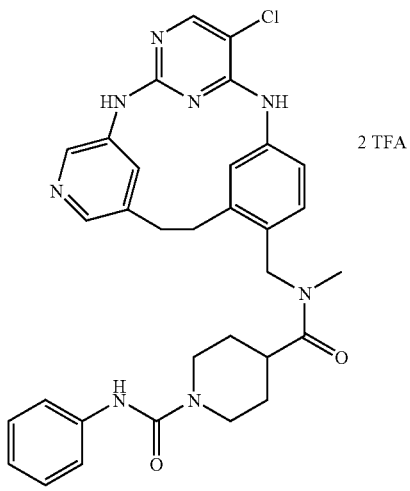 [SMILES: CN(Cc1ccc2cc1CCc1cncc(c1)Nc1ncc(Cl)c(n1)N2)C(=O)C1CCN(C(=O)Nc2ccccc2)CC1 ; "2 TFA"]

The desired compound was prepared according to the procedure of Example B183, using N-{[6-chloro-2,4,8,18,22-pentaazatetracyclo[14.3.1.1(3,7).1(9,13)]docosa-1(20),3(22),4,6,9(21),10,12,16,18-nonaen-12-yl]methyl}-N-methylpiperidine-4-carboxamide trihydrochloride and phenyl isocyanate as the starting materials in 53% yield. LCMS for $C_{32}H_{34}ClN_8O_2(M+H)^+$: m/z=597.3.

Example B338

N-{[6-Chloro-2,4,8,18,22-pentaazatetracyclo[14.3.1.1(3,7).1(9,13)]docosa-1(20),3(22),4,6,9(21),10,12,16,18-nonaen-12-yl]methyl}-N-methyl-1-pyrimidin-2-ylpiperidine-4-carboxamide tris(trifluoroacetate)

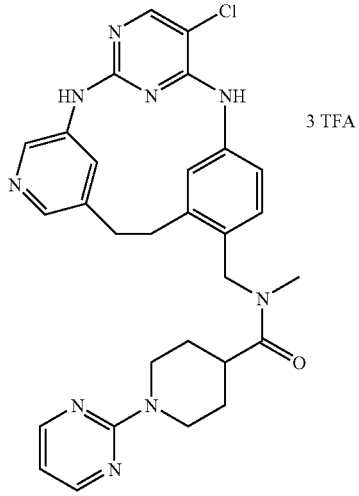 [SMILES: CN(Cc1ccc2cc1CCc1cncc(c1)Nc1ncc(Cl)c(n1)N2)C(=O)C1CCN(c2ncccn2)CC1]

The desired compound was prepared according to the procedure of Example B276, using N-{[6-Chloro-2,4,8,18,22-pentaazatetracyclo[14.3.1.1(3,7).1(9,13)]docosa-1(20),3(22),4,6,9(21),10,12,16,18-nonaen-12-yl]methyl}-N-methylpiperidine-4-carboxamide trihydrochloride and 2-chloropyrimidine as the starting materials in 34% yield. LCMS for $C_{29}H_{31}ClN_9O$ $(M+H)^+$: m/z=556.3.

Example B339

1-[6-Chloro-2,4,8,18,22-pentaazatetracyclo[14.3.1.1(3,7).1(9,13)]docosa-1(20),3(22),4,6,9(21),10,12,16,18-nonaen-12-yl]-N-methyl-N-(piperidin-4-ylmethyl)methanamine Tetrahydrochloride

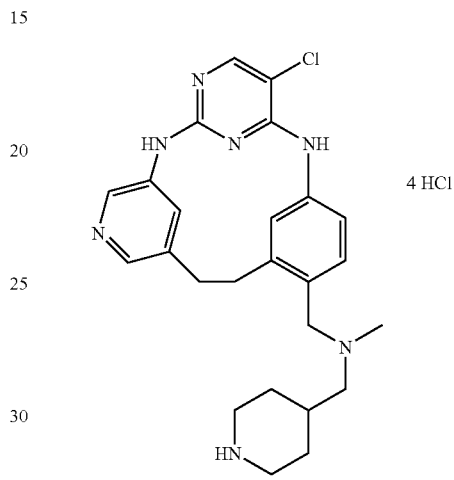

Step A: tert-Butyl 4-{[{[6-chloro-2,4,8,18,22-pentaazatetracyclo[14.3.1.1(3,7).1(9,13)]docosa-1(20),3(22),4,6,9(21),10,12,16,18-nonaen-12-yl]methyl}(methyl)amino]methyl}piperidine-1-carboxylate tris(trifluoroacetate)

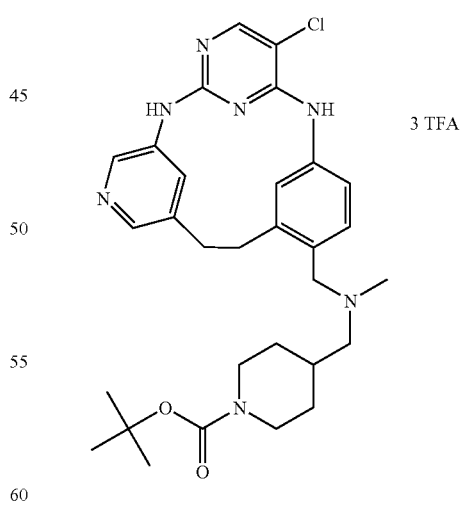

The desired compound was prepared according to the procedure of Example B192, using 1-[6-chloro-2,4,8,18,22-pentaazatetracyclo[14.3.1.1(3,7).1(9,13)]docosa-1(20),3(22),4,6,9(21),10,12,16,18-nonaen-12-yl]-N-methylmethanamine trihydrochloride and tert-butyl 4-formylpiperidine-1-carboxylate as the starting materials in 46% yield. LCMS for $C_{30}H_{39}ClN_7O_2(M+H)^+$: m/z=564.5.

Step B: 1-[6-Chloro-2,4,8,18,22-pentaazatetracyclo[14.3.1.1(3,7).1(9,13)]docosa-1(20),3(22),4,6,9(21),10,12,16,18-nonaen-12-yl]-N-methyl-N-(piperidin-4-ylmethyl)methanamine Tetrahydrochloride The desired compound was prepared according to the procedure of Example B21, step B, using tert-butyl 4-{[{[6-chloro-2,4,8,18,22-pentaazatetracyclo[14.3.1.1(3,7).1(9,13)]docosa-1(20),3(22),4,6,9(21),10,12,16,18-nonaen-12-yl]methyl}(methyl)amino]methyl}piperidine-1-carboxylate tris(trifluoroacetate) as the starting material in 91% yield. LCMS for $C_{25}H_{31}ClN_7$ (M+H)$^+$: m/z=464.3.

Example B340
2-[(4-{[{[6-Chloro-2,4,8,18,22-pentaazatetracyclo[14.3.1.1(3,7).1(9,13)]docosa-1(20),3(22),4,6,9(21),10,12,16,18-nonaen-12-yl]methyl}(methyl)amino]methyl}piperidin-1-yl)sulfonyl]benzonitrile tris(trifluoroacetate)

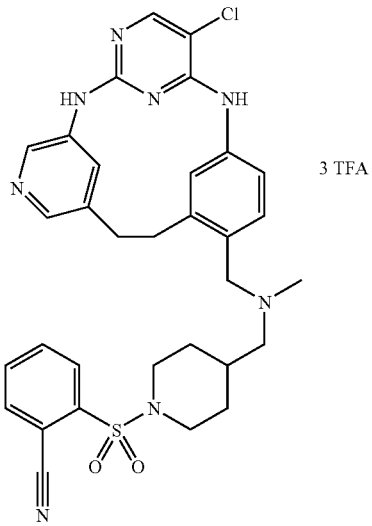 [SMILES: "3 TFA" ; CN(Cc1ccc2cc1CCc1cncc(c1)Nc1ncc(Cl)c(n1)N2)CC1CCN(S(=O)(=O)c2ccccc2C#N)CC1]

The desired compound was prepared according to the procedure of Example B136, using 1-[6-chloro-2,4,8,18,22-pentaazatetracyclo[14.3.1.1(3,7).1(9,13)]docosa-1(20),3(22),4,6,9(21),10,12,16,18-nonaen-12-yl]-N-methyl-N-(piperidin-4-ylmethyl)methanamine tetrahydrochloride and 2-cyanobenzenesulfonyl chloride as the starting materials in 55% yield. LCMS for $C_{32}H_{34}ClN_8O_2S$ (M+H)$^+$: m/z=629.2.

Example B341
1-[6-Chloro-2,4,8,18,22-pentaazatetracyclo[14.3.1.1(3,7).1(9,13)]docosa-1(20),3(22),4,6,9(21),10,12,16,18-nonaen-12-yl]-N-methyl-N-{[1-(phenylsulfonyl)piperidin-4-yl]methyl}methanamine tris(trifluoroacetate)

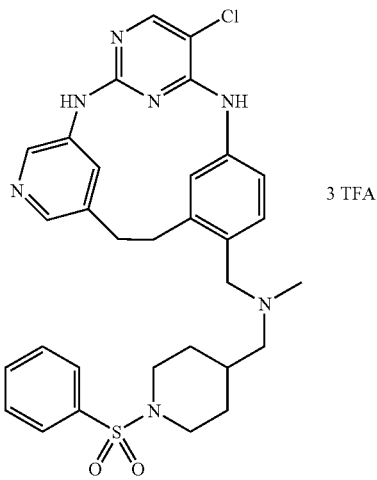 [SMILES: "3 TFA" ; CN(Cc1ccc2cc1CCc1cncc(c1)Nc1ncc(Cl)c(n1)N2)CC1CCN(S(=O)(=O)c2ccccc2)CC1]

The desired compound was prepared according to the procedure of Example B136, using 1-[6-chloro-2,4,8,18,22-pentaazatetracyclo[14.3.1.1(3,7).1(9,13)]docosa-1(20),3(22),4,6,9(21),10,12,16,18-nonaen-12-yl]-N-methyl-N-(piperidin-4-ylmethyl)methanamine tetrahydrochloride and benzenesulfonyl chloride as the starting materials in 42% yield. LCMS for $C_{31}H_{35}ClN_7O_2S$ (M+H)$^+$: m/z=604.3.

Example B342
1-[6-Chloro-2,4,8,18,22-pentaazatetracyclo[14.3.1.1(3,7).1(9,13)]docosa-1(20),3(22),4,6,9(21),10,12,16,18-nonaen-12-yl]-N-methyl-N-({1-[(5-methylisoxazol-4-yl)sulfonyl]piperidin-4-yl}methyl)methanamine tris(trifluoroacetate)

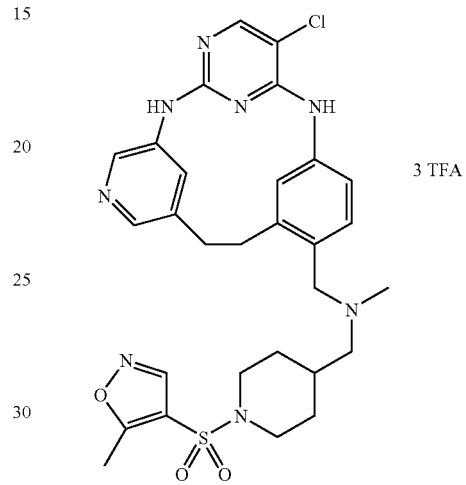

The desired compound was prepared according to the procedure of Example B136, using 1-[6-chloro-2,4,8,18,22-pentaazatetracyclo[14.3.1.1(3,7).1(9,13)]docosa-1(20),3(22),4,6,9(21),10,12,16,18-nonaen-12-yl]-N-methyl-N-(piperidin-4-ylmethyl)methanamine tetrahydrochloride and 5-methylisoxazole-4-sulfonyl chloride as the starting materials in 32% yield. LCMS for $C_{29}H_{34}ClN_8O_3S$ (M+H)$^+$: m/z=609.4.

Example B343
1-[6-Chloro-2,4,8,18,22-pentaazatetracyclo[14.3.1.1(3,7).1(9,13)]docosa-1(20),3(22),4,6,9(21),10,12,16,18-nonaen-12-yl]-N-({1-[(1,2-dimethyl-1H-imidazol-4-yl)sulfonyl]piperidin-4-yl}methyl)-N-methylmethanamine tris(trifluoroacetate)

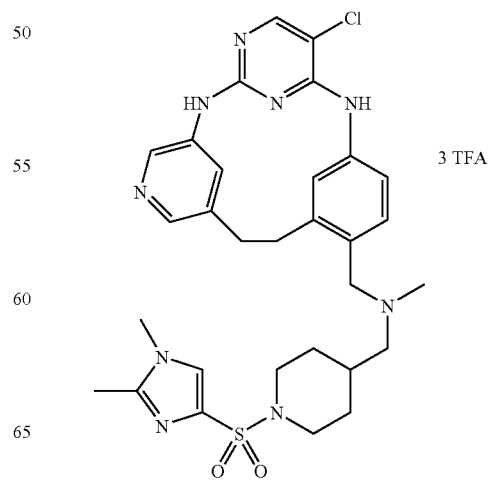

The desired compound was prepared according to the procedure of Example B136, using 1-[6-chloro-2,4,8,18,22-pentaazatetracyclo[14.3.1.1(3,7).1(9,13)]docosa-1(20),3(22),4,6,9(21),10,12,16,18-nonaen-12-yl]-N-methyl-N-(piperidin-4-ylmethyl)methanamine tetrahydrochloride and 1,2-dimethyl-1H-imidazole-4-sulfonyl chloride as the starting materials in 28% yield. LCMS for $C_{30}H_{37}ClN_9O_2S$ (M+H)$^+$: m/z=622.3.

Example B344

1-[6-Chloro-2,4,8,18,22-pentaazatetracyclo[14.3.1.1(3,7).1(9,13)]docosa-1(20),3(22),4,6,9(21),10,12,16,18-nonaen-12-yl]-N-methyl-N-({1-[(5-methylisoxazol-3-yl)carbonyl]piperidin-4-yl}methyl)methanamine tris(trifluoroacetate)

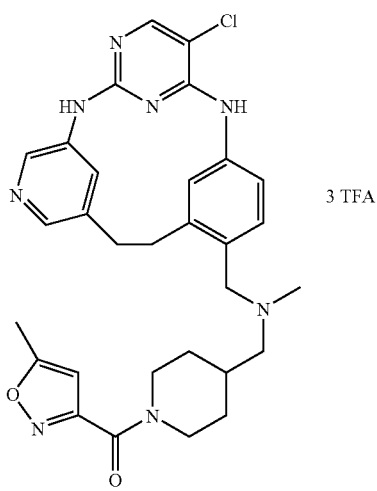 [SMILES: "3 TFA" ; Cc1cc(C(=O)N2CCC(CN(C)Cc3ccc4cc3CCc3cncc(c3)Nc3ncc(Cl)c(n3)N4)CC2)no1]

3 TFA

The desired compound was prepared according to the procedure of Example B267, using 1-[6-chloro-2,4,8,18,22-pentaazatetracyclo[14.3.1.1(3,7).1(9,13)]docosa-1(20),3(22),4,6,9(21),10,12,16,18-nonaen-12-yl]-N-methyl-N-(piperidin-4-ylmethyl)methanamine tetrahydrochloride and 5-methylisoxazole-3-carboxylic acid as the starting materials in 48% yield. LCMS for $C_{30}H_{34}ClN_8O_2$(M+H)$^+$: m/z=573.4.

Example B345

1-[6-Chloro-2,4,8,18,22-pentaazatetracyclo[14.3.1.1(3,7).1(9,13)]docosa-1(20),3(22),4,6,9(21),10,12,16,18-nonaen-12-yl]-N-{[1-(isoxazol-5-ylcarbonyl)piperidin-4-yl]methyl}-N-methylmethanamine tris(trifluoroacetate)

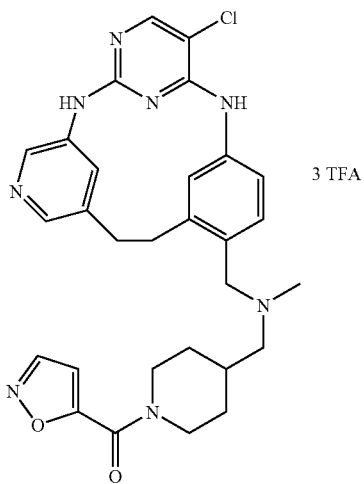 [SMILES: "3 TFA" ; CN(Cc1ccc2cc1CCc1cncc(c1)Nc1ncc(Cl)c(n1)N2)CC1CCN(C(=O)c2ccno2)CC1]

3 TFA

The desired compound was prepared according to the procedure of Example B267, using 1-[6-chloro-2,4,8,18,22-pentaazatetracyclo[14.3.1.1(3,7).1(9,13)]docosa-1(20),3(22),4,6,9(21),10,12,16,18-nonaen-12-yl]-N-methyl-N-(piperidin-4-ylmethyl)methanamine tetrahydrochloride and isoxazole-5-carboxylic acid as the starting materials in 36% yield. LCMS for $C_{29}H_{32}ClN_8O_2$(M+H)$^+$: m/z=559.4.

Example B346

1-(1-Acetylpiperidin-4-yl)-N-{[6-chloro-2,4,8,18,22-pentaazatetracyclo[14.3.1.1(3,7).1(9,13)]docosa-1(20),3(22),4,6,9(21),10,12,16,18-nonaen-12-yl]methyl}-N-methylmethanamine tris(trifluoroacetate)

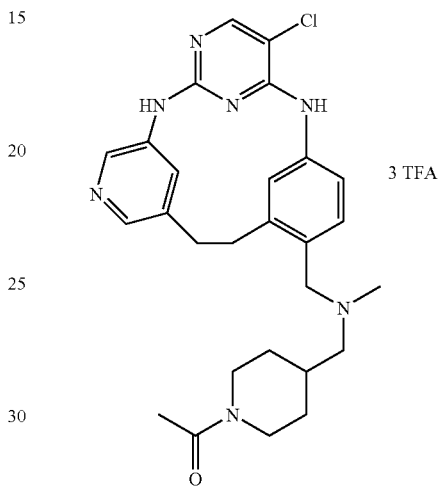

3 TFA

The desired compound was prepared according to the procedure of Example B26, using 1-[6-chloro-2,4,8,18,22-pentaazatetracyclo[14.3.1.1(3,7).1(9,13)]docosa-1(20),3(22),4,6,9(21),10,12,16,18-nonaen-12-yl]-N-methyl-N-(piperidin-4-ylmethyl)methanamine tetrahydrochloride and acetyl chloride as the starting materials in 22% yield. LCMS for $C_{27}H_{33}ClN_7O$ (M+H)$^+$: m/z=506.4.

Example B347

1-[6-Chloro-2,4,8,18,22-pentaazatetracyclo[14.3.1.1(3,7).1(9,13)]docosa-1(20),3(22),4,6,9(21),10,12,16,18-nonaen-12-yl]-N-methyl-N-({1-[(4-methyl-1,3-oxazol-5-yl)carbonyl]piperidin-4-yl}methyl)methanamine tris(trifluoroacetate)

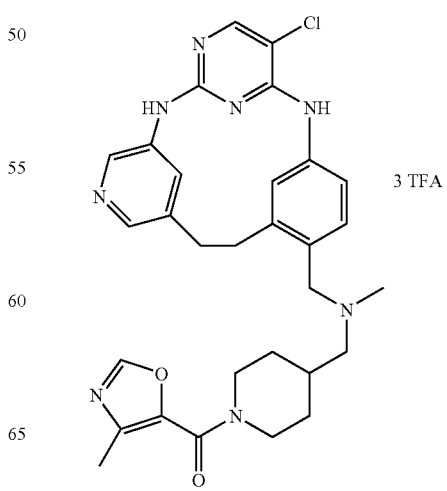

3 TFA

The desired compound was prepared according to the procedure of Example B26, using 1-[6-chloro-2,4,8,18,22-pentaazatetracyclo[14.3.1.1(3,7).1(9,13)]docosa-1(20),3(22),4,6,9(21),10,12,16,18-nonaen-12-yl]-N-methyl-N-(piperidin-4-ylmethyl)methanamine tetrahydrochloride and 4-methyl-1,3-oxazole-5-carbonyl chloride as the starting materials in 16% yield. LCMS for $C_{30}H_{34}ClN_8O_2(M+H)^+$: m/z=573.4.

Example B348

4-{[{[6-Chloro-2,4,8,18,22-pentaazatetracyclo[14.3.1.1(3,7).1(9,13)]docosa-1(20),3(22),4,6,9(21),10,12,16,18-nonaen-12-yl]methyl}(methyl)amino]methyl}-N-pyridin-3-ylpiperidine-1-carboxamide tetrakis(trifluoroacetate)

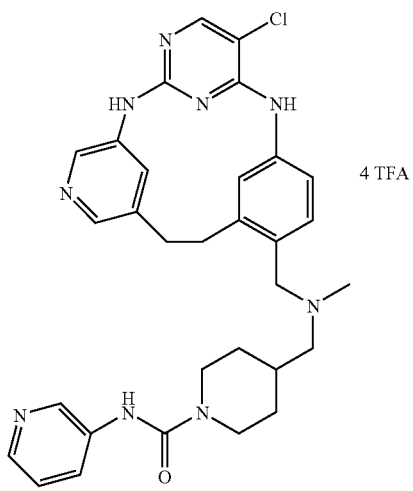 [SMILES: CN(Cc1ccc2cc1CCc1cncc(c1)Nc1ncc(Cl)c(n1)N2)CC1CCN(C(=O)Nc2cccnc2)CC1 ; "4 TFA"]

The desired compound was prepared according to the procedure of Example B83, using 1-[6-chloro-2,4,8,18,22-pentaazatetracyclo[14.3.1.1(3,7).1(9,13)]docosa-1(20),3(22),4,6,9(21),10,12,16,18-nonaen-12-yl]-N-methyl-N-(piperidin-4-ylmethyl)methanamine tetrahydrochloride and 3-isocyanatopyridine as the starting materials in 19% yield. LCMS for $C_{31}H_{35}ClN_9O$ (M+H)$^+$: m/z=584.4.

Example B349

4-{[{[6-Chloro-2,4,8,18,22-pentaazatetracyclo[14.3.1.1(3,7).1(9,13)]docosa-1(20),3(22),4,6,9(21),10,12,16,18-nonaen-12-yl]methyl}(methyl)amino]methyl}-N-(2-methyl-3-furyl)piperidine-1-carboxamide tris(trifluoroacetate)

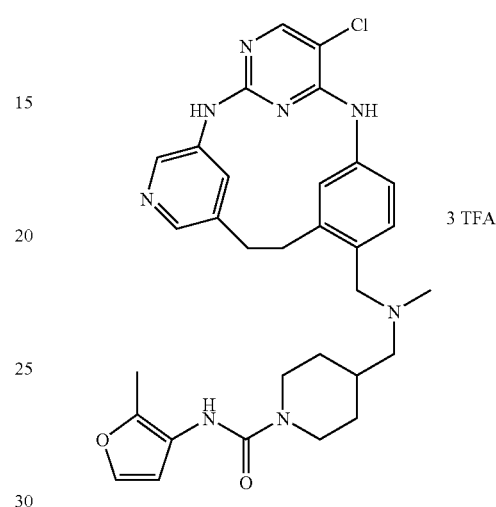

The desired compound was prepared according to the procedure of Example B83, using 1-[6-chloro-2,4,8,18,22-pentaazatetracyclo[14.3.1.1(3,7).1(9,13)]docosa-1(20),3(22),4,6,9(21),10,12,16,18-nonaen-12-yl]-N-methyl-N-(piperidin-4-ylmethyl)methanamine tetrahydrochloride and 3-isocyanato-2-methylfuran as the starting materials in 14% yield. LCMS for $C_{31}H_{36}ClN_8O_2(M+H)^+$: m/z=587.4.

Example B350

6-Chloro-12-(1H-pyrazol-4-yl)-2,4,8,18,22-pentaazatetracyclo[14.3.1.1(3,7).1(9,13)]docosa-1(20),3(22),4,6,9(21),10,12,16,18-nonaene tris(trifluoroacetate)

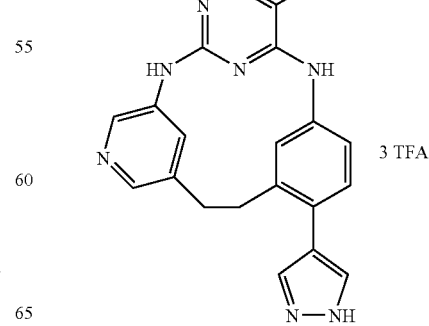

491

Step A: 6-Chloro-12-iodo-2,4,8,18,22-pentaazatetra-cyclo[14.3.1.1(3,7).1(9,13)]docosa-1(20),3(22),4,6,9(21),10,12,16,18-nonaene

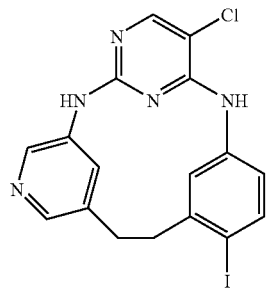 [SMILES: Clc1cnc2nc1Nc1ccc(I)c(c1)CCc1cncc(c1)N2]

To a solution of 6-chloro-2,4,8,18,22-pentaazatetracyclo[14.3.1.1(3,7).1(9,13)]docosa-1(20),3(22),4,6,9(21),10,12,16,18-nonaen-12-amine trihydrochloride (161 mg, 0.359 mmol) in 2.0 M of sulfuric acid in water (1.8 mL, 3.59 mmol) was added a solution of sodium nitrite (37.2 mg, 0.539 mmol) in water dropwise at 0° C. The reaction solution was stirred at same temperature for 1 h, then a solution of potassium iodide (89.4 mg, 0.539 mmol) in water was added at 0° C. The reaction solution was stirred at room temperature for 48 h. The precipitate was filtered and washed by water and dried under vacuum to give the desired product (103 mg, 64%). LCMS for $C_{17}H_{14}ClIN_5 (M+H)^+$: m/z=450.1.

Step B: 6-Chloro-12-(1H-pyrazol-4-yl)-2,4,8,18,22-pentaazatetracyclo[14.3.1.1(3,7).1(9,13)]docosa-1(20),3(22),4,6,9(21),10,12,16,18-nonaene tris(trifluoroacetate)

A mixture of 6-chloro-12-iodo-2,4,8,18,22-pentaazatetracyclo[14.3.1.1(3,7).1(9,13)]docosa-1(20),3(22),4,6,9(21),10,12,16,18-nonaene (14.1 mg, 0.0314 mmol), 1-(1-ethoxyethyl)-4-(4,4,5,5-tetramethyl-1,3,2-dioxaborolan-2-yl)-1H-pyrazole (10.0 mg, 0.0376 mmol), [1,1'-bis(diphenylphosphino)ferrocene]dichloropalladium (II), complex with dichloromethane (1:1) (1.5 mg, 0.0019 mmol) and potassium phosphate (20 mg, 0.094 mmol) in 1,4-dioxane (0.8 mL) and water (0.2 mL) was degassed and heated at 120° C. for 2 h. The reaction solution was concentrated and diluted with methanol and purified with preparative LCMS. The resulting intermediate was treated with TFA (0.3 mL) and stirred at room temperature for 2 h. The reaction solution was diluted with methanol and purified with preparative LCMS to give the desired product (8.4 mg, 37%). LCMS for $C_{20}H_{17}ClN_7 (M+H)^+$: m/z=390.3.

492

Example C1

6-Chloro-2,4,8,15,22-pentaazatetracyclo[14.3.1.1(3,7).1(9,13)]docosa-1(20),3(22),4,6,9(21),10,12,16,18-nonaen-14-one hydrochloride

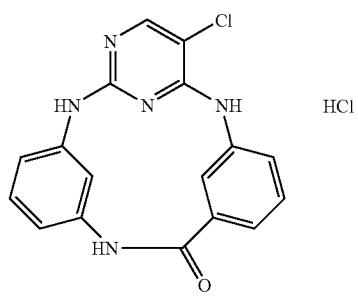 [SMILES: O=C1Nc2cccc(c2)Nc2ncc(Cl)c(n2)Nc2cccc1c2 ; Cl]

Step A: tert-Butyl {3-[(3-nitrobenzoyl)amino]phenyl}carbamate

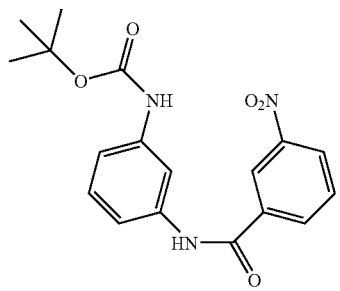 [SMILES: CC(C)(C)OC(=O)Nc1cccc(NC(=O)c2cccc([N+](=O)[O-])c2)c1]

To a stirring solution of tert-butyl (3-aminophenyl)carbamate (2.00 g, 9.6 mmol) and triethylamine (1.40 mL, 10 mol) in dry tetrahydrofuran (27.3 mL) at 0° C. was slowly added a solution of 3-nitrobenzoyl chloride (1.87 g, 10.1 mmol) in tetrahydrofuran (7.8 mL). The resulting mixture was slowly warmed up to rt and stirred for one additional hour at rt. The reaction mixture was treated with $Na_2CO_3$ (aq). The aqueous layer was extracted with EtOAc three times. The combined organic layers were dried, filtered and concentrated to give the desired product as a white powder (3.4 g, 99%). LCMS for $C_{18}H_{19}N_3O_5$ (M-tBu+H)$^+$: m/z=302.0. $^1$H NMR (400 MHz, $CD_3OD$): δ 8.79 (t, J=2.0 Hz, 1H), 8.43 (ddd, J=8.0, 2.0, 1.2 Hz, 1H), 8.31 (ddd, J=6.4, 2.4, 1.2 Hz, 1H), 7.87 (t, J=2.1 Hz, 1H), 7.77 (t, J=8.0 Hz, 1H), 7.60 (ddd, J=8.0, 4.0, 2.4, 1H), 7.25 (t, J=8.0 Hz, 1H), 7.19 (d, J=1.2 Hz, 1H), 1.52 (s, 9H).

Step B: tert-Butyl {3-[(3-aminobenzoyl)amino]phenyl}carbamate

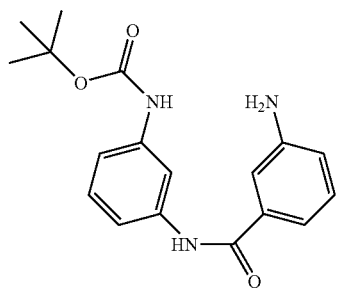 [SMILES: CC(C)(C)OC(=O)Nc1cccc(NC(=O)c2cccc(N)c2)c1]

To a solution of tert-butyl {3-[(3-nitrobenzoyl)amino]phenyl}carbamate (2.00 g, 5.6 mmol) in water (4 mL), methanol (22 mL) and acetic acid (8.6 mL) was added iron (0.782 g, 14.0 mmol) powder in small quantities. When the addition was completed, the mixture was stirred in water bath for 3 h. The mixture was filtered, and the cake was washed with MeOH/EtOAc. The brown filtrate was concentrated and diluted with $H_2O$, and the aqueous layer was extracted with EtOAc three times. The combined organic layers were dried, filtered and concentrated to give the desired product as an off-white powder (1.6 g, 87%). LCMS for $C_{18}H_{21}N_3O_3$ $(M+H)^+$: m/z=328.1.

Step C: tert-Butyl [3-({3-[(2,5-dichloropyrimidin-4-yl)amino]benzoyl}amino)phenyl]carbamate

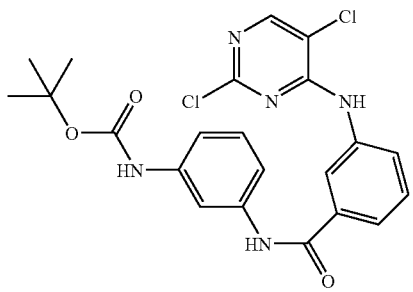 [SMILES: CC(C)(C)OC(=O)Nc1cccc(NC(=O)c2cccc(Nc3nc(Cl)ncc3Cl)c2)c1]

To a solution of tert-butyl {3-[(3-aminobenzoyl)amino]phenyl}carbamate (0.500 g, 1.53 mol) and 2,4,5-trichloropyrimidine (0.25 g, 1.4 mmol) in DMF (3.7 mL) was added potassium carbonate (0.29 g, 2.1 mmol). The resulting mixture was stirred overnight at room temperature. The reaction was quenched with saturated (sat'd) $NH_4Cl$ and water. EtOAc was added and the layers separated. The aqueous layer was extracted with EtOAc twice and the combined organics were washed with water, dried, filtered and concentrated to give 800 mg of crude product, which was purified by Combi-Flash column chromatography (12 g column, 0 to 30% EtOAc in hexane) to give the desired product (66 mg, 10%). LCMS for $C_{22}H_{21}Cl_2N_5O_3$ $(M-tBu+H)^+$: m/z=420.0, 418.1. $^1H$ NMR (400 MHz, $CD_3OD$): δ 8.26 (s, 1H), 8.11 (t, J=2.0 Hz, 1H), 7.89 (ddd, J=8.0, 2.0, 1.2 Hz, 1H), 7.85 (t, J=2.0 Hz, 1H), 7.74 (ddd, J=7.6, 2.0, 0.8 Hz, 1H), 7.53 (t, J=8.0 Hz, 1H), 7.32 (dd, J=8.0, 1.2 Hz, 1H), 7.24 (t, J=8.0 Hz, 1H), 7.19 (m, 1H), 1.52 (s, 9H).

Step D: 6-Chloro-2,4,8,15,22-pentaazatetracyclo[14.3.1.1(3,7).1(9,13)]docosa-1(20),3(22),4,6,9(21),10,12,16,18-nonaen-14-one hydrochloride To a solution of tert-butyl [3-({3-[(2,5-dichloropyrimidin-4-yl)amino]benzoyl}amino)phenyl]carbamate (20.0 mg, 0.042 mmol) in 2-methoxyethanol (0.2 mL) was added 4.0 M of hydrogen chloride in 1,4-dioxane (63 µL). The resulting mixture was heated at 150° C. in the microwave for 15 min. After filtration of the reaction mixture, the crude was triturated with MeOH/EtOAc to give the desired product as an off-white powder (2 mg, 14%). LCMS for $C_{17}H_{12}ClN_5O$ $(M+H)^+$: m/z=338.0. $^1H$ NMR (400 MHz, $CD_3OD$): δ 9.57 (s, 1H), 9.42 (s, 1H), 8.33 (s, 1H), 8.16 (s, 1H), 7.91 (s, 1H), 7.29 (dd, J=7.9, 7.6 Hz, 1H), 7.15 (d, J=7.9 Hz, 1H), 7.10-7.05 (m, 2H), 6.90 (dd, J=8.2, 0.9 Hz, 1H), 6.84-6.81 (m, 1H), 4.11 (s, 2H).

Example C2

6-Chloro-2,4,8,14,22-pentaazatetracyclo[14.3.1.1(3,7).1(9,13)]docosa-1(20),3(22),4,6,9(21),10,12,16,18-nonaen-15-one hydrochloride

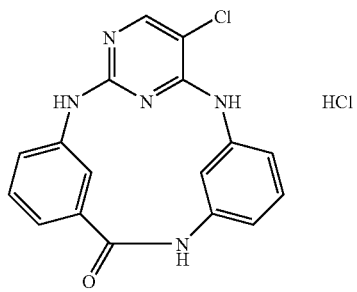 [SMILES: O=C1Nc2cccc(c2)Nc2nc(ncc2Cl)Nc2cccc1c2 ; Cl]

Step A: N-(3-Aminophenyl)-3-nitrobenzamide hydrochloride

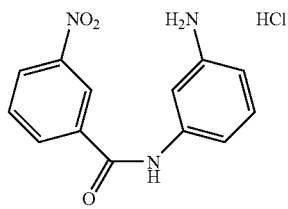 [SMILES: Nc1cccc(NC(=O)c2cccc([N+](=O)[O-])c2)c1 ; Cl]

tert-Butyl {3-[(3-nitrobenzoyl)amino]phenyl}carbamate (0.60 g, 1.7 mmol) was mixed with 4 M of hydrogen chloride in 1,4-dioxane (7 mL) and stirred at rt for 2 h. After concentration, the desired white powder solid product (0.49 g, 99%) as a HCl salt was used in the next step. MF=$C_{13}H_{11}N_3O_3$; LCMS calculated for $C_{13}H_{11}N_3O_3$ $(M+H)^+$: m/z=258.0. $^1H$ NMR (400 MHz, $CD_3OD$): δ 8.82 (t, J=2.0 Hz, 1H), 8.46 (ddd, J=8.4, 2.4, 1.2 Hz, 1H), 8.36 (ddd, J=8.4, 2.4, 1.2 Hz, 1H), 8.21 (t, J=2.0 Hz, 1H), 7.80 (t, J=8.0 Hz, 1H), 7.68 (ddd, J=8.0, 4.0, 2.4, 1H), 7.54 (t, J=8.4 Hz, 1H), 7.19 (ddd, J=8.0, 2.0, 1.2 Hz, 1H).

Step B: N-{3-[(2,5-Dichloropyrimidin-4-yl)amino]phenyl}-3-nitrobenzamide

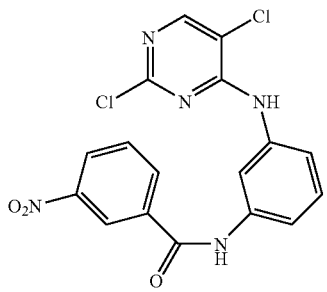

To a solution of N-(3-aminophenyl)-3-nitrobenzamide hydrochloride (0.200 g, 0.681 mmol) and 2,4,5-trichloropyrimidine (0.071 mL, 0.619 mmol) in DMF (1.6 mL) was added potassium carbonate (0.30 g, 2.2 mmol). The resulting mixture was stirred overnight at room temperature. The reaction was quenched with sat'd NH$_4$Cl and water. EtOAc was added and the layers separated. The aqueous layer was extracted with EtOAc twice. The combined organics were washed with water, dried, filtered and concentrated to give the desired product as a light brown powder (330 mg). LCMS for C$_{17}$H$_{11}$Cl$_2$N$_5$O$_3$ (M+H)$^+$: m/z=403.9, 405.9, 407.9. $^1$H NMR (400 MHz, CD$_3$OD): δ 8.82 (t, J=2.0 Hz, 1H), 8.45 (ddd, J=8.0, 2.0, 1.2 Hz, 1H), 8.34 (ddd, J=7.6, 2.0, 1.2 Hz, 1H), 8.24 (s, 1H), 7.97 (br, 2H), 7.76 (t, J=8.0 Hz, 1H), 7.56 (m, 1H), 7.43 (ddd, J=8.0, 2.0, 1.2 Hz, 1H).

Step C: 3-Amino-N-{3-[(2,5-dichloropyrimidin-4-yl)amino]phenyl}benzamide

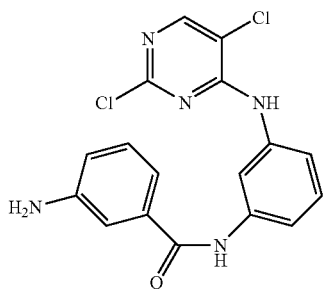 [SMILES: O=C(Nc1cccc(Nc2nc(Cl)ncc2Cl)c1)c1cccc([N+](=O)[O-])c1]

To a solution N-{3-[(2,5-dichloropyrimidin-4-yl)amino]phenyl}-3-nitrobenzamide (50.0 mg, 0.124 mmol) in water (0.09 mL), methanol (0.48 mL) and acetic acid (0.19 mL) was added iron (17 mg, 0.31 mmol) powder in small quantities. When the addition was completed, the mixture was stirred at 0° C. for 3 h, 3 eq additional iron powder was added. The mixture was filtered, and the cake was washed with MeOH/EtOAc. The brown filtrate was concentrated and diluted with H$_2$O, and the aqueous layer was extracted with EtOAc three times. The combined organic layers were dried, filtered and concentrated to give the desired product as a light brown powder (32 mg, 69%). LCMS for C$_{17}$H$_{13}$Cl$_2$N$_5$O (M+H)$^+$: m/z=374.0, 376.0. $^1$H NMR (400 MHz, CD$_3$OD): δ 9.57 (s, 1H), 9.42 (s, 1H), 8.33 (s, 1H), 8.16 (s, 1H), 7.91 (s, 1H), 7.29 (dd, J=7.9, 7.6 Hz, 1H), 7.15 (d, J=7.9 Hz, 1H), 7.10-7.05 (m, 2H), 6.90 (dd, J=8.2, 0.9 Hz, 1H), 6.84-6.81 (m, 1H), 4.11 (s, 2H).

Step D: 6-Chloro-2,4,8,14,22-pentaazatetracyclo[14.3.1.1(3,7).1(9,13)]docosa-1(20),3(22),4,6,9(21),10,12,16,18-nonaen-15-one hydrochloride To a solution of 3-amino-N-{3-[(2,5-dichloropyrimidin-4-yl)amino]phenyl}benzamide (20.0 mg, 0.053 mmol) in 2-methoxyethanol (0.295 mL) was added 4.0 M of hydrogen chloride in 1,4-dioxane (67 μL). The resulting mixture was heated at 150° C. in a microwave for 15 min. After filtration of the reaction mixture, the crude was triturated with MeOH/EtOAc to give the desired product as an off-white powder (12 mg, 66%). LCMS for C$_{17}$H$_{12}$ClN$_5$O (M+H)$^+$: m/z=337.9. $^1$H NMR (400 MHz, DMSO-d$_6$): δ 10.32 (s, 1H), 10.16 (ddd, J=8.0, 2.0, 1.2 Hz, 1H), 9.66 (ddd, J=7.6, 2.0, 1.2 Hz, 1H), 9.38 (s, 1H), 6.30 (br, 1H), 8.24 (m, 1H), 7.38 (ddd, J=8.0, 2.0, 1.2 Hz, 1H), 7.50 (t, J=8.0 Hz, 1H), 7.25 (m, 2H), 7.16 (m, 1H), 6.95 (t, J=2.0 Hz, 1H).

Example C3

6-Chloro-16-thia-2,4,8,15,23-pentaazatetracyclo[15.3.1.1(3,7).1(9,13)]tricosa-1(21),3(23),4,6,9(22),10,12,17,19-nonaene 16,16-dioxide

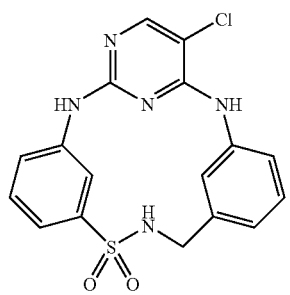 [SMILES: O=S1(=O)NCc2cccc(c2)Nc2nc(ncc2Cl)Nc2cccc1c2]

Step A: tert-Butyl [3-({[(3-nitrophenyl)sulfonyl]amino}methyl)phenyl]carbamate

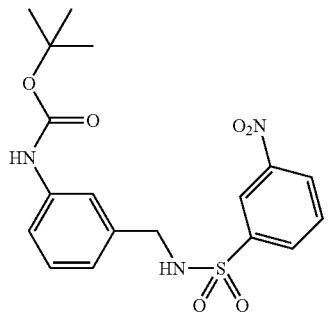 [SMILES: CC(C)(C)OC(=O)Nc1cccc(CNS(=O)(=O)c2cccc([N+](=O)[O-])c2)c1]

To a stirring solution of tert-butyl [3-(aminomethyl)phenyl]carbamate (2.00 g, 9.0 mmol) and triethylamine (1.32 mL, 9.45 mmol) in dry tetrahydrofuran (25.5 mL) at 0° C. was slowly added a solution of m-nitrobenzenesulfonyl chloride (2.09 g, 9.45 mmol) in tetrahydrofuran (7.3 mL). The resulting mixture was slowly warmed up to rt and stirred for one additional hour at rt. The reaction mixture was treated with Na$_2$CO$_3$ (aq) and layers separated. The aqueous layer was extracted with EtOAc three times. The combined organic layers were dried, filtered and concentrated to give the desired product as an off-white powder (4.0 g, 100%). LCMS for C$_{18}$H$_{21}$N$_3$O$_6$S (M-Boc+H)$^+$: m/z=308.0. $^1$H NMR (400 MHz, CD$_3$OD): δ 8.43 (t, J=2.0 Hz, 1H), 8.31 (ddd, J=8.0, 2.0, 1.2 Hz, 1H), 8.04 (dt, J=8.0, 2.8 Hz, 1H), 7.64 (t, J=8.0 Hz, 1H), 7.19 (br, 1H), 7.04 (m, 2H), 6.77 (dt, J=7.2, 1.2 Hz, 1H), 4.13 (s, 2H).

Step B: N-(3-Aminobenzyl)-3-nitrobenzenesulfonamide hydrochloride

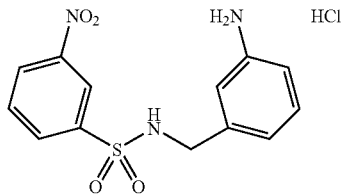 [SMILES: Nc1cccc(CNS(=O)(=O)c2cccc([N+](=O)[O-])c2)c1 ; Cl]

tert-Butyl [3-({[(3-nitrophenyl)sulfonyl]amino}methyl)phenyl]carbamate (1.00 g, 2.45 mmol) was mixed with 4 M of hydrogen chloride in 1,4-dioxane (10 mL) and stirred at rt for 2 h. After concentration, the crude off-white powder product (0.97 g) was used in the next step. (Molecular Formula (MF)= $C_{13}H_{13}N_3O_4S$; LCMS calculated for $C_{13}H_{13}N_3O_4S$ $(M+H)^+$: m/z=308.0. $^1$H NMR (400 MHz, $CD_3OD$): δ 8.55 (t, J=2.0 Hz, 1H), 8.44 (ddd, J=8.4, 2.4, 1.2 Hz, 1H), 8.20 (ddd, J=7.6, 2.4, 1.2 Hz, 1H), 7.81 (t, J=8.0 Hz, 1H), 7.40 (m, 2H), 7.36 (dd, J=7.6, 1.2 Hz, 1H), 7.23 (ddd, J=8.0, 2.4, 1.2 Hz, 1H), 4.21 (s, 2H).

Step C: N-{3-[(2,5-Dichloropyrimidin-4-yl)amino]benzyl}-3-nitrobenzenesulfonamide

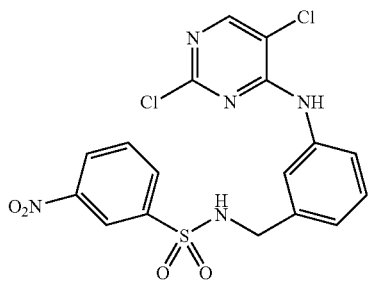 [SMILES: O=[N+]([O-])c1cccc(S(=O)(=O)NCc2cccc(Nc3nc(Cl)ncc3Cl)c2)c1]

To a solution of N-(3-aminobenzyl)-3-nitrobenzenesulfonamide hydrochloride (0.400 g, 1.16 mmol) and 2,4,5-trichloropyrimidine (0.12 mL, 1.06 mmol) in DMF (2.8 mL) was added potassium carbonate (0.51 g, 3.7 mmol). The resulting mixture was stirred overnight at room temperature. The reaction was quenched with saturated (sat'd) $NH_4Cl$ and water. EtOAc was added and the layers separated. The aqueous layer was extracted with EtOAc twice. The combined organics were washed with water, dried, filtered and concentrated to give 660 mg of crude residue, which was purified by Combi-Flash column chromatography (12 g column, 0 to 30% EtOAc in hexane) to give the desired product (135 mg, 28%). LCMS for $C_{17}H_{13}Cl_2N_5O_4S$ $(M+H)^+$: m/z=453.9, 455.9, 457.9. $^1$H NMR (400 MHz, $CD_3OD$): δ 8.85 (s, 1H), 8.48 (t, J=2.0 Hz, 1H), 8.29 (ddd, J=8.0, 2.0, 1.2 Hz, 1H), 8.21 (s, 1H), 8.08 (ddd, J=8.0, 1.6, 0.8 Hz, 1H), 7.64 (t, J=8.0 Hz, 1H), 7.41 (m, 2H), 7.17 (t, J=8.0 Hz, 1H), 4.21 (s, 2H).

Step D: 3-Amino-N-{3-[(2,5-dichloropyrimidin-4-yl)amino]benzyl}benzenesulfonamide

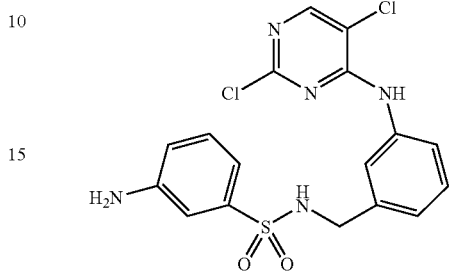

To a solution N-{3-[(2,5-dichloropyrimidin-4-yl)amino]benzyl}-3-nitrobenzenesulfonamide (50.0 mg, 0.11 mmol) in water (0.08 mL), methanol (0.42 mL) and acetic acid (0.17 mL) was added iron (15 mg, 0.28 mmol) powder in small quantities. When the addition was completed, the mixture was stirred in water bath for 3 h and the reaction was complete. The mixture was filtered and the cake was washed with MeOH/EtOAc. The brown filtrate was concentrated and diluted with $H_2O$, and the aqueous layer was extracted with EtOAc three times. The combined organic layers were dried, filtered and concentrated to give the desired product as a light brown powder (42 mg, 90%). LCMS for $C_{17}H_{15}Cl_2N_5O_2S$ $(M+H)^+$: m/z=424.0, 426.0, 428.0. $^1$H NMR (400 MHz, $CD_3OD$): δ 8.22 (t, J=2.0 Hz, 1H), 8.52 (ddd, J=8.0, 2.0, 1.2 Hz, 1H), 7.48 (m, 1H), 7.40 (t, J=8.0 Hz, 1H), 7.28 (m, 1H), 7.20 (t, J=8.0 Hz, 1H), 7.08 (ddd, J=8.4, 2.0, 1.2 Hz, 1H), 6.84 (ddd, J=8.0, 1.6, 1.2 Hz, 1H), 4.21 (s, 2H).

Step E: 6-Chloro-16-thia-2,4,8,15,23-pentaazatetracyclo[15.3.1.1(3,7).1(9,13)]tricosa-1(21),3(23),4,6,9(22),10,12,17,19-nonaene 16,16-dioxide To a solution of 3-amino-N-{3-[(2,5-dichloropyrimidin-4-yl)amino]benzyl}benzenesulfonamide (38.0 mg, 0.089 mmol) in 2-methoxyethanol (0.49 mL) was added 4.0 M of hydrogen chloride in 1,4-dioxane (45 µL). The resulting mixture was heated at 150° C. in the microwave for 15 min. The mixture was diluted with $Na_2CO_3$ (aq), extracted with EtOAc three times. The combined organic layers were dried, filtered and concentrated to give the crude, which was purified by Combi-Flash column chromatography (4 g column, 0 to 50% EtOAc in Hex) to give the desired product as a white powder (7 mg, 20%). LCMS for $C_{17}H_{14}ClN_5O_2S$ $(M+H)^+$: m/z=388.0, 390.0. $^1$H NMR (400 MHz, $CD_3OD$): δ 7.62 (m, 1H), 7.54 (s, 1H), 7.28 (t, J=2.0 Hz, 1H), 7.08 (ddd, J=8.0, 2.0, 1.2 Hz, 1H), 6.78 (t, J=8.0 Hz, 1H), 6.35 (m, 1H), 6.18 (ddd, J=8.0, 1.6, 1.0 Hz, 1H), 5.98 (m, 1H), 5.82 (ddd, J=7.6, 2.0, 1.0, 1H), 4.20 (s, 2H).

Example C4

6-Chloro-2,4,8,15,23-pentaazatetracyclo[15.3.1.1(3,7).1(9,13)]tricosa-1(21),3(23),4,6,9(22),10,12,17,19-nonaen-14-one

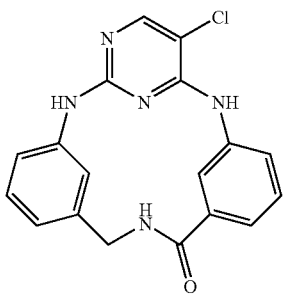 [SMILES: O=C1NCc2cccc(c2)Nc2ncc(Cl)c(n2)Nc2cccc1c2]

Step A: tert-Butyl (3-{[(3-nitrobenzoyl)amino]methyl}phenyl)carbamate

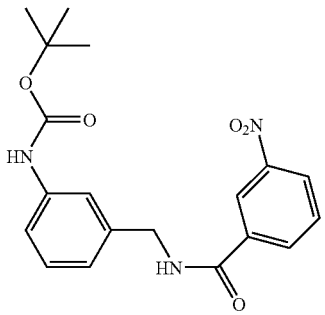 [SMILES: CC(C)(C)OC(=O)Nc1cccc(CNC(=O)c2cccc([N+](=O)[O-])c2)c1]

To a stirring solution of tert-butyl [3-(aminomethyl)phenyl]carbamate (2.0 g, 9.0 mmol) and triethylamine (1.3 mL, 9.4 mmol) in dry tetrahydrofuran (25 mL) at 0° C. slowly added a solution of 3-nitrobenzoyl chloride (1.75 g, 9.45 mmol) in tetrahydrofuran (7.3 mL). The resulting mixture was slowly warmed up to rt and stirred for one additional hour at rt. The reaction mixture was treated with Na$_2$CO$_3$ (aq), separated. The aqueous layer was extracted with EtOAc three times. The combined organic layers were dried, filtered and concentrated to give the desired product as an off-white powder (3.5 g, 100%). LCMS for C$_{19}$H$_{21}$N$_3$O$_5$ (M-tBu+H)$^+$: m/z=316.0. $^1$H NMR (400 MHz, CD$_3$OD): δ 8.71 (t, J=2.0 Hz, 1H), 8.38 (ddd, J=8.4, 1.6, 1.2 Hz, 1H), 8.23 (ddd, J=8.0, 1.6, 0.8 Hz, 1H), 7.70 (t, J=8.0 Hz, 1H), 7.44 (s, 1H), 7.28 (m, 1H), 7.20 (t, J=7.6, 1H), 7.00 (d J=7.6 Hz, 1H), 4.90 (s, 2H), 1.49 (s, 9H).

Step B: tert-Butyl (3-{[(3-aminobenzoyl)amino]methyl}phenyl)carbamate

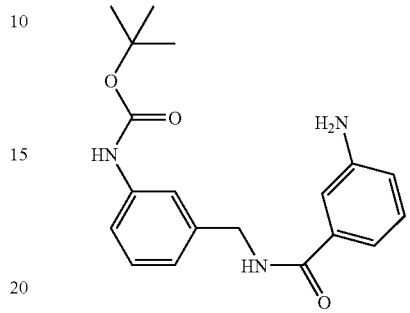

To a solution tert-butyl (3-[{(3-nitrobenzoyl)amino]methyl}phenyl)carbamate (1.50 g, 4.04 mmol) in water (2.91 mL), methanol (16 mL) and acetic acid (6.2 mL) was added iron (0.564 g, 10.1 mmol) powder in small quantities. When the addition was completed, the mixture was stirred in water bath for 4 h, and the reaction was complete. The mixture was filtered, and the cake was washed with MeOH/EtOAc. The brown filtrate was concentrated and diluted with H$_2$O, and the aqueous layer was extracted with EtOAc three times. The combined organic layers were dried, filtered and concentrated to give the desired product as a brown solid (1.8 g). LCMS for C$_{19}$H$_{23}$N$_3$O$_3$ (M+H)$^+$: m/z=342.1. $^1$H NMR (400 MHz, CD$_3$OD): δ 7.38 (t, J=2.0 Hz, 1H), 7.28 (ddd, J=8.0, 2.0, 1.2 Hz, 1H), 7.22 (t, J=8.0 Hz, 1H), 7.16 (s, 1H), 7.14 (t, J=8.0 Hz, 1H), 7.08 (m, 1H), 6.96 (ddd, J=8.0, 2.4, 1.2 Hz, 1H), 6.85 (ddd, J=8.0, 2.0, 1.2, 1H), 4.50 (s, 2H), 1.50 (s, 9H).

Step C. tert-Butyl {3-[({3-[(2,5-dichloropyrimidin-4-yl)amino]benzoyl}amino)methyl]phenyl}carbamate

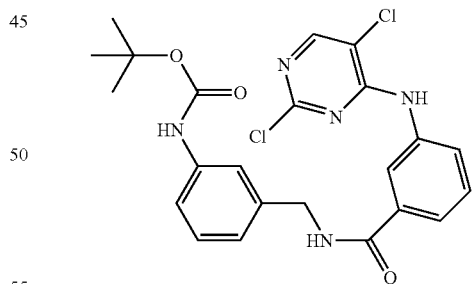

To a solution of tert-butyl (3-{[(3-aminobenzoyl)amino]methyl}phenyl)carbamate (0.60 g, 1.8 mmol) and 2,4,5-trichloropyrimidine (0.183 mL, 1.6 mmol) in DMF (4.3 mL) was added potassium carbonate (0.331 g, 2.4 mmol). The resulting mixture was stirred overnight at room temperature. The reaction was quenched with sat'd NH$_4$Cl and water. EtOAc was added and the layers separated. The aqueous layer was extracted with EtOAc twice. The combined organics were washed with water, dried, filtered and concentrated to give the crude, which was purified by silica gel column chromatography to give the desired product (138 mg, 18%).

LCMS for $C_{23}H_{23}Cl_2N_5O_3$ (M-tBu+H)$^+$: m/z=432.0, 434.0, 436.0. $^1$H NMR (400 MHz, CD$_3$OD): δ 8.23 (s, 1H), 8.04 (t, J=2.0 Hz, 1H), 7.96 (s, 1H), 7.83 (ddd, J=8.0, 2.0, 1.2 Hz, 1H), 7.67 (ddd, J=7.6, 2.4, 1.2 Hz, 1H), 7.48 (m, 2H), 7.21 (t, J=8.0 Hz, 1H), 7.00 (d, J=7.6 Hz, 1H), 4.54 (s, 2H), 1.49 (s, 9H).

Step D: 6-Chloro-2,4,8,15,23-pentaazatetracyclo[15.3.1.1(3,7).1(9,13)]tricosa-1(21),3(23),4,6,9(22),10,12,17,19-nonaen-14-one To a solution of tert-butyl {3-[({3-[(2,5-dichloropyrimidin-4-yl)amino]benzoyl}amino)methyl]phenyl}carbamate (40.0 mg, 0.0819 mmol) in 2-methoxyethanol (0.452 mL) was added 4.0 M of hydrogen chloride in 1,4-dioxane (100 μL). The resulting mixture was heated at 150° C. in the microwave for 15 min. The cloudy mixture was diluted with Na$_2$CO$_3$ (aq), filtered, washed with water. The crude cake was triturated with MeOH to give the desired product as an off-white powder (18 mg, 62%). LCMS for $C_{18}H_{14}ClN_5O$ (M+H)$^+$: m/z=352.0. $^1$H NMR (400 MHz, DMSO-d$_6$): δ 10.24 (s, 1H), 10.05 (t, J=2.0 Hz, 1H), 9.66 (s, 1H), 9.05 (ddd, J=8.0, 2.0, 1.2 Hz, 1H), 8.62 (t, J=2.0 Hz, 1H), 8.25 (t, J=8.0 Hz, 1H), 8.00 (m, 1H), 7.76 (ddd, J=7.6, 2.0, 1.2 Hz, 1H), 7.52 (m, 1H), 7.36 (t, J=7.6 Hz, 1H), 7.02 (m, 1H), 6.90 (m, 1H), 4.32 (s, 2H).

Example C5

6-Chloro-2,4,8,15,23-pentaazatetracyclo[15.3.1.1(3,7).1(9,13)]tricosa-1(21),3(23),4,6,9(22),10,12,17,19-nonaen-16-one hydrochloride

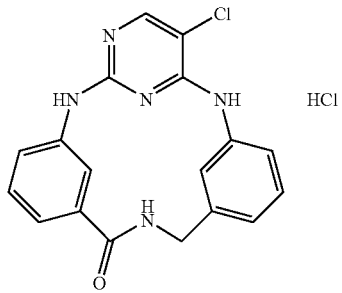 [SMILES: O=C1NCc2cccc(c2)Nc2nc(ncc2Cl)Nc2cccc1c2 ; Cl]

Step A: N-(3-Aminobenzyl)-3-nitrobenzamide hydrochloride

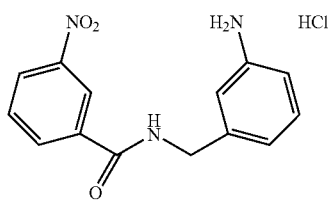 [SMILES: Nc1cccc(CNC(=O)c2cccc([N+](=O)[O-])c2)c1 ; Cl]

tert-butyl (3-{[(3-nitrobenzoyl)amino]methyl}phenyl)carbamate (1.00 g, 2.69 mmol) was mixed with 4 M of hydrogen chloride in 1,4-dioxane (10 mL) and stirred at rt for 2 h. After concentration, the desired product was isolated as a white powder (0.82 grams, 99% yield) and used in the next step without further purification. MF=$C_{14}H_{13}N_3O_3$; LCMS calculated for $C_{14}H_{13}N_3O_3$ (M+H)$^+$: m/z=272.0. $^1$H NMR (400 MHz, CD$_3$OD): δ 8.73 (t, J=2.0 Hz, 1H), 8.42 (ddd, J=8.4, 2.4, 1.2 Hz, 1H), 8.28 (ddd, J=8.0, 2.4, 1.2 Hz, 1H), 7.76 (t, J=8.4 Hz, 1H), 7.52 (m, 2H), 7.45 (s, 1H), 7.31 (ddd, J=8.4, 2.0, 1.2 Hz, 1H), 4.66 (s, 2H).

Step B: N-{3-[(2,5-Dichloropyrimidin-4-yl)amino]benzyl}-3-nitrobenzamide

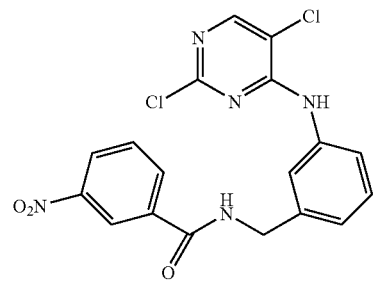

To a solution of N-(3-aminobenzyl)-3-nitrobenzamide hydrochloride (0.70 g, 2.3 mmol) and 2,4,5-trichloropyrimidine (0.237 mL, 2.07 mmol) in DMF (5.5 mL) was added potassium carbonate (1.0 g, 7.2 mmol). The resulting mixture was stirred overnight at room temperature. The reaction was quenched with sat'd NH$_4$Cl and water. EtOAc was added and the layers separated. The aqueous layer was extracted with EtOAc twice. The combined organics were washed with water, dried, filtered and concentrated to give 1.25 grams of crude material, which was triturated with MeOH/EtOAc to give the desired product as an off-white powder (665 mg, 77%). LCMS for $C_{18}H_{13}Cl_2N_5O_3$ (M+H)$^+$: m/z=418.0, 420.0, 422.0. $^1$H NMR (400 MHz, DMSO-d$_6$): δ 9.53 (s, 1H), 9.49 (t, J=2.0 Hz, 1H), 8.74 (t, J=2.0 Hz, 1H), 8.36 (m, 3H), 7.78 (t, J=8.0 Hz, 1H), 7.52 (s, 1H), 7.47 (d, J=8.0 Hz, 1H), 7.34 (t, J=7.6 Hz, 1H), 7.15 (d, J=8.0, 1H), 4.52 (d, J=6.0 Hz, 2H).

Step C: 3-Amino-N-{3-[(2,5-dichloropyrimidin-4-yl)amino]benzyl}benzamide

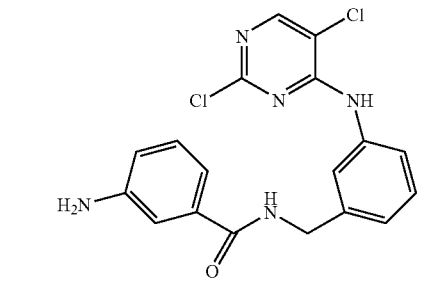 [SMILES: O=C(NCc1cccc(Nc2nc(Cl)ncc2Cl)c1)c1cccc([N+](=O)[O-])c1]

To a solution N-{3-[(2,5-dichloropyrimidin-4-yl)amino]benzyl}-3-nitrobenzamide (400.0 mg, 0.956 mmol) in water (0.7 mL), methanol (3.7 mL) and acetic acid (1.5 mL) was added iron (130 mg, 2.4 mmol) powder in small quantities. When the addition was completed, the very cloudy mixture was stirred at 0° C. for 1 h and then heat at 40° C. for 3 h. The mixture was filtered, and the cake was washed with MeOH/EtOAc. The filtrate was concentrated and the residue was diluted with H₂O, then the aqueous layer was extracted with EtOAc three times. The combined organic layers were dried, filtered and concentrated to give the desired product as an off-white powder (435 mg). LCMS for $C_{18}H_{15}Cl_2N_5O$ (M+H)⁺: m/z=388.0, 390.0, 392.0. ¹H NMR (400 MHz, CD₃OD): δ 8.20 (s, 1H), 7.59 (t, J=2.0 Hz, 1H), 7.52 (d, J=8.0 Hz, 1H), 7.36 (t, J=8.0 Hz, 1H), 7.24 (m, 2H), 7.20 (m, 2H), 6.93 (m, 1H), 4.60 (s, 2H).

Step D: 6-Chloro-2,4,8,15,23-pentaazatetracyclo [15.3.1.1(3,7).1(9,13)]tricosa-1(21),3(23),4,6,9(22), 10,12,17,19-nonaen-16-one hydrochloride To a solution of 3-amino-N-{3-[(2,5-dichloropyrimidin-4-yl)amino]benzyl}benzamide (80.0 mg, 0.206 mmol) in 2-methoxyethanol (1.1 mL) was added 4.0 M of hydrogen chloride in 1,4-dioxane (154 µL). The resulting mixture was heated at 150° C. in a microwave for 15 min. The cloudy mixture was filtered. The crude cake was recrystallized from MeOH to give the desired product as an off-white powder (25 mg, 34%). LCMS for $C_{18}H_{14}ClN_5O$ (M+H)⁺: m/z=352.0. ¹H NMR (400 MHz, DMSO-d₆): δ 10.06 (s, 1H), 9.50 (t, J=2.0 Hz, 1H), 9.05 (t, J=2.0 Hz, 1H), 8.24 (m, 1H), 7.86 (s, 1H), 7.75 (d, J=8.0 Hz, 1H), 7.50 (t, J=8.0 Hz, 1H), 7.42 (d, J=8.0 Hz, 1H), 7.28 (m, 2H), 7.10 (t, J=7.6 Hz, 1H), 6.96 (d, J=8.0 Hz, 1H), 4.42 (d, J=6.0 Hz, 2H).

Example C6

6-Chloro-15-thia-2,4,8,14,22-pentaazatetracyclo [14.3.1.1(3,7).1(9,13)]docosa-1(20),3(22),4,6,9(21), 10,12,16,18-nonaene 15,15-dioxide trifluoroacetate

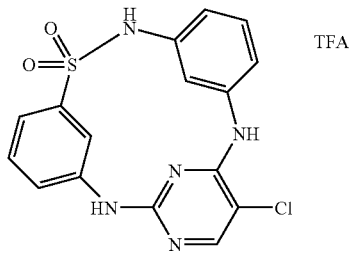 [SMILES: O=S1(=O)Nc2cccc(c2)Nc2nc(ncc2Cl)Nc2cccc1c2]

Step A:
N-(3-Aminophenyl)-3-nitrobenzenesulfonamide

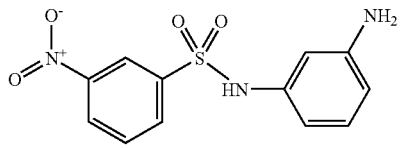 [SMILES: Nc1cccc(NS(=O)(=O)c2cccc([N+](=O)[O-])c2)c1]

Into a 1-neck round-bottom flask were added m-phenylenediamine (1.6 g, 14 mmol) and tetrahydrofuran (30 mL) and triethylamine (2.0 mL, 14 mmol). The mixture was cooled in ice bath and then m-nitrobenzenesulfonyl chloride (2.1 g, 9.6 mmol) was slowly added. The resultant mixture was warmed up to rt. after 1 h and EtOAc and water were then added. Aqueous layer was extracted again with EtOAc. The organics layers were combined, dried over Na₂SO₄ and the solvent was removed under vacuum. The crude was purified by silica gel column chromatography to give the desired product (2.5 g, 89%). LCMS for $C_{12}H_{11}N_3O_4S$ (M+H)⁺: m/z=294.0. ¹H NMR (300 MHz, CD₃OD): δ 8.56 (t, J=2.0 Hz, 1H), 8.40 (ddd, J=8.2, 2.3, 1.2 Hz, 1H), 8.09 (ddd, J=7.8, 1.7, 1.0 HZ, 1H), 7.73 (t, J=8.1 Hz, 1H), 6.91 (t, J=8.1 Hz, 1H), 6.51 (t, J=2.2 Hz, 1H), 6.42 (ddd, J=8.1, 2.2, 1.0 Hz, 1H), 6.36 (ddd, J=7.9, 2.1, 1.0 Hz, 1H).

Step B: N-{3-[(2,5-Dichloropyrimidin-4-yl)amino] phenyl}-3-nitrobenzenesulfonamide

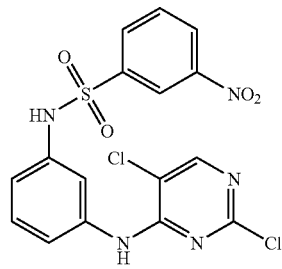 [SMILES: O=[N+]([O-])c1cccc(S(=O)(=O)Nc2cccc(Nc3nc(Cl)ncc3Cl)c2)c1]

To a solution of N-(3-aminophenyl)-3-nitrobenzenesulfonamide (1.00 g, 3.41 mmol) and 2,4,5-trichloropyrimidine (0.57 g, 3.1 mmol) in DMF (10 mL) was added potassium carbonate (0.52 g, 3.7 mmol). The resulting mixture was stirred overnight at room temperature. The reaction was quenched with sat'd NH₄Cl and water. EtOAc was added and the layers separated. The aqueous was extracted with EtOAc. The combined organics were washed with water and brine then dried (MgSO₄), filtered, and concentrated. The crude was purified by combi-flash column chromatography to give the desired product (1.2 g, 88%). LCMS for $C_{16}H_{11}Cl_2N_5O_4S$ (M+H)⁺: m/z=439.9, 441.9. ¹H NMR (400 MHz, DMSO-d₆): δ 10.65 (s, 1H), 9.51 (s, 1H), 8.54 (t, J=2.1 Hz, 1H), 8.43 (ddd, J=8.2, 2.0, 1.0 Hz, 1H), 8.37 (s, 1H), 8.18 (ddd, J=8.0, 2.0, 1.0 Hz, 1H), 7.84 (t, J=8.0 Hz, 1H), 7.50 (t, J=2.0 Hz, 1H), 7.29 (ddd, J=8.2, 2.0, 1.2 Hz, 1H), 7.24 (m, 1H), 6.88 (ddd, J=8.0, 2.0, 1.2 Hz, 1H).

Step C: 3-Amino-N-{3-[(2,5-dichloropyrimidin-4-yl) amino]phenyl}benzenesulfonamide

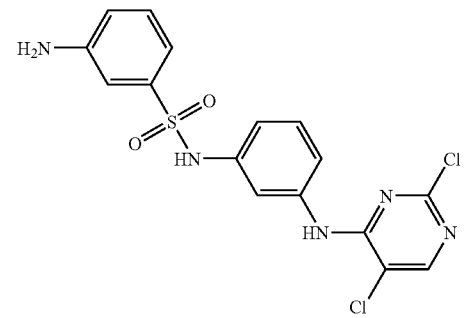 [SMILES: Nc1cccc(S(=O)(=O)Nc2cccc(Nc3nc(Cl)ncc3Cl)c2)c1]

To a solution N-{3-[(2,5-dichloropyrimidin-4-yl)amino] phenyl}-3-nitrobenzenesulfonamide (0.5 g, 1.0 mmol) in water (0.9 mL), methanol (4.4 mL) and acetic acid (1.7 mL) was added iron (250 mg, 4.5 mmol) powder in one portion.

The mixture was stirred at 0° C. for 1 h and then mixed with celite and filtered. The crude cake was washed with EtOAc. The brown filtrate was concentrated and mixed with EtOAc and NaHCO$_3$/water. The aqueous phase was extracted once with EtOAc. The organic phases were combined and dried over Na$_2$SO$_4$. The volatiles were removed under vacuum to give the desired product (0.45 g, 100%). LCMS for C$_{16}$H$_{13}$Cl$_2$N$_5$O$_2$S (M+H)$^+$: m/z=410.0, 411.9. $^1$H NMR (400 MHz, DMSO-d$_6$): δ 9.57 (s, 1H), 9.42 (s, 1H), 8.33 (s, 1H), 8.16 (s, 1H), 7.91 (s, 1H), 7.29 (dd, J=7.9, 7.6 Hz, 1H), 7.15 (d, J=7.9 Hz, 1H), 7.10-7.05 (m, 2H), 6.90 (dd, J=8.2, 0.9 Hz, 1H), 6.84-6.81 (m, 1H), 4.11 (s, 2H).

Step D: 6-Chloro-15-thia-2,4,8,14,22-pentaazatetracyclo[14.3.1.1(3,7).1(9,13)]docosa-1(20),3(22),4,6,9(21),10,12,16,18-nonaene 15,15-dioxide trifluoroacetate To a solution of 3-amino-N-{3-[(2,5-dichloropyrimidin-4-yl)amino]phenyl}benzenesulfonamide (80 mg, 0.2 mmol) and in 2-methoxyethanol (1 mL) was added 4.0 M of hydrogen chloride in 1,4-dioxane (49 μL). The resulting mixture was heated at 150° C. in a microwave for 15 min. The mixture was condensed and diluted with MeOH to 5 mL and purified using preparative LCMS (pH 2). Pure fraction was freeze dried to give the desired product (25 mg, 34%). LCMS for C$_{16}$H$_{12}$ClN$_5$O$_2$S (M+H)$^+$: m/z=374.0. $^1$H NMR (400 MHz, DMSO-d$_6$): δ 10.22 (s, 1H), 9.69 (s, 1H), 9.11 (s, 1H), 8.27 (t, J=2.0 Hz, 1H), 8.14 (s, 1H), 7.79 (t, J=2.0 Hz, 1H), 7.45 (m, 1H), 7.22 (ddd, J=7.8, 2.0, 1.2 Hz, 1H), 7.15 (t, J=8.0 Hz, 1H), 7.06 (s, 1H), 6.94 (s, 1H), 6.70 (ddd, J=8.0, 2.2, 1.0 Hz, 1H).

Example C7

6-Chloro-14-thia-2,4,8,15,22-pentaazatetracyclo[14.3.1.1(3,7).1(9,13)]docosa-1(20),3(22),4,6,9(21),10,12,16,18-nonaene 14,14-dioxide trifluoroacetate

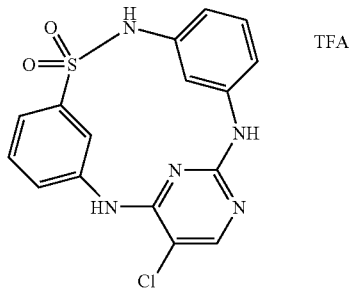 [SMILES: O=S1(=O)Nc2cccc(c2)Nc2ncc(Cl)c(n2)Nc2cccc1c2]

Step A: tert-Butyl (3-{[(3-nitrophenyl)sulfonyl]amino}phenyl)carbamate

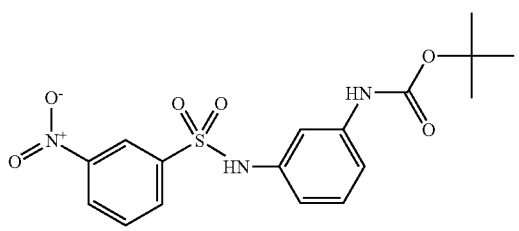 [SMILES: CC(C)(C)OC(=O)Nc1cccc(NS(=O)(=O)c2cccc([N+](=O)[O-])c2)c1]

Into a 1-neck round-bottom flask were added tert-butyl (3-aminophenyl)carbamate (2.0 g, 9.6 mmol) and tetrahydrofuran (30 mL) and triethylamine (2.0 mL, 14 mmol). The mixture was stirred at 0° C. and m-nitrobenzenesulfonyl chloride (2.1 g, 9.6 mmol) was slowly added. The reaction was warmed to rt and stirred for 1 h. The solvent was removed under vacuum and EtOAc and water were added. The aqueous phase was extracted again with EtOAc. The organics were combined, dried over Na$_2$SO$_4$ and the solvents were removed under vacuum. The crude was purified by combi-flash column chromatography to give the desired product (1.5 g, 39%). LCMS for C$_{17}$H$_{19}$N$_3$O$_6$S (M-tBu+H)$^+$: m/z=338.0. $^1$H NMR (400 MHz, DMSO-d$_6$): δ 10.47 (s, 1H), 9.35 (s, 1H), 8.51 (t, J=2.0 Hz, 1H), 8.43 (ddd, J=8.2, 2.2, 1.0 Hz, 1H), 8.12 (ddd, J=7.8, 1.8, 1.0 Hz, 1H), 7.84 (t, J=8.0 Hz, 1H), 7.35 (br, 1H), 7.07 (m, 1H), 7.06 (s, 1H), 6.68 (dt, J=7.0, 2.0 Hz, 1H), 1.42 (s, 9H).

Step B: tert-Butyl (3-{[(3-aminophenyl)sulfonyl]amino}phenyl)carbamate

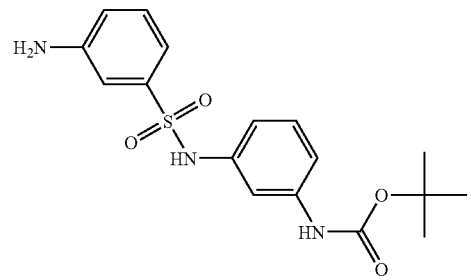 [SMILES: CC(C)(C)OC(=O)Nc1cccc(NS(=O)(=O)c2cccc(N)c2)c1]

To a solution tert-butyl (3-{[(3-nitrophenyl)sulfonyl]amino}phenyl)carbamate (0.51 g, 0.0013 mol) in water (1 mL), methanol (5 mL) and acetic acid (2 mL) was added iron (290 mg, 5.2 mmol) powder in one batch. The mixture was stirred at 0° C. for 0.5 h. The reaction mixture was mixed with celite, filtered, and the cake was washed with EtOAc. The brown filtrate was concentrated, followed by the addition of EtOAc and NaHCO$_3$/water. The aqueous phase was extracted with EtOAc. The organics were combined, dried over Na$_2$SO$_4$ and concentrated to give the desired product as a yellow powder (0.46 g, 98%). LCMS for C$_{17}$H$_{21}$N$_3$O$_4$S (M-tBu+H)$^+$: m/z=308.0. $^1$H NMR (400 MHz, DMSO-d$_6$): δ 10.02 (s, 1H), 9.31 (s, 1H), 7.33 (br, 1H), 7.10 (t, J=8.0 Hz, 1H), 7.02 (m, 1H), 6.93 (t, J=2.0 Hz, 1H), 6.85 (ddd, J=7.6, 1.8, 1.0 Hz, 1H), 6.67 (m, 1H), 5.53 (s, 1H), 1.43 (s, 9H).

Step C: tert-Butyl {3-[({3-[(2,5-dichloropyrimidin-4-yl)amino]phenyl}sulfonyl)amino]phenyl}carbamate

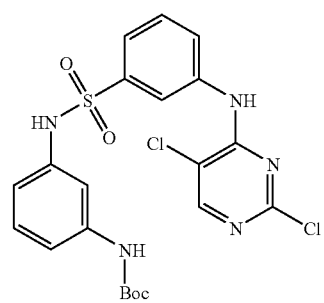 [SMILES: CC(C)(C)OC(=O)Nc1cccc(NS(=O)(=O)c2cccc(Nc3nc(Cl)ncc3Cl)c2)c1]

To a solution of tert-butyl (3-{[(3-aminophenyl)sulfonyl]amino}phenyl)carbamate (0.30 g, 0.82 mmol) and 2,4,5-trichloropyrimidine (0.14 g, 0.75 mmol) in DMF (2 mL) was added potassium carbonate (0.12 g, 0.90 mmol). The resulting mixture was stirred overnight at room temperature. The reaction was quenched with sat'd NH$_4$Cl and water. EtOAc was added and the layers separated. The aqueous phase was extracted with EtOAc. The combined organics were washed with water and brine then dried (MgSO$_4$), filtered, and concentrated. The resulted crude mixture was purified by column chromatography to give the desired product (70 mg, 18%). LCMS for C$_{21}$H$_{21}$Cl$_2$N$_5$O$_4$S (M-tBu+H)$^+$: m/z=454.0, 455.9. $^1$H NMR (500 MHz, DMSO-d$_6$): δ 9.28 (s, 1H), 8.41 (s, 1H), 8.12 (br, 1H), 7.85 (dt, J=7.4, 1.8 Hz, 1H), 7.55 (br, 1H), 7.57 (dt, J=7.9, 1.8 Hz, 1H), 7.39 (s, 1H), 7.04 (m, 1H), 7.02 (dt, J=8.2, 2.0 Hz, 1H), 6.71 (dt, J=7.5, 1.8 Hz, 1H), 1.43 (s, 9H).

Step D: 6-Chloro-14-thia-2,4,8,15,22-pentaazatetracyclo[14.3.1.1(3,7).1(9,13)]docosa-1(20),3(22),4,6,9(21),10,12,16,18-nonaene 14,14-dioxide trifluoroacetate To a solution of tert-butyl {3-[({3-[(2,5-dichloropyrimidin-4-yl)amino]phenyl}sulfonyl)amino]phenyl}carbamate (20 mg, 0.04 mmol) and in 2-methoxyethanol (1 mL) was added 4.0 M of hydrogen chloride in 1,4-dioxane (60 µL). The resulting mixture was heated at 150° C. in a microwave for 15 min. The mixture was condensed and diluted with MeOH to 5 mL and purified using preparative LCMS (pH 2) to give the desired product (10 mg, 68%). LCMS for C$_{16}$H$_{12}$ClN$_5$O$_2$S (M+H)$^+$: m/z=374.0. $^1$H NMR (400 MHz, DMSO-d$_6$): δ 10.24 (s, 1H), 9.61 (s, 1H), 9.53 (s, 1H), 8.29 (br, 1H), 8.17 (s, 1H), 7.94 (t, J=2.2 Hz, 1H), 7.55 (m, 1H), 7.44 (m, 1H), 7.06 (m, 1H), 6.94 (s, 1H), 6.71 (ddd, J=7.8, 2.0, 0.9 Hz, 1H), 6.52 (ddd, J=8.0, 2.2, 0.9 Hz, 1H).

Example C8

6-Chloro-15-thia-2,4,8,16,23-pentaazatetracyclo[15.3.1.1(3,7).1(9,13)]tricosa-1(21),3(23),4,6,9(22),10,12,17,19-nonaene 15,15-dioxide trifluoroacetate

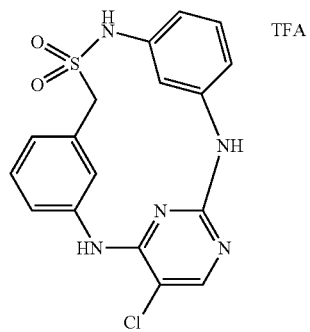 [SMILES: O=S1(=O)Cc2cccc(c2)Nc2nc(ncc2Cl)Nc2cccc(c2)N1]

Step A: tert-Butyl (3-{[(3-nitrobenzyl)sulfonyl]amino}phenyl)carbamate

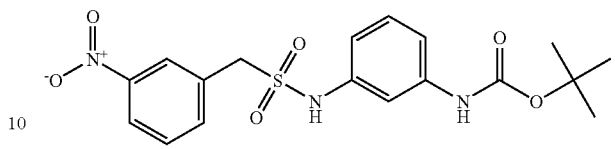

Into a 1-neck round-bottom flask was added tert-butyl (3-aminophenyl)carbamate (1.0 g, 4.8 mmol) and tetrahydrofuran (20 mL) and triethylamine (1.0 mL, 7.2 mmol). The mixture was cooled in an ice bath and (3-nitrophenyl)methanesulfonyl chloride (1.1 g, 4.8 mmol) was slowly added. The resultant mixture was warmed to rt. The solvent was removed under vacuum and EtOAc and water added. The aqueous phase was extracted again with EtOAc. The organic layers were combined, dried over Na$_2$SO$_4$ and the solvent removed under vacuum to give the desired product (1.94 g, 99%). LCMS for C$_{18}$H$_{21}$N$_3$O$_6$S (M-Boc+H)$^+$: m/z=308.0. $^1$H NMR (400 MHz, DMSO-d$_6$): δ 9.84 (s, 1H), 9.37 (s, 1H), 8.98 (s, 1H), 8.19 (ddd, J=8.1, 2.3, 1.1 Hz, 1H), 8.11 (t, J=1.9 Hz, 1H), 7.71 (dt, J=7.7, 1.3 Hz, 1H), 7.63 (t, J=7.9 Hz, 1H), 7.44 (t, J=2.0 Hz, 1H), 7.15 (t, J=8.0 Hz, 1H), 7.10 (m, 1H), 6.81 (t, J=8.0 Hz, 1H), 6.78 (br, 1H), 6.75 (ddd, J=7.4, 2.2, 1.6 Hz, 1H), 1.46 (s, 9H).

Step B: tert-Butyl (3-{[(3-aminobenzyl)sulfonyl]amino}phenyl)carbamate

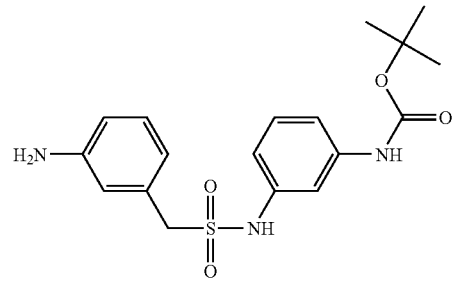 [SMILES: CC(C)(C)OC(=O)Nc1cccc(NS(=O)(=O)Cc2cccc(N)c2)c1]

To a solution tert-butyl (3-{[(3-nitrobenzyl)sulfonyl]amino}phenyl)carbamate (1.1 g, 2.7 mmol) in water (2 mL), methanol (100 mL) and acetic acid (4.1 mL) was added iron (0.60 g, 11.0 mmol) powder in one batch. The mixture was stirred at 0° C. for 2 h. The mixture was mixed with celite, filtered, and the cake was washed with EtOAc. The brown filtrate was concentrated and EtOAc and NaHCO$_3$/water were added. The water layer was extracted with EtOAc once more. The organic layers were combined, dried over Na$_2$SO$_4$ and concentrated to give the desired product as a yellow powder (0.9 g, 90%). LCMS for C$_{18}$H$_{23}$N$_3$O$_4$S (M-tBu+H)$^+$: m/z=322.0. $^1$H NMR (400 MHz, DMSO-d$_6$): δ 9.72 (s, 1H), 9.39 (s, 1H), 7.44 (br, 1H), 7.16 (t, J=8.2 Hz, 1H), 7.12 (m, 1H), 6.94 (t, J=7.7 Hz, 1H), 7.79 (dt, J=7.2, 2.1 Hz, 1H), 6.50 (m, 1H), 6.49 (s, 1H), 6.35 (m, 1H).

Step C: tert-Butyl {3-[({3-[(2,5-dichloropyrimidin-4-yl)amino]benzyl}sulfonyl)amino]phenyl}carbamate

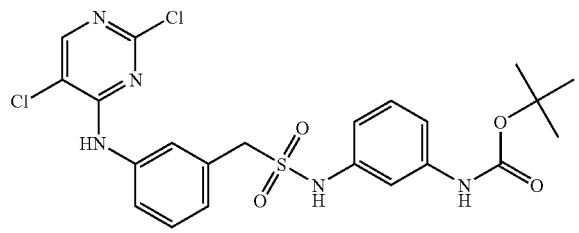 [SMILES: CC(C)(C)OC(=O)Nc1cccc(NS(=O)(=O)Cc2cccc(Nc3nc(Cl)ncc3Cl)c2)c1]

To a solution of tert-butyl (3-{[(3-aminobenzyl)sulfonyl]amino}phenyl)carbamate (0.64 g, 1.7 mmol) and 2,4,5-trichloropyrimidine (0.28 g, 1.5 mmol) in DMF (5 mL) was added potassium carbonate (0.26 g, 1.8 mmol). The resulting mixture was stirred overnight at room temperature. The reaction was quenched with sat'd NH₄Cl and water. EtOAc was then added and the layers separated. The aqueous phase was extracted with EtOAc. The combined organics were washed with water and brine then dried (MgSO₄), filtered, and concentrated to give the desired product (0.75 g, 92%). LCMS for $C_{22}H_{23}Cl_2N_5O_4S$ (M-tBu+H)⁺: m/z=467.9, 469.9.

Step D: 6-Chloro-15-thia-2,4,8,16,23-pentaazatetracyclo[15.3.1.1(3,7).1(9,13)]tricosa-1(21),3(23),4,6,9 (22),10,12,17,19-nonaene 15,15-dioxide trifluoroacetate To a solution of tert-butyl {3-[({3-[(2,5-dichloropyrimidin-4-yl)amino]benzyl}sulfonyl)amino]phenyl}carbamate (40 mg, 0.08 mmol) and in 2-methoxyethanol (1 mL) was added 4.0 M of hydrogen chloride in 1,4-dioxane (60 μL). The resulting mixture was heated at 150° C. in the microwave for 15 min. The mixture was condensed and diluted with MeOH to 5 mL and purified using preparative LCMS (pH 2) to give the desired product (25 mg, 84%). LCMS for $C_{17}H_{14}ClN_5O_2S$ (M+H)⁺: m/z=388.0, 390.0. ¹H NMR (400 MHz, DMSO-d₆): δ 9.63 (s, 1H), 9.34 (s, 1H), 8.97 (s, 1H), 8.23 (t, J=1.8 Hz, 1H), 8.19 (s, 1H), 8.00 (t, J=2.0 Hz, 1H), 7.40 (dt, J=8.4, 1.8 Hz, 1H), 7.35 (t, J=8.0 Hz, 1H), 7.23 (t, J=8.0 Hz, 1H), 7.20 (dt, J=7.4, 1.5 Hz, 1H), 6.99 (ddd, J=8.0, 2.0, 1.0 Hz, 1H), 6.95 (ddd, J=8.0, 2.1, 1.0 Hz, 1H), 4.17 (s, 2H).

Example C9

6-Chloro-15-thia-2,4,8,14,23-pentaazatetracyclo [15.3.1.1(3,7).1(9,13)]tricosa-1(21),3(23),4,6,9(22), 10,12,17,19-nonaene 15,15-dioxide trifluoroacetate

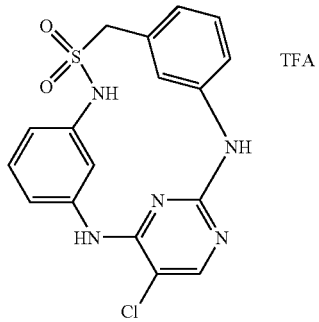 [SMILES: O=S1(=O)Cc2cccc(c2)Nc2ncc(Cl)c(n2)Nc2cccc(c2)N1]

Step A: N-(3-Aminophenyl)-1-(3-nitrophenyl)methanesulfonamide hydrochloride

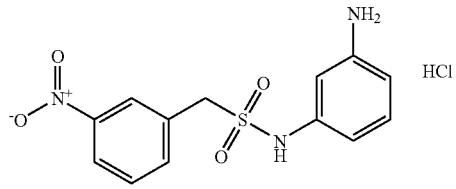

tert-Butyl (3-{[(3-nitrobenzyl)sulfonyl]amino}phenyl) carbamate (0.50 g, 1.2 mmol) and 4.0 M of hydrogen chloride were dissolved in 1,4-dioxane (3 mL) and stirred at rt for 2 h. The solvent was removed under vacuum and the white powder product (0.37 g, 98%) as a HCl salt was used in the next step without further purification. LCMS for $C_{13}H_{13}N_3O_4S$ (M+H)⁺: m/z=308.0.

Step B: N-{3-[(2,5-Dichloropyrimidin-4-yl)amino] phenyl}-1-(3-nitrophenyl)methanesulfonamide

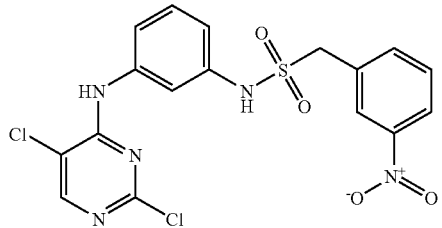

To a solution of N-(3-aminophenyl)-1-(3-nitrophenyl) methanesulfonamide-hydrogen chloride (0.10 g, 0.29 mmol) and 2,4,5-trichloropyrimidine (0.065 g, 0.35 mmol) in DMF (1 mL) was added potassium carbonate (0.20 g, 1.4 mmol). The resulting mixture was stirred overnight at room temperature. Additional triethylamine (0.099 mL, 0.71 mmol) was added and stirred again overnight. The reaction was then quenched with sat'd NH₄Cl and water. EtOAc was added and the layers separated. The aqueous phase was extracted with EtOAc. The combined organics were washed with water and brine then dried (MgSO₄), filtered, and concentrated. The crude was purified by column chromatography to give the desired product (0.080 g, 60%). LCMS for $C_{17}H_{13}Cl_2N_5O_4S$ (M+H)⁺: m/z=453.9, 455.9.

Step C: 1-(3-Aminophenyl)-N-{3-[(2,5-dichloropyrimidin-4-yl)amino]phenyl}methanesulfonamide

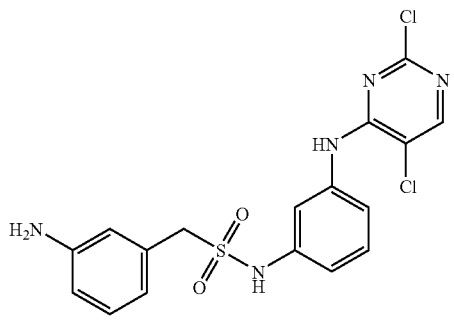 [SMILES: Nc1cccc(CS(=O)(=O)Nc2cccc(Nc3nc(Cl)ncc3Cl)c2)c1]

To a solution of N-{3-[(2,5-dichloropyrimidin-4-yl)amino]phenyl}-1-(3-nitrophenyl)methanesulfonamide (0.060 g, 0.13 mmol) in water (0.1 mL), methanol (0.5 mL) and acetic acid (0.20 mL) was added iron (0.030 g, 0.53 mmol) powder in one batch. The mixture was stirred at 0° C. for 0.5 h. The reaction was mixed with celite, filtered, and the cake was washed with EtOAc. The brown filtrate was concentrated and EtOAc and NaHCO$_3$/water added. Water phase was extracted with EtOAc twice. The organics were combined, dried over Na$_2$SO$_4$ and concentrated to give the desired product as a yellow powder (0.050 g, 89%. LCMS for C$_{17}$H$_{15}$Cl$_2$N$_5$O$_2$S (M+H)$^+$: m/z=423.9, 426.0.

Step D: 6-Chloro-15-thia-2,4,8,14,23-pentaazatetracyclo[15.3.1.1(3,7).1(9,13)]tricosa-1(21),3(23),4,6,9(22),10,12,17,19-nonaene 15,15-dioxide trifluoroacetate To a solution of 1-(3-aminophenyl)-N-{3-[(2,5-dichloropyrimidin-4-yl)amino]phenyl}methanesulfonamide (20 mg, 0.05 mmol) and in 2-methoxyethanol (1 mL) was added 4.0 M of hydrogen chloride in 1,4-dioxane (24 μL). The resulting mixture was heated at 150° C. in a microwave for 15 min. The mixture was concentrated, then diluted with MeOH to 5 mL and purified using preparative LCMS (pH 2) to give the desired product (10 mg, 55%). LCMS for C$_{17}$H$_{14}$ClN$_5$O$_2$S (M+H)$^+$: m/z=388.0, 390.0. $^1$H NMR (400 MHz, DMSO-d$_6$): δ 9.61 (s, 1H), 9.53 (s, 1H), 9.21 (s, 1H), 8.21 (t, J=1.9 Hz, 1H), 8.18 (s, 1H), 7.91 (t, J=2.0 Hz, 1H), 7.33 (t, J=8.0 Hz, 1H), 7.25 (t, J=7.8 Hz, 1H), 7.20 (ddd, J=8.0, 2.1, 1.0 Hz, 1H), 7.13 (m, 2H), 6.99 (dt, J=7.8, 1.2 Hz, 1H), 4.13 (s, 2H).

Example C10

6-Chloro-2,4,8,14,23-pentaazatetracyclo[15.3.1.1(3,7).1(9,13)]tricosa-1(21),3(23),4,6,9(22),10,12,17,19-nonaen-15-one trifluoroacetate

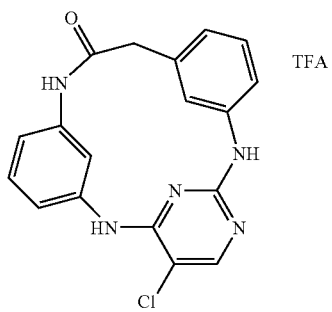 [SMILES: O=C1Cc2cccc(c2)Nc2ncc(Cl)c(n2)Nc2cccc(c2)N1]

Step A: tert-Butyl (3-{[(3-nitrophenyl)acetyl]amino}phenyl)carbamate

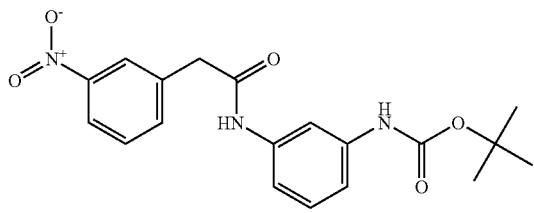 [SMILES: CC(C)(C)OC(=O)Nc1cccc(NC(=O)Cc2cccc([N+](=O)[O-])c2)c1]

tert-Butyl (3-aminophenyl)carbamate (1.0 g, 4.8 mmol) was dissolved in methylene chloride (4 mL) and then thionyl chloride (2.0 mL, 27 mmol) was added. The mixture was heated at 80° C. for 1 h. The solvent was removed under vacuum. Tetrahydrofuran (20 mL), triethylamine (2.3 mL, 17 mmol) and (3-nitrophenyl)acetic acid (0.87 g, 4.8 mmol) were then added and the mixture was stirred at rt for 1 h. The solvent was removed under vacuum and then EtOAc and water were added. The aqueous phase was extracted again with EtOAc. The organics were combined, dried over Na$_2$SO$_4$ and concentrated to give the desired product as a white powder (1.70 g, 95%). LCMS for C$_{19}$H$_{21}$N$_3$O$_5$ (M-tBu+H)$^+$: m/z=316.0.

Step B: N-(3-Aminophenyl)-2-(3-nitrophenyl)acetamide hydrochloride

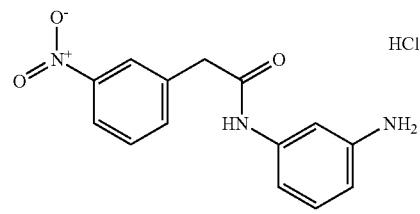 [SMILES: Nc1cccc(NC(=O)Cc2cccc([N+](=O)[O-])c2)c1 ; Cl]

Into the reaction was added tert-butyl (3-{[(3-nitrophenyl)acetyl]amino}phenyl)carbamate (0.46 g, 1.2 mmol) and 4.0 M of hydrogen chloride in 1,4-dioxane (3 mL). The mixture was stirred at rt for 2 h. The solvent was removed under vacuum to give the desired product (0.34 g, 100%) as a white powder. LCMS for C$_{14}$H$_{13}$N$_3$O$_3$ (M+H)$^+$: m/z=272.0.

Step C: N-{3-[(2,5-Dichloropyrimidin-4-yl)amino]phenyl}-2-(3-nitrophenyl)acetamide

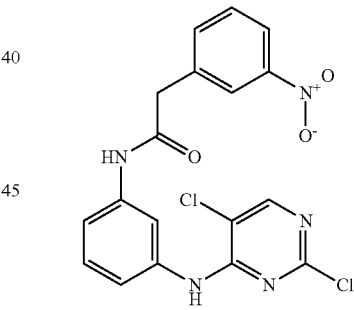

To a solution of N-(3-aminophenyl)-2-(3-nitrophenyl)acetamide-hydrogen chloride (0.11 g, 0.35 mmol) and 2,4,5-trichloropyrimidine (0.065 g, 0.35 mmol) in DMF (1 mL) was added potassium carbonate (0.20 g, 1.4 mmol). The resulting mixture was stirred overnight at room temperature. Additional triethylamine (0.099 mL, 0.71 mmol) was then added an stirred overnight again. The reaction was quenched with sat'd NH$_4$Cl and water. EtOAc was added and the layers separated. The aqueous was extracted with EtOAc. The combined organics were washed with water and brine then dried (MgSO$_4$), filtered, and concentrated. The resulted mixture was purified by column chromatography to give the desired product (0.080 g, 53%). LCMS for C$_{18}$H$_{13}$Cl$_2$N$_5$O$_3$ (M+H)$^+$: m/z=418.0, 419.9. $^1$H NMR (400 MHz, DMSO-d$_6$): δ 10.33 (s, 1H), 9.53 (s, 1H), 8.35 (s, 1H), 8.23 (t, J=2.0 Hz, 1H), 8.12 (ddd, J=8.2, 2.4, 1.0 Hz, 1H), 7.82 (t, J=2.0 Hz, 1H), 7.78 (dt, J=7.8, 1.4 Hz, 1H), 7.62 (t, J=7.9 Hz, 1H), 7.36 (dt, J=8.0, 1.7 Hz, 1H), 7.30 (t, J=7.8 Hz, 1H), 7.25 (dt, J=8.0, 1.7 Hz, 1H).

Step D: 2-(3-Aminophenyl)-N-{3-[(2,5-dichloropyrimidin-4-yl)amino]phenyl}acetamide

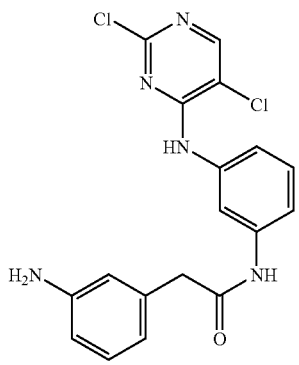 [SMILES: Nc1cccc(CC(=O)Nc2cccc(Nc3nc(Cl)ncc3Cl)c2)c1]

To a solution N-{3-[(2,5-dichloropyrimidin-4-yl)amino]phenyl}-2-(3-nitrophenyl)acetamide (0.055 g, 0.13 mmol) in water (0.1 mL), methanol (0.5 mL) and acetic acid (0.20 mL) was added iron (0.030 g, 0.53 mmol) powder in one batch. The mixture was stirred at 0° C. for 0.5 h. The reaction was mixed with celite, filtered, and the cake was washed with EtOAc. The brown filtrate was concentrated and EtOAc and NaHCO$_3$/water added. The aqueous phase was extracted with EtOAc. The organics were combined, died over Na$_2$SO$_4$ and concentrated to give the desired product as a yellow powder (30 mg, 58%). LCMS for C$_{18}$H$_{15}$Cl$_2$N$_5$O (M+H)$^+$: m/z=388.0, 390.0.

Step E: 6-Chloro-2,4,8,14,23-pentaazatetracyclo[15.3.1.1(3,7).1(9,13)]tricosa-1(21),3(23),4,6,9(22),10,12,17,19-nonaen-15-one trifluoroacetate To a solution of 2-(3-aminophenyl)-N-{3-[(2,5-dichloropyrimidin-4-yl)amino]phenyl}acetamide (20 mg, 0.05 mmol) and in 2-methoxyethanol (1 mL) was added 4.0 M of hydrogen chloride in 1,4-dioxane (24 μL). The resulting mixture was heated at 150° C. in the microwave for 15 min. The mixture was concentrated, diluted with MeOH to 5 mL and purified using preparative LCMS (pH 2) to give the desired product (4.0 mg, 22%). LCMS for C$_{18}$H$_{14}$ClN$_5$O (M+H)$^+$: m/z=351.9.

Example C11

6-Chloro-2,4,8,16,23-pentaazatetracyclo[15.3.1.1(3,7).1(9,13)]tricosa-1(21),3(23),4,6,9(22),10,12,17,19-nonaen-15-one trifluoroacetate

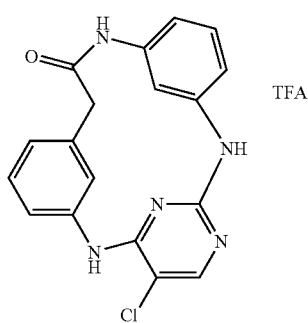 [SMILES: O=C1Cc2cccc(c2)Nc2nc(ncc2Cl)Nc2cccc(c2)N1]

Step A: tert-Butyl (3-{[(3-aminophenyl)acetyl]amino}phenyl)carbamate

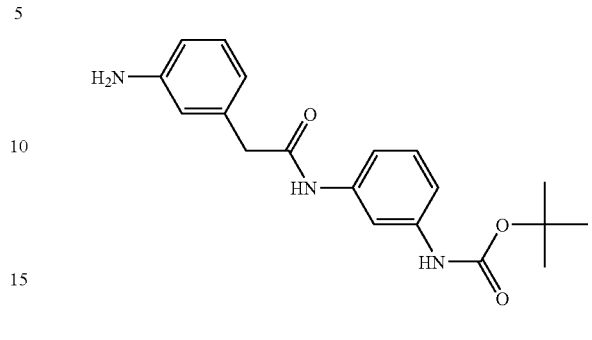

To a solution of tert-butyl (3-{[(3-nitrophenyl)acetyl]amino}phenyl)carbamate (0.35 g, 0.94 mmol) in methanol (100 mL) was added 10% palladium on carbon (1:10, Palladium:carbon black, 0.15 g, 0.13 mmol). The reaction was shaken under 60 psi hydrogen gas overnight. The crude mixture was filtered through celite and concentrated under vacuum to give the desired product (0.30 g, 94%). LCMS for C$_{19}$H$_{23}$N$_3$O$_3$ (M-tBu+H)$^+$: m/z=286.0.

Step B: tert-Butyl {3-[({3-[(2,5-dichloropyrimidin-4-yl)amino]phenyl}acetyl)amino]phenyl}carbamate

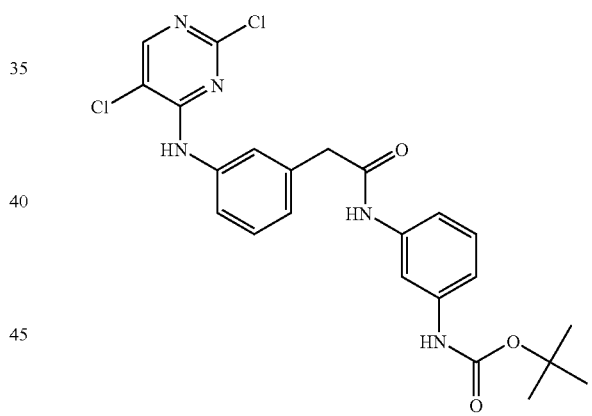

To a solution of tert-butyl (3-{[(3-aminophenyl)acetyl]amino}phenyl)carbamate (0.31 g, 0.91 mmol) and 2,4,5-trichloropyrimidine (0.15 g, 0.82 mmol) in DMF (3 mL) was added potassium carbonate (0.14 g, 0.99 mmol). The resulting mixture was stirred overnight at rt. The reaction was quenched with sat'd NH$_4$Cl and water. EtOAc was added and the layers separated. The aqueous was extracted with EtOAc and the combined organics were washed with water and brine then dried (MgSO$_4$), filtered, and concentrated. The crude mixture was purified by column chromatography to give the desired product (0.25 g, 62%). LCMS for C$_{23}$H$_{23}$Cl$_2$N$_5$O$_3$ (M-tBu+H)$^+$: m/z=432.0, 434.0. $^1$H NMR (400 MHz, DMSO-d$_6$): δ 10.12 (s, 1H), 9.54 (s, 1H), 9.32 (s, 1H), 8.35 (s, 1H), 7.93 (s, 1H), 7.78 (t, J=2.1 Hz, 1H), 7.47 (s, 1H), 7.46 (m, 1H), 7.33 (dd, J=8.7, 7.5 Hz, 1H), 7.31 (m, 1H), 7.15 (m, 1H), 7.11 (t, J=8.0 Hz, 1H), 6.98 (m, 1H).

Step C: 6-Chloro-2,4,8,16,23-pentaazatetracyclo [15.3.1.1(3,7).1(9,13)]tricosa-1(21),3(23),4,6,9(22), 10,12,17,19-nonaen-15-one trifluoroacetate To a solution of tert-butyl {3-[({3-[(2,5-dichloropyrimidin-4-yl)amino]phenyl}acetyl)amino]phenyl}carbamate (20 mg, 0.04 mmol) and in 2-methoxyethanol (1 mL) was added 4.0 M of hydrogen chloride in 1,4-dioxane (50 μL). The resulting mixture was heated at 150° C. in a microwave for 15 min. The mixture was condensed and diluted with DMSO to 5 mL and purified using preparative LCMS (pH 2) to give the desired product (5.0 mg, 35%). LCMS for $C_{18}H_{14}ClN_5O$ $(M+H)^+$: m/z=352.2.

Example C12

6-Chloro-2,4,8,17,22-pentaazatetracyclo[14.3.1.1(3,7).1(9,13)]docosa-1(20),3(22),4,6,9(21),10,12,16,18-nonaene

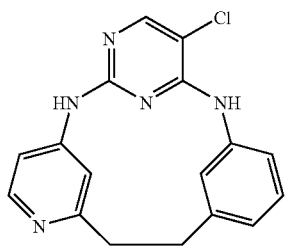

Step A: tert-Butyl {2-[(3-aminophenyl)ethynyl]pyridin-4-yl}carbamate

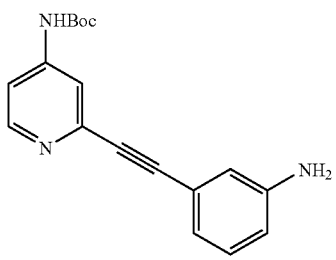 [SMILES: CC(C)(C)OC(=O)Nc1ccnc(C#Cc2cccc(N)c2)c1]

tert-Butyl (2-iodopyridin-4-yl)carbamate (2.41 g, 7.5 mmol), copper(I) iodide (50 mg, 0.3 mmol) and bis(triphenylphosphine)palladium(II) chloride (200 mg, 0.3 mmol) were stirred in tetrahydrofuran (22 mL) with triethylamine (1.1 mL, 8.1 mmol) under $N_2$ at rt. 3-Ethynylaniline (0.75 mL, 7.2 mmol) was added and the mixture was stirred at rt for 40 hours. The reaction mixture was diluted with water. After removal of the solvent, the aqueous residue was extracted with EtOAc three times, followed by drying, filtration, and concentration to give the desired product as a brown solid (1.97 g, 89%). LCMS for $C_{18}H_{20}N_3O_2$ $(M+H)^+$: m/z=310.1.

Step B: tert-Butyl [2-({3-[(2,5-dichloropyrimidin-4-yl)amino]phenyl}ethynyl)pyridin-4-yl]carbamate

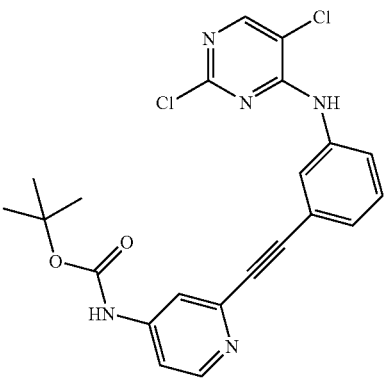 [SMILES: CC(C)(C)OC(=O)Nc1ccnc(C#Cc2cccc(Nc3nc(Cl)ncc3Cl)c2)c1]

To a solution of tert-butyl {2-[(3-aminophenyl)ethynyl]pyridin-4-yl}carbamate (0.50 g, 1.6 mmol) and 2,4,5-trichloropyrimidine (0.19 mL, 1.7 mmol) in N,N-dimethylformamide (5.0 mL) was added potassium carbonate (0.670 g, 4.85 mmol). The resultant mixture was stirred for 40 hours at room temperature. The reaction was quenched with water. EtOAc was added and the layers were separated. The aqueous layer was extracted with EtOAc twice. The combined organic layers were washed with water and brine then dried $(Na_2SO_4)$, filtered and concentrated to give the desired product as a light brown gum (0.665 g, 90%). LCMS for $C_{22}H_{20}Cl_2N_5O_2$ $(M+H)^+$: m/z=456.0, 458.0.

Step C: tert-Butyl [2-(2-{3-[(2,5-dichloropyrimidin-4-yl)amino]phenyl}ethyl)pyridin-4-yl]carbamate

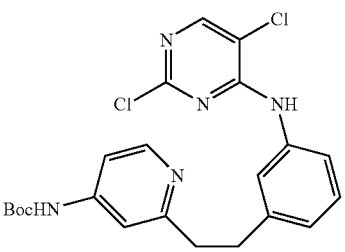

To a mixture of tert-butyl [2-({3-[(2,5-dichloropyrimidin-4-yl)amino]phenyl}ethynyl)pyridin-4-yl]carbamate (740 mg, 1.6 mmol) in methanol (15 mL) and tetrahydrofuran (15 mL) was added 10% palladium on carbon (148 mg, 0.139 mmol). The resultant mixture was hydrogenated at 55 psi for 20 hours. The crude mixture was filtered and concentrated to give the desired product as a light yellow solid (0.65 g, 87%). LCMS for $C_{22}H_{24}Cl_2N_5O_2$ (M+H)$^+$: m/z=460.0, 462.0.

Step D: N-{3-[2-(4-Aminopyridin-2-yl)ethyl]phenyl}-2,5-dichloropyrimidin-4-amine dihydrochloride

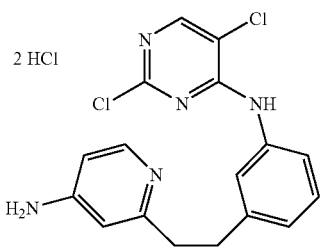 [SMILES: "2 HCl" ; Nc1ccnc(CCc2cccc(Nc3nc(Cl)ncc3Cl)c2)c1]

To a mixture of tert-butyl [2-(2-{3-[(2,5-dichloropyrimidin-4-yl)amino]phenyl}ethyl)pyridin-4-yl]carbamate (0.75 g, 1.6 mmol) in 1,4-dioxane (3.0 mL) was added 4 M hydrogen chloride in 1,4-dioxane (7.1 mL). The resultant reaction mixture was stirred at rt for 2 hours. The reaction mixture was concentrated under vacuum to give the desired product as a light yellow powder (0.67 g, 95%). LCMS for $C_{17}H_{16}Cl_2N_5$ (M+H)$^+$: m/z=360.2, 362.0.

Step E: 6-Chloro-2,4,8,17,22-pentaazatetracyclo [14.3.1.1(3,7).1(9,13)]docosa-1(20),3(22),4,6,9(21), 10,12,16,18-nonaene To a mixture of N-{3-[2-(4-aminopyridin-2-yl)ethyl]phenyl}-2,5-dichloropyrimidin-4-amine dihydrochloride (90.0 mg, 0.21 mmol) and triethylamine (0.087 mL, 0.62 mmol) in dry 1,4-dioxane (1.8 mL) was added (9,9-dimethyl-9H-xanthene-4,5-diyl)bis(diphenylphosphine) (7.2 mg, 0.013 mmol), palladium acetate (1.9 mg, 0.008 mmol) and cesium carbonate (135 mg, 0.42 mmol). The mixture was degassed by bubbling N$_2$ through the solution. The sealed tube was then microwaved at 150° C. for 30 min. The reaction mixture was diluted with THF/MeOH, filtered, and concentrated to give the residue, which was purified by silica gel column chromatography to provide the desired product (24 mg, 36%) as a white powder. LCMS for $C_{17}H_{15}ClN_5$ (M+H)$^+$: m/z=324.0. $^1$H NMR (400 MHz, DMSO-d$_6$): δ 9.69 (s, 1H), 9.28 (s, 1H), 8.15 (m, 3H), 7.74 (d, J=1.6 Hz, 1H), 7.27 (dd, J=16.0, 8.0 Hz, 1H), 7.07 (dd, J=12.4, 3.2 Hz, 2H), 6.84 (dd, J=5.6, 2.0 Hz, 1H), 2.93 (m, 4H).

Example C13

6-Fluoro-2,4,8,17,22-pentaazatetracyclo[14.3.1.1(3, 7).1(9,13)]docosa-1(20),3(22),4,6,9(21),10,12,16,18-nonaene

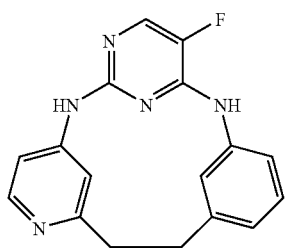 [SMILES: Fc1cnc2nc1Nc1cccc(c1)CCc1cc(ccn1)N2]

Step A: tert-Butyl {2-[2-(3-aminophenyl)ethyl]pyridin-4-yl}carbamate

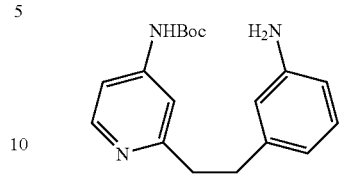

To a mixture of tert-butyl {2-[(3-aminophenyl)ethynyl]pyridin-4-yl}carbamate (250 mg, 1.62 mmol) (prepared in Example C12, step A) in methanol (10 mL) was added 10% palladium on carbon (0.30 g, 0.24 mmol). The reaction mixture was hydrogenated at 50 psi overnight. The resultant mixture was filtered and concentrated to provide the desired product (240 mg, 95%) as a white solid. LCMS for $C_{18}H_{24}N_3O_2$ (M+H)$^+$: m/z=314.0.

Step B: tert-Butyl [2-(2-{3-[(2-chloro-5-fluoropyrimidin-4-yl)amino]phenyl}ethyl)pyridin-4-yl]carbamate

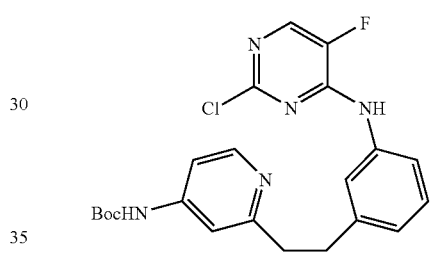

To a solution of tert-butyl {2-[2-(3-aminophenyl)ethyl]pyridin-4-yl}carbamate (240 mg, 0.76 mmol) and 2,4-dichloro-5-fluoropyrimidine (134 mg, 0.80 mmol) in N,N-dimethylformamide (3.5 mL) was added potassium carbonate (318 mg, 0.23 mmol). The resultant mixture was stirred overnight at room temperature. The reaction mixture was filtered first to remove K$_2$CO$_3$, followed by quenching with water. EtOAc was added and the layers were separated. The aqueous layer was extracted with EtOAc twice. The combined organic layers were washed with water and brine, then dried (Na$_2$SO$_4$), filtered and concentrated to give the residue, which was purified by silica gel column chromatography to give the desired product as an off-white solid (123 mg, 36%). LCMS for $C_{22}H_{24}ClFN_5O_2$ (M+H)$^+$: m/z=444.1.

Step C: N-{3-[2-(4-Aminopyridin-2-yl)ethyl]phenyl}-2-chloro-5-fluoropyrimidin-4-amine dihydrochloride

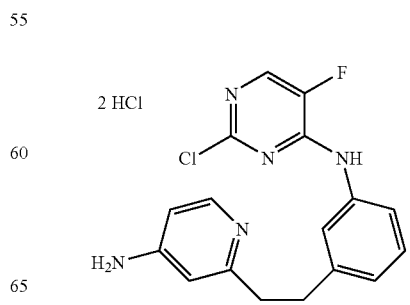

To a mixture of tert-butyl [2-(2-{3-[(2-chloro-5-fluoropyrimidin-4-yl)amino]phenyl}ethyl)pyridin-4-yl]carbamate (123 mg, 0.28 mmol) in 1,4-dioxane (0.51 mL) was added 4 M hydrogen chloride in 1,4-dioxane (1.21 mL). The resultant reaction mixture was stirred at rt for 1 hour. The reaction mixture was concentrated under vacuum to provide the desired product as an off-white powder (113 mg, 98%). LCMS for $C_{17}H_{16}ClFN_5$ (M+H)$^+$: m/z=344.0.

Step D: 6-fluoro-2,4,8,17,22-pentaazatetracyclo [14.3.1.1(3,7).1(9,13)]docosa-1(20),3(22),4,6,9(21), 10,12,16,18-nonaene To a mixture of N-{3-[2-(4-aminopyridin-2-yl)ethyl]phenyl}-2-chloro-5-fluoropyrimidin-4-amine dihydrochloride (50.0 mg, 0.12 mmol) and triethylamine (0.05 mL, 0.36 mmol) in dry 1,4-dioxane (1.0 mL) was added (9,9-dimethyl-9H-xanthene-4,5-diyl)bis(diphenylphosphine) (4.16 mg, 0.007 mmol), palladium acetate (1.1 mg, 0.0048 mmol) and cesium carbonate (78.2 mg, 0.24 mmol). The cloudy mixture was degassed by bubbling $N_2$ through the solution. The sealed tube was then microwaved at 150° C. for 30 min. The reaction mixture was diluted with THF, filtered and concentrated to give the residue, which was then triturated with MeOH/THF/EtOAc to provide the desired product as a white powder (15 mg, 41%). LCMS for $C_{17}H_{15}FN_5$ (M+H)$^+$: m/z=308.0. $^1$H NMR (400 MHz, DMSO-$d_6$): δ 9.68 (s, 1H), 9.58 (s, 1H), 8.14 (m, 3H), 7.84 (s, 1H), 7.26 (dd, J=15.2, 7.2 Hz, 1H), 7.04 (dd, J=7.2, 2.0 Hz, 2H), 6.84 (dd, J=5.6, 2.0 Hz, 1H), 2.90 (m, 4H).

Example C14

(14Z)-6-Chloro-2,4,8,17,22-pentaazatetracyclo [14.3.1.1(3,7).1(9,13)]docosa-1(20),3(22),4,6,9(21), 10,12,14,16,18-decaene

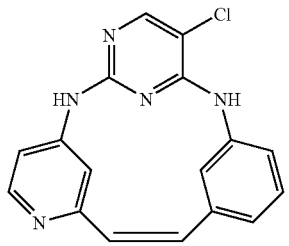 [SMILES: Clc1cnc2nc1Nc1cccc(c1)/C=C\c1cc(ccn1)N2]

Step A: tert-Butyl {2-[(Z)-2-(3-aminophenyl)vinyl] pyridin-4-yl}carbamate

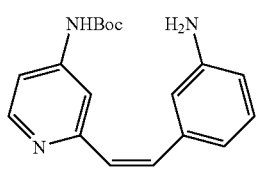

To a mixture of tert-butyl {2-[(3-aminophenyl)ethynyl] pyridin-4-yl}carbamate (430 mg, 1.4 mmol) in methanol (15 mL) was added 10% palladium on carbon (150 mg, 0.14 mmol) and hydrogenated at 60 psi for 20 hours. After filtration and concentration, the crude residue was purified by silica gel column chromatography to give the desired product (160 mg, 37%). LCMS for $C_{18}H_{22}N_3O_2$ (M+H)$^+$: m/z=312.1

Step B: tert-Butyl [2-((Z)-2-{3-[(2,5-dichloropyrimidin-4-yl)amino]phenyl}vinyl)pyridin-4-yl]carbamate

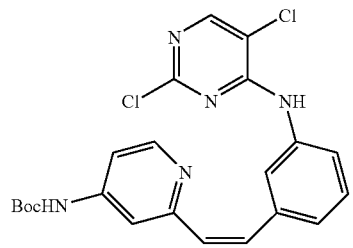 [SMILES: CC(C)(C)OC(=O)Nc1ccnc(/C=C\c2cccc(Nc3nc(Cl)ncc3Cl)c2)c1]

To a solution of tert-butyl {2-[(Z)-2-(3-aminophenyl)vinyl]pyridin-4-yl}carbamate (50.0 mg, 0.16 mmol) and 2,4,5-trichloropyrimidine (0.019 mL, 0.17 mmol) in N,N-dimethylformamide (0.50 mL) was added potassium carbonate (66.6 mg, 0.48 mmol). The resultant mixture was stirred for 16 hours at room temperature. The reaction was quenched with water. EtOAc was added and the layers were separated. The aqueous layer was extracted with EtOAc twice. The combined organic layers were washed with water and brine then dried ($Na_2SO_4$), filtered and concentrated to give the desired product as a light brown gum (66 mg, 90%). LCMS for $C_{22}H_{22}Cl_2N_5O_2$ (M+H)$^+$: m/z=458.0, 460.0.

Step C: N-{3-[(Z)-2-(4-Aminopyridin-2-yl)vinyl] phenyl}-2,5-dichloropyrimidin-4-amine dihydrochloride

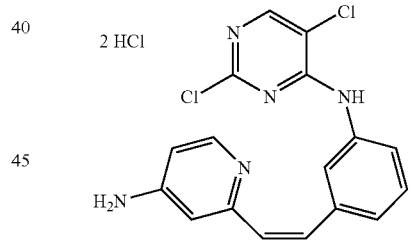

To a mixture of tert-butyl [2-((Z)-2-{3-[(2,5-dichloropyrimidin-4-yl)amino]phenyl}vinyl)pyridin-4-yl]carbamate (73.6 mg, 0.16 mmol) in 1,4-dioxane (0.50 mL) was added 4 M of hydrogen chloride in 1,4-dioxane (0.70 mL). The resultant reaction mixture was stirred at rt for 1 hour. The reaction mixture was concentrated under vacuum to give the desired product as a light yellow powder (66 mg, 95%). LCMS for $C_{17}H_{14}Cl_2N_5$ (M+H)$^+$: m/z=358.0.

Step D: (14Z)-6-Chloro-2,4,8,17,22-pentaazatetracyclo[14.3.1.1(3,7).1(9,13)]docosa-1(20),3(22),4,6,9 (21),10,12,14,16,18-decaene To a mixture of N-{3-[(Z)-2-(4-aminopyridin-2-yl)vinyl] phenyl}-2,5-dichloropyrimidin-4-amine dihydrochloride (34.6 mg, 0.08 mmol) and triethylamine (0.034 mL, 0.24 mmol) in dry 1,4-dioxane (0.70 mL) was added (9,9-dimethyl-9H-xanthene-4,5-diyl)bis(diphenylphosphine) (2.8 mg, 0.0048 mmol), palladium acetate (0.7 mg, 0.003 mmol) and cesium carbonate (52.3 mg, 0.16 mmol). The mixture was degassed by bubbling $N_2$ through the solution. The sealed tube was then microwaved at 150° C. for 30 min. The reaction mixture was diluted with THF/MeOH, filtered and concentrated to give the residue, which was then triturated with MeOH/EtOAc/THF to provide the desired product as a light yellow powder (9 mg, 35%). LCMS for $C_{17}H_{13}ClN_5$ (M+H)$^+$: m/z=322.0. $^1$H NMR (300 MHz, DMSO-d$_6$): δ 9.81 (s, 1H), 9.33 (s, 1H), 9.15 (s, 1H), 8.49 (s, 1H), 8.26 (m, 1H), 8.19 (s, 1H), 7.33 (m, 1H), 7.24 (m, 1H), 7.08 (d, J=5.7 Hz, 1H), 6.93 (dd, J=5.7, 2.1 Hz, 1H), 6.83 (m, 1H), 6.58 (d, J=13.5 Hz, 1H).

Example C15

6-Chloro-2,4,8,19,22-pentaazatetracyclo[14.3.1.1(3,7).1(9,13)]docosa-1(20),3(22),4,6,9(21),10,12,16,18-nonaene

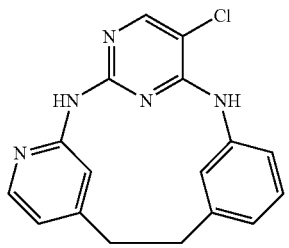 [SMILES: Clc1cnc2nc1Nc1cccc(c1)CCc1ccnc(c1)N2]

Step A: tert-Butyl (4-bromopyridin-2-yl)carbamate

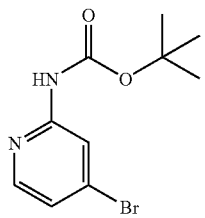

A solution of 4-bromopyridin-2-amine (1.60 g, 9.25 mmol) in tetrahydrofuran (16 mL) was slowly added to a stirring solution of 1 M sodium bis(trimethylsilyl)amide in tetrahydrofuran (17.8 mL, 19.4 mmol) at rt. After the mixture was stirred at rt for 1 hour, a solution of di-tert-butyldicarbonate (2.2 g, 10.0 mmol) in tetrahydrofuran (16 mL) was slowly added. The mixture was stirred at rt for 1 hour. The reaction mixture was quenched with NH$_4$Cl (aq) and THF was removed under vacuum. The aqueous layer was extracted with EtOAc three times. The combined organic layers were dried, filtered and concentrated to give the desired product (2.32 g, 92%) as a light brown powder. LCMS for $C_6H_6BrN_2O_2$ ([M-(tBu)+H]+H)$^+$: m/z=216.9, 218.9.

Step B: tert-Butyl [4-[(3-aminophenyl)ethynyl]pyridin-2-yl]carbamate

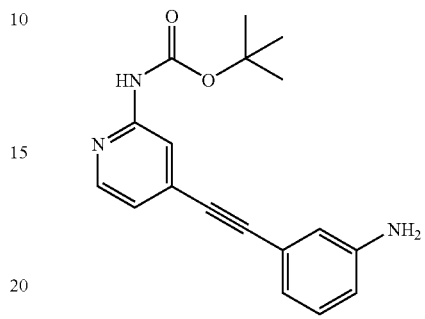

tert-Butyl (4-bromopyridin-2-yl)carbamate (1.935 g, 7.09 mmol), copper(I) iodide (0.67 g, 3.5 mmol) and bis(triphenylphosphine)palladium(II) chloride (0.20 g, 0.28 mmol) were stirred in tetrahydrofuran (22 mL) with triethylamine (1.09 mL, 7.82 mmol) under $N_2$ at rt. 3-Ethynylaniline (0.815 mL, 7.79 mmol) was added and the mixture was heated at 70° C. for 2 hours and only very little product was observed. Thus more 3-ethynylaniline (0.41 mL, 3.9 mmol) was added and the mixture was heated at 70° C. over the weekend. The reaction mixture was filtered and concentrated to give a brown residue, which was purified by silica gel column chromatography to give the desired product (340 mg, 16%). LCMS for $C_{18}H_{20}N_3O_2$ (M+H)$^+$: m/z=310.1

Step C: tert-Butyl [4-[2-(3-aminophenyl)ethyl]pyridin-2-yl]carbamate

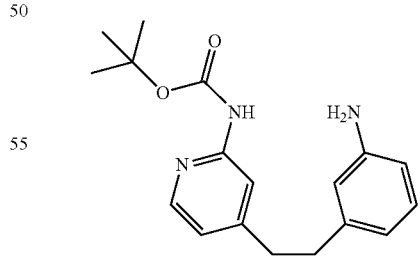

To a mixture of tert-butyl {4-[(3-aminophenyl)ethynyl]pyridin-2-yl}carbamate (328 mg, 1.06 mmol) in methanol (8 mL) and methylene chloride (8 mL) was added 10% palladium on carbon (100 mg, 0.09 mmol). The resultant mixture was hydrogenated at 30 psi for 18 hours. The reaction mixture was filtered, washed with MeOH/DCM and concentrated to give the desired product (326 mg, 98%) as a light brown powder. LCMS for $C_{18}H_{24}N_3O_2$ (M+H)$^+$: m/z=314.1.

Step D: tert-Butyl [4-(2-{3-[(2,5-dichloropyrimidin-4-yl)amino]phenyl}ethyl)pyridin-2-yl]carbamate

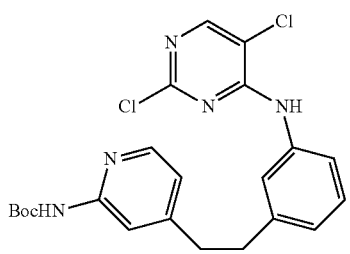 [SMILES: CC(C)(C)OC(=O)Nc1cc(CCc2cccc(Nc3nc(Cl)ncc3Cl)c2)ccn1]

To a solution of tert-butyl {4-[2-(3-aminophenyl)ethyl]pyridin-2-yl}carbamate (160 mg, 0.51 mmol) and 2,4,5-trichloropyrimidine (98.3 mg, 0.54 mol) in N,N-dimethylformamide (2.3 mL) was added potassium carbonate (212 mg, 1.53 mmol). The resultant mixture was stirred at room temperature for 4 hours. The reaction mixture was filtered first to remove $K_2CO_3$, followed by quenching with water. EtOAc was added and the layers were separated. The aqueous layer was extracted with EtOAc twice. The combined organic layers were washed with water and then dried ($Na_2SO_4$), filtered and concentrated to give the residue, which was purified by trituration with cold EtOAc to give the desired product (123 mg, 36%) as an off-white powder. LCMS for $C_{22}H_{24}Cl_2N_5O_2$ (M+H)$^+$: m/z=460.1, 462.0.

Step E: N-{3-[2-(2-Aminopyridin-4-yl)ethyl]phenyl}-2,5-dichloropyrimidin-4-amine dihydrochloride

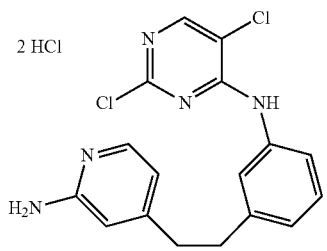 [SMILES: "2 HCl" ; Nc1cc(CCc2cccc(Nc3nc(Cl)ncc3Cl)c2)ccn1]

To a mixture of tert-butyl [4-(2-{3-[(2,5-dichloropyrimidin-4-yl)amino]phenyl}ethyl)pyridin-2-yl]carbamate (128 mg, 0.28 mmol) in 1,4-dioxane (0.64 mL) was added 4 M of hydrogen chloride in 1,4-dioxane (3.0 mL). The resultant reaction mixture was stirred at rt for 2 hours. The reaction mixture was concentrated under vacuum to give the desired product (120 mg, 100%) as a very hygroscopic off-white powder. LCMS for $C_{17}H_{16}Cl_2N_5$ (M+H)$^+$: m/z=360.0

Step F: 6-Chloro-2,4,8,19,22-pentaazatetracyclo[14.3.1.1(3,7).1(9,13)]docosa-1(20),3(22),4,6,9(21),10,12,16,18-nonaene To a mixture of N-{3-[2-(2-aminopyridin-4-yl)ethyl]phenyl}-2,5-dichloropyrimidin-4-amine dihydrochloride (35.0 mg, 0.08 mmol) and triethylamine (0.034 mL, 0.24 mmol) in a mixed solvent of 1,4-dioxane (0.70 mL) and N,N-dimethylformamide (0.70 mL) at rt were added (9,9-dimethyl-9H-xanthene-4,5-diyl)bis(diphenylphosphine) (5.6 mg, 0.010 mmol), palladium acetate (2.2 mg, 0.010 mmol) and cesium carbonate (52.6 mg, 0.16 mmol). The mixture was degassed by bubbling $N_2$ through the solution. The sealed tube was then microwaved at 160° C. for 20 min. The reaction mixture was diluted with THF/MeOH, filtered and concentrated to give a residue, which was triturated with MeOH/EtOAc (1:1) to provide the desired product (16 mg, 61%) as a light brown powder. LCMS for $C_{17}H_{15}ClN_5$ (M+H)$^+$: m/z=324.0. $^1$H NMR (400 MHz, DMSO-d$_6$): δ 9.44 (s, 1H), 9.22 (s, 1H), 8.18 (m, 1H), 8.06 (m, 1H), 7.86 (m, 1H), 7.68 (m, 1H), 7.40 (m, 1H), 7.28 (m, 1H), 7.05 (m, 1H), 6.28 (m, 1H), 3.05 (m, 4H).

Example C16

6-Fluoro-2,4,8,19,22-pentaazatetracyclo[14.3.1.1(3,7).1(9,13)]docosa-1(20),3(22),4,6,9(21),10,12,16,18-nonaene

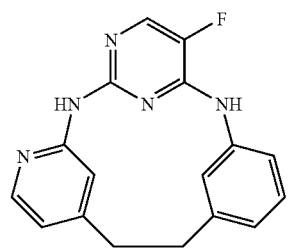 [SMILES: Fc1cnc2nc1Nc1cccc(c1)CCc1ccnc(c1)N2]

Step A: tert-Butyl [4-(2-{3-[(2-chloro-5-fluoropyrimidin-4-yl)amino]phenyl}ethyl)pyridin-2-yl]carbamate

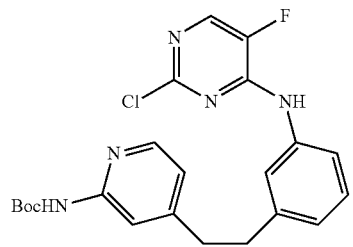 [SMILES: CC(C)(C)OC(=O)Nc1cc(CCc2cccc(Nc3nc(Cl)ncc3F)c2)ccn1]

To a solution of tert-butyl {4-[2-(3-aminophenyl)ethyl]pyridin-2-yl}carbamate (160 mg, 0.51 mmol) (prepared in Example C15, step C) and 2,4-dichloro-5-fluoropyrimidine (89.5 mg, 0.54 mmol) in N,N-dimethylformamide (2.3 mL) was added potassium carbonate (212 mg, 1.53 mmol). The resultant mixture was stirred overnight at room temperature. The reaction mixture was filtered first to remove $K_2CO_3$, followed by quenching with water. EtOAc was added and the layers were separated. The aqueous layer was extracted with EtOAc twice. The combined organic layers were washed with water and then dried ($Na_2SO_4$), filtered and concentrated to give the residue, which was purified by silica gel column chromatography to give the desired product as an off-white solid (93 mg, 41%). LCMS for $C_{22}H_{24}ClFN_5O_2$ (M+H)$^+$: m/z=444.1.

Step B: N-{3-[2-(2-Aminopyridin-4-yl)ethyl]phenyl}-2-chloro-5-fluoropyrimidin-4-amine dihydrochloride

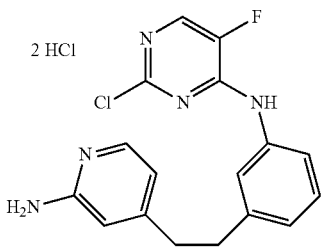 [SMILES: "2 HCl" ; Nc1cc(CCc2cccc(Nc3nc(Cl)ncc3F)c2)ccn1]

To a mixture of tert-butyl [4-(2-{3-[(2-chloro-5-fluoropyrimidin-4-yl)amino]phenyl}ethyl)pyridin-2-yl]carbamate (88 mg, 0.20 mmol) in 1,4-dioxane (0.50 mL) was added 4 M hydrogen chloride in 1,4-dioxane (2.0 mL). The resultant reaction mixture was stirred at 40° C. for 1 hour. The reaction mixture was concentrated under vacuum to give the desired product as a very hygroscopic white powder (83 mg, 100%). LCMS for $C_{17}H_{16}ClFN_5$ (M+H)$^+$: m/z=344.1.

Step C: 6-Fluoro-2,4,8,19,22-pentaazatetracyclo[14.3.1.1(3,7).1(9,13)]docosa-1(20),3(22),4,6,9(21),10,12,16,18-nonaene To a mixture of N-{3-[2-(2-aminopyridin-4-yl)ethyl]phenyl}-2-chloro-5-fluoropyrimidin-4-amine dihydrochloride (35.0 mg, 0.084 mmol) and triethylamine (0.035 mL, 0.25 mmol) in a mixed solvent of 1,4-dioxane (0.70 mL) and N,N-dimethylformamide (0.70 mL) were added (9,9-dimethyl-9H-xanthene-4,5-diyl)bis(diphenylphosphine) (5.8 mg, 0.01 mmol), palladium acetate (2.3 mg, 0.01 mmol) and cesium carbonate (54.7 mg, 0.17 mmol). The mixture was degassed by bubbling N$_2$ through the solution. The sealed tube was then microwaved at 160° C. for 30 min. The reaction mixture was diluted with THF/MeOH, filtered and concentrated to give the residue, which was purified by silica gel column chromatography to provide the desired product as a white powder (7.8 mg, 30%). LCMS for $C_{17}H_{15}FN_5$ (M+H)$^+$: m/z=308.1. $^1$H NMR (400 MHz, CD$_3$OD): δ 8.09 (d, J=5.2 Hz, 1H), 8.00 (s, 1H), 7.96 (d, J=4.0 Hz, 1H), 7.81 (d, J=1.6 Hz, 1H), 7.31 (m, 1H), 7.04 (m, 2H), 6.91 (m, 1H).

Example C17

6-Chloro-2,4,8,20,22-pentaazatetracyclo[14.3.1.1(3,7).1(9,13)]docosa-1(20),3(22),4,6,9(21),10,12,16,18-nonaene

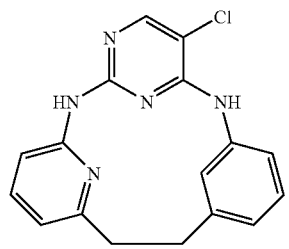 [SMILES: Clc1cnc2nc1Nc1cccc(c1)CCc1cccc(n1)N2]

Step A: tert-Butyl {6-[(3-aminophenyl)ethynyl]pyridin-2-yl}carbamate

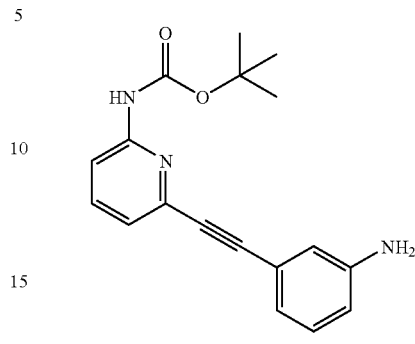

tert-Butyl (6-iodopyridin-2-yl)carbamate (1.50 g, 4.68 mmol), copper(I) iodide (68.0 mg, 0.36 mmol) and bis(triphenylphosphine)palladium(II) chloride (100 mg, 0.2 mmol) were stirred in tetrahydrofuran (14 mL) with triethylamine (0.70 mL, 5.0 mmol) under N$_2$ at rt. 3-Ethynylaniline (0.47 mL, 4.5 mmol) was added and the mixture was heated at 60° C. overnight. The mixture was filtered, washed with EtOAc and concentrated under vacuum to give the desired product as a brown solid (1.23 g, 89%). LCMS for $C_{14}H_{12}N_3O_2$ ([M-(tBu)+H]+H)$^+$: m/z=254.1.

Step B: tert-Butyl {6-[2-(3-aminophenyl)ethyl]pyridin-2-yl}carbamate

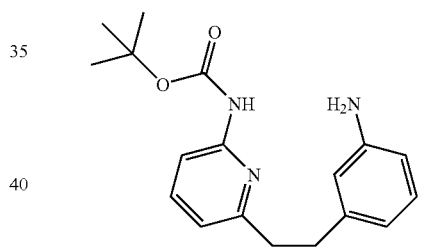

To a mixture of tert-butyl {6-[(3-aminophenyl)ethynyl]pyridin-2-yl}carbamate (70.0 mg, 2.3 mmol) in methanol (25 mL) and was added 10% palladium on carbon (700 mg, 0.60 mmol). The resultant mixture was hydrogenated at 60 psi for 3 hours. The reaction mixture was filtered, washed with MeOH and concentrated to give the desired product (680 mg, 96%). LCMS for $C_{18}H_{24}N_3O_2$ (M+H)$^+$: m/z=314.1.

Step C: tert-Butyl [6-(2-{3-[(2,5-dichloropyrimidin-4-yl)amino]phenyl}ethyl)pyridin-2-yl]carbamate

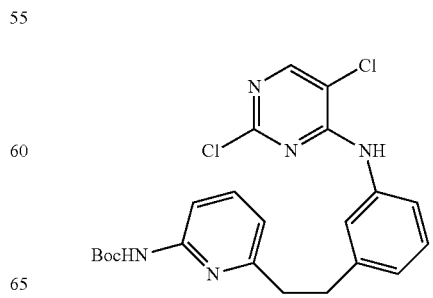

To a solution of tert-butyl {6-[2-(3-aminophenyl)ethyl]pyridin-2-yl}carbamate (200 mg, 0.64 mmol) and 2,4,5-trichloropyrimidine (123 mg, 0.67 mmol) in N,N-dimethylformamide (2.9 mL) was added potassium carbonate (264 mg, 1.91 mmol). The resultant mixture was stirred overnight at room temperature. The reaction mixture was filtered first to remove $K_2CO_3$, followed by quenching with water. EtOAc was added and the layers were separated. The aqueous layer was extracted with EtOAc twice. The combined organic layers were washed with water and then dried ($Na_2SO_4$), filtered and concentrated to give the residue, which was purified by silica gel column chromatography to give the desired product as a light brown gel (231 mg, 79%). LCMS for $C_{17}H_{16}Cl_2N_5$ [(M-Boc+H)+H]$^+$: m/z=360.0, 362.0.

Step D: N-{3-[2-(6-Aminopyridin-2-yl)ethyl]phenyl}-2,5-dichloropyrimidin-4-amine dihydrochloride

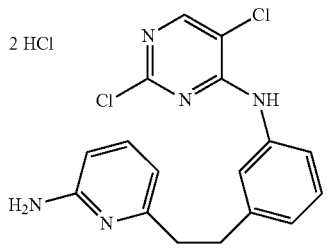 [SMILES: "2 HCl" ; Nc1cccc(CCc2cccc(Nc3nc(Cl)ncc3Cl)c2)n1]

To a mixture of tert-butyl [6-(2-{3-[(2,5-dichloropyrimidin-4-yl)amino]phenyl}ethyl)pyridin-2-yl]carbamate (230 mg, 0.50 mmol) in 1,4-dioxane (1.0 mL) was added 4 M hydrogen chloride in 1,4-dioxane (5.0 mL). The resultant reaction mixture was stirred at rt for 2 hours. The reaction mixture was concentrated under vacuum to give the desired product (212 mg, 98%) as a very hydroscopic light yellow powder. LCMS for $C_{17}H_{16}Cl_2N_5$ (M+H)$^+$: m/z=360.0.

Step E: 6-Chloro-2,4,8,20,22-pentaazatetracyclo[14.3.1.1(3,7).1(9,13)]docosa-1(20),3(22),4,6,9(21),10,12,16,18-nonaene To a mixture of N-{3-[2-(6-aminopyridin-2-yl)ethyl]phenyl}-2,5-dichloropyrimidin-4-amine dihydrochloride (50 mg, 0.12 mmol) and triethylamine (0.048 mL, 0.35 mmol) in a mixed solvent of 1,4-dioxane (0.80 mL) and N,N-dimethylformamide (0.80 mL) were added (9,9-dimethyl-9H-xanthene-4,5-diyl)bis(diphenylphosphine) (8.0 mg, 0.014 mmol), palladium acetate (3.1 mg, 0.014 mmol) and cesium carbonate (75.2 mg, 0.23 mmol). The mixture was degassed by bubbling $N_2$ through the solution. The sealed tube was then microwaved at 160° C. for 30 min. The reaction mixture was diluted with THF/MeOH, filtered and concentrated to give the residue, which was purified by silica gel column chromatography to provide the desired product as a white powder (14 mg, 37%). LCMS for $C_{17}H_{15}ClN_5$ (M+H)$^+$: m/z=324.0. $^1$H NMR (400 MHz, $CD_3OD$): δ 8.70 (s, 1H), 8.02 (s, 1H), 7.63 (d, J=7.6 Hz, 1H), 7.07 (m, 2H), 6.90 (dd, J=8.0, 1.6 Hz, 1H), 6.84 (d, J=8.0 Hz, 1H), 6.79 (d, J=8.0 Hz, 1H), 3.22 (s, 4H).

Example C18

6-Fluoro-2,4,8,20,22-pentaazatetracyclo[14.3.1.1(3,7).1(9,13)]docosa-1(20),3(22),4,6,9(21),10,12,16,18-nonaene

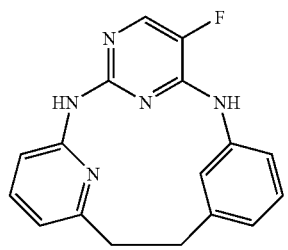 [SMILES: Fc1cnc2nc1Nc1cccc(c1)CCc1cccc(n1)N2]

Step A: tert-Butyl [6-(2-{3-[(2-chloro-5-fluoropyrimidin-4-yl)amino]phenyl}ethyl)pyridin-2-yl]carbamate

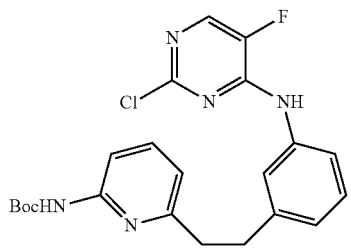 [SMILES: CC(C)(C)OC(=O)Nc1cccc(CCc2cccc(Nc3nc(Cl)ncc3F)c2)n1]

To a solution of tert-butyl {6-[2-(3-aminophenyl)ethyl]pyridin-2-yl}carbamate (200 mg, 0.64 mmol) (prepared in Example C17, step B) and 2,4-dichloro-5-fluoropyrimidine (112 mg, 0.67 mmol) in N,N-dimethylformamide (2.9 mL) was added potassium carbonate (264 mg, 1.91 mmol). The resultant mixture was stirred overnight at room temperature. The reaction mixture was filtered first to remove $K_2CO_3$. The filtrate was concentrated to give the residue, which was purified by silica gel column chromatography to give the desired product as a light yellow gum (216 mg, 76%). LCMS for $C_{22}H_{24}ClFN_5O_2$ (M+H)$^+$: m/z=444.0.

Step B: N-{3-[2-(6-Aminopyridin-2-yl)ethyl]phenyl}-2-chloro-5-fluoropyrimidin-4-amine dihydrochloride

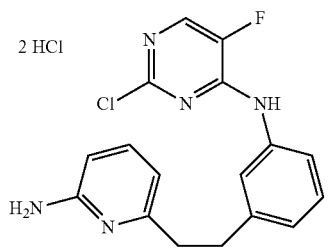 [SMILES: "2 HCl" ; Nc1cccc(CCc2cccc(Nc3nc(Cl)ncc3F)c2)n1]

To a mixture of tert-butyl [6-(2-{3-[(2-chloro-5-fluoropyrimidin-4-yl)amino]phenyl}ethyl)pyridin-2-yl]carbamate (215 mg, 0.48 mmol) in 1,4-dioxane (0.90 mL) was added 4 M of hydrogen chloride in 1,4-dioxane (4.5 mL). The resultant reaction mixture was stirred at 35° C. for 3 hours. The reaction mixture was concentrated under vacuum to give the desired product as a very hydroscopic light yellow powder (194 mg, 96%). LCMS for $C_{17}H_{16}ClFN_5$ $(M+H)^+$: m/z=344.1.

Step C: 6-Fluoro-2,4,8,20,22-pentaazatetracyclo[14.3.1.1(3,7).1(9,13)]docosa-1(20),3(22),4,6,9(21),10,12,16,18-nonaene To a mixture of N-{3-[2-(6-aminopyridin-2-yl)ethyl]phenyl}-2-chloro-5-fluoropyrimidin-4-amine dihydrochloride (35.0 mg, 0.084 mmol) and triethylamine (0.035 mL, 0.25 mmol) in a mixed solvent of 1,4-dioxane (0.70 mL) and N,N-dimethylformamide (0.70 mL) was added (9,9-dimethyl-9H-xanthene-4,5-diyl)bis(diphenylphosphine) (5.8 mg, 0.01 mmol), palladium acetate (2.3 mg, 0.01 mmol) and cesium carbonate (54.7 mg, 0.17 mmol). The mixture was degassed by bubbling $N_2$ through the solution. The sealed tube was then microwaved at 160° C. for 1 hour. The reaction mixture was diluted with THF/MeOH, filtered and concentrated to give a residue, which was purified by silica gel column chromatography to provide the desired product as a white powder (6.4 mg, 25%). LCMS for $C_{17}H_{15}FN_5$ $(M+H)^+$: m/z=308.1.

Example C19

6-Chloro-2,4,8,18,22-pentaazatetracyclo[14.3.1.1(3,7).1(9,13)]docosa-1(20),3(22),4,6,9(21),10,12,16,18-nonaene bis(trifluoroacetate)

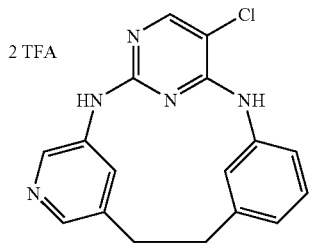 [SMILES: "2 TFA" ; Clc1cnc2nc1Nc1cccc(c1)CCc1cncc(c1)N2]

Step A: tert-Butyl {5-[(3-aminophenyl)ethynyl]pyridin-3-yl}carbamate

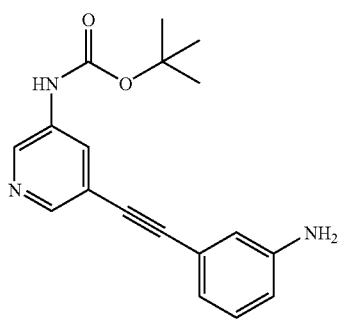

Into the reaction flask were added tert-butyl (5-bromopyridin-3-yl)carbamate (2.00 g, 7.32 mmol), copper(I) iodide (56 mg, 0.29 mmol), bis(triphenylphosphine)palladium(II) chloride (0.20 g, 0.29 mmol), tetrahydrofuran (20 mL) and triethylamine (1.1 mL, 8.0 mmol). The reaction mixture was stirred under $N_2$ bubbling for 5 min. 3-Ethynylaniline (0.849 g, 7.3 mmol) was then added. The reaction mixture was heated at 50° C. overnight. After removal of the solvent, the residue was treated with EtOAc and water. The organic layer was dried over $Na_2SO_4$ and concentrated under vacuum. The crude was purified by silica gel column chromatography to give the desired product as a yellow gel (0.60 g, 49%). LCMS for $C_{14}H_{12}N_3O_2$ $([M-(tBu)+H]+H)^+$: m/z=254.0.

Step B: tert-Butyl {5-[2-(3-aminophenyl)ethyl]pyridin-3-yl}carbamate

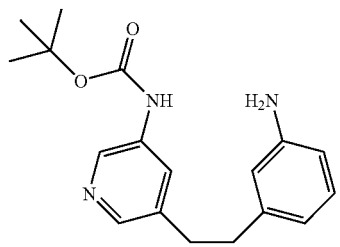 [SMILES: CC(C)(C)OC(=O)Nc1cncc(CCc2cccc(N)c2)c1]

Into the reaction flask was added tert-butyl {5-[(3-aminophenyl)ethynyl]pyridin-3-yl}carbamate (0.50 g, 1.6 mmol), 50 mL of methanol and 10% palladium on carbon (100 mg, 0.094 mmol). The mixture was hydrogenated at 50 psi for 3 h. The reaction mixture was filtered to remove the catalyst and then concentrated under vacuum to give the desired product as an off-white powder (0.50 g, 99%). LCMS for $C_{18}H_{24}N_3O_2$ $(M+H)^+$: m/z=314.1.

Step C: tert-Butyl [5-(2-{3-[(2,5-dichloropyrimidin-4-yl)amino]phenyl}ethyl)pyridin-3-yl]carbamate

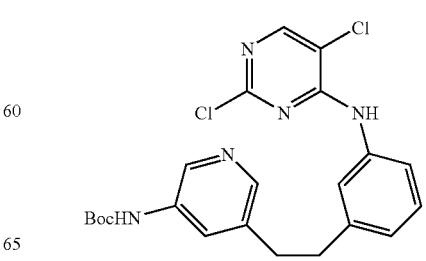

To a solution of tert-butyl {5-[2-(3-aminophenyl)ethyl]pyridin-3-yl}carbamate (0.50 g, 1.6 mmol) and 2,4,5-trichloropyrimidine (0.30 g, 1.6 mmol) in N,N-dimethylformamide (4 mL) was added potassium carbonate (0.43 g, 3.11 mmol). The resultant mixture was stirred overnight at room temperature. The reaction was quenched with water. EtOAc was added and the layers were separated. The aqueous layer was extracted with EtOAc once. The combined organic layers were washed with water and brine then dried (Na$_2$SO$_4$), filtered, and concentrated. The crude mixture was purified by silica gel column chromatography to give the desired product as a white powder (0.60 g, 82%). LCMS for C$_{22}$H$_{24}$Cl$_2$N$_5$O$_2$ (M+H)$^+$: m/z=460.1, 462.1.

Step D: N-{3-[2-(5-Aminopyridin-3-yl)ethyl]phenyl}-2,5-dichloropyrimidin-4-amine dihydrochloride

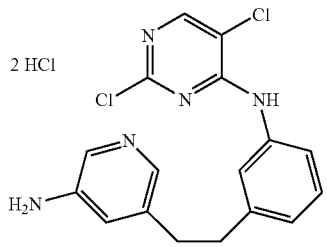 [SMILES: "2 HCl" ; Nc1cncc(CCc2cccc(Nc3nc(Cl)ncc3Cl)c2)c1]

Into the reaction vessel were added tert-butyl [5-(2-{3-[(2,5-dichloropyrmidin-4-yl)amino]phenyl}ethyl)pyridin-3-yl]carbamate (0.20 g, 0.43 mmol) and methanol (2.0 mL) and 4.0 M hydrogen chloride in 1,4-dioxane (2.0 mL). The reaction mixture was stirred at rt for 2 h and then concentrated under vacuum to give the desired product as an off-white powder (140 mg, 96%). LCMS for C$_{17}$H$_{16}$Cl$_2$N$_5$ (M+H)$^+$: m/z=360.0, 362.0.

Step E: 6-Chloro-2,4,8,18,22-pentaazatetracyclo[14.3.1.1(3,7).1(9,13)]docosa-1(20),3(22),4,6,9(21),10,12,16,18-nonaene bis(trifluoroacetate)

Into a reaction vial were added N-{3-[2-(5-aminopyridin-3-yl)ethyl]phenyl}-2,5-dichloropyrimidin-4-amine (100 mg, 0.28 mmol) and 1,4-dioxane (2 mL) and triethylamine (0.116 mL, 0.83 mmol). The mixture was stirred at rt for 5 min, followed by the addition of palladium acetate (1.2 mg, 0.006 mmol), (9,9-dimethyl-9H-xanthene-4,5-diyl)bis(diphenylphosphine) (4.8 mg, 0.008 mmol) and cesium carbonate (0.181 g, 0.56 mmol). The reaction mixture was degassed with N$_2$ bubbling. The vial was sealed and heated in a 150° C. oil bath for 1 hour. After filtration and concentration, the crude was purified by prep-HPLC to give the desired product as an off-white powder (25 mg, 28%). LCMS for C$_{17}$H$_{15}$ClN$_5$ (M+H)$^+$: m/z=324.0. $^1$H NMR (400 MHz, DMSO-d$_6$): δ 10.02 (s, 1H), 9.39 (s, 1H), 8.92 (d, J=2.0 Hz, 1H), 8.36 (d, J=1.5 Hz, 1H), 8.33 (d, J=2.3 Hz, 1H), 8.22 (s, 1H), 7.64 (d, J=1.8 Hz, 1H), 7.30 (d, J=7.8 Hz, 1H), 7.09 (m, 2H), 2.99 (m, 4H).

Example C20

(14Z)-6-Chloro-2,4,8,18,22-pentaazatetracyclo[14.3.1.1(3,7).1(9,13)]docosa-1(20),3(22),4,6,9(21),10,12,14,16,18-decaene bis(trifluoroacetate)

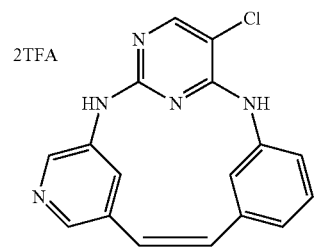 [SMILES: "2TFA" ; Clc1cnc2nc1Nc1cccc(c1)/C=C\c1cncc(c1)N2]

Step A: tert-Butyl {5-[(Z)-2-(3-aminophenyl)vinyl]pyridin-3-yl}carbamate

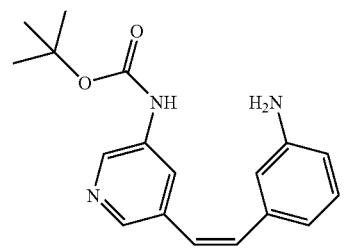 [SMILES: CC(C)(C)OC(=O)Nc1cncc(/C=C\c2cccc(N)c2)c1]

Into a reaction flask were added tert-butyl {5-[(3-aminophenyl)ethynyl]pyridin-3-yl}carbamate (0.45 g, 1.4 mmol) (prepared in Example C19, step A), methanol (15 mL) and 100 mg of Lindlar's catalyst. The reaction mixture was hydrogenated at 35 psi for 2 h. After removal of the solvent, the crude was purified by silica gel column chromatography to give the desired product as a white powder (0.19 g, 42%). LCMS for C$_{18}$H$_{22}$N$_3$O$_2$ (M+H)$^+$: m/z=312.0.

Step B: tert-Butyl [S—((Z)-2-{3-[(2,5-dichloropyrimidin-4-yl)amino]phenyl}vinyl)pyridin-3-yl]carbamate

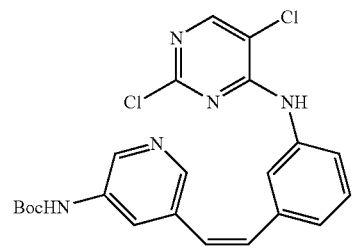 [SMILES: CC(C)(C)OC(=O)Nc1cncc(/C=C\c2cccc(Nc3nc(Cl)ncc3Cl)c2)c1]

Into a reaction flask were added tert-butyl {5-[(Z)-2-(3-aminophenyl)vinyl]pyridin-3-yl}carbamate (80 mg, 0.26 mmol) and 2,4,5-trichloropyrimidine (57 mg, 0.31 mmol) and potassium carbonate (71 mg, 0.51 mmol) and N,N-dimethylformamide (2 mL). The resultant mixture was stirred over the weekend at room temperature. The reaction was quenched with water. EtOAc was added and the layers were separated. The aqueous layer was extracted with EtOAc twice. The combined organic layers were washed with water and brine, and then dried (Na$_2$SO$_4$), filtered, and concentrated. The crude mixture was purified by silica gel column chromatography to give the desired product as a brown oil (55 mg, 47%). LCMS for C$_{22}$H$_{22}$Cl$_2$N$_5$O$_2$ (M+H)$^+$: m/z=458.0, 460.0.

Step C: N-{3-(Z)-[2-(5-Aminopyridin-3-yl)ethyl]phenyl}-2,5-dichloropyrimidin-4-amine dihydrochloride

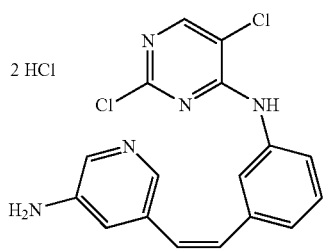 [SMILES: "2 HCl" ; Nc1cncc(/C=C\c2cccc(Nc3nc(Cl)ncc3Cl)c2)c1]

Into a reaction flask were added tert-butyl [5-((Z)-2-{3-[(2,5-dichloropyrimidin-4-yl)amino]phenyl}vinyl)pyridin-3-yl]carbamate (55 mg, 0.12 mmol), methanol (1.0 mL) and 4.0 M of hydrogen chloride in 1,4-dioxane (1.0 mL). The reaction mixture was stirred at rt for 2 h and then concentrated under vacuum to give the desired product as a white powder (39 mg, 98%). LCMS for C$_{17}$H$_{14}$Cl$_2$N$_5$ (M+H)$^+$: m/z=358.0, 360.0.

Step D: (14Z)-6-Chloro-2,4,8,18,22-pentaazatetracyclo[14.3.1.1(3,7).1(9,13)]docosa-1(20),3(22),4,6,9(21),10,12,14,16,18-decaene bis(trifluoroacetate)

Into a reaction vial were added N-{3-[(Z)-2-(5-aminopyridin-3-yl)vinyl]phenyl}-2,5-dichloropyrimidin-4-amine (50 mg, 0.14 mmol), 1,4-dioxane (2 mL) and triethylamine (0.058 mL, 0.42 mmol). The mixture was stirred at rt for 5 min, followed by the addition of palladium acetate (0.6 mg, 0.003 mmol), (9,9-dimethyl-9H-xanthene-4,5-diyl)bis(diphenylphosphine) (2.4 mg, 0.004 mmol) and cesium carbonate (91 mg, 0.28 mmol). The reaction mixture was degassed with N$_2$ bubbling. The vial was sealed and heated in a 150° C. oil bath for 1 h. The solvent was removed under vacuum and the crude was purified by prep-HPLC to give the desired product as a white powder (15 mg, 30%). LCMS for C$_{17}$H$_{13}$ClN$_5$ (M+H)$^+$: m/z=322.0. $^1$H NMR (400 MHz, DMSO-d$_6$): δ 9.89 (s, 1H), 9.48 (d, J=2.0 Hz, 1H), 9.35 (s, 1H), 8.40 (s, 1H), 8.31 (s, 2H), 8.22 (s, 1H), 7.33 (d, J=7.9 Hz, 1H), 7.24 (ddd, J=7.9, 2.0, 1.2 Hz, 1H), 7.08 (d, J=7.7 Hz, 1H), 6.91 (d, J=13.0 Hz, 1H), 6.67 (d, J=13.2 Hz, 1H).

Example C21

6-Fluoro-2,4,8,18,22-pentaazatetracyclo[14.3.1.1(3,7).1(9,13)]docosa-1(20),3(22),4,6,9(21),10,12,16,18-nonaene bis(trifluoroacetate)

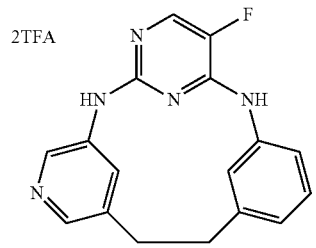 [SMILES: "2TFA" ; Fc1cnc2nc1Nc1cccc(c1)CCc1cncc(c1)N2]

Step A: tert-Butyl [5-(2-{3-[(2-chloro-5-fluoropyrimidin-4-yl)amino]phenyl}ethyl)pyridin-3-yl]carbamate

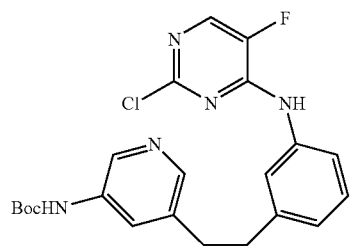

To a solution of tert-butyl {5-[2-(3-aminophenyl)ethyl]pyridin-3-yl}carbamate (0.20 g, 0.64 mmol) (prepared in Example C19, step B) and 2,4-dichloro-5-fluoropyrimidine (200 mg, 1.2 mmol) in N,N-dimethylformamide (4 mL) was added potassium carbonate (0.430 g, 3.1 mmol). The resultant mixture was stirred overnight at room temperature. The reaction was quenched with water. EtOAc was added and the layers were separated. The aqueous layer was extracted with EtOAc once. The combined organic layers were washed with water and brine, and then dried (Na$_2$SO$_4$), filtered, and concentrated. The crude was purified by silica gel column chromatography to give the desired product as a light yellow oil (60 mg, 20%). LCMS for C$_{22}$H$_{24}$ClFN$_5$O$_2$ (M+H)$^+$: m/z=444.0.

Step B: N-{3-[2-(5-Aminopyridin-3-yl)ethyl]phenyl}-2-chloro-5-fluoropyrimidin-4-amine dihydrochloride

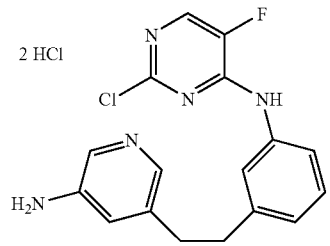 [SMILES: "2 HCl" ; Nc1cncc(CCc2cccc(Nc3nc(Cl)ncc3F)c2)c1]

Into a reaction flask were added tert-butyl [5-(2-{3-[(2-chloro-5-fluoropyrimidin-4-yl)amino]phenyl}ethyl)pyridin-3-yl]carbamate (48 mg, 0.11 mmol), methanol (0.50 mL) and 4.0 M of hydrogen chloride in 1,4-dioxane (0.50 mL). The reaction mixture was stirred at rt for 2 h and then concentrated under vacuum to give the desired product as an off-white powder (35 mg, 97%). LCMS for C$_{17}$H$_{16}$ClFN$_5$ (M+H)$^+$: m/z=344.0.

Step C: 6-Fluoro-2,4,8,18,22-pentaazatetracyclo
[14.3.1.1(3,7).1(9,13)]docosa-1(20),3(22),4,6,9(21),
10,12,16,18-nonaene bis(trifluoroacetate)

Into a reaction vial were added N-{3-[2-(5-aminopyridin-3-yl)ethyl]phenyl}-2-chloro-5-fluoropyrimidin-4-amine dihydrochloride (30 mg, 0.087 mmol), 1,4-dioxane (1 mL) and triethylamine (0.037 mL, 0.26 mmol). The mixture was stirred at rt for 5 min, followed by the addition of palladium acetate (0.4 mg, 0.0017 mmol), (9,9-dimethyl-9H-xanthene-4,5-diyl)bis(diphenylphosphine) (1.5 mg, 0.0026 mmol) and cesium carbonate (56.9 mg, 0.17 mmol). The reaction mixture was degassed with $N_2$ bubbling. The vial was sealed and heated in a 150° C. oil bath for 2 h. After concentration, the crude was purified by prep-HPLC to give the desired product as an off-white powder (10 mg, 37%). LCMS for $C_{17}H_{15}FN_5$ (M+H)$^+$: m/z=308.1. $^1$H NMR (400 MHz, DMSO-$d_6$): δ 9.99 (s, 1H), 9.84 (s, 1H), 8.97 (d, J=2.0 Hz, 1H), 8.40 (d, J=1.5 Hz, 1H), 8.36 (d, J=2.3 Hz, 1H), 8.20 (d, J=4.1 Hz, 1H), 7.71 (d, J=1.8 Hz, 1H), 7.30 (d, J=7.9 Hz, 1H), 7.07 (m, 2H), 3.01 (m, 2H), 2.94 (m, 2H).

Example C22

14-Benzoyl-6-chloro-2,4,8,14,22-pentaazatetracyclo
[14.3.1.1(3,7).1(9,13)]docosa-1(20),3(22),4,6,9(21),
10,12,16,18-nonaene

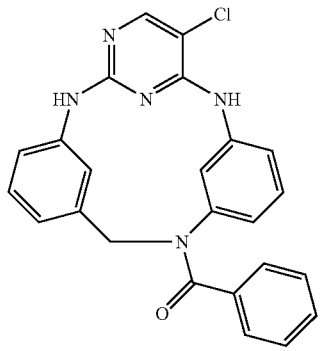

Step A: tert-Butyl {3-[(3-nitrobenzyl)amino]
phenyl}carbamate

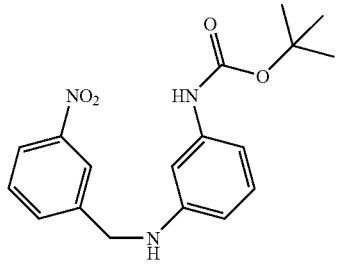 [SMILES: CC(C)(C)OC(=O)Nc1cccc(NCc2cccc([N+](=O)[O-])c2)c1]

To a solution of 1-(bromomethyl)-3-nitro-benzene (4.50 g, 0.021 mol) and tert-butyl (3-aminophenyl)carbamate (4.34 g, 0.021 mol) in N,N-dimethylformamide (50 mL) was added potassium carbonate (4.32 g, 0.03 mol). The resultant mixture was stirred at room temperature overnight and the reaction was complete. The reaction mixture was filtered first to remove $K_2CO_3$, and then quenched with water. EtOAc was added and the layers were separated. The aqueous layer was extracted with EtOAc twice. The combined organic layers were washed with water and then dried ($Na_2SO_4$), filtered and concentrated to give the desired product as a light brown gel (6.94 g, 97%). LCMS for $C_{18}H_{22}N_3O_4$ (M+H)+: m/z=344.1.

Step B: N-(3-Nitrobenzyl)benzene-1,3-diamine
dihydrochloride

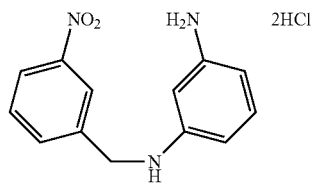 [SMILES: Nc1cccc(NCc2cccc([N+](=O)[O-])c2)c1 ; "2HCl"]

tert-Butyl {3-[(3-nitrobenzyl)amino]phenyl}carbamate (7.15 g, 0.021 mol) was mixed with 4 M of hydrogen chloride in 1,4-dioxane (68.3 mL) and stirred at rt for 1 hour and concentrated to give the desired product (6.32 g, 96%) as an off-white powder. LCMS for $C_{13}H_{14}N_3O_2$ (M+H)+: m/z=244.1.

Step C: N-(2,5-Dichloropyrimidin-4-yl)-N'-(3-nitrobenzyl)benzene-1,3-diamine

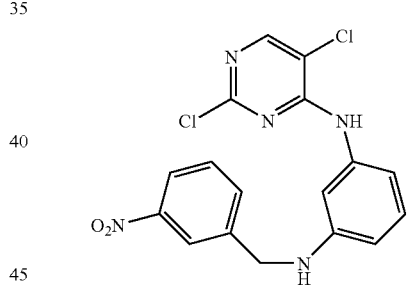

To a solution of N-(3-nitrobenzyl)benzene-1,3-diamine dihydrochloride (6.58 g, 0.021 mol) and 2,4,5-trichloropyrimidine (2.38 mL, 0.021 mol) in N,N-dimethylformamide (70 mL) was added potassium carbonate (10.1 g, 0.073 mol). The resultant mixture was stirred for 60 h at room temperature. The reaction mixture was filtered first to remove $K_2CO_3$, and then quenched with water. EtOAc was added and the layers were separated. The aqueous layer was extracted with EtOAc twice. The combined organic layers were washed with water and then dried ($Na_2SO_4$), filtered and concentrated to give the residue (10.5 g), which was purified by silica gel column chromatography to give the desired product as a light yellow powder (6.19 g, 76%). LCMS for $C_{17}H_{14}Cl_2N_5O_2$ (M+H)$^+$: m/z=389.9.

Step D: N-(3-Aminobenzyl)-N'-(2,5-dichloropyrimi-din-4-yl)benzene-1,3-diamine

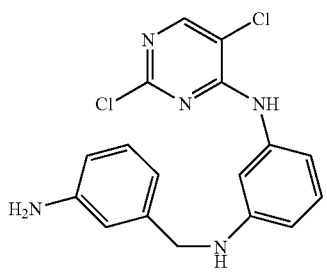 [SMILES: O=[N+]([O-])c1cccc(CNc2cccc(Nc3nc(Cl)ncc3Cl)c2)c1]

To a solution of N-(2,5-dichloropyrimidin-4-yl)-N'-(3-nitrobenzyl)benzene-1,3-diamine (2.00 g, 5.12 mmol) in methanol (30 mL) was added 10% palladium on carbon (200 mg, 0.2 mmol). The resultant mixture was hydrogenated at 25 psi for 18 h. The reaction mixture was filtered, washed with MeOH and concentrated to give the desired product (1.72 g, 93%) as a light yellow powder. LCMS for $C_{17}H_{16}Cl_2N_5$ (M+H)$^+$: m/z=360.2.

Step E: 6-Chloro-2,4,8,14,22-pentaazatetracyclo[14.3.1.1(3,7).1(9,13)]docosa-1(20),3(22),4,6,9(21),10,12,16,18-nonaene

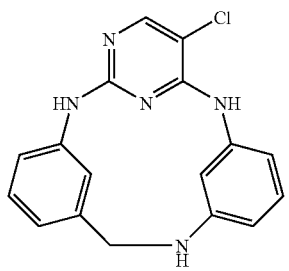 [SMILES: Clc1cnc2nc1Nc1cccc(c1)NCc1cccc(c1)N2]

To a solution of N-(3-aminobenzyl)-N'-(2,5-dichloropyrimidin-4-yl)benzene-1,3-diamine (900 mg, 2.0 mmol) in 2-methoxyethanol (18 mL) was added 4.00 M of hydrogen chloride in 1,4-dioxane (1.88 mL). The resultant mixture was heated at 150° C. in the microwave for 5 min. After cooling, water and NaOH (12 N) were added to neutralize the mixture to pH=7. The aqueous layer was extracted with EtOAc four times. The combined organic layers were dried, filtered and concentrated. The residue was purified by silica gel column chromatography to give the desired product as an off-white powder (66 mg, 8%). LCMS for $C_{17}H_{15}ClN_5$ (M+H)$^+$: m/z=324.0.

Step F: 14-Benzoyl-6-chloro-2,4,8,14,22-pentaazatetracyclo[14.3.1.1(3,7).1(9,13)]docosa-1(20),3(22),4,6,9(21),10,12,16,18-nonaene To a stirring solution of 6-chloro-2,4,8,14,22-pentaazatetracyclo[14.3.1.1(3,7).1(9,13)]docosa-1(20),3(22),4,6,9(21),10,12,16,18-nonaene (20.0 mg, 0.0618 mmol) in N,N-dimethylformamide (0.24 mL) was added triethylamine (17.2 μL), followed by the addition of benzoyl chloride (17.4 mg, 0.12 mmol). The resultant solution was stirred at rt for 30 min. The mixture was quenched with H$_2$O and concentrated. The residue was purified by silica gel column chromatography to give the desired product as an off-white powder (11 mg, 42%). LCMS for $C_{24}H_{19}ClN_5O$ (M+H)$^+$: m/z=428.1. $^1$H NMR (300 MHz, DMSO-d$_6$): δ 9.42 (s, 1H), 9.11 (s, 1H), 8.12 (s, 2H), 7.82 (s, 1H), 7.25 (m, 4H), 7.15 (m, 4H), 7.03 (m, 3H), 4.86 (m, 2H).

Example C23

6-Chloro-14-(pyridin-2-ylcarbonyl)-2,4,8,14,22-pentaazatetracyclo[14.3.1.1(3,7).1(9,13)]docosa-1(20),3(22),4,6,9(21),10,12,16,18-nonaene

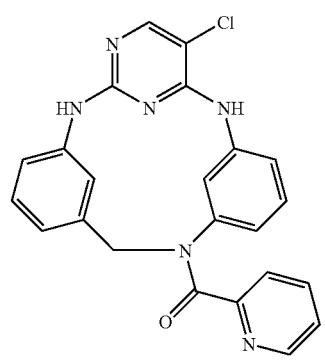 [SMILES: O=C(c1ccccn1)N1Cc2cccc(c2)Nc2ncc(Cl)c(n2)Nc2cccc1c2]

The desired compound was prepared as a white powder according to the procedure of Example C22, step F, using 6-chloro-2,4,8,14,22-pentaazatetracyclo[14.3.1.1(3,7).1(9,13)]docosa-1(20),3(22),4,6,9(21),10,12,16,18-nonaene and pyridine-2-carbonyl chloride hydrochloride as the starting materials in 29% yield. LCMS for $C_{23}H_{18}ClN_6O$ (M+H)$^+$: m/z=429.0.

Example C24

6-Chloro-14-(4-methylbenzoyl)-2,4,8,14,22-pentaazatetracyclo[14.3.1.1(3,7).1(9,13)]docosa-1(20),3(22),4,6,9(21),10,12,16,18-nonaene

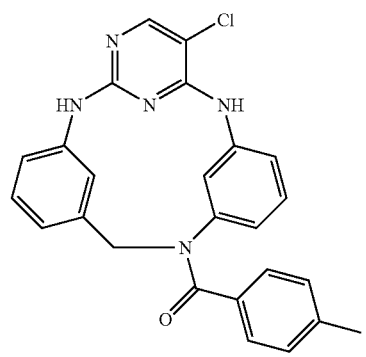 [SMILES: Cc1ccc(C(=O)N2Cc3cccc(c3)Nc3ncc(Cl)c(n3)Nc3cccc2c3)cc1]

The desired compound was prepared as a white powder according to the procedure of Example C22, step F, using 6-chloro-2,4,8,14,22-pentaazatetracyclo[14.3.1.1(3,7).1(9,13)]docosa-1(20),3(22),4,6,9(21),10,12,16,18-nonaene and 4-methylbenzoic acid chloride as the starting materials in 48% yield. LCMS for $C_{25}H_{21}ClN_5O$ (M+H)$^+$: m/z=442.0.

Example C25

6-Chloro-14-(2-thienylcarbonyl)-2,4,8,14,22-pentaazatetracyclo[14.3.1.1(3,7).1(9,13)]docosa-1(20),3(22),4,6,9(21),10,12,16,18-nonaene

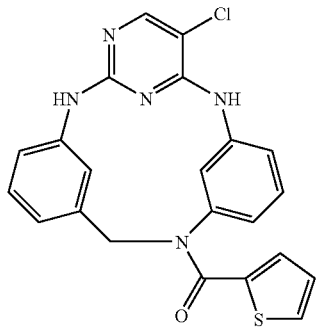 [SMILES: O=C(c1cccs1)N1Cc2cccc(c2)Nc2ncc(Cl)c(n2)Nc2cccc1c2]

The desired compound was prepared as a white powder according to the procedure of Example C22, step F, using 6-chloro-2,4,8,14,22-pentaazatetracyclo[14.3.1.1(3,7).1(9,13)]docosa-1(20),3(22),4,6,9(21),10,12,16,18-nonaene and 2-thiophenecarbonyl chloride as the starting materials in 34% yield. LCMS for $C_{22}H_{17}ClN_5OS$ (M+H)$^+$: m/z=434.0.

Example C26

14-Butyryl-6-chloro-2,4,8,14,22-pentaazatetracyclo [14.3.1.1(3,7).1(9,13)]docosa-1(20),3(22),4,6,9(21),10,12,16,18-nonaene

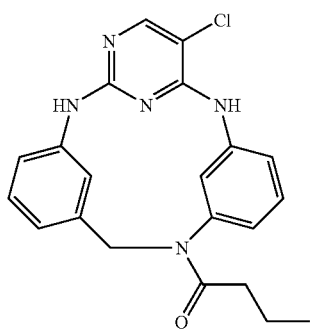 [SMILES: CCCC(=O)N1Cc2cccc(c2)Nc2ncc(Cl)c(n2)Nc2cccc1c2]

The desired compound was prepared as a white powder according to the procedure of Example C22, step F, using 6-chloro-2,4,8,14,22-pentaazatetracyclo[14.3.1.1(3,7).1(9,13)]docosa-1(20),3(22),4,6,9(21),10,12,16,18-nonaene and butyryl chloride as the starting materials in 50% yield. LCMS for $C_{21}H_{21}ClN_5O$ (M+H)$^+$: m/z=394.1.

Example C27

6-Chloro-14-(pyridin-3-ylcarbonyl)-2,4,8,14,22-pentaazatetracyclo[14.3.1.1(3,7).1(9,13)]docosa-1(20),3(22),4,6,9(21),10,12,16,18-nonaene

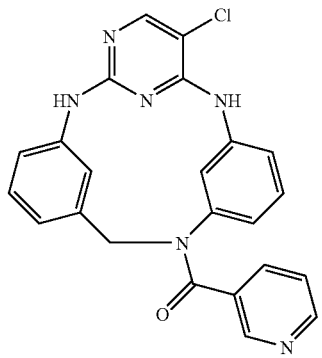 [SMILES: O=C(c1cccnc1)N1Cc2cccc(c2)Nc2ncc(Cl)c(n2)Nc2cccc1c2]

The desired compound was prepared as a white powder according to the procedure of Example C22, step F, using 6-chloro-2,4,8,14,22-pentaazatetracyclo[14.3.1.1(3,7).1(9,13)]docosa-1(20),3(22),4,6,9(21),10,12,16,18-nonaene and nicotinoyl chloride hydrochloride as the starting materials in 60% yield. LCMS for $C_{23}H_{18}ClN_6O$ (M+H)$^+$: m/z=429.0. $^1$H NMR (300 MHz, DMSO-d$_6$): δ 9.43 (s, 1H), 9.15 (s, 1H), 8.40 (s, 1H), 8.14 (s, 2H), 7.89 (s, 1H), 7.62 (s, 1H), 7.23 (m, 4H), 7.10 (m, 4H), 4.85 (m, 2H).

Example C28

Methyl 6-chloro-2,4,8,18,22-pentaazatetracyclo [14.3.1.1(3,7).1(9,13)]docosa-1(20),3(22),4,6,9(21),10,12,16,18-nonaene-12-carboxylate

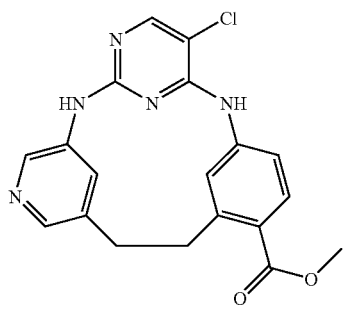 [SMILES: COC(=O)c1ccc2cc1CCc1cncc(c1)Nc1ncc(Cl)c(n1)N2]

Step A: 6-Chloro-12-iodo-2,4,8,18,22-pentaazatetra-
cyclo[14.3.1.1(3,7).1(9,13)]docosa-1(20),3(22),4,6,9
(21),10,12,16,18-nonaene

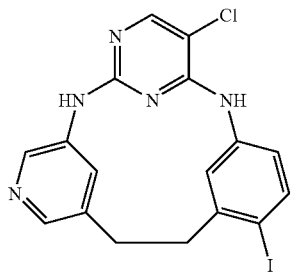 [SMILES: Clc1cnc2nc1Nc1ccc(I)c(c1)CCc1cncc(c1)N2]

To a suspension of 6-chloro-2,4,8,18,22-pentaazatetracy-clo[14.3.1.1(3,7).1(9,13)]docosa-1(20),3(22),4,6,9(21),10,12,16,18-nonaen-12-amine trihydrochloride (30.0 mg, 0.067 mmol) (prepared in Example B19, step F) in 2.0 M of sulfuric acid in water (0.502 mL) was added a solution of sodium nitrite (6.93 mg, 0.10 mmol) in water dropwise at 0° C. After addition, the resultant cloudy solution was stirred at same temperature for 1 h. Then this cold solution was added dropwise to a solution of potassium iodide (16.7 mg, 0.10 mmol) and copper cyanide (0.90 mg, 0.01 mmol) in water at 0° C. The resultant mixture was stirred at rt overnight. The precipite was filtered and washed by water and dried to give the desired product as a light brown powder (28 mg, 93%). LCMS for $C_{17}H_{14}ClIN_5$ (M+H)$^+$: m/z=449.9.

Step B: Methyl 6-chloro-2,4,8,18,22-pentaazatetra-
cyclo[14.3.1.1(3,7).1(9,13)]docosa-1(20),3(22),4,6,9
(21),10,12,16,18-nonaene-12-carboxylate The mixture of 6-chloro-12-iodo-2,4,8,18,22-pentaazatet-racyclo[14.3.1.1(3,7).1(9,13)]docosa-1(20),3(22),4,6,9(21),10,12,16,18-nonaene (20.0 mg, 0.0445 mmol) in methanol (2.0 mL) was added triethylamine (0.0248 mL, 0.178 mmol) and [1,1'-bis(diphenylphosphino)ferrocene]dichloropalladium(II), complex with dichloromethane (1:1) (20.0 mg, 0.025 mmol). The mixture was refluxed under a CO balloon overnight. The mixture was filtered and concentrated. The residue was purified by silica gel column chromatography to give the desired product as an off-white powder (7 mg, 41%). LCMS for $C_{19}H_{17}ClN_5O_2$ (M+H)$^+$: m/z=382.0.

Example C29

N-[6-Chloro-2,4,8,22-tetraazatetracyclo[14.3.1.1(3,
7).1(9,13)]docosa-1(20),3(22),4,6,9(21),10,12,16,18-
nonaen-12-yl]-2-(1H-indol-3-yl)acetamide bis(trif-
luoroacetate)

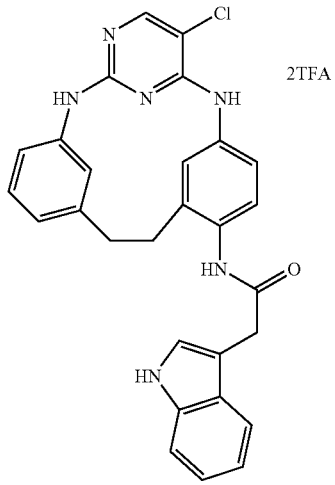 [SMILES: O=C(Cc1c[nH]c2ccccc12)Nc1ccc2cc1CCc1cccc(c1)Nc1ncc(Cl)c(n1)N2 ; "2TFA"]

A solution of indole-3-acetic acid (6.5 mg, 0.037 mmol), N,N,N',N'-tetramethyl-O-(7-azabenzotriazol-1-yl)uronium hexafluorophosphate (38 mg, 0.10 mmol) in N,N-dimethyl-formamide (0.5 mL) and N,N-diisopropylethylamine (15 μL, 0.086 mmol) was stirred for 15 minutes. A solution of 6-chloro-2,4,8,22-tetraazatetracyclo[14.3.1.1(3,7).1(9,13)] docosa-1(20),3(22),4,6,9(21),10,12,16,18-nonaen-12-amine dihydrochloride (15 mg, 0.036 mmol) (prepared in Example C20, step H) in N,N-dimethylformamide (0.2 mL) and N,N-diisopropylethylamine (15 μL, 0.086 mmol) was added to the previous solution and the reaction mixture was stirred overnight. The reaction mixture was concentrated and purified by preparative LCMS (pH 2) to afford the desired product as a tristrifluoroacetic acid salt (10 mg, 55%). LCMS for $C_{28}H_{24}ClN_6O$ (M+H)$^+$: m/z=495.1. $^1$H NMR (300 MHz, DMSO-d$_6$): δ 10.96 (s, 1H), 9.36 (s, 1H), 9.25 (s, 1H), 8.10 (s, 1H), 7.93 (s, 1H), 7.66 (m, 2H), 7.38 (d, J=8.1 Hz, 1H), 7.30 (m, 2H), 7.10 (m, 2H), 7.01 (m, 3H), 6.82 (m, 1H), 6.53 (m, 1H), 3.76 (s, 2H), 2.76 (m, 4H).

Example C30

N-[6-Chloro-2,4,8,22-tetraazatetracyclo[14.3.1.1(3,
7).1(9,13)]docosa-1(20),3(22),4,6,9(21),10,12,16,18-
nonaen-12-yl]-2-(3-methylisoxazol-5-yl)acetamide
trifluoroacetate

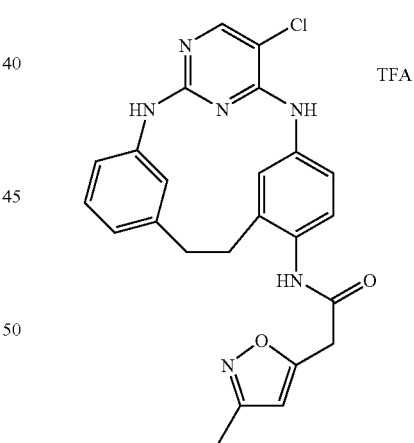

The desired compound was prepared according to the procedure of Example C29, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and (3-methylisoxazol-5-yl)acetic acid as the starting materials in 36% yield (6 mg). LCMS for $C_{24}H_{22}ClN_6O_2$ (M+H)$^+$: m/z=461.0. $^1$H NMR (300 MHz, DMSO-d$_6$): δ 9.67 (s, 1H), 9.37 (s, 1H), 9.26 (s, 1H), 8.11 (s, 1H), 7.98 (s, 1H), 7.76 (d, J=2.7 Hz, 1H), 7.25 (m, 1H), 7.06 (m, 2H), 6.86 (m, 1H), 6.75 (m, 1H), 6.27 (s, 1H), 3.91 (s, 2H), 2.84 (m, 4H), 2.21 (s, 3H).

Example C31

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-(1H-tetrazol-5-yl)acetamide trifluoroacetate

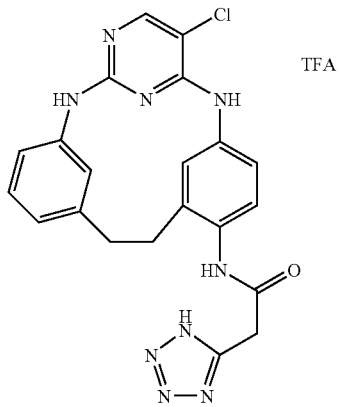 [SMILES: "TFA" ; O=C(Cc1nnn[nH]1)Nc1ccc2cc1CCc1cccc(c1)Nc1ncc(Cl)c(n1)N2]

The desired compound was prepared according to the procedure of Example C29, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 1H-tetrazol-5-ylacetic acid as the starting materials in 50% yield. LCMS for $C_{21}H_{19}ClN_9O$ (M+H)$^+$: m/z=448.0. $^1$H NMR (300 MHz, DMSO-$d_6$): δ 9.81 (s, 1H), 9.31 (s, 1H), 9.15 (s, 1H), 8.09 (s, 1H), 8.00 (m, 1H), 7.78 (m, 1H), 7.28 (m, 1H), 7.07 (m, 2H), 6.87 (m, 1H), 6.76 (m, 1H), 4.17 (s, 2H), 2.86 (s, 4H).

Example C32

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-(3-thienyl)acetamide trifluoroacetate

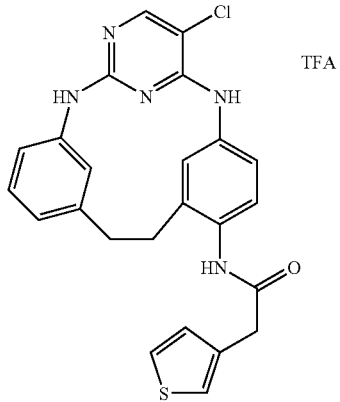 [SMILES: "TFA" ; O=C(Cc1ccsc1)Nc1ccc2cc1CCc1cccc(c1)Nc1ncc(Cl)c(n1)N2]

The desired compound was prepared according to the procedure of Example C29, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 3-thienylacetic acid as the starting materials in 25% yield. LCMS for $C_{24}H_{21}ClN_5OS$ (M+H)$^+$: m/z=462.0. $^1$H NMR (300 MHz, DMSO-$d_6$): δ 9.46 (s, 1H), 9.40 (s, 1H), 9.30 (s, 1H), 8.11 (s, 1H), 7.96 (s, 1H), 7.72 (d, J=2.4 Hz, 1H), 7.52 (dd, J=4.9, 3.0 Hz, 1H), 7.36 (m, 1H), 7.26 (d, J=8.4 Hz, 1H), 7.13 (dd, J=5.0, 1.2 Hz, 1H), 7.06 (t, J=7.9 Hz, 1H), 7.02 (dd, J=8.6, 2.2 Hz, 1H), 6.85 (d, J=8.5 Hz, 1H), 6.70 (d, J=7.7 Hz, 1H), 3.68 (s, 2H), 2.75 (m, 4H).

Example C33

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-(1H-imidazol-4-yl)acetamide bis(trifluoroacetate)

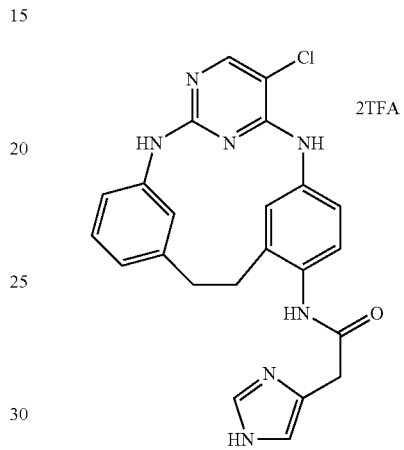

The desired compound was prepared according to the procedure of Example C29, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 1H-imidazol-4-ylacetic acid hydrochloride as the starting materials in 31% yield. LCMS for $C_{23}H_{21}ClN_7O$ (M+H)$^+$: m/z=446.1.

Example C34

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-(2-methyl-1H-indol-3-yl)acetamide trifluoroacetate

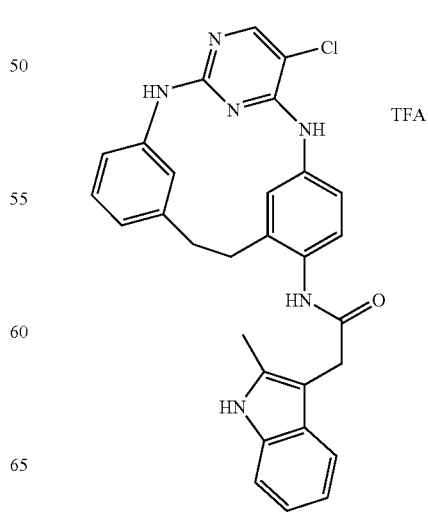

The desired compound was prepared according to the procedure of Example C29, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and (2-methyl-1H-indol-3-yl)acetic acid as the starting materials in 54% yield. LCMS for $C_{29}H_{26}ClN_6O$ (M+H)$^+$: m/z=509.1. $^1$H NMR (300 MHz, DMSO-$d_6$): δ 10.87 (s, 1H), 9.32 (s, 1H), 9.20 (s, 1H), 9.10 (s, 1H), 8.08 (s, 1H), 7.94 (s, 1H), 7.67 (m, 1H), 7.59 (m, 1H), 7.32 (m, 1H), 7.26 (m, 2H), 7.00 (m, 5H), 6.82 (m, 2H), 6.54 (m, 1H), 3.70 (s, 2H), 2.70 (s, 4H).

Example C35

2-(1-Benzothien-3-yl)-N-[6-chloro-2,4,8,22-tetraazatetracyclo[14.3.1.1(3,7).1(9,13)]docosa-1(20),3(22),4,6,9(21),10,12,16,18-nonaen-12-yl]acetamide trifluoroacetate

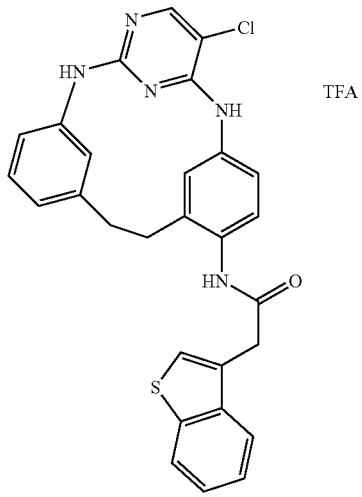 [SMILES: O=C(Cc1csc2ccccc12)Nc1ccc2cc1CCc1cccc(c1)Nc1ncc(Cl)c(n1)N2]

The desired compound was prepared according to the procedure of Example C29, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and benzo[b]thiophene-3-acetic acid as the starting materials in 64% yield. LCMS for $C_{28}H_{23}ClN_5OS$ (M+H)$^+$: m/z=512.0.

Example C36

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-(2-furyl)acetamide trifluoroacetate

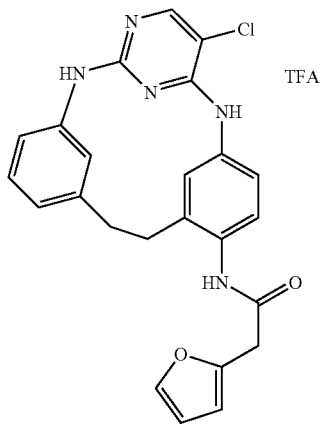 [SMILES: O=C(Cc1ccco1)Nc1ccc2cc1CCc1cccc(c1)Nc1ncc(Cl)c(n1)N2]

The desired compound was prepared according to the procedure of Example C29, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 2-furylacetic acid as the starting materials in 61% yield. LCMS for $C_{24}H_{21}ClN_5O_2$ (M+H)$^+$: m/z=446.1. $^1$H NMR (300 MHz, DMSO-$d_6$): δ 9.51 (s, 1H), 9.36 (s, 1H), 9.24 (s, 1H), 8.11 (s, 1H), 7.99 (s, 1H), 7.74 (d, J=2.3 Hz, 1H), 7.61 (m, 1H), 7.25 (d, J=8.5 Hz, 1H), 7.06 (m, 2H), 6.86 (m, 1H), 6.74 (m, 1H), 6.42 (dd, J=3.2, 2.0 Hz, 1H), 6.29 (m, 1H), 3.75 (s, 2H), 2.82 (m, 4H).

Example C37

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-(1-methyl-1H-indol-3-yl)acetamide trifluoroacetate

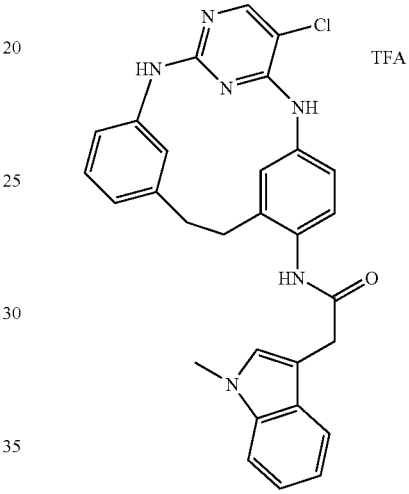

The desired compound was prepared according to the procedure of Example C29, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 1-methyl-3-indoleacetic acid as the starting materials in 54% yield. LCMS for $C_{29}H_{26}ClN_6O$ (M+H)$^+$: m/z=509.2.

Example C38

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-(2-methyl-1,3-thiazol-4-yl)acetamide trifluoroacetate

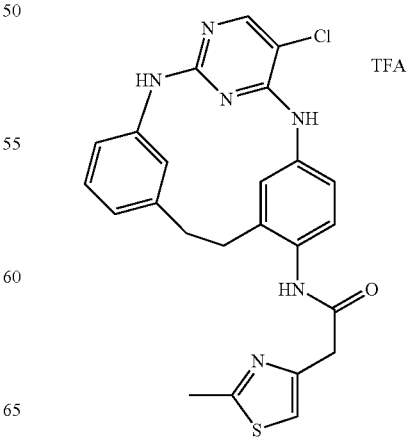

The desired compound was prepared according to the procedure of Example C29, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and (2-methyl-1,3-thiazol-4-yl)acetic acid as the starting materials in 57% yield. LCMS for $C_{24}H_{22}ClN_6OS$ (M+H)$^+$: m/z=477.0.

Example C39

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-pyridin-3-ylacetamide bis(trifluoroacetate)

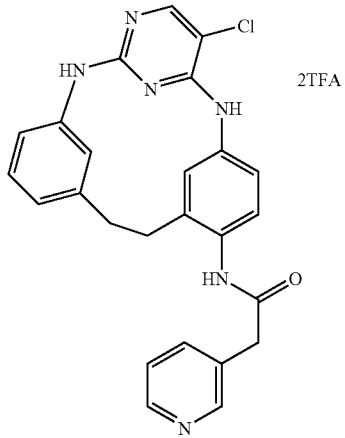 [SMILES: O=C(Cc1cccnc1)Nc1ccc2cc1CCc1cccc(c1)Nc1ncc(Cl)c(n1)N2 ; "2TFA"]

The desired compound was prepared according to the procedure of Example C29, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and pyridin-3-ylacetic acid as the starting materials in 48% yield. LCMS for $C_{25}H_{22}ClN_6O$ (M+H)$^+$: m/z=457.1.

Example C40

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-pyridin-4-ylacetamide bis(trifluoroacetate)

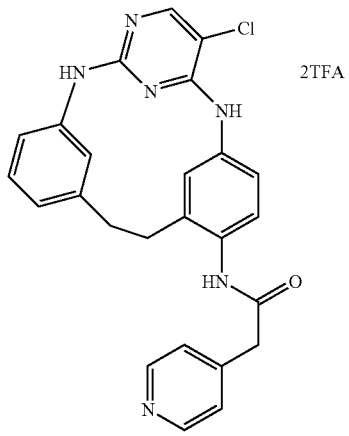 [SMILES: O=C(Cc1ccncc1)Nc1ccc2cc1CCc1cccc(c1)Nc1ncc(Cl)c(n1)N2 ; "2TFA"]

The desired compound was prepared according to the procedure of Example C29, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and pyridin-4-ylacetic acid as the starting materials in 45% yield. LCMS for $C_{25}H_{22}ClN_6O$ (M+H)$^+$: m/z=457.0.

Example C41

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-pyridin-2-ylacetamide bis(trifluoroacetate)

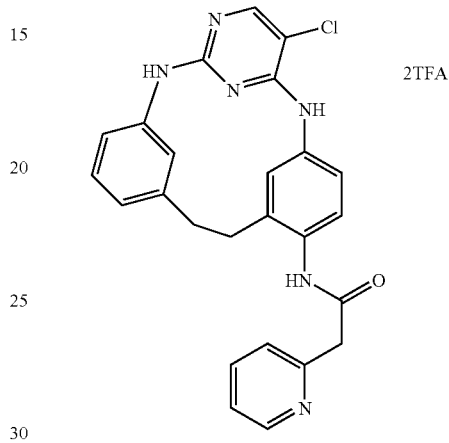

The desired compound was prepared according to the procedure of Example C29, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and pyridin-2-ylacetic acid as the starting materials in 45% yield. LCMS for $C_{25}H_{22}ClN_6O$ (M+H)$^+$: m/z=457.2.

Example C42

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-(2-thienyl)acetamide trifluoroacetate

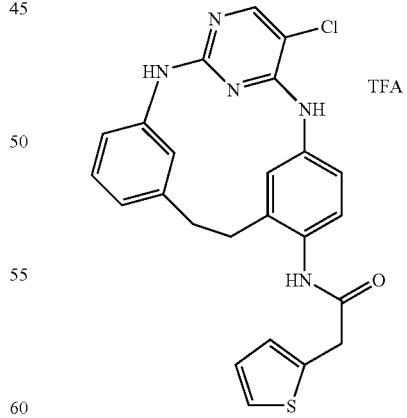

The desired compound was prepared according to the procedure of Example C29, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 2-thienylacetic acid as the starting materials in 20% yield. LCMS for $C_{24}H_{21}ClN_5OS$ (M+H)$^+$: m/z=462.0.

Example C43

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-(2,4-dimethyl-1,3-thiazol-5-yl)acetamide trifluoroacetate

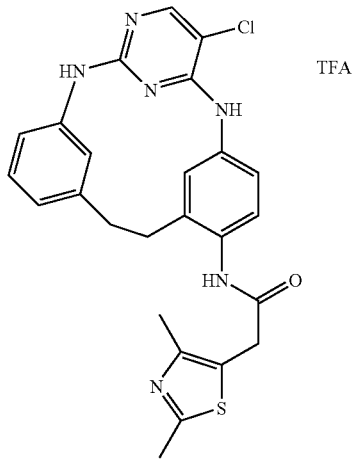 [SMILES: Cc1nc(C)c(CC(=O)Nc2ccc3cc2CCc2cccc(c2)Nc2ncc(Cl)c(n2)N3)s1]

The desired compound was prepared according to the procedure of Example C29, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and (2,4-dimethyl-1,3-thiazol-5-yl)acetic acid as the starting materials in 42% yield. LCMS for $C_{25}H_{24}ClN_6OS$ (M+H)$^+$: m/z=491.0.

Example C44

2-(1H-Benzimidazol-2-yl)-N-[6-chloro-2,4,8,22-tetraazatetracyclo[14.3.1.1(3,7).1(9,13)]docosa-1(20),3(22),4,6,9(21),10,12,16,18-nonaen-12-yl]acetamide bis(trifluoroacetate)

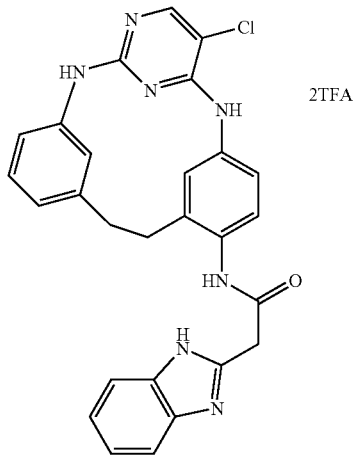 [SMILES: O=C(Cc1nc2ccccc2[nH]1)Nc1ccc2cc1CCc1cccc(c1)Nc1ncc(Cl)c(n1)N2 ; "2TFA"]

The desired compound was prepared according to the procedure of Example C29, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 1H-benzimidazol-2-ylacetic acid as the starting materials in 23% yield. LCMS for $C_{27}H_{23}ClN_7O$ (M+H)$^+$: m/z=496.0.

Example C45

2-(1,2-Benzisoxazol-3-yl)-N-[6-chloro-2,4,8,22-tetraazatetracyclo[14.3.1.1(3,7).1(9,13)]docosa-1(20),3(22),4,6,9(21),10,12,16,18-nonaen-12-yl]acetamide trifluoroacetate

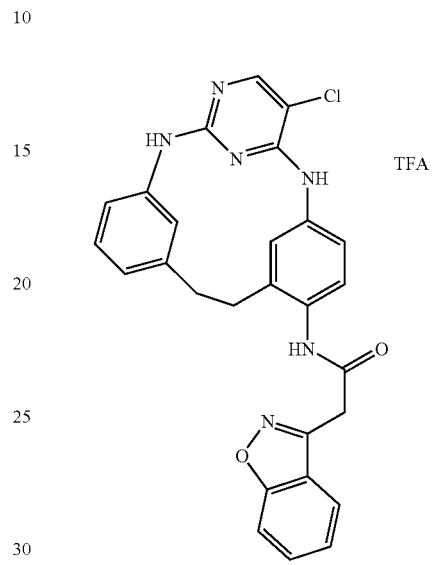

The desired compound was prepared according to the procedure of Example C29, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 1,2-benzisoxazol-3-ylacetic acid as the starting materials in 10% yield. LCMS for $C_{27}H_{22}ClN_6O_2$ (M+H)$^+$: m/z=497.1.

Example C46

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-(2,5-dimethyl-1,3-thiazol-4-yl)acetamide trifluoroacetate

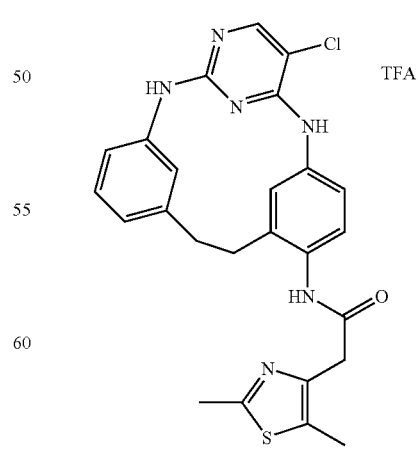

The desired compound was prepared according to the procedure of Example C29, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and (2,5-dimethyl-1,3-thiazol-4-yl)acetic acid as the starting materials in 42% yield. LCMS for $C_{25}H_{24}ClN_6OS$ $(M+H)^+$: m/z=491.0.

Example C47

2-(1-Benzofuran-3-yl)-N-[6-chloro-2,4,8,22-tetraazatetracyclo[14.3.1.1(3,7).1(9,13)]docosa-1(20),3(22),4,6,9(21),10,12,16,18-nonaen-12-yl]acetamide trifluoroacetate

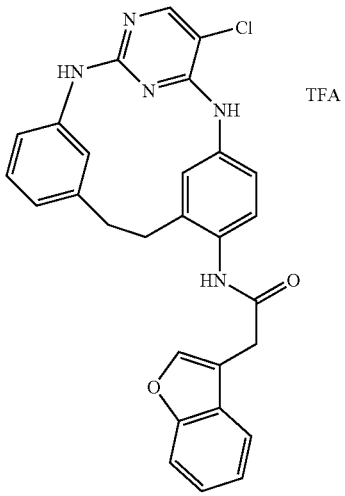 [SMILES: O=C(Cc1coc2ccccc12)Nc1ccc2cc1CCc1cccc(c1)Nc1ncc(Cl)c(n1)N2]

The desired compound was prepared according to the procedure of Example C29, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 1-benzofuran-3-ylacetic acid as the starting materials in 28% yield. LCMS for $C_{28}H_{23}ClN_5O_2$ $(M+H)^+$: m/z=496.0.

Example C48

N-[6-Chloro-2,4,8,22-tetraazatetracyclo[14.3.1.1(3,7).1(9,13)]docosa-1(20),3(22),4,6,9(21),10,12,16,18-nonaen-12-yl]-3-(4-methyl-1,3-thiazol-5-yl)propanamide trifluoroacetate

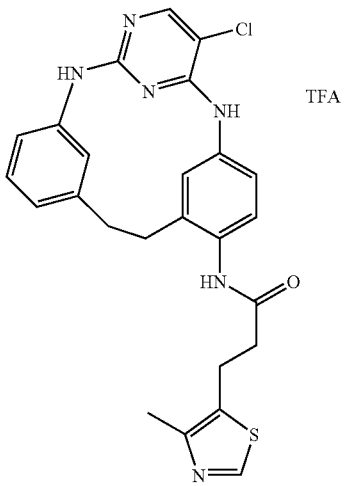 [SMILES: Cc1ncsc1CCC(=O)Nc1ccc2cc1CCc1cccc(c1)Nc1ncc(Cl)c(n1)N2]

The desired compound was prepared according to the procedure of Example C29, using 6-chloro-2,4,8,22-tetraazatetracyclo[14.3.1.1(3,7).1(9,13)]docosa-1(20),3(22),4,6,9(21),10,12,16,18-nonaen-12-amine dihydrochloride and 3-(4-methyl-1,3-thiazol-5-yl)propanoic acid as the starting materials in 42% yield. LCMS for $C_{25}H_{24}ClN_6OS$ $(M+H)^+$: m/z=491.0. $^1$H NMR (300 MHz, DMSO-$d_6$): δ 9.52 (s, 1H), 9.45 (s, 1H), 9.35 (s, 1H), 8.88 (s, 1H), 8.81 (dd, J=4.5, 1.5 Hz, 1H), 8.14 (s, 1H), 8.67 (dd, J=8.4, 1.3 Hz, 1H), 7.92 (s, 1H), 7.71 (d, J=2.4 Hz, 1H), 7.61 (dd, J=8.5, 4.4 Hz, 1H), 7.20 (d, J=8.6 Hz, 1H), 7.08 (d, J=7.6 Hz, 1H), 7.00 (dd, J=8.5, 2.3 Hz, 1H), 6.85 (d, J=7.6 Hz, 1H), 6.75 (d, J=7.6 Hz, 1H), 3.08 (t, J=7.1 Hz, 2H), 3.23 (s, 3H), 3.00 (s, 1H), 2.64 (m, 2H).

Example C49

N-[6-Fluoro-2,4,8,18,22-pentaazatetracyclo[14.3.1.1(3,7).1(9,13)]docosa-1(20),3(22),4,6,9(21),10,12,16,18-nonaen-12-yl]-2-{1-[(5-methylisoxazol-3-yl)carbonyl]piperidin-4-yl}acetamide trifluoroacetate

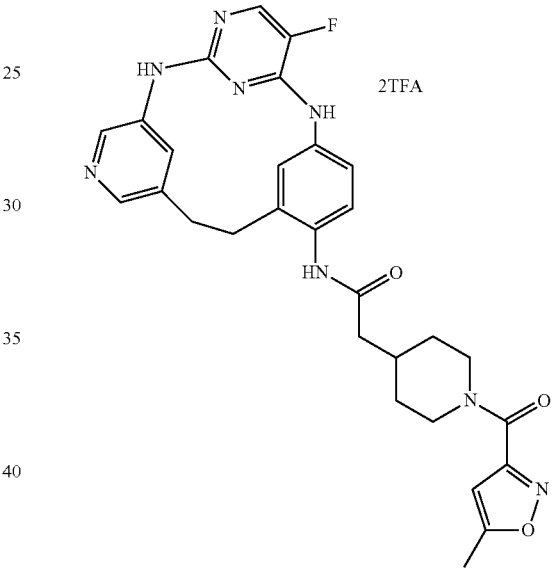

Step A: tert-Butyl (2-iodo-4-nitrophenyl)carbamate

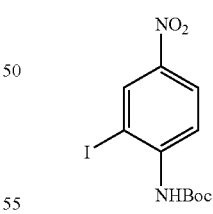

Into the reaction flask was added 2-iodo-4-nitroaniline (2.0 g, 7.6 mmol) and N,N-dimethylformamide (30 mL). Sodium hydride (0.22 g, 9.1 mmol) was added at 0° C., followed by the addition of di-tert-butyldicarbonate (1.8 g, 8.3 mmol). The mixture was warmed up to rt and stirred over the weekend. To it was added water and EtOAc. The aqueous layer was extracted again with EtOAc. The organic layers were combined and dried over $Na_2SO_4$. After filtration and concentration, the crude was purified by silica gel column chromatography to give the desired product (1.5 g, 55%). LCMS for $C_{11}H_{141}N_2O_4$ $(M+H)^+$: m/z=364.9.

Step B: tert-Butyl [5-({2-[(tert-butoxycarbonyl)amino]-5-nitrophenyl}ethynyl)pyridin-3-yl]carbamate

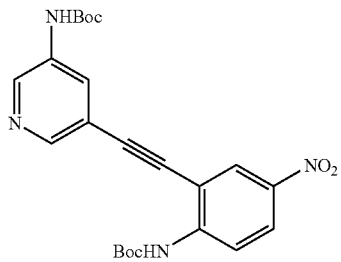 [SMILES: CC(C)(C)OC(=O)Nc1cncc(C#Cc2cc([N+](=O)[O-])ccc2NC(=O)OC(C)(C)C)c1]

Into the reaction flask was added tert-butyl (2-iodo-4-nitrophenyl)carbamate (1.5 g, 4.1 mmol) and copper(I) iodide (0.031 g, 0.16 mmol), bis(triphenylphosphine)palladium(II) chloride (0.12 g, 0.16 mmol), tetrahydrofuran (10 mL), and triethylamine (0.63 mL). The mixture was stirred under bubbling $N_2$ for 5 min, and tert-butyl (5-ethynylpyridin-3-yl)carbamate (0.90 g, 4.1 mmol) was then added. The reaction mixture was stirred at 65° C. for 1 h. After concentration, the residue was diluted with EtOAc and water. The aqueous layer was extracted again with EtOAc. The organic layers were combined and dried over $Na_2SO_4$. After filtration and concentration, the crude was purified by silica gel column chromatography to give the desired product (1.6 g, 85%). LCMS for $C_{23}H_{27}N_4O_6$ $(M+H)^+$: m/z=455.1.

Step C: tert-Butyl [5-({5-amino-2-[(tert-butoxycarbonyl)amino]phenyl}ethynyl)pyridin-3-yl]carbamate

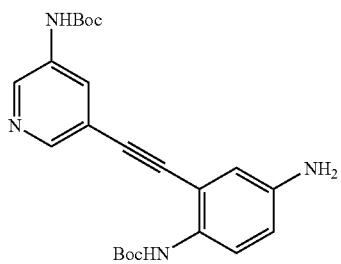 [SMILES: CC(C)(C)OC(=O)Nc1cncc(C#Cc2cc(N)ccc2NC(=O)OC(C)(C)C)c1]

Into the reaction flask was added tert-butyl [5-({2-[(tert-butoxycarbonyl)amino]-5-nitrophenyl}ethynyl)pyridin-3-yl]carbamate (1.6 g, 3.5 mmol), methanol (40 mL), acetic acid (7 mL), and water (4 mL). Then iron (0.90 g, 0.016 mol) powder was added. The reaction mixture was heated at 60° C. for 3 h. After filtration, the cake was rinsed with EtOAc. The filtrate was concentrated and the residue was diluted with $NaHCO_3$ and EtOAc. After layer separation, the organic layer was dried, filtered and concentrated to give the desired product (1.4 g, 94%). LCMS for $C_{23}H_{29}N_4O_4$ $(M+H)^+$: m/z=425.1.

Step D: tert-Butyl [5-(2-{5-amino-2-[(tert-butoxycarbonyl)amino]phenyl}ethyl)pyridin-3-yl]carbamate

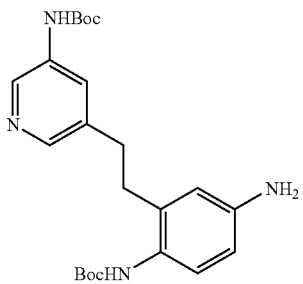 [SMILES: CC(C)(C)OC(=O)Nc1cncc(CCc2cc(N)ccc2NC(=O)OC(C)(C)C)c1]

Into the reaction flask was added tert-butyl [5-({5-amino-2-[(tert-butoxycarbonyl)amino]phenyl}ethynyl)pyridin-3-yl]carbamate (1.5 g, 3.5 mmol) and methanol (30 mL) and 10% palladium on carbon (0.15 g, 0.14 mmol). The reaction mixture was hydrogenated at 25 psi for 2 h. The mixture was filtered and concentrated to give the desired product (1.4 g, 92%). LCMS for $C_{23}H_{33}N_4O_4$ $(M+H)^+$: m/z=429.1.

Step E: tert-Butyl [5-(2-{2-[(tert-butoxycarbonyl)amino]-5-[(2-chloro-5-fluoropyrimidin-4-yl)amino]phenyl}ethyl)pyridin-3-yl]carbamate

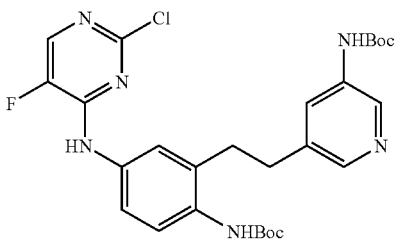 [SMILES: CC(C)(C)OC(=O)Nc1cncc(CCc2cc(Nc3nc(Cl)ncc3F)ccc2NC(=O)OC(C)(C)C)c1]

To a solution of tert-butyl [5-(2-{5-amino-2-[(tert-butoxycarbonyl)amino]phenyl}ethyl)pyridin-3-yl]carbamate (0.27 g, 0.63 mmol) and 2,4-dichloro-5-fluoropyrimidine (0.105 g, 0.63 mmol) in N,N-dimethylformamide (4 mL) was added potassium carbonate (0.446 g, 3.23 mmol). The resultant mixture was stirred overnight at rt. The reaction was quenched with water. EtOAc was added and the layers were separated. The aqueous layer was extracted with EtOAc twice. The combined organic layers were washed with brine, dried ($Na_2SO_4$), filtered and concentrated. The residue was purified by silica gel column chromatography to give the desired product (50 mg, 14%). LCMS for $C_{27}H_{33}ClFN_6O_4$ $(M+H)^+$: m/z=559.2.

Step F: 2-[2-(5-Aminopyridin-3-yl)ethyl]-N(4)-(2-chloro-5-fluoropyrimidin-4-yl)benzene-1,4-diamine trihydrochloride

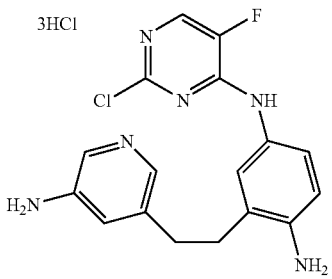 [SMILES: "3HCl" ; Nc1cncc(CCc2cc(Nc3nc(Cl)ncc3F)ccc2N)c1]

Into the reaction flask was added tert-butyl [5-(2-{2-[(tert-butoxycarbonyl)amino]-5-[(2-chloro-5-fluoropyrimidin-4-yl)amino]phenyl}ethyl)pyridin-3-yl]carbamate (0.050 g, 0.089 mmol), methanol (0.6 mL), and 4.0 M of hydrogen chloride in 1,4-dioxane (1 mL). The mixture was stirred at rt overnight and concentrated under vacuum to give the desired product (10 mg, 95%). LCMS for $C_{17}H_{17}ClFN_6$ (M+H)$^+$: m/z=359.0.

Step G: 6-Fluoro-2,4,8,18,22-pentaazatetracyclo[14.3.1.1(3,7).1(9,13)]docosa-1(20),3(22),4,6,9(21),10,12,16,18-nonaen-12-amine tris(trifluoroacetate)

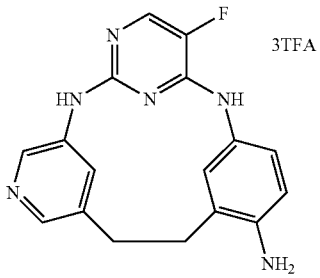 [SMILES: Nc1ccc2cc1CCc1cncc(c1)Nc1ncc(F)c(n1)N2]

Into the reaction flask was added 2-[2-(5-aminopyridin-3-yl)ethyl]-N(4)-(2-chloro-5-fluoropyrimidin-4-yl)benzene-1,4-diamine trihydrochloride (0.034 g, 0.095 mmol), 1,4-dioxane (0.6 mL), and triethylamine (0.04 mL). The mixture was stirred at rt for 5 min. To it was then added palladium acetate (1 mg, 0.004 mmol) and (9,9-dimethyl-9H-xanthene-4,5-diyl)bis(diphenylphosphine) (2 mg, 0.003 mmol) and cesium carbonate (60 mg, 0.2 mmol). The mixture was degassed with N$_2$ bubbling. The tube was sealed and heated at 160° C. for 20 min under microwave irradiation. After filtration and concentration, the crude was purified by preparative HPLC (pH 2) to give the desired product (2.5 mg, 8%), LCMS for $C_{17}H_{16}FN_6$ (M+H)$^+$: m/z=323.1.

Step H: Methyl {1-[(S-methylisoxazol-3-yl)carbonyl]piperidin-4-yl}acetate

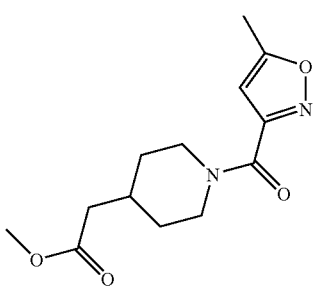 [SMILES: COC(=O)CC1CCN(C(=O)c2cc(C)on2)CC1]

Into the reaction flask was added methyl piperidin-4-ylacetate (2.2 g, 14 mmol), tetrahydrofuran (50 mL), and triethylamine (1.7 mL) and 5-methylisoxazole-3-carbonyl chloride (2.0 g, 14 mmol). The mixture was stirred at rt for 5 min. To it was added water and EtOAc. The water phase was extracted again with EtOAc. The organic layers were combined and dried over Na$_2$SO$_4$. After filtration and concentration, the desired product (2.8 g, 75%) was used without further purification. LCMS for $C_{13}H_{19}N_2O_4$ (M+H)$^+$: m/z=267.0

Step I: {1-[(5-Methylisoxazol-3-yl)carbonyl]piperidin-4-yl}acetic acid

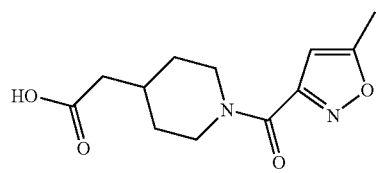 [SMILES: Cc1cc(C(=O)N2CCC(CC(=O)O)CC2)no1]

Into the reaction flask was added methyl {1-[(5-methylisoxazol-3-yl)carbonyl]piperidin-4-yl}acetate (2.8 g, 10.0 mmol) and methanol (10 mL) and 3 M of sodium hydroxide in water (10 mL). The mixture was stirred at rt for 2 h. After concentration, the residue was neutralized to pH=7. The mixture was extracted with EtOAc twice. The combined organic layers were dried and concentrated to give the desired product (0.30 g, 11%). LCMS for $C_{12}H_{17}N_2O_4$ (M+H)$^+$: m/z=253.1

Step J: N-[6-Fluoro-2,4,8,18,22-pentaazatetracyclo[14.3.1.1(3,7).1(9,13)]docosa-1(20),3(22),4,6,9(21),10,12,16,18-nonaen-12-yl]-2-{1-[(5-methylisoxazol-3-yl)carbonyl]piperidin-4-yl}acetamide bis(trifluoroacetate)

A solution of {1-[(5-methylisoxazol-3-yl)carbonyl]piperidin-4-yl}acetic acid (2.0 mg, 0.0079 mmol), N,N,N',N'-tetramethyl-O-(7-azabenzotriazol-1-yl)uronium hexafluorophosphate (8.1 mg, 0.021 mmol) in N,N-dimethylformamide (0.1 mL) and N,N-diisopropylethylamine (3.2 uL) was stirred for 15 minutes. A solution of 6-fluoro-2,4,8,18,22-pentaazatetracyclo[14.3.1.1(3,7).1(9,13)]docosa-1(20),3(22),4,6,9(21),10,12,16,18-nonaen-12-amine tris(trifluoroacetate) (2.5 mg, 0.0078 mmol) in N,N-dimethylformamide (0.04 mL) and was added to the previous solution and stirred overnight. The reaction mixture was purified by preparative HPLC (pH 2) to give the desired product (0.5 mg, 14%). LCMS for $C_{29}H_{30}FN_8O_3$ (M+H)$^+$: m/z=557.1.

Example C50

6-Methyl-2,4,8,18,22-pentaazatetracyclo[14.3.1.1(3,7).1(9,13)]docosa-1(20),3(22),4,6,9(21),10,12,16,18-nonaen-12-amine tris(trifluoroacetate)

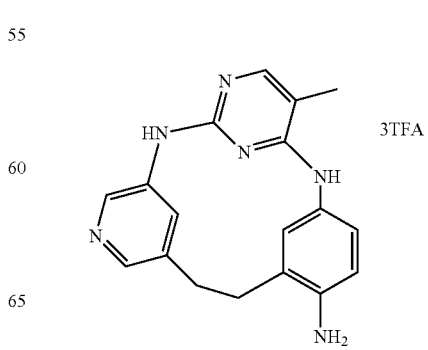

Step A: tert-Butyl [5-(2-{2-[(tert-butoxycarbonyl)amino]-5-[(2-chloro-5-methylpyrimidin-4-yl)amino]phenyl}ethyl)pyridin-3-yl]carbamate

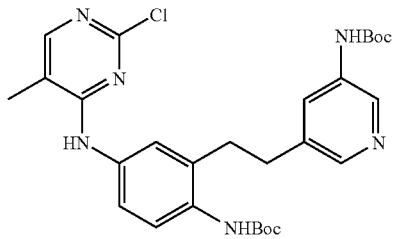 [SMILES: Cc1cnc(Cl)nc1Nc1ccc(NC(=O)OC(C)(C)C)c(CCc2cncc(NC(=O)OC(C)(C)C)c2)c1]

To a solution of tert-butyl [5-(2-{5-amino-2-[(tert-butoxycarbonyl)amino]phenyl}ethyl)pyridin-3-yl]carbamate (0.27 g, 0.63 mmol) (prepared in Example C49, step D) and 2,4-dichloro-5-methylpyrimidine (0.103 g, 0.63 mmol) in N,N-dimethylformamide (4 mL) was added potassium carbonate (0.446 g, 3.23 mmol). The resultant mixture was stirred overnight at rt overnight. The reaction was quenched with water. EtOAc was added and the layers were separated. The aqueous layer was extracted with EtOAc twice. The combined organic layers were washed with brine, dried ($Na_2SO_4$), filtered and concentrated. The crude was purified by silica gel column chromatography to give the desired product (30 mg, 9%). LCMS for $C_{28}H_{34}ClN_6O_4$ $(M+H)^+$: m/z=555.2.

Step B: 2-[2-(5-Aminopyridin-3-yl)ethyl]-N(4)-(2-chloro-5-methylpyrimidin-4-yl)benzene-1,4-diamine trihydrochloride

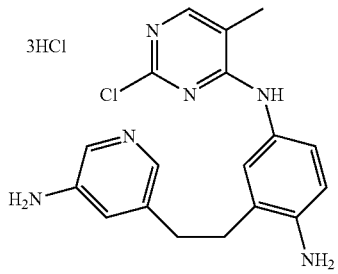 [SMILES: "3HCl" ; Cc1cnc(Cl)nc1Nc1ccc(N)c(CCc2cncc(N)c2)c1]

Into the reaction flask was added tert-butyl [5-(2-{2-[(tert-butoxycarbonyl)amino]-5-[(2-chloro-5-methylpyrimidin-4-yl)amino]phenyl}ethyl)pyridin-3-yl]carbamate (0.030 g, 0.054 mmol), methanol (0.6 mL), and 4.0 M of hydrogen chloride in 1,4-dioxane (1 mL). The mixture was stirred at rt overnight and concentrated to give the desired product (21 mg, 95%). LCMS for $C_{18}H_{20}ClN_6$ $(M+H)^+$: m/z=355.1.

Step C: 6-Methyl-2,4,8,18,22-pentaazatetracyclo[14.3.1.1(3,7).1(9,13)]docosa-1(20),3(22),4,6,9(21),10,12,16,18-nonaen-12-amine tris(trifluoroacetate)

Into the reaction flask was added 2-[2-(5-aminopyridin-3-yl)ethyl]-N(4)-(2-chloro-5-methylpyrimidin-4-yl)benzene-1,4-diamine trihydrochloride (0.019 g, 0.054 mmol), 1,4-dioxane (0.4 mL), and triethylamine (0.02 mL). The mixture was stirred at rt for 5 min. To it was added palladium acetate (0.6 mg, 0.002 mmol), (9,9-dimethyl-9H-xanthene-4,5-diyl)bis(diphenylphosphine) (1 mg, 0.002 mmol), and cesium carbonate (40 mg, 0.1 mmol). The mixture was degassed with $N_2$ bubbling. The tube was sealed and heated at 160° C. for 20 min in a microwave. The mixture was filtered and purified by preparative HPLC (pH 2) to give the desired product (8.5 mg, 50%). LCMS for $C_{18}H_{19}N_6$ $(M+H)^+$: m/z=319.2.

Example C51

2-{1-[(5-Methylisoxazol-3-yl)carbonyl]piperidin-4-yl}-N-[6-methyl-2,4,8,18,22-pentaazatetracyclo[14.3.1.1(3,7).1(9,13)]docosa-1(20),3(22),4,6,9(21),10,12,16,18-nonaen-12-yl]acetamide bis(trifluoroacetate)

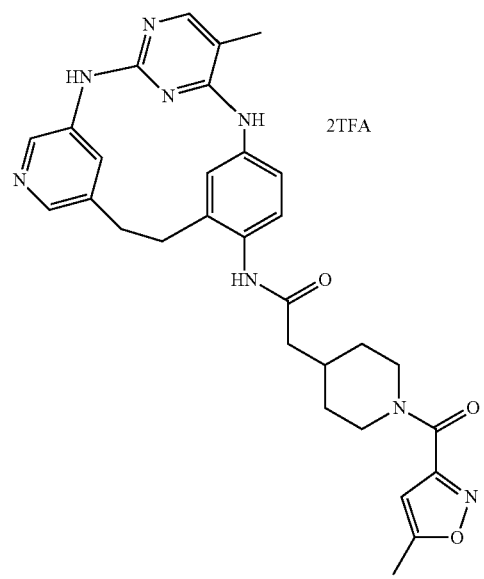 [SMILES: Cc1cc(C(=O)N2CCC(CC(=O)Nc3ccc4cc3CCc3cncc(c3)Nc3ncc(C)c(n3)N4)CC2)no1 ; "2TFA"]

A solution of {1-[(5-methylisoxazol-3-yl)carbonyl]piperidin-4-yl}acetic acid (4.8 mg, 0.019 mmol) (prepared in Example C49, step I), N,N,N',N'-tetramethyl-O-(7-azabenzotriazol-1-yl)uronium hexafluorophosphate (19 mg, 0.050 mmol) in N,N-dimethylformamide (0.2 mL) and N,N-diisopropylethylamine (7.6 uL) was stirred for 15 minutes. A solution of 6-methyl-2,4,8,18,22-pentaazatetracyclo[14.3.1.1(3,7).1(9,13)]docosa-1(20),3(22),4,6,9(21),10,12,16,18-nonaen-12-amine tris(trifluoroacetate) (6.0 mg, 0.019 mmol) (prepared in Example C29, step C) in N,N-dimethylformamide (0.1 mL) and was added to the previous solution and was stirred overnight. The reaction mixture was purified by preparative HPLC (pH 2) to give the desired product (0.5 mg, 19%). LCMS for $C_{30}H_{33}N_8O_3$ $(M+H)^+$: m/z=553.2. $^1$H NMR (300 MHz, DMSO-$d_6$): δ 9.83 (s, 1H), 9.38 (s, 1H), 9.34 (s, 1H), 8.52 (s, 1H), 8.19 (s, 1H), 8.12 (s, 1H), 7.90 (s, 1H), 7.62 (d, J=2.4 Hz, 1H), 7.28 (d, J=8.7 Hz, 1H), 7.00 (dd, J=8.3, 2.2 Hz, 1H), 6.41 (dd, J=8.1, 0.8 Hz, 1H), 4.42 (m, 4H), 3.86 (m, 4H), 2.90-3.10 (m, 6H), 2.10-2.30 (m, 4H), 2.66 (s, 3H).

Example C52

N-[6-Fluoro-2,4,8,22-tetraazatetracyclo[14.3.1.1(3,7).1(9,13)]docosa-1(20),3(22),4,6,9(21),10,12,16,18-nonaen-12-yl]-2-{1-[(5-methylisoxazol-3-yl)carbonyl]piperidin-4-yl}acetamide trifluoroacetate

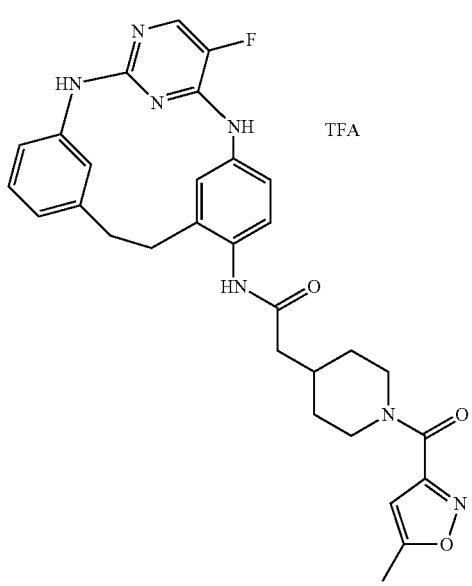 [SMILES: "TFA" ; Cc1cc(C(=O)N2CCC(CC(=O)Nc3ccc4cc3CCc3cccc(c3)Nc3ncc(F)c(n3)N4)CC2)no1]

Step A: tert-Butyl [3-({2-[(tert-butoxycarbonyl)amino]-5-nitrophenyl}ethynyl)phenyl]carbamate

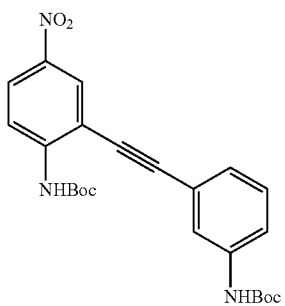 [SMILES: CC(C)(C)OC(=O)Nc1cccc(C#Cc2cc([N+](=O)[O-])ccc2NC(=O)OC(C)(C)C)c1]

Into the reaction flask was added tert-butyl (2-iodo-4-nitrophenyl)carbamate (2.71 g, 7.44 mmol), copper(I) iodide (0.057 g, 0.30 mmol), bis(triphenylphosphine)palladium(II) chloride (0.21 g, 0.30 mmol), tetrahydrofuran (20 mL), and triethylamine (1.1 mL). It was stirred under $N_2$ bubbling for 5 min. tert-Butyl (3-ethynylphenyl)carbamate (1.62 g, 7.44 mmol) was then added. The reaction mixture was stirred at 65° C. for 3 h. After concentration, the residue was diluted with EtOAc and water. The aqueous layer was extracted again with fresh EtOAc. The organic layers were combined and dried over $Na_2SO_4$. After filtration and concentration, the crude was purified by silica gel column chromatography to give the desired product (2.7 g, 80%). LCMS for $C_{24}H_{28}N_3O_6$ $(M+H)^+$: m/z=454.1.

Step B: tert-Butyl [3-({5-amino-2-[(tert-butoxycarbonyl)amino]phenyl}ethynyl)phenyl]carbamate

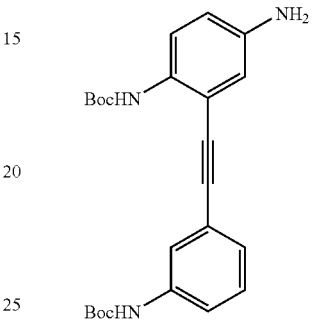

Into the reaction flask was added tert-butyl [3-({2-[(tert-butoxycarbonyl)amino]-5-nitrophenyl}ethynyl)phenyl]carbamate (2.7 g, 6.0 mmol), methanol (70 mL), acetic acid (10 mL), and water (7 mL). Then iron powder (1.8 g, 30 mmol) was added. The reaction mixture was heated at 60° C. for 3 h. After filtration, the cake was rinsed with EtOAc. The filtrate was concentrated and the residue was diluted with $NaHCO_3$ (aq) and EtOAc. After the layers were separated, the organic layer was dried, filtered and concentrated to give the desired product (2.3 g, 91%). LCMS for $C_{24}H_{30}N_3O_4$ $(M+H)^+$: m/z=424.2.

Step C: tert-Butyl [3-(2-{5-amino-2-[(tert-butoxycarbonyl)amino]phenyl}ethyl)phenyl]carbamate

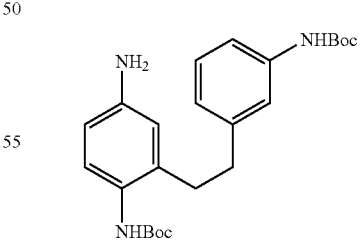

Into the reaction flask was added tert-butyl [3-({5-amino-2-[(tert-butoxycarbonyl)amino]phenyl}ethynyl)phenyl]carbamate (1.0 g, 2.4 mmol), 50 mL of methanol, and 10% palladium on carbon (0.10 g, 0.097 mmol). The reaction mixture was hydrogenated at 25 psi for 3 h. The mixture was filtered and concentrated to give the desired product (0.9 g, 89%). LCMS for $C_{24}H_{33}NaN_3O_4$ (M+Na)$^+$: m/z=450.2

Step D: tert-Butyl [3-(2-{2-[(tert-butoxycarbonyl)amino]-5-[(2-chloro-5-fluoropyrimidin-4-yl)amino]phenyl}ethyl)phenyl]carbamate

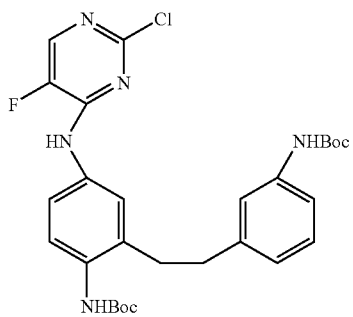 [SMILES: CC(C)(C)OC(=O)Nc1cccc(CCc2cc(Nc3nc(Cl)ncc3F)ccc2NC(=O)OC(C)(C)C)c1]

To a solution of tert-butyl [3-(2-{5-amino-2-[(tert-butoxycarbonyl)amino]phenyl}ethyl)phenyl]carbamate (0.4 g, 0.9 mmol) and 2,4-dichloro-5-fluoropyrimidine (0.156 g, 0.936 mmol) in N,N-dimethylformamide (7 mL) was added potassium carbonate (0.662 g, 4.79 mmol). The resultant mixture was stirred overnight at rt overnight. The reaction was quenched with water. EtOAc was added and the layers were separated. The aqueous layer was extracted with EtOAc twice. The combined organic layers were washed with brine, dried (Na$_2$SO$_4$), filtered and concentrated. The residue was purified by silica gel column chromatography to give the desired product (0.32 g, 61%). LCMS for $C_{28}H_{33}ClFNaN_5O_4$ (M+Na)$^+$: m/z=580.2.

Step E: 2-[2-(3-Aminophenyl)ethyl]-N(4)-(2-chloro-5-fluoropyrimidin-4-yl)benzene-1,4-diamine trihydrochloride

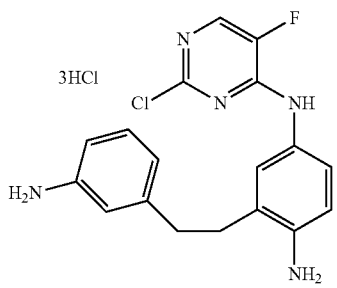 [SMILES: Nc1cccc(CCc2cc(Nc3nc(Cl)ncc3F)ccc2N)c1 ; "3HCl"]

Into the reaction flask was added tert-butyl [3-(2-{2-[(tert-butoxycarbonyl)amino]-5-[(2-chloro-5-fluoropyrimidin-4-yl)amino]phenyl}ethyl)phenyl]carbamate (0.32 g, 0.57 mmol), methanol (3 mL), and 4.0 M of hydrogen chloride in 1,4-dioxane (5 mL). The mixture was stirred at rt overnight and concentrated under vacuum to give the desired product as a HCl salt (220 mg, 98%). LCMS for $C_{18}H_{18}ClFN_5$ (M+H)$^+$: m/z=358.1.

Step F: 6-Fluoro-2,4,8,22-tetraazatetracyclo[14.3.1.1(3,7).1(9,13)]docosa-1(20),3(22),4,6,9(21),10,12,16,18-nonaen-12-amine bis(trifluoroacetate)

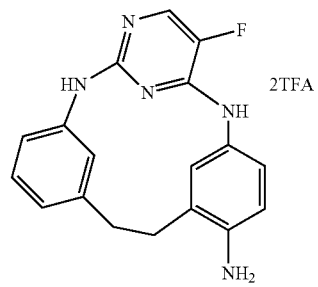 [SMILES: Nc1ccc2cc1CCc1cccc(c1)Nc1ncc(F)c(n1)N2 ; "2TFA"]

To a solution of 2-[2-(3-aminophenyl)ethyl]-N(4)-(2-chloro-5-fluoropyrimidin-4-yl)benzene-1,4-diamine trihydrochloride (0.20 g, 0.56 mmol) in 2-methoxyethanol (3 mL) was added 4.00 M of hydrogen chloride in 1,4-dioxane (140 µL). The resultant mixture was heated at 150° C. in the microwave for 15 min. After cooling down and filtration, the cake was further purified by preparative HPLC (pH 2) to give the desired product (100 mg, 56%). LCMS for $C_{18}H_{17}FN_5$ (M+H)$^+$: m/z=322.1.

Step G: N-[6-Fluoro-2,4,8,22-tetraazatetracyclo[14.3.1.1(3,7).1(9,13)]docosa-1(20),3(22),4,6,9(21),10,12,16,18-nonaen-12-yl]-2-{1-[(5-ethylisoxazol-3-yl)carbonyl]piperidin-4-yl}acetamide bis(trifluoroacetate)

A solution of {1-[(5-methylisoxazol-3-yl)carbonyl]piperidin-4-yl}acetic acid (16 mg, 0.063 mmol) (prepared in Example C49, step I), N,N,N',N'-tetramethyl-O-(7-azabenzotriazol-1-yl)uronium hexafluorophosphate (65 mg, 0.17 mmol) in N,N-dimethylformamide (0.8 mL) and N,N-diisopropylethylamine (26 µL) was stirred for 15 minutes. A solution of 6-fluoro-2,4,8,22-tetraazatetracyclo[14.3.1.1(3,7).1(9,13)]docosa-1(20),3(22),4,6,9(21),10,12,16,18-nonaen-12-amine bis(trifluoroacetate) (20 mg, 0.06 mmol) in N,N-dimethylformamide (0.3 mL) and was added to the previous solution and stirred overnight. The reaction mixture was purified by preparative HPLC (pH 2) to give the desired product (4 mg, 12%). LCMS for $C_{30}H_{31}FN_7O_3$ (M+H)$^+$: m/z=556.2

Example C53

N-[6-Methyl-2,4,8,22-tetraazatetracyclo[14.3.1.1(3,7).1(9,13)]docosa-1(20),3(22),4,6,9(21),10,12,16,18-nonaen-12-yl]-2-[1-(1,3,4-thiadiazol-2-yl)piperidin-4-yl]acetamide trifluoroacetate

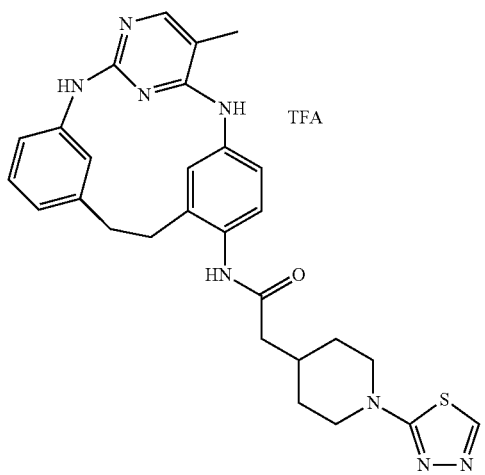 [SMILES: "TFA" ; Cc1cnc2nc1Nc1ccc(NC(=O)CC3CCN(c4nncs4)CC3)c(c1)CCc1cccc(c1)N2]

Step A: tert-Butyl [3-(2-{2-[(tert-butoxycarbonyl)amino]-5-[(2-chloro-5-methylpyrimidin-4-yl)amino]phenyl}ethyl)phenyl]carbamate

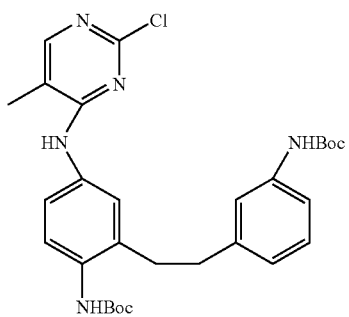 [SMILES: Cc1cnc(Cl)nc1Nc1ccc(NC(=O)OC(C)(C)C)c(CCc2cccc(NC(=O)OC(C)(C)C)c2)c1]

To a solution of tert-butyl [3-(2-{5-amino-2-[(tert-butoxycarbonyl)amino]phenyl}ethyl)phenyl]carbamate (0.4 g, 0.9 mmol) (prepared in Example C52, step C) and 2,4-dichloro-5-methylpyrimidine (0.152 g, 0.936 mmol) in N,N-dimethylformamide (7 mL) was added potassium carbonate (0.662 g, 4.79 mmol). The resultant mixture was stirred overnight at rt overnight. The reaction was quenched with water. EtOAc was added and the layers were separated. The aqueous layer was extracted with EtOAc twice. The combined organic layers were washed with water and then dried (Na$_2$SO$_4$), filtered and concentrated to give the residue, which was purified by silica gel column chromatography to give the desired product (0.25 g, 39%). LCMS for $C_{29}H_{37}ClN_5O_4$ (M+H)$^+$: m/z=554.2.

Step B: 2-[2-(3-Aminophenyl)ethyl]-N(4)-(2-chloro-5-methylpyrimidin-4-yl)benzene-1,4-diamine trihydrochloride

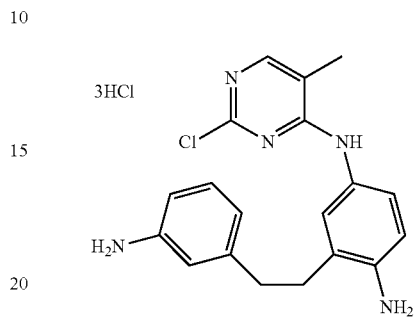

Into the reaction flask was added tert-butyl [3-(2-{2-[(tert-butoxycarbonyl)amino]-5-[(2-chloro-5-methylpyrimidin-4-yl)amino]phenyl}ethyl)phenyl]carbamate (0.25 g, 0.45 mmol), methanol (3 mL), and 4.0 M of hydrogen chloride in 1,4-dioxane (5 mL). The reaction mixture was stirred at rt for 16 h and concentrated to give the desired product (0.21 g, 90%). LCMS for $C_{19}H_{21}ClN_5$ (M+H)$^+$: m/z=354.1.

Step C: 6-Methyl-2,4,8,22-tetraazatetracyclo[14.3.1.1(3,7).1(9,13)]docosa-1(20),3(22),4,6,9(21),10,12,16,18-nonaen-12-amine

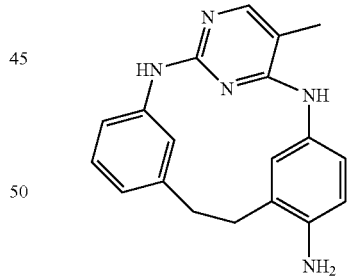

To a solution of 2-[2-(3-aminophenyl)ethyl]-N(4)-(2-chloro-5-methylpyrimidin-4-yl)benzene-1,4-diamine trihydrochloride (0.16 g, 0.45 mmol) in 2-methoxyethanol (2 mL) was added 4.0 M of hydrogen chloride in 1,4-dioxane (110 μL). The resultant mixture was heated at 150° C. in the microwave for 15 min. After cooling, water and NaOH (12 N) were added to neutralize the mixture to pH=7. The aqueous layer was extracted with EtOAc four times. The combined organic layers were dried, filtered and concentrated. The residue was purified by silica gel column chromatography to give the desired product as an off-white powder (60 mg, 48%). LCMS for $C_{19}H_{20}N_5$ (M+H)$^+$: m/z=318.2.

Step D:
[1-(1,3,4-Thiadiazol-2-yl)piperidin-4-yl]acetic acid

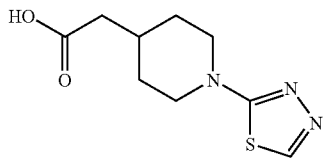 [SMILES: O=C(O)CC1CCN(c2nncs2)CC1]

Into the reaction flask was added 2-bromo-1,3,4-thiadiazole (0.21 g, 1.3 mmol), methyl piperidin-4-ylacetate (0.20 g, 1.3 mmol), N-methylpyrrolidinone (2 mL), and triethylamine (0.39 mL). The reaction was sealed and put under microwave at 150° C. for 10 min. After concentration, the crude was purified by silica gel column chromatography to give the ester. The resultant pure ester was then mixed with methanol (2.0 mL) and 1.0 M of sodium hydroxide in water (2.0 mL). The mixture was stirred at rt for 3 h. The mixture was neutralized with HCl (3 M), the white precipitate was collected by vacuum filtration to give the desired product (0.09 g, 80%) as a white solid. LCMS for $C_9H_{14}N_3O_2S$ (M+H)$^+$: m/z=228.1.

Step E: N-[6-Methyl-2,4,8,22-tetraazatetracyclo [14.3.1.1(3,7).1(9,13)]docosa-1(20),3(22),4,6,9(21), 10,12,16,18-nonaen-12-yl]-2-[1-(1,3,4-thiadiazol-2-yl)piperidin-4-yl]acetamide bis(trifluoroacetate)

A solution of [1-(1,3,4-thiadiazol-2-yl)piperidin-4-yl]acetic acid (14 mg, 0.063 mmol), N,N,N',N'-tetramethyl-O-(7-azabenzotriazol-1-yl)uronium hexafluorophosphate (65 mg, 0.17 mmol) in N,N-dimethylformamide (0.8 mL) and N,N-diisopropylethylamine (26 µL) was stirred for 15 minutes. A solution of 6-methyl-2,4,8,22-tetraazatetracyclo[14.3.1.1(3,7).1(9,13)]docosa-1(20),3(22),4,6,9(21),10,12,16,18-nonaen-12-amine (20 mg, 0.06 mmol) in N,N-dimethylformamide (0.3 mL) was added to the previous solution and stirred overnight. The reaction mixture was purified by preparative HPLC (pH 2) to give the desired product (4 mg, 14%). LCMS for $C_{28}H_{31}N_8OS$ (M+H)$^+$: m/z=527.1

Example C54

2-{1-[(5-Methylisoxazol-3-yl)carbonyl]piperidin-4-yl}-N-[6-methyl-2,4,8,22-tetraazatetracyclo[14.3.1.1 (3,7).1(9,13)]docosa-1(20),3(22),4,6,9(21),10,12,16, 18-nonaen-12-yl]acetamide trifluoroacetate

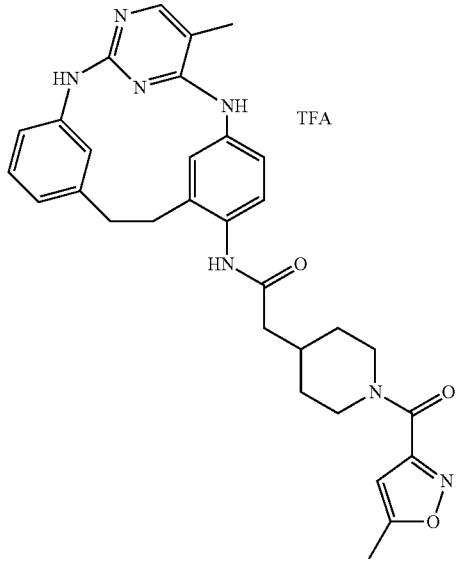 [SMILES: Cc1cc(C(=O)N2CCC(CC(=O)Nc3ccc4cc3CCc3cccc(c3)Nc3ncc(C)c(n3)N4)CC2)no1]

The desired compound was prepared as a white powder according to the procedure of Example C53, step E, using 6-methyl-2,4,8,22-tetraazatetracyclo[14.3.1.1(3,7).1(9,13)] docosa-1(20),3(22),4,6,9(21),10,12,16,18-nonaen-12-amine (15 mg, 47.3 mmol) and {1-[(5-methylisoxazol-3-yl)carbonyl]piperidin-4-yl}acetic acid as the starting materials in 29% yield. LCMS for $C_{31}H_{34}N_7O_3$ (M+H)$^+$: m/z=552.2.

Example C55

6-Chloro-12-(pyrrolidin-3-ylmethoxy)-2,4,8,18,22-pentaazatetracyclo[14.3.1.1(3,7).1(9,13)]docosa-1 (20),3(22),4,6,9(21),10,12,16,18-nonaene trihydrochloride

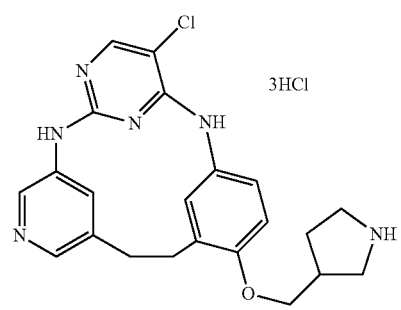 [SMILES: Clc1cnc2nc1Nc1ccc(OCC3CCNC3)c(c1)CCc1cncc(c1)N2 ; "3HCl"]

Step A: 2-Iodo-4-methoxyaniline

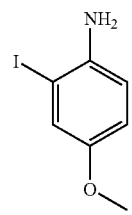

To a suspension of 3-iodo-4-nitrophenyl methyl ether (5.0 g, 0.018 mol) in methanol (50 mL), water (5 mL), and acetic acid (10 mL) was added iron (3.00 g, 0.0538 mol) powder in small quantities. When the addition was completed, the reaction mixture was heated at 70° C. overnight. After filtration, the cake was rinsed with EtOAc. The filtrate was concentrated and the residue was diluted with NaHCO$_3$ (aq) and EtOAc. After layer separation, the organic layer was dried, filtered and concentrated to give the desired product (4.0 g, 90%).

Step B: 2,5-Dichloro-N-(3-iodo-4-methoxyphenyl) pyrimidin-4-amine

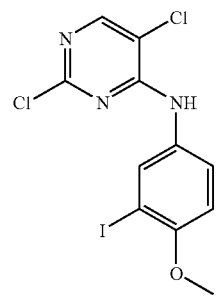 [SMILES: COc1ccc(Nc2nc(Cl)ncc2Cl)cc1I]

To a suspension of 3-iodo-4-methoxyaniline (8.0 g, 0.021 mol) and 2,4,5-trichloropyrimidine (4.13 g, 0.0225 mol) in N,N-dimethylformamide (57 mL) was added potassium carbonate (7.40 g, 0.0536 mol). The resultant mixture was stirred overnight at room temperature. The reaction mixture was filtered to remove $K_2CO_3$ and concentrated to give the residue (10 grams). The residue was triturated with EtOAc, and filtered under vacuum. The residue was purified by silica gel column chromatography to give the desired product (2.54 g, 30%). LCMS for $C_{11}H_9Cl_2I N_3O$ (M+H)$^+$: m/z=396.0, 398.0.

Step C: N-[3-[(E)-2-(S-Aminopyridin-3-yl)vinyl]-4-methoxyphenyl]-2,5-dichloropyrimidin-4-amine

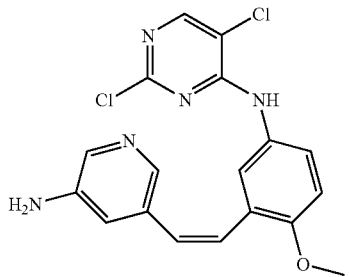 [SMILES: COc1ccc(Nc2nc(Cl)ncc2Cl)cc1/C=C\c1cncc(N)c1]

To a solution of 2,5-dichloro-N-(3-iodo-4-methoxyphenyl)pyrimidin-4-amine (2.54 g, 6.41 mmol) in acetonitrile (40 mL), tetrahydrofuran (30 mL), and water (30 mL) was added 5-vinylpyridin-3-amine (1.54 g, 12.8 mmol), sodium carbonate (1.36 g, 12.8 mmol), palladium acetate (43.2 mg, 0.192 mmol), and trisodium 3,3',3"-phosphinetriyltris(4,6-dimethylbenzenesulfonate) (377 mg, 0.577 mmol). The reaction flask was flushed with nitrogen for 10 min. The reaction mixture was heated at 80° C. for 16 hours. LCMS showed clean conversion of iodide. The mixture was concentrated under vacuum. To the residue water (40 mL) and MeOH (20 mL) were added. The resultant solid was collected by vacuum filtration. The cake was washed with water and then fresh methanol to give the desired product (2.22 g, 90%) as a red-yellow solid. LCMS for $C_{18}H_{16}Cl_2N_5O$ (M+H)$^+$: m/z=388.1.

Step D: N-{3-[2-(5-Aminopyridin-3-yl)ethyl]-4-methoxyphenyl}-2,5-dichloropyrimidin-4-amine

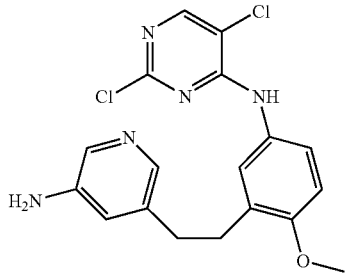 [SMILES: COc1ccc(Nc2nc(Cl)ncc2Cl)cc1CCc1cncc(N)c1]

To a solution of N-{3-[(E)-2-(5-aminopyridin-3-yl)vinyl]-4-methoxyphenyl}-2,5-dichloropyrimidin-4-amine (2.25 g, 5.80 mmol) in 1,2-dimethoxyethane (2.0 mL), and tetrahydrofuran (100 mL) was added p-toluenesulfonylhydrazide (16.2 g, 86.9 mmol). The reaction mixture was heated to 90°

C. when a solution of sodium acetate (11.4 g, 139 mmol) in water (120 mL) was added dropwise over 4 h. The reaction mixture was stirred at 90° C. for 3 h. The reaction mixture was diluted with ethyl acetate. The aqueous layer was extracted with ethyl acetate twice. The combined organic layers were combined, dried over $Na_2SO_4$, filtered and concentrated. The residue was purified by silica gel column chromatography to give the desired product as a yellow foam (1.75 g, 77%). LCMS for $C_{18}H_{18}Cl_2N_5O$ (M+H)$^+$: m/z=390.1

Step E: 6-Chloro-12-methoxy-2,4,8,18,22-pentaazatetracyclo[14.3.1.1(3,7).1(9,13)]docosa-1(20),3(22),4,6,9(21),10,12,16,18-nonaene

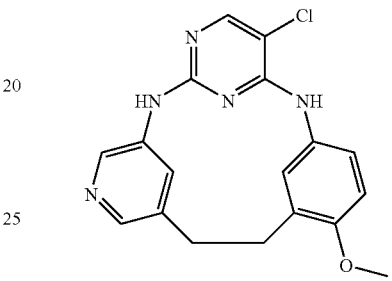

Into the reaction was added N-{3-[2-(5-aminopyridin-3-yl)ethyl]-4-methoxyphenyl}-2,5-dichloropyrimidin-4-amine (1.75 g, 4.48 mmol), 1,4-dioxane (29 mL), N,N-dimethylformamide (29 mL), palladium acetate (30 mg, 0.1 mmol), (9,9-dimethyl-9H-xanthene-4,5-diyl)bis(diphenylphosphine) (90 mg, 0.2 mmol), and cesium carbonate (2.92 g, 8.97 mmol). The mixture was degassed with $N_2$ bubbling and then microwaved at 150° C. for 20 min. After concentration to remove the solvent, 20 mL of water was added to the residue. The formed precipitate was then collected by vacuum filtration and air dried overnight to give the desired product (1.35 g, 85%). LCMS for $C_{18}H_{17}ClN_5O$ (M+H)$^+$: m/z=354.1.

Step F: 6-Chloro-2,4,8,18,22-pentaazatetracyclo[14.3.1.1(3,7).1(9,13)]docosa-1(20),3(22),4,6,9(21),10,12,16,18-nonaen-12-ol

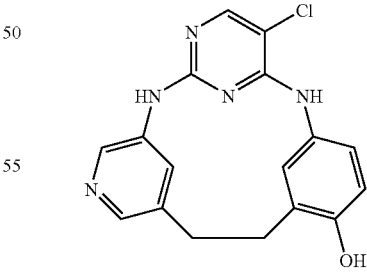

Into the reaction flask was added 6-chloro-12-methoxy-2,4,8,18,22-pentaazatetracyclo[14.3.1.1(3,7).1(9,13)]docosa-1(20),3(22),4,6,9(21),10,12,16,18-nonaene (1.35 g, 3.82 mmol), methylene chloride (20 mL), and 1.0 M of boron tribromide in methylene chloride (19.1 mL). The reaction mixture was stirred at rt overnight. To the mixture was added 1.0 M of sodium bicarbonate in water (30 mL). The precipi- Step G: tert-Butyl 3-{[(methylsulfonyl)oxy]methyl}pyrrolidine-1-carboxylate

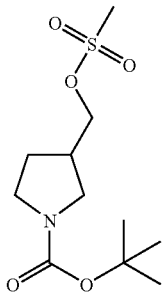 [SMILES: CC(C)(C)OC(=O)N1CCC(COS(C)(=O)=O)C1]

Into the reaction flask was added tert-butyl 3-(hydroxymethyl)pyrrolidine-1-carboxylate (0.80 g, 4.0 mmol), methylene chloride (20 mL), and methanesulfonyl chloride (0.55 g, 4.8 mmol). The mixture was stirred at 0° C. when triethylamine (1.4 mL) was slowly added. The reaction mixture was stirred at rt for 2 h, followed by the addition of water (5 mL). The aqueous layer was extracted twice with methylene chloride. The combined organic layers were dried over Na$_2$SO$_4$, filtered and concentrated to give the desired product (0.85 g crude) which was used without further purification.

Step H: tert-Butyl 3-({[6-chloro-2,4,8,18,22-pentaazatetracyclo[14.3.1.1(3,7).1(9,13)]docosa-1(20),3(22),4,6,9(21),10,12,16,18-nonaen-12-yl]oxy}methyl)pyrrolidine-1-carboxylate

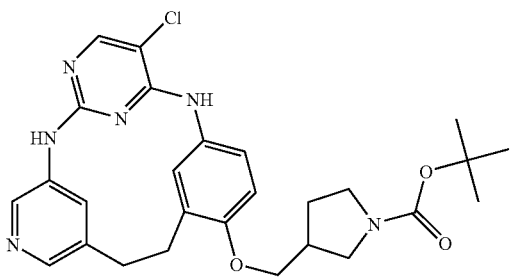 [SMILES: CC(C)(C)OC(=O)N1CCC(COc2ccc3cc2CCc2cncc(c2)Nc2ncc(Cl)c(n2)N3)C1]

Into the reaction was added 6-chloro-2,4,8,18,22-pentaazatetracyclo[4.3.1.1(3,7).1(9,13)]docosa-1(20),3(22),4,6,9(21),10,12,16,18-nonaen-12-ol (0.10 g, 0.29 mmol), N,N-dimethylformamide (2 mL) and sodium tert-butoxide (0.034 g, 0.35 mmol). The mixture was stirred at rt for 5 min, then tert-butyl 3-{[(methylsulfonyl)oxy]methyl}pyrrolidine-1-carboxylate (0.2 g, 0.7 mmol) was added. The reaction mixture was heated at 75° C. overnight. The mixture was purified by preparative LCMS (pH 10) to give the desired product (25 mg, 16%). LCMS for C$_{27}$H$_{32}$ClN$_6$O$_3$ (M+H)$^+$: m/z=523.2.
$^1$H NMR (500 MHz, DMSO-d$_6$): δ 9.55 (s, 1H), 9.12 (s, 1H), 8.27 (s, 1H), 7.19 (d, J=2.4 Hz, 1H), 8.09 (s, 1H), 7.99 (s, 1H), 7.47 (d, J=2.6 Hz, 1H), 7.03 (dd, J=8.5, 2.7 Hz, 1H), 6.93 (d, J=8.5 Hz, 1H), 4.20 (m, 6H), 2.85 (m, 1H), 2.55 (m, 2H), 1.95 (m, 2H), 1.64 (m, 2H), 1.40 (s, 9H).

Step I: 6-Chloro-12-(pyrrolidin-3-ylmethoxy)-2,4,8,18,22-pentaazatetracyclo[14.3.1.1(3,7).1(9,13)]docosa-1(20), 3(22),4,6,9(21),10,12,16,18-nonaene trihydrochloride Into the reaction was added tert-butyl 3-({[6-chloro-2,4,8,18,22-pentaazatetracyclo[14.3.1.1(3,7).1(9,13)]docosa-1(20),3(22),4,6,9(21),10,12,16,18-nonaen-12-yl]oxy}methyl)pyrrolidine-1-carboxylate (0.024 g, 0.046 mmol), methanol (0.5 mL), and 4.0 M of hydrogen chloride in 1,4-dioxane (0.5 mL). The mixture was stirred at rt overnight and concentrated under vacuum to give the desired product (19 mg, 92%). LCMS for C$_{22}$H$_{24}$ClN$_6$O (M+H)$^+$: m/z=423.2.

Example C56

12-[(1-Acetylpyrrolidin-3-yl)methoxy]-6-chloro-2,4, 8,18,22-pentaazatetracyclo[14.3.1.1(3,7).1(9,13)] docosa-1(20),3(22),4,6,9(21),10,12,16,18-nonaene bis(trifluoroacetate)

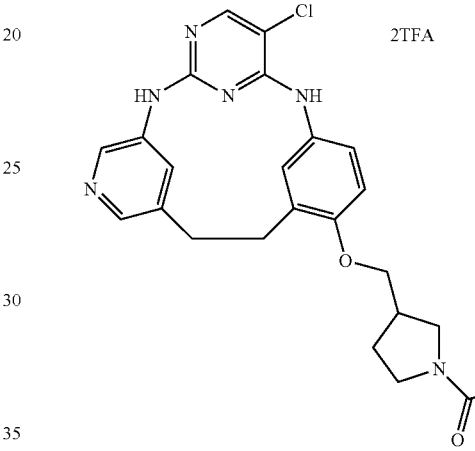

Into the reaction flask was added 6-chloro-12-(pyrrolidin-3-ylmethoxy)-2,4,8,18,22-pentaazatetracyclo[14.3.1.1(3,7).1(9,13)]docosa-1(20),3(22),4,6,9(21),10,12,16,18-nonaene trihydrochloride (6 mg, 0.01 mmol) and N,N-dimethylformamide (0.25 mL), triethylamine (0.0040 mL) and acetyl chloride (14 mg). The mixture was stirred at rt for 5 min. The reaction mixture was diluted with 4 mL of DMF and purified by preparative HPLC (pH 2) to give the desired product (3 mg, 40%). LCMS for C$_{24}$H$_{26}$ClN$_6$O$_2$ (M+H)$^+$: m/z=465.1.

Example C57

2-{[3-({[6-Chloro-2,4,8,18,22-pentaazatetracyclo [14.3.1.1(3,7).1(9,13)]docosa-1(20),3(22),4,6,9(21), 10,12,16,18-nonaen-12-yl]oxy}methyl)pyrrolidin-1-yl]sulfonyl}benzonitrile bis(trifluoroacetate)

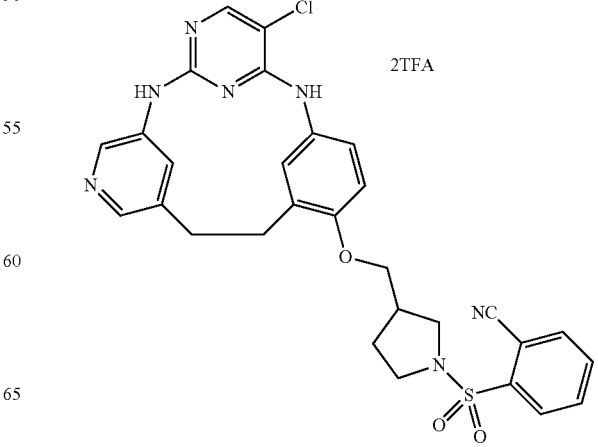

The desired compound was prepared as a white powder according to the procedure of Example C56, using 6-chloro-12-(pyrrolidin-3-ylmethoxy)-2,4,8,18,22pentaazatetracyclo[14.3.1.1(3,7).1(9,13)]docosa-1(20),3(22),4,6,9(21),10,12,16,18-nonaene trihydrochloride and 2-cyanobenzenesulfonyl chloride as the starting materials in 44% yield. LCMS for $C_{29}H_{27}ClN_7O_3S$ (M+H)$^+$: m/z=588.2. $^1$H NMR (300 MHz, DMSO-d$_6$): δ 9.86 (s, 1H), 9.26 (s, 1H), 8.80 (s, 1H), 8.27 (d, J=2.2 Hz, 1H), 8.22 (d, J=2.2 Hz, 1H), 8.15 (s, 1H), 8.13 (dd, J=7.5, 1.5 Hz, 1H), 8.06 (dd, J=7.7, 1.5 Hz, 1H), 7.92 (dd, J=7.7, 1.5 Hz, 1H), 7.85 (dd, J=7.5, 1.4 Hz, 1H), 7.50 (d, J=2.5 Hz, 1H), 7.01 (dd, J=8.6, 2.6 Hz, 1H), 6.84 (d, J=8.6 Hz, 1H), 3.93 (m, 1H), 3.80 (dd, J=9.3, 7.2 Hz, 1H), 3.56 (t, J=7.7 Hz, 1H), 3.40 (m, 1H), 3.22 (dd, J=9.8, 7.0 Hz, 1H), 3.08 (m, 1H), 2.86 (m, 4H), 2.67 (m, 1H), 2.06 (m, 1H), 1.76 (m, 1H).

Example C58

6-Chloro-12-({1-[(5-methylisoxazol-3-yl)carbonyl]pyrrolidin-3-yl}methoxy)-2,4,8,18,22-pentaazatetracyclo[14.3.1.1(3,7).1(9,13)]docosa-1(20),3(22),4,6,9(21),10,12,16,18-nonaene bis(trifluoroacetate)

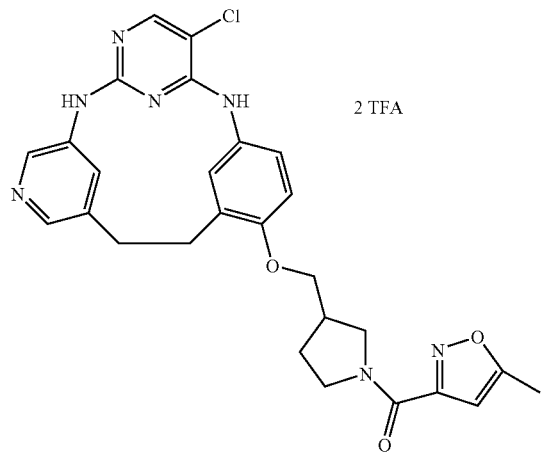 [SMILES: Cc1cc(C(=O)N2CCC(COc3ccc4cc3CCc3cncc(c3)Nc3ncc(Cl)c(n3)N4)C2)no1 ; "2 TFA"]

The desired compound was prepared as a white powder according to the procedure of Example C56, using 6-chloro-12-(pyrrolidin-3-ylmethoxy)-2,4,8,18,22-pentaazatetracyclo[14.3.1.1(3,7).1(9,13)]docosa-1(20),3(22),4,6,9(21),10,12,16,18-nonaene trihydrochloride and 5-methylisoxazole-3-carbonyl chloride as the starting materials in 25% yield. LCMS for $C_{27}H_{27}ClN_7O_3$ (M+H)$^+$: m/z=532.2.

Example C59

3-({[6-Chloro-2,4,8,18,22-pentaazatetracyclo[14.3.1.1(3,7).1(9,13)]docosa-1(20),3(22),4,6,9(21),10,12,16,18-nonaen-12-yl]oxy}methyl)-N-phenylpyrrolidine-1-carboxamide bis(trifluoroacetate)

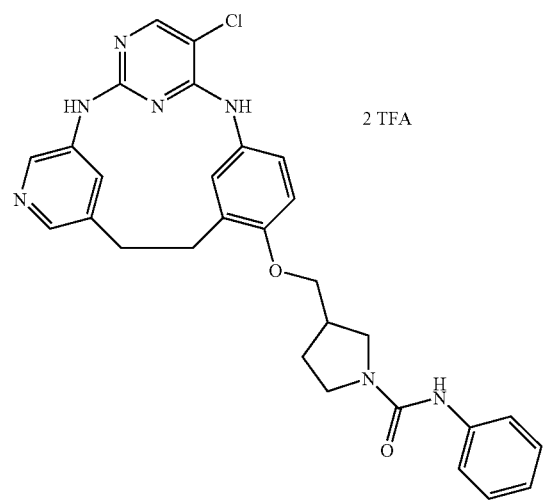 [SMILES: O=C(Nc1ccccc1)N1CCC(COc2ccc3cc2CCc2cncc(c2)Nc2ncc(Cl)c(n2)N3)C1 ; "2 TFA"]

The desired compound was prepared as a white powder according to the procedure of Example C56, using 6-chloro-12-(pyrrolidin-3-ylmethoxy)-2,4,8,18,22-pentaazatetracyclo[14.3.1.1(3,7).1(9,13)]docosa-1(20),3(22),4,6,9(21),10,12,16,18-nonaene trihydrochloride and phenyl isocyanate as the starting materials in 40% yield. LCMS for $C_{29}H_{29}ClN_7O_2$ (M+H)$^+$: m/z=542.1.

Example D1

6-Chloro-14-thia-2,4,8,22-tetraazatetracyclo[14.3.1.1(3,7).1(9,13)]docosa-1(20),3(22),4,6,9(21),10,12,16,18-nonaene trifluoroacetate

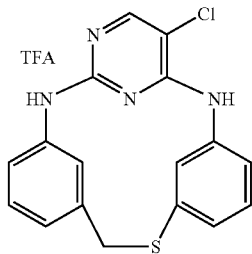 [SMILES: "TFA" ; Clc1cnc2nc1Nc1cccc(c1)SCc1cccc(c1)N2]

Step A: 3-[(3-Nitrobenzyl)thio]aniline

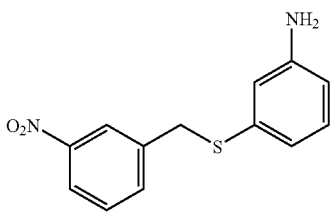 [SMILES: Nc1cccc(SCc2cccc([N+](=O)[O-])c2)c1]

A solution of 3-aminobenzenethiol (0.51 mL, 4.8 mmol) and sodium methoxide (0.31 g, 5.8 mmol) in N,N-dimethylformamide (5.3 mL) was stirred at 25° C. for 10 minutes (min). The reaction mixture was treated with a solution of 1-(bromomethyl)-3-nitro-benzene (1.0 g, 4.8 mmol) in N,N-dimethylformamide (4.5 mL) dropwise and stirred at 25° C. for 1 h. The reaction mixture was poured into water (50 mL) and extracted with ethyl acetate (100 mL). The organic layer was separated and washed with brine (25 mL), dried over anhydrous sodium sulfate, filtered, and evaporated to give a crude brown oil. This material was purified by flash column chromatography to give the desired product (1.2 g, 95%) as a tan oil. LCMS for $C_{13}H_{13}N_2O_2S$ (M+H)$^+$: m/z=261.0.

Step B: 2,5-Dichloro-N-{3-[(3-nitrobenzyl)thio]phenyl}pyrimidin-4-amine

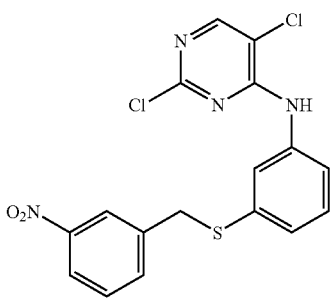 [SMILES: O=[N+]([O-])c1cccc(CSc2cccc(Nc3nc(Cl)ncc3Cl)c2)c1]

A solution of 3-[(3-nitrobenzyl)thio]aniline (0.50 g, 1.9 mmol) in N,N-dimethylformamide (4 mL) at 0° C. was treated with sodium hydride (0.15 g, 3.8 mmol) and stirred at 0° C. for 5 min. The reaction mixture was treated with 2,4,5-trichloropyrimidine dropwise and stirred at 0° C. for 30 min and at 25° C. for 16 h. The reaction mixture was quenched with saturated ammonium chloride (50 mL), poured into saturated sodium bicarbonate (50 mL), and extracted with ethyl acetate (2×100 mL). The combined organic extracts were washed with brine (50 mL), dried over anhydrous sodium sulfate, filtered, and evaporated to give a crude brown gum. This material was purified by flash column chromatography but the desired product contained impurities. Repurification by preparative LCMS gave the desired product as a TFA salt. This material was dissolved in ethyl acetate (50 mL) and washed with saturated sodium bicarbonate. The ethyl acetate layer was dried over anhydrous sodium sulfate, filtered, and evaporated to give the desired product (0.21 g, 27%) as a free base. LCMS for $C_{17}H_{13}Cl_2N_4O_2S$ (M+H)$^+$: m/z=406.9, 409.0.

Step C: N-{3-[(3-Aminobenzyl)thio]phenyl}-2,5-dichloropyrimidin-4-amine trifluoroacetate

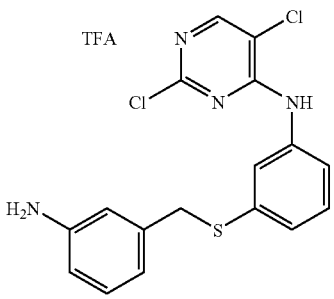 [SMILES: Nc1cccc(CSc2cccc(Nc3nc(Cl)ncc3Cl)c2)c1]

A degassed solution of 2,5-dichloro-N-{3-[(3-nitrobenzyl)thio]phenyl}pyrimidin-4-amine (69 mg, 0.17 mmol) in ethyl acetate (260 mL) was treated with 5% palladium on carbon (sulfided) (10 mg) and stirred under an atmosphere of hydrogen using a balloon for 1 h. The reaction mixture was treated with two additional aliquots of 5% palladium on carbon (sulfided) (20 mg) with stirring of 1 h after each addition. The reaction mixture was filtered, washed with ethyl acetate, and concentrated to a crude residue. This material was purified by preparative LCMS to give the desired product (34 mg, 41%) as a TFA salt. LCMS for $C_{17}H_{15}Cl_2N_4S$ (M+H)$^+$: m/z=377.0, 379.0.

Step D: 6-Chloro-14-thia-2,4,8,22-tetraazatetracyclo[14.3.1.1(3,7).1(9,13)]docosa-1(20),3(22),4,6,9(21),10,12,16,18-nonaene trifluoroacetate A solution of N-{3-[(3-aminobenzyl)thio]phenyl}-2,5-dichloropyrimidin-4-amine trifluoroacetate (33 mg, 67 μmol) in 2-methoxyethanol (6.6 mL) was treated with 3.5 M HCl in ethanol (3 mL) and heated in the microwave at 150° C. for 5 min. The reaction mixture was degassed to remove the HCl and concentrated to a crude residue. This material was purified by preparative LCMS to give the desired product (8.4 mg, 27%) as a TFA salt. LCMS for $C_{17}H_{14}ClN_4S$ (M+H)$^+$: m/z=341.0. $^1$H NMR (300 MHz, DMSO-d$_6$): δ 9.59 (s, 1H), 9.20 (s, 1H), 8.17 (s, 2H), 7.93 (s, 1H), 7.21-7.15 (m, 3H), 7.08-7.05 (m, 1H), 7.00-6.97 (m, 1H), 6.91-6.88 (m, 1H), 4.03 (s, 2H).

Example D2

6-Chloro-15-thia-2,4,8,22-tetraazatetracyclo[14.3.1.1(3,7).1(9,13)]docosa-1(20),3(22),4,6,9(21),10,12,16,18-nonaene trifluoroacetate

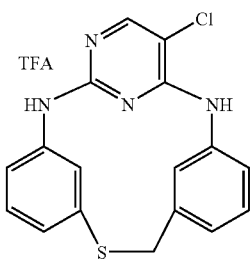 [SMILES: "TFA" ; Clc1cnc2nc1Nc1cccc(c1)CSc1cccc(c1)N2]

Step A: tert-Butyl {3-[(3-nitrobenzyl)thio]phenyl}carbamate

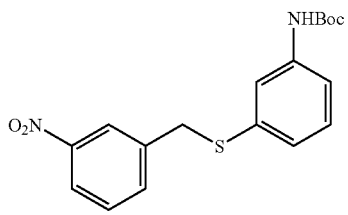 [SMILES: CC(C)(C)OC(=O)Nc1cccc(SCc2cccc([N+](=O)[O-])c2)c1]

A solution of 3-[(3-nitrobenzyl)thio]aniline (0.60 g, 2.3 mmol) in ethanol (2.5 mL) was treated with di-tert-butyldicarbonate (0.65 g, 3.0 mmol) and stirred at 25° C. for 7 h. The reaction mixture was treated with additional di-tert-butyldicarbonate (0.25 g, 1.1 mmol) and stirred at 25° C. for 16 h. The reaction mixture was concentrated to a crude oil. This material was purified by flash column chromatography to give the desired product (0.83 g, quantitative yield) as a clear oil. LCMS for $C_{18}H_{20}N_2O_4SNa$ (M+Na)$^+$: m/z=383.1.

Step B: tert-Butyl {3-[(3-aminobenzyl)thio]phenyl}carbamate

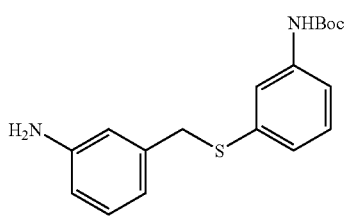

A mixture of iron (0.62 g, 11 mmol) in ethanol (22 mL) was treated with 1 M HCl in water (1.1 mL) and heated at 60° C. for 2 h. The reaction mixture was cooled to 55-60° C. and treated with 5 M ammonium chloride in water (1.9 mL). The reaction mixture was then treated with a solution of tert-butyl {3-[(3-nitrobenzyl)thio]phenyl}carbamate (0.80 g, 2.2 mmol) in ethanol (2.5 mL) while the temperature was kept at 60° C. The resulting suspension was stirred at 60-65° C. for 30 min. The reaction mixture was cooled to 40° C., diluted with ethanol, treated with celite, filtered over a pad of celite, and washed with ethanol. The filtrate was concentrated to a tan solid that was diluted with ethyl acetate (50 mL) and saturated sodium bicarbonate (50 mL). The organic layer was separated and washed with brine (25 mL), dried over anhydrous sodium sulfate, filtered, and evaporated to give a crude tan oil. This material was purified by flash column chromatography to give the desired product (0.63 g, 85%). LCMS for $C_{18}H_{23}N_2O_2S$ (M+H)$^+$: m/z=331.1.

Step C: tert-Butyl [3-({3-[(2,5-dichloropyrimidin-4-yl)amino]benzyl}thio)phenyl]carbamate

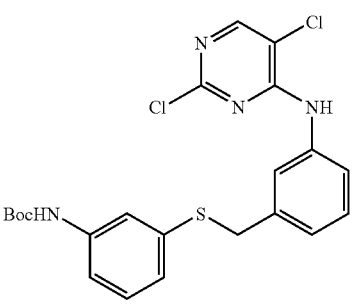 [SMILES: CC(C)(C)OC(=O)Nc1cccc(SCc2cccc(Nc3nc(Cl)ncc3Cl)c2)c1]

A solution of tert-butyl {3-[(3-aminobenzyl)thio]phenyl}carbamate (0.55 g, 1.7 mmol) in N,N-dimethylformamide (5.0 mL) was treated with potassium carbonate (0.30 g, 2.2 mmol) and stirred at 25° C. for 5 min. The reaction mixture was treated with 2,4,5-trichloropyrimidine (0.25 mL, 2.2 mmol) and stirred at 25° C. for 16 h. The reaction mixture was poured into water (50 mL) and extracted with ethyl acetate (100 mL). The organic layer was separated and washed with brine (25 mL), dried over anhydrous sodium sulfate, filtered, and evaporated to give a crude gum. This material was purified by flash column chromatography to give the desired product (0.67 g, 84%) as a solid. LCMS for $C_{22}H_{22}Cl_2N_4O_2SNa$ (M+Na)$^+$: m/z=499.0, 501.0.

Step D: 6-Chloro-15-thia-2,4,8,22-tetraazatetracyclo [14.3.1.1(3,7).1(9,13)]docosa-1(20),3(22),4,6,9(21), 10,12,16,18-nonaene trifluoroacetate A solution of tert-butyl [3-({3-[(2,5-dichloropyrimidin-4-yl)amino]benzyl}thio)phenyl]carbamate (0.15 g, 0.31 mmol) in 2-methoxyethanol (15 mL) was treated with 4 M HCl in 1,4-dioxane (8 mL) and heated in the microwave at 150° C. for 5 min. The reaction mixture was concentrated to a crude residue. This material was purified by preparative LCMS to give the desired product (72 mg, 50%) as a TFA salt. LCMS for $C_{17}H_{14}ClN_4S$ (M+H)$^+$: m/z=341.0. $^1$H NMR (300 MHz, DMSO-d$_6$): δ 9.57 (s, 1H), 9.42 (s, 1H), 8.33 (s, 1H), 8.16 (s, 1H), 7.91 (s, 1H), 7.29 (dd, J=7.9, 7.6 Hz, 1H), 7.15 (d, J=7.9 Hz, 1H), 7.10-7.05 (m, 2H), 6.90 (dd, J=8.2, 0.9 Hz, 1H), 6.84-6.81 (m, 1H), 4.11 (s, 2H).

Example D3

6-Chloro-15-thia-2,4,8,22-tetraazatetracyclo[14.3.1.1 (3,7).1(9,13)]docosa-1(20),3(22),4,6,9(21),10,12,16, 18-nonaene 15-oxide trifluoroacetate

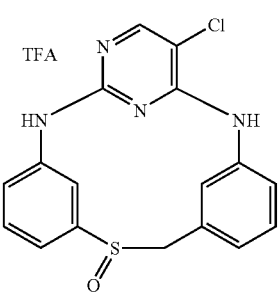 [SMILES: O=S1Cc2cccc(c2)Nc2nc(ncc2Cl)Nc2cccc1c2]

Example D4

6-Chloro-15-thia-2,4,8,22-tetraazatetracyclo[14.3.1.1
(3,7).1(9,13)]docosa-1(20),3(22),4,6,9(21),10,12,16,
18-nonaene 15,15-dioxide trifluoroacetate

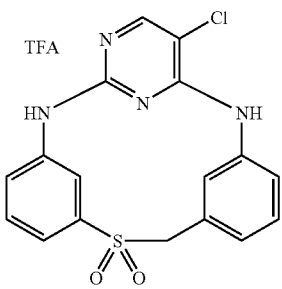 [SMILES: O=S1(=O)Cc2cccc(c2)Nc2nc(ncc2Cl)Nc2cccc1c2]

A solution of 6-chloro-15-thia-2,4,8,22-tetraazatetracyclo[14.3.1.1(3,7).1(9,13)]docosa-1(20),3(22),4,6,9(21),10,12,16,18-nonaene trifluoroacetate (45 mg, 0.13 mmol) in dichloromethane (7 mL) was treated with m-chloroperbenzoic acid (44 mg, 0.20 mmol) and was stirred at 0° C. for 1.5 h. The reaction mixture was concentrated and diluted with ethyl acetate (40 mL). The organic layer was washed with 10% $NaHSO_3$ (20 mL), saturated sodium bicarbonate (30 mL), and brine (10 mL), dried over anhydrous sodium sulfate, filtered, and evaporated to give a crude solid. This material was purified by preparative HPLC to give the desired products Example D3 (13 mg, 12%) and Example D4 (24 mg, 37%) as white solids.

Example D3: LCMS for $C_{17}H_{14}ClN_4OS$ $(M+H)^+$: m/z=357.0. $^1$H NMR (300 MHz, DMSO-$d_6$): δ 9.70 (s, 1H), 9.20 (s, 1H), 8.18 (s, 1H), 8.08 (dd, J=1.8, 1.8 Hz, 1H), 7.84 (s, 1H), 7.55-7.49 (m, 1H), 7.43-7.30 (m, 5H), 4.39 (d, J=12.0 Hz, 1H), 4.23 (d, J=12.0 Hz, 1H).

Example D4: LCMS for $C_{17}H_{14}ClN_4O_2S$ $(M+H)^+$: m/z=373.0. $^1$H NMR (300 MHz, DMSO-$d_6$): δ 9.81 (s, 1H), 9.22 (s, 1H), 8.40 (s, 1H), 8.21 (s, 1H), 7.97 (s, 1H), 7.54-7.52 (m, 2H), 7.50-7.45 (m, 1H), 7.37-7.34 (m, 2H), 7.23-7.20 (m, 1H), 4.70 (s, 2H).

Example D5

6-Chloro-16-oxa-2,4,8,23-tetraazatetracyclo[15.3.1.1
(3,7).1(9,13)]tricosa-1(21),3(23),4,6,9(22),10,12,17,
19-nonaene trifluoroacetate

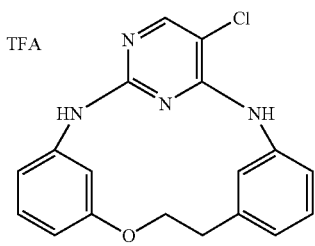 [SMILES: Clc1cnc2nc1Nc1cccc(c1)CCOc1cccc(c1)N2]

Step A: 2-{3-[(2,5-Dichloropyrimidin-4-yl)amino]phenyl}ethanol

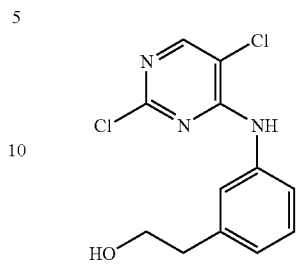

The desired compound was prepared according to the procedure of Example D2, step C, using 2-(3-aminophenyl)ethanol [Bioorg. Med. Chem. 2005, 13, 6703-6712] as the starting material in 86% yield. LCMS for $C_{12}H_{12}Cl_2N_3O$ $(M+H)^+$: m/z=284.0, 286.0.

Step B: 3-[(5-Chloro-4-{[3-(2-hydroxyethyl)phenyl]amino}pyrimidin-2-yl)amino]phenol

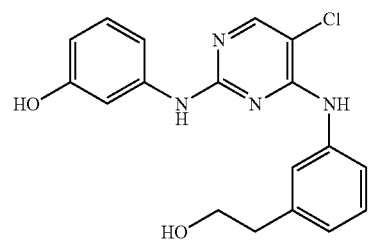 [SMILES: OCCc1cccc(Nc2nc(Nc3cccc(O)c3)ncc2Cl)c1]

A solution of 2-{3-[(2,5-dichloropyrimidin-4-yl)amino]phenyl}ethanol (0.10 g, 0.35 mmol) and 3-aminophenol (58 mg, 0.53 mmol) in 1,4-dioxane (3.5 mL) was treated with p-toluenesulfonic acid monohydrate (54 mg, 0.28 mmol) and heated at 100° C. for 1 h. The reaction mixture was treated with additional 3-aminophenol (19 mg, 0.18 mmol) and heated at 100° C. for 1 h. The reaction mixture was poured into 10% potassium carbonate (20 mL) and extracted with ethyl acetate (2×50 mL). The combined organic layers were washed with brine (25 mL), dried over anhydrous sodium sulfate, filtered, and evaporated to a crude brown oil. This material was purified by flash column chromatography to give the desired product (0.12 g, 96%) as a light brown solid. LCMS for $C_{18}H_{18}ClN_4O_2$ $(M+H)^+$: m/z=357.0.

Step C: 6-Chloro-16-oxa-2,4,8,23-tetraazatetracyclo[15.3.1.1(3,7).1(9,13)]tricosa-1(21),3(23),4,6,9(22),10,12,17,19-nonaene trifluoroacetate A solution of 3-[(5-chloro-4-{[3-(2-hydroxyethyl)phenyl]amino}pyrimidin-2-yl)amino]phenol (50 mg, 0.10 mmol) and triphenylphospine (44 mg, 0.17 mmol) in tetrahydrofuran (10 mL) at 0° C. was treated with 0.1 M of diisopropylazodicarboxylate in tetrahydrofuran (1.8 mL, 0.18 mmol) and stirred at 25° C. for 2 h. The reaction mixture was concentrated and purified by preparative LCMS to give the desired product (11 mg, 20%) as a white solid. LCMS for $C_{18}H_{16}ClN_4O$ $(M+H)^+$: m/z=339.1. $^1$H NMR (300 MHz, DMSO-$d_6$): δ 9.40 (s, 1H), 9.01 (s, 1H), 8.09 (s, 1H), 7.87-

7.85 (m, 2H), 7.21 (dd, J=7.6, 7.6 Hz, 1H), 7.06-7.00 (m, 3H), 6.64-6.61 (m, 1H), 6.51 (dd, J=7.9, 1.8 Hz, 1H), 4.48-4.45 (m, 2H), 2.85-2.81 (m, 2H).

Example D6

6-Chloro-15-oxa-2,4,8,22-tetraazatetracyclo[14.3.1.1(3,7).1(9,13)]docosa-1(20),3(22),4,6,9(21),10,12,16,18-nonaene trifluoroacetate

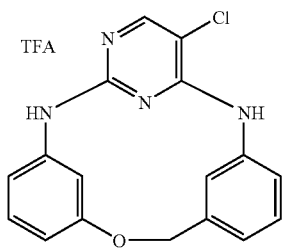 [SMILES: Clc1cnc2nc1Nc1cccc(c1)COc1cccc(c1)N2]

Step A: {3-[(2,5-Dichloropyrimidin-4-yl)amino]phenyl}methanol

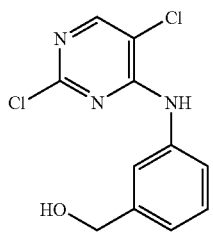 [SMILES: OCc1cccc(Nc2nc(Cl)ncc2Cl)c1]

The desired compound was prepared according to the procedure of Example D2, step C, using 3-aminobenzyl alcohol as the starting material in 93% yield. LCMS for $C_{11}H_{10}Cl_2N_3O$ (M+H)$^+$: m/z=270.0, 272.0.

Step B: 3-[(5-Chloro-4-{[3-(hydroxymethyl)phenyl]amino}pyrimidin-2-yl)amino]phenol

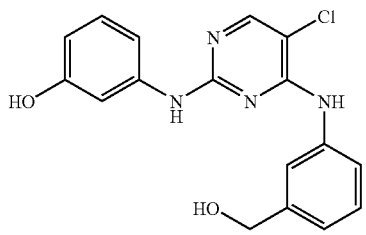 [SMILES: OCc1cccc(Nc2nc(Nc3cccc(O)c3)ncc2Cl)c1]

The desired compound was prepared according to the procedure of Example D5, step B, using {3-[(2,5-dichloropyrimidin-4-yl)amino]phenyl}methanol and 3-aminophenol as the starting materials in 85% yield. LCMS for $C_{17}H_{16}ClN_4O_2$ (M+H)$^+$: m/z=343.1.

Step C: 6-Chloro-15-oxa-2,4,8,22-tetraazatetracyclo[14.3.1.1(3,7).1(9,13)]docosa-1(20),3(22),4,6,9(21),10,12,16,18-nonaene trifluoroacetate The desired compound was prepared according to the procedure of Example D5, step C, using 3-[(5-chloro-4-{[3-(hydroxymethyl)phenyl]amino}pyrimidin-2-yl)amino]phenol as the starting material in 48% yield. LCMS for $C_{17}H_{14}ClN_4O$ (M+H)$^+$: m/z=325.0. $^1$H NMR (400 MHz, DMSO-d$_6$): δ 9.73 (s, 1H), 9.58 (s, 1H), 8.16 (s, 1H), 7.93 (s, 1H), 7.70 (s, 1H), 7.27 (dd, J=7.6, 7.6 Hz, 1H), 7.20 (d, J=7.8 Hz, 1H), 7.04 (d, J=8.2 Hz, 1H), 6.97 (dd, J=8.0, 8.0 Hz, 1H), 6.50 (d, J=8.6 Hz, 1H), 6.44 (d, J=8.2, 2.0 Hz, 1H), 5.14 (s, 2H).

Example D7

6-Chloro-14-oxa-2,4,8,22-tetraazatetracyclo[14.3.1.1(3,7).1(9,13)]docosa-1(20),3(22),4,6,9(21),10,12,16,18-nonaene trifluoroacetate

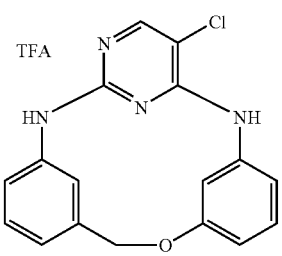 [SMILES: Clc1cnc2nc1Nc1cccc(c1)OCc1cccc(c1)N2]

Step A: 2-(3-Nitrophenoxy)tetrahydro-2H-pyran

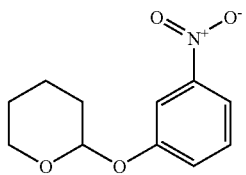 [SMILES: O=[N+]([O-])c1cccc(OC2CCCCO2)c1]

A solution of m-nitrophenol (1.8 g, 13 mmol) in dichloromethane (13 mL) was treated with dihydropyran (1.7 mL, 19 mmol) followed by pyridinium p-toluenesulfonate (0.32 g, 1.2 mmol) and stirred at 25° C. for 16 h. The reaction mixture was diluted with dichloromethane and washed with 1:1 brine/water (50 mL). The organic layer was dried over anhydrous sodium sulfate, filtered, and evaporated to give a crude oil. This material was purified by flash column chromatography to give the desired product (2.5 g, 88%) as a clear oil.

Step B: 3-(Tetrahydro-2H-pyran-2-yloxy)aniline

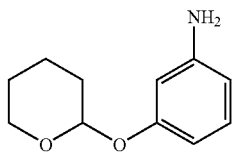 [SMILES: Nc1cccc(OC2CCCCO2)c1]

A solution of 2-(3-nitrophenoxy)tetrahydro-2H-pyran (1.0 g, 4.5 mmol) in methanol (13 mL) was degassed with nitrogen (3×) and treated with 10% Pd/C (wet Degussa type) (12 mg). The reaction mixture was degassed and stirred under an atmosphere of hydrogen at 25° C. for 2 h. The reaction mixture was filtered to give the desired product (0.87 g, quantitative) as a tan oil. LCMS for $C_{11}H_{16}NO_2$ (M+H)+: m/z=194.0.

Step C: 2,5-Dichloro-N-[3-(tetrahydro-2H-pyran-2-yloxy)phenyl]pyrimidin-4-amine

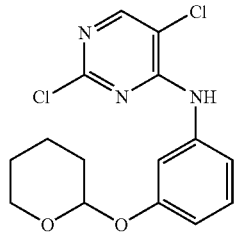 [SMILES: Clc1ncc(Cl)c(Nc2cccc(OC3CCCCO3)c2)n1]

The desired compound was prepared according to the procedure of Example D2, step C, using 3-(tetrahydro-2H-pyran-2-yloxy)aniline as the starting material in 60% yield. LCMS for $C_{15}H_{16}Cl_2N_3O_2$ (M+H)+: m/z=340.0, 342.0.

Step D: 3-[(5-Chloro-2-{[3-(hydroxymethyl)phenyl]amino}pyrimidin-4-yl)amino]phenol

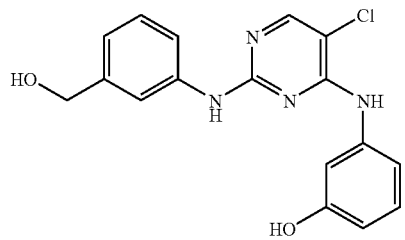 [SMILES: OCc1cccc(Nc2ncc(Cl)c(Nc3cccc(O)c3)n2)c1]

The desired compound was prepared according to the procedure of Example D5, step B, using 2,5-dichloro-N-[3-(tetrahydro-2H-pyran-2-yloxy)phenyl]pyrimidin-4-amine and 3-aminobenzyl alcohol as the starting materials in 53% yield. LCMS for $C_{17}H_{16}ClN_4O_2$ (M+H)+: m/z=343.0.

Step E: 6-Chloro-14-oxa-2,4,8,22-tetraazatetracyclo[14.3.1.1(3,7).1(9,13)]docosa-1(20),3(22),4,6,9(21),10,12,16,18-nonaene trifluoroacetate The desired compound was prepared according to the procedure of Example D5, step C, using 3-[(5-chloro-2-{[3-(hydroxymethyl)phenyl]amino}pyrimidin-4-yl)amino]phenol as the starting material in 54% yield. LCMS for $C_{17}H_{14}ClN_4O$ (M+H)+: m/z=325.1. ¹H NMR (300 MHz, DMSO-$d_6$): δ 9.66 (s, 1H), 9.40 (s, 1H), 8.15 (s, 1H), 7.88 (s, 1H), 7.59 (s, 1H), 7.20 (dd, J=7.6, 7.6 Hz, 1H), 7.11-7.01 (m, 2H), 6.89 (d, J=8.2 Hz, 1H), 6.71 (d, J=7.9 Hz, 1H), 6.56 (dd, J=8.2, 1.8 Hz, 1H), 5.14 (s, 2H).

Example D8

6-Chloro-14-oxa-2,4,8,23-tetraazatetracyclo[15.3.1.1(3,7).1(9,13)]tricosa-1(21),3(23),4,6,9(22),10,12,17,19-nonaene trifluoroacetate

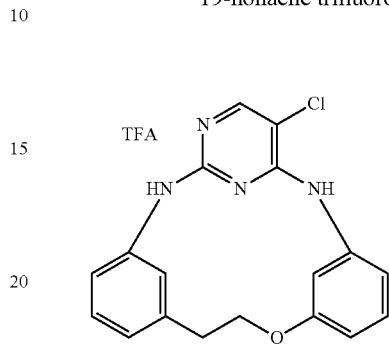

Step A: 3-[(5-Chloro-2-{[3-(2-hydroxyethyl)phenyl]amino}pyrimidin-4-yl)amino]phenol

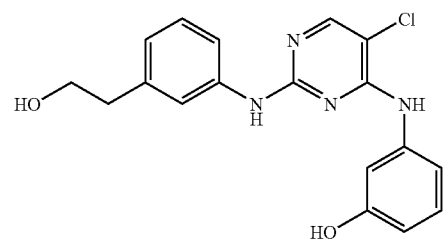 [SMILES: OCCc1cccc(Nc2ncc(Cl)c(Nc3cccc(O)c3)n2)c1]

The desired compound was prepared according to the procedure of Example D5, step B, using 2,5-dichloro-N-[3-(tetrahydro-2H-pyran-2-yloxy)phenyl]pyrimidin-4-amine and 2-(3-aminophenyl)ethanol [Bioorg. Med. Chem. 2005, 13, 6703-6712] as the starting materials in 65% yield. LCMS for $C_{18}H_{18}ClN_4O_2$ (M+H)+: m/z=357.1.

Step B: 6-Chloro-14-oxa-2,4,8,23-tetraazatetracyclo[15.3.1.1(3,7).1(9,13)]tricosa-1(21),3(23),4,6,9(22),10,12,17,19-nonaene trifluoroacetate The desired compound was prepared according to the procedure of Example D5, step C, using 3-[(5-chloro-2-{[3-(2-hydroxyethyl)phenyl]amino}pyrimidin-4-yl)amino]phenol as the starting material in 66% yield. LCMS for $C_{18}H_{16}ClN_4O$ (M+H)+: m/z=339.1. ¹H NMR (300 MHz, DMSO-$d_6$): δ 9.52 (s, 1H), 9.27 (s, 1H), 8.17 (s, 1H), 7.90 (s, 1H), 7.67-7.66 (m, 1H), 7.23-7.13 (m, 2H), 6.92-6.89 (m, 3H), 6.48-6.81 (m, 1H), 4.49-4.54 (m, 2H), 2.75-2.72 (m, 2H).

Example D9

6-Chloro-8-methyl-14-oxa-2,4,8,23-tetraazatetracyclo[15.3.1.1(3,7).1(9,13)]tricosa-1(21),3(23),4,6,9(22),10,12,17,19-nonaene trifluoroacetate

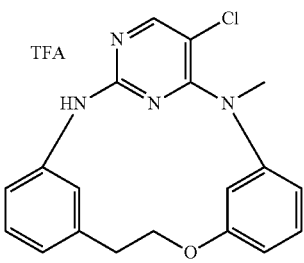 [SMILES: CN1c2cccc(c2)OCCc2cccc(c2)Nc2ncc(Cl)c1n2]

Step A: 2,5-Dichloro-N-methyl-N-[3-(tetrahydro-2H-pyran-2-yloxy)phenyl]pyrimidin-4-amine

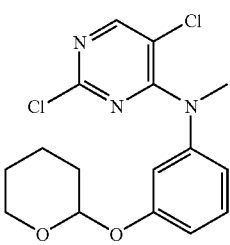 [SMILES: CN(c1cccc(OC2CCCCO2)c1)c1nc(Cl)ncc1Cl]

A solution of 2,5-dichloro-N-[3-(tetrahydro-2H-pyran-2-yloxy)phenyl]pyrimidin-4-amine (110 mg, 0.32 mmol) in acetonitrile (3 mL) was treated with potassium carbonate (89 mg, 0.65 mmol) followed by methyl iodide (60 µL, 0.97 mmol) and heated at 70° C. for 16 h. The reaction mixture was treated with additional methyl iodide (60 µL, 0.97 mmol) and heated at 70° C. for 11 h. The reaction mixture was cooled to 25° C., poured into water (30 mL), and extracted with ethyl acetate (50 mL). The organic layer was separated and washed with brine (20 mL), dried over anhydrous sodium sulfate, filtered, and evaporated to give a crude oil. This material was purified by flash column chromatography to give the desired product (68 mg, 59%) as a clear oil. LCMS for $C_{16}H_{18}Cl_2N_3O_2$ (M+H)$^+$: m/z=354.0, 356.0.

Step B: 3-[(5-Chloro-2-{[3-(2-hydroxyethyl)phenyl]amino}pyrimidin-4-yl)(methyl)amino]phenol

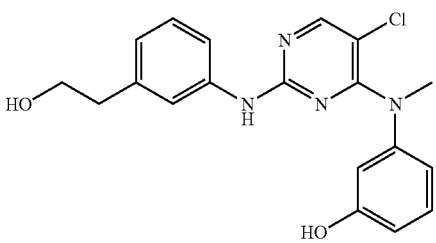 [SMILES: CN(c1cccc(O)c1)c1nc(Nc2cccc(CCO)c2)ncc1Cl]

The desired compound was prepared according to the procedure of Example D5, step B, using 2,5-dichloro-N-methyl-N-[3-(tetrahydro-2H-pyran-2-yloxy)phenyl]pyrimidin-4-amine and 2-(3-aminophenyl)ethanol [Bioorg. Med. Chem. 2005, 13, 6703-6712] as the starting materials in 59% yield. LCMS for $C_{19}H_{20}ClN_4O_2$ (M+H)$^+$: m/z=371.1.

Step C: 6-Chloro-8-methyl-14-oxa-2,4,8,23-tetraazatetracyclo[15.3.1.1(3,7).1(9,13)]tricosa-1(21),3(23),4,6,9(22),10,12,17,19-nonaene trifluoroacetate The desired compound was prepared according to the procedure of Example D5, step C, using 3-[(5-chloro-2-{[3-(2-hydroxyethyl)phenyl]amino}pyrimidin-4-yl)(methyl)amino]phenol as the starting material in 53% yield. LCMS for $C_{19}H_{18}ClN_4O$ (M+H)$^+$: m/z=353.1. $^1$H NMR (300 MHz, DMSO-d$_6$): δ 9.33 (s, 1H), 8.21 (s, 1H), 7.41 (s, 1H), 7.26 (dd, J=8.2, 7.9 Hz, 1H), 7.13-7.06 (m, 2H), 6.89-6.82 (m, 4H), 4.50-4.46 (m, 2H), 3.59 (s, 3H), 2.76-2.73 (m, 2H).

Example D10

6-Chloro-14,17-dioxa-2,4,8,24-tetraazatetracyclo[16.3.1.1(3,7).1(9,13)]tetracosa-1(22),3(24),4,6,9(23),10,12,18,20-nonaene trifluoroacetate

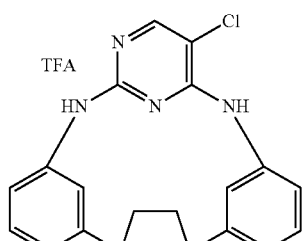

Step A: 2-(3-Nitrophenoxy)ethanol

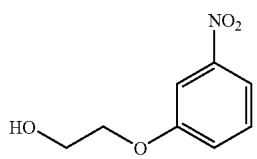 [SMILES: O=[N+]([O-])c1cccc(OCCO)c1]

A solution of m-nitrophenol (2.0 g, 14 mmol), 2-bromoethanol (1.4 mL, 20 mmol), and potassium carbonate (3.0 g, 22 mmol) in N,N-dimethylformamide (10 mL) was heated at 70° C. for 7 h. The reaction mixture was treated with additional 2-bromoethanol (0.5 mL, 7.2 mmol) and potassium carbonate (1.0 g, 7.2 mmol) and heated at 70° C. for 20 h. The reaction mixture was poured into water (50 mL) and extracted with ethyl acetate (150 mL). The organic layer was separated and washed with brine (50 mL), dried over anhydrous sodium sulfate, filtered, and evaporated to a crude residue. This material was purified by flash column chromatography to give the desired product (1.9 g, 70%) as a white solid. LCMS for C$_8$H$_{10}$NO$_4$ (M+H)$^+$: m/z=183.9.

Step B: 2-(3-Aminophenoxy)ethanol

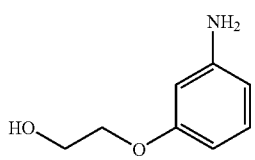 [SMILES: Nc1cccc(OCCO)c1]

The desired compound was prepared according to the procedure of Example D7, step B, using 2-(3-nitrophenoxy)ethanol as the starting material in quantitative yield. LCMS for C$_8$H$_{12}$NO$_2$ (M+H)$^+$: m/z=154.1.

Step C: 2-{3-[(2,5-Dichloropyrimidin-4-yl)amino]phenoxy}ethanol

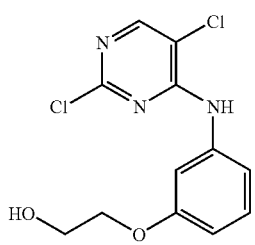 [SMILES: OCCOc1cccc(Nc2nc(Cl)ncc2Cl)c1]

The desired compound was prepared according to the procedure of Example D2, step C, using 2-(3-aminophenoxy)ethanol as the starting material in 30% yield. LCMS for C$_{12}$H$_{12}$Cl$_2$N$_3$O$_2$ (M+H)$^+$: m/z=300.0, 302.0.

Step D: 3-[(5-Chloro-4-{[3-(2-hydroxyethoxy)phenyl]amino}pyrimidin-2-yl)amino]phenol

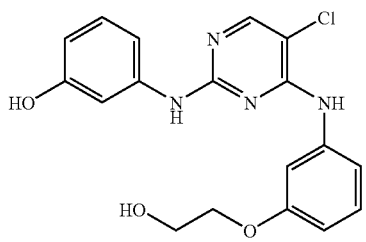 [SMILES: OCCOc1cccc(Nc2nc(Nc3cccc(O)c3)ncc2Cl)c1]

The desired compound was prepared according to the procedure of Example D5, step B, using 2-{3-[(2,5-dichloropyrimidin-4-yl)amino]phenoxy}ethanol and 3-aminophenol as the starting materials in 34% yield. LCMS for C$_{18}$H$_{18}$ClN$_4$O$_3$ (M+H)$^+$: m/z=373.0.

Step E: 6-Chloro-14,17-dioxa-2,4,8,24-tetraazatetracyclo[16.3.1.1(3,7).1(9,13)]tetracosa-1(22),3(24),4,6,9(23),10,12,18,20-nonaene trifluoroacetate The desired compound was prepared according to the procedure of Example D5, step C, using 3-[(5-chloro-4-{[3-(2-hydroxyethoxy)phenyl]amino}pyrimidin-2-yl)amino]phenol as the starting material in 22% yield. LCMS for C$_{18}$H$_{16}$ClN$_4$O$_2$ (M+H)$^+$: m/z=355.1. $^1$H NMR (300 MHz, DMSO-d$_6$): δ 9.56 (s, 1H), 8.74 (s, 1H), 8.18 (s, 1H), 7.94 (dd, J=2.1, 1.8 Hz, 1H), 7.87 (dd, J=2.1, 1.8 Hz, 1H), 7.24 (dd, J=8.2, 7.9 Hz, 1H), 7.13 (dd, J=8.2, 7.9 Hz, 1H), 6.99 (d, J=8.2 Hz, 1H), 6.81-6.75 (m, 2H), 6.54 (dd, J=8.2, 1.8 Hz, 1H), 4.35-4.31 (m, 2H), 4.22-4.18 (m, 2H).

Example D11

6-Chloro-17-oxa-14-thia-2,4,8,24-tetraazatetracyclo[16.3.1.1(3,7).1(9,13)]tetracosa-1(22),3(24),4,6,9(23),10,12,18,20-nonaene trifluoroacetate

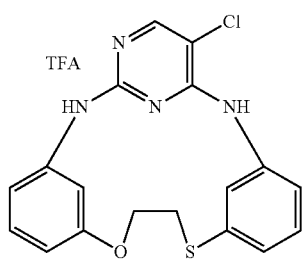 [SMILES: Clc1cnc2nc1Nc1cccc(c1)SCCOc1cccc(c1)N2]

Step A: 3-{[2-(3-Nitrophenoxy)ethyl]thio}aniline

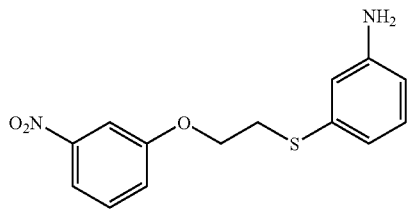 [SMILES: Nc1cccc(SCCOc2cccc([N+](=O)[O-])c2)c1]

The desired compound was prepared according to the procedure of Example D1, step A, using 1-(2-bromoethoxy)-3-nitrobenzene as the starting material in 95% yield. LCMS for C$_{14}$H$_{15}$N$_2$O$_3$S (M+H)$^+$: m/z=291.0.

Step B: 2,5-Dichloro-N-(3-{[2-(3-nitrophenoxy)ethyl]thio}phenyl)pyrimidin-4-amine

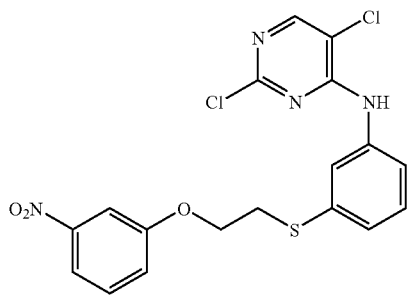

The desired compound was prepared according to the procedure of Example D2, step C, using 3-{[2-(3-nitrophenoxy)

ethyl]thio}aniline as the starting material in 91% yield. LCMS for $C_{18}H_{15}Cl_2N_4O_3S$ (M+H)$^+$: m/z=437.0, 439.0.

Step C: N-(3-{[2-(3-Aminophenoxy)ethyl]thio}phenyl)-2,5-dichloropyrimidin-4-amine

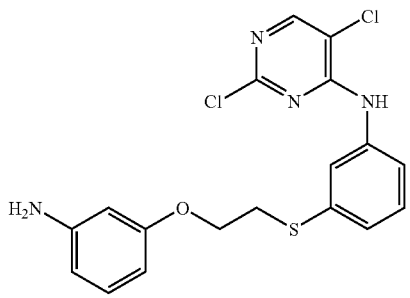 [SMILES: O=[N+]([O-])c1cccc(OCCSc2cccc(Nc3nc(Cl)ncc3Cl)c2)c1]

The desired compound was prepared according to the procedure of Example D2, step B, using 2,5-dichloro-N-(3-{[2-(3-nitrophenoxy)ethyl]thio}phenyl)pyrimidin-4-amine as the starting material in 83% yield. LCMS for $C_{18}H_{17}Cl_2N_4OS$ (M+H)$^+$: m/z=407.1, 409.0.

Step D: 6-Chloro-17-oxa-14-thia-2,4,8,24-tetraazatetracyclo[16.3.1.1(3,7).1(9,13)]tetracosa-1(22),3(24),4,6,9(23),10,12,18,20-nonaene trifluoroacetate The desired compound was prepared according to the procedure of Example D2, step D, using N-(3-{[2-(3-aminophenoxy)ethyl]thio}phenyl)-2,5-dichloropyrimidin-4-amine as the starting material in 40% yield. LCMS for $C_{18}H_{16}ClN_4OS$ (M+H)$^+$: m/z=371.0. $^1$H NMR (300 MHz, DMSO-d$_6$): δ 9.54 (s, 1H), 8.87 (s, 1H), 8.18 (s, 1H), 7.96 (s, 1H), 7.82 (dd, J=2.1, 2.1 Hz, 1H), 7.36-7.20 (m, 3H), 7.08 (dd, J=8.2, 7.9 Hz, 1H), 6.75 (d, J=9.1 Hz, 1H), 6.42 (dd, J=8.2, 1.8 Hz, 1H), 4.07 (t, J=6.4 Hz, 2H), 3.23 (t, J=6.4 Hz, 2H).

Example D12

6-Chloro-14,15-dithia-2,4,8,22-tetraazatetracyclo[14.3.1.1(3,7).1(9,13)]docosa-1(20),3(22),4,6,9(21),10,12,16,18-nonaene trifluoroacetate

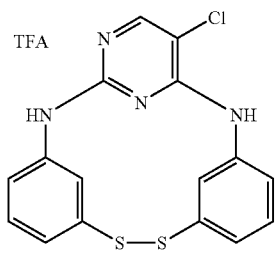 [SMILES: Clc1cnc2nc1Nc1cccc(c1)SSc1cccc(c1)N2]

Step A: 3,3'-Dithiodianiline

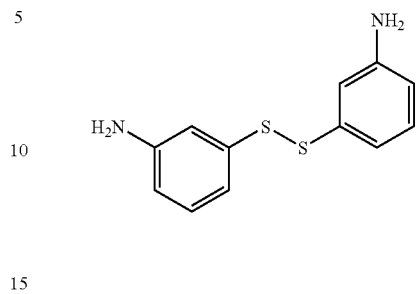

A solution of 3-aminobenzenethiol (0.85 mL, 8.0 mmol) in dimethyl sulfoxide (0.57 mL, 8.0 mmol) was heated at 85° C. for 4 h. The reaction mixture was poured into a solution of brine (25 mL) and water (25 mL) and extracted with ethyl acetate (100 mL). The organic layer was separated and washed with brine (25 mL), dried over anhydrous sodium sulfate, filtered, and evaporated to a crude oil. This material was purified by flash column chromatography to give the desired product (0.97 g, 98%) as a yellow oil. LCMS for $C_{12}H_{13}N_2S_2$ (M+H)$^+$: m/z=249.0.

Step B: N-{3-[(3-Aminophenyl)dithio]phenyl}-2,5-dichloropyrimidin-4-amine

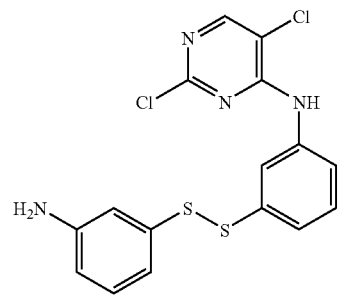 [SMILES: Nc1cccc(SSc2cccc(Nc3nc(Cl)ncc3Cl)c2)c1]

The desired compound was prepared according to the procedure of Example D2, step C, using 3,3'-dithiodianiline as the starting material. The desired compound decomposed during the purification, therefore, the crude material was used without further purification.

Step C: 6-Chloro-14,15-dithia-2,4,8,22-tetraazatetracyclo[14.3.1.1(3,7).1(9,13)]docosa-1(20),3(22),4,6,9(21),10,12,16,18-nonaene trifluoroacetate The desired compound was prepared according to the procedure of Example D2, step D, using N-{3-[(3-aminophenyl)dithio]phenyl}-2,5-dichloropyrimidin-4-amine as the starting material in 6% yield (2 steps). LCMS for $C_{16}H_{12}ClN_4S_2$ (M+H)$^+$: m/z=359.0. $^1$H NMR (300 MHz, DMSO-d$_6$): δ 9.77 (s, 1H), 9.27 (s, 1H), 8.73 (s, 1H), 8.58 (s, 1H), 8.22 (s, 1H), 7.48-7.45 (m, 1H), 7.41-7.39 (m, 2H), 7.23-7.15 (m, 2H), 7.11-7.09 (m, 1H).

Example D13

6-Chloro-17-oxa-14-thia-2,4,8,24-tetraazatetracyclo[16.3.1.1(3,7).1(9,13)]tetracosa-1(22),3(24),4,6,9(23),10,12,18,20-nonaene 14-oxide trifluoroacetate

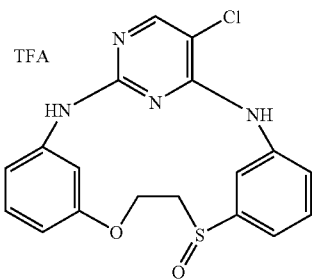 [SMILES: O=S1CCOc2cccc(c2)Nc2ncc(Cl)c(n2)Nc2cccc1c2]

Example D14

6-Chloro-17-oxa-14-thia-2,4,8,24-tetraazatetracyclo[16.3.1.1(3,7).1(9,13)]tetracosa-1(22),3(24),4,6,9(23),10,12,18,20-nonaene 14,14-dioxide trifluoroacetate

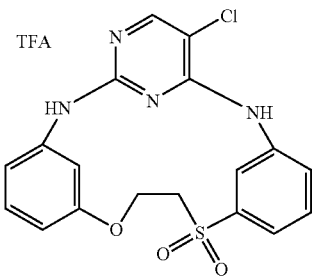 [SMILES: O=S1(=O)CCOc2cccc(c2)Nc2ncc(Cl)c(n2)Nc2cccc1c2]

The desired compounds were prepared according to the procedures of Example D3 and D4 using 6-chloro-17-oxa-14-thia-2,4,8,24-tetraazatetracyclo[16.3.1.1(3,7).1(9,13)]tetracosa-1(22),3(24),4,6,9(23),10,12,18,20-nonaene trifluoroacetate as the starting material in 40% and 35% yields respectively.

Example D13: LCMS for $C_{18}H_{16}ClN_4O_2S$ $(M+H)^+$: m/z=387.1. $^1$H NMR (300 MHz, DMSO-$d_6$): δ 9.60 (s, 1H), 9.18 (s, 1H), 8.20 (s, 1H), 8.01 (s, 1H), 7.69-7.60 (m, 2H), 7.52 (d, J=7.9 Hz, 1H), 7.44 (d, J=8.2 Hz, 1H), 7.07 (dd, J=8.2, 7.9 Hz, 1H), 6.75 (d, J=8.2 Hz, 1H), 6.46 (dd, J=7.9, 1.5 Hz, 1H), 4.22-4.15 (m, 1H), 3.94-3.85 (m, 1H), 3.60-3.50 (m, 1H), 3.40-3.33 (m, 1H).

Example D14: LCMS for $C_{18}H_{16}ClN_4O_3S$ $(M+H)^+$: m/z=403.1. $^1$H NMR (300 MHz, DMSO-$d_6$): δ 9.64 (s, 1H), 9.28 (s, 1H), 8.19 (s, 1H), 8.05 (s, 1H), 7.86-7.81 (m, 2H), 7.68 (dd, J=7.9, 7.9 Hz, 1H), 7.58 (d, J=8.5 Hz, 1H), 7.09 (dd, J=8.2, 7.9 Hz, 1H), 6.77 (dd, J=7.9, 1.5 Hz, 1H), 6.50 (dd, J=7.9, 1.8 Hz, 1H), 4.28-4.15 (m, 2H), 3.93-3.89 (m, 2H).

Example D15

6-Chloro-14-oxa-17-thia-2,4,8,24-tetraazatetracyclo[16.3.1.1(3,7).1(9,13)]tetracosa-1(22),3(24),4,6,9(23),10,12,18,20-nonaene trifluoroacetate

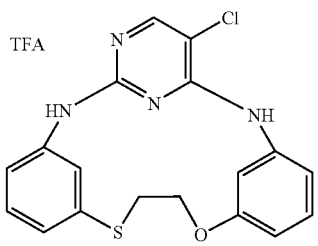 [SMILES: Clc1cnc2nc1Nc1cccc(c1)OCCSc1cccc(c1)N2]

Step A: tert-Butyl (3-{[2-(3-nitrophenoxy)ethyl]thio}phenyl)carbamate

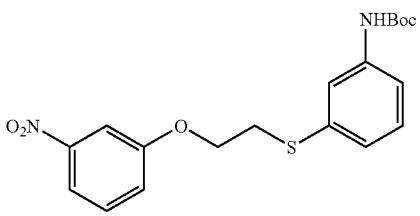 [SMILES: CC(C)(C)OC(=O)Nc1cccc(SCCOc2cccc(N)c2)c1]

A solution of 3-{[2-(3-nitrophenoxy)ethyl]thio}aniline (0.80 g, 2.8 mmol) in ethanol (5 mL) was treated with di-tert-butyldicarbonate (1.2 g, 5.5 mmol) and stirred at 25° C. for 16 h. The reaction mixture was concentrated to an oil that was purified by flash column chromatography to give the desired product (1.1 g, 98%). LCMS for $C_{19}H_{22}N_2O_5SNa$ $(M+Na)^+$: m/z=413.0.

Step B: tert-Butyl (3-{[2-(3-aminophenoxy)ethyl]thio}phenyl)carbamate

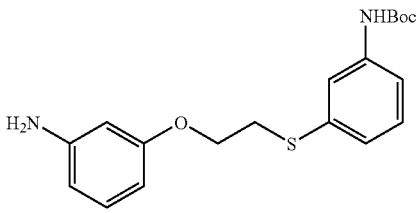

The desired compound was prepared according to the procedure of Example D2, step B, using tert-butyl (3-{[2-(3- nitrophenoxy)ethyl]thio}phenyl)carbamate as the starting material in 74% yield. LCMS for $C_{19}H_{25}N_2O_3S$ (M+H)$^+$: m/z=361.0.

Step C: tert-Butyl {3-[(2-{3-[(2,5-dichloropyrimidin-4-yl)amino]phenoxy}ethyl)thio]phenyl}carbamate

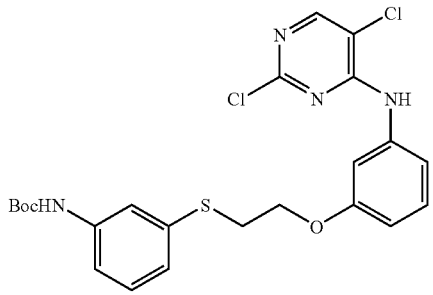 [SMILES: CC(C)(C)OC(=O)Nc1cccc(SCCOc2cccc(Nc3nc(Cl)ncc3Cl)c2)c1]

The desired compound was prepared according to the procedure of Example D2, step C, using tert-butyl (3-{[2-(3-aminophenoxy)ethyl]thio}phenyl)carbamate as the starting material in 97% yield. LCMS for $C_{23}H_{25}Cl_2N_4O_3S$ (M+H)$^+$: m/z=507.0, 509.0.

Step D: 6-Chloro-14-oxa-17-thia-2,4,8,24-tetraaza-tetracyclo[16.3.1.1(3,7).1(9,13)]tetracosa-1(22),3(24),4,6,9(23),10,12,18,20-nonaene trifluoroacetate The desired compound was prepared according to the procedure of Example D2, step D, using tert-butyl {3-[(2-{3-[(2,5-dichloropyrimidin-4-yl)amino]phenoxy}ethyl)thio]phenyl}carbamate as the starting material in 26% yield. LCMS for $C_{18}H_{16}ClN_4OS$ (M+H)$^+$: m/z=371.1. $^1$H NMR (300 MHz, DMSO-d$_6$): δ 9.58 (s, 1H), 8.65 (s, 1H), 8.19-8.18 (m, 2H), 7.88 (s, 1H), 7.25-7.17 (m, 2H), 7.09-7.04 (m, 2H), 6.96 (d, J=8.5 Hz, 1H), 6.64 (dd, J=8.2, 1.8 Hz, 1H), 4.22-4.18 (m, 2H), 3.12-3.08 (m, 2H).

Example D16

6-Chloro-2,4,8,14,22-pentaazatetracyclo[14.3.1.1(3,7).1(9,13)]docosa-1(20),3(22),4,6,9(21),10,12,16,18-nonaene bis(trifluoroacetate)

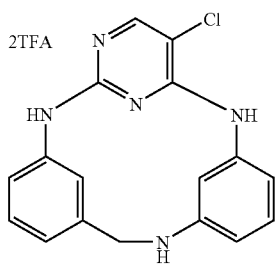 [SMILES: "2TFA" ; Clc1cnc2nc1Nc1cccc(c1)NCc1cccc(c1)N2]

Step A: tert-Butyl {3-[(3-nitrobenzyl)amino]phenyl}carbamate

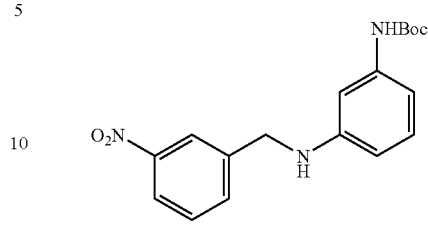

A solution of tert-butyl (3-aminophenyl)carbamate (0.51 g, 2.4 mmol) and potassium carbonate (0.61 g, 4.4 mmol) in N,N-dimethylformamide (7 mL) was treated with a solution of 1-(bromomethyl)-3-nitrobenzene (0.50 g, 2.3 mmol) in N,N-dimethylformamide (3 mL) and stirred at 25° C. for 16 h. The reaction mixture was diluted with water (80 mL) and extracted with ethyl acetate (3×75 mL). The combined organic layers were washed with water (3×50 mL) and brine (50 mL), dried over anhydrous sodium sulfate, filtered, and evaporated to give a crude residue. This material was purified by flash column chromatography to give the desired product (0.78 g, 88% [90% pure]) as a solid. LCMS for $C_{18}H_{22}N_3O_4$ (M+H)$^+$: m/z=344.2.

Step B: N-(3-Nitrobenzyl)benzene-1,3-diamine bis(trifluoroacetate)

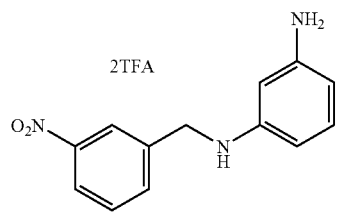 [SMILES: Nc1cccc(NCc2cccc([N+](=O)[O-])c2)c1 ; "2TFA"]

A solution of tert-butyl {3-[(3-nitrobenzyl)amino]phenyl}carbamate (100 mg, 0.3 mmol) in dichloromethane (3 mL) and trifluoroacetic acid (3 mL) was stirred at 25° C. for 1 h. The reaction mixture was concentrated to a crude residue. This material was purified by preparative LCMS to give the desired product (110 mg, 79%) as a solid. LCMS for $C_{13}H_{14}N_3O_2$ (M+H)$^+$: m/z=244.0.

Step C: N-(2,5-Dichloropyrimidin-4-yl)-N'-(3-nitrobenzyl)benzene-1,3-diamine trifluoroacetate

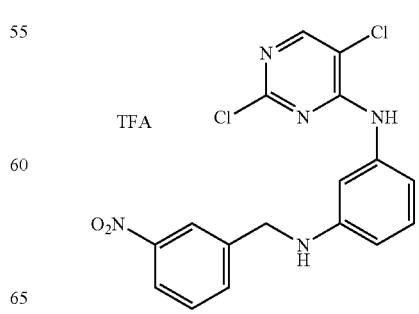

593

The desired compound was prepared according to the procedure of Example D2, step C, using N-(3-nitrobenzyl)benzene-1,3-diamine bis(trifluoroacetate) as the starting material in 63% yield after purification by preparative LCMS. LCMS for $C_{17}H_{14}Cl_2N_5O_2$ (M+H)$^+$: m/z=389.9, 391.9.

Step D: N-(3-Aminobenzyl)-N'-(2,5-dichloropyrimidin-4-yl)benzene-1,3-diamine

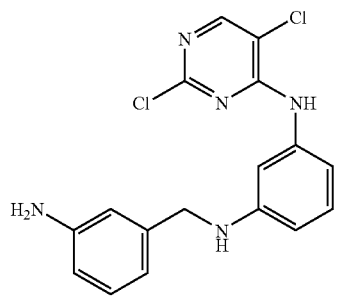

A solution of N-(2,5-dichloropyrimidin-4-yl)-N'-(3-nitrobenzyl)benzene-1,3-diamine trifluoroacetate (67 mg, 0.13 mmol) in methanol (0.51 mL), acetic acid (0.20 mL), and water (0.10 mL) was treated with iron (30 mg, 0.53 mmol) and stirred at 25° C. for 1 h. The reaction mixture was treated with additional iron (25 mg, 0.45 mmol) and stirred at 25° C. for 16 h. The reaction mixture was diluted with methanol (2 mL) and celite was added. The resulting suspension was filtered through a pad of celite and rinsed with methanol. The filtrate was concentrated to give the desired product as a crude residue that was used without further purification.

Step E: 6-Chloro-2,4,8,14,22-pentaazatetracyclo[14.3.1.1(3,7).1(9,13)]docosa-1(20),3(22),4,6,9(21),10,12,16,18-nonaene bis(trifluoroacetate)

The desired compound was prepared according to the procedure of Example D2, step D, using N-(3-aminobenzyl)-N'-(2,5-dichloropyrimidin-4-yl)benzene-1,3-diamine as the starting material in 14% yield (2 steps: Steps D and E). LCMS for $C_{17}H_{15}ClN_5$ (M+H)$^+$: m/z=324.0. $^1$H NMR (400 MHz, DMSO-d$_6$): δ 9.70 (s, 1H), 9.31 (s, 1H), 8.15 (s, 1H), 7.70 (s, 1H), 7.24 (s, 1H), 7.18 (dd, J=7.8, 7.6 Hz, 1H), 7.05 (d, J=7.6 Hz, 1H), 6.93 (dd, J=7.6, 7.4 Hz, 1H), 6.85 (d, J=7.4 Hz, 1H), 6.50-6.40 (m, 2H), 4.19 (s, 2H).

Example D17

6-Chloro-2,4,8,15,22-pentaazatetracyclo[14.3.1.1(3,7).1(9,13)]docosa-1(20),3(22),4,6,9(21),10,12,16,18-nonaene bis(trifluoroacetate)

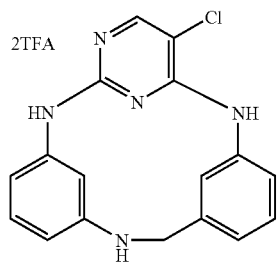 [SMILES: "2TFA" ; Clc1cnc2nc1Nc1cccc(c1)CNc1cccc(c1)N2]

594

Step A: tert-Butyl {3-[(3-aminobenzyl)amino]phenyl}carbamate

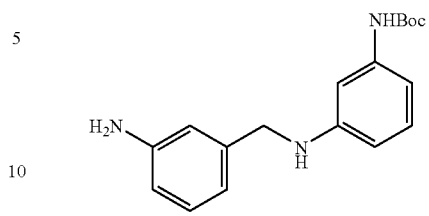

The desired compound was prepared according to the procedure of Example D2, step B, using tert-butyl {3-[(3-nitrobenzyl)amino]phenyl}carbamate as the starting material in 82% yield after purification by preparative LCMS. LCMS for $C_{18}H_{24}N_3O_2$ (M+H)$^+$: m/z=314.1.

Step B: tert-Butyl [3-({3-[(2,5-dichloropyrimidin-4-yl)amino]benzyl}amino)phenyl]carbamate

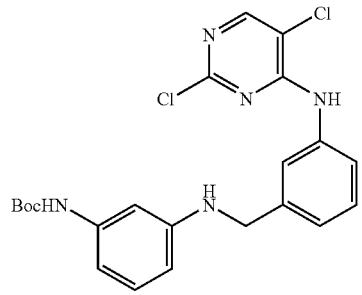 [SMILES: CC(C)(C)OC(=O)Nc1cccc(NCc2cccc(Nc3nc(Cl)ncc3Cl)c2)c1]

The desired compound was prepared according to the procedure of Example D2, step C, using tert-butyl {3-[(3-nitrobenzyl)amino]phenyl}carbamate as the starting material in 44% yield. LCMS for $C_{22}H_{24}Cl_2N_5O_2$ (M+H)$^+$: m/z=460.1, 462.0.

Step C: 6-Chloro-2,4,8,15,22-pentaazatetracyclo[14.3.1.1(3,7).1(9,13)]docosa-1(20),3(22),4,6,9(21),10,12,16,18-nonaene bis(trifluoroacetate)

The desired compound was prepared according to the procedure of Example D2, step D, using tert-butyl [3-({3-[(2,5-dichloropyrimidin-4-yl)amino]benzyl}amino)phenyl]carbamate as the starting material in 27% yield. LCMS for $C_{17}H_{15}ClN_5$ (M+H)$^+$: m/z=324.0. $^1$H NMR (300 MHz, DMSO-d$_6$): δ 9.90 (s, 1H), 9.65 (s, 1H), 8.19 (s, 1H), 7.77 (s, 1H), 7.33 (s, 1H), 7.27 (dd, J=7.6, 7.6 Hz, 1H), 7.16 (d, J=7.6 Hz, 1H), 7.01 (d, J=7.9 Hz, 1H), 6.88 (dd, J=7.9, 7.9 Hz, 1H), 6.37-6.27 (m, 2H), 4.20 (s, 2H).

Example D18

6-Chloro-14-thia-2,4,8,23-tetraazatetracyclo[15.3.1.1(3,7).1(9,13)]tricosa-1(21),3(23),4,6,9(22),10,12,17,19-nonaene trifluoroacetate

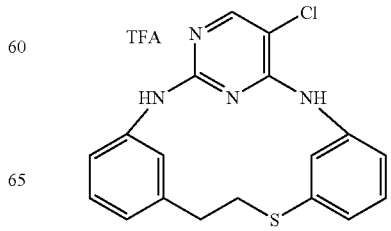

Step A: 3-{[2-(3-Nitrophenyl)ethyl]thio}aniline

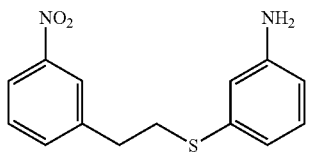 [SMILES: Nc1cccc(SCCc2cccc([N+](=O)[O-])c2)c1]

The desired compound was prepared according to the procedure of Example D1, step A, using 2-(3-nitrophenyl)ethyl methanesulfonate [WO05/014552] as the starting material in 84% yield. LCMS for $C_{14}H_{15}N_2O_2S$ (M+H)$^+$: m/z=275.0.

Step B: 2,5-Dichloro-N-(3-{[2-(3-nitrophenyl)ethyl]thio}phenyl)pyrimidin-4-amine

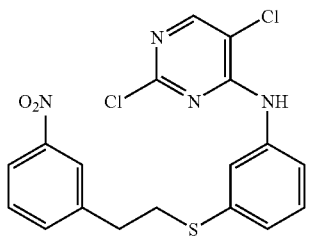 [SMILES: O=[N+]([O-])c1cccc(CCSc2cccc(Nc3nc(Cl)ncc3Cl)c2)c1]

The desired compound was prepared according to the procedure of Example D2, step C, using 3-{[2-(3-nitrophenyl)ethyl]thio}aniline as the starting material in 93% yield. LCMS for $C_{18}H_{15}Cl_2N_4O_2S$ (M+H)$^+$: m/z=420.9, 422.9.

Step C: N-(3-{[2-(3-Aminophenyl)ethyl]thio}phenyl)-2,5-dichloropyrimidin-4-amine

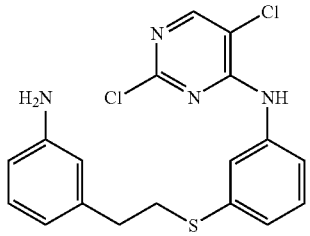 [SMILES: Nc1cccc(CCSc2cccc(Nc3nc(Cl)ncc3Cl)c2)c1]

The desired compound was prepared according to the procedure of Example D2, step B, using 2,5-dichloro-N-(3-{[2-(3-nitrophenyl)ethyl]thio}phenyl)pyrimidin-4-amine as the starting material in 79% yield. LCMS for $C_{18}H_{17}Cl_2N_4S$ (M+H)$^+$: m/z=390.9, 393.0.

Step D: 6-Chloro-14-thia-2,4,8,23-tetraazatetracyclo[15.3.1.1(3,7).1(9,13)]tricosa-1(21),3(23),4,6,9(22),10,12,17,19-nonaene trifluoroacetate The desired compound was prepared according to the procedure of Example D2, step D, using N-(3-{[2-(3-aminophenyl)ethyl]thio}phenyl)-2,5-dichloropyrimidin-4-amine as the starting material in 51% yield. LCMS for $C_{18}H_{16}ClN_4S$ (M+H)$^+$: m/z=354.9. $^1$H NMR (300 MHz, DMSO-d$_6$): δ 9.55 (s, 1H), 9.22 (s, 1H), 8.18 (s, 1H), 8.05 (s, 1H), 7.98 (s, 1H), 7.37-7.20 (m, 3H), 7.15 (dd, J=7.9, 7.6 Hz, 1H), 6.94-6.91 (m, 1H), 6.82 (d, J=7.3 Hz, 1H), 3.25-3.20 (m, 2H), 2.57-2.53 (m, 2H).

Example D19

6-Chloro-16-thia-2,4,8,23-tetraazatetracyclo[15.3.1.1(3,7).1(9,13)]tricosa-1(21),3(23),4,6,9(22),10,12,17,19-nonaene hydrochloride

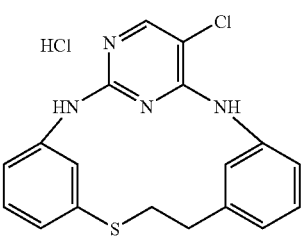 [SMILES: Clc1cnc2nc1Nc1cccc(c1)CCSc1cccc(c1)N2 ; Cl]

Step A: tert-Butyl (3-{[2-(3-nitrophenyl)ethyl]thio}phenyl)carbamate

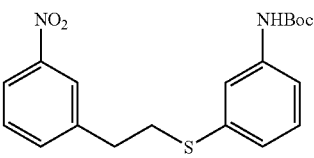 [SMILES: CC(C)(C)OC(=O)Nc1cccc(SCCc2cccc([N+](=O)[O-])c2)c1]

The desired compound was prepared according to the procedure of Example D2, step A, using 3-{[2-(3-nitrophenyl)ethyl]thio}aniline as the starting material in quantitative yield. LCMS for $C_{19}H_{22}N_2O_4SNa$ (M+Na)$^+$: m/z=397.0.

Step B: tert-Butyl (3-{[2-(3-aminophenyl)ethyl]thio}phenyl)carbamate

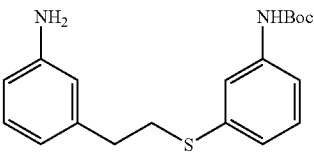 [SMILES: CC(C)(C)OC(=O)Nc1cccc(SCCc2cccc(N)c2)c1]

The desired compound was prepared according to the procedure of Example D2, step B, using tert-butyl (3-{[2-(3- nitrophenyl)ethyl]thio}phenyl)carbamate as the starting material in quantitative yield. LCMS for $C_{19}H_{25}N_2O_2S$ (M+H)$^+$: m/z=345.0.

Step C: tert-Butyl {3-[(2-{3-[(2,5-dichloropyrimidin-4-yl)amino]phenyl}ethyl)thio]phenyl}carbamate

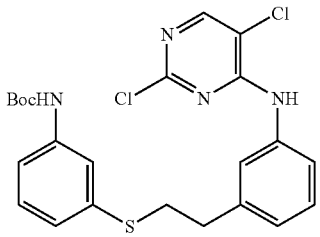

The desired compound was prepared according to the procedure of Example D2, step C, using tert-butyl (3-{[2-(3-aminophenyl)ethyl]thio}phenyl)carbamate as the starting material in 82% yield. LCMS for $C_{23}H_{25}Cl_2N_4O_2S$ (M+H)$^+$: m/z=490.9, 492.9.

Step D: 6-Chloro-16-thia-2,4,8,23-tetraazatetracyclo[15.3.1.1(3,7).1(9,13)]tricosa-1(21),3(23),4,6,9(22),10,12,17,19-nonaene hydrochloride The desired compound was prepared according to the procedure of Example D2, step D, using tert-butyl {3-[(2-{3-[(2,5-dichloropyrimidin-4-yl)amino]phenyl}ethyl)thio]phenyl}carbamate as the starting material in 35% yield. LCMS for $C_{18}H_{16}ClN_4S$ (M+H)$^+$: m/z=355.0. $^1$H NMR (300 MHz, DMSO-d$_6$): δ 9.79 (s, 1H), 9.34 (s, 1H), 8.21 (s, 1H), 8.13 (s, 1H), 7.86 (s, 1H), 7.29-7.24 (m, 1H), 7.19-7.11 (m, 2H), 7.04-6.94 (m, 3H), 3.37-3.25 (m, 2H), 2.76-2.72 (m, 2H).

Example D20

6-Chloro-15-thia-2,4,8,23-tetraazatetracyclo[15.3.1.1(3,7).1(9,13)]tricosa-1(21),3(23),4,6,9(22),10,12,17,19-nonaene trifluoroacetate

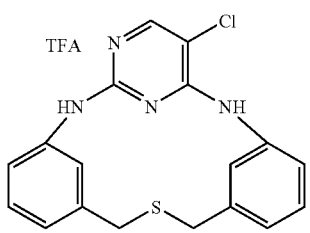 [SMILES: "TFA" ; Clc1cnc2nc1Nc1cccc(c1)CSCc1cccc(c1)N2]

Step A: 3-[(tert-Butoxycarbonyl)amino]benzyl methanesulfonate

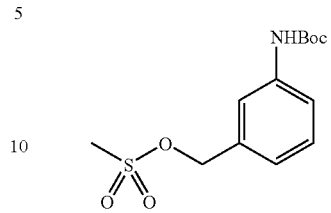

A solution of tert-butyl [3-(hydroxymethyl)phenyl]carbamate (0.6 g, 2.7 mmol) [J. Med. Chem. 1989, 32, 807-826] in dichloromethane (8.4 mL) at −10° C. was treated with N,N-diisopropylethylamine (0.7 mL, 4.0 mmol) followed by methanesulfonyl chloride (0.31 mL, 4.0 mmol and stirred at −10° C. for 1 h. The reaction mixture was quenched with water (50 mL) and extracted with dichloromethane (100 mL). The organic layer was separated, dried over anhydrous sodium sulfate, filtered, and evaporated to give the desired product as a crude yellow oil that was used without further purification. LCMS for $C_{13}H_{19}NO_5SNa$ (M+Na)$^+$: m/z=323.9.

Step B: tert-Butyl (3-{[(3-nitrobenzyl)thio]methyl}phenyl)carbamate

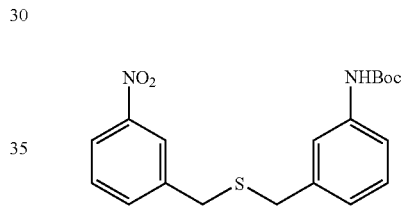

A solution of cesium carbonate (0.57 g, 1.8 mmol) in N,N-dimethylformamide (1.8 mL) at 0° C. was treated with (3-nitrophenyl)methanethiol (0.22 mL, 1.6 mmol) dropwise and stirred at 0° C. for 10 min. The reaction mixture was treated with a solution of 3-[(tert-butoxycarbonyl)amino]benzyl methanesulfonate (0.41 g, 1.3 mmol) in N,N-dimethylformamide (2.4 mL) dropwise and stirred at 0° C. for 30 min. The reaction mixture was diluted with ethyl acetate (50 mL) and washed with water (40 mL) and brine (20 mL). The organic layer was separated, dried over anhydrous sodium sulfate, filtered, and evaporated to a crude brown oil. This material was purified by flash column chromatography to give the desired product (0.42 g, 84% for 2 steps) as a yellow oil. LCMS for $C_{19}H_{22}N_2O_4SNa$ (M+Na)$^+$: m/z=396.7.

Step C: tert-Butyl (3-{[(3-aminobenzyl)thio]methyl}phenyl)carbamate

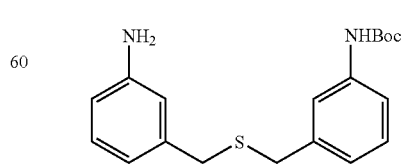

The desired compound was prepared according to the procedure of Example D2, step B, using tert-butyl (3-{[(3-nitrobenzyl)thio]methyl}phenyl)carbamate as the starting material in 76% yield. LCMS for $C_{19}H_{25}N_2O_2S$ (M+H)$^+$: m/z=345.0.

Step D: tert-Butyl {3-[({3-[(2,5-dichloropyrimidin-4-yl)amino]benzyl}thio)methyl]phenyl}carbamate

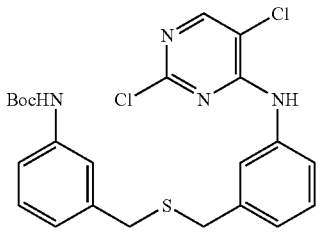

The desired compound was prepared according to the procedure of Example D2, step C, using tert-butyl (3-{[(3-aminobenzyl)thio]methyl}phenyl)carbamate as the starting material in 84% yield. LCMS for $C_{23}H_{24}Cl_2N_4O_2SNa$ (M+Na)$^+$: m/z=513.0, 515.0.

Step E: 6-Chloro-15-thia-2,4,8,23-tetraazatetracyclo[15.3.1.1(3,7).1(9,13)]tricosa-1(21),3(23),4,6,9(22),10,12,17,19-nonaene trifluoroacetate The desired compound was prepared according to the procedure/conditions of Example D5, step B, using tert-butyl {3-[({3-[(2,5-dichloropyrimidin-4-yl)amino]benzyl}thio)methyl]phenyl}carbamate as the starting material in 15% yield. LCMS for $C_{18}H_{16}ClN_4S$ (M+H)$^+$: m/z=355.0. $^1$H NMR (300 MHz, DMSO-d$_6$): δ 9.60 (s, 1H), 9.17 (s, 1H), 8.18 (s, 1H), 7.99 (s, 1H), 7.93 (s, 1H), 7.38-7.33 (m, 1H), 7.25-7.19 (m, 3H), 7.00-6.94 (m, 2H), 3.44 (s, 2H), 3.30 (s, 2H).

Example D21

6-Chloro-15-oxa-2,4,8,23-tetraazatetracyclo[15.3.1.1(3,7).1(9,13)]tricosa-1(21),3(23),4,6,9(22),10,12,17,19-nonaene trifluoroacetate

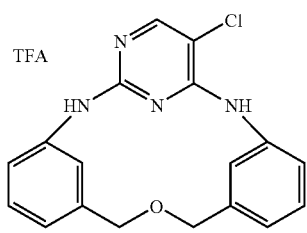 [SMILES: Clc1cnc2nc1Nc1cccc(c1)COCc1cccc(c1)N2]

Step A: tert-Butyl (3-{[(3-nitrobenzyl)oxy]methyl}phenyl)carbamate

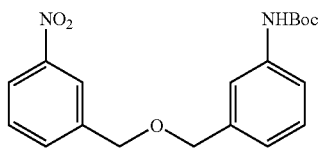

The desired compound was prepared according to the procedure of Example D20, step B, using 3-nitro-benzenemethanol as the starting material in 38% yield. LCMS for $C_{19}H_{22}N_2O_5Na$ (M+Na)$^+$: m/z=381.0.

Step B: tert-Butyl (3-{[(3-aminobenzyl)oxy]methyl}phenyl)carbamate

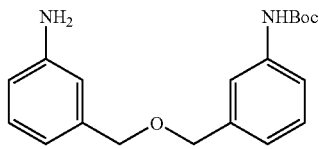 [SMILES: CC(C)(C)OC(=O)Nc1cccc(COCc2cccc(N)c2)c1]

The desired compound was prepared according to the procedure of Example D2, step B, using tert-butyl (3-{[(3-nitrobenzyl)oxy]methyl}phenyl)carbamate as the starting material in quantitative yield. LCMS for $C_{19}H_{25}N_2O_3$ (M+H)$^+$: m/z=329.1.

Step C: tert-Butyl {3-[({3-[(2,5-dichloropyrimidin-4-yl)amino]benzyl}oxy)methyl]phenyl}carbamate

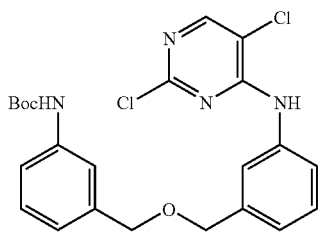 [SMILES: CC(C)(C)OC(=O)Nc1cccc(COCc2cccc(Nc3nc(Cl)ncc3Cl)c2)c1]

The desired compound was prepared according to the procedure of Example D2, step C, using tert-butyl (3-{[(3-aminobenzyl)oxy]methyl}phenyl)carbamate as the starting material in 79% yield. LCMS for $C_{23}H_{24}Cl_2N_4O_3Na$ (M+Na)$^+$: m/z=497.0, 499.0.

Step D: 6-Chloro-15-oxa-2,4,8,23-tetraazatetracyclo[15.3.1.1(3,7).1(9,13)]tricosa-1(21),3(23),4,6,9(22),10,12,17,19-nonaene trifluoroacetate The desired compound was prepared according to the procedure/conditions of Example D5, step B, using tert-butyl {3-[({3-[(2,5-dichloropyrimidin-4-yl)amino]benzyl}oxy)methyl]phenyl}carbamate as the starting material in 47% yield. LCMS for $C_{18}H_{16}ClN_4O$ (M+H)$^+$: m/z=339.0. $^1$H NMR (300 MHz, DMSO-d$_6$): δ 9.60 (s, 1H), 9.18 (s, 1H), 8.35 (s, 1H), 8.17 (s, 1H), 8.12 (s, 1H), 7.32-7.21 (m, 2H), 7.15 (dd, J=7.9, 7.6 Hz, 1H), 7.07 (d, J=7.3 Hz, 1H), 7.00-7.96 (m, 1H), 6.84 (d, J=7.3 Hz, 1H), 4.49 (s, 2H), 4.39 (s, 2H).

Example D22

19-Bromo-6-chloro-14-oxa-2,4,8,23-tetraazatetracyclo[15.3.1.1(3,7).1(9,13)]tricosa-1(21),3(23),4,6,9(22),10,12,17,19-nonaene trifluoroacetate

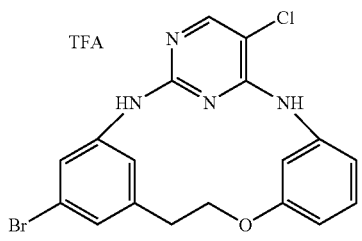 [SMILES: Clc1cnc2nc1Nc1cccc(c1)OCCc1cc(Br)cc(c1)N2]

Step A:
3-Bromo-5-[(tert-butoxycarbonyl)amino]benzoic acid

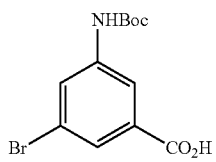

A solution of 3-amino-5-bromobenzoic acid (10 g, 46 mmol) in 1,4-dioxane (46 mL) and water (46 mL) was treated with triethylamine (10 mL, 69 mmol) followed by a solution of di-tert-butyldicarbonate (15 g, 69 mmol) in 1,4-dioxane (46 mL) at 0° C. The reaction mixture was stirred at 20° C. for 16 h, treated with additional triethylamine (3.2 mL, 23 mmol) and di-tert-butyldicarbonate (5.1 g, 23 mmol), and stirred for another 16 h. The reaction mixture was concentrated, diluted with ethyl acetate (200 mL), and washed with 1 N HCl (2×100 mL) and brine (50 mL). The organic layer was separated, dried over anhydrous sodium sulfate, filtered, and evaporated to give the desired product as a crude tan solid. This material was stirred in boiling toluene (100 mL), cooled, filtered, washed with cold toluene, and dried to give the desired product (13.6 g, 93%) as an off-white solid. LCMS for $C_{12}H_{15}BrNO_4$ (M+H)$^+$: m/z=316.0, 318.0.

Step B: tert-Butyl [3-bromo-5-(hydroxymethyl)phenyl]carbamate

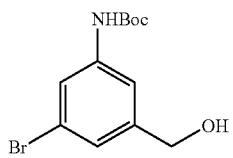 [SMILES: CC(C)(C)OC(=O)Nc1cc(Br)cc(CO)c1]

A solution of 3-bromo-5-[(tert-butoxycarbonyl)amino]benzoic acid (13.6 g, 43.1 mol) in tetrahydrofuran (44 mL) at 0° C. was treated with 1 M borane in THF (64.6 mL, 64.6 mmol) dropwise and stirred at 20° C. for 1 h. The reaction mixture was concentrated, diluted with ethyl acetate (200 mL), and washed with 1 M HCl (100 mL) and brine (50 mL). The organic layer was separated, dried over anhydrous sodium sulfate, filtered, and evaporated to give the desired product as a colorless oil that was used without further purification. LCMS for $C_{12}H_{16}BrNO_3Na$ (M+Na)$^+$: m/z=323.9, 325.9.

Step C: tert-Butyl (3-bromo-5-formylphenyl)carbamate

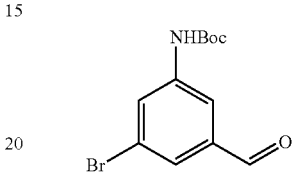

A solution of tert-butyl [3-bromo-5-(hydroxymethyl)phenyl]carbamate (13.3 g, 44.2 mmol) and manganese(IV) oxide (19.2 g, 221 mmol) in 1,2-dichloroethane (88 mL) was stirred at 80° C. for 3 h. The reaction mixture was treated with additional manganese(IV) oxide (11.5 g, 132 mmol) and stirred at 80° C. for 16 h. The reaction mixture was filtered over celite (2×) and washed with dichloromethane. The filtrate was concentrated to give the desired product (10.9 g, 82% for 2 steps) as a white solid. LCMS for $C_{12}H_{14}BrNO_3Na$ (M+Na)$^+$: m/z=321.9, 323.9.

Step D: tert-Butyl (3-bromo-5-vinylphenyl)carbamate

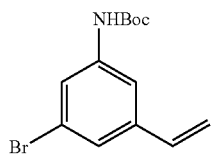 [SMILES: C=Cc1cc(Br)cc(NC(=O)OC(C)(C)C)c1]

A solution of triphenylmethylphosphonium bromide (28.4 g, 79.5 mmol) in tetrahydrofuran (152 mL) at 0° C. was treated with 2.5 M n-butyllithium in hexanes (31.8 mL, 79.5 mmol) dropwise and stirred at 0° C. for 15 min and at 20° C. for 1 h. The reaction mixture was cooled to 0° C., treated with a solution of tert-butyl (3-bromo-5-formylphenyl)carbamate (10.9 g, 36.2 mmol) in tetrahydrofuran (55 mL), and stirred at 20° C. for 1 h. The reaction mixture was cooled to 0° C., quenched with water (50 mL), concentrated to remove most of the tetrahydrofuran, poured into water (150 mL), and extracted with ethyl acetate (200 mL). The aqueous layer was separated and extracted with additional ethyl acetate (100 mL). The combined organic extracts were washed with brine (100 mL), dried over anhydrous sodium sulfate, filtered, and evaporated to give the desired product as a crude tan oil. This material was purified by flash column chromatography to give the desired product (9.9 g, 92%) as a white solid. LCMS for C₉H₉BrNO₂ ([M-(t-Bu)+H]+H)⁺: m/z=241.9, 243.8.

Step E: tert-Butyl [3-bromo-5-(2-hydroxyethyl)phenyl]carbamate

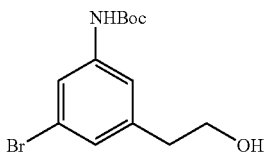 [SMILES: CC(C)(C)OC(=O)Nc1cc(Br)cc(CCO)c1]

A solution of tert-butyl (3-bromo-5-vinylphenyl)carbamate (0.80 g, 2.7 mmol) in tetrahydrofuran (2.7 mL) was treated with 9-BBN in tetrahydrofuran (16.1 mL, 8.1 mol) dropwise and stirred for 2 h. The reaction mixture was cooled to 0° C. and treated with ethanol (5 mL), 3 M sodium hydroxide (3.2 mL) and 9 M hydrogen peroxide (3 mL) dropwise. The reaction mixture was heated at 50° C. for 30 min, cooled to 20° C., poured into brine (25 mL), and extracted with ethyl acetate (100 mL). A small amount of water was added to dissolve the solids that were insoluble in the brine. The organic layer was separated and washed with brine (25 mL), dried over anhydrous sodium sulfate, filtered, and evaporated to give the desired product as a crude tan oil. This material was purified by flash column chromatography to give the desired product (0.66 g, 78%) as a colorless foam. LCMS for C₉H₁₁BrNO₃ ([M-(t-Bu)+H]+H)⁺: m/z=259.9, 261.8.

Step F: N-(3-{[tert-Butyl(dimethyl)silyl]oxy}phenyl)-2,5-dichloropyrimidin-4-amine

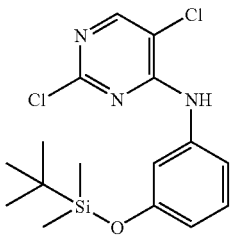 [SMILES: CC(C)(C)[Si](C)(C)Oc1cccc(Nc2nc(Cl)ncc2Cl)c1]

The desired compound was prepared according to the procedure of Example D1, step B, using 3-{[tert-butyl(dimethyl)silyl]oxy}aniline [WO2005113556] as the starting material in 84% yield. LCMS for C₁₆H₂₂Cl₂N₃OSi (M+H)⁺: m/z=370.0, 372.0.

Step G: 3-[(2-{[3-Bromo-5-(2-hydroxyethyl)phenyl]amino}-5-chloropyrimidin-4-yl)amino]phenol

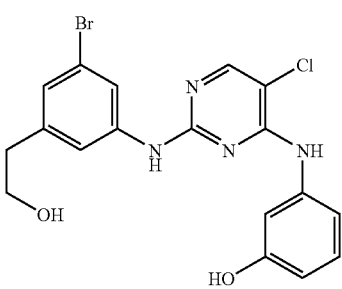 [SMILES: OCCc1cc(Br)cc(Nc2ncc(Cl)c(Nc3cccc(O)c3)n2)c1]

The desired compound was prepared according to the procedure of Example D5, step B, using N-(3-{[tert-butyl(dimethyl)silyl]oxy}phenyl)-2,5-dichloropyrimidin-4-amine and tert-butyl [3-bromo-5-(2-hydroxyethyl)phenyl]carbamate as the starting materials in 77% yield. LCMS for C₁₈H₁₇BrClN₄O₂ (M+H)⁺: m/z=434.9, 436.9.

Step H: 19-Bromo-6-chloro-14-oxa-2,4,8,23-tetraazatetracyclo[15.3.1.1(3,7).1(9,13)]tricosa-1(21),3(23),4,6,9(22),10,12,17,19-nonaene trifluoroacetate The desired compound was prepared according to the procedure of Example D5, step C, using 3-[(2-{[3-bromo-5-(2-hydroxyethyl)phenyl]amino}-5-chloropyrimidin-4-yl)amino]phenol as the starting material in 36% yield. LCMS for C₁₈H₁₅BrClN₄O (M+H)⁺: m/z=416.8, 418.9. ¹H NMR (300 MHz, DMSO-d₆): δ 9.55 (s, 1H), 9.23 (s, 1H), 8.17 (s, 1H), 7.93 (s, 1H), 7.59 (dd, J=2.1, 2.1 Hz, 1H), 7.23 (dd, J=8.2, 7.9 Hz, 1H), 7.12 (s, 2H), 6.93-6.86 (m, 2H), 4.47-4.43 (m, 2H), 2.70-2.67 (m, 2H).

Example D23

6-Chloro-14-thia-2,4,8,23-tetraazatetracyclo[15.3.1.1(3,7).1(9,13)]tricosa-1(21),3(23),4,6,9(22),10,12,17,19-nonaene 14-oxide trifluoroacetate

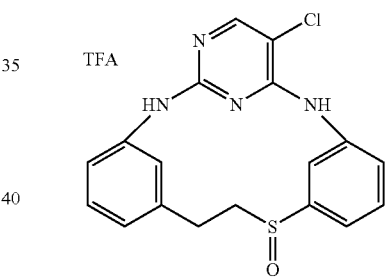

Example D24

6-chloro-14-thia-2,4,8,23-tetraazatetracyclo[15.3.1.1(3,7).1(9,13)]tricosa-1(21),3(23),4,6,9(22),10,12,17,19-nonaene 14,14-dioxide trifluoroacetate

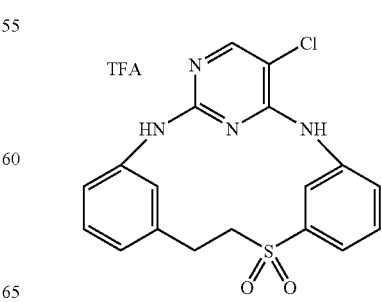

The desired compounds were prepared according to the procedures of Examples D3 and D4 using 6-chloro-14-thia-2,4,8,23-tetraazatetracyclo[15.3.1.1(3,7).1(9,13)]tricosa-1(21),3(23),4,6,9(22),10,12,17,19-nonaene as the starting material in 18% and 32% yields respectively.

Example D23: LCMS for $C_{18}H_{16}ClN_4OS$ (M+H)$^+$: m/z=370.9. $^1$H NMR (300 MHz, DMSO-d$_6$): δ 9.60 (s, 1H), 9.37 (s, 1H), 8.20 (s, 2H), 7.88 (s, 1H), 7.65 (dd, J=7.9, 7.6 Hz, 1H), 7.58-7.50 (m, 2H), 7.16 (dd, J=7.9, 7.6 Hz, 1H), 6.98-6.90 (m, 2H), 3.64-3.54 (m, 1H), 3.41-3.33 (m, 1H), 2.91-2.82 (m, 1H), 2.19-2.11 (m, 1H).

Example D24: LCMS for $C_{18}H_{16}ClN_4O_2S$ (M+H)$^+$: m/z=386.9. $^1$H NMR (300 MHz, DMSO-d$_6$): δ 9.61 (s, 1H), 9.42 (s, 1H), 8.47 (s, 1H), 8.23 (s, 1H), 7.99 (s, 1H), 7.70-7.64 (m, 3H), 7.14 (dd, J=7.9, 7.6 Hz, 1H), 6.94-6.87 (m, 2H), 2.57-2.53 (m, 1H).

Example D25

6-Chloro-19-pyridin-4-yl-14-oxa-2,4,8,23-tetraazatetracyclo[15.3.1.1(3,7).1(9,13)]tricosa-1(21),3(23),4,6,9(22),10,12,17,19-nonaene bis(trifluoroacetate)

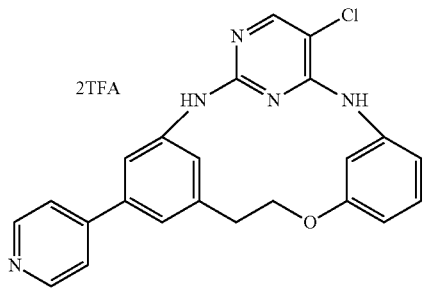 [SMILES: Clc1cnc2nc1Nc1cccc(c1)OCCc1cc(cc(-c3ccncc3)c1)N2 ; "2TFA"]

A solution of 19-bromo-6-chloro-14-oxa-2,4,8,23-tetraazatetracyclo[15.3.1.1(3,7).1(9,13)]tricosa-1(21),3(23),4,6,9(22),10,12,17,19-nonaene trifluoroacetate (40 mg, 96 μmol), 4-pyridinylboronic acid (13 mg, 0.11 mmol), and 2 M sodium carbonate (0.14 mL, 0.29 mmol) in toluene (0.36 mL) and ethanol (0.36 mL) was degassed with nitrogen, treated with tetrakis(triphenylphosphine)palladium(O) (8 mg, 6.7 μmol), and heated at 85° C. for 12 h. The reaction mixture was concentrated and purified by preparative LCMS to give the desired product (4 mg, 7%) as a white solid. LCMS for $C_{23}H_{19}ClN_5O$ (M+H)$^+$: m/z=416.0. $^1$H NMR (400 MHz, DMSO-d$_6$): δ 9.62 (s, 1H), 9.20 (s, 1H), 8.90 (br s, 2H), 8.19 (s, 1H), 8.13-8.05 (m, 3H), 7.65 (s, 1H), 7.52 (s, 1H), 7.45 (s, 1H), 7.24 (dd, J=8.2, 8.0 Hz, 1H), 6.94-6.86 (m, 2H), 4.57-4.54 (m, 2H), 2.85-2.78 (m, 2H).

Example D26

6-Chloro-19-pyridin-3-yl-14-oxa-2,4,8,23-tetraazatetracyclo[15.3.1.1(3,7).1(9,13)]tricosa-1(21),3(23),4,6,9(22),10,12,17,19-nonaene bis(trifluoroacetate)

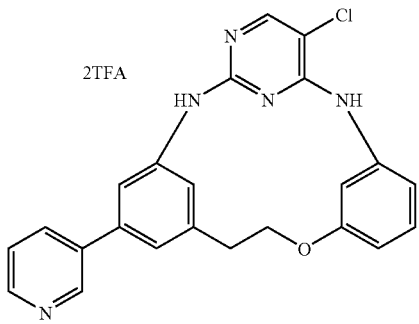 [SMILES: Clc1cnc2nc1Nc1cccc(c1)OCCc1cc(cc(-c3cccnc3)c1)N2 ; "2TFA"]

The desired compound was prepared according to the procedure of Example D25 using 3-pyridylboronic acid as the starting material in 24% yield. LCMS for $C_{23}H_{19}ClN_5O$ (M+H)$^+$: m/z=416.0. $^1$H NMR (300 MHz, DMSO-d$_6$): δ 9.61 (s, 1H), 9.24 (s, 1H), 8.99 (s, 1H), 8.72 (d, J=4.4 Hz, 1H), 8.37 (d, J=7.9 Hz, 1H), 8.19 (s, 1H), 8.03 (s, 1H), 7.80 (dd, J=7.3, 5.6 Hz, 1H), 7.68 (s, 1H), 7.36 (s, 1H), 7.29-7.20 (m, 2H), 6.94-6.85 (m, 2H), 4.55 (br s, 2H), 2.82 (br s, 2H).

Example D27

6-Chloro-19-(2-piperazin-1-ylpyridin-4-yl)-14-oxa-2,4,8,23-tetraazatetracyclo[15.3.1.1(3,7).1(9,13)]tricosa-1(21),3(23),4,6,9(22),10,12,17,19-nonaene tris(trifluoroacetate)

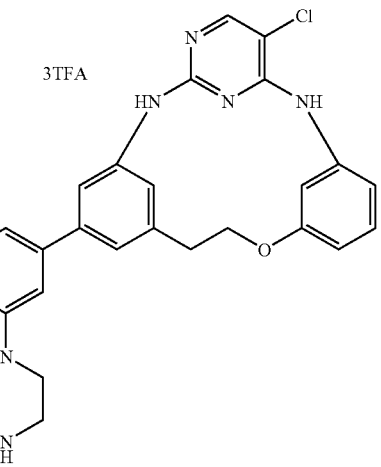

A solution of 19-bromo-6-chloro-14-oxa-2,4,8,23-tetraazatetracyclo[15.3.1.1(3,7).1(9,13)]tricosa-1(21),3(23),4,6,9(22),10,12,17,19-nonaene trifluoroacetate (40 mg, 96 μmol), tert-butyl 4-[4-(4,4,5,5-tetramethyl-1,3,2-dioxaborolan-2-yl)pyridin-2-yl]piperazine-1-carboxylate (45 mg, 0.12 mmol), and 2 M sodium carbonate (0.14 mL, 0.29 mmol) in toluene (0.36 mL) and ethanol (0.36 mL) was degassed with nitrogen, treated with tetrakis(triphenylphosphine)palladium (O) (8 mg, 6.7 μmol), and heated at 85° C. for 9 h. The reaction mixture was concentrated, stirred in TFA (1.5 mL) for 30 min, concentrated, and purified by preparative LCMS to give the desired product (11 mg, 14%) as a white solid. LCMS for $C_{27}H_{27}ClN_7O$ (M+H)$^+$: m/z=500.0. $^1$H NMR (300 MHz, DMSO-d$_6$): δ 9.59 (s, 1H), 9.25 (s, 1H), 8.88 (br s, 2H), 8.21-8.18 (m, 2H), 8.00 (s, 1H), 7.67 (s, 1H), 7.35-7.29 (m, 2H), 7.25-7.16 (m, 2H), 7.00-6.80 (m, 3H), 4.55 (br s, 2H), 3.80 (br s, 4H), 3.21 (br s, 4H), 2.82 (br s, 2H).

Example D28

6-Chloro-19-phenyl-14-oxa-2,4,8,23-tetraazatetracyclo[15.3.1.1(3,7).1(9,13)]tricosa-1(21),3(23),4,6,9(22),10,12,17,19-nonaene trifluoroacetate

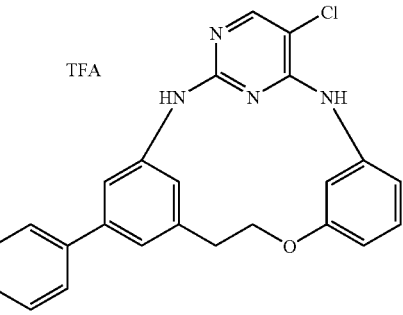

The desired compound was prepared according to the procedure of Example D25 using phenylboronic acid as the starting material in 57% yield. LCMS for C$_{24}$H$_{20}$ClN$_4$O (M+H)$^+$: m/z=415.0. $^1$H NMR (300 MHz, DMSO-d$_6$): δ 9.59 (s, 1H), 9.31 (s, 1H), 8.19 (s, 1H), 7.91 (s, 1H), 7.69 (s, 1H), 7.60-7.57 (m, 2H), 7.47-7.42 (m, 2H), 7.36-7.31 (m, 1H), 7.25-7.19 (m, 3H), 6.93-6.84 (m, 2H), 4.55-4.51 (m, 2H), 2.85-2.80 (m, 2H).

Example D29

6-Chloro-19-[4-(methylsulfonyl)phenyl]-14-oxa-2,4,8,23-tetraazatetracyclo[15.3.1.1(3,7).1(9,13)]tricosa-1(21),3(23),4,6,9(22),10,12,17,19-nonaene trifluoroacetate

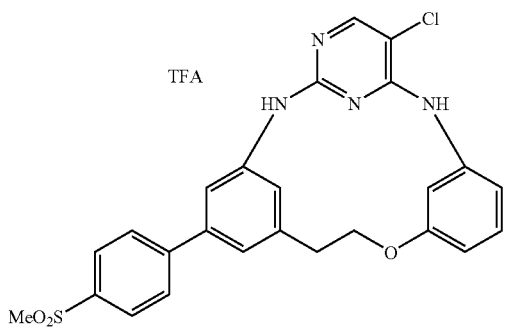 [SMILES: "TFA" ; CS(=O)(=O)c1ccc(-c2cc3cc(c2)Nc2ncc(Cl)c(n2)Nc2cccc(c2)OCC3)cc1]

The desired compound was prepared according to the procedure of Example D25 using [4-(methylsulfonyl)phenyl]boronic acid as the starting material in 29% yield. LCMS for C$_{25}$H$_{22}$ClN$_4$O$_3$S (M+H)$^+$: m/z=492.9. $^1$H NMR (300 MHz, DMSO-d$_6$): δ 9.60 (s, 1H), 9.27 (s, 1H), 8.19 (s, 1H), 8.01-7.97 (m, 3H), 7.87-7.84 (m, 2H), 7.68 (s, 1H), 7.31-7.20 (m, 3H), 6.94-6.86 (m, 2H), 4.59-4.50 (m, 2H), 3.25 (s, 3H), 2.85-2.78 (m, 2H).

Example D30

6-Chloro-19-(3,5-dimethyl-1H-pyrazol-4-yl)-14-oxa-2,4,8,23-tetraazatetracyclo[15.3.1.1(3,7).1(9,13)]tricosa-1(21),3(23),4,6,9(22),10,12,17,19-nonaene bis(trifluoroacetate)

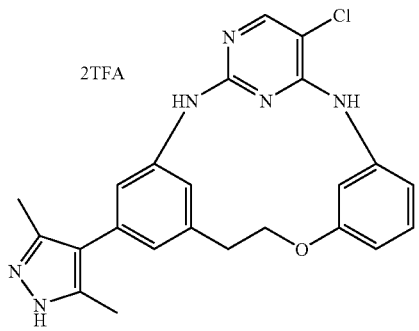 [SMILES: Cc1n[nH]c(C)c1-c1cc2cc(c1)Nc1ncc(Cl)c(n1)Nc1cccc(c1)OCC2 ; "2TFA"]

The desired compound was prepared according to the procedure of Example D25 using 3,5-dimethyl-4-(4,4,5,5-tetramethyl-1,3,2-dioxaborolan-2-yl)-1H-pyrazole as the starting material in 41% yield. LCMS for C$_{23}$H$_{22}$ClN$_6$O (M+H)$^+$: m/z=433.0. $^1$H NMR (300 MHz, DMSO-d$_6$): δ 9.58 (s, 1H), 9.32 (s, 1H), 8.19 (s, 1H), 7.87 (s, 1H), 7.69 (s, 1H), 7.24 (dd, J=8.2, 7.9 Hz, 1H), 6.94-6.85 (m, 3H), 4.54-4.45 (m, 2H), 2.80-2.70 (m, 2H), 2.22 (s, 6H).

Example D31

6-Chloro-19-(2-piperazin-1-ylpyrimidin-5-yl)-14-oxa-2,4,8,23-tetraazatetracyclo[15.3.1.1(3,7).1(9,13)]tricosa-1(21),3(23),4,6,9(22),10,12,17,19-nonaene tris(trifluoroacetate)

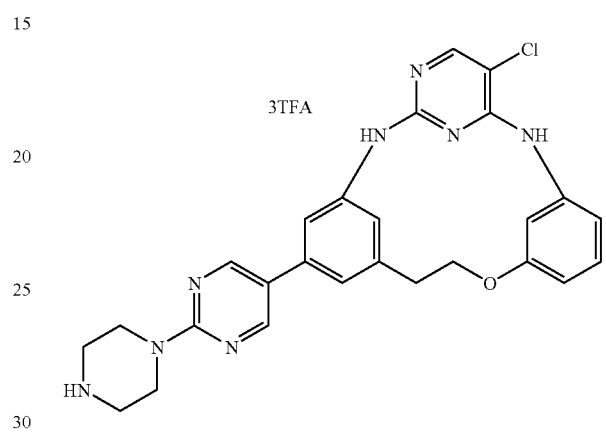

The desired compound was prepared according to the procedure of Example D27 using tert-butyl 4-[5-(4,4,5,5-tetramethyl-1,3,2-dioxaborolan-2-yl)pyrimidin-2-yl]piperazine-1-carboxylate as the starting material in 38% yield. LCMS for C$_{26}$H$_{26}$ClN$_8$O (M+H)$^+$: m/z=501.0. $^1$H NMR (300 MHz, DMSO-d$_6$): δ 9.50 (s, 1H), 9.19 (s, 1H), 8.81 (br s, 2H), 8.68 (s, 2H), 8.17 (s, 1H), 7.91 (s, 1H), 7.69 (s, 1H), 7.24-7.18 (m, 2H), 7.15 (s, 1H), 6.93-6.89 (m, 1H), 6.84 (dd, J=8.2, 2.1 Hz, 1H), 4.57-4.49 (m, 2H), 3.99-3.93 (m, 4H), 3.19 (br s, 4H), 2.80-2.78 (m, 2H).

Example D32

6-Chloro-15-thia-2,4,8,24-tetraazatetracyclo[16.3.1.1(3,7).1(9,13)]tetracosa-1(22),3(24),4,6,9(23),10,12,18,20-nonaene trifluoroacetate

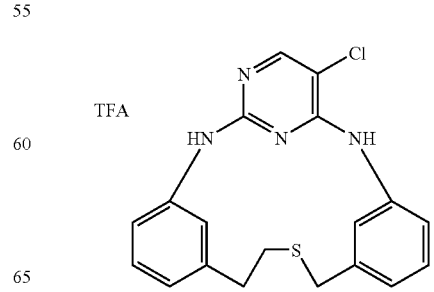

Step A: tert-Butyl
[3-(2-hydroxyethyl)phenyl]carbamate

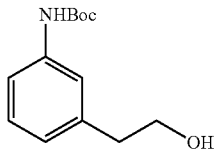 [SMILES: CC(C)(C)OC(=O)Nc1cccc(CCO)c1]

The desired compound was prepared according to the procedure of Example D15, step A, using 2-(3-aminophenyl)ethanol as the starting material in quantitative yield. LCMS for $C_{13}H_{19}NO_3Na$ (M+Na)$^+$: m/z=260.0.

Step B: 2-{3-[(tert-Butoxycarbonyl)amino]phenyl}ethyl methanesulfonate

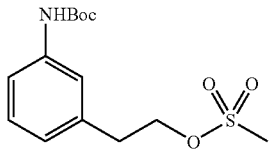 [SMILES: CC(C)(C)OC(=O)Nc1cccc(CCOS(C)(=O)=O)c1]

The desired compound was prepared according to the procedure of Example D20, step A, using tert-butyl [3-(2-hydroxyethyl)phenyl]carbamate as the starting material in quantitative yield. LCMS for $C_{14}H_{21}NO_5SNa$ (M+Na)$^+$: m/z=338.0.

Step C: tert-Butyl (3-{2-[(3-nitrobenzyl)thio]ethyl}phenyl)carbamate

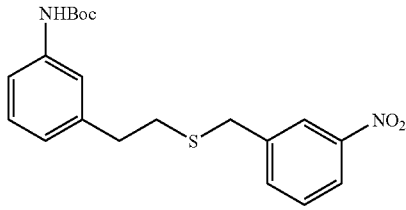 [SMILES: CC(C)(C)OC(=O)Nc1cccc(CCSCc2cccc([N+](=O)[O-])c2)c1]

The desired compound was prepared according to the procedure of Example D20, step B, using 2-{3-[(tert-butoxycarbonyl)amino]phenyl}ethyl methanesulfonate as the starting material in 80% yield. LCMS for $C_{20}H_{24}N_2O_4SNa$ (M+Na)$^+$: m/z=411.0.

Step D: tert-Butyl (3-{2-[(3-aminobenzyl)thio]ethyl}phenyl)carbamate

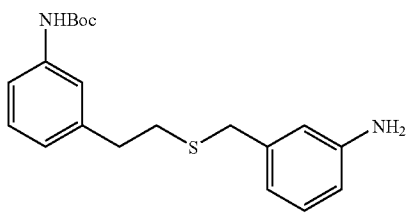

The desired compound was prepared according to the procedure of Example D2, step B, using tert-butyl (3-{2-[(3-nitrobenzyl)thio]ethyl}phenyl)carbamate as the starting material in 71% yield. LCMS for $C_{20}H_{27}N_2O_2S$ (M+H)$^+$: m/z=359.0.

Step E: tert-Butyl {3-[2-({3-[(2,5-dichloropyrimidin-4-yl)amino]benzyl}thio)ethyl]phenyl}carbamate

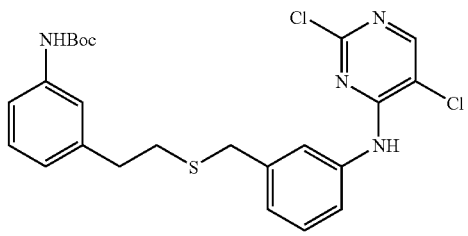 [SMILES: CC(C)(C)OC(=O)Nc1cccc(CCSCc2cccc(Nc3nc(Cl)ncc3Cl)c2)c1]

The desired compound was prepared according to the procedure of Example D2, step C, using tert-butyl (3-{2-[(3-aminobenzyl)thio]ethyl}phenyl)carbamate as the starting material in 83% yield. LCMS for $C_{24}H_{27}Cl_2N_4O_2S$ (M+H)$^+$: m/z=504.9, 506.9.

Step F: 6-Chloro-15-thia-2,4,8,24-tetraazatetracyclo[16.3.1.1(3,7).1(9,13)]tetracosa-1(22),3(24),4,6,9(23),10,12,18,20-nonaene trifluoroacetate A solution of tert-butyl {3-[2-({3-[(2,5-dichloropyrimidin-4-yl)amino]benzyl}thio)ethyl]phenyl}carbamate (0.14 g, 0.27 mmol) in 1,4-dioxane (11 mL) was treated with p-toluenesulfonic acid monohydrate (92 mg, 0.48 mmol) and heated at 98° C. for 16 h. The reaction mixture was concentrated and diluted with ethyl acetate (100 mL), saturated sodium bicarbonate (25 mL), and water (25 mL). The organic layer was separated and washed with brine, dried over anhydrous sodium sulfate, filtered, and evaporated to give the desired product as a crude tan solid. This material was purified by preparative LCMS to give the desired product (24 mg, 18%) as a solid. LCMS for $C_{19}H_{18}ClN_4S$ (M+H)$^+$: m/z=368.9. $^1$H NMR (300 MHz, DMSO-d$_6$): δ 9.50 (s, 1H), 9.04 (s, 1H), 8.15 (s, 1H), 7.92 (s, 1H), 7.69 (s, 1H), 7.35-7.23 (m, 2H), 7.12-7.04 (m, 2H), 6.88 (d, J=9.1 Hz, 1H), 6.71 (d, J=7.3 Hz, 1H), 3.71 (s, 2H), 2.60-2.50 (m, 4H).

Example D33

6-Chloro-19-(6-piperazin-1-ylpyridin-3-yl)-14-oxa-2,4,8,23-tetraazatetracyclo[15.3.1.1(3,7).1(9,13)]tricosa-1(21),3(23),4,6,9(22),10,12,17,19-nonaene tris(trifluoroacetate)

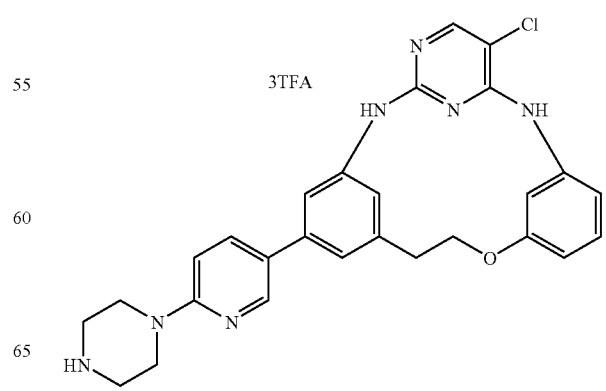

The desired compound was prepared according to the procedure of Example D25 using 1-[5-(4,4,5,5-tetramethyl-1,3,2-dioxaborolan-2-yl)pyridin-2-yl]piperazine as the starting material in 76% yield. LCMS for $C_{27}H_{27}ClN_7O$ (M+H)$^+$: m/z=500.0. $^1$H NMR (300 MHz, DMSO-d$_6$): δ 9.54 (s, 1H), 9.24 (s, 1H), 8.77 (br s, 2H), 8.40 (d, J=2.6 Hz, 1H), 8.18 (s, 1H), 7.88-7.84 (m, 2H), 7.69 (d, J=2.1 Hz, 1H), 7.24-7.15 (m, 3H), 7.03 (d, J=8.8 Hz, 1H), 6.92 (d, J=7.6 Hz, 1H), 6.84 (dd, J=8.2, 1.8 Hz, 1H), 4.55-4.50 (m, 2H), 3.77-3.73 (m, 4H), 3.20 (br s, 4H), 2.79 (br s, 2H).

Example D34

6-Chloro-16-thia-2,4,8,24-tetraazatetracyclo[16.3.1.1(3,7).1(9,13)]tetracosa-1(22),3(24),4,6,9(23),10,12,18,20-nonaene trifluoroacetate

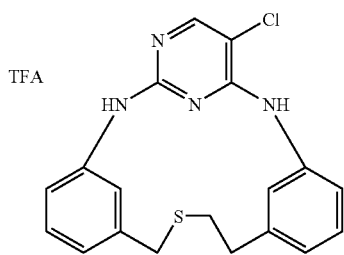 [SMILES: "TFA" ; Clc1cnc2nc1Nc1cccc(c1)CCSCc1cccc(c1)N2]

Step A: 3-{2-[(3-Nitrobenzyl)thio]ethyl}aniline

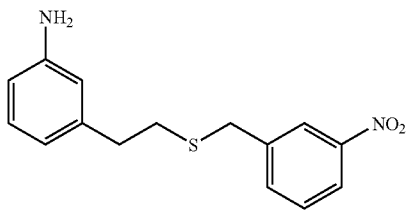 [SMILES: Nc1cccc(CCSCc2cccc([N+](=O)[O-])c2)c1]

A solution of tert-butyl (3-{2-[(3-nitrobenzyl)thio]ethyl}phenyl)carbamate (0.38 g, 0.97 mmol) in dichloromethane (2 mL) was treated with trifluoroacetic acid and stirred for 30 min. The reaction mixture was concentrated and poured into 10% potassium carbonate (30 mL) and ethyl acetate (100 mL). The organic layer was separated, washed with brine (25 mL), dried over anhydrous sodium sulfate, filtered, and evaporated to give the desired product as a crude orange oil. This material was purified by flash column chromatography to give the desired product (0.19 g, 67%) as an orange oil. LCMS for $C_{15}H_{17}N_2O_2S$ (M+H)$^+$: m/z=289.0.

Step B: 2,5-Dichloro-N-(3-{2-[(3-nitrobenzyl)thio]ethyl}phenyl)pyrimidin-4-amine

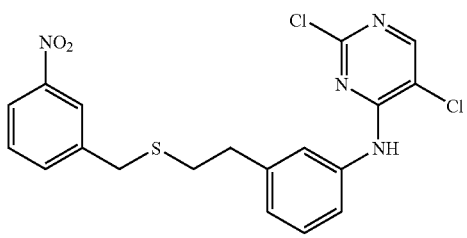 [SMILES: O=[N+]([O-])c1cccc(CSCCc2cccc(Nc3nc(Cl)ncc3Cl)c2)c1]

The desired compound was prepared according to the procedure of Example D2, step C, using 3-{2-[(3-nitrobenzyl)thio]ethyl}aniline as the starting material in 91% yield. LCMS for $C_{19}H_{17}Cl_2N_4O_2S$ (M+H)$^+$: m/z=434.9, 436.9.

Step C: N-(3-{2-[(3-Aminobenzyl)thio]ethyl}phenyl)-2,5-dichloropyrimidin-4-amine

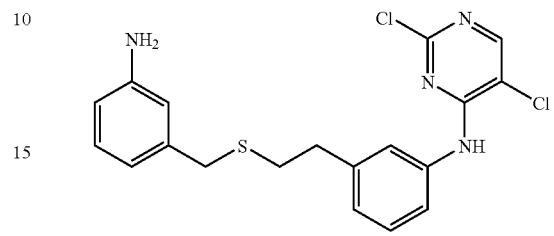

The desired compound was prepared according to the procedure of Example D2, step B, using 2,5-dichloro-N-(3-{2-[(3-nitrobenzyl)thio]ethyl}phenyl)pyrimidin-4-amine as the starting material in 87% yield. LCMS for $C_{19}H_{19}Cl_2N_4S$ (M+H)$^+$: m/z=404.9, 406.9.

Step D: 6-Chloro-16-thia-2,4,8,24-tetraazatetracyclo[16.3.1.1(3,7).1(9,13)]tetracosa-1(22), 3(24),4,6,9(23),10,12,18,20-nonaene trifluoroacetate The desired compound was prepared according to the procedure of Example D32, step F, using N-(3-{2-[(3-aminobenzyl)thio]ethyl}phenyl)-2,5-dichloropyrimidin-4-amine as the starting material in 44% yield. LCMS for $C_{19}H_{18}ClN_4S$ (M+H)$^+$: m/z=369.0. $^1$H NMR (300 MHz, DMSO-d$_6$): δ 9.61 (s, 1H), 9.20 (s, 1H), 8.17 (s, 1H), 7.96 (s, 1H), 7.57 (s, 1H), 7.31 (dd, J=7.6, 7.6 Hz, 1H), 7.18-7.10 (m, 3H), 6.93 (dd, J=7.9, 1.2 Hz, 1H), 6.85 (d, J=7.6 Hz, 1H), 3.16 (s, 2H), 2.86-2.81 (m, 2H).

Example D35

19-[2-(4-Acetylpiperazin-1-yl)pyridin-4-yl]-6-chloro-14-oxa-2,4,8,23-tetraazatetracyclo[15.3.1.1(3,7).1(9,13)]tricosa-1(21),3(23),4,6,9(22),10,12,17,19-nonaene bis(trifluoroacetate)

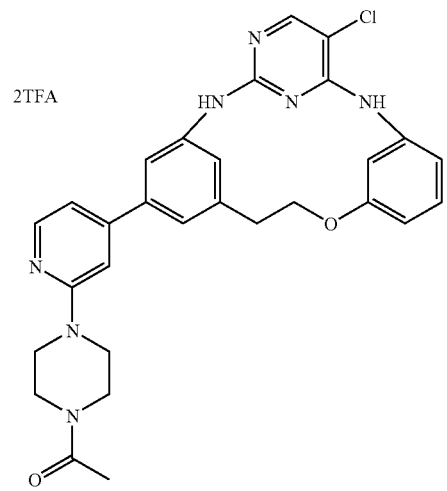 [SMILES: "2TFA" ; CC(=O)N1CCN(c2cc(-c3cc4cc(c3)Nc3ncc(Cl)c(n3)Nc3cccc(c3)OCC4)ccn2)CC1]

A solution of 6-chloro-19-(2-piperazin-1-ylpyridin-4-yl)-14-oxa-2,4,8,23-tetraazatetracyclo[15.3.1.1(3,7).1(9,13)]tricosa-1(21),3(23),4,6,9(22),10,12,17,19-nonaene (40 mg, 80 µmol) in dichloromethane (1.2 mL) was treated with triethylamine (22 µL, 0.16 mmol), cooled to 0° C., and treated with 0.2 M acetyl chloride in dichloromethane (0.48 mL, 96 µmol) dropwise. The reaction mixture was stirred at 20° C. for 1 h, quenched with methanol, and purified by preparative LCMS to give the desired product (37 mg, 52%) as a white solid. LCMS for $C_{29}H_{29}ClN_7O_2$ (M+H)$^+$: m/z=542.1. $^1$H NMR (300 MHz, DMSO-d$_6$): δ 9.57 (s, 1H), 9.25 (s, 1H), 8.19 (s, 1H), 8.14 (d, J=6.2 Hz, 1H), 8.06 (s, 1H), 7.66 (dd, J=2.1, 2.1 Hz, 1H), 7.44 (s, 1H), 7.37-7.34 (m, 2H), 7.23 (dd, J=8.2, 7.9 Hz, 1H), 7.09 (d, J=6.2 Hz, 1H), 6.92 (d, J=7.9 Hz, 1H), 6.86 (dd, J=8.2, 2.1 Hz, 1H), 4.59-4.53 (m, 2H), 3.78-3.61 (m, 8H), 2.86-2.80 (m, 2H).

Example D36

6-Chloro-19-{2-[4-(methylsulfonyl)piperazin-1-yl]pyridin-4-yl}-14-oxa-2,4,8,23-tetraazatetracyclo[15.3.1.1(3,7).1(9,13)]tricosa-1(21),3(23),4,6,9(22),10,12,17,19-nonaene bis(trifluoroacetate)

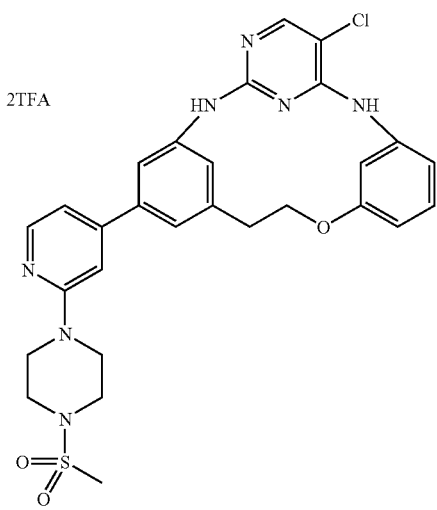 [SMILES: "2TFA" ; CS(=O)(=O)N1CCN(c2cc(-c3cc4cc(c3)Nc3ncc(Cl)c(n3)Nc3cccc(c3)OCC4)ccn2)CC1]

A solution of 6-chloro-19-(2-piperazin-1-ylpyridin-4-yl)-14-oxa-2,4,8,23-tetraazatetracyclo[15.3.1.1(3,7).1(9,13)]tricosa-1(21),3(23),4,6,9(22),10,12,17,19-nonaene (40 mg, 80 µmol) in dichloromethane (1.2 mL) was treated with triethylamine (22 µL, 0.16 mmol) followed by 0.2 M methanesulfonyl chloride in dichloromethane (0.48 mL, 96 µmol) dropwise. The reaction mixture was stirred at 20° C. for 1 h, quenched with methanol, and purified by preparative LCMS to give the desired product (36 mg, 49%) as a white solid. LCMS for $C_{28}H_{29}ClN_7O_3S$ (M+H)$^+$: m/z=578.0. $^1$H NMR (300 MHz, DMSO-d$_6$): δ 9.57 (s, 1H), 9.26 (s, 1H), 8.19-8.15 (m, 2H), 8.03 (s, 1H), 7.66 (s, 1H), 7.40 (s, 1H), 7.34 (s, 1H), 7.28 (s, 1H), 7.22 (dd, J=8.2, 7.9 Hz, 1H), 7.04 (d, J=5.9 Hz, 1H), 6.92 (d, J=7.9 Hz, 1H), 6.87-6.83 (m, 1H), 4.59-4.53 (m, 2H), 3.77 (br s, 4H), 3.24 (br s, 4H), 2.83 (br s, 2H).

Example D37

19-[6-(4-Acetylpiperazin-1-yl)pyridin-3-yl]-6-chloro-14-oxa-2,4,8,23-tetraazatetracyclo[15.3.1.1(3,7).1(9,13)]tricosa-1(21),3(23),4,6,9(22),10,12,17,19-nonaene tris(trifluoroacetate)

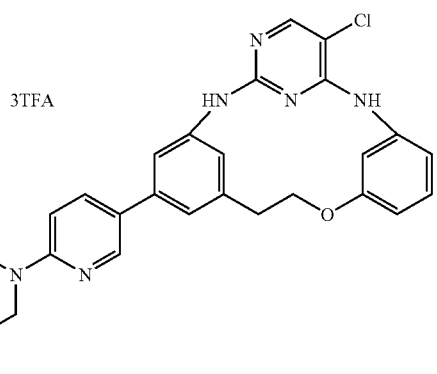

The desired compound was prepared according to the procedure of Example D35 using 6-chloro-19-(6-piperazin-1-ylpyridin-3-yl)-14-oxa-2,4,8,23-tetraazatetracyclo[15.3.1.1(3,7).1(9,13)]tricosa-1(21),3(23),4,6,9(22),10,12,17,19-nonaene as the starting material in 37% yield. LCMS for $C_{29}H_{29}ClN_7O_2$ (M+H)$^+$: m/z=542.0. $^1$H NMR (300 MHz, DMSO-d$_6$): δ 9.58 (s, 1H), 9.31 (s, 1H), 8.32 (d, J=2.3 Hz, 1H), 8.19 (s, 1H), 7.96 (d, J=8.8 Hz, 1H), 7.88 (s, 1H), 6.68 (s, 1H), 7.24-7.11 (m, 4H), 6.91 (d, J=7.9 Hz, 1H), 6.84 (dd, J=8.2, 1.8 Hz, 1H), 4.54 (br s, 2H), 3.65-3.56 (m, 8H), 2.80 (br s, 2H).

Example D38

6-Chloro-19-{6-[4-(methylsulfonyl)piperazin-1-yl]pyridin-3-yl}-14-oxa-2,4,8,23-tetraazatetracyclo[15.3.1.1(3,7).1(9,13)]tricosa-1(21),3(23),4,6,9(22),10,12,17,19-nonaene bis(trifluoroacetate)

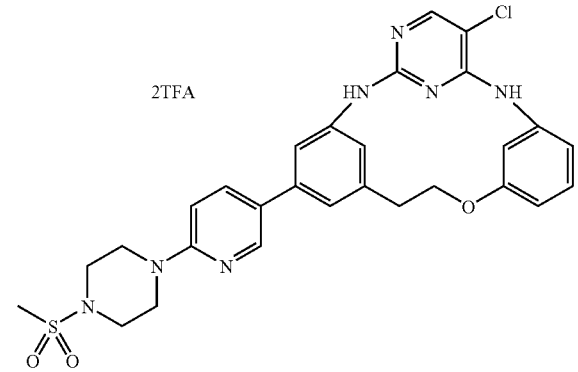 [SMILES: CS(=O)(=O)N1CCN(c2ccc(-c3cc4cc(c3)Nc3ncc(Cl)c(n3)Nc3cccc(c3)OCC4)cn2)CC1 ; "2TFA"]

The desired compound was prepared according to the procedure of Example D36 using 6-chloro-19-(6-piperazin-1-ylpyridin-3-yl)-14-oxa-2,4,8,23-tetraazatetracyclo[15.3.1.1(3,7).1(9,13)]tricosa-1(21),3(23),4,6,9(22),10,12,17,19-nonaene as the starting material in 45% yield. LCMS for $C_{28}H_{29}ClN_7O_3S$ (M+H)$^+$: m/z=578.0. $^1$H NMR (300 MHz, DMSO-d$_6$): δ 9.58 (s, 1H), 9.33 (s, 1H), 8.36 (d, J=2.3 Hz, 1H), 8.19 (s, 1H), 7.92-7.87 (m, 2H), 7.68 (s, 1H), 7.24-7.15 (m, 3H), 7.08 (d, J=9.1 Hz, 1H), 6.91 (d, J=8.2 Hz, 1H), 6.85 (d, J=7.9 Hz, 1H), 4.54 (br s, 2H), 3.69-3.67 (m, 4H), 3.23-3.21 (m, 4H), 2.80 (br s, 2H).

Example D39

4-{4-[6-Chloro-14-oxa-2,4,8,23-tetraazatetracyclo [15.3.1.1(3,7).1(9,13)]tricosa-1(21),3(23),4,6,9(22), 10,12,17,19-nonaen-19-yl]pyridin-2-yl}piperazine-1-carboxamide bis(trifluoroacetate)

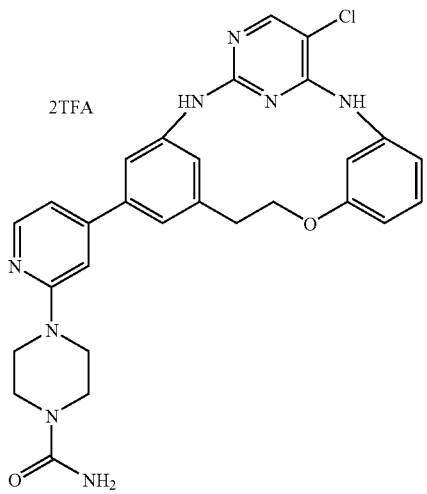 [SMILES: "2TFA" ; NC(=O)N1CCN(c2cc(-c3cc4cc(c3)Nc3ncc(Cl)c(n3)Nc3cccc(c3)OCC4)ccn2)CC1]

A solution of 6-chloro-19-(2-piperazin-1-ylpyridin-4-yl)-14-oxa-2,4,8,23-tetraazatetracyclo[15.3.1.1(3,7).1(9,13)]tricosa-1(21),3(23),4,6,9(22),10,12,17,19-nonaene (40 mg, 80 μmol) in dichloromethane (1 mL) was treated with triethylamine (22 μL, 0.16 mol) followed by 0.2 M 2-isocyanato-2-methylpropane in dichloromethane (0.5 mL, 100 μmol) dropwise. The reaction mixture was stirred at 20° C. for 16 h, concentrated, treated with trifluoroacetic acid (1.5 mL), and heated at 80° C. for 2 h. The reaction mixture was concentrated and purified by preparative LCMS to give the desired product (25 mg, 35%) as a white solid. LCMS for C$_{28}$H$_{28}$ClN$_8$O$_2$ (M+H)$^+$: m/z=543.0. $^1$H NMR (300 MHz, DMSO-d$_6$): δ 9.53 (s, 1H), 9.21 (s, 1H), 8.18 (s, 1H), 8.12 (dd, J=6.2 Hz, 1H), 8.07 (s, 1H), 7.66 (s, 1H), 7.44 (s, 1H), 7.37 (s, 2H), 7.23 (dd, J=8.2, 7.9 Hz, 1H), 7.09 (d, J=6.2 Hz, 1H), 6.92 (d, J=7.9 Hz, 1H), 6.86 (d, J=6.4 Hz, 1H), 4.56 (br s, 2H), 3.67 (br s, 4H), 3.48 (br s, 4H), s.83 (br s, 2H).

Example D40

4-{5-[6-Chloro-14-oxa-2,4,8,23-tetraazatetracyclo [15.3.1.1(3,7).1(9,13)]tricosa-1(21),3(23),4,6,9(22), 10,12,17,19-nonaen-19-yl]pyridin-2-yl}piperazine-1-carboxamide bis(trifluoroacetate)

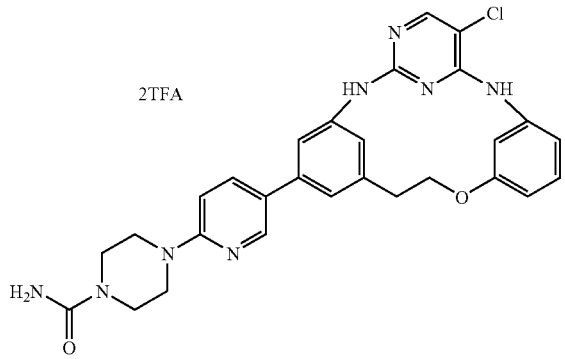 [SMILES: NC(=O)N1CCN(c2ccc(-c3cc4cc(c3)Nc3ncc(Cl)c(n3)Nc3cccc(c3)OCC4)cn2)CC1 ; "2TFA"]

The desired compound was prepared according to the procedure of Example D39 using 6-chloro-19-(6-piperazin-1-ylpyridin-3-yl)-14-oxa-2,4,8,23-tetraazatetracyclo[15.3.1.1 (3,7).1(9,13)]tricosa-1(21),3(23),4,6,9(22),10,12,17,19-nonaene as the starting material in 59% yield. LCMS for C$_{28}$H$_{28}$ClN$_8$O$_2$ (M+H)$^+$: m/z=543.0. $^1$H NMR (300 MHz, DMSO-d$_6$): δ 9.58 (s, 1H), 9.30 (s, 1H), 8.28 (d, J=2.3 Hz, 1H), 8.19 (s, 1H), 7.99 (d, J=8.8 Hz, 1H), 7.89 (s, 1H), 7.68 (d, J=1.8 Hz, 1H), 7.25-7.16 (m, 4H), 6.91 (d, J=9.1 Hz, 1H), 6.85 (dd, J=8.2, 2.1 Hz, 1H), 4.56-4.50 (m, 2H), 3.58-3.56 (m, 4H), 3.46-3.43 (m, 4H), 2.80 (br s, 2H).

Example D41

N-(tert-Butyl)-4-{4-[6-chloro-14-oxa-2,4,8,23-tetraazatetracyclo[15.3.1.1(3,7).1(9,13)]tricosa-1(21),3 (23),4,6,9(22),10,12,17,19-nonaen-19-yl]pyridin-2-yl}piperazine-1-carboxamide bis(trifluoroacetate)

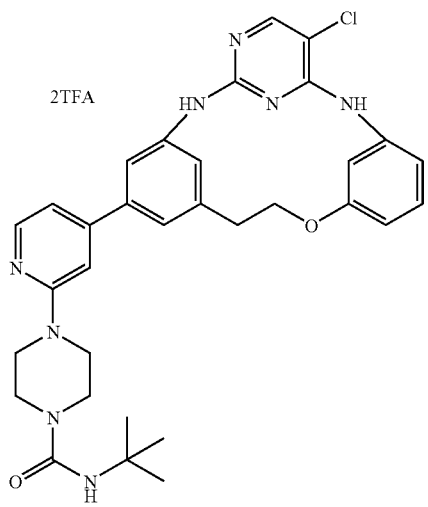 [SMILES: "2TFA" ; CC(C)(C)NC(=O)N1CCN(c2cc(-c3cc4cc(c3)Nc3ncc(Cl)c(n3)Nc3cccc(c3)OCC4)ccn2)CC1]

A solution of 6-chloro-19-(2-piperazin-1-ylpyridin-4-yl)-14-oxa-2,4,8,23-tetraazatetracyclo[15.3.1.1(3,7).1(9,13)]tricosa-1(21),3(23),4,6,9(22),10,12,17,19-nonaene (25 mg, 50 μmol) in dichloromethane (1 mL) was treated with triethylamine (21 μL, 0.15 mmol) followed by 2-isocyanato-2-methylpropane (10 μL, 90 μmol) dropwise. The reaction mixture was stirred at 20° C. for 4 h, concentrated, and purified by preparative HPLC to give the desired product (21 mg, 45%) as a white solid. LCMS for C$_{32}$H$_{36}$ClN$_8$O$_2$ (M+H)$^+$: m/z=599.1. $^1$H NMR (300 MHz, DMSO-d$_6$): δ 9.55 (s, 1H), 9.22 (s, 1H), 8.18 (s, 1H), 8.13 (d, J=6.2 Hz, 1H), 8.07 (s, 1H), 7.66 (s, 1H), 7.44 (s, 1H), 7.37 (s, 2H), 7.23 (dd, J=8.2, 7.9 Hz, 1H), 7.09 (d, J=5.9 Hz, 1H), 6.92 (d, J=7.6 Hz, 1H), 6.86 (dd, J=7.9, 1.5 Hz, 1H), 5.95 (s, 1H), 4.58-4.50 (m, 2H), 3.66 (br s, 4H), 3.45 (br s, 4H), 2.87-2.80 (m, 2H), 1.26 (s, 9H).

Example D42

4-{5-[6-Chloro-14-oxa-2,4,8,23-tetraazatetracyclo[15.3.1.1(3,7).1(9,13)]tricosa-1(21),3(23),4,6,9(22),10,12,17,19-nonaen-19-yl]pyridin-2-yl}-N-phenylpiperazine-1-carboxamide bis(trifluoroacetate)

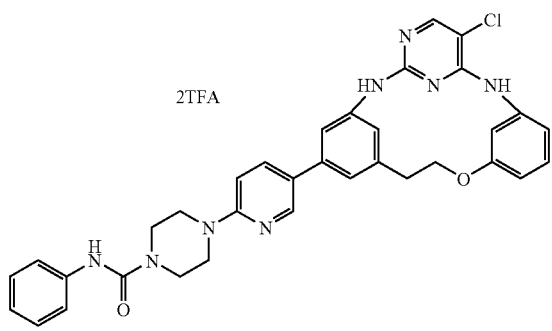 [SMILES: O=C(Nc1ccccc1)N1CCN(c2ccc(-c3cc4cc(c3)Nc3ncc(Cl)c(n3)Nc3cccc(c3)OCC4)cn2)CC1 ; "2TFA"]

The desired compound was prepared according to the procedure of Example D41 using 6-chloro-19-(6-piperazin-1-ylpyridin-3-yl)-14-oxa-2,4,8,23-tetraazatetracyclo[15.3.1.1(3,7).1(9,13)]tricosa-1(21),3(23),4,6,9(22),10,12,17,19-nonaene and phenyl isocyanate as the starting materials in 79% yield. LCMS for $C_{34}H_{32}ClN_8O_2$ (M+H)$^+$: m/z=619.1. $^1$H NMR (300 MHz, DMSO-$d_6$): δ 9.61 (s, 1H), 9.34 (s, 1H), 8.62 (s, 1H), 8.31 (d, J=2.1 Hz, 1H), 8.20 (s, 1H), 8.01 (d, J=9.1 Hz, 1H), 7.89 (s, 1H), 7.68 (s, 1H), 7.46 (d, J=7.6 Hz, 2H), 7.26-7.17 (m, 5H), 6.96-6.82 (m, 3H), 4.54 (br s, 2H), 3.66-3.62 (m, 8H), 2.83-2.78 (m, 2H).

Example D43

Methyl 6-chloro-17-oxa-14-thia-2,4,8,24-tetraazatetracyclo[16.3.1.1(3,7).1(9,13)]tetracosa-1(22),3(24),4,6,9(23),10,12,18,20-nonaene-20-carboxylate trifluoroacetate

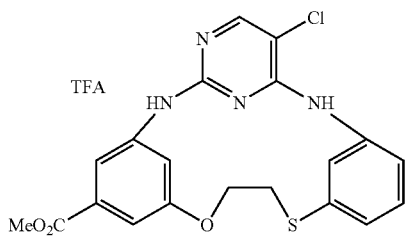 [SMILES: COC(=O)c1cc2cc(c1)OCCSc1cccc(c1)Nc1nc(ncc1Cl)N2]

Step A: 2-({3-[(2,5-Dichloropyrimidin-4-yl)amino]phenyl}thio)ethanol

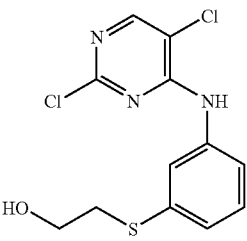

A solution of sodium methoxide (2.4 g, 44 mmol) in N,N-dimethylformamide (80 mL) was treated with 3-aminobenzenethiol (4.6 g, 37 mmol) and stirred at 20° C. for 15 min. The reaction mixture was cooled to 0° C., treated with a solution of 2-bromoethanol (3.4 mL, 48 mmol) in N,N-dimethylformamide (10 mL), and stirred at 0° C. for 15 min and at 20° C. for 1 h. The reaction mixture was treated with potassium carbonate (10 g, 74 mmol) followed by 2,4,5-trichloropyrimidine (5.5 mL, 48 mmol) and heated at 60° C. for 1 h and stirred at 20° C. for 18 h. The reaction mixture was diluted with 4:1 water:brine (1 L) and extracted with ethyl acetate (2×250 mL). The combined organic layers were washed with water (3×300 mL) and brine (100 mL), dried over anhydrous sodium sulfate, filtered, and evaporated to a crude product. This material was purified by flash column chromatography give the desired product (7.8 g, 68%) as a solid. LCMS for $C_{12}H_{12}Cl_2N_3OS$ (M+H)$^+$: m/z=315.9, 317.9.

Step B: Methyl 3-{[5-chloro-4-({3-[(2-hydroxyethyl)thio]phenyl}amino)pyrimidin-2-yl]amino}-5-hydroxybenzoate

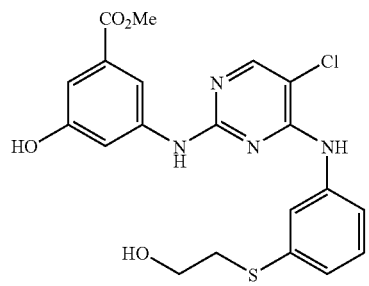 [SMILES: COC(=O)c1cc(O)cc(Nc2ncc(Cl)c(Nc3cccc(SCCO)c3)n2)c1]

The desired compound was prepared according to the procedure of Example D5, step B, using 2-({3-[(2,5-dichloropyrimidin-4-yl)amino]phenyl}thio)ethanol and methyl 3-amino-5-hydroxybenzoate as the starting materials in 99% yield. LCMS for $C_{20}H_{20}ClN_4O_4S$ (M+H)$^+$: m/z=446.9.

Step C: Methyl 6-chloro-17-oxa-14-thia-2,4,8,24-tetraazatetracyclo[16.3.1.1(3,7).1(9,13)]tetracosa-1(22),3(24),4,6,9(23),10,12,18,20-nonaene-20-carboxylate trifluoroacetate The desired compound was prepared according to the procedure of Example D5, step C, using methyl 3-{[5-chloro-4-({3-[(2-hydroxyethyl)thio]phenyl}amino)pyrimidin-2-yl]amino}-5-hydroxybenzoate as the starting material in 28% yield. LCMS for $C_{20}H_{18}ClN_4O_3S$ (M+H)⁺: m/z=428.9. ¹H NMR (300 MHz, DMSO-d₆): δ 9.76 (s, 1H), 8.93 (s, 1H), 8.19 (s, 1H), 8.11 (dd, J=2.1, 2.1 Hz, 1H), 7.90 (s, 1H), 7.45 (s, 1H), 7.37-7.29 (m, 2H), 7.22-7.18 (m, 1H), 6.94 (dd, J=1.8, 1.5 Hz, 1H), 4.16-4.12 (m, 2H), 3.80 (s, 3H), 3.28-3.24 (m, 2H).

Example D44

4-{4-[6-Chloro-14-oxa-2,4,8,23-tetraazatetracyclo[15.3.1.1(3,7).1(9,13)]tricosa-1(21),3(23),4,6,9(22),10,12,17,19-nonaen-19-yl]pyridin-2-yl}-N-phenylpiperazine-1-carboxamide bis(trifluoroacetate)

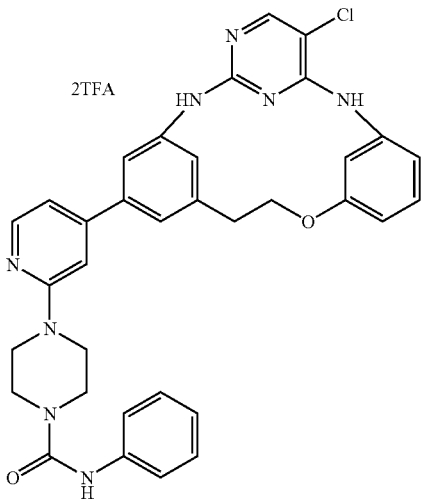 [SMILES: "2TFA" ; O=C(Nc1ccccc1)N1CCN(c2cc(-c3cc4cc(c3)Nc3ncc(Cl)c(n3)Nc3cccc(c3)OCC4)ccn2)CC1]

The desired compound was prepared according to the procedure of Example D41 using phenyl isocyanate as the starting material in 44% yield. LCMS for $C_{34}H_{32}ClN_8O_2$ (M+H)⁺: m/z=619.0. ¹H NMR (300 MHz, DMSO-d₆): δ 9.58 (s, 1H), 9.25 (s, 1H), 8.64 (s, 1H), 8.19 (s, 1H), 8.15 (d, J=6.2 Hz, 1H), 8.07 (s, 1H), 7.66 (s, 1H), 7.47-7.38 (m, 5H), 7.26-7.20 (m, 3H), 7.11 (d, J=5.9 Hz, 1H), 6.96-6.84 (m, 3H), 4.57 (br s, 2H), 3.75 (br s, 4H), 3.67 (br s, 4H), 2.84 (br s, 2H).

Example D45

N-Benzyl-4-{4-[6-chloro-14-oxa-2,4,8,23-tetraazatetracyclo[15.3.1.1(3,7).1(9,13)]tricosa-1(21),3(23),4,6,9(22),10,12,17,19-nonaen-19-yl]pyridin-2-yl}piperazine-1-carboxamide bis(trifluoroacetate)

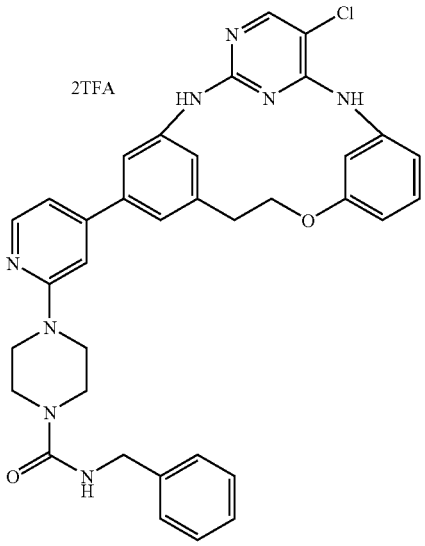 [SMILES: "2TFA" ; O=C(NCc1ccccc1)N1CCN(c2cc(-c3cc4cc(c3)Nc3ncc(Cl)c(n3)Nc3cccc(c3)OCC4)ccn2)CC1]

The desired compound was prepared according to the procedure of Example D41 using benzyl isocyanate as the starting material in 35% yield. LCMS for $C_{35}H_{34}ClN_8O_2$ (M+H)⁺: m/z=633.1. ¹H NMR (300 MHz, DMSO-d₆): δ 9.53 (s, 1H), 9.21 (s, 1H), 8.18 (s, 1H), 8.13 (d, J=6.4 Hz, 1H), 8.07 (s, 1H), 7.66 (s, 1H), 7.44 (s, 1H), 7.37 (s, 2H), 7.32-7.20 (m, 7H), 7.09 (d, J=5.9 Hz, 1H), 6.92 (d, J=7.9 Hz, 1H), 6.86 (dd, J=8.2, 1.8 Hz, 1H), 4.56 (br s, 2H), 4.26 (d, J=5.3 Hz, 2H), 3.70 (br s, 4H), 3.53 (br s, 4H), 2.83 (br s, 2H).

Example D46

4-{4-[6-Chloro-14-oxa-2,4,8,23-tetraazatetracyclo[15.3.1.1(3,7).1(9,13)]tricosa-1(21),3(23),4,6,9(22),10,12,17,19-nonaen-19-yl]pyridin-2-yl}-N-cyclopentylpiperazine-1-carboxamide bis(trifluoroacetate)

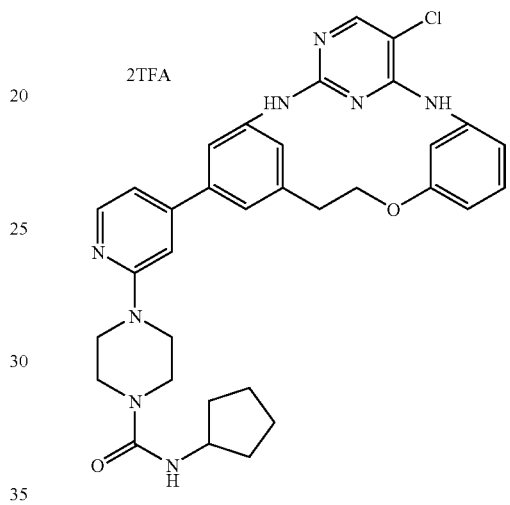

The desired compound was prepared according to the procedure of Example D41 using isocyanatocyclopentane as the starting material in 44% yield. LCMS for $C_{33}H_{36}ClN_8O_2$ (M+H)⁺: m/z=611.0. ¹H NMR (300 MHz, DMSO-d₆): δ 9.56 (s, 1H), 9.24 (s, 1H), 8.19 (s, 1H), 8.12 (d, J=6.2 Hz, 1H), 8.07 (s, 1H), 7.66 (s, 1H), 7.44 (s, 1H), 7.37 (s, 2H), 7.23 (dd, J=8.2, 7.9 Hz, 1H), 7.10 (d, J=6.2 Hz, 1H), 6.92 (d, J=7.9 Hz, 1H), 6.86 (d, J=10.0 Hz, 1H), 6.39 (d, J=6.4 Hz, 1H), 4.56 (s, 2H), 3.92-3.88 (m, 1H), 3.66 (br s, 4H), 3.48 (br s, 4H), 2.83 (br s, 2H), 1.82-1.70 (m, 2H), 1.62-1.50 (m, 2H), 1.49-1.34 (m, 4H).

Example D47

N-(tert-Butyl)-4-{4-[6-chloro-14-oxa-2,4,8,23-tetraazatetracyclo[15.3.1.1(3,7).1(9,13)]tricosa-1(21),3(23),4,6,9(22),10,12,17,19-nonaen-19-yl]pyridin-2-yl}piperazine-1-carboxamide bis(trifluoroacetate)

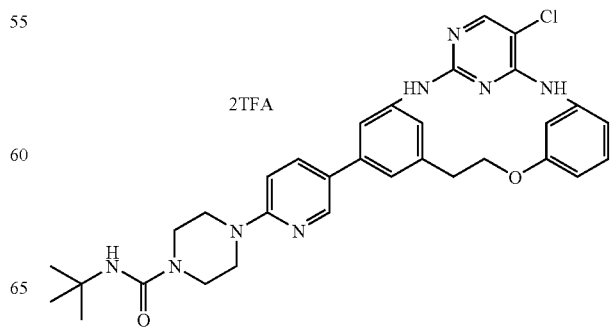

The desired compound was prepared according to the procedure of Example D41 using 6-chloro-19-(6-piperazin-1-ylpyridin-3-yl)-14-oxa-2,4,8,23-tetraazatetracyclo[15.3.1.1(3,7).1(9,13)]tricosa-1(21),3(23),4,6,9(22),10,12,17,19-nonaene and 2-isocyanato-2-methylpropane as the starting materials in 72% yield. LCMS for $C_{32}H_{36}ClN_8O_2$ (M+H)$^+$: m/z=599.1. $^1$H NMR (300 MHz, DMSO-d$_6$): δ 9.60 (s, 1H), 9.31 (s, 1H), 8.28 (d, J=2.3 Hz, 1H), 8.20 (s, 1H), 8.01 (d, J=9.7 Hz, 1H), 7.89 (s, 1H), 7.68 (s, 1H), 7.25-7.16 (m, 4H), 6.91 (d, J=9.4 Hz, 1H), 6.84 (dd, J=8.2, 2.1 Hz, 1H), 5.92 (br s, 1H), 4.56-4.52 (m, 2H), 3.58-3.54 (m, 4H), 3.44-3.40 (m, 4H), 2.83-2.78 (m, 2H), 1.25 (s, 9H).

Example D48

N-Benzyl-4-{4-[6-chloro-14-oxa-2,4,8,23-tetraazatetracyclo[15.3.1.1(3,7).1(9,13)]tricosa-1(21),3(23), 4,6,9(22),10,12,17,19-nonaen-19-yl]pyridin-2-yl}piperazine-1-carboxamide bis(trifluoroacetate)

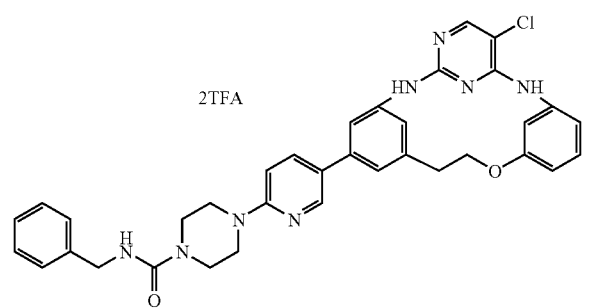 [SMILES: O=C(NCc1ccccc1)N1CCN(c2ccc(-c3cc4cc(c3)Nc3ncc(Cl)c(n3)Nc3cccc(c3)OCC4)cn2)CC1 ; "2TFA"]

The desired compound was prepared according to the procedure of Example D41 using 6-chloro-19-(6-piperazin-1-ylpyridin-3-yl)-14-oxa-2,4,8,23-tetraazatetracyclo[15.3.1.1(3,7).1(9,13)]tricosa-1(21),3(23),4,6,9(22),10,12,17,19-nonaene and benzyl isocyanate as the starting materials in 51% yield. LCMS for $C_{35}H_{34}ClN_8O_2$ (M+H)$^+$: m/z=633.1. $^1$H NMR (300 MHz, DMSO-d$_6$): δ 9.58 (s, 1H), 9.30 (s, 1H), 8.29 (d, J=2.1 Hz, 1H), 8.19 (s, 1H), 7.98 (d, J=8.5 Hz, 1H), 7.89 (s, 1H), 7.68 (s, 1H), 7.32-7.16 (m, 10H), 6.91 (d, J=9.1 Hz, 1H), 6.84 (dd, J=7.9, 2.1 Hz, 1H), 4.54 (br s, 2H), 4.26 (d, J=5.3 Hz, 2H), 3.60 (d, J=2.9 Hz, 4H), 3.50 (d, J=2.9 Hz, 4H), 2.80 (br s, 2H).

Example D49

4-{4-[6-Chloro-14-oxa-2,4,8,23-tetraazatetracyclo [15.3.1.1(3,7).1(9,13)]tricosa-1(21),3(23),4,6,9(22), 10,12,17,19-nonaen-19-yl]pyridin-2-yl}-N-cyclopentylpiperazine-1-carboxamide bis(trifluoroacetate)

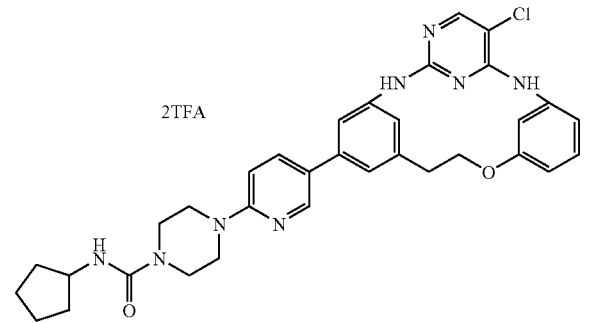 [SMILES: O=C(NC1CCCC1)N1CCN(c2ccc(-c3cc4cc(c3)Nc3ncc(Cl)c(n3)Nc3cccc(c3)OCC4)cn2)CC1 ; "2TFA"]

The desired compound was prepared according to the procedure of Example D41 using 6-chloro-19-(6-piperazin-1-ylpyridin-3-yl)-14-oxa-2,4,8,23-tetraazatetracyclo[15.3.1.1(3,7).1(9,13)]tricosa-1(21),3(23),4,6,9(22),10,12,17,19-nonaene and isocyanatocyclopentane as the starting materials in 52% yield. LCMS for $C_{33}H_{36}ClN_8O_2$ (M+H)$^+$: m/z=611.1. $^1$H NMR (300 MHz, DMSO-d$_6$): δ 9.57 (s, 1H), 9.29 (s, 1H), 8.29 (d, J=2.1 Hz, 1H), 8.19 (s, 1H), 7.98 (d, J=8.8 Hz, 1H), 7.89 (s, 1H), 7.68 (s, 1H), 7.25-7.16 (m, 4H), 6.93-6.90 (m, 1H), 6.84 (dd, J=8.5, 1.8 Hz, 1H), 6.36 (d, J=5.6 Hz, 1H), 4.54 (br s, 2H), 3.93-3.87 (m, 1H), 3.57-3.55 (m, 4H), 3.50-3.40 (m, 4H), 2.80 (br s, 2H), 1.83-1.70 (m, 2H), 1.63-1.51 (m, 2H), 1.48-1.34 (m, 4H).

Example D50

6-Chloro-N-phenyl-17-oxa-14-thia-2,4,8,24-tetraazatetracyclo[16.3.1.1(3,7).1(9,13)]tetracosa-1(22), 3(24),4,6,9(23),10,12,18,20-nonaene-20-carboxamide trifluoroacetate

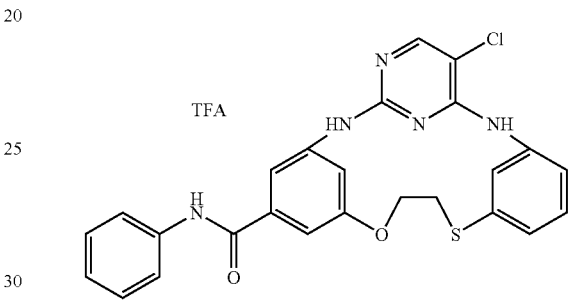

A solution of methyl 6-chloro-17-oxa-14-thia-2,4,8,24-tetraazatetracyclo[16.3.1.1(3,7).1(9,13)]tetracosa-1(22),3 (24),4,6,9(23),10,12,18,20-nonaene-20-carboxylate (30 mg, 70 μmol) and aniline (13 μL, 0.14 mmol) in dichloromethane (1 mL) was cooled to 0° C. and treated with 2 M trimethylaluminum in toluene (70 μL, 0.14 mmol) dropwise and stirred at 20° C. for 60 h. The reaction mixture was cooled to 0° C., treated with additional aniline (13 μL, 0.14 mmol) and 2 M trimethylaluminum in toluene (70 μL, 0.14 mmol), and stirred at 20° C. for 60 h. The reaction mixture was diluted with methanol and a small amount of TFA and the resultant suspension was filtered. The filtrate was purified by preparative LCMS to give the desired product (6 mg, 14%) as a solid. LCMS for $C_{25}H_{21}ClN_5O_2S$ (M+H)$^+$: m/z=489.9. $^1$H NMR (300 MHz, DMSO-d$_6$): δ 10.15 (s, 1H), 9.74 (s, 1H), 8.93 (s, 1H), 8.21 (s, 1H), 7.99 (d, J=11.1 Hz, 2H), 7.72 (d, J=7.6 Hz, 2H), 7.38-7.22 (m, 6H), 7.07 (dd, J=7.0, 7.0 Hz, 1H), 6.99 (s, 1H), 4.18 (br s, 2H), 3.28 (br s, 2H).

Example D51

N-Benzyl-6-chloro-17-oxa-14-thia-2,4,8,24-tetraazatetracyclo[16.3.1.1(3,7).1(9,13)]tetracosa-1(22),3 (24),4,6,9(23),10,12,18,20-nonaene-20-carboxamide trifluoroacetate

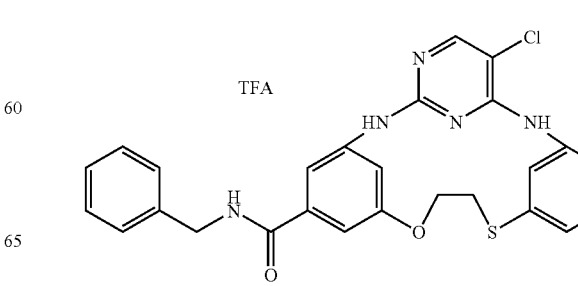

Step A: 6-Chloro-17-oxa-14-thia-2,4,8,24-tetraaza-tetracyclo[16.3.1.1(3,7).1(9,13)]tetracosa-1(22),3(24),4,6,9(23),10,12,18,20-nonaene-20-carboxylic acid

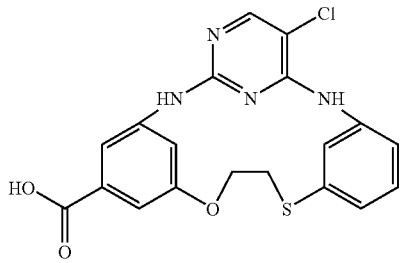 [SMILES: O=C(O)c1cc2cc(c1)OCCSc1cccc(c1)Nc1nc(ncc1Cl)N2]

A solution of methyl 6-chloro-17-oxa-14-thia-2,4,8,24-tetraazatetracyclo[16.3.1.1(3,7).1(9,13)]tetracosa-1(22),3(24),4,6,9(23),10,12,18,20-nonaene-20-carboxylate (450 mg, 1.1 mmol) in methanol (2.3 mL) and tetrahydrofuran (4.5 mL) was treated with 1 M sodium hydroxide (2.1 mL, 2.1 mmol) dropwise and heated at 60° C. for 16 h. The reaction mixture was cooled to 0° C. and quenched with 1 M HCl (3.2 mL). The resultant suspension was diluted with a small amount of water, filtered, and washed with cold acetonitrile to give the desired product (420 mg, 97%) as a white solid. LCMS for $C_{19}H_{16}ClN_4O_3S$ (M+H)+: m/z=414.9.

Step B: N-Benzyl-6-chloro-17-oxa-14-thia-2,4,8,24-tetraazatetracyclo[16.3.1.1(3,7).1(9,13)]tetracosa-1(22),3(24),4,6,9(23),10,12,18,20-nonaene-20-carboxamide trifluoroacetate A solution of 6-chloro-17-oxa-14-thia-2,4,8,24-tetraazatetracyclo[16.3.1.1(3,7).1(9,13)]tetracosa-1(22),3(24),4,6,9(23),10,12,18,20-nonaene-20-carboxylic acid (30 mg, 72 μmol) and benzylamine (12 μL, 0.11 mmol) in N,N-dimethylformamide (1 mL) was treated with N,N-diisopropylethylamine (50 μL, 0.29 mmol) followed by 0.5 M O-(benzotriazol-1-yl)-N,N,N',N'-tetramethyluronium hexafluorophosphate in N,N-dimethylformamide (0.19 mL, 94 μmol) and stirred at 20° C. for 16 h. The reaction mixture was diluted with methanol (4.9 mL) and TFA (0.1 mL) and the resultant suspension was filtered. The filtrate was purified by preparative LCMS to give the desired product (7 mg, 16%) as a solid. LCMS for $C_{26}H_{23}ClN_5O_2S$ (M+H)+: m/z=503.9. $^1$H NMR (300 MHz, DMSO-$d_6$): δ 9.66 (s, 1H), 8.91-8.88 (m, 2H), 8.18 (s, 1H), 7.96 (d, J=5.6 Hz, 2H), 7.37-7.21 (m, 9H), 6.94 (s, 1H), 4.41 (d, J=5.9 Hz, 2H), 4.16-4.11 (m, 2H), 3.28-3.23 (m, 2H).

Example D52

4-{4-[6-Chloro-14-oxa-2,4,8,23-tetraazatetracyclo[15.3.1.1(3,7).1(9,13)]tricosa-1(21),3(23),4,6,9(22),10,12,17,19-nonaen-19-yl]pyridin-2-yl}-N-cyclopentylpiperazine-1-carboxamide trifluoroacetate

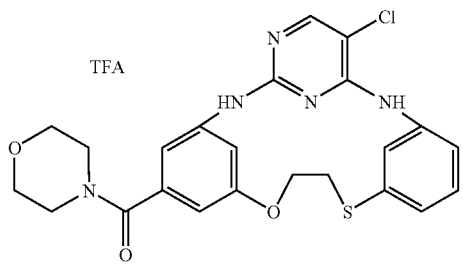 [SMILES: O=C(c1cc2cc(c1)OCCSc1cccc(c1)Nc1nc(ncc1Cl)N2)N1CCOCC1]

The desired compound was prepared according to the procedure of Example D51, step B, using morpholine as the starting material in 74% yield. LCMS for $C_{23}H_{23}ClN_5O_3S$ (M+H)+: m/z=483.9. $^1$H NMR (300 MHz, DMSO-$d_6$): δ 9.71 (s, 1H), 8.98 (s, 1H), 8.21 (s, 1H), 7.94 (s, 1H), 7.88 (dd, J=2.1, 1.8 Hz, 1H), 7.37-7.28 (m, 2H), 7.22 (dd, J=7.3, 1.8 Hz, 1H), 6.78 (s, 1H), 6.44 (d, J=1.2 Hz, 1H), 4.13-4.08 (m, 2H), 3.60-3.20 (m, 10H).

Example D53

6-Chloro-20-[(4-phenylpiperazin-1-yl)carbonyl]-17-oxa-14-thia-2,4,8,24-tetraazatetracyclo[16.3.1.1(3,7).1(9,13)]tetracosa-1(22),3(24),4,6,9(23),10,12,18,20-nonaene bis(trifluoroacetate)

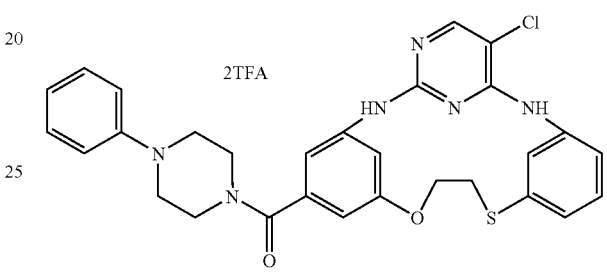

The desired compound was prepared according to the procedure of Example D51, step B, using 1-phenylpiperazine as the starting material in 63% yield. LCMS for $C_{29}H_{28}ClN_6O_2S$ (M+H)+: m/z=559.0. $^1$H NMR (300 MHz, DMSO-$d_6$): δ 9.72 (s, 1H), 8.98 (s, 1H), 8.21 (s, 1H), 7.95 (s, 1H), 7.90 (s, 1H), 7.38-7.28 (m, 2H), 7.25-7.19 (m, 3H), 6.96 (d, J=7.9 Hz, 2H), 6.83-6.78 (m, 2H), 6.47 (s, 1H), 4.14-4.09 (m, 2H), 3.70 (br s, 2H), 3.45 (br s, 2H), 3.29-3.24 (m, 2H), 3.15 (br s, 4H).

Example D54

6-Chloro-N-1,3-thiazol-2-yl-17-oxa-14-thia-2,4,8,24-tetraazatetracyclo[16.3.1.1(3,7).1(9,13)]tetracosa-1(22),3(24),4,6,9(23),10,12,18,20-nonaene-20-carboxamide trifluoroacetate

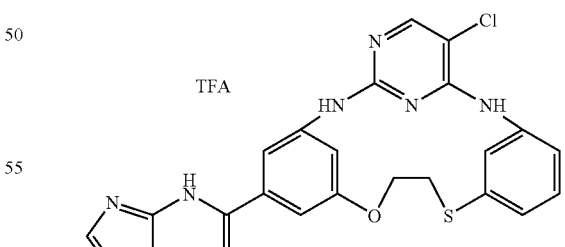

The desired compound was prepared according to the procedure of Example D51, step B, using 1,3-thiazol-2-amine as the starting material in 10% yield. LCMS for $C_{22}H_{18}ClN_6O_2S_2$ (M+H)+: m/z=496.9. $^1$H NMR (300 MHz, DMSO-$d_6$): δ 9.80 (s, 1H), 9.00 (s, 1H), 8.21 (s, 1H), 8.08 (s, 1H), 7.90 (s, 1H), 7.54 (d, J=3.2 Hz, 1H), 7.39-7.34 (m, 3H), 7.27-7.21 (m, 3H), 4.23-4.20 (m, 2H), 3.33-3.30 (m, 2H).

Example D55

6-Chloro-N-(1-methyl-1H-benzimidazol-2-yl)-17-oxa-14-thia-2,4,8,24-tetraazatetracyclo[16.3.1.1(3,7).1(9,13)]tetracosa-1(22),3(24),4,6,9(23),10,12,18,20-nonaene-20-carboxamide bis(trifluoroacetate)

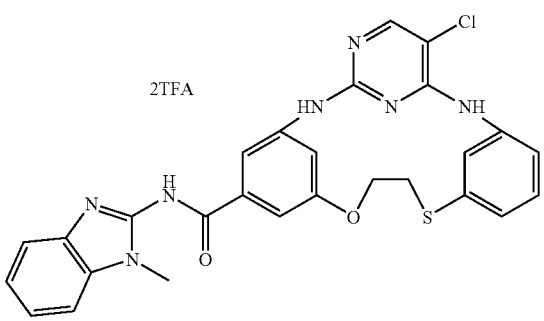 [SMILES: Cn1c(NC(=O)c2cc3cc(c2)OCCSc2cccc(c2)Nc2nc(ncc2Cl)N3)nc2ccccc21 ; "2TFA"]

The desired compound was prepared according to the procedure of Example D51, step B, using 1-methyl-1H-benzimidazol-2-amine as the starting material in 40% yield. LCMS for $C_{27}H_{23}ClN_7O_2S$ (M+H)$^+$: m/z=544.0. $^1$H NMR (300 MHz, DMSO-d$_6$): δ 9.85 (s, 1H), 9.01 (s, 1H), 8.23 (s, 1H), 7.98-7.96 (m, 2H), 7.74 (s, 1H), 7.55-7.49 (m, 2H), 7.36-7.22 (m, 7H), 4.17-4.13 (m, 2H), 3.75 (s, 3H), 3.30-3.26 (m, 2H).

Example D56

6-Chloro-N-1H-indol-5-yl-17-oxa-14-thia-2,4,8,24-tetraazatetracyclo[16.3.1.1(3,7).1(9,13)]tetracosa-1(22),3(24),4,6,9(23),10,12,18,20-nonaene-20-carboxamide trifluoroacetate

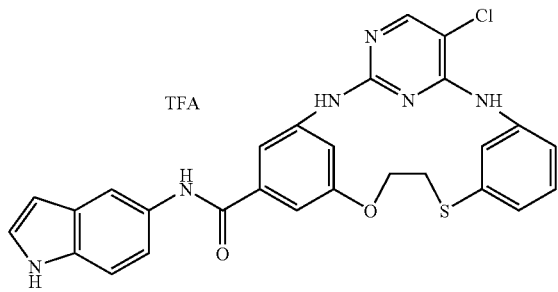 [SMILES: "TFA" ; O=C(Nc1ccc2[nH]ccc2c1)c1cc2cc(c1)OCCSc1cccc(c1)Nc1nc(ncc1Cl)N2]

The desired compound was prepared according to the procedure of Example D51, step B, using 5-aminoindole as the starting material in 28% yield. LCMS for $C_{27}H_{22}ClN_6O_2S$ (M+H)$^+$: m/z=529.0. $^1$H NMR (300 MHz, DMSO-d$_6$): δ 11.02 (s, 1H), 9.97 (s, 1H), 9.74 (s, 1H), 8.96 (s, 1H), 8.21 (s, 1H), 7.99-7.94 (m, 3H), 7.39-7.22 (m, 7H), 7.02 (s, 1H), 6.38 (dd, J=2.3, 2.3 Hz, 1H), 4.21-4.16 (m, 2H), 3.31-3.26 (m, 2H).

Example D57

N-[6-Chloro-17-oxa-14-thia-2,4,8,24-tetraazatetracyclo[16.3.1.1(3,7).1(9,13)]tetracosa-1(22),3(24),4,6,9(23),10,12,18,20-nonaen-20-yl]benzamide trifluoroacetate

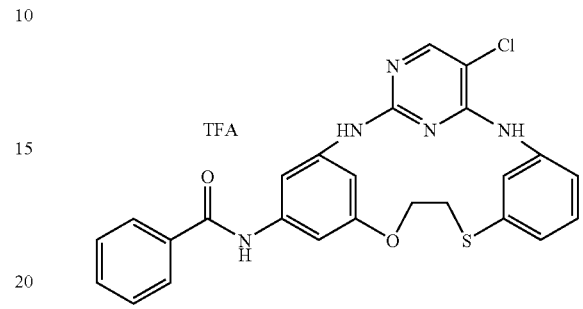

Step A: 6-Chloro-17-oxa-14-thia-2,4,8,24-tetraazatetracyclo[16.3.1.1(3,7).1(9,13)]tetracosa-1(22),3(24),4,6,9(23),10,12,18,20-nonaen-20-amine

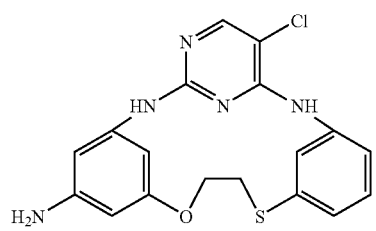 [SMILES: Nc1cc2cc(c1)OCCSc1cccc(c1)Nc1nc(ncc1Cl)N2]

A solution of 6-chloro-17-oxa-14-thia-2,4,8,24-tetraazatetracyclo[16.3.1.1(3,7).1(9,13)]tetracosa-1(22),3(24),4,6,9(23),10,12,18,20-nonaene-20-carboxylic acid (0.40 g, 0.95 mmol) in tetrahydrofuran (10 mL) at 0° C. was treated with triethylamine (0.53 mL, 3.8 mmol) and diphenylphosphonic acid (0.45 mL, 2.1 mmol) and stirred at 20° C. for 2 h. The reaction mixture was poured into water (50 mL) and ethyl acetate (150 mL). The ethyl acetate layer was separated, diluted with water (50 mL) and heated at 100° C. for 8 h. The reaction mixture was filtered and the organic layer from the filtrate was separated and washed with brine (50 mL), dried over anhydrous sodium sulfate, filtered, and evaporated to give the desired product as a crude yellow. This material was treated with ethyl acetate and filtered. The filtrate was concentrated to give the desired product (0.29 g, 78%) as a tan solid. LCMS for $C_{18}H_{17}ClN_5OS$ (M+H)$^+$: m/z=385.9.

Step B: N-[6-Chloro-17-oxa-14-thia-2,4,8,24-tetraazatetracyclo[16.3.1.1(3,7).1(9,13)]tetracosa-1(22),3(24),4,6,9(23),10,12,18,20-nonaen-20-yl]benzamide trifluoroacetate A solution of 6-chloro-17-oxa-14-thia-2,4,8,24-tetraazatetracyclo[16.3.1.1(3,7).1(9,13)]tetracosa-1(22),3(24),4,6,9(23),10,12,18,20-nonaen-20-amine (25 mg, 65 μmol) in tetrahydrofuran (0.5 mL) was treated with 0.2 M benzoyl chloride in dichloromethane (0.24 mL, 49 μmol) and stirred at 20° C. for 1 h. The reaction mixture was concentrated and purified by preparative LCMS to give the desired product (5 mg, 10%) as a solid. LCMS for $C_{25}H_{21}ClN_5O_2S$ (M+H)$^+$: m/z=490.0. $^1$H NMR (300 MHz, DMSO-d$_6$): δ 10.16 (s, 1H), 9.64 (s, 1H), 8.92 (s, 1H), 8.20 (s, 1H), 8.00 (s, 1H), 7.90 (d, J=6.7 Hz, 2H), 7.60-7.47 (m, 4H), 7.36-7.22 (m, 4H), 6.90 (s, 1H), 4.11-4.06 (m, 2H), 3.26-3.22 (m, 2H).

Example D58

N-[6-Chloro-17-oxa-14-thia-2,4,8,24-tetraazatetracyclo[16.3.1.1(3,7).1(9,13)]tetracosa-1(22),3(24),4,6,9(23),10,12,18,20-nonaen-20-yl]-5-methylisoxazole-3-carboxamide trifluoroacetate

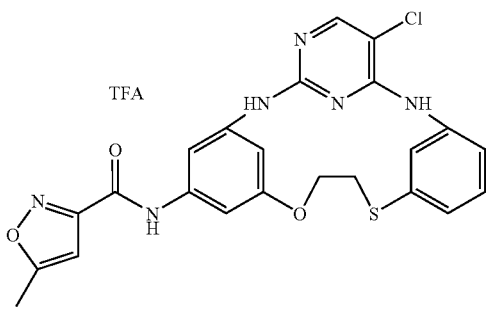 [SMILES: Cc1cc(C(=O)Nc2cc3cc(c2)OCCSc2cccc(c2)Nc2nc(ncc2Cl)N3)no1]

The desired compound was prepared according to the procedure of Example D57, step B, using 5-methylisoxazole-3-carbonyl chloride as the starting material in 10% yield. LCMS for $C_{23}H_{20}ClN_6O_3S$ (M+H)$^+$: m/z=495.0. $^1$H NMR (300 MHz, DMSO-d$_6$): δ 10.50 (s, 1H), 9.63 (s, 1H), 8.87 (s, 1H), 8.19 (s, 1H), 7.99 (s, 1H), 7.62 (s, 1H), 7.36-7.20 (m, 4H), 6.87 (s, 1H), 6.63 (s, 1H), 4.09-4.05 (m, 2H), 3.25-3.21 (m, 2H).

Example D59

N-[6-Chloro-17-oxa-14-thia-2,4,8,24-tetraazatetracyclo[16.3.1.1(3,7).1(9,13)]tetracosa-1(22),3(24),4,6,9(23),10,12,18,20-nonaen-20-yl]isoxazole-5-carboxamide trifluoroacetate

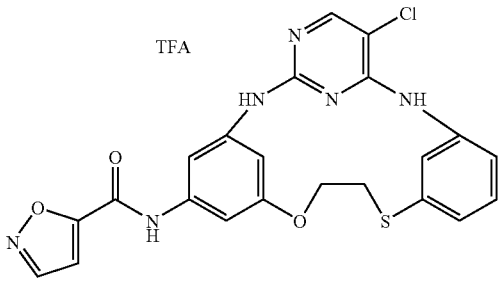 [SMILES: O=C(Nc1cc2cc(c1)OCCSc1cccc(c1)Nc1nc(ncc1Cl)N2)c1ccno1]

The desired compound was prepared according to the procedure of Example D57, step B, using isoxazole-5-carbonyl chloride as the starting material in 31% yield. LCMS for $C_{22}H_{18}ClN_6O_3S$ (M+H)$^+$: m/z=480.9. $^1$H NMR (300 MHz, DMSO-d$_6$): δ 10.64 (s, 1H), 9.71 (s, 1H), 8.94 (s, 1H), 8.79 (d, J=1.5 Hz, 1H), 8.20 (s, 1H), 7.99 (s, 1H), 7.64 (s, 1H), 7.37-7.18 (m, 5H), 6.88 (s, 1H), 4.11-4.06 (m, 2H), 3.26-3.22 (m, 2H).

Example D60

N-[6-Chloro-17-oxa-14-thia-2,4,8,24-tetraazatetracyclo[16.3.1.1(3,7).1(9,13)]tetracosa-1(22),3(24),4,6,9(23),10,12,18,20-nonaen-20-yl]isonicotinamide bis(trifluoroacetate)

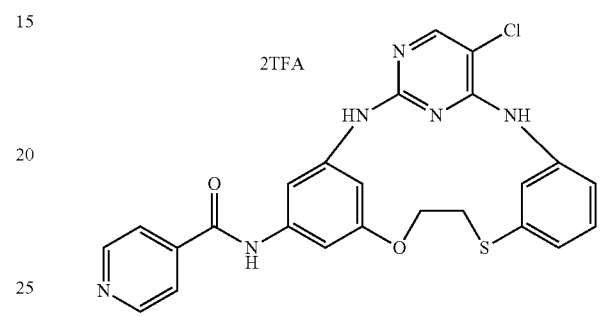

The desired compound was prepared according to the procedure of Example D57, step B, using isonicotinoyl chloride as the starting material in 26% yield. LCMS for $C_{24}H_{20}ClN_6O_2S$ (M+H)$^+$: m/z=491.0. $^1$H NMR (300 MHz, DMSO-d$_6$): δ 10.46 (s, 1H), 9.71 (s, 1H), 8.94 (s, 1H), 8.80-8.78 (m, 2H), 8.20 (s, 1H), 8.00 (s, 1H), 7.89-7.86 (m, 2H), 7.64 (s, 1H), 7.37-7.19 (m, 4H), 6.91 (s, 1H), 4.11-4.07 (m, 2H), 3.27-3.22 (m, 2H).

Example D61

N-[6-Chloro-17-oxa-14-thia-2,4,8,24-tetraazatetracyclo[16.3.1.1(3,7).1(9,13)]tetracosa-1(22),3(24),4,6,9(23),10,12,18,20-nonaen-20-yl]-1-benzofuran-5-carboxamide trifluoroacetate

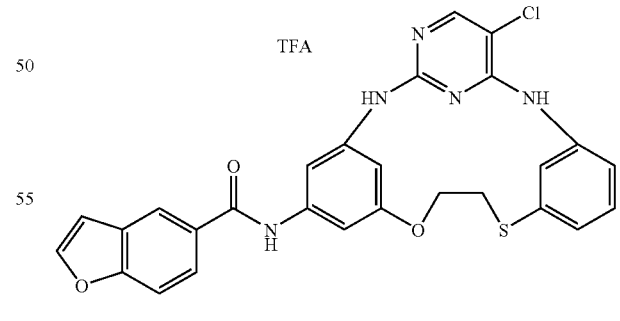

The desired compound was prepared according to the procedure of Example D57, step B, using 1-benzofuran-5-carbonyl chloride as the starting material in 36% yield. LCMS for $C_{27}H_{21}ClN_5O_3S$ (M+H)$^+$: m/z=529.9. $^1$H NMR (300 MHz, DMSO-d$_6$): δ 10.21 (s, 1H), 9.72 (s, 1H), 9.02 (s, 1H), 8.26 (d, J=1.2 Hz, 1H), 8.22 (s, 1H), 8.10 (d, J=2.3 Hz, 1H), 8.00 (s, 1H), 7.88 (dd, J=8.8, 1.5 Hz, 1H), 7.71 (d, J=8.5 Hz, 1H), 7.58 (s, 1H), 7.37-7.22 (m, 4H), 7.09 (d, J=1.5 Hz, 1H), 6.92 (s, 1H), 4.11-4.07 (m, 2H), 3.27-3.23 (m, 2H).

Example D62

N-[6-Chloro-17-oxa-14-thia-2,4,8,24-tetraazatetracyclo[16.3.1.1(3,7).1(9,13)]tetracosa-1(22),3(24),4,6,9(23),10,12,18,20-nonaen-20-yl]-2-furamide trifluoroacetate

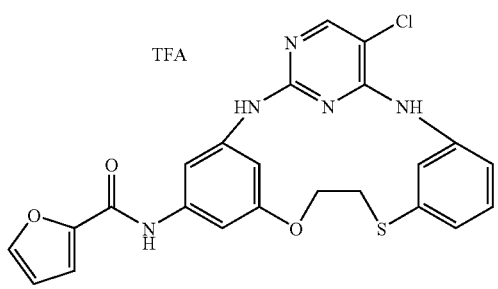 [SMILES: O=C(Nc1cc2cc(c1)OCCSc1cccc(c1)Nc1nc(ncc1Cl)N2)c1ccco1]

The desired compound was prepared according to the procedure of Example D57, step B, using 2-furancarbonyl chloride as the starting material in 36% yield. LCMS for $C_{23}H_{19}ClN_5O_3S$ (M+H)$^+$: m/z=479.9. $^1$H NMR (300 MHz, DMSO-d$_6$): δ 10.06 (s, 1H), 9.67 (s, 1H), 8.97 (s, 1H), 8.20 (s, 1H), 7.99 (s, 1H), 7.91 (d, J=0.9 Hz, 1H), 7.58 (s, 1H), 7.36-7.18 (m, 5H), 6.86 (dd, J=2.1, 1.8 Hz, 1H), 6.67 (dd, J=3.5, 1.8 Hz, 1H), 4.10-4.05 (m, 2H), 3.26-3.21 (m, 2H).

Example D63

N-[6-Chloro-17-oxa-14-thia-2,4,8,24-tetraazatetracyclo[16.3.1.1(3,7).1(9,13)]tetracosa-1(22),3(24),4,6,9(23),10,12,18,20-nonaen-20-yl]thiophene-2-carboxamide trifluoroacetate

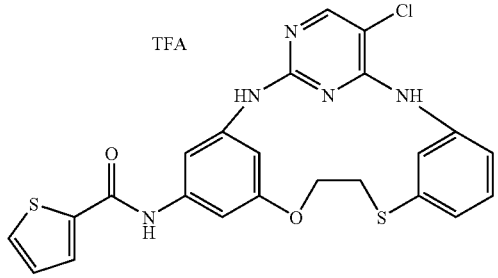 [SMILES: O=C(Nc1cc2cc(c1)OCCSc1cccc(c1)Nc1nc(ncc1Cl)N2)c1cccs1]

The desired compound was prepared according to the procedure of Example D57, step B, using 2-thiophenecarbonyl chloride as the starting material in 28% yield. LCMS for $C_{23}H_{19}ClN_5O_2S_2$ (M+H)$^+$: m/z=495.9. $^1$H NMR (300 MHz, DMSO-d$_6$): δ 10.14 (s, 1H), 9.67 (s, 1H), 8.95 (s, 1H), 8.20 (s, 1H), 7.99 (d, J=3.2 Hz, 2H), 7.83 (d, J=5.0 Hz, 1H), 7.60 (s, 1H), 7.37-7.13 (m, 5H), 6.86 (s, 1H), 4.11-4.06 (m, 2H), 3.27-3.22 (m, 2H).

Example D64

N-[6-Chloro-17-oxa-14-thia-2,4,8,24-tetraazatetracyclo[16.3.1.1(3,7).1(9,13)]tetracosa-1(22),3(24),4,6,9(23),10,12,18,20-nonaen-20-yl]thiophene-2-carboxamide trifluoroacetate

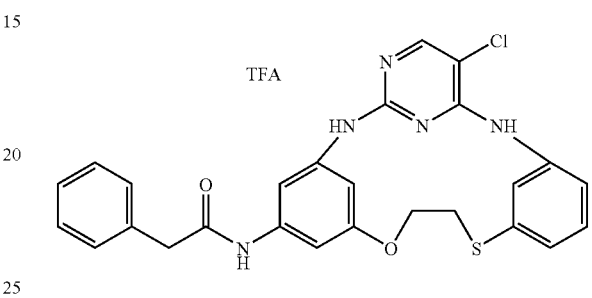

The desired compound was prepared according to the procedure of Example D57, step B, using benzeneacetyl chloride as the starting material in 30% yield. LCMS for $C_{26}H_{23}ClN_5O_2S$ (M+H)$^+$: m/z=504.0. $^1$H NMR (300 MHz, DMSO-d$_6$): δ 10.06 (s, 1H), 9.62 (s, 1H), 8.92 (s, 1H), 8.18 (s, 1H), 7.97 (s, 1H), 7.52 (s, 1H), 7.35-7.20 (m, 8H), 6.92 (s, 1H), 6.84 (s, 1H), 4.06-4.01 (m, 2H), 3.59 (s, 2H), 3.23-3.18 (m, 2H).

Example D65

N-[6-Chloro-17-oxa-14-thia-2,4,8,24-tetraazatetracyclo[16.3.1.1(3,7).1(9,13)]tetracosa-1(22),3(24),4,6,9(23),10,12,18,20-nonaen-20-yl]-N'-phenylurea trifluoroacetate

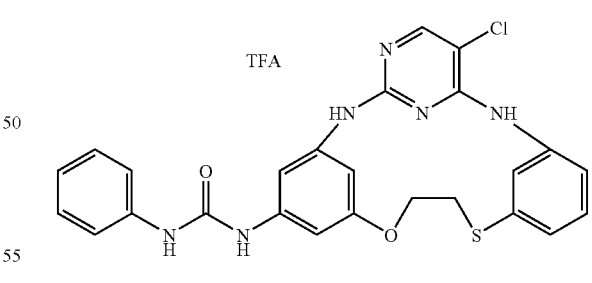

A solution of 6-chloro-17-oxa-14-thia-2,4,8,24-tetraazatetracyclo[16.3.1.1(3,7).1(9,13)]tetracosa-1(22),3(24),4,6,9(23),10,12,18,20-nonaen-20-amine (25 mg, 0.65 mmol) in tetrahydrofuran (0.5 mL) was treated with phenyl isocyanate (9.2 μL, 84 μmol) followed by triethylamine (0.53 mL, 3.8 mmol) and stirred at 20° C. for 2 h. The reaction mixture was concentrated and purified by preparative LCMS to give the desired product (7 mg, 20%) as a solid. LCMS for $C_{25}H_{22}ClN_6O_2S$ (M+H)$^+$: m/z=505.0. $^1$H NMR (300 MHz, DMSO-d$_6$): δ 9.60 (s, 1H), 8.90 (s, 1H), 8.62 (d, J=18.7 Hz, 2H), 8.19 (s, 1H), 7.99 (s, 1H), 7.47-7.22 (m, 8H), 6.94 (dd, J=7.3, 7.0 Hz, 1H), 6.84 (s, 1H), 6.67 (s, 1H), 4.08-4.03 (m, 2H), 3.25-3.20 (m, 2H).

Example D66

N-Benzyl-N'-[6-chloro-17-oxa-14-thia-2,4,8,24-tetraazatetracyclo[16.3.1.1(3,7).1(9,13)]tetracosa-1(22),3(24),4,6,9(23),10,12,18,20-nonaen-20-yl]urea trifluoroacetate

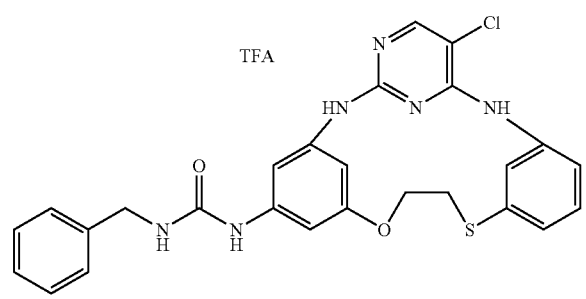 [SMILES: O=C(NCc1ccccc1)Nc1cc2cc(c1)OCCSc1cccc(c1)Nc1nc(ncc1Cl)N2]

The desired compound was prepared according to the procedure of Example D65 using benzyl isocyanate as the starting material in 29% yield. LCMS for $C_{26}H_{24}ClN_6O_2S$ (M+H)$^+$: m/z=519.0. $^1$H NMR (300 MHz, DMSO-d$_6$): δ 9.48 (s, 1H), 8.80 (s, 1H), 8.42 (s, 1H), 8.16 (s, 1H), 7.98 (s, 1H), 7.41 (s, 1H), 7.34-7.19 (m, 8H), 6.81 (s, 1H), 6.59-6.54 (m, 2H), 4.25 (d, J=5.9 Hz, 2H), 4.05-4.00 (m, 2H), 3.22-3.18 (m, 2H).

Example D67

N-[6-Chloro-17-oxa-14-thia-2,4,8,24-tetraazatetracyclo[16.3.1.1(3,7).1(9,13)]tetracosa-1(22),3(24),4,6,9(23),10,12,18,20-nonaen-20-yl]-N'-(2-furylmethyl)urea trifluoroacetate

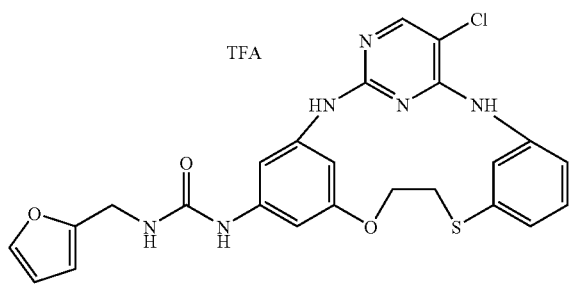 [SMILES: O=C(NCc1ccco1)Nc1cc2cc(c1)OCCSc1cccc(c1)Nc1nc(ncc1Cl)N2]

The desired compound was prepared according to the procedure of Example D65 using 2-(isocyanatomethyl)furan as the starting material in 20% yield. LCMS for $C_{24}H_{22}ClN_6O_3S$ (M+H)$^+$: m/z=509.0. $^1$H NMR (300 MHz, DMSO-d$_6$): δ 9.49 (s, 1H), 8.82 (s, 1H), 8.39 (s, 1H), 8.17 (s, 1H), 7.98 (s, 1H), 7.56 (d, J=0.9 Hz, 1H), 7.41 (s, 1H), 7.34-7.29 (m, 2H), 7.25-7.20 (m, 2H), 6.79 (s, 1H), 7.58 (s, 1H), 6.49 (dd, J=5.6, 5.6 Hz, 1H), 6.37 (dd, J=3.2, 2.1 Hz, 1H), 6.22 (d, J=2.9 Hz, 1H), 4.23 (d, J=5.6 Hz, 2H), 4.05-4.01 (m, 2H), 3.22-3.18 (m, 2H).

Example D68

N-[6-Chloro-17-oxa-14-thia-2,4,8,24-tetraazatetracyclo[16.3.1.1(3,7).1(9,13)]tetracosa-1(22),3(24),4,6,9(23),10,12,18,20-nonaen-20-yl]benzenesulfonamide trifluoroacetate NaCl

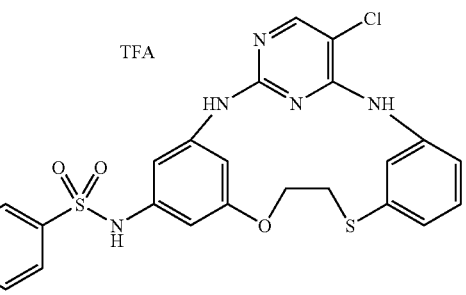

A solution of 6-chloro-17-oxa-14-thia-2,4,8,24-tetraazatetracyclo[16.3.1.1(3,7).1(9,13)]tetracosa-1(22),3(24),4,6,9(23),10,12,18,20-nonaen-20-amine (25 mg, 0.65 mmol) in tetrahydrofuran (0.5 mL) was treated with benzenesulfonyl chloride (8.3 μL, 65 μmol) followed by triethylamine (18 μL, 0.13 mmol) and stirred at 20° C. for 16 h. The reaction mixture was concentrated and purified by preparative LCMS to give the desired product (9 mg, 20%) as a solid. LCMS for $C_{24}H_{21}ClN_5O_3S_2$ (M+H)$^+$: m/z=525.9. $^1$H NMR (300 MHz, DMSO-d$_6$): δ 10.23 (s, 1H), 9.66 (s, 1H), 8.91 (s, 1H), 8.18 (s, 1H), 7.91 (s, 1H), 7.80 (d, J=7.0 Hz, 2H), 7.59-7.46 (m, 4H), 7.33-7.18 (m, 3H), 6.63 (s, 1H), 6.14 (s, 1H), 3.97-3.93 (m, 2H), 3.18-3.13 (m, 2H).

Example D69

N-[6-Chloro-17-oxa-14-thia-2,4,8,24-tetraazatetracyclo[16.3.1.1(3,7).1(9,13)]tetracosa-1(22),3(24),4,6,9(23),10,12,18,20-nonaen-20-yl]-1,2-dimethyl-1H-imidazole-4-sulfonamide bis(trifluoroacetate)

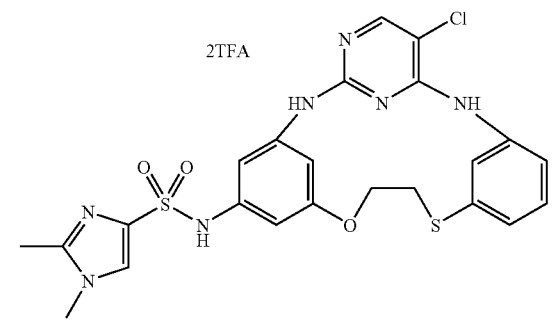 [SMILES: Cc1nc(S(=O)(=O)Nc2cc3cc(c2)OCCSc2cccc(c2)Nc2nc(ncc2Cl)N3)cn1C ; "2TFA"]

The desired compound was prepared according to the procedure of Example D68 using 1,2-dimethyl-1H-imidazole-4-sulfonyl chloride as the starting material in 20% yield (the reaction was heated at 60° C. for 16 h). LCMS for $C_{23}H_{23}ClN_7O_3S_2$ (M+H)$^+$: m/z=543.9. $^1$H NMR (300 MHz, DMSO-d$_6$): δ 10.12 (s, 1H), 9.57 (s, 1H), 8.89 (s, 1H), 8.18 (s, 1H), 7.94 (s, 1H), 7.78 (s, 1H), 7.42 (s, 1H), 7.34-7.19 (m, 3H), 6.56 (s, 1H), 6.25 (s, 1H), 3.98-3.96 (m, 2H), 3.53 (s, 3H), 3.20-3.15 (m, 2H), 2.33 (s, 3H).

Example D70

6-Chloro-14-oxa-2,4,8,17,24-pentaazatetracyclo[16.3.1.1(3,7).1(9,13)]tetracosa-1(22),3(24),4,6,9(23),10,12,18,20-nonaene bis(trifluoroacetate)

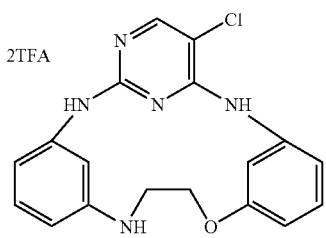 [SMILES: "2TFA" ; Clc1cnc2nc1Nc1cccc(c1)OCCNc1cccc(c1)N2]

Step A: tert-Butyl (3-{[2-(3-nitrophenoxy)ethyl]amino}phenyl)carbamate

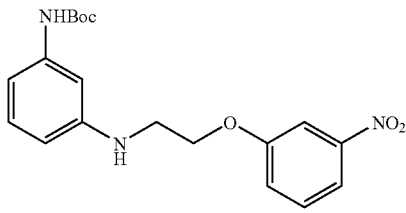 [SMILES: CC(C)(C)OC(=O)Nc1cccc(NCCOc2cccc([N+](=O)[O-])c2)c1]

A solution of tert-butyl (3-aminophenyl)carbamate (1.0 g, 4.8 mmol) and potassium carbonate (1.3 g, 9.6 mmol) in N,N-dimethylformamide (10 mL) was treated with a solution of 1-(2-bromoethoxy)-3-nitrobenzene (1.2 g, 5.0 mmol) in N,N-dimethylformamide (5 mL) was stirred at 20° C. for 2 h and at 80° C. for 16 h. The reaction mixture was diluted with water (100 mL) and extracted with ethyl acetate (3×80 mL). The combined organic layers were washed with water and brine, dried over anhydrous sodium sulfate, filtered, and evaporated to give the desired product as a crude residue. This material was purified by flash column chromatography to give the desired product (1.0 g, 56%) as a yellow gum. LCMS for $C_{19}H_{24}N_3O_5$ (M+H)$^+$: m/z=374.2.

Step B: tert-Butyl (3-{[2-(3-aminophenoxy)ethyl]amino}phenyl)carbamate

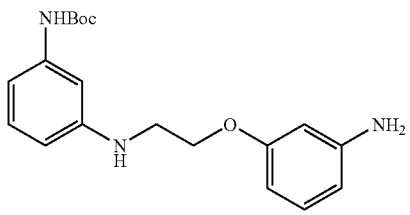

The desired compound was prepared according to the procedure of Example D2, step B, using tert-butyl (3-{[2-(3-nitrophenoxy)ethyl]amino}phenyl)carbamate as the starting material in 92% yield. LCMS for $C_{19}H_{26}N_3O_3$ (M+H)$^+$: m/z=344.1.

Step C: tert-Butyl {3-[(2-{3-[(2,5-dichloropyrimidin-4-yl)amino]phenoxy}ethyl)amino]phenyl}carbamate

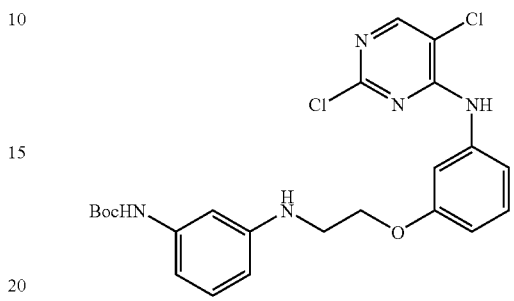

The desired compound was prepared according to the procedure of Example D2, step C, using tert-butyl (3-{[2-(3-aminophenoxy)ethyl]amino}phenyl)carbamate as the starting material in 70% yield. LCMS for $C_{23}H_{26}Cl_2N_5O_3$ (M+H)$^+$: m/z=490.0, 492.0.

Step D: 6-Chloro-14-oxa-2,4,8,17,24-pentaazatetracyclo[16.3.1.1(3,7).1(9,13)]tetracosa-1(22),3(24),4,6,9(23),10,12,18,20-nonaene bis(trifluoroacetate)

The desired compound was prepared according to the procedure of Example D2, step D, using tert-butyl {3-[(2-{3-[(2,5-dichloropyrimidin-4-yl)amino]phenoxy}ethyl)amino]phenyl}carbamate as the starting material in 12% yield. LCMS for $C_{18}H_{17}ClN_5O$ (M+H)$^+$: m/z=354.0. $^1$H NMR (400 MHz, DMSO-$d_6$): δ 9.34 (s, 1H), 8.39 (s, 1H), 8.18 (s, 1H), 8.13 (dd, J=2.0, 2.0 Hz, 1H), 7.54 (s, 1H), 7.20 (dd, J=8.2, 8.0 Hz, 1H), 7.02 (d, J=8.8 Hz, 1H), 6.88 (dd, J=8.0, 7.8 Hz, 1H), 6.60-6.57 (m, 1H), 6.40 (d, J=8.6 Hz, 1H), 6.17 (dd, J=8.0, 1.2 Hz, 1H), 5.81 (dd, J=6.8, 6.6 Hz, 1H), 4.14-4.10 (m, 2H), 3.30-3.24 (m, 2H).

Example D71

15-Acetyl-6-chloro-2,4,8,15,22-pentaazatetracyclo[14.3.1.1(3,7).1(9,13)]docosa-1(20),3(22),4,6,9(21),10,12,16,18-nonaene trifluoroacetate

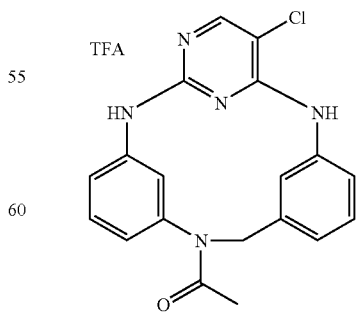

A solution of 6-chloro-2,4,8,15,22-pentaazatetracyclo[14.3.1.1(3,7).1(9,13)]docosa-1(20),3(22),4,6,9(21),10,12, 16,18-nonaene bis(trifluoroacetate) (10 mg, 18 μmol) in acetonitrile (0.28 mL) was treated with pyridine (7.3 μL, 91 μmol) followed by acetic anhydride (2.1 μL, 22 μmol) and stirred for 16 h. The reaction mixture was quenched with a few drops of acetic acid and purified by preparative LCMS to give the desired product (5 mg, 58%) as a solid. LCMS for $C_{19}H_{17}ClN_5O$ (M+H)$^+$: m/z=366.0. $^1$H NMR (400 MHz, DMSO-d$_6$): δ 9.61 (s, 1H), 9.24 (s, 1H), 8.16 (s, 1H), 8.06 (dd, J=2.0, 1.8 Hz, 1H), 7.93 (s, 1H), 7.32-7.21 (m, 4H), 7.13 (dd, J=8.2, 1.4 Hz, 1H), 6.97 (dd, J=7.8, 1.2 Hz, 1H), 4.61 (br s, 2H), 1.73 (s, 3H).

Example D72

6-Chloro-17-oxa-2,4,8,14,24-pentaazatetracyclo[16.3.1.1(3,7).1(9,13)]tetracosa-1(22),3(24),4,6,9(23),10,12,18,20-nonaene bis(trifluoroacetate)

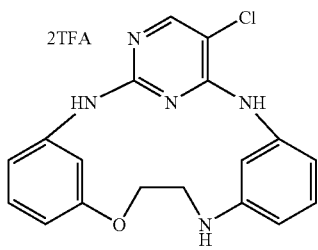 [SMILES: "2TFA" ; Clc1cnc2nc1Nc1cccc(c1)NCCOc1cccc(c1)N2]

Step A: N-[2-(3-Nitrophenoxy)ethyl]benzene-1,3-diamine

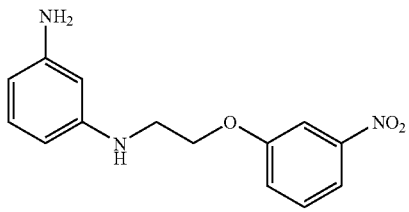 [SMILES: Nc1cccc(NCCOc2cccc([N+](=O)[O-])c2)c1]

The desired compound was prepared according to the procedure of D34, step A, using tert-butyl (3-{[2-(3-nitrophenoxy)ethyl]amino}phenyl)carbamate as the starting material in 82% yield. LCMS for $C_{14}H_{16}N_3O_3$ (M+H)$^+$: m/z=274.0.

Step B: N-(2,5-Dichloropyrimidin-4-yl)-N'-[2-(3-nitrophenoxy)ethyl]benzene-1,3-diamine bis(trifluoroacetate)

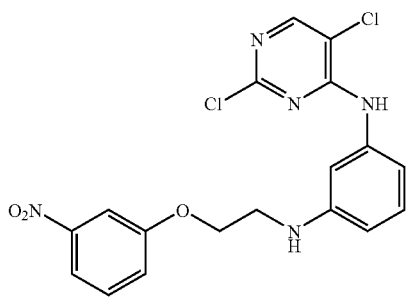

The desired compound was prepared according to the procedure of Example D2, step C, using N-[2-(3-nitrophenoxy)ethyl]benzene-1,3-diamine as the starting material in 54% yield. LCMS for $C_{18}H_{16}Cl_2N_5O_3$ (M+H)$^+$: m/z=419.9, 421.9.

Step C: N-[2-(3-Aminophenoxy)ethyl]-N'-(2,5-dichloropyrimidin-4-yl)benzene-1,3-diamine

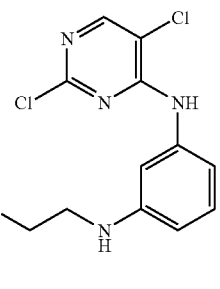

A solution of N-(2,5-dichloropyrimidin-4-yl)-N'-[2-(3-nitrophenoxy)ethyl]benzene-1,3-diamine bis(trifluoroacetate) (100 mg, 0.15 mmol) in methanol (0.63 mL) was treated with acetic acid (0.25 mL, 4.4 mmol), water (0.13 mL, 7.0 mmol), and iron (43 mg, 0.77 mmol) and stirred at 20° C. for 16 h. The reaction mixture was diluted with methanol and treated with celite. The suspension was filtered over a pad of celite and washed with methanol. The filtrate was concentrated to give the desired product (63 mg, 94%) as a crude residue that was used without further purification.

Step D: 6-Chloro-17-oxa-2,4,8,14,24-pentaazatetracyclo[16.3.1.1(3,7).1(9,13)]tetracosa-1(22),3(24),4,6,9(23),10,12,18,20-nonaene bis(trifluoroacetate)

The desired compound was prepared according to the procedure of Example D2, step C, using N-[2-(3-aminophenoxy)ethyl]-N'-(2,5-dichloropyrimidin-4-yl)benzene-1,3-diamine as the starting material in 21% yield (2 steps). LCMS for $C_{18}H_{17}ClN_5O$ (M+H)$^+$: m/z=354.0. $^1$H NMR (300 MHz, DMSO-d$_6$): δ 9.61 (s, 1H), 8.33 (s, 1H), 8.19 (s, 1H), 7.98 (s, 1H), 7.68 (s, 1H), 7.14-7.00 (m, 2H), 6.78 (d, J=8.5 Hz, 1H), 6.63 (d, J=8.5 Hz, 1H), 6.47-6.41 (m, 2H), 4.10-4.04 (m, 2H), 3.39-3.33 (m, 2H).

Example D73

6-Chloro-2,4,8,15,23-pentaazatetracyclo[15.3.1.1(3,7).1(9,13)]tricosa-1(21),3(23),4,6,9(22),10,12,17,19-nonaene bis(trifluoroacetate)

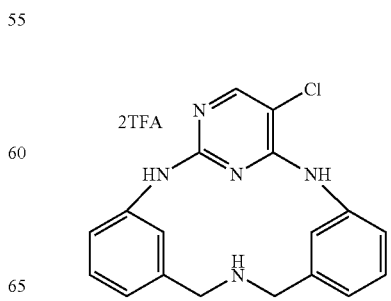

Step A: tert-Butyl (3-{[(3-nitrobenzoyl)amino]methyl}phenyl)carbamate

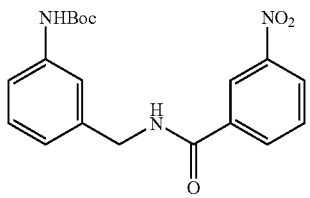 [SMILES: CC(C)(C)OC(=O)Nc1cccc(CNC(=O)c2cccc([N+](=O)[O-])c2)c1]

A solution of tert-butyl [3-(aminomethyl)phenyl]carbamate (2.0 g, 9 mmol) and triethylamine (1.3 mL, 9.5 mmol) in tetrahydrofuran (26 mL) at 0° C. was treated with a solution of 3-nitrobenzoyl chloride (1.8 g, 9.5 mmol) in tetrahydrofuran (7.3 mL) and stirred at 20° C. for 1 h. The reaction mixture was treated with saturated sodium bicarbonate and the aqueous layer was separated and extracted with ethyl acetate (3×15 mL). The combined organic layers were dried over anhydrous sodium sulfate, filtered, and evaporated to give the desired product (3.5 g, 105%) as a crude off-white solid that was used without further purification. LCMS for $C_{15}H_{14}N_3O_5$ ([M-(t-Bu)+H]+H)$^+$: m/z=316.0.

Step B: N-(3-Aminobenzyl)-3-nitrobenzamide hydrochloride

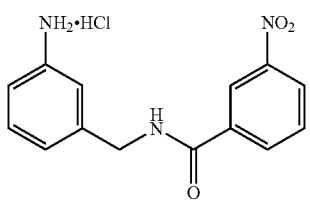

The desired compound was prepared according to the procedure of Example A27, step A, using tert-butyl (3-{[(3-nitrobenzoyl)amino]methyl}phenyl)carbamate as the starting material in 99% yield (2 steps: Steps A and B). LCMS for $C_{14}H_{14}N_3O_3$ (M+H)$^+$: m/z=272.0.

Step C: N-{3-[(2,5-Dichloropyrimidin-4-yl)amino]benzyl}-3-nitrobenzamide

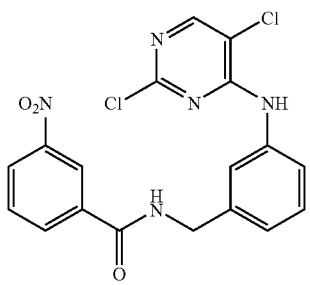 [SMILES: O=C(NCc1cccc(Nc2nc(Cl)ncc2Cl)c1)c1cccc([N+](=O)[O-])c1]

The desired compound was prepared according to the procedure of Example D2, step C, using N-(3-aminobenzyl)-3-nitrobenzamide hydrochloride as the starting material in 77% yield. LCMS for $C_{18}H_{14}Cl_2N_5O_3$ (M+H)$^+$: m/z=418.0, 420.0.

Step D: 3-Amino-N-{3-[(2,5-dichloropyrimidin-4-yl)amino]benzyl}benzamide

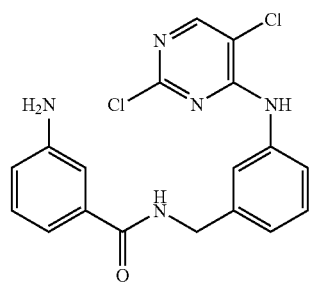 [SMILES: Nc1cccc(C(=O)NCc2cccc(Nc3nc(Cl)ncc3Cl)c2)c1]

The desired compound was prepared according to the procedure of Example D16, step D, using N-{3-[(2,5-dichloropyrimidin-4-yl)amino]benzyl}-3-nitrobenzamide as the starting material and used in the next step without further purification. LCMS for $C_{18}H_{16}Cl_2N_5O$ (M+H)$^+$: m/z=388.0.

Step E: 6-Chloro-2,4,8,15,23-pentaazatetracyclo[15.3.1.1(3,7).1(9,13)]tricosa-1(21),3(23),4,6,9(22),10,12,17,19-nonaen-16-one

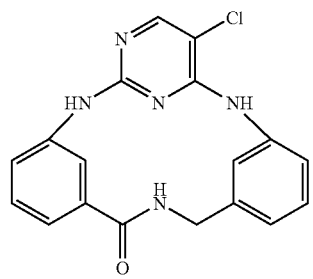 [SMILES: O=C1NCc2cccc(c2)Nc2nc(ncc2Cl)Nc2cccc1c2]

The desired compound was prepared according to the procedure of Example D2, step D, using 6-chloro-2,4,8,15,23-pentaazatetracyclo[15.3.1.1(3,7).1(9,13)]tricosa-1(21),3(23),4,6,9(22),10,12,17,19-nonaen-16-one as the starting material and used in the next step without further purification.

Step F: 6-Chloro-2,4,8,15,23-pentaazatetracyclo[15.3.1.1(3,7).1(9,13)]tricosa-1(21),3(23),4,6,9(22),10,12,17,19-nonaene bis(trifluoroacetate)

A solution of 6-chloro-2,4,8,15,23-pentaazatetracyclo[15.3.1.1(3,7).1(9,13)]tricosa-1(21),3(23),4,6,9(22),10,12,17,19-nonaen-16-one (25 mg, 71 µmol) in tetrahydrofuran (4 mL) was treated with 1 M borane in tetrahydrofuran (0.26 mL, 0.26 mmol) and refluxed for 3 h. The reaction mixture was concentrated and the crude residue purified by preparative LCMS to give the desired product (3 mg, 2% for 3 steps). LCMS for $C_{18}H_{17}ClN_5$ (M+H)$^+$: m/z=337.9

Example D74

15-Acetyl-6-chloro-2,4,8,15,23-pentaazatetracyclo[15.3.1.1(3,7).1(9,13)]tricosa-1(21),3(23),4,6,9(22),10,12,17,19-nonaene trifluoroacetate

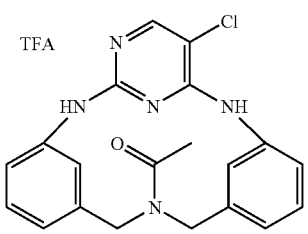 [SMILES: CC(=O)N1Cc2cccc(c2)Nc2ncc(Cl)c(n2)Nc2cccc(c2)C1]

Step A: tert-Butyl (3-{[(3-nitrobenzyl)amino]methyl}phenyl)carbamate trifluoroacetate

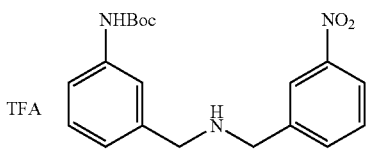 [SMILES: CC(C)(C)OC(=O)Nc1cccc(CNCc2cccc([N+](=O)[O-])c2)c1]

A solution of tert-butyl [3-(aminomethyl)phenyl]carbamate (0.15 g, 0.65 mmol) and N,N-diisopropylethylamine (0.23 mL, 1.3 mmol) in acetonitrile (2 mL) at 60° C. was treated with a solution of 1-(bromomethyl)-3-nitrobenzene (0.15 g, 0.69 mmol) in acetonitrile (1 mL) and stirred at 60° C. for 1 h. The reaction mixture was cooled and purified by preparative LCMS to give the desired product (0.27 g, 87%). LCMS for $C_{19}H_{24}N_3O_4$ (M+H)$^+$: m/z=358.1.

Step B: tert-Butyl (3-{[acetyl(3-nitrobenzyl)amino]methyl}phenyl)carbamate

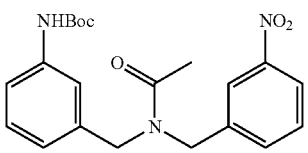 [SMILES: CC(=O)N(Cc1cccc(NC(=O)OC(C)(C)C)c1)Cc1cccc([N+](=O)[O-])c1]

A solution of tert-butyl (3-{[(3-nitrobenzyl)amino]methyl}phenyl)carbamate trifluoroacetate (0.16 g, 0.34 mmol) in acetonitrile (5.2 mL) was treated with 4-dimethylaminopyridine (8.3 mg, 68 µmol), pyridine (0.14 mL, 1.7 mmol), and acetic anhydride (35 µL, 0.37 mmol) and stirred at 20° C. for 16 h. The reaction mixture was purified by preparative LCMS to give the desired product (95 mg, 70%). LCMS for $C_{21}H_{25}N_3O_5Na$ (M+Na)$^+$: m/z=422.0.

Step C: tert-Butyl (3-{[acetyl(3-aminobenzyl)amino]methyl}phenyl)carbamate trifluoroacetate

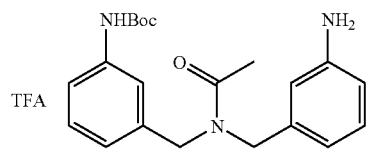 [SMILES: CC(=O)N(Cc1cccc(N)c1)Cc1cccc(NC(=O)OC(C)(C)C)c1]

The desired compound was prepared according to the procedure of Example D2, step B, using tert-butyl (3-{[acetyl(3-nitrobenzyl)amino]methyl}phenyl)carbamate as the starting material in 70% yield. LCMS for $C_{21}H_{27}N_3O_3Na$ (M+Na)$^+$: m/z=392.0.

Step D: tert-Butyl {3-[(acetyl{3-[(2,5-dichloropyrimidin-4-yl)amino]benzyl}amino)methyl]phenyl}carbamate trifluoroacetate

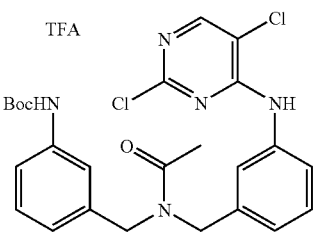 [SMILES: CC(=O)N(Cc1cccc(NC(=O)OC(C)(C)C)c1)Cc1cccc(Nc2nc(Cl)ncc2Cl)c1]

The desired compound was prepared according to the procedure of Example D2, step C, using tert-butyl (3-{[acetyl(3-aminobenzyl)amino]methyl}phenyl)carbamate trifluoroacetate as the starting material in 43% yield. LCMS for $C_{21}H_{20}Cl_2N_5O_3$ ([M-(t-Bu)+H]+H)$^+$: m/z=459.9, 461.1.

Step E: 15-Acetyl-6-chloro-2,4,8,15,23-pentaazatetracyclo[15.3.1.1(3,7).1(9,13)]tricosa-1(21),3(23),4,6,9(22),10,12,17,19-nonaene trifluoroacetate A solution of tert-butyl {3-[(acetyl{3-[(2,5-dichloropyrimidin-4-yl)amino]benzyl}amino)methyl]phenyl}carbamate trifluoroacetate (10 mg, 16 µmol) in acetonitrile (1.5 mL) was treated with trifluoroacetic acid (75 µL, 0.97 mmol) and heated at 70° C. for 16 h. The reaction mixture was cooled and purified by preparative LCMS to give the desired product (2.5 mg, 32%) as a solid. LCMS for $C_{20}H_{19}ClN_5O$ (M+H)$^+$: m/z=380.0. $^1$H NMR (300 MHz, CD$_3$OD): δ 8.14 (d, J=1.8 Hz, 1H), 7.78 (s, 1H), 7.63-7.61 (m, 1H), 7.40-7.21 (m, 2H), 7.19-7.05 (m, 3H), 6.98-6.96 (m, 1H), 4.71-4.62 (m, 4H).

Example D75

6-Chloro-2,4,8,14,24-pentaazatetracyclo[16.3.1.1(3,7).1(9,13)]tetracosa-1(22),3(24),4,6,9(23),10,12,18,20-nonaene bis(trifluoroacetate)

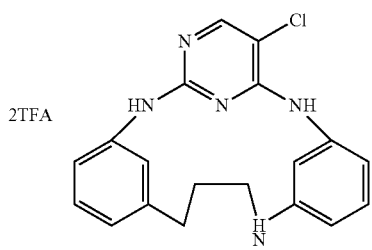 [SMILES: "2TFA" ; Clc1cnc2nc1Nc1cccc(c1)NCCCc1cccc(c1)N2]

Step A: tert-Butyl (3-{[3-(3-nitrophenyl)propanoyl]amino}phenyl)carbamate

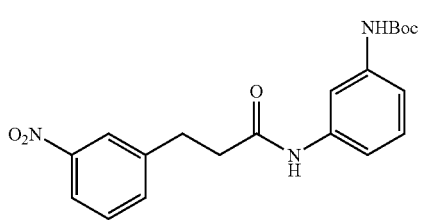 [SMILES: CC(C)(C)OC(=O)Nc1cccc(NC(=O)CCc2cccc([N+](=O)[O-])c2)c1]

A solution of 3-(3-nitrophenyl)propanoic acid (0.43 g, 2.2 mmol) and tert-butyl (3-aminophenyl)carbamate (0.50 g, 2.4 mmol) in acetonitrile (16 mL) was treated with O-(benzotriazol-1-yl)-N,N,N',N'-tetramethyluronium hexafluorophosphate (1.2 g, 3.3 mmol) followed by N,N-diisopropylethylamine (0.57 mL, 3.3 mmol) and stirred for 16 h. The reaction mixture was concentrated and diluted with brine (80 mL) and extracted with ethyl acetate (3×50 mL). The combined organic layers were washed with water and brine, dried over anhydrous sodium sulfate, filtered, and evaporated to give the desired product as a crude residue. This material was purified by flash column chromatography to give the desired product (0.87 g, 98%) as an off-white foam. LCMS for $C_{16}H_{16}N_3O_5$ ([M-(t-Bu)+H]+H)$^+$: m/z=330.0.

Step B: N-[3-(3-Nitrophenyl)propyl]benzene-1,3-diamine trifluoroacetate

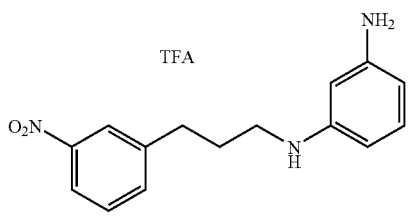 [SMILES: Nc1cccc(NCCCc2cccc([N+](=O)[O-])c2)c1]

A solution of tert-butyl (3-{[3-(3-nitrophenyl)propanoyl]amino}phenyl)carbamate (0.10 g, 0.26 mmol) in tetrahydrofuran (2 mL) was treated slowly with a solution of 1 M borane in tetrahydrofuran (0.54 mL, 0.54 mmol) and refluxed for 2 h. The reaction mixture was cooled and treated with 6 M HCl (2 mL) and stirred at 20° C. for 1 h. The reaction mixture was concentrated and purified by preparative LCMS to give the desired product (41 mg, 41%) as a solid. LCMS for $C_{15}H_{18}N_3O_2$ (M+H)$^+$: m/z=272.0.

Step C: N-(2,5-Dichloropyrimidin-4-yl)-N'-[3-(3-nitrophenyl)propyl]benzene-1,3-diamine trifluoroacetate

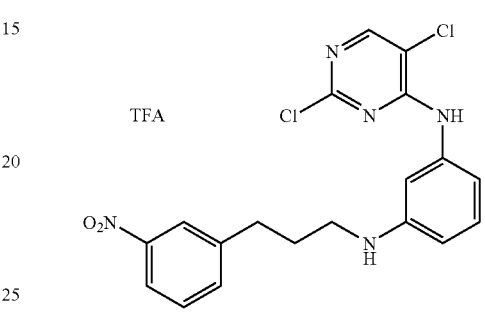

The desired compound was prepared according to the procedure of Example D2, step C, using N-[3-(3-nitrophenyl)propyl]benzene-1,3-diamine trifluoroacetate as the starting material in 55% yield. LCMS for $C_{19}H_{18}Cl_2N_5O_2$ (M+H)$^+$: m/z=418.0, 419.9.

Step D: N-[3-(3-Aminophenyl)propyl]-N'-(2,5-dichloropyrimidin-4-yl)benzene-1,3-diamine

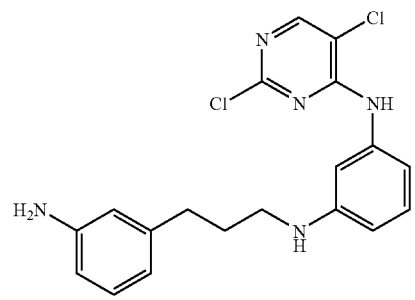

The desired compound was prepared according to the procedure of Example D72, step C, using N-(2,5-dichloropyrimidin-4-yl)-N'-[3-(3-nitrophenyl)propyl]benzene-1,3-diamine trifluoroacetate as the starting material and used in the next step without further purification.

Step E: 6-Chloro-2,4,8,14,24-pentaazatetracyclo[16.3.1.1(3,7).1(9,13)]tetracosa-1(22), 3(24),4,6,9(23),10,12,18,20-nonaene bis(trifluoroacetate)

The desired compound was prepared according to the procedure of Example D2, step D, using N-[3-(3-aminophenyl)propyl]-N'-(2,5-dichloropyrimidin-4-yl)benzene-1,3-diamine as the starting material in 12% yield (2 steps). LCMS for $C_{19}H_{19}ClN_5$ (M+H)$^+$: m/z=352.0.

Example D76

6-Chloro-2,4,8,17,24-pentaazatetracyclo[16.3.1.1(3,7).1(9,13)]tetracosa-1(22),3(24),4,6,9(23),10,12,18,20-nonaen-16-one trifluoroacetate

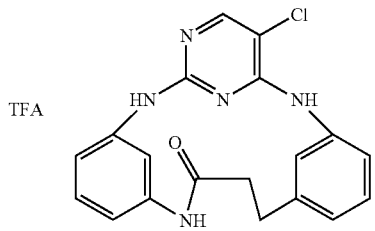 [SMILES: "TFA" ; O=C1CCc2cccc(c2)Nc2nc(ncc2Cl)Nc2cccc(c2)N1]

Step A: tert-Butyl (3-{[3-(3-aminophenyl)propanoyl]amino}phenyl)carbamate

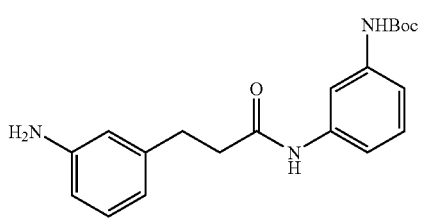

The desired compound was prepared according to the procedure of Example D2, step B, using tert-butyl (3-{[3-(3-nitrophenyl)propanoyl]amino}phenyl)carbamate as the starting material in 97% yield. LCMS for $C_{20}H_{26}N_3O_3$ (M+H)$^+$: m/z=356.0.

Step B: tert-Butyl {3-[(3-{3-[(2,5-dichloropyrimidin-4-yl)amino]phenyl}propanoyl)amino]phenyl}carbamate

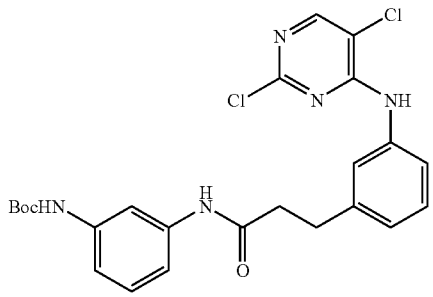 [SMILES: CC(C)(C)OC(=O)Nc1cccc(NC(=O)CCc2cccc(Nc3nc(Cl)ncc3Cl)c2)c1]

The desired compound was prepared according to the procedure of Example D2, step C, using tert-butyl (3-{[3-(3-aminophenyl)propanoyl]amino}phenyl)carbamate as the starting material in 85% yield. LCMS for $C_{20}H_{18}Cl_2N_5O_3$ ([M-(t-Bu)+H]+H)$^+$: m/z=445.9, 448.0.

Step C: 6-Chloro-2,4,8,17,24-pentaazatetracyclo[16.3.1.1(3,7).1(9,13)]tetracosa-1(22), 3(24),4,6,9(23),10,12,18,20-nonaen-16-one trifluoroacetate The desired compound was prepared according to the procedure of Example D32, step F, using tert-butyl {3-[(3-{3-[(2,5-dichloropyrimidin-4-yl)amino]phenyl}propanoyl)amino]phenyl}carbamate as the starting material in 11% yield. LCMS for $C_{19}H_{17}ClN_5O$ (M+H)$^+$: m/z=366.0.

Example D77

6-Chloro-2,4,8,17,24-pentaazatetracyclo[16.3.1.1(3,7).1(9,13)]tetracosa-1(22),3(24),4,6,9(23),10,12,18,20-nonaene bis(trifluoroacetate)

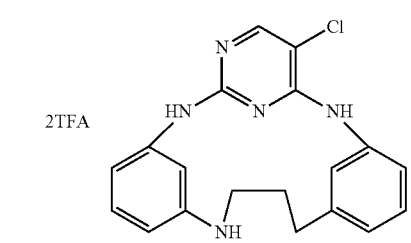 [SMILES: "2TFA" ; Clc1cnc2nc1Nc1cccc(c1)CCCNc1cccc(c1)N2]

Step A: tert-Butyl {3-[(3-{3-[(2,5-dichloropyrimidin-4-yl)amino]phenyl}propyl)amino]phenyl}carbamate

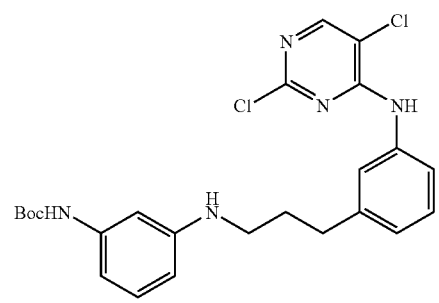

The desired compound was prepared according to the procedure of Example D73, step F, using tert-butyl {3-[(3-{3-[(2,5-dichloropyrimidin-4-yl)amino]phenyl}propanoyl)amino]phenyl}carbamate as the starting material and used in the next step without further purification.

Step B: 6-Chloro-2,4,8,17,24-pentaazatetracyclo[16.3.1.1(3,7).1(9,13)]tetracosa-1(22),3(24),4,6,9(23),10,12,18,20-nonaene bis(trifluoroacetate)

The desired compound was prepared according to the procedure of Example D2, step D, using tert-butyl {3-[(3-{3-[(2,5-dichloropyrimidin-4-yl)amino]phenyl}propyl)amino]phenyl}carbamate as the starting material in 6% yield (2 steps). LCMS for $C_{19}H_{19}ClN_5$ (M+H)$^+$: m/z=352.0. $^1$H NMR (400 MHz, DMSO-d$_6$): δ 9.52 (s, 1H), 8.94 (s, 1H), 8.20 (s, 1H), 7.82 (s, 1H), 7.46 (s, 1H), 7.27 (dd, J=7.8, 7.6 Hz, 1H), 7.17 (d, J=8.8 Hz, 1H), 7.02-6.96 (m, 2H), 6.57 (br s, 1H), 6.40 (br s, 1H), 2.88-2.84 (m, 2H), 2.73-2.69 (m, 2H), 1.97-1.86 (m, 2H).

Example D78

6-Chloro-2,4,8,16,23-pentaazatetracyclo[15.3.1.1(3,7).1(9,13)]tricosa-1(21), 3(23),4,6,9(22),10,12,17,19-nonaene bis(trifluoroacetate)

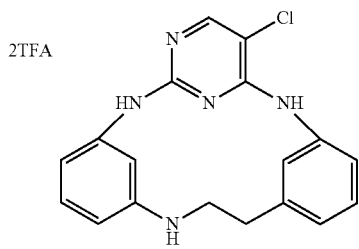 [SMILES: "2TFA" ; Clc1cnc2nc1Nc1cccc(c1)CCNc1cccc(c1)N2]

A solution of tert-butyl {3-[({3-[(2,5-dichloropyrimidin-4-yl)amino]phenyl}acetyl)amino]phenyl}carbamate (85 mg, 0.17 mmol) in tetrahydrofuran (1.3 mL) was treated with 1 M borane in tetrahydrofuran (0.37 mL, 0.37 mmol) slowly and refluxed for 1 h. The reaction mixture was concentrated and purified by preparative LCMS to give the uncyclized intermediate. This material, upon concentration of the acidic preparative LCMS fractions, spontaneously cyclized to the desired product (20 mg, 20%) which was purified by preparative LCMS. LCMS for $C_{18}H_{17}ClN_5$ $(M+H)^+$: m/z=338.0.

Example D79

6-Chloro-2,4,8,16,23-pentaazatetracyclo[15.3.1.1(3,7).1(9,13)]tricosa-1(21), 3(23),4,6,9(22),10,12,17,19-nonaene bis(trifluoroacetate)

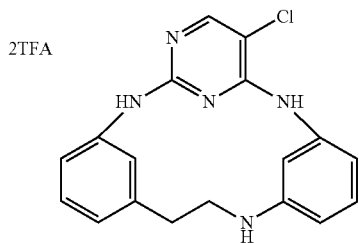 [SMILES: "2TFA" ; Clc1cnc2nc1Nc1cccc(c1)NCCc1cccc(c1)N2]

Step A: tert-Butyl (3-{[(3-nitrophenyl)acetyl]amino}phenyl)carbamate

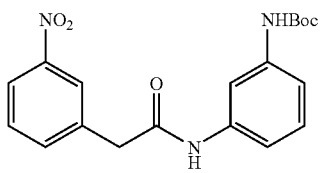 [SMILES: CC(C)(C)OC(=O)Nc1cccc(NC(=O)Cc2cccc([N+](=O)[O-])c2)c1]

The desired compound was prepared according to the procedure of Example D75, step A, using (3-nitrophenyl)acetic acid as the starting material in quantitative yield. LCMS for $C_{15}H_{14}N_3O_5$ $([M-(t-Bu)+H]+H)^+$: m/z=316.0.

Step B: N-(3-Aminophenyl)-2-(3-nitrophenyl)acetamide trifluoroacetate

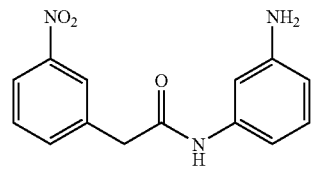

The desired compound was prepared according to the procedure of Example D34, step A, using tert-butyl (3-{[(3-nitrophenyl)acetyl]amino}phenyl)carbamate as the starting material and used in the next step without further purification.

Step C: N-{3-[(2,5-Dichloropyrimidin-4-yl)amino]phenyl}-2-(3-nitrophenyl)acetamide

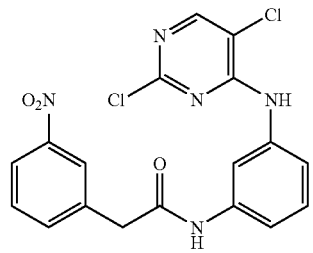 [SMILES: O=C(Cc1cccc([N+](=O)[O-])c1)Nc1cccc(Nc2nc(Cl)ncc2Cl)c1]

The desired compound was prepared according to the procedure of Example D2, step C, using N-(3-aminophenyl)-2-(3-nitrophenyl)acetamide trifluoroacetate as the starting material in 72% yield (2 steps). LCMS for $C_{18}H_{14}Cl_2N_5O_3$ $(M+H)^+$: m/z=417.9, 419.9.

Step D: N-(2,5-Dichloropyrimidin-4-yl)-N'-[2-(3-nitrophenyl)ethyl]benzene-1,3-diamine

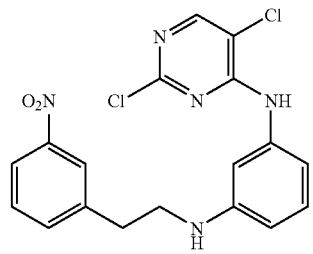 [SMILES: O=[N+]([O-])c1cccc(CCNc2cccc(Nc3nc(Cl)ncc3Cl)c2)c1]

The desired compound was prepared according to the procedure of Example D73, step F, using N-{3-[(2,5-dichloropyrimidin-4-yl)amino]phenyl}-2-(3-nitrophenyl)acetamide as the starting material in 23% yield. LCMS for $C_{18}H_{16}Cl_2N_5O_2$ (M+H)+: m/z=403.9, 405.9

Step E: N-[2-(3-Aminophenyl)ethyl]-N'-(2,5-dichloropyrimidin-4-yl)benzene-1,3-diamine

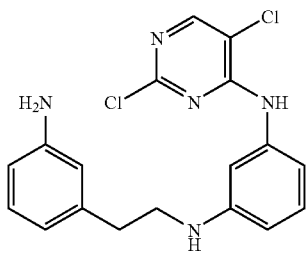 [SMILES: Nc1cccc(CCNc2cccc(Nc3nc(Cl)ncc3Cl)c2)c1]

The desired compound was prepared according to the procedure of Example D72, step C, using N-(2,5-dichloropyrimidin-4-yl)-N'-[2-(3-nitrophenyl)ethyl]benzene-1,3-diamine as the starting material and used in the next step without further purification.

Step F: 6-Chloro-2,4,8,16,23-pentaazatetracyclo [15.3.1.1(3,7).1(9,13)]tricosa-1(21),3(23),4,6,9(22), 10,12,17,19-nonaene bis(trifluoroacetate)

The desired compound was prepared according to the procedure of Example D2, step D, using N-[2-(3-aminophenyl)ethyl]-N'-(2,5-dichloropyrimidin-4-yl)benzene-1,3-diamine as the starting material in 10% yield (2 steps). LCMS for $C_{18}H_{17}ClN_5$ (M+H)+: m/z=338.0. $^1$H NMR (300 MHz, CD$_3$OD): δ 8.18 (s, 1H), 8.13 (s, 1H), 7.94 (s, 1H), 7.55 (dd, J=8.2, 8.2 Hz, 1H), 7.40-7.29 (m, 2H), 7.23-7.16 (m, 2H), 7.05-7.03 (m, 1H), 3.89-3.85 (m, 2H), 2.81-2.77 (m, 2H).

Example D80

6-Chloro-14-thia-2,4,8,17,24-pentaazatetracyclo [16.3.1.1(3,7).1(9,13)]tetracosa-1(22),3(24),4,6,9 (23),10,12,18,20-nonaene bis(trifluoroacetate)

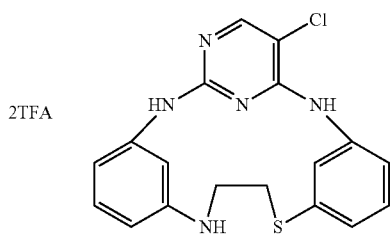 [SMILES: "2TFA" ; Clc1cnc2nc1Nc1cccc(c1)SCCNc1cccc(c1)N2]

Step A: 2-({3-[(2,5-Dichloropyrimidin-4-yl)amino] phenyl}thio)ethanol

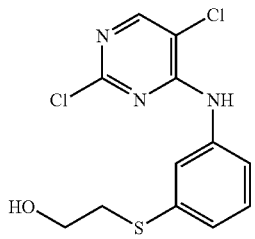

A solution of sodium methoxide (2.4 g, 44 mmol) in N,N-dimethylformamide (80 mL) was treated with 3-aminobenzenethiol (4.6 g, 37 mmol) and stirred at 20° C. for 15 min. The reaction mixture was cooled to 0° C., treated with a solution of 2-bromoethanol (3.4 mL, 48 mmol) in N,N-dimethylformamide (10 mL), and stirred at 0° C. for 15 min and at 20° C. for 1 h. The reaction mixture was treated with potassium carbonate (10 g, 74 mmol) followed by 2,4,5-trichloropyrimidine (5.5 mL, 48 mmol), heated at 60° C. for 1 h, and stirred at 20° C. for 16 h. The reaction mixture was diluted with 4:1 water/brine (1 L) and extracted with ethyl acetate (2×250 mL). The combined organic layers were washed with water (3×300 mL) and brine, dried over anhydrous sodium sulfate, filtered, and evaporated to a crude brown oil. This material was purified by flash column chromatography to give the desired product (7.8 g, 68%) as a solid after lyophilization. LCMS for $C_{12}H_{12}Cl_2N_3OS$ (M+H)+: m/z=315.9, 317.9.

Step B: 2-({3-[(2,5-Dichloropyrimidin-4-yl)amino] phenyl}thio)ethyl methanesulfonate

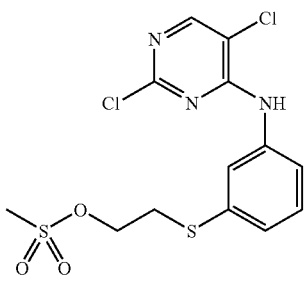 [SMILES: CS(=O)(=O)OCCSc1cccc(Nc2nc(Cl)ncc2Cl)c1]

The desired compound was prepared according to the procedure of Example D20, step A, using 2-({3-[(2,5-dichloropyrimidin-4-yl)amino]phenyl}thio)ethanol as the starting material and used in the next step without further purification.

Step C: tert-Butyl (3-{[2-({3-[(2,5-dichloropyrimidin-4-yl)amino]phenyl}thio)ethyl]amino}phenyl) carbamate

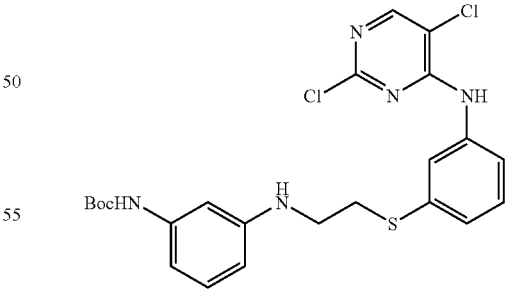

A solution of 2-({3-[(2,5-dichloropyrimidin-4-yl)amino] phenyl}thio)ethyl methanesulfonate (0.17 g, 0.43 mmol) in N,N-dimethylformamide (2 mL) was treated with potassium carbonate (0.15 g, 1.1 mmol) followed by tert-butyl (3-aminophenyl)carbamate (0.17 g, 0.81 mmol) and stirred at 20° C. for 16 h. The reaction mixture was purified by preparative LCMS to give the desired product (23 mg, 10% for 2 steps). LCMS for $C_{23}H_{26}Cl_2N_5O_2S$ (M+H)+: m/z=505.9, 508.0.

Step D: 6-Chloro-14-thia-2,4,8,17,24-pentaazatetra-
cyclo[16.3.1.1(3,7).1(9,13)]tetracosa-1(22),3(24),4,
6,9(23),10,12,18,20-nonaene bis(trifluoroacetate)

The desired compound was prepared according to the procedure of Example D2, step D, using tert-butyl (3-{[2-({3-[(2,5-dichloropyrimidin-4-yl)amino]phenyl}thio)ethyl]amino}phenyl)carbamate as the starting material in 37% yield. LCMS for $C_{18}H_{17}ClN_5S$ (M+H)$^+$: m/z=370.0. $^1$H NMR (400 MHz, DMSO-d$_6$): δ 9.41 (s, 1H), 8.84 (s, 1H), 8.21 (s, 1H), 8.05 (s, 1H), 7.32-7.26 (m, 3H), 7.20-7.17 (m, 1H), 6.89 (dd, J=8.0, 8.0 Hz, 1H), 6.40 (d, J=7.8 Hz, 1H), 6.18 (d, J=9.2 Hz, 1H), 3.11-3.07 (m, 2H), 2.98-2.94 (m, 2H).

Example D81

6-Chloro-17-oxa-14-thia-2,4,8,24-tetraazatetracyclo
[16.3.1.1(3,7).1(9,13)]tetracosa-1(22),3(24),4,6,9
(23),10,12,18,20-nonaene-19-carbonitrile trifluoroacetate

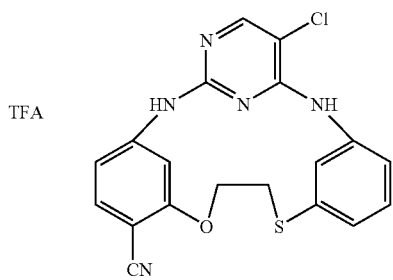 [SMILES: "TFA" ; N#Cc1ccc2cc1OCCSc1cccc(c1)Nc1nc(ncc1Cl)N2]

Step A: 2-{[2-({3-[(2,5-Dichloropyrimidin-4-yl)
amino]phenyl}thio)ethyl]amino}-4-nitrobenzonitrile
trifluoroacetate

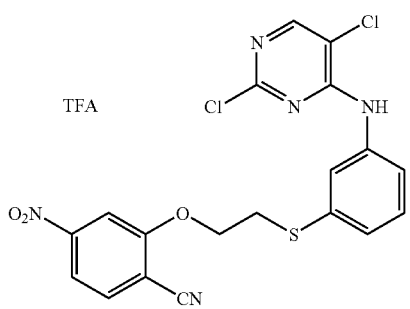 [SMILES: N#Cc1ccc([N+](=O)[O-])cc1OCCSc1cccc(Nc2nc(Cl)ncc2Cl)c1]

A solution of 2-({3-[(2,5-dichloropyrimidin-4-yl)amino]phenyl}thio)ethanol (0.2 g, 0.63 mmol) in dichloromethane (4.7 mL) was treated with N,N-diisopropylethylamine (0.22 mL, 1.3 mmol) followed by methanesulfonyl chloride (73 µL, 0.95 mmol) and stirred at 20° C. for 1 h. The reaction mixture was concentrated to give the intermediate mesylate which was diluted with N,N-dimethylformamide (2.4 mL), treated with sodium bromide (0.20 g, 1.9 mmol), and stirred at 70° C. for 2 h. The reaction mixture was diluted with ethyl acetate (100 mL) and washed with water and brine, dried over anhydrous sodium sulfate, filtered, and evaporated to a crude mixture of the intermediate bromide and chloride. This mixture was diluted with N,N-dimethylformamide (3 mL), treated with potassium carbonate (0.17 g, 1.3 mmol) followed by 2-hydroxy-4-nitrobenzonitrile (0.16 g, 0.95 mmol), and stirred at 50° C. for 16 h. An attempt to convert the remaining chloro intermediate into product with cesium carbonate (0.25 g, 0.77 mmol) at 80° C. for 6 h was unsuccessful and the chloro intermediate remained unreacted. The reaction mixture was diluted with ethyl acetate (100 mL) and washed with water and brine, dried over anhydrous sodium sulfate, filtered, and evaporated to a crude residue. Purification by preparative LCMS gave the desired product (0.12 g, 32%) as a solid. LCMS for $C_{19}H_{14}Cl_2N_5O_3S$ (M+H)$^+$: m/z=461.9, 463.9.

Step B: 4-Amino-2-[2-({3-[(2,5-dichloropyrimidin-
4-yl)amino]phenyl}thio)ethoxy]benzonitrile

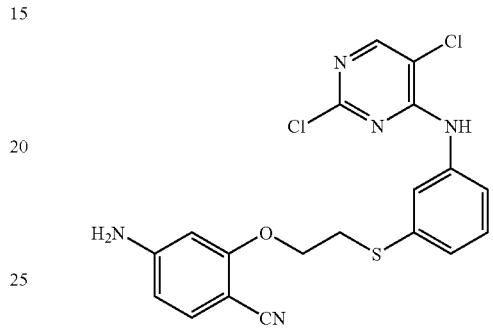

The desired compound was prepared according to the procedure of Example D72, step C, using 2-{[2-({3-[(2,5-dichloropyrimidin-4-yl)amino]phenyl}thio)ethyl]amino}-4-nitrobenzonitrile as the starting material and used in the next step without further purification.

Step C: 6-Chloro-17-oxa-14-thia-2,4,8,24-tetraaza-
tetracyclo[16.3.1.1(3,7).1(9,13)]tetracosa-1(22),3
(24),4,6,9(23),10,12,18,20-nonaene-19-carbonitrile
trifluoroacetate The desired compound was prepared according to the procedure of Example D32, step F, using 4-amino-2-[2-({3-[(2,5-dichloropyrimidin-4-yl)amino]phenyl}thio)ethoxy]benzonitrile as the starting material in 8% yield (2 steps). LCMS for $C_{19}H_{15}ClN_5OS$ (M+H)$^+$: m/z=395.9. $^1$H NMR (400 MHz, DMSO-d$_6$): δ 10.06 (s, 1H), 8.92 (s, 1H), 8.28 (s, 1H), 8.08 (s, 1H), 7.84 (d, J=1.6 Hz, 1H), 7.50 (d, J=8.6 Hz, 1H), 7.33-7.22 (m, 3H), 6.88 (dd, J=8.6, 1.8 Hz, 1H), 4.19-4.15 (m, 2H), 3.27-3.23 (m, 2H).

Example D82

6-Chloro-17-oxa-14-thia-2,4,8,24-tetraazatetracyclo
[16.3.1.1(3,7).1(9,13)]tetracosa-1(22),3(24),4,6,9
(23),10,12,18,20-nonaene-19-carbonitrile trifluoroacetate

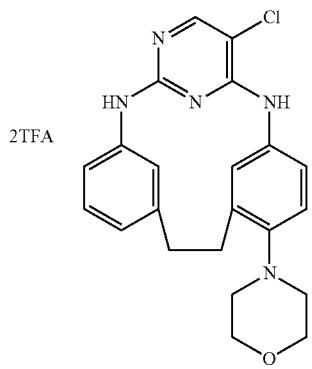 [SMILES: "2TFA" ; Clc1cnc2nc1Nc1ccc(N3CCOCC3)c(c1)CCc1cccc(c1)N2]

Step A: 4-(2-Bromo-4-nitrophenyl)morpholine

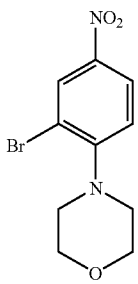

A solution of 2-bromo-1-fluoro-4-nitrobenzene (0.94 g, 4.3 mmol) in N,N-dimethylformamide (10 mL) was treated with potassium carbonate (1.5 g, 11 mmol) followed by morpholine (0.56 mL, 6.4 mmol) and stirred at 20° C. for 3 h. The reaction mixture was diluted with sodium bicarbonate and extracted with ethyl acetate. The organic layer was separated, dried over anhydrous sodium sulfate, filtered, and evaporated to give the desired product (1.0 g, quantitative) which was used without further purification.

Step B: tert-Butyl {3-[(2-morpholin-4-yl-5-nitrophenyl)ethynyl]phenyl}carbamate

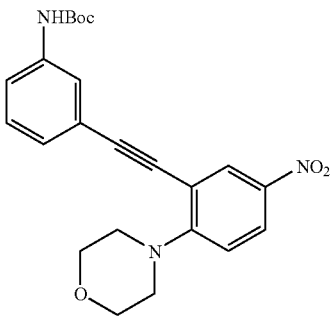 [SMILES: CC(C)(C)OC(=O)Nc1cccc(C#Cc2cc([N+](=O)[O-])ccc2N2CCOCC2)c1]

A solution of 4-(2-bromo-4-nitrophenyl)morpholine (0.27 g, 0.95 mmol), tert-butyl (3-ethynylphenyl)carbamate, and bis(triphenylphosphine)palladium(II) chloride (67 mg, 95 μmol) in N,N-dimethylformamide (4.4 mL) was treated with N,N-diisopropylethylamine (0.21 mL, 1.2 mmol) and stirred at 80° C. for 16 h. The reaction mixture was diluted with ethyl acetate, washed with brine, dried over anhydrous sodium sulfate, filtered, and evaporated to give a crude residue. This material was purified by flash column chromatography to give the desired product (0.28 g, 70%) as a solid. LCMS for $C_{23}H_{26}N_3O_5$ $(M+H)^+$: m/z=424.0.

Step C: tert-Butyl {3-[2-(5-amino-2-morpholin-4-ylphenyl)ethyl]phenyl}carbamate

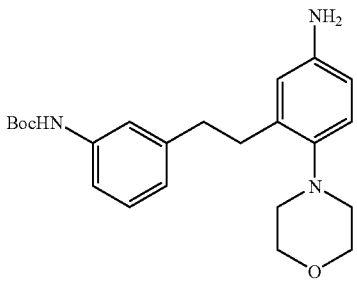 [SMILES: CC(C)(C)OC(=O)Nc1cccc(CCc2cc(N)ccc2N2CCOCC2)c1]

A solution of tert-butyl {3-[(2-morpholin-4-yl-5-nitrophenyl)ethynyl]phenyl}carbamate (0.33 g, 0.78 mmol) in methanol (20 mL) was degassed with nitrogen, treated with 10% palladium on carbon (wet Degussa type) (0.33 g, 100 wt %), degassed with nitrogen, and shaken under an atmosphere of hydrogen (50 psi) for 48 h. The reaction mixture was filtered over celite and the filtrate concentrated to give the desired product (0.29 g, 92%) which was used without further purification. LCMS for $C_{23}H_{32}N_3O_3$ $(M+H)^+$: m/z=398.1.

Step D: tert-Butyl [3-(2-{5-[(2,5-dichloropyrimidin-4-yl)amino]-2-morpholin-4-ylphenyl}ethyl)phenyl]carbamate

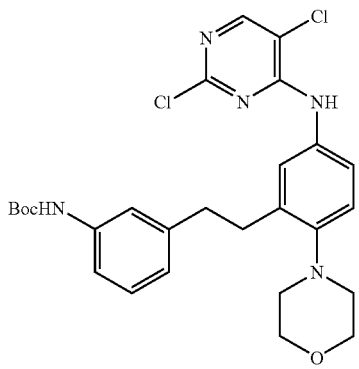 [SMILES: CC(C)(C)OC(=O)Nc1cccc(CCc2cc(Nc3nc(Cl)ncc3Cl)ccc2N2CCOCC2)c1]

The desired compound was prepared according to the procedure of Example D2, step C, using tert-butyl {3-[2-(5-amino-2-morpholin-4-ylphenyl)ethyl]phenyl}carbamate as the starting material in 80% yield. LCMS for $C_{27}H_{32}Cl_2N_5O_3$ $(M+H)^+$: m/z=544.0, 546.0.

Step E: 6-Chloro-17-oxa-14-thia-2,4,8,24-tetraazatetracyclo[16.3.1.1(3,7).1(9,13)]tetracosa-1(22),3(24),4,6,9(23),10,12,18,20-nonaene-19-carbonitrile trifluoroacetate The desired compound was prepared according to the procedure of Example B19, step F, using tert-butyl [3-(2-{5-[(2,5-dichloropyrimidin-4-yl)amino]-2-morpholin-4-ylphenyl}ethyl)phenyl]carbamate as the starting material in 50% yield. LCMS for $C_{22}H_{23}ClN_5O$ $(M+H)^+$: m/z=408.0. $^1H$ NMR (400 MHz, DMSO-$d_6$): δ 9.38 (s, 1H), 9.18 (s, 1H), 8.10 (s, 1H), 7.97 (s, 1H), 7.78 (d, J=2.1 Hz, 1H), 7.10-7.05 (m, 3H), 6.86 (dd, J=8.0, 1.0 Hz, 1H), 6.80 (d, J=7.6 Hz, 1H), 3.74-3.72 (m, 2H), 3.15 (s, 2H), 2.94 (s, 4H), 2.81-2.78 (m, 4H).

Example D83

6-Chloro-12-piperazin-1-yl-2,4,8,22-tetraazatetracyclo[14.3.1.1(3,7).1(9,13)]docosa-1(20),3(22),4,6,9(21),10,12,16,18-nonaene bis(trifluoroacetate)

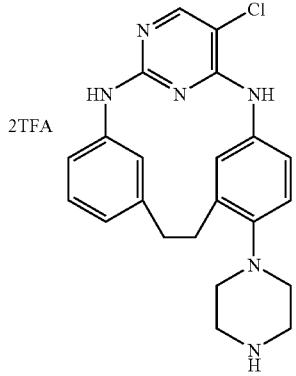 [SMILES: "2TFA" ; Clc1cnc2nc1Nc1ccc(N3CCNCC3)c(c1)CCc1cccc(c1)N2]

Step A: tert-Butyl 4-(2-bromo-4-nitrophenyl)piperazine-1-carboxylate

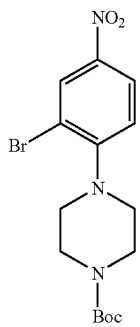

A solution of 2-bromo-1-fluoro-4-nitrobenzene (0.1 g, 0.45 mmol) and tert-butyl piperazine-1-carboxylate (85 mg, 0.45 mmol) in N,N-dimethylformamide (0.9 mL) was treated with potassium carbonate (94 mg, 0.68 mmol) and stirred at 20° C. for 23 h and at 60° C. for 3.5 h. The reaction mixture was diluted with water (10 mL) and ethyl acetate (20 mL). The organic layer was separated, washed with water (10 mL) and brine (10 mL), dried over anhydrous sodium sulfate, filtered, and evaporated to give a yellow oil. This material was purified by flash column chromatography to give the desired product (0.15 g, 87%) as a yellow solid. LCMS for $C_{15}H_{20}BrN_3O_4Na$ (M+Na)$^+$: m/z=407.9, 410.1.

Step B: 1-(2-Bromo-4-nitrophenyl)piperazine dihydrochloride

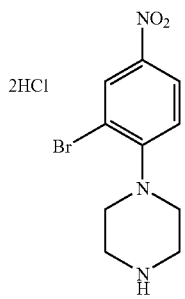

A solution of tert-butyl 4-(2-bromo-4-nitrophenyl)piperazine-1-carboxylate (2.3 g, 5.9 mmol) in dichloromethane (15 mL) was treated with 4 M HCl in 1,4-dioxane (15 mL, 59 mmol) and stirred at 20° C. for 3 h. The reaction mixture was concentrated, diluted with a minimal amount of methanol (~15 mL), and added dropwise to ether (300 mL) that was cooled 0° C. The solid that precipitated was collected by filtration and dried to give the desired product (1.9 g, 89%) which was used in the next step without further purification.

Step C: 2-(Trimethylsilyl)ethyl 4-(2-bromo-4-nitrophenyl)piperazine-1-carboxylate

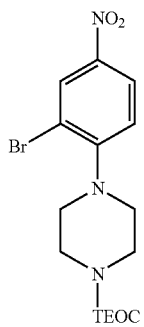

A solution of 1-(2-bromo-4-nitrophenyl)piperazine dihydrochloride (1.9 g, 5.8 mmol) in acetonitrile (50 mL) was treated with 1-({[2-(trimethylsilyl)ethoxy]carbonyl}oxy)pyrrolidine-2,5-dione (1.5 g, 5.9 mmol) followed by water (15 mL) and sodium carbonate (1.9 g, 18 mmol) and stirred at 20° C. for 6 h. The reaction mixture was diluted with ethyl acetate (400 mL) and washed with water and brine, dried over anhydrous sodium sulfate, filtered, and evaporated to give a residue. This material was purified by flash column chromatography to give the desired product (2.4 g, 87%) as a solid. [TEOC: (2-(trimethylsilyl)ethoxy)carbonyl]

Step D: 2-(Trimethylsilyl)ethyl 4-[2-({3-[(tert-butoxycarbonyl)amino]phenyl}ethynyl)-4-nitrophenyl]piperazine-1-carboxylate

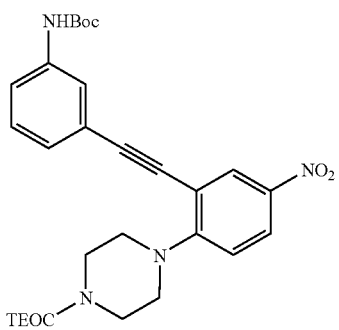

The desired compound was prepared according to the procedure of D82, step B, using 2-(trimethylsilyl)ethyl 4-(2-bromo-4-nitrophenyl)piperazine-1-carboxylate as the starting material in 94% yield. LCMS for $C_{29}H_{38}N_4O_6SiNa$ (M+Na)$^+$: m/z=589.1.

Step E: tert-Butyl {3-[2-(5-amino-2-morpholin-4-ylphenyl)ethyl]phenyl}carbamate

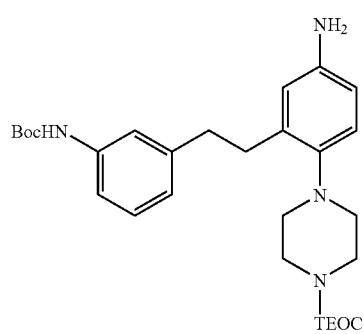

The desired compound was prepared according to the procedure of D82, step C, using 2-(trimethylsilyl)ethyl 4-[2-({3-[(tert-butoxycarbonyl)amino]phenyl}ethynyl)-4-nitrophenyl]piperazine-1-carboxylate as the starting material in 97% yield. LCMS for $C_{29}H_{45}N_4O_4Si$ (M+H)$^+$: m/z=541.2.

Step F: 2-(Trimethylsilyl)ethyl 4-{2-(2-{3-[(tert-butoxycarbonyl)amino]phenyl}ethyl)-4-[(2,5-dichloropyrimidin-4-yl)amino]phenyl}piperazine-1-carboxylate

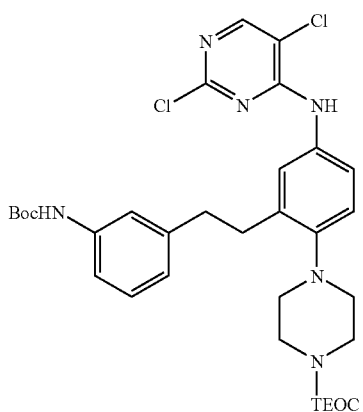

The desired compound was prepared according to the procedure of Example D2, step C, using tert-butyl {3-[2-(5-amino-2-morpholin-4-ylphenyl)ethyl]phenyl}carbamate as the starting material in 79% yield. LCMS for $C_{33}H_{45}Cl_2N_6O_4Si$ (M+H)$^+$: m/z=687.0, 689.0.

Step G: 6-Chloro-12-piperazin-1-yl-2,4,8,22-tetraazatetracyclo[14.3.1.1(3,7).1(9,13)]docosa-1(20),3(22),4,6,9(21),10,12,16,18-nonaene bis(trifluoroacetate)

The desired compound was prepared according to the procedure of Example D32, step F, using 2-(trimethylsilyl)ethyl 4-{2-(2-{3-[(tert-butoxycarbonyl)amino]phenyl}ethyl)-4-[(2,5-dichloropyrimidin-4-yl)amino]phenyl}piperazine-1-carboxylate as the starting material in 55% yield. LCMS for $C_{22}H_{24}ClN_6$ (M+H)$^+$: m/z=407.0. $^1$H NMR (400 MHz, DMSO-d$_6$): δ 9.41 (s, 1H), 9.18 (s, 1H), 8.71 (br s, 2H), 8.11 (s, 1H), 7.97 (s, 1H), 7.81 (s, 1H), 7.11-7.07 (m, 3H), 6.88-6.85 (m, 1H), 6.80 (d, J=7.6 Hz, 1H), 3.25 (br s, 4H), 3.00-2.97 (m, 4H), 2.93 (s, 4H).

Example D84

N-(tert-Butyl)-4-[6-chloro-2,4,8,22-tetraazatetracyclo[14.3.1.1(3,7).1(9,13)]docosa-1(20),3(22),4,6,9(21),10,12,16,18-nonaen-12-yl]piperazine-1-carboxamide bis(trifluoroacetate)

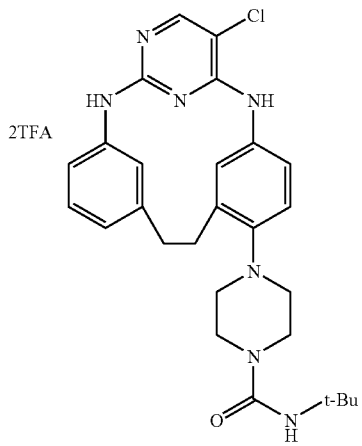 [SMILES: "2TFA" ; CC(C)(C)NC(=O)N1CCN(c2ccc3cc2CCc2cccc(c2)Nc2ncc(Cl)c(n2)N3)CC1]

The desired compound was prepared according to the procedure of Example D41 using 6-chloro-12-piperazin-1-yl-2,4,8,22-tetraazatetracyclo[14.3.1.1(3,7).1(9,13)]docosa-1(20),3(22),4,6,9(21),10,12,16,18-nonaene bis(trifluoroacetate) as the starting material in 46% yield. LCMS for $C_{27}H_{33}ClN_7O$ (M+H)$^+$: m/z=506.1. $^1$H NMR (400 MHz, DMSO-d$_6$): δ 9.48 (s, 1H), 9.33 (br s, 1H), 8.12 (s, 1H), 7.94 (s, 1H), 7.76 (d, J=1.6 Hz, 1H), 7.09-7.03 (m, 3H), 6.87-6.80 (m, 2H), 5.84 (s, 1H), 3.40 (br s, 4H), 2.95 (s, 4H), 2.75-2.73 (m, 4H), 1.26 (s, 9H).

Example D85

12-(4-Acetylpiperazin-1-yl)-6-chloro-2,4,8,22-tetraazatetracyclo[14.3.1.1(3,7).1(9,13)]docosa-1(20),3(22),4,6,9(21),10,12,16,18-nonaene bis(trifluoroacetate)

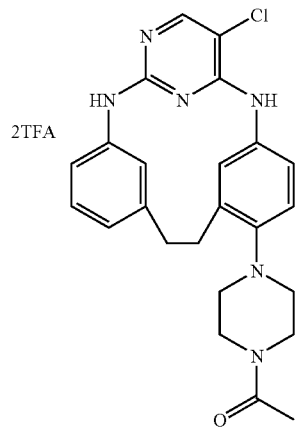 [SMILES: "2TFA" ; CC(=O)N1CCN(c2ccc3cc2CCc2cccc(c2)Nc2ncc(Cl)c(n2)N3)CC1]

A solution of 6-chloro-12-piperazin-1-yl-2,4,8,22-tetraazatetracyclo[14.3.1.1(3,7).1(9,13)]docosa-1(20),3(22),4,6,9(21),10,12,16,18-nonaene bis(trifluoroacetate) (20 mg, 32 μmol) and N,N-diisopropylethylamine (27 μL, 0.16 mmol) in tetrahydrofuran (0.5 mL) was treated with acetic anhydride (15 μL, 0.16 mmol) and stirred at 20° C. for 16 h. The reaction mixture was treated with 2 M sodium hydroxide (0.16 mL, 0.32 mmol) and stirred at 20° C. for 16 h to remove the undesired acetamide. The reaction mixture was purified by preparative LCMS to give the desired product (10 mg, 47%) as a solid. LCMS for $C_{24}H_{26}ClN_6O$ (M+H)$^+$: m/z=449.0.

Example D86

4-[6-Chloro-2,4,8,22-tetraazatetracyclo[14.3.1.1(3,7).1(9,13)]docosa-1(20),3(22),4,6,9(21),10,12,16,18-nonaen-12-yl]-1,1-dimethylpiperazin-1-ium bis(trifluoroacetate)

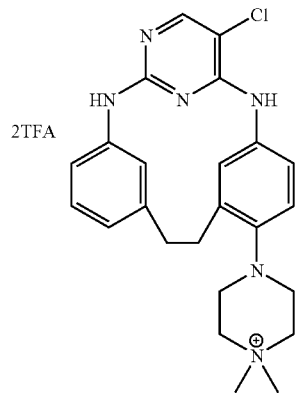 [SMILES: "2TFA" ; C[N+]1(C)CCN(c2ccc3cc2CCc2cccc(c2)Nc2ncc(Cl)c(n2)N3)CC1]

A solution of 6-chloro-12-piperazin-1-yl-2,4,8,22-tetraazatetracyclo[14.3.1.1(3,7).1(9,13)]docosa-1(20),3(22),4,6,9(21),10,12,16,18-nonaene bis(trifluoroacetate) (20 mg, 32 μmol) and N,N-diisopropylethylamine (27 μL, 0.16 mmol) in dichloromethane (0.3 mL) was treated with methyl iodide (10 μL, 0.16 mmol) and stirred for 16 h. The reaction mixture was purified by preparative LCMS to give the desired product (15 mg, 72%) as a solid. LCMS for $C_{24}H_{28}ClN_6$ (M)$^+$: m/z=435.1. $^1$H NMR (400 MHz, DMSO-$d_6$): δ 9.41 (s, 1H), 9.17 (s, 1H), 8.11 (s, 1H), 7.98 (s, 1H), 7.81 (d, J=2.3 Hz, 1H), 7.30 (d, J=8.6 Hz, 1H), 7.11-7.07 (m, 2H), 6.87 (d, J=9.2 Hz, 1H), 6.79 (d, J=7.4 Hz, 1H), 3.55-3.53 (m, 4H), 3.22 (s, 6H), 3.15 (br s, 4H), 2.95-2.90 (m, 4H).

Example D87

4-[6-Chloro-2,4,8,22-tetraazatetracyclo[14.3.1.1(3,7).1(9,13)]docosa-1(20),3(22),4,6,9(21),10,12,16,18-nonaen-12-yl]piperazine-1-carboxamide bis(trifluoroacetate)

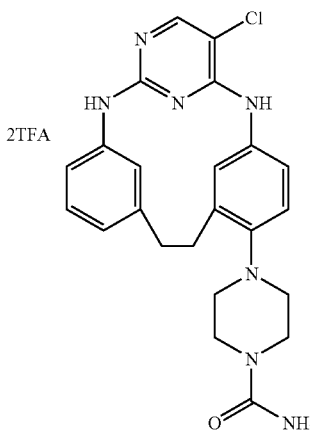

A solution of N-(tert-butyl)-4-[6-chloro-2,4,8,22-tetraazatetracyclo[14.3.1.1(3,7).1(9,13)]docosa-1(20),3(22),4,6,9(21),10,12,16,18-nonaen-12-yl]piperazine-1-carboxamide bis(trifluoroacetate) (12 mg, 16 μmol) in trifluoroacetic acid (1 mL) was stirred at 20° C. for 4 h. The reaction mixture was purified by preparative LCMS to give the desired product (8 mg, 72%) as a solid. LCMS for $C_{23}H_{25}ClN_7O$ (M+H)$^+$: m/z=450.0. $^1$H NMR (300 MHz, CD$_3$OD): δ 8.09 (s, 1H), 7.74-7.69 (m, 2H), 7.22-7.11 (m, 2H), 7.04-7.00 (m, 2H), 6.87 (d, J=7.9 Hz, 1H), 3.60 (br s, 4H), 3.14 (s, 4H), 2.89-2.87 (m, 4H).

Example D88

1-[6-Chloro-2,4,8,22-tetraazatetracyclo[14.3.1.1(3,7). 1(9,13)]docosa-1(20),3(22),4,6,9(21),10,12,16,18-nonaen-12-yl]pyrrolidin-3-amine tris(trifluoroacetate)

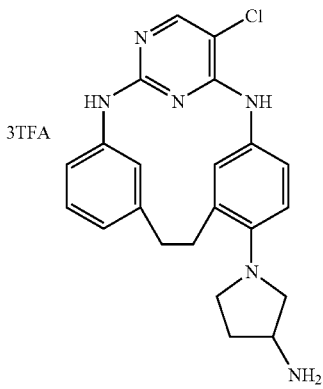 [SMILES: "3TFA" ; NC1CCN(c2ccc3cc2CCc2cccc(c2)Nc2ncc(Cl)c(n2)N3)C1]

Step A: tert-Butyl [1-(2-bromo-4-nitrophenyl)pyrrolidin-3-yl]carbamate

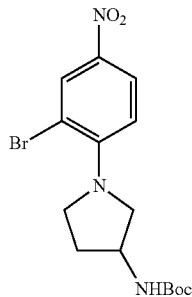 [SMILES: CC(C)(C)OC(=O)NC1CCN(c2ccc([N+](=O)[O-])cc2Br)C1]

The desired compound was prepared according to the procedure of Example D83, step A, using tert-butyl pyrrolidin-3-ylcarbamate as the starting material in 93% yield. LCMS for $C_{15}H_{21}BrN_3O_4$ (M+H)$^+$: m/z=385.9, 387.9.

Step B: 1-(2-Bromo-4-nitrophenyl)pyrrolidin-3-amine dihydrochloride

The desired compound was prepared according to the procedure of Example D83, step B, using tert-butyl [1-(2-bromo-4-nitrophenyl)pyrrolidin-3-yl]carbamate as the starting material in quantitative yield.

Step C: 2-(Trimethylsilyl)ethyl [1-(2-bromo-4-nitrophenyl)pyrrolidin-3-yl]carbamate The desired compound was prepared according to the procedure of Example D83, step C, using 1-(2-bromo-4-nitrophenyl)pyrrolidin-3-amine dihydrochloride as the starting material in 91% yield. LCMS for $C_{16}H_{25}BrN_3O_4Si$ (M+H)+: m/z=429.9, 431.9.

Step D: 2-(Trimethylsilyl)ethyl {1-[2-({3-[(tert-butoxycarbonyl)amino]phenyl}ethynyl)-4-nitrophenyl]pyrrolidin-3-yl}carbamate

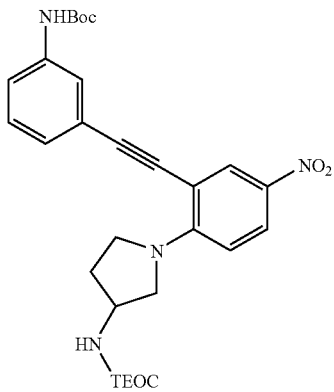

The desired compound was prepared according to the procedure of Example A11, step C, using 2-(trimethylsilyl)ethyl [1-(2-bromo-4-nitrophenyl)pyrrolidin-3-yl]carbamate and tert-butyl (3-ethynylphenyl)carbamate as the starting materials in 91% yield. LCMS for $C_{29}H_{39}N_4O_6Si$ (M+H)+: m/z=567.2.

Step E: 2-(Trimethylsilyl)ethyl {1-[4-amino-2-(2-{3-[(tert-butoxycarbonyl)amino]phenyl}ethyl)phenyl]pyrrolidin-3-yl}carbamate

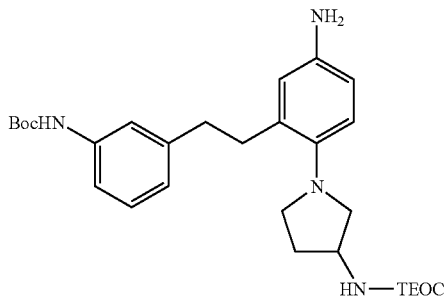

The desired compound was prepared according to the procedure of Example D7, step B, using 2-(trimethylsilyl)ethyl {1-[2-({3-[(tert-butoxycarbonyl)amino]phenyl}ethynyl)-4-nitrophenyl]pyrrolidin-3-yl}carbamate as the starting material in 84% yield. LCMS for $C_{29}H_{45}N_4O_4Si$ (M+H)+: m/z=541.2.

Step F: 2-(Trimethylsilyl)ethyl (1-{2-(2-{3-[(tert-butoxycarbonyl)amino]phenyl}ethyl)-4-[(2,5-dichloropyrimidin-4-yl)amino]phenyl}pyrrolidin-3-yl)carbamate

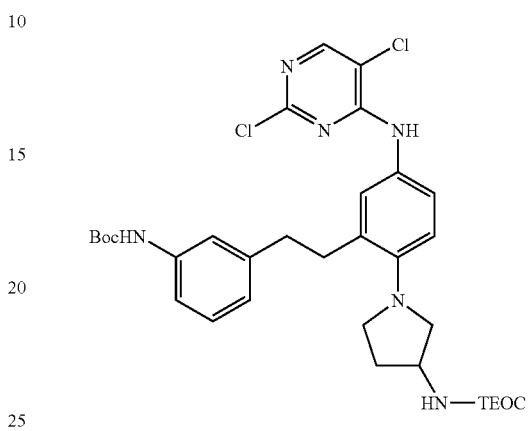

The desired compound was prepared according to the procedure of Example D2, step C, using 2-(trimethylsilyl)ethyl {1-[4-amino-2-(2-{3-[(tert-butoxycarbonyl)amino]phenyl}ethyl)phenyl]pyrrolidin-3-yl}carbamate as the starting material in 86% yield. LCMS for $C_{33}H_{45}Cl_2N_6O_4Si$ (M+H)+: m/z=687.1, 689.1.

Step G: 1-[6-Chloro-2,4,8,22-tetraazatetracyclo[14.3.1.1(3,7).1(9,13)]docosa-1(20),3(22),4,6,9(21),10,12,16,18-nonaen-12-yl]pyrrolidin-3-amine tris(trifluoroacetate)

The desired compound was prepared according to the procedure of Example D32, step F, using 2-(trimethylsilyl)ethyl (1-{2-(2-{3-[(tert-butoxycarbonyl)amino]phenyl}ethyl)-4-[(2,5-dichloropyrimidin-4-yl)amino]phenyl}pyrrolidin-3-yl)carbamate as the starting material in 22% yield. LCMS for $C_{22}H_{24}ClN_6$ (M+H)+: m/z=407.0.

Example D89

4-[6-Chloro-2,4,8,22-tetraazatetracyclo[14.3.1.1(3,7).1(9,13)]docosa-1(20),3(22),4,6,9(21),10,12,16,18-nonaen-12-yl]-N-(3-cyanophenyl)piperazine-1-carboxamide bis(trifluoroacetate)

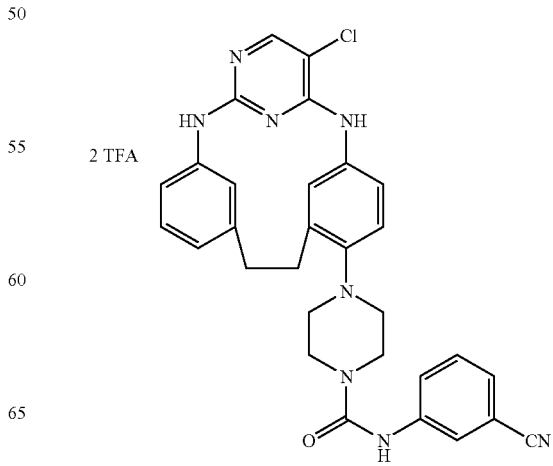

The desired compound was prepared according to the procedure of Example D41 using 6-chloro-12-piperazin-1-yl-2,4,8,22-tetraazatetracyclo[14.3.1.1(3,7).1(9,13)]docosa-1(20),3(22),4,6,9(21),10,12,16,18-nonaene bis(trifluoroacetate) and 3-isocyanatobenzonitrile as the starting materials in 35% yield. LCMS for $C_{30}H_{28}ClN_8O$ (M+H)$^+$: m/z=551.0. $^1$H NMR (300 MHz, DMSO-d$_6$): δ 9.49 (s, 1H), 9.34 (s, 1H), 8.95 (s, 1H), 8.14 (s, 1H), 7.97-7.96 (m, 2H), 7.79-7.75 (m, 2H), 7.48-7.37 (m, 2H), 7.13-7.03 (m, 3H), 6.89-6.82 (m, 2H), 3.63 (br s, 4H), 2.99 (s, 4H), 2.84 (brs, 4H).

Example D90

4-[6-Chloro-2,4,8,22-tetraazatetracyclo[14.3.1.1(3,7).1(9,13)]docosa-1(20),3(22),4,6,9(21),10,12,16,18-nonaen-12-yl]-N-[4-(trifluoromethyl)phenyl]piperazine-1-carboxamide bis(trifluoroacetate)

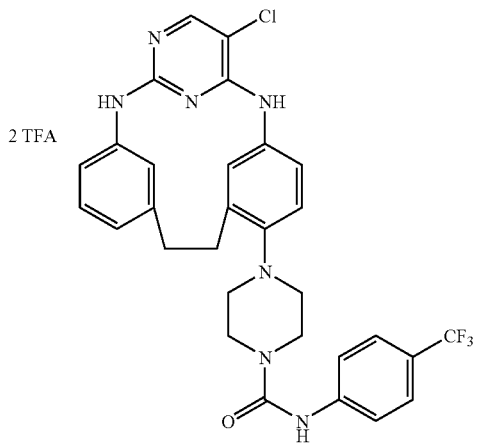 [SMILES: "2 TFA" ; O=C(Nc1ccc(C(F)(F)F)cc1)N1CCN(c2ccc3cc2CCc2cccc(c2)Nc2ncc(Cl)c(n2)N3)CC1]

The desired compound was prepared according to the procedure of Example D41 using 6-chloro-12-piperazin-1-yl-2,4,8,22-tetraazatetracyclo[14.3.1.1(3,7).1(9,13)]docosa-1(20),3(22),4,6,9(21),10,12,16,18-nonaene bis(trifluoroacetate) and 1-isocyanato-4-(trifluoromethyl)benzene as the starting materials in 41% yield. LCMS for $C_{30}H_{28}ClF_3N_7O$ (M+H)$^+$: m/z=594.0. $^1$H NMR (400 MHz, DMSO-d$_6$): δ 9.49 (s, 1H), 9.32 (br s, 1H), 9.00 (s, 1H), 8.13 (s, 1H), 7.96 (s, 1H), 7.79 (d, J=2.3 Hz, 1H), 7.72-7.70 (m, 2H), 7.60-7.57 (m, 2H), 7.12-7.03 (m, 3H), 6.88-6.82 (m, 2H), 3.64 (br s, 4H), 2.99 (s, 4H), 2.84 (br s, 4H).

Example D91

4-[6-Chloro-2,4,8,22-tetraazatetracyclo[14.3.1.1(3,7).1(9,13)]docosa-1(20),3(22),4,6,9(21),10,12,16,18-nonaen-12-yl]-N-[3-(trifluoromethyl)phenyl]piperazine-1-carboxamide bis(trifluoroacetate)

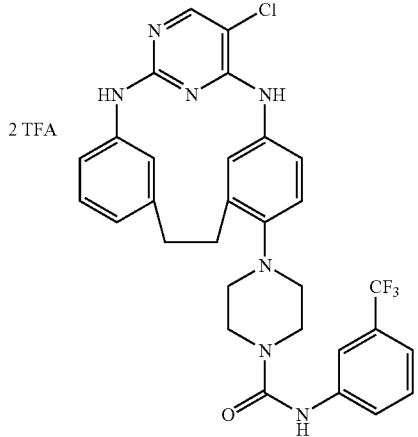 [SMILES: "2 TFA" ; O=C(Nc1cccc(C(F)(F)F)c1)N1CCN(c2ccc3cc2CCc2cccc(c2)Nc2ncc(Cl)c(n2)N3)CC1]

The desired compound was prepared according to the procedure of Example D41 using 6-chloro-12-piperazin-1-yl-2,4,8,22-tetraazatetracyclo[14.3.1.1(3,7).1(9,13)]docosa-1(20),3(22),4,6,9(21),10,12,16,18-nonaene bis(trifluoroacetate) and 1-isocyanato-3-(trifluoromethyl)benzene as the starting materials in 44% yield. LCMS for $C_{30}H_{28}ClF_3N_7O$ (M+H)$^+$: m/z=594.0. $^1$H NMR (400 MHz, DMSO-d$_6$): δ 9.67 (br s, 1H), 9.55 (br s, 1H), 8.94 (s, 1H), 8.18 (s, 1H), 7.95-7.92 (m, 2H), 7.77-7.75 (m, 2H), 7.47 (dd, J=8.0, 8.0 Hz, 1H), 7.27 (d, J=7.8 Hz, 1H), 7.14-7.02 (m, 3H), 6.88-6.85 (m, 2H), 3.64 (br s, 4H), 3.01 (s, 4H), 2.85-2.82 (m, 4H).

Example D92

4-[6-Chloro-2,4,8,22-tetraazatetracyclo[14.3.1.1(3,7).1(9,13)]docosa-1(20),3(22),4,6,9(21),10,12,16,18-nonaen-12-yl]-N-phenylpiperazine-1-carboxamide bis(trifluoroacetate)

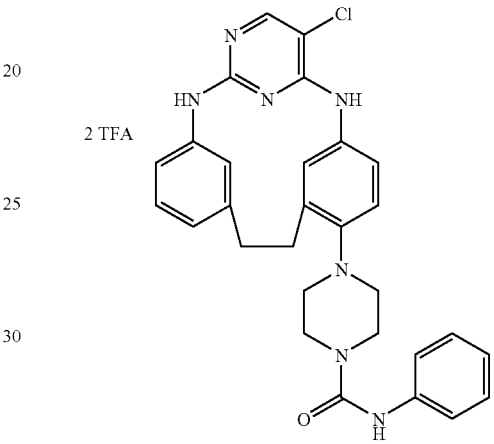

The desired compound was prepared according to the procedure of Example D41 using 6-chloro-12-piperazin-1-yl-2,4,8,22-tetraazatetracyclo[14.3.1.1(3,7).1(9,13)]docosa-1(20),3(22),4,6,9(21),10,12,16,18-nonaene bis(trifluoroacetate) and phenyl isocyanate as the starting materials in 39% yield. LCMS for $C_{29}H_{29}ClN_7O$ (M+H)$^+$: m/z=526.1. $^1$H NMR (400 MHz, DMSO-d$_6$): δ 9.51 (s, 1H), 9.35 (br s, 1H), 8.59 (s, 1H), 8.14 (s, 1H), 7.96 (s, 1H), 7.78 (s, 1H), 7.49-7.46 (m, 2H), 7.25-7.21 (m, 2H), 7.13-7.04 (m, 3H), 6.95-6.83 (m, 3H), 3.61 (br s, 4H), 2.99 (s, 4H), 2.84 (br s, 4H).

Example D93

4-[6-Chloro-2,4,8,22-tetraazatetracyclo[14.3.1.1(3,7).1(9,13)]docosa-1(20),3(22),4,6,9(21),10,12,16,18-nonaen-12-yl]-N-(4-cyanophenyl)piperazine-1-carboxamide bis(trifluoroacetate)

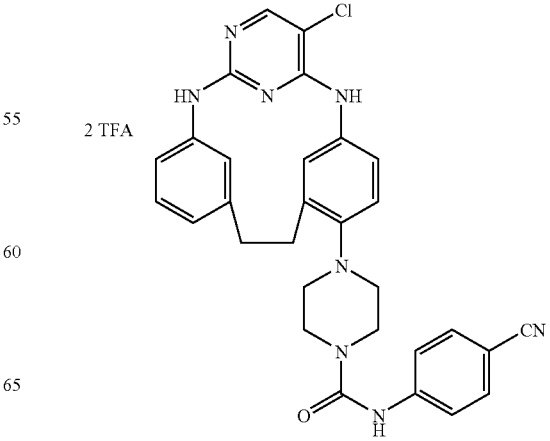

The desired compound was prepared according to the procedure of Example D41 using 6-chloro-12-piperazin-1-yl-2,4,8,22-tetraazatetracyclo[14.3.1.1(3,7).1(9,13)]docosa-1(20),3(22),4,6,9(21),10,12,16,18-nonaene bis(trifluoroacetate) and 4-isocyanatobenzonitrile as the starting materials in 38% yield. LCMS for $C_{30}H_{28}ClN_8O$ (M+H)$^+$: m/z=551.0. $^1$H NMR (400 MHz, DMSO-d$_6$): δ 9.46 (br s, 1H), 9.29 (br s, 1H), 9.09 (s, 1H), 8.13 (s, 1H), 7.97 (s, 1H), 7.79 (d, J=2.3 Hz, 1H), 7.69 (s, 4H), 7.12-7.03 (m, 3H), 6.88-6.82 (m, 2H), 3.64 (br s, 4H), 2.98 (s, 4H), 2.84 (brs, 4H).

Example D94

12-(4-Benzoylpiperazin-1-yl)-6-chloro-2,4,8,22-tetraazatetracyclo[14.3.1.1(3,7).1(9,13)]docosa-1(20),3(22),4,6,9(21),10,12,16,18-nonaene bis(trifluoroacetate)

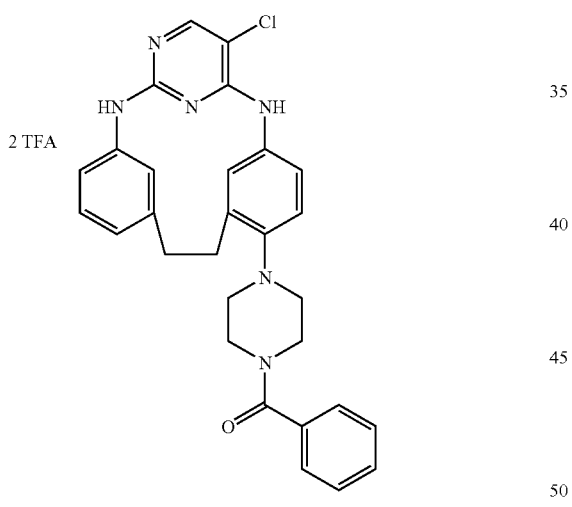

A solution of 6-chloro-12-piperazin-1-yl-2,4,8,22-tetraazatetracyclo[14.3.1.1(3,7).1(9,13)]docosa-1(20),3(22),4,6,9(21),10,12,16,18-nonaene bis(trifluoroacetate) (30 mg, 47 µmol) and N,N-diisopropylethylamine (41 µL, 0.24 mmol) in dichloromethane was treated with benzoyl chloride (11 µL, 95 µmol) and stirred for 16 h. The reaction mixture was purified by preparative LCMS to give the desired product (14 mg, 40%) as a solid. LCMS for $C_{29}H_{27}ClN_6O$ (M+H)$^+$: m/z=511.1. $^1$H NMR (400 MHz, DMSO-d$_6$): δ 9.54 (br s, 1H), 9.38 (br s, 1H), 8.14 (s, 1H), 7.94 (s, 1H), 7.77 (d, J=2.3 Hz, 1H), 7.47-7.43 (m, 4H), 7.12-7.02 (m, 3H), 6.87-6.82 (m, 2H), 3.79 (br s, 2H), 3.49 (br s, 2H), 2.97 (s, 4H), 2.87-2.79 (m, 4H).

Example D95

4-({4-[6-Chloro-2,4,8,22-tetraazatetracyclo[14.3.1.1(3,7).1(9,13)]docosa-1(20),3(22),4,6,9(21),10,12,16,18-nonaen-12-yl]piperazin-1-yl}carbonyl)benzonitrile bis(trifluoroacetate)

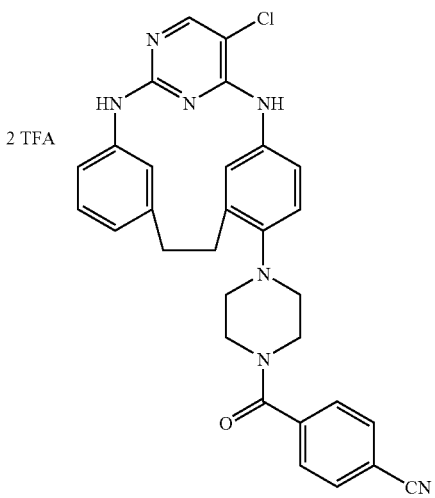 [SMILES: "2 TFA" ; N#Cc1ccc(C(=O)N2CCN(c3ccc4cc3CCc3cccc(c3)Nc3ncc(Cl)c(n3)N4)CC2)cc1]

The desired compound was prepared according to the procedure of Example D94 using 4-cyanobenzoyl chloride as the starting material in 17% yield. LCMS for $C_{30}H_{27}ClN_7O$ (M+H)$^+$: m/z=536.1. $^1$H NMR (400 MHz, DMSO-d$_6$): δ 9.47 (br s, 1H), 9.28 (br s, 1H), 8.12 (s, 1H), 7.96-7.93 (m, 3H), 7.77 (s, 1H), 7.66-7.63 (m, 2H), 7.10-7.03 (m, 3H), 6.87-6.80 (m, 2H), 3.42 (br s, 4H), 2.96 (s, 4H), 2.89 (br s, 2H), 2.78 (br s, 2H).

Example D96

6-Chloro-12-{4-[4-(trifluoromethyl)benzoyl]piperazin-1-yl}-2,4,8,22-tetraazatetracyclo[14.3.1.1(3,7).1(9,13)]docosa-1(20),3(22),4,6,9(21),10,12,16,18-nonaene bis(trifluoroacetate)

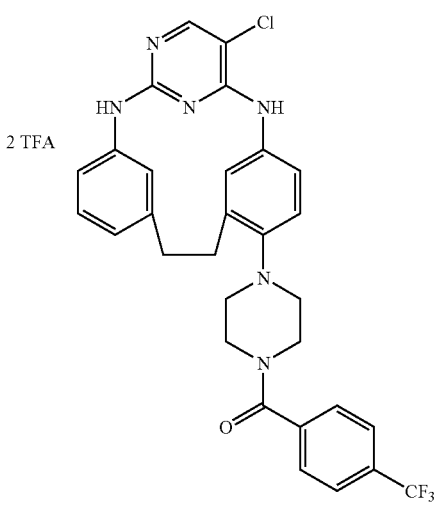 [SMILES: "2 TFA" ; O=C(c1ccc(C(F)(F)F)cc1)N1CCN(c2ccc3cc2CCc2cccc(c2)Nc2ncc(Cl)c(n2)N3)CC1]

The desired compound was prepared according to the procedure of Example D94 using 4-(trifluoromethyl)benzoyl chloride as the starting material in 32% yield. LCMS for $C_{30}H_{27}ClF_3N_6O$ (M+H)$^+$: m/z=579.1. $^1$H NMR (400 MHz, DMSO-d$_6$): δ 9.52 (br s, 1H), 9.36 (br s, 1H), 8.14 (s, 1H), 7.94 (s, 1H), 7.85-7.82 (m, 2H), 7.77 (d, J=2.0 Hz, 1H), 7.69-7.66 (m, 2H), 7.11-7.03 (m, 3H), 6.87-6.81 (m, 2H), 3.82 (br s, 2H), 3.44 (br s, 2H), 2.97 (s, 4H), 2.90 (br s, 2H), 2.78 (br s, 2H).

Example D97

(3R)-3-(2-{[6-Chloro-2,4,8,18,22-pentaazatetracyclo [14.3.1.1(3,7).1(9,13)]docosa-1(20),3(22),4,6,9(21), 10,12,16,18-nonaen-12-yl]amino}-2-oxoethyl)-N-phenylpyrrolidine-1-carboxamide bis (trifluoroacetate)

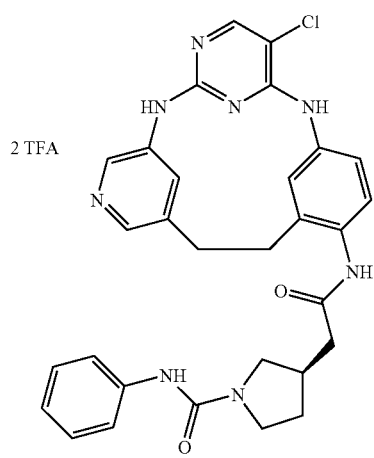 [SMILES: "2 TFA" ; O=C(C[C@H]1CCN(C(=O)Nc2ccccc2)C1)Nc1ccc2cc1CCc1cncc(c1)Nc1ncc(Cl)c(n1)N2]

Step A: tert-Butyl (3R)-3-(2-{[6-chloro-2,4,8,18,22-pentaazatetracyclo[14.3.1.1(3,7).1(9,13)]docosa-1 (20),3(22),4,6,9(21),10,12,16,18-nonaen-12-yl] amino}-2-oxoethyl)pyrrolidine-1-carboxylate

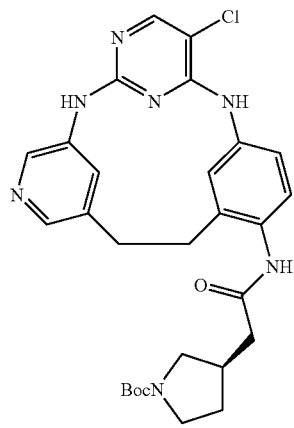

A solution of 6-chloro-2,4,8,18,22-pentaazatetracyclo [14.3.1.1(3,7).1(9,13)]docosa-1(20),3(22),4,6,9(21),10,12, 16,18-nonaen-12-amine (0.64 g, 1.9 mmol) and [(3R)-1-(tert-butoxycarbonyl)pyrrolidin-3-yl]acetic acid (0.5 g, 2.2 mmol) in dichloromethane (7 mL) and N,N-dimethylformamide (4.5 mL) was treated with N,N-diisopropylethylamine (0.5 mL, 2.8 mmol) followed by 2.0 M of 1-hydroxy-7-azabenzotriazole in N,N-dimethylformamide (0.19 mL) and N-(3-dimethylaminopropyl)-N'-ethylcarbodiimide hydrochloride (0.55 g, 2.8 mmol) and the reaction mixture was stirred at 20° C. overnight. The reaction mixture was concentrated and the resultant solution was added slowly to ice cold water (~200 mL). The solid that precipitated was filtered and collected to give the crude Boc intermediate. This material was used immediately in the next step.

Step B: N-[6-Chloro-2,4,8,18,22-pentaazatetracyclo [14.3.1.1(3,7).1(9,13)]docosa-1(20),3(22),4,6,9(21), 10,12,16,18-nonaen-12-yl]-2-[(3R)-pyrrolidin-3-yl] acetamidetris(trifluoroacetate)

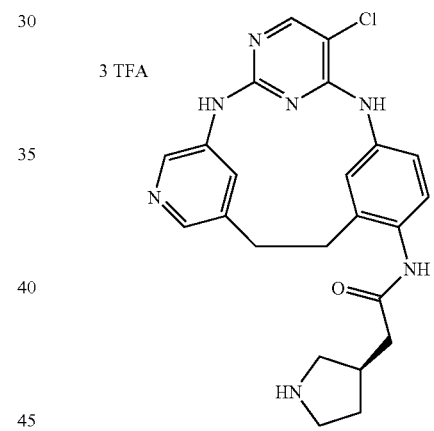

The crude Boc intermediate from Step A was dissolved in dichloromethane (10 mL), treated with 4.0 M hydrogen chloride in 1,4-dioxane (10 mL) and stirred at 20° C. for 4 h. The reaction mixture was concentrated and purified by preparative LCMS to give the desired product (0.75 g, 50%) as a solid. LCMS for $C_{23}H_{25}ClN_7O$ (M+H)$^+$: m/z=450.0.

Step C: (3R)-3-(2-{[6-Chloro-2,4,8,18,22-pentaazatetracyclo[14.3.1.1(3,7).1(9,13)]docosa-1(20),3(22), 4,6,9(21),10,12,16,18-nonaen-12-yl]amino}-2-oxoethyl)-N-phenylpyrrolidine-1-carboxamide bis (trifluoroacetate)

The desired compound was prepared according to the procedure of Example D41 using N-[6-chloro-2,4,8,18,22-pentaazatetracyclo[14.3.1.1(3,7).1(9,13)]docosa-1(20),3(22),4, 6,9(21),10,12,16,18-nonaen-12-yl]-2-[(3R)-pyrrolidin-3-yl]

acetamidetris(trifluoroacetate) and phenyl isocyanate as the starting materials in 83% yield. LCMS for $C_{30}H_{30}ClN_8O_2$ (M+H)⁺: m/z=569.0.

Example D98

(3R)-3-(2-{[6-Chloro-2,4,8,18,22-pentaazatetracyclo [14.3.1.1(3,7).1(9,13)]docosa-1(20),3(22),4,6,9(21), 10,12,16,18-nonaen-12-yl]amino}-2-oxoethyl)-N-(4-cyanophenyl)pyrrolidine-1-carboxamide bis (trifluoroacetate)

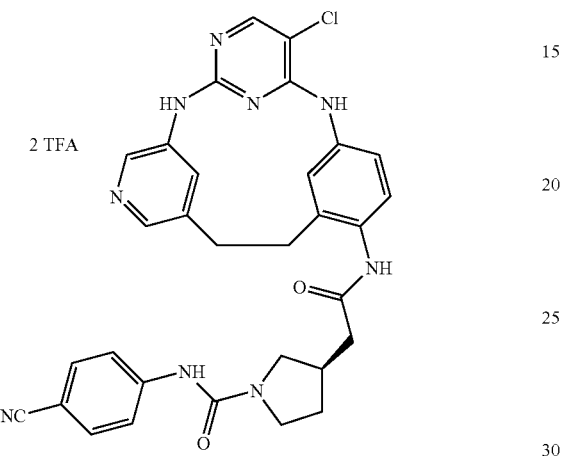

The desired compound was prepared according to the procedure of Example D41 using N-[6-chloro-2,4,8,18,22-pentaazatetracyclo[14.3.1.1(3,7).1(9,13)]docosa-1(20),3(22),4, 6,9(21),10,12,16,18-nonaen-12-yl]-2-[(3R)-pyrrolidin-3-yl] acetamidetris(trifluoroacetate) and 4-isocyanatobenzonitrile as the starting materials in 51% yield. LCMS for $C_{31}H_{29}ClN_9O_2$ (M+H)⁺: m/z=594.0.

Example D99

(3R)-3-(2-{[6-Chloro-2,4,8,18,22-pentaazatetracyclo [14.3.1.1(3,7).1(9,13)]docosa-1(20),3(22),4,6,9(21), 10,12,16,18-nonaen-12-yl]amino}-2-oxoethyl)-N-(3-cyanophenyl)pyrrolidine-1-carboxamide bis (trifluoroacetate)

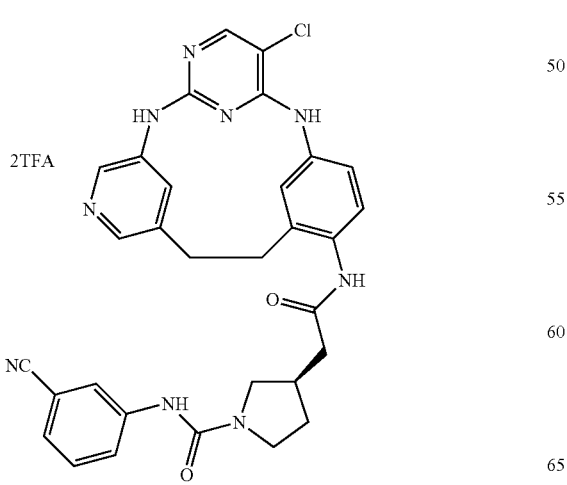

The desired compound was prepared according to the procedure of Example D41 using N-[6-chloro-2,4,8,18,22-pentaazatetracyclo[14.3.1.1(3,7).1(9,13)]docosa-1(20),3(22),4, 6,9(21),10,12,16,18-nonaen-12-yl]-2-[(3R)-pyrrolidin-3-yl] acetamidetris(trifluoroacetate) and 3-isocyanatobenzonitrile as the starting materials in 64% yield. LCMS for $C_{31}H_{29}ClN_9O_2$ (M+H)⁺: m/z=594.0.

Example D100

(3R)-3-(2-{[6-Chloro-2,4,8,18,22-pentaazatetracyclo [14.3.1.1(3,7).1(9,13)]docosa-1(20),3(22),4,6,9(21), 10,12,16,18-nonaen-12-yl]amino}-2-oxoethyl)-N-(2-cyanophenyl)pyrrolidine-1-carboxamide bis (trifluoroacetate)

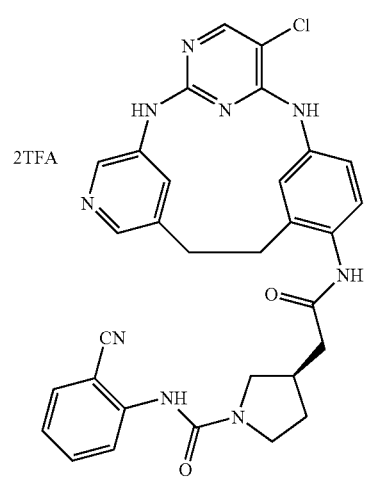 [SMILES: "2TFA" ; N#Cc1ccccc1NC(=O)N1CC[C@H](CC(=O)Nc2ccc3cc2CCc2cncc(c2)Nc2ncc(Cl)c(n2)N3)C1]

The desired compound was prepared according to the procedure of Example D41 using N-[6-chloro-2,4,8,18,22-pentaazatetracyclo[14.3.1.1(3,7).1(9,13)]docosa-1(20),3(22),4, 6,9(21),10,12,16,18-nonaen-12-yl]-2-[(3R)-pyrrolidin-3-yl] acetamidetris(trifluoroacetate) and 2-isocyanatobenzonitrile as the starting materials in 48% yield. LCMS for $C_{31}H_{29}ClN_9O_2$ (M+H)⁺: m/z=594.0.

Example D101

(3R)-3-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-pyridin-3-ylpyrrolidine-1-carboxamide tris(trifluoroacetate)

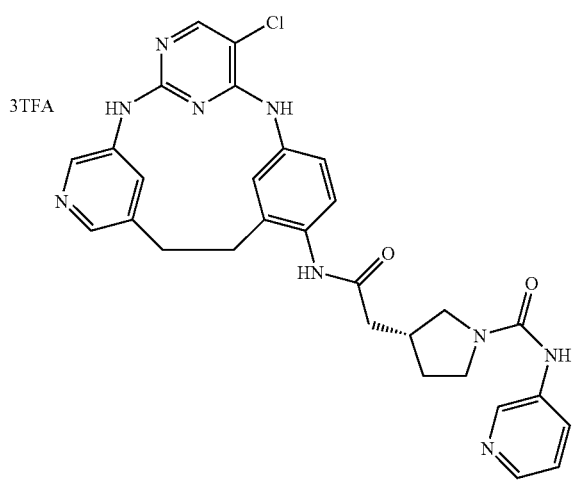 [SMILES: O=C(C[C@H]1CCN(C(=O)Nc2cccnc2)C1)Nc1ccc2cc1CCc1cncc(c1)Nc1ncc(Cl)c(n1)N2]

The desired compound was prepared according to the procedure of Example D41 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-[(3R)-pyrrolidin-3-yl]acetamide tris(trifluoroacetate) and 2-isocyanatopyridine as the starting materials in 84% yield. LCMS for $C_{29}H_{29}ClN_9O_2$ (M+H)$^+$: m/z=570.0.

Example D102

(3R)-3-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-(4-fluorophenyl)pyrrolidine-1-carboxamide bis(trifluoroacetate)

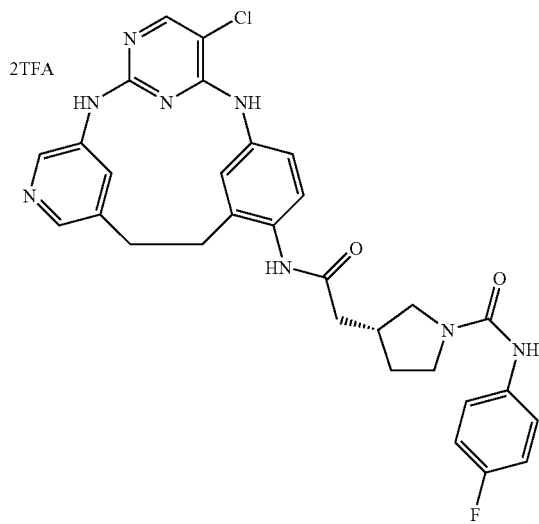 [SMILES: "2TFA" ; O=C(C[C@H]1CCN(C(=O)Nc2ccc(F)cc2)C1)Nc1ccc2cc1CCc1cncc(c1)Nc1ncc(Cl)c(n1)N2]

The desired compound was prepared according to the procedure of Example D41 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-[(3R)-pyrrolidin-3-yl]acetamide tris(trifluoroacetate) and 1-fluoro-4-isocyanatobenzene as the starting materials in 73% yield. LCMS for $C_{30}H_{29}ClFN_8O_2$ (M+H)$^+$: m/z=587.0.

Example D103

(3R)-3-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-(3-fluorophenyl)pyrrolidine-1-carboxamide bis(trifluoroacetate)

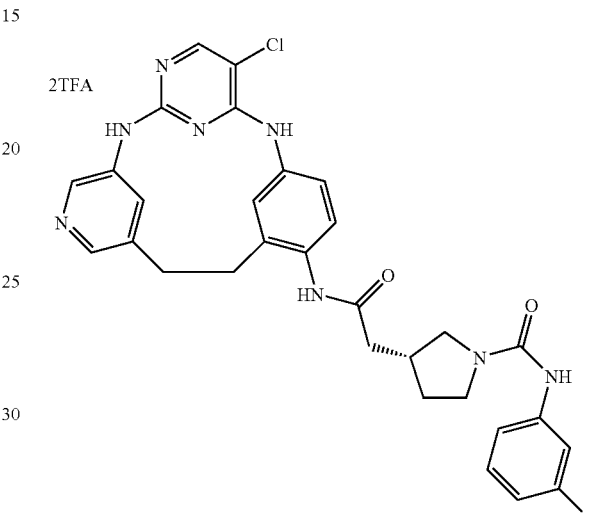

The desired compound was prepared according to the procedure of Example D41 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-[(3R)-pyrrolidin-3-yl]acetamide tris(trifluoroacetate) and 1-fluoro-3-isocyanatobenzene as the starting materials in 58% yield. LCMS for $C_{30}H_{29}ClFN_8O_2$ (M+H)$^+$: m/z=587.0.

Example D104

(3R)-3-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-(2-fluorophenyl)pyrrolidine-1-carboxamide bis(trifluoroacetate)

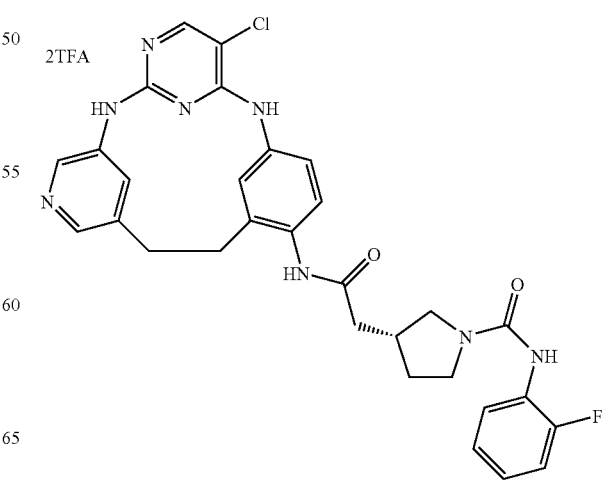

The desired compound was prepared according to the procedure of Example D41 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-[(3R)-pyrrolidin-3-yl]acetamidetris(trifluoroacetate) and 1-fluoro-2-isocyanatobenzene as the starting materials in 85% yield. LCMS for $C_{30}H_{29}ClFN_8O_2$ (M+H)$^+$: m/z=587.1.

Example D105

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[(3R)-1-(isoxazol-5-ylcarbonyl)pyrrolidin-3-yl]acetamide bis(trifluoroacetate)

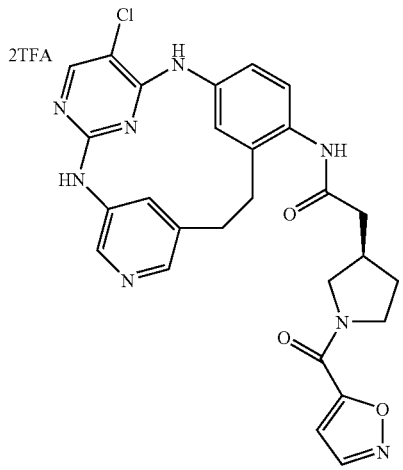 [SMILES: "2TFA" ; O=C(C[C@H]1CCN(C(=O)c2ccno2)C1)Nc1ccc2cc1CCc1cncc(c1)Nc1ncc(Cl)c(n1)N2]

The desired compound was prepared according to the procedure of Example D94 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-[(3R)-pyrrolidin-3-yl]acetamidetris(trifluoroacetate) and isoxazole-5-carbonyl chloride as the starting materials in 59% yield. LCMS for $C_{27}H_{26}ClN_8O_3$ (M+H)$^+$: m/z=545.1.

Example D106

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{(3R)-1-[(1-methyl-1H-pyrazol-3-yl)carbonyl]pyrrolidin-3-yl}acetamide bis(trifluoroacetate)

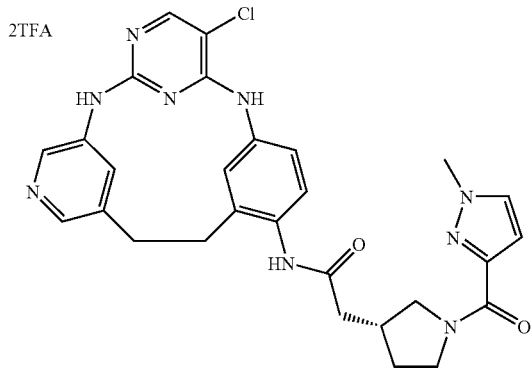 [SMILES: "2TFA" ; Cn1ccc(C(=O)N2CC[C@H](CC(=O)Nc3ccc4cc3CCc3cncc(c3)Nc3ncc(Cl)c(n3)N4)C2)n1]

The desired compound was prepared according to the procedure of Example D94 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-[(3R)-pyrrolidin-3-yl]acetamidetris(trifluoroacetate) and 1-methyl-1H-pyrazole-3-carbonyl chloride as the starting materials in 67% yield. LCMS for $C_{28}H_{29}ClN_9O_2$ (M+H)$^+$: m/z=558.1.

Example D107

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{(3R)-1-[(1-methyl-1H-pyrazol-4-yl)carbonyl]pyrrolidin-3-yl}acetamide bis(trifluoroacetate)

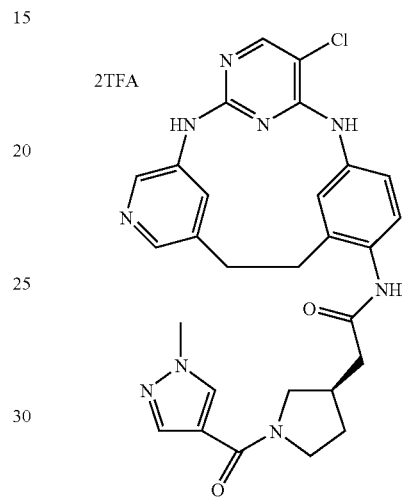

The desired compound was prepared according to the procedure of Example D94 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-[(3R)-pyrrolidin-3-yl]acetamidetris(trifluoroacetate) and 1-methyl-1H-pyrazole-4-carbonyl chloride as the starting materials in 67% yield. LCMS for $C_{28}H_{29}ClN_9O_2$ (M+H)$^+$: m/z=558.0.

Example D108

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{(3R)-1-[(5-methylisoxazol-4-yl)carbonyl]pyrrolidin-3-yl}acetamide bis(trifluoroacetate)

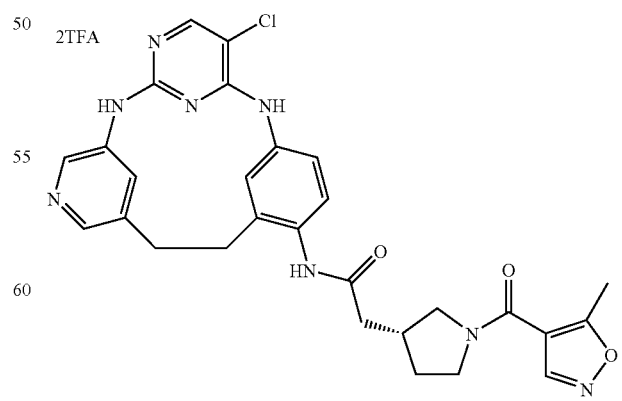

The desired compound was prepared according to the procedure of Example D94 using N-[6-chloro-2,4,8,18,22-pentaazatetracyclo[14.3.1.1(3,7).1(9,13)]docosa-1(20),3(22),4, 6,9(21),10,12,16,18-nonaen-12-yl]-2-[(3R)-pyrrolidin-3-yl]acetamidetris(trifluoroacetate) and 5-methylisoxazole-4-carbonyl chloride as the starting materials in 92% yield. LCMS for $C_{28}H_{28}ClN_8O_3$ (M+H)$^+$: m/z=559.1.

Example D109

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{(3R)-1-[(5-methylisoxazol-3-yl)carbonyl]pyrrolidin-3-yl}acetamide bis(trifluoroacetate)

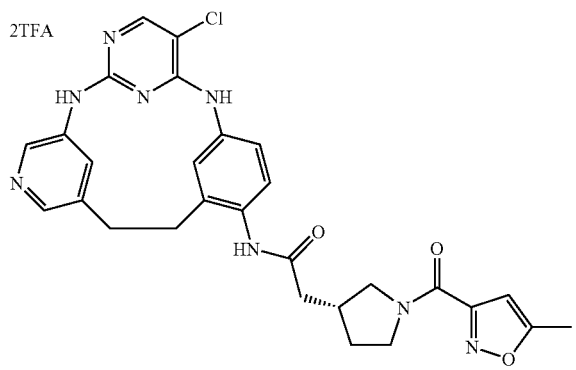 [SMILES: "2TFA" ; Cc1cc(C(=O)N2CC[C@H](CC(=O)Nc3ccc4cc3CCc3cncc(c3)Nc3ncc(Cl)c(n3)N4)C2)no1]

The desired compound was prepared according to the procedure of Example D94 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-[(3R)-pyrrolidin-3-yl]acetamidetris(trifluoroacetate) and 5-methylisoxazole-3-carbonyl chloride as the starting materials in 46% yield. LCMS for $C_{28}H_{28}ClN_8O_3$ (M+H)$^+$: m/z=559.0.

Example D110

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[(3R)-1-(1,3-thiazol-2-ylcarbonyl)pyrrolidin-3-yl]acetamide bis(trifluoroacetate)

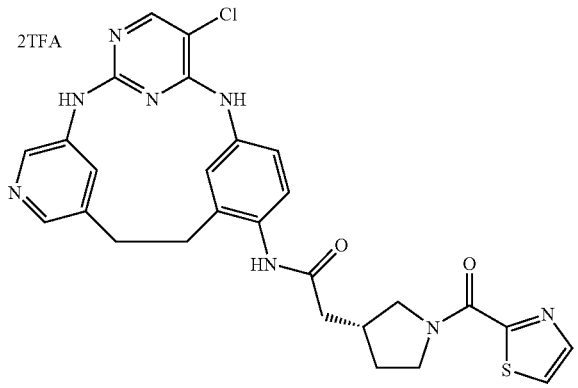 [SMILES: "2TFA" ; O=C(C[C@H]1CCN(C(=O)c2nccs2)C1)Nc1ccc2cc1CCc1cncc(c1)Nc1ncc(Cl)c(n1)N2]

The desired compound was prepared according to the procedure of Example D94 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-[(3R)-pyrrolidin-3-yl]acetamidetris(trifluoroacetate) and 1,3-thiazole-2-carbonyl chloride as the starting materials in 57% yield. LCMS for $C_{27}H_{26}ClN_8O_2S$ (M+H)$^+$: m/z=561.1.

Example D111

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{(3R)-1-[(1-methyl-1H-imidazol-5-yl)carbonyl]pyrrolidin-3-yl}acetamide tris(trifluoroacetate)

The desired compound was prepared according to the procedure of Example D94 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-[(3R)-pyrrolidin-3-yl]acetamidetris(trifluoroacetate) and 1-methyl-1H-imidazole-5-carbonyl chloride hydrochloride as the starting materials in 23% yield. LCMS for $C_{28}H_{29}ClN_9O_2$ (M+H)$^+$: m/z=558.1.

Example D112

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[(3R)-1-(methylsulfonyl)pyrrolidin-3-yl]acetamide bis(trifluoroacetate)

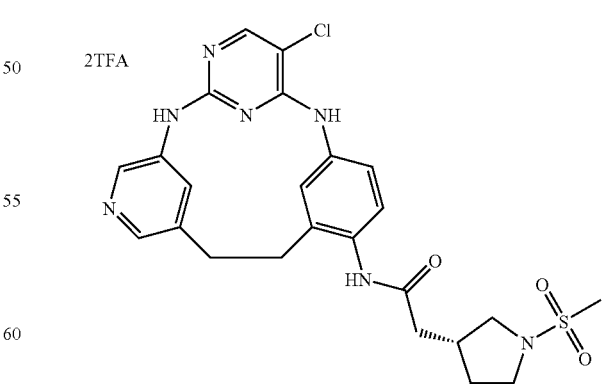

The desired compound was prepared according to the procedure of Example D20, step A, using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-[(3R)- pyrrolidin-3-yl]acetamidetris(trifluoroacetate) as the starting material in 75% yield. LCMS for $C_{24}H_{27}ClN_7O_3S$ (M+H)$^+$: m/z=528.1.

Example D113

(3S)-3-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-phenylpyrrolidine-1-carboxamide bis(trifluoroacetate)

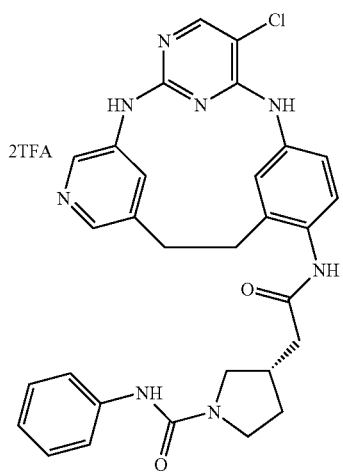 [SMILES: "2TFA" ; O=C(C[C@@H]1CCN(C(=O)Nc2ccccc2)C1)Nc1ccc2cc1CCc1cncc(c1)Nc1ncc(Cl)c(n1)N2]

Step A: N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[(3S)-pyrrolidin-3-yl]acetamide tris(trifluoroacetate)

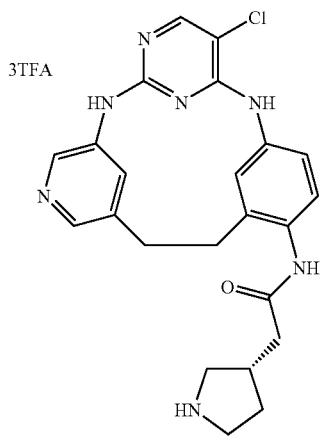 [SMILES: O=C(C[C@@H]1CCNC1)Nc1ccc2cc1CCc1cncc(c1)Nc1ncc(Cl)c(n1)N2]

The desired compound was prepared according to the procedure of Example D97, step A, using [(3S)-1-(tert-butoxycarbonyl)pyrrolidin-3-yl]acetic acid as the starting material in 54% yield. LCMS for $C_{23}H_{25}ClN_7O$ (M+H)$^+$: m/z=450.0.

Step B: (3S)-3-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-phenylpyrrolidine-1-carboxamide bis(trifluoroacetate)

The desired compound was prepared according to the procedure of Example D41 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-[(3S)-pyrrolidin-3-yl]acetamide tris(trifluoroacetate) and phenyl isocyanate as the starting materials in 99% yield. LCMS for $C_{30}H_{30}ClN_8O_2$ (M+H)$^+$: m/z=569.1.

Example D114

(3S)-3-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-(4-cyanophenyl)pyrrolidine-1-carboxamide bis(trifluoroacetate)

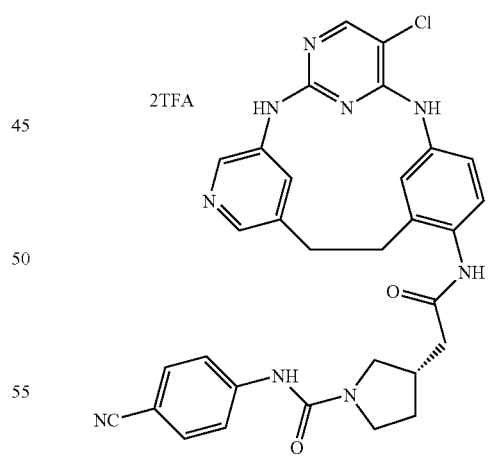

The desired compound was prepared according to the procedure of Example D41 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-[(3S)-pyrrolidin-3-yl]acetamide tris(trifluoroacetate) and 4-isocyanatobenzonitrile as the starting materials in 60% yield. LCMS for $C_{31}H_{29}ClN_9O_2$ (M+H)$^+$: m/z=594.0.

Example D115

(3S)-3-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-(3-cyanophenyl)pyrrolidine-1-carboxamide bis(trifluoroacetate)

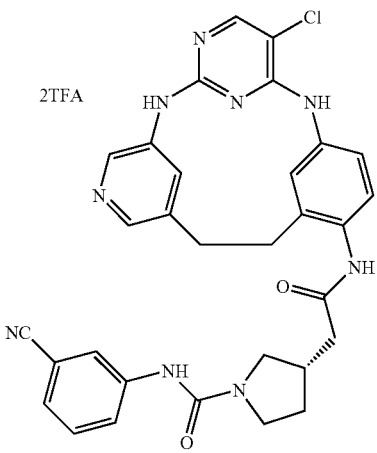

The desired compound was prepared according to the procedure of Example D41 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-[(3S)-pyrrolidin-3-yl]acetamide tris(trifluoroacetate) and 3-isocyanatobenzonitrile as the starting materials in 77% yield. LCMS for $C_{31}H_{29}ClN_9O_2$ (M+H)$^+$: m/z=594.1.

Example D116

(3S)-3-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-(2-cyanophenyl)pyrrolidine-1-carboxamide bis(trifluoroacetate)

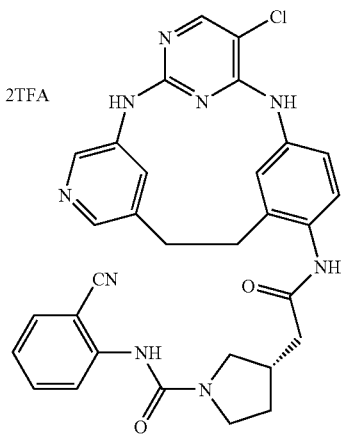 [SMILES: "2TFA" ; N#Cc1ccccc1NC(=O)N1CC[C@@H](CC(=O)Nc2ccc3cc2CCc2cncc(c2)Nc2ncc(Cl)c(n2)N3)C1]

The desired compound was prepared according to the procedure of Example D41 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-[(3S)-pyrrolidin-3-yl]acetamide tris(trifluoroacetate) and 2-isocyanatobenzonitrile as the starting materials in 77% yield. LCMS for $C_{31}H_{29}ClN_9O_2$ (M+H)$^+$: m/z=594.1.

Example D117

(3S)-3-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-pyridin-3-ylpyrrolidine-1-carboxamide tris(trifluoroacetate)

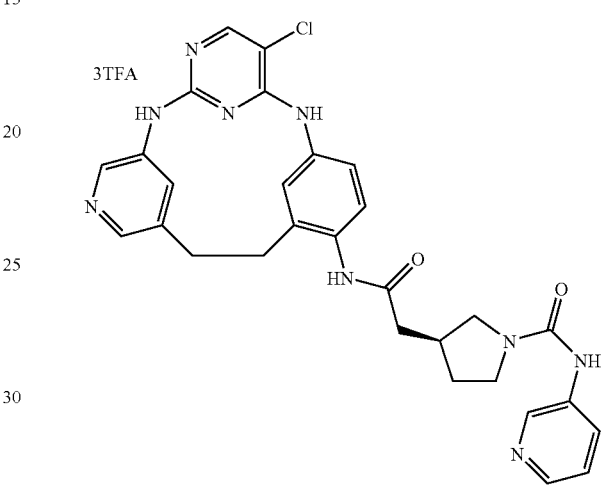

The desired compound was prepared according to the procedure of Example D41 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-[(3S)-pyrrolidin-3-yl]acetamide tris(trifluoroacetate) and 3-isocyanatopyridine as the starting materials in 93% yield. LCMS for $C_{29}H_{29}ClN_9O_2$ (M+H)$^+$: m/z=570.0.

Example D118

(3S)-3-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-(4-fluorophenyl)pyrrolidine-1-carboxamide bis(trifluoroacetate)

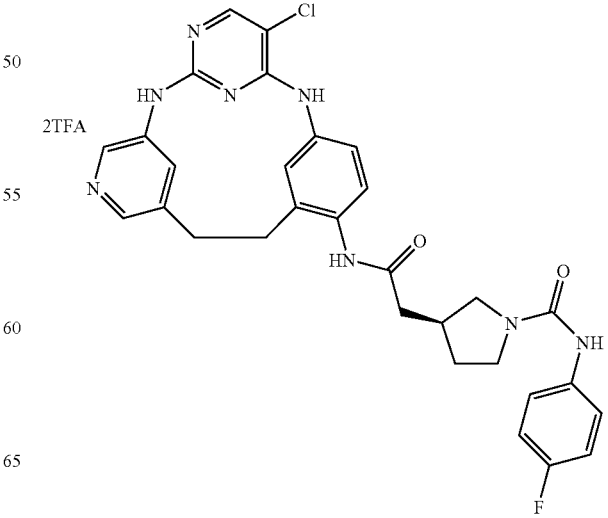

The desired compound was prepared according to the procedure of Example D41 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-[(3S)-pyrrolidin-3-yl]acetamide tris(trifluoroacetate) and 1-fluoro-4-isocyanatobenzene as the starting materials in 79% yield. LCMS for $C_{30}H_{29}ClFN_8O_2$ (M+H)$^+$: m/z=587.0.

Example D119

(3S)-3-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-(3-fluorophenyl)pyrrolidine-1-carboxamide bis(trifluoroacetate)

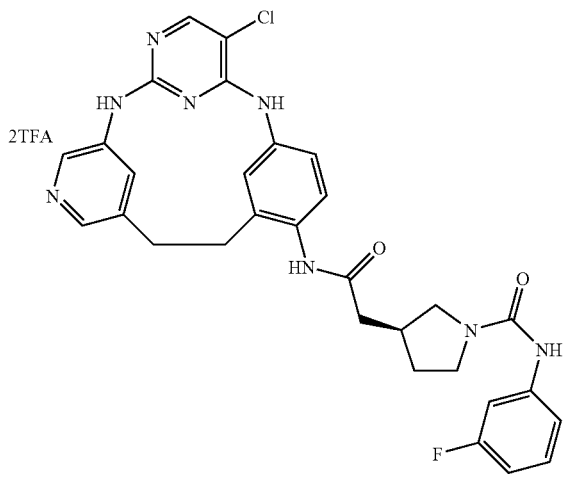 [SMILES: "2TFA" ; O=C(C[C@@H]1CCN(C(=O)Nc2cccc(F)c2)C1)Nc1ccc2cc1CCc1cncc(c1)Nc1ncc(Cl)c(n1)N2]

The desired compound was prepared according to the procedure of Example D41 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-[(3S)-pyrrolidin-3-yl]acetamide tris(trifluoroacetate) and 1-fluoro-3-isocyanatobenzene as the starting materials in 80% yield. LCMS for $C_{30}H_{29}ClFN_8O_2$ (M+H)$^+$: m/z=587.0.

Example D120

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[(3S)-1-(isoxazol-5-ylcarbonyl)pyrrolidin-3-yl]acetamide bis(trifluoroacetate)

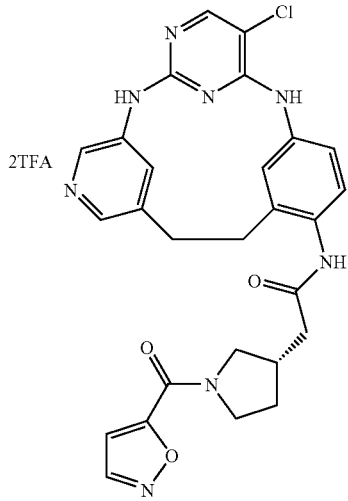 [SMILES: "2TFA" ; O=C(C[C@@H]1CCN(C(=O)c2ccno2)C1)Nc1ccc2cc1CCc1cncc(c1)Nc1ncc(Cl)c(n1)N2]

The desired compound was prepared according to the procedure of Example D94 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-[(3S)-pyrrolidin-3-yl]acetamide tris(trifluoroacetate) and isoxazole-5-carbonyl chloride as the starting materials in 81% yield. LCMS for $C_{27}H_{26}ClN_8O_3$ (M+H)$^+$: m/z=545.0.

Example D121

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{(3S)-1-[(1-methyl-1H-pyrazol-3-yl)carbonyl]pyrrolidin-3-yl}acetamide bis(trifluoroacetate)

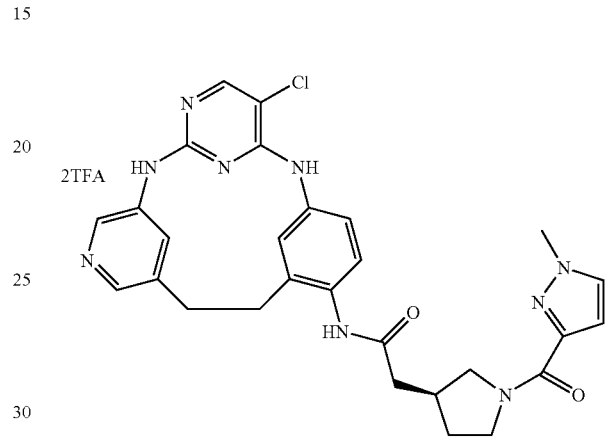

The desired compound was prepared according to the procedure of Example D94 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-[(3S)-pyrrolidin-3-yl]acetamide tris(trifluoroacetate) and 1-methyl-1H-pyrazole-3-carbonyl chloride as the starting materials in 82% yield. LCMS for $C_{28}H_{29}ClN_9O_2$ (M+H)$^+$: m/z=558.1.

Example D122

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{(3S)-1-[(1-methyl-1H-pyrazol-4-yl)carbonyl]pyrrolidin-3-yl}acetamide bis(trifluoroacetate)

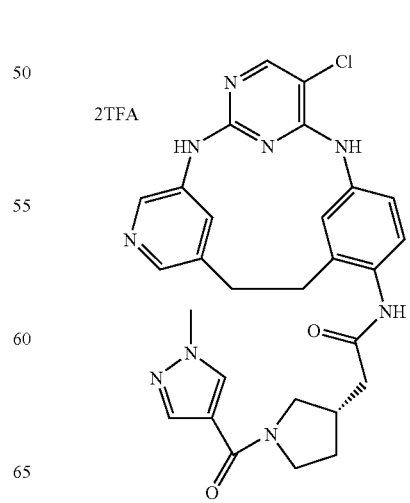

The desired compound was prepared according to the procedure of Example D94 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-[(3S)-pyrrolidin-3-yl]acetamide tris(trifluoroacetate) and 1-methyl-1H-pyrazole-4-carbonyl chloride as the starting materials in 72% yield. LCMS for $C_{28}H_{29}ClN_9O_2$ (M+H)$^+$: m/z=558.1.

Example D123

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{(3S)-1-[(5-methylisoxazol-4-yl)carbonyl]pyrrolidin-3-yl}acetamide bis(trifluoroacetate)

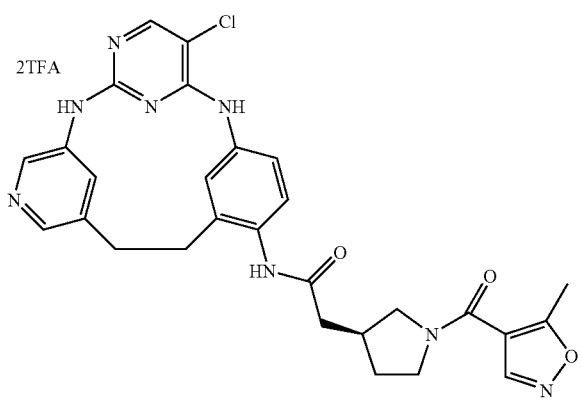 [SMILES: "2TFA" ; Cc1oncc1C(=O)N1CC[C@@H](CC(=O)Nc2ccc3cc2CCc2cncc(c2)Nc2ncc(Cl)c(n2)N3)C1]

The desired compound was prepared according to the procedure of Example D94 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-[(3S)-pyrrolidin-3-yl]acetamide tris(trifluoroacetate) and 5-methylisoxazole-4-carbonyl chloride as the starting materials in 91% yield. LCMS for $C_{28}H_{28}ClN_8O_3$ (M+H)$^+$: m/z=559.0.

Example D124

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{(3S)-1-[(5-methylisoxazol-3-yl)carbonyl]pyrrolidin-3-yl}acetamide bis(trifluoroacetate)

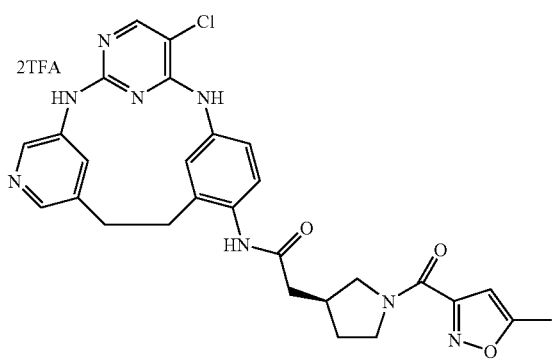 [SMILES: "2TFA" ; Cc1cc(C(=O)N2CC[C@@H](CC(=O)Nc3ccc4cc3CCc3cncc(c3)Nc3ncc(Cl)c(n3)N4)C2)no1]

The desired compound was prepared according to the procedure of Example D94 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-[(3S)-pyrrolidin-3-yl]acetamide tris(trifluoroacetate) and 5-methylisoxazole-3-carbonyl chloride as the starting materials in 76% yield. LCMS for $C_{28}H_{28}ClN_8O_3$ (M+H)$^+$: m/z=559.0.

Example D125

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[(3S)-1-(1,3-thiazol-2-ylcarbonyl)pyrrolidin-3-yl]acetamide bis(trifluoroacetate)

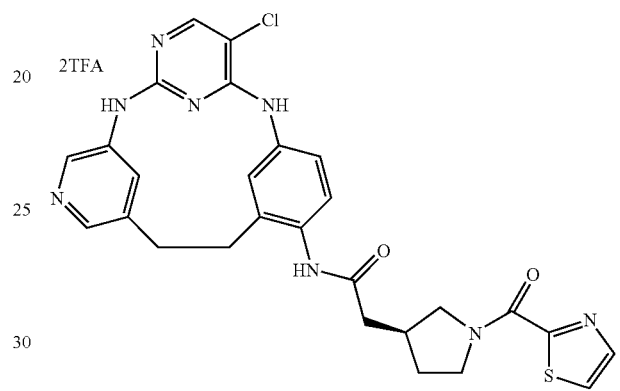

The desired compound was prepared according to the procedure of Example D94 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-[(3S)-pyrrolidin-3-yl]acetamide tris(trifluoroacetate) and 1,3-thiazole-2-carbonyl chloride as the starting materials in 83% yield. LCMS for $C_{27}H_{26}ClN_8O_2S$ (M+H)$^+$: m/z=561.0.

Example D126

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{(3S)-1-[(1-methyl-1H-imidazol-5-yl)carbonyl]pyrrolidin-3-yl}acetamide tris(trifluoroacetate)

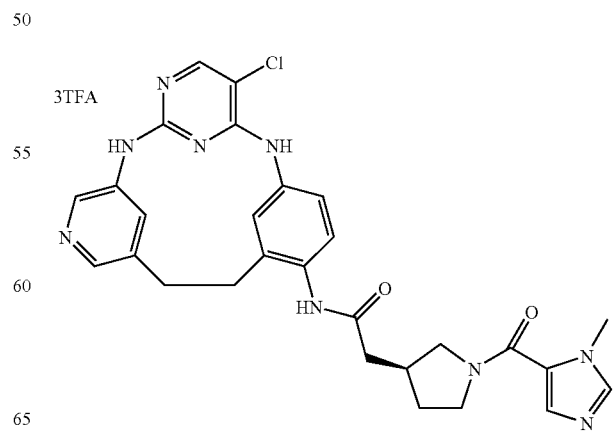

The desired compound was prepared according to the procedure of Example D94 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-[(3S)-pyrrolidin-3-yl]acetamide tris(trifluoroacetate) and 1-methyl-1H-imidazole-5-carbonyl chloride hydrochloride as the starting materials in 20% yield. LCMS for $C_{28}H_{29}ClN_9O_2$ (M+H)$^+$: m/z=558.0.

Example D127

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[(3S)-1-(methylsulfonyl)pyrrolidin-3-yl]acetamide bis(trifluoroacetate)

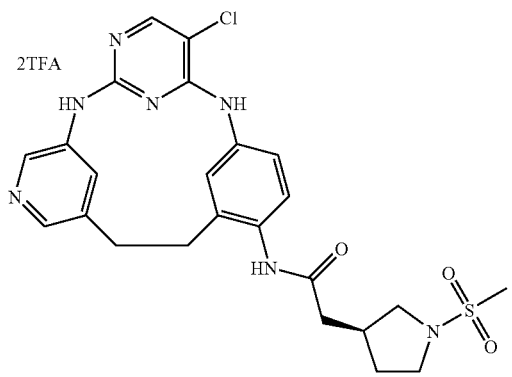 [SMILES: "2TFA" ; CS(=O)(=O)N1CC[C@@H](CC(=O)Nc2ccc3cc2CCc2cncc(c2)Nc2ncc(Cl)c(n2)N3)C1]

The desired compound was prepared according to the procedure of Example D20, step A, using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-[(3S)-pyrrolidin-3-yl]acetamide tris(trifluoroacetate) as the starting material in 78% yield. LCMS for $C_{24}H_{27}ClN_7O_3S$ (M+H)$^+$: m/z=528.0.

Example D128

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[(3R)-1-(1H-1,2,4-triazol-3-ylcarbonyl)pyrrolidin-3-yl]acetamide bis(trifluoroacetate)

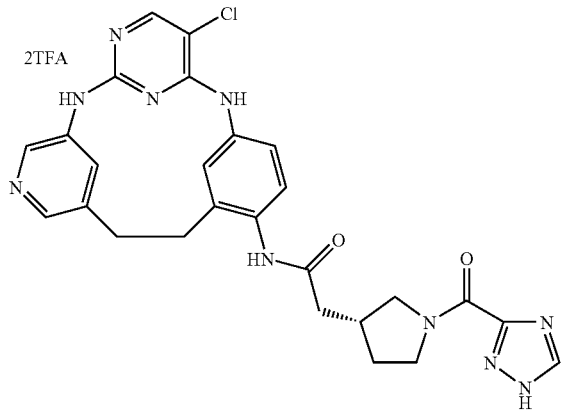 [SMILES: "2TFA" ; O=C(C[C@H]1CCN(C(=O)c2nc[nH]n2)C1)Nc1ccc2cc1CCc1cncc(c1)Nc1ncc(Cl)c(n1)N2]

The desired compound was prepared according to the procedure of Example D97, step A, using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-[(3R)-pyrrolidin-3-yl]acetamidetris(trifluoroacetate) and 1H-1,2,4-triazole-3-carboxylic acid as the starting materials in 58% yield. LCMS for $C_{26}H_{26}ClN_{10}O_2$ (M+H)$^+$: m/z=545.0.

Example D129-a

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[(3R)-1-(1H-1,2,3-triazol-4-ylcarbonyl)pyrrolidin-3-yl]acetamide bis(trifluoroacetate)

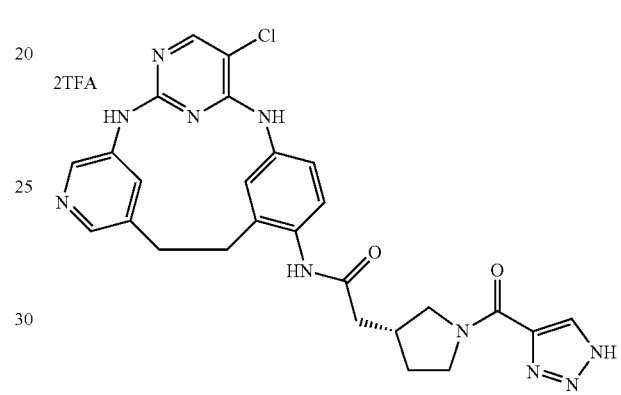

The desired compound was prepared according to the procedure of Example D97, step A, using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-[(3R)-pyrrolidin-3-yl]acetamidetris(trifluoroacetate) and 4-carboxy-1,2,3-triazole as the starting materials in 78% yield. LCMS for $C_{26}H_{26}ClN_{10}O_2$ (M+H)$^+$: m/z=545.0.

Example D129-b

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[(3R)-1-(1H-pyrazol-4-ylcarbonyl)pyrrolidin-3-yl]acetamide bis(trifluoroacetate)

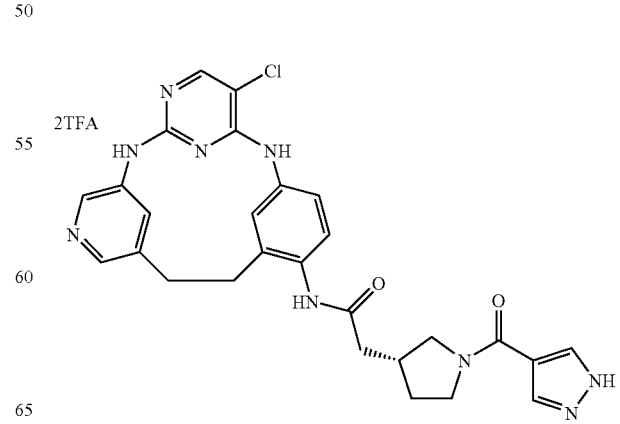

The desired compound was prepared according to the procedure of Example D97, step A, using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-[(3R)-pyrrolidin-3-yl]acetamidetris(trifluoroacetate) and 1H-pyrazole-4-carboxylic acid as the starting materials in 51% yield. LCMS for $C_{27}H_{27}ClN_9O_2$ (M+H)$^+$: m/z=544.0.

Example D130

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[(3R)-1-(1H-pyrazol-3-ylcarbonyl)pyrrolidin-3-yl]acetamide bis(trifluoroacetate)

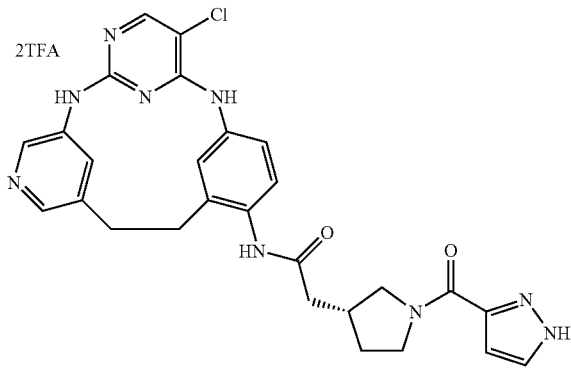 [SMILES: "2TFA" ; O=C(C[C@H]1CCN(C(=O)c2cc[nH]n2)C1)Nc1ccc2cc1CCc1cncc(c1)Nc1ncc(Cl)c(n1)N2]

The desired compound was prepared according to the procedure of Example D97, step A, using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-[(3R)-pyrrolidin-3-yl]acetamidetris(trifluoroacetate) and 1H-pyrazole-3-carboxylic acid as the starting materials in 62% yield. LCMS for $C_{27}H_{27}ClN_9O_2$ (M+H)$^+$: m/z=544.0.

Example D131

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[(3S)-1-(1H-1,2,4-triazol-3-yl-carbonyl)pyrrolidin-3-yl]acetamide bis(trifluoroacetate)

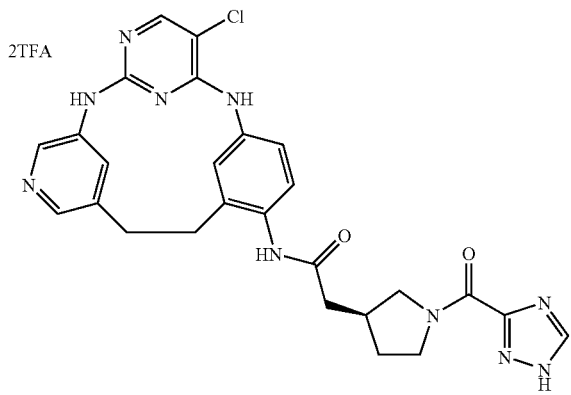 [SMILES: "2TFA" ; O=C(C[C@@H]1CCN(C(=O)c2nc[nH]n2)C1)Nc1ccc2cc1CCc1cncc(c1)Nc1ncc(Cl)c(n1)N2]

The desired compound was prepared according to the procedure of Example D97, step A, using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-[(3S)-pyrrolidin-3-yl]acetamide tris(trifluoroacetate) and 1H-1,2,4-triazole-3-carboxylic acid as the starting materials in 68% yield. LCMS for $C_{26}H_{26}ClN_{10}O_2$ (M+H)$^+$: m/z=545.0.

Example D132

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[(3S)-1-(1H-1,2,3-triazol-4-yl-carbonyl)pyrrolidin-3-yl]acetamide bis(trifluoroacetate)

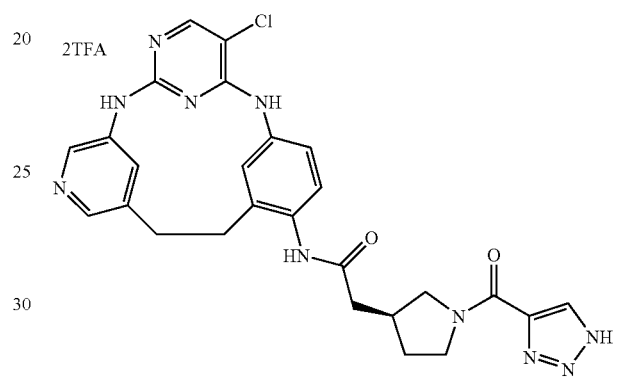

The desired compound was prepared according to the procedure of Example D97, step A, using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-[(3S)-pyrrolidin-3-yl]acetamide tris(trifluoroacetate) and 4-carboxy-1,2,3-triazole as the starting materials in 87% yield. LCMS for $C_{26}H_{26}ClN_{10}O_2$ (M+H)$^+$: m/z=545.0.

Example D133

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[(3S)-1-(1H-pyrazol-4-ylcarbonyl)pyrrolidin-3-yl]acetamide bis(trifluoroacetate)

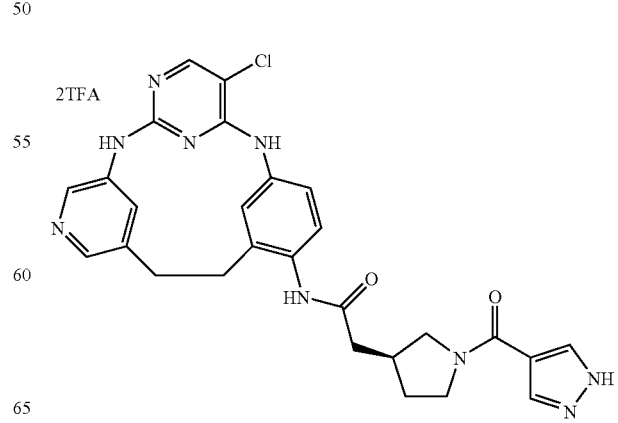

The desired compound was prepared according to the procedure of Example D97, step A, using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-[(3S)-pyrrolidin-3-yl]acetamide tris(trifluoroacetate) and 1H-pyrazole-4-carboxylic acid as the starting materials in 66% yield. LCMS for $C_{27}H_{27}ClN_9O_2$ (M+H)$^+$: m/z=544.0.

Example D134

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[(3S)-1-(1H-pyrazol-3-ylcarbonyl)pyrrolidin-3-yl]acetamide bis(trifluoroacetate)

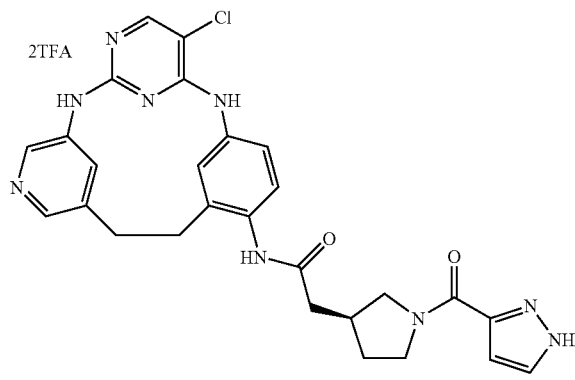 [SMILES: "2TFA" ; O=C(C[C@@H]1CCN(C(=O)c2cc[nH]n2)C1)Nc1ccc2cc1CCc1cncc(c1)Nc1ncc(Cl)c(n1)N2]

The desired compound was prepared according to the procedure of Example D97, step A, using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-[(3S)-pyrrolidin-3-yl]acetamide tris(trifluoroacetate) and 1H-pyrazole-3-carboxylic acid as the starting materials in 66% yield. LCMS for $C_{27}H_{27}ClN_9O_2$ (M+H)$^+$: m/z=544.0.

Example D135

(3S)-3-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-(2-fluorophenyl)pyrrolidine-1-carboxamide bis(trifluoroacetate)

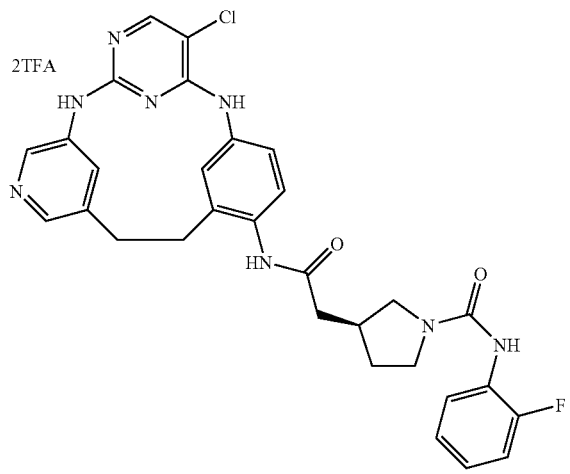 [SMILES: "2TFA" ; O=C(C[C@@H]1CCN(C(=O)Nc2ccccc2F)C1)Nc1ccc2cc1CCc1cncc(c1)Nc1ncc(Cl)c(n1)N2]

The desired compound was prepared according to the procedure of Example D41 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-[(3S)-pyrrolidin-3-yl]acetamide tris(trifluoroacetate) and 1-fluoro-2-isocyanatobenzene as the starting materials in 87% yield. LCMS for $C_{30}H_{29}ClFN_8O_2$ (M+H)$^+$: m/z=587.0.

Example D136

2-[(3R)-1-(1,3-Benzothiazol-2-yl)pyrrolidin-3-yl]-N-[6-chloro-2,4,8,18,22-pentaazatetracyclo[14.3.1.1(3,7).1(9,13)]docosa-1(20),3(22),4,6,9(21),10,12,16,18-nonaen-12-yl]acetamide tris(trifluoroacetate)

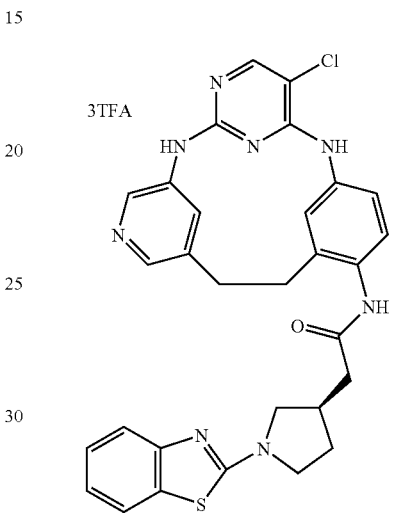

The desired compound was prepared according to the procedure of Example A157 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-[(3R)-pyrrolidin-3-yl]acetamide tris(trifluoroacetate) as the starting material in 60% yield. LCMS for $C_{30}H_{28}ClN_8OS$ (M+H)$^+$: m/z=583.0.

Example D137

2-[(3S)-1-(1,3-Benzothiazol-2-yl)pyrrolidin-3-yl]-N-[6-chloro-2,4,8,18,22-pentaazatetracyclo[14.3.1.1(3,7).1(9,13)]docosa-1(20),3(22),4,6,9(21),10,12,16,18-nonaen-12-yl]acetamide tris(trifluoroacetate)

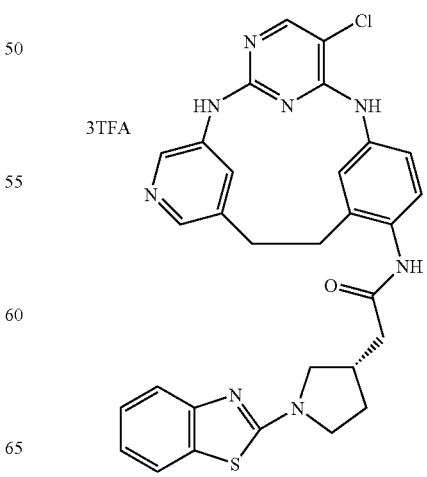

The desired compound was prepared according to the procedure of Example A157 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-[(3S)-pyrrolidin-3-yl]acetamide tris(trifluoroacetate) as the starting material in 69% yield. LCMS for $C_{30}H_{28}ClN_8OS$ (M+H)$^+$: m/z=583.0.

Example D138

2-[1-(1,3-Benzothiazol-2-yl)azetidin-3-yl]-N-[6-chloro-2,4,8,18,22-pentaazatetracyclo[14.3.1.1(3,7).1(9,13)]docosa-1(20),3(22),4,6,9(21),10,12,16,18-nonaen-12-yl]acetamide tris(trifluoroacetate)

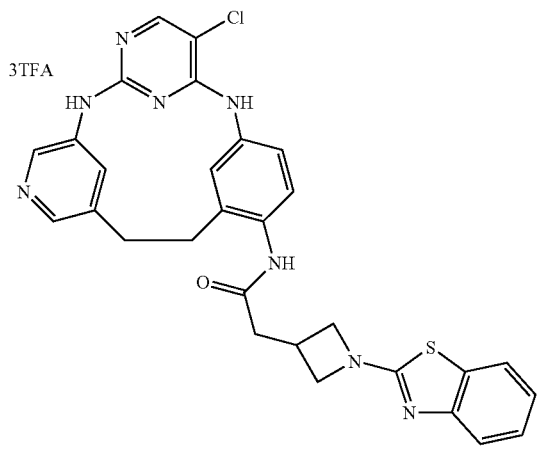 [SMILES: O=C(CC1CN(c2nc3ccccc3s2)C1)Nc1ccc2cc1CCc1cncc(c1)Nc1ncc(Cl)c(n1)N2]

The desired compound was prepared according to the procedure of Example A157 using 2-azetidin-3-yl-N-[6-chloro-2,4,8,18,22-pentaazatetracyclo[14.3.1.1(3,7).1(9,13)]docosa-1(20),3(22),4,6,9(21),10,12,16,18-nonaen-12-yl]acetamide tris(trifluoroacetate) as the starting material in 35% yield. LCMS for $C_{29}H_{26}ClN_8OS$ (M+H)$^+$: m/z=569.0.

Example D139

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[(3R)-1-[1,3]oxazolo[5,4-b]pyridin-2-ylpyrrolidin-3-yl]acetamide tris(trifluoroacetate)

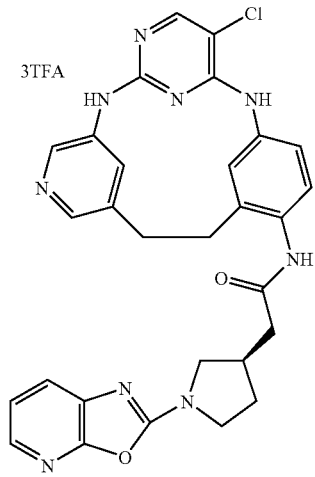 [SMILES: O=C(C[C@H]1CCN(c2nc3cccnc3o2)C1)Nc1ccc2cc1CCc1cncc(c1)Nc1ncc(Cl)c(n1)N2]

The desired compound was prepared according to the procedure of Example A118 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-[(3R)-pyrrolidin-3-yl]acetamide tris(trifluoroacetate) as the starting material in 7% yield. LCMS for $C_{29}H_{27}ClN_9O_2$ (M+H)$^+$: m/z=568.1.

Example D140

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[(3S)-1-[1,3]oxazolo[5,4-b]pyridin-2-ylpyrrolidin-3-yl]acetamide tris(trifluoroacetate)

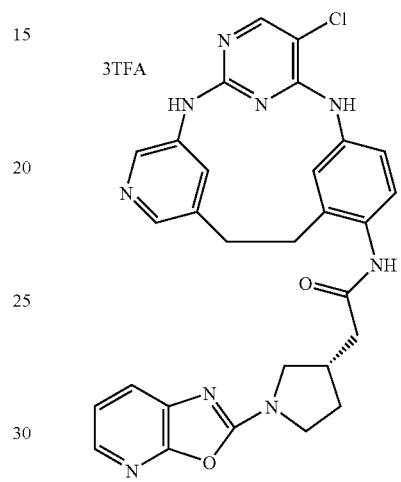

The desired compound was prepared according to the procedure of Example A118 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-[(3S)-pyrrolidin-3-yl]acetamide tris(trifluoroacetate) as the starting material in 10% yield. LCMS for $C_{29}H_{27}ClN_9O_2$ (M+H)$^+$: m/z=568.1.

Example D141

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-(1-[1,3]oxazolo[5,4-b]pyridin-2-ylazetidin-3-yl)acetamide tris(trifluoroacetate)

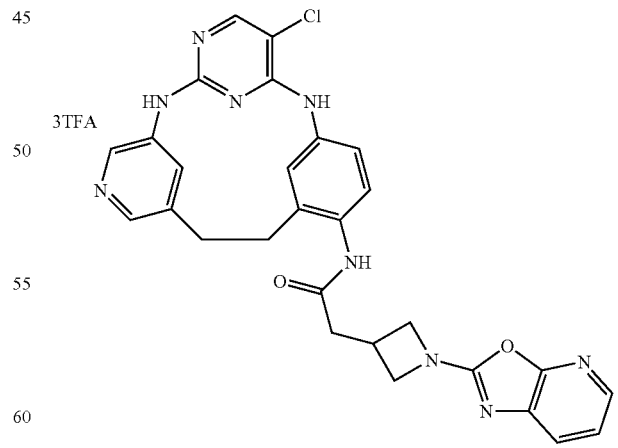

The desired compound was prepared according to the procedure of Example A118 using 2-azetidin-3-yl-N-[6-chloro-2,4,8,18,22-pentaazatetracyclo[14.3.1.1(3,7).1(9,13)]docosa-1(20),3(22),4,6,9(21),10,12,16,18-nonaen-12-yl]acetamide tris(trifluoroacetate) as the starting material in 28% yield. LCMS for $C_{28}H_{25}ClN_9O_2$ (M+H)$^+$: m/z=554.0.

Example D142

N-[6-Chloro-2,4,8,18,22-pentaazatetracyclo[14.3.1.1 (3,7).1(9,13)]docosa-1(20),3(22),4,6,9(21),10,12,16, 18-nonaen-12-yl]-2-{1-[(1-methyl-1H-pyrazol-4-yl) carbonyl]azetidin-3-yl}acetamide bis (trifluoroacetate)

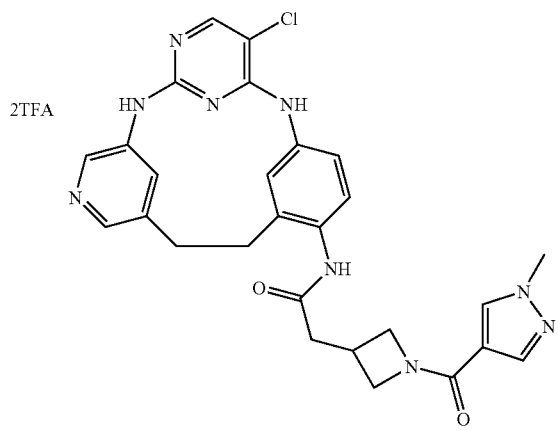 [SMILES: "2TFA" ; Cn1cc(C(=O)N2CC(CC(=O)Nc3ccc4cc3CCc3cncc(c3)Nc3ncc(Cl)c(n3)N4)C2)cn1]

The desired compound was prepared according to the procedure of Example D94 using 2-azetidin-3-yl-N-[6-chloro-2, 4,8,18,22-pentaazatetracyclo[14.3.1.1(3,7).1(9,13)]docosa-1(20),3(22),4,6,9(21),10,12,16,18-nonaen-12-yl]acetamide tris(trifluoroacetate) and 1-methyl-1H-pyrazole-4-carbonyl chloride as the starting materials in 50% yield. LCMS for $C_{27}H_{27}ClN_9O_2$ (M+H)$^+$: m/z=544.0.

Example D143

N-[6-Chloro-2,4,8,18,22-pentaazatetracyclo[14.3.1.1 (3,7).1(9,13)]docosa-1(20),3(22),4,6,9(21),10,12,16, 18-nonaen-12-yl]-2-{1-[(5-methylisoxazol-3-yl) carbonyl]azetidin-3-yl}acetamide bis (trifluoroacetate)

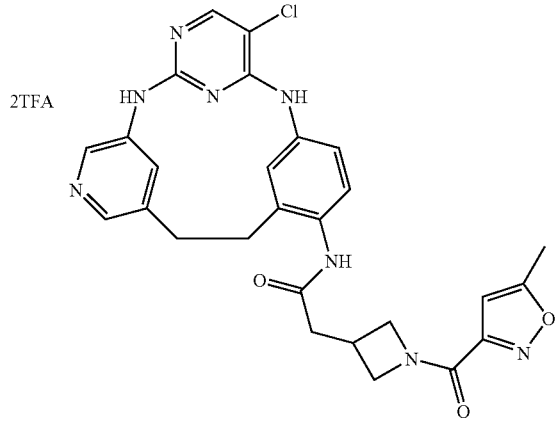 [SMILES: "2TFA" ; Cc1cc(C(=O)N2CC(CC(=O)Nc3ccc4cc3CCc3cncc(c3)Nc3ncc(Cl)c(n3)N4)C2)no1]

The desired compound was prepared according to the procedure of Example D94 using 2-azetidin-3-yl-N-[6-chloro-2, 4,8,18,22-pentaazatetracyclo[14.3.1.1(3,7).1(9,13)]docosa-1(20),3(22),4,6,9(21),10,12,16,18-nonaen-12-yl]acetamide tris(trifluoroacetate) and 5-methylisoxazole-3-carbonyl chloride as the starting materials in 87% yield. LCMS for $C_{27}H_{26}ClN_8O_3$ (M+H)$^+$: m/z=545.0.

Example D144

N-[6-Chloro-2,4,8,18,22-pentaazatetracyclo[14.3.1.1 (3,7).1(9,13)]docosa-1(20),3(22),4,6,9(21),10,12,16, 18-nonaen-12-yl]-2-[1-(isoxazol-5-ylcarbonyl)azetidin-3-yl]acetamide bis(trifluoroacetate)

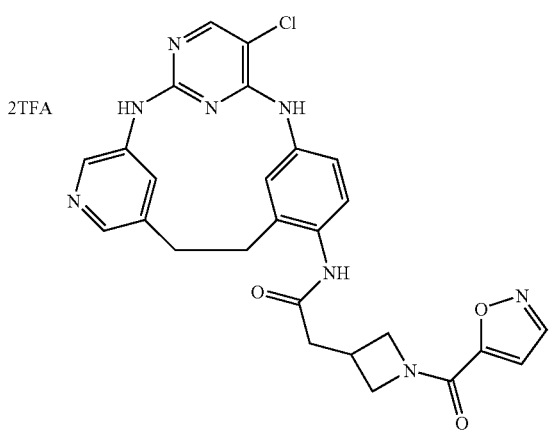 [SMILES: "2TFA" ; O=C(CC1CN(C(=O)c2ccno2)C1)Nc1ccc2cc1CCc1cncc(c1)Nc1ncc(Cl)c(n1)N2]

The desired compound was prepared according to the procedure of Example D94 using 2-azetidin-3-yl-N-[6-chloro-2, 4,8,18,22-pentaazatetracyclo[14.3.1.1(3,7).1(9,13)]docosa-1(20),3(22),4,6,9(21),10,12,16,18-nonaen-12-yl]acetamide tris(trifluoroacetate) and isoxazole-5-carbonyl chloride as the starting materials in 68% yield. LCMS for $C_{26}H_{24}ClN_8O_3$ (M+H)$^+$: m/z=531.0.

Example D145

N-[6-Chloro-2,4,8,18,22-pentaazatetracyclo[14.3.1.1 (3,7).1(9,13)]docosa-1(20),3(22),4,6,9(21),10,12,16, 18-nonaen-12-yl]-2-[1-(1,3-thiazol-2-ylcarbonyl) azetidin-3-yl]acetamide bis(trifluoroacetate)

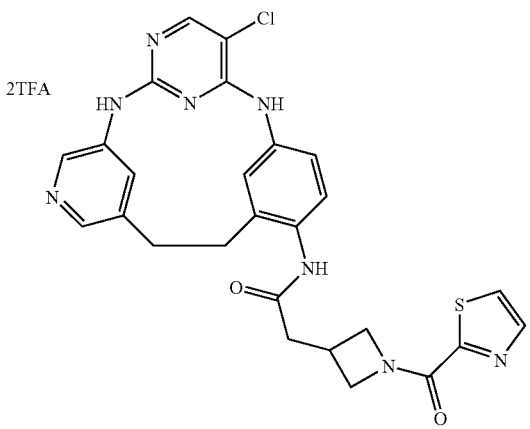 [SMILES: "2TFA" ; O=C(CC1CN(C(=O)c2nccs2)C1)Nc1ccc2cc1CCc1cncc(c1)Nc1ncc(Cl)c(n1)N2]

The desired compound was prepared according to the procedure of Example D94 using 2-azetidin-3-yl-N-[6-chloro-2, 4,8,18,22-pentaazatetracyclo[14.3.1.1(3,7).1(9,13)]docosa-1(20),3(22),4,6,9(21),10,12,16,18-nonaen-12-yl]acetamide tris(trifluoroacetate) and 1,3-thiazole-2-carbonyl chloride as the starting materials in 66% yield. LCMS for $C_{26}H_{24}ClN_8O_2S$ (M+H)$^+$: m/z=547.2.

Example D146

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(methylsulfonyl)azetidin-3-yl]acetamide bis(trifluoroacetate)

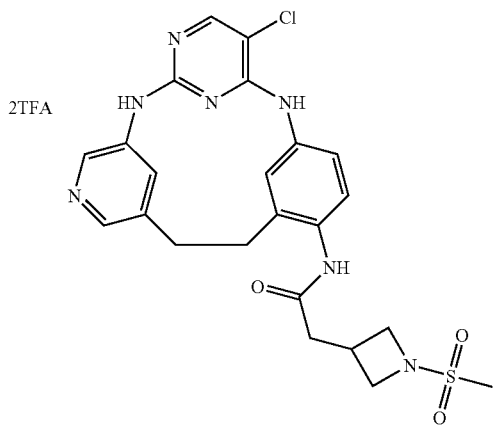 [SMILES: "2TFA" ; CS(=O)(=O)N1CC(CC(=O)Nc2ccc3cc2CCc2cncc(c2)Nc2ncc(Cl)c(n2)N3)C1]

The desired compound was prepared according to the procedure of Example D20, step A, using 2-azetidin-3-yl-N-[6-chloro-2,4,8,18,22-pentaazatetracyclo[14.3.1.1(3,7).1(9,13)]docosa-1(20),3(22),4,6,9(21),10,12,16,18-nonaen-12-yl]acetamide tris(trifluoroacetate) as the starting material in 19% yield. LCMS for $C_{23}H_{25}ClN_7O_3S$ (M+H)$^+$: m/z=514.0.

Example D147

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(1H-1,2,4-triazol-3-ylcarbonyl)azetidin-3-yl]acetamide bis(trifluoroacetate)

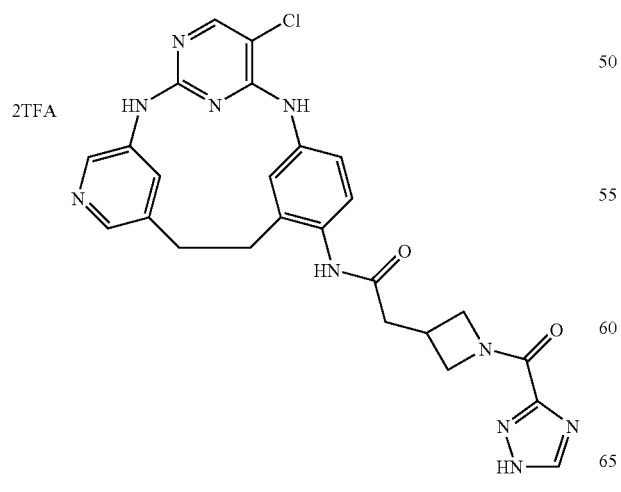

The desired compound was prepared according to the procedure of Example D97, step A, using 2-azetidin-3-yl-N-[6-chloro-2,4,8,18,22-pentaazatetracyclo[14.3.1.1(3,7).1(9,13)]docosa-1(20),3(22),4,6,9(21),10,12,16,18-nonaen-12-yl]acetamide tris(trifluoroacetate) and 1H-1,2,4-triazole-3-carboxylic acid as the starting materials in 57% yield. LCMS for $C_{25}H_{24}ClN_{10}O_2$ (M+H)$^+$: m/z=531.0.

Example D148

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(1H-1,2,3-triazol-4-ylcarbonyl)azetidin-3-yl]acetamide bis(trifluoroacetate)

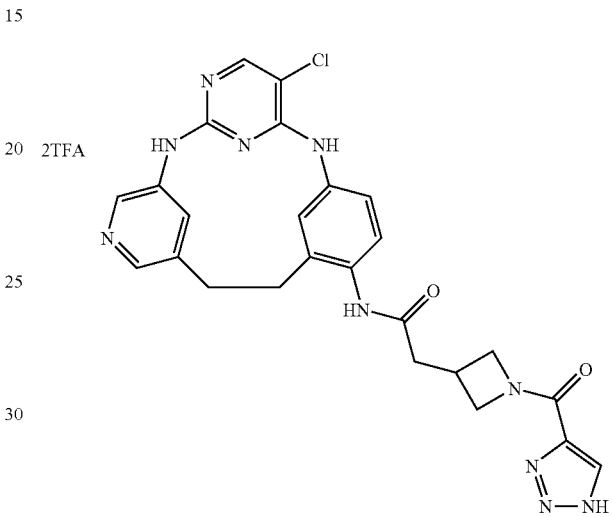

The desired compound was prepared according to the procedure of Example D97, step A, using 2-azetidin-3-yl-N-[6-chloro-2,4,8,18,22-pentaazatetracyclo[14.3.1.1(3,7).1(9,13)]docosa-1(20),3(22),4,6,9(21),10,12,16,18-nonaen-12-yl]acetamide tris(trifluoroacetate) and 4-carboxy-1,2,3-triazole as the starting materials in 72% yield. LCMS for $C_{25}H_{24}ClN_{10}O_2$ (M+H)$^+$: m/z=531.0.

Example D149

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(1H-pyrazol-4-ylcarbonyl)azetidin-3-yl]acetamide bis(trifluoroacetate)

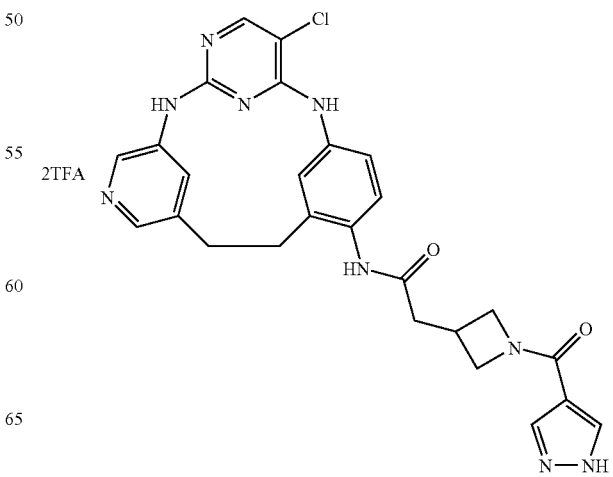

The desired compound was prepared according to the procedure of Example D97, step A, using 2-azetidin-3-yl-N-[6-chloro-2,4,8,18,22-pentaazatetracyclo[14.3.1.1(3,7).1(9,13)]docosa-1(20),3(22),4,6,9(21),10,12,16,18-nonaen-12-yl]acetamide tris(trifluoroacetate) and 1H-pyrazole-4-carboxylic acid as the starting materials in 49% yield. LCMS for $C_{26}H_{25}ClN_9O_2$ (M+H)$^+$: m/z=530.0.

Example D150

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(1H-pyrazol-5-ylcarbonyl)azetidin-3-yl]acetamide bis(trifluoroacetate)

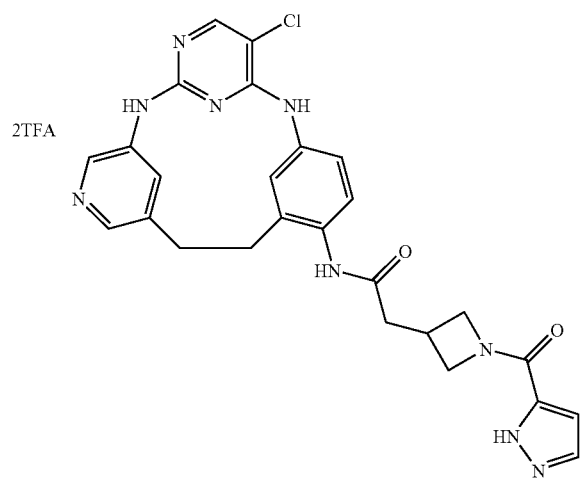 [SMILES: "2TFA" ; O=C(CC1CN(C(=O)c2ccn[nH]2)C1)Nc1ccc2cc1CCc1cncc(c1)Nc1ncc(Cl)c(n1)N2]

The desired compound was prepared according to the procedure of Example D97, step A, using 2-azetidin-3-yl-N-[6-chloro-2,4,8,18,22-pentaazatetracyclo[14.3.1.1(3,7).1(9,13)]docosa-1(20),3(22),4,6,9(21),10,12,16,18-nonaen-12-yl]acetamide tris(trifluoroacetate) and 1H-pyrazole-5-carboxylic acid as the starting materials in 66% yield. LCMS for $C_{26}H_{25}ClN_9O_2$ (M+H)$^+$: m/z=530.0.

Example D151

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(1,3,4-thiadiazol-2-yl)azetidin-3-yl]acetamide tris(trifluoroacetate)

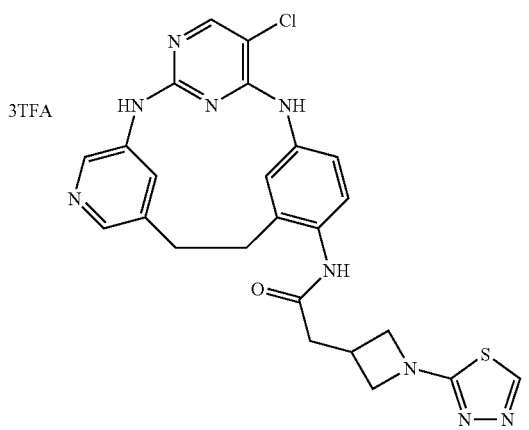 [SMILES: "3TFA" ; O=C(CC1CN(c2nncs2)C1)Nc1ccc2cc1CCc1cncc(c1)Nc1ncc(Cl)c(n1)N2]

The desired compound was prepared according to the procedure of Example A157 using 2-azetidin-3-yl-N-[6-chloro-2,4,8,18,22-pentaazatetracyclo[14.3.1.1(3,7).1(9,13)]docosa-1(20),3(22),4,6,9(21),10,12,16,18-nonaen-12-yl]acetamide tris(trifluoroacetate) and 2-bromo-1,3,4-thiadiazole as the starting materials in 20% yield. LCMS for $C_{24}H_{23}ClN_9OS$ (M+H)$^+$: m/z=520.0.

Example D152

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(1,3-thiazol-2-yl)azetidin-3-yl]acetamide tris(trifluoroacetate)

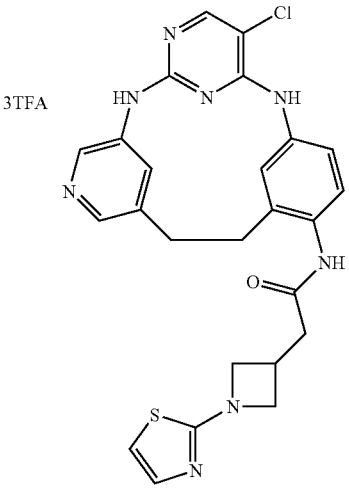 [SMILES: "3TFA" ; O=C(CC1CN(c2nccs2)C1)Nc1ccc2cc1CCc1cncc(c1)Nc1ncc(Cl)c(n1)N2]

A solution of 6-chloro-2,4,8,18,22-pentaazatetracyclo[14.3.1.1(3,7).1(9,13)]docosa-1(20),3(22),4,6,9(21),10,12,16,18-nonaen-12-amine (15 mg, 0.04 mmol), [1-(1,3-thiazol-2-yl)azetidin-3-yl]acetic acid (11 mg, 0.06 mmol), and N,N,',N'-tetramethyl-O-(7-azabenzotriazol-1-yl)uronium hexafluorophosphate (59 mg, 0.16 mmol) in N,N-dimethylformamide (0.5 mL) was treated with triethylamine (22 µL, 0.16 mmol) and stirred at room temperature overnight. The reaction mixture was purified via preparative LCMS to give the desired product (3 mg, 8%) as a solid. LCMS for $C_{25}H_{24}ClN_8OS$ (M+H)$^+$: m/z=519.1.

Example D153

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-(1-pyridin-2-ylazetidin-3-yl)acetamide tris(trifluoroacetate)

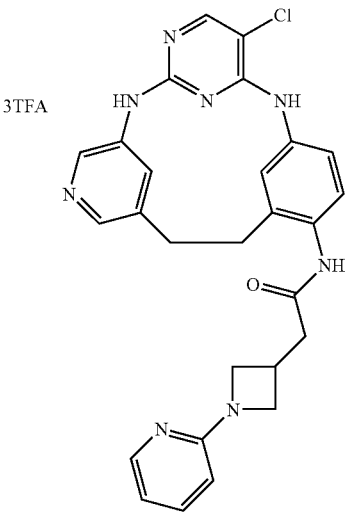 [SMILES: "3TFA" ; O=C(CC1CN(c2ccccn2)C1)Nc1ccc2cc1CCc1cncc(c1)Nc1ncc(Cl)c(n1)N2]

The desired compound was prepared according to the procedure of Example D152 using (1-pyridin-2-ylazetidin-3-yl)acetic acid as the starting materials in 13% yield. LCMS for $C_{27}H_{26}ClN_8O$ (M+H)+: m/z=513.1.

Example D154

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(1,3-thiazol-2-yl)pyrrolidin-3-yl]acetamide tris(trifluoroacetate)

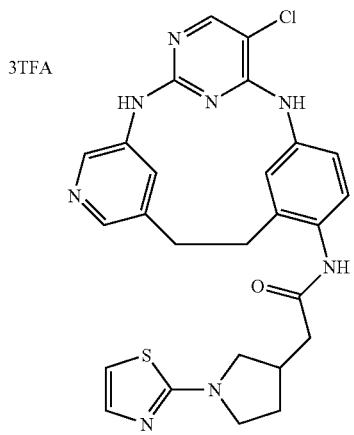 [SMILES: "3TFA" ; O=C(CC1CCN(c2nccs2)C1)Nc1ccc2cc1CCc1cncc(c1)Nc1ncc(Cl)c(n1)N2]

The desired compound was prepared according to the procedure of Example D152 using [1-(1,3-thiazol-2-yl)pyrrolidin-3-yl]acetic acid as the starting materials in 8% yield. LCMS for $C_{26}H_{26}ClN_8OS$ (M+H)+: m/z=533.1.

Example D155

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(1,3,4-thiadiazol-2-yl)pyrrolidin-3-yl]acetamide tris(trifluoroacetate)

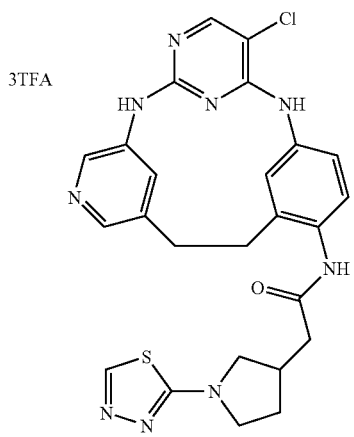 [SMILES: "3TFA" ; O=C(CC1CCN(c2nncs2)C1)Nc1ccc2cc1CCc1cncc(c1)Nc1ncc(Cl)c(n1)N2]

The desired compound was prepared according to the procedure of Example D152 using [1-(1,3,4-thiadiazol-2-yl)pyr-rolidin-3-yl]acetic acid as the starting materials in 8% yield. LCMS for $C_{25}H_{25}ClN_9OS$ (M+H)+: m/z=534.2.

Example D156

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-(1-pyridin-2-ylpyrrolidin-3-yl)acetamide tris(trifluoroacetate)

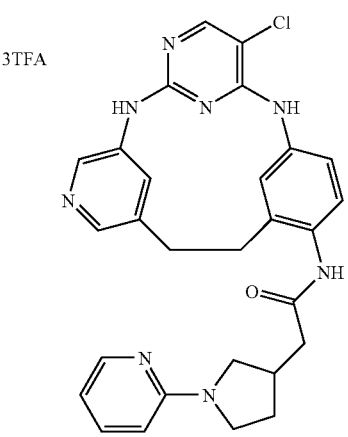 [SMILES: "3TFA" ; O=C(CC1CCN(c2ccccn2)C1)Nc1ccc2cc1CCc1cncc(c1)Nc1ncc(Cl)c(n1)N2]

The desired compound was prepared according to the procedure of Example D152 using (1-pyridin-2-ylpyrrolidin-3-yl)acetic acid as the starting materials in 21% yield. LCMS for $C_{28}H_{28}ClN_8O$ (M+H)+: m/z=527.2.

Example D157

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-(1-pyridin-4-ylpyrrolidin-3-yl)acetamide tris(trifluoroacetate)

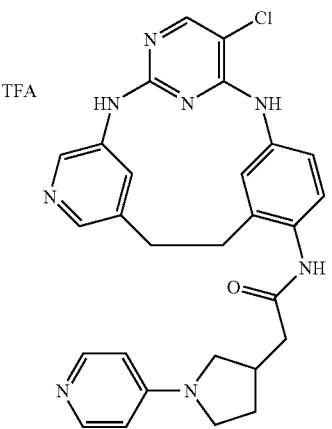

The desired compound was prepared according to the procedure of Example D152 using (1-pyridin-4-ylpyrrolidin-3- yl)acetic acid as the starting material in 13% yield. LCMS for $C_{28}H_{28}ClN_8O$ (M+H)$^+$: m/z=527.2.

Example D158

N-(1-Acetylpiperidin-4-yl)-6-chloro-2,4,8,18,22-pentaazatetracyclo[14.3.1.1(3,7).1(9,13)]docosa-1(20),3(22),4,6,9(21),10,12,16,18-nonaen-12-amine tris(trifluoroacetate)

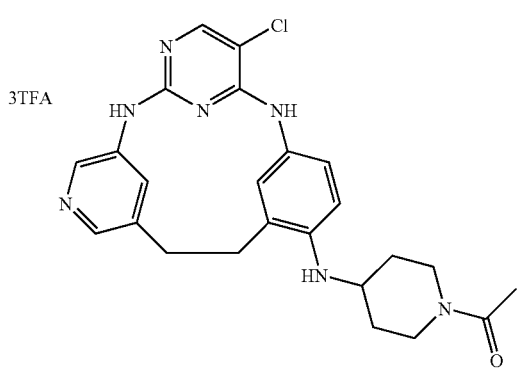 [SMILES: CC(=O)N1CCC(Nc2ccc3cc2CCc2cncc(c2)Nc2ncc(Cl)c(n2)N3)CC1]

Step A: Benzyl 4-[(2-iodo-4-nitrophenyl)amino]piperidine-1-carboxylate

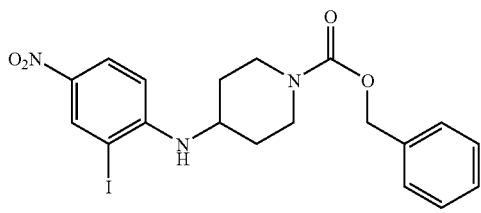 [SMILES: O=C(OCc1ccccc1)N1CCC(Nc2ccc([N+](=O)[O-])cc2I)CC1]

The desired compound was prepared according to the procedure of Example D83, step A, using 1-fluoro-2-iodo-4-nitrobenzene and benzyl 4-aminopiperidine-1-carboxylate as the starting materials in 64% yield. LCMS for $C_{19}H_{21}IN_3O_4$ (M+H)$^+$: m/z=482.0.

Step B: Benzyl 4-[(4-amino-2-iodophenyl)amino]piperidine-1-carboxylate

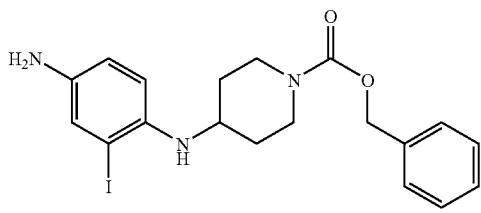

The desired compound was prepared according to the procedure of Example D16, step D, using benzyl 4-[(2-iodo-4-nitrophenyl)amino]piperidine-1-carboxylate as the starting material in 51% yield. LCMS for $C_{19}H_{23}IN_3O_2$ (M+H)$^+$: m/z=452.0.

Step C: Benzyl 4-({4-[(2,5-dichloropyrimidin-4-yl)amino]-2-iodophenyl}amino)piperidine-1-carboxylate

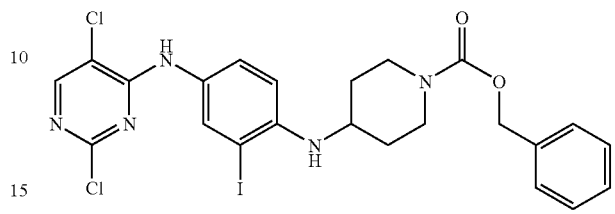

The desired compound was prepared according to the procedure of Example D2, step C, using benzyl 4-[(4-amino-2-iodophenyl)amino]piperidine-1-carboxylate as the starting material in 85% yield. LCMS for $C_{23}H_{23}Cl_2IN_5O_2$ (M+H)$^+$: m/z=598.0, 600.0.

Step D: Benzyl 4-({2-[(E)-2-(5-aminopyridin-3-yl)vinyl]-4-[(2,5-dichloropyrimidin-4-yl)amino]phenyl}amino)piperidine-1-carboxylate

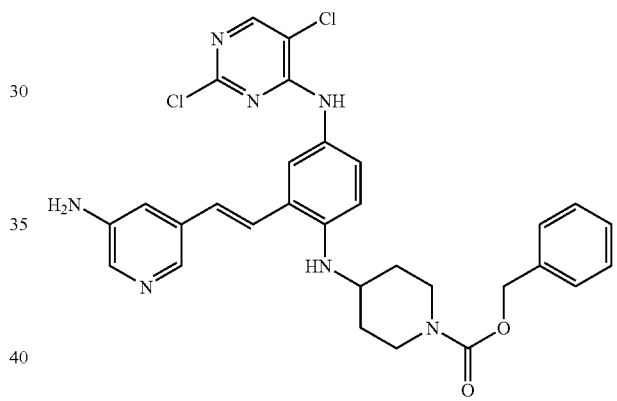

The desired compound was prepared according to the procedure of Example B334, step G, using benzyl 4-({4-[(2,5-dichloropyrimidin-4-yl)amino]-2-iodophenyl}amino)piperidine-1-carboxylate and 5-vinylpyridin-3-amine as the starting materials in 75% yield. LCMS for $C_{30}H_{30}Cl_2N_7O_2$ (M+H)$^+$: m/z=590.2, 592.1.

Step E: Benzyl 4-({2-[2-(5-aminopyridin-3-yl)ethyl]-4-[(2,5-dichloropyrimidin-4-yl)amino]phenyl}amino)piperidine-1-carboxylate

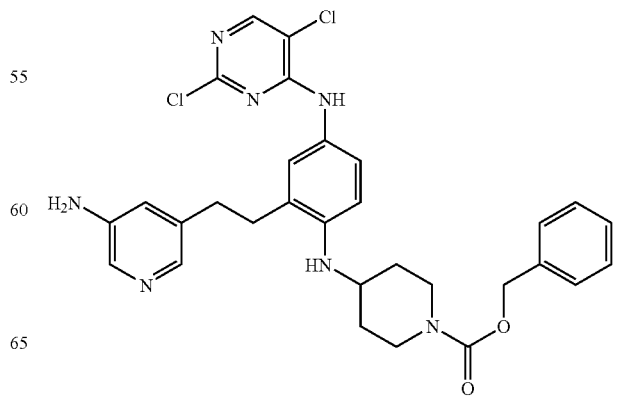

The desired compound was prepared according to the procedure of Example B334, step H, using benzyl 4-({2-[(E)-2-(5-aminopyridin-3-yl)vinyl]-4-[(2,5-dichloropyrimidin-4-yl)amino]phenyl}amino)piperidine-1-carboxylate as the starting material in 85% yield. LCMS for $C_{30}H_{32}Cl_2N_7O_2$ (M+H)$^+$: m/z=592.2, 594.2.

Step F: Benzyl 4-{[6-chloro-2,4,8,18,22-pentaazatetracyclo[14.3.1.1(3,7).1(9,13)]docosa-1(20),3(22),4,6,9(21),10,12,16,18-nonaen-12-yl]amino}piperidine-1-carboxylate

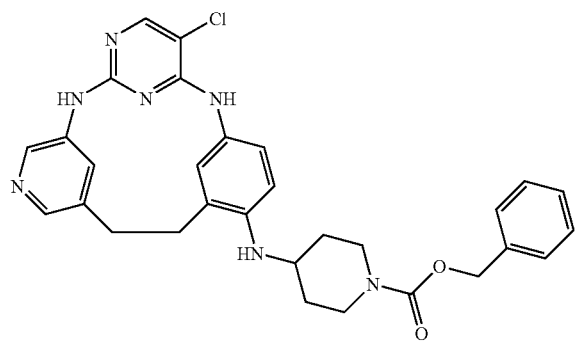 [SMILES: O=C(OCc1ccccc1)N1CCC(Nc2ccc3cc2CCc2cncc(c2)Nc2ncc(Cl)c(n2)N3)CC1]

The desired compound was prepared according to the procedure of Example B20, step H, using benzyl 4-({2-[2-(5-aminopyridin-3-yl)ethyl]-4-[(2,5-dichloropyrimidin-4-yl)amino]phenyl}amino)piperidine-1-carboxylate as the starting material in 63% yield. LCMS for $C_{30}H_{31}ClN_7O_2$ (M+H)$^+$: m/z=556.2.

Step G: 6-Chloro-N-piperidin-4-yl-2,4,8,18,22-pentaazatetracyclo[14.3.1.1(3,7).1(9,13)]docosa-1(20),3(22),4,6,9(21),10,12,16,18-nonaen-12-amine tetrakis(trifluoroacetate)

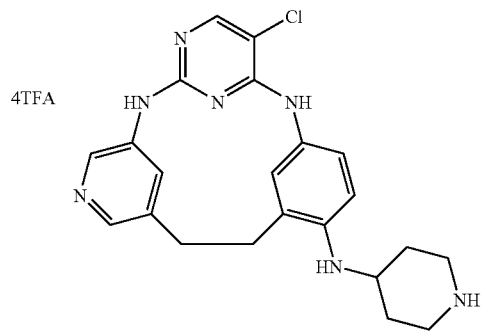 [SMILES: "4TFA" ; Clc1cnc2nc1Nc1ccc(NC3CCNCC3)c(c1)CCc1cncc(c1)N2]

A solution of benzyl 4-{[6-chloro-2,4,8,18,22-pentaazatetracyclo[14.3.1.1(3,7).1(9,13)]docosa-1(20),3(22),4,6,9(21),10,12,16,18-nonaen-12-yl]amino}piperidine-1-carboxylate (0.22 g, 0.39 mmol) in dichloromethane (8 mL) was treated with iodotrimethylsilane (0.14 mL, 0.98 mmol) and stirred at 25° C. for 30 min. The reaction mixture was quenched with 1 M HCl (0.2 mL) and concentrated to a crude residue. This material was purified by preparative LCMS to give the desired product (0.20 g, 66%) as a solid. LCMS for $C_{22}H_{25}ClN_7$ (M+H)$^+$: m/z=422.1.

Step H: N-(1-Acetylpiperidin-4-yl)-6-chloro-2,4,8,18,22-pentaazatetracyclo[14.3.1.1(3,7).1(9,13)]docosa-1(20),3(22),4,6,9(21),10,12,16,18-nonaen-12-amine tris(trifluoroacetate)

The desired compound was prepared according to the procedure of Example D94 using 6-chloro-N-piperidin-4-yl-2,4,8,18,22-pentaazatetracyclo[14.3.1.1(3,7).1(9,13)]docosa-1(20),3(22),4,6,9(21),10,12,16,18-nonaen-12-amine tris(trifluoroacetate) and acetyl chloride as the starting materials in 57% yield. LCMS for $C_{24}H_{27}ClN_7O$ (M+H)$^+$: m/z=464.2.

Example D159

6-Chloro-N-[1-(phenylacetyl)piperidin-4-yl]-2,4,8,18,22-pentaazatetracyclo[14.3.1.1(3,7).1(9,13)]docosa-1(20),3(22),4,6,9(21),10,12,16,18-nonaen-12-amine tris(trifluoroacetate)

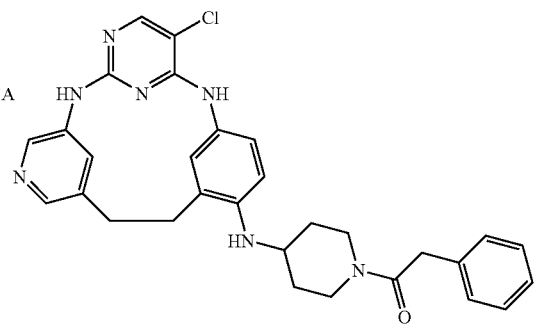

The desired compound was prepared according to the procedure of Example D94 using 6-chloro-N-piperidin-4-yl-2,4,8,18,22-pentaazatetracyclo[14.3.1.1(3,7).1(9,13)]docosa-1(20),3(22),4,6,9(21),10,12,16,18-nonaen-12-amine tris(trifluoroacetate) and benzeneacetyl chloride as the starting materials in 29% yield. LCMS for $C_{30}H_{31}ClN_7O$ (M+H)$^+$: m/z=540.2.

Example D160

6-Chloro-N-{1-[(5-methylisoxazol-3-yl)carbonyl]piperidin-4-yl}-2,4,8,18,22-pentaazatetracyclo[14.3.1.1(3,7).1(9,13)]docosa-1(20),3(22),4,6,9(21),10,12,16,18-nonaen-12-amine tris(trifluoroacetate)

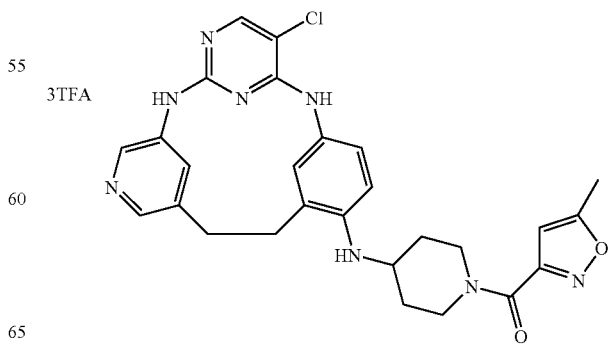

The desired compound was prepared according to the procedure of Example D94 using 6-chloro-N-piperidin-4-yl-2,4,8,18,22-pentaazatetracyclo[14.3.1.1(3,7).1(9,13)]docosa-1(20),3(22),4,6,9(21),10,12,16,18-nonaen-12-amine tris(trifluoroacetate) and 5-methylisoxazole-3-carbonyl chloride as the starting materials in 52% yield. LCMS for $C_{27}H_{28}ClN_8O_2$ (M+H)$^+$: m/z=531.2.

Example D161

12-[2-(1-Acetylpiperidin-4-yl)ethoxy]-6-chloro-2,4,8,18,22-pentaazatetracyclo[14.3.1.1(3,7).1(9,13)]docosa-1(20),3(22),4,6,9(21),10,12,16,18-nonaene bis(trifluoroacetate)

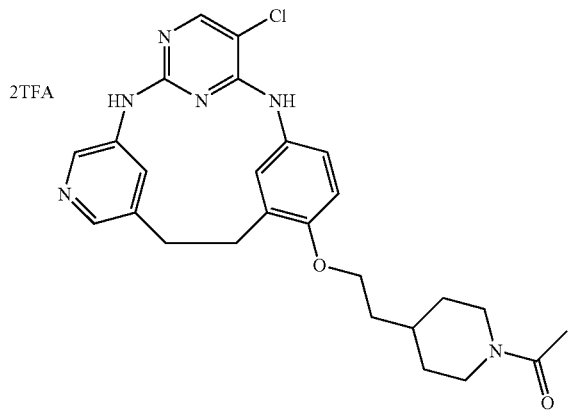 [SMILES: "2TFA" ; CC(=O)N1CCC(CCOc2ccc3cc2CCc2cncc(c2)Nc2ncc(Cl)c(n2)N3)CC1]

Step A: 2-Iodo-4-nitroaniline

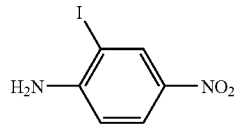 [SMILES: Nc1ccc([N+](=O)[O-])cc1I]

A solution of iodine monochloride (25.8 mL, 514 mmol) in water (220 mL) at 0° C. was treated with concentrated hydrogen chloride (87 mL, 2800 mmol) and stirred until the iodine monochloride dissolved. This cooled ICl solution was then added to a solution of p-nitroaniline (71 g, 510 mmol) in water (590 mL) and concentrated hydrogen chloride (50 mL, 2000 mmol) and stirred at 20° C. for 3 hours. The reaction mixture was filtered, washed with water, and dried to give the desired product (132 g, 94%) as a yellow solid. LCMS for $C_6H_{61}N_2O_2$ (M+H)$^+$: m/z=264.7.

Step B: 1-Fluoro-2-iodo-4-nitrobenzene

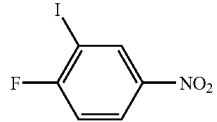 [SMILES: O=[N+]([O-])c1ccc(F)c(I)c1]

A solution of nitrosonium tetrafluoroborate (24 g, 0.21 mol) in dichloromethane (200 mL) at 0° C. was treated with a solution of 2-iodo-4-nitroaniline (50 g, 0.19 mol) in dichloromethane (350 mL) and stirred at 0° C. for 1 h. The dichloromethane was concentrated to about half volume and the reaction mixture was treated with 1,2-dichlorobenzene (300 mL). The remaining dichloromethane was further concentrated in vacuo. The resultant 1,2-dichlorobenzene suspension was heated at 110° C. for 1 h, cooled to 20° C., and treated with water (200 mL) and dichloromethane (500 mL). The reaction mixture was filtered over celite and the celite was washed with dichloromethane and water. The aqueous layer of the filtrate was separated and extracted with dichloromethane (2×). The combined organic layers were washed with 20% sodium thiosulfate and brine, dried over anhydrous sodium sulfate, and filtered. The dichloromethane was removed under standard conditions while the 1,2-dichlorobenzene was removed via vacuum distillation to give a crude dark oil. This material was purified by distillation to give the desired product (19 g, 38%) as a solid.

Step C: tert-Butyl 4-[2-(2-iodo-4-nitrophenoxy)ethyl]piperidine-1-carboxylate

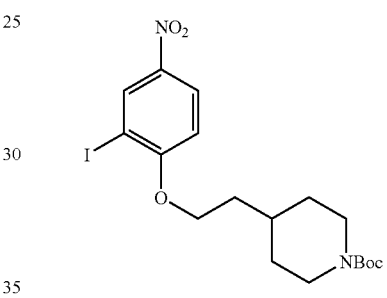

A solution of sodium hydride (0.16 g, 3.9 mmol) in tetrahydrofuran (10 mL) at 0° C. was treated with a solution of tert-butyl 4-(2-hydroxyethyl)piperidine-1-carboxylate (0.82 mL, 3.7 mmol) in tetrahydrofuran (5 mL) and stirred at 0° C. for 30 minutes. The reaction mixture was treated with a solution of 1-fluoro-2-iodo-4-nitrobenzene (1.0 g, 3.7 mmol) in tetrahydrofuran (5 mL) and heated at 70° C. for 16 h. The reaction mixture was concentrated, diluted with ethyl acetate, and washed with water. The aqueous layer was separated and extracted with additional ethyl acetate. The combined organic extracts were washed with brine, dried with sodium sulfate, filtered, and concentrated to a crude brown oil. Purification by flash column chromatography gave the desired product (1.4 g, 81%) as a yellow oil. LCMS for $C_{18}H_{25}IN_2O_5Na$ (M+Na)$^+$: m/z=499.0.

Step D: tert-Butyl 4-[2-(4-amino-2-iodophenoxy)ethyl]piperidine-1-carboxylate

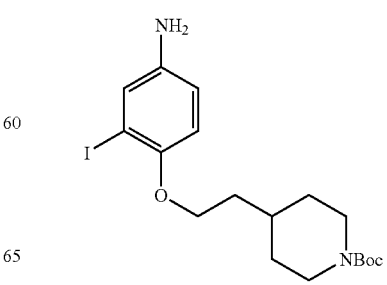

The desired compound was prepared according to the procedure of Example D2, step B, using tert-butyl 4-[2-(2-iodo-4-nitrophenoxy)ethyl]piperidine-1-carboxylate as the starting material in 99% yield. LCMS for $C_{18}H_{271}N_2O_3Na$ (M+Na)$^+$: m/z=469.0.

Step E: tert-Butyl 4-(2-{4-[(2,5-dichloropyrimidin-4-yl)amino]-2-iodophenoxy}ethyl)piperidine-1-carboxylate

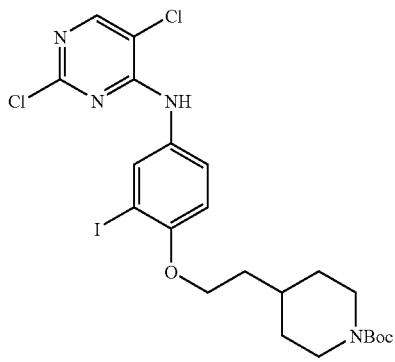 [SMILES: CC(C)(C)OC(=O)N1CCC(CCOc2ccc(Nc3nc(Cl)ncc3Cl)cc2I)CC1]

The desired compound was prepared according to the procedure of Example D2, step C, using tert-butyl 4-[2-(4-amino-2-iodophenoxy)ethyl]piperidine-1-carboxylate as the starting material in 87% yield. LCMS for $C_{22}H_{27}Cl_{21}N_4O_3Na$ (M+Na)$^+$: m/z=615.0.

Step F: tert-Butyl 4-(2-{2-[(E)-2-(5-aminopyridin-3-yl)vinyl]-4-[(2,5-dichloropyrimidin-4-yl)amino]phenoxy}ethyl)piperidine-1-carboxylate

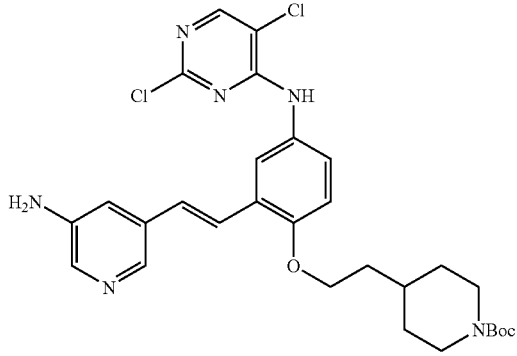 [SMILES: CC(C)(C)OC(=O)N1CCC(CCOc2ccc(Nc3nc(Cl)ncc3Cl)cc2/C=C/c2cncc(N)c2)CC1]

The desired compound was prepared according to the procedure of Example B334, step G, using tert-butyl 4-(2-{4-[(2,5-dichloropyrimidin-4-yl)amino]-2-iodophenoxy}ethyl)piperidine-1-carboxylate and 5-vinylpyridine-3-amine as the starting materials in 99% yield. LCMS for $C_{29}H_{35}Cl_2N_6O_3$ (M+H)$^+$: m/z=585.3, 587.2.

Step G: tert-Butyl 4-(2-{2-[2-(5-aminopyridin-3-yl)ethyl]-4-[(2,5-dichloropyrimidin-4-yl)amino]phenoxy}ethyl)piperidine-1-carboxylate

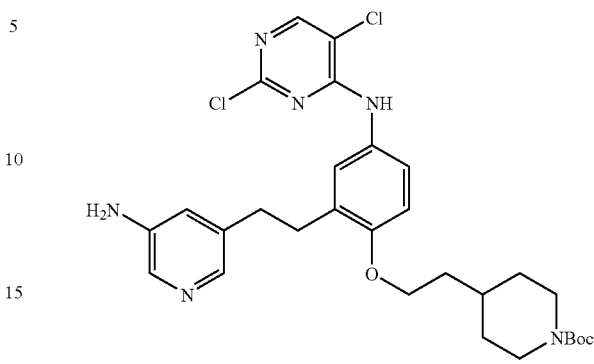

The desired compound was prepared according to the procedure of Example B334, step H, using tert-butyl 4-(2-{2-[(E)-2-(5-aminopyridin-3-yl)vinyl]-4-[(2,5-dichloropyrimidin-4-yl)amino]phenoxy}ethyl)piperidine-1-carboxylate as the starting material in 86% yield. LCMS for $C_{29}H_{37}Cl_2N_6O_3$ (M+H)$^+$: m/z=587.2, 589.2.

Step H: tert-Butyl 4-(2-{[6-chloro-2,4,8,18,22-pentaazatetracyclo[14.3.1.1(3,7).1(9,13)]docosa-1(20),3(22),4,6,9(21),10,12,16,18-nonaen-12-yl]oxy}ethyl)piperidine-1-carboxylate

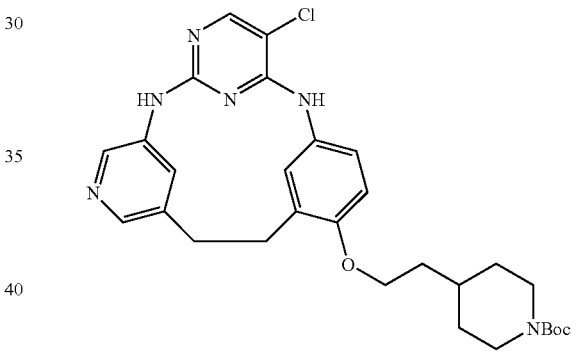

The desired compound was prepared according to the procedure of Example B20, step H, using tert-butyl 4-(2-{2-[2-(5-aminopyridin-3-yl)ethyl]-4-[(2,5-dichloropyrimidin-4-yl)amino]phenoxy}ethyl)piperidine-1-carboxylate as the starting material. This material was used in the next step without further purification.

Step I: 6-Chloro-12-(2-piperidin-4-ylethoxy)-2,4,8,18,22-pentaazatetracyclo[14.3.1.1(3,7).1(9,13)]docosa-1(20),3(22),4,6,9(21),10,12,16,18-nonaene tris(trifluoroacetate)

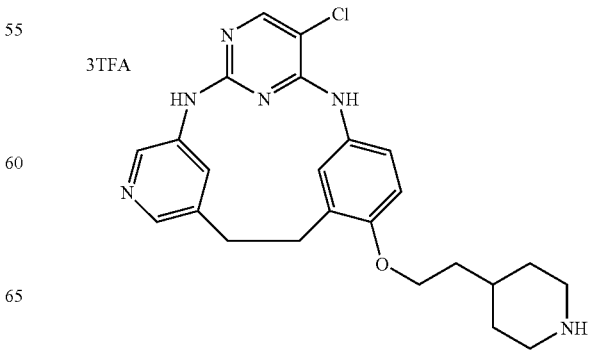

The desired compound was prepared according to the procedure of Example D16, step B, using tert-butyl 4-(2-{[6-chloro-2,4,8,18,22-pentaazatetracyclo[14.3.1.1(3,7).1(9,13)]docosa-1(20),3(22),4,6,9(21),10,12,16,18-nonaen-12-yl]oxy}ethyl)piperidine-1-carboxylate as the starting material in 48% yield (2 steps). LCMS for $C_{24}H_{28}ClN_6O$ (M+H)$^+$: m/z=451.1.

Step J: 12-[2-(1-Acetylpiperidin-4-yl)ethoxy]-6-chloro-2,4,8,18,22-pentaazatetracyclo[14.3.1.1(3,7).1(9,13)]docosa-1(20),3(22),4,6,9(21),10,12,16,18-nonaene bis(trifluoroacetate)

The desired compound was prepared according to the procedure of Example D94 using 6-chloro-12-(2-piperidin-4-ylethoxy)-2,4,8,18,22-pentaazatetracyclo[14.3.1.1(3,7).1(9,13)]docosa-1(20),3(22),4,6,9(21),10,12,16,18-nonaene tris(trifluoroacetate) and acetyl chloride as the starting materials in 66% yield. LCMS for $C_{26}H_{30}ClN_6O_2$ (M+H)$^+$: m/z=493.1.

Example D162

4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]oxy}ethyl)-N-phenylpiperidine-1-carboxamide bis(trifluoroacetate)

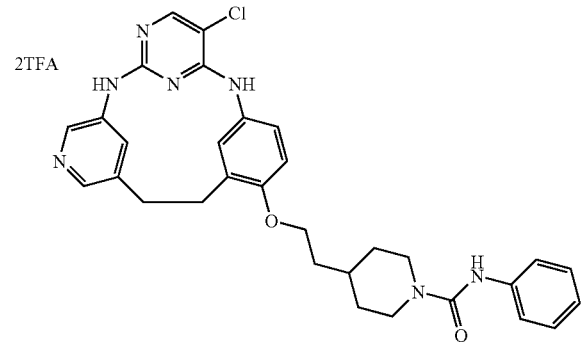 [SMILES: "2TFA" ; O=C(Nc1ccccc1)N1CCC(CCOc2ccc3cc2CCc2cncc(c2)Nc2ncc(Cl)c(n2)N3)CC1]

The desired compound was prepared according to the procedure of Example D41 using 6-chloro-12-(2-piperidin-4-ylethoxy)-2,4,8,18,22-pentaazatetracyclo[14.3.1.1(3,7).1(9,13)]docosa-1(20),3(22),4,6,9(21),10,12,16,18-nonaene tris(trifluoroacetate) and phenyl isocyanate as the starting materials in 50% yield. LCMS for $C_{31}H_{33}ClN_7O_2$ (M+H)$^+$: m/z=570.1.

Example D163

2-{[4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]oxy}ethyl)piperidin-1-yl]sulfonyl}benzonitrilebis(trifluoroacetate)

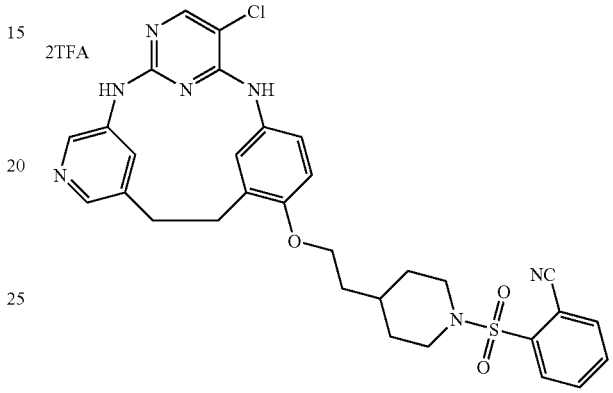

The desired compound was prepared according to the procedure of Example D20, step A, using 6-chloro-12-(2-piperidin-4-ylethoxy)-2,4,8,18,22-pentaazatetracyclo[14.3.1.1(3,7).1(9,13)]docosa-1(20),3(22),4,6,9(21),10,12,16,18-nonaene tris(trifluoroacetate) and 2-cyanobenzenesulfonyl chloride as the starting materials in 62% yield. LCMS for $C_{31}H_{31}ClN_7O_3S$ (M+H)$^+$: m/z=616.0.

Example D164

4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]oxy}ethyl)-N-(2-methyl-3-furyl)piperidine-1-carboxamide bis(trifluoroacetate)

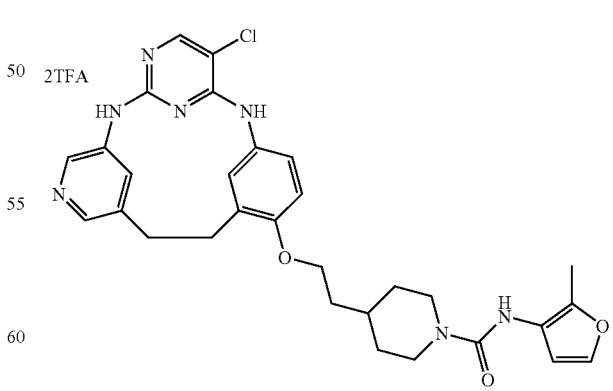

The desired compound was prepared according to the procedure of Example D41 using 6-chloro-12-(2-piperidin-4-ylethoxy)-2,4,8,18,22-pentaazatetracyclo[14.3.1.1(3,7).1(9,13)]docosa-1(20),3(22),4,6,9(21),10,12,16,18-nonaene tris (trifluoroacetate) and 3-isocyanato-2-methylfuran as the starting materials in 8% yield. LCMS for $C_{30}H_{33}ClN_7O_3$ (M+H)+: m/z=574.1.

Example D165

4-(2-{[6-Chloro-2,4,8,18,22-pentaazatetracyclo [14.3.1.1(3,7).1(9,13)]docosa-1(20),3(22),4,6,9(21), 10,12,16,18-nonaen-12-yl]oxy}ethyl)-N-(2-furylmethyl)piperidine-1-carboxamide bis(trifluoroacetate)

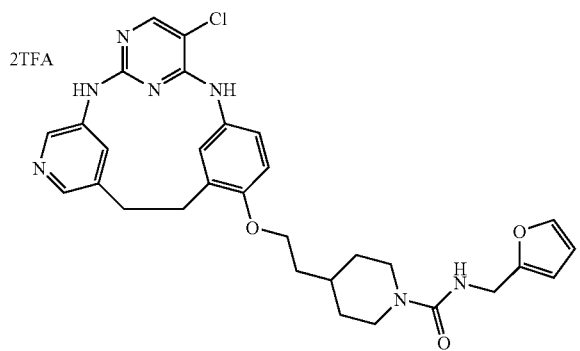 [SMILES: "2TFA" ; O=C(NCc1ccco1)N1CCC(CCOc2ccc3cc2CCc2cncc(c2)Nc2ncc(Cl)c(n2)N3)CC1]

The desired compound was prepared according to the procedure of Example D41 using 6-chloro-12-(2-piperidin-4-ylethoxy)-2,4,8,18,22-pentaazatetracyclo[14.3.1.1(3,7).1(9,13)]docosa-1(20),3(22),4,6,9(21),10,12,16,18-nonaene tris (trifluoroacetate) and 2-(isocyanatomethyl)furan as the starting materials in 40% yield. LCMS for $C_{30}H_{33}ClN_7O_3$ (M+H)+: m/z=574.1.

Example D166

4-(2-{[6-Chloro-2,4,8,18,22-pentaazatetracyclo [14.3.1.1(3,7).1(9,13)]docosa-1(20),3(22),4,6,9(21), 10,12,16,18-nonaen-12-yl]oxy}ethyl)-N-3-thienylpiperidine-1-carboxamide bis(trifluoroacetate)

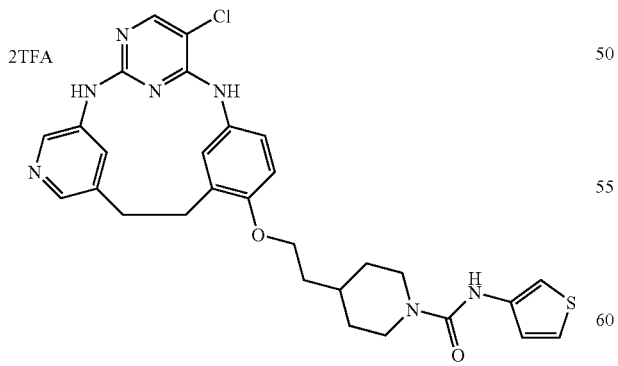

The desired compound was prepared according to the procedure of Example D41 using 6-chloro-12-(2-piperidin-4-ylethoxy)-2,4,8,18,22-pentaazatetracyclo[14.3.1.1(3,7).1(9,13)]docosa-1(20),3(22),4,6,9(21),10,12,16,18-nonaene tris (trifluoroacetate) and 3-isocyanatothiophene as the starting materials in 30% yield. LCMS for $C_{29}H_{31}ClN_7O_2S$ (M+H)+: m/z=576.0.

Example D167

4-(2-{[6-Chloro-2,4,8,18,22-pentaazatetracyclo [14.3.1.1(3,7).1(9,13)]docosa-1(20),3(22),4,6,9(21), 10,12,16,18-nonaen-12-yl]oxy}ethyl)-N-2-thienylpiperidine-1-carboxamide bis(trifluoroacetate)

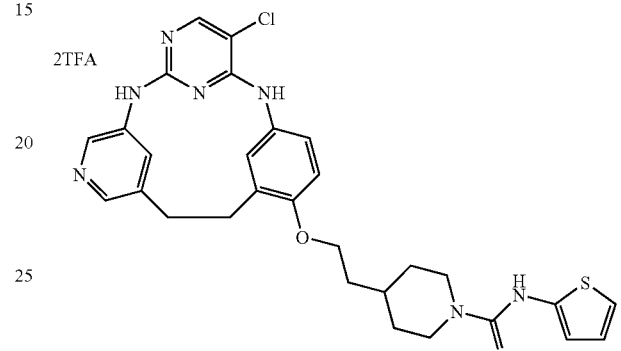

The desired compound was prepared according to the procedure of Example D41 using 6-chloro-12-(2-piperidin-4-ylethoxy)-2,4,8,18,22-pentaazatetracyclo[14.3.1.1(3,7).1(9,13)]docosa-1(20),3(22),4,6,9(21),10,12,16,18-nonaene tris (trifluoroacetate) and 2-isocyanatothiophene as the starting materials in 20% yield. LCMS for $C_{29}H_{31}ClN_7O_2S$ (M+H)+: m/z=576.0.

Example D168

4-(2-{[6-Chloro-2,4,8,18,22-pentaazatetracyclo [14.3.1.1(3,7).1(9,13)]docosa-1(20),3(22),4,6,9(21), 10,12,16,18-nonaen-12-yl]oxy}ethyl)-N-(4-fluorophenyl)piperidine-1-carboxamide bis (trifluoroacetate)

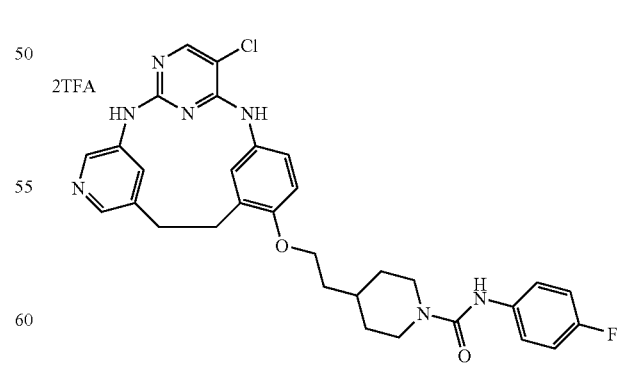

The desired compound was prepared according to the procedure of Example D41 using 6-chloro-12-(2-piperidin-4-ylethoxy)-2,4,8,18,22-pentaazatetracyclo[14.3.1.1(3,7).1(9,13)]docosa-1(20),3(22),4,6,9(21),10,12,16,18-nonaene tris (trifluoroacetate) and 1-fluoro-4-isocyanatobenzene as the starting materials in 40% yield. LCMS for $C_{31}H_{32}ClFN_7O_2$ (M+H)$^+$: m/z=588.2.

Example D169

4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]oxy}ethyl)-N-(3-fluorophenyl)piperidine-1-carboxamide bis (trifluoroacetate)

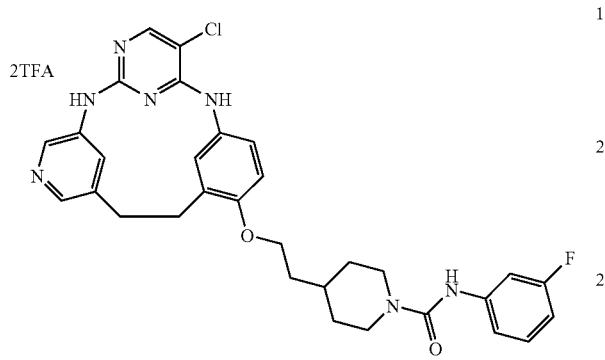

The desired compound was prepared according to the procedure of Example D41 using 6-chloro-12-(2-piperidin-4-ylethoxy)-2,4,8,18,22-pentaazatetracyclo[14.3.1.1(3,7).1(9,13)]docosa-1(20),3(22),4,6,9(21),10,12,16,18-nonaene tris (trifluoroacetate) and 1-fluoro-3-isocyanatobenzene as the starting materials in 60% yield. LCMS for $C_{31}H_{32}ClFN_7O_2$ (M+H)$^+$: m/z=588.1.

Example D170

4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]oxy}ethyl)-N-(2-fluorophenyl)piperidine-1-carboxamide bis (trifluoroacetate)

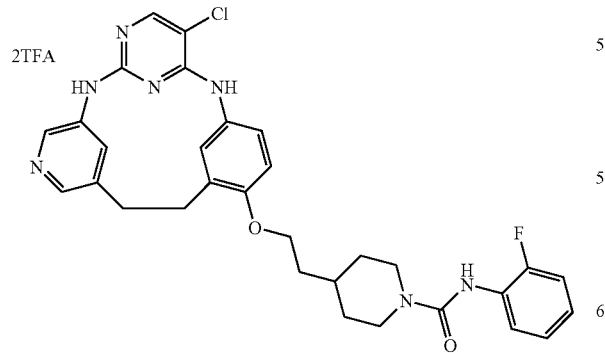

The desired compound was prepared according to the procedure of Example D41 using 6-chloro-12-(2-piperidin-4-ylethoxy)-2,4,8,18,22-pentaazatetracyclo[14.3.1.1(3,7).1(9,13)]docosa-1(20),3(22),4,6,9(21),10,12,16,18-nonaene tris (trifluoroacetate) and 1-fluoro-2-isocyanatobenzene as the starting materials in 40% yield. LCMS for $C_{31}H_{32}ClFN_7O_2$ (M+H)$^+$: m/z=588.1.

Example D171

4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]oxy}ethyl)-N-(3,5-dimethylisoxazol-4-yl)piperidine-1-carboxamide bis (trifluoroacetate)

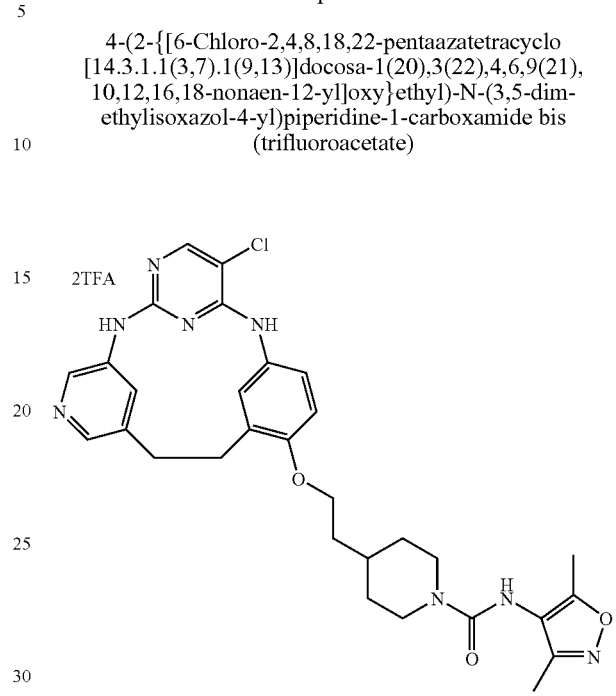

The desired compound was prepared according to the procedure of Example D41 using 6-chloro-12-(2-piperidin-4-ylethoxy)-2,4,8,18,22-pentaazatetracyclo[14.3.1.1(3,7).1(9,13)]docosa-1(20),3(22),4,6,9(21),10,12,16,18-nonaene tris (trifluoroacetate) and 4-isocyanato-3,5-dimethylisoxazole as the starting materials in 50% yield. LCMS for $C_{30}H_{34}ClN_8O_3$ (M+H)$^+$: m/z=589.1.

Example D172

4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]oxy}ethyl)-N-(4-methyl-2-thienyl)piperidine-1-carboxamide bis (trifluoroacetate)

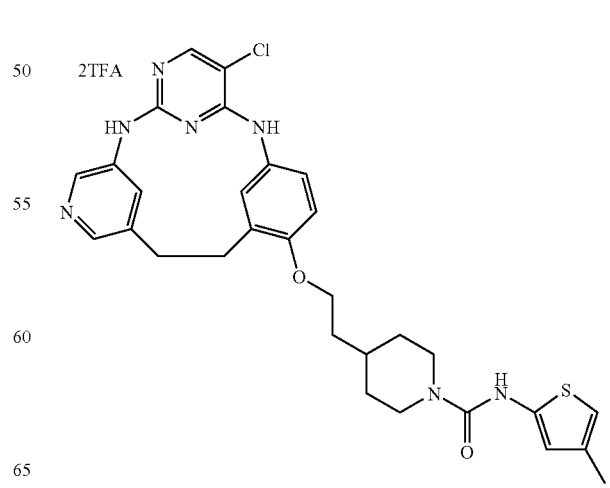

The desired compound was prepared according to the procedure of Example D41 using 6-chloro-12-(2-piperidin-4-ylethoxy)-2,4,8,18,22-pentaazatetracyclo[14.3.1.1(3,7).1(9,13)]docosa-1(20),3(22),4,6,9(21),10,12,16,18-nonaene tris(trifluoroacetate) and 2-isocyanato-4-methylthiophene as the starting materials in 34% yield. LCMS for $C_{30}H_{33}ClN_7O_2S$ (M+H)$^+$: m/z=590.0.

Example D173

4-(2-{[6-Chloro-2,4,8,18,22-pentaazatetracyclo [14.3.1.1(3,7).1(9,13)]docosa-1(20),3(22),4,6,9(21), 10,12,16,18-nonaen-12-yl]oxy}ethyl)-N-(2-cyanophenyl)piperidine-1-carboxamide bis (trifluoroacetate)

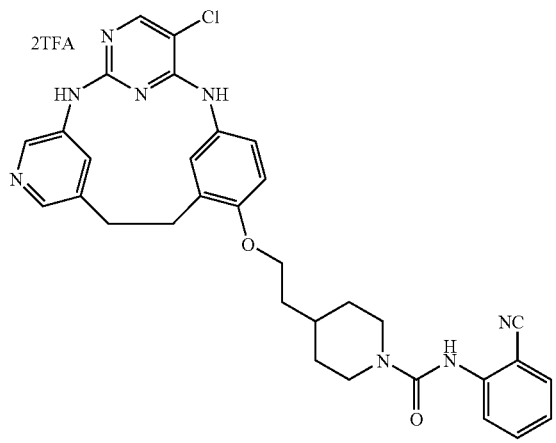

The desired compound was prepared according to the procedure of Example D41 using 6-chloro-12-(2-piperidin-4-ylethoxy)-2,4,8,18,22-pentaazatetracyclo[14.3.1.1(3,7).1(9,13)]docosa-1(20),3(22),4,6,9(21),10,12,16,18-nonaene tris(trifluoroacetate) and 2-isocyanatobenzonitrile as the starting materials in 40% yield. LCMS for $C_{32}H_{32}ClN_8O_2$ (M+H)$^+$: m/z=595.0.

Example D174

4-(2-{[6-Chloro-2,4,8,18,22-pentaazatetracyclo [14.3.1.1(3,7).1(9,13)]docosa-1(20),3(22),4,6,9(21), 10,12,16,18-nonaen-12-yl]oxy}ethyl)-N-(4-cyanophenyl)piperidine-1-carboxamide bis (trifluoroacetate)

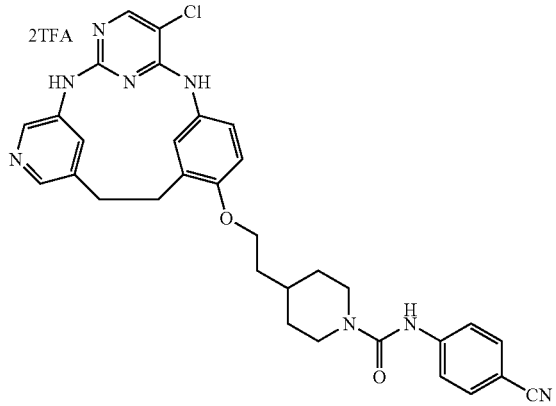 [SMILES: "2TFA" ; N#Cc1ccc(NC(=O)N2CCC(CCOc3ccc4cc3CCc3cncc(c3)Nc3ncc(Cl)c(n3)N4)CC2)cc1]

The desired compound was prepared according to the procedure of Example D41 using 6-chloro-12-(2-piperidin-4-ylethoxy)-2,4,8,18,22-pentaazatetracyclo[14.3.1.1(3,7).1(9,13)]docosa-1(20),3(22),4,6,9(21),10,12,16,18-nonaene tris (trifluoroacetate) and 4-isocyanatobenzonitrile as the starting materials in 40% yield. LCMS for $C_{32}H_{32}ClN_8O_2$ (M+H)$^+$: m/z=595.0.

Example D175

4-(2-{[6-Chloro-2,4,8,18,22-pentaazatetracyclo [14.3.1.1(3,7).1(9,13)]docosa-1(20),3(22),4,6,9(21), 10,12,16,18-nonaen-12-yl]oxy}ethyl)-N-(2,2-dimethyl-2,3-dihydro-1-benzofuran-7-yl)piperidine-1-carboxamide bis(trifluoroacetate)

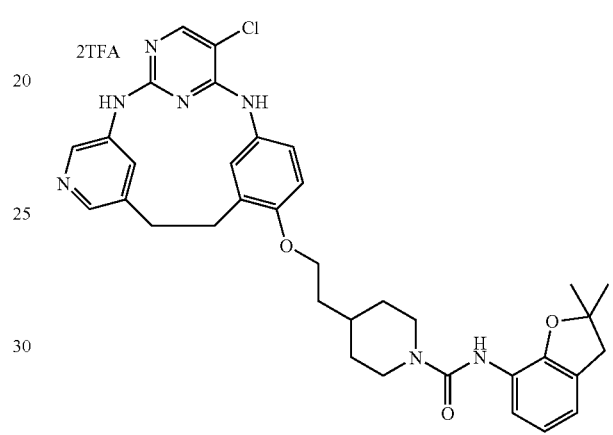

The desired compound was prepared according to the procedure of Example D41 using 6-chloro-12-(2-piperidin-4-ylethoxy)-2,4,8,18,22-pentaazatetracyclo[14.3.1.1(3,7).1(9,13)]docosa-1(20),3(22),4,6,9(21),10,12,16,18-nonaene tris (trifluoroacetate) and 7-isocyanato-2,2-dimethyl-2,3-dihydro-1-benzofuran as the starting materials in 60% yield. LCMS for $C_{35}H_{39}ClN_7O_3$ (M+H)$^+$: m/z=640.1.

Example D176

4-(2-{[6-Chloro-2,4,8,18,22-pentaazatetracyclo [14.3.1.1(3,7).1(9,13)]docosa-1(20),3(22),4,6,9(21), 10,12,16,18-nonaen-12-yl]oxy}ethyl)-N-(6-morpholin-4-ylpyridin-2-yl)piperidine-1-carboxamide tris (trifluoroacetate)

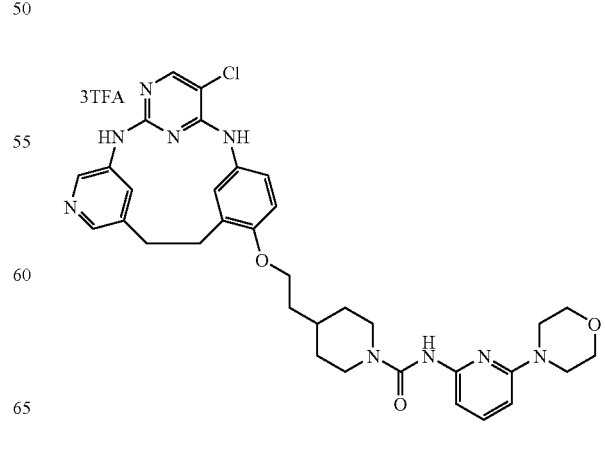

The desired compound was prepared according to the procedure of Example D41 using 6-chloro-12-(2-piperidin-4-ylethoxy)-2,4,8,18,22-pentaazatetracyclo[14.3.1.1(3,7).1(9,13)]docosa-1(20),3(22),4,6,9(21),10,12,16,18-nonaene tris(trifluoroacetate) and 4-(6-isocyanatopyridin-2-yl)morpholine as the starting materials in 45% yield. LCMS for $C_{34}H_{39}ClN_9O_3$ (M+H)$^+$: m/z=656.2.

Example D177

6-Chloro-12-{2-[1-(pyrazin-2-ylcarbonyl)piperidin-4-yl]ethoxy}-2,4,8,18,22-pentaazatetracyclo[14.3.1.1(3,7).1(9,13)]docosa-1(20),3(22),4,6,9(21),10,12,16,18-nonaene tris(trifluoroacetate)

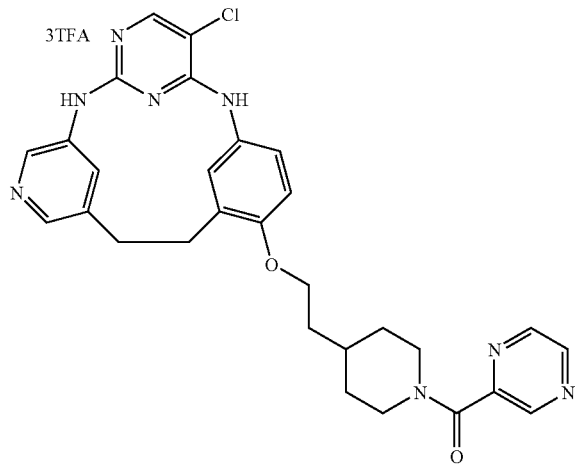 [SMILES: "3TFA" ; O=C(c1cnccn1)N1CCC(CCOc2ccc3cc2CCc2cncc(c2)Nc2ncc(Cl)c(n2)N3)CC1]

The desired compound was prepared according to the procedure of Example D94 using 6-chloro-12-(2-piperidin-4-ylethoxy)-2,4,8,18,22-pentaazatetracyclo[14.3.1.1(3,7).1(9,13)]docosa-1(20),3(22),4,6,9(21),10,12,16,18-nonaene tris(trifluoroacetate) and pyrazine-2-carbonyl chloride as the starting materials in 50% yield. LCMS for $C_{29}H_{30}ClN_8O_2$ (M+H)$^+$: m/z=557.0.

Example D178

6-Chloro-12-(2-{1-[(5-methylisoxazol-4-yl)carbonyl]piperidin-4-yl}ethoxy)-2,4,8,18,22-pentaazatetracyclo[14.3.1.1(3,7).1(9,13)]docosa-1(20),3(22),4,6,9(21),10,12,16,18-nonaene bis(trifluoroacetate)

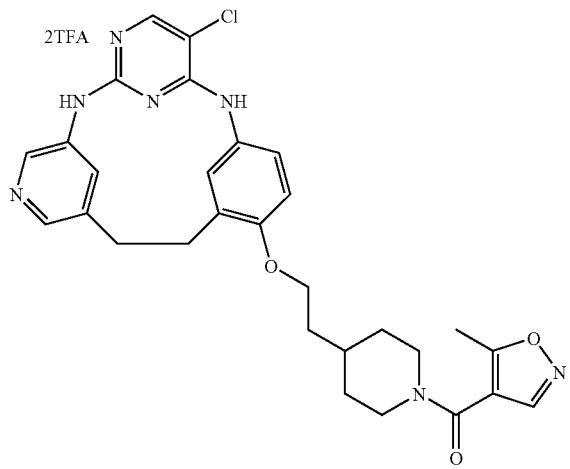 [SMILES: "2TFA" ; Cc1oncc1C(=O)N1CCC(CCOc2ccc3cc2CCc2cncc(c2)Nc2ncc(Cl)c(n2)N3)CC1]

The desired compound was prepared according to the procedure of Example D94 using 6-chloro-12-(2-piperidin-4-ylethoxy)-2,4,8,18,22-pentaazatetracyclo[14.3.1.1(3,7).1(9,13)]docosa-1(20),3(22),4,6,9(21),10,12,16,18-nonaene tris(trifluoroacetate) and 5-methylisoxazole-4-carbonyl chloride as the starting materials in 40% yield. LCMS for $C_{29}H_{31}ClN_7O_3$ (M+H)$^+$: m/z=560.0.

Example D179

6-Chloro-12-(2-{1-[(2-chloropyridin-3-yl)carbonyl]piperidin-4-yl}ethoxy)-2,4,8,18,22-pentaazatetracyclo[14.3.1.1(3,7).1(9,13)]docosa-1(20),3(22),4,6,9(21),10,12,16,18-nonaene tris(trifluoroacetate)

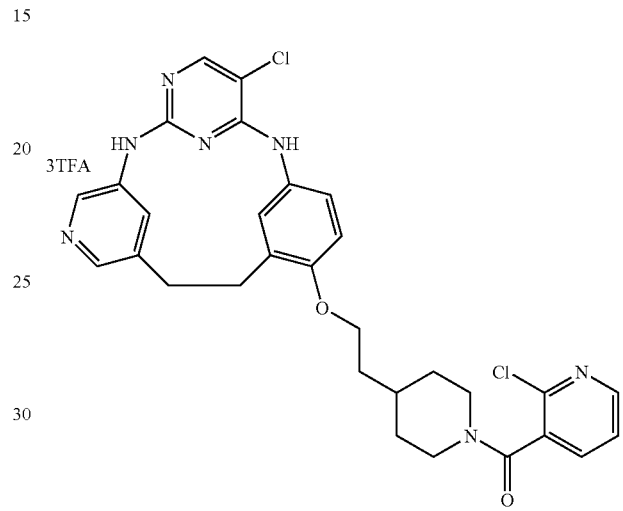

The desired compound was prepared according to the procedure of Example D94 using 6-chloro-12-(2-piperidin-4-ylethoxy)-2,4,8,18,22-pentaazatetracyclo[14.3.1.1(3,7).1(9,13)]docosa-1(20),3(22),4,6,9(21),10,12,16,18-nonaene tris(trifluoroacetate) and 2-chloronicotinoyl chloride as the starting materials in 30% yield. LCMS for $C_{30}H_{30}Cl_2N_7O_2$ (M+H)$^+$: m/z=590.0, 592.0.

Example D180

6-Chloro-12-{2-[1-(pyridin-3-ylcarbonyl)piperidin-4-yl]ethoxy}-2,4,8,18,22-pentaazatetracyclo[14.3.1.1(3,7).1(9,13)]docosa-1(20),3(22),4,6,9(21),10,12,16,18-nonaene tris(trifluoroacetate)

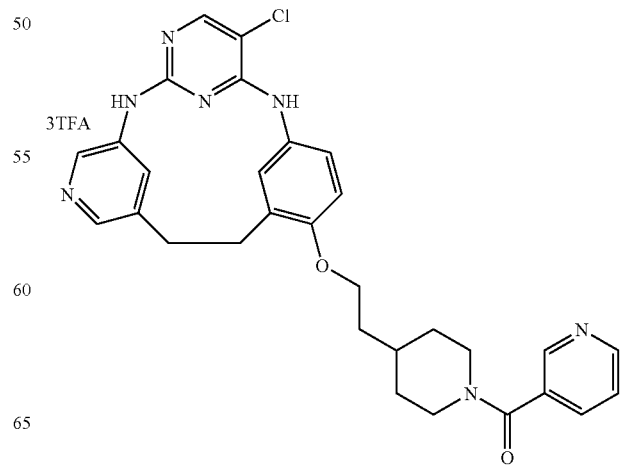

The desired compound was prepared according to the procedure of Example D94 using 6-chloro-12-(2-piperidin-4-ylethoxy)-2,4,8,18,22-pentaazatetracyclo[14.3.1.1(3,7).1(9,13)]docosa-1(20),3(22),4,6,9(21),10,12,16,18-nonaene tris(trifluoroacetate) and nicotinoyl chloride hydrochloride as the starting materials in 50% yield. LCMS for $C_{30}H_{31}ClN_7O_2$ (M+H)$^+$: m/z=556.1.

Example D181

6-Chloro-12-[2-(1-isonicotinoylpiperidin-4-yl)ethoxy]-2,4,8,18,22-pentaazatetracyclo[14.3.1.1(3,7).1(9,13)]docosa-1(20),3(22),4,6,9(21),10,12,16,18-nonaene tris(trifluoroacetate)

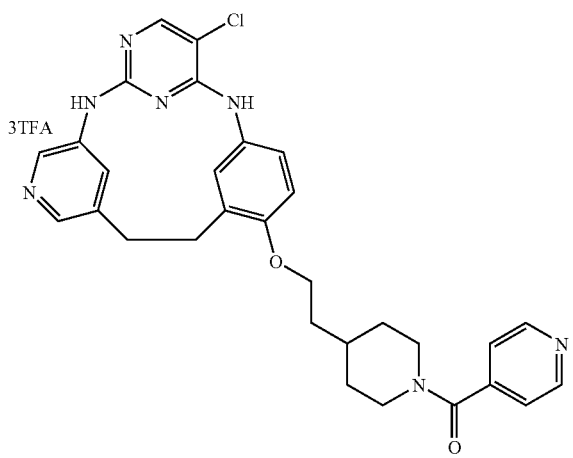 [SMILES: "3TFA" ; O=C(c1ccncc1)N1CCC(CCOc2ccc3cc2CCc2cncc(c2)Nc2ncc(Cl)c(n2)N3)CC1]

The desired compound was prepared according to the procedure of Example D94 using 6-chloro-12-(2-piperidin-4-ylethoxy)-2,4,8,18,22-pentaazatetracyclo[14.3.1.1(3,7).1(9,13)]docosa-1(20),3(22),4,6,9(21),10,12,16,18-nonaene tris(trifluoroacetate) and isonicotinoyl chloride hydrochloride as the starting materials in 30% yield. LCMS for $C_{30}H_{31}ClN_7O_2$ (M+H)$^+$: m/z=556.1.

Example D182

4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]oxy}ethyl)-N-pyridin-3-ylpiperidine-1-carboxamide tris(trifluoroacetate)

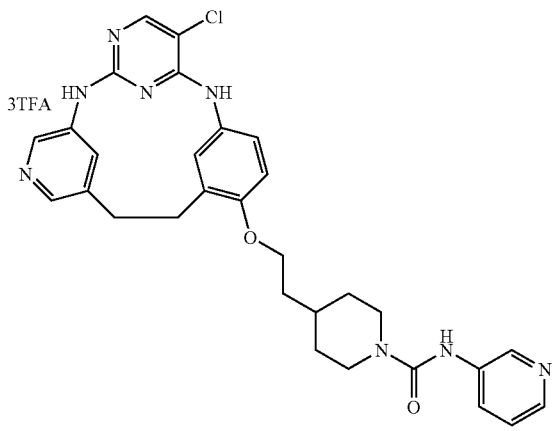 [SMILES: "3TFA" ; O=C(Nc1cccnc1)N1CCC(CCOc2ccc3cc2CCc2cncc(c2)Nc2ncc(Cl)c(n2)N3)CC1]

The desired compound was prepared according to the procedure of Example D41 using 6-chloro-12-(2-piperidin-4-ylethoxy)-2,4,8,18,22-pentaazatetracyclo[14.3.1.1(3,7).1(9,13)]docosa-1(20),3(22),4,6,9(21),10,12,16,18-nonaene tris(trifluoroacetate) and 3-isocyanatopyridine as the starting materials in 20% yield. LCMS for $C_{30}H_{32}ClN_8O_2$ (M+H)$^+$: m/z=571.0.

Example D183

Methyl [4-chloro-19-oxo-18-oxa-2,6,8,20,25-pentaazapentacyclo[14.6.1.1(3,7).1(9,13).0(17,21)]pentacosa-1(23),3(25),4,6,9(24),10,12,16,21-nonaen-20-yl]acetate trifluoroacetate

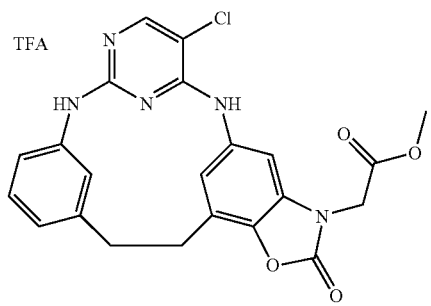 [SMILES: COC(=O)Cn1c(=O)oc2c3cc(cc21)Nc1nc(ncc1Cl)Nc1cccc(c1)CC3]

Step A: tert-Butyl (2-hydroxy-5-nitrophenyl)carbamate

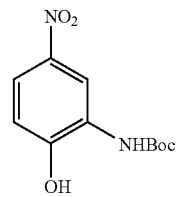 [SMILES: CC(C)(C)OC(=O)Nc1cc([N+](=O)[O-])ccc1O]

The desired compound was prepared according to the procedure of Example D2, step A, using 2-amino-4-nitrophenol as the starting material in 82% yield. LCMS for $C_{11}H_{14}N_2O_5Na$ (M+Na)$^+$: m/z=277.0.

Step B: tert-Butyl (2-hydroxy-3-iodo-5-nitrophenyl)carbamate

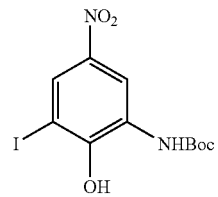 [SMILES: CC(C)(C)OC(=O)Nc1cc([N+](=O)[O-])cc(I)c1O]

A solution of tert-butyl (2-hydroxy-5-nitrophenyl)carbamate (4.2 g, 16 mmol) in methanol (18 mL) at 0° C. was treated with sodium bicarbonate (3.0 g, 36 mmol) followed by N,N,N-trimethyl(phenyl)methanaminium dichloroiodanuide (6.3 g, 18 mmol) and stirred at 20° C. for 16 h. The reaction mixture was filtered and washed with 25% MeOH/CH$_2$Cl$_2$ (200 mL). The filtrate was concentrated and diluted with ethyl acetate (300 mL) and 0.5 M HCl (100 mL). The organic layer was separated and washed with brine, dried over anhydrous sodium sulfate, filtered, and concentrated to give a crude gummy solid. This material was concentrated from hexanes (2×) to give the desired product (5.7 g, 91%) as an orange solid. LCMS for C$_{11}$H$_{131}$N$_2$O$_5$Na (M+Na)$^+$: m/z=402.8.

Step C: 7-Iodo-5-nitro-1,3-benzoxazol-2(3H)-one

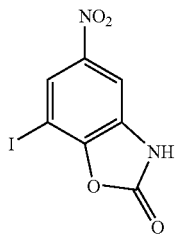 [SMILES: O=c1[nH]c2cc([N+](=O)[O-])cc(I)c2o1]

A solution of tert-butyl (2-hydroxy-3-iodo-5-nitrophenyl)carbamate (1.0 g, 2.6 mmol) and N,N-carbonyldiimidazole (0.47 g, 2.9 mmol) in THF (6 mL) was stirred at reflux for 1 h. The reaction mixture was concentrated, diluted with ethyl acetate (100 mL), washed with 1 N HCl (50 mL), water (20 mL), and brine (20 mL), dried over anhydrous sodium sulfate, filtered, and concentrated to give a crude solid. This material was concentrated from hexanes (2×) to give the desired product (5.7 g, 91%) as an orange solid. This material was purified by flash column chromatography to give the desired product (0.66 g, 82%) as a yellow solid. LCMS for C$_7$H$_{41}$N$_2$O$_4$ (M+H)$^+$: m/z=306.8.

Step D: Methyl (7-iodo-5-nitro-2-oxo-1,3-benzoxazol-3(2H)-yl)acetate

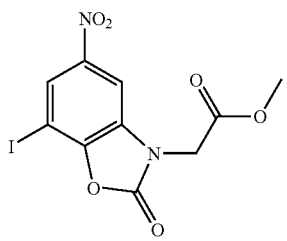 [SMILES: COC(=O)Cn1c(=O)oc2c(I)cc([N+](=O)[O-])cc21]

A solution of 7-iodo-5-nitro-1,3-benzoxazol-2(3H)-one (1.6 g, 5.3 mmol) in N,N-dimethylformamide (11 mL) at 0° C. was treated with potassium carbonate (1.2 g, 8.4 mmol) followed by methyl bromoacetate (0.75 mL, 7.9 mmol) and stirred at 20° C. for 2 h. The reaction mixture was added dropwise to a solution of 1M HCl (100 mL) at 0° C. and extracted with ethyl acetate (2×100 mL). The combined organic extracts were washed with brine (50 mL), dried over anhydrous sodium sulfate, filtered, and concentrated to give a crude solid. This material was washed with cold methanol to give the desired product (1.6 g, 79%) as a solid. LCMS for C$_{10}$H$_{81}$N$_2$O$_6$ (M+H)$^+$: m/z=378.8.

Step E: Methyl [7-({3-[(tert-butoxycarbonyl)amino]phenyl}ethynyl)-5-nitro-2-oxo-1,3-benzoxazol-3(2H)-yl]acetate

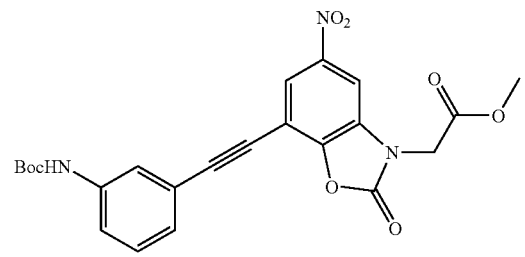 [SMILES: COC(=O)Cn1c(=O)oc2c(C#Cc3cccc(NC(=O)OC(C)(C)C)c3)cc([N+](=O)[O-])cc21]

The desired compound was prepared according to the procedure of Example B5, step C, using methyl (7-iodo-5-nitro-2-oxo-1,3-benzoxazol-3(2H)-yl)acetate and tert-butyl (3-ethynylphenyl)carbamate as the starting materials in quantitative yield. LCMS for C$_{23}$H$_{21}$N$_3$O$_8$Na (M+Na)$^+$: m/z=490.0.

Step F: Methyl [5-amino-7-(2-{3-[(tert-butoxycarbonyl)amino]phenyl}ethyl)-2-oxo-1,3-benzoxazol-3(2H)-yl]acetate

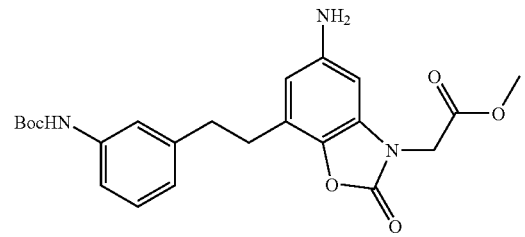 [SMILES: COC(=O)Cn1c(=O)oc2c(CCc3cccc(NC(=O)OC(C)(C)C)c3)cc(N)cc21]

The desired compound was prepared according to the procedure of Example D82, step C, using methyl [7-({3-[(tert-butoxycarbonyl)amino]phenyl}ethynyl)-5-nitro-2-oxo-1,3-benzoxazol-3(2H)-yl]acetate as the starting material in 94% yield. LCMS for C$_{23}$H$_{27}$N$_3$O$_6$Na (M+Na)$^+$: m/z=464.0.

Step G: Methyl [7-(2-{3-[(tert-butoxycarbonyl)amino]phenyl}ethyl)-5-[(2,5-dichloropyrimidin-4-yl)amino]-2-oxo-1,3-benzoxazol-3(2H)-yl]acetate

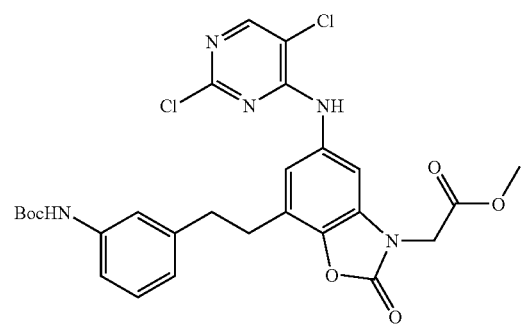 [SMILES: COC(=O)Cn1c(=O)oc2c(CCc3cccc(NC(=O)OC(C)(C)C)c3)cc(Nc3nc(Cl)ncc3Cl)cc21]

The desired compound was prepared according to the procedure of Example D2, step C, using methyl [5-amino-7-(2-{3-[(tert-butoxycarbonyl)amino]phenyl}ethyl)-2-oxo-1,3-benzoxazol-3(2H)-yl]acetate as the starting material in 70% yield. LCMS for $C_{27}H_{27}Cl_2N_5O_6Na$ (M+Na)$^+$: m/z=609.9.

Step H: Methyl [4-chloro-19-oxo-18-oxa-2,6,8,20,25-pentaazapentacyclo[14.6.1.1(3,7).1(9,13).0(17,21)]pentacosa-1(23),3(25),4,6,9(24),10,12,16,21-nonaen-20-yl]acetate trifluoroacetate The desired compound was prepared according to the procedure of Example D32, step F, using methyl [7-(2-{3-[(tert-butoxycarbonyl)amino]phenyl}ethyl)-5-[(2,5-dichloropyrimidin-4-yl)amino]-2-oxo-1,3-benzoxazol-3(2H)-yl]acetate as the starting material in 20% yield. LCMS for $C_{22}H_{19}ClN_5O_4$ (M+H)$^+$: m/z=452.0.

Example D184

4-Chloro-18-oxa-2,6,8,20,25-pentaazapentacyclo[14.6.1.1(3,7).1(9,13).0(17,21)]pentacosa-1(23),3(25),4,6,9(24),10,12,16,21-nonaen-19-one

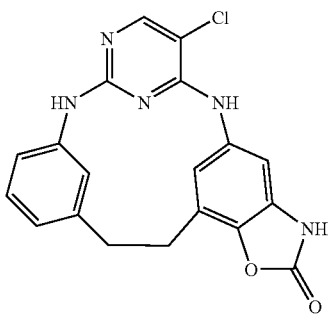 [SMILES: O=c1[nH]c2cc3cc(c2o1)CCc1cccc(c1)Nc1ncc(Cl)c(n1)N3]

Step A: 7-Iodo-5-nitro-3-{[2-(trimethylsilyl)ethoxy]methyl}-1,3-benzoxazol-2(3H)-one

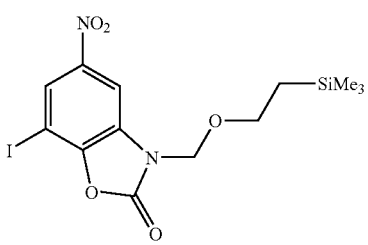 [SMILES: C[Si](C)(C)CCOCn1c(=O)oc2c(I)cc([N+](=O)[O-])cc21]

A solution of 7-iodo-5-nitro-1,3-benzoxazol-2(3H)-one (0.76 g, 2.5 mmol) in N,N-dimethylformamide (5 mL) at 0° C. was treated with N,N-diisopropylethylamine (0.65 mL, 3.7 mmol) followed by [β-(trimethylsilyl)ethoxy]methyl chloride (0.61 mL, 3.5 mmol) dropwise and stirred at 20° C. for 1 h. The reaction mixture was diluted with ethyl acetate (100 mL) and washed with 0.5 M HCl (50 mL), brine (25 mL), dried over anhydrous sodium sulfate, filtered, and concentrated to a crude oil. This material was purified by flash column chromatography to give the desired product (0.93 g, 86%) as a yellow oil.

Step B: tert-Butyl {3-[(5-nitro-2-oxo-3-{[2-(trimethylsilyl)ethoxy]methyl}-2,3-dihydro-1,3-benzoxazol-7-yl)ethynyl]phenyl}carbamate

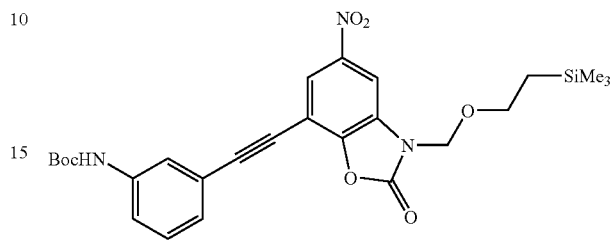

The desired compound was prepared according to the procedure of Example B5, step C, using 7-iodo-5-nitro-3-{[2-(trimethylsilyl)ethoxy]methyl}-1,3-benzoxazol-2(3H)-on and tert-butyl (3-ethynylphenyl)carbamate as the starting materials in quantitative yield. LCMS for $C_{26}H_{31}N_3O_7SiNa$ (M+Na)$^+$: m/z=548.0.

Step C: tert-Butyl {3-[2-(5-amino-2-oxo-3-{[2-(trimethylsilyl)ethoxy]methyl}-2,3-dihydro-1,3-benzoxazol-7-yl)ethyl]phenyl}carbamate

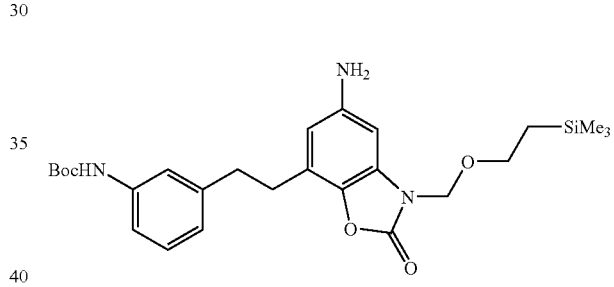

The desired compound was prepared according to the procedure of Example D82, step C, using tert-butyl {3-[(5-nitro-2-oxo-3-{[2-(trimethylsilyl)ethoxy]methyl}-2,3-dihydro-1,3-benzoxazol-7-yl)ethynyl]phenyl}carbamate as the starting material in 46% yield. LCMS for $C_{26}H_{37}N_3O_5SiNa$ (M+Na)$^+$: m/z=522.1.

Step D: tert-Butyl {3-[2-(5-[(2,5-dichloropyrimidin-4-yl)amino]-2-oxo-3-{[2-(trimethylsilyl)ethoxy]methyl}-2,3-dihydro-1,3-benzoxazol-7-yl)ethyl]phenyl}carbamate

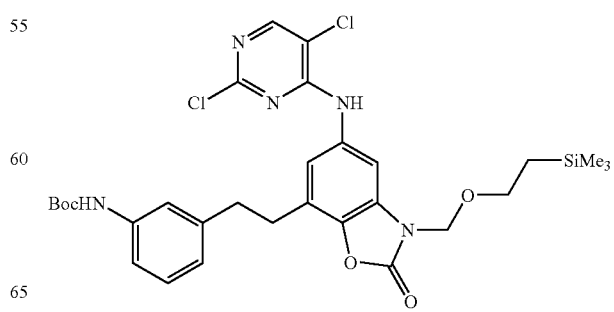

The desired compound was prepared according to the procedure of Example D2, step C, using tert-butyl {3-[2-(5-amino-2-oxo-3-{[2-(trimethylsilyl)ethoxy]methyl}-2,3-dihydro-1,3-benzoxazol-7-yl)ethyl]phenyl}carbamate as the starting material in 92% yield. LCMS for $C_{30}H_{37}Cl_2N_5O_5SiNa$ (M+Na)$^+$: m/z=668.0.

Step E: 4-Chloro-20-{[2-(trimethylsilyl)ethoxy]methyl}-18-oxa-2,6,8,20,25-pentaazapentacyclo[14.6.1.1(3,7).1(9,13).0(17,21)]pentacosa-1(23),3(25),4,6,9(24),10,12,16,21-nonaen-19-one

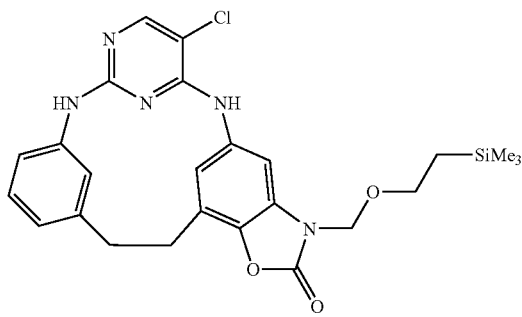 [SMILES: C[Si](C)(C)CCOCn1c(=O)oc2c3cc(cc21)Nc1nc(ncc1Cl)Nc1cccc(c1)CC3]

The desired compound was prepared according to the procedure of Example D32, step F, using tert-butyl {3-[2-(5-[(2,5-dichloropyrimidin-4-yl)amino]-2-oxo-3-{[2-(trimethylsilyl)ethoxy]methyl}-2,3-dihydro-1,3-benzoxazol-7-yl)ethyl]phenyl}carbamate as the starting material in 51% yield. LCMS for $C_{25}H_{29}ClN_5O_3Si$ (M+H)$^+$: m/z=510.0.

Step F: 4-Chloro-18-oxa-2,6,8,20,25-pentaazapentacyclo[14.6.1.1(3,7).1(9,13).0(17,21)]pentacosa-1(23),3(25),4,6,9(24),10,12,16,21-nonaen-19-one A solution of 4-chloro-20-{[2-(trimethylsilyl)ethoxy]methyl}-18-oxa-2,6,8,20,25-pentaazapentacyclo[14.6.1.1(3,7).1(9,13).0(17,21)]pentacosa-1(23),3(25),4,6,9(24),10,12,16,21-nonaen-19-one (25 mg, 49 μmol) in TFA (1.5 mL) was stirred at 20° C. for 30 min. The reaction mixture was concentrated and reconcentrated from dichloromethane to a residue. This residue was dissolved in THF (1.5 mL) and treated with 20 M of ammonia in water (1 mL, 20 mmol) dropwise and stirred at 20° C. for 1 h. The reaction mixture was poured into water (20 mL) and ethyl acetate (50 mL). The organic layer was separated and washed with brine (10 mL), dried over anhydrous sodium sulfate, filtered, and evaporated to give the desired product (19 mg, quantitative) as a white solid. LCMS for $C_{19}H_{15}ClN_5O_2$ (M+H)$^+$: m/z=380.0.

Example D185

2-[4-Chloro-19-oxo-18-oxa-2,6,8,20,25-pentaazapentacyclo[14.6.1.1(3,7).1(9,13).0(17,21)]pentacosa-1(23),3(25),4,6,9(24),10,12,16,21-nonaen-20-yl]-N-phenylacetamide trifluoroacetate

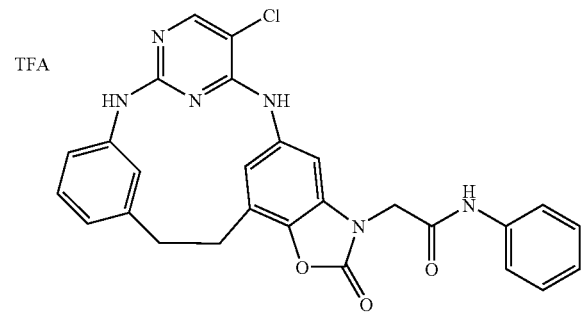 [SMILES: O=C(Cn1c(=O)oc2c3cc(cc21)Nc1nc(ncc1Cl)Nc1cccc(c1)CC3)Nc1ccccc1]

Step A: [4-Chloro-19-oxo-18-oxa-2,6,8,20,25-pentaazapentacyclo[14.6.1.1(3,7).1(9,13).0(17,21)]pentacosa-1(23),3(25),4,6,9(24),10,12,16,21-nonaen-20-yl]aceticacid

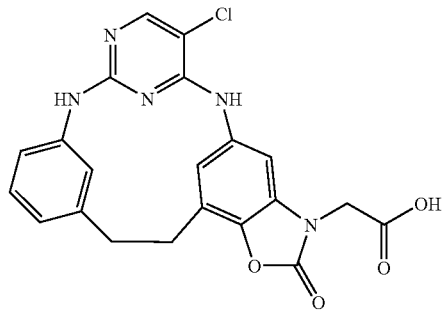 [SMILES: O=C(O)Cn1c(=O)oc2c3cc(cc21)Nc1nc(ncc1Cl)Nc1cccc(c1)CC3]

A solution of methyl [4-chloro-19-oxo-18-oxa-2,6,8,20,25-pentaazapentacyclo[14.6.1.1(3,7).1(9,13).0(17,21)]pentacosa-1(23),3(25),4,6,9(24),10,12,16,21-nonaen-20-yl]acetate (0.23 g, 0.51 mmol) in dichloromethane (15 mL) at −78° C. was treated with 1 M of boron tribromide in dichloromethane (1.5 mL, 1.5 mmol) and stirred at 20° C. for 16 h. The reaction mixture was cooled to 0° C., treated with additional 1 M of boron tribromide in dichloromethane (1.5 mL, 1.5 mmol), and stirred at 20° C. for 6 h. The reaction mixture was cooled to 0° C., quenched with 0.5 M HCl (10 mL) dropwise, concentrated and filtered. The brown solid that was collected was washed with water and dried. This material was diluted with dichloromethane (20 mL), cooled to 0° C., treated with 1 M of boron tribromide in dichloromethane (1.5 mL, 1.5 mmol), and stirred at 20° C. for 24 h. The reaction mixture was cooled to 0° C., quenched with 0.5 M HCl (10 mL) dropwise, concentrated and filtered. The brown solid that was collected was washed with water and dried to give the desired product (0.15 g, 67%) as a tan solid. LCMS for $C_{21}H_{17}ClN_5O_4$ (M+H)$^+$: m/z=438.0.

Step B: 2-[4-Chloro-19-oxo-18-oxa-2,6,8,20,25-pentaazapentacyclo[14.6.1.1(3,7).1(9,13).0(17,21)]pentacosa-1(23),3(25),4,6,9(24),10,12,16,21-nonaen-20-yl]-N-phenylacetamide trifluoroacetate The desired compound was prepared according to the procedure of Example D152 using [4-chloro-19-oxo-18-oxa-2,6,8,20,25-pentaazapentacyclo[14.6.1.1(3,7).1(9,13).0(17,21)]pentacosa-1(23),3(25),4,6,9(24),10,12,16,21-nonaen-20-yl]aceticacid and aniline as the starting materials in 20% yield. LCMS for $C_{27}H_{22}ClN_6O_3$ (M+H)$^+$: m/z=513.0.

Example D186

N-Benzyl-2-[4-chloro-19-oxo-18-oxa-2,6,8,20,25-pentaazapentacyclo[14.6.1.1(3,7).1(9,13).0(17,21)]pentacosa-1(23),3(25),4,6,9(24),10,12,16,21-nonaen-20-yl]acetamide trifluoroacetate

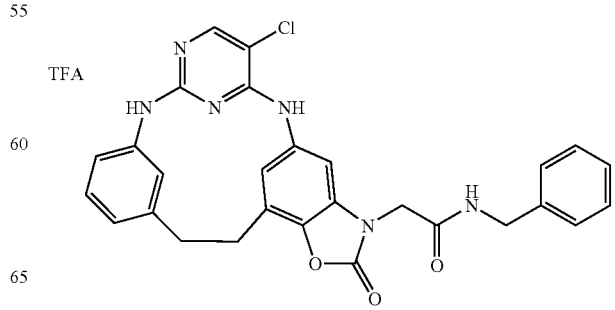

The desired compound was prepared according to the procedure of Example D152 using [4-chloro-19-oxo-18-oxa-2,6,8,20,25-pentaazapentacyclo[14.6.1.1(3,7).1(9,13).0(17,21)]pentacosa-1(23),3(25),4,6,9(24),10,12,16,21-nonaen-20-yl]aceticacid and benzylamine as the starting materials in 30% yield. LCMS for $C_{28}H_{24}ClN_6O_3$ (M+H)$^+$: m/z=527.0.

Example D187

4-Chloro-20-(2-morpholin-4-yl-2-oxoethyl)-18-oxa-2,6,8,20,25-pentaazapentacyclo[14.6.1.1(3,7).1(9,13).0(17,21)]pentacosa-1(23),3(25),4,6,9(24),10,12,16,21-nonaen-19-one trifluoroacetate

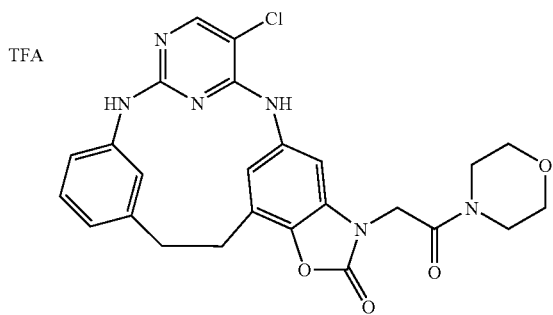 [SMILES: O=C(Cn1c(=O)oc2c3cc(cc21)Nc1nc(ncc1Cl)Nc1cccc(c1)CC3)N1CCOCC1]

The desired compound was prepared according to the procedure of Example D152 using [4-chloro-19-oxo-18-oxa-2,6,8,20,25-pentaazapentacyclo[14.6.1.1(3,7).1(9,13).0(17,21)]pentacosa-1(23),3(25),4,6,9(24),10,12,16,21-nonaen-20-yl]aceticacid and morpholine as the starting materials in 31% yield. LCMS for $C_{25}H_{24}ClN_6O_4$ (M+H)$^+$: m/z=507.0.

Example D188

4-Chloro-20-[2-oxo-2-(4-phenylpiperazin-1-yl)ethyl]-18-oxa-2,6,8,20,25-pentaazapentacyclo[14.6.1.1(3,7).1(9,13).0(17,21)]pentacosa-1(23),3(25),4,6,9(24),10,12,16,21-nonaen-19-one bis(trifluoroacetate)

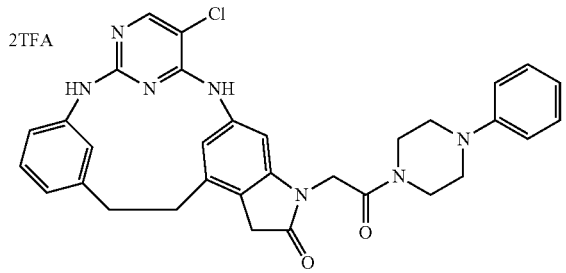 [SMILES: "2TFA" ; O=C(CN1C(=O)Cc2c3cc(cc21)Nc1nc(ncc1Cl)Nc1cccc(c1)CC3)N1CCN(c2ccccc2)CC1]

The desired compound was prepared according to the procedure of Example D152 using [4-chloro-19-oxo-18-oxa-2,6,8,20,25-pentaazapentacyclo[14.6.1.1(3,7).1(9,13).0(17,21)]pentacosa-1(23),3(25),4,6,9(24),10,12,16,21-nonaen-20-yl]aceticacid and 1-phenyl-piperazine as the starting materials in 26% yield. LCMS for $C_{31}H_{29}ClN_7O_3$ (M+H)$^+$: m/z=582.0.

Example D189

6-Chloro-19-(morpholin-4-ylmethyl)-14-oxa-2,4,8,23-tetraazatetracyclo[15.3.1.1(3,7).1(9,13)]tricosa-1(21),3(23),4,6,9(22),10,12,17,19-nonaene bis(trifluoroacetate)

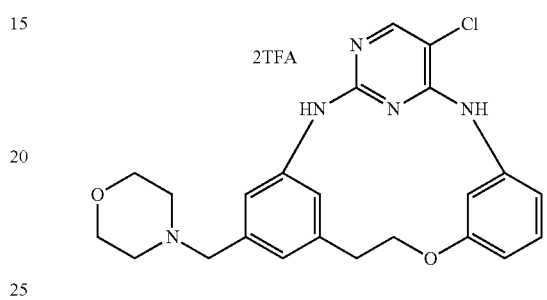

A solution of 19-bromo-6-chloro-14-oxa-2,4,8,23-tetraazatetracyclo[15.3.1.1(3,7).1(9,13)]tricosa-1(21),3(23),4,6,9(22),10,12,17,19-nonaene (25 mg, 60 µmol), potassium trifluoro(morpholin-4-ylmethyl)borate(1-) (15 mg, 72 µmol), cesium carbonate (59 mg, 0.18 mmol), dicyclohexyl(2',4',6'-triisopropylbiphenyl-2-yl)phosphine (3.4 mg, 7.2 µmol), and palladium acetate (0.81 mg, 36 µmol) in 5.1 M of water in THF (0.5 mL, 2.5 mmol) that was previously degassed with nitrogen was heated in a sealed tube at 80° C. for 24 h. The reaction mixture was concentrated and purified by preparative LCMS to give the desired product (14 mg, 35%) as a white solid. LCMS for $C_{23}H_{25}ClN_5O_2$ (M+H)$^+$: m/z=438.0.

Example D190

6-Chloro-19-[(4-methylpiperazin-1-yl)methyl]-14-oxa-2,4,8,23-tetraazatetracyclo[15.3.1.1(3,7).1(9,13)]tricosa-1(21),3(23),4,6,9(22),10,12,17,19-nonaene tris(trifluoroacetate)

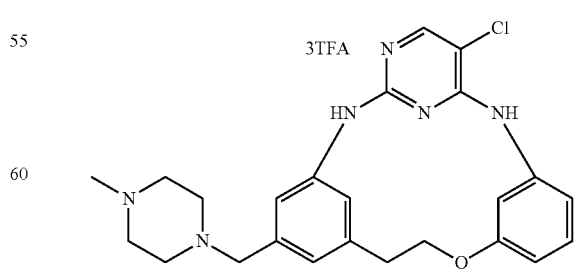

The desired compound was prepared according to the procedure of Example D189 using potassium trifluoro[(4-methylpiperazin-1-yl)methyl]borate(1-) as the starting material in 38% yield. LCMS for $C_{24}H_{28}ClN_6O$ (M+H)$^+$: m/z=451.0.

Example D191

6-Chloro-19-(piperazin-1-ylmethyl)-14-oxa-2,4,8,23-tetraazatetracyclo[15.3.1.1(3,7).1(9,13)]tricosa-1(21),3(23),4,6,9(22),10,12,17,19-nonaene tris(trifluoroacetate)

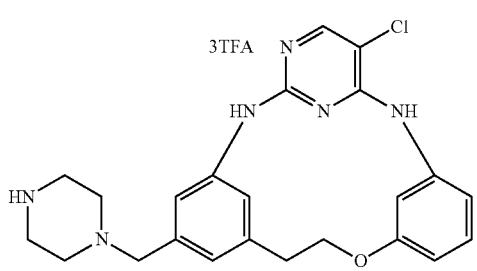 [SMILES: "3TFA" ; Clc1cnc2nc1Nc1cccc(c1)OCCc1cc(CN3CCNCC3)cc(c1)N2]

Step A: tert-Butyl 4-{[6-chloro-14-oxa-2,4,8,23-tetraazatetracyclo[15.3.1.1(3,7).1(9,13)]tricosa-1(21),3(23),4,6,9(22),10,12,17,19-nonaen-19-yl]methyl}piperazine-1-carboxylate

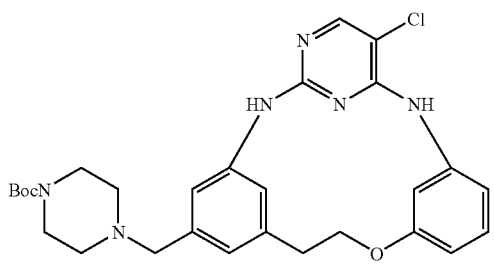 [SMILES: CC(C)(C)OC(=O)N1CCN(Cc2cc3cc(c2)Nc2ncc(Cl)c(n2)Nc2cccc(c2)OCC3)CC1]

The desired compound was prepared according to the procedure of Example D189 using potassium {[4-(tert-butoxycarbonyl)piperazin-1-yl]methyl}(trifluoro)borate(1-) as the starting material. The desired product was used in the next step without further purification.

Step B: 6-Chloro-19-(piperazin-1-ylmethyl)-14-oxa-2,4,8,23-tetraazatetracyclo[15.3.1.1(3,7).1(9,13)]tricosa-1(21),3(23),4,6,9(22),10,12,17,19-nonaene tris(trifluoroacetate)

A solution of tert-butyl 4-{[6-chloro-14-oxa-2,4,8,23-tetraazatetracyclo[15.3.1.1(3,7).1(9,13)]tricosa-1(21),3(23),4,6,9(22),10,12,17,19-nonaen-19-yl]methyl}piperazine-1-carboxylate in TFA (1.5 mL) was stirred at 20° C. for 15 min, concentrated, and purified by preparative LCMS to give the desired product (15 mg, 32% for 2 steps) as a white solid. LCMS for $C_{23}H_{26}ClN_6O$ (M+H)$^+$: m/z=437.0.

Example D192

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-[(3S)-piperidin-3-yl]acetamidebis(trifluoroacetate)

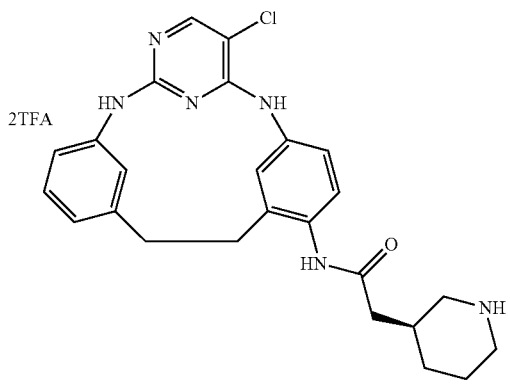 [SMILES: "2TFA" ; O=C(C[C@@H]1CCCNC1)Nc1ccc2cc1CCc1cccc(c1)Nc1ncc(Cl)c(n1)N2]

Step A: tert-Butyl 4-{[6-chloro-14-oxa-2,4,8,23-tetraazatetracyclo[15.3.1.1(3,7).1(9,13)]tricosa-1(21),3(23),4,6,9(22),10,12,17,19-nonaen-19-yl]methyl}piperazine-1-carboxylate

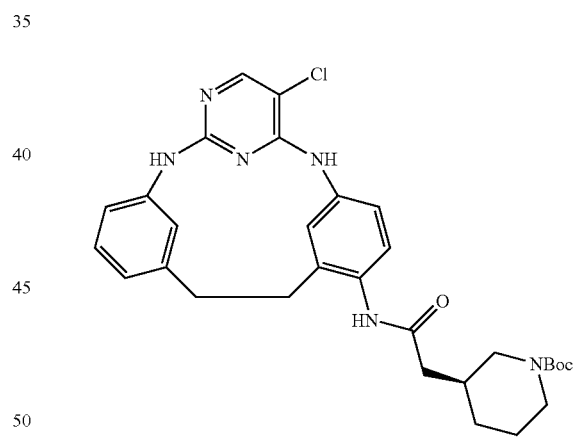

The desired compound was prepared according to the procedure of Example D152 using 6-chloro-2,4,8,22-tetraazatetracyclo[14.3.1.1(3,7).1(9,13)]docosa-1(20),3(22),4,6,9(21),10,12,16,18-nonaen-12-amine bis(trifluoroacetate) and [(3S)-1-(tert-butoxycarbonyl)piperidin-3-yl]acetic acid as the starting materials. The crude reaction product was purified by preparative LCMS to give the desired product which was used immediately in the next step.

Step B: N-[6-Chloro-2,4,8,22-tetraazatetracyclo[14.3.1.1(3,7).1(9,13)]docosa-1(20),3(22),4,6,9(21),10,12,16,18-nonaen-12-yl]-2-[(3S)-piperidin-3-yl]acetamidebis(trifluoroacetate)

A solution of tert-butyl (3S)-3-(2-{[6-chloro-2,4,8,22-tetraazatetracyclo[14.3.1.1(3,7).1(9,13)]docosa-1(20),3(22),4, 6,9(21),10,12,16,18-nonaen-12-yl]amino}-2-oxoethyl)piperidine-1-carboxylate in TFA (2 mL) was stirred at 20° C. for 15 min, concentrated, and purified by preparative LCMS to give the desired product (63 mg, 21% for 2 steps) as a solid. LCMS for $C_{25}H_{28}ClN_6O$ (M+H)$^+$: m/z=463.0.

Example D193

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-[(3R)-piperidin-3-yl]acetamidebis(trifluoroacetate)

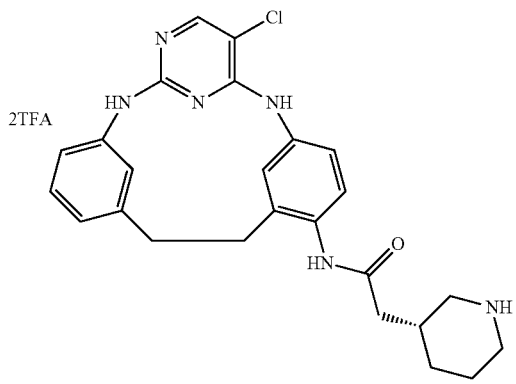 [SMILES: "2TFA" ; O=C(C[C@H]1CCCNC1)Nc1ccc2cc1CCc1cccc(c1)Nc1ncc(Cl)c(n1)N2]

The desired compound was prepared according to the procedure of Example D192 using [(3R)-1-(tert-butoxycarbonyl)piperidin-3-yl]acetic acid as the starting material in 15% yield. LCMS for $C_{25}H_{28}ClN_6O$ (M+H)$^+$: m/z=463.0.

Example D194

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[(3S)-piperidin-3-yl]acetamide-tris(trifluoroacetate)

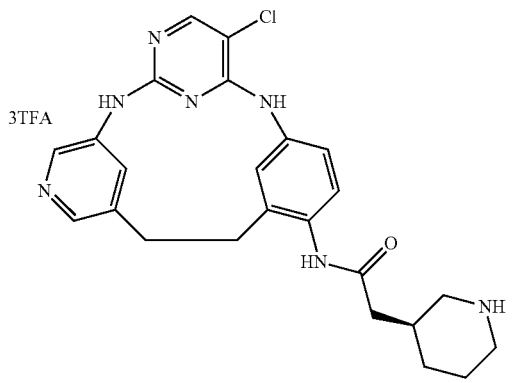 [SMILES: "3TFA" ; O=C(C[C@@H]1CCCNC1)Nc1ccc2cc1CCc1cncc(c1)Nc1ncc(Cl)c(n1)N2]

The desired compound was prepared according to the procedure of Example D192 using 6-chloro-2,4,8,18,22-pentaazatetracyclo[14.3.1.1(3,7).1(9,13)]docosa-1(20),3(22),4,6,9(21),10,12,16,18-nonaen-12-amine tris(trifluoroacetate) as the starting material in 44% yield. LCMS for $C_{24}H_{27}ClN_7O$ (M+H)$^+$: m/z=464.0.

Example D195

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[(3R)-piperidin-3-yl]acetamide-tris(trifluoroacetate)

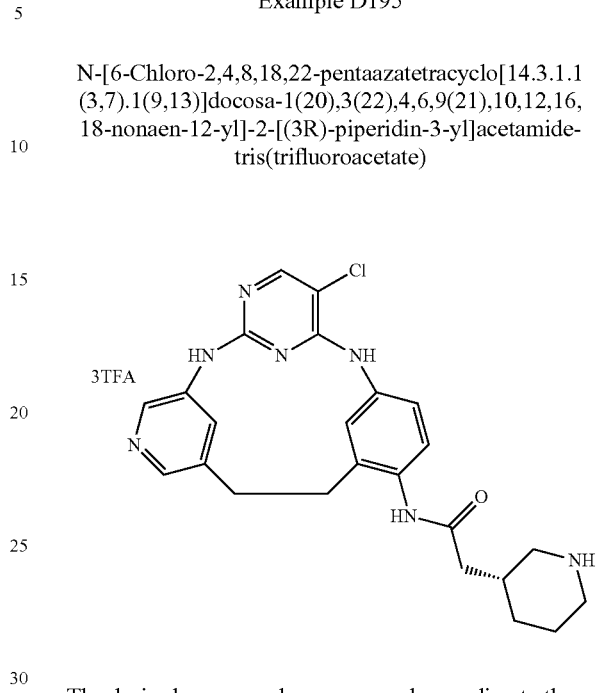

The desired compound was prepared according to the procedure of Example D192 using 6-chloro-2,4,8,18,22-pentaazatetracyclo[14.3.1.1(3,7).1(9,13)]docosa-1(20),3(22),4,6,9(21),10,12,16,18-nonaen-12-amine tris(trifluoroacetate) and [(3R)-1-(tert-butoxycarbonyl)piperidin-3-yl]acetic acid as the starting materials in 39% yield. LCMS for $C_{24}H_{27}ClN_7O$ (M+H)$^+$: m/z=464.0.

Example D196

(3S)-3-(2-{[6-Chloro-2,4,8,22-tetraazatetracyclo[14.3.1.1(3,7).1(9,13)]docosa-1(20),3(22),4,6,9(21),10,12,16,18-nonaen-12-yl]amino}-2-oxoethyl)-N-phenylpiperidine-1-carboxamide trifluoroacetate

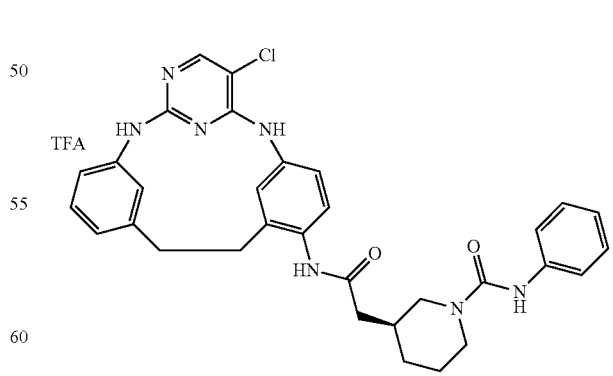

The desired compound was prepared according to the procedure of Example D41 using N-[6-chloro-2,4,8,22-tetraazatetracyclo[14.3.1.1(3,7).1(9,13)]docosa-1(20),3(22),4,6,9(21),10,12,16,18-nonaen-12-yl]-2-[(3S)-piperidin-3-yl]

acetamide bis(trifluoroacetate) and phenyl isocyanate as the starting materials in 40% yield. LCMS for $C_{32}H_{33}ClN_7O_2$ (M+H)$^+$: m/z=582.2.

Example D197

(3R)-3-(2-{[6-Chloro-2,4,8,22-tetraazatetracyclo[14.3.1.1(3,7).1(9,13)]docosa-1(20),3(22),4,6,9(21),10,12,16,18-nonaen-12-yl]amino}-2-oxoethyl)-N-phenylpiperidine-1-carboxamide trifluoroacetate

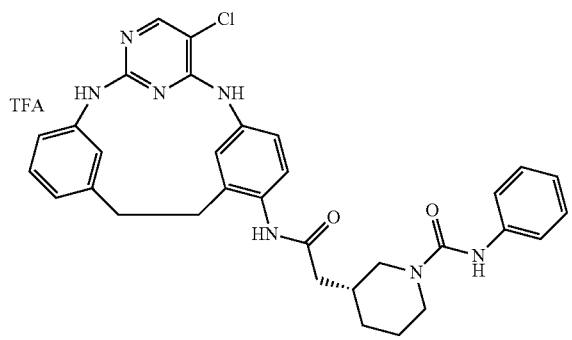 [SMILES: "TFA" ; O=C(C[C@H]1CCCN(C(=O)Nc2ccccc2)C1)Nc1ccc2cc1CCc1cccc(c1)Nc1ncc(Cl)c(n1)N2]

The desired compound was prepared according to the procedure of Example D41 using N-[6-chloro-2,4,8,22-tetraazatetracyclo[14.3.1.1(3,7).1(9,13)]docosa-1(20),3(22),4,6,9(21),10,12,16,18-nonaen-12-yl]-2-[(3R)-piperidin-3-yl]acetamide bis(trifluoroacetate) and phenyl isocyanate as the starting materials in 50% yield. LCMS for $C_{32}H_{33}ClN_7O_2$ (M+H)$^+$: m/z=582.0.

Example D198

(3S)-3-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-phenylpiperidine-1-carboxamide bis(trifluoroacetate)

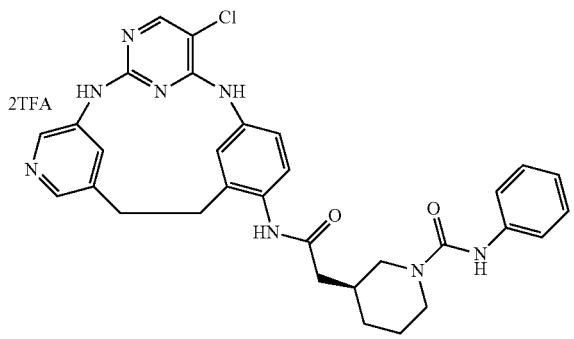 [SMILES: "2TFA" ; O=C(C[C@@H]1CCCN(C(=O)Nc2ccccc2)C1)Nc1ccc2cc1CCc1cncc(c1)Nc1ncc(Cl)c(n1)N2]

The desired compound was prepared according to the procedure of Example D41 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-[(3S)-piperidin-3-yl]

Example D199

(3R)-3-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-phenylpiperidine-1-carboxamide bis(trifluoroacetate)

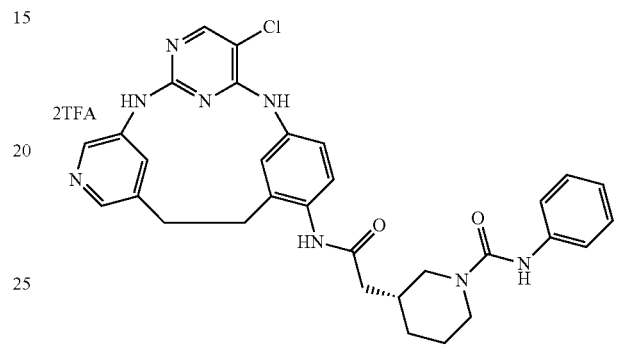

The desired compound was prepared according to the procedure of Example D41 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-[(3R)-piperidin-3-yl]acetamide tris(trifluoroacetate) and phenyl isocyanate as the starting materials in 60% yield. LCMS for $C_{31}H_{32}ClN_8O_2$ (M+H)$^+$: m/z=583.1.

Example D200

2-[(3S)-1-Acetylpiperidin-3-yl]-N-[6-chloro-2,4,8,22-tetraazatetracyclo[14.3.1.1(3,7).1(9,13)]docosa-1(20),3(22),4,6,9(21),10,12,16,18-nonaen-12-yl]acetamide trifluoroacetate

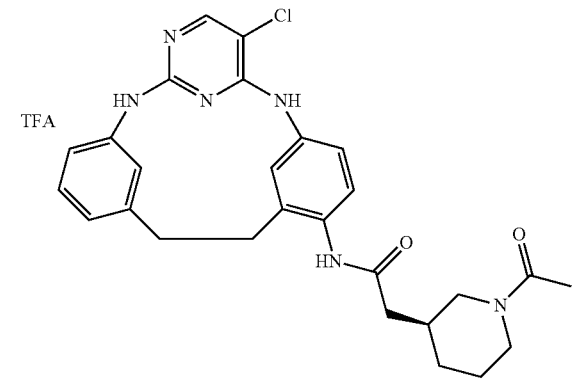 [SMILES: "TFA" ; CC(=O)N1CCC[C@@H](CC(=O)Nc2ccc3cc2CCc2cccc(c2)Nc2ncc(Cl)c(n2)N3)C1]

The desired compound was prepared according to the procedure of Example D94 using N-[6-chloro-2,4,8,22-tetraazatetracyclo[14.3.1.1(3,7).1(9,13)]docosa-1(20),3(22),4,6,9(21),10,12,16,18-nonaen-12-yl]-2-[(3S)-piperidin-3-yl]

acetamide bis(trifluoroacetate) and acetyl chloride as the starting materials in 67% yield. LCMS for $C_{27}H_{30}ClN_6O_2$ (M+H)⁺: m/z=505.1.

Example D201

2-[(3R)-1-Acetylpiperidin-3-yl]-N-[6-chloro-2,4,8,22-tetraazatetracyclo[14.3.1.1(3,7).1(9,13)]docosa-1(20),3(22),4,6,9(21),10,12,16,18-nonaen-12-yl]acetamide trifluoroacetate

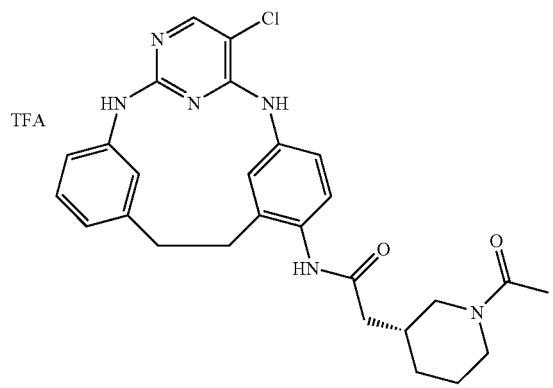 [SMILES: CC(=O)N1CCC[C@H](CC(=O)Nc2ccc3cc2CCc2cccc(c2)Nc2ncc(Cl)c(n2)N3)C1]

The desired compound was prepared according to the procedure of Example D94 using N-[6-chloro-2,4,8,22-tetraazatetracyclo[14.3.1.1(3,7).1(9,13)]docosa-1(20),3(22),4,6,9(21),10,12,16,18-nonaen-12-yl]-2-[(3R)-piperidin-3-yl]acetamide bis(trifluoroacetate) and acetyl chloride as the starting materials in 78% yield. LCMS for $C_{27}H_{30}ClN_6O_2$ (M+H)⁺: m/z=505.0.

Example D202

2-[(3S)-1-Benzoylpiperidin-3-yl]-N-[6-chloro-2,4,8,22-tetraazatetracyclo[14.3.1.1(3,7).1(9,13)]docosa-1(20),3(22),4,6,9(21),10,12,16,18-nonaen-12-yl]acetamide trifluoroacetate

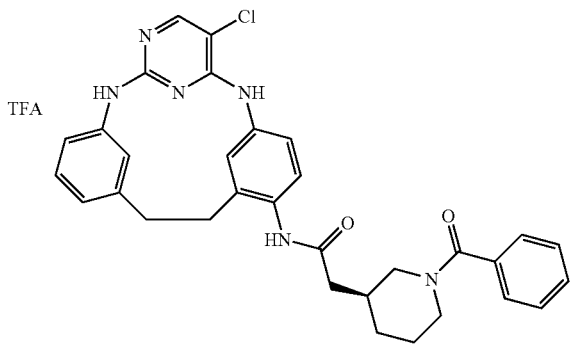 [SMILES: O=C(C[C@@H]1CCCN(C(=O)c2ccccc2)C1)Nc1ccc2cc1CCc1cccc(c1)Nc1ncc(Cl)c(n1)N2]

The desired compound was prepared according to the procedure of Example D94 using N-[6-chloro-2,4,8,22-tetraazatetracyclo[14.3.1.1(3,7).1(9,13)]docosa-1(20),3(22),4,6,9(21),10,12,16,18-nonaen-12-yl]-2-[(3S)-piperidin-3-yl]

acetamide bis(trifluoroacetate) and benzoyl chloride as the starting materials in 71% yield. LCMS for $C_{32}H_{32}ClN_6O_2$ (M+H)⁺: m/z=567.0.

Example D203

2-[(3R)-1-Benzoylpiperidin-3-yl]-N-[6-chloro-2,4,8,22-tetraazatetracyclo[14.3.1.1(3,7).1(9,13)]docosa-1(20),3(22),4,6,9(21),10,12,16,18-nonaen-12-yl]acetamide trifluoroacetate

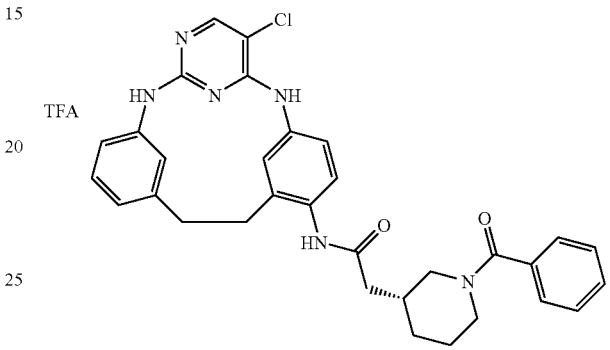

The desired compound was prepared according to the procedure of Example D94 using N-[6-chloro-2,4,8,22-tetraazatetracyclo[14.3.1.1(3,7).1(9,13)]docosa-1(20),3(22),4,6,9(21),10,12,16,18-nonaen-12-yl]-2-[(3R)-piperidin-3-yl]acetamide bis(trifluoroacetate) and benzoyl chloride as the starting materials in 71% yield. LCMS for $C_{32}H_{32}ClN_6O_2$ (M+H)⁺: m/z=567.0.

Example D204

2-[(3S)-1-Acetylpiperidin-3-yl]-N-[6-chloro-2,4,8,18,22-pentaazatetracyclo[14.3.1.1(3,7).1(9,13)]docosa-1(20),3(22),4,6,9(21),10,12,16,18-nonaen-12-yl]acetamide bis(trifluoroacetate)

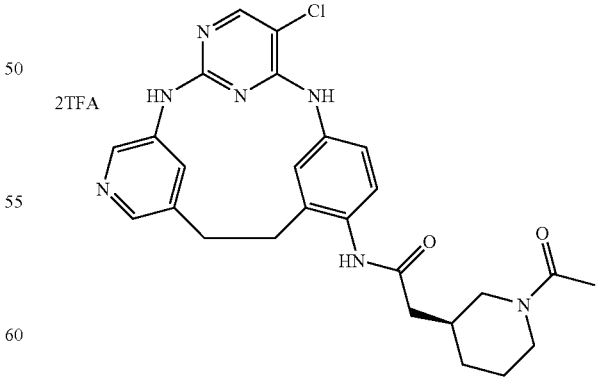

The desired compound was prepared according to the procedure of Example D94 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-[(3S)-piperidin-3-yl]

acetamide tris(trifluoroacetate) and acetyl chloride as the starting materials in 77% yield. LCMS for $C_{26}H_{29}ClN_7O_2$ (M+H)$^+$: m/z=506.0.

Example D205

2-[(3R)-1-Acetylpiperidin-3-yl]-N-[6-chloro-2,4,8,18,22-pentaazatetracyclo[14.3.1.1(3,7).1(9,13)]docosa-1(20),3(22),4,6,9(21),10,12,16,18-nonaen-12-yl]acetamide bis(trifluoroacetate)

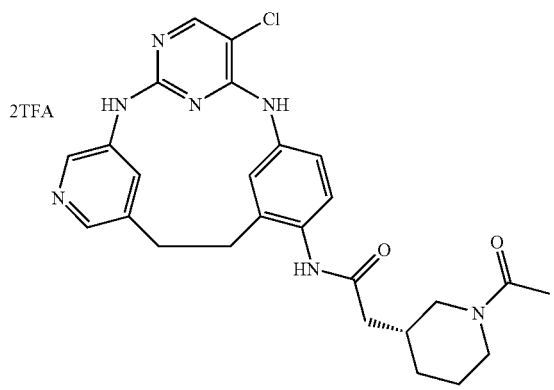 [SMILES: "2TFA" ; CC(=O)N1CCC[C@H](CC(=O)Nc2ccc3cc2CCc2cncc(c2)Nc2ncc(Cl)c(n2)N3)C1]

The desired compound was prepared according to the procedure of Example D94 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-[(3R)-piperidin-3-yl]acetamide tris(trifluoroacetate) and acetyl chloride as the starting materials in 55% yield. LCMS for $C_{26}H_{29}ClN_7O_2$ (M+H)$^+$: m/z=506.0.

Example D206

2-[(3S)-1-Benzoylpiperidin-3-yl]-N-[6-chloro-2,4,8,18,22-pentaazatetracyclo[14.3.1.1(3,7).1(9,13)]docosa-1(20),3(22),4,6,9(21),10,12,16,18-nonaen-12-yl]acetamide bis(trifluoroacetate)

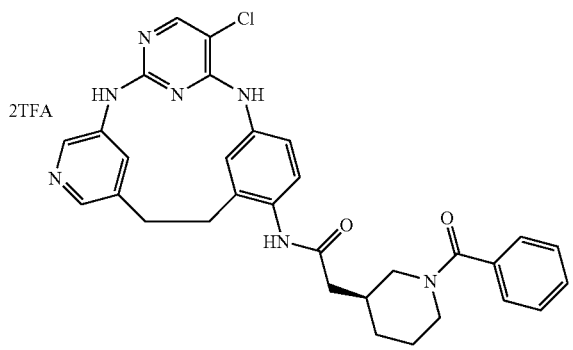 [SMILES: "2TFA" ; O=C(C[C@@H]1CCCN(C(=O)c2ccccc2)C1)Nc1ccc2cc1CCc1cncc(c1)Nc1ncc(Cl)c(n1)N2]

The desired compound was prepared according to the procedure of Example D94 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-[(3S)-piperidin-3-yl]

acetamide tris(trifluoroacetate) and benzoyl chloride as the starting materials in 61% yield. LCMS for $C_{31}H_{31}ClN_7O_2$ (M+H)$^+$: m/z=568.0.

Example D207

2-[(3R)-1-Benzoylpiperidin-3-yl]-N-[6-chloro-2,4,8,18,22-pentaazatetracyclo[14.3.1.1(3,7).1(9,13)]docosa-1(20),3(22),4,6,9(21),10,12,16,18-nonaen-12-yl]acetamide bis(trifluoroacetate)

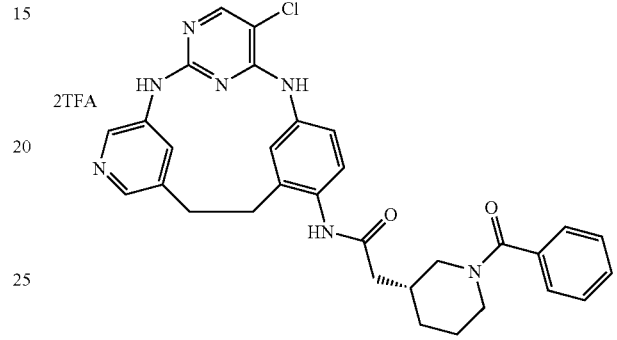

The desired compound was prepared according to the procedure of Example D94 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-[(3R)-piperidin-3-yl]acetamide tris(trifluoroacetate) and benzoyl chloride as the starting materials in 51% yield. LCMS for $C_{31}H_{31}ClN_7O_2$ (M+H)$^+$: m/z=568.0.

Example D208

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{(3S)-1-[(5-methylisoxazol-3-yl)carbonyl]piperidin-3-yl}acetamide bis(trifluoroacetate)

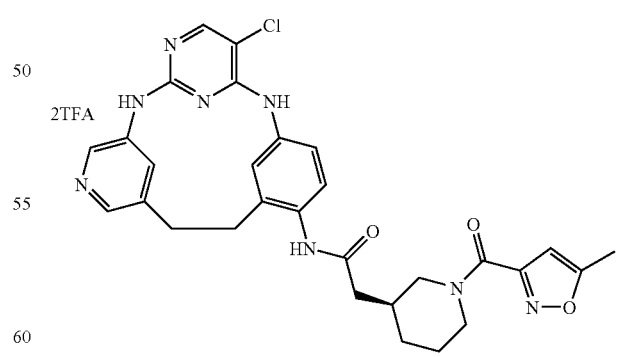

The desired compound was prepared according to the procedure of Example D94 using N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-[(3S)-piperidin-3-yl]acetamide tris(trifluoroacetate) and 5-methylisoxazole-3- carbonyl chloride as the starting materials in 60% yield. LCMS for $C_{29}H_{30}ClN_8O_3$ $(M+H)^+$: m/z=573.0.

Example D209

N-[6-Chloro-2,4,8,18,22-pentaazatetracyclo[14.3.1.1 (3,7).1(9,13)]docosa-1(20),3(22),4,6,9(21),10,12,16, 18-nonaen-12-yl]-2-{(3R)-1-[(5-methylisoxazol-3-yl)carbonyl]piperidin-3-yl}acetamide bis (trifluoroacetate)

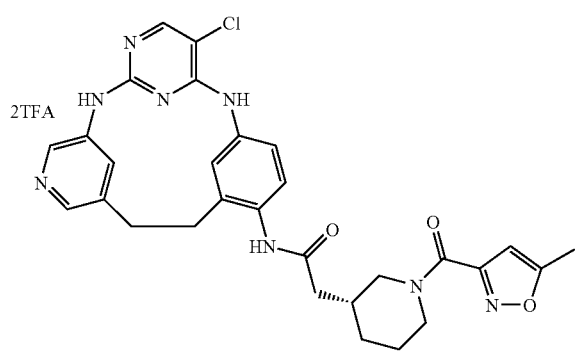 [SMILES: "2TFA" ; Cc1cc(C(=O)N2CCC[C@H](CC(=O)Nc3ccc4cc3CCc3cncc(c3)Nc3ncc(Cl)c(n3)N4)C2)no1]

The desired compound was prepared according to the procedure of Example D94 using N-[6-chloro-2,4,8,18,22-pentaazatetracyclo[14.3.1.1(3,7).1(9,13)]docosa-1(20),3(22),4, 6,9(21),10,12,16,18-nonaen-12-yl]-2-[(3R)-piperidin-3-yl] acetamide tris(trifluoroacetate) and 5-methylisoxazole-3-carbonyl chloride as the starting materials in 60% yield. LCMS for $C_{29}H_{30}ClN_8O_3$ $(M+H)^+$: m/z=573.1.

Example D210

N-[6-Chloro-2,4,8,18,22-pentaazatetracyclo[14.3.1.1 (3,7).1(9,13)]docosa-1(20),3(22),4,6,9(21),10,12,16, 18-nonaen-12-yl]-2-(1,3-dioxo-1,3-dihydro-2H-isoindol-2-yl)ethanesulfonamide bis(trifluoroacetate)

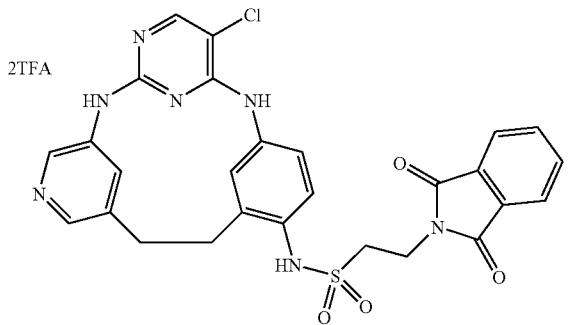 [SMILES: "2TFA" ; O=C1c2ccccc2C(=O)N1CCS(=O)(=O)Nc1ccc2cc1CCc1cncc(c1)Nc1ncc(Cl)c(n1)N2]

The desired compound was prepared according to the procedure of Example D20, step A, using 6-chloro-2,4,8,18,22-pentaazatetracyclo[14.3.1.1(3,7).1(9,13)]docosa-1(20),3 (22),4,6,9(21),10,12,16,18-nonaen-12-amine tris (trifluoroacetate) and 2-(1,3-dioxo-1,3-dihydro-2H-isoindol- 2-yl)ethanesulfonyl chloride as the starting materials in 20% yield. LCMS for $C_{27}H_{23}ClN_7O_4S$ $(M+H)^+$: m/z=575.9.

Example D211

2-[(3S)-1-(1,3-Benzothiazol-2-yl)piperidin-3-yl]-N-[6-chloro-2,4,8,18,22-pentaazatetracyclo[14.3.1.1(3, 7).1(9,13)]docosa-1(20),3(22),4,6,9(21),10,12,16,18-nonaen-12-yl]acetamide tris(trifluoroacetate)

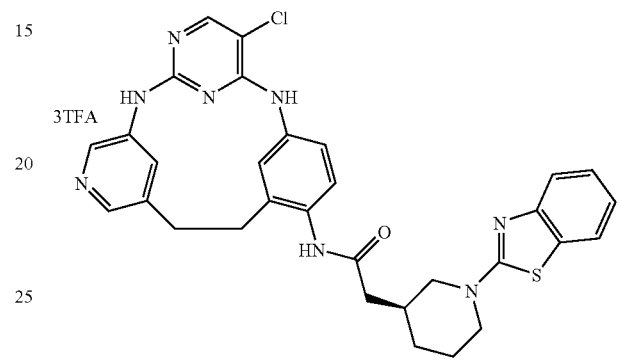

The desired compound was prepared according to the procedure of Example A157 using N-[6-chloro-2,4,8,18,22-pentaazatetracyclo[14.3.1.1(3,7).1(9,13)]docosa-1(20),3(22),4, 6,9(21),10,12,16,18-nonaen-12-yl]-2-[(3S)-piperidin-3-yl] acetamide tris(trifluoroacetate) as the starting material in 40% yield. LCMS for $C_{31}H_{30}ClN_8OS$ $(M+H)^+$: m/z=597.0.

Example D212

2-[(3R)-1-(1,3-Benzothiazol-2-yl)piperidin-3-yl]-N-[6-chloro-2,4,8,18,22-pentaazatetracyclo[14.3.1.1(3, 7).1(9,13)]docosa-1(20),3(22),4,6,9(21),10,12,16,18-nonaen-12-yl]acetamide tris(trifluoroacetate)

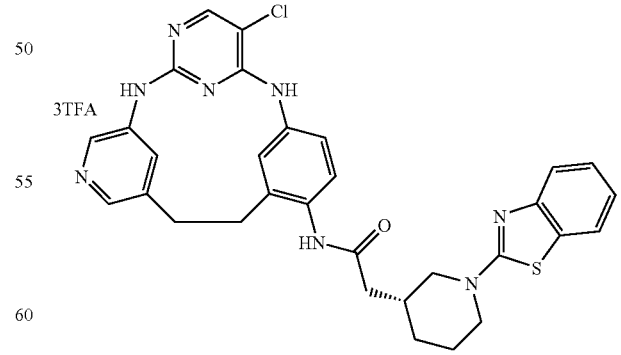

The desired compound was prepared according to the procedure of Example A157 using N-[6-chloro-2,4,8,18,22-pentaazatetracyclo[14.3.1.1(3,7).1(9,13)]docosa-1(20),3(22),4, 6,9(21),10,12,16,18-nonaen-12-yl]-2-[(3R)-piperidin-3-yl]

acetamide tris(trifluoroacetate) as the starting material in 30% yield. LCMS for $C_{31}H_{30}ClN_8OS$ (M+H)$^+$: m/z=597.0.

Example D213

N-[6-Chloro-2,4,8,18,22-pentaazatetracyclo[14.3.1.1 (3,7).1(9,13)]docosa-1(20),3(22),4,6,9(21),10,12,16, 18-nonaen-12-yl]-2-[(3S)-1-[1,3]oxazolo[5,4-b]pyridin-2-ylpiperidin-3-yl]acetamide tris (trifluoroacetate)

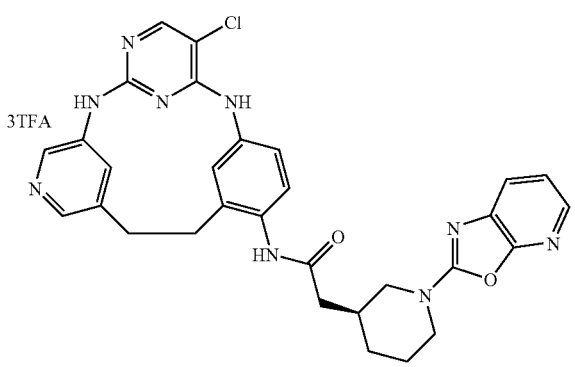 [SMILES: "3TFA" ; O=C(C[C@@H]1CCCN(c2nc3cccnc3o2)C1)Nc1ccc2cc1CCc1cncc(c1)Nc1ncc(Cl)c(n1)N2]

The desired compound was prepared according to the procedure of Example A118 using N-[6-chloro-2,4,8,18,22-pentaazatetracyclo[14.3.1.1(3,7).1(9,13)]docosa-1(20),3(22),4, 6,9(21),10,12,16,18-nonaen-12-yl]-2-[(3S)-piperidin-3-yl] acetamide tris(trifluoroacetate) as the starting material in 20% yield. LCMS for $C_{30}H_{29}ClN_9O_2$ (M+H)$^+$: m/z=582.0.

Example D214

N-[6-Chloro-2,4,8,18,22-pentaazatetracyclo[14.3.1.1 (3,7).1(9,13)]docosa-1(20),3(22),4,6,9(21),10,12,16, 18-nonaen-12-yl]-2-[(3R)-1-[1,3]oxazolo[5,4-b]pyridin-2-ylpiperidin-3-yl]acetamide tris (trifluoroacetate)

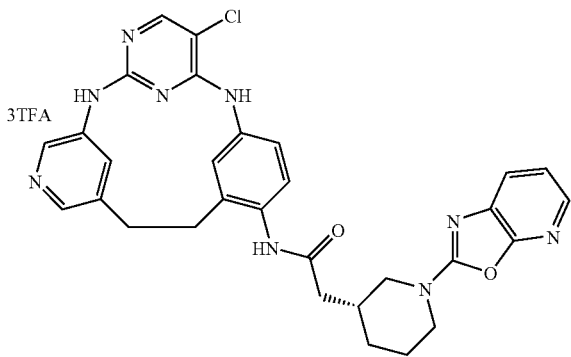 [SMILES: "3TFA" ; O=C(C[C@H]1CCCN(c2nc3cccnc3o2)C1)Nc1ccc2cc1CCc1cncc(c1)Nc1ncc(Cl)c(n1)N2]

The desired compound was prepared according to the procedure of Example A118 using N-[6-chloro-2,4,8,18,22-pentaazatetracyclo[14.3.1.1(3,7).1(9,13)]docosa-1(20),3(22),4, 6,9(21),10,12,16,18-nonaen-12-yl]-2-[(3R)-piperidin-3-yl]

acetamide tris(trifluoroacetate) as the starting material in 20% yield. LCMS for $C_{30}H_{29}ClN_9O_2$ (M+H)$^+$: m/z=582.0.

Example D215

Benzyl 4-(2-{[6-chloro-2,4,8,18,22-pentaazatetracyclo[14.3.1.1(3,7).1(9,13)]docosa-1(20),3(22),4,6,9 (21),10,12,16,18-nonaen-12-yl]amino}ethyl)piperidine-1-carboxylate

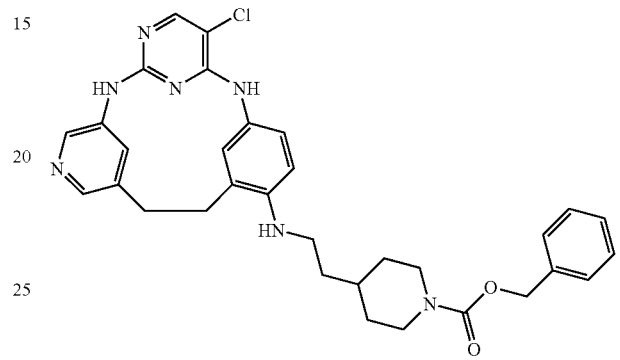

Step A: Benzyl 4-[2-({2-[2-(5-aminopyridin-3-yl) ethyl]-4-[(2,5-dichloropyrimidin-4-yl)amino] phenyl}amino)ethyl]piperidine-1-carboxylate

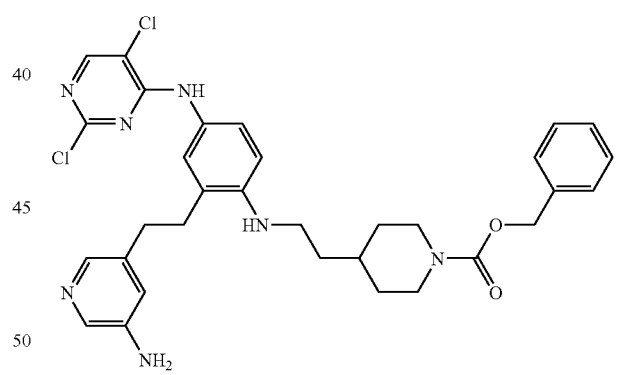

The desired compound was prepared according to the procedure of Example D158, steps A-E, using benzyl 4-(2-aminoethyl)piperidine-1-carboxylate as the starting material. LCMS for $C_{32}H_{36}Cl_2N_7O_2$ (M+H)$^+$: m/z=620.2, 622.1.

Step B: Benzyl 4-(2-{[6-chloro-2,4,8,18,22-pentaazatetracyclo[14.3.1.1(3,7).1(9,13)]docosa-1(20),3 (22),4,6,9(21),10,12,16,18-nonaen-12-yl] amino}ethyl)piperidine-1-carboxylate The desired compound was prepared according to the procedure of Example B20, step H, using benzyl 4-[2-({2-[2-(5-aminopyridin-3-yl)ethyl]-4-[(2,5-dichloropyrimidin-4-yl)

amino]phenyl}amino)ethyl]piperidine-1-carboxylate as the starting material in 58% yield. LCMS for $C_{32}H_{35}ClN_7O_2$ (M+H)$^+$: m/z=584.2.

Example D216

6-Chloro-N-(2-piperidin-4-ylethyl)-2,4,8,18,22-pentaazatetracyclo[14.3.1.1(3,7).1(9,13)]docosa-1(20),3(22),4,6,9(21),10,12,16,18-nonaen-12-amine tetrakis (trifluoroacetate)

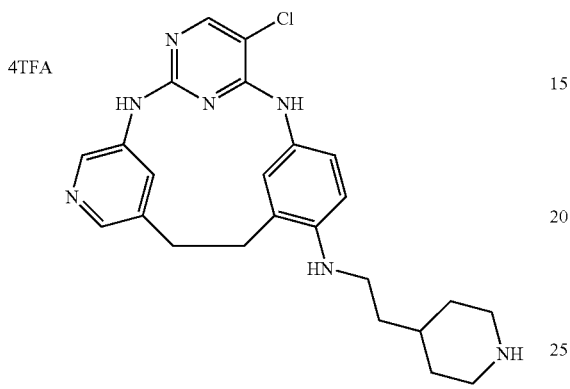

A solution of benzyl 4-(2-{[6-chloro-2,4,8,18,22-pentaazatetracyclo[14.3.1.1(3,7).1(9,13)]docosa-1(20),3(22),4,6,9(21),10,12,16,18-nonaen-12-yl]amino}ethyl)piperidine-1-carboxylate (25 mg, 43 µmol) in acetic acid (0.7 mL) and ethanol (2 mL) was degassed with nitrogen and treated with 10% palladium on carbon (25 mg, 21 µmol) followed by 1,4-cyclohexadiene (41 µL, 0.43 mmol) and stirred at 20° C. for 60 h. The reaction mixture was filtered over celite and purified by preparative LCMS to give the desired product (11 mg, 28%) as a yellow solid. LCMS for $C_{24}H_{29}ClN_7$ (M+H)$^+$: m/z=450.2.

Example D217

2,4,8,18,22-Pentaazatetracyclo[14.3.1.1(3,7).1(9,13)]docosa-1(20),3(22),4,6,9(21),10,12,16,18-nonaene bis(trifluoroacetate)

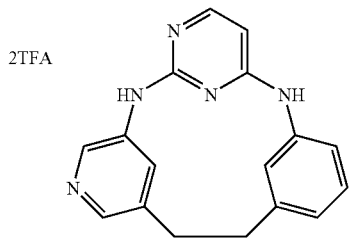 [SMILES: "2TFA" ; c1cc2cc(c1)Nc1ccnc(n1)Nc1cncc(c1)CC2]

Step A:
2-Chloro-N-(3-iodophenyl)pyrimidin-4-amine

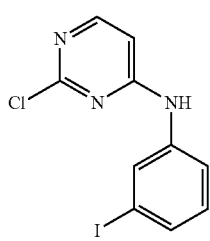 [SMILES: Clc1nccc(Nc2cccc(I)c2)n1]

A solution of 2,4-dichloropyrimidine (3.0 g, 20 mmol) and N,N-diisopropylethylamine (4.2 mL, 24 mmol) in N-methylpyrrolidinone (20 mL) was treated with 3-iodoaniline (2.4 mL, 20 mmol) dropwise and heated at 120° C. for 2 h. The reaction mixture was concentrated, diluted with ethyl acetate (150 mL), and washed with water (150 mL). The aqueous layer was separated and extracted with ethyl acetate (150 mL). The combined organic extracts were washed with brine (100 mL), dried over anhydrous sodium sulfate, filtered, and concentrated to a crude oil. This material was purified by flash column chromatography to give the desired product (3.2 mg, 48%) as a tan solid. LCMS for $C_{10}H_8ClIN_3$ (M+H)$^+$: m/z=331.9.

Step B: N-{3-[(E)-2-(5-Aminopyridin-3-yl)vinyl]phenyl}-2-chloropyrimidin-4-amine

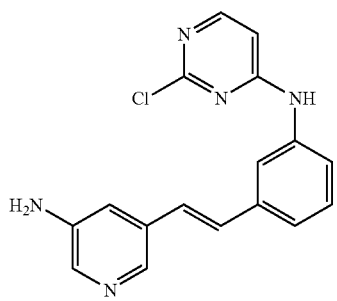 [SMILES: Nc1cncc(/C=C/c2cccc(Nc3ccnc(Cl)n3)c2)c1]

The desired compound was prepared according to the procedure of Example B334, step G, using 2-chloro-N-(3-iodophenyl)pyrimidin-4-amine as the starting material in 70% yield. LCMS for $C_{17}H_{15}ClN_5$ (M+H)$^+$: m/z=324.1.

Step C: N-{3-[2-(5-Aminopyridin-3-yl)ethyl]phenyl}-2-chloropyrimidin-4-amine

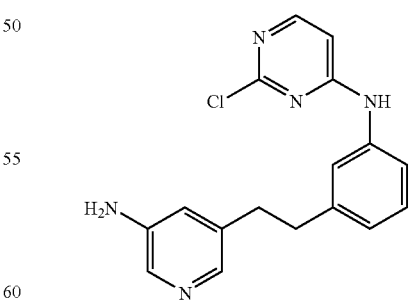

The desired compound was prepared according to the procedure of Example B334, step H, using N-{3-[(E)-2-(5-aminopyridin-3-yl)vinyl]phenyl}-2-chloropyrimidin-4-amine as the starting material in 65% yield. LCMS for $C_{17}H_{17}ClN_5$ (M+H)$^+$: m/z=326.1.

Step D: 2,4,8,18,22-Pentaazatetracyclo[14.3.1.1(3,7).1(9,13)]docosa-1(20),3(22),4,6,9(21),10,12,16,18-nonaene bis(trifluoroacetate)

The desired compound was prepared according to the procedure of Example B20, step H, using N-{3-[2-(5-aminopyridin-3-yl)ethyl]phenyl}-2-chloropyrimidin-4-amine as the starting material in 40% yield. LCMS for $C_{17}H_{16}N_5$ (M+H)$^+$: m/z=290.1.

Example D218

6-Chloro-N-(2-{1-[(5-methylisoxazol-3-yl)carbonyl]piperidin-4-yl}ethyl)-2,4,8,18,22-pentaazatetracyclo[14.3.1.1(3,7).1(9,13)]docosa-1(20),3(22),4,6,9(21),10,12,16,18-nonaen-12-amine tris(trifluoroacetate)

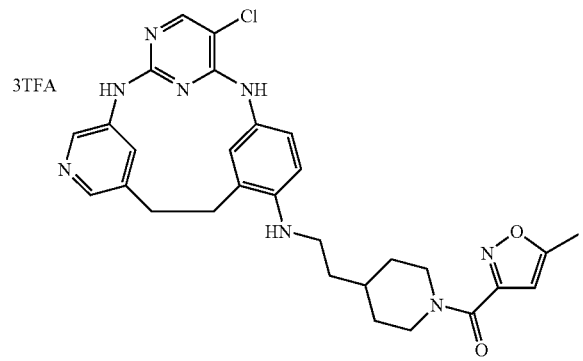 [SMILES: "3TFA" ; Cc1cc(C(=O)N2CCC(CCNc3ccc4cc3CCc3cncc(c3)Nc3ncc(Cl)c(n3)N4)CC2)no1]

The desired compound was prepared according to the procedure of Example D94 using 6-chloro-N-(2-piperidin-4-ylethyl)-2,4,8,18,22-pentaazatetracyclo[14.3.1.1(3,7).1(9,13)]docosa-1(20),3(22),4,6,9(21),10,12,16,18-nonaen-12-amine tetrakis(trifluoroacetate) and 5-methylisoxazole-3-carbonyl chloride as the starting materials in 55% yield. LCMS for $C_{29}H_{32}ClN_8O_2$ (M+H)$^+$: m/z=559.2.

Example D219

N-[2-(1-Acetylpiperidin-4-yl)ethyl]-6-chloro-2,4,8,18,22-pentaazatetracyclo[14.3.1.1(3,7).1(9,13)]docosa-1(20),3(22),4,6,9(21),10,12,16,18-nonaen-12-amine tris(trifluoroacetate)

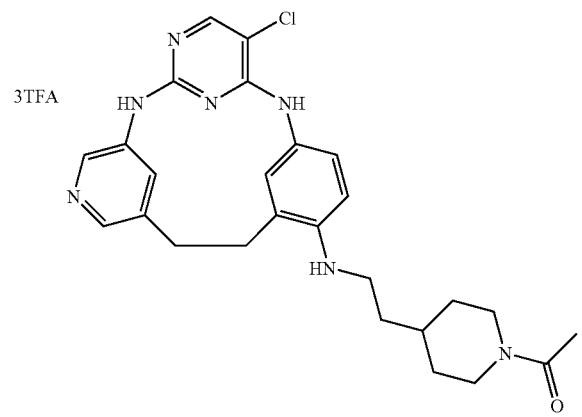 [SMILES: "3TFA" ; CC(=O)N1CCC(CCNc2ccc3cc2CCc2cncc(c2)Nc2ncc(Cl)c(n2)N3)CC1]

The desired compound was prepared according to the procedure of Example D94 using 6-chloro-N-(2-piperidin-4-ylethyl)-2,4,8,18,22-pentaazatetracyclo[14.3.1.1(3,7).1(9,13)]docosa-1(20),3(22),4,6,9(21),10,12,16,18-nonaen-12-amine tetrakis(trifluoroacetate) and acetyl chloride as the starting materials in 50% yield. LCMS for $C_{26}H_{31}ClN_7O$ (M+H)$^+$: m/z=492.1.

Example D220

6-Chloro-N-{2-[1-(2,4-difluorobenzoyl)piperidin-4-yl]ethyl}-2,4,8,18,22-pentaazatetracyclo[14.3.1.1(3,7).1(9,13)]docosa-1(20),3(22),4,6,9(21),10,12,16,18-nonaen-12-amine tris(trifluoroacetate)

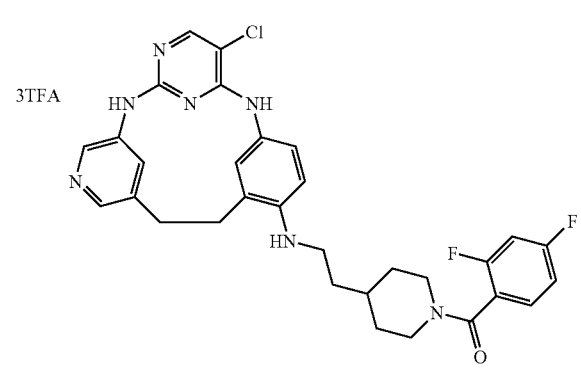 [SMILES: "3TFA" ; O=C(c1ccc(F)cc1F)N1CCC(CCNc2ccc3cc2CCc2cncc(c2)Nc2ncc(Cl)c(n2)N3)CC1]

The desired compound was prepared according to the procedure of Example D94 using 6-chloro-N-(2-piperidin-4-ylethyl)-2,4,8,18,22-pentaazatetracyclo[14.3.1.1(3,7).1(9,13)]docosa-1(20),3(22),4,6,9(21),10,12,16,18-nonaen-12-amine tetrakis(trifluoroacetate) and 2,4-difluorobenzoyl chloride as the starting materials in 30% yield. LCMS for $C_{31}H_{31}ClF_2N_7O$ (M+H)$^+$: m/z=590.1.

Example D221

6-Chloro-N-(2-{1-[(2-fluorophenyl)sulfonyl]piperidin-4-yl}ethyl)-2,4,8,18,22-pentaazatetracyclo[14.3.1.1(3,7).1(9,13)]docosa-1(20),3(22),4,6,9(21),10,12,16,18-nonaen-12-amine tris(trifluoroacetate)

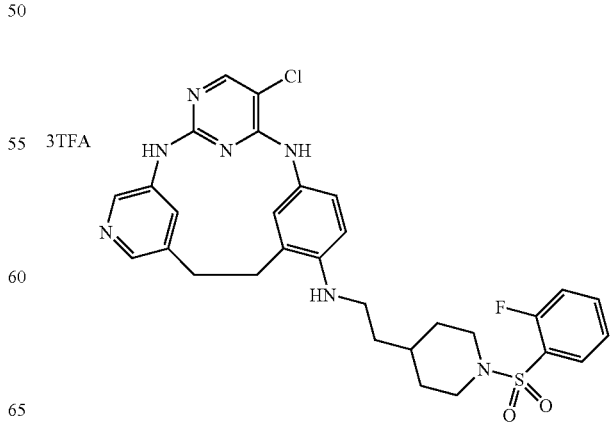

The desired compound was prepared according to the procedure of Example D20, step A, using 6-chloro-N-(2-piperidin-4-ylethyl)-2,4,8,18,22-pentaazatetracyclo[14.3.1.1(3,7).1(9,13)]docosa-1(20),3(22),4,6,9(21),10,12,16,18-nonaen-12-amine tetrakis(trifluoroacetate) and 2-fluorobenzenesulphonyl chloride as the starting materials in 50% yield. LCMS for $C_{30}H_{32}ClFN_7O_2S$ (M+H)$^+$: m/z=608.1.

Example D222

2-{[4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}ethyl)piperidin-1-yl]sulfonyl}benzonitrile tris(trifluoroacetate)

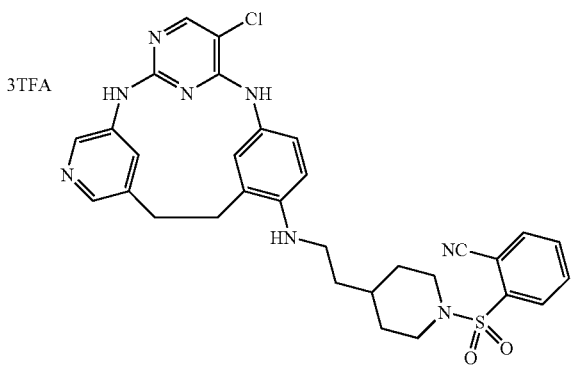

The desired compound was prepared according to the procedure of Example D20, step A, using 6-chloro-N-(2-piperidin-4-ylethyl)-2,4,8,18,22-pentaazatetracyclo[14.3.1.1(3,7).1(9,13)]docosa-1(20),3(22),4,6,9(21),10,12,16,18-nonaen-12-amine tetrakis(trifluoroacetate) and 2-cyanobenzenesulfonyl chloride as the starting materials in 60% yield. LCMS for $C_{31}H_{32}ClN_8O_2S$ (M+H)$^+$: m/z=615.2.

Example D223

8-Methyl-2,4,8,22-tetraazatetracyclo[14.3.1.1(3,7).1(9,13)]docosa-1(20),3(22),4,6,9(21),10,12,16,18-nonaene trifluoroacetate

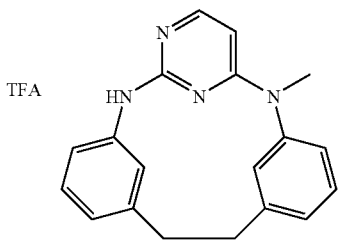 [SMILES: "TFA" ; CN1c2cccc(c2)CCc2cccc(c2)Nc2nccc1n2]

Step A: 2-Chloro-N-(3-iodophenyl)-N-methylpyrimidin-4-amine

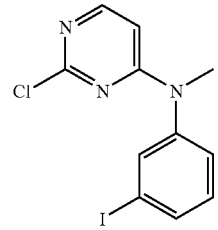 [SMILES: CN(c1cccc(I)c1)c1ccnc(Cl)n1]

A solution of 2-chloro-N-(3-iodophenyl)pyrimidin-4-amine (1.1 g, 3.3 mmol) and potassium carbonate (0.92 g, 6.6 mmol) in N,N-dimethylformamide (6.6 mL) was treated with methyl iodide (0.52 mL, 8.3 mmol) and stirred at 20° C. for 5 h. The reaction mixture was poured into water (50 mL) and extracted with ethyl acetate (200 mL). The organic layer was separated and washed with brine (50 mL), dried over anhydrous sodium sulfate, filtered, and concentrated to a crude solid. This material was purified by flash column chromatography to give the desired product (0.87 g, 75%) as a tan oil. LCMS for $C_{11}H_{10}ClIN_3$ (M+H)$^+$: m/z=346.0.

Step B: tert-Butyl [3-((E)-2-{3-[(2-chloropyrimidin-4-yl)(ethyl)amino]phenyl}vinyl)phenyl]carbamate

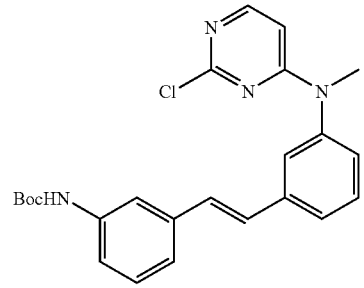 [SMILES: CN(c1cccc(/C=C/c2cccc(NC(=O)OC(C)(C)C)c2)c1)c1ccnc(Cl)n1]

The desired compound was prepared according to the procedure of Example B334, step G, using 2-chloro-N-(3-iodophenyl)-N-methylpyrimidin-4-amine and tert-butyl (3-vinylphenyl)carbamate as the starting materials in 76% yield. LCMS for $C_{24}H_{26}ClN_4O_2$ (M+H)$^+$: m/z=437.1.

Step C: tert-Butyl [3-(2-{3-[(2-chloropyrimidin-4-yl)(methyl)amino]phenyl}ethyl)phenyl]carbamate

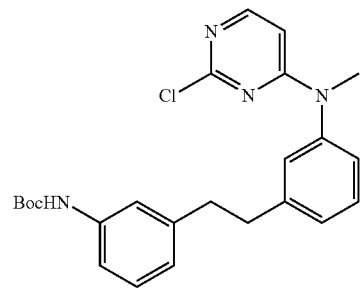 [SMILES: CN(c1cccc(CCc2cccc(NC(=O)OC(C)(C)C)c2)c1)c1ccnc(Cl)n1]

The desired compound was prepared according to the procedure of Example B334, step H, using tert-butyl [3-((E)-2-{3-[(2-chloropyrimidin-4-yl)(methyl)amino]phenyl}vinyl)phenyl]carbamate as the starting material in 65% yield. LCMS for $C_{24}H_{28}ClN_4O_2$ (M+H)$^+$: m/z=439.1.

Step D: 8-Methyl-2,4,8,22-tetraazatetracyclo[14.3.1.1(3,7).1(9,13)]docosa-1(20),3(22),4,6,9(21),10,12,16,18-nonaene trifluoroacetate The desired compound was prepared according to the procedure of Example D2, step D, using tert-butyl [3-(2-{3-[(2-chloropyrimidin-4-yl)(methyl)amino]phenyl}ethyl)phenyl]carbamate as the starting material in 20% yield. LCMS for $C_{19}H_{19}N_4$ (M+H)$^+$: m/z=303.1.

Example D224

8-Methyl-2,4,8,18,22-pentaazatetracyclo[14.3.1.1(3,7).1(9,13)]docosa-1(20),3(22),4,6,9(21),10,12,16,18-nonaene bis(trifluoroacetate)

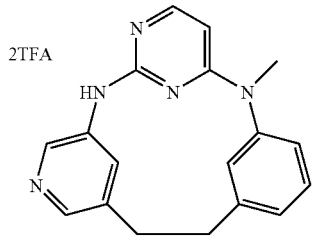 [SMILES: "2TFA" ; CN1c2cccc(c2)CCc2cncc(c2)Nc2nccc1n2]

Step A: N-{3-[(E)-2-(5-aminopyridin-3-yl)vinyl]phenyl}-2-chloro-N-methylpyrimidin-4-amine

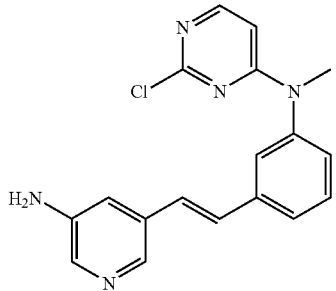 [SMILES: CN(c1cccc(/C=C/c2cncc(N)c2)c1)c1ccnc(Cl)n1]

The desired compound was prepared according to the procedure of Example B334, step G, using 2-chloro-N-(3-iodophenyl)-N-methylpyrimidin-4-amine as the starting material in 90% yield. LCMS for $C_{18}H_{17}ClN_5$ (M+H)$^+$: m/z=338.1.

Step B: N-{3-[2-(5-Aminopyridin-3-yl)ethyl]phenyl}-2-chloro-N-methylpyrimidin-4-amine

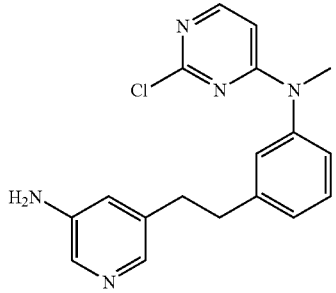 [SMILES: CN(c1cccc(CCc2cncc(N)c2)c1)c1ccnc(Cl)n1]

The desired compound was prepared according to the procedure of Example B334, step H, using N-{3-[(E)-2-(5-aminopyridin-3-yl)vinyl]phenyl}-2-chloro-N-methylpyrimidin-4-amine as the starting material in 49% yield. LCMS for $C_{18}H_{19}ClN_5$ (M+H)$^+$: m/z=340.0.

Step C: 8-Methyl-2,4,8,18,22-pentaazatetracyclo[14.3.1.1(3,7).1(9,13)]docosa-1(20),3(22),4,6,9(21),10,12,16,18-nonaene bis(trifluoroacetate)

The desired compound was prepared according to the procedure of Example B20, step H, using N-{3-[2-(5-aminopyridin-3-yl)ethyl]phenyl}-2-chloro-N-methylpyrimidin-4-amine as the starting material in 32% yield. LCMS for $C_{18}H_{18}N_5$ (M+H)$^+$: m/z=304.1.

Example D225

6-Chloro-12-(piperidin-4-ylmethoxy)-2,4,8,18,22-pentaazatetracyclo[14.3.1.1(3,7).1(9,13)]docosa-1(20),3(22),4,6,9(21),10,12,16,18-nonaene tris(trifluoroacetate)

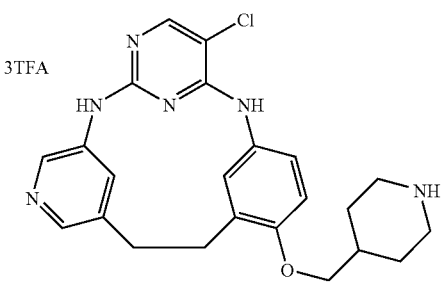 [SMILES: "3TFA" ; Clc1cnc2nc1Nc1ccc(OCC3CCNCC3)c(c1)CCc1cncc(c1)N2]

The desired compound was prepared according to the procedure of Example D161, steps C-I using 4-hydroxymethyl-piperidine-1-carboxylic acid tert-butyl ester as the starting material. LCMS for $C_{23}H_{26}ClN_6O$ (M+H)$^+$: m/z=437.1.

Example D226

6-Chloro-12-({1-[(5-methylisoxazol-3-yl)carbonyl]piperidin-4-yl}methoxy)-2,4,8,18,22-pentaazatetracyclo[14.3.1.1(3,7).1(9,13)]docosa-1(20),3(22),4,6,9(21),10,12,16,18-nonaene bis(trifluoroacetate)

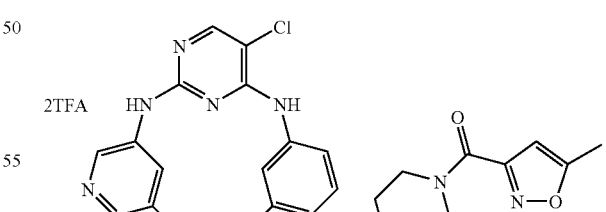

The desired compound was prepared according to the procedure of Example D94 using 6-chloro-12-(piperidin-4-ylmethoxy)-2,4,8,18,22-pentaazatetracyclo[14.3.1.1(3,7).1(9,13)]docosa-1(20),3(22),4,6,9(21),10,12,16,18-nonaene tris(trifluoroacetate) and 5-methylisoxazole-3-carbonyl chloride as the starting materials in 60% yield. LCMS for $C_{28}H_{29}ClN_7O_3$ (M+H)$^+$: m/z=546.2.

Example D227

12-[(1-Acetylpiperidin-4-yl)methoxy]-6-chloro-2,4,8,18,22-pentaazatetracyclo[14.3.1.1(3,7).1(9,13)]docosa-1(20),3(22),4,6,9(21),10,12,16,18-nonaene bis(trifluoroacetate)

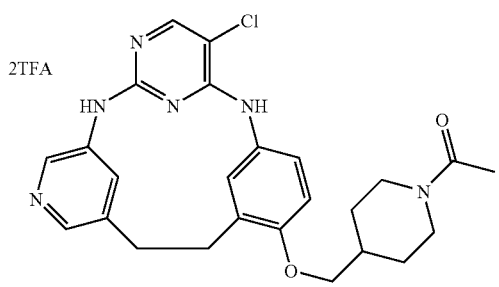 [SMILES: "2TFA" ; CC(=O)N1CCC(COc2ccc3cc2CCc2cncc(c2)Nc2ncc(Cl)c(n2)N3)CC1]

The desired compound was prepared according to the procedure of Example D94 using 6-chloro-12-(piperidin-4-ylmethoxy)-2,4,8,18,22-pentaazatetracyclo[14.3.1.1(3,7).1(9,13)]docosa-1(20),3(22),4,6,9(21),10,12,16,18-nonaene tris(trifluoroacetate) and acetyl chloride as the starting materials in 66% yield. LCMS for $C_{25}H_{28}ClN_6O_2$ (M+H)$^+$: m/z=479.1.

Example D228

4-({[6-Chloro-2,4,8,18,22-pentaazatetracyclo[14.3.1.1(3,7).1(9,13)]docosa-1(20),3(22),4,6,9(21),10,12,16,18-nonaen-12-yl]oxy}methyl)-N-phenylpiperidine-1-carboxamide bis(trifluoroacetate)

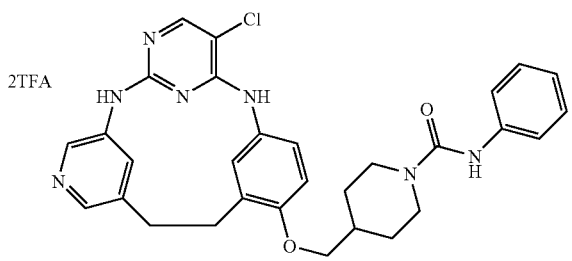 [SMILES: "2TFA" ; O=C(Nc1ccccc1)N1CCC(COc2ccc3cc2CCc2cncc(c2)Nc2ncc(Cl)c(n2)N3)CC1]

The desired compound was prepared according to the procedure of Example D41 using 6-chloro-12-(piperidin-4-ylmethoxy)-2,4,8,18,22-pentaazatetracyclo[14.3.1.1(3,7).1(9,13)]docosa-1(20),3(22),4,6,9(21),10,12,16,18-nonaene tris(trifluoroacetate) and phenyl isocyanate as the starting materials in 40% yield. LCMS for $C_{30}H_{31}ClN_7O_2$ (M+H)$^+$: m/z=556.1.

Example D229

6-Chloro-12-(2-oxo-2-piperazin-1-ylethoxy)-2,4,8,18,22-pentaazatetracyclo[14.3.1.1(3,7).1(9,13)]docosa-1(20),3(22),4,6,9(21),10,12,16,18-nonaene tris(trifluoroacetate)

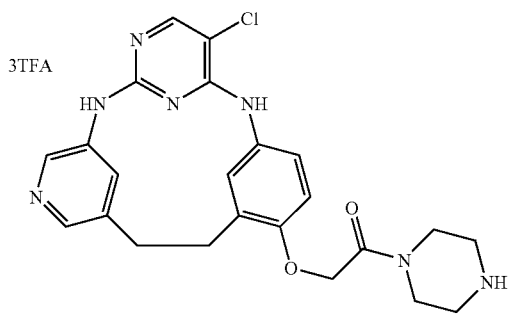 [SMILES: "3TFA" ; O=C(COc1ccc2cc1CCc1cncc(c1)Nc1ncc(Cl)c(n1)N2)N1CCNCC1]

Step A: tert-Butyl (2-iodo-4-nitrophenoxy)acetate

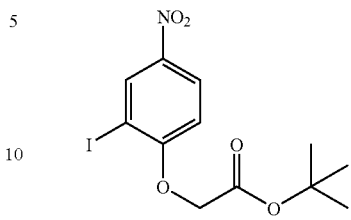

A solution of 2-iodo-4-nitrophenol (2.2 g, 8.3 mmol), tert-butyl bromoacetate (1.6 mL, 11 mmol), and potassium carbonate (2.3 g, 17 mmol) in N,N-dimethylformamide (20 mL) was stirred at 20° C. for 60 h. The reaction mixture was poured into water (300 mL) and extracted with ethyl acetate (500 mL). The organic layer was separated and washed with brine, dried over anhydrous sodium sulfate, filtered, and concentrated to a crude oil. This material was purified by flash column chromatography to give the desired product (2.0 g, 60%).

Step B: tert-Butyl (4-amino-2-iodophenoxy)acetate

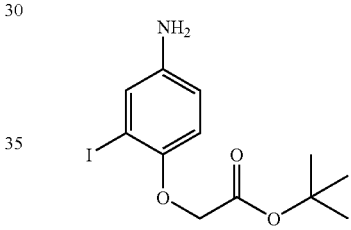

The desired compound was prepared according to the procedure of Example D2, step B, using tert-butyl (2-iodo-4-nitrophenoxy)acetate as the starting material in quantitative yield. LCMS for $C_{12}H_{17}INO_3$ (M+H)$^+$: m/z=350.1.

Step C: tert-Butyl {4-[(2,5-dichloropyrimidin-4-yl)amino]-2-iodophenoxy}acetate

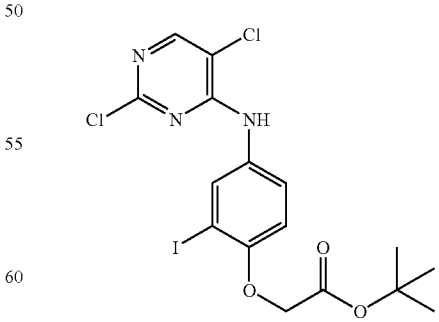

The desired compound was prepared according to the procedure of Example D2, step C, using tert-butyl (4-amino-2-iodophenoxy)acetate as the starting material in 89% yield. LCMS for $C_{16}H_{17}Cl_2IN_3O_3$ (M+H)$^+$: m/z=495.9, 497.9.

Step D: tert-Butyl {4-[(2,5-dichloropyrimidin-4-yl)amino]-2-iodophenoxy}acetate

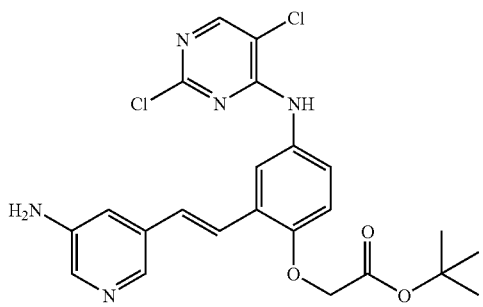 [SMILES: CC(C)(C)OC(=O)COc1ccc(Nc2nc(Cl)ncc2Cl)cc1/C=C/c1cncc(N)c1]

The desired compound was prepared according to the procedure of Example B334, step G, using tert-butyl {4-[(2,5-dichloropyrimidin-4-yl)amino]-2-iodophenoxy}acetate as the starting material in 76% yield. LCMS for $C_{23}H_{24}Cl_2N_5O_3$ (M+H)$^+$: m/z=488.0, 490.0.

Step E: tert-Butyl {2-[2-(5-aminopyridin-3-yl)ethyl]-4-[(2,5-dichloropyrimidin-4-yl)amino]phenoxy}acetate

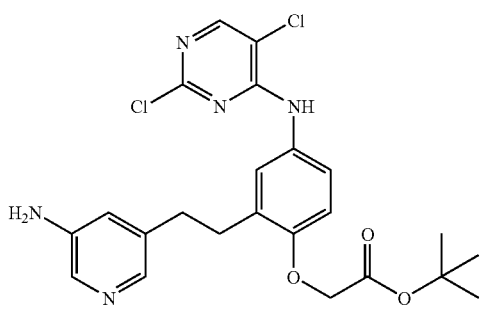 [SMILES: CC(C)(C)OC(=O)COc1ccc(Nc2nc(Cl)ncc2Cl)cc1CCc1cncc(N)c1]

The desired compound was prepared according to the procedure of Example B334, step H, using tert-butyl {4-[(2,5-dichloropyrimidin-4-yl)amino]-2-iodophenoxy}acetate as the starting material in 92% yield. LCMS for $C_{23}H_{26}Cl_2N_5O_3$ (M+H)$^+$: m/z=490.0, 492.0.

Step F: tert-Butyl {[6-chloro-2,4,8,18,22-pentaazatetracyclo[14.3.1.1(3,7).1(9,13)]docosa-1(20),3(22),4,6,9(21),10,12,16,18-nonaen-12-yl]oxy}acetate

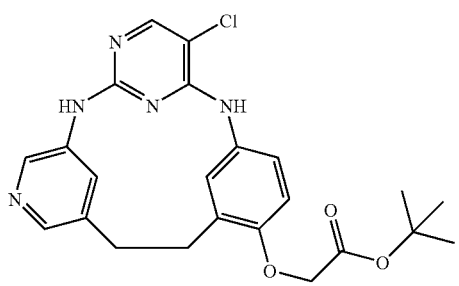 [SMILES: CC(C)(C)OC(=O)COc1ccc2cc1CCc1cncc(c1)Nc1ncc(Cl)c(n1)N2]

The desired compound was prepared according to the procedure of Example B20, step H, using tert-butyl {2-[2-(5-aminopyridin-3-yl)ethyl]-4-[(2,5-dichloropyrimidin-4-yl)amino]phenoxy}acetate as the starting material in 60% yield. LCMS for $C_{23}H_{25}ClN_5O_3$ (M+H)$^+$: m/z=454.1.

Step G: {[6-Chloro-2,4,8,18,22-pentaazatetracyclo[14.3.1.1(3,7).1(9,13)]docosa-1(20),3(22),4,6,9(21),10,12,16,18-nonaen-12-yl]oxy}acetic acid dihydrochloride

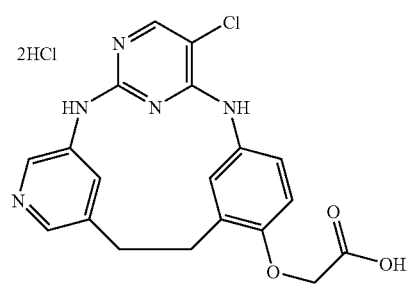 [SMILES: "2HCl" ; O=C(O)COc1ccc2cc1CCc1cncc(c1)Nc1ncc(Cl)c(n1)N2]

A solution of tert-butyl {[6-chloro-2,4,8,18,22-pentaazatetracyclo[14.3.1.1(3,7).1(9,13)]docosa-1(20),3(22),4,6,9(21),10,12,16,18-nonaen-12-yl]oxy}acetate (0.76 g, 1.7 mmol) in 4 M HCl in 1,4 dioxane (30 mL, 120 mmol) was heated at 70° C. for 1 h. The reaction mixture was concentrated to a solid that was suspended in diethyl ether, filtered, and washed with diethyl ether to give the desired product (0.82 g, 104%) as a white solid. LCMS for $C_{19}H_{17}ClN_5O_3$ (M+H)$^+$: m/z=398.0.

Step H: tert-Butyl 4-({[6-chloro-2,4,8,18,22-pentaazatetracyclo[14.3.1.1(3,7).1(9,13)]docosa-1(20),3(22),4,6,9(21),10,12,16,18-nonaen-12-yl]oxy}acetyl)piperazine-1-carboxylate

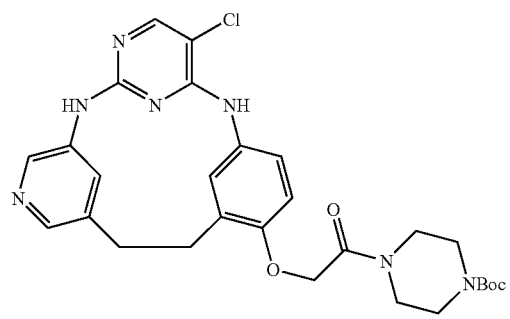 [SMILES: CC(C)(C)OC(=O)N1CCN(C(=O)COc2ccc3cc2CCc2cncc(c2)Nc2ncc(Cl)c(n2)N3)CC1]

The desired compound was prepared according to the procedure of Example D152 using {[6-chloro-2,4,8,18,22-pentaazatetracyclo[14.3.1.1(3,7).1(9,13)]docosa-1(20),3(22),4,6,9(21),10,12,16,18-nonaen-12-yl]oxy}acetic acid dihydrochloride and tert-butyl piperazine-1-carboxylate as the starting materials. LCMS for $C_{23}H_{25}ClN_5O_3$ (M+H)$^+$: m/z=454.1. This material was used immediately in the next step.

Step I: 6-Chloro-12-(2-oxo-2-piperazin-1-ylethoxy)-2,4,8,18,22-pentaazatetracyclo[14.3.1.1(3,7).1(9,13)]docosa-1(20),3(22),4,6,9(21),10,12,16,18-nonaene tris(trifluoroacetate)

The desired compound was prepared according to the procedure of Example D192, step B, using tert-butyl 4-({[6-chloro-2,4,8,18,22-pentaazatetracyclo[14.3.1.1(3,7).1(9,13)]docosa-1(20),3(22),4,6,9(21),10,12,16,18-nonaen-12-yl]oxy}acetyl)piperazine-1-carboxylate as the starting material in 44% yield (2 steps). LCMS for $C_{23}H_{25}ClN_7O_2$ (M+H)$^+$: m/z=466.2.

Example D230

6-Chloro-12-{2-oxo-2-[4-(1,3-thiazol-2-yl)piperazin-1-yl]ethoxy}-2,4,8,18,22-pentaazatetracyclo[14.3.1.1(3,7).1(9,13)]docosa-1(20),3(22),4,6,9(21),10,12,16,18-nonaene tris(trifluoroacetate)

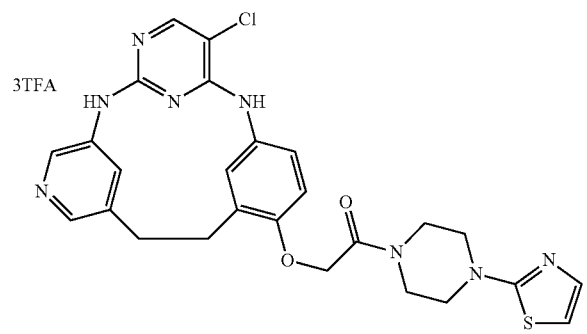 [SMILES: O=C(COc1ccc2cc1CCc1cncc(c1)Nc1ncc(Cl)c(n1)N2)N1CCN(c2nccs2)CC1]

The desired compound was prepared according to the procedure of Example D152 using {[6-chloro-2,4,8,18,22-pentaazatetracyclo[14.3.1.1(3,7).1(9,13)]docosa-1(20),3(22),4,6,9(21),10,12,16,18-nonaen-12-yl]oxy}acetic acid dihydrochloride and 1-(1,3-thiazol-2-yl)piperazine as the starting materials in 63% yield. LCMS for $C_{26}H_{26}ClN_8O_2S$ (M+H)$^+$: m/z=549.0.

Example D231

6-Chloro-12-[2-oxo-2-(4-pyridin-2-ylpiperazin-1-yl)ethoxy]-2,4,8,18,22-pentaazatetracyclo[14.3.1.1(3,7).1(9,13)]docosa-1(20),3(22),4,6,9(21),10,12,16,18-nonaene tris(trifluoroacetate)

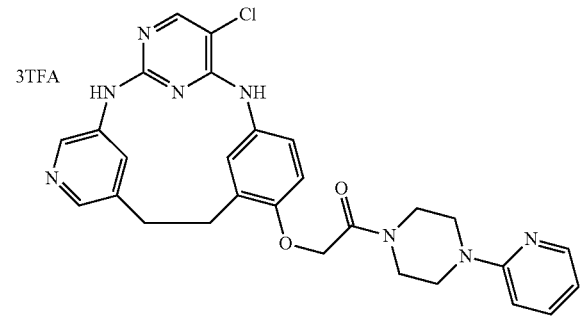 [SMILES: O=C(COc1ccc2cc1CCc1cncc(c1)Nc1ncc(Cl)c(n1)N2)N1CCN(c2ccccn2)CC1]

The desired compound was prepared according to the procedure of Example D152 using {[6-chloro-2,4,8,18,22-pentaazatetracyclo[14.3.1.1(3,7).1(9,13)]docosa-1(20),3(22),4,6,9(21),10,12,16,18-nonaen-12-yl]oxy}acetic acid dihydrochloride and N-(2-pyridyl)piperazine as the starting materials in 64% yield. LCMS for $C_{28}H_{28}ClN_8O_2$ (M+H)$^+$: m/z=543.0.

Example D232

6-Chloro-12-[2-oxo-2-(4-pyrazin-2-ylpiperazin-1-yl)ethoxy]-2,4,8,18,22-pentaazatetracyclo[14.3.1.1(3,7).1(9,13)]docosa-1(20),3(22),4,6,9(21),10,12,16,18-nonaene tris(trifluoroacetate)

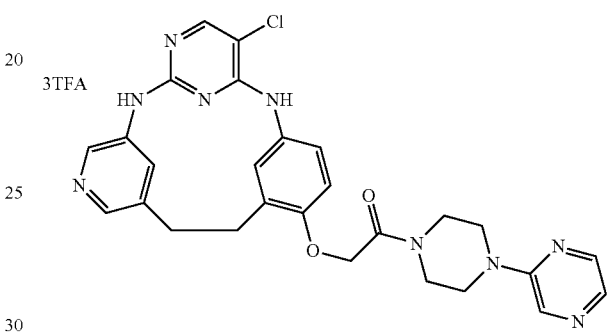

The desired compound was prepared according to the procedure of Example D152 using {[6-chloro-2,4,8,18,22-pentaazatetracyclo[14.3.1.1(3,7).1(9,13)]docosa-1(20),3(22),4,6,9(21),10,12,16,18-nonaen-12-yl]oxy}acetic acid dihydrochloride and 2-piperazin-1-ylpyrazine as the starting materials in 60% yield. LCMS for $C_{27}H_{27}ClN_9O_2$ (M+H)$^+$: m/z=544.0.

Example D233

6-Chloro-12-[2-oxo-2-(4-pyrimidin-2-ylpiperazin-1-yl)ethoxy]-2,4,8,18,22-pentaazatetracyclo[14.3.1.1(3,7).1(9,13)]docosa-1(20),3(22),4,6,9(21),10,12,16,18-nonaene tris(trifluoroacetate)

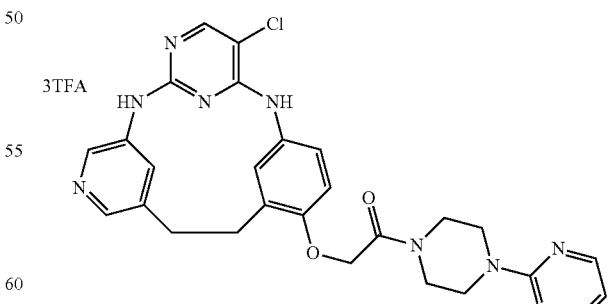

The desired compound was prepared according to the procedure of Example D152 using {[6-chloro-2,4,8,18,22-pentaazatetracyclo[14.3.1.1(3,7).1(9,13)]docosa-1(20),3(22),4,6,9(21),10,12,16,18-nonaen-12-yl]oxy}acetic acid dihydrochloride and 2-piperazin-1-ylpyrimidine as the starting materials in 60% yield. LCMS for $C_{27}H_{27}ClN_9O_2$ (M+H)+: m/z=544.0.

Example D234

6-Chloro-12-[2-oxo-2-(4-phenylpiperazin-1-yl)ethoxy]-2,4,8,18,22-pentaazatetracyclo[14.3.1.1(3,7).1(9,13)]docosa-1(20),3(22),4,6,9(21),10,12,16,18-nonaene tris(trifluoroacetate)

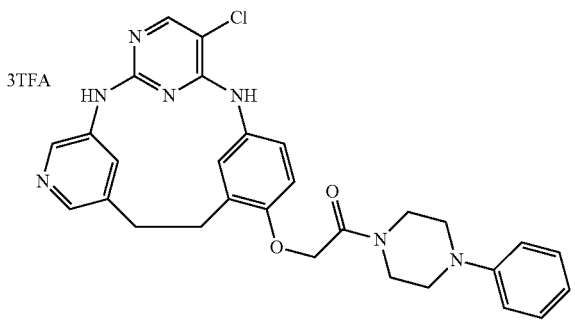 [SMILES: O=C(COc1ccc2cc1CCc1cncc(c1)Nc1ncc(Cl)c(n1)N2)N1CCN(c2ccccc2)CC1]

The desired compound was prepared according to the procedure of Example D152 using {[6-chloro-2,4,8,18,22-pentaazatetracyclo[14.3.1.1(3,7).1(9,13)]docosa-1(20),3(22),4,6,9(21),10,12,16,18-nonaen-12-yl]oxy}acetic acid dihydrochloride and 1-phenylpiperazine as the starting materials in 53% yield. LCMS for $C_{29}H_{29}ClN_7O_2$ (M+H)+: m/z=542.0.

Example D235

2-[4-({[6-Chloro-2,4,8,18,22-pentaazatetracyclo[14.3.1.1(3,7).1(9,13)]docosa-1(20),3(22),4,6,9(21),10,12,16,18-nonaen-12-yl]oxy}acetyl)piperazin-1-yl]benzonitrile tris(trifluoroacetate)

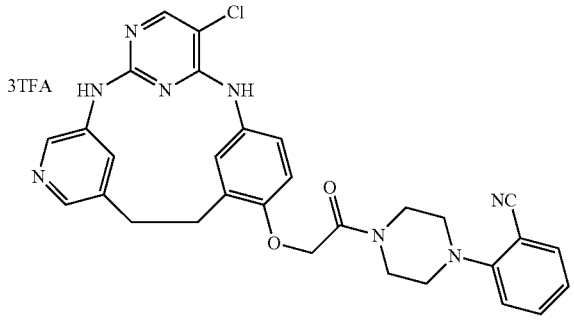 [SMILES: N#Cc1ccccc1N1CCN(C(=O)COc2ccc3cc2CCc2cncc(c2)Nc2ncc(Cl)c(n2)N3)CC1]

The desired compound was prepared according to the procedure of Example D152 using {[6-chloro-2,4,8,18,22-pentaazatetracyclo[14.3.1.1(3,7).1(9,13)]docosa-1(20),3(22),4,6,9(21),10,12,16,18-nonaen-12-yl]oxy}acetic acid dihydrochloride and 2-piperazin-1-ylbenzonitrile as the starting materials in 45% yield. LCMS for $C_{30}H_{28}ClN_8O_2$ (M+H)+: m/z=567.1.

Example D236

4-[4-({[6-Chloro-2,4,8,18,22-pentaazatetracyclo[14.3.1.1(3,7).1(9,13)]docosa-1(20),3(22),4,6,9(21),10,12,16,18-nonaen-12-yl]oxy}acetyl)piperazin-1-yl]benzonitrile tris(trifluoroacetate)

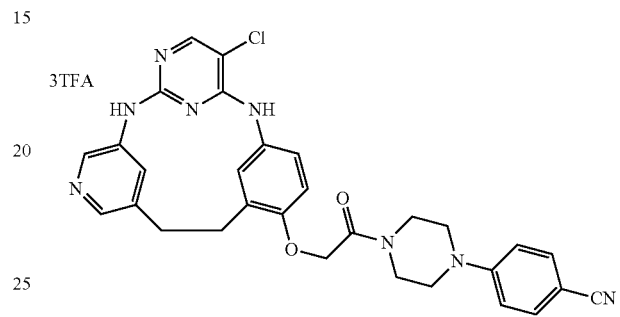

The desired compound was prepared according to the procedure of Example D152 using {[6-chloro-2,4,8,18,22-pentaazatetracyclo[14.3.1.1(3,7).1(9,13)]docosa-1(20),3(22),4,6,9(21),10,12,16,18-nonaen-12-yl]oxy}acetic acid dihydrochloride and 4-piperazin-1-ylbenzonitrile as the starting materials in 48% yield. LCMS for $C_{30}H_{28}ClN_8O_2$ (M+H)+: m/z=567.0.

Example D237

6-Chloro-12-{2-[4-(4-methylpyridin-2-yl)piperazin-1-yl]-2-oxoethoxy}-2,4,8,18,22-pentaazatetracyclo[14.3.1.1(3,7).1(9,13)]docosa-1(20),3(22),4,6,9(21),10,12,16,18-nonaene tris(trifluoroacetate)

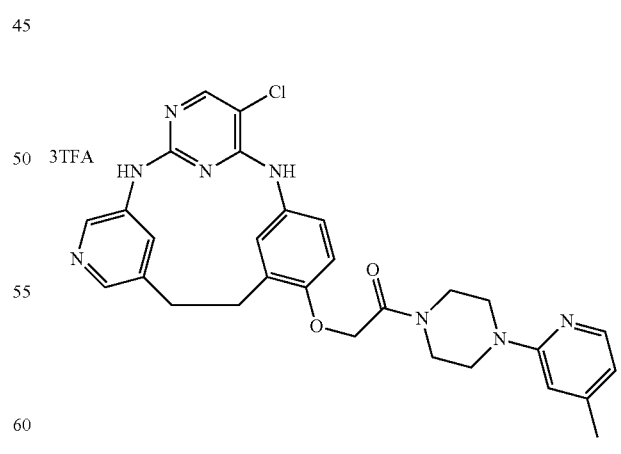

The desired compound was prepared according to the procedure of Example D152 using {[6-chloro-2,4,8,18,22-pentaazatetracyclo[14.3.1.1(3,7).1(9,13)]docosa-1(20),3(22),4,6,9(21),10,12,16,18-nonaen-12-yl]oxy}acetic acid dihydrochloride and 1-(4-methylpyridin-2-yl)piperazine as the starting materials in 52% yield. LCMS for $C_{29}H_{30}ClN_8O_2$ $(M+H)^+$: m/z=557.0.

Example D238

2-[4-({[6-Chloro-2,4,8,18,22-pentaazatetracyclo [14.3.1.1(3,7).1(9,13)]docosa-1(20),3(22),4,6,9(21), 10,12,16,18-nonaen-12-yl]oxy}acetyl)piperazin-1-yl]nicotinonitrile tris(trifluoroacetate)

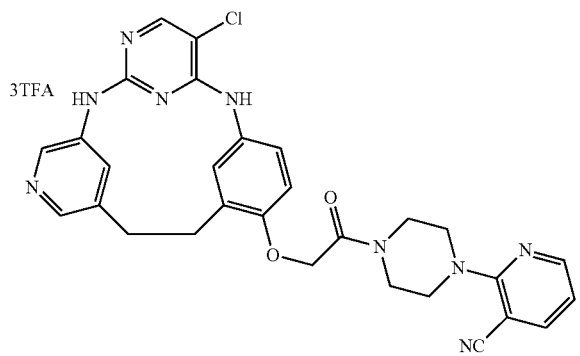 [SMILES: N#Cc1cccnc1N1CCN(C(=O)COc2ccc3cc2CCc2cncc(c2)Nc2ncc(Cl)c(n2)N3)CC1]

The desired compound was prepared according to the procedure of Example D152 using {[6-chloro-2,4,8,18,22-pentaazatetracyclo[14.3.1.1(3,7).1(9,13)]docosa-1(20),3(22),4,6,9(21),10,12,16,18-nonaen-12-yl]oxy}acetic acid dihydrochloride and 2-piperazin-1-ylnicotinonitrile as the starting materials in 20% yield. LCMS for $C_{29}H_{27}ClN_9O_2$ $(M+H)^+$: m/z=568.0.

Example D239

6-[4-({[6-Chloro-2,4,8,18,22-pentaazatetracyclo [14.3.1.1(3,7).1(9,13)]docosa-1(20),3(22),4,6,9(21), 10,12,16,18-nonaen-12-yl]oxy}acetyl)piperazin-1-yl]nicotinonitrile tris(trifluoroacetate)

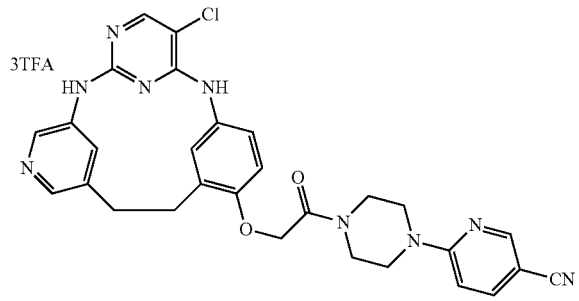 [SMILES: N#Cc1ccc(N2CCN(C(=O)COc3ccc4cc3CCc3cncc(c3)Nc3ncc(Cl)c(n3)N4)CC2)nc1]

The desired compound was prepared according to the procedure of Example D152 using {[6-chloro-2,4,8,18,22-pentaazatetracyclo[14.3.1.1(3,7).1(9,13)]docosa-1(20),3(22),4, 6,9(21),10,12,16,18-nonaen-12-yl]oxy}acetic acid dihydrochloride and 6-piperazin-1-ylnicotinonitrile as the starting materials in 45% yield. LCMS for $C_{29}H_{27}ClN_9O_2$ $(M+H)^+$: m/z=568.0.

Example D240

6-Chloro-12-{2-[4-(6-chloropyridin-2-yl)piperazin-1-yl]-2-oxoethoxy}-2,4,8,18,22-pentaazatetracyclo [14.3.1.1(3,7).1(9,13)]docosa-1(20),3(22),4,6,9(21), 10,12,16,18-nonaene tris(trifluoroacetate)

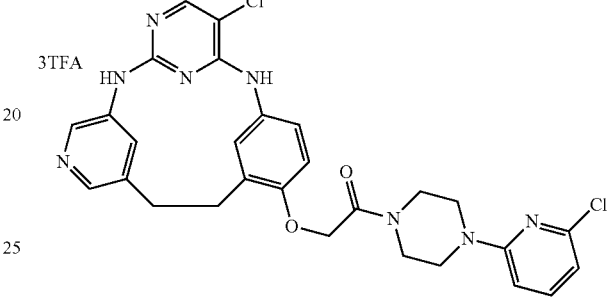

The desired compound was prepared according to the procedure of Example D152 using {[6-chloro-2,4,8,18,22-pentaazatetracyclo[14.3.1.1(3,7).1(9,13)]docosa-1(20),3(22),4, 6,9(21),10,12,16,18-nonaen-12-yl]oxy}acetic acid dihydrochloride and 1-(6-chloropyridin-2-yl)piperazine as the starting materials in 61% yield. LCMS for $C_{28}H_{27}Cl_2N_8O_2$ $(M+H)^+$: m/z=577.0.

Example D241

6-Chloro-12-{2-[4-(2-methoxyphenyl)piperazin-1-yl]-2-oxoethoxy}-2,4,8,18,22-pentaazatetracyclo [14.3.1.1(3,7).1(9,13)]docosa-1(20),3(22),4,6,9(21), 10,12,16,18-nonaene tris(trifluoroacetate)

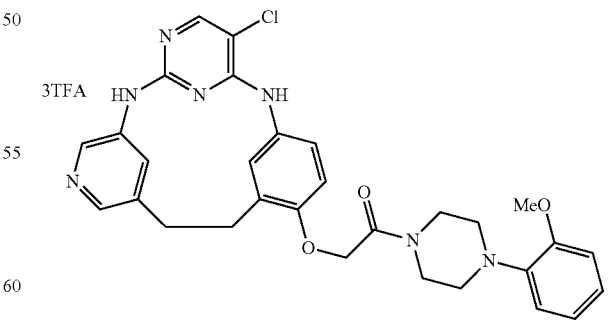

The desired compound was prepared according to the procedure of Example D152 using {[6-chloro-2,4,8,18,22-pentaazatetracyclo[14.3.1.1(3,7).1(9,13)]docosa-1(20),3(22),4, 6,9(21),10,12,16,18-nonaen-12-yl]oxy}acetic acid dihydrochloride and 1-(2-methoxyphenyl)piperazine as the starting materials in 51% yield. LCMS for $C_{30}H_{31}ClN_7O_3$ (M+H)$^+$: m/z=572.1.

Example D242

6-Chloro-12-{2-[4-(4-fluorophenyl)piperazin-1-yl]-2-oxoethoxy}-2,4,8,18,22-pentaazatetracyclo[14.3.1.1(3,7).1(9,13)]docosa-1(20),3(22),4,6,9(21),10,12,16,18-nonaene tris(trifluoroacetate)

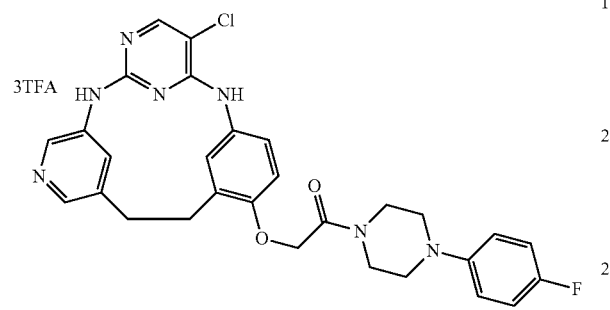

The desired compound was prepared according to the procedure of Example D152 using {[6-chloro-2,4,8,18,22-pentaazatetracyclo[14.3.1.1(3,7).1(9,13)]docosa-1(20),3(22),4,6,9(21),10,12,16,18-nonaen-12-yl]oxy}acetic acid dihydrochloride and N-(4-fluorophenyl)piperazine as the starting materials in 42% yield. LCMS for $C_{29}H_{28}ClFN_7O_2$ (M+H)$^+$: m/z=560.0.

Example D243

6-Chloro-12-[2-oxo-2-(4-pyridin-4-ylpiperazin-1-yl)ethoxy]-2,4,8,18,22-pentaazatetracyclo[14.3.1.1(3,7).1(9,13)]docosa-1(20),3(22),4,6,9(21),10,12,16,18-nonaene tris(trifluoroacetate)

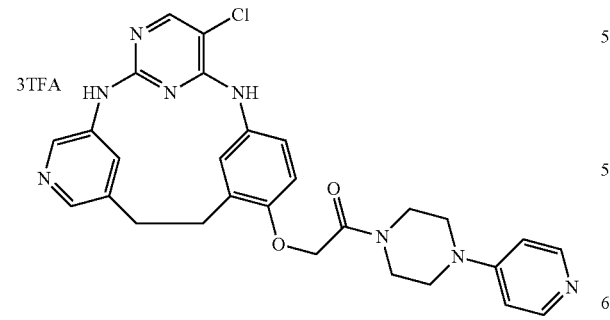 [SMILES: O=C(COc1ccc2cc1CCc1cncc(c1)Nc1ncc(Cl)c(n1)N2)N1CCN(c2ccc(F)cc2)CC1]

The desired compound was prepared according to the procedure of Example D152 using {[6-chloro-2,4,8,18,22-pentaazatetracyclo[14.3.1.1(3,7).1(9,13)]docosa-1(20),3(22),4,6,9(21),10,12,16,18-nonaen-12-yl]oxy}acetic acid dihydrochloride and 1-pyridin-4-ylpiperazine as the starting materials in 42% yield. LCMS for $C_{28}H_{28}ClN_8O_2$ (M+H)$^+$: m/z=543.1.

Example D244

6-Chloro-12-{2-[4-(4-chloropyridin-2-yl)piperazin-1-yl]-2-oxoethoxy}-2,4,8,18,22-pentaazatetracyclo[14.3.1.1(3,7).1(9,13)]docosa-1(20),3(22),4,6,9(21),10,12,16,18-nonaene tris(trifluoroacetate)

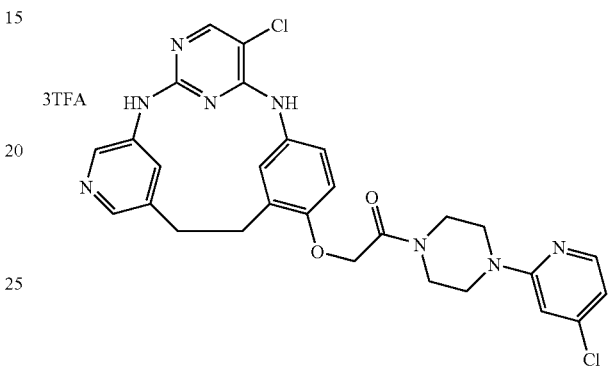

The desired compound was prepared according to the procedure of Example D152 using {[6-chloro-2,4,8,18,22-pentaazatetracyclo[14.3.1.1(3,7).1(9,13)]docosa-1(20),3(22),4,6,9(21),10,12,16,18-nonaen-12-yl]oxy}acetic acid dihydrochloride and 1-(4-chloropyridin-2-yl)piperazine as the starting materials in 44% yield. LCMS for $C_{28}H_{27}Cl_2N_8O_2$ (M+H)$^+$: m/z=577.0.

Example D245

6-Chloro-12-[2-(4-furo[3,2-c]pyridin-4-ylpiperazin-1-yl)-2-oxoethoxy]-2,4,8,18,22-pentaazatetracyclo[14.3.1.1(3,7).1(9,13)]docosa-1(20),3(22),4,6,9(21),10,12,16,18-nonaene tris(trifluoroacetate)

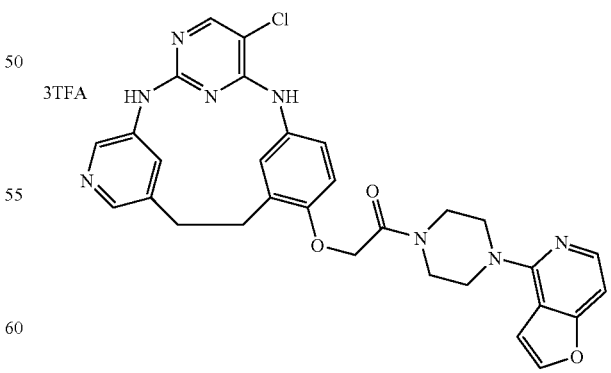

The desired compound was prepared according to the procedure of Example D152 using {[6-chloro-2,4,8,18,22-pentaazatetracyclo[14.3.1.1(3,7).1(9,13)]docosa-1(20),3(22),4,6,9(21),10,12,16,18-nonaen-12-yl]oxy}acetic acid dihydrochloride and 4-piperazin-1-ylfuro[3,2-c]pyridine as the starting materials in 47% yield. LCMS for $C_{30}H_{28}ClN_8O_3$ (M+H)$^+$: m/z=583.1.

Example D246

6-Chloro-12-{2-[4-(5-methylpyridin-2-yl)piperazin-1-yl]-2-oxoethoxy}-2,4,8,18,22-pentaazatetracyclo[14.3.1.1(3,7).1(9,13)]docosa-1(20),3(22),4,6,9(21),10,12,16,18-nonaene tris(trifluoroacetate)

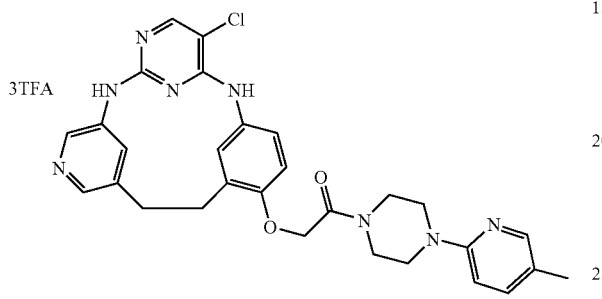

The desired compound was prepared according to the procedure of Example D152 using {[6-chloro-2,4,8,18,22-pentaazatetracyclo[14.3.1.1(3,7).1(9,13)]docosa-1(20),3(22),4,6,9(21),10,12,16,18-nonaen-12-yl]oxy}acetic acid dihydrochloride and 1-(5-methylpyridin-2-yl)piperazine as the starting materials in 49% yield. LCMS for $C_{29}H_{30}ClN_8O_2$ (M+H)$^+$: m/z=557.0.

Example D247

6-Chloro-12-{2-[4-(4,6-dichloropyridin-2-yl)piperazin-1-yl]-2-oxoethoxy}-2,4,8,18,22-pentaazatetracyclo[14.3.1.1(3,7).1(9,13)]docosa-1(20),3(22),4,6,9(21),10,12,16,18-nonaene tris(trifluoroacetate)

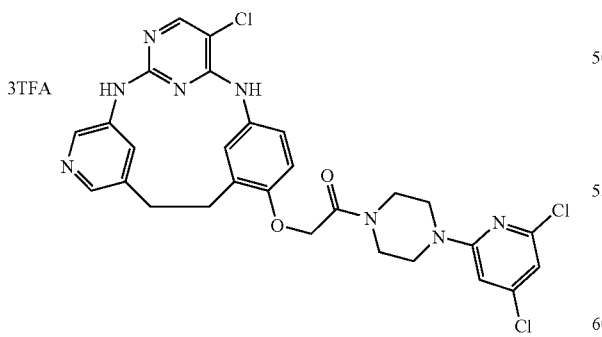

The desired compound was prepared according to the procedure of Example D152 using {[6-chloro-2,4,8,18,22-pentaazatetracyclo[14.3.1.1(3,7).1(9,13)]docosa-1(20),3(22),4,6,9(21),10,12,16,18-nonaen-12-yl]oxy}acetic acid dihydrochloride and 1-(4,6-dichloropyridin-2-yl)piperazine as the starting materials in 30% yield. LCMS for $C_{28}H_{26}Cl_3N_8O_2$ (M+H)$^+$: m/z=611.0, 613.0.

Example D248

6-Chloro-12-(2-oxo-2-{4-[6-(trifluoromethyl)pyridin-2-yl]piperazin-1-yl}ethoxy)-2,4,8,18,22-pentaazatetracyclo[14.3.1.1(3,7).1(9,13)]docosa-1(20),3(22),4,6,9(21),10,12,16,18-nonaene tris(trifluoroacetate)

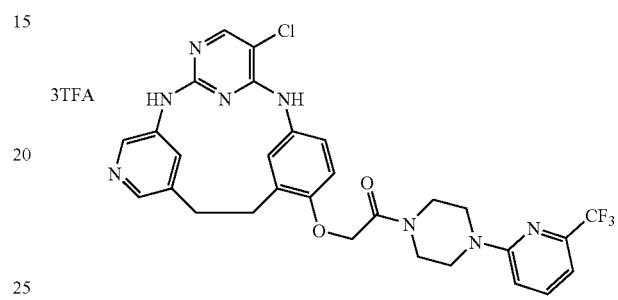

The desired compound was prepared according to the procedure of Example D152 using {[6-chloro-2,4,8,18,22-pentaazatetracyclo[14.3.1.1(3,7).1(9,13)]docosa-1(20),3(22),4,6,9(21),10,12,16,18-nonaen-12-yl]oxy}acetic acid dihydrochloride and 1-[6-(trifluoromethyl)pyridin-2-yl]piperazine as the starting materials in 40% yield. LCMS for $C_{29}H_{27}ClF_3N_8O_2$ (M+H)$^+$: m/z=611.0.

Example D249

6-Chloro-12-{2-[4-(3-methoxypyridin-2-yl)piperazin-1-yl]-2-oxoethoxy}-2,4,8,18,22-pentaazatetracyclo[14.3.1.1(3,7).1(9,13)]docosa-1(20),3(22),4,6,9(21),10,12,16,18-nonaene tris(trifluoroacetate)

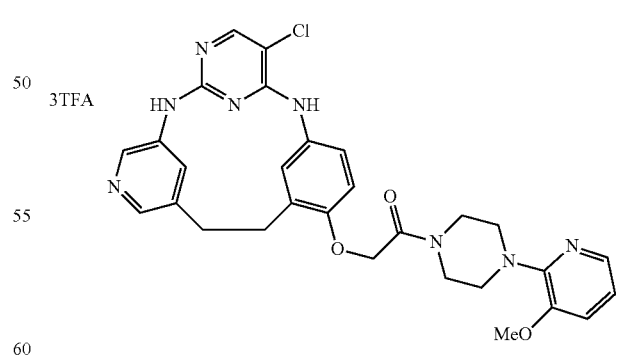

The desired compound was prepared according to the procedure of Example D152 using {[6-chloro-2,4,8,18,22-pentaazatetracyclo[14.3.1.1(3,7).1(9,13)]docosa-1(20),3(22),4,6,9(21),10,12,16,18-nonaen-12-yl]oxy}acetic acid dihydrochloride and 1-(3-methoxypyridin-2-yl)piperazine as the starting materials in 51% yield. LCMS for $C_{29}H_{30}ClN_8O_3$ (M+H)$^+$: m/z=573.1.

Example D250

12-{2-[4-(1,2-Benzisoxazol-3-yl)piperazin-1-yl]-2-oxoethoxy}-6-chloro-2,4,8,18,22-pentaazatetracyclo[14.3.1.1(3,7).1(9,13)]docosa-1(20),3(22),4,6,9(21),10,12,16,18-nonaene tris(trifluoroacetate)

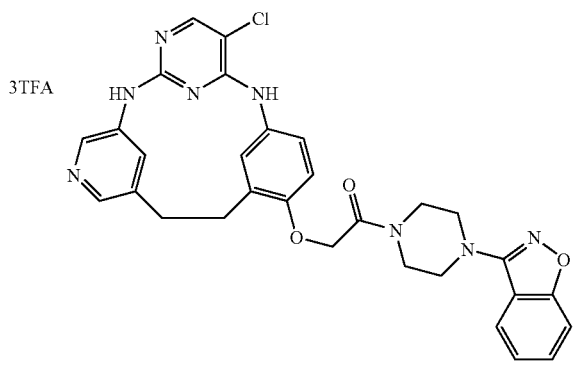 [SMILES: O=C(COc1ccc2cc1CCc1cncc(c1)Nc1ncc(Cl)c(n1)N2)N1CCN(c2noc3ccccc23)CC1]

The desired compound was prepared according to the procedure of Example D152 using {[6-chloro-2,4,8,18,22-pentaazatetracyclo[14.3.1.1(3,7).1(9,13)]docosa-1(20),3(22),4,6,9(21),10,12,16,18-nonaen-12-yl]oxy}acetic acid dihydrochloride and 3-piperazin-1-yl-1,2-benzisoxazole as the starting materials in 30% yield. LCMS for $C_{30}H_{28}ClN_8O_3$ (M+H)$^+$: m/z=583.1.

Example D251

6-Chloro-12-(2-{4-[(5-methylisoxazol-3-yl)carbonyl]piperazin-1-yl}-2-oxoethoxy)-2,4,8,18,22-pentaazatetracyclo[14.3.1.1(3,7).1(9,13)]docosa-1(20),3(22),4,6,9(21),10,12,16,18-nonaene bis(trifluoroacetate)

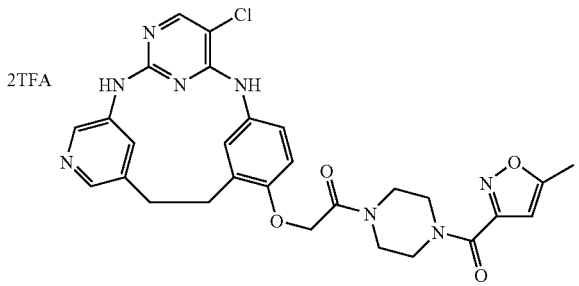 [SMILES: "2TFA" ; Cc1cc(C(=O)N2CCN(C(=O)COc3ccc4cc3CCc3cncc(c3)Nc3ncc(Cl)c(n3)N4)CC2)no1]

The desired compound was prepared according to the procedure of Example D94 using 6-chloro-12-(2-oxo-2-piperazin-1-ylethoxy)-2,4,8,18,22-pentaazatetracyclo[14.3.1.1(3,7).1(9,13)]docosa-1(20),3(22),4,6,9(21),10,12,16,18-nonaene tris(trifluoroacetate) and 5-methylisoxazole-3-carbonyl chloride as the starting materials in 80% yield. LCMS for $C_{28}H_{28}ClN_8O_4$ (M+H)$^+$: m/z=575.0.

Example D252

12-[2-(4-Acetylpiperazin-1-yl)-2-oxoethoxy]-6-chloro-2,4,8,18,22-pentaazatetracyclo[14.3.1.1(3,7).1(9,13)]docosa-1(20),3(22),4,6,9(21),10,12,16,18-nonaene bis(trifluoroacetate)

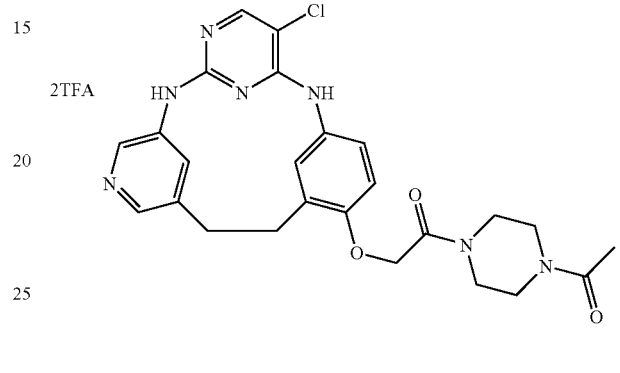

The desired compound was prepared according to the procedure of Example D94 using 6-chloro-12-(2-oxo-2-piperazin-1-ylethoxy)-2,4,8,18,22-pentaazatetracyclo[14.3.1.1(3,7).1(9,13)]docosa-1(20),3(22),4,6,9(21),10,12,16,18-nonaene tris(trifluoroacetate) and acetyl chloride as the starting materials in 88% yield. LCMS for $C_{25}H_{27}ClN_7O_3$ (M+H)$^+$: m/z=508.0.

Example D253

6-Chloro-12-(2-{4-[(2-fluorophenyl)sulfonyl]piperazin-1-yl}-2-oxoethoxy)-2,4,8,18,22-pentaazatetracyclo[14.3.1.1(3,7).1(9,13)]docosa-1(20),3(22),4,6,9(21),10,12,16,18-nonaene bis(trifluoroacetate)

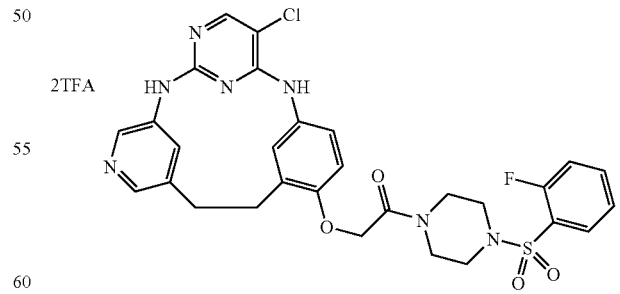

The desired compound was prepared according to the procedure of Example D20, step A, using 6-chloro-12-(2-oxo-2-piperazin-1-ylethoxy)-2,4,8,18,22-pentaazatetracyclo[14.3.1.1(3,7).1(9,13)]docosa-1(20),3(22),4,6,9(21),10,12,16,18-nonaene tris(trifluoroacetate) and 2-fluorobenzenesulphonyl chloride as the starting materials in 50% yield. LCMS for $C_{29}H_{28}ClFN_7O_4S$ (M+H)$^+$: m/z=624.0.

Example D254

2-{[4-({[6-Chloro-2,4,8,18,22-pentaazatetracyclo [14.3.1.1(3,7).1(9,13)]docosa-1(20),3(22),4,6,9(21), 10,12,16,18-nonaen-12-yl]oxy}acetyl)piperazin-1-yl]sulfonyl}benzonitrile bis(trifluoroacetate)

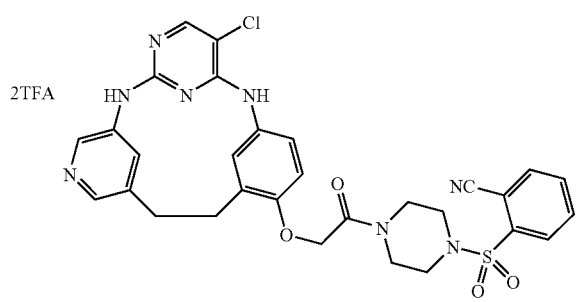

The desired compound was prepared according to the procedure of Example D20, step A, using 6-chloro-12-(2-oxo-2-piperazin-1-ylethoxy)-2,4,8,18,22-pentaazatetracyclo [14.3.1.1(3,7).1(9,13)]docosa-1(20),3(22),4,6,9(21),10,12, 16,18-nonaene tris(trifluoroacetate) and 2-cyanobenzenesulfonyl chloride as the starting materials in 50% yield. LCMS for $C_{30}H_{28}ClN_8O_4S$ (M+H)$^+$: m/z=631.0.

Example D255

6-Chloro-12-{2-oxo-2-[4-(pyridin-3-ylmethyl)piperazin-1-yl]ethoxy}-2,4,8,18,22-pentaazatetracyclo [14.3.1.1(3,7).1(9,13)]docosa-1(20),3(22),4,6,9(21), 10,12,16,18-nonaene tris(trifluoroacetate)

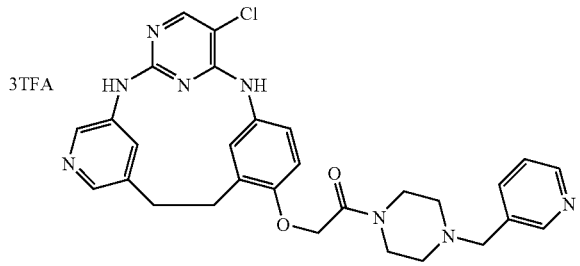 [SMILES: "3TFA" ; O=C(COc1ccc2cc1CCc1cncc(c1)Nc1ncc(Cl)c(n1)N2)N1CCN(Cc2cccnc2)CC1]

The desired compound was prepared according to the procedure of Example D152 using {[6-chloro-2,4,8,18,22-pentaazatetracyclo[14.3.1.1(3,7).1(9,13)]docosa-1(20),3(22),4, 6,9(21),10,12,16,18-nonaen-12-yl]oxy}acetic acid dihydrochloride and 1-(pyridin-3-ylmethyl)piperazine dihydrochloride as the starting materials in 42% yield. LCMS for $C_{29}H_{30}ClN_8O_2$ (M+H)$^+$: m/z=557.0.

Example D256

6-Chloro-12-{2-oxo-2-[4-(pyridin-4-ylmethyl)piperazin-1-yl]ethoxy}-2,4,8,18,22-pentaazatetracyclo [14.3.1.1(3,7).1(9,13)]docosa-1(20),3(22),4,6,9(21), 10,12,16,18-nonaene tris(trifluoroacetate)

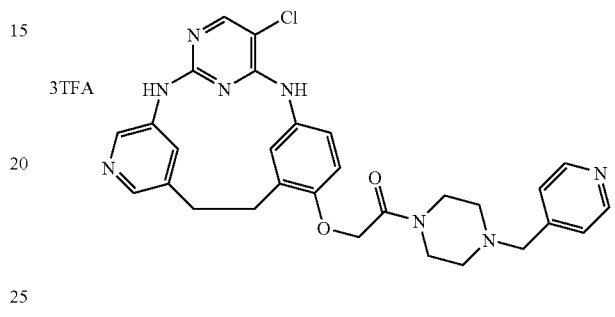

The desired compound was prepared according to the procedure of Example D152 using {[6-chloro-2,4,8,18,22-pentaazatetracyclo[14.3.1.1(3,7).1(9,13)]docosa-1(20),3(22),4, 6,9(21),10,12,16,18-nonaen-12-yl]oxy}acetic acid dihydrochloride and 1-(pyridin-4-ylmethyl)piperazine as the starting materials in 45% yield. LCMS for $C_{29}H_{30}ClN_8O_2$ (M+H)$^+$: m/z=557.1.

Example D257

6-Chloro-12-(2-oxo-2-{4-[5-(2-thienyl)-1H-pyrazol-3-yl]piperidin-1-yl}ethoxy)-2,4,8,18,22-pentaazatetracyclo[14.3.1.1(3,7).1(9,13)]docosa-1(20),3(22),4, 6,9(21),10,12,16,18-nonaene tris(trifluoroacetate)

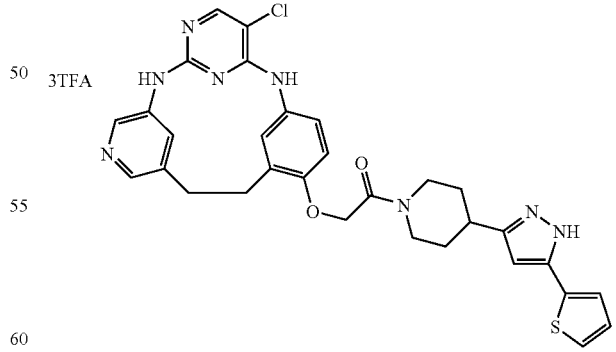

The desired compound was prepared according to the procedure of Example D152 using {[6-chloro-2,4,8,18,22-pentaazatetracyclo[14.3.1.1(3,7).1(9,13)]docosa-1(20),3(22),4, 6,9(21),10,12,16,18-nonaen-12-yl]oxy}acetic acid dihydrochloride and 4-[5-(2-thienyl)-1H-pyrazol-3-yl]piperidine dihydrochloride as the starting materials in 39% yield. LCMS for $C_{31}H_{30}ClN_8O_2S$ (M+H)+: m/z=613.0.

Example D258

6-Chloro-12-(2-oxo-2-{4-[3-(2-thienyl)-1,2,4-oxadiazol-5-yl]piperidin-1-yl}ethoxy)-2,4,8,18,22-pentaazatetracyclo[14.3.1.1(3,7).1(9,13)]docosa-1(20),3(22),4,6,9(21),10,12,16,18-nonaene bis(trifluoroacetate)

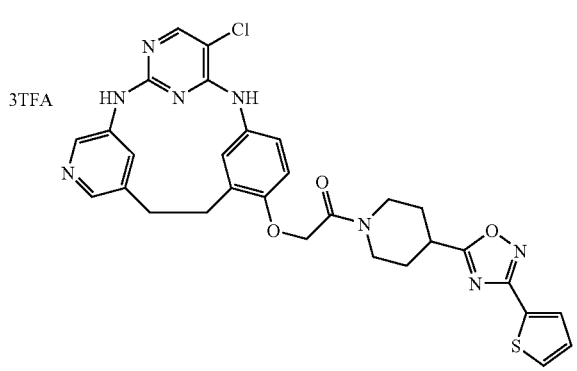 [SMILES: "3TFA" ; O=C(COc1ccc2cc1CCc1cncc(c1)Nc1ncc(Cl)c(n1)N2)N1CCC(c2nc(-c3cccs3)no2)CC1]

The desired compound was prepared according to the procedure of Example D152 using {[6-chloro-2,4,8,18,22-pentaazatetracyclo[14.3.1.1(3,7).1(9,13)]docosa-1(20),3(22),4,6,9(21),10,12,16,18-nonaen-12-yl]oxy}acetic acid dihydrochloride and 4-[3-(2-thienyl)-1,2,4-oxadiazol-5-yl]piperidine as the starting materials in 41% yield. LCMS for $C_{30}H_{28}ClN_8O_3S$ (M+H)+: m/z=615.0.

Example D259

6-Chloro-12-{2-[4-(2,4-difluorobenzoyl)piperazin-1-yl]-2-oxoethoxy}-2,4,8,18,22-pentaazatetracyclo[14.3.1.1(3,7).1(9,13)]docosa-1(20),3(22),4,6,9(21),10,12,16,18-nonaene bis(trifluoroacetate)

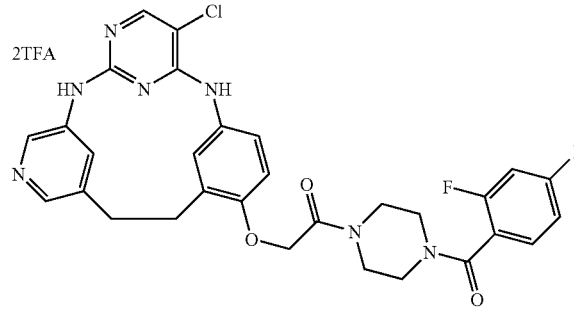

The desired compound was prepared according to the procedure of Example D94 using 6-chloro-12-(2-oxo-2-piperazin-1-ylethoxy)-2,4,8,18,22-pentaazatetracyclo[14.3.1.1(3,7).1(9,13)]docosa-1(20),3(22),4,6,9(21),10,12,16,18-nonaene tris(trifluoroacetate) and 2,4-difluorobenzoyl chloride as the starting materials in 30% yield. LCMS for $C_{30}H_{27}ClF_2N_7O_3$ (M+H)+: m/z=606.0.

Example D260

6-Chloro-12-{2-[4-(isoxazol-5-ylcarbonyl)piperazin-1-yl]-2-oxoethoxy}-2,4,8,18,22-pentaazatetracyclo[14.3.1.1(3,7).1(9,13)]docosa-1(20),3(22),4,6,9(21),10,12,16,18-nonaene bis(trifluoroacetate)

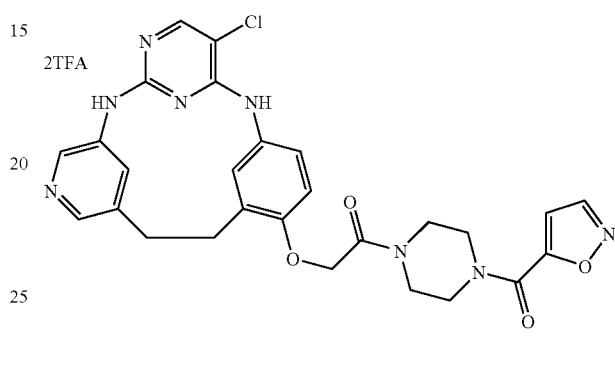

The desired compound was prepared according to the procedure of Example D94 using 6-chloro-12-(2-oxo-2-piperazin-1-ylethoxy)-2,4,8,18,22-pentaazatetracyclo[14.3.1.1(3,7).1(9,13)]docosa-1(20),3(22),4,6,9(21),10,12,16,18-nonaene tris(trifluoroacetate) and isoxazole-5-carbonyl chloride as the starting materials in 60% yield. LCMS for $C_{27}H_{26}ClN_8O_4$ (M+H)+: m/z=561.0.

Example D261

Methyl 4-({[6-chloro-2,4,8,18,22-pentaazatetracyclo[14.3.1.1(3,7).1(9,13)]docosa-1(20),3(22),4,6,9(21),10,12,16,18-nonaen-12-yl]oxy}acetyl)piperazine-1-carboxylate bis(trifluoroacetate)

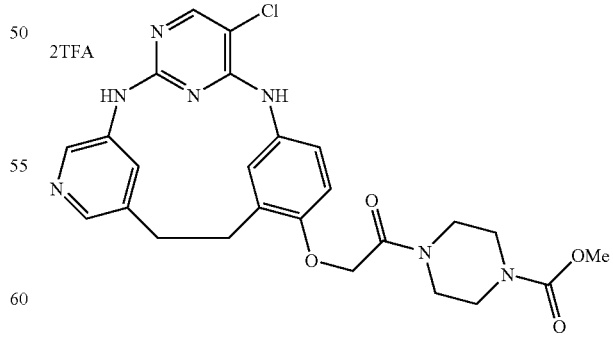

The desired compound was prepared according to the procedure of Example D94 using 6-chloro-12-(2-oxo-2-piperazin-1-ylethoxy)-2,4,8,18,22-pentaazatetracyclo[14.3.1.1(3,7).1(9,13)]docosa-1(20),3(22),4,6,9(21),10,12,16,18- nonaene tris(trifluoroacetate) and methyl chloroformate as the starting materials in 60% yield. LCMS for $C_{25}H_{27}ClN_7O_4$ (M+H)$^+$: m/z=524.1.

Example D262

6-Chloro-12-{2-[4-(methoxyacetyl)piperazin-1-yl]-2-oxoethoxy}-2,4,8,18,22-pentaazatetracyclo[14.3.1.1(3,7).1(9,13)]docosa-1(20),3(22),4,6,9(21),10,12,16,18-nonaene bis(trifluoroacetate)

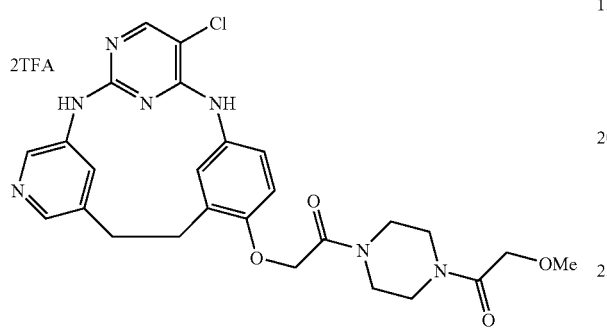

The desired compound was prepared according to the procedure of Example D94 using 6-chloro-12-(2-oxo-2-piperazin-1-ylethoxy)-2,4,8,18,22-pentaazatetracyclo[14.3.1.1(3,7).1(9,13)]docosa-1(20),3(22),4,6,9(21),10,12,16,18-nonaene tris(trifluoroacetate) and methoxyacetyl chloride as the starting materials in 77% yield. LCMS for $C_{26}H_{29}ClN_7O_4$ (M+H)$^+$: m/z=538.1.

Example D263

6-Chloro-12-{2-[4-(ethylsulfonyl)piperazin-1-yl]-2-oxoethoxy}-2,4,8,18,22-pentaazatetracyclo[14.3.1.1(3,7).1(9,13)]docosa-1(20),3(22),4,6,9(21),10,12,16,18-nonaene bis(trifluoroacetate)

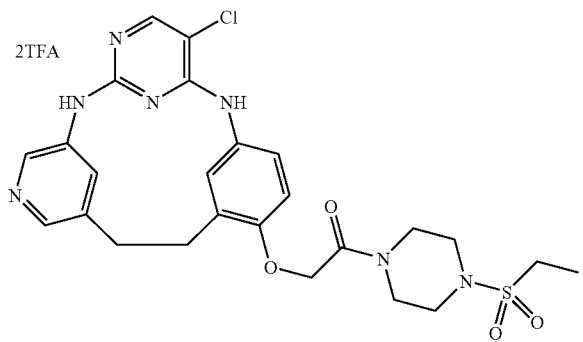 [SMILES: "2TFA" ; CCS(=O)(=O)N1CCN(C(=O)COc2ccc3cc2CCc2cncc(c2)Nc2ncc(Cl)c(n2)N3)CC1]

The desired compound was prepared according to the procedure of Example D20, step A, using 6-chloro-12-(2-oxo-2-piperazin-1-ylethoxy)-2,4,8,18,22-pentaazatetracyclo[14.3.1.1(3,7).1(9,13)]docosa-1(20),3(22),4,6,9(21),10,12,16,18-nonaene tris(trifluoroacetate) and ethanesulfonyl chloride as the starting materials in 60% yield. LCMS for $C_{25}H_{29}ClN_7O_4S$ (M+H)$^+$: m/z=558.0.

Example D264

4-({[6-Chloro-2,4,8,18,22-pentaazatetracyclo[14.3.1.1(3,7).1(9,13)]docosa-1(20),3(22),4,6,9(21),10,12,16,18-nonaen-12-yl]oxy}acetyl)-N-phenylpiperazine-1-carboxamide bis(trifluoroacetate)

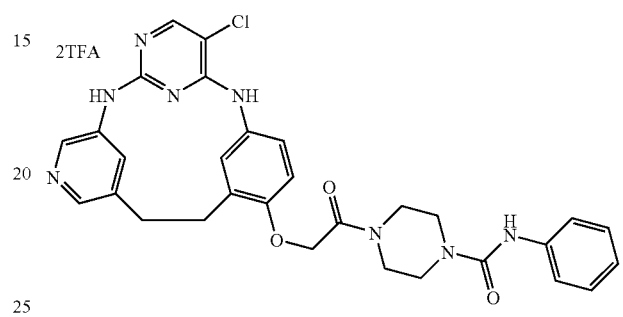

The desired compound was prepared according to the procedure of Example D41 using 6-chloro-12-(2-oxo-2-piperazin-1-ylethoxy)-2,4,8,18,22-pentaazatetracyclo[14.3.1.1(3,7).1(9,13)]docosa-1(20),3(22),4,6,9(21),10,12,16,18-nonaene tris(trifluoroacetate) and phenyl isocyanate as the starting materials in 70% yield. LCMS for $C_{30}H_{30}ClN_8O_3$ (M+H)$^+$: m/z=585.0.

Example D265

4-({[6-Chloro-2,4,8,18,22-pentaazatetracyclo[14.3.1.1(3,7).1(9,13)]docosa-1(20),3(22),4,6,9(21),10,12,16,18-nonaen-12-yl]oxy}acetyl)-N-methylpiperazine-1-carboxamide bis(trifluoroacetate)

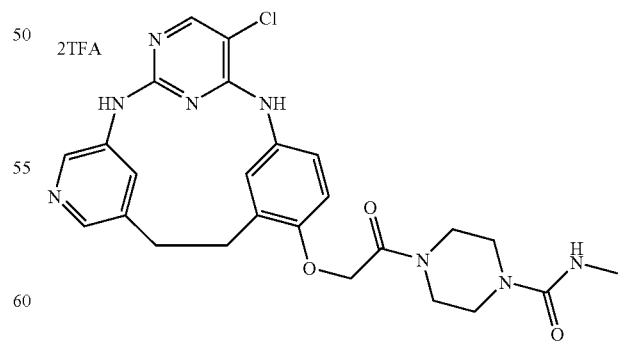

The desired compound was prepared according to the procedure of Example D41 using 6-chloro-12-(2-oxo-2-piperazin-1-ylethoxy)-2,4,8,18,22-pentaazatetracyclo[14.3.1.1(3,7).1(9,13)]docosa-1(20),3(22),4,6,9(21),10,12,16,18- nonaene tris(trifluoroacetate) and methyl isocyanate as the starting materials in 70% yield. LCMS for $C_{25}H_{28}ClN_8O_3$ $(M+H)^+$: m/z=523.1.

Example D266

6-Chloro-12-(2-{4-[(5-methyl-1H-pyrazol-3-yl)carbonyl]piperazin-1-yl}-2-oxoethoxy)-2,4,8,18,22-pentaazatetracyclo[14.3.1.1(3,7).1(9,13)]docosa-1(20),3(22),4,6,9(21),10,12,16,18-nonaene tris(trifluoroacetate)

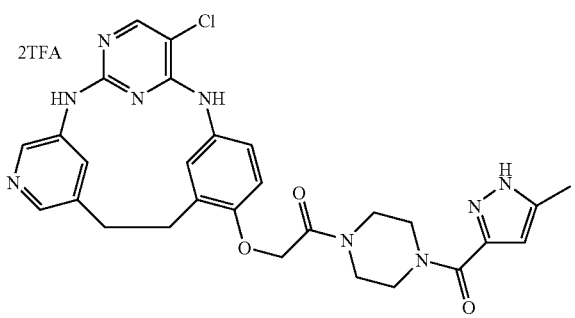 [SMILES: "2TFA" ; Cc1cc(C(=O)N2CCN(C(=O)COc3ccc4cc3CCc3cncc(c3)Nc3ncc(Cl)c(n3)N4)CC2)n[nH]1]

The desired compound was prepared according to the procedure of Example D152 using 6-chloro-12-(2-oxo-2-piperazin-1-ylethoxy)-2,4,8,18,22-pentaazatetracyclo[14.3.1.1(3,7).1(9,13).1]docosa-1(20),3(22),4,6,9(21),10,12,16,18-nonaenetris(trifluoroacetate) and 5-methyl-1H-pyrazole-3-carboxylic acid as the starting materials in 50% yield. LCMS for $C_{28}H_{29}ClN_9O_3$ $(M+H)^+$: m/z=574.0.

Example D267

1-{[4-({[6-Chloro-2,4,8,18,22-pentaazatetracyclo[14.3.1.1(3,7).1(9,13)]docosa-1(20),3(22),4,6,9(21),10,12,16,18-nonaen-12-yl]oxy}acetyl)piperazin-1-yl]carbonyl}cyclopropanecarbonitrile bis(trifluoroacetate)

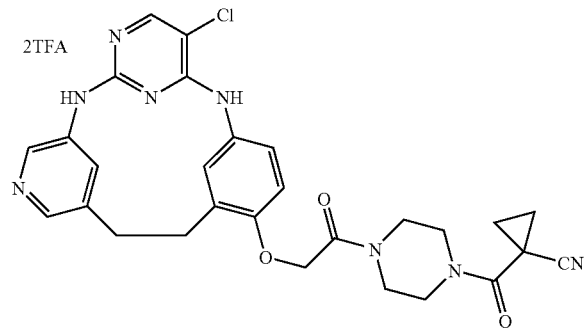 [SMILES: "2TFA" ; N#CC1(C(=O)N2CCN(C(=O)COc3ccc4cc3CCc3cncc(c3)Nc3ncc(Cl)c(n3)N4)CC2)CC1]

The desired compound was prepared according to the procedure of Example D152 using 6-chloro-12-(2-oxo-2-piperazin-1-ylethoxy)-2,4,8,18,22-pentaazatetracyclo[14.3.1.1(3,7).1(9,13)]docosa-1(20),3(22),4,6,9(21),10,12,16,18-nonaenetris(trifluoroacetate) and 1-cyanocyclopropanecarboxylic acid as the starting materials in 60% yield. LCMS for $C_{28}H_{28}ClN_8O_3$ $(M+H)^+$: m/z=559.1.

Example D268

4-({[6-Chloro-2,4,8,18,22-pentaazatetracyclo[14.3.1.1(3,7).1(9,13)]docosa-1(20),3(22),4,6,9(21),10,12,16,18-nonaen-12-yl]oxy}acetyl)piperazine-1-sulfonamide bis(trifluoroacetate)

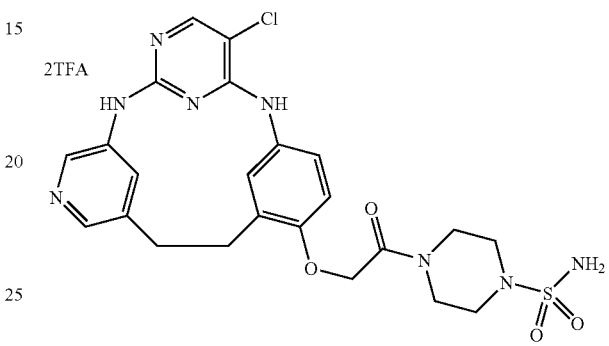

The desired compound was prepared according to the procedure of Example A72 using 6-chloro-12-(2-oxo-2-piperazin-1-ylethoxy)-2,4,8,18,22-pentaazatetracyclo[14.3.1.1(3,7).1(9,13)]docosa-1(20),3(22),4,6,9(21),10,12,16,18-nonaenetris(trifluoroacetate) as the starting material in 30% yield. LCMS for $C_{23}H_{26}ClN_8O_4S$ $(M+H)^+$: m/z=545.0.

Example D269

3-[4-({[6-Chloro-2,4,8,18,22-pentaazatetracyclo[14.3.1.1(3,7).1(9,13)]docosa-1(20),3(22),4,6,9(21),10,12,16,18-nonaen-12-yl]oxy}acetyl)piperazin-1-yl]-3-oxopropanenitrile bis(trifluoroacetate)

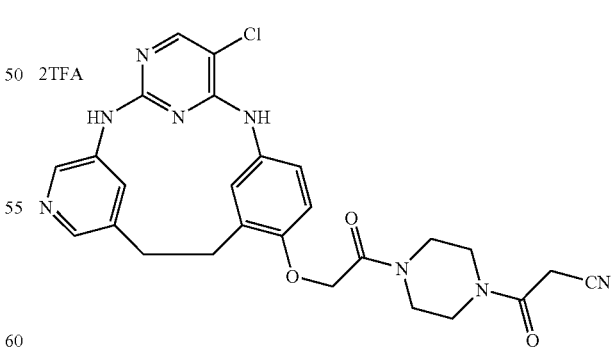

The desired compound was prepared according to the procedure of Example D94 using 6-chloro-12-(2-oxo-2-piperazin-1-ylethoxy)-2,4,8,18,22-pentaazatetracyclo[14.3.1.1(3,7).1(9,13)]docosa-1(20),3(22),4,6,9(21),10,12,16,18-nonaene tris(trifluoroacetate) and 3-[(2,5-dioxopyrrolidin-1- yl)oxy]-3-oxopropanenitrile as the starting materials in 60% yield. LCMS for $C_{26}H_{26}ClN_8O_3$ (M+H)$^+$: m/z=533.0.

Example D270

4-({[6-Chloro-2,4,8,18,22-pentaazatetracyclo[14.3.1.1(3,7).1(9,13)]docosa-1(20),3(22),4,6,9(21),10,12,16,18-nonaen-12-yl]oxy}acetyl)piperazine-1-carboxamide bis(trifluoroacetate)

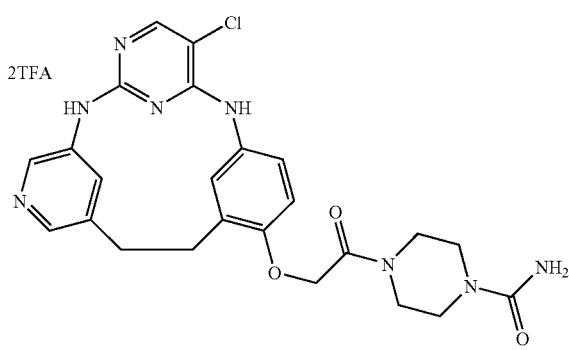 [SMILES: "2TFA" ; NC(=O)N1CCN(C(=O)COc2ccc3cc2CCc2cncc(c2)Nc2ncc(Cl)c(n2)N3)CC1]

The desired compound was prepared according to the procedures of Example D41, using 6-chloro-12-(2-oxo-2-piperazin-1-ylethoxy)-2,4,8,18,22-pentaazatetracyclo[14.3.1.1(3,7).1(9,13)]docosa-1(20),3(22),4,6,9(21),10,12,16,18-nonaene tris(trifluoroacetate) and 2-isocyanato-2-methylpropane as the starting materials, and Example D87 in 60% yield (2 steps). LCMS for $C_{24}H_{26}ClN_8O_3$ (M+H)$^+$: m/z=509.0.

Example D271

6-Chloro-12-{2-oxo-2-[4-(tetrahydrofuran-3-ylcarbonyl)piperazin-1-yl]ethoxy}-2,4,8,18,22-pentaazatetracyclo[14.3.1.1(3,7).1(9,13)]docosa-1(20),3(22),4,6,9(21),10,12,16,18-nonaene bis(trifluoroacetate)

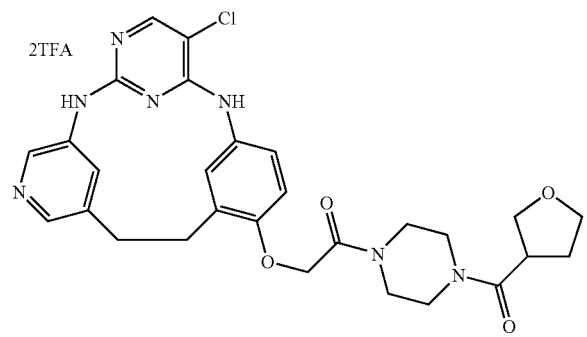 [SMILES: "2TFA" ; O=C(COc1ccc2cc1CCc1cncc(c1)Nc1ncc(Cl)c(n1)N2)N1CCN(C(=O)C2CCOC2)CC1]

The desired compound was prepared according to the procedure of Example D152 using 6-chloro-12-(2-oxo-2-piperazin-1-ylethoxy)-2,4,8,18,22-pentaazatetracyclo[14.3.1.1(3,7).1(9,13)]docosa-1(20),3(22),4,6,9(21),10,12,16,18-nonaenetris(trifluoroacetate) and tetrahydrofuran-3-carboxylic acid as the starting materials in 50% yield. LCMS for $C_{28}H_{31}ClN_7O_4$ (M+H)$^+$: m/z=564.1.

Example D272

6-Chloro-12-{2-oxo-2-[4-(tetrahydrofuran-2-ylcarbonyl)piperazin-1-yl]ethoxy}-2,4,8,18,22-pentaazatetracyclo[14.3.1.1(3,7).1(9,13)]docosa-1(20),3(22),4,6,9(21),10,12,16,18-nonaene bis(trifluoroacetate)

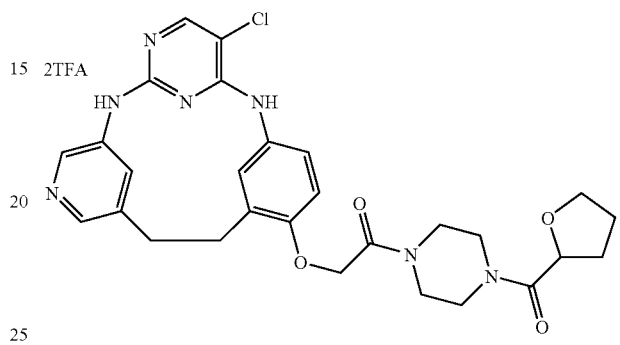

The desired compound was prepared according to the procedure of Example D152 using 6-chloro-12-(2-oxo-2-piperazin-1-ylethoxy)-2,4,8,18,22-pentaazatetracyclo[14.3.1.1(3,7).1(9,13)]docosa-1(20),3(22),4,6,9(21),10,12,16,18-nonaenetris(trifluoroacetate) and tetrahydro-2-furancarboxylic acid as the starting materials in 70% yield. LCMS for $C_{28}H_{31}ClN_7O_4$ (M+H)$^+$: m/z=564.1.

Example AA1

In Vitro JAK Kinase Assay

One or more compounds herein were tested for inhibitory activity of JAK targets according to the following in vitro assay described in Park et al., *Analytical Biochemistry* 1999, 269, 94-104. The catalytic domains of human JAK1 (a.a. 837-1142), JAK2 (a.a. 828-1132) and JAK3 (a.a. 781-1124) with an N-terminal His tag were expressed using baculovirus in insect cells and purified. The catalytic activity of JAK1, JAK2 or JAK3 was assayed by measuring the phosphorylation of a biotinylated peptide. The phosphorylated peptide was detected by homogenous time resolved fluorescence (HTRF). IC$_{50}$s of compounds were measured for each kinase in the reactions that contain the enzyme, ATP and 500 nM peptide in 50 mM Tris (pH 7.8) buffer with 100 mM NaCl, 5 mM DTT, and 0.1 mg/mL (0.01%) BSA. The ATP concentration in the reactions was 90 µM for JAK1, 30 µM for JAK2 and 3 µM for JAK3. Reactions were carried out at room temperature for 1 hr and then stopped with 20 µL 45 mM EDTA, 300 nM SA-APC, 6 nM Eu-Py20 in assay buffer (Perkin Elmer, Boston, Mass.). Binding to the Europium labeled antibody took place for 40 minutes and HTRF signal was measured on a Fusion plate reader (Perkin Elmer, Boston, Mass.).

Example AA2

In Vitro JAK Kinase Assay

One or more compounds herein were tested for inhibitory activity of JAK targets according to the following in vitro assay described in Park et al., *Analytical Biochemistry* 1999, 269, 94-104. The catalytic domains of human JAK1 (a.a. 837-1142), JAK2 (a.a. 828-1132) and JAK3 (a.a. 781-1124) with an N-terminal His tag were expressed using baculovirus in insect cells and purified. The catalytic activity of JAK1, JAK2 or JAK3 was assayed by measuring the phosphorylation of a biotinylated peptide. The phosphorylated peptide was detected by homogenous time resolved fluorescence (HTRF). $IC_{50}$s of compounds were measured for each kinase in the reactions that contain the enzyme, 1000 µM ATP, and 500 nM peptide in 50 mM Tris (pH 7.8) buffer with 100 mM NaCl, 5 mM DTT, and 0.1 mg/mL (0.01%) BSA. Reactions were carried out at room temperature for 1 hr and then stopped with 20 µL 45 mM EDTA, 300 nM SA-APC, 6 nM Eu-Py20 in assay buffer (Perkin Elmer, Boston, Mass.). Binding to the Europium labeled antibody took place for 40 minutes and HTRF signal was measured on a Fusion plate reader (Perkin Elmer, Boston, Mass.).

Example BB

Cellular Assays

One or more compounds herein were tested for inhibitory activity of JAK targets according to at least one of the following cellular assays.

Cancer cell lines dependent on cytokines and hence JAK/STAT signal transduction, for growth, were plated at 6000 cells per well (96 well plate format) in RPMI 1640, 10% FBS, and 1 nG/mL of appropriate cytokine. Compounds were added to the cells in DMSO/media (final concentration 0.2% DMSO) and incubated for 72 hours at 37° C., 5% $CO_2$. The effect of compound on cell viability was assessed using the CellTiter-Glo Luminescent Cell Viability Assay (Promega) followed by TopCount (Perkin Elmer, Boston, Mass.) quantitation. Potential off-target effects of compounds were measured in parallel using a non-JAK driven cell line with the same assay readout. All experiments were performed in duplicate.

The above cell lines can also be used to examine the effects of compounds on phosphorylation of JAK kinases or potential downstream substrates such as STAT proteins, Akt, Shp2, or Erk. These experiments can be performed following an overnight cytokine starvation, followed by a brief preincubation with compound (2 hours or less) and cytokine stimulation of approximately 1 hour or less. Proteins are then extracted from cells and analyzed by techniques familiar to those schooled in the art including Western blotting or ELISAs using antibodies that can differentiate between phosphorylated and total protein. These experiments can utilize normal or cancer cells to investigate the activity of compounds on tumor cell survival biology or on mediators of inflammatory disease. For example, with regards to the latter, cytokines such as IL-6, IL-12, IL-23, or IFN can be used to stimulate JAK activation resulting in phosphorylation of STAT protein (s) and potentially in transcriptional profiles (assessed by array or qPCR technology) or production and/or secretion of proteins, such as IL-17. The ability of compounds to inhibit these cytokine mediated effects can be measured using techniques common to those schooled in the art.

Compounds herein can also be tested in cellular models designed to evaluate their potency and activity against mutant JAKs, for example, the JAK2V617F mutation found in myeloid proliferative disorders. These experiments often utilize cytokine dependent cells of hematological lineage (e.g. BaF/3) into which the wild-type or mutant JAK kinases are ectopically expressed (James, C., et al. *Nature* 434:1144-1148; Staerk, J., et al. *JBC* 280:41893-41899). Endpoints include the effects of compounds on cell survival, proliferation, and phosphorylated JAK, STAT, Akt, or Erk proteins.

Certain compounds herein have been or can be evaluated for their activity inhibiting T-cell proliferation. Such as assay can be considered a second cytokine (i.e. JAK) driven proliferation assay and also a simplistic assay of immune suppression or inhibition of immune activation. The following is a brief outline of how such experiments can be performed. Peripheral blood mononuclear cells (PBMCs) are prepared from human whole blood samples using Ficoll Hypaque separation method and T-cells (fraction 2000) can be obtained from PBMCs by elutriation. Freshly isolated human T-cells can be maintained in culture medium (RPMI 1640 supplemented with 10% fetal bovine serum, 100 U/mL penicillin, 100 µg/mL streptomycin) at a density of $2\times10^6$ cells/mL at 37° C. for up to 2 days. For IL-2 stimulated cell proliferation analysis, T-cells are first treated with Phytohemagglutinin (PHA) at a final concentration of 10 µg/mL for 72 hours. After washing once with PBS, 6000 cells/well are plated in 96-well plates and treated with compounds at different concentrations in the culture medium in the presence of 100 U/mL human IL-2 (ProSpec-Tany TechnoGene; Rehovot, Israel). The plates are incubated at 37° C. for 72 hours and the proliferation index is assessed using CellTiter-Glo Luminescent reagents following the manufactory suggested protocol (Promega; Madison, Wis.).

Example CC

In Vivo Anti-Tumor Efficacy

Compounds herein can be evaluated in human tumor xenograft models in immune compromised mice. For example, a tumorigenic variant of the INA-6 plasmacytoma cell line can be used to inoculate SCID mice subcutaneously (Burger, R., et al. *Hematol J.* 2:42-53, 2001). Tumor bearing animals can then be randomized into drug or vehicle treatment groups and different doses of compounds can be administered by any number of the usual routes including oral, i.p., or continuous infusion using implantable pumps. Tumor growth is followed over time using calipers. Further, tumor samples can be harvested at any time after the initiation of treatment for analysis as described above (Example B) to evaluate compound effects on JAK activity and downstream signaling pathways. In addition, selectivity of the compound(s) can be assessed using xenograft tumor models that are driven by other know kinases (e.g. Bcr-Abl) such as the $K_{562}$ tumor model.

Example DD

Murine Skin Contact Delayed Hypersensitivity Response Test

Compounds herein can also be tested for their efficacies (of inhibiting JAK targets) in the T-cell driven murine delayed hypersensitivity test model. The murine skin contact delayed-type hypersensitivity (DTH) response is considered to be a valid model of clinical contact dermatitis, and other T-lymphocyte mediated immune disorders of the skin, such as psoriasis (*Immunol Today.* 1998 January; 19(1):37-44). Murine DTH shares multiple characteristics with psoriasis, including the immune infiltrate, the accompanying increase in inflammatory cytokines, and keratinocyte hyperproliferation. Furthermore, many classes of agents that are efficacious in treating psoriasis in the clinic are also effective inhibitors of the DTH response in mice (Agents Actions. 1993 January; 38(1-2):116-21).

On Day 0 and 1, Balb/c mice are sensitized with a topical application, to their shaved abdomen with the antigen 2,4, dinitro-fluorobenzene (DNFB). On day 5, ears are measured for thickness using an engineer's micrometer. This measurement is recorded and used as a baseline. Both of the animals' ears are then challenged by a topical application of DNFB in a total of 20 µL (10 µL on the internal pinna and 10 µL on the external pinna) at a concentration of 0.2%. Twenty-four to seventy-two hours after the challenge, ears are measured again. Treatment with the test compounds was given throughout the sensitization and challenge phases (day −1 to day 7) or prior to and throughout the challenge phase (usually afternoon of day 4 to day 7). Treatment of the test compounds (in different concentration) was administered either systemically or topically (topical application of the treatment to the ears). Efficacies of the test compounds are indicated by a reduction in ear swelling comparing to the situation without the treatment. Compounds causing a reduction of 20% or more were considered efficacious. In some experiments, the mice are challenged but not sensitized (negative control).

The inhibitive effect (inhibiting activation of the JAK-STAT pathways) of the test compounds can be confirmed by immunohistochemical analysis. Activation of the JAK-STAT pathway(s) results in the formation and translocation of functional transcription factors. Further, the influx of immune cells and the increased proliferation of keratinocytes should also provide unique expression profile changes in the ear that can be investigated and quantified. Formalin fixed and paraffin embedded ear sections (harvested after the challenge phase in the DTH model) are subjected to immunohistochemical analysis using an antibody that specifically interacts with phosphorylated STAT3 (clone 58E12, Cell Signaling Technologies). The mouse ears are treated with test compounds, vehicle, or dexamethasone (a clinically efficacious treatment for psoriasis), or without any treatment, in the DTH model for comparisons. Test compounds and the dexamethasone can produce similar transcriptional changes both qualitatively and quantitatively, and both the test compounds and dexamethasone can reduce the number of infiltrating cells. Both systemically and topical administration of the test compounds can produce inhibitive effects, i.e., reduction in the number of infiltrating cells and inhibition of the transcriptional changes.

Example EE

In Vivo Anti-Inflammatory Activity

Compounds herein can be evaluated in rodent or non-rodent models designed to replicate a single or complex inflammation response. For instance, rodent models of arthritis can be used to evaluate the therapeutic potential of compounds dosed preventatively or therapeutically. These models include but are not limited to mouse or rat collagen-induced arthritis, rat adjuvant-induced arthritis, and collagen antibody-induced arthritis. Autoimmune diseases including, but not limited to, multiple sclerosis, type I-diabetes mellitus, uveoretinitis, thyroditis, myasthenia gravis, immunoglobulin nephropathies, myocarditis, airway sensitization (asthma), lupus, or colitis may also be used to evaluate the therapeutic potential of compounds herein. These models are well established in the research community and are familiar to those schooled in the art (Current Protocols in Immunology, Vol 3., Coligan, J. E. et al, Wiley Press.; *Methods in Molecular Biology*: Vol. 225, Inflammation Protocols., Winyard, P. G. and Willoughby, D. A., Humana Press, 2003.).

Example FF pALK Assay

To determine the activity of numerous compounds on the phosphorylation of ALK in cells, an ELISA method testing lymphoma cell lysates was developed. Human lymphoma cells were treated with examples for 4 hours. Cells were lysed in lysis buffer (Cell Signaling #9803, Danvers, Mass.) supplemented with complete mini protease inhibitor cocktail tablets (Roche Applied Science, Indianapolis, Ind.) on ice and after 15 minutes, lysates were cleared by centrifugation. According to the manufacturer's instructions, lysates were placed in wells precoated with anti-phospho-ALK antibody (Cell Signaling #7324, Danvers, Mass.) and allowed to incubate overnight at 4° C. After washing, an anti-ALK antibody is added to wells. Colorimetric (TMB) detection of HRP-linked anti-mouse IgG is used to quantify relative levels of phospho-ALK.

Example GG

Cell Proliferation Assay

The activity of numerous compounds on ALK driven proliferation was assessed using Karpas-299 human anaplastic lymphoma cells. Cells were seeded at 2500 cells per well in clear bottom 96 well plates. On the first day, replicate plates were treated with various concentrations of compounds or processed using the manufacturer's instructions for Cell Titer Glo (Promega, Madison, Wis.) to determine baseline levels. After 72 hours, the dosed plate was processed using Cell Titer Glo. After calculating the specific proliferation of cells in the presence of compounds, $IC_{50}$s were determined using Prism software (GraphPad Software, San Diego, Calif.).

Example HH

ALK HTRF Kinase Assay

Materials: Recombinant Human Anaplastic Lymphoma Kinase was purchased from Invitrogen, Carlsbad, Calif. Peptide substrate (Biotin-KKKGPWLEEEEEAYGWLDF-amide) was custom synthesized at EZBiolab, Westfield, Ind. Streptavidin conjugated SureLight-Allophycocyania and LANCE Eu-W1024 labeled anti-phosphotyrosine antibody were from Perkin-Elmer, Boston, Mass. Microplates were from Corning Inc., Acton, Mass. All other reagents were from Sigma, St. Louis, Mo.

HTRF kinase assay: 40 µL reactions were run in black 384 well polystyrene plates in assay buffer (50 mM Tris, pH 7.8, 100 mM NaCl, 0.1 mg/mL BSA, 5 mM DTT), containing 0.5 µM Biotinylated peptide substrate, 10 mM $MgCl_2$, 90 µM ATP, and 0.25 nM enzyme for 2 hours at 25° C. Reactions were stopped by addition of 20 µL assay buffer supplemented with an additional 50 mM NaCl, 0.4 mg/mL BSA, 45 mM EDTA, 4.5 nM LANCE Eu-W1024 labeled anti-phosphotyrosine antibody and 200 nM streptavidin conjugated Sure-Light-allophycocyanin. Plates were read in Fusion α-FP instrument (Perkin-Elmer). The concentrations needed to reach 50% inhibition, the $IC_{50}$ value, were determined by fitting the assay signal to the following equation using Graphpad Prizm.

$$Signal = Bottom + (Top - Bottom)/(1 + 10^{((Log(IC50) - Log[I]) * Hill Slope)})$$

Bottom and Top refer to the post and pre-transition baselines, respectively.

The $IC_{50}$ values (or the percentage inhibition of the sample compounds at a concentration of 500 nM or 1 mM) for the example compounds of invention with respect one or more of JAK/ALK according to one or more methods in Examples AA1, AA2, and HH are provided in Tables A1, B1, C1, and D1 as follows.

TABLE A1

| Example Number | JAK1 $IC_{50}$ (nM) | JAK2 $IC_{50}$ (nM) | JAK3 $IC_{50}$ (nM) | TYK2 $IC_{50}$ (nM) | ALK $IC_{50}$ (nM) or % of inhibition at a concentration of 500 nM or 1 mM |
|---|---|---|---|---|---|
| Example A1 | 6 | 2.7 | 8.5 | 4.7 | 415 |
| Example A2 | 12 | 9.3 | 26 | 35 | 657 |
| Example A3 | 50 | 15 | 45 | 55 | 2037 |
| Example A4 | 87 | 54 | 45 | >100 | 925 |
| Example A5 | >100 | 56 | >100 | >100 | 6180 |
| Example A6 | 700 | 8.7 | 802 | 76 | 497 |
| Example A7 | 128 | 32 | 300 | 150 | 523 |
| Example A8 | 51 | 52 | 20 | 80 | 80 |
| Example A9 | 9.1 | 19 | 67 | 22 | 0% |
| Example A10 | 14 | 21 | 104 | 50 | 5% |
| Example A11 | 3.4 | 5.6 | 16 | 9.5 | 12% |
| Example A12 | 9.4 | 11 | 65 | 30 | 17% |
| Example A13 | 1 | 2.6 | 44 | 42 | 20% |
| Example A14 | 74 | 42 | 144 | 116 | 0% |
| Example A15 | 2.9 | 1.1 | 4.8 | 3.4 | 79% |
| Example A16 | 12 | 10 | 60 | 32 | 21% |
| Example A17 | 85 | 87 | 217 | 200 | 7% |
| Example A18 | 4.5 | 3.3 | 23 | 11 | 59% |
| Example A19 | 17 | 54 | >100 | 100 | 17% |
| Example A20 | 12 | 8.2 | 78 | 27 | 17% |
| Example A21 | 57 | 6.2 | 26 | 98 | 65% |
| Example A22 | 11 | 6.2 | 10 | 22 | 54% |
| Example A23 | 12 | 1 | 22 | 37 | 33% |
| Example A24 | 47 | 4.3 | 58 | 139 | 11% |
| Example A25 | 38 | 21 | 14 | 122 | 130 |
| Example A26 | 36 | 11 | 9.2 | 45 | 350 |
| Example A27 | 61 | 56 | 124 | 43 | 21% |
| Example A28 | 56 | 61 | 99 | 175 | 30% |
| Example A29 | 42 | 31 | 31 | 65 | 30% |
| Example A30 | 28 | 45 | 110 | 84 | 34% |
| Example A31 | 42 | 49 | 108 | 115 | 26% |
| Example A32 | 30 | 29 | 35 | 66 | 30% |
| Example A33 | 30 | 38 | 102 | 75 | 26% |
| Example A34 | 446 | 220 | >1000 | 343 | 5% |
| Example A35 | 42 | 62 | 82 | 228 | 38% |
| Example A36 | 2.4 | 6.7 | 26 | 27 | 48% |
| Example A37 | 9 | 11 | 24 | 21 | — |
| Example A38 | 6.6 | 16 | 46 | 48 | 55% |
| Example A39 | 19 | 36 | 66 | 77 | 39% |
| Example A40 | 16 | 15 | 30 | 18 | — |
| Example A41 | 5.8 | 12 | 157 | 102 | 58% |
| Example A42 | 21 | 24 | 58 | 183 | 34% |
| Example A43 | 1 | 4.8 | 36 | 48 | 32% |
| Example A44 | 26 | 52 | 71 | 169 | 21% |
| Example A45 | 9.6 | 20 | 31 | 39 | 29% |
| Example A46 | 10 | 16 | 49 | 42 | 20% |
| Example A47 | 17 | 6.9 | 25 | 39 | 26% |
| Example A48 | 27 | 13 | 56 | 92 | 28% |
| Example A49 | 14 | 7.5 | 11 | 39 | 24% |
| Example A50 | 2.4 | 6.5 | 13 | 21 | 37% |
| Example A51 | 13 | 5 | 10 | 21 | 30% |
| Example A52 | 2.2 | 4.5 | 7.8 | 15 | 35% |
| Example A53 | 6.1 | 1.2 | 3.2 | 14 | 35% |
| Example A54 | 4 | 2.9 | 3.5 | 12 | 54% |
| Example A55 | 1.5 | 2.4 | 54 | 2.3 | 23% |
| Example A56 | 4.2 | 7.3 | 90 | 10 | 26% |
| Example A57 | 5.5 | 7.3 | 60 | 8.8 | 24% |
| Example A58 | 0.2 | 1.1 | 22 | 9.9 | 38% |
| Example A59 | 26 | 6.9 | 19 | 15 | 39% |
| Example A60 | 31 | 6.5 | 14 | 22 | 28% |
| Example A61 | 29 | 11 | 16 | 22 | 41% |
| Example A62 | 7 | 5.6 | 9.1 | 12 | 26% |
| Example A63 | 9 | 2.5 | 2.6 | 13 | 29% |

TABLE A1-continued

| Example Number | JAK1 IC$_{50}$ (nM) | JAK2 IC$_{50}$ (nM) | JAK3 IC$_{50}$ (nM) | TYK2 IC$_{50}$ (nM) | ALK IC$_{50}$ (nM) or % of inhibition at a concentration of 500 nM or 1 mM |
|---|---|---|---|---|---|
| Example A64 | 13 | 6.5 | 30 | 23 | 23% |
| Example A65 | 9 | 11 | 7.3 | 17 | 39% |
| Example A66 | 9 | 3.1 | 6.2 | 21 | 26% |
| Example A67 | 8 | 2.8 | 7.7 | 10 | 40% |
| Example A68 | 2 | 2.8 | 4.1 | 11 | 46% |
| Example A69 | 41 | 7.7 | 16 | 39 | 27% |
| Example A70 | 20 | 57 | 195 | 110 | 18% |
| Example A71 | 19 | 69 | 112 | 57 | 26% |
| Example A72 | 18 | 3.7 | 10 | 16 | 34% |
| Example A73 | 10 | 0.7 | 3 | 8 | 49% |
| Example A74 | 6 | 3 | 3.3 | 17 | 48% |
| Example A75 | 0.2 | 0.2 | 3.2 | 0.3 | 51% |
| Example A76 | 2 | 4.1 | 124 | 3.9 | 21% |
| Example A77 | 0.6 | 0.7 | 35 | 4 | 35% |
| Example A78 | 0.4 | 0.3 | 12 | 0.3 | 39% |
| Example A79 | 0.5 | 1.9 | 46 | 3.6 | 33% |
| Example A80 | 8.1 | 4.4 | 62 | 5.3 | 21% |
| Example A81 | 4.7 | 1.6 | 24 | 4.3 | 29% |
| Example A82 | 7.3 | 3.7 | 17 | 13 | 31% |
| Example A83 | 1.9 | 2.5 | 12 | 2.5 | 41% |
| Example A84 | 24 | 9 | 49 | 16 | 31% |
| Example A85 | 49 | 13 | 147 | 33 | 19% |
| Example A86 | 0.8 | 2.2 | 29 | 1.5 | 32% |
| Example A87 | 14 | 9.8 | 56 | 12 | 31% |
| Example A88 | 14 | 24 | 86 | 47 | 22% |
| Example A89 | 6.5 | 3.7 | 57 | 3 | 29% |
| Example A90 | 4.9 | 5.4 | 68 | 4.9 | 30% |
| Example A91 | 3.7 | 5.9 | 44 | 14 | 29% |
| Example A92 | 1.4 | 6.1 | 79 | 21 | 61% |
| Example A93 | 22 | 24 | 112 | 43 | 30% |
| Example A94 | 21 | 17 | 86 | 32 | 26% |
| Example A95 | 9.1 | 23 | 160 | 9 | 18% |
| Example A96 | 4.5 | 6.6 | 80 | 11 | 26% |
| Example A97 | 3.9 | 7.5 | 34 | 11 | 31% |
| Example A98 | 1 | 2.7 | 55 | 5.3 | 34% |
| Example A99 | 15 | 24 | 133 | 24 | 25% |
| Example A100 | 1.5 | 5.8 | 58 | 3 | 28% |
| Example A101 | 0.5 | 10 | 128 | 3.4 | 29% |
| Example A102 | 10 | 20 | 170 | 19 | 21% |
| Example A103 | 10 | 21 | 156 | 15 | 24% |
| Example A104 | 81 | 8.3 | 148 | 4.4 | 26% |
| Example A105 | 29 | 40 | 112 | 44 | 23% |
| Example A106 | 18 | 10 | 6.2 | 22 | 21% |
| Example A107 | 4 | 10 | 8.2 | 4.2 | 39% |
| Example A108 | 6 | 32 | 26 | 15 | 32% |
| Example A109 | 5 | 11 | 7.3 | 7.5 | 33% |
| Example A110 | 32 | 26 | 14 | 15 | 45% |
| Example A111 | 45 | 103 | 298 | 148 | 23% |
| Example A112 | 8 | 38 | 239 | 61 | 20% |
| Example A113 | 17 | 54 | 238 | 61 | 14% |
| Example A114 | 25 | 13 | 59 | 33 | 19% |
| Example A115 | 34 | 42 | 300 | 45 | 20% |
| Example A116 | 14 | 20 | 44 | 33 | 27% |
| Example A117 | 10 | 29 | 160 | 44 | 25% |
| Example A118 | 0.9 | 16 | 150 | 20 | 29% |
| Example A119 | 3.6 | 16 | 174 | 8.6 | 15% |
| Example A120 | 21 | 16 | 112 | 37 | 42% |
| Example A121 | 14 | 4.2 | 11 | 14 | 41% |
| Example A122 | 7.2 | 3.9 | 7.3 | 17 | 52% |
| Example A123 | 7.2 | 9.6 | 68 | 8.3 | 26% |
| Example A124 | 0.6 | 2.5 | 39 | 5.4 | 34% |
| Example A125 | 1.7 | 4.9 | 90 | 5.3 | 25% |
| Example A126 | 0.5 | 2.6 | 34 | 7.5 | — |
| Example A127 | 31 | 64 | 350 | 59 | 15% |
| Example A128 | 0.6 | 4.1 | 64 | 1.6 | 34% |
| Example A129 | 12 | 17 | 178 | 24 | 32% |
| Example A130 | 1.2 | 9.2 | 203 | 4.8 | 26% |
| Example A131 | 6.6 | 36 | 225 | 45 | 20% |
| Example A132 | 7.9 | 18 | 248 | 17 | 23% |
| Example A133 | 2.1 | 11 | 73 | 5.5 | 32% |
| Example A134 | 6.2 | 18 | 226 | 25 | 30% |
| Example A135 | 0.4 | 2.3 | 79 | 0.9 | 30% |
| Example A136 | 0.4 | 2.4 | 57 | 2.1 | 38% |
| Example A137 | 0.6 | 3 | 41 | 1 | 54% |

TABLE A1-continued

| Example Number | JAK1 IC$_{50}$ (nM) | JAK2 IC$_{50}$ (nM) | JAK3 IC$_{50}$ (nM) | TYK2 IC$_{50}$ (nM) | ALK IC$_{50}$ (nM) or % of inhibition at a concentration of 500 nM or 1 mM |
|---|---|---|---|---|---|
| Example A138 | 2 | 7.2 | 30 | 8 | 46% |
| Example A139 | 1.1 | 7.6 | 178 | 3.4 | 27% |
| Example A140 | 38 | 46 | 117 | 68 | 18% |
| Example A141 | 3.5 | 12 | >100 | 13 | 19% |
| Example A142 | 2.4 | 4.8 | >100 | 6.5 | 41% |
| Example A143 | 2.2 | 1.8 | >100 | 1.2 | 63% |
| Example A144 | 1.2 | 6.4 | >100 | 11.0 | 35% |
| Example A145 | 16 | 30 | >100 | 43 | 21% |
| Example A146 | 0.9 | 3.6 | >100 | 7.1 | 34% |
| Example A147 | 0.3 | 1.9 | >100 | 7.4 | 46% |
| Example A148 | 0.2 | 1.5 | >100 | 3.9 | 42% |
| Example A149 | 0.5 | 3.1 | >100 | 6.9 | 35% |
| Example A150 | 0.3 | 1.1 | >100 | 5.1 | 48% |
| Example A151 | 0.3 | 1.4 | >100 | 3.8 | 45% |
| Example A152 | 0.4 | 2.4 | >100 | 2.4 | 37% |
| Example A153 | 0.5 | 1.1 | >100 | 5.7 | 52% |
| Example A154 | 0.6 | 2.6 | >100 | 3.1 | 51% |
| Example A155 | 2.4 | 4.2 | >100 | 3.8 | 47% |
| Example A156 | 96 | 917 | >10000 | 2500 | 17% |
| Example A157 | 2.6 | 102 | >10000 | 617 | 15% |
| Example A158 | 11 | 244 | >10000 | 675 | 18% |
| Example A159 | 3.6 | 87 | — | — | 24% |
| Example A160 | 5 | 271 | — | — | 19% |
| Example A161 | 15 | 300 | — | — | 27% |
| Example A162 | 8.2 | 289 | — | — | 33% |
| Example A163 | 0.5 | 36 | >100 | 3 | 29% |
| Example A164 | 5.3 | 175 | — | — | 14% |
| Example A165 | 64 | >1000 | — | — | 23% |
| Example A166 | 6.5 | 300 | — | — | 32% |
| Example A167 | 0.6 | 59 | — | — | 33% |
| Example A168 | 22 | 400 | — | — | 27% |
| Example A169 | 26 | 131 | >1000 | 319 | 23% |
| Example A170 | 7.8 | 165 | >1000 | 250 | 37% |
| Example A171 | 12 | 118 | >1000 | 300 | 29% |
| Example A172 | 11 | 199 | >1000 | 237 | 28% |
| Example A173 | 8 | 89 | >1000 | 105 | 40% |
| Example A174 | 4.1 | 124 | >1000 | 72 | 33% |
| Example A175 | 1 | 13 | >200 | 1.8 | 28% |
| Example A176 | 51 | >200 | >200 | >200 | 25% |
| Example A177 | 14 | 95 | >200 | >200 | 34% |
| Example A178 | 68 | >200 | >200 | >200 | 26% |
| Example A179 | 18 | 83 | >200 | >200 | 43% |
| Example A180 | 13 | >200 | >200 | >200 | 13% |
| Example A181 | 6.3 | 81 | >200 | 89 | 42% |
| Example A182 | 48 | >200 | >200 | >200 | 32% |
| Example A183 | 3.6 | 22 | >200 | 30 | 40% |
| Example A184 | 43 | 79 | >200 | >200 | 29% |
| Example A185 | 62 | >200 | >200 | >200 | 33% |
| Example A186 | 58 | 185 | >200 | >200 | 38% |
| Example A187 | 52 | 132 | >200 | >200 | 37% |
| Example A188 | 34 | >200 | >200 | >200 | 26% |
| Example A189 | 116 | >200 | >200 | >200 | 21% |
| Example A190 | 100 | >200 | >200 | >200 | 27% |
| Example A191 | 67 | >200 | >200 | >200 | 25% |
| Example A192 | 21 | >200 | >200 | >200 | 31% |
| Example A193 | 12 | >200 | >200 | >200 | 31% |
| Example A194 | 7.3 | 150 | >200 | >200 | 31% |
| Example A195 | 7.1 | 80 | >200 | 140 | 35% |
| Example A196 | 15 | 100 | >200 | >200 | 34% |
| Example A197 | 30 | >200 | >200 | >200 | 39% |
| Example A198 | 0.4 | 50 | >200 | 50 | 56% |
| Example A199 | 32 | 199 | >200 | >200 | 41% |
| Example A200 | 8.5 | 101 | >200 | >200 | 25% |
| Example A201 | 9.3 | 100 | >200 | 150 | 31% |
| Example A202 | 0.7 | 14 | >200 | 150 | 42% |
| Example A203 | 38 | 150 | >200 | >200 | 38% |
| Example A204 | 20 | 100 | >200 | >200 | 28% |
| Example A205 | 52 | 199 | >200 | >200 | 23% |
| Example A206 | 100 | >200 | >200 | >200 | 15% |
| Example A207 | 85 | 199 | >200 | >200 | 23% |
| Example A208 | 1.6 | 41 | >200 | 150 | 17% |
| Example A209 | 60 | 120 | >200 | >200 | 19% |
| Example A210 | 35 | 90 | >200 | >200 | 20% |
| Example A211 | 12 | 66 | >200 | 150 | 37% |

TABLE A1-continued

| Example Number | JAK1 IC$_{50}$ (nM) | JAK2 IC$_{50}$ (nM) | JAK3 IC$_{50}$ (nM) | TYK2 IC$_{50}$ (nM) | ALK IC$_{50}$ (nM) or % of inhibition at a concentration of 500 nM or 1 mM |
|---|---|---|---|---|---|
| Example A212 | 1.3 | 8.6 | >200 | 85 | 45% |
| Example A213 | 58 | >200 | >200 | >200 | 27% |
| Example A214 | 50 | >200 | >200 | >200 | 15% |
| Example A215 | 16 | 185 | >200 | 160 | 32% |
| Example A216 | 80 | >200 | >200 | >200 | 29% |
| Example A217 | 4.2 | 68 | >200 | 55 | 23% |
| Example A218 | 74 | >200 | >200 | >200 | 26% |
| Example A219 | 12 | 90 | >200 | 180 | 20% |
| Example A220 | 13 | 180 | >200 | 190 | 18% |
| Example A221 | 44 | >200 | >200 | >200 | 22% |
| Example A222 | 3.2 | >200 | >200 | >200 | 5.6% |
| Example A223 | 5 | 90 | >400 | >400 | 41% |
| Example A224 | 14 | >400 | >400 | >400 | 30% |
| Example A225 | 7.2 | 180 | >400 | >400 | 36% |
| Example A226 | 5.3 | 100 | >400 | >400 | 55% |
| Example A227 | 10 | >400 | >400 | >400 | 22% |
| Example A228 | 6.9 | 114 | >400 | 109 | 62% |
| Example A229 | 8 | 75 | >400 | 120 | 55% |
| Example A230 | 15 | 130 | >400 | 255 | 50% |
| Example A231 | 9.7 | 85 | >400 | 98 | 46% |
| Example A232 | 12 | 94 | >400 | 326 | 43% |
| Example A233 | 0.4 | 19 | >400 | 26 | 24% |
| Example A234 | 1.5 | 80 | >400 | 72 | 13% |
| Example A235 | 12 | 326 | >400 | >400 | 4.6% |
| Example A236 | 1.7 | 150 | >400 | >400 | 16% |
| Example A237 | 90 | >400 | >400 | >400 | 5.9% |
| Example A238 | 18 | 244 | >400 | 200 | 15% |
| Example A239 | 16 | 226 | >400 | >400 | 17% |
| Example A240 | 1.5 | 80 | >400 | 244 | 29% |
| Example A241 | 42 | >400 | >400 | >400 | 14% |
| Example A242 | 40 | >400 | >400 | >400 | 31% |
| Example A243 | 20 | 119 | >400 | 235 | 38% |
| Example A244 | 30 | 171 | >400 | 170 | 66% |
| Example A245 | 3.2 | 117 | >400 | 41 | 47% |
| Example A246 | 15 | 120 | >200 | >200 | 39% |
| Example A247 | 6.9 | 72 | >200 | 84 | 35% |
| Example A248 | 8.7 | 30 | >200 | 82 | 50% |
| Example A249 | 226 | >400 | >400 | >400 | 28% | a. when the experiment limit is set as "a" and the IC$_{50}$ measurement of the example compound exceeds the limit, then the IC$_{50}$ data is shown as "> a"
b. "—" designates that the IC$_{50}$ is not available due to no measurement
c. when the data is shown as a number in percentage, the measurement is the percentage inhibition of the example compound at a concentration of 500 nM or 1 mM.

TABLE B1

| Example Number | JAK1 IC$_{50}$ (nM) | JAK2 IC$_{50}$ (nM) | JAK3 IC$_{50}$ (nM) | TYK2 IC$_{50}$ (nM) | ALK IC$_{50}$ (nM) or % of inhibition at a concentration of 500 nM or 1 mM |
|---|---|---|---|---|---|
| Example B1 | 11 | 5.1 | >100 | 17 | 786 |
| Example B2 | 11 | 8.4 | 277 | 19 | >1000 |
| Example B3 | 9.2 | 3.5 | 67 | 15 | 976 |
| Example B5 | 107 | 44 | 83 | 165 | >1000 |
| Example B6 | >1000 | 800 | >1000 | >1000 | >1000 |
| Example B7 | >1000 | 700 | >1000 | >1000 | >10000 |
| Example B8 | 500 | 350 | >1000 | >1000 | >1000 |
| Example B9 | 263 | 130 | >1000 | 683 | >1000 |
| Example B10 | 68 | 12 | 51 | 172 | 1956 |
| Example B11 | 97 | 92 | 144 | 275 | 2370 |
| Example B12 | 235 | 112 | 450 | 312 | >10000 |
| Example B13 | 900 | 171 | 682 | >1000 | >1000 |
| Example B14 | 232 | 119 | 314 | >1000 | >1000 |
| Example B15 | 160 | 111 | 365 | >1000 | >1000 |
| Example B16 | 52 | 7.5 | 182 | 206 | >10000 |
| Example B17 | 71 | 11 | 126 | 152 | >10000 |
| Example B18 | 107 | 23 | 64 | 178 | >1000 |
| Example B19 | 1.3 | 0.97 | 7.5 | 2.5 | 610 |
| Example B20 | 1.0 | 1.3 | 6.7 | 1.6 | 51% |
| Example B21 | 18 | 6.3 | 21 | 32 | 1500 |

TABLE B1-continued

| Example Number | JAK1 IC$_{50}$ (nM) | JAK2 IC$_{50}$ (nM) | JAK3 IC$_{50}$ (nM) | TYK2 IC$_{50}$ (nM) | ALK IC$_{50}$ (nM) or % of inhibition at a concentration of 500 nM or 1 mM |
|---|---|---|---|---|---|
| Example B22 | 144 | 11 | 104 | 41 | 1440 |
| Example B23 | 0.2 | 0.8 | 1.2 | 1.8 | 75% |
| Example B24 | 14 | 2.3 | 5.8 | 18 | 781 |
| Example B25 | 12 | 36 | 153 | 50 | 14% |
| Example B26 | 6.5 | 4.1 | 7.4 | 15 | 1100 |
| Example B27 | 5.2 | 3.7 | 8.5 | 15 | 880 |
| Example B28 | 8.2 | 4.1 | 10 | 20 | 1800 |
| Example B29 | 0.24 | 0.48 | 3.3 | 1.7 | 96 |
| Example B30 | 0.87 | 0.78 | 2.9 | 2.5 | 260 |
| Example B31 | 5.4 | 3.7 | 69 | 10 | >10000 |
| Example B32 | 2.8 | 1.6 | 5.5 | 2.7 | 940 |
| Example B33 | 2.1 | 2.6 | 44 | 9.7 | 820 |
| Example B34 | 0.85 | 1 | 13 | 5.6 | 470 |
| Example B35 | 0.6 | 0.35 | 1.4 | 1.3 | 76 |
| Example B36 | 13 | 7.7 | 42 | 21 | >1000 |
| Example B37 | 7.6 | 8.3 | 87 | 21 | >10000 |
| Example B38 | 1.4 | 0.26 | 4 | 0.97 | 210 |
| Example B39 | 0.2 | 0.12 | 2.7 | 0.66 | 86 |
| Example B40 | 1.4 | 0.55 | 3.6 | 2.1 | 430 |
| Example B41 | 1.7 | 0.63 | 6.5 | 2.3 | 140 |
| Example B42 | 1.7 | 0.75 | 7 | 3.9 | 310 |
| Example B43 | 0.79 | 1.1 | 6.7 | 2.9 | 170 |
| Example B44 | 13 | 2.9 | 48 | 22 | 300 |
| Example B45 | 0.88 | 0.6 | 3.7 | 0.53 | 95 |
| Example B46 | 2.5 | 2.3 | 9.7 | 3.6 | 330 |
| Example B47 | 0.7 | 1.5 | 9.5 | 3.2 | 180 |
| Example B48 | 0.96 | 0.44 | 2.6 | 1.7 | 160 |
| Example B49 | 0.59 | 0.54 | 3.6 | 1.4 | 80 |
| Example B50 | 0.44 | 0.28 | 2.5 | 2.3 | 230 |
| Example B51 | 2.7 | 0.91 | 4.7 | 3.3 | 300 |
| Example B52 | 3.7 | 1.8 | 17 | 6.3 | 910 |
| Example B53 | 2.8 | 2.3 | 17 | 8 | 720 |
| Example B54 | 4.9 | 3.9 | 5.9 | 14 | 970 |
| Example B55 | 12 | 2.7 | 1.1 | 23 | 930 |
| Example B56 | 5.9 | 2 | 1.5 | 14 | 720 |
| Example B57 | 12 | 5.3 | 18 | 39 | 2200 |
| Example B58 | 365 | 47 | 107 | 228 | >1000 |
| Example B59 | 2.4 | 2.4 | 5.1 | 5.3 | 700 |
| Example B60 | 22 | 8.4 | 20 | 47 | >1000 |
| Example B61 | 19 | 1.4 | 3 | 34 | 680 |
| Example B62 | 1.8 | 1.9 | 4.8 | 2.7 | 210 |
| Example B63 | 18 | 12 | 56 | 34 | 600 |
| Example B64 | 1.2 | 0.73 | 10 | 3.2 | 150 |
| Example B65 | 3.4 | 1.8 | 8.8 | 5.9 | 290 |
| Example B66 | 3 | 1.6 | 13 | 4.5 | 310 |
| Example B67 | 3.2 | 1.9 | 15 | 6 | 220 |
| Example B68 | 1.4 | 2.3 | 19 | 3.6 | 19% |
| Example B69 | 0.45 | 0.6 | 3.6 | 2.3 | 68% |
| Example B70 | 1.5 | 0.64 | 2.4 | 2.5 | 82% |
| Example B71 | 1.9 | 4.9 | 24 | 9.6 | 43% |
| Example B72 | 200 | 55 | >500 | 77 | 12% |
| Example B73 | 80 | 103 | 178 | 154 | 21% |
| Example B74 | >1000 | 400 | >1000 | >1000 | — |
| Example B75 | 4.7 | 30 | 80 | 30 | 17% |
| Example B76 | 33 | 14 | 61 | 25 | 28% |
| Example B77 | 0.84 | 2.2 | 7.6 | 8 | 54% |
| Example B78 | 11 | 12 | 57 | 29 | 44% |
| Example B79 | 0.83 | 0.58 | 2.8 | 1.7 | 91% |
| Example B80 | 0.56 | 0.53 | 1.7 | 1.2 | 73% |
| Example B81 | 109 | 123 | 475 | 221 | — |
| Example B82 | 7.9 | 7.6 | 44 | 14 | 39% |
| Example B83 | 0.56 | 1.7 | 27 | 5.2 | 780 |
| Example B84 | 0.39 | 1.3 | 9.7 | 4.2 | 730 |
| Example B85 | 1.4 | 2.7 | 39 | 2.2 | >1000 |
| Example B86 | 2.7 | 2.6 | 27 | 6.4 | >1000 |
| Example B87 | 5.3 | 4.5 | 42 | 16 | >1000 |
| Example B88 | 0.74 | 1.7 | 29 | 6.3 | 930 |
| Example B89 | 2.4 | 2.9 | 40 | 16 | >1000 |
| Example B90 | 5.2 | 7.7 | 73 | 20 | >1000 |
| Example B91 | 2.1 | 2.7 | 28 | 13 | >1000 |
| Example B92 | 4 | 5.3 | 61 | 9.7 | >1000 |
| Example B93 | 2.6 | 3.4 | 43 | 12 | >1000 |
| Example B94 | 3.1 | 3.8 | 51 | 13 | >1000 |
| Example B95 | 2.1 | 4.1 | 67 | 7.8 | >1000 |

TABLE B1-continued

| Example Number | JAK1 IC$_{50}$ (nM) | JAK2 IC$_{50}$ (nM) | JAK3 IC$_{50}$ (nM) | TYK2 IC$_{50}$ (nM) | ALK IC$_{50}$ (nM) or % of inhibition at a concentration of 500 nM or 1 mM |
|---|---|---|---|---|---|
| Example B96 | 1 | 6 | 45 | 12 | >1000 |
| Example B97 | 3.9 | 9 | 35 | 16 | 40% |
| Example B98 | 13 | 26 | 91 | 38 | 41% |
| Example B99 | 7 | 20 | 151 | 33 | 37% |
| Example B100 | 0.92 | 4.7 | 40 | 8.7 | 44% |
| Example B101 | 4.5 | 10 | 26 | 19 | 39% |
| Example B102 | 2 | 3.8 | 33 | 8.9 | 54% |
| Example B103 | 9 | 31 | 124 | 46 | 49% |
| Example B104 | 4.9 | 11 | 81 | 26 | 55% |
| Example B105 | 3.9 | 10 | 43 | 13 | 52% |
| Example B106 | 4.3 | 9.6 | 90 | 18 | 5.7% |
| Example B107 | 0.62 | 2.3 | 16 | 6.8 | 9.3% |
| Example B108 | 1.6 | 4.6 | 23 | 2.1 | 21% |
| Example B109 | 9.6 | 56 | 261 | 72 | 0% |
| Example B110 | 4.3 | 5.2 | 92 | 15 | 7.1% |
| Example B111 | 3.7 | 6 | 21 | 5 | 14% |
| Example B112 | 11 | 34 | 165 | 33 | 3.3% |
| Example B113 | 4.7 | 7.4 | 48 | 17 | 9.5% |
| Example B114 | 0.81 | 2.9 | 13 | 5.4 | 24% |
| Example B115 | 1.4 | 5.2 | 29 | 8.8 | 23% |
| Example B116 | 3.1 | 3.5 | 26 | 10 | 20% |
| Example B117 | 1.1 | 2.8 | 17 | 4.5 | 21% |
| Example B118 | 1.3 | 2.1 | 20 | 7.7 | 22% |
| Example B119 | 2.9 | 3.3 | 48 | 9.8 | 19% |
| Example B120 | 6.7 | 7.9 | 68 | 25 | 16% |
| Example B121 | 2.2 | 7.9 | 50 | 19 | 39% |
| Example B122 | 5.6 | 6.7 | 30 | 24 | 13% |
| Example B123 | 7.9 | 15 | 110 | 32 | 16% |
| Example B124 | 3.9 | 4.6 | 33 | 13 | 17% |
| Example B125 | 2.8 | 10 | 76 | 30 | 34% |
| Example B126 | 8.9 | 20 | 164 | 52 | 6.1% |
| Example B127 | 25 | 27 | 182 | 89 | 6.1% |
| Example B128 | 0.69 | 1.8 | 13 | 9.2 | 32% |
| Example B129 | 3.7 | 9.5 | 184 | 32 | 7.3% |
| Example B130 | 11 | 11 | 331 | 64 | 0% |
| Example B131 | 7.3 | 13 | 63 | 33 | 5.9% |
| Example B132 | 11 | 27 | 198 | 96 | 5% |
| Example B133 | 44 | 85 | 376 | 288 | 2.5% |
| Example B134 | 0.75 | 1.7 | 23 | 2.8 | — |
| Example B135 | 0.69 | 4.3 | 30 | 6.8 | 13% |
| Example B136 | 0.24 | 0.1 | 2.3 | 0.76 | 240 |
| Example B137 | 0.42 | 0.11 | 6.4 | 0.27 | 580 |
| Example B138 | 0.25 | 0.1 | 0.33 | 0.35 | 100 |
| Example B139 | 0.5 | 0.1 | 5.1 | 0.84 | 290 |
| Example B140 | 0.51 | 0.2 | 1.3 | 0.89 | 150 |
| Example B141 | 0.8 | 0.2 | 3 | 1.2 | 740 |
| Example B142 | 0.85 | 0.31 | 4.6 | 1.5 | 990 |
| Example B143 | 11 | 2.8 | 104 | 13 | >1000 |
| Example B144 | 0.34 | 0.2 | 4.2 | 0.5 | 600 |
| Example B145 | 0.8 | 0.17 | 12 | 0.84 | 1200 |
| Example B146 | 0.5 | 0.11 | 2.6 | 0.61 | 130 |
| Example B147 | 2.5 | 1.5 | 37 | 6.6 | 1800 |
| Example B148 | 0.49 | 0.13 | 1.1 | 0.53 | 150 |
| Example B149 | 0.15 | 0.22 | 2.4 | 0.51 | 350 |
| Example B150 | 0.41 | 0.15 | 6.3 | 0.86 | 180 |
| Example B151 | 2.9 | 1.2 | 36 | 1.4 | 1000 |
| Example B152 | 0.35 | 0.14 | 11 | 0.5 | 430 |
| Example B153 | 0.69 | 0.1 | 0.48 | 0.44 | 70 |
| Example B154 | 0.6 | 0.1 | 5.3 | 0.83 | 280 |
| Example B155 | 1.3 | 2.4 | 40 | 2.2 | >1000 |
| Example B156 | 0.75 | 1.5 | 17 | 2.7 | 28% |
| Example B157 | 0.51 | 0.15 | 0.3 | 0.62 | 87% |
| Example B158 | 0.15 | 0.15 | 0.64 | 0.49 | 71% |
| Example B159 | 1.3 | 0.46 | 3.1 | 1.6 | 82% |
| Example B160 | 12 | 6.4 | 102 | 2.4 | 4.6% |
| Example B161 | 1.6 | 1.1 | 8.5 | 2.6 | 58% |
| Example B162 | 1.7 | 2.7 | 26 | 4.3 | 16% |
| Example B163 | 0.54 | 0.24 | 1.1 | 0.97 | 80% |
| Example B164 | 8 | 8.4 | 200 | 8.1 | 4.6% |
| Example B165 | 13 | 10 | 83 | 20 | 10% |
| Example B166 | 3.6 | 7.4 | 39 | 17 | 15% |
| Example B167 | 3.7 | 12 | 43 | 30 | 17% |
| Example B168 | 2.8 | 12 | 67 | 17 | 21% |
| Example B169 | 3.3 | 12 | 47 | 26 | 17% |

TABLE B1-continued

| Example Number | JAK1 IC$_{50}$ (nM) | JAK2 IC$_{50}$ (nM) | JAK3 IC$_{50}$ (nM) | TYK2 IC$_{50}$ (nM) | ALK IC$_{50}$ (nM) or % of inhibition at a concentration of 500 nM or 1 mM |
|---|---|---|---|---|---|
| Example B170 | 1.6 | 17 | 228 | 34 | 12% |
| Example B171 | 2.8 | 12 | 51 | 30 | 15% |
| Example B172 | 0.82 | 1.1 | 17 | 2.6 | 24% |
| Example B173 | 3.5 | 23 | 163 | 55 | 14% |
| Example B174 | 15 | 27 | 124 | 62 | 12% |
| Example B175 | 9 | 18 | 69 | 31 | 18% |
| Example B176 | 5.7 | 7.8 | 60 | 25 | 19% |
| Example B177 | 3.1 | 5.4 | 46 | 39 | 20% |
| Example B178 | 0.82 | 1.1 | 17 | 2.6 | 24% |
| Example B179 | 0.23 | 0.84 | 1.3 | 2.8 | 43% |
| Example B180 | 91 | 97 | 500 | 450 | 3.5% |
| Example B181 | 70 | 177 | 236 | 226 | 3.7% |
| Example B182 | 1.2 | 6.2 | 44 | 17 | 29% |
| Example B183 | 2.1 | 1 | 14 | 7 | 26% |
| Example B184 | 0.1 | 0.1 | 0.1 | 0.14 | 82% |
| Example B185 | 0.62 | 3.9 | 46 | 4 | 12% |
| Example B186 | 4 | 8.2 | 35 | 9.6 | 21% |
| Example B187 | 0.9 | 0.4 | 2.4 | 1.9 | 29% |
| Example B188 | 4 | 7.7 | 52 | 13 | 24% |
| Example B189 | 5 | 6.7 | 35 | 22 | 15% |
| Example B190 | 5 | 10 | 61 | 19 | 11% |
| Example B191 | 93 | 27 | 205 | 378 | 1530 |
| Example B192 | 21 | 23 | 308 | 341 | >1000 |
| Example B193 | 55 | 47 | 500 | 950 | >1000 |
| Example B194 | 36 | 12 | 108 | 251 | >1000 |
| Example B195 | >1000 | 91 | >1000 | >1000 | >10000 |
| Example B196 | 3.5 | 0.88 | 48 | 111 | >10000 |
| Example B197 | 18 | 2.2 | 138 | 188 | >1000 |
| Example B198 | 39 | 10 | 161 | 289 | >10000 |
| Example B199 | 4.9 | 2.7 | 64 | 154 | >1000 |
| Example B200 | 82 | 17 | 118 | 85 | 4400 |
| Example B201 | 119 | 410 | 454 | >1000 | >10000 |
| Example B202 | 36 | 56 | 101 | 205 | 3600 |
| Example B203 | 44 | 19 | 102 | 34 | >10000 |
| Example B204 | >1000 | 500 | >1000 | >1000 | >10000 |
| Example B205 | 188 | 146 | 509 | >1000 | >10000 |
| Example B206 | 16 | 15 | 41 | 46 | >10000 |
| Example B207 | 176 | 125 | 200 | 700 | >10000 |
| Example B208 | 209 | 57 | 84 | 150 | >1000 |
| Example B209 | 64 | 51 | 140 | 110 | >1000 |
| Example B210 | 62 | 42 | 76 | 357 | >1000 |
| Example B211 | 56 | 20 | 135 | 191 | 1000 |
| Example B212 | 400 | 238 | 312 | 500 | 14% |
| Example B213 | 70 | 173 | 184 | 206 | 11% |
| Example B214 | >1000 | 281 | 231 | >1000 | 39% |
| Example B215 | 91 | 43 | 189 | 766 | 31% |
| Example B216 | 48 | 29 | 166 | 66 | 1.3% |
| Example B217 | 225 | 71 | 199 | >1000 | >10000 |
| Example B218 | 164 | 25 | 400 | 900 | >10000 |
| Example B219 | 6.6 | 16 | 29 | 29 | 26% |
| Example B220 | 7.4 | 12 | 36 | 28 | 25% |
| Example B221 | 12 | 19 | 59 | 43 | 8.1% |
| Example B222 | 20 | 14 | 40 | 54 | 34% |
| Example B223 | 17 | 7.4 | 29 | 42 | 41% |
| Example B224 | 19 | 8.9 | 41 | 41 | 28% |
| Example B225 | 31 | 10 | 37 | 46 | 27% |
| Example B226 | 4 | 42 | 306 | 62 | 15% |
| Example B227 | 1 | 29 | 245 | 33 | 25% |
| Example B228 | 6 | 11 | 63 | 19 | 10% |
| Example B229 | 9 | 17 | 76 | 19 | 6.5% |
| Example B230 | 2 | 7 | 50 | 15 | 11% |
| Example B231 | 4 | 5.5 | 65 | 16 | 8.1% |
| Example B232 | 4 | 11 | 72 | 26 | 10% |
| Example B233 | 7 | 11 | 102 | 24 | 5.8% |
| Example B234 | 4 | 6.5 | 40 | 11 | 31% |
| Example B235 | 6 | 21 | 213 | 36 | 7.3% |
| Example B236 | 1.7 | 1.7 | 9.7 | 6.1 | 29% |
| Example B237 | 7.9 | 18 | 122 | 16 | 6.2% |
| Example B238 | 8.1 | 17 | 274 | 50 | 15% |
| Example B239 | 6.4 | 8.9 | 35 | 24 | 21% |
| Example B240 | 1.5 | 0.74 | 10 | 4 | 15% |
| Example B241 | 1.1 | 1.5 | 10 | 3.5 | 22% |
| Example B242 | 2.8 | 2 | 12 | 6.9 | 16% |
| Example B243 | 0.92 | 1.5 | 16 | 3.1 | 14% |

TABLE B1-continued

| Example Number | JAK1 IC$_{50}$ (nM) | JAK2 IC$_{50}$ (nM) | JAK3 IC$_{50}$ (nM) | TYK2 IC$_{50}$ (nM) | ALK IC$_{50}$ (nM) or % of inhibition at a concentration of 500 nM or 1 mM |
|---|---|---|---|---|---|
| Example B244 | 9.2 | 19 | 2.6 | 1.6 | 63% |
| Example B245 | 17 | 78 | 20 | 8.5 | 41% |
| Example B246 | 12 | 25 | 21 | 3.4 | 23% |
| Example B247 | 6.5 | 4 | 73 | 20 | 7.5% |
| Example B248 | 77 | 171 | 46 | 25 | 32% |
| Example B249 | 6 | 8.6 | 103 | 30 | 35% |
| Example B250 | 28 | 28 | 6.3 | 5.5 | 66% |
| Example B251 | 53 | 37 | 4.2 | 14 | 44% |
| Example B252 | 13 | 26 | 119 | 62 | 20% |
| Example B253 | 90 | 72 | 695 | 173 | 4.9% |
| Example B254 | 2 | 2.4 | 26 | 8.2 | 18% |
| Example B255 | 5.5 | 14 | 53 | 25 | 32% |
| Example B256 | 4.2 | 13 | 77 | 21 | 23% |
| Example B257 | 7.3 | 9.5 | 64 | 18 | 14% |
| Example B258 | 4.9 | 10 | 83 | 24 | 29% |
| Example B259 | 3.8 | 7 | 52 | 23 | 13% |
| Example B260 | 4.7 | 9.9 | 51 | 20 | 26% |
| Example B261 | 9.5 | 29 | 81 | 81 | 24% |
| Example B262 | 2.6 | 4.7 | 38 | 8.7 | 19% |
| Example B263 | 6.7 | 9.3 | 110 | 22 | 29% |
| Example B264 | 14 | 25 | 216 | 54 | 27% |
| Example B265 | 14 | 141 | 85 | 15 | 23% |
| Example B266 | 17 | 601 | 100 | 25 | 22% |
| Example B267 | 27 | 765 | >10000 | 887 | 12% |
| Example B268 | 9.8 | 273 | >10000 | 541 | 16% |
| Example B269 | 13 | 409 | >10000 | 727 | 10% |
| Example B270 | 20 | 279 | >10000 | 607 | 10% |
| Example B271 | 8.7 | 440 | >10000 | 847 | 10% |
| Example B272 | 14 | 316 | >10000 | 575 | 23% |
| Example B273 | 117 | 1629 | >10000 | 3829 | 3.2% |
| Example B274 | 60 | 192 | >10000 | 325 | 18% |
| Example B275 | 14 | 129 | >10000 | 348 | 9.8% |
| Example B276 | 6.5 | 11 | 1172 | 34 | 22% |
| Example B277 | 4.8 | 5.9 | 359 | 62 | 54% |
| Example B278 | 47 | 126 | 1846 | 222 | 10% |
| Example B279 | 86 | 158 | >10000 | 549 | 0.76% |
| Example B280 | 276 | 446 | >10000 | 1786 | 4.6% |
| Example B281 | 15 | 150 | 1400 | 2300 | 24% |
| Example B282 | >1000 | >1000 | | | 0% |
| Example B283 | 141 | 165 | >1000 | 550 | 30% |
| Example B284 | 72 | 368 | >1000 | 409 | 25% |
| Example B285 | 100 | >200 | >200 | >200 | 38% |
| Example B286 | 43 | >200 | >200 | >200 | 51% |
| Example B287 | 15 | 90 | >200 | >200 | 46% |
| Example B288 | 42 | 180 | >200 | >200 | 18% |
| Example B289 | 17 | 134 | >200 | 85 | 65% |
| Example B290 | 82 | 89 | >200 | 59 | 50% |
| Example B291 | 28 | 100 | >200 | 199 | 58% |
| Example B292 | 32 | >200 | >200 | 100 | 68% |
| Example B293 | 60 | >200 | >200 | 150 | 45% |
| Example B294 | 19 | 150 | >200 | 85 | 54% |
| Example B295 | 30 | 199 | >200 | 150 | 50% |
| Example B296 | 8.3 | 26 | >200 | 48 | 33% |
| Example B297 | 27 | 67 | >400 | 36 | 66% |
| Example B298 | 29 | 341 | >400 | 208 | 62% |
| Example B299 | 30 | 180 | >400 | 82 | 74% |
| Example B300 | 16 | 160 | >400 | 27 | 77% |
| Example B301 | 35 | >400 | >400 | 75 | 58% |
| Example B302 | 119 | >400 | >400 | 200 | 69% |
| Example B303 | 19 | 161 | >400 | 36 | 81% |
| Example B304 | 58 | 300 | >400 | 90 | 67% |
| Example B305 | 15 | 148 | >400 | 38 | 79% |
| Example B306 | 27 | 265 | >400 | 43 | 72% |
| Example B307 | 36 | 217 | >400 | 66 | 74% |
| Example B308 | 16 | 83 | >400 | 34 | 79% |
| Example B309 | 21 | 133 | >400 | 67 | 68% |
| Example B310 | 24 | 61 | >400 | 44 | 74% |
| Example B311 | 20 | 170 | >400 | 146 | 67% |
| Example B312 | 5 | 70 | >400 | 42 | 40% |
| Example B313 | 48 | 371 | >400 | >400 | 20% |
| Example B314 | 28 | 108 | >400 | 67 | 69% |
| Example B315 | 47 | >400 | >400 | 235 | 50% |
| Example B316 | 16 | 180 | >400 | 208 | 64% |
| Example B317 | 57 | >400 | >400 | 356 | 50% |

TABLE B1-continued

| Example Number | JAK1 IC$_{50}$ (nM) | JAK2 IC$_{50}$ (nM) | JAK3 IC$_{50}$ (nM) | TYK2 IC$_{50}$ (nM) | ALK IC$_{50}$ (nM) or % of inhibition at a concentration of 500 nM or 1 mM |
|---|---|---|---|---|---|
| Example B318 | 24 | 371 | >400 | 70 | 61% |
| Example B319 | 42 | >400 | >400 | 288 | 58% |
| Example B320 | 79 | >400 | >400 | >400 | 57% |
| Example B321 | 75 | 371 | >400 | >400 | 36% |
| Example B322 | 32 | 313 | >400 | 160 | 74% |
| Example B323 | 12 | 14 | 2.1 | 0.89 | 20% |
| Example B324 | 20 | 56 | 7.5 | 2.8 | 16% |
| Example B325 | 2 | 1.6 | 6.4 | 5.5 | 19% |
| Example B326 | 3 | 3.4 | 7.8 | 6.9 | 19% |
| Example B327 | 2 | 1.8 | 4.2 | 5 | 19% |
| Example B328 | 18 | 25 | 24 | 7.1 | 16% |
| Example B329 | 3 | 3.2 | 6.5 | 5.8 | 20% |
| Example B330 | 4 | 6.1 | 7.1 | 16 | 21% |
| Example B331 | 2 | 3.6 | 2.7 | 16 | 27% |
| Example B332 | 3 | 3.4 | 26 | 8.2 | 23% |
| Example B333 | 6.8 | 15 | 1 | 1.2 | 55% |
| Example B334 | 44 | 199 | >200 | >200 | 72% |
| Example B335 | 45 | 77 | >200 | >200 | 18% |
| Example B336 | 52 | 140 | >200 | >200 | 11% |
| Example B337 | 41 | 171 | >200 | >200 | 21% |
| Example B338 | 70 | 130 | >200 | >200 | 21% |
| Example B339 | 172 | >400 | >400 | >400 | 41% |
| Example B340 | 1.2 | 41 | >400 | 180 | 24% |
| Example B341 | 13 | 146 | >400 | >400 | 27% |
| Example B342 | 7.7 | 60 | >400 | 226 | 37% |
| Example B343 | 3.8 | 130 | >400 | 180 | 42% |
| Example B344 | 14 | 90 | >400 | 276 | 43% |
| Example B345 | 17 | 179 | >400 | 98 | 40% |
| Example B346 | 13 | 91 | >400 | >400 | 38% |
| Example B347 | 58 | 371 | >400 | >400 | 45% |
| Example B348 | 3.4 | 45 | >400 | >400 | 47% |
| Example B349 | 11 | 150 | 371 | 300 | 61% |
| Example B350 | 90 | 66 | >400 | 244 | 58% | a. when the experiment limit is set as "a" and the IC$_{50}$ measurement of the example compound exceeds the limit, then the IC$_{50}$ data is shown as "> a"
b. "—" designates that the IC$_{50}$ is not available due to no measurement
c. when the data is shown as a number in percentage, the measurement is the percentage inhibition of the example compound at a concentration of 500 nM or 1 mM.

TABLE C1

| Example Number | JAK1 IC$_{50}$ (nM) | JAK2 IC$_{50}$ (nM) | JAK3 IC$_{50}$ (nM) | TYK2 IC$_{50}$ (nM) | ALK IC$_{50}$ (nM) or % inhibition at a concentration of 500 nM or 1 mM |
|---|---|---|---|---|---|
| Example C1 | >1,000 | 900 | >1,000 | >1,000 | >10,000 |
| Example C2 | >1,000 | >1,000 | >1,000 | >1,000 | >1,000 |
| Example C3 | 81 | 37 | 115 | 91 | 6600 |
| Example C4 | 361 | 350 | 317 | >1,000 | >1,000 |
| Example C5 | >1,000 | >1,000 | >1,000 | >1,000 | >1,000 |
| Example C6 | 220 | 70 | 377 | 240 | >10,000 |
| Example C7 | 63 | 36 | 82 | 32 | 1900 |
| Example C8 | 200 | 66 | 242 | 400 | >1,000 |
| Example C9 | 144 | 93 | 412 | 353 | >1,000 |
| Example C10 | 154 | 303 | >1,000 | 60 | >10,000 |
| Example C11 | >1,000 | >1,000 | >1,000 | >1,000 | >10,000 |
| Example C12 | 14 | 9.5 | 39 | 13 | 26% |
| Example C13 | 70 | 17 | 154 | 16 | 18% |
| Example C14 | 10 | 2.8 | 17 | 5.7 | 19% |
| Example C15 | 700 | 87 | 400 | 106 | 6% |
| Example C16 | >1,000 | 60 | 350 | 83 | 14% |
| Example C17 | >1,000 | >1,000 | >1,000 | >1,000 | 1% |
| Example C18 | >1,000 | >1,000 | >1,000 | >1,000 | 3% |
| Example C19 | 2.9 | 7.0 | 28 | 10 | 45% |
| Example C20 | 2.9 | 2.3 | 13 | 4.4 | 26% |
| Example C21 | 13 | 28 | 111 | 15 | 26% |
| Example C22 | 24 | 32 | >400 | 88 | — |
| Example C23 | 162 | 281 | >10,000 | 1135 | — |
| Example C24 | 95 | 154 | 1205 | 1031 | — |
| Example C25 | 91 | 173 | >10,000 | 793 | — |

TABLE C1-continued

| Example Number | JAK1 IC$_{50}$ (nM) | JAK2 IC$_{50}$ (nM) | JAK3 IC$_{50}$ (nM) | TYK2 IC$_{50}$ (nM) | ALK IC$_{50}$ (nM) or % inhibition at a concentration of 500 nM or 1 mM |
|---|---|---|---|---|---|
| Example C26 | 228 | 357 | >10,000 | 1418 | — |
| Example C27 | 43 | 59 | 1294 | 501 | — |
| Example C28 | 120 | 100 | >200 | >200 | — |
| Example C29 | 43 | 68 | 1031 | 227 | — |
| Example C30 | 31 | 56 | 990 | 136 | — |
| Example C31 | 140 | 24 | 404 | 481 | — |
| Example C32 | 34 | 20 | 658 | 44 | — |
| Example C33 | 17 | 35 | 733 | 217 | — |
| Example C34 | 265 | 178 | 4,000 | 775 | — |
| Example C35 | 232 | 203 | >10,000 | 549 | — |
| Example C36 | 33 | 42 | 663 | 103 | — |
| Example C37 | 496 | 276 | 2622 | 581 | — |
| Example C38 | 37 | 47 | 1069 | 39 | — |
| Example C39 | 54 | 29 | 1222 | 195 | — |
| Example C40 | 62 | 56 | 804 | 291 | — |
| Example C41 | 112 | 65 | 1166 | 246 | — |
| Example C42 | 37 | 23 | 346 | 96 | — |
| Example C43 | 22 | 31 | 1136 | 88 | — |
| Example C44 | 70 | 53 | 779 | 478 | — |
| Example C45 | 165 | 321 | >10,000 | 544 | — |
| Example C46 | 79 | 170 | 1487 | 165 | — |
| Example C47 | 67 | 134 | 1141 | 300 | — |
| Example C48 | 52 | 74 | 1152 | 647 | — |
| Example C49 | 50 | >400 | >400 | 326 | — |
| Example C50 | 33 | 111 | >400 | 80 | — |
| Example C51 | 13 | 371 | >400 | 100 | — |
| Example C52 | >200 | >200 | >200 | >200 | — |
| Example C53 | 39 | >200 | >200 | 199 | — |
| Example C54 | 65 | 199 | >200 | 199 | — |
| Example C55 | 96 | >400 | >400 | >400 | — |
| Example C56 | 216 | 255 | >400 | >400 | — |
| Example C57 | >400 | 288 | >400 | >400 | — |
| Example C58 | 217 | >400 | >400 | >400 | — |
| Example C59 | 102 | >400 | >400 | 371 | — | a. when the experiment limit is set as "a" and the IC$_{50}$ measurement of the example compound exceeds the limit, then the IC$_{50}$ data is shown as "> a"
b. when the data is shown as a number in percentage, the measurement is the percentage inhibition of the example compound at a concentration of 500 nM or 1 mM.
c. "—" designates that the IC$_{50}$ is not available due to no measurement

TABLE D1

| Example Number | JAK1 IC$_{50}$ (nM) | JAK2 IC$_{50}$ (nM) | JAK3 IC$_{50}$ (nM) | TYK2 IC$_{50}$ (nM) | ALK IC$_{50}$ (nM) |
|---|---|---|---|---|---|
| Example D1 | 13 | 9.6 | 16 | 14 | 620 |
| Example D2 | 19 | 7.3 | 13 | 25 | 774 |
| Example D3 | 25 | 6.3 | 13 | 40 | 1108 |
| Example D4 | 91 | 16 | 25 | 50 | 774 |
| Example D5 | 30 | 15 | 36 | 12 | 509 |
| Example D6 | 36 | 37 | >100 | 16 | 4190 |
| Example D7 | 100 | 61 | >100 | >100 | >10000 |
| Example D8 | 7.9 | 5.4 | 13 | 19 | 351 |
| Example D9 | 183 | 47 | 489 | 137 | >952 |
| Example D10 | 8.2 | 2.4 | 10 | 8.1 | 791 |
| Example D11 | 3.4 | 5.4 | 24 | 9.9 | 480 |
| Example D12 | 178 | 290 | 369 | 324 | >10000 |
| Example D13 | 3.6 | 2.1 | 24 | 12 | 1743 |
| Example D14 | 2.2 | 2.2 | 11 | 5 | 732 |
| Example D15 | 93 | 61 | 135 | 88 | >10000 |
| Example D16 | 144 | 113 | 325 | 400 | >10000 |
| Example D17 | 63 | 32 | 165 | 77 | >1000 |
| Example D18 | 5.4 | 6.6 | 24 | 19 | 327 |
| Example D19 | 150 | 16 | 39 | 149 | 562 |
| Example D20 | 41 | 32 | 88 | 102 | 598 |
| Example D21 | 8.1 | 13 | 45 | 27 | 984 |
| Example D22 | 4.2 | 7.9 | 41 | 28 | 489 |
| Example D23 | 5.9 | 4.9 | 21 | 23 | 1210 |
| Example D24 | 5 | 6 | 20 | 16 | 1370 |
| Example D25 | 1.1 | 0.3 | 8.8 | 2.1 | 110 |
| Example D26 | 1.2 | 0.6 | 8.5 | 2.7 | 138 |
| Example D27 | 1.5 | 0.3 | 3.5 | 3.9 | 32 |
| Example D28 | 6.2 | 5.2 | 53 | 25 | 525 |
| Example D29 | 2 | 0.5 | 14 | 3.4 | 238 |
| Example D30 | 4.1 | 0.6 | 49 | 15 | 157 |
| Example D31 | 0.9 | 0.2 | 6.7 | 2 | 104 |
| Example D32 | 41 | 43 | 84 | 45 | >1000 |
| Example D33 | 1.8 | 0.7 | 12 | 4 | 108 |
| Example D34 | 123 | 91 | 136 | 211 | >1000 |
| Example D35 | 0.7 | 0.4 | 7.7 | 4.3 | 150 |
| Example D36 | 1.3 | 0.4 | 4.9 | 4.9 | 225 |
| Example D37 | 0.9 | 0.7 | 9.9 | 1.4 | 248 |
| Example D38 | 1.1 | 0.9 | 19 | 4 | 442 |
| Example D39 | 0.5 | 0.5 | 6.4 | 1.8 | 91 |
| Example D40 | 0.9 | 0.7 | 7.2 | 2.1 | 182 |
| Example D41 | 3.1 | 0.4 | 17 | 6.2 | 280 |
| Example D42 | 2.2 | 2.1 | 20 | 4 | 730 |
| Example D43 | 2.9 | 5.3 | 66 | 37 | 390 |
| Example D44 | 2.6 | 1.5 | 18 | 15 | 480 |
| Example D45 | 8.1 | 3 | 36 | 13 | 340 |
| Example D46 | 4.7 | 0.9 | 21 | 8.2 | 390 |
| Example D47 | 1.4 | 0.8 | 27 | 4.4 | 610 |
| Example D48 | 4.9 | 2.1 | 27 | 8.3 | >1000 |
| Example D49 | 1.9 | 1 | 14 | 6.2 | 560 |
| Example D50 | 7.3 | 4.1 | 55 | 16 | 1500 |
| Example D51 | 1.8 | 1.2 | 14 | 4.5 | 910 |
| Example D52 | 1.5 | 1.2 | 13 | 4.4 | 420 |

TABLE D1-continued

| Example Number | JAK1 IC$_{50}$ (nM) | JAK2 IC$_{50}$ (nM) | JAK3 IC$_{50}$ (nM) | TYK2 IC$_{50}$ (nM) | ALK IC$_{50}$ (nM) |
|---|---|---|---|---|---|
| Example D53 | 27 | 34 | 273 | 28 | 1150 |
| Example D54 | 18 | 15 | 132 | 27 | 1220 |
| Example D55 | 56 | 40 | 129 | 88 | >10000 |
| Example D56 | 10 | 4.8 | 42 | 14 | 1940 |
| Example D57 | 11 | 2.3 | 21 | 7.4 | 430 |
| Example D58 | 6.5 | 1.3 | 21 | 2.5 | 490 |
| Example D59 | 2.3 | 0.6 | 7.1 | 2.1 | 200 |
| Example D60 | 2 | 0.6 | 5 | 1.3 | 130 |
| Example D61 | 18 | 2.1 | 41 | 8 | >10000 |
| Example D62 | 7.3 | 2.1 | 18 | 6.1 | 380 |
| Example D63 | 6.8 | 1.5 | 19 | 5.4 | 610 |
| Example D64 | 3.8 | 0.2 | 8.4 | 3.7 | 450 |
| Example D65 | 18 | 5.1 | 16 | 6.4 | >1000 |
| Example D66 | 7.3 | 3 | 9.6 | 3.4 | 770 |
| Example D67 | 3.2 | 1.8 | 8.4 | 2.4 | >1000 |
| Example D68 | 14 | 5.8 | 36 | 32 | 340 |
| Example D69 | 3.5 | 1.4 | 8.6 | 8.4 | 160 |
| Example D70 | 9 | 2.1 | 8.1 | 5 | 375 |
| Example D71 | 151 | 187 | 65 | 300 | >1000 |
| Example D72 | 12 | 2.2 | 7.4 | 6.9 | 772 |
| Example D73 | 83 | 106 | 67 | 191 | 1332 |
| Example D74 | 160 | 83 | 225 | 343 | >1000 |
| Example D75 | 50 | 26 | 80 | 60 | 1250 |
| Example D76 | 11 | 18 | 117 | 13 | 2050 |
| Example D77 | 8.9 | 3.1 | 11 | 5.6 | 400 |
| Example D78 | 30 | 10 | 30 | 19 | 791 |
| Example D79 | 17 | 17 | 35 | 44 | 1460 |
| Example D80 | 7.4 | 4.9 | 23 | 8.8 | 570 |
| Example D81 | 12 | 16 | 130 | 53 | >10000 |
| Example D82 | 21 | 4.7 | 21 | 17 | — |
| Example D83 | 126 | 26 | 57 | 129 | — |
| Example D84 | 21 | 7.3 | 37 | 45 | — |
| Example D85 | 24 | 6.6 | 31 | 40 | — |
| Example D86 | 295 | 87 | 169 | 268 | — |
| Example D87 | 18 | 3.3 | 34 | 30 | — |
| Example D88 | 19 | 7.7 | 15 | 14 | — |
| Example D89 | 66 | 6.7 | 77 | 53 | — |
| Example D90 | 127 | 23 | 108 | 70 | — |
| Example D91 | 146 | 32 | 133 | 156 | — |
| Example D92 | 16 | 4.9 | 36 | 25 | — |
| Example D93 | 46 | 14 | 69 | 71 | — |
| Example D94 | 79 | 43 | 138 | 160 | — |
| Example D95 | 25 | 15 | 87 | 106 | — |
| Example D96 | 112 | 49 | 149 | 195 | — |
| Example D97 | 3.3 | 84 | — | — | — |
| Example D98 | 12 | 122 | — | — | — |
| Example D99 | 15 | 107 | — | — | — |
| Example D100 | 20 | 191 | — | — | — |
| Example D101 | 14 | 172 | — | — | — |
| Example D102 | 2.5 | 78 | — | — | — |
| Example D103 | 6.7 | 113 | — | — | — |
| Example D104 | 8.5 | 255 | — | — | — |
| Example D105 | 25 | 216 | — | — | — |
| Example D106 | 32 | 256 | — | — | — |
| Example D107 | 25 | 185 | — | — | — |
| Example D108 | 62 | 246 | — | — | — |
| Example D109 | 16 | 189 | — | — | — |
| Example D110 | 22 | 222 | — | — | — |
| Example D111 | 61 | 689 | — | — | — |
| Example D112 | 9.9 | 142 | — | — | — |
| Example D113 | 11 | 161 | — | — | — |
| Example D114 | 9 | 83 | — | — | — |
| Example D115 | 19 | 163 | — | — | — |
| Example D116 | 23 | 577 | — | — | — |
| Example D117 | 39 | 392 | — | — | — |
| Example D118 | 12 | 236 | — | — | — |
| Example D119 | 10 | 198 | — | — | — |
| Example D120 | 20 | 397 | — | — | — |
| Example D121 | 75 | 550 | — | — | — |
| Example D122 | 43 | 500 | — | — | — |
| Example D123 | 50 | 999 | — | — | — |
| Example D124 | 16 | 200 | — | — | — |
| Example D125 | 34 | 400 | — | — | — |
| Example D126 | 98 | 999 | — | — | — |
| Example D127 | 12 | 199 | — | — | — |
| Example D128 | 21 | 199 | — | — | — |
| Example D129-a | 15 | 84 | — | — | — |
| Example D129-b | 33 | 600 | — | — | — |
| Example D130 | 23 | 200 | — | — | — |
| Example D131 | 8.6 | 125 | — | — | — |
| Example D132 | 3.2 | 43 | — | — | — |
| Example D133 | 73 | 900 | — | — | — |
| Example D134 | 44 | 357 | — | — | — |
| Example D135 | 60 | 314 | >1000 | >1000 | — |
| Example D136 | 6.6 | 53 | >1000 | 106 | — |
| Example D137 | 1.6 | 15 | >1000 | 66 | — |
| Example D138 | 12 | 96 | >1000 | 500 | — |
| Example D139 | 12 | 159 | >1000 | 282 | — |
| Example D140 | 8.6 | 83 | >1000 | 226 | — |
| Example D141 | 9 | 106 | >1000 | 262 | — |
| Example D142 | 37 | 144 | >1000 | 193 | — |
| Example D143 | 26 | 132 | >1000 | 304 | — |
| Example D144 | 32 | 172 | >1000 | 260 | — |
| Example D145 | 31 | 123 | >1000 | 775 | — |
| Example D146 | 24 | 149 | >1000 | 270 | — |
| Example D147 | 26 | 85 | >1000 | 401 | — |
| Example D148 | 15 | 34 | >1000 | 414 | — |
| Example D149 | 18 | 94 | >1000 | 170 | — |
| Example D150 | 33 | 136 | >1000 | 435 | — |
| Example D151 | 76 | >200 | >200 | >200 | — |
| Example D152 | 21 | 95 | >400 | 265 | — |
| Example D153 | 30 | 150 | >400 | >400 | — |
| Example D154 | 7.8 | 59 | >400 | 226 | — |
| Example D155 | 29 | 120 | >400 | >400 | — |
| Example D156 | 24 | 29 | >400 | 217 | — |
| Example D157 | 39 | >400 | >400 | >400 | — |
| Example D158 | 150 | >400 | >400 | >400 | — |
| Example D159 | 313 | >400 | >400 | >400 | — |
| Example D160 | 244 | 341 | >400 | >400 | — |
| Example D161 | 85 | 276 | >400 | >400 | — |
| Example D162 | 10 | 71 | >400 | >400 | — |
| Example D163 | 190 | >400 | >400 | >400 | — |
| Example D164 | 39 | 75 | >400 | >400 | — |
| Example D165 | 52 | 208 | >400 | >400 | — |
| Example D166 | 14 | 58 | >400 | >400 | — |
| Example D167 | 57 | 244 | >400 | >400 | — |
| Example D168 | 34 | 255 | >400 | >400 | — |
| Example D169 | 39 | 235 | >400 | >400 | — |
| Example D170 | 23 | 130 | >400 | >400 | — |
| Example D171 | 117 | 244 | >400 | >400 | — |
| Example D172 | 130 | >400 | >400 | >400 | — |
| Example D173 | 100 | >400 | >400 | >400 | — |
| Example D174 | 160 | >400 | >400 | >400 | — |
| Example D175 | 150 | >400 | >400 | >400 | — |
| Example D176 | 124 | 208 | >400 | >400 | — |
| Example D177 | 150 | 265 | >400 | >400 | — |
| Example D178 | 265 | >400 | >400 | >400 | — |
| Example D179 | 226 | >400 | >400 | >400 | — |
| Example D180 | 255 | >400 | >400 | >400 | — |
| Example D181 | 115 | 313 | >400 | >400 | — |
| Example D182 | 68 | 180 | >400 | >400 | — |
| Example D183 | 12 | 22 | 64 | 166 | — |
| Example D184 | 0.9 | 2.8 | 21 | 1.8 | — |
| Example D185 | 108 | 49 | 196 | 742 | — |
| Example D186 | 53 | 40 | 162 | 792 | — |
| Example D187 | 200 | 185 | 130 | >1000 | — |
| Example D188 | 32 | 32 | 79 | >1000 | — |
| Example D189 | 7.6 | 0.5 | 7.3 | 5.2 | — |
| Example D190 | 24 | 0.9 | 3 | 3.5 | — |
| Example D191 | 34 | 1.4 | 5.7 | 8.9 | — |
| Example D192 | 4.7 | 9.8 | 104 | 13 | — |
| Example D193 | 1.4 | 8.3 | 32 | 6.1 | — |
| Example D194 | 5.8 | 46 | 144 | 23 | — |
| Example D195 | 18 | 54 | 355 | 31 | — |
| Example D196 | 11 | 6.4 | 57 | 31 | — |
| Example D197 | 16 | 9 | 44 | 34 | — |
| Example D198 | 5.7 | 10 | 69 | 27 | — |
| Example D199 | 5.7 | 8 | 65 | 21 | — |
| Example D200 | 8.1 | 9.3 | 34 | 12 | — |
| Example D201 | 19 | 10 | 29 | 35 | — |
| Example D202 | 22 | 12 | 65 | 30 | — |
| Example D203 | 32 | 13 | 85 | 70 | — |

TABLE D1-continued

| Example Number | JAK1 IC$_{50}$ (nM) | JAK2 IC$_{50}$ (nM) | JAK3 IC$_{50}$ (nM) | TYK2 IC$_{50}$ (nM) | ALK IC$_{50}$ (nM) |
|---|---|---|---|---|---|
| Example D204 | 7.2 | 12 | 101 | 12 | — |
| Example D205 | 7.1 | 15 | 107 | 25 | — |
| Example D206 | 9.2 | 14 | 147 | 13 | — |
| Example D207 | 9.4 | 5.4 | 109 | 56 | — |
| Example D208 | 18 | 15 | 64 | 82 | — |
| Example D209 | 65 | 462 | | | — |
| Example D210 | 1 | 14 | | | — |
| Example D211 | 4.2 | 160 | | | — |
| Example D212 | 64 | >1000 | | | — |
| Example D213 | 11 | 999 | | | — |
| Example D214 | 12 | >1000 | | | — |
| Example D215 | 13 | 44 | >400 | 276 | — |
| Example D216 | 23 | 276 | >400 | 300 | — |
| Example D217 | 53 | 103 | >400 | >400:255 | — |
| Example D218 | 13 | 64 | >400 | 46 | — |
| Example D219 | 14 | 49 | >400 | 38 | — |
| Example D220 | 14 | 40 | >400 | 38 | — |
| Example D221 | 20 | 70 | >400 | 59 | — |
| Example D222 | 21 | 111 | >400 | 90 | — |
| Example D223 | >400 | 106 | >400 | >400 | — |
| Example D224 | 300 | 126 | >400 | >400 | — |
| Example D225 | 180 | >400 | >400 | >400 | — |
| Example D226 | 255 | >400 | >400 | >400 | — |
| Example D227 | 72 | 148 | >400 | >400 | — |
| Example D228 | >400 | 371 | >400 | >400 | — |
| Example D229 | 153 | 235 | >400 | >400 | — |
| Example D230 | 25 | 47 | >400 | >400 | — |
| Example D231 | 52 | 217 | >400 | >400 | — |
| Example D232 | 32 | 160 | >400 | >400 | — |
| Example D233 | 100 | >400 | >400 | >400 | — |
| Example D234 | 41 | 160 | >400 | >400 | — |
| Example D235 | 64 | >400 | >400 | >400 | — |
| Example D236 | 90 | 288 | >400 | >400 | — |
| Example D237 | 29 | 180 | >400 | >400 | — |
| Example D238 | 41 | >400 | >400 | >400 | — |
| Example D239 | 101 | 208 | >400 | >400 | — |
| Example D240 | 255 | >400 | >400 | >400 | — |
| Example D241 | 41 | 180 | >400 | >400 | — |
| Example D242 | 46 | 159 | >400 | >400 | — |
| Example D243 | 60 | 300 | >400 | 326 | — |
| Example D244 | 80 | 358 | >400 | >400 | — |
| Example D245 | 75 | >400 | >400 | >400 | — |
| Example D246 | 30 | 226 | >400 | >400 | — |
| Example D247 | 82 | >400 | >400 | >400 | — |
| Example D248 | 59 | >400 | >400 | >400 | — |
| Example D249 | 71 | >400 | >400 | >400 | — |
| Example D250 | 43 | 49 | >400 | >400 | — |
| Example D251 | 18 | 17 | >400 | >400 | — |
| Example D252 | 65 | 244 | >400 | >400 | — |
| Example D253 | 35 | 67 | >400 | >400 | — |
| Example D254 | 8.1 | 49 | >400 | 356 | — |
| Example D255 | 90 | 226 | >400 | >400 | — |
| Example D256 | 150 | 217 | >400 | >400 | — |
| Example D257 | 63 | 112 | >400 | >400 | — |
| Example D258 | 70 | 113 | >400 | >400 | — |
| Example D259 | 42 | 37 | >400 | >400 | — |
| Example D260 | 15 | 22 | >400 | 288 | — |
| Example D261 | 31 | 106 | >400 | >400 | — |
| Example D262 | 150 | >400 | >400 | >400 | — |
| Example D263 | 80 | 180 | >400 | >400 | — |
| Example D264 | 6.1 | 22 | >400 | 300 | — |
| Example D265 | 34 | 235 | >400 | >400 | — |
| Example D266 | 31 | 21 | >400 | >400 | — |
| Example D267 | 84 | 300 | >400 | >400 | — |
| Example D268 | 15 | 36 | >400 | 49 | — |
| Example D269 | 29 | 226 | >400 | >400 | — |
| Example D270 | 23 | 80 | >400 | 265 | — |
| Example D271 | 75 | >400 | >400 | >400 | — |
| Example D272 | 38 | 288 | >400 | >400 | — | a. when the experiment limit is set as "a" and the IC$_{50}$ measurement of the example compound exceeds the limit, then the IC$_{50}$ data is shown as ">a"
b. "—" designates that the IC$_{50}$ is not available due to no measurement Various modifications of the invention, in addition to those described herein, will be apparent to those skilled in the art from the foregoing description. Such modifications are also intended to fall within the scope of the appended claims. Each reference cited in the present application is herein incorporated by reference in its entirety.

What is claimed is:
1. A compound of Formula I:

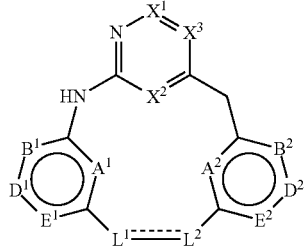

or pharmaceutically acceptable salt thereof or quaternary ammonium salt thereof, wherein:
===== represents a single bond or a double bond;
$X^1$ is $CR^1$;
$X^2$ is N;
$X^3$ is $CR^3$;
Y is $NR^4$;
$A^1$ and $A^2$ are each, independently, selected from $CR^2$, N, $NR^6$, O, and S;
$B^1, B^2, E^1$, and $E^2$ are each, independently, selected from $CR^5$, N, $NR^6$, O, and S;
$D^1$ and $D^2$ are each, independently, selected from a bond, $CR^5$, N, $NR^6$, O, and S;
wherein the ring containing $A^1$, $B^1$, $D^1$, and $E^1$ is a 6-membered aromatic ring selected from pyridine and wherein the ring containing $A^2$, $B^2$, $D^2$, and $E^2$ is a 6-membered aromatic ring;
$L^1$ and $L^2$ are each, independently selected from a bond, $-(CR^7R^8)_n-$, $-O-(CR^7R^8)_m-CR^{10}=$, $-S-(CR^7R^8)_m-CR^{10}=$, $-(CR^7R^8)_m-CR^{10}=$, $-(CR^7R^8)_m-NR^9-$, $-(CR^7R^8)_m-N=$, $-(CR^7R^8)_m-O-$, $-(CR^7R^8)_m-S-$, $-(CR^7R^8)_m-S(O)-$, $-(CR^7R^8)_m-S(O)_2-$, $-(CR^7R^8)_m-C(O)-$, $-C(O)NR^9-$, $-(CR^7R^8)_m-C(O)O-$, $-(CR^7R^8)_m-NR^9C(O)NR^9-$, $-(CR^7R^8)_m-OC(O)NR^9-$, $-(CR^7R^8)_m-NR^9C(O)O-$, $-(CR^7R^8)_m-NR^9-S(O)_2NR^9-$, $-(CR^7R^8)_m-S(O)NR^9-$, and $-(CR^7R^8)_m-S(O)_2NR^9-$;
wherein at least one of $L^1$ and $L^2$ is other than a bond;
$R^1$ and $R^3$ are each, independently, selected from H, halo, $C_{1-6}$ alkyl, $C_{2-6}$ alkenyl, $C_{2-6}$ alkynyl, $C_{1-6}$ haloalkyl, CN, $NO_2$, $SF_5$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^g)NR^{c2}R^{d2}$, $NR^{c2}C(=NR^g)NR^{c2}R^{d2}$, $NR^{c2}S(O)_2NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

each $R^2$ is, independently, selected from H, halo, $C_{1-6}$ alkyl, $C_{2-6}$ alkenyl, $C_{2-6}$ alkynyl, $C_{1-6}$ haloalkyl, CN, $NO_2$, $SF_5$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^g)NR^{c2}R^{d2}$, $NR^{c2}C(=NR^g)NR^{c2}R^{d2}$, $NR^{c2}S(O)_2NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

each $R^5$ is, independently, H, $Cy^1$, halo, $C_{1-6}$ alkyl, $C_{2-6}$ alkenyl, $C_{2-6}$ alkynyl, $C_{1-6}$ haloalkyl, arylalkyl, heteroarylalkyl, cycloalkylalkyl, heterocycloalkylalkyl, halosulfanyl, CN, $NO_2$, $SF_5$, $OR^{a1}$, $SR^{a1}$, $C(O)R^{b1}$, $C(O)NR^{c1}R^{d1}$, $C(S)R^{b1}$, $C(S)NR^{c1}R^{d1}$, $C(O)OR^{a1}$, $OC(O)R^{b1}$, —$W^1$-$Q^1$-$Y^1$-$Z^1$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(S)R^{b1}$, $NR^{c1}C(S)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, $P(R^{f1})_2$, $P(OR^{e1})_2$, $P(O)R^{e1}R^{f1}$, or $P(O)OR^{e1}OR^{f1}$, wherein each of said $C_{1-6}$ alkyl, $C_{2-6}$ alkenyl, $C_{2-6}$ alkynyl, $C_{1-6}$ haloalkyl, arylalkyl, heteroarylalkyl, cycloalkylalkyl, or heterocycloalkylalkyl, is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $Cy^1$, halosulfanyl, CN, $NO_2$, $SF_5$, $OR^{a1}$, $SR^{a1}$, $C(O)R^{b1}$, $C(O)NR^{c1}R^{d1}$, $C(S)R^{b1}$, $C(S)NR^{c1}R^{d1}$, $C(O)OR^{a1}$, $OC(O)R^{b1}$, -$W^1$-$Q^1$-$Y^1$-$Z^1$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(S)R^{b1}$, $NR^{c1}C(S)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)NR^{c1}R^{d1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, $P(R^{f1})_2$, $P(OR^{e1})_2$, $P(O)R^{e1}R^{f1}$, and $P(O)OR^{e1}OR^{f1}$; or two adjacent $R^5$ on the same ring can link to form a fused cycloalkyl or fused heterocycloalkyl group, each optionally substituted by 1, 2, or 3 substituents independently selected from halo, $C_{1-6}$ alkyl, $C_{2-6}$ alkenyl, $C_{2-6}$ alkynyl, $C_{1-6}$ haloalkyl, arylalkyl, heteroarylalkyl, cycloalkylalkyl, heterocycloalkylalkyl, halosulfanyl, $Cy^1$, CN, $NO_2$, $OR^{a1}$, $SR^{a1}$, $C(O)R^{b1}$, $C(O)NR^{c1}R^{d1}$, $SF_5$, $C(S)R^{b1}$, $C(S)NR^{c1}R^{d1}$, $C(O)OR^{a1}$, $OC(O)R^{b1}$, -$W^1$-$Q^1$-$Y^1$-$Z^1$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(S)R^{b1}$, $NR^{c1}C(S)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)NR^{c1}R^{d1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, $P(R^{f1})_2$, $P(OR^{e1})_2$, $P(O)R^{e1}R^{f1}$, and $P(O)OR^{e1}OR^{f1}$, wherein each of said $C_{1-6}$ alkyl, $C_{2-6}$ alkenyl, $C_{2-6}$ alkynyl, $C_{1-6}$ haloalkyl, arylalkyl, heteroarylalkyl, cycloalkylalkyl, or heterocycloalkylalkyl, is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $Cy^1$, -$W^1$-$Q^1$-$Y^1$-$Z^1$, halosulfanyl, CN, $NO_2$, $SF_5$, OR $SR^{a1}$, $C(O)R^{b1}$, $C(O)NR^{c1}R^{d1}$, $C(O)OR^{a1}$, $OC(O)R^{b1}$, $OCH_2C(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)NR^{c1}R^{d1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, $P(R^{f1})_2$, $P(OR^{e1})_2$, $P(O)R^{e1}R^{f1}$, and $P(O)OR^{e1}OR^{f1}$;

$R^4$ and $R^6$ are each, independently, selected from H, $Cy^2$, $C_{1-6}$ alkyl, $C_{2-6}$ alkenyl, $C_{2-6}$ alkynyl, $C_{1-6}$ haloalkyl, arylalkyl, heteroarylalkyl, cycloalkylalkyl, heterocycloalkylalkyl, -$W^2$-$X^2$-$Y^2$-$Z^2$, $C(O)R^{b1}$, $C(O)NR^{c1}R^{d1}$, $C(O)OR^{a1}$, $C(=NR^g)NR^{c1}R^{d1}$, $S(O)R^{b1}$, $S(O)NR^{c1}R^{d1}$, $S(O)_2R^{b1}$, $S(O)_2NR^{c1}R^{d1}$, $P(R^{f1})_2$, $P(OR^{e1})_2$, $P(O)R^{e1}R^{f1}$, and $P(O)OR^{e1}OR^{f1}$, wherein each of said $C_{1-6}$ alkyl, $C_{2-6}$ alkenyl, $C_{2-6}$ alkynyl, $C_{1-6}$ haloalkyl, arylalkyl, heteroarylalkyl, cycloalkylalkyl, or heterocycloalkylalkyl is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $Cy^2$, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, -$W^2$-$Q^2$-$Y^2$-$Z^2$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, $P(R^{f1})_2$, $P(OR^{e1})_2$, $P(O)R^{e1}R^{f1}$, and $P(O)OR^{e1}OR^{f1}$;

$R^7$, $R^8$, and $R^{10}$ are each, independently, selected from H, $Cy^3$, halo, $C_{1-6}$ alkyl, $C_{2-6}$ alkenyl, $C_{2-6}$ alkynyl, $C_{1-6}$ haloalkyl, arylalkyl, heteroarylalkyl, cycloalkylalkyl, heterocycloalkylalkyl, -$W^3$-$Q^3$-$Y^3$-$Z^3$, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, $P(R^{f1})_2$, $P(OR^{e1})_2$, $P(O)R^{e1}R^{f1}$, and $P(O)OR^{e1}OR^{f1}$, wherein each of said $C_{1-6}$ alkyl, $C_{2-6}$ alkenyl, $C_{2-6}$ alkynyl, $C_{1-6}$ haloalkyl, arylalkyl, heteroarylalkyl, cycloalkylalkyl, or heterocycloalkylalkyl is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $Cy^3$, -$W^3$-$Q^3$-$Y^3$-$Z^3$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, $P(R^{f1})_2$, $P(OR^{e1})_2$, $P(O)R^{e1}R^{f1}$, and $P(O)OR^{e1}OR^{f1}$;

each $R^9$ is, independently, H, $Cy^4$, $C_{1-6}$ alkyl, $C_{2-6}$ alkenyl, $C_{2-6}$ alkynyl, $C_{1-6}$ haloalkyl, arylalkyl, heteroarylalkyl, cycloalkylalkyl, heterocycloalkylalkyl, -$W^4$-$Q^4$-$Y^4$-$Z^4$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^g)NR^{c1}R^{d1}$, $S(O)R^{b1}$, $S(O)NR^{c1}R^{d1}$, $S(O)_2R^{b1}$, $S(O)_2NR^{c1}R^{d1}$, $P(R^{f1})_2$, $P(OR^{e1})_2$, $P(O)R^{e1}R^{f1}$, or $P(O)OR^{e1}OR^{f1}$, wherein each of said $C_{1-6}$ alkyl, $C_{2-6}$ alkenyl, $C_{2-6}$ alkynyl, $C_{1-6}$ haloalkyl, arylalkyl, heteroarylalkyl, cycloalkylalkyl, or heterocycloalkylalkyl is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $Cy^4$, -$W^4$-$Q^4$-$Y^4$-$Z^4$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, $P(R^{f1})_2$, $P(OR^{e1})_2$, $P(O)R^{e1}R^{f1}$, and $P(O)OR^{e1}OR^{f1}$;

$R^{11a}$, $R^{11b}$, $R^{12a}$, $R^{12b}$, and $R^{13}$ are each, independently, selected from H, $Cy^3$, halo, $C_{1-6}$ alkyl, $C_{2-6}$ alkenyl, $C_{2-6}$ alkynyl, $C_{1-6}$ haloalkyl, arylalkyl, heteroarylalkyl, cycloalkylalkyl, heterocycloalkylalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, $P(R^{f1})_2$, $P(OR^{e1})_2$, $P(O)R^{e1}R^{f1}$, and $P(O)OR^{e1}OR^{f1}$, wherein each of said $C_{1-6}$ alkyl, $C_{2-6}$ alkenyl, $C_{2-6}$ alkynyl, $C_{1-6}$ haloalkyl, arylalkyl, heteroarylalkyl, cycloalkylalkyl, or heterocycloalkylalkyl is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, NO$_2$, OR$^{a1}$, SR$^{a1}$, SF$_5$, C(O)R$^{b1}$, C(O)NR$^{c1}$R$^{d1}$, C(O)OR$^{a1}$, OC(O)R$^{b1}$, Cy$^3$, -W$^3$-Q$^3$-Y$^3$-Z$^3$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, C(=NR$^g$)NR$^{c1}$R$^{d1}$, NR$^{c1}$C(=NR$^g$)NR$^{c1}$R$^{d1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, S(O)$_2$NR$^{c1}$R$^{d1}$, P(R$^{f1}$)$_2$, P(OR$^{e1}$)$_2$, P(O)R$^{e1}$R$^{f1}$, and P(O)OR$^{e1}$OR$^{f1}$;

R' and R" are each, independently, selected from H, halo, C$_{1-4}$ alkyl, C$_{2-4}$ alkenyl, C$_{2-4}$ alkynyl, C$_{1-4}$ haloalkyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, C(=NR$^g$)NR$^{c2}$R$^{d2}$, NR$^{c2}$C(=NR$^g$)NR$^{c2}$R$^{d2}$, NR$^{c1}$S(O)$_2$NR$^{c1}$R$^{d1}$, S(O)R$^{b2}$, S(O)NR$^{c2}$R$^{d2}$, S(O)$_2$R$^{b2}$, NR$^{c2}$S(O)$_2$R$^{b2}$, and S(O)$_2$NR$^{c2}$R$^{d2}$;

W$^1$, W$^2$, W$^3$, W$^4$, and W$^5$ are each, independently, selected from absent, W$^6$, C$_{1-6}$ alkylenyl, C$_{2-6}$ alkenylenyl, C$_{2-6}$ alkynylenyl, (CR$^{11a}$R$^{11b}$)$_{p1}$O(CR$^{11a}$R$^{11b}$)$_{p2}$, (CR$^{11a}$R$^{11b}$)$_{p1}$S(CR$^{11a}$R$^{11b}$)$_{p2}$, (CR$^{11a}$R$^{11b}$)$_{p1}$NR$^e$(CR$^{11a}$R$^{11b}$)$_{p2}$, (CR$^{11a}$R$^{11b}$)$_{p1}$C(O)(CR$^{11a}$R$^{11b}$)$_{p2}$, (CR$^{11a}$R$^{11b}$)$_{p1}$C(S)(CR$^{11a}$R$^{11b}$)$_{p2}$, (CR$^{11a}$R$^{11b}$)$_{p1}$C(O)O(CR$^{11a}$R$^{11b}$)$_{p2}$, (CR$^{11a}$R$^{11b}$)$_{p1}$C(O)NR$^e$(CR$^{11a}$R$^{11b}$)$_{p2}$, (CR$^{11a}$R$^{11b}$)$_{p1}$C(S)NR$^e$(CR$^{11a}$R$^{11b}$)$_{p2}$, (CR$^{11a}$R$^{11b}$)$_{p1}$S(O)(CR$^{11a}$R$^{11b}$)$_{p2}$, (CR$^{11a}$R$^{11b}$)$_{p1}$S(O)$_2$(CR$^{11a}$R$^{11b}$)$_{p2}$, (CR$^{11a}$R$^{11b}$)$_{p1}$S(O)NR$^e$(CR$^{11a}$R$^{11b}$)$_{p2}$, (CR$^{11a}$R$^{11b}$)$_{p1}$S(O)$_2$NR$^e$(CR$^{11a}$R$^{11b}$)$_{p2}$, (CR$^{11a}$R$^{11b}$)$_{p1}$NR$^e$C(O)NR$^f$(CR$^{11a}$R$^{11b}$)$_{p2}$, (CR$^{11a}$R$^{11b}$)$_{p1}$NR$^e$C(S)NR$^f$(CR$^{11a}$R$^{11b}$)$_{p2}$, (CR$^{11a}$R$^{11b}$)$_{p1}$NR$^e$S(O)$_2$NR$^f$(CR$^{11a}$R$^{11b}$)$_{p2}$, (CR$^{11a}$R$^{11b}$)$_{p1}$C(=NR$^g$)NR$^e$(CR$^{11a}$R$^{11b}$)$_{p2}$, (C$^{11a}$R$^{11b}$)$_{p1}$NR$^e$C(=NR$^g$)NR$^f$(CR$^{11a}$R$^{11b}$)$_{p2}$, O(CR$^{11a}$R$^{11b}$)$_{q1}$C(O), S(CR$^{11a}$R$^{11b}$)$_{q1}$ C(O), NR$^e$(CR$^{11a}$R$^{11b}$)$_{q1}$C(O), C(O)(CR$^{11a}$R$^{11b}$)$_{q1}$ C(O), NR$^e$(CR$^{11a}$R$^{11b}$)$_{q1}$NR$^f$, O(CR$^{11a}$R$^{11b}$)$_{q1}$ NR$^f$, and O(CR$^{11a}$R$^{11b}$)$_{q1}$O, wherein each of the C$_{1-6}$ alkylenyl, C$_{2-6}$ alkenylenyl and C$_{2-6}$ alkynylenyl is optionally substituted by 1, 2, or 3 substituents independently selected from halo, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$ R$^d$, NR$^c$C(O)OR$^a$, C(=NR$^g$)NR$^c$R$^d$, NR$^c$C(=NR$^g$)NR$^c$R$^d$, NR$^c$S(O)$_2$NR$^c$R$^d$, S(O)R$^b$, S(O)NR$^c$R$^d$, S(O)$_2$ R$^b$, NR$^c$S(O)$_2$R$^b$, and S(O)$_2$NR$^c$R$^d$;

each W$^6$ is independently selected from NR$^{e100}$C(O)NR$^{f100}$ and NR$^{e200}$C(O)CR$^{13}$R$^{f200}$, wherein R$^{e100}$ and R$^{f100}$ together with the intervening NC(O)N moiety to which they are attached form a 4-7 membered heterocycloalkyl group which is optionally substituted by 1, 2, or 3 substituents each independently selected from C$_{1-6}$ alkyl, C$_{1-6}$ haloalkyl, C$_{2-6}$ alkenyl, C$_{2-6}$ alkynyl, halo, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, C(=NR$^g$)NR$^c$R$^d$, NR$^c$C(=NR$^g$)NR$^c$R$^d$, NR$^c$S(O)$_2$NR$^c$R$^d$, S(O)R$^b$, S(O)NR$^c$R$^d$, S(O)$_2$R$^b$, NR$^c$S(O)$_2$ R$^b$, and S(O)$_2$NR$^c$R$^d$, and wherein R$^{e200}$ and R$^{f200}$ together with the intervening NC(O)CR$^{13}$ moiety to which they are attached form a 4-7 membered heterocycloalkyl group which is optionally substituted by 1, 2, or 3 substituents each independently selected from C$_{1-6}$ alkyl, C$_{1-6}$ haloalkyl, C$_{2-6}$ alkenyl, C$_{2-6}$ alkynyl, halo, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, C(=NR$^g$)NR$^c$R$^d$, NR$^c$C(=NR$^g$)NR$^c$R$^d$, NR$^c$S(O)$_2$NR$^c$R$^d$, S(O)R$^b$, S(O)NR$^c$R$^d$, S(O)$_2$R$^b$, NR$^c$S(O)$_2$ R$^b$, and S(O)$_2$NR$^c$R$^d$;

Q$^1$, Q$^2$, Q$^3$, Q$^4$, and Q$^5$ are each, independently, selected from aryl, cycloalkyl, heteroaryl, heterocycloalkyl, arylalkyl, heteroarylalkyl, cycloalkylalkyl, and heterocycloalkylalkyl, each optionally substituted by 1, 2, 3, 4, or 5 substituents independently selected from C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, heterocycloalkylalkyl, halo, CN, NO$_2$, OR$^a$, SR$^a$, SF$_5$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, C(=NR$^g$)NR$^c$R$^d$, NR$^c$C(=NR$^g$)NR$^c$R$^d$, NR$^c$S(O)$_2$NR$^c$R$^d$, S(O)R$^b$, S(O)NR$^c$R$^d$, S(O)$_2$R$^b$, NR$^c$S(O)$_2$R$^b$, and S(O)$_2$NR$^c$R$^d$;

Y$^1$, Y$^2$, Y$^3$, Y$^4$, and Y$^5$ are each, independently, selected from absent, C$_{1-6}$ alkylenyl, C$_{2-6}$ alkenylenyl, C$_{2-6}$ alkynylenyl, (CR$^{12a}$R$^{12b}$)$_{p3}$O(CR$^{12a}$R$^{12b}$)$_{p4}$, (CR$^{12a}$R$^{12b}$)$_{p3}$S(CR$^{12a}$R$^{12b}$)$_{p4}$, (CR$^{12a}$R$^{12b}$)$_{p3}$NR$^e$(CR$^{12a}$R$^{12b}$)$_{p4}$, (CR$^{12a}$R$^{12b}$)$_{p3}$C(O)(CR$^{12a}$R$^{12b}$)$_{p4}$, (CR$^{12a}$R$^{12b}$)$_{p3}$C(S)(CR$^{12a}$R$^{12b}$)$_{p4}$, (CR$^{12a}$R$^{12b}$)$_{p3}$C(O)O(CR$^{12a}$R$^{12b}$)$_{p4}$, (CR$^{12a}$R$^{12b}$)$_{p3}$C(O)NR$^e$(CR$^{12a}$R$^{12b}$)$_{p4}$, (CR$^{12a}$R$^{12b}$)$_{p3}$C(S)NR$^e$(CR$^{12a}$R$^{12b}$)$_{p4}$, (CR$^{12a}$R$^{12b}$)$_{p3}$S(O)(CR$^{12a}$R$^{12b}$)$_{p4}$, (CR$^{12a}$R$^{12b}$)$_{p3}$ S(O)$_2$(CR$^{12a}$R$^{12b}$)$_{p4}$, (CR$^{12a}$R$^{12b}$)$_{p3}$S(O)NR$^e$(CR$^{12a}$R$^{12b}$)$_{p4}$, (CR$^{12a}$R$^{12b}$)$_{p3}$S(O)$_2$NR$^e$(CR$^{12a}$R$^{12b}$)$_{p4}$, (CR$^{12a}$R$^{12b}$)$_{p3}$NR$^e$C(O)NR$^f$(CR$^{12a}$R$^{12b}$)$_{p4}$, (CR$^{12a}$R$^{12b}$)$_{p3}$NR$^e$C(S)NR$^f$(CR$^{12a}$R$^{12b}$)$_{p4}$, (CR$^{12a}$R$^{12b}$)$_{p3}$NR$^e$S(O)$_2$NR$^f$(CR$^{12a}$R$^{12b}$)$_{p4}$, (CR$^{12a}$R$^{12b}$)$_{p3}$C(=NR$^g$)NR$^e$(CR$^{12a}$R$^{12b}$)$_{p4}$, (CR$^{12a}$R$^{12b}$)$_{p3}$NR$^e$C(=NR$^g$)NR$^f$(CR$^{12a}$R$^{12b}$)$_{p4}$, O(CR$^{12a}$R$^{12b}$)$_{q2}$C(O), S(CR$^{12a}$R$^{12b}$)$_{q2}$ C(O), NR$^e$(CR$^{12a}$R$^{12b}$)$_{q2}$C(O), NR$^e$ (CR$^{12a}$R$^{12b}$)$_{q2}$ NR$^f$, O(CR$^{12a}$R$^{12b}$)$_{q2}$NR$^f$, and O(CR$^{12a}$R$^{12b}$)$_{q2}$O, wherein each of the C$_{1-6}$ alkylenyl, C$_{2-6}$ alkenylenyl and C$_{2-6}$ alkynylenyl is optionally substituted by 1, 2 or 3 substituents independently selected from C$_{1-6}$ alkyl, C$_{1-6}$ haloalkyl, C$_{2-6}$ alkenyl, C$_{2-6}$ alkynyl, halo, CN, NO$_2$, OR$^a$, SR$^a$, SF$_5$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, C(=NR$^g$)NR$^c$R$^d$, NR$^c$C(=NR$^g$)NR$^c$R$^d$, NR$^c$S(O)$_2$NR$^c$R$^d$, S(O)R$^b$, S(O)NR$^c$R$^d$, S(O)$_2$R$^b$, NR$^c$S(O)$_2$R$^b$, and S(O)$_2$NR$^c$R$^d$;

Z$^1$, Z$^2$, Z$^3$, Z$^4$, and Z$^5$ are each, independently, selected from H, halo, CN, NO$_2$, OH, C$_{1-6}$ alkoxy, C$_{1-6}$ haloalkoxy, amino, C$_{1-6}$ alkylamino, C$_{2-8}$ dialkylamino, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of the C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted by 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, aryl, cycloalkyl, heteroaryl, heterocycloalkyl, CN, NO$_2$, OR$^a$, SR$^a$, SF$_5$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, NR$^c$S(O)$_2$R$^b$, NR$^c$S(O)$_2$NR$^c$R$^d$; S(O)R$^b$, S(O)NR$^c$R$^d$, S(O)$_2$R$^b$, and S(O)$_2$NR$^c$R$^d$;

Cy$^1$, Cy$^2$, Cy$^3$, and Cy$^4$ are each, independently, selected from aryl, cycloalkyl, heteroaryl, and heterocycloalkyl, each optionally substituted by 1, 2, 3, 4, or 5 substituents independently selected from halo, C$_{1-6}$ alkyl, C$_{2-6}$ alkenyl, C$_{2-6}$ alkynyl, aryl, cycloalkyl, heteroaryl, heterocycloalkyl, $SF_5$, $Cy^5$, -$L^{b1}$-$Cy^5$, -$W^5$-$Q^5$-$Y^5$-$Z^5$, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$;

$Cy^5$ and $Cy^6$ are each, independently, selected from aryl, cycloalkyl, heteroaryl, and heterocycloalkyl, each optionally substituted by 1, 2, 3, 4, or 5 substituents independently selected from halo, $C_{1-6}$ alkyl, $C_{2-6}$ alkenyl, $C_{2-6}$ alkynyl, aryl, cycloalkyl, heteroaryl, heterocycloalkyl, $C_{1-6}$ haloalkyl, arylalkyl, heteroarylalkyl, cycloalkylalkyl, heterocycloalkylalkyl, halosulfanyl, CN, $NO_2$, $OR^{a2}$, $SR^{a2}$, $SF_5$, $C(O)R^{b2}$, $C(O)NR^{c2}R^{d2}$, $C(S)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^g)NR^{c2}R^{d2}$, $NR^{c2}C(=NR^g)NR^{c2}R^{d2}$, $NR^{c2}S(O)_2NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

$L^{b1}$ and $L^{b2}$ are each, independently, selected from $C_{1-4}$ alkylenyl, O, S, C(O), C(S), $C(O)NR^{c2}$, $C(S)NR^{c2}$, C(O)O, $OC(O)NR^{c2}$, $NR^{c2}$, $NR^{c2}C(O)NR^{d2}$, $NR^{c2}C(S)NR^{d2}$, $C(=NR^g)NR^{c2}$, $NR^{c2}C(=NR^g)NR^{d2}$, $NR^{c2}S(O)_2NR^{d2}$, S(O), $S(O)NR^{c2}$, $S(O)_2$, and $S(O)_2NR^{c2}$, wherein said $C_{1-4}$ alkylenyl is optionally substituted by 1, 2, 3, 4, 5, 6, 7, or 8 substituents each independently selected from halo, CN, $C_{1-6}$ alkyl, $C_{1-6}$ haloalkyl, OH, $C_{1-6}$ alkoxy, $C_{1-6}$ haloalkoxy, $NH_2$, $NH(C_{1-4}$ alkyl), and $N(C_{1-4}$ alkyl$)_2$;

$R^{a1}$, $R^{b1}$, $R^{c1}$, and $R^{d1}$ are each, independently, selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted with 1, 2, 3, 4, or 5 substituents independently selected from $C_{1-6}$ alkyl, halo, CN, $Cy^6$, -$L^{b2}$-$Cy^6$, $OR^{a2}$, $SR^{a2}$, $SF_5$, $C(O)R^{b2}$, $C(O)NR^{c2}R^{d2}$, $C(S)R^{b2}$, $C(S)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(S)R^{b2}$, $NR^{c2}C(S)NR^{c2}R^{d2}$, $NR^{c2}C(O)OR^{a2}$, $C(=NR^g)NR^{c2}R^{d2}$, $NR^{c2}C(=NR^g)NR^{c2}R^{d2}$, $NR^{c2}S(O)_2NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

or $R^{c1}$ and $R^{d1}$ together with the N atom to which they are attached form a 4-, 5-, 6- or 7-membered heterocycloalkyl group or heteroaryl group, each optionally substituted with 1, 2, or 3 substituents independently selected from $C_{1-6}$ alkyl, $C_{1-6}$ haloalkyl, halo, CN, $Cy^6$, -$L^{b2}$-$Cy^6$, $OR^{a2}$, $SR^{a2}$, $SF_5$, $C(O)R^{b2}$, $C(O)NR^{c2}R^{d2}$, $C(S)R^{b2}$, $C(S)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(S)R^{b2}$, $NR^{c2}C(S)NR^{c2}R^{d2}$, $NR^{c2}C(O)OR^{a2}$, $C(=NR^g)NR^{c2}R^{d2}$, $NR^{c2}C(=NR^g)NR^{c2}R^{d2}$, $NR^{c2}S(O)_2NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

each $R^{e1}$ is, independently, H, $C_{1-6}$ alkyl, $C_{1-6}$ haloalkyl, $C_{2-6}$ alkenyl, $(C_{1-6}$ alkoxy)-$C_{1-6}$ alkyl, $C_{2-6}$ alkynyl, aryl, cycloalkyl, heteroaryl, heterocycloalkyl, arylalkyl, cycloalkylalkyl, heteroarylalkyl, or heterocycloalkylalkyl;

each $R^{f1}$ is, independently, H, $C_{1-6}$ alkyl, $C_{1-6}$ haloalkyl, $C_{2-6}$ alkenyl, $C_{2-6}$ alkynyl, aryl, cycloalkyl, heteroaryl, or heterocycloalkyl;

$R^{a2}$, $R^{b2}$, $R^{c2}$, and $R^{d2}$ are each, independently, selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

or $R^{c2}$ and $R^{d2}$ together with the N atom to which they are attached form a 4-, 5-, 6- or 7-membered heterocycloalkyl group or heteroaryl group, each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

each $R^a$ is independently selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl and heterocycloalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl and heterocycloalkyl is optionally substituted with 1, 2, 3, 4, or 5 substituents each independently selected from OH, CN, amino, halo, $C_{1-6}$ alkyl, $C_{1-6}$ haloalkyl, $C_{1-6}$ alkoxy, $C_{1-6}$ haloalkyl, aryl, arylalkyl, heteroaryl, heteroarylalkyl, cycloalkyl, and heterocycloalkyl;

each $R^b$ is independently selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl and heterocycloalkylalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl and heterocycloalkylalkyl is optionally substituted with 1, 2, 3, 4, or 5 substituents each independently selected from OH, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl, and heterocycloalkyl;

$R^c$ and $R^d$ are independently selected from H, $C_{1-10}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein each of the $C_{1-10}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, and heterocycloalkylalkyl is optionally substituted with 1, 2, 3, 4, or 5 substituents each independently selected from OH, amino, halo, $C_{1-6}$ haloalkyl, $C_{1-6}$ haloalkyl, aryl, arylalkyl, heteroaryl, heteroarylalkyl, cycloalkyl, and heterocycloalkyl;

or $R^c$ and $R^d$ together with the N atom to which they are attached form a 4-, 5-, 6- or 7-membered heterocycloalkyl group that is optionally substituted with 1, 2, 3, 4, or 5 substituents each independently selected from OH, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl, and heterocycloalkyl; and $R^e$ and $R^f$ are each, independently, selected from H, $C_{1-10}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein each of the $C_{1-10}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl is optionally substituted by OH, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl, and heterocycloalkyl;

each $R^g$ is, independently, H, CN, or $NO_2$;
each p1 is, independently, 0, 1, or 2;
each p2 is, independently, 0, 1, or 2;
each p3 is, independently, 0, 1, or 2;
each p4 is, independently, 0, 1, or 2;
each q1 is, independently, 1 or 2;
each q2 is, independently, 1 or 2;
each n is, independently, 1, 2, or 3; and
each m is, independently, 0, 1, or 2.

2. The compound of claim 1, or pharmaceutically acceptable salt thereof or quaternary ammonium salt thereof, wherein $D^1$ is N.

3. The compound of claim 1, or pharmaceutically acceptable salt thereof or quaternary ammonium salt thereof, wherein $E^1$ is N.

4. The compound of claim 1, or pharmaceutically acceptable salt thereof or quaternary ammonium salt thereof, wherein $B^1$ is N.

5. The compound of claim 1, or pharmaceutically acceptable salt thereof or quaternary ammonium salt thereof, wherein the ring containing $A^2$, $B^2$, $D^2$, and $E^2$ is a 6-membered aromatic ring; $B^2$, $D^2$, and $E^2$ are each, independently, $CR^5$; and $A^2$ is $CR^2$.

6. The compound of claim 1, or pharmaceutically acceptable salt thereof or quaternary ammonium salt thereof, wherein Y is $NR^4$.

7. The compound of claim 1, or pharmaceutically acceptable salt thereof or quaternary ammonium salt thereof, wherein Y is NH.

8. The compound of claim 1, or pharmaceutically acceptable salt thereof or quaternary ammonium salt thereof, wherein $L^1$ and $L^2$ are each, independently, selected from a bond, $-(CR^7R^8)_n-$, $-O-(CR^7R^8)_m-CR^{10}=$, $-S-(CR^7R^8)_m-CR^{10}=$, $-(CR^7R^8)_m-CR^{10}=$, $-(CR^7R^8)_m-NR^9-$, $-(CR^7R^8)_m-O-$, $-(CR^7R^8)_m-S-$, $-(CR^7R^8)_m-S(O)-$, $-(CR^7R^8)_m-S(O)_2-$, $-(CR^7R^8)_m-C(O)-$, $-C(O)NR^9-$, $-(CR^7R^8)_m-C(O)O-$, $-(CR^7R^8)_m-NR^9C(O)NR^9-$, $-(CR^7R^8)_m-OC(O)NR^9-$, $-(CR^7R^8)_m-NR^9C(O)O-$, $-(CR^7R^8)_m-NR^9-S(O)_2NR^9-$, $-(CR^7R^8)_m-S(O)NR^9-$, and $-(CR^7R^8)_m-S(O)_2 NR^9-$.

9. The compound of claim 1, or pharmaceutically acceptable salt thereof or quaternary ammonium salt thereof, wherein $L^1$ and $L^2$ together form $-CR^{10}=CR^{10}-$, $-(CH_2)_2-$, $-(CH_2)-O-$, $-(CH_2)-S-$, $-(CH_2)-S(O)-$, $-(CH_2)-S(O)_2-$, $-(CH_2)-NR^9-$, $-C(O)-NR^9-$, $-S(O)_2-NR^9-$, $-S-S-$, $-(CH_2)_2-O-$, $-(CH_2)_2-S-$, $-(CH_2)_2-S(O)-$, $-(CH_2)_2-S(O)_2-$, $-(CH_2)_2-C(O)-$, $-(CH_2)_2-NR^9-$, $-(CH_2)-S(O)_2-NH-$, $-(CH_2)-NH-S(O)_2-$, $-(CH_2)-C(O)-NH-$, $-(CH_2)-NH-C(O)-$, $-(CH_2)-O-(CH_2)-$, $-(CH_2)-S-(CH_2)-$, $-(CH_2)-NR^9-(CH_2)-$, $-(CH_2)_3-NR^9-$, $-(CH_2)_2-S-(CH_2)-$, $-O-(CH_2)_2-O-$, $-O-(CH_2)_2-S-$, $-O-(CH_2)_2-S(O)-$, $-O-(CH_2)_2-S(O)_2-$, $-S-(CH_2)_2-S-$, $-NR^9-(CH_2)_2-S-$, or $-NR^9-C(O)-(CH_2)_2-$.

10. The compound of claim 1, or pharmaceutically acceptable salt thereof or quaternary ammonium salt thereof, wherein $L^1$ and $L^2$ together form $-CH=CH-$, $-(CH_2)_2-$, $-(CH_2)-O-$, $-(CH_2)-S-$, $-(CH_2)-S(O)-$, $-(CH_2)-S(O)_2-$, $-(CH_2)-NR^9-$, $-C(O)-NH-$, $-S(O)_2-NH-$, $-S-S-$, $-(CH_2)_2-O-$, $-(CH_2)_2-S-$, $-(CH_2)_2-S(O)-$, $-(CH_2)_2-S(O)_2-$, $-(CH_2)_2-C(O)-$, $-(CH_2)_2-NR^9-$, $-(CH_2)-S(O)_2-NH-$, $-(CH_2)-NH-S(O)_2-$, $-(CH_2)-C(O)-NH-$, $-(CH_2)-NH-C(O)-$, $-(CH_2)-O-(CH_2)-$, $-(CH_2)-S-(CH_2)-$, $-(CH_2)-NR^9-(CH_2)-$, $-(CH_2)_3-NR^9-$, $-(CH_2)_2-S-(CH_2)-$, $-O-(CH_2)_2-O-$, $-O-(CH_2)_2-S-$, $-O-(CH_2)_2-S(O)-$, $-O-(CH_2)_2-S(O)_2-$, $-S-(CH_2)_2-S-$, $-NR^9-(CH_2)_2-S-$, or $-NH-C(O)-(CH_2)_2-$, wherein each $R^9$ is independently selected from H, $C_{1-6}$ alkyl, and $C(O)R^{b1}$, and wherein $R^{b1}$ is selected from $C_{1-6}$ alkyl, aryl, and heteroaryl, each optionally substituted with 1, 2, or 3 substituents independently selected from halo, $C_{1-6}$ alkyl, and $C_{1-6}$ haloalkyl.

11. The compound of claim 1, or pharmaceutically acceptable salt thereof or quaternary ammonium salt thereof, wherein $L^1$ and $L^2$ together form $-(CH_2)_2-$.

12. The compound of claim 1, or pharmaceutically acceptable salt thereof or quaternary ammonium salt thereof, wherein one of $L^1$ and $L^2$ is selected from $-(CR^7R^8)_m-O-$, $-(CR^7R^8)_m-S-$, $-(CR^7R^8)_m-S(O)-$, and $-(CR^7R^8)_m-S(O)_2-$; and the other is selected from a bond, $-(CR^7R^8)_n-$, $-(CR^7R^8)_m-O-$, $-(CR^7R^8)_m-S-$, $-(CR^7R^8)_m-S(O)-$, and $-(CR^7R^8)_m-S(O)_2-$.

13. A compound of claim 1, or pharmaceutically acceptable salt thereof or quaternary ammonium salt thereof, wherein:

$L^1$ and $L^2$ together form $-(CR^7R^8)_{t1}-S-$, $-(CR^7R^8)_{t1}-O-$, $-(CR^7R^8)_{t1}-S(O)-$, $-(CR^7R^8)_{t1}-S(O)_2-$, $-S-(CR^7R^8)_{t2}-S-$, $-O-(CR^7R^8)_{t2}-S-$, $-O-(CR^7R^8)_{t2}-S(O)-$, $-O-(CR^7R^8)_{t2}-S(O)_2-$, $-S-S-$, $-(CR^7R^8)_{t3}-O-(CR^7R^8)_{t4}-$, $-(CR^7R^8)_{t3}-S-(CR^7R^8)_{t4}-$, $-(CR^7R^8)_{t3}-S(O)-(CR^7R^8)_{t4}-$, or $-(CR^7R^8)_{t3}-S(O)_2-(CR^7R^8)_{t4}-$;

t1 is 1, 2, or 3;
t2 is 1 or 2;
t3 is 1, 2, or 3; and
t4 is 1 or 2.

14. The compound of claim 1, or pharmaceutically acceptable salt thereof or quaternary ammonium salt thereof, wherein $L^1$ and $L^2$ together form $-(CH_2)-S-$, $-(CH_2)-S(O)-$, $-(CH_2)-S(O)_2-$, $-(CH_2)-O-$, $-(CH_2)_2-O-$, $-O-(CH_2)_2-O-$, $-O-(CH_2)_2-S-$, $-O-(CH_2)_2-S(O)-$, or $-O-(CH_2)_2-S(O)_2-$.

15. The compound of claim 1, or pharmaceutically acceptable salt thereof or quaternary ammonium salt thereof, wherein $R^1$ and $R^3$ are each, independently, selected from H, halo, $C_{1-3}$ alkyl, and $C_{1-3}$ haloalkyl.

16. The compound of claim 1, or pharmaceutically acceptable salt thereof or quaternary ammonium salt thereof, wherein $R^1$ is H and $R^3$ is selected from H, halo, $C_{1-3}$ alkyl, and $C_{1-3}$ haloalkyl.

17. The compound of claim 1, or pharmaceutically acceptable salt thereof or quaternary ammonium salt thereof, wherein $R^1$ is H and $R^3$ is selected from halo, $C_1$ alkyl, and $C_1$ haloalkyl.

18. The compound of claim 1, or pharmaceutically acceptable salt thereof or quaternary ammonium salt thereof, wherein $R^1$ is H and $R^3$ is selected from halo.

19. The compound of any one of claims 1, 2-4, 5, 6, 7 and 8-14, or pharmaceutically acceptable salt thereof or quaternary ammonium salt thereof, wherein $R^1$ is H and $R^3$ is Cl.

20. The compound of claim 1, or pharmaceutically acceptable salt thereof or quaternary ammonium salt thereof, wherein each $R^2$ is, independently, selected from H, F, Cl, $CH_3$, and $CF_3$.

21. The compound of claim 1, or pharmaceutically acceptable salt thereof or quaternary ammonium salt thereof, wherein each $R^2$ is H.

22. The compound of claim 1, or pharmaceutically acceptable salt thereof or quaternary ammonium salt thereof, wherein each $R^5$ is, independently, selected from H, halo, $C_{1-6}$ alkyl, $C_{1-6}$ haloalkyl, $Cy^1$, $-W^1-Q^1-Y^1-Z^1$, CN, $NO_2$, $SF_5$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $S(O)_2R^{b1}$, $NR^{c1}S(O)_2NR^{c1}R^{d1}$, $NR^{c1}S(O)_2R^{b1}$, and $S(O)_2NR^{c1}R^{d1}$, wherein each of said $C_{1-6}$ alkyl, $C_{2-6}$ alkenyl, $C_{2-6}$ alkynyl, or $C_{1-6}$ haloalkyl is optionally substituted by 1, 2, 3, 4, or 5 substituents each independently selected from halo, $C_{1-6}$ alkyl, $C_{2-6}$ alkenyl, $C_{2-6}$ alkynyl, $C_{1-6}$ haloalkyl, halosulfanyl, $Cy^1$, $-W^1-Q^1-Y^1-Z^1$, CN, $NO_2$, $SF_5$, $OR^{a1}$, $SR^{a2}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)_2NR^{c1}R^{d1}S(O)R^{b1}$, $S(O)NR^{c1}R^{d1}$ $S(O)_2R^{b1}$ $NR^{c1}S(O)_2R^{b1}$, $S(O)_2NR^{c1}R^{d1}$, $P(R^{f1})_2$, $P(OR^{e1})_2$, $P(O)R^{e1}R^{f1}$, and $P(O)OR^{e1}OR^{f1}$.

23. The compound of claim 1, or pharmaceutically acceptable salt thereof or quaternary ammonium salt thereof, wherein:

each $R^5$ is, independently, selected from H, halo, $C_{1-6}$ alkyl, $C_{2-6}$ alkenyl, $C_{2-6}$ alkynyl, $C_{1-6}$ haloalkyl, $Cy^1$, $-W^1-Q^1-Y^1-Z^1$, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)NR^{c1}R^{d1}$, $NR^{c1}S(O)_2NR^{c1}R^{d1}$, $S(O)_2R^{b1}$, $NR^{c1}S(O)_2R^{b1}$, and $S(O)_2NR^{c1}R^{d1}$, wherein each of said $C_{1-6}$ alkyl, $C_{2-6}$ alkenyl, $C_{2-6}$ alkynyl, or $C_{1-6}$ haloalkyl, is optionally substituted by 1, 2, 3, 4 or 5 substituents each independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $SF_5$, $OR^{a1}$, $SR^{a2}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$;

$R^{a1}$, $R^{b1}$, $R^{c1}$, and $R^{d1}$ are each, independently, selected from H, $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of said $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted with 1, 2, 3, 4, or 5 substituents independently selected from halo, $C_{1-4}$ alkyl, $C_{1-4}$ haloalkyl, $C_{1-4}$ hydroxylalkyl, $C_{1-4}$ cyanoalkyl, aryl, cycloalkyl, heteroaryl, heterocycloalkyl, CN, $NO_2$, OH, SH, $O(C_{1-4}$ alkyl), $O(C_{1-4}$ haloalkyl), O(aryl), O(arylalkyl), $S(C_{1-4}$ alkyl), $S(C_{1-4}$ haloalkyl), S(aryl), S(arylalkyl), amino, $C_{1-4}$ alkylamino, $C_{2-8}$ dialkylamino, $C(=O)H$, $C(=O)-(C_{1-4}$ alkyl), $C(=O)-(arylalkyl)$, $C(=O)NH_2$, $C(=O)NH(C_{1-4}$ alkyl), $C(=O)N(C_{1-4}$ alkyl)$_2$, $CO(=O)H$, $CO(=O)-(C_{1-4}$ alkyl), $CO(=O)-(arylalkyl)$, $OC(=O)H$, $OC(=O)-(C_{1-4}$ alkyl), $OC(=O)-(arylalkyl)$, $OC(=O)NH_2$, $OC(=O)NH(C_{1-4}$ alkyl), $OC(=O)NH-(arylalkyl)$, $OC(=O)N(C_{1-4}$ alkyl)$_2$, $NHC(=O)-(C_{1-4}$ alkyl), $NHC(=O)-(arylalkyl)$, $NHC(=O)-(C_{1-4}$ alkyl), $NHC(=O)O-(arylalkyl)$, $NHS(=O)_2-(C_{1-4}$ alkyl), $NHS(=O)_2-(arylalkyl)$, $NHS(=O)_2-NH(C_{1-4}$ alkyl), $NHS(=O)_2-N(C_{1-4}$ alkyl)$_2$, $NHS(=O)_2-NH(arylalkyl)$, $S(=O)_2-(C_{1-4}$ alkyl), $S(=O)_2-(arylalkyl)$, $S(=O)_2NH_2$, $S(=O)_2NH(C_{1-4}$ alkyl), and $S(=O)_2NH(arylalkyl)$;

or $R^{c1}$ and $R^{d1}$ together with the N atom to which they are attached form a 4-, 5-, 6- or 7-membered heterocycloalkyl group or heteroaryl group, each optionally substituted with 1, 2, or 3 substituents independently selected from halo, $C_{1-4}$ alkyl, $C_{1-4}$ haloalkyl, $C_{1-4}$ hydroxylalkyl, $C_{1-4}$ cyanoalkyl, aryl, cycloalkyl, heteroaryl, heterocycloalkyl, CN, $NO_2$, OH, SH, $O(C_{1-4}$ alkyl), $O(C_{1-4}$ haloalkyl), O(aryl), O(arylalkyl), $S(C_{1-4}$ alkyl), $S(C_{1-4}$ haloalkyl), S(aryl), S(arylalkyl), amino, $C_{1-4}$ alkylamino, $C_{2-8}$ dialkylamino, $C(=O)H$, $C(=O)-(C_{1-4}$ alkyl), $C(=O)-(arylalkyl)$, $C(=O)NH_2$, $C(=O)NH(C_{1-4}$ alkyl), $C(=O)N(C_{1-4}$ alkyl)$_2$, $C(=O)OH$, $CO(=O)-(C_{1-4}$ alkyl), $CO(=O)-(arylalkyl)$, $OC(=O)H$, $OC(=O)-(C_{1-4}$ alkyl), $OC(=O)-(arylalkyl)$, $OC(=O)NH_2$, $OC(=O)NH(C_{1-4}$ alkyl), $OC(=O)NH-(arylalkyl)$, $OC(=O)N(C_{1-4}$ alkyl)$_2$, $NHC(=O)-(C_{1-4}$ alkyl), $NHC(=O)O-(arylalkyl)$, $NHC(=O)-(C_{1-4}$ alkyl), $NHC(=O)O-(arylalkyl)$, $NHS(=O)_2-(C_{1-4}$ alkyl), $NHS(=O)_2-(arylalkyl)$, $NHS(=O)_2-NH(C_{1-4}$ alkyl), $NHS(=O)_2-N(C_{1-4}$ alkyl)$_2$, $NHS(=O)_2-NH(arylalkyl)$, $S(=O)_2-(C_{1-4}$ alkyl), $S(=O)_2-(arylalkyl)$, $S(=O)_2NH_2$, $S(=O)_2NH(C_{1-4}$ alkyl), and $S(=O)_2NH(arylalkyl)$.

24. The compound of any one of claims 1, 2-4, 5, 6, 7, 8-18, 20 and 21, or pharmaceutically acceptable salt thereof or quaternary ammonium salt thereof, wherein each $R^5$ is, independently, selected from H, halo, $C_{1-6}$ alkyl, $C_{1-6}$ haloalkyl, $Cy^1$, $-W^1-Q^1-Y^1-Z^1$, CN, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $S(O)_2R^{b1}$, $NR^{c1}S(O)_2NR^{c1}R^{d1}$, $NR^{c1}S(O)_2R^{b1}$, and $S(O)_2NR^{c1}R^{d1}$, wherein each of said $C_{1-6}$ alkyl, $C_{2-6}$ alkenyl, $C_{2-6}$ alkynyl, or $C_{1-6}$ haloalkyl is optionally substituted by 1, 2, 3, 4, or 5 substituents each independently selected from halo, $C_{1-6}$ alkyl, $C_{2-6}$ alkenyl, $C_{2-6}$ alkynyl, $C_{1-6}$ haloalkyl, halosulfanyl, $Cy^1$, $-W^1-Q^1-Y^1-Z^1$, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, and $S(O)_2 NR^{c1}R^{d1}$.

25. The compound of claim 1, or pharmaceutically acceptable salt thereof or quaternary ammonium salt thereof, wherein at least one $R^5$ is $Cy^1$.

26. The compound of claim 1, or pharmaceutically acceptable salt thereof or quaternary ammonium salt thereof, wherein:

at least one $R^5$ is $Cy^1$;

each $Cy^1$ is independently selected from aryl and heteroaryl, each optionally substituted with 1, 2, or 3 substituents independently selected from $C_{1-6}$ alkyl, $C(O)-O-(C_{1-4}$ alkyl), $S(O)_2-(C_{1-4}$ alkyl), and piperazinyl, wherein the piperazinyl is optionally substituted with 1 or 2 substituents independently selected from $C_{1-6}$ alkyl, arylalkyl, aryl, heteroaryl, $C(O)R^{b1}$, $S(O)_2 R^{b1}$, $C(O)NR^{c1}R^{d1}$, and $S(O)_2NR^{c1}R^{d1}$.

27. The compound of claim 1, or pharmaceutically acceptable salt thereof or quaternary ammonium salt thereof, wherein at least one $R^5$ is $-W^1-Q^1-Y^1-Z^1$.

28. The compound of claim 1, or pharmaceutically acceptable salt thereof or quaternary ammonium salt thereof, wherein at least one $R^5$ is $-Q^1-Y^1-Z^1$, $-(CH_2)-Q^1-Y^1-Z^1$, $-O(CR^{11a}R^{11b})_{q1}C(O)-Q^1-Y^1-Z^1$, $-O(CR^{11a}R^{11b})_{p2}-Q^1-Y^1-Z^1$, $-(CR^{11a}R^{11b})_{p1}C(O)NR^e(CR^{11a}R^{11b})_{p2}-Q^1-Y^1-Z^1$, $-(CR^{11a}R^{11b})_{p1}C(O)NR^e-Q^1-Y^1-Z^1$, $-NR^e(CR^{11a}R^{11b})_{p2}-Q^1-Y^1-Z^1$, $(CR^{11a}R^{11b})_{p2}NR^eC(O)-Q^1-Y^1-Z^1$, $-(CR^{11a}R^{11b})_{p1}NR^e-Q^1-Y^1-Z^1$, $-(CR^{11a}R^{11b})_{p1}O(CR^{11a}R^{11b})_{p2}-Q^1-Y^1-Z^1$, $-(CR^{11a}R^{11b})_{p1}S(CR^{11a}R^{11b})_{p2}-Q^1-Y^1-Z^1$, $-(CR^{11a}R^{11b})_{p1}S(O)(CR^{11a}R^{11b})_{p2}-Q^1-Y^1-Z^1$, $-(CR^{11a}R^{11b})_{p1}S(O)_2(CR^{11a}R^{11b})_{p2}-Q^1-Y^1-Z^1$, $-(CR^{11a}R^{11b})_{p1}NR^e(CR^{11a}R^{11b})_{p2}-Q^1-Y^1-Z^1$, $-NR^eS(O)(CR^{11a}R^{11b})_{p1}-Q^1-Y^1-Z^1$, $-S(O)NR^e(CR^{11a}R^{11b})_{p2}-Q^1-Y^1-Z^1$, $-NR^eS(O)_2(CR^{11a}R^{11b})_{p1}-Q^1-Y^1-Z^1$, $-S(O)_2NR^e(CR^{11a}R^{11b})_{p2}-Q^1-Y^1-Z^1$, $-NR^eC(O)(CR^{11a}R^{11b})_{p1}-Q^1-Y^1-Z^1$, $-C(O)NR^e(CR^{11a}R^{11b})_{p2}-Q^1-Y^1-Z^1$, or $-NR^eC(O)NR^f(CR^{11a}R^{11b})_{p2}-Q^1-Y^1-Z^1$.

29. The compound of claim 1, or pharmaceutically acceptable salt thereof or quaternary ammonium salt thereof, wherein at least one $R^5$ is $-(CR^{11a}R^{11b})_{p1}O(CR^{11a}R^{11b})_{p2}-Q^1-Y^1-Z^1$, $-(CR^{11a}R^{11b})_{p1}S(CR^{11a}R^{11b})_{p2}-Q^1-Y^1-Z^1$, $-(CR^{11a}R^{11b})_{p1}S(O)(CR^{11a}R^{11b})_{p2}-Q^1-Y^1-Z^1$, $-(CR^{11a}R^{11b})_{p1}S(O)_2(CR^{11a}R^{11b})_{p2}-Q^1-Y^1-Z^1$, $-(CR^{11a}R^{11b})_{p1}NR^e(CR^{11a}R^{11b})_{p2}-Q^1-Y^1-Z^1$, $-NR^eS(O)(CR^{11a}R^{11b})_{p1}-Q^1-Y^1-Z^1$, $-S(O)NR^3(CR^{11a}R^{11b})_{p2}-Q^1-Y^1-Z^1$, $-NR^eS(O)_2(CR^{11a}R^{11b})_{p1}-Q^1-Y^1-Z^1$, $-S(O)_2NR^e(CR^{11a}R^{11b})_{p2}-Q^1-Y^1-Z^1$, $-NR^eC(O)(CR^{11a}R^{11b})_{p1}-Q^1-Y^1-Z^1$, $-C(O)NR^e(CR^{11a}R^{11b})_{p2}-Q^1-Y^1-Z^1$, or $-NR^eC(O)NR^f(CR^{11a}R^{11b})_{p2}-Q^1-Y^1-Z^1$.

30. The compound of claim 1, or pharmaceutically acceptable salt thereof or quaternary ammonium salt thereof, wherein at least one $R^5$ is $-Q^1-Y^1-Z^1$, $-(CH_2)-Q^1-Y^1-Z^1$, $-O(CR^{11a}R^{11b})_{q1}C(O)-Q^1-Y^1-Z^1$, $-O(CR^{11a}R^{11b})_{p2}-Q^1-Y^1-Z^1$, $-(CR^{11a}R^{11b})_{p1}C(O)NR^e(CR^{11a}R^{11b})_{p2}-Q^1-Y^1-Z^1$, $-(CR^{11a}R^{11b})_{p1}C(O)NR^e-Q^1-Y^1-Z^1$, $-NR^e(CR^{11a}R^{11b})_{p2}-Q^1-Y^1-Z^1$, $(CR^{11a}R^{11b})_{p2}NR^eC(O)-Q^1-Y^1-Z^1$, $-(CR^{11a}R^{11b})_{p1}NR^e-Q^1-Y^1-Z^1$, $-(CR^{11a}R^{11b})_{p1}O(CR^{11a}R^{11b})_{p2}-Q^1-Y^1-Z^1$, $-(CR^{11a}R^{11b})_{p1}NR^e(CR^{11a}R^{11b})_{p2}-Q^1-Y^1-Z^1$, $-NR^eS(O)_2(CR^{11a}R^{11b})_{p1}-Q^1-Y^1-Z^1$, $-NR^eC(O)(CR^{11a}R^{11b})_{p1}-Q^1-Y^1-Z^1$, $-C(O)NR^e(CR^{11a}R^{11b})_{p2}-Q^1-Y^1-Z^1$, or $-NR^eC(O)NR^f(CR^{11a}R^{11b})_{p2}-Q^1-Y^1-Z^1$.

31. The compound of claim 27, or pharmaceutically acceptable salt thereof or quaternary ammonium salt thereof, wherein each $Q^1$ is independently selected from aryl, heteroaryl, cycloalkyl, and heterocycloalkyl, each optionally substituted by 1, 2, 3, 4, or 5 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^a$, $C(O)NR^cR^d$, amino, $C_{1-6}$ alkylamino and $C_{2-8}$ dialkylamino.

32. The compound of claim 27, or pharmaceutically acceptable salt thereof or quaternary ammonium salt thereof, wherein each $Q^1$ is independently selected from cycloalkyl and heterocycloalkyl, each optionally substituted by 1, 2, 3, 4, or 5 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^a$, $C(O)NR^cR^d$, amino, $C_{1-6}$ alkylamino and $C_{2-8}$ dialkylamino.

33. The compound of claim 27, or pharmaceutically acceptable salt thereof or quaternary ammonium salt thereof, wherein each $Q^1$ is independently selected from cyclopropyl, cyclobutyl, cyclopentyl, cyclohexyl, azetidinyl, pyrrolidinyl, piperidinyl, and piperazinyl, each optionally substituted by 1, 2, 3, 4, or 5 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^a$, $C(O)NR^cR^d$, amino, $C_{1-6}$ alkylamino and $C_{2-8}$ dialkylamino.

34. The compound of claim 1, or pharmaceutically acceptable salt thereof or quaternary ammonium salt thereof, wherein at least one $R^5$ is $-W^6-Q^1-Y^1-Z^1$.

35. The compound of claim 27, or pharmaceutically acceptable salt thereof or quaternary ammonium salt thereof, wherein each $Y^1$ is independently selected from absent, $(CH_2)$, $(CR^{12a}R^{12b})_{p3}O(CR^{12a}R^{12b})_{p4}$, $(CR^{12a}R^{12b})_{p3}S(CR^{12a}R^{12b})_{p4}$, $(CR^{12a}R^{12b})_{p3}NR^e(CR^{12a}R^{12b})_{p4}$, $(CR^{12a}R^{12b})_{p3}C(O)(CR^{12a}R^{12b})_{p4}$, $(CR^{12a}R^{12b})_3C(O)O(CR^{12a}R^{12b})_{p4}$, $C(S)NR^e$, $(CR^{12a}R^{12b})_{p3}C(O)NR^e(CR^{12a}R^{12b})_{p4}$, $(CR^{12a}R^{12b})_{p3}S(O)_2(CR^{12a}R^{12b})_{p4}$, $(CR^{12a}R^{12b})_{p3}S(O)_2NR^e(CR^{12a}R^{12b})_{p4}$, and $(CR^{12a}R^{12b})_{p3}NR^eC(O)NR^f(CR^{12a}R^{12b})_{p4}$.

36. The compound of claim 27, or pharmaceutically acceptable salt thereof or quaternary ammonium salt thereof, wherein each $Y^1$ is independently selected from absent, $(CR^{12a}R^{12b})_{p3}O(CR^{12a}R^{12b})_{p4}$, $(CR^{12a}R^{12b})_{p3}S(CR^{12a}R^{12b})_{p4}$, $(CR^{12a}R^{12b})_{p3}NR^e(CR^{12a}R^{12b})_{p4}$, $(CR^{12a}R^{12b})_{p3}C(O)(CR^{12a}R^{12b})_{p4}$, $(CR^{12a}R^{12b})_{p3}C(O)NR^e(CR^{12a}R^{12b})_{p4}$, $(CR^{12a}R^{12b})_{p3}S(O)_2(CR^{12a}R^{12b})_4$, $(CR^{12a}R^{12b})_{p3}S(O)_2NR^e(CR^{12a}R^{12b})_{p4}$, and $(CR^{12a}R^{12b})_{p3}NR^eC(O)NR^f(CR^{12a}R^{12b})_{p4}$.

37. The compound of claim 27, or pharmaceutically acceptable salt thereof or quaternary ammonium salt thereof, wherein each $Y^1$ is independently selected from absent, $(CH_2)$, $(CR^{12a}R^{12b})_{p3}C(O)(CR^{12a}R^{12b})_{p4}$, $(CR^{12a}R^{12b})_{p3}C(O)O(CR^{12a}R^{12b})_{p4}$, $C(S)NR^e$, $(CR^{12a}R^{12b})_{p3}C(O)NR^e(CR^{12a}R^{12b})_{p4}$, $(CR^{12a}R^{12b})_{p3}S(O)_2(CR^{12a}R^{12b})_{p4}$, and $(CR^{12a}R^{12b})_{p3}NR^eC(O)NR^f(CR^{12a}R^{12b})_{p4}$.

38. The compound of claim 27, or pharmaceutically acceptable salt thereof or quaternary ammonium salt thereof, wherein each $Z^1$ is independently selected from H, OH, CN, $C_{1-6}$ alkyl, aryl, cycloalkyl, heteroaryl, and heterocycloalkyl, wherein each of the $C_{1-6}$ alkyl, aryl, cycloalkyl, heteroaryl, and heterocycloalkyl is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $NR^cS(O)_2R^b$, $NR^cS(O)_2S(O)_2NR^cR^d$, $S(O)R^b$, $S(O)NR^cR^d$, $S(O)_2R^b$, and $S(O)_2NR^cR^d$.

39. The compound of claim 27, or pharmaceutically acceptable salt thereof or quaternary ammonium salt thereof, wherein each $Z^1$ is independently selected from aryl, cycloalkyl, heteroaryl and heterocycloalkyl, each optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $NR^cS(O)_2R^b$, $NR^cS(O)_2S(O)_2NR^cR^d$, $S(O)R^b$, $S(O)NR^cR^d$, $S(O)_2R^b$, and $S(O)_2NR^cR^d$.

40. The compound of claim 1, or pharmaceutically acceptable salt thereof or quaternary ammonium salt thereof, wherein $R^7$, $R^8$, and $R^{10}$ are each, independently, selected from H, $C_{1-4}$ alkyl, OH, $C_{1-6}$ alkoxy, $C_{1-6}$ haloalkoxy, and $C_{2-8}$ alkoxyalkoxy.

41. The compound of claim 1, or pharmaceutically acceptable salt thereof or quaternary ammonium salt thereof, wherein each n is, independently, 1 or 2.

42. The compound of claim 1, or pharmaceutically acceptable salt thereof or quaternary ammonium salt thereof, wherein each m is, independently, 0 or 1.

43. The compound of claim 1 or pharmaceutically acceptable salt thereof or quaternary ammonium salt thereof, wherein the compound is a compound of Formula IIIa, IIIb, IIIc, IIId, IIIe, IIIf, IIIg, IIIh, IVa, IVb, IVc, IVd, or Va:

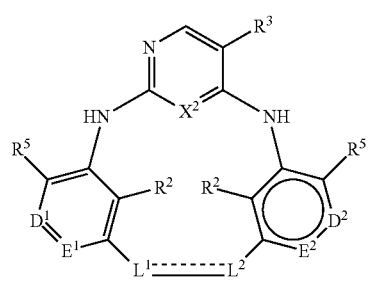

IIIa

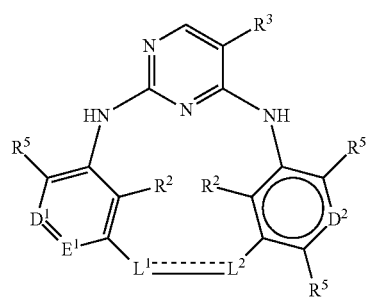

IIIb

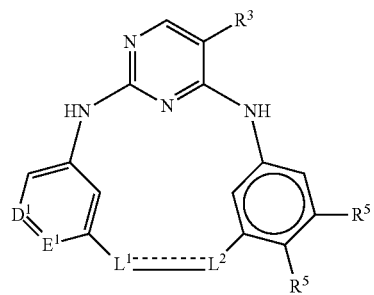

IIIc

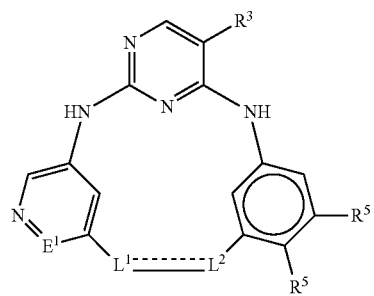

IIId

-continued

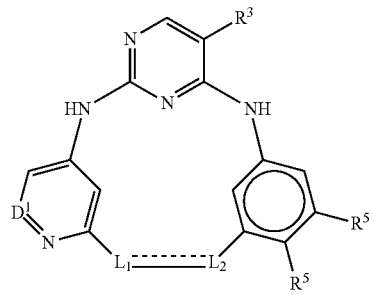

IIIe

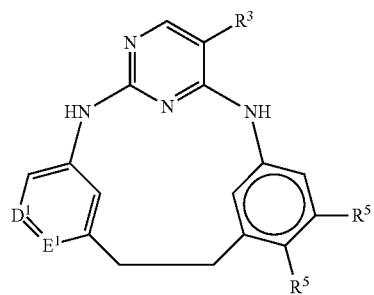

IIIf

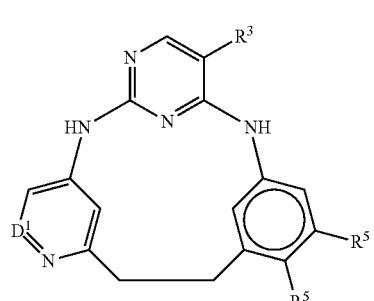

IIIg

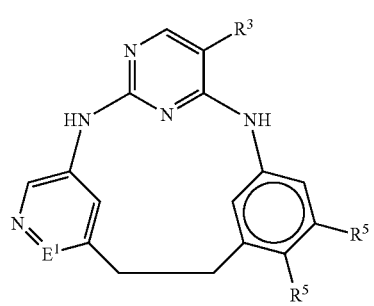

IIIh

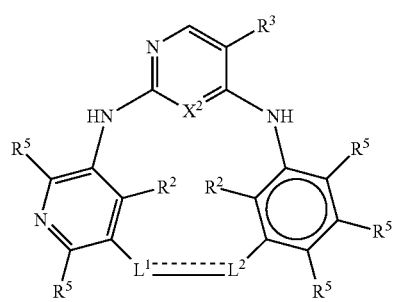

IVa

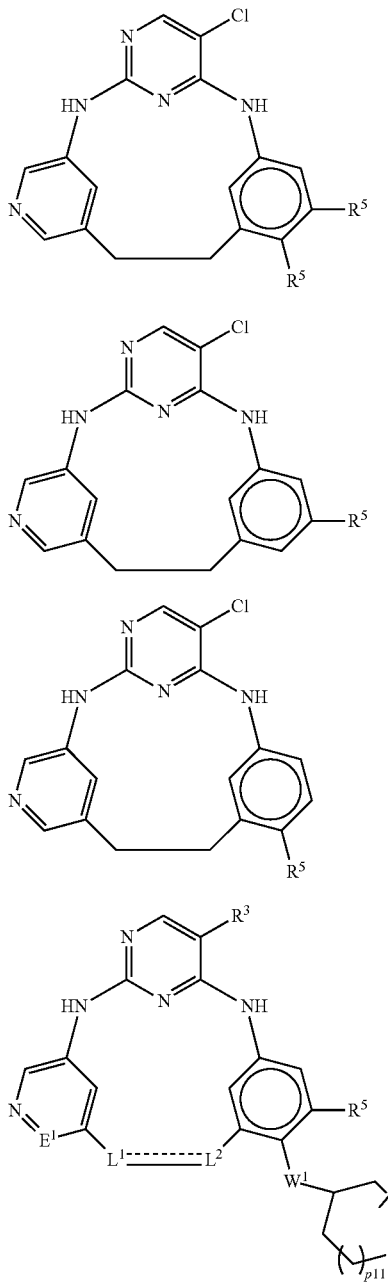

wherein:
D¹, E¹, D², and E² are each, independently, CR⁵ or N;
each $R^Q$ is independently selected from selected from $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, heterocycloalkylalkyl, halo, CN, NO₂, OR$^a$, SR$^a$, SF₅, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, C(=NR$^g$)NR$^c$R$^d$, NR$^c$C(=NR$^g$)NR$^c$R$^d$, NR$^c$S(O)₂NR$^c$R$^d$, S(O)R$^b$, S(O)NR$^c$R$^d$, S(O)₂R$^b$, NR$^c$S(O)₂R$^b$, and S(O)₂NR$^c$R$^d$;
p10 is 0 or 1;
p11 is 0 or 1; and
t10 is 0, 1, 2, 3, 4, or 5.

44. The compound of claim 43 or pharmaceutically acceptable salt thereof or quaternary ammonium salt thereof, wherein:
each R⁵ is, independently, H, Cy¹, halo, $C_{1-6}$ alkyl, $C_{2-6}$ alkenyl, $C_{2-6}$ alkynyl, $C_{1-6}$ haloalkyl, halosulfanyl, CN, NO₂, SF₅, OR$^{a1}$, SR$^{a1}$, C(O)R$^{b1}$, C(O)NR$^{c1}$R$^{d1}$, C(S)R$^{b1}$, C(S)NR$^{c1}$R$^{d1}$, C(O)OR$^{a1}$, OC(O)R$^{b1}$, OC(O)NR$^{c1}$R$^{d1}$, NR$^{c1}$R$^{d1}$C(O)R$^{b1}$, NR$^{c1}$C(O)NR$^{c1}$R$^{d1}$, NR$^{c1}$C(S)R$^{b1}$, NR$^{c1}$C(S)NR$^{c1}$R$^{d1}$, NR$^{c1}$C(O)R$^{a1}$, NR$^{c1}$S(O)₂NR$^{c1}$R$^{d1}$, S(O)R$^{b1}$, S(O)NR$^{c1}$R$^{d1}$, S(O)₂R$^{b1}$, NR$^{c1}$S(O)₂R$^{b1}$, S(O)₂NR$^{c1}$R$^{d1}$, or -W¹-Q¹-Y¹-Z¹;

or two adjacent R⁵ on the same ring can link to form a fused cycloalkyl or fused heterocycloalkyl group, each optionally substituted by 1, 2, or 3 substituents independently selected from halo, $C_{1-6}$ alkyl, $C_{2-6}$ alkenyl, $C_{2-6}$ alkynyl, $C_{1-6}$ haloalkyl, arylalkyl, heteroarylalkyl, cycloalkylalkyl, heterocycloalkylalkyl, Cy¹, CN, NO₂, OR$^{a1}$, SR$^{a1}$, C(O)R$^{b1}$, C(O)NR$^{c1}$R$^{d1}$, SF₅, C(S)R$^{b1}$, C(S)NR$^{c1}$R$^{d1}$, C(O)OR$^{a1}$, OC(O)R$^{b1}$, -W¹-Q¹-Y¹-Z¹, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(S)R$^{b1}$, NR$^{c1}$C(S)NR$^{c1}$R$^{d1}$, NR$^{c1}$C(O)OR$^{a1}$, C(=NR$^g$)NR$^{c1}$R$^{d1}$, NR$^{c1}$C(=NR$^g$)NR$^{c1}$R$^{d1}$, NR$^{c1}$S(O)NR$^{c1}$R$^{d1}$, S(O)R$^{b1}$, S(O)NR$^{c1}$R$^{d1}$, S(O)₂R$^{b1}$, NR$^{c1}$S(O)₂R$^{b1}$, and S(O)₂NR$^{c1}$R$^{d1}$, wherein each of the $C_{1-6}$ alkyl, $C_{2-6}$ alkenyl, $C_{2-6}$ alkynyl, $C_{1-6}$ haloalkyl, arylalkyl, heteroarylalkyl, cycloalkylalkyl, or heterocycloalkylalkyl is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, Cy¹, -W¹-Q¹-Y¹-Z¹, CN, NO₂, SF₅, OR$^{a1}$, SR$^{a2}$, C(O)R$^{b1}$, C(O)NR$^{c1}$R$^{d1}$, C(O)OR$^{a1}$, OC(O)R$^{b1}$, OCH₂C(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, C(=NR$^g$)NR$^{c1}$R$^{d1}$, NR$^{c1}$C(=NR$^g$)NR$^{c1}$R$^{d1}$, NR$^{c1}$S(O)NR$^{c1}$R$^{d1}$, S(O)R$^{b1}$, S(O)NR$^{c1}$R$^{d1}$, S(O)₂R$^{b1}$, NR$^{c1}$S(O)₂R$^{b1}$, and S(O)₂NR$^{c1}$R$^{d1}$.

45. The compound of claim 43 or pharmaceutically acceptable salt thereof or quaternary ammonium salt thereof, wherein at least one R⁵ is -W¹-Q¹-Y¹-Z¹.

46. The compound of claim 43, or pharmaceutically acceptable salt thereof or quaternary ammonium salt thereof, wherein at least one R⁵ is -Q¹-Y¹-Z¹, —(CH₂)-Q¹-Y¹-Z¹, —O(CR$^{11a}$R$^{11b}$)$_{q1}$C(O)-Q¹-Y¹-Z¹, —O(CR$^{11a}$R$^{11b}$)$_{p2}$-Q¹-Y¹-Z¹, —(CR$^{11a}$R$^{11b}$)$_{p1}$C(O)NR$^e$(CR$^{11a}$R$^{11b}$)$_{p2}$-Q¹-Y¹-Z¹, —(CR$^{11a}$R$^{11b}$)$_{p1}$C(O)NR$^e$-Q¹-Y¹-Z¹, —NR$^e$(CR$^{11a}$R$^{11b}$)$_{p2}$- Q¹-Y¹-Z¹, —(CR$^{11a}$R$^{11b}$)$_{p2}$NR$^e$C(O)-Q¹-Y¹-Z¹, —(CR$^{11a}$R$^{11b}$)$_{p1}$NR$^e$-Q¹-Y¹-Z¹, —(CR$^{11a}$R$^{11b}$)$_{p1}$O(CR$^{11a}$R$^{11b}$)$_{p2}$-Q¹-Y¹-Z¹, —(CR$^{11a}$R$^{11b}$)$_{p1}$NR$^e$(CR$^{11a}$R$^{11b}$)$_{p2}$- Q¹-Y¹-Z¹, —NR$^e$S(O)₂(CR$^{11a}$R$^{11b}$)$_{p1}$-Q¹-Y¹-Z¹, —NR$^e$C(O)(CR$^{11a}$R$^{11b}$)$_{p1}$-Q¹-Y¹-Z¹, —C(O)NR$^e$(CR$^{11a}$R$^{11b}$)$_{p2}$-Q¹-Y¹-Z¹, or —NR$^e$C(O)NR$^f$(CR$^{11a}$R$^{11b}$)$_{p2}$-Q¹-Y¹-Z¹.

47. The compound of claim 45, or pharmaceutically acceptable salt thereof or quaternary ammonium salt thereof, wherein each Q¹ is independently selected from aryl, heteroaryl, cycloalkyl, and heterocycloalkyl, each optionally substituted by 1, 2, 3, 4, or 5 substituents independently selected from halo, CN, NO₂, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, C(O)OR$^a$, C(O)NR$^c$R$^d$, amino, $C_{1-6}$ alkylamino and $C_{2-8}$ dialkylamino.

48. The compound of claim 45, or pharmaceutically acceptable salt thereof or quaternary ammonium salt thereof, wherein each Q¹ is independently selected from cycloalkyl and heterocycloalkyl, each optionally substituted by 1, 2, 3, 4, or 5 substituents independently selected from halo, CN, NO₂, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^a$, $C(O)NR^cR^d$, amino, $C_{1-6}$ alkylamino and $C_{2-8}$ dialkylamino.

49. The compound of claim 45, or pharmaceutically acceptable salt thereof or quaternary ammonium salt thereof, wherein each $Q^1$ is independently selected from cyclopropyl, cyclobutyl, cyclopentyl, cyclohexyl, azetidinyl, pyrrolidinyl, piperidinyl, and piperazinyl, each optionally substituted by 1, 2, 3, 4, or 5 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^a$, $C(O)NR^cR^d$, amino, $C_{1-6}$ alkylamino and $C_{2-8}$ dialkylamino.

50. The compound of claim 45, or pharmaceutically acceptable salt thereof or quaternary ammonium salt thereof, wherein each $Y^1$ is independently selected from absent, $(CH_2)$, $(CR^{12a}R^{12b})_{p3}C(O)(CR^{12a}R^{12b})_{p4}$, $(CR^{12a}R^{12b})_{p3}C(O)O(CR^{12a}R^{12b})_{p4}$, $(CR^{12a}R^{12b})_{p3}C(O)NR^e(CR^{12a}R^{12b})_{p4}$, $(CR^{12a}R^{12b})_{p3}S(O)_2(CR^{12a}R^{12b})_{p4}$, and $(CR^{12a}R^{12b})_{p3}NR^eC(O)NR^f(CR^{12a}R^{12b})_{p4}$.

51. The compound of claim 45, or pharmaceutically acceptable salt thereof or quaternary ammonium salt thereof, wherein each $Z^1$ is independently selected from H, OH, CN, $C_{1-6}$ alkyl, aryl, cycloalkyl, heteroaryl, and heterocycloalkyl, wherein each of the $C_{1-6}$ alkyl, aryl, cycloalkyl, heteroaryl, and heterocycloalkyl is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $NR^cS(O)_2R^b$, $NR^cS(O)_2S(O)_2NR^cR^d$, $S(O)R^b$, $S(O)NR^cR^d$, $S(O)_2R^b$, and $S(O)_2NR^cR^d$.

52. A compound selected from:
(14Z)-6-Chloro-2,4,8,22-tetraazatetracyclo[14.3.1.1(3,7).1(9,13)]docosa-1(20),3(22),4,6,9(21),10,12,14,16,18-decaene;
6-Chloro-2,4,8,22-tetraazatetracyclo[14.3.1.1(3,7).1(9,13)]docosa-1(20),3(22),4,6,9(21),10,12,16,18-nonaene;
2,4,8,22-Tetraazatetracyclo[14.3.1.1(3,7).1(9,13)]docosa-1(20),3(22),4,6,9(21),10,12,16,18-nonaene;
6-Chloro-2,4,8,23-tetraazatetracyclo[15.3.1.1(3,7).1(9,13)]tricosa-1(21),3(23),4,6,9(22),10,12,17,19-nonaene;
6-Chloro-2,4,8,23-tetraazatetracyclo[15.3.1.1(3,7).1(9,13)]tricosa-1(21),3(23),4,6,9(22),10,12,17,19-nonaen-16-one;
6-Chloro-19-methyl-17-morpholin-4-yl-2,4,8,22-tetraazatetracyclo[14.3.1.1(3,7).1(9,13)]docosa-1(20),3(22),4,6,9(21),10,12,16,18-nonaene;
6-Chloro-19-methyl-2,4,8,22-tetraazatetracyclo[14.3.1.1(3,7).1(9,13)]docosa-1(20),3(22),4,6,9(21),10,12,16,18-nonaene;
6-Chloro-10-(isopropylsulfonyl)-2,4,8,22-tetraazatetracyclo[14.3.1.1(3,7).1(9,13)]docosa-1(20),3(22),4,6,9(21),10,12,16,18-nonaene;
(14Z)-6-Methyl-2,4,8,22-tetraazatetracyclo[14.3.1.1(3,7).1(9,13)]docosa-1(20),3(22),4,6,9(21),10,12,14,16,18-decaene;
6-Methyl-2,4,8,22-tetraazatetracyclo[14.3.1.1(3,7).1(9,13)]docosa-1(20),3(22),4,6,9(21),10,12,16,18-nonaene;
Methyl 6-chloro-2,4,8,22-tetraazatetracyclo[14.3.1.1(3,7).1(9,13)]docosa-1(20),3(22),4,6,9(21),10,12,16,18-nonaene-11-carboxylate;
6-Bromo-2,4,8,22-tetraazatetracyclo[14.3.1.1(3,7).1(9,13)]docosa-1(20),3(22),4,6,9(21),10,12,16,18-nonaene;
6-Chloro-2,4,8,22-tetraazatetracyclo[14.3.1.1(3,7).1(9,13)]docosa-1(20),3(22),4,6,9(21),10,12,16,18-nonaene-11-carboxylic acid;
6-Chloro-N-(3-chloro-4-fluorophenyl)-2,4,8,22-tetraazatetracyclo[14.3.1.1(3,7).1(9,13)]docosa-1(20),3(22),4,6,9(21),10,12,16,18-nonaene-11-carboxamide;
6-Chloro-11-[(4-methylpiperazin-1-yl)carbonyl]-2,4,8,22-tetraazatetracyclo[14.3.1.1(3,7).1(9,13)]docosa-1(20),3(22),4,6,9(21),10,12,16,18-nonaene;
6-Chloro-N-(4-morpholin-4-ylphenyl)-2,4, 8,22-tetraazatetracyclo[14.3.1.1(3,7).1(9,13)]docosa-1(20),3(22),4,6,9(21),10,12,16,18-nonaene-11-carboxamide;
6-Chloro-N-[4-(2-hydroxyethyl)phenyl]-2,4,8,22-tetraazatetracyclo[14.3.1.1(3,7).1(9,13)]docosa-1(20),3(22),4,6,9(21),10,12,16,18-nonaene-11-carboxamide;
6-Chloro-N-(pyridin-4-ylmethyl)-2,4, 8,22-tetraazatetracyclo[14.3.1.1(3,7).1(9,13)]docosa-1(20),3(22),4,6,9(21),10,12,16,18-nonaene-11-carboxamide;
1-{[6-Chloro-2,4,8,22-tetraazatetracyclo[14.3.1.1(3,7).1(9,13)]docosa-1(20),3(22),4,6,9(21),10,12,16,18-nonaen-11-yl]carbonyl}piperidin-3-ol;
6-Chloro-N-(3-chlorophenyl)-2,4,8,22-tetraazatetracyclo[14.3.1.1(3,7).1(9,13)]docosa-1(20),3(22),4,6,9(21),10,12,16,18-nonaene-11-carboxamide;
6-Chloro-N-(2-chlorophenyl)-2,4,8,22-tetraazatetracyclo[14.3.1.1(3,7).1(9,13)]docosa-1(20),3(22),4,6,9(21),10,12,16,18-nonaene-11-carboxamide;
6-Chloro-N-(4-chlorophenyl)-2,4,8,22-tetraazatetracyclo[14.3.1.1(3,7).1(9,13)]docosa-1(20),3(22),4,6,9(21),10,12,16,18-nonaene-11-carboxamide;
N-(tert-Butyl)-6-chloro-2,4,8,22-tetraazatetracyclo[14.3.1.1(3,7).1(9,13)]docosa-1(20),3(22),4,6,9(21),10,12,16,18-nonaene-11-sulfonamide;
6-Bromo-N-(tert-butyl)-2,4,8,22-tetraazatetracyclo[14.3.1.1(3,7).1(9,13)]docosa-1(20),3(22),4,6,9(21),10,12,16,18-nonaene-11-sulfonamide;
6-Bromo-2,4,8,22-tetraazatetracyclo[14.3.1.1(3,7).1(9,13)]docosa-1(20),3(22),4,6,9(21),10,12,16,18-nonaene-11-sulfonamide;
6-Chloro-2,4,8,15,22-pentaazatetracyclo[14.3.1.1(3,7).1(9,13)]docosa-1(20),3(22),4,6,9(21),10,12,16,18-nonaen-14-one;
6-Chloro-16-thia-2,4,8,15,23-pentaazatetracyclo[15.3.1.1(3,7).1(9,13)]tricosa-1(21),3(23),4,6,9(22),10,12,17,19-nonaene 16,16-dioxide;
6-Chloro-2,4,8,15,23-pentaazatetracyclo[15.3.1.1(3,7).1(9,13)]tricosa-1(21),3(23),4,6,9(22),10,12,17,19-nonaen-14-one;
6-Chloro-2,4,8,15,23-pentaazatetracyclo[15.3.1.1(3,7).1(9,13)]tricosa-1(21),3(23),4,6,9(22),10,12,17,19-nonaen-16-one;
6-Chloro-15-thia-2,4,8,14,22-pentaazatetracyclo[14.3.1.1(3,7).1(9,13)]docosa-1(20),3(22),4,6,9(21),10,12,16,18-nonaene 15,15-dioxide;
6-Chloro-14-thia-2,4,8,15,22-pentaazatetracyclo[14.3.1.1(3,7).1(9,13)]docosa-1(20),3(22),4,6,9(21),10,12,16,18-nonaene 14,14-dioxide;
6-Chloro-15-thia-2,4,8,16,23-pentaazatetracyclo[15.3.1.1(3,7).1(9,13)]tricosa-1(21),3(23),4,6,9(22),10,12,17,19-nonaene 15,15-dioxide;
6-Chloro-15-thia-2,4,8,14,23-pentaazatetracyclo[15.3.1.1(3,7).1(9,13)]tricosa-1(21),3(23),4,6,9(22),10,12,17,19-nonaene 15,15-dioxide;

6-Chloro-2,4,8,14,23-pentaazatetracyclo[15.3.1.1(3,7).1(9,13)]tricosa-1(21),3(23),4,6,9(22),10,12,17,19-nonaen-15-one;
6-Chloro-14-thia-2,4,8,22-tetraazatetracyclo[14.3.1.1(3,7).1(9,13)]docosa-1(20),3 (22),4,6,9(21),10,12,16,18-nonaene;
6-Chloro-15-thia-2,4,8,22-tetraazatetracyclo[14.3.1.1(3,7).1(9,13)]docosa-1(20),3 (22),4,6,9(21),10,12,16,18-nonaene;
6-Chloro-15-thia-2,4,8,22-tetraazatetracyclo[14.3.1.1(3,7).1(9,13)]docosa-1(20),3(22),4,6,9(21),10,12,16,18-nonaene 15-oxide;
6-Chloro-15-thia-2,4,8,22-tetraazatetracyclo[14.3.1.1(3,7).1(9,13)]docosa-1(20),3(22),4,6,9(21),10,12,16,18-nonaene 15,15-dioxide;
6-Chloro-16-oxa-2,4,8,23-tetraazatetracyclo[15.3.1.1(3,7).1(9,13)]tricosa-1(21),3(23),4,6,9(22),10,12,17,19-nonaene;
6-Chloro-15-oxa-2,4,8,22-tetraazatetracyclo[14.3.1.1(3,7).1(9,13)]docosa-1(20),3 (22),4,6,9(21),10,12,16,18-nonaene;
6-Chloro-14-oxa-2,4,8,22-tetraazatetracyclo[14.3.1.1(3,7).1(9,13)]docosa-1(20),3 (22),4,6,9(21),10,12,16,18-nonaene;
6-Chloro-14-oxa-2,4,8,23-tetraazatetracyclo[15.3.1.1(3,7).1(9,13)]tricosa-1(21),3(23),4,6,9(22),10,12,17,19-nonaene;
6-Chloro-8-methyl-14-oxa-2,4,8,23-tetraazatetracyclo[15.3.1.1(3,7).1(9,13)]tricosa-1(21),3(23),4,6,9(22),10,12,17,19-nonaene;
6-Chloro-14,17-dioxa-2,4,8,24-tetraazatetracyclo[16.3.1.1(3,7).1(9,13)]tetracosa-1(22),3(24),4,6,9(23),10,12,18,20-nonaene;
6-Chloro-17-oxa-14-thia-2,4,8,24-tetraazatetracyclo[16.3.1.1(3,7).1(9,13)]tetracosa-1(22),3 (24),4,6,9(23),10,12,18,20-nonaene;
6-Chloro-14,15-dithia-2,4,8,22-tetraazatetracyclo[14.3.1.1(3,7).1(9,13)]docosa-1(20),3 (22),4,6,9(21),10,12,16,18-nonaene;
6-Chloro-17-oxa-14-thia-2,4,8,24-tetraazatetracyclo[16.3.1.1(3,7).1(9,13)]tetracosa-1(22),3(24),4,6,9(23),10,12,18,20-nonaene 14-oxide;
6-Chloro-17-oxa-14-thia-2,4,8,24-tetraazatetracyclo[16.3.1.1(3,7).1(9,13)]tetracosa-1(22),3(24),4,6,9(23),10,12,18,20-nonaene 14,14-dioxide;
6-Chloro-14-oxa-17-thia-2,4,8,24-tetraazatetracyclo[16.3.1.1(3,7).1(9,13)]tetracosa-1(22),3(24),4,6,9(23),10,12,18,20-nonaene; and
6-Chloro-2,4,8,14,22-pentaazatetracyclo[14.3.1.1(3,7).1(9,13)]docosa-1(20),3(22),4,6,9(21),10,12,16,18-nonaene,
or pharmaceutically acceptable salt thereof.

53. A compound selected from:
(14Z)-6-Chloro-2,4,8,22-tetraazatetracyclo[14.3.1.1(3,7).1(9,13)]docosa-1(20),3(22),4,6,9(21),10,12,14,16,18-decaene;
6-Chloro-2,4,8,22-tetraazatetracyclo[14.3.1.1(3,7).1(9,13)]docosa-1(20),3(22),4,6,9(21),10,12,16,18-nonaene;
2,4,8,22-Tetraazatetracyclo[14.3.1.1(3,7).1(9,13)]docosa-1(20),3(22),4,6,9(21),10,12,16,18-nonaene;
6-Chloro-2,4,8,23-tetraazatetracyclo[15.3.1.1(3,7).1(9,13)]tricosa-1(21),3(23),4,6,9(22),10,12,17,19-nonaene;
6-Chloro-2,4,8,23-tetraazatetracyclo[15.3.1.1(3,7).1(9,13)]tricosa-1(21),3(23),4,6,9(22),10,12,17,19-nonaen-16-one;
6-Chloro-19-methyl-17-morpholin-4-yl-2,4,8,22-tetraazatetracyclo[14.3.1.1(3,7).1(9,13)]docosa-1(20),3(22),4,6,9(21),10,12,16,18-nonaene;
6-Chloro-19-methyl-2,4,8,22-tetraazatetracyclo[14.3.1.1(3,7).1(9,13)]docosa-1(20),3(22),4,6,9(21),10,12,16,18-nonaene;
6-Chloro-10-(isopropylsulfonyl)-2,4,8,22-tetraazatetracyclo[14.3.1.1(3,7).1(9,13)]docosa-1(20),3(22),4,6,9(21),10,12,16,18-nonaene;
4-({[6-Chloro-2,4,8,22-tetraazatetracyclo[14.3.1.1(3,7).1(9,13)]docosa-1(20),3(22),4,6,9(21),10,12,16,18-nonaen-12-yl]oxy}acetyl)-N-(4-cyanophenyl)piperazine-1-carboxamide;
4-(6-Chloropyridin-3-yl)-4-({[6-chloro-2,4,8,22-tetraazatetracyclo[14.3.1.1(3,7).1(9,13)]docosa-1(20),3(22),4,6,9(21),10,12,16,18-nonaen-12-yl]oxy}acetyl)piperazine-1-carboxamide;
4-({[6-Chloro-2,4,8,22-tetraazatetracyclo[14.3.1.1(3,7).1(9,13)]docosa-1(20),3(22),4,6,9(21),10,12,16,18-nonaen-12-yl]oxy}acetyl)-N-(1-methyl-1H-indol-4-yl)piperazine-1-carboxamide;
12-[2-(4-Acetylpiperazin-1-yl)-2-oxoethoxy]-6-chloro-2,4,8,22-tetraazatetracyclo[14.3.1.1(3,7).1(9,13)]docosa-1(20),3(22),4,6,9(21),10,12,16,18-nonaene;
4-({[6-Chloro-2,4,8,22-tetraazatetracyclo[14.3.1.1(3,7).1(9,13)]docosa-1(20),3(22),4,6,9(21),10,12,16,18-nonaen-12-yl]oxy}acetyl)-N-phenylpiperazine-1-carboxamide;
6-Chloro-12-(cyclopentyloxy)-2,4,8,22-tetraazatetracyclo[14.3.1.1(3,7).1(9,13)]docosa-1(20),3(22),4,6,9(21),10,12,16,18-nonaene;
2-{[6-Chloro-2,4,8,22-tetraazatetracyclo[14.3.1.1(3,7).1(9,13)]docosa-1(20),3(22),4,6,9(21),10,12,16,18-nonaen-12-yl]oxy}acetamide;
2-{[6-Chloro-2,4,8,22-tetraazatetracyclo[14.3.1.1(3,7).1(9,13)]docosa-1(20),3(22),4,6,9(21),10,12,16,18-nonaen-12-yl]oxy}-N-phenylpropanamide;
tert-Butyl 4-({[6-chloro-2,4,8,22-tetraazatetracyclo[14.3.1.1(3,7).1(9,13)]docosa-1(20),3(22),4,6,9(21),10,12,16,18-nonaen-12-yl]oxy}acetyl)piperazine-1-carboxylate;
2-{[6-Chloro-2,4,8,22-tetraazatetracyclo[14.3.1.1(3,7).1(9,13)]docosa-1(20),3(22),4,6,9(21),10,12,16,18-nonaen-12-yl]oxy}-N-phenylacetamide;
N-Benzyl-4-(2-{[6-chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)piperidine-1-carboxamide;
12-[2-(4-Acetylpiperazin-1-yl)-2-oxoethoxy]-6-chloro-2,4,8,22-tetraazatetracyclo[14.3.1.1(3,7).1(9,13)]docosa-1(20),3(22),4,6,9(21),10,12,16,18-nonaene;
6-Chloro-11-methoxy-2,4,8,22-tetraazatetracyclo[14.3.1.1(3,7).1(9,13)]docosa-1(20),3(22),4,6,9(21),10,12,16,18-nonaene;
6-Chloro-2,4,8,22-tetraazatetracyclo[14.3.1.1(3,7).1(9,13)]docosa-1(20),3(22),4,6,9(21),10,12,16,18-nonaen-11-ol;
2-{[6-Chloro-2,4,8,22-tetraazatetracyclo[14.3.1.1(3,7).1(9,13)]docosa-1(20),3(22),4,6,9(21),10,12,16,18-nonaen-11-yl]oxy}acetyl)acetamide;
2-{[6-Chloro-2,4,8,22-tetraazatetracyclo[14.3.1.1(3,7).1(9,13)]docosa-1(20),3(22),4,6,9(21),10,12,16,18-nonaen-11-yl]oxy}-N-phenylacetamide;
6-Chloro-10-methoxy-2,4,8,22-tetraazatetracyclo[14.3.1.1(3,7).1(9,13)]docosa-1(20),3(22),4,6,9(21),10,12,16,18-nonaene;

6-Chloro-2,4,8,22-tetraazatetracyclo[14.3.1.1(3,7).1(9,13)]docosa-1(20),3(22),4,6,9(21),10,12,16,18-nonaen-10-ol;

tert-Butyl 4-({[6-chloro-2,4,8,22-tetraazatetracyclo[14.3.1.1(3,7).1(9,13)]docosa-1(20),3(22),4,6,9(21),10,12,16,18-nonaen-12-yl]amino}carbonyl)piperidine-1-carboxylate;

N-[6-Chloro-2,4,8,22-tetraazatetracyclo[14.3.1.1(3,7).1(9,13)]docosa-1(20),3(22),4,6,9(21),10,12,16,18-nonaen-12-yl]piperidine-4-carboxamide;

1-Acetyl-N-[6-chloro-2,4,8,22-tetraazatetracyclo[14.3.1.1(3,7).1(9,13)]docosa-1(20),3(22),4,6,9(21),10,12,16,18-nonaen-12-yl]piperidine-4-carboxamide;

1-Benzoyl-N-[6-chloro-2,4,8,22-tetraazatetracyclo[14.3.1.1(3,7).1(9,13)]docosa-1(20),3(22),4,6,9(21),10,12,16,18-nonaen-12-yl]piperidine-4-carboxamide;

1-(1,3-Benzodioxol-5-ylcarbonyl)-N-[6-chloro-2,4,8,22-tetraazatetracyclo[14.3.1.1(3,7).1(9,13)]docosa-1(20),3(22),4,6,9(21),10,12,16,18-nonaen-12-yl]piperidine-4-carboxamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-1-(2-furoyl)piperidine-4-carboxamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-1-(4-cyanobenzoyl)piperidine-4-carboxamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-1-[(3,5-dimethylisoxazol-4-yl)carbonyl]piperidine-4-carboxamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-1-(phenylacetyl)piperidine-4-carboxamide;

N(4)-[6-Chloro-2,4,8,22-tetraazatetracyclo[14.3.1.1(3,7).1(9,13)]docosa-1(20),3(22),4,6,9(21),10,12,16,18-nonaen-12-yl]-N(1)-phenylpiperidine-1,4-dicarboxamide;

N(4)-[6-Chloro-2,4,8,22-tetraazatetracyclo[14.3.1.1(3,7).1(9,13)]docosa-1(20),3(22),4,6,9(21),10,12,16,18-nonaen-12-yl]-N(1)-(4-cyanophenyl)piperidine-1,4-dicarboxamide;

N(4)-[6-Chloro-2,4,8,22-tetraazatetracyclo[14.3.1.1(3,7).1(9,13)]docosa-1(20),3(22),4,6,9(21),10,12,16,18-nonaen-12-yl]-N(1)-(3-methoxyphenyl)piperidine-1,4-dicarboxamide;

N(4)-[6-Chloro-2,4,8,22-tetraazatetracyclo[14.3.1.1(3,7).1(9,13)]docosa-1(20),3(22),4,6,9(21),10,12,16,18-nonaen-12-yl]-N(1)-[2-(methylthio)phenyl]piperidine-1,4-dicarboxamide;

N(1)-(6-Chloropyridin-3-yl)-N(4)-[6-chloro-2,4,8,22-tetraazatetracyclo[14.3.1.1(3,7).1(9,13)]docosa-1(20),3(22),4,6,9(21),10,12,16,18-nonaen-12-yl]piperidine-1,4-dicarboxamide;

N(4)-[6-Chloro-2,4,8,22-tetraazatetracyclo[14.3.1.1(3,7).1(9,13)]docosa-1(20),3(22),4,6,9(21),10,12,16,18-nonaen-12-yl]-N(1)-(1-methyl-1H-indol-4-yl)piperidine-1,4-dicarboxamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-1-(phenylsulfonyl)piperidine-4-carboxamide;

1-(Anilinocarbonothioyl)-N-[6-chloro-2,4,8,22-tetraazatetracyclo[14.3.1.1(3,7).1(9,13)]docosa-1(20),3(22),4,6,9(21),10,12,16,18-nonaen-12-yl]piperidine-4-carboxamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]piperidine-3-carboxamide;

(3R)—N-[6-chloro-2,4,8,22-tetraazatetracyclo[14.3.1.1(3,7).1(9,13)]docosa-1(20),3(22),4,6,9(21),10,12,16,18-nonaen-12-yl]pyrrolidine-3-carboxamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-piperidin-4-ylacetamide;

1-Acetyl-N-[6-chloro-2,4,8,22-tetraazatetracyclo[14.3.1.1(3,7).1(9,13)]docosa-1(20),3(22),4,6,9(21),10,12,16,18-nonaen-12-yl]piperidine-3-carboxamide;

1-Benzoyl-N-[6-chloro-2, 4, 8, 22-tetraazatetracyclo[14.3.1.1(3,7).1(9,13)]docosa-1(20),3(22),4,6,9(21),10,12,16,18-nonaen-12-yl]piperidine-3-carboxamide;

N(3)-[6-Chloro-2,4,8,22-tetraazatetracyclo[14.3.1.1(3,7).1(9,13)]docosa-1(20),3(22),4,6,9(21),10,12,16,18-nonaen-12-yl]-N(1)-ethylpiperidine-1,3-dicarboxamide;

N(3)-[6-Chloro-2,4,8,22-tetraazatetracyclo[14.3.1.1(3,7).1(9,13)]docosa-1(20),3(22),4,6,9(21),10,12,16,18-nonaen-12-yl]-N(1)-phenylpiperidine-1,3-dicarboxamide;

(3R)-1-Acetyl-N-[6-chloro-2,4,8,22-tetraazatetracyclo[14.3.1.1(3,7).1(9,13)]docosa-1(20),3(22),4,6,9(21),10,12,16,18-nonaen-12-yl]pyrrolidine-3-carboxamide;

(3R)-1-Benzoyl-N-[6-chloro-2, 4, 8, 22-tetraazatetracyclo[14.3.1.1(3,7).1(9,13)]docosa-1(20),3(22),4,6,9(21),10,12,16,18-nonaen-12-yl]pyrrolidine-3-carboxamide;

(3R)—N(3)-[6-Chloro-2,4,8,22-tetraazatetracyclo[14.3.1.1(3,7).1(9,13)]docosa-1(20),3(22),4,6,9(21),10,12,16,18-nonaen-12-yl]-N(1)-ethylpyrrolidine-1,3-dicarboxamide;

(3R)—N(3)-[6-Chloro-2,4,8,22-tetraazatetracyclo[14.3.1.1(3,7).1(9,13)]docosa-1(20),3(22),4,6,9(21),10,12,16,18-nonaen-12-yl]-N(1)-phenylpyrrolidine-1,3-dicarboxamide;

2-(1-Acetylpiperidin-4-yl)-N-[6-chloro-2,4,8,22-tetraazatetracyclo[14.3.1.1(3,7).1(9,13)]docosa-1(20),3(22),4,6,9(21),10,12,16,18-nonaen-12-yl]acetamide;

2-(1-Benzoylpiperidin-4-yl)-N-[6-chloro-2,4,8,22-tetraazatetracyclo[14.3.1.1(3,7).1(9,13)]docosa-1(20),3(22),4,6,9(21),10,12,16,18-nonaen-12-yl]acetamide;

4-(2-{[6-Chloro-2,4,8,22-tetraazatetracyclo[14.3.1.1(3,7). 1(9,13)]docosa-1(20),3(22),4,6,9(21),10,12,16,18-nonaen-12-yl]amino}-2-oxoethyl)-N-ethylpiperidine-1-carboxamide;

4-(2-{[6-Chloro-2,4,8,22-tetraazatetracyclo[14.3.1.1(3,7). 1(9,13)]docosa-1(20),3(22),4,6,9(21),10,12,16,18-nonaen-12-yl]amino}-2-oxoethyl)-N-phenylpiperidine-1-carboxamide;

N(4)-[6-Chloro-2,4,8,22-tetraazatetracyclo[14.3.1.1(3,7).1(9,13)]docosa-1(20),3(22),4,6,9(21),10,12,16,18-nonaen-12-yl]-N(1)-ethylpiperidine-1,4-dicarboxamide;

Ethyl ({[4-({[6-chloro-2,4,8,22-tetraazatetracyclo[14.3.1.1(3,7).1(9,13)]docosa-1(20),3(22),4,6,9(21),10,12,16,18-nonaen-12-yl]amino}carbonyl)piperidin-1-yl]carbonyl}amino)acetate;

N(4)-[6-Chloro-2,4,8,22-tetraazatetracyclo[14.3.1.1(3,7).1(9,13)]docosa-1(20),3(22),4,6,9(21),10,12,16,18-nonaen-12-yl]-N(1)-cyclopentylpiperidine-1,4-dicarboxamide;

N(3)-[6-Chloro-2,4,8,22-tetraazatetracyclo[14.3.1.1(3,7).1(9,13)]docosa-1(20),3(22),4,6,9(21),10,12,16,18-nonaen-12-yl]-N(1)-cyclopentylpiperidine-1,3-dicarboxamide;

(3R)—N(3)-[6-Chloro-2,4,8,22-tetraazatetracyclo[14.3.1.1(3,7).1(9,13)]docosa-1(20),3(22),4,6,9(21),10,12,16,18-nonaen-12-yl]-N(1)-cyclopentylpyrrolidine-1,3-dicarboxamide;

4-(2-{[6-Chloro-2,4,8,22-tetraazatetracyclo[14.3.1.1(3,7). 1(9,13)]docosa-1(20),3(22),4,6,9(21),10,12,16,18-nonaen-12-yl]amino}-2-oxoethyl)-N-cyclopentylpiperidine-1-carboxamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-cyanoacetamide;

2-[(Anilinocarbonyl)amino]-N-[6-chloro-2,4,8,22-tetraazatetracyclo[14.3.1.1(3,7).1(9,13)]docosa-1(20),3(22),4,6,9(21),10,12,16,18-nonaen-12-yl]acetamide;

3-[(Anilinocarbonyl)amino]-N-[6-chloro-2,4,8,22-tetraazatetracyclo[14.3.1.1(3,7).1(9,13)]docosa-1(20),3(22),4,6,9(21),10,12,16,18-nonaen-12-yl]propanamide;

(2S)-2-[(Anilinocarbonyl)amino]-N-[6-chloro-2,4,8,22-tetraazatetracyclo[14.3.1.1(3,7).1(9,13)]docosa-1(20),3(22),4,6,9(21),10,12,16,18-nonaen-12-yl]-3-hydroxypropanamide;

(2S)—N(2)-[6-Chloro-2,4,8,22-tetraazatetracyclo[14.3.1.1(3,7).1(9,13)]docosa-1(20),3(22),4,6,9(21),10,12,16,18-nonaen-12-yl]-N(1)-phenylpyrrolidine-1,2-dicarboxamide;

tert-Butyl 4-(2-{[6-chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)piperidine-1-carboxylate;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-piperidin-4-ylacetamide;

1-(Aminosulfonyl)-N-[6-chloro-2,4,8,22-tetraazatetracyclo[14.3.1.1(3,7).1(9,13)]docosa-1(20),3(22),4,6,9(21),10,12,16,18-nonaen-12-yl]piperidine-4-carboxamide;

1-(Aminosulfonyl)-N-[6-chloro-2,4,8,22-tetraazatetracyclo[14.3.1.1(3,7).1(9,13)]docosa-1(20),3(22),4,6,9(21),10,12,16,18-nonaen-12-yl]piperidine-3-carboxamide;

(3R)-1-(Aminosulfonyl)-N-[6-chloro-2,4,8,22-tetraazatetracyclo[14.3.1.1(3,7).1(9,13)]docosa-1(20),3(22),4,6,9(21),10,12,16,18-nonaen-12-yl]pyrrolidine-3-carboxamide;

2-[1-(Aminosulfonyl)piperidin-4-yl]-N-[6-chloro-2,4,8,22-tetraazatetracyclo[14.3.1.1(3,7).1(9,13)]docosa-1(20),3(22),4,6,9(21),10,12,16,18-nonaen-12-yl]acetamide;

2-(1-Acetylpiperidin-4-yl)-N-[6-chloro-2,4,8,18,22-pentaazatetracyclo[14.3.1.1(3,7).1(9,13)]docosa-1(20),3(22),4,6,9(21),10,12,16,18-nonaen-12-yl]acetamide; and 4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-phenylpiperidine-1-carboxamide, or pharmaceutically acceptable salts thereof or quaternary ammonium salt thereof.

54. A compound selected from:

2-[1-(Aminosulfonyl)piperidin-4-yl]-N-[6-chloro-2,4,8,18,22pentaazatetracyclo[14.3.1.1(3,7).1(9,13)]docosa-1(20),3(22),4,6,9(21),10,12,16,18-nonaen-12-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(methylsulfonyl)piperidin-4-yl]acetamide;

4-(2-{[6-Chloro-2,4,8,22-tetraazatetracyclo[14.3.1.1(3,7). 1(9,13)]docosa-1(20),3(22),4,6,9(21),10,12,16,18-nonaen-12-yl]amino}-2-oxoethyl)-N,N-dimethylpiperidine-1-carboxamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-{1-[(dimethylamino)sulfonyl]piperidin-4-yl}acetamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-[1-(isopropylsulfonyl)piperidin-4-yl]acetamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-[1-(ethylsulfonyl)piperidin-4-yl]acetamide;

4-(2-{[6-Chloro-2,4,8,22-tetraazatetracyclo[14.3.1.1(3,7).1(9,13)]docosa-1(20),3(22),4,6,9(21),10,12,16,18-nonaen-12-yl]amino}-2-oxoethyl)-N-isopropylpiperidine-1-carboxamide;

N-(tert-Butyl)-4-(2-{[6-chloro-2,4,8,22-tetraazatetracyclo[14.3.1.1(3,7).1(9,13)]docosa-1(20),3(22),4,6,9(21),10,12,16,18-nonaen-12-yl]amino}-2-oxoethyl)piperidine-1-carboxamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-{14(5-methylisoxazol-3-yl)carbonyl]piperidin-4-yl}acetamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-[1-(pyrazin-2-ylcarbonyl)piperidin-4-yl]acetamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-[1-(2,2-dimethylpropanoyl)piperidin-4-yl]acetamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-(1-isobutyrylpiperidin-4-yl)acetamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-(1-propionylpiperidin-4-yl)acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(methylsulfonyl)pyrrolidin-3-yl]acetamide;

3-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-phenylpyrrolidine-1-carboxamide;

3-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-methylpyrrolidine-1-carboxamide;

2-(1-Acetylpyrrolidin-3-yl)-N-[6-chloro-2,4,8,18,22-pentaazatetracyclo[14.3.1.1(3,7).1(9,13)]docosa-1(20),3(22),4,6,9(21),10,12,16,18-nonaen-12-yl]acetamide;

4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N,N-dimethylpiperidine-1-carboxamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(dimethylamino)sulfonyl]piperidin-4-yl}acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(isopropylsulfonyl)piperidin-4-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(ethylsulfonyl)piperidin-4-yl]acetamide;

4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-isopropylpiperidine-1-carboxamide;

4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-methylpiperidine-1-carboxamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(5-methylisoxazol-3-yl)carbonyl]piperidin-4-yl}acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(pyrazin-2-ylcarbonyl)piperidin-4-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-(1-isobutyrylpiperidin-4-yl)acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-(1-propionylpiperidin-4-yl)acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-pyrrolidin-3-ylacetamide;

(2S)—N-[6-Chloro-2,4,8,22-tetraazatetracyclo[14.3.1.1(3,7).1(9,13)]docosa-1(20),3(22),4,6,9(21),10,12,16,18-nonaen-12-yl]-2-hydroxypropanamide;

2-Amino-N-[6-chloro-2,4,8,22-tetraazatetracyclo[14.3.1.1(3,7).1(9,13)]docosa-1(20),3(22),4,6,9(21),10,12,16,18-nonaen-12-yl]acetamide;

3-Amino-N-[6-chloro-2,4,8,22-tetraazatetracyclo[14.3.1.1(3,7).1(9,13)]docosa-1(20),3(22),4,6,9(21),10,12,16,18-nonaen-12-yl]propanamide;

(2S)-2-Amino-N-[6-chloro-2,4,8,22-tetraazatetracyclo[14.3.1.1(3,7).1(9,13)]docosa-1(20),3(22),4,6,9(21),10,12,16,18-nonaen-12-yl]-3-hydroxypropanamide;

(2S)—N-[6-Chloro-2,4,8,22-tetraazatetracyclo[14.3.1.1(3,7).1(9,13)]docosa-1(20),3(22),4,6,9(21),10,12,16,18-nonaen-12-yl]pyrrolidine-2-carboxamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(2,2-dimethylpropanoyl)piperidin-4-yl]acetamide;

N-(tert-Butyl)-4-(2-{[6-chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)piperidine-1-carboxamide;

tert-Butyl-4-(2-{[6-chloro-2,4,8,22-tetraazatetracyclo[14.3.1.1(3,7).1(9,13)]docosa-1(20),3(22),4,6,9(21),10,12,16,18-nonaen-12-yl]amino}-2-oxoethyl)piperazine-1-carboxylate;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-piperazin-1-acetamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-3piperidin-4-ylpropanamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-3piperidin-4-ylpropanamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-(4-[1,3]oxazolo[5,4-b]pyridin-2-ylpiperazin-1-yl)acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{4-[(5-methylisoxazol-3-yl)carbonyl]piperazin-1-yl}acetamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-1-[(5-methylisoxazol-3-yl)carbonyl]piperidine-4-carboxamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-1-[(5-methylisoxazol-3-yl)carbonyl]piperidine-3-carboxamide;

(3R)—N-[6-Chloro-2,4,8,22-tetraazatetracyclo[14.3.1.1(3,7).1(9,13)]docosa-1(20),3(22),4,6,9(21),10,12,16,18-nonaen-12-yl]-1-[(5-methylisoxazol-3-yl)carbonyl]pyrrolidine-4-carboxamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-{4-[(5-methylisoxazol-3-yl)carbonyl]piperazin-1-yl}acetamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-3-{1-[(5-methylisoxazol-3-yl)carbonyl]piperidin-4-yl}propanamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-3-{1-[(5-methylisoxazol-3-yl)carbonyl]piperidin-4-yl}propanamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-(1-[1,3]oxazolo[5,4-b]pyridin-2-ylpiperidin-4-yl)acetamide;

2-(4-Acetylpiperazin-1-yl)-N-[6-chloro-2,4, 8,18,22-pentaazatetracyclo[14.3.1.1(3,7).1(9,13)]docosa-1(20),3(22),4,6,9(21),10,12,16,18-nonaen-12-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(isoxazol-5-ylcarbonyl)piperidin-4-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(1-methyl-1H-pyrazol-4-yl)carbonyl]piperidin-4-yl}acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(1-methyl-1H-pyrazol-3-yl)carbonyl]piperidin-4-yl}acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(5-methylisoxazol-4-yl)carbonyl]piperidin-4-yl}acetamide;

N-[6-Chloro-2,4,8,18,22-pentaazatetracyclo[14.3.1.1(3,7).1(9,13)]docosa-1(20),3(22),4,6,9(21),10,12,16,18- nonaen-12-yl]-2-{1-[(4-methyl-1,3-oxazol-5-yl)carbonyl]piperidin-4-yl}acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(1,3-thiazol-2-ylcarbonyl)piperidin-4-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(1-methyl-1H-imidazol-5yl)carbonyl]piperidin-4-yl}acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(isoxazol-3-ylcarbonyl)piperidin-4-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(1H-1,2,4-triazol-3-ylcarbonyl)piperidin-4-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(1H-1,2,3-triazol-4-ylcarbonyl)piperidin-4-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(1,2,5-oxadiazol-3-ylcarbonyl)piperidin-4-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(1,3-oxazol-2-ylcarbonyl)piperidin-4-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-(1-isopropylpiperidin-4-yl)acetamide;

4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-(2-cyanophenyl)piperidine-1-carboxamide;

4-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-(3-cyanophenyl)piperidine-1-carboxamide;

4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-(4-cyanophenyl)piperidine-1-carboxamide;

4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-pyridin-3-ylpiperidine-1-carboxamide;

4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-(3,5-dimethylisoxazol-4-yl)piperidine-1-carboxamide;

4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-(2-fluorophenyl)piperidine-1-carboxamide;

4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-(3-fluorophenyl)piperidine-1-carboxamide;

4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-(4-fluorophenyl)piperidine-1-carboxamide;

4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-(2-methylphenyl)piperidine-1-carboxamide;

4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-(3-methylphenyl)piperidine-1-carboxamide;

4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-(4-methylphenyl)piperidine-1-carboxamide;

4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-(2-methoxyphenyl)piperidine-1-carboxamide;

4-(2-{[6-chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-(3-methoxyphenyl)piperidine-1-carboxamide;

4-(2-{[6-Chloro-2,4,8,18,22-pentaazatetracyclo[14.3.1.1(3,7).1(9,13)]docosa-1(20),3 (22),4,6,9(21),10,12,16,18-nonaen-12-yl]amino}-2-oxo ethyl)-N-(4-methoxyphenyl)piperidine-1-carboxamide; and N-Benzyl-4-(2-{[6-chloro-2,4,8,18,22-pentaazatetracyclo[14.3.1.1(3,7).1(9,13)]docosa-1(20),3 (22),4,6,9(21),10,12,16,18-nonaen-12-yl]amino}-2-oxo ethyl)piperidine-1-carboxamide, or pharmaceutically acceptable salts thereof or quaternary ammonium salt thereof, or 4-(2-{[6-Chloro-2,4,8,22-tetraazatetracyclo[14.3.1.1(3,7).1(9,13)]docosa-1(20),3 (22),4,6,9(21),10,12,16,18-nonaen-12-yl]amino}-2-oxo ethyl)-1,1-dimethylpiperidinium bis(trifluoroacetate).

55. A compound selected from:

(14Z)-6-Methyl-2,4,8,22-tetraazatetracyclo[14.3.1.1(3,7).1(9,13)]docosa-1(20),3(22),4,6,9(21),10,12,14,16,18-decaene;

6-Methyl-2,4,8,22-tetraazatetracyclo[14.3.1.1(3,7).1(9,13)]docosa-1(20),3(22),4,6,9(21),10,12,16,18-nonaene;

6-Bromo-2,4,8,22-tetraazatetracyclo[14.3.1.1(3,7).1(9,13)]docosa-1(20),3(22),4,6,9(21),10,12,16,18-nonaene;

Methyl 6-chloro-2,4,8,22-tetraazatetracyclo[14.3.1.1(3,7).1(9,13)]docosa-1(20),3(22),4,6,9(21),10,12,16,18-nonaene-11-carboxylate;

6-Chloro-2,4,8,22-tetraazatetracyclo[14.3.1.1(3,7).1(9,13)]docosa-1(20),3(22),4,6,9(21),10,12,16,18-nonaene-11-carboxylic acid;

6-Chloro-N-(3-chloro-4-fluorophenyl)-2,4,8,22-tetraazatetracyclo[14.3.1.1(3,7).1(9,13)]docosa-1(20),3(22),4,6,9(21),10,12,16,18-nonaene-11-carboxamide;

6-Chloro-11-[(4-methylpiperazin-1-yl)carbonyl]-2,4,8,22-tetraazatetracyclo[14.3.1.1(3,7).1(9,13)]docosa-1(20),3(22),4,6,9(21),10,12,16,18-nonaene;

6-Chloro-N-(4-morpholin-4-ylphenyl)-2,4,8,22-tetraazatetracyclo[14.3.1.1(3,7).1(9,13)]docosa-1(20),3(22),4,6,9(21),10,12,16,18-nonaene-11-carboxamide;

6-Chloro-N-[4-(2-hydroxyethyl)phenyl]-2,4,8,22-tetraazatetracyclo[14.3.1.1(3,7).1(9,13)]docosa-1(20),3(22),4,6,9(21),10,12,16,18-nonaene-11-carboxamide;

6-Chloro-N-(pyridin-4-ylmethyl)-2,4,8,22-tetraazatetracyclo[14.3.1.1(3,7).1(9,13)]docosa-1(20),3(22),4,6,9(21),10,12,16,18-nonaene-11-carboxamide;

1-{[6-Chloro-2,4,8,22-tetraazatetracyclo[14.3.1.1(3,7).1(9,13)]docosa-1(20),3(22),4,6,9(21),10,12,16,18-nonaen-11-yl]carbonyl}piperidin-3-ol;

6-Chloro-N-(3-chlorophenyl)-2,4,8,22-tetraazatetracyclo[14.3.1.1(3,7).1(9,13)]docosa-1(20),3(22),4,6,9(21),10,12,16,18-nonaene-11-carboxamide;

6-Chloro-N-(2-chlorophenyl)-2,4,8,22-tetraazatetracyclo[14.3.1.1(3,7).1(9,13)]docosa-1(20),3(22),4,6,9(21),10,12,16,18-nonaene-11-carboxamide;

6-Chloro-N-(4-chlorophenyl)-2,4,8,22-tetraazatetracyclo[14.3.1.1(3,7).1(9,13)]docosa-1(20),3(22),4,6,9(21),10,12,16,18-nonaene-11-carboxamide;

N-(tert-Butyl)-6-chloro-2,4,8,22-tetraazatetracyclo[14.3.1.1(3,7).1(9,13)]docosa-1(20),3(22),4,6,9(21),10,12,16,18-nonaene-11-sulfonamide;

6-Bromo-N-(tert-butyl)-2,4,8,22-tetraazatetracyclo[14.3.1.1(3,7).1(9,13)]docosa-1(20),3(22),4,6,9(21),10,12,16,18-nonaene-11-sulfonamide;

6-Bromo-2,4,8,22-tetraazatetracyclo[14.3.1.1(3,7).1(9,13)]docosa-1(20),3(22),4,6,9(21),10,12,16,18-nonaene-11-sulfonamide;

6-Chloro-2,4,8,22-tetraazatetracyclo[14.3.1.1(3,7).1(9,13)]docosa-1(20),3(22),4,6,9(21),10,12,16,18-nonaen-12-amine di;

6-Chloro-2,4,8,18,22-pentaazatetracyclo[14.3.1.1(3,7).1(9,13)]docosa-1(20),3(22),4,6,9(21),10,12,16,18-nonaen-12-amine;

6-Chloro-2,4,8,22-tetraazatetracyclo[14.3.1.1(3,7).1(9,13)]docosa-1(20),3(22),4,6,9(21),10,12,16,18-nonaen-11-amine;

Methyl 6-chloro-2,4,8,22-tetraazatetracyclo[14.3.1.1(3,7).1(9,13)]docosa-1(20),3(22),4,6,9(21),10,12,16,18-nonaene-12-carboxylate;

[6-Chloro-2,4,8,22-tetraazatetracyclo[14.3.1.1(3,7).1(9,13)]docosa-1(20),3(22),4,6,9(21),10,12,16,18-nonaen-12-yl]methanol;

[6-Chloro-2,4,8,22-tetraazatetracyclo[14.3.1.1(3,7).1(9,13)]docosa-1(20),3(22),4,6,9(21),10,12,16,18-nonaen-11-yl]methanol;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-N'-[(3S)-pyrrolidin-3-yl]urea tri;

N-[6-Chloro-2,4,8,22-tetraazatetracyclo[14.3.1.1(3,7).1(9,13)]docosa-1(20),3(22),4,6,9(21),10,12,16,18-nonaen-12-yl]acetamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]cyclopropanecarboxamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-methoxyacetamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]benzamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]nicotinamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-1-methyl-1H-pyrazole-3-carboxamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-phenylacetamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-furamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]thiophene-2-carboxamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-methylbenzamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-methoxybenzamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]pyridine-2-carboxamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-fluorobenzamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]isonicotinamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-3,5-dimethylisoxazole-4-carboxamide;

2-Chloro-N-[6-chloro-2,4,8,22-tetraazatetracyclo[14.3.1.1(3,7).1(9,13)]docosa-1(20),3(22),4,6,9(21),10,12,16,18-nonaen-12-yl]benzamide;

3-Chloro-N-[6-chloro-2,4,8,22-tetraazatetracyclo[14.3.1.1(3,7).1(9,13)]docosa-1(20),3(22),4,6,9(21),10,12,16,18-nonaen-12-yl]benzamide;

4-Chloro-N-[6-chloro-2,4,8,22-tetraazatetracyclo[14.3.1.1(3,7).1(9,13)]docosa-1(20),3(22),4,6,9(21),10,12,16,18-nonaen-12-yl]benzamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]pyrazine-2-carboxamide;

4-(Acetylamino)-N-[6-chloro-2,4,8,22-tetraazatetracyclo[14.3.1.1(3,7).1(9,13)]docosa-1(20),3(22),4,6,9(21),10,12,16,18-nonaen-12-yl]benzamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-3-methylbenzamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-4-methylbenzamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-3-fluorobenzamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-4-fluorobenzamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-1-methyl-1H-pyrrole-2-carboxamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-1-methyl-1H-imidazole-5-carboxamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-1,3-thiazole-2-carboxamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]isoxazole-5-carboxamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]propanamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-methylpropanamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]butanamide;

N-[6-Chloro-2,4,8,22-tetraazatetracyclo[14.3.1.1(3,7).1
(9,13)]docosa-1(20),3(22),4,6,9(21),10,12,16,18-
nonaen-12-yl]cyclobutanecarboxamide;
N-[6-Chloro-2,4,8,22-tetraazatetracyclo[14.3.1.1(3,7).1
(9,13)]docosa-1(20),3(22),4,6,9(21),10,12,16,18-
nonaen-12-yl]-2,2-dimethylpropanamide;
N-[6-Chloro-2,4,8,22-tetraazatetracyclo[14.3.1.1(3,7).1
(9,13)]docosa-1(20),3(22),4,6,9(21),10,12,16,18-
nonaen-12-yl]-3-furamide;
N-[6-Chloro-2,4,8,22-tetraazatetracyclo[14.3.1.1(3,7).1
(9,13)]docosa-1(20),3(22),4,6,9(21),10,12,16,18-
nonaen-12-yl]cyclopentanecarboxamide;
N-[6-Chloro-2,4,8,22-tetraazatetracyclo[14.3.1.1(3,7).1
(9,13)]docosa-1(20),3(22),4,6,9(21),10,12,16,18-
nonaen-12-yl]-2-methylbutanamide;
N-[6-Chloro-2,4,8,22-tetraazatetracyclo[14.3.1.1(3,7).1
(9,13)]docosa-1(20),3(22),4,6,9(21),10,12,16,18-
nonaen-12-yl]thiophene-3-carboxamide;
N-[6-Chloro-2,4,8,22-tetraazatetracyclo[14.3.1.1(3,7).1
(9,13)]docosa-1(20),3(22),4,6,9(21),10,12,16,18-
nonaen-12-yl]cyclohexanecarboxamide;
N-[6-Chloro-2,4,8,22-tetraazatetracyclo[14.3.1.1(3,7).1
(9,13)]docosa-1(20),3(22),4,6,9(21),10,12,16,18-
nonaen-12-yl]-4-cyanobenzamide;
N-[6-Chloro-2,4,8,22-tetraazatetracyclo[14.3.1.1(3,7).1
(9,13)]docosa-1(20),3(22),4,6,9(21),10,12,16,18-
nonaen-12-yl]-3-cyanobenzamide;
N-[6-Chloro-2,4,8,22-tetraazatetracyclo[14.3.1.1(3,7).1
(9,13)]docosa-1(20),3(22),4,6,9(21),10,12,16,18-
nonaen-12-yl]-3-methoxybenzamide;
N-[6-Chloro-2,4,8,22-tetraazatetracyclo[14.3.1.1(3,7).1
(9,13)]docosa-1(20),3(22),4,6,9(21),10,12,16,18-
nonaen-12-yl]-4-methoxybenzamide;
N-[6-Chloro-2,4,8,22-tetraazatetracyclo[14.3.1.1(3,7).1
(9,13)]docosa-1(20),3(22),4,6,9(21),10,12,16,18-
nonaen-12-yl]-5-methylisoxazole-3-carboxamide;
6-Chloro-N-[6-chloro-2,4,8,22-tetraazatetracyclo
[14.3.1.1(3,7).1(9,13)]docosa-1(20),3(22),4,6,9(21),
10,12,16,18-nonaen-12-yl]nicotinamide;
2-Chloro-N-[6-chloro-2,4,8,22-tetraazatetracyclo
[14.3.1.1(3,7).1(9,13)]docosa-1(20),3(22),4,6,9(21),
10,12,16,18-nonaen-12-yl]nicotinamide;
N-[6-Chloro-2,4,8,22-tetraazatetracyclo[14.3.1.1(3,7).1
(9,13)]docosa-1(20),3(22),4,6,9(21),10,12,16,18-
nonaen-12-yl]-1,3-benzodioxole-5-carboxamide;
N-[6-Chloro-2,4,8,22-tetraazatetracyclo[14.3.1.1(3,7).1
(9,13)]docosa-1(20),3(22),4,6,9(21),10,12,16,18-
nonaen-12-yl]quinoxaline-2-carboxamide;
4-tert-Butyl-N-[6-chloro-2,4,8,22-tetraazatetracyclo
[14.3.1.1(3,7).1(9,13)]docosa-1(20),3(22),4,6,9(21),
10,12,16,18-nonaen-12-yl]benzamide;
N-[6-Chloro-2,4,8,22-tetraazatetracyclo[14.3.1.1(3,7).1
(9,13)]docosa-1(20),3(22),4,6,9(21),10,12,16,18-
nonaen-12-yl]-1,3-benzothiazole-2-carboxamide;
N-[6-Chloro-2,4,8,22-tetraazatetracyclo[14.3.1.1(3,7).1
(9,13)]docosa-1(20),3(22),4,6,9(21),10,12,16,18-
nonaen-12-yl]-4-(trifluoromethyl)benzamide;
N-[6-Chloro-2,4,8,22-tetraazatetracyclo[14.3.1.1(3,7).1
(9,13)]docosa-1(20),3(22),4,6,9(21),10,12,16,18-
nonaen-12-yl]-3-(trifluoromethyl)benzamide;
N-[6-Chloro-2,4,8,22-tetraazatetracyclo[14.3.1.1(3,7).1
(9,13)]docosa-1(20),3(22),4,6,9(21),10,12,16,18-
nonaen-12-yl]-6-(trifluoromethyl)nicotinamide;
N-[6-Chloro-2,4,8,22-tetraazatetracyclo[14.3.1.1(3,7).1
(9,13)]docosa-1(20),3(22),4,6,9(21),10,12,16,18-
nonaen-12-yl]-4-methyl-1,3-oxazole-5-carboxamide;
and
N-[6-Chloro-2,4,8,22-tetraazatetracyclo[14.3.1.1(3,7).1
(9,13)]docosa-1(20),3(22),4,6,9(21),10,12,16,18-
nonaen-12-yl]-1-benzofuran-5-carboxamide, or pharmaceutically acceptable salts thereof or quaternary ammonium salt thereof.

56. A compound of claim 1 selected from:
N-[6-Chloro-2,4,8,22-tetraazatetracyclo[14.3.1.1(3,7).1
(9,13)]docosa-1(20),3(22),4,6,9(21),10,12,16,18-
nonaen-12-yl]pyrazolo[1,5-a]pyridine-3-carboxamide;
N-[6-Chloro-2,4,8,22-tetraazatetracyclo[14.3.1.1(3,7).1
(9,13)]docosa-1(20),3(22),4,6,9(21),10,12,16,18-
nonaen-12-yl]pyrrolidine-1-carboxamide;
N-[6-Chloro-2,4,8,22-tetraazatetracyclo[14.3.1.1(3,7).1
(9,13)]docosa-1(20),3 (22),4,6,9(21),10,12,16,18-
nonaen-12-yl]-4-(dimethylamino)benzamide;
N-[6-Chloro-2,4,8,22-tetraazatetracyclo[14.3.1.1(3,7).1
(9,13)]docosa-1(20),3(22),4,6,9(21),10,12,16,18-
nonaen-12-yl]-N'-phenylurea;
N-(2-Chlorophenyl)-N'46-chloro-2,4,8,22-tetraazatetra-
cyclo[14.3.1.1(3,7).1(9,13)]docosa-1(20),3(22),4,6,9
(21),10,12,16,18-nonaen-12-yl]urea;
N-(3-Chlorophenyl)-N'46-chloro-2,4,8,22-tetraazatetra-
cyclo[14.3.1.1(3,7).1(9,13)]docosa-1(20),3(22),4,6,9
(21),10,12,16,18-nonaen-12-yl]urea;
N-(4-Chlorophenyl)-N'46-chloro-2,4,8,22-tetraazatetra-
cyclo[14.3.1.1(3,7).1(9,13)]docosa-1(20),3(22),4,6,9
(21),10,12,16,18-nonaen-12-yl]urea;
N-(tert-Butyl)-N'46-chloro-2,4,8,22-tetraazatetracyclo
[14.3.1.1(3,7).1(9,13)]docosa-1(20),3(22),4,6,9(21),
10,12,16,18-nonaen-12-yl]urea;
N-[6-Chloro-2,4,8,22-tetraazatetracyclo[14.3.1.1(3,7).1
(9,13)]docosa-1(20),3(22),4,6,9(21),10,12,16,18-
nonaen-12-yl]-N'-cyclopentylurea;
N-[6-Chloro-2,4,8,22-tetraazatetracyclo[14.3.1.1(3,7).1
(9,13)]docosa-1(20),3(22),4,6,9(21),10,12,16,18-
nonaen-12-yl]-N'-3-thienylurea;
N-[6-Chloro-2,4,8,22-tetraazatetracyclo[14.3.1.1(3,7).1
(9,13)]docosa-1(20),3(22),4,6,9(21),10,12,16,18-
nonaen-12-yl]-N'-(3-methylphenyl)urea;
N-[6-Chloro-2,4,8,22-tetraazatetracyclo[14.3.1.1(3,7).1
(9,13)]docosa-1(20),3(22),4,6,9(21),10,12,16,18-
nonaen-12-yl]-N'-(2-methylphenyl)urea;
N-[6-Chloro-2,4,8,22-tetraazatetracyclo[14.3.1.1(3,7).1
(9,13)]docosa-1(20),3(22),4,6,9(21),10,12,16,18-
nonaen-12-yl]-N'-(4-methylphenyl)urea;
N-benzyl-N'-[6-chloro-2,4,8,22-tetraazatetracyclo
[14.3.1.1(3,7).1(9,13)]docosa-1(20),3(22),4,6,9(21),
10,12,16,18-nonaen-12-yl]urea;
N-[6-Chloro-2,4,8,22-tetraazatetracyclo[14.3.1.1(3,7).1
(9,13)]docosa-1(20),3(22),4,6,9(21),10,12,16,18-
nonaen-12-A-N'-(3,5-dimethylisoxazol-4-yl)urea;
N-[6-Chloro-2,4,8,22-tetraazatetracyclo[14.3.1.1(3,7).1
(9,13)]docosa-1(20),3(22),4,6,9(21),10,12,16,18-
nonaen-12-yl]-N'-(3-cyanophenyl)urea;
N-[6-Chloro-2,4,8,22-tetraazatetracyclo[14.3.1.1(3,7).1
(9,13)]docosa-1(20),3(22),4,6,9(21),10,12,16,18-
nonaen-12-yl]-N'-(4-cyanophenyl)urea;
N-[6-Chloro-2,4,8,22-tetraazatetracyclo[14.3.1.1(3,7).1
(9,13)]docosa-1(20),3(22),4,6,9(21),10,12,16,18-
nonaen-12-yl]-N'-(2-ethylphenyl)urea;
N-[6-Chloro-2,4,8,22-tetraazatetracyclo[14.3.1.1(3,7).1
(9,13)]docosa-1(20),3(22),4,6,9(21),10,12,16,18-
nonaen-12-yl]-N'-(4-ethylphenyl)urea;
N-[6-Chloro-2,4,8,22-tetraazatetracyclo[14.3.1.1(3,7).1
(9,13)]docosa-1(20),3(22),4,6,9(21),10,12,16,18-
nonaen-12-yl]-N'-(3-ethylphenyl)urea;

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-(3-methoxyphenyl)urea;

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-(4-methoxyphenyl)urea;

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-(2-methoxyphenyl)urea;

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-(2,3-dihydro-1H-inden-5-yl)urea;

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-(2-isopropylphenyl)urea;

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-(2-propylphenyl)urea;

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-(2-ethoxyphenyl)urea;

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-[2-(methylthio)phenyl]urea;

N42-(Chloromethyl)phenyl]-N'46-chloro-2,4,8,22-tetraazatetracyclo[14.3.1.1(3,7).1(9,13)]docosa-1(20),3(22),4,6,9(21),10,12,16,18-nonaen-12-yl]urea;

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-(5,6,7,8-tetrahydronaphthalen-1-yl)urea;

N-(2-tert-Butylphenyl)-N'-[6-chloro-2,4,8,22-tetraazatetracyclo[14.3.1.1(3,7).1(9,13)]docosa-1(20),3(22),4,6,9(21),10,12,16,18-nonaen-12-yl]urea;

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-[2-(trifluoromethyl)phenyl]urea;

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-[3-(trifluoromethyl)phenyl]urea;

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-(2,6-dichlorophenyl)urea;

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-methylurea;

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-ethylurea;

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-isopropylurea;

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-(2-furylmethyl)urea;

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-(2-methyl-3-furyl)urea;

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-cyclohexylurea;

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-(4-methyl-2-thienyl)urea;

N-(6-Chloropyridin-3-yl)-N'-[6-chloro-2,4,8,22-tetraazatetracyclo[14.3.1.1(3,7).1(9,13)]docosa-1(20),3(22),4,6,9(21),10,12,16,18-nonaen-12-yl]urea;

N-(2-Chloro-6-methylphenyl)-N'-[6-chloro-2,4,8,22-tetraazatetracyclo[14.3.1.1(3,7).1(9,13)]docosa-1(20),3(22),4,6,9(21),10,12,16,18-nonaen-12-yl]urea;

N-(5-Chloro-2-methylphenyl)-N'-[6-chloro-2,4,8,22-tetraazatetracyclo[14.3.1.1(3,7).1(9,13)]docosa-1(20),3(22),4,6,9(21),10,12,16,18-nonaen-12-yl]urea;

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-1-naphthylurea;

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-(1-methyl-1H-indol-4-yl)urea;

N-(2-sec-Butylphenyl)-N'-[6-chloro-2,4,8,22-tetraazatetracyclo[14.3.1.1(3,7).1(9,13)]docosa-1(20),3(22),4,6,9(21),10,12,16,18-nonaen-12-yl]urea;

N-1-Adamantyl-N'-[6-chloro-2,4,8,22-tetraazatetracyclo[14.3.1.1(3,7).1(9,13)]docosa-1(20),3(22),4,6,9(21),10,12,16,18-nonaen-12-yl]urea;

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-[2-(difluoromethoxy)phenyl]urea;

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-(2,2-dimethyl-2,3-dihydro-1-benzofuran-7-yl)urea;

N-Biphenyl-2-yl-N'-[6-chloro-2,4,8,22-tetraazatetracyclo[14.3.1.1(3,7).1(9,13)]docosa-1(20),3(22),4,6,9(21),10,12,16,18-nonaen-12-yl]urea;

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-[2-(trifluoromethoxy)phenyl]urea;

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-[4-(trifluoromethoxy)phenyl]urea;

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-(6-morpholin-4-ylpyridin-2-yl)urea;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-N'-(2-furylmethyl)urea;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-N'-methylurea;

N-[6-Chloro-2,4,8,22-tetraazatetracyclo[14.3.1.1(3,7).1(9,13)]docosa-1(20),3(22),4,6,9(21),10,12,16,18-nonaen-12-yl]benzenesulfonamide;

2-Chloro-N-[6-chloro-2,4,8,22-tetraazatetracyclo[14.3.1.1(3,7).1(9,13)]docosa-1(20),3(22),4,6,9(21),10,12,16,18-nonaen-12-yl]benzenesulfonamide;

3-Chloro-N-[6-chloro-2,4,8,22-tetraazatetracyclo[14.3.1.1(3,7).1(9,13)]docosa-1(20),3(22),4,6,9(21),10,12,16,18-nonaen-12-yl]benzenesulfonamide;

4-Chloro-N-[6-chloro-2,4,8,22-tetraazatetracyclo[14.3.1.1(3,7).1(9,13)]docosa-1(20),3(22),4,6,9(21),10,12,16,18-nonaen-12-yl]benzenesulfonamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]methanesulfonamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]ethanesulfonamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]propane-1-sulfonamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]propane-2-sulfonamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-1-methyl-1H-imidazole-4-sulfonamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-5-methylisoxazole-4-sulfonamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]thiophene-2-sulfonamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-1-phenylmethanesulfonamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-3-methylbenzenesulfonamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-methylbenzenesulfonamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-4-methylbenzenesulfonamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-1,2-dimethyl-1H-imidazole-4-sulfonamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-3,5-dimethylisoxazole-4-sulfonamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-3-cyanobenzenesulfonamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-4-cyanobenzenesulfonamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-cyanobenzenesulfonamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-4-methoxybenzenesulfonamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-3-methoxybenzenesulfonamide; and N-[6-Chloro-2,4,8,22-tetraazatetracyclo[14.3.1.1(3,7).1(9,13)]docosa-1(20),3(22),4,6,9(21),10,12,16,18-nonaen-12-yl]cyclopropanesulfonamide, or pharmaceutically acceptable salts thereof or quaternary ammonium salt thereof.

57. A compound selected from:

3-({[6-Chloro-2,4,8,22-tetraazatetracyclo[14.3.1.1(3,7).1(9,13)]docosa-1(20),3(22),4,6,9(21),10,12,16,18-nonaen-12-yl]amino}sulfonyl)benzoic acid;

N-[6-Chloro-2,4,8,22-tetraazatetracyclo[14.3.1.1(3,7).1(9,13)]docosa-1(20),3(22),4,6,9(21),10,12,16,18-nonaen-12-yl]quinoline-8-sulfonamide;

N-[4-({[6-Chloro-2,4,8,22-tetraazatetracyclo[14.3.1.1(3,7).1(9,13)]docosa-1(20),3(22),4,6,9(21),10,12,16,18-nonaen-12-yl]amino}sulfonyl)phenyl]acetamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-4-(trifluoromethyl)benzenesulfonamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-3-(trifluoromethyl)benzenesulfonamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-(trifluoromethyl)benzenesulfonamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-4-methyl-3,4-dihydro-2H-1,4-benzoxazine-7-sulfonamide;

tert-Butyl (3S)-3-[({[6-chloro-2,4,8,22-tetraazatetracyclo[14.3.1.1(3,7).1(9,13)]docosa-1(20),3(22),4,6,9(21),10,12,16,18-nonaen-12-yl]amino}carbonyl)amino]pyrrolidine-1-carboxylate;

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-[(3S)-pyrrolidin-3-yl]urea;

N-[(3S)-1-Acetylpyrrolidin-3-yl]-N'-[6-chloro-2,4,8,22-tetraazatetracyclo[14.3.1.1(3,7).1(9,13)]docosa-1(20),3(22),4,6,9(21),10,12,16,18-nonaen-12-yl]urea;

(3S)-3-[({[6-Chloro-2,4,8,22-tetraazatetracyclo[14.3.1.1(3,7).1(9,13)]docosa-1(20),3(22),4,6,9(21),10,12,16,18-nonaen-12-yl]amino}carbonyl)amino]-N-methylpyrrolidine-1-carboxamide;

N-[(3S)-1-Benzoylpyrrolidin-3-yl]-N'-[6-chloro-2,4,8,22-tetraazatetracyclo[14.3.1.1(3,7).1(9,13)]docosa-1(20),3(22),4,6,9(21),10,12,16,18-nonaen-12-yl]urea;

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-[(3S)-1-(pyridin-3-ylcarbonyl)pyrrolidin-3-yl]urea;

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-[(3S)-1-(methylsulfonyl)pyrrolidin-3-yl]urea;

N-[(3S)-1-Benzylpyrrolidin-3-yl]-N'-[6-chloro-2,4,8,22-tetraazatetracyclo[14.3.1.1(3,7).1(9,13)]docosa-1(20),3(22),4,6,9(21),10,12,16,18-nonaen-12-yl]urea;

tert-Butyl (3R)-3-[({[6-chloro-2,4,8,22-tetraazatetracyclo[14.3.1.1(3,7).1(9,13)]docosa-1(20),3(22),4,6,9(21),10,12,16,18-nonaen-12-yl]amino}carbonyl)amino]pyrrolidine-1-carboxylate;

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-[(3R)-pyrrolidin-3-yl]urea;

N-[(3R)-1-Benzoylpyrrolidin-3-yl]-N'-[6-chloro-2,4,8,22-tetraazatetracyclo[14.3.1.1(3,7).1(9,13)]docosa-1(20),3(22),4,6,9(21),10,12,16,18-nonaen-12-yl]urea;

N-[(3R)-1-Acetylpyrrolidin-3-yl]-N'-[6-chloro-2,4,8,22-tetraazatetracyclo[14.3.1.1(3,7).1(9,13)]docosa-1(20),3(22),4,6,9(21),10,12,16,18-nonaen-12-yl]urea;

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-[(3R)-1-(methylsulfonyl)pyrrolidin-3-yl]urea;

(3R)-3-[({[6-Chloro-2,4,8,22-tetraazatetracyclo[14.3.1.1(3,7).1(9,13)]docosa-1(20),3(22),4,6,9(21),10,12,16,18-nonaen-12-yl]amino}carbonyl)amino]pyrrolidine-1-sulfonamide;

tert-Butyl 4-[({[6-chloro-2,4,8,22-tetraazatetracyclo[14.3.1.1(3,7).1(9,13)]docosa-1(20),3(22),4,6,9(21),10,12,16,18-nonaen-12-yl]amino}carbonyl)amino]piperidine-1-carboxylate;

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-piperidin-4-ylurea;

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-[1-(methylsulfonyl)piperidin-4-yl]urea;

4-[({[6-Chloro-2,4,8,22-tetraazatetracyclo[14.3.1.1(3,7).1(9,13)]docosa-1(20),3(22),4,6,9(21),10,12,16,18-nonaen-12-yl]amino}carbonyl)amino]piperidine-1-sulfonamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]sulfamide;

tert-Butyl {2-[({[6-chloro-2,4,8,22-tetraazatetracyclo[14.3.1.1(3,7).1(9,13)]docosa-1(20),3(22),4,6,9(21),10,12,16,18-nonaen-12-yl]amino}carbonyl)amino]ethyl}carbamate;

N-{2-[({[6-Chloro-2,4,8,22-tetraazatetracyclo[14.3.1.1(3,7).1(9,13)]docosa-1(20),3(22),4,6,9(21),10,12,16,18-nonaen-12-yl]amino}carbonyl)amino]ethyl}acetamide;

N-{2-[({[6-Chloro-2,4,8,22-tetraazatetracyclo[14.3.1.1(3,7).1(9,13)]docosa-1(20),3(22),4,6,9(21),10,12,16,18-nonaen-12-yl]amino}carbonyl)amino]ethyl}methanesulfonamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-(2-{[(isopropylamino)carbonyl]amino}ethyl)urea;

N-{2-[({[6-Chloro-2,4,8,22-tetraazatetracyclo[14.3.1.1(3,7).1(9,13)]docosa-1(20),3(22),4,6,9(21),10,12,16,18-nonaen-12-yl]amino}carbonyl)amino]ethyl}benzamide;

N-{2-[({[6-Chloro-2,4,8,22-tetraazatetracyclo[14.3.1.1(3,7).1(9,13)]docosa-1(20),3(22),4,6,9(21),10,12,16,18-nonaen-12-yl]amino}carbonyl)amino]ethyl}pyridine-2-carboxamide;

6-Chloro-11-(piperazin-1-ylmethyl)-2,4,8,22-tetraazatetracyclo[14.3.1.1(3,7).1(9,13)]docosa-1(20),3(22),4,6,9(21),10,12,16,18-nonaene;

6-Chloro-11-{[4-(4-fluorobenzyl)piperazin-1-yl]methyl}-2,4,8,22-tetraazatetracyclo[14.3.1.1(3,7).1(9,13)]docosa-1(20),3(22),4,6,9(21),10,12,16,18-nonaene;

6-Chloro-11-({4-[4-(pyrimidin-2-yloxy)benzyl]piperazin-1-yl}methyl)-2,4,8,22-tetraazatetracyclo[14.3.1.1(3,7).1(9,13)]docosa-1(20),3(22),4,6,9(21),10,12,16,18-nonaene;

6-Chloro-11-{[4-(4-nitrobenzyl)piperazin-1-yl]methyl}-2,4,8,22-tetraazatetracyclo[14.3.1.1(3,7).1(9,13)]docosa-1(20),3(22),4,6,9(21),10,12,16,18-nonaene;

6-Chloro-11-[(4-{4-[(4-chlorophenyl)sulfonyl]benzyl}piperazin-1-yl)methyl]-2,4,8,22-tetraazatetracyclo[14.3.1.1(3,7).1(9,13)]docosa-1(20),3(22),4,6,9(21),10,12,16,18-nonaene;

11-({4-[(4-Bromo-2-thienyl)methyl]piperazin-1-yl}methyl)-6-chloro-2,4,8,22-tetraazatetracyclo[14.3.1.1(3,7).1(9,13)]docosa-1(20),3(22),4,6,9(21),10,12,16,18-nonaene;

6-Chloro-11-{[4-(4-methoxybenzyl)piperazin-1-yl]methyl}-2,4,8,22-tetraazatetracyclo[14.3.1.1(3,7).1(9,13)]docosa-1(20),3(22),4,6,9(21),10,12,16,18-nonaene;

6-Chloro-11-{[4-(3-methoxybenzyl)piperazin-1-yl]methyl}-2,4,8,22-tetraazatetracyclo[14.3.1.1(3,7).1(9,13)]docosa-1(20),3(22),4,6,9(21),10,12,16,18-nonaene;

6-Chloro-11-{[4-(4-chlorobenzyl)piperazin-1-yl]methyl}-2,4,8,22-tetraazatetracyclo[14.3.1.1(3,7).1(9,13)]docosa-1(20),3(22),4,6,9(21),10,12,16,18-nonaene;

6-Chloro-N-phenyl-2,4,8,22-tetraazatetracyclo[14.3.1.1(3,7).1(9,13)]docosa-1(20),3(22),4,6,9(21),10,12,16,18-nonaene-12-carboxamide;

N-[6-Chloro-2,4,8,22-tetraazatetracyclo[14.3.1.1(3,7).1(9,13)]docosa-1(20),3(22),4,6,9(21),10,12,16,18-nonaen-11-yl]pyridine-2-carboxamide;

N-[6-Chloro-2,4,8,22-tetraazatetracyclo[14.3.1.1(3,7).1(9,13)]docosa-1(20),3(22),4,6,9(21),10,12,16,18-nonaen-11-yl]-N'-phenylurea;

N-[6-Chloro-2,4,8,22-tetraazatetracyclo[14.3.1.1(3,7).1(9,13)]docosa-1(20),3(22),4,6,9(21),10,12,16,18-nonaen-11-yl]benzenesulfonamide;

N-[6-Chloro-2,4,8,22-tetraazatetracyclo[14.3.1.1(3,7).1(9,13)]docosa-1(20),3(22),4,6,9(21),10,12,16,18-nonaen-11-yl]-1,3-benzothiazole-2-carboxamide;

N-[6-Chloro-2,4,8,22-tetraazatetracyclo[14.3.1.1(3,7).1(9,13)]docosa-1(20),3(22),4,6,9(21),10,12,16,18-nonaen-11-yl]-5-methylisoxazole-3-carboxamide;

N-[6-Chloro-2,4,8,22-tetraazatetracyclo[14.3.1.1(3,7).1(9,13)]docosa-1(20),3(22),4,6,9(21),10,12,16,18-nonaen-11-yl]isoxazole-5-carboxamide;

N-[6-Chloro-2,4,8,22-tetraazatetracyclo[14.3.1.1(3,7).1(9,13)]docosa-1(20),3(22),4,6,9(21),10,12,16,18-nonaen-11-yl]-1-methyl-1H-pyrazole-3-carboxamide;

N-[6-Chloro-2,4,8,22-tetraazatetracyclo[14.3.1.1(3,7).1(9,13)]docosa-1(20),3(22),4,6,9(21),10,12,16,18-nonaen-11-yl]-1-methyl-1H-imidazole-5-carboxamide;

N-[6-Chloro-2,4,8,22-tetraazatetracyclo[14.3.1.1(3,7).1(9,13)]docosa-1(20),3(22),4,6,9(21),10,12,16,18-nonaen-11-yl]-1,3-thiazole-2-carboxamide;

N-[6-Chloro-2,4,8,22-tetraazatetracyclo[14.3.1.1(3,7).1(9,13)]docosa-1(20),3(22),4,6,9(21),10,12,16,18-nonaen-11-yl]-4-methyl-1,3-oxazole-5-carboxamide;

N-[6-Chloro-2,4,8,22-tetraazatetracyclo[14.3.1.1(3,7).1(9,13)]docosa-1(20),3(22),4,6,9(21),10,12,16,18-nonaen-11-yl]cyclobutanecarboxamide;

N-[6-Chloro-2,4,8,22-tetraazatetracyclo[14.3.1.1(3,7).1(9,13)]docosa-1(20),3(22),4,6,9(21),10,12,16,18-nonaen-11-yl]-N'-(4-cyanophenyl)urea;

N-[6-Chloro-2,4,8,22-tetraazatetracyclo[14.3.1.1(3,7).1(9,13)]docosa-1(20),3(22),4,6,9(21),10,12,16,18-nonaen-11-yl]-N'-(2-fluorophenyl)urea;

N-[6-Chloro-2,4,8,22-tetraazatetracyclo[14.3.1.1(3,7).1(9,13)]docosa-1(20),3(22),4,6,9(21),10,12,16,18-nonaen-11-yl]-N'-(3-fluorophenyl)urea;

N-[6-Chloro-2,4,8,22-tetraazatetracyclo[14.3.1.1(3,7).1(9,13)]docosa-1(20),3(22),4,6,9(21),10,12,16,18-nonaen-11-yl]-N'-cyclopentylurea;

N-[6-Chloro-2,4,8,22-tetraazatetracyclo[14.3.1.1(3,7).1(9,13)]docosa-1(20),3(22),4,6,9(21),10,12,16,18-nonaen-11-yl]-2-cyanobenzenesulfonamide;

6-Chloro-11-{[4-(6-chloropyridin-2-yl)piperazin-1-yl]methyl}-2,4,8,22-tetraazatetracyclo[14.3.1.1(3,7).1(9,13)]docosa-1(20),3(22),4,6,9(21),10,12,16,18-nonaene;

6-Chloro-11-{[4-(2-chloropyrimidin-4-yl)piperazin-1-yl]methyl}-2,4,8,22-tetraazatetracyclo[14.3.1.1(3,7).1(9,13)]docosa-1(20),3(22),4,6,9(21),10,12,16,18-nonaene;

tert-Butyl (3R)-3-({[6-chloro-2,4,8,22-tetraazatetracyclo[14.3.1.1(3,7).1(9,13)]docosa-1(20),3(22),4,6,9(21),10,12,16,18-nonaen-12-yl]methyl}amino)pyrrolidine-1-carboxylate;

tert-Butyl (3S)-3-({[6-chloro-2,4,8,22-tetraazatetracyclo[14.3.1.1(3,7).1(9,13)]docosa-1(20),3(22),4,6,9(21),10,12,16,18-nonaen-12-yl]methyl}amino)pyrrolidine-1-carboxylate;

tert-Butyl 4-{[6-chloro-2,4,8,22-tetraazatetracyclo[14.3.1.1(3,7).1(9,13)]docosa-1(20),3(22),4,6,9(21),10,12,16,18-nonaen-12-yl]methyl}piperazine-1-carboxylate;

(3R)—N-{[6-Chloro-2,4,8,22-tetraazatetracyclo[14.3.1.1(3,7).1(9,13)]docosa-1(20),3(22),4,6,9(21),10,12,16,18-nonaen-12-yl]methyl}pyrrolidin-3-amine;

(3S)—N-{[6-Chloro-2,4,8,22-tetraazatetracyclo[14.3.1.1(3,7).1(9,13)]docosa-1(20),3(22),4,6,9(21),10,12,16,18-nonaen-12-yl]methyl}pyrrolidin-3-amine;

6-Chloro-12-(piperazin-1-ylmethyl)-2,4,8,22-tetraazatetracyclo[14.3.1.1(3,7).1(9,13)]docosa-1(20),3(22),4,6,9(21),10,12,16,18-nonaene;

12-[(4-Acetylpiperazin-1-yl)methyl]-6-chloro-2,4,8,22-tetraazatetracyclo[14.3.1.1(3,7).1(9,13)]docosa-1(20),3(22),4,6,9(21),10,12,16,18-nonaene;

N-[(3S)-1-Acetylpyrrolidin-3-yl]-N'-[6-chloro-2,4,8,18,22-pentaazatetracyclo[14.3.1.1(3,7).1(9,13)]docosa-1(20),3(22),4,6,9(21),10,12,16,18-nonaen-12-yl]urea;

N-[(3S)-1-benzoylpyrrolidin-3-yl]-N'-[6-chloro-2,4,8,18,22-pentaazatetracyclo[14.3.1.1(3,7).1(9,13)]docosa-1(20),3(22),4,6,9(21),10,12,16,18-nonaen-12-yl]urea;

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-[(3S)-1-(cyclopropylcarbonyl)pyrrolidin-3-yl]urea;

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-[(3S)-1-isobutyrylpyrrolidin-3-yl]urea;

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-[(3S)-1-(isoxazol-5-ylcarbonyl)pyrrolidin-3-yl]urea;

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-[(3S)-1-(1,3-thiazol-2-ylcarbonyl)pyrrolidin-3-yl]urea;

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-{(3S)-1-[(1-methyl-1H-pyrazol-3-yl)carbonyl]pyrrolidin-3-yl}urea;

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-[(3S)-1-(pyridin-2-ylcarbonyl)pyrrolidin-3-yl]urea;

N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-[(3S)-1-isonicotinoylpyrrolidin-3-yl]urea; and N-[6-Chloro-2,4,8,22-tetraazatetracyclo[14.3.1.1(3,7).1(9,13)]docosa-1(20),3(22),4,6,9(21),10,12,16,18-nonaen-12-yl]-N'-[(3S)-1-(4-cyanobenzoyl)pyrrolidin-3-yl]urea, or pharmaceutically acceptable salts thereof or quaternary ammonium salt thereof.

58. A compound selected from:

6-Chloro-2,4,8,15,22-pentaazatetracyclo[14.3.1.1(3,7).1(9,13)]docosa-1(20),3(22),4,6,9(21),10,12,16,18-nonaen-14-one;

6-Chloro-2,4,8,14,22-pentaazatetracyclo[14.3.1.1(3,7).1(9,13)]docosa-1(20),3(22),4,6,9(21),10,12,16,18-nonaen-15-one;

6-Chloro-16-thia-2,4,8,15,23-pentaazatetracyclo[15.3.1.1(3,7).1(9,13)]tricosa-1(21),3(23),4,6,9(22),10,12,17,19-nonaene 16,16-dioxide;

6-Chloro-2,4,8,15,23-pentaazatetracyclo[15.3.1.1(3,7).1(9,13)]tricosa-1(21),3(23),4,6,9(22),10,12,17,19-nonaen-14-one;

6-Chloro-2,4,8,15,23-pentaazatetracyclo[15.3.1.1(3,7).1(9,13)]tricosa-1(21),3(23),4,6,9(22),10,12,17,19-nonaen-16-one;

6-Chloro-15-thia-2,4,8,14,22-pentaazatetracyclo[14.3.1.1(3,7).1(9,13)]docosa-1(20),3(22),4,6,9(21),10,12,16,18-nonaene 15,15-dioxide;

6-Chloro-14-thia-2,4,8,15,22-pentaazatetracyclo[14.3.1.1(3,7).1(9,13)]docosa-1(20),3(22),4,6,9(21),10,12,16,18-nonaene 14,14-dioxide;

6-Chloro-15-thia-2,4,8,16,23-pentaazatetracyclo[15.3.1.1(3,7).1(9,13)]tricosa-1(21),3(23),4,6,9(22),10,12,17,19-nonaene 15,15-dioxide;

6-Chloro-15-thia-2,4,8,14,23-pentaazatetracyclo[15.3.1.1(3,7).1(9,13)]tricosa-1(21),3(23),4,6,9(22),10,12,17,19-nonaene 15,15-dioxide;

6-Chloro-2,4,8,14,23-pentaazatetracyclo[15.3.1.1(3,7).1(9,13)]tricosa-1(21),3(23),4,6,9(22),10,12,17,19-nonaen-15-one;

6-Chloro-2,4,8,16,23-pentaazatetracyclo[15.3.1.1(3,7).1(9,13)]tricosa-1(21),3(23),4,6,9(22),10,12,17,19-nonaen-15-one;

6-Chloro-2,4,8,17,22-pentaazatetracyclo[14.3.1.1(3,7).1(9,13)]docosa-1(20),3(22),4,6,9(21),10,12,16,18-nonaene;

6-Fluoro-2,4,8,17,22-pentaazatetracyclo[14.3.1.1(3,7).1(9,13)]docosa-1(20),3(22),4,6,9(21),10,12,16,18-nonaene;

(14Z)-6-Chloro-2,4,8,17,22-pentaazatetracyclo[14.3.1.1(3,7).1(9,13)]docosa-1(20),3(22),4,6,9(21),10,12,14,16,18-decaene;

6-Chloro-2,4,8,19,22-pentaazatetracyclo[14.3.1.1(3,7).1(9,13)]docosa-1(20),3(22),4,6,9(21),10,12,16,18-nonaene;

6-Fluoro-2,4,8,19,22-pentaazatetracyclo[14.3.1.1(3,7).1(9,13)]docosa-1(20),3(22),4,6,9(21),10,12,16,18-nonaene;

6-Chloro-2,4,8,20,22-pentaazatetracyclo[14.3.1.1(3,7).1(9,13)]docosa-1(20),3(22),4,6,9(21),10,12,16,18-nonaene;

6-Fluoro-2,4,8,20,22-pentaazatetracyclo[14.3.1.1(3,7).1(9,13)]docosa-1(20),3(22),4,6,9(21),10,12,16,18-nonaene;

6-Chloro-2,4,8,18,22-pentaazatetracyclo[14.3.1.1(3,7).1(9,13)]docosa-1(20),3(22),4,6,9(21),10,12,16,18-nonaene;

(14Z)-6-Chloro-2,4,8,18,22-pentaazatetracyclo[14.3.1.1(3,7).1(9,13)]docosa-1(20),3(22),4,6,9(21),10,12,14,16,18-decaene; and 6-Fluoro-2,4,8,18,22-pentaazatetracyclo[14.3.1.1(3,7).1(9,13)]docosa-1(20),3(22),4,6,9(21),10,12,16,18-nonaene, or pharmaceutically acceptable salts thereof or quaternary ammonium salt thereof.

59. A compound selected from:

6-Chloro-14-thia-2,4,8,22-tetraazatetracyclo[14.3.1.1(3,7).1(9,13)]docosa-1(20),3(22),4,6,9(21),10,12,16,18-nonaene;

6-Chloro-15-thia-2,4,8,22-tetraazatetracyclo[14.3.1.1(3,7).1(9,13)]docosa-1(20),3(22),4,6,9(21),10,12,16,18-nonaene;

6-Chloro-15-thia-2,4,8,22-tetraazatetracyclo[14.3.1.1(3,
  7).1(9,13)]docosa-1(20),3(22),4,6,9(21),10,12,16,18-
  nonaene 15-oxide;
6-Chloro-15-thia-2,4,8,22-tetraazatetracyclo[14.3.1.1(3,
  7).1(9,13)]docosa-1(20),3(22),4,6,9(21),10,12,16,18-
  nonaene 15,15-dioxide;
6-Chloro-16-oxa-2,4,8,23-tetraazatetracyclo[15.3.1.1(3,
  7).1(9,13)]tricosa-1(21),3(23),4,6,9(22),10,12,17,19-
  nonaene;
6-Chloro-15-oxa-2,4,8,22-tetraazatetracyclo[14.3.1.1(3,
  7).1(9,13)]docosa-1(20),3(22),4,6,9(21),10,12,16,18-
  nonaene;
6-Chloro-14-oxa-2,4,8,22-tetraazatetracyclo[14.3.1.1(3,
  7).1(9,13)]docosa-1(20),3(22),4,6,9(21),10,12,16,18-
  nonaene;
6-Chloro-14-oxa-2,4,8,23-tetraazatetracyclo[15.3.1.1(3,
  7).1(9,13)]tricosa-1(21),3(23),4,6,9(22),10,12,17,19-
  nonaene;
6-Chloro-8-methyl-14-oxa-2,4,8,23-tetraazatetracyclo
  [15.3.1.1(3,7).1(9,13)]tricosa-1(21),3(23),4,6,9(22),10,
  12,17,19-nonaene;
6-Chloro-14,17-dioxa-2,4,8,24-tetraazatetracyclo
  [16.3.1.1(3,7).1(9,13)]tetracosa-1(22),3(24),4,6,9(23),
  10,12,18,20-nonaene;
6-Chloro-17-oxa-14-thia-2,4,8,24-tetraazatetracyclo
  [16.3.1.1(3,7).1(9,13)]tetracosa-1(22),3(24),4,6,9(23),
  10,12,18,20-nonaene;
6-Chloro-14,15-dithia-2,4,8,22-tetraazatetracyclo
  [14.3.1.1(3,7).1(9,13)]docosa-1(20),3(22),4,6,9(21),
  10,12,16,18-nonaene;
6-Chloro-17-oxa-14-thia-2,4,8,24-tetraazatetracyclo
  [16.3.1.1(3,7).1(9,13)]tetracosa-1(22),3(24),4,6,9(23),
  10,12,18,20-nonaene 14-oxide;
6-Chloro-17-oxa-14-thia-2,4,8,24-tetraazatetracyclo
  [16.3.1.1(3,7).1(9,13)]tetracosa-1(22),3(24),4,6,9(23),
  10,12,18,20-nonaene 14,14-dioxide;
6-Chloro-14-oxa-17-thia-2,4,8,24-tetraazatetracyclo
  [16.3.1.1(3,7).1(9,13)]tetracosa-1(22),3(24),4,6,9(23),
  10,12,18,20-nonaene;
6-Chloro-2,4,8,14,22-pentaazatetracyclo[14.3.1.1(3,7).1
  (9,13)]docosa-1(20),3(22),4,6,9(21),10,12,16,18-
  nonaene;
6-Chloro-2,4,8,15,22-pentaazatetracyclo[14.3.1.1(3,7).1
  (9,13)]docosa-1(20),3(22),4,6,9(21),10,12,16,18-
  nonaene;
6-Chloro-14-thia-2,4,8,23-tetraazatetracyclo[15.3.1.1(3,
  7).1(9,13)]tricosa-1(21),3(23),4,6,9(22),10,12,17,19-
  nonaene;
6-Chloro-16-thia-2,4,8,23-tetraazatetracyclo[15.3.1.1(3,
  7).1(9,13)]tricosa-1(21),3(23),4,6,9(22),10,12,17,19-
  nonaene;
6-Chloro-15-thia-2,4,8,23-tetraazatetracyclo[15.3.1.1(3,
  7).1(9,13)]tricosa-1(21),3(23),4,6,9(22),10,12,17,19-
  nonaene;
6-Chloro-15-oxa-2,4,8,23-tetraazatetracyclo[15.3.1.1(3,
  7).1(9,13)]tricosa-1(21),3(23),4,6,9(22),10,12,17,19-
  nonaene;
19-Bromo-6-chloro-14-oxa-2,4,8,23-tetraazatetracyclo
  [15.3.1.1(3,7).1(9,13)]tricosa-1(21),3(23),4,6,9(22),10,
  12,17,19-nonaene;
6-Chloro-14-oxa-2,4,8,23-tetraazatetracyclo[15.3.1.1(3,
  7).1(9,13)]tricosa-1(21),3(23),4,6,9(22),10,12,17,19-
  nonaene 14-oxide;
6-chloro-14-thia-2,4,8,23-tetraazatetracyclo[15.3.1.1(3,7)
  .1(9,13)]tricosa-1(21),3(23),4,6,9(22),10,12,17,19-
  nonaene 14,14-dioxide;
6-Chloro-19-pyridin-4-yl-14-oxa-2,4,8,23-tetraazatetra-
  cyclo[15.3.1.1(3,7).1(9,13)]tricosa-1(21),3(23),4,6,9
  (22),10,12,17,19-nonaene;
6-Chloro-19-pyridin-3-yl-14-oxa-2,4,8,23-tetraazatetra-
  cyclo[15.3.1.1(3,7).1(9,13)]tricosa-1(21),3(23),4,6,9
  (22),10,12,17,19-nonaene;
6-Chloro-19-(2-piperazin-1-ylpyridin-4-yl)-14-oxa-2,4,8,
  23-tetraazatetracyclo[15.3.1.1(3,7).1(9,13)]tricosa-1
  (21),3(23),4,6,9(22),10,12,17,19-nonaene;
6-Chloro-19-phenyl-14-oxa-2,4,8,23-tetraazatetracyclo
  [15.3.1.1(3,7).1(9,13)]tricosa-1(21),3(23),4,6,9(22),10,
  12,17,19-nonaene;
6-Chloro-1944-(methylsulfonyl)phenyl]-14-oxa-2,4,8,
  23-tetraazatetracyclo[15.3.1.1(3,7).1(9,13)]tricosa-1
  (21),3(23),4,6,9(22),10,12,17,19-nonaene;
6-Chloro-19-(3,5-dimethyl-1H-pyrazol-4-yl)-14-oxa-2,4,
  8,23-tetraazatetracyclo[15.3.1.1(3,7).1(9,13)]tricosa-1
  (21),3(23),4,6,9(22),10,12,17,19-nonaene;
6-Chloro-19-(2-piperazin-1-ylpyrimidin-5-yl)-14-oxa-2,
  4,8,23-tetraazatetracyclo[15.3.1.1(3,7).1(9,13)]tricosa-
  1(21),3(23),4,6,9(22),10,12,17,19-nonaene;
6-Chloro-15-thia-2,4,8,24-tetraazatetracyclo[16.3.1.1(3,
  7).1(9,13)]tetracosa-1(22),3(24),4,6,9(23),10,12,18,
  20-nonaene;
6-Chloro-19-(6-piperazin-1-ylpyridin-3-yl)-14-oxa-2,4,8,
  23-tetraazatetracyclo[15.3.1.1(3,7).1(9,13)]tricosa-1
  (21),3(23),4,6,9(22),10,12,17,19-nonaene;
6-Chloro-16-thia-2,4,8,24-tetraazatetracyclo[16.3.1.1(3,
  7).1(9,13)]tetracosa-1(22),3(24),4,6,9(23),10,12,18,
  20-nonaene;
19-[2-(4-Acetylpiperazin-1-yl)pyridin-4-yl]-6-chloro-14-
  oxa-2,4,8,23-tetraazatetracyclo[15.3.1.1(3,7).1(9,13)]
  tricosa-1(21),3(23),4,6,9(22),10,12,17,19-nonaene;
6-Chloro-19-{2-[4-(methylsulfonyl)piperazin-1-yl]pyri-
  din-4-yl}-14-oxa-2,4,8,23-tetraazatetracyclo[15.3.1.1
  (3,7).1(9,13)]tricosa-1(21),3(23),4,6,9(22),10,12,17,
  19-nonaene;
19-[6-(4-Acetylpiperazin-1-yl)pyridin-3-yl]-6-chloro-14-
  oxa-2,4,8,23-tetraazatetracyclo[15.3.1.1(3,7).1(9,13)]
  tricosa-1(21),3(23),4,6,9(22),10,12,17,19-nonaene;
6-Chloro-19-{6-[4-(methylsulfonyl)piperazin-1-yl]pyri-
  din-3-yl}-14-oxa-2,4,8,23-tetraazatetracyclo[15.3.1.1
  (3,7).1(9,13)]tricosa-1(21),3(23),4,6,9(22),10,12,17,
  19-nonaene;
4-{4-[6-Chloro-14-oxa-2,4,8,23-tetraazatetracyclo
  [15.3.1.1(3,7).1(9,13)]tricosa-1(21),3(23),4,6,9(22),10,
  12,17,19-nonaen-19-yl]pyridin-2-yl}piperazine-1-car-
  boxamide;
4-{5-[6-Chloro-14-oxa-2,4,8,23-tetraazatetracyclo
  [15.3.1.1(3,7).1(9,13)]tricosa-1(21),3(23),4,6,9(22),10,
  12,17,19-nonaen-19-yl]pyridin-2-yl}piperazine-1-car-
  boxamide;
N-(tert-Butyl)-4-{4-[6-chloro-14-oxa-2,4,8,23-tetraaza-
  tetracyclo[15.3.1.1(3,7).1(9,13)]tricosa-1(21),3(23),4,
  6,9(22),10,12,17,19-nonaen-19-yl]pyridin-2-
  yl}piperazine-1-carboxamide;
4-{5-[6-Chloro-14-oxa-2,4,8,23-tetraazatetracyclo
  [15.3.1.1(3,7).1(9,13)]tricosa-1(21),3(23),4,6,9(22),10,
  12,17,19-nonaen-19-yl]pyridin-2-yl}-N-phenylpipera-
  zine-1-carboxamide;
Methyl 6-chloro-17-oxa-14-thia-2,4,8,24-tetraazatetracy-
  clo[16.3.1.1(3,7).1(9,13)]tetracosa-1(22),3(24),4,6,9
  (23),10,12,18,20-nonaene-2O-carboxylate;
4-{4-[6-Chloro-14-oxa-2,4,8,23-tetraazatetracyclo
  [15.3.1.1(3,7).1(9,13)]tricosa-1(21),3(23),4,6,9(22),10,
  12,17,19-nonaen-19-yl]pyridin-2-yl}-N-phenylpipera-
  zine-1-carboxamide;

N-Benzyl-4-{4-[6-chloro-14-oxa-2,4,8,23-tetraazatetracyclo[15.3.1.1(3,7).1(9,13)]tricosa-1(21),3(23),4,6,9(22),10,12,17,19-nonaen-19-yl]pyridin-2-yl}piperazine-1-carboxamide;

4-{4-[6-Chloro-14-oxa-2,4,8,23-tetraazatetracyclo[15.3.1.1(3,7).1(9,13)]tricosa-1(21),3(23),4,6,9(22),10,12,17,19-nonaen-19-yl]pyridin-2-yl}-N-cyclopentylpiperazine-1-carboxamide;

N-(tert-Butyl)-4-{4-[6-chloro-14-oxa-2,4,8,23-tetraazatetracyclo[15.3.1.1(3,7).1(9,13)]tricosa-1(21),3(23),4,6,9(22),10,12,17,19-nonaen-19-yl]pyridin-2-yl}piperazine-1-carboxamide;

N-Benzyl-4-{4-[6-chloro-14-oxa-2,4,8,23-tetraazatetracyclo[15.3.1.1(3,7).1(9,13)]tricosa-1(21),3(23),4,6,9(22),10,12,17,19-nonaen-19-yl]pyridin-2-yl}piperazine-1-carboxamide;

4-{4-[6-Chloro-14-oxa-2,4,8,23-tetraazatetracyclo[15.3.1.1(3,7).1(9,13)]tricosa-1(21),3(23),4,6,9(22),10,12,17,19-nonaen-19-yl]pyridin-2-yl}-N-cyclopentylpiperazine-1-carboxamide;

6-Chloro-N-phenyl-17-oxa-14-thia-2,4,8,24-tetraazatetracyclo[16.3.1.1(3,7).1(9,13)]tetracosa-1(22),3(24),4,6,9(23),10,12,18,20-nonaene-2O-carboxamide;

N-Benzyl-6-chloro-17-oxa-14-thia-2,4,8,24-tetraazatetracyclo[16.3.1.1(3,7).1(9,13)]tetracosa-1(22),3(24),4,6,9(23),10,12,18,20-nonaene-2O-carboxamide;

4-{4-[6-Chloro-14-oxa-2,4,8,23-tetraazatetracyclo[15.3.1.1(3,7).1(9,13)]tricosa-1(21),3(23),4,6,9(22),10,12,17,19-nonaen-19-yl]pyridin-2-yl}-N-cyclopentylpiperazine-1-carboxamide;

6-Chloro-20-[(4-phenylpiperazin-1-yl)carbonyl]-17-oxa-14-thia-2,4,8,24-tetraazatetracyclo[16.3.1.1(3,7).1(9,13)]tetracosa-1(22),3(24),4,6,9(23),10,12,18,20-nonaene;

6-Chloro-N-1,3-thiazol-2-yl-17-oxa-14-thia-2,4,8,24-tetraazatetracyclo[16.3.1.1(3,7).1(9,13)]tetracosa-1(22),3(24),4,6,9(23),10,12,18,20-nonaene-2O-carboxamide;

6-Chloro-N-(1-methyl-1H-benzimidazol-2-yl)-17-oxa-14-thia-2,4,8,24-tetraazatetracyclo[16.3.1.1(3,7).1(9,13)]tetracosa-1(22),3(24),4,6,9(23),10,12,18,20-nonaene-2O-carboxamide;

6-Chloro-N-1H-indol-5-yl-17-oxa-14-thia-2,4,8,24-tetraazatetracyclo[16.3.1.1(3,7).1(9,13)]tetracosa-1(22),3(24),4,6,9(23),10,12,18,20-nonaene-2O-carboxamide;

N-[6-Chloro-17-oxa-14-thia-2,4,8,24-tetraazatetracyclo[16.3.1.1(3,7).1(9,13)]tetracosa-1(22),3(24),4,6,9(23),10,12,18,20-nonaen-20-yl]benzamide;

N-[6-Chloro-17-oxa-14-thia-2,4,8,24-tetraazatetracyclo[16.3.1.1(3,7).1(9,13)]tetracosa-1(22),3(24),4,6,9(23),10,12,18,20-nonaen-20-yl]-5-methylisoxazole-3-carboxamide;

N-[6-Chloro-17-oxa-14-thia-2,4,8,24-tetraazatetracyclo[16.3.1.1(3,7).1(9,13)]tetracosa-1(22),3(24),4,6,9(23),10,12,18,20-nonaen-20-yl]isoxazole-5-carboxamide;

N-[6-Chloro-17-oxa-14-thia-2,4,8,24-tetraazatetracyclo[16.3.1.1(3,7).1(9,13)]tetracosa-1(22),3(24),4,6,9(23),10,12,18,20-nonaen-20-yl]isonicotinamide;

N-[6-Chloro-17-oxa-14-thia-2,4,8,24-tetraazatetracyclo[16.3.1.1(3,7).1(9,13)]tetracosa-1(22),3(24),4,6,9(23),10,12,18,20-nonaen-20-yl]-1-benzofuran-5-carboxamide;

N-[6-Chloro-17-oxa-14-thia-2,4,8,24-tetraazatetracyclo[16.3.1.1(3,7).1(9,13)]tetracosa-1(22),3(24),4,6,9(23),10,12,18,20-nonaen-20-yl]-2-furamide;

N-[6-Chloro-17-oxa-14-thia-2,4,8,24-tetraazatetracyclo[16.3.1.1(3,7).1(9,13)]tetracosa-1(22),3(24),4,6,9(23),10,12,18,20-nonaen-20-yl]thiophene-2-carboxamide;

N-[6-Chloro-17-oxa-14-thia-2,4,8,24-tetraazatetracyclo[16.3.1.1(3,7).1(9,13)]tetracosa-1(22),3(24),4,6,9(23),10,12,18,20-nonaen-20-yl]thiophene-2-carboxamide;

N-[6-Chloro-17-oxa-14-thia-2,4,8,24-tetraazatetracyclo[16.3.1.1(3,7).1(9,13)]tetracosa-1(22),3(24),4,6,9(23),10,12,18,20-nonaen-20-yl]-N'-phenylurea;

N-Benzyl-N'-[6-chloro-17-oxa-14-thia-2,4,8,24-tetraazatetracyclo[16.3.1.1(3,7).1(9,13)]tetracosa-1(22),3(24),4,6,9(23),10,12,18,20-nonaen-20-yl]urea;

N-[6-Chloro-17-oxa-14-thia-2,4,8,24-tetraazatetracyclo[16.3.1.1(3,7).1(9,13)]tetracosa-1(22),3(24),4,6,9(23),10,12,18,20-nonaen-20-yl]-N'-(2-furylmethyl)urea;

N-[6-Chloro-17-oxa-14-thia-2,4,8,24-tetraazatetracyclo[16.3.1.1(3,7).1(9,13)]tetracosa-1(22),3(24),4,6,9(23),10,12,18,20-nonaen-20-yl]benzenesulfonamide;

N-[6-Chloro-17-oxa-14-thia-2,4,8,24-tetraazatetracyclo[16.3.1.1(3,7).1(9,13)]tetracosa-1(22),3(24),4,6,9(23),10,12,18,20-nonaen-20-yl]-1,2-dimethyl-1H-imidazole-4-sulfonamide;

6-Chloro-14-oxa-2,4,8,17,24-pentaazatetracyclo[16.3.1.1(3,7).1(9,13)]tetracosa-1(22),3(24),4,6,9(23),10,12,18,20-nonaene;

15-Acetyl-6-chloro-2,4,8,15,22-pentaazatetracyclo[14.3.1.1(3,7).1(9,13)]docosa-1(20),3(22),4,6,9(21),10,12,16,18-nonaene;

6-Chloro-17-oxa-2,4,8,14,24-pentaazatetracyclo[16.3.1.1(3,7).1(9,13)]tetracosa-1(22),3(24),4,6,9(23),10,12,18,20-nonaene;

6-Chloro-2,4,8,15,23-pentaazatetracyclo[15.3.1.1(3,7).1(9,13)]tricosa-1(21),3(23),4,6,9(22),10,12,17,19-nonaene;

15-Acetyl-6-chloro-2,4,8,15,23-pentaazatetracyclo[15.3.1.1(3,7).1(9,13)]tricosa-1(21),3(23),4,6,9(22),10,12,17,19-nonaene;

6-Chloro-2,4,8,14,24-pentaazatetracyclo[16.3.1.1(3,7).1(9,13)]tetracosa-1(22),3(24),4,6,9(23),10,12,18,20-nonaene;

6-Chloro-2,4,8,17,24-pentaazatetracyclo[16.3.1.1(3,7).1(9,13)]tetracosa-1(22),3(24),4,6,9(23),10,12,18,20-nonaen-16-one;

6-Chloro-2,4,8,17,24-pentaazatetracyclo[16.3.1.1(3,7).1(9,13)]tetracosa-1(22),3(24),4,6,9(23),10,12,18,20-nonaene;

6-Chloro-2,4,8,16,23-pentaazatetracyclo[15.3.1.1(3,7).1(9,13)]tricosa-1(21),3(23),4,6,9(22),10,12,17,19-nonaene;

6-Chloro-2,4,8,16,23-pentaazatetracyclo[15.3.1.1(3,7).1(9,13)]tricosa-1(21),3(23),4,6,9(22),10,12,17,19-nonaene;

6-Chloro-14-thia-2,4,8,17,24-pentaazatetracyclo[16.3.1.1(3,7).1(9,13)]tetracosa-1(22),3(24),4,6,9(23),10,12,18,20-nonaene;

6-Chloro-17-oxa-14-thia-2,4,8,24-tetraazatetracyclo[16.3.1.1(3,7).1(9,13)]tetracosa-1(22),3(24),4,6,9(23),10,12,18,20-nonaene-19-carbonitrile;

6-Chloro-17-oxa-14-thia-2,4,8,24-tetraazatetracyclo[16.3.1.1(3,7).1(9,13)]tetracosa-1(22),3(24),4,6,9(23),10,12,18,20-nonaene-19-carbonitrile;

6-Chloro-12-piperazin-1-yl-2,4,8,22-tetraazatetracyclo[14.3.1.1(3,7).1(9,13)]docosa-1(20),3(22),4,6,9(21),10,12,16,18-nonaene;

N-(tert-Butyl)-4-[6-chloro-2,4,8,22-tetraazatetracyclo[14.3.1.1(3,7).1(9,13)]docosa-1(20),3(22),4,6,9(21),10,12,16,18-nonaen-12-yl]piperazine-1-carboxamide;

12-(4-Acetylpiperazin-1-yl)-6-chloro-2,4,8,22-tetraazatetracyclo[14.3.1.1(3,7).1(9,13)]docosa-1(20),3(22),4,6,9(21),10,12,16,18-nonaene;

4-[6-Chloro-2,4,8,22-tetraazatetracyclo[14.3.1.1(3,7).1(9,13)]docosa-1(20),3(22),4,6,9(21),10,12,16,18-nonaen-12-yl]piperazine-1-carboxamide;

1-[6-Chloro-2,4,8,22-tetraazatetracyclo[14.3.1.1(3,7).1(9,13)]docosa-1(20),3(22),4,6,9(21),10,12,16,18-nonaen-12-yl]pyrrolidin-3-amine;

4-[6-Chloro-2,4,8,22-tetraazatetracyclo[14.3.1.1(3,7).1(9,13)]docosa-1(20),3(22),4,6,9(21),10,12,16,18-nonaen-12-yl]-N-(3-cyanophenyl)piperazine-1-carboxamide;

4-[6-Chloro-2,4,8,22-tetraazatetracyclo[14.3.1.1(3,7).1(9,13)]docosa-1(20),3(22),4,6,9(21),10,12,16,18-nonaen-12-yl]-N44-(trifluoromethyl)phenyl]piperazine-1-carboxamide;

4-[6-Chloro-2,4,8,22-tetraazatetracyclo[14.3.1.1(3,7).1(9,13)]docosa-1(20),3(22),4,6,9(21),10,12,16,18-nonaen-12-yl]-N43-(trifluoromethyl)phenyl]piperazine-1-carboxamide;

4-[6-Chloro-2,4,8,22-tetraazatetracyclo[14.3.1.1(3,7).1(9,13)]docosa-1(20),3(22),4,6,9(21),10,12,16,18-nonaen-12-yl]-N-phenylpiperazine-1-carboxamide;

4-[6-Chloro-2,4,8,22-tetraazatetracyclo[14.3.1.1(3,7).1(9,13)]docosa-1(20),3(22),4,6,9(21),10,12,16,18-nonaen-12-yl]-N-(4-cyanophenyl)piperazine-1-carboxamide;

12-(4-Benzoylpiperazin-1-yl)-6-chloro-2,4,8,22-tetraazatetracyclo[14.3.1.1(3,7).1(9,13)]docosa-1(20),3(22),4,6,9(21),10,12,16,18-nonaene;

4-({4-[6-Chloro-2,4,8,22-tetraazatetracyclo[14.3.1.1(3,7).1(9,13)]docosa-1(20),3(22),4,6,9(21),10,12,16,18-nonaen-12-yl]piperazin-1-yl}carbonyl)benzonitrile; and 6-Chloro-12-{4-[4-(trifluoromethyl)benzoyl]piperazin-1-yl}-2,4,8,22-tetraazatetracyclo[14.3.1.1(3,7).1(9,13)]docosa-1(20),3(22),4,6,9(21),10,12,16,18-nonaene, or pharmaceutically acceptable salts thereof or quaternary ammonium salt thereof, or 4-[6-Chloro-2,4,8,22-tetraazatetracyclo[14.3.1.1(3,7).1(9,13)]docosa-1(20),3(22),4,6,9(21),10,12,16,18-nonaen-12-yl]-1,1-dimethylpiperazin-1-ium bis(trifluoroacetate).

60. A compound selected from:

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(3,5-dimethylisoxazol-4-yl)carbonyl]piperidin-4-yl}acetamide;

2-[1-(1,3-Benzothiazol-2-yl)piperidin-4-yl]-N-[6-chloro-2,4,8,18,22-pentaazatetracyclo[14.3.1.1(3,7).1(9,13)]docosa-1(20),3(22),4,6,9(21),10,12,16,18-nonaen-12-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-(1-[1,3]oxazolo[5,4-b]pyridin-2-ylpiperidin-4-yl)acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(1,3-thiazol-2-yl)piperidin-4-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(2-methyl-3-furoyl)piperidin-4-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(3-methyl-2-furoyl)piperidin-4-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(5-methyl-2-furoyl)piperidin-4-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{14(5-methyl-1H-pyrazol-3-yl)carbonyl]piperidin-4-yl}acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{14(1-methyl-1H-imidazol-2-yl)carbonyl]piperidin-4-yl}acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(3-methylisoxazol-4-yl)carbonyl]piperidin-4-yl}acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(4-methyl-1,2,5-oxadiazol-3-yl)carbonyl]piperidin-4-yl}acetamide;

2-{1-[(4-Amino-1,2,5-oxadiazol-3-yl)carbonyl]piperidin-4-yl}-N-[6-chloro-2,4,8,18,22-pentaazatetracyclo[14.3.1.1(3,7).1(9,13)]docosa-1(20),3(22),4,6,9(21),10,12,16,18-nonaen-12-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(isothiazol-5-ylcarbonyl)piperidin-4-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(5-fluoropyrimidin-2-yl)piperidin-4-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-(1-pyridin-2-ylpiperidin-4-yl)acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-(1-pyrazin-2-ylpiperidin-4-yl)acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-(1-pyrimidin-2-ylpiperidin-4-yl)acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(6-methylpyridazin-3-yl)piperidin-4-yl]acetamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-[1-(1,3,4-thiadiazol-2-yl)piperidin-4-yl]acetamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-{1-[(5-methyl-1H-pyrazol-3-yl)carbonyl]piperidin-4-yl}acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(4-methylpyridin-2-yl)piperidin-4-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(3-cyanopyridin-2-yl)piperidin-4-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(4-cyanopyridin-2-yl)piperidin-4-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(5-cyanopyridin-2-yl)piperidin-4-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(6-chloropyridin-2-yl)piperidin-4-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(6-fluoropyridin-2-yl)piperidin-4-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(2-methylpyrimidin-4-yl)piperidin-4-yl]acetamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-[1-(1,3,4-thiadiazol-2-yl)piperidin-4-yl]acetamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-[1-(pyridin-3-ylcarbonyl)piperidin-4-yl]acetamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-(1-isonicotinoylpiperidin-4-yl)acetamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-[1-(4-cyanobenzoyl)piperidin-4-yl]acetamide trifluoroacetate;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-[1-(3-cyanobenzoyl)piperidin-4-yl]acetamide trifluoroacetate;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(pyridin-3-ylcarbonyl)piperidin-4-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-(1-isonicotinoylpiperidin-4-yl)acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(4-cyanobenzoyl)piperidin-4-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(3-cyanobenzoyl)piperidin-4-yl]acetamide;

2-(1-Benzoylpiperidin-4-yl)-N-[6-chloro-2,4,8,18,22-pentaazatetracyclo[14.3.1.1(3,7).1(9,13)]docosa-1(20),3(22),4,6,9(21),10,12,16,18-nonaen-12-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(4-fluorobenzoyl)piperidin-4-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(2,4-difluorobenzoyl)piperidin-4-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(phenylsulfonyl)piperidin-4-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(3-methoxyphenyl)sulfonyl]piperidin-4-yl}acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(4-methoxyphenyl)sulfonyl]piperidin-4-yl}acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(2-cyanophenyl)sulfonyl]piperidin-4-yl}acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(4-cyanophenyl)sulfonyl]piperidin-4-yl}acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(5-methylisoxazol-4-yl)sulfonyl]piperidin-4-yl}acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(2-furylsulfonyl)piperidin-4-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(pyridin-3-ylsulfonyl)piperidin-4-yl]acetamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-[1-(4-fluorobenzoyl)piperidin-4-yl]acetamide trifluoroacetate;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-[1-(2,4-difluorobenzoyl)piperidin-4-yl]acetamide trifluoroacetate;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-[1-(phenylsulfonyl)piperidin-4-yl]acetamide trifluoroacetate;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-{1-[(3-methoxyphenyl)sulfonyl]piperidin-4-yl}acetamide trifluoroacetate;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-{1-[(4-methoxyphenyl)sulfonyl]piperidin-4-yl}acetamide trifluoroacetate;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-{1-[(2-cyanophenyl)sulfonyl]piperidin-4-yl}acetamide trifluoroacetate;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-{1-[(4-cyanophenyl)sulfonyl]piperidin-4-yl}acetamide trifluoroacetate;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-{1-[(5-methylisoxazol-4-yl)sulfonyl]piperidin-4-yl}acetamide trifluoroacetate;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-[1-(2-furylsulfonyl)piperidin-4-yl]acetamide trifluoroacetate;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-[1-(pyridin-3-ylsulfonyl)piperidin-4-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(5-cyclopropylisoxazol-4-yl)carbonyl]piperidin-4-yl}acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(5-isopropylisoxazol-3-yl)carbonyl]piperidin-4-yl}acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(3-methoxyisoxazol-5-yl)carbonyl]piperidin-4-yl}acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(4-methyl-1,3-thiazol-5-yl)carbonyl]piperidin-4-yl}acetamide;

2-{1-[(2-Amino-1,3-thiazol-4-yl)carbonyl]piperidin-4-yl}-N-[6-chloro-2,4,8,18,22-pentaazatetracyclo[14.3.1.1(3,7).1(9,13)]docosa-1(20),3(22),4,6,9(21),10,12,16,18-nonaen-12-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(5-isopropylisoxazol-4-yl)carbonyl]piperidin-4-yl}acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-(1-phenylpiperidin-4-yl)acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(2-cyanophenyl)piperidin-4-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(4-cyanophenyl)piperidin-4-yl]acetamide;

2-[1-(3-Chloro-2-cyanophenyl)piperidin-4-yl]-N-[6-chloro-2,4,8,18,22-pentaazatetracyclo[14.3.1.1(3,7).1(9,13)]docosa-1(20),3(22),4,6,9(21),10,12,16,18-nonaen-12-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(2-chlorophenyl)sulfonyl]piperidin-4-yl}acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-(1-{[2-(trifluoromethyl)phenyl]sulfonyl}piperidin-4-yl)acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(2-methylphenyl)sulfonyl]piperidin-4-yl}acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(2-fluorophenyl)sulfonyl]piperidin-4-yl}acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-(1-{[2-(trifluoromethoxy)phenyl]sulfonyl}piperidin-4-yl)acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(3-cyanophenyl)sulfonyl]piperidin-4-yl}acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(1-methyl-1H-imidazol-4-yl)sulfonyl]piperidin-4-yl}acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(1,2-dimethyl-1H-imidazol-4-yl)sulfonyl]piperidin-4-yl}acetamide;

N-[6-chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(3,5-dimethylisoxazol-4-yl)sulfonyl]piperidin-4-yl}acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[(2,4-dimethyl-1,3-thiazol-5-yl)sulfonyl]piperidin-4-yl}acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(2-cyano-3-methoxyphenyl)piperidin-4-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(2-cyano-3-fluorophenyl)piperidin-4-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[2-cyano-3-(trifluoromethyl)phenyl]piperidin-4-yl}acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(2-cyano-3-methylphenyl)piperidin-4-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{1-[2-cyano-5-(trifluoromethyl)phenyl]piperidin-4-yl}acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(3-cyano-6-methylpyridin-2-yl)piperidin-4-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(3-cyano-4,6-dimethylpyridin-2-yl)piperidin-4-yl]acetamide;

2-[1-(5-Chloro-4-cyanopyridin-3-yl)piperidin-4-yl]-N-[6-chloro-2,4,8,18,22-pentaazatetracyclo[14.3.1.1(3,7).1(9,13)]docosa-1(20),3(22),4,6,9(21),10,12,16,18-nonaen-12-yl]acetamide;

2-[1-(6-Chloro-3-cyano-5-fluoropyridin-2-yl)piperidin-4-yl]-N-[6-chloro-2,4,8,18,22-pentaazatetracyclo[14.3.1.1(3,7).1(9,13)]docosa-1(20),3(22),4,6,9(21),10,12,16,18-nonaen-12-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-(1-pyridin-4-ylpiperidin-4-yl)acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(3-fluoropyridin-4-yl)piperidin-4-yl]acetamide;

N-[6-Chloro-2,4,8,18,22-pentaazatetracyclo[14.3.1.1(3, 7).1(9,13)]docosa-1(20),3(22),4,6,9(21),10,12,16,18-nonaen-12-yl]-2-[1-(2-fluoropyridin-4-yl)piperidin-4-yl]acetamide;

N-[6-Chloro-2,4,8,18,22-pentaazatetracyclo[14.3.1.1(3, 7).1(9,13)]docosa-1(20),3(22),4,6,9(21),10,12,16,18-nonaen-12-yl]-2-[1-(cyanoacetyl)piperidin-4-yl]acetamide;

N-[6-Chloro-2,4,8,18,22-pentaazatetracyclo[14.3.1.1(3, 7).1(9,13)]docosa-1(20),3(22),4,6,9(21),10,12,16,18-nonaen-12-yl]-2-[1(1,3-oxazol-2-yl)piperidin-4-yl]acetamide;

N-[6-Chloro-2,4,8,18,22-pentaazatetracyclo[14.3.1.1(3, 7).1(9,13)]docosa-1(20),3(22),4,6,9(21),10,12,16,18-nonaen-12-yl]-2-[1-(5-methylisoxazol-3-yl)piperidin-4-yl]acetamide;

N-[6-Chloro-2,4,8,22-tetraazatetracyclo[14.3.1.1(3,7).1 (9,13)]docosa-1(20),3(22),4,6,9(21),10,12,16,18-nonaen-12-yl]-2-[1-(5-methylisoxazol-3-yl)piperidin-4-yl]acetamide trifluoroacetate;

6-Chloro-12-{2-oxo-2-[3-(trifluoromethyl)-5,6-dihydro[1,2,4]triazolo[4,3-a]pyrazin-7(8H)-yl]ethoxy}-2,4,8, 18,22pentaazatetracyclo[14.3.1.1(3,7).1(9,13)]docosa 1(20),3(22),4,6,9(21),10,12,16,18-nonaene;

tert-Butyl [(3R)-1-({[6-chloro-2,4,8,22-tetraazatetracyclo [14.3.1.1(3,7).1(9,13)]docosa-1(20),3(22),4,6,9(21), 10,12,16,18-nonaen-12-yl]amino}carbonyl)pyrrolidin-3-yl]carbamate;

tert-Butyl 3-[({[6-chloro-2,4,8,22-tetraazatetracyclo [14.3.1.1(3,7).1(9,13)]docosa-1(20),3(22),4,6,9(21), 10,12,16,18-nonaen-12-yl]amino}carbonyl)amino]piperidine-1-carboxylate;

N-[6-Chloro-2,4,8,22-tetraazatetracyclo[14.3.1.1(3,7).1 (9,13)]docosa-1(20),3(22),4,6,9(21),10,12,16,18-nonaen-12-yl]-N'-piperidin-3-ylurea;

N'-[6-Chloro-2,4,8,22-tetraazatetracyclo[14.3.1.1(3,7).1 (9,13)]docosa-1(20),3(22),4,6,9(21),10,12,16,18-nonaen-12-yl]-N,N-dimethylurea;

N-[6-Chloro-2,4,8,22-tetraazatetracyclo[14.3.1.1(3,7).1 (9,13)]docosa-1(20),3(22),4,6,9(21),10,12,16,18-nonaen-12-yl]-N'-cyclopropylurea;

N-[6-Chloro-2,4,8,22-tetraazatetracyclo[14.3.1.1(3,7).1 (9,13)]docosa-1(20),3(22),4,6,9(21),10,12,16,18-nonaen-12-yl]-N'-(2-hydroxyethyl)urea;

N-[6-Chloro-2,4,8,22-tetraazatetracyclo[14.3.1.1(3,7).1 (9,13)]docosa-1(20),3(22),4,6,9(21),10,12,16,18-nonaen-12-yl]-N'-(2-hydroxy-1-methylethyl)urea;

N-[6-Chloro-2,4,8,22-tetraazatetracyclo[14.3.1.1(3,7).1 (9,13)]docosa-1(20),3(22),4,6,9(21),10,12,16,18-nonaen-12-yl]-N'-(2-methoxyethyl)urea;

N-[6-Chloro-2,4,8,22-tetraazatetracyclo[14.3.1.1(3,7).1 (9,13)]docosa-1(20),3(22),4,6,9(21),10,12,16,18-nonaen-12-yl]-N'-1H-1,2,4-triazol-3-ylurea;

N-[6-Chloro-2,4,8,22-tetraazatetracyclo[14.3.1.1(3,7).1 (9,13)]docosa-1(20),3(22),4,6,9(21),10,12,16,18-nonaen-12-yl]-N'-1,3-thiazol-2-ylurea;

N-[6-Chloro-2,4,8,22-tetraazatetracyclo[14.3.1.1(3,7).1 (9,13)]docosa-1(20),3(22),4,6,9(21),10,12,16,18-nonaen-12-yl]-N'-(pyridin-4-ylmethyl)urea;

N-[6-Chloro-2,4,8,22-tetraazatetracyclo[14.3.1.1(3,7).1 (9,13)]docosa-1(20),3(22),4,6,9(21),10,12,16,18-nonaen-12-yl]-N'-(2-methoxy-1-methylethyl)urea;

N-[6-Chloro-2,4,8,22-tetraazatetracyclo[14.3.1.1(3,7).1 (9,13)]docosa-1(20),3(22),4,6,9(21),10,12,16,18-nonaen-12-yl]-N'-(5-methyl-1,3-thiazol-2-yl)urea;

N-[6-Chloro-2,4,8,22-tetraazatetracyclo[14.3.1.1(3,7).1 (9,13)]docosa-1(20),3(22),4,6,9(21),10,12,16,18-nonaen-12-yl]-N'-(4-methyl-1,3-thiazol-2-yl)urea;

2-[({[6-Chloro-2,4,8,22-tetraazatetracyclo[14.3.1.1(3,7) .1(9,13)]docosa-1(20),3(22),4,6,9(21),10,12,16,18-nonaen-12-yl]amino}carbonyl)amino]-1,3-thiazole-4-carboxylic acid;

N-[6-Chloro-2,4,8,22-tetraazatetracyclo[14.3.1.1(3,7).1 (9,13)]docosa-1(20),3(22),4,6,9(21),10,12,16,18-nonaen-12-yl]-N'-1H-tetrazol-5-ylurea;

N-[6-Chloro-2,4,8,22-tetraazatetracyclo[14.3.1.1(3,7).1 (9,13)]docosa-1(20),3(22),4,6,9(21),10,12,16,18-nonaen-12-yl]-N'-(5-chloro-1,3-thiazol-2-yl)urea;

N-[6-Chloro-2,4,8,22-tetraazatetracyclo[14.3.1.1(3,7).1 (9,13)]docosa-1(20),3(22),4,6,9(21),10,12,16,18-nonaen-12-yl]-N'-pyridin-2-ylurea;

N-[6-Chloro-2,4,8,22-tetraazatetracyclo[14.3.1.1(3,7).1 (9,13)]docosa-1(20),3(22),4,6,9(21),10,12,16,18-nonaen-12-yl]-N'-(2-morpholin-4-ylethyl)urea;

N-[6-Chloro-2,4,8,22-tetraazatetracyclo[14.3.1.1(3,7).1 (9,13)]docosa-1(20),3(22),4,6,9(21),10,12,16,18-nonaen-12-yl]-N'-(2-pyrrolidin-1-ylethyl)urea;

N-[6-Chloro-2,4,8,22-tetraazatetracyclo[14.3.1.1(3,7).1 (9,13)]docosa-1(20),3(22),4,6,9(21),10,12,16,18-nonaen-12-yl]-N'42-(1-methylpyrrolidin-2-yl)ethyl]urea;

N-[6-Chloro-2,4,8,22-tetraazatetracyclo[14.3.1.1(3,7).1 (9,13)]docosa-1(20),3(22),4,6,9(21),10,12,16,18-nonaen-12-yl]-N'-[2-(2-oxopyrrolidin-1-yl)ethyl]urea;

N-[6-Chloro-2,4,8,22-tetraazatetracyclo[14.3.1.1(3,7).1 (9,13)]docosa-1(20),3(22),4,6,9(21),10,12,16,18-nonaen-12-yl]-N'-(2-piperidin-1-ylethyl)urea;

tert-Butyl 4-{2-[({[6-chloro-2,4,8,22-tetraazatetracyclo [14.3.1.1(3,7).1(9,13)]docosa-1(20),3(22),4,6,9(21), 10,12,16,18-nonaen-12-yl]amino}carbonyl)amino] ethyl}piperazine-1-carboxylate;

N-[6-Chloro-2,4,8,22-tetraazatetracyclo[14.3.1.1(3,7).1 (9,13)]docosa-1(20),3(22),4,6,9(21),10,12,16,18-nonaen-12-yl]-N'-(2-piperazin-1-ylethyl)urea;

N-[6-Chloro-2,4,8,22-tetraazatetracyclo[14.3.1.1(3,7).1 (9,13)]docosa-1(20),3(22),4,6,9(21),10,12,16,18-nonaen-12-yl]-N'-[(3S)-1-methylpyrrolidin-3-yl]urea;

N-[6-Chloro-2,4,8,22-tetraazatetracyclo[14.3.1.1(3,7).1 (9,13)]docosa-1(20),3(22),4,6,9(21),10,12,16,18-nonaen-12-yl]-N'-[(3S)-1-pyrimidin-2-ylpyrrolidin-3-yl]urea;

N-[6-Chloro-2,4,8,22-tetraazatetracyclo[14.3.1.1(3,7).1 (9,13)]docosa-1(20),3(22),4,6,9(21),10,12,16,18-nonaen-12-yl]-N'-{1-[(5-methylisoxazol-3-yl)carbonyl]piperidin-4-yl}urea;

N-[6-chloro-2,4,8,22-tetraazatetracyclo[14.3.1.1(3,7).1 (9,13)]docosa-1(20),3(22),4,6,9(21),10,12,16,18-nonaen-12-yl]-N'-{1-[(5-methylisoxazol-4-yl)carbonyl]piperidin-4-yl}urea;

N-[6-Chloro-2,4,8,18,22-pentaazatetracyclo[14.3.1.1(3, 7).1(9,13)]docosa-1(20),3(22),4,6,9(21),10,12,16,18-nonaen-12-yl]-N'-{(3S)-1-[(5-methylisoxazol-3-yl) carbonyl]pyrrolidin-3-yl}urea;

N-[6-Chloro-2,4,8,18,22-pentaazatetracyclo[14.3.1.1(3, 7).1(9,13)]docosa-1(20),3(22),4,6,9(21),10,12,16,18-nonaen-12-yl]-N'-{(3S)-1-[(5-methylisoxazol-4-yl) carbonyl]pyrrolidin-3-yl}urea;

N-[6-chloro-2,4,8,18,22-pentaazatetracyclo[14.3.1.1(3,7) .1(9,13)]docosa-1(20),3(22),4,6,9(21),10,12,16,18-nonaen-12-yl]-N'-[(3S)-1-(1H-pyrazol-4-ylcarbonyl) pyrrolidin-3-yl]urea;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-N'-[(3S)-1-(1H-pyrazol-5-ylcarbonyl)pyrrolidin-3-yl]urea;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-N'-{(3S)-1-[(1-methyl-1H-pyrazol-4-yl)carbonyl]pyrrolidin-3-yl}urea;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-N'-{(3S)-1-[(5-cyclopropylisoxazol-3-yl)carbonyl]pyrrolidin-3-yl}urea;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-N'-[(3S)-1-(isoxazol-5-ylcarbonyl)pyrrolidin-3-yl]urea;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-N'-{(3S)-1-[(1-methyl-1H-pyrazol-3-yl)carbonyl]pyrrolidin-3-yl}urea;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-N'-{(3S)-1-[(4-methyl-1,3-oxazol-5-yl)carbonyl]pyrrolidin-3-yl}urea;

N-[6-chloro-2,4,8,18,22-pentaazatetracyclo[14.3.1.1(3,7). 1(9,13)]docosa-1(20),3(22),4,6,9(21),10,12,16,18-nonaen-12-yl]-N'-{(3S)-1-[(3,5-dimethylisoxazol-4-yl)carbonyl]pyrrolidin-3-yl}urea;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-N'-[(3S)-1-[1,3]oxazolo[5,4-b]pyridin-2-ylpyrrolidin-3-yl]urea;

6-Chloro-N-(4-methylpyrimidin-2-yl)-2,4, 8,22-tetraazatetracyclo[14.3.1.1(3,7).1(9,13)]docosa-1(20),3(22),4,6,9(21),10,12,16,18-nonaen-12-amine;

2-{[6-Chloro-2,4,8,22-tetraazatetracyclo[14.3.1.1(3,7).1(9,13)]docosa-1(20),3(22),4,6,9(21),10,12,16,18-nonaen-12-yl]amino}pyrimidin-4-ol;

Ethyl 2-{[6-chloro-2,4,8,22-tetraazatetracyclo[14.3.1.1(3,7).1(9,13)]docosa-1(20),3(22),4,6,9(21),10,12,16,18-nonaen-12-yl]amino}-1,3-oxazole-4-carboxylate;

6-Chloro-N-(4-phenylpyrimidin-2-yl)-2,4, 8,22-tetraazatetracyclo[14.3.1.1(3,7).1(9,13)]docosa-1(20),3(22),4,6,9(21),10,12,16,18-nonaen-12-amine;

2-Chloro-N-[6-chloro-2,4,8,22-tetraazatetracyclo[14.3.1.1(3,7).1(9,13)]docosa-1(20),3(22),4,6,9(21),10,12,16,18-nonaen-12-yl]-6-methylpyrimidine-4-carboxamide;

N-[4-(4-Aminopiperidin-1-yl)pyrimidin-2-yl]-6-chloro-2,4,8,22-tetraazatetracyclo[14.3.1.1(3,7).1(9,13)]docosa-1(20),3(22),4,6,9(21),10,12,16,18-nonaen-12-amine;

N-[4-(4-Aminopiperidin-1-yl)pyrimidin-2-yl]-6-chloro-2,4, 8,18,22-pentaazatetracyclo[14.3.1.1(3,7).1(9,13)]docosa-1(20),3(22),4,6,9(21),10,12,16,18-nonaen-12-amine;

N-[(3S)-1-Benzylpyrrolidin-3-yl]-N'-[6-chloro-2,4,8,22-tetraazatetracyclo[14.3.1.1(3,7).1(9,13)]docosa-1(20),3(22),4,6,9(21),10,12,16,18-nonaen-12-yl]-N-methylurea;

N-[(3S)-1-Benzylpyrrolidin-3-yl]-N'-[6-chloro-2,4, 8, 18,22-pentaazatetracyclo[14.3.1.1(3,7).1(9,13)]docosa-1(20),3(22),4,6,9(21),10,12,16,18-nonaen-12-yl]-N-methylurea;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]piperazine-1-carboxamide;

4-Benzoyl-N-[6-chloro-2,4,8,18,22-pentaazatetracyclo[14.3.1.1(3,7).1(9,13)]docosa-1(20),3(22),4,6,9(21),10,12,16,18-nonaen-12-yl]piperazine-1-carboxamide;

4-Benzyl-N-[6-chloro-2,4,8,18,22-pentaazatetracyclo[14.3.1.1(3,7).1(9,13)]docosa-1(20),3(22),4,6,9(21),10,12,16,18-nonaen-12-yl]piperazine-1-carboxamide;

N'-[6-Chloro-2,4,8,18,22-pentaazatetracyclo[14.3.1.1(3,7).1(9,13)]docosa-1(20),3(22),4,6,9(21),10,12,16,18-nonaen-12-A-N-methyl-N-[(3S)-pyrrolidin-3-yl]urea;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-4-pyridin-2-ylpiperazine-1-carboxamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-4-pyridin-2-ylpiperazine-1-carboxamide;

N-[(3S)-1-Benzoylpyrrolidin-3-yl]-N'-[6-chloro-2,4,8,18,22-pentaazatetracyclo[14.3.1.1(3,7).1(9,13)]docosa-1(20),3(22),4,6,9(21),10,12,16,18-nonaen-12-yl]-N-methylurea;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-4-phenylpiperazine-1-carboxamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-4-pyridin-4-ylpiperazine-1-carboxamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-4-pyrazin-2-ylpiperazine-1-carboxamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-4-(2-fluorophenyl)piperazine-1-carboxamide;

6-Chloro-N-[4-(hexahydropyrrolo[1,2-a]pyrazin-2(1H)-ylcarbonyl)-1,3-oxazol-2-yl]-2,4,8,22-tetraazatetracyclo[14.3.1.1(3,7).1(9,13)]docosa-1(20),3(22),4,6,9(21),10,12,16,18-nonaen-12-amine;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-4-(4-fluorophenyl)piperazine-1-carboxamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-4-(2-methoxyphenyl)piperazine-1-carboxamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-4-(4-methoxyphenyl)piperazine-1-carboxamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-4-(2-cyanophenyl)piperazine-1-carboxamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-4-[5-(trifluoromethyl)pyridin-2-yl]piperazine-1-carboxamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-4-[3-chloro-5-(trifluoromethyl)pyridin-2-yl]piperazine-1-carboxamide;

N-[6-Chloro-2,4,8,18,22-pentaazatetracyclo[14.3.1.1(3,
7).1(9,13)]docosa-1(20),3(22),4,6,9(21),10,12,16,18-
nonaen-12-yl]-4-(4-cyanophenyl)piperazine-1-car-
boxamide;
N-[6-Chloro-2,4,8,18,22-pentaazatetracyclo[14.3.1.1(3,
7).1(9,13)]docosa-1(20),3(22),4,6,9(21),10,12,16,18-
nonaen-12-yl]-4-(3-methoxyphenyl)piperazine-1-car-
boxamide;
N-[6-Chloro-2,4,8,18,22-pentaazatetracyclo[14.3.1.1(3,
7).1(9,13)]docosa-1(20),3(22),4,6,9(21),10,12,16,18-
nonaen-12-yl]-4-(2-chlorophenyl)piperazine-1-car-
boxamide;
N-[6-Chloro-2,4,8,18,22-pentaazatetracyclo[14.3.1.1(3,
7).1(9,13)]docosa-1(20),3(22),4,6,9(21),10,12,16,18-
nonaen-12-yl]-4-(3-chlorophenyl)piperazine-1-car-
boxamide;
N-[6-Chloro-2,4,8,18,22-pentaazatetracyclo[14.3.1.1(3,
7).1(9,13)]docosa-1(20),3(22),4,6,9(21),10,12,16,18-
nonaen-12-yl]-4-(4-chlorophenyl)piperazine-1-car-
boxamide;
N-[6-Chloro-2,4,8,18,22-pentaazatetracyclo[14.3.1.1(3,
7).1(9,13)]docosa-1(20),3(22),4,6,9(21),10,12,16,18-
nonaen-12-yl]-4-(6-methylpyrazin-2-yl)piperazine-1-
carboxamide;
N-[6-Chloro-2,4,8,18,22-pentaazatetracyclo[14.3.1.1(3,
7).1(9,13)]docosa-1(20),3(22),4,6,9(21),10,12,16,18-
nonaen-12-yl]-4-pyrimidin-2-ylpiperazine-1-carboxa-
mide;
N-[6-Chloro-2,4,8,18,22-pentaazatetracyclo[14.3.1.1(3,
7).1(9,13)]docosa-1(20),3(22),4,6,9(21),10,12,16,18-
nonaen-12-yl]-4-(5-cyanopyridin-2-yl)piperazine-1-
carboxamide;
N-[6-Chloro-2,4,8,18,22-pentaazatetracyclo[14.3.1.1(3,
7).1(9,13)]docosa-1(20),3(22),4,6,9(21),10,12,16,18-
nonaen-12-yl]-4-(3-cyanopyridin-2-yl)piperazine-1-
carboxamide;
N-[6-Chloro-2,4,8,18,22-pentaazatetracyclo[14.3.1.1(3,
7).1(9,13)]docosa-1(20),3(22),4,6,9(21),10,12,16,18-
nonaen-12-yl]-3-phenylpyrrolidine-1-carboxamide;
N-[6-Chloro-2,4,8,18,22-pentaazatetracyclo[14.3.1.1(3,
7).1(9,13)]docosa-1(20),3(22),4,6,9(21),10,12,16,18-
nonaen-12-yl]-3-pyrazin-2-ylpyrrolidine-1-carboxam-
ide;
N-[6-Chloro-2,4,8,18,22-pentaazatetracyclo[14.3.1.1(3,
7).1(9,13)]docosa-1(20),3(22),4,6,9(21),10,12,16,18-
nonaen-12-yl]-4-phenylpiperidine-1-carboxamide;
N-[6-Chloro-2,4,8,18,22-pentaazatetracyclo[14.3.1.1(3,
7).1(9,13)]docosa-1(20),3(22),4,6,9(21),10,12,16,18-
nonaen-12-yl]hexahydropyrrolo[1,2-a]pyrazine-2(1H)-
carboxamide;
N-[6-Chloro-2,4,8,18,22-pentaazatetracyclo[14.3.1.1(3,
7).1(9,13)]docosa-1(20),3(22),4,6,9(21),10,12,16,18-
nonaen-12-yl]-3-(trifluoromethyl)-5,6-dihydro[1,2,4]
triazolo[4,3-a]pyrazine-7(8H)-carboxamide;
4-Acetyl-N-[6-chloro-2,4,8,18,22-pentaazatetracyclo
[14.3.1.1(3,7).1(9,13)]docosa-1(20),3(22),4,6,9(21),
10,12,16,18-nonaen-12-yl]piperazine-1-carboxamide;
N-[6-Chloro-2,4,8,18,22-pentaazatetracyclo[14.3.1.1(3,
7).1(9,13)]docosa-1(20),3(22),4,6,9(21),10,12,16,18-
nonaen-12-yl]-4-(methylsulfonyl)piperazine-1-car-
boxamide;
N-[6-Chloro-2,4,8,18,22-pentaazatetracyclo[14.3.1.1(3,
7).1(9,13)]docosa-1(20),3(22),4,6,9(21),10,12,16,18-
nonaen-12-yl]-4-(phenylsulfonyl)piperazine-1-car-
boxamide;
N-[6-Chloro-2,4,8,18,22-pentaazatetracyclo[14.3.1.1(3,
7).1(9,13)]docosa-1(20),3(22),4,6,9(21),10,12,16,18-
nonaen-12-yl]-3-methyl-4-phenylpiperazine-1-car-
boxamide;
N-[6-Chloro-2,4,8,18,22-pentaazatetracyclo[14.3.1.1(3,
7).1(9,13)]docosa-1(20),3(22),4,6,9(21),10,12,16,18-
nonaen-12-yl]-3-(phenylsulfonyl)pyrrolidine-1-car-
boxamide;
N-[6-Chloro-2,4,8,18,22-pentaazatetracyclo[14.3.1.1(3,
7).1(9,13)]docosa-1(20),3(22),4,6,9(21),10,12,16,18-
nonaen-12-yl]-4-cyano-4-phenylpiperidine-1-carboxa-
mide;
N-[6-chloro-2,4,8,22-tetraazatetracyclo[14.3.1.1(3,7).1
(9,13)]docosa-1(20),3(22),4,6,9(21),10,12,16,18-
nonaen-12-yl]-N'-cyanourea;
N-[6-Chloro-2,4,8,22-tetraazatetracyclo[14.3.1.1(3,7).1
(9,13)]docosa-1(20),3(22),4,6,9(21),10,12,16,18-
nonaen-12-yl]-N'-hydroxyurea;
N-{2-[({[6-Chloro-2,4,8,22-tetraazatetracyclo[14.3.1.1
(3,7).1(9,13)]docosa-1(20),3(22),4,6,9(21),10,12,16,
18-nonaen-12-yl]amino}carbonyl)amino]
ethyl}ethanesulfonamide;
N-{2-[({[6-Chloro-2,4,8,22-tetraazatetracyclo[14.3.1.1
(3,7).1(9,13)]docosa-1(20),3(22),4,6,9(21),10,12,16,
18-nonaen-12-yl]amino}carbonyl)amino]
ethyl}propane-1-sulfonamide;
N-{2-[({[6-Chloro-2,4,8,22-tetraazatetracyclo[14.3.1.1
(3,7).1(9,13)]docosa-1(20),3(22),4,6,9(21),10,12,16,
18-nonaen-12-yl]amino}carbonyl)amino]
ethyl}cyclopropanesulfonamide;
N-[6-chloro-2,4,8,22-tetraazatetracyclo[14.3.1.1(3,7).1
(9,13)]docosa-1(20),3(22),4,6,9(21),10,12,16,18-
nonaen-12-yl]-N'-(2-{[(dimethylamino)sulfonyl]
amino}ethyl)urea;
N-{2-[({[6-Chloro-2,4,8,22-tetraazatetracyclo[14.3.1.1
(3,7).1(9,13)]docosa-1(20),3(22),4,6,9(21),10,12,16,
18-nonaen-12-yl]amino}carbonyl)amino]
ethyl}benzenesulfonamide;
5-Chloro-N-{2-[({[6-chloro-2,4,8,22-tetraazatetracyclo
[14.3.1.1(3,7).1(9,13)]docosa-1(20),3(22),4,6,9(21),
10,12,16,18-nonaen-12-yl]amino}carbonyl)amino]
ethyl}thiophene-2-sulfonamide;
6-Chloro-N-{2-[({[6-chloro-2,4,8,22-tetraazatetracyclo
[14.3.1.1(3,7).1(9,13)]docosa-1(20),3(22),4,6,9(21),
10,12,16,18-nonaen-12-yl]amino}carbonyl)amino]
ethyl}pyridine-3-sulfonamide;
N-{2-[({[6-chloro-2,4,8,22-tetraazatetracyclo[14.3.1.1(3,
7).1(9,13)]docosa-1(20),3(22),4,6,9(21),10,12,16,18-
nonaen-12-yl]amino}carbonyl)amino]ethyl}-1-me-
thyl-1H-pyrazole-3-sulfonamide;
6-Chloro-N-[1,3]oxazolo[5,4-b]pyridin-2-yl-2,4,8,22-tet-
raazatetracyclo[14.3.1.1(3,7).1(9,13)]docosa-1(20),3
(22),4,6,9(21),10,12,16,18-nonaen-12-amine;
1-[6-Chloro-2,4,8,18,22-pentaazatetracyclo[14.3.1.1(3,7)
.1(9,13)]docosa-1(20),3(22),4,6,9(21),10,12,16,18-
nonaen-12-yl]-N-methylmethanamine;
N-{[6-Chloro-2,4,8,18,22-pentaazatetracyclo[14.3.1.1(3,
7).1(9,13)]docosa-1(20),3(22),4,6,9(21),10,12,16,18-
nonaen-12-yl]methyl}-N-methyl-1-[(5-methylisox-
azol-3-yl)carbonyl]piperidine-4-carboxamide;
N-{[6-Chloro-2,4,8,18,22-pentaazatetracyclo[14.3.1.1(3,
7).1(9,13)]docosa-1(20),3(22),4,6,9(21),10,12,16,18-
nonaen-12-yl]methyl}-1-(isoxazol-5-ylcarbonyl)-N-
methylpiperidine-4-carboxamide;
N(4)-{[6-chloro-2,4,8,18,22-pentaazatetracyclo[14.3.1.1
(3,7).1(9,13)]docosa-1(20),3(22),4,6,9(21),10,12,16, 18-nonaen-12-yl]methyl}-N(4)-methyl-N(1)-phenylpiperidine-1,4-dicarboxamide;

N-{[6-Chloro-2,4,8,18,22-pentaazatetracyclo[14.3.1.1(3,7).1(9,13)]docosa-1(20),3(22),4,6,9(21),10,12,16,18-nonaen-12-yl]methyl}-N-methyl-1-pyrimidin-2-ylpiperidine-4-carboxamide;

1-[6-Chloro-2,4,8,18,22-pentaazatetracyclo[14.3.1.1(3,7).1(9,13)]docosa-1(20),3(22),4,6,9(21),10,12,16,18-nonaen-12-yl]-N-methyl-N-(piperidin-4-ylmethyl)methanamine;

2-[(4-{[{[6-Chloro-2,4,8,18,22-pentaazatetracyclo[14.3.1.1(3,7).1(9,13)]docosa-1(20),3(22),4,6,9(21),10,12,16,18-nonaen-12-yl]methyl}(methyl)amino]methyl}piperidin-1-yl)sulfonyl]benzonitrile;

1-[6-Chloro-2,4,8,18,22-pentaazatetracyclo[14.3.1.1(3,7).1(9,13)]docosa-1(20),3(22),4,6,9(21),10,12,16,18-nonaen-12-yl]-N-methyl-N-{1-(phenylsulfonyl)piperidin-4-yl]methyl}methanamine;

1-[6-Chloro-2,4,8,18,22-pentaazatetracyclo[14.3.1.1(3,7).1(9,13)]docosa-1(20),3(22),4,6,9(21),10,12,16,18-nonaen-12-yl]-N-methyl-N-({1-[(5-methylisoxazol-4-yl)sulfonyl]piperidin-4-yl}methyl)methanamine;

1-[6-Chloro-2,4,8,18,22-pentaazatetracyclo[14.3.1.1(3,7).1(9,13)]docosa-1(20),3(22),4,6,9(21),10,12,16,18-nonaen-12-yl]-N-({1-[(1,2-dimethyl-1H-imidazol-4-yl)sulfonyl]piperidin-4-yl}methyl)-N-methylmethanamine;

1-[6-Chloro-2,4,8,18,22-pentaazatetracyclo[14.3.1.1(3,7).1(9,13)]docosa-1(20),3(22),4,6,9(21),10,12,16,18-nonaen-12-yl]-N-methyl-N-({1-[(5-methylisoxazol-3-yl)carbonyl]piperidin-4-yl}methyl)methanamine;

1-[6-Chloro-2,4,8,18,22-pentaazatetracyclo[14.3.1.1(3,7).1(9,13)]docosa-1(20),3(22),4,6,9(21),10,12,16,18-nonaen-12-yl]-N-{[1-(isoxazol-5-ylcarbonyl)piperidin-4-yl]methyl}-N-methylmethanamine;

1-(1-Acetylpiperidin-4-yl)-N-{[6-chloro-2,4,8,18,22-pentaazatetracyclo[14.3.1.1(3,7).1(9,13)]docosa-1(20),3(22),4,6,9(21),10,12,16,18-nonaen-12-yl]methyl}-N-methylmethanamine;

1-[6-Chloro-2,4,8,18,22-pentaazatetracyclo[14.3.1.1(3,7).1(9,13)]docosa-1(20),3(22),4,6,9(21),10,12,16,18-nonaen-12-yl]-N-methyl-N-({14(4-methyl-1,3-oxazol-5-yl)carbonyl]piperidin-4-yl}methyl)methanamine;

4-{[{[6-Chloro-2,4,8,18,22-pentaazatetracyclo[14.3.1.1(3,7).1(9,13)]docosa-1(20),3(22),4,6,9(21),10,12,16,18-nonaen-12-yl]methyl}(methyl)amino]methyl}-N-pyridin-3-ylpiperidine-1-carboxamide;

4-{[{[6-Chloro-2,4,8,18,22-pentaazatetracyclo[14.3.1.1(3,7).1(9,13)]docosa-1(20),3(22),4,6,9(21),10,12,16,18-nonaen-12-yl]methyl}(methyl)amino]methyl}-N-(2-methyl-3-furyl)piperidine-1-carboxamide; and 6-Chloro-12-(1H-pyrazol-4-yl)-2,4,8,18,22-pentaazatetracyclo[14.3.1.1(3,7).1(9,13)]docosa-1(20),3(22),4,6,9(21),10,12,16,18-nonaene, or pharmaceutically acceptable salts thereof or quaternary ammonium salt thereof.

61. A compound selected from:

14-Benzoyl-6-chloro-2,4,8,14,22-pentaazatetracyclo[14.3.1.1(3,7).1(9,13)]docosa-1(20),3(22),4,6,9(21),10,12,16,18-nonaene;

6-Chloro-14-(pyridin-2-ylcarbonyl)-2,4,8,14,22-pentaazatetracyclo[14.3.1.1(3,7).1(9,13)]docosa-1(20),3(22),4,6,9(21),10,12,16,18-nonaene;

6-Chloro-14-(4-methylbenzoyl)-2,4,8,14,22-pentaazatetracyclo[14.3.1.1(3,7).1(9,13)]docosa-1(20),3(22),4,6,9(21),10,12,16,18-nonaene;

6-Chloro-14-(2-thienylcarbonyl)-2,4,8,14,22-pentaazatetracyclo[14.3.1.1(3,7).1(9,13)]docosa-1(20),3(22),4,6,9(21),10,12,16,18-nonaene;

14-Butyryl-6-chloro-2,4,8,14,22-pentaazatetracyclo[14.3.1.1(3,7).1(9,13)]docosa-1(20),3(22),4,6,9(21),10,12,16,18-nonaene;

6-Chloro-14-(pyridin-3-ylcarbonyl)-2,4,8,14,22-pentaazatetracyclo[14.3.1.1(3,7).1(9,13)]docosa-1(20),3(22),4,6,9(21),10,12,16,18-nonaene;

Methyl 6-chloro-2,4,8,18,22-pentaazatetracyclo[14.3.1.1(3,7).1(9,13)]docosa-1(20),3(22),4,6,9(21),10,12,16,18-nonaene-12-carboxylate;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-(1H-indol-3-yl)acetamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-[3-methylisoxazol-5-yl)acetamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-[1H-tetrazol-5-yl)acetamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-(3-thienyl)acetamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-(1H-imidazol-4-yl)acetamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-[2-methyl-1H-indol-3-yl)acetamide;

2-(1-Benzothien-3-yl)-N-[6-chloro-2,4,8,22-tetraazatetracyclo[14.3.1.1(3,7).1(9,13)]docosa-1(20),3(22),4,6,9(21),10,12,16,18-nonaen-12-yl]acetamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-(2-furyl)acetamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-[1-methyl-1H-indol-3-yl)acetamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-[2-methyl-1,3-thiazol-4-yl)acetamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-pyridin-3-ylacetamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-pyridin-4-ylacetamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-pyridin-2-ylacetamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-(2-thienyl)acetamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-[2,4-dimethyl-1,3-thiazol-5-yl)acetamide;

2-(1H-Benzimidazol-2-yl)-N46-chloro-2,4,8,22-tetraazatetracyclo[14.3.1.1(3,7).1(9,13)]docosa-1(20),3(22),4,6,9(21),10,12,16,18-nonaen-12-yl]acetamide;

2-(1,2-Benzisoxazol-3-yl)-N-[6-chloro-2,4,8,22-tetraazatetracyclo[14.3.1.1(3,7).1(9,13)]docosa-1(20),3(22),4,6,9(21),10,12,16,18-nonaen-12-yl]acetamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-[2,5-dimethyl-1,3-thiazol-4-yl)acetamide;

2-(1-Benzofuran-3-yl)-N-[6-chloro-2,4,8,22-tetraazatetracyclo[14.3.1.1(3,7).1(9,13)]docosa-1(20),3(22),4,6,9(21),10,12,16,18-nonaen-12-yl]acetamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-3-[4-methyl-1,3-thiazol-5-yl)propanamide;

N-[6-Fluoro-2,4,8,18,22-pentaazatetracyclo[14.3.1.1(3,7).1(9,13)]docosa-1(20),3(22),4,6,9(21),10,12,16,18-nonaen-12-yl]-2-{1-[(5-methylisoxazol-3-yl)carbonyl]piperidin-4-yl}acetamide;

6-Methyl-2,4,8,18,22-pentaazatetracyclo[14.3.1.1(3,7).1(9,13)]docosa-1(20),3(22),4,6,9(21),10,12,16,18-nonaen-12-amine;

2-{1-[(5-Methylisoxazol-3-yl)carbonyl]piperidin-4-yl}-N-[6-methyl-2,4,8,18,22-pentaazatetracyclo[14.3.1.1(3,7).1(9,13)]docosa-1(20),3(22),4,6,9(21),10,12,16,18-nonaen-12-yl]acetamide;

N-[6-Fluoro-2,4,8,22-tetraazatetracyclo[14.3.1.1(3,7).1(9,13)]docosa-1(20),3(22),4,6,9(21),10,12,16,18-nonaen-12-yl]-2-{1-[(5-methylisoxazol-3-yl)carbonyl]piperidin-4-yl}acetamide;

N-[6-Methyl-2,4,8,22-tetraazatetracyclo[14.3.1.1(3,7).1(9,13)]docosa-1(20),3(22),4,6,9(21),10,12,16,18-nonaen-12-yl]-2-[1-(1,3,4-thiadiazol-2-yl)piperidin-4-yl]acetamide;

2-{1-[(5-Methylisoxazol-3-yl)carbonyl]piperidin-4-yl}-N-[6-methyl-2,4,8,22-tetraazatetracyclo[14.3.1.1(3,7).1(9,13)]docosa-1(20),3(22),4,6,9(21),10,12,16,18-nonaen-12-yl]acetamide;

6-Chloro-12-(pyrrolidin-3-ylmethoxy)-2,4,8,18,22-pentaazatetracyclo[14.3.1.1(3,7).1(9,13)]docosa-1(20),3(22),4,6,9(21),10,12,16,18-nonaene;

12-[(1-Acetylpyrrolidin-3-yl)methoxy]-6-chloro-2,4,8,18,22-pentaazatetracyclo[14.3.1.1(3,7).1(9,13)]docosa-1(20),3(22),4,6,9(21),10,12,16,18-nonaene;

2-{[3-({[6-Chloro-2,4,8,18,22-pentaazatetracyclo[14.3.1.1(3,7).1(9,13)]docosa-1(20),3(22),4,6,9(21),10,12,16,18-nonaen-12-yl]oxy}methyl)pyrrolidin-1-yl]sulfonyl}benzonitrile;

6-Chloro-12-({1-[(5-methylisoxazol-3-yl)carbonyl]pyrrolidin-3-yl}methoxy)-2,4,8,18,22-pentaazatetracyclo[14.3.1.1(3,7).1(9,13)]docosa-1(20),3(22),4,6,9(21),10,12,16,18-nonaene;

3-({[6-Chloro-2,4,8,18,22-pentaazatetracyclo[14.3.1.1(3,7).1(9,13)]docosa-1(20),3(22),4,6,9(21),10,12,16,18-nonaen-12-yl]oxy}methyl)-N-phenylpyrrolidine-1-carboxamide;

(3R)-3-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-phenylpyrrolidine-1-carboxamide;

(3R)-3-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-(4-cyanophenyl)pyrrolidine-1-carboxamide;

(3R)-3-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-(3-cyanophenyl)pyrrolidine-1-carboxamide;

(3R)-3-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-(2-cyanophenyl)pyrrolidine-1-carboxamide;

(3R)-3-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-pyridin-3-ylpyrrolidine-1-carboxamide;

(3R)-3-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-(4-fluorophenyl)pyrrolidine-1-carboxamide;

(3R)-3-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-(3-fluorophenyl)pyrrolidine-1-carboxamide;

(3R)-3-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-(2-fluorophenyl)pyrrolidine-1-carboxamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[(3R)-1-(isoxazol-5-ylcarbonyl)pyrrolidin-3-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{(3R)-1-[(1-methyl-1H-pyrazol-3-yl)carbonyl]pyrrolidin-3-yl}acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{(3R)-1-[(1-methyl-1H-pyrazol-4-yl)carbonyl]pyrrolidin-3-yl}acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{(3R)-1-[(5-methylisoxazol-4-yl)carbonyl]pyrrolidin-3-yl}acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{(3R)-1-[(5-methylisoxazol-3-yl)carbonyl]pyrrolidin-3-yl}acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{(3R)-1-(1,3-thiazol-2-ylcarbonyl)pyrrolidin-3-yl}acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{(3R)-1-[(1-methyl-1H-imidazol-5-yl)carbonyl]pyrrolidin-3-yl}acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-24(3R)-1-(methylsulfonyl)pyrrolidin-3-yl]acetamide;

(3S)-3-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-phenylpyrrolidine-1-carboxamide;

(3S)-3-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-(4-cyanophenyl)pyrrolidine-1-carboxamide;

(3S)-3-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-(3-cyanophenyl)pyrrolidine-1-carboxamide;

(3S)-3-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]amino}-2-oxoethyl)-N-(2-cyanophenyl)pyrrolidine-1-carboxamide;

(3S)-3-(2-{[6-Chloro-2,4,8,18,22-pentaazatetracyclo
[14.3.1.1(3,7).1(9,13)]docosa-1(20),3(22),4,6,9(21),
10,12,16,18-nonaen-12-yl]amino}-2-oxoethyl)-N-py-
ridin-3-ylpyrrolidine-1-carboxamide;
(3S)-3-(2-{[6-Chloro-2,4,8,18,22-pentaazatetracyclo
[14.3.1.1(3,7).1(9,13)]docosa-1(20),3(22),4,6,9(21),
10,12,16,18-nonaen-12-yl]amino}-2-oxoethyl)-N-(4-
fluorophenyl)pyrrolidine-1-carboxamide;
(3S)-3-(2-{[6-Chloro-2,4,8,18,22-pentaazatetracyclo
[14.3.1.1(3,7).1(9,13)]docosa-1(20),3(22),4,6,9(21),
10,12,16,18-nonaen-12-yl]amino}-2-oxoethyl)-N-(3-
fluorophenyl)pyrrolidine-1-carboxamide;
N-[6-Chloro-2,4,8,18,22-pentaazatetracyclo[14.3.1.1(3,
7).1(9,13)]docosa-1(20),3(22),4,6,9(21),10,12,16,18-
nonaen-12-yl]-24(3S)-1-(isoxazol-5-ylcarbonyl)pyrro-
lidin-3-yl]acetamide;
N-[6-Chloro-2,4,8,18,22-pentaazatetracyclo[14.3.1.1(3,
7).1(9,13)]docosa-1(20),3(22),4,6,9(21),10,12,16,18-
nonaen-12-yl]-2-{(3S)-1-[(1-methyl-1H-pyrazol-3-yl)
carbonyl]pyrrolidin-3-yl}acetamide;
N-[6-Chloro-2,4,8,18,22-pentaazatetracyclo[14.3.1.1(3,
7).1(9,13)]docosa-1(20),3(22),4,6,9(21),10,12,16,18-
nonaen-12-yl]-2-{(3S)-1-[(1-methyl-1H-pyrazol-4-yl)
carbonyl]pyrrolidin-3-yl}acetamide;
N-[6-Chloro-2,4,8,18,22-pentaazatetracyclo[14.3.1.1(3,
7).1(9,13)]docosa-1(20),3(22),4,6,9(21),10,12,16,18-
nonaen-12-yl]-2-{(3S)-1-[(5-methylisoxazol-4-yl)car-
bonyl]pyrrolidin-3-yl}acetamide;
N-[6-Chloro-2,4,8,18,22-pentaazatetracyclo[14.3.1.1(3,
7).1(9,13)]docosa-1(20),3(22),4,6,9(21),10,12,16,18-
nonaen-12-yl]-2-{(3S)-1-[(5-methylisoxazol-3-yl)car-
bonyl]pyrrolidin-3-yl}acetamide;
N-[6-Chloro-2,4,8,18,22-pentaazatetracyclo[14.3.1.1(3,
7).1(9,13)]docosa-1(20),3(22),4,6,9(21),10,12,16,18-
nonaen-12-yl]-2-[(3S)-1-(1,3-thiazol-2-ylcarbonyl)
pyrrolidin-3-yl]acetamide;
N-[6-Chloro-2,4,8,18,22-pentaazatetracyclo[14.3.1.1(3,
7).1(9,13)]docosa-1(20),3(22),4,6,9(21),10,12,16,18-
nonaen-12-yl]-2-{(3S)-1-[(1-methyl-1H-imidazol-5-
yl)carbonyl]pyrrolidin-3-yl}acetamide;
N-[6-Chloro-2,4,8,18,22-pentaazatetracyclo[14.3.1.1(3,
7).1(9,13)]docosa-1(20),3(22),4,6,9(21),10,12,16,18-
nonaen-12-yl]-24(3S)-1-(methylsulfonyl)pyrrolidin-3-
yl]acetamide;
N-[6-Chloro-2,4,8,18,22-pentaazatetracyclo[14.3.1.1(3,
7).1(9,13)]docosa-1(20),3(22),4,6,9(21),10,12,16,18-
nonaen-12-yl]-2-[(3R)-1-(1H-1,2,4-triazol-3-ylcarbo-
nyl)pyrrolidin-3-yl]acetamide;
N-[6-Chloro-2,4,8,18,22-pentaazatetracyclo[14.3.1.1(3,
7).1(9,13)]docosa-1(20),3(22),4,6,9(21),10,12,16,18-
nonaen-12-yl]-2-[(3R)-1-(1H-1,2,3-triazol-4-ylcarbo-
nyl)pyrrolidin-3-yl]acetamide;
N-[6-Chloro-2,4,8,18,22-pentaazatetracyclo[14.3.1.1(3,
7).1(9,13)]docosa-1(20),3(22),4,6,9(21),10,12,16,18-
nonaen-12-yl]-2-[3R)-1-(1H-pyrazol-4-ylcarbonyl)
pyrrolidin-3-yl]acetamide;
N-[6-Chloro-2,4,8,18,22-pentaazatetracyclo[14.3.1.1(3,
7).1(9,13)]docosa-1(20),3(22),4,6,9(21),10,12,16,18-
nonaen-12-yl]-2-[3R)-1-(1H-pyrazol-3-ylcarbonyl)
pyrrolidin-3-yl]acetamide;
N-[6-Chloro-2,4,8,18,22-pentaazatetracyclo[14.3.1.1(3,
7).1(9,13)]docosa-1(20),3(22),4,6,9(21),10,12,16,18-
nonaen-12-yl]-2-[(3S)-1-(1H-1,2,4-triazol-3-ylcarbo-
nyl)pyrrolidin-3-yl]acetamide;
N-[6-Chloro-2,4,8,18,22-pentaazatetracyclo[14.3.1.1(3,
7).1(9,13)]docosa-1(20),3(22),4,6,9(21),10,12,16,18-
nonaen-12-yl]-2-[(3S)-1-(1H-1,2,3-triazol-4-ylcarbo-
nyl)pyrrolidin-3-yl]acetamide;
N-[6-Chloro-2,4,8,18,22-pentaazatetracyclo[14.3.1.1(3,
7).1(9,13)]docosa-1(20),3(22),4,6,9(21),10,12,16,18-
nonaen-12-yl]-2-[(3S)-1-(1H-pyrazol-4-ylcarbonyl)
pyrrolidin-3-yl]acetamide;
N-[6-Chloro-2,4,8,18,22-pentaazatetracyclo[14.3.1.1(3,
7).1(9,13)]docosa-1(20),3(22),4,6,9(21),10,12,16,18-
nonaen-12-yl]-2-[(3S)-1-(1H-pyrazol-3-ylcarbonyl)
pyrrolidin-3-yl]acetamide;
(3S)-3-(2-{[6-Chloro-2,4,8,18,22-pentaazatetracyclo
[14.3.1.1(3,7).1(9,13)]docosa-1(20),3(22),4,6,9(21),
10,12,16,18-nonaen-12-yl]amino}-2-oxoethyl)-N-(2-
fluorophenyl)pyrrolidine-1-carboxamide;
2-[(3R)-1-(1,3-Benzothiazol-2-yl)pyrrolidin-3-yl]-N-[6-
chloro-2,4,8,18,22-pentaazatetracyclo[14.3.1.1(3,7).1
(9,13)]docosa-1(20),3(22),4,6,9(21),10,12,16,18-
nonaen-12-yl]acetamide;
2-[(3S)-1-(1,3-Benzothiazol-2-yl)pyrrolidin-3-yl]-N-[6-
chloro-2,4,8,18,22-pentaazatetracyclo[14.3.1.1(3,7).1
(9,13)]docosa-1(20),3(22),4,6,9(21),10,12,16,18-
nonaen-12-yl]acetamide;
2-[1-(1,3-Benzothiazol-2-yl)azetidin-3-yl]-N-[6-chloro-
2,4,8,18,22-pentaazatetracyclo[14.3.1.1(3,7).1(9,13)]
docosa-1(20),3(22),4,6,9(21),10,12,16,18-nonaen-12-
yl]acetamide;
N-[6-Chloro-2,4,8,18,22-pentaazatetracyclo[14.3.1.1(3,
7).1(9,13)]docosa-1(20),3(22),4,6,9(21),10,12,16,18-
nonaen-12-yl]-2-[(3R)-1-[1,3]oxazolo[5,4-b]pyridin-
2-ylpyrrolidin-3-yl]acetamide;
N-[6-Chloro-2,4,8,18,22-pentaazatetracyclo[14.3.1.1(3,
7).1(9,13)]docosa-1(20),3(22),4,6,9(21),10,12,16,18-
nonaen-12-yl]-24(3S)-1-[1,3]oxazolo[5,4-b]pyridin-2-
ylpyrrolidin-3-yl]acetamide;
N-[6-Chloro-2,4,8,18,22-pentaazatetracyclo[14.3.1.1(3,
7).1(9,13)]docosa-1(20),3(22),4,6,9(21),10,12,16,18-
nonaen-12-yl]-2-(1-[1,3]oxazolo[5,4-b]pyridin-2-
ylazetidin-3-yl)acetamide;
N-[6-Chloro-2,4,8,18,22-pentaazatetracyclo[14.3.1.1(3,
7).1(9,13)]docosa-1(20),3(22),4,6,9(21),10,12,16,18-
nonaen-12-yl]-2-{1-[(1-methyl-1H-pyrazol-4-yl)car-
bonyl]azetidin-3-yl}acetamide;
N-[6-Chloro-2,4,8,18,22-pentaazatetracyclo[14.3.1.1(3,
7).1(9,13)]docosa-1(20),3(22),4,6,9(21),10,12,16,18-
nonaen-12-yl]-2-{1-[(5-methylisoxazol-3-yl)carbonyl]
azetidin-3-yl}acetamide;
N-[6-Chloro-2,4,8,18,22-pentaazatetracyclo[14.3.1.1(3,
7).1(9,13)]docosa-1(20),3(22),4,6,9(21),10,12,16,18-
nonaen-12-yl]-2-[1-(isoxazol-5-ylcarbonyl)azetidin-3-
yl]acetamide;
N-[6-Chloro-2,4,8,18,22-pentaazatetracyclo[14.3.1.1(3,
7).1(9,13)]docosa-1(20),3(22),4,6,9(21),10,12,16,18-
nonaen-12-yl]-2-[1-(1,3-thiazol-2-ylcarbonyl)azetidin-
3-yl]acetamide;
N-[6-Chloro-2,4,8,18,22-pentaazatetracyclo[14.3.1.1(3,
7).1(9,13)]docosa-1(20),3(22),4,6,9(21),10,12,16,18-
nonaen-12-yl]-2-[1-(methylsulfonyl)azetidin-3-yl]ac-
etamide;
N-[6-Chloro-2,4,8,18,22-pentaazatetracyclo[14.3.1.1(3,
7).1(9,13)]docosa-1(20),3(22),4,6,9(21),10,12,16,18-
nonaen-12-yl]-2-[1-(1H-1,2,4-triazol-3-ylcarbonyl)
azetidin-3-yl]acetamide;
N-[6-Chloro-2,4,8,18,22-pentaazatetracyclo[14.3.1.1(3,
7).1(9,13)]docosa-1(20),3(22),4,6,9(21),10,12,16,18-
nonaen-12-yl]-2-[1-(1H-1,2,3-triazol-4-ylcarbonyl)
azetidin-3-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(1H-pyrazol-4-ylcarbonyl)azetidin-3-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(1H-pyrazol-5-ylcarbonyl)azetidin-3-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(1,3,4-thiadiazol-2-yl)azetidin-3-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1(1,3-thiazol-2-yl)azetidin-3-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-(1-pyridin-2-ylazetidin-3-yl)acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(1,3-thiazol-2-yl)pyrrolidin-3-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[1-(1,3,4-thiadiazol-2-yl)pyrrolidin-3-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-(1-pyridin-2-ylpyrrolidin-3-yl)acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-(1-pyridin-4-ylpyrrolidin-3-yl)acetamide;

N-(1-Acetylpiperidin-4-yl)-6-chloro-2,4,8,18,22-pentaazatetracyclo[14.3.1.1(3,7).1(9,13)]docosa-1(20),3(22),4,6,9(21),10,12,16,18-nonaen-12-amine;

6-Chloro-N-[1-(phenylacetyl)piperidin-4-yl]-2,4,8,18,22-pentaazatetracyclo[14.3.1.1(3,7).1(9,13)]docosa-1(20),3(22),4,6,9(21),10,12,16,18-nonaen-12-amine;

6-Chloro-N-{1-[(5-methylisoxazol-3-yl)carbonyl]piperidin-4-yl}-2,4,8,18,22-pentaazatetracyclo[14.3.1.1(3,7).1(9,13)]docosa-1(20),3(22),4,6,9(21),10,12,16,18-nonaen-12-amine;

12-[2-(1-Acetylpiperidin-4-yl)ethoxy]-6-chloro-2,4,8,18,22-pentaazatetracyclo[14.3.1.1(3,7).1(9,13)]docosa-1(20),3(22),4,6,9(21),10,12,16,18-nonaene;

4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]oxy}ethyl)-N-phenylpiperidine-1-carboxamide;

2-{[4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]oxy}ethyl)piperidin-1-yl]sulfonyl}benzonitrile;

4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]oxy}ethyl)-N-(2-methyl-3-furyl)piperidine-1-carboxamide;

4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]oxy}ethyl)-N-(2-furylmethyl)piperidine-1-carboxamide;

4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]oxy}ethyl)-N-3-thienylpiperidine-1-carboxamide;

4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]oxy}ethyl)-N-2-thienylpiperidine-1-carboxamide;

4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]oxy}ethyl)-N-(4-fluorophenyl)piperidine-1-carboxamide;

4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]oxy}ethyl)-N-(3-fluorophenyl)piperidine-1-carboxamide;

4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]oxy}ethyl)-N-(2-fluorophenyl)piperidine-1-carboxamide;

4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]oxy}ethyl)-N-(3,5-dimethylisoxazol-4-yl)piperidine-1-carboxamide;

4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]oxy}ethyl)-N-(4-methyl-2-thienyl)piperidine-1-carboxamide;

4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]oxy}ethyl)-N-(2-cyanophenyl)piperidine-1-carboxamide;

4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]oxy}ethyl)-N-(4-cyanophenyl)piperidine-1-carboxamide;

4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]oxy}ethyl)-N-(2,2-dimethyl-2,3-dihydro-1-benzofuran-7-yl)piperidine-1-carboxamide;

4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]oxy}ethyl)-N-(6-morpholin-4-ylpyridin-2-yl)piperidine-1-carboxamide;

6-Chloro-12-{2-[1-(pyrazin-2-ylcarbonyl)piperidin-4-yl]ethoxy}-2,4,8,18,22-pentaazatetracyclo[14.3.1.1(3,7).1(9,13)]docosa-1(20),3(22),4,6,9(21),10,12,16,18-nonaene;

6-Chloro-12-(2-{1-[(5-methylisoxazol-4-yl)carbonyl]piperidin-4-yl}ethoxy)-2,4,8,18,22-pentaazatetracyclo[14.3.1.1(3,7).1(9,13)]docosa-1(20),3(22),4,6,9(21),10,12,16,18-nonaene;

6-Chloro-12-(2-{1-[(2-chloropyridin-3-yl)carbonyl]piperidin-4-yl}ethoxy)-2,4,8,18,22-pentaazatetracyclo[14.3.1.1(3,7).1(9,13)]docosa-1(20),3(22),4,6,9(21),10,12,16,18-nonaene;

6-Chloro-12-{2-[1-(pyridin-3-ylcarbonyl)piperidin-4-yl]ethoxy}-2,4,8,18,22-pentaazatetracyclo[14.3.1.1(3,7).1(9,13)]docosa-1(20),3(22),4,6,9(21),10,12,16,18-nonaene;

6-Chloro-12-[2-(1-isonicotinoylpiperidin-4-yl)ethoxy]-2,4,8,18,22-pentaazatetracyclo[14.3.1.1(3,7).1(9,13)]docosa-1(20),3(22),4,6,9(21),10,12,16,18-nonaene;

4-(2-{[6-Chloro-2,4,8,18,22-pentaazatetracyclo[14.3.1.1(3,7).1(9,13)]docosa-1(20),3(22),4,6,9(21),10,12,16,18-nonaen-12-yl]oxy}ethyl)-N-pyridin-3-ylpiperidine-1-carboxamide;

Methyl [4-chloro-19-oxo-18-oxa-2,6,8,20,25-pentaazapentacyclo[14.6.1.1(3,7).1(9,13).0(17,21)]pentacosa-1(23),3(25),4,6,9(24),10,12,16,21-nonaen-20-yl]acetate;

4-Chloro-18-oxa-2,6,8,20,25-pentaazapentacyclo [14.6.1.1(3,7).1(9,13).0(17,21)]pentacosa-1(23),3(25),4,6,9(24),10,12,16,21-nonaen-19-one;

2-[4-Chloro-19-oxo-18-oxa-2,6,8,20,25-pentaazapentacyclo[14.6.1.1(3,7).1(9,13).0(17,21)]pentacosa-1(23),3(25),4,6,9(24),10,12,16,21-nonaen-20-yl]-N-phenylacetamide;

N-Benzyl-2-[4-chloro-19-oxo-18-oxa-2,6,8,20,25-pentaazapentacyclo[14.6.1.1(3,7).1(9,13).0(17,21)]pentacosa-1(23),3(25),4,6,9(24),10,12,16,21-nonaen-20-yl]acetamide;

4-Chloro-20-(2-morpholin-4-yl-2-oxoethyl)-18-oxa-2,6,8,20,25-pentaazapentacyclo[14.6.1.1(3,7).1(9,13).0(17,21)]pentacosa-1(23),3(25),4,6,9(24),10,12,16,21-nonaen-19-one;

4-Chloro-20-[2-oxo-2-(4-phenylpiperazin-1-yl)ethyl]-18-oxa-2,6,8,20,25-pentaazapentacyclo[14.6.1.1(3,7).1(9,13).0(17,21)]pentacosa-1(23),3(25),4,6,9(24),10,12,16,21-nonaen-19-one;

6-Chloro-19-(morpholin-4-ylmethyl)-14-oxa-2,4,8,23-tetraazatetracyclo[15.3.1.1(3,7).1(9,13)]tricosa-1(21),3(23),4,6,9(22),10,12,17,19-nonaene;

6-Chloro-19-[(4-methylpiperazin-1-yl)methyl]-14-oxa-2,4,8,23-tetraazatetracyclo[15.3.1.1(3,7).1(9,13)]tricosa-1(21),3(23),4,6,9(22),10,12,17,19-nonaene;

6-Chloro-19-(piperazin-1-ylmethyl)-14-oxa-2,4,8,23-tetraazatetracyclo[15.3.1.1(3,7).1(9,13)]tricosa-1(21),3(23),4,6,9(22),10,12,17,19-nonaene;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-[(3S)-piperidin-3-yl]acetamide;

N-[6-Chloro-2,4,8,22-tetraazatetracyclo[14.3.1.1(3,7).1(9,13)]docosa-1(20),3(22),4,6,9(21),10,12,16,18-nonaen-12-yl]-2-[(3R)-piperidin-3-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[(3S)-piperidin-3-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[(3R)-piperidin-3-yl]acetamide;

(3S)-3-(2-{[6-Chloro-2,4,8,22-tetraazatetracyclo[14.3.1.1(3,7).1(9,13)]docosa-1(20),3(22),4,6,9(21),10,12,16-nonaen-12-yl]amino}-2-oxoethyl)-N-phenylpiperidine-1-carboxamide;

(3R)-3-(2-{[6-Chloro-2,4,8,22-tetraazatetracyclo[14.3.1.1(3,7).1(9,13)]docosa-1(20),3(22),4,6,9(21),10,12,16-nonaen-12-yl]amino}-2-oxoethyl)-N-phenylpiperidine-1-carboxamide;

(3S)-3-(2-{[6-Chloro-2,4,8,18,22-pentaazatetracyclo[14.3.1.1(3,7).1(9,13)]docosa-1(20),3(22),4,6,9(21),10,12,16-nonaen-12-yl]amino}-2-oxoethyl)-N-phenylpiperidine-1-carboxamide;

(3R)-3-(2-{[6-Chloro-2,4,8,18,22-pentaazatetracyclo[14.3.1.1(3,7).1(9,13)]docosa-1(20),3(22),4,6,9(21),10,12,16-nonaen-12-yl]amino}-2-oxoethyl)-N-phenylpiperidine-1-carboxamide;

2-[(3S)-1-Acetylpiperidin-3-yl]-N-[6-chloro-2,4,8,22-tetraazatetracyclo[14.3.1.1(3,7).1(9,13)]docosa-1(20),3(22),4,6,9(21),10,12,16,18-nonaen-12-yl]acetamide;

2-[(3R)-1-Acetylpiperidin-3-yl]-N-[6-chloro-2,4,8,22-tetraazatetracyclo[14.3.1.1(3,7).1(9,13)]docosa-1(20),3(22),4,6,9(21),10,12,16,18-nonaen-12-yl]acetamide;

2-[(3S)-1-Benzoylpiperidin-3-yl]-N-[6-chloro-2,4,8,22-tetraazatetracyclo[14.3.1.1(3,7).1(9,13)]docosa-1(20),3(22),4,6,9(21),10,12,16,18-nonaen-12-yl]acetamide;

2-[(3R)-1-Benzoylpiperidin-3-yl]-N-[6-chloro-2,4,8,22-tetraazatetracyclo[14.3.1.1(3,7).1(9,13)]docosa-1(20),3(22),4,6,9(21),10,12,16,18-nonaen-12-yl]acetamide;

2-[(3S)-1-Acetylpiperidin-3-yl]-N-[6-chloro-2,4,8,18,22-pentaazatetracyclo[14.3.1.1(3,7).1(9,13)]docosa-1(20),3(22),4,6,9(21),10,12,16,18-nonaen-12-yl]acetamide;

2-[(3R)-1-Acetylpiperidin-3-yl]-N-[6-chloro-2,4,8,18,22-pentaazatetracyclo[14.3.1.1(3,7).1(9,13)]docosa-1(20),3(22),4,6,9(21),10,12,16,18-nonaen-12-yl]acetamide;

2-[(3S)-1-Benzoylpiperidin-3-yl]-N-[6-chloro-2,4,8,18,22-pentaazatetracyclo[14.3.1.1(3,7).1(9,13)]docosa-1(20),3(22),4,6,9(21),10,12,16,18-nonaen-12-yl]acetamide;

2-[(3R)-1-Benzoylpiperidin-3-yl]-N-[6-chloro-2,4,8,18,22-pentaazatetracyclo[14.3.1.1(3,7).1(9,13)]docosa-1(20),3(22),4,6,9(21),10,12,16,18-nonaen-12-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{(3S)-1-[(5-methylisoxazol-3-yl)carbonyl]piperidin-3-yl}acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-{(3R)-1-[(5-methylisoxazol-3-yl)carbonyl]piperidin-3-yl}acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-(1,3-dioxo-1,3-dihydro-2H-isoindol-2-yl)ethanesulfonamide;

2-[(3S)-1-(1,3-Benzothiazol-2-yl)piperidin-3-yl]-N46-chloro-2,4,8,18,22-pentaazatetracyclo[14.3.1.1(3,7).1(9,13)]docosa-1(20),3(22),4,6,9(21),10,12,16,18-nonaen-12-yl]acetamide;

2-[(3R)-1-(1,3-Benzothiazol-2-yl)piperidin-3-yl]-N46-chloro-2,4,8,18,22-pentaazatetracyclo[14.3.1.1(3,7).1(9,13)]docosa-1(20),3(22),4,6,9(21),10,12,16,18-nonaen-12-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-24(3S)-1-[1,3]oxazolo[5,4-b]pyridin-2-ylpiperidin-3-yl]acetamide;

N-[6-Chloro-2,4,8,18,22-pentaazatetracyclo[14.3.1.1(3,7).1(9,13)]docosa-1(20),3(22),4,6,9(21),10,12,16,18-nonaen-12-yl]-2-[(3R)-1-[1,3]oxazolo[5,4-b]pyridin-2-ylpiperidin-3-yl]acetamide;

Benzyl 4-(2-{[6-chloro-2,4,8,18,22-pentaazatetracyclo[14.3.1.1(3,7).1(9,13)]docosa-1(20),3(22),4,6,9(21),10,12,16,18-nonaen-12-yl]amino}ethyl)piperidine-1-carboxylate;

6-Chloro-N-(2-piperidin-4-ylethyl)-2,4, 8,18,22-pentaazatetracyclo[14.3.1.1(3,7).1(9,13)]docosa-1(20),3(22),4,6,9(21),10,12,16,18-nonaen-12-amine;

2,4,8,18,22-Pentaazatetracyclo[14.3.1.1(3,7).1(9,13)]docosa-1(20),3(22),4,6,9(21),10,12,16,18-nonaene;

6-Chloro-N-(2-{1-[(5-methylisoxazol-3-yl)carbonyl]piperidin-4-yl}ethyl)-2,4,8,18,22-pentaazatetracyclo[14.3.1.1(3,7).1(9,13)]docosa-1(20),3(22),4,6,9(21),10,12,16,18-nonaen-12-amine;

N-[2-(1-Acetylpiperidin-4-yl)ethyl]-6-chloro-2,4,8,18,22-pentaazatetracyclo[14.3.1.1(3,7).1(9,13)]docosa-1(20),3(22),4,6,9(21),10,12,16,18-nonaen-12-amine;

6-Chloro-N-{2-[1-(2,4-difluorobenzoyl)piperidin-4-yl]
ethyl}-2,4,8,18,22-pentaazatetracyclo[14.3.1.1(3,7).1
(9,13)]docosa-1(20),3(22),4,6,9(21),10,12,16,18-
nonaen-12-amine;

6-Chloro-N-(2-{1-[(2-fluorophenyl)sulfonyl]piperidin-4-
yl}ethyl)-2,4,8,18,22-pentaazatetracyclo[14.3.1.1(3,7)
.1(9,13)]docosa-1(20),3(22),4,6,9(21),10,12,16,18-
nonaen-12-amine;

2-{[4-(2-{[6-Chloro-2,4,8,18,22-pentaazatetracyclo
[14.3.1.1(3,7).1(9,13)]docosa-1(20),3(22),4,6,9(21),
10,12,16,18-nonaen-12-yl]amino}ethyl)piperidin-1-yl]
sulfonyl}benzonitrile;

8-Methyl-2,4,8,22-tetraazatetracyclo[14.3.1.1(3,7).1(9,
13)]docosa-1(20),3(22),4,6,9(21),10,12,16,18-
nonaene;

8-Methyl-2,4, 8,18,22-pentaazatetracyclo[14.3.1.1(3,7).1
(9,13)]docosa-1(20),3(22),4,6,9(21),10,12,16,18-
nonaene;

6-Chloro-12-(piperidin-4-ylmethoxy)-2,4,8,18,22-pen-
taazatetracyclo[14.3.1.1(3,7).1(9,13)]docosa-1(20),3
(22),4,6,9(21),10,12,16,18-nonaene;

6-Chloro-12-({1-[(5-methylisoxazol-3-yl)carbonyl]pip-
eridin-4-yl}methoxy)-2,4,8,18,22-pentaazatetracyclo
[14.3.1.1(3,7).1(9,13)]docosa-1(20),3(22),4,6,9(21),
10,12,16,18-nonaene;

12-[(1-Acetylpiperidin-4-yl)methoxy]-6-chloro-2,4,8,18,
22-pentaazatetracyclo[14.3.1.1(3,7).1(9,13)]docosa-1
(20),3(22),4,6,9(21),10,12,16,18-nonaene;

4-({[6-Chloro-2,4,8,18,22-pentaazatetracyclo[14.3.1.1(3,
7).1(9,13)]docosa-1(20),3(22),4,6,9(21),10,12,16,18-
nonaen-12-yl]oxy}methyl)-N-phenylpiperidine-1-car-
boxamide;

6-Chloro-12-(2-oxo-2-piperazin-1-ylethoxy)-2,4,8,18,22-
pentaazatetracyclo[14.3.1.1(3,7).1(9,13)]docosa-1(20),
3(22),4,6,9(21),10,12,16,18-nonaene;

6-Chloro-12-{2-oxo-2-[4-(1,3-thiazol-2-yl)piperazin-1-
yl]ethoxy}-2,4,8,18,22-pentaazatetracyclo[14.3.1.1(3,
7).1(9,13)]docosa-1(20),3(22),4,6,9(21),10,12,16,18-
nonaene;

6-Chloro-12-[2-oxo-2-(4-pyridin-2-ylpiperazin-1-yl)
ethoxy]-2,4,8,18,22-pentaazatetracyclo[14.3.1.1(3,7).1
(9,13)]docosa-1(20),3(22),4,6,9(21),10,12,16,18-
nonaene;

6-Chloro-12-[2-oxo-2-(4-pyrazin-2-ylpiperazin-1-yl)
ethoxy]-2,4,8,18,22-pentaazatetracyclo[14.3.1.1(3,7).1
(9,13)]docosa-1(20),3(22),4,6,9(21),10,12,16,18-
nonaene;

6-Chloro-12-[2-oxo-2-(4-pyrimidin-2-ylpiperazin-1-yl)
ethoxy]-2,4,8,18,22-pentaazatetracyclo[14.3.1.1(3,7).1
(9,13)]docosa-1(20),3(22),4,6,9(21),10,12,16,18-
nonaene;

6-Chloro-12-[2-oxo-2-(4-phenylpiperazin-1-yl)ethoxy]-
2,4,8,18,22-pentaazatetracyclo[14.3.1.1(3,7).1(9,13)]
docosa-1(20),3(22),4,6,9(21),10,12,16,18-nonaene;

2-[4-({[6-Chloro-2,4,8,18,22-pentaazatetracyclo[14.3.1.1
(3,7).1(9,13)]docosa-1(20),3(22),4,6,9(21),10,12,16,
18-nonaen-12-yl]oxy}acetyl)piperazin-1-yl]benzoni-
trile;

4-[4-({[6-Chloro-2,4,8,18,22-pentaazatetracyclo[14.3.1.1
(3,7).1(9,13)]docosa-1(20),3(22),4,6,9(21),10,12,16,
18-nonaen-12-yl]oxy}acetyl)piperazin-1-yl]benzoni-
trile;

6-Chloro-12-{2-[4-(4-methylpyridin-2-yl)piperazin-1-
yl]-2-oxoethoxy}-2,4,8,18,22-pentaazatetracyclo
[14.3.1.1(3,7).1(9,13)]docosa-1(20),3(22),4,6,9(21),
10,12,16,18-nonaene;

2-[4-({[6-Chloro-2,4,8,18,22-pentaazatetracyclo[14.3.1.1
(3,7).1(9,13)]docosa-1(20),3(22),4,6,9(21),10,12,16,
18-nonaen-12-yl]oxy}acetyl)piperazin-1-yl]nicotino-
nitrile;

6-[4-({[6-Chloro-2,4,8,18,22-pentaazatetracyclo[14.3.1.1
(3,7).1(9,13)]docosa-1(20),3(22),4,6,9(21),10,12,16,
18-nonaen-12-yl]oxy}acetyl)piperazin-1-yl]nicotino-
nitrile;

6-Chloro-12-{2-[4-(6-chloropyridin-2-yl)piperazin-1-yl]-
2-oxoethoxy}-2,4,8,18,22-pentaazatetracyclo[14.3.1.1
(3,7).1(9,13)]docosa-1(20),3(22),4,6,9(21),10,12,16,
18-nonaene;

6-Chloro-12-{2-[4-(2-methoxyphenyl)piperazin-1-yl]-2-
oxoethoxy}-2,4,8,18,22-pentaazatetracyclo[14.3.1.1(3,
7).1(9,13)]docosa-1(20),3(22),4,6,9(21),10,12,16,18-
nonaene;

6-Chloro-12-{2-[4-(4-fluorophenyl)piperazin-1-yl]-2-
oxoethoxy}-2,4,8,18,22-pentaazatetracyclo[14.3.1.1(3,
7).1(9,13)]docosa-1(20),3(22),4,6,9(21),10,12,16,18-
nonaene;

6-Chloro-12-[2-oxo-2-(4-pyridin-4-ylpiperazin-1-yl)
ethoxy]-2,4,8,18,22-pentaazatetracyclo[14.3.1.1(3,7).1
(9,13)]docosa-1(20),3(22),4,6,9(21),10,12,16,18-
nonaene;

6-Chloro-12-{2-[4-(4-chloropyridin-2-yl)piperazin-1-yl]-
2-oxoethoxy}-2,4,8,18,22-pentaazatetracyclo[14.3.1.1
(3,7).1(9,13)]docosa-1(20),3(22),4,6,9(21),10,12,16,
18-nonaene;

6-Chloro-12-[2-(4-furo[3,2-c]pyridin-4-ylpiperazin-1-
yl)-2-oxoethoxy]-2,4,8,18,22-pentaazatetracyclo
[14.3.1.1(3,7).1(9,13)]docosa-1(20),3(22),4,6,9(21),
10,12,16,18-nonaene;

6-Chloro-12-{2-[4-(5-methylpyridin-2-yl)piperazin-1-
yl]-2-oxoethoxy}-2,4,8,18,22-pentaazatetracyclo
[14.3.1.1(3,7).1(9,13)]docosa-1(20),3(22),4,6,9(21),
10,12,16,18-nonaene;

6-Chloro-12-{2-[4-(4,6-dichloropyridin-2-yl)piperazin-
1-yl]-2-oxoethoxy}-2,4,8,18,22-pentaazatetracyclo
[14.3.1.1(3,7).1(9,13)]docosa-1(20),3(22),4,6,9(21),
10,12,16,18-nonaene;

6-Chloro-12-(2-oxo-2-{4-[6-(trifluoromethyl)pyridin-2-
yl]piperazin-1-yl}ethoxy)-2,4,8,18,22-pentaazatetra-
cyclo[14.3.1.1(3,7).1(9,13)]docosa-1(20),3(22),4,6,9
(21),10,12,16,18-nonaene;

6-Chloro-12-{2-[4-(3-methoxypyridin-2-yl)piperazin-1-
yl]-2-oxoethoxy}-2,4,8,18,22-pentaazatetracyclo
[14.3.1.1(3,7).1(9,13)]docosa-1(20),3(22),4,6,9(21),
10,12,16,18-nonaene;

12-{2-[4-(1,2-Benzisoxazol-3-yl)piperazin-1-yl]-2-oxo-
ethoxy}-6-chloro-2,4,8,18,22-pentaazatetracyclo
[14.3.1.1(3,7).1(9,13)]docosa-1(20),3(22),4,6,9(21),
10,12,16,18-nonaene;

6-Chloro-12-(2-{4-[(5-methylisoxazol-3-yl)carbonyl]
piperazin-1-yl}-2-oxoethoxy)-2,4,8,18,22-pentaazatet-
racyclo[14.3.1.1(3,7).1(9,13)]docosa-1(20),3(22),4,6,9
(21),10,12,16,18-nonaene;

12-[2-(4-Acetylpiperazin-1-yl)-2-oxoethoxy]-6-chloro-2,
4, 8,18,22-pentaazatetracyclo[14.3.1.1(3,7).1(9,13)]
docosa-1(20),3(22),4,6,9(21),10,12,16,18-nonaene;

6-Chloro-12-(2-{4-[(2-fluorophenyl)sulfonyl]piperazin-
1-yl}-2-oxoethoxy)-2,4, 8,18,22-pentaazatetracyclo
[14.3.1.1(3,7).1(9,13)]docosa-1(20),3(22),4,6,9(21),
10,12,16,18-nonaene;

2-{[4-({[6-Chloro-2,4,8,18,22-pentaazatetracyclo
[14.3.1.1(3,7).1(9,13)]docosa-1(20),3(22),4,6,9(21),
10,12,16,18-nonaen-12-yl]oxy}acetyl)piperazin-1-yl]
sulfonyl}benzonitrile;

6-Chloro-12-{2-oxo-2-[4-(pyridin-3-ylmethyl)piperazin-1-yl]ethoxy}-2,4,8,18,22-pentaazatetracyclo[14.3.1.1(3,7).1(9,13)]docosa-1(20),3(22),4,6,9(21),10,12,16,18-nonaene;

6-Chloro-12-{2-oxo-2-[4-(pyridin-4-ylmethyl)piperazin-1-yl]ethoxy}-2,4,8,18,22-pentaazatetracyclo[14.3.1.1(3,7).1(9,13)]docosa-1(20),3(22),4,6,9(21),10,12,16,18-nonaene;

6-Chloro-12-(2-oxo-2-{4-[5-(2-thienyl)-1H-pyrazol-3-yl]piperidin-1-yl}ethoxy)-2,4,8,18,22-pentaazatetracyclo[14.3.1.1(3,7).1(9,13)]docosa-1(20),3(22),4,6,9(21),10,12,16,18-nonaene;

6-Chloro-12-(2-oxo-2-{4-[3-(2-thienyl)-1,2,4-oxadiazol-5-yl]piperidin-1-yl}ethoxy)-2,4,8,18,22-pentaazatetracyclo[14.3.1.1(3,7).1(9,13)]docosa-1(20),3(22),4,6,9(21),10,12,16,18-nonaene;

6-Chloro-12-{2-[4-(2,4-difluorobenzoyl)piperazin-1-yl]-2-oxoethoxy}-2,4,8,18,22-pentaazatetracyclo[14.3.1.1(3,7).1(9,13)]docosa-1(20),3(22),4,6,9(21),10,12,16,18-nonaene;

6-Chloro-12-{2-[4-(isoxazol-5-ylcarbonyl)piperazin-1-yl]-2-oxoethoxy}-2,4,8,18,22-pentaazatetracyclo[14.3.1.1(3,7).1(9,13)]docosa-1(20),3(22),4,6,9(21),10,12,16,18-nonaene;

Methyl 4-({[6-chloro-2,4,8,18,22-pentaazatetracyclo[14.3.1.1(3,7).1(9,13)]docosa-1(20),3(22),4,6,9(21),10,12,16,18-nonaen-12-yl]oxy}acetyl)piperazine-1-carboxylate;

6-Chloro-12-{2-[4-(methoxyacetyl)piperazin-1-yl]-2-oxoethoxy}-2,4,8,18,22-pentaazatetracyclo[14.3.1.1(3,7).1(9,13)]docosa-1(20),3(22),4,6,9(21),10,12,16,18-nonaene;

6-Chloro-12-{2-[4-(ethylsulfonyl)piperazin-1-yl]-2-oxoethoxy}-2,4,8,18,22-pentaazatetracyclo[14.3.1.1(3,7).1(9,13)]docosa-1(20),3(22),4,6,9(21),10,12,16,18-nonaene;

4-({[6-Chloro-2,4,8,18,22-pentaazatetracyclo[14.3.1.1(3,7).1(9,13)]docosa-1(20),3(22),4,6,9(21),10,12,16,18-nonaen-12-yl]oxy}acetyl)-N-phenylpiperazine-1-carboxamide;

4-({[6-Chloro-2,4,8,18,22-pentaazatetracyclo[14.3.1.1(3,7).1(9,13)]docosa-1(20),3(22),4,6,9(21),10,12,16,18-nonaen-12-yl]oxy}acetyl)-N-methylpiperazine-1-carboxamide;

6-Chloro-12-(2-{4-[(5-methyl-1H-pyrazol-3-yl)carbonyl]piperazin-1-yl}-2-oxoethoxy)-2,4,8,18,22-pentaazatetracyclo[14.3.1.1(3,7).1(9,13)]docosa-1(20),3(22),4,6,9(21),10,12,16,18-nonaene;

1-{[4-({[6-Chloro-2,4,8,18,22-pentaazatetracyclo[14.3.1.1(3,7).1(9,13)]docosa-1(20),3(22),4,6,9(21),10,12,16,18-nonaen-12-yl]oxy}acetyl)piperazin-1-yl]carbonyl}cyclopropanecarbonitrile;

4-({[6-Chloro-2,4,8,18,22-pentaazatetracyclo[14.3.1.1(3,7).1(9,13)]docosa-1(20),3(22),4,6,9(21),10,12,16,18-nonaen-12-yl]oxy}acetyl)piperazine-1-sulfonamide;

3-[4-({[6-Chloro-2,4,8,18,22-pentaazatetracyclo[14.3.1.1(3,7).1(9,13)]docosa-1(20),3(22),4,6,9(21),10,12,16,18-nonaen-12-yl]oxy}acetyl)piperazin-1-yl]-3-oxopropanenitrile;

4-({[6-Chloro-2,4,8,18,22-pentaazatetracyclo[14.3.1.1(3,7).1(9,13)]docosa-1(20),3(22),4,6,9(21),10,12,16,18-nonaen-12-yl]oxy}acetyl)piperazine-1-carboxamide;

6-Chloro-12-{2-oxo-2-[4-(tetrahydrofuran-3-ylcarbonyl)piperazin-1-yl]ethoxy}-2,4,8,18,22-pentaazatetracyclo[14.3.1.1(3,7).1(9,13)]docosa-1(20),3(22),4,6,9(21),10,12,16,18-nonaene;

6-Chloro-12-{2-oxo-2-[4-(tetrahydrofuran-2-ylcarbonyl)piperazin-1-yl]ethoxy}-2,4,8,18,22-pentaazatetracyclo[14.3.1.1(3,7).1(9,13)]docosa-1(20),3(22),4,6,9(21),10,12,16,18-nonaene;

or pharmaceutically acceptable salts thereof or quaternary ammonium salt thereof.

62. A pharmaceutical composition comprising a compound of claim 1, or pharmaceutically acceptable salt thereof or quaternary ammonium salt thereof, and at least one pharmaceutically acceptable carrier.

\* \* \* \* \*